US009999671B2

(12) United States Patent
Liu et al.

(10) Patent No.: US 9,999,671 B2
(45) Date of Patent: Jun. 19, 2018

(54) DELIVERY OF NEGATIVELY CHARGED PROTEINS USING CATIONIC LIPIDS

(71) Applicant: President and Fellows of Harvard College, Cambridge, MA (US)

(72) Inventors: David R. Liu, Lexington, MA (US); David B. Thompson, Cambridge, MA (US); John Anthony Zuris, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 460 days.

(21) Appl. No.: 14/529,010

(22) Filed: Oct. 30, 2014

(65) Prior Publication Data

US 2015/0118216 A1 Apr. 30, 2015

Related U.S. Application Data

(63) Continuation-in-part of application No. PCT/US2014/054247, filed on Sep. 5, 2014, which is a continuation of application No. 14/462,163, filed on Aug. 18, 2014, now Pat. No. 9,526,784, and a continuation of application No. 14/462,189, filed on Aug. 18, 2014, now Pat. No. 9,737,604, application No. 14/529,010, which is a continuation-in-part of application No. 14/462,163, filed on Aug. 18, 2014, now Pat. No. 9,526,784, and a continuation-in-part of application No. 14/462,189, filed on Aug. 18, 2014, now Pat. No. 9,737,604.

(60) Provisional application No. 61/874,746, filed on Sep. 6, 2013.

(51) Int. Cl.

| | |
|---|---|
| ***C12N 15/88*** | (2006.01) |
| ***C12N 15/113*** | (2010.01) |
| ***A61K 47/12*** | (2006.01) |
| ***A61K 9/127*** | (2006.01) |
| ***A61K 38/45*** | (2006.01) |
| ***C12N 9/12*** | (2006.01) |
| ***C12N 9/96*** | (2006.01) |
| ***A61K 38/46*** | (2006.01) |
| ***C07K 14/435*** | (2006.01) |
| ***C12N 9/22*** | (2006.01) |
| ***C07K 14/195*** | (2006.01) |
| ***A61K 38/17*** | (2006.01) |
| ***C07K 14/46*** | (2006.01) |
| ***C07K 14/47*** | (2006.01) |
| ***C12N 9/14*** | (2006.01) |
| ***C07K 14/00*** | (2006.01) |

(52) U.S. Cl.

CPC .............. *A61K 47/12* (2013.01); *A61K 9/127* (2013.01); *A61K 38/1767* (2013.01); *A61K 38/45* (2013.01); *A61K 38/465* (2013.01); *C07K 14/00* (2013.01); *C07K 14/195* (2013.01); *C07K 14/43595* (2013.01); *C07K 14/463* (2013.01); *C07K 14/4702* (2013.01); *C12N 9/1241* (2013.01); *C12N 9/14* (2013.01); *C12N 9/22* (2013.01); *C12N 9/96* (2013.01); *C07K 2319/60* (2013.01); *C07K 2319/80* (2013.01); *C07K 2319/85* (2013.01); *C12Y 207/07* (2013.01); *C12Y 301/00* (2013.01)

(58) Field of Classification Search

CPC ..... C12N 15/88; C12N 15/113; C12N 15/111; C12N 2320/30; C12N 2310/3519; A61K 47/48323; C07K 2319/85; Y10S 436/829; Y10S 977/798; Y10S 977/907

See application file for complete search history.

(56) References Cited

U.S. PATENT DOCUMENTS

| | | | |
|---|---|---|---|
| 4,235,871 | A | 11/1980 | Papahadjopoulos et al. |
| 4,501,728 | A | 2/1985 | Geho et al. |
| 4,737,323 | A | 4/1988 | Martin et al. |
| 4,837,028 | A | 6/1989 | Allen |

(Continued)

FOREIGN PATENT DOCUMENTS

| | | |
|---|---|---|
| AU | 2012244264 | 11/2012 |
| AU | 2015252023 A1 | 11/2015 |

(Continued)

OTHER PUBLICATIONS

Zelphati et al (Intracellular Delivery of Proteins with a New Lipid-mediated Delivery System. The Journal of Biological Chemistry vol. 276, No. 37, Issue of Sep. 14, pp. 35103-35110, 2001.*

(Continued)

*Primary Examiner* — Kagnew H Gebreyesus
(74) *Attorney, Agent, or Firm* — Wolf, Greenfield & Sacks, P.C.

(57) ABSTRACT

Compositions, methods, strategies, kits, and systems for the delivery of negatively charged proteins, protein complexes, and fusion proteins, using cationic polymers or lipids are provided. Delivery of proteins into cells can be effected in vivo, ex vivo, or in vitro. Proteins that can be delivered using the compositions, methods, strategies, kits, and systems provided herein include, without limitation, enzymes, transcription factors, genome editing proteins, Cas9 proteins, TALEs, TALENs, nucleases, binding proteins (e.g., ligands, receptors, antibodies, antibody fragments; nucleic acid binding proteins, etc.), structural proteins, and therapeutic proteins (e.g., tumor suppressor proteins, therapeutic enzymes, growth factors, growth factor receptors, transcription factors, proteases, etc.), as well as variants and fusions of such proteins.

29 Claims, 59 Drawing Sheets

(56) References Cited

U.S. PATENT DOCUMENTS

| | | | |
|---|---|---|---|
| 5,767,099 | A | 6/1998 | Harris et al. |
| 5,780,053 | A | 7/1998 | Ashley et al. |
| 5,830,430 | A | 11/1998 | Unger et al. |
| 5,851,548 | A | 12/1998 | Dattagupta et al. |
| 5,855,910 | A | 1/1999 | Ashley et al. |
| 6,057,153 | A | 5/2000 | Shaji et al. |
| 6,453,242 | B1 | 9/2002 | Eisenberg et al. |
| 6,503,717 | B2 | 1/2003 | Case et al. |
| 6,534,261 | B1 | 3/2003 | Cox, III et al. |
| 6,599,692 | B1 | 7/2003 | Case et al. |
| 6,607,882 | B1 | 8/2003 | Cox, III et al. |
| 6,824,978 | B1 | 11/2004 | Cox, III et al. |
| 6,933,113 | B2 | 8/2005 | Case et al. |
| 6,979,539 | B2 | 12/2005 | Cox, III et al. |
| 7,013,219 | B2 | 3/2006 | Case et al. |
| 7,163,824 | B2 | 1/2007 | Cox, III et al. |
| 7,479,573 | B2 | 1/2009 | Chu et al. |
| 7,794,931 | B2 | 9/2010 | Breaker et al. |
| 7,919,277 | B2 | 4/2011 | Russell et al. |
| 7,993,672 | B2 | 8/2011 | Huang et al. |
| 8,361,725 | B2 | 1/2013 | Russell et al. |
| 8,546,553 | B2 | 10/2013 | Terns et al. |
| 8,569,256 | B2 | 10/2013 | Heyes et al. |
| 8,680,069 | B2 | 3/2014 | de Fougerolles et al. |
| 8,691,750 | B2 | 4/2014 | Constien et al. |
| 8,697,359 | B1 | 4/2014 | Zhang |
| 8,709,466 | B2 | 4/2014 | Coady et al. |
| 8,728,526 | B2 | 5/2014 | Heller |
| 8,748,667 | B2 | 6/2014 | Budzik et al. |
| 8,758,810 | B2 | 6/2014 | Okada et al. |
| 8,759,103 | B2 | 6/2014 | Kim et al. |
| 8,759,104 | B2 * | 6/2014 | Unciti-Broceta A61K 47/48046 435/458 |
| 8,771,728 | B2 | 7/2014 | Huang et al. |
| 8,790,664 | B2 | 7/2014 | Pitard et al. |
| 8,795,965 | B2 | 8/2014 | Zhang et al. |
| 8,846,578 | B2 | 9/2014 | McCray et al. |
| 8,993,233 | B2 | 3/2015 | Zhang et al. |
| 8,999,641 | B2 | 4/2015 | Zhang et al. |
| 9,068,179 | B1 | 6/2015 | Liu et al. |
| 9,163,284 | B2 | 10/2015 | Liu et al. |
| 9,228,207 | B2 | 1/2016 | Liu et al. |
| 9,234,213 | B2 | 1/2016 | Wu et al. |
| 9,322,006 | B2 | 4/2016 | Liu et al. |
| 9,322,037 | B2 | 4/2016 | Liu et al. |
| 9,340,799 | B2 | 5/2016 | Liu et al. |
| 9,340,800 | B2 | 5/2016 | Liu et al. |
| 9,359,599 | B2 | 6/2016 | Liu et al. |
| 9,388,430 | B2 | 7/2016 | Liu et al. |
| 9,512,446 | B1 | 12/2016 | Joung et al. |
| 9,526,724 | B2 | 12/2016 | Oshlack et al. |
| 9,737,604 | B2 | 8/2017 | Liu et al. |
| 2004/0003420 | A1 | 1/2004 | Kuhn et al. |
| 2004/0115184 | A1 | 6/2004 | Smith et al. |
| 2005/0222030 | A1 | 10/2005 | Allison et al. |
| 2006/0088864 | A1 | 4/2006 | Smolke et al. |
| 2007/0264692 | A1 | 11/2007 | Liu et al. |
| 2008/0124725 | A1 | 5/2008 | Barrangou et al. |
| 2008/0182254 | A1 | 7/2008 | Hall et al. |
| 2009/0130718 | A1 | 5/2009 | Short |
| 2009/0234109 | A1 | 9/2009 | Han et al. |
| 2010/0076057 | A1 | 3/2010 | Sontheimer et al. |
| 2010/0093617 | A1 | 4/2010 | Barrangou et al. |
| 2010/0104690 | A1 | 4/2010 | Barrangou et al. |
| 2010/0316643 | A1 | 12/2010 | Eckert et al. |
| 2011/0059160 | A1 | 3/2011 | Essner et al. |
| 2011/0104787 | A1 | 5/2011 | Church et al. |
| 2011/0189776 | A1 | 8/2011 | Terns et al. |
| 2011/0217739 | A1 | 9/2011 | Terns et al. |
| 2012/0129759 | A1 | 5/2012 | Liu et al. |
| 2012/0141523 | A1 | 6/2012 | Castado et al. |
| 2012/0270273 | A1 | 10/2012 | Zhang et al. |
| 2013/0117869 | A1 | 5/2013 | Duchateau et al. |
| 2013/0130248 | A1 | 5/2013 | Haurwitz et al. |
| 2013/0158245 | A1 | 6/2013 | Russell et al. |
| 2013/0165389 | A1 | 6/2013 | Schellenberger et al. |
| 2013/0344117 | A1 | 12/2013 | Mirosevich et al. |
| 2014/0004280 | A1 | 1/2014 | Loomis |
| 2014/0005269 | A1 | 1/2014 | Ngwuluka et al. |
| 2014/0017214 | A1 | 1/2014 | Cost |
| 2014/0018404 | A1 | 1/2014 | Chen et al. |
| 2014/0044793 | A1 | 2/2014 | Goll et al. |
| 2014/0065711 | A1 | 3/2014 | Liu et al. |
| 2014/0068797 | A1 | 3/2014 | Doudna et al. |
| 2014/0127752 | A1 | 5/2014 | Zhou et al. |
| 2014/0141094 | A1 | 5/2014 | Smyth et al. |
| 2014/0141487 | A1 | 5/2014 | Feldman et al. |
| 2014/0186843 | A1 | 7/2014 | Zhang et al. |
| 2014/0186958 | A1 | 7/2014 | Zhang et al. |
| 2014/0234289 | A1 | 8/2014 | Liu et al. |
| 2014/0248702 | A1 | 9/2014 | Cong |
| 2014/0273037 | A1 | 9/2014 | Wu |
| 2014/0273226 | A1 | 9/2014 | Wu |
| 2014/0273230 | A1 | 9/2014 | Chen et al. |
| 2014/0295556 | A1 | 10/2014 | Joung et al. |
| 2014/0295557 | A1 | 10/2014 | Joung et al. |
| 2014/0342456 | A1 | 11/2014 | Mali et al. |
| 2014/0342457 | A1 | 11/2014 | Mali et al. |
| 2014/0342458 | A1 | 11/2014 | Mali et al. |
| 2014/0349400 | A1 | 11/2014 | Jakimo et al. |
| 2014/0356867 | A1 | 12/2014 | Peter et al. |
| 2014/0356956 | A1 | 12/2014 | Church et al. |
| 2014/0356958 | A1 | 12/2014 | Mali et al. |
| 2014/0356959 | A1 | 12/2014 | Church et al. |
| 2014/0357523 | A1 | 12/2014 | Zeiner et al. |
| 2014/0377868 | A1 | 12/2014 | Joung et al. |
| 2015/0010526 | A1 | 1/2015 | Liu et al. |
| 2015/0031089 | A1 | 1/2015 | Lindstrom |
| 2015/0031132 | A1 | 1/2015 | Church et al. |
| 2015/0031133 | A1 | 1/2015 | Church et al. |
| 2015/0044191 | A1 | 2/2015 | Liu et al. |
| 2015/0044192 | A1 | 2/2015 | Liu et al. |
| 2015/0044772 | A1 | 2/2015 | Zhao |
| 2015/0050699 | A1 | 2/2015 | Siksnys et al. |
| 2015/0056177 | A1 | 2/2015 | Liu et al. |
| 2015/0056629 | A1 | 2/2015 | Guthrie-Honea |
| 2015/0064138 | A1 | 3/2015 | Lu et al. |
| 2015/0064789 | A1 | 3/2015 | Paschon et al. |
| 2015/0071898 | A1 | 3/2015 | Liu et al. |
| 2015/0071899 | A1 | 3/2015 | Liu et al. |
| 2015/0071900 | A1 | 3/2015 | Liu et al. |
| 2015/0071901 | A1 | 3/2015 | Liu et al. |
| 2015/0071902 | A1 | 3/2015 | Liu et al. |
| 2015/0071903 | A1 | 3/2015 | Liu et al. |
| 2015/0071906 | A1 | 3/2015 | Liu et al. |
| 2015/0079680 | A1 | 3/2015 | Bradley et al. |
| 2015/0098954 | A1 | 4/2015 | Hyde et al. |
| 2015/0132269 | A1 | 5/2015 | Orkin et al. |
| 2015/0140664 | A1 | 5/2015 | Byrne et al. |
| 2015/0159172 | A1 | 6/2015 | Miller et al. |
| 2015/0165054 | A1 | 6/2015 | Liu et al. |
| 2015/0166980 | A1 | 6/2015 | Liu et al. |
| 2015/0166981 | A1 | 6/2015 | Liu et al. |
| 2015/0166982 | A1 | 6/2015 | Liu et al. |
| 2015/0166984 | A1 | 6/2015 | Liu et al. |
| 2015/0166985 | A1 | 6/2015 | Liu et al. |
| 2015/0191744 | A1 | 7/2015 | Wolfe et al. |
| 2015/0197759 | A1 | 7/2015 | Xu et al. |
| 2015/0211058 | A1 | 7/2015 | Carstens et al. |
| 2015/0218573 | A1 | 8/2015 | Loque et al. |
| 2015/0225773 | A1 | 8/2015 | Farmer et al. |
| 2015/0252358 | A1 | 9/2015 | Maeder et al. |
| 2015/0315252 | A1 | 11/2015 | Haugwitz et al. |
| 2016/0015682 | A2 | 1/2016 | Cawthorne et al. |
| 2016/0017393 | A1 | 1/2016 | Jacobson et al. |
| 2016/0017396 | A1 | 1/2016 | Cann et al. |
| 2016/0032353 | A1 | 2/2016 | Braman et al. |
| 2016/0046952 | A1 | 2/2016 | Hittinger et al. |
| 2016/0046961 | A1 | 2/2016 | Jinek et al. |
| 2016/0046962 | A1 | 2/2016 | May et al. |
| 2016/0053272 | A1 | 2/2016 | Wurtzel et al. |
| 2016/0053304 | A1 | 2/2016 | Wurtzel et al. |
| 2016/0074535 | A1 | 3/2016 | Ranganathan et al. |
| 2016/0076093 | A1 | 3/2016 | Shendure et al. |

(56) References Cited

U.S. PATENT DOCUMENTS

| | | | |
|---|---|---|---|
| 2016/0090603 | A1 | 3/2016 | Carnes et al. |
| 2016/0090622 | A1 | 3/2016 | Liu et al. |
| 2016/0138046 | A1 | 5/2016 | Wu et al. |
| 2016/0186214 | A1 | 6/2016 | Brouns et al. |
| 2016/0200779 | A1 | 7/2016 | Liu et al. |
| 2016/0201040 | A1 | 7/2016 | Liu et al. |
| 2016/0201089 | A1 | 7/2016 | Gersbach et al. |
| 2016/0206566 | A1 | 7/2016 | Lu et al. |
| 2016/0208243 | A1 | 7/2016 | Zhang et al. |
| 2016/0208288 | A1 | 7/2016 | Liu et al. |
| 2016/0215275 | A1 | 7/2016 | Zhong |
| 2016/0215276 | A1 | 7/2016 | Liu et al. |
| 2016/0215300 | A1 | 7/2016 | May et al. |
| 2016/0244784 | A1 | 8/2016 | Jacobson et al. |
| 2016/0244829 | A1 | 8/2016 | Bang et al. |
| 2016/0304846 | A1 | 10/2016 | Liu et al. |
| 2016/0304855 | A1 | 10/2016 | Stark et al. |
| 2016/0312304 | A1 | 10/2016 | Sorrentino et al. |
| 2016/0333389 | A1 | 11/2016 | Liu et al. |
| 2016/0345578 | A1 | 12/2016 | Barrangou et al. |
| 2016/0346360 | A1 | 12/2016 | Quake et al. |
| 2016/0346361 | A1 | 12/2016 | Quake et al. |
| 2016/0346362 | A1 | 12/2016 | Quake et al. |
| 2016/0348074 | A1 | 12/2016 | Quake et al. |
| 2016/0350476 | A1 | 12/2016 | Quake et al. |
| 2016/0369262 | A1 | 12/2016 | Reik et al. |
| 2017/0009242 | A1 | 1/2017 | McKinley et al. |
| 2017/0014449 | A1 | 1/2017 | Bangera et al. |
| 2017/0020922 | A1 | 1/2017 | Wagner et al. |
| 2017/0037432 | A1 | 2/2017 | Donohue et al. |
| 2017/0044520 | A1 | 2/2017 | Liu et al. |
| 2017/0044592 | A1 | 2/2017 | Peter et al. |
| 2017/0053729 | A1 | 2/2017 | Kotani et al. |
| 2017/0058271 | A1 | 3/2017 | Joung et al. |
| 2017/0058272 | A1 | 3/2017 | Carter et al. |
| 2017/0058298 | A1 | 3/2017 | Kennedy et al. |
| 2017/0073663 | A1 | 3/2017 | Wang et al. |
| 2017/0087224 | A1 | 3/2017 | Quake et al. |
| 2017/0087225 | A1 | 3/2017 | Quake et al. |
| 2017/0088587 | A1 | 3/2017 | Quake et al. |
| 2017/0088828 | A1 | 3/2017 | Quake et al. |
| 2017/0107560 | A1 | 4/2017 | Peter et al. |
| 2017/0114367 | A1 | 4/2017 | Hu et al. |
| 2017/0121693 | A1 | 5/2017 | Liu et al. |
| 2017/0145394 | A1 | 5/2017 | Yeo et al. |
| 2017/0145405 | A1 | 5/2017 | Tang et al. |
| 2017/0145438 | A1 | 5/2017 | Kantor |
| 2017/0152787 | A1 | 6/2017 | Kubo et al. |
| 2017/0159033 | A1 | 6/2017 | Kamtekar et al. |
| 2017/0166928 | A1 | 6/2017 | Vyas et al. |
| 2017/0175104 | A1 | 6/2017 | Doudna et al. |
| 2017/0191047 | A1 | 7/2017 | Terns et al. |
| 2017/0198277 | A1 | 7/2017 | Kmiec et al. |
| 2017/0198302 | A1 | 7/2017 | Feng et al. |
| 2017/0226522 | A1 | 8/2017 | Hu et al. |
| 2017/0233703 | A1 | 8/2017 | Xie et al. |
| 2017/0233756 | A1 | 8/2017 | Begemann et al. |
| 2017/0247671 | A1 | 8/2017 | Yung et al. |
| 2017/0247703 | A1 | 8/2017 | Sloan et al. |
| 2017/0268022 | A1 | 9/2017 | Liu et al. |
| 2017/0283797 | A1 | 10/2017 | Robb et al. |
| 2017/0314016 | A1 | 11/2017 | Kim et al. |

FOREIGN PATENT DOCUMENTS

| | | | |
|---|---|---|---|
| AU | 2015101792 | | 1/2016 |
| CA | 2 852 593 | A1 | 11/2015 |
| CN | 103233028 | A | 8/2013 |
| CN | 103388006 | A | 11/2013 |
| CN | 103614415 | A | 3/2014 |
| CN | 103642836 | A | 3/2014 |
| CN | 103668472 | A | 3/2014 |
| CN | 103820441 | A | 5/2014 |
| CN | 103820454 | A | 5/2014 |
| CN | 103911376 | A | 7/2014 |
| CN | 103923911 | A | 7/2014 |
| CN | 103981211 | A | 8/2014 |
| CN | 103981212 | A | 8/2014 |
| CN | 104004778 | A | 8/2014 |
| CN | 104004782 | A | 8/2014 |
| CN | 104017821 | A | 9/2014 |
| CN | 104109687 | A | 10/2014 |
| CN | 104178461 | A | 12/2014 |
| CN | 104342457 | | 2/2015 |
| CN | 104404036 | A | 3/2015 |
| CN | 104450774 | A | 3/2015 |
| CN | 104480144 | A | 4/2015 |
| CN | 104498493 | A | 4/2015 |
| CN | 104504304 | A | 4/2015 |
| CN | 104531704 | A | 4/2015 |
| CN | 104531705 | A | 4/2015 |
| CN | 104560864 | A | 4/2015 |
| CN | 104561095 | A | 4/2015 |
| CN | 104593418 | A | 5/2015 |
| CN | 104593422 | A | 5/2015 |
| CN | 104611370 | A | 5/2015 |
| CN | 104651392 | A | 5/2015 |
| CN | 104651398 | A | 5/2015 |
| CN | 104651399 | A | 5/2015 |
| CN | 104651401 | A | 5/2015 |
| CN | 104673816 | A | 6/2015 |
| CN | 104726449 | A | 6/2015 |
| CN | 104726494 | A | 6/2015 |
| CN | 104745626 | A | 7/2015 |
| CN | 104762321 | A | 7/2015 |
| CN | 104805078 | A | 7/2015 |
| CN | 104805099 | A | 7/2015 |
| CN | 104805118 | A | 7/2015 |
| CN | 104846010 | A | 8/2015 |
| CN | 104894068 | A | 9/2015 |
| CN | 104894075 | A | 9/2015 |
| CN | 104928321 | A | 9/2015 |
| CN | 105039339 | A | 11/2015 |
| CN | 105039399 | A | 11/2015 |
| CN | 105063061 | A | 11/2015 |
| CN | 105087620 | A | 11/2015 |
| CN | 105112422 | A | 12/2015 |
| CN | 105112445 | A | 12/2015 |
| CN | 105112519 | A | 12/2015 |
| CN | 105132427 | A | 12/2015 |
| CN | 105132451 | A | 12/2015 |
| CN | 105177038 | A | 12/2015 |
| CN | 105177126 | A | 12/2015 |
| CN | 105210981 | A | 1/2016 |
| CN | 105219799 | A | 1/2016 |
| CN | 105238806 | A | 1/2016 |
| CN | 105255937 | A | 1/2016 |
| CN | 105274144 | A | 1/2016 |
| CN | 105296518 | A | 2/2016 |
| CN | 105296537 | A | 2/2016 |
| CN | 105316324 | A | 2/2016 |
| CN | 105316327 | A | 2/2016 |
| CN | 105316337 | A | 2/2016 |
| CN | 105331607 | A | 2/2016 |
| CN | 105331608 | A | 2/2016 |
| CN | 105331609 | A | 2/2016 |
| CN | 105331627 | A | 2/2016 |
| CN | 105400773 | A | 3/2016 |
| CN | 105400779 | A | 3/2016 |
| CN | 105400810 | A | 3/2016 |
| CN | 105441451 | A | 3/2016 |
| CN | 105462968 | A | 4/2016 |
| CN | 105463003 | A | 4/2016 |
| CN | 105463027 | A | 4/2016 |
| CN | 105492608 | A | 4/2016 |
| CN | 105492609 | A | 4/2016 |
| CN | 105505976 | A | 4/2016 |
| CN | 105505979 | A | 4/2016 |
| CN | 105518134 | A | 4/2016 |
| CN | 105518135 | A | 4/2016 |
| CN | 105518137 | A | 4/2016 |
| CN | 105518138 | A | 4/2016 |
| CN | 105518139 | A | 4/2016 |
| CN | 105518140 | A | 4/2016 |

(56) References Cited

FOREIGN PATENT DOCUMENTS

| | | | |
|---|---|---|---|
| CN | 105543228 | A | 5/2016 |
| CN | 105543266 | A | 5/2016 |
| CN | 105543270 | A | 5/2016 |
| CN | 105567688 | A | 5/2016 |
| CN | 105567689 | A | 5/2016 |
| CN | 105567734 | A | 5/2016 |
| CN | 105567735 | A | 5/2016 |
| CN | 105567738 | A | 5/2016 |
| CN | 105593367 | A | 5/2016 |
| CN | 105594664 | A | 5/2016 |
| CN | 105602987 | A | 5/2016 |
| CN | 105624146 | A | 6/2016 |
| CN | 105624187 | A | 6/2016 |
| CN | 105646719 | A | 6/2016 |
| CN | 105647922 | A | 6/2016 |
| CN | 105647962 | A | 6/2016 |
| CN | 105647968 | A | 6/2016 |
| CN | 105647969 | A | 6/2016 |
| CN | 105671070 | A | 6/2016 |
| CN | 105671083 | A | 6/2016 |
| CN | 105695485 | A | 6/2016 |
| CN | 105779448 | A | 7/2016 |
| CN | 105779449 | A | 7/2016 |
| CN | 105802980 | A | 7/2016 |
| CN | 105821039 | A | 8/2016 |
| CN | 105821040 | A | 8/2016 |
| CN | 105821049 | A | 8/2016 |
| CN | 105821072 | A | 8/2016 |
| CN | 105821075 | A | 8/2016 |
| CN | 105821116 | A | 8/2016 |
| CN | 105838733 | A | 8/2016 |
| CN | 105861547 | A | 8/2016 |
| CN | 105861552 | A | 8/2016 |
| CN | 105861554 | A | 8/2016 |
| CN | 105886498 | A | 8/2016 |
| CN | 105886534 | A | 8/2016 |
| CN | 105886616 | A | 8/2016 |
| CN | 105907758 | A | 8/2016 |
| CN | 105907785 | A | 8/2016 |
| CN | 105925608 | A | 9/2016 |
| CN | 105950560 | A | 9/2016 |
| CN | 105950626 | A | 9/2016 |
| CN | 105950633 | A | 9/2016 |
| CN | 105950639 | A | 9/2016 |
| CN | 105985985 | A | 10/2016 |
| CN | 106011150 | A | 10/2016 |
| CN | 106011167 | A | 10/2016 |
| CN | 106011171 | A | 10/2016 |
| CN | 106032540 | A | 10/2016 |
| CN | 106047803 | A | 10/2016 |
| CN | 106047877 | A | 10/2016 |
| CN | 106047930 | A | 10/2016 |
| CN | 106086008 | A | 11/2016 |
| CN | 106086028 | A | 11/2016 |
| CN | 106086061 | A | 11/2016 |
| CN | 106086062 | A | 11/2016 |
| CN | 106109417 | A | 11/2016 |
| CN | 106119275 | A | 11/2016 |
| CN | 106119283 | A | 11/2016 |
| CN | 106148286 | A | 11/2016 |
| CN | 106148370 | A | 11/2016 |
| CN | 106148416 | A | 11/2016 |
| CN | 106167525 | A | 11/2016 |
| CN | 106167808 | A | 11/2016 |
| CN | 106167810 | A | 11/2016 |
| CN | 106167821 | A | 11/2016 |
| CN | 106172238 | A | 12/2016 |
| CN | 106190903 | A | 12/2016 |
| CN | 106191057 | A | 12/2016 |
| CN | 106191061 | A | 12/2016 |
| CN | 106191062 | A | 12/2016 |
| CN | 106191064 | A | 12/2016 |
| CN | 106191071 | A | 12/2016 |
| CN | 106191099 | A | 12/2016 |
| CN | 106191107 | A | 12/2016 |
| CN | 106191113 | A | 12/2016 |
| CN | 106191114 | A | 12/2016 |
| CN | 106191116 | A | 12/2016 |
| CN | 106191124 | A | 12/2016 |
| CN | 106222177 | A | 12/2016 |
| CN | 106222193 | A | 12/2016 |
| CN | 106222203 | A | 12/2016 |
| CN | 106244555 | A | 12/2016 |
| CN | 106244591 | A | 12/2016 |
| CN | 106244609 | A | 12/2016 |
| CN | 106282241 | A | 1/2017 |
| CN | 106318934 | A | 1/2017 |
| CN | 106318973 | A | 1/2017 |
| CN | 106350540 | A | 1/2017 |
| CN | 106367435 | A | 2/2017 |
| CN | 106399306 | A | 2/2017 |
| CN | 106399311 | A | 2/2017 |
| CN | 106399360 | A | 2/2017 |
| CN | 106399367 | A | 2/2017 |
| CN | 106399375 | A | 2/2017 |
| CN | 106399377 | A | 2/2017 |
| CN | 106434651 | A | 2/2017 |
| CN | 106434663 | A | 2/2017 |
| CN | 106434688 | A | 2/2017 |
| CN | 106434737 | A | 2/2017 |
| CN | 106434748 | A | 2/2017 |
| CN | 106434752 | A | 2/2017 |
| CN | 106434782 | A | 2/2017 |
| CN | 106446600 | A | 2/2017 |
| CN | 106479985 | A | 3/2017 |
| CN | 106480027 | A | 3/2017 |
| CN | 106480036 | A | 3/2017 |
| CN | 106480067 | A | 3/2017 |
| CN | 106480083 | A | 3/2017 |
| CN | 106480097 | A | 3/2017 |
| CN | 106544351 | A | 3/2017 |
| CN | 106544353 | A | 3/2017 |
| CN | 106544357 | A | 3/2017 |
| CN | 106554969 | A | 4/2017 |
| CN | 106566838 | A | 4/2017 |
| CN | 106701763 | A | 5/2017 |
| CN | 106701808 | A | 5/2017 |
| CN | 106701818 | A | 5/2017 |
| CN | 106701823 | A | 5/2017 |
| CN | 106701830 | A | 5/2017 |
| CN | 106754912 | A | 5/2017 |
| CN | 106755026 | A | 5/2017 |
| CN | 106755077 | A | 5/2017 |
| CN | 106755088 | A | 5/2017 |
| CN | 106755091 | A | 5/2017 |
| CN | 106755097 | A | 5/2017 |
| CN | 106755424 | A | 5/2017 |
| CN | 106801056 | A | 6/2017 |
| CN | 106834323 | A | 6/2017 |
| CN | 106834341 | A | 6/2017 |
| CN | 106834347 | A | 6/2017 |
| CN | 106845151 | A | 6/2017 |
| CN | 106868008 | A | 6/2017 |
| CN | 106868031 | A | 6/2017 |
| CN | 106906240 | A | 6/2017 |
| CN | 106906242 | A | 6/2017 |
| CN | 106916820 | A | 7/2017 |
| CN | 106916852 | A | 7/2017 |
| CN | 106939303 | A | 7/2017 |
| CN | 106947750 | A | 7/2017 |
| CN | 106947780 | A | 7/2017 |
| CN | 106957830 | A | 7/2017 |
| CN | 106957831 | A | 7/2017 |
| CN | 106957844 | A | 7/2017 |
| CN | 106957855 | A | 7/2017 |
| CN | 106957858 | A | 7/2017 |
| CN | 106967697 | A | 7/2017 |
| CN | 106967726 | A | 7/2017 |
| CN | 106978428 | A | 7/2017 |
| CN | 106987570 | A | 7/2017 |
| CN | 106987757 | A | 7/2017 |
| CN | 107012164 | A | 8/2017 |
| CN | 107012174 | A | 8/2017 |
| CN | 107012213 | A | 8/2017 |

(56) References Cited

FOREIGN PATENT DOCUMENTS

| | | | |
|---|---|---|---|
| CN | 107012250 | A | 8/2017 |
| CN | 107022562 | A | 8/2017 |
| CN | 107034188 | A | 8/2017 |
| CN | 107034218 | A | 8/2017 |
| CN | 107034229 | A | 8/2017 |
| CN | 107043775 | A | 8/2017 |
| CN | 107043779 | A | 8/2017 |
| CN | 107043787 | A | 8/2017 |
| CN | 107058320 | A | 8/2017 |
| CN | 107058328 | A | 8/2017 |
| CN | 107058358 | A | 8/2017 |
| CN | 107058372 | A | 8/2017 |
| CN | 107083392 | A | 8/2017 |
| CN | 107099533 | A | 8/2017 |
| CN | 107099850 | A | 8/2017 |
| CN | 107119053 | A | 9/2017 |
| CN | 107119071 | A | 9/2017 |
| CN | 107129999 | A | 9/2017 |
| CN | 107130000 | A | 9/2017 |
| CN | 107142272 | A | 9/2017 |
| CN | 107142282 | A | 9/2017 |
| CN | 107177591 | A | 9/2017 |
| CN | 107177595 | A | 9/2017 |
| CN | 107177631 | A | 9/2017 |
| CN | 107190006 | A | 9/2017 |
| CN | 107190008 | A | 9/2017 |
| CN | 107217042 | A | 9/2017 |
| CN | 107217075 | A | 9/2017 |
| CN | 107227307 | A | 10/2017 |
| CN | 107227352 | A | 10/2017 |
| CN | 107236737 | A | 10/2017 |
| CN | 107236739 | A | 10/2017 |
| CN | 107236741 | A | 10/2017 |
| CN | 107245502 | A | 10/2017 |
| CN | 107254485 | A | 10/2017 |
| CN | 107266541 | A | 10/2017 |
| CN | 107267515 | A | 10/2017 |
| CN | 107287245 | A | 10/2017 |
| CN | 107298701 | | 10/2017 |
| CN | 107299114 | A | 10/2017 |
| CN | 107304435 | A | 10/2017 |
| CN | 107312785 | A | 11/2017 |
| CN | 107312793 | A | 11/2017 |
| CN | 107312795 | A | 11/2017 |
| CN | 107312798 | A | 11/2017 |
| CN | 107326042 | A | 11/2017 |
| CN | 107326046 | A | 11/2017 |
| CN | 107354156 | | 11/2017 |
| CN | 107354173 | | 11/2017 |
| EP | 2 604 255 | A1 | 6/2013 |
| EP | 2 966 170 | A1 | 1/2016 |
| EP | 3 009 511 | A2 | 4/2016 |
| EP | 3199632 | A1 | 8/2017 |
| GB | 2 528 177 | A | 1/2016 |
| GB | 2 531 454 | A1 | 4/2016 |
| GB | 2542653 | A | 3/2017 |
| JP | 2007-501626 | A | 2/2007 |
| JP | 2010-539929 | A | 12/2010 |
| KR | 101584933 | B1 | 1/2016 |
| KR | 2016/0133380 | A | 11/2016 |
| KR | 20170037025 | A | 4/2017 |
| KR | 20170037028 | A | 4/2017 |
| KR | 101748575 | B1 | 6/2017 |
| RU | 2016104674 | A | 8/2017 |
| RU | 2634395 | C1 | 10/2017 |
| WO | WO-2001/38547 | A2 | 5/2001 |
| WO | WO 2002/068676 | A2 | 9/2002 |
| WO | WO 2002/103028 | A2 | 12/2002 |
| WO | WO-2004/007684 | A2 | 1/2004 |
| WO | WO-2005/014791 | A2 | 2/2005 |
| WO | WO 2006/002547 | A1 | 1/2006 |
| WO | WO 2006/042112 | A2 | 4/2006 |
| WO | WO 2007/025097 | A2 | 3/2007 |
| WO | WO 2007/136815 | A2 | 11/2007 |
| WO | WO 2007/143574 | A1 | 12/2007 |
| WO | WO 2008/108989 | A2 | 9/2008 |
| WO | WO 2009/134808 | A2 | 11/2009 |
| WO | WO 2010/011961 | A2 | 1/2010 |
| WO | WO 2010/054108 | A2 | 5/2010 |
| WO | WO 2010/054154 | A2 | 5/2010 |
| WO | WO 2010/068289 | A2 | 6/2010 |
| WO | WO 2010/075424 | A2 | 7/2010 |
| WO | WO 2010/102257 | A2 | 9/2010 |
| WO | WO 2010/129019 | A2 | 11/2010 |
| WO | WO 2010/129023 | A2 | 11/2010 |
| WO | WO 2010/144150 | A2 | 12/2010 |
| WO | WO-2011/002503 | A1 | 1/2011 |
| WO | WO 2011/017293 | A2 | 2/2011 |
| WO | WO 2011/053868 | A1 | 5/2011 |
| WO | WO 2011/053982 | A2 | 5/2011 |
| WO | WO 2011/075627 | A1 | 6/2011 |
| WO | WO 2011/091311 | A2 | 7/2011 |
| WO | WO 2011/109031 | A1 | 9/2011 |
| WO | WO 2011/143124 | A2 | 11/2011 |
| WO | WO 2012/054726 | A1 | 4/2012 |
| WO | WO 2012/065043 | A2 | 5/2012 |
| WO | WO-2012/125445 | A2 | 9/2012 |
| WO | WO 2012/138927 | A2 | 10/2012 |
| WO | WO 2012/158985 | A2 | 11/2012 |
| WO | WO 2012/158986 | A2 | 11/2012 |
| WO | WO 2012/164565 | A1 | 12/2012 |
| WO | WO 2013/012674 | A1 | 1/2013 |
| WO | WO 2013/013105 | A2 | 1/2013 |
| WO | WO 2013/066438 | A2 | 5/2013 |
| WO | WO 2013/098244 | A1 | 7/2013 |
| WO | WO 2013/119602 | A1 | 8/2013 |
| WO | WO 2013/126794 | A1 | 8/2013 |
| WO | WO 2013/130824 | A1 | 9/2013 |
| WO | WO 2013/141680 | A1 | 9/2013 |
| WO | WO 2013/142378 | A9 | 9/2013 |
| WO | WO 2013/142578 | A2 | 9/2013 |
| WO | WO 2013/160230 | A1 | 10/2013 |
| WO | WO 2013/166315 | A1 | 11/2013 |
| WO | WO 2013/169398 | A2 | 11/2013 |
| WO | WO 2013/169802 | A1 | 11/2013 |
| WO | WO 2013/176772 | A2 | 11/2013 |
| WO | WO 2013/176915 | A1 | 11/2013 |
| WO | WO 2013/176916 | A1 | 11/2013 |
| WO | WO 2013/181440 | A1 | 12/2013 |
| WO | WO 2013/186754 | A2 | 12/2013 |
| WO | WO 2013/188037 | A2 | 12/2013 |
| WO | WO 2013/188522 | A2 | 12/2013 |
| WO | WO 2013/188638 | A2 | 12/2013 |
| WO | WO 2013/192278 | A1 | 12/2013 |
| WO | WO 2014/005042 | A2 | 1/2014 |
| WO | WO 2014/011237 | A1 | 1/2014 |
| WO | WO 2014/011901 | A2 | 1/2014 |
| WO | WO 2014/018423 | A2 | 1/2014 |
| WO | WO 2014/020608 | A1 | 2/2014 |
| WO | WO 2014/022120 | A1 | 2/2014 |
| WO | WO 2014/022702 | A2 | 2/2014 |
| WO | WO 2014/036219 | A2 | 3/2014 |
| WO | WO 2014/039513 | A2 | 3/2014 |
| WO | WO 2014/039523 | A1 | 3/2014 |
| WO | WO 2014/039684 | A1 | 3/2014 |
| WO | WO 2014/039692 | A2 | 3/2014 |
| WO | WO 2014/039702 | A2 | 3/2014 |
| WO | WO 2014/039872 | A1 | 3/2014 |
| WO | WO 2014/039970 | A1 | 3/2014 |
| WO | WO 2014/041327 | A1 | 3/2014 |
| WO | WO 2014/043143 | A1 | 3/2014 |
| WO | WO 2014/047103 | A2 | 3/2014 |
| WO | WO 2014/059173 | A2 | 4/2014 |
| WO | WO 2014/059255 | A1 | 4/2014 |
| WO | WO 2014/065596 | A1 | 5/2014 |
| WO | WO 2014/066505 | A1 | 5/2014 |
| WO | WO 2014/068346 | A2 | 5/2014 |
| WO | WO 2014/070887 | A1 | 5/2014 |
| WO | WO 2014/071006 | A1 | 5/2014 |
| WO | WO 2014/071219 | A1 | 5/2014 |
| WO | WO 2014/071235 | A1 | 5/2014 |
| WO | WO 2014/072941 | A1 | 5/2014 |
| WO | WO 2014/081729 | A1 | 5/2014 |
| WO | WO 2014/081730 | A1 | 5/2014 |

(56) References Cited

FOREIGN PATENT DOCUMENTS

| | | | |
|---|---|---|---|
| WO | WO 2014/081855 | A1 | 5/2014 |
| WO | WO 2014/082644 | A1 | 6/2014 |
| WO | WO 2014/085261 | A1 | 6/2014 |
| WO | WO 2014/085593 | A1 | 6/2014 |
| WO | WO 2014/085830 | A2 | 6/2014 |
| WO | WO 2014/089212 | A1 | 6/2014 |
| WO | WO 2014/089290 | A1 | 6/2014 |
| WO | WO 2014/089348 | A1 | 6/2014 |
| WO | WO 2014/089513 | A1 | 6/2014 |
| WO | WO 2014/089533 | A2 | 6/2014 |
| WO | WO 2014/089541 | A2 | 6/2014 |
| WO | WO 2014/093479 | A1 | 6/2014 |
| WO | WO 2014/093595 | A1 | 6/2014 |
| WO | WO 2014/093622 | A2 | 6/2014 |
| WO | WO 2014/093635 | A1 | 6/2014 |
| WO | WO 2014/093655 | A2 | 6/2014 |
| WO | WO 2014/093661 | A2 | 6/2014 |
| WO | WO 2014/093694 | A1 | 6/2014 |
| WO | WO 2014/093701 | A1 | 6/2014 |
| WO | WO 2014/093709 | A1 | 6/2014 |
| WO | WO 2014/093712 | A1 | 6/2014 |
| WO | WO 2014/093718 | A1 | 6/2014 |
| WO | WO 2014/093736 | A1 | 6/2014 |
| WO | WO 2014/093768 | A1 | 6/2014 |
| WO | WO 2014/093852 | A1 | 6/2014 |
| WO | WO 2014/096972 | A2 | 6/2014 |
| WO | WO 2014/099744 | A1 | 6/2014 |
| WO | WO 2014/099750 | A2 | 6/2014 |
| WO | WO 2014/104878 | A1 | 7/2014 |
| WO | WO 2014/110006 | A1 | 7/2014 |
| WO | WO 2014/110552 | A1 | 7/2014 |
| WO | WO 2014/113493 | A1 | 7/2014 |
| WO | WO 2014/123967 | A2 | 8/2014 |
| WO | WO 2014/124226 | A1 | 8/2014 |
| WO | WO 2014/125668 | A1 | 8/2014 |
| WO | WO 2014/127287 | A1 | 8/2014 |
| WO | WO 2014/128324 | A1 | 8/2014 |
| WO | WO 2014/128659 | A1 | 8/2014 |
| WO | WO 2014/130706 | A1 | 8/2014 |
| WO | WO 2014/130955 | A1 | 8/2014 |
| WO | WO 2014/131833 | A1 | 9/2014 |
| WO | WO 2014/138379 | A1 | 9/2014 |
| WO | WO 2014/143381 | A1 | 9/2014 |
| WO | WO 2014/144094 | A1 | 9/2014 |
| WO | WO 2014/144155 | A1 | 9/2014 |
| WO | WO 2014/144288 | A1 | 9/2014 |
| WO | WO 2014/144592 | A2 | 9/2014 |
| WO | WO 2014/144761 | A2 | 9/2014 |
| WO | WO 2014/144951 | A1 | 9/2014 |
| WO | WO 2014/145599 | A2 | 9/2014 |
| WO | WO 2014/145736 | A2 | 9/2014 |
| WO | WO 2014/150624 | A1 | 9/2014 |
| WO | WO 2014/152432 | A2 | 9/2014 |
| WO | WO 2014/153118 | A1 | 9/2014 |
| WO | WO 2014/153470 | A2 | 9/2014 |
| WO | WO 2014/161821 | A1 | 10/2014 |
| WO | WO 2014/164466 | A1 | 10/2014 |
| WO | WO 2014/165177 | A1 | 10/2014 |
| WO | WO 2014/165349 | A1 | 10/2014 |
| WO | WO 2014/165612 | A2 | 10/2014 |
| WO | WO 2014/165707 | A2 | 10/2014 |
| WO | WO 2014/165825 | A2 | 10/2014 |
| WO | WO 2014/172458 | A1 | 10/2014 |
| WO | WO 2014/172470 | A | 10/2014 |
| WO | WO 2014/172489 | A2 | 10/2014 |
| WO | WO 2014/173955 | A1 | 10/2014 |
| WO | WO 2014/182700 | A1 | 11/2014 |
| WO | WO 2014/183071 | A2 | 11/2014 |
| WO | WO 2014/184143 | A1 | 11/2014 |
| WO | WO 2014/184741 | A1 | 11/2014 |
| WO | WO 2014/184744 | A1 | 11/2014 |
| WO | WO 2014/186585 | A2 | 11/2014 |
| WO | WO 2014/186686 | A2 | 11/2014 |
| WO | WO 2014/190181 | A1 | 11/2014 |
| WO | WO 2014/191128 | A1 | 12/2014 |
| WO | WO 2014/191518 | A1 | 12/2014 |
| WO | WO 2014/191521 | A2 | 12/2014 |
| WO | WO 2014/191525 | A1 | 12/2014 |
| WO | WO 2014/191527 | A1 | 12/2014 |
| WO | WO 2014/193583 | A2 | 12/2014 |
| WO | WO 2014/194190 | A1 | 12/2014 |
| WO | WO 2014/197568 | A2 | 12/2014 |
| WO | WO 2014/197748 | A2 | 12/2014 |
| WO | WO 2014/199358 | A1 | 12/2014 |
| WO | WO 2014/200659 | A1 | 12/2014 |
| WO | WO 2014/201015 | A2 | 12/2014 |
| WO | WO 2014/204578 | A1 | 12/2014 |
| WO | WO 2014/204723 | A1 | 12/2014 |
| WO | WO 2014/204724 | A1 | 12/2014 |
| WO | WO 2014/204725 | A1 | 12/2014 |
| WO | WO 2014/204726 | A1 | 12/2014 |
| WO | WO 2014/204727 | A1 | 12/2014 |
| WO | WO 2014/204728 | A1 | 12/2014 |
| WO | WO 2014/204729 | A1 | 12/2014 |
| WO | WO 2014/205192 | A2 | 12/2014 |
| WO | WO 2014/207043 | A1 | 12/2014 |
| WO | WO 2015/002780 | A1 | 1/2015 |
| WO | WO 2015/004241 | A2 | 1/2015 |
| WO | WO 2015/006290 | A1 | 1/2015 |
| WO | WO 2015/006294 | A2 | 1/2015 |
| WO | WO 2015/006437 | A1 | 1/2015 |
| WO | WO 2015/006498 | A2 | 1/2015 |
| WO | WO 2015/006747 | A2 | 1/2015 |
| WO | WO 2015/007194 | A1 | 1/2015 |
| WO | WO 2015/010114 | A1 | 1/2015 |
| WO | WO 2015/011483 | A1 | 1/2015 |
| WO | WO 2015/013583 | A2 | 1/2015 |
| WO | WO 2015/017866 | A1 | 2/2015 |
| WO | WO 2015/018503 | A1 | 2/2015 |
| WO | WO 2015/021353 | A1 | 2/2015 |
| WO | WO 2015/021426 | A1 | 2/2015 |
| WO | WO 2015/021990 | A1 | 2/2015 |
| WO | WO 2015/024017 | A2 | 2/2015 |
| WO | WO 2015/024986 | A1 | 2/2015 |
| WO | WO 2015/026883 | A1 | 2/2015 |
| WO | WO 2015/026885 | A1 | 2/2015 |
| WO | WO 2015/026886 | A1 | 2/2015 |
| WO | WO 2015/026887 | A1 | 2/2015 |
| WO | WO 2015/027134 | A1 | 2/2015 |
| WO | WO 2015/028969 | A2 | 3/2015 |
| WO | WO 2015/030881 | A1 | 3/2015 |
| WO | WO 2015/031619 | A1 | 3/2015 |
| WO | WO 2015/031775 | A1 | 3/2015 |
| WO | WO 2015/032494 | A2 | 3/2015 |
| WO | WO 2015/033293 | A1 | 3/2015 |
| WO | WO 2015/034872 | A2 | 3/2015 |
| WO | WO 2015/034885 | A1 | 3/2015 |
| WO | WO 2015/035136 | A2 | 3/2015 |
| WO | WO 2015/035139 | A2 | 3/2015 |
| WO | WO 2015/035162 | A2 | 3/2015 |
| WO | WO 2015/040075 | A1 | 3/2015 |
| WO | WO 2015/040402 | A1 | 3/2015 |
| WO | WO 2015/042585 | A1 | 3/2015 |
| WO | WO 2015/048577 | A2 | 4/2015 |
| WO | WO 2015/048690 | A1 | 4/2015 |
| WO | WO 2015/048707 | A2 | 4/2015 |
| WO | WO 2015/049897 | A1 | 4/2015 |
| WO | WO 2015/051191 | A1 | 4/2015 |
| WO | WO 2015/052133 | A1 | 4/2015 |
| WO | WO 2015/052231 | A2 | 4/2015 |
| WO | WO 2015/052335 | A1 | 4/2015 |
| WO | WO 2015/053995 | A1 | 4/2015 |
| WO | WO 2015/054253 | A1 | 4/2015 |
| WO | WO 2015/054315 | A1 | 4/2015 |
| WO | WO 2015/057671 | A1 | 4/2015 |
| WO | WO 2015/057834 | A1 | 4/2015 |
| WO | WO 2015/057852 | A1 | 4/2015 |
| WO | WO 2015/057976 | A1 | 4/2015 |
| WO | WO 2015/057980 | A1 | 4/2015 |
| WO | WO 2015/059265 | A1 | 4/2015 |
| WO | WO 2015/065964 | A1 | 5/2015 |
| WO | WO 2015/066119 | A1 | 5/2015 |
| WO | WO 2015/066634 | A2 | 5/2015 |
| WO | WO 2015/066636 | A2 | 5/2015 |

(56) References Cited

FOREIGN PATENT DOCUMENTS

| | | | |
|---|---|---|---|
| WO | WO 2015/066637 | A1 | 5/2015 |
| WO | WO 2015/066638 | A2 | 5/2015 |
| WO | WO 2015/066643 | A1 | 5/2015 |
| WO | WO 2015/069682 | A2 | 5/2015 |
| WO | WO 2015/070083 | A1 | 5/2015 |
| WO | WO 2015/070193 | A1 | 5/2015 |
| WO | WO 2015/070212 | A1 | 5/2015 |
| WO | WO 2015/071474 | A2 | 5/2015 |
| WO | WO 2015/073683 | A2 | 5/2015 |
| WO | WO 2015/073867 | A1 | 5/2015 |
| WO | WO 2015/073990 | A1 | 5/2015 |
| WO | WO 2015/075056 | A1 | 5/2015 |
| WO | WO 2015/075154 | A2 | 5/2015 |
| WO | WO 2015/075175 | A1 | 5/2015 |
| WO | WO 2015/075195 | A1 | 5/2015 |
| WO | WO 2015/075557 | A2 | 5/2015 |
| WO | WO 2015/077058 | A2 | 5/2015 |
| WO | WO 2015/077290 | A2 | 5/2015 |
| WO | WO 2015/077318 | A1 | 5/2015 |
| WO | WO 2015/079056 | A1 | 6/2015 |
| WO | WO 2015/079057 | A2 | 6/2015 |
| WO | WO 2015/086795 | A2 | 6/2015 |
| WO | WO 2015/086798 | A1 | 6/2015 |
| WO | WO 2015/088643 | A1 | 6/2015 |
| WO | WO 2015/089046 | A1 | 6/2015 |
| WO | WO 2015/089077 | A2 | 6/2015 |
| WO | WO 2015/089277 | A1 | 6/2015 |
| WO | WO 2015/089351 | A1 | 6/2015 |
| WO | WO 2015/089354 | A1 | 6/2015 |
| WO | WO 2015/089364 | A1 | 6/2015 |
| WO | WO 2015/089406 | A1 | 6/2015 |
| WO | WO 2015/089419 | A2 | 6/2015 |
| WO | WO 2015/089427 | A1 | 6/2015 |
| WO | WO 2015/089462 | A1 | 6/2015 |
| WO | WO 2015/089465 | A1 | 6/2015 |
| WO | WO 2015/089473 | A1 | 6/2015 |
| WO | WO 2015/089486 | A1 | 6/2015 |
| WO | WO 2015/095804 | A1 | 6/2015 |
| WO | WO 2015/099850 | A1 | 7/2015 |
| WO | WO 2015/100929 | A1 | 7/2015 |
| WO | WO 2015/103057 | A1 | 7/2015 |
| WO | WO 2015/103153 | A1 | 7/2015 |
| WO | WO 2015/105928 | A1 | 7/2015 |
| WO | WO 2015/108993 | A1 | 7/2015 |
| WO | WO 2015/109752 | A1 | 7/2015 |
| WO | WO 2015/110474 | A1 | 7/2015 |
| WO | WO 2015/112790 | A2 | 7/2015 |
| WO | WO 2015/112896 | A2 | 7/2015 |
| WO | WO 2015/113063 | A1 | 7/2015 |
| WO | WO 2015/114365 | A1 | 8/2015 |
| WO | WO 2015/115903 | A1 | 8/2015 |
| WO | WO 2015/116686 | A1 | 8/2015 |
| WO | WO 2015/116969 | A2 | 8/2015 |
| WO | WO 2015/117021 | A1 | 8/2015 |
| WO | WO 2015/117041 | A1 | 8/2015 |
| WO | WO 2015/117081 | A2 | 8/2015 |
| WO | WO 2015/118156 | A1 | 8/2015 |
| WO | WO 2015/119941 | A2 | 8/2015 |
| WO | WO 2015/121454 | A1 | 8/2015 |
| WO | WO 2015/122967 | A1 | 8/2015 |
| WO | WO 2015/123339 | A1 | 8/2015 |
| WO | WO 2015/124715 | A1 | 8/2015 |
| WO | WO 2015/124718 | A1 | 8/2015 |
| WO | WO 2015/126927 | A2 | 8/2015 |
| WO | WO 2015/127428 | A1 | 8/2015 |
| WO | WO 2015/127439 | A1 | 8/2015 |
| WO | WO 2015/129686 | A1 | 9/2015 |
| WO | WO 2015/131101 | A1 | 9/2015 |
| WO | WO 2015/133554 | A1 | 9/2015 |
| WO | WO 2015/134812 | A1 | 9/2015 |
| WO | WO 2015/136001 | A1 | 9/2015 |
| WO | WO 2015/138510 | A1 | 9/2015 |
| WO | WO 2015/138739 | A2 | 9/2015 |
| WO | WO 2015/138855 | A1 | 9/2015 |
| WO | WO 2015/138870 | A2 | 9/2015 |
| WO | WO 2015/139008 | A1 | 9/2015 |
| WO | WO 2015/139139 | A1 | 9/2015 |
| WO | WO 2015/143046 | A2 | 9/2015 |
| WO | WO 2015/143177 | A1 | 9/2015 |
| WO | WO 2015/145417 | A1 | 10/2015 |
| WO | WO 2015/148431 | A1 | 10/2015 |
| WO | WO 2015/148670 | A1 | 10/2015 |
| WO | WO 2015/148680 | A1 | 10/2015 |
| WO | WO 2015/148761 | A1 | 10/2015 |
| WO | WO 2015/148860 | A1 | 10/2015 |
| WO | WO 2015/148863 | A2 | 10/2015 |
| WO | WO 2015/153760 | A2 | 10/2015 |
| WO | WO 2015/153780 | A1 | 10/2015 |
| WO | WO 2015/153789 | A1 | 10/2015 |
| WO | WO 2015/153791 | A1 | 10/2015 |
| WO | WO 2015/153889 | A2 | 10/2015 |
| WO | WO 2015/153940 | A1 | 10/2015 |
| WO | WO 2015/155341 | A1 | 10/2015 |
| WO | WO 2015/155686 | A2 | 10/2015 |
| WO | WO 2015/157070 | A2 | 10/2015 |
| WO | WO 2015/157534 | A1 | 10/2015 |
| WO | WO 2015/159068 | A1 | 10/2015 |
| WO | WO 2015/159086 | A1 | 10/2015 |
| WO | WO 2015/159087 | A1 | 10/2015 |
| WO | WO 2015/160683 | A1 | 10/2015 |
| WO | WO 2015/161276 | A2 | 10/2015 |
| WO | WO 2015/163733 | A1 | 10/2015 |
| WO | WO 2015/164740 | A1 | 10/2015 |
| WO | WO 2015/164748 | A1 | 10/2015 |
| WO | WO-2015/165274 | A1 | 11/2015 |
| WO | WO-2015/165275 | A1 | 11/2015 |
| WO | WO-2015/165276 | A1 | 11/2015 |
| WO | WO 2015/166272 | A2 | 11/2015 |
| WO | WO 2015/167766 | A1 | 11/2015 |
| WO | WO 2015/167956 | A1 | 11/2015 |
| WO | WO 2015/168125 | A1 | 11/2015 |
| WO | WO 2015/168158 | A1 | 11/2015 |
| WO | WO 2015/168404 | A1 | 11/2015 |
| WO | WO 2015/168547 | A2 | 11/2015 |
| WO | WO 2015/168800 | A1 | 11/2015 |
| WO | WO 2015/171603 | A1 | 11/2015 |
| WO | WO 2015/171894 | A1 | 11/2015 |
| WO | WO 2015/171932 | A1 | 11/2015 |
| WO | WO 2015/172128 | A1 | 11/2015 |
| WO | WO 2015/173436 | A1 | 11/2015 |
| WO | WO 2015/175642 | A2 | 11/2015 |
| WO | WO 2015/179540 | A1 | 11/2015 |
| WO | WO-2015/183025 | A1 | 12/2015 |
| WO | WO-2015/183026 | A1 | 12/2015 |
| WO | WO 2015/183885 | A1 | 12/2015 |
| WO | WO 2015/184259 | A1 | 12/2015 |
| WO | WO 2015/184262 | A1 | 12/2015 |
| WO | WO 2015/184268 | A1 | 12/2015 |
| WO | WO 2015/188056 | A1 | 12/2015 |
| WO | WO-2015/188065 | A1 | 12/2015 |
| WO | WO 2015/188094 | A1 | 12/2015 |
| WO | WO 2015/188109 | A1 | 12/2015 |
| WO | WO 2015/188132 | A1 | 12/2015 |
| WO | WO 2015/188135 | A1 | 12/2015 |
| WO | WO 2015/188191 | A1 | 12/2015 |
| WO | WO 2015/189693 | A1 | 12/2015 |
| WO | WO 2015/191693 | A2 | 12/2015 |
| WO | WO 2015/191899 | A1 | 12/2015 |
| WO | WO 2015/191911 | A2 | 12/2015 |
| WO | WO 2015/193858 | A1 | 12/2015 |
| WO | WO 2015/195547 | A1 | 12/2015 |
| WO | WO 2015/195621 | A1 | 12/2015 |
| WO | WO 2015/195798 | A1 | 12/2015 |
| WO | WO 2015/198020 | A1 | 12/2015 |
| WO | WO 2015/200334 | A1 | 12/2015 |
| WO | WO 2015/200378 | A1 | 12/2015 |
| WO | WO 2015/200555 | A2 | 12/2015 |
| WO | WO 2015/200805 | A2 | 12/2015 |
| WO | WO-2016/001978 | A1 | 1/2016 |
| WO | WO 2016/004010 | A1 | 1/2016 |
| WO | WO 2016/007347 | A1 | 1/2016 |
| WO | WO 2016/007604 | A1 | 1/2016 |
| WO | WO 2016/007948 | A1 | 1/2016 |
| WO | WO 2016/011080 | A2 | 1/2016 |

(56) References Cited

FOREIGN PATENT DOCUMENTS

WO WO 2016/011210 A2 1/2016
WO WO 2016/011428 A1 1/2016
WO WO 2016/012544 A2 1/2016
WO WO-2016/012552 A1 1/2016
WO WO 2016/014409 A1 1/2016
WO WO-2016/014565 A2 1/2016
WO WO 2016/014794 A1 1/2016
WO WO 2016/014837 A1 1/2016
WO WO 2016/016119 A1 2/2016
WO WO 2016/016358 A1 2/2016
WO WO 2016/019144 A2 2/2016
WO WO 2016/020399 A1 2/2016
WO WO 2016/021972 A1 2/2016
WO WO 2016/021973 A1 2/2016
WO WO 2016/022363 A2 2/2016
WO WO 2016/022866 A1 2/2016
WO WO 2016/022931 A1 2/2016
WO WO 2016/025131 A1 2/2016
WO WO 2016/025469 A1 2/2016
WO WO 2016/025759 A1 2/2016
WO WO 2016/026444 A1 2/2016
WO WO 2016/028682 A1 2/2016
WO WO 2016/028843 A1 2/2016
WO WO 2016/028887 A1 2/2016
WO WO 2016/033088 A1 3/2016
WO WO-2016/033230 A1 3/2016
WO WO 2016/033246 A1 3/2016
WO WO 2016/033298 A1 3/2016
WO WO 2016/035044 A1 3/2016
WO WO 2016/036754 A1 3/2016
WO WO 2016/037157 A2 3/2016
WO WO 2016/040030 A1 3/2016
WO WO 2016/040594 A1 3/2016
WO WO-2016/044182 A1 3/2016
WO WO 2016/044416 A1 3/2016
WO WO-2016/046635 A1 3/2016
WO WO 2016/049024 A2 3/2016
WO WO 2016/049163 A2 3/2016
WO WO 2016/049230 A1 3/2016
WO WO 2016/049251 A1 3/2016
WO WO 2016/049258 A2 3/2016
WO WO 2015/048801 A2 4/2016
WO WO-2016/053397 A2 4/2016
WO WO 2016/054326 A1 4/2016
WO WO 2016/057061 A2 4/2016
WO WO 2016/057821 A2 4/2016
WO WO 2016/057835 A2 4/2016
WO WO 2016/057850 A2 4/2016
WO WO 2016/057951 A2 4/2016
WO WO 2016/057961 A2 4/2016
WO WO 2016/061073 A1 4/2016
WO WO 2016/061374 A1 4/2016
WO WO-2016/061481 A1 4/2016
WO WO 2016/061523 A1 4/2016
WO WO-2016/069282 A1 5/2016
WO WO-2016/069283 A1 5/2016
WO WO 2016/069591 A2 5/2016
WO WO 2016/069910 A1 5/2016
WO WO 2016/069912 A1 5/2016
WO WO 2016/070037 A2 5/2016
WO WO 2016/070070 A1 5/2016
WO WO 2016/070129 A1 5/2016
WO WO 2016/072399 A1 5/2016
WO WO 2016/072936 A1 5/2016
WO WO 2016/073433 A1 5/2016
WO WO 2016/073559 A1 5/2016
WO WO 2016/073990 A2 5/2016
WO WO 2016/075662 A2 5/2016
WO WO 2016/077273 A1 5/2016
WO WO 2016/077350 A1 5/2016
WO WO 2016/080097 A1 5/2016
WO WO-2016/080795 A1 5/2016
WO WO 2016/081923 A2 5/2016
WO WO 2016/081924 A1 5/2016
WO WO 2016/082135 A1 6/2016
WO WO 2016/083811 A1 6/2016
WO WO 2016/084084 A1 6/2016
WO WO 2016/084088 A1 6/2016
WO WO 2016/086177 A2 6/2016
WO WO 2016/089433 A1 6/2016
WO WO 2016/089866 A1 6/2016
WO WO 2016/089883 A1 6/2016
WO WO 2016/090385 A1 6/2016
WO WO 2016/094845 A2 6/2016
WO WO 2016/094867 A1 6/2016
WO WO 2016/094872 A1 6/2016
WO WO 2016/094874 A1 6/2016
WO WO 2016/094880 A1 6/2016
WO WO 2016/094888 A1 6/2016
WO WO 2016/097212 A1 6/2016
WO WO 2016/097231 A2 6/2016
WO WO 2016/097751 A1 6/2016
WO WO 2016/099887 A1 6/2016
WO WO 2016/100272 A1 6/2016
WO WO 2016/100389 A1 6/2016
WO WO 2016/100568 A1 6/2016
WO WO 2016/100571 A1 6/2016
WO WO 2016/100951 A2 6/2016
WO WO 2016/100955 A2 6/2016
WO WO 2016/100974 A1 6/2016
WO WO 2016/103233 A2 6/2016
WO WO 2016/104716 A1 6/2016
WO WO 2016/106236 A1 6/2016
WO WO 2016/106244 A1 6/2016
WO WO 2016/106338 A2 6/2016
WO WO 2016/108926 A1 7/2016
WO WO 2016/109255 A1 7/2016
WO WO 2016/109840 A2 7/2016
WO WO 2016/110214 A1 7/2016
WO WO 2016/110453 A1 7/2016
WO WO 2016/110511 A1 7/2016
WO WO 2016/110512 A1 7/2016
WO WO 2016/112351 A1 7/2016
WO WO 2016/112963 A1 7/2016
WO WO 2016/114972 A1 7/2016
WO WO 2016/115179 A1 7/2016
WO WO 2016/115326 A1 7/2016
WO WO 2016/115355 A1 7/2016
WO WO 2016/116032 A1 7/2016
WO WO 2016/120480 A1 8/2016
WO WO 2016/123071 A1 8/2016
WO WO 2016/123230 A1 8/2016
WO WO 2016/123243 A1 8/2016
WO WO 2016/123578 A1 8/2016
WO WO 2016/130600 A2 8/2016
WO WO 2016/130697 A1 8/2016
WO WO 2016/132122 A1 8/2016
WO WO 2016/135507 A1 9/2016
WO WO 2016/135557 A2 9/2016
WO WO 2016/135558 A2 9/2016
WO WO 2016/135559 A2 9/2016
WO WO 2016/137774 A1 9/2016
WO WO 2016/137949 A1 9/2016
WO WO 2016/141224 A1 9/2016
WO WO 2016/141893 A1 9/2016
WO WO 2016/142719 A1 9/2016
WO WO 2016/145150 A2 9/2016
WO WO 2016/148994 A1 9/2016
WO WO 2016/149484 A2 9/2016
WO WO 2016/149547 A1 9/2016
WO WO 2016/150336 A1 9/2016
WO WO 2016/150855 A1 9/2016
WO WO 2016/154016 A2 9/2016
WO WO 2016/154579 A2 9/2016
WO WO 2016/154596 A1 9/2016
WO WO 2016/155482 A1 10/2016
WO WO 2016/161004 A1 10/2016
WO WO 2016/161207 A1 10/2016
WO WO 2016/161260 A1 10/2016
WO WO 2016/161380 A1 10/2016
WO WO-2016/161446 A1 10/2016
WO WO 2016/164356 A1 10/2016
WO WO 2016/164797 A1 10/2016
WO WO 2016/166340 A1 10/2016

(56) References Cited

FOREIGN PATENT DOCUMENTS

WO WO-2016/167300 A1 10/2016
WO WO 2016/170484 A1 10/2016
WO WO 2016/172359 A2 10/2016
WO WO 2016/172727 A1 10/2016
WO WO 2016/174056 A1 11/2016
WO WO 2016/174151 A1 11/2016
WO WO 2016/174250 A1 11/2016
WO WO 2016/176191 A1 11/2016
WO WO 2016/176404 A1 11/2016
WO WO 2016/176690 A2 11/2016
WO WO 2016/177682 A1 11/2016
WO WO 2016/178207 A1 11/2016
WO WO 2016/179038 A1 11/2016
WO WO 2016/179112 A1 11/2016
WO WO 2016/181357 A1 11/2016
WO WO 2016/182893 A1 11/2016
WO WO 2016/182917 A1 11/2016
WO WO 2016/182959 A1 11/2016
WO WO 2016/183236 A1 11/2016
WO WO 2016/183298 A2 11/2016
WO WO 2016/183345 A1 11/2016
WO WO 2016/183402 A2 11/2016
WO WO 2016/183438 A1 11/2016
WO WO 2016/183448 A1 11/2016
WO WO 2016/184955 A2 11/2016
WO WO 2016/184989 A1 11/2016
WO WO 2016/185411 A1 11/2016
WO WO 2016/186745 A1 11/2016
WO WO 2016/186772 A2 11/2016
WO WO 2016/186946 A1 11/2016
WO WO 2016/186953 A1 11/2016
WO WO 2016/187717 A1 12/2016
WO WO 2016/187904 A1 12/2016
WO WO 2016/191684 A1 12/2016
WO WO 2016/191869 A1 12/2016
WO WO 2016/196273 A1 12/2016
WO WO 2016/196282 A1 12/2016
WO WO 2016/196308 A1 12/2016
WO WO-2016/196361 A1 12/2016
WO WO 2016/196499 A1 12/2016
WO WO 2016/196539 A2 12/2016
WO WO 2016/196655 A1 12/2016
WO WO 2016/196805 A1 12/2016
WO WO 2016/196887 A1 12/2016
WO WO 2016/197132 A1 12/2016
WO WO 2016/197133 A1 12/2016
WO WO 2016/197354 A1 12/2016
WO WO 2016/197355 A1 12/2016
WO WO 2016/197356 A1 12/2016
WO WO 2016/197357 A1 12/2016
WO WO 2016/197358 A1 12/2016
WO WO 2016/197359 A1 12/2016
WO WO 2016/197360 A1 12/2016
WO WO 2016/197361 A1 12/2016
WO WO 2016/197362 A1 12/2016
WO WO 2016/198361 A1 12/2016
WO WO 2016/198500 A1 12/2016
WO WO 2016/200263 A1 12/2016
WO WO 2016/201047 A1 12/2016
WO WO 2016/201138 A1 12/2016
WO WO 2016/201152 A1 12/2016
WO WO 2016/201153 A1 12/2016
WO WO 2016/201155 A1 12/2016
WO WO 2016/205276 A1 12/2016
WO WO 2016/205613 A1 12/2016
WO WO 2016/205623 A1 12/2016
WO WO 2016/205680 A1 12/2016
WO WO 2016/205688 A2 12/2016
WO WO 2016/205703 A1 12/2016
WO WO 2016/205711 A1 12/2016
WO WO 2016/205728 A1 12/2016
WO WO 2016/205745 A2 12/2016
WO WO 2016/205749 A1 12/2016
WO WO 2016/205759 A2 12/2016
WO WO 2016/205764 A2 12/2016
WO WO 2017/001572 A1 1/2017
WO WO-2017/001988 A1 1/2017
WO WO 2017/004261 A1 1/2017
WO WO 2017/004279 A2 1/2017
WO WO 2017/004616 A1 1/2017
WO WO 2017/005807 A1 1/2017
WO WO 2017/009399 A1 1/2017
WO WO 2017/011519 A1 1/2017
WO WO 2017/011721 A1 1/2017
WO WO 2017/011804 A1 1/2017
WO WO 2017/015015 A1 1/2017
WO WO 2017/015101 A1 1/2017
WO WO 2017/015567 A1 1/2017
WO WO 2017/015637 A1 1/2017
WO WO 2017/017016 A1 2/2017
WO WO 2017/019867 A1 2/2017
WO WO 2017/019895 A1 2/2017
WO WO 2017/023803 A1 2/2017
WO WO 2017/023974 A1 2/2017
WO WO 2017/024047 A1 2/2017
WO WO 2017/024319 A1 2/2017
WO WO 2017/024343 A1 2/2017
WO WO-2017/024602 A1 2/2017
WO WO-2017/025323 A1 2/2017
WO WO 2017/027423 A1 2/2017
WO WO 2017/028768 A1 2/2017
WO WO 2017/029664 A1 2/2017
WO WO 2017/031360 A1 2/2017
WO WO 2017/031483 A1 2/2017
WO WO 2017/035416 A2 3/2017
WO WO 2017/040348 A1 3/2017
WO WO 2017/040511 A1 3/2017
WO WO 2017/040709 A1 3/2017
WO WO 2017/040786 A1 3/2017
WO WO 2017/040793 A1 3/2017
WO WO 2017/040813 A2 3/2017
WO WO-2017/043573 A1 3/2017
WO WO-2017/043656 A1 3/2017
WO WO 2017/044419 A1 3/2017
WO WO 2017/044776 A1 3/2017
WO WO 2017/044857 A2 3/2017
WO WO-2017/049129 A2 3/2017
WO WO 2017/050963 A1 3/2017
WO WO 2017/053312 A1 3/2017
WO WO 2017/053431 A2 3/2017
WO WO 2017/053713 A1 3/2017
WO WO 2017/053729 A1 3/2017
WO WO 2017/053753 A1 3/2017
WO WO 2017/053762 A1 3/2017
WO WO 2017/053879 A1 3/2017
WO WO-2017/058658 A2 4/2017
WO WO-2017/062605 A1 4/2017
WO WO-2017/062723 A1 4/2017
WO WO-2017/062754 A1 4/2017
WO WO-2017/062855 A1 4/2017
WO WO-2017/062886 A1 4/2017
WO WO-2017/062983 A1 4/2017
WO WO-2017/064439 A1 4/2017
WO WO-2017/064546 A1 4/2017
WO WO-2017/064566 A2 4/2017
WO WO-2017/066175 A1 4/2017
WO WO-2017/066497 A2 4/2017
WO WO-2017/066588 A2 4/2017
WO WO-2017/068377 A1 4/2017
WO WO-2017/069829 A2 4/2017
WO WO-2017/070029 A1 4/2017
WO WO-2017/070032 A1 4/2017
WO WO-2017/070169 A1 4/2017
WO WO-2017/070284 A1 4/2017
WO WO-2017/070598 A1 4/2017
WO WO-2017/070605 A1 4/2017
WO WO-2017/070632 A2 4/2017
WO WO-2017/070633 A2 4/2017
WO WO-2017/072590 A1 5/2017
WO WO-2017/074526 A1 5/2017
WO WO-2017/074962 A1 5/2017
WO WO-2017/075261 A1 5/2017
WO WO-2017/075475 A1 5/2017
WO WO-2017/077135 A1 5/2017

(56) References Cited

FOREIGN PATENT DOCUMENTS

WO WO-2017/077329 A2 5/2017
WO WO-2017/078751 A1 5/2017
WO WO-2017/079400 A1 5/2017
WO WO-2017/079428 A1 5/2017
WO WO-2017/079673 A1 5/2017
WO WO-2017/079724 A1 5/2017
WO WO-2017/081097 A1 5/2017
WO WO-2017/081288 A1 5/2017
WO WO-2017/083368 A1 5/2017
WO WO-2017/083722 A1 5/2017
WO WO-2017/083766 A1 5/2017
WO WO-2017/087395 A1 5/2017
WO WO-2017/090724 A1 6/2017
WO WO-2017/091510 A1 6/2017
WO WO-2017/091630 A1 6/2017
WO WO-2017/092201 A1 6/2017
WO WO-2017/093370 A1 6/2017
WO WO-2017/095111 A1 6/2017
WO WO-2017/096041 A1 6/2017
WO WO-2017/096237 A1 6/2017
WO WO-2017/100158 A1 6/2017
WO WO-2017/100431 A2 6/2017
WO WO-2017/104404 A1 6/2017
WO WO-2017/105251 A1 6/2017
WO WO-2017/105350 A1 6/2017
WO WO-2017/105991 A1 6/2017
WO WO-2017/106414 A1 6/2017
WO WO-2017/106528 A2 6/2017
WO WO-2017/106537 A2 6/2017
WO WO-2017/106569 A1 6/2017
WO WO-2017/106616 A1 6/2017
WO WO-2017/106657 A1 6/2017
WO WO-2017/106767 A1 6/2017
WO WO-2017/112620 A1 6/2017
WO WO-2017/115268 A1 7/2017
WO WO-2017/117395 A1 7/2017
WO WO-2017/118720 A1 7/2017
WO WO-2017/123609 A1 7/2017
WO WO-2017/123910 A1 7/2017
WO WO-2017/124086 A1 7/2017
WO WO-2017/124100 A1 7/2017
WO WO-2017/124652 A1 7/2017
WO WO-2017/126987 A1 7/2017
WO WO-2017/127807 A1 7/2017
WO WO-2017/131237 A1 8/2017
WO WO-2017/132112 A1 8/2017
WO WO-2017/136520 A1 8/2017
WO WO-2017/136629 A1 8/2017
WO WO-2017/136794 A1 8/2017
WO WO-2017/139264 A1 8/2017
WO WO-2017/139505 A2 8/2017
WO WO-2017/142835 A1 8/2017
WO WO-2017/142999 A2 8/2017
WO WO-2017/143042 A2 8/2017
WO WO-2017/147278 A1 8/2017
WO WO-2017/147432 A1 8/2017
WO WO-2017/147446 A1 8/2017
WO WO-2017/147555 A1 8/2017
WO WO-2017/151444 A1 9/2017
WO WO-2017/152015 A1 9/2017
WO WO-2017/157422 A1 9/2017
WO WO-2017/158153 A1 9/2017
WO WO-2017/160689 A1 9/2017
WO WO-2017/160752 A1 9/2017
WO WO-2017/160890 A1 9/2017
WO WO-2017/161068 A1 9/2017
WO WO-2017/165826 A1 9/2017
WO WO-2017/165862 A1 9/2017
WO WO-2017/172644 A2 10/2017
WO WO-2017/172645 A2 10/2017
WO WO-2017/172860 A1 10/2017
WO WO-2017/173004 A1 10/2017
WO WO-2017/173092 A1 10/2017
WO WO-2017/174329 A1 10/2017
WO WO-2017/176529 A1 10/2017
WO WO-2017/178590 A1 10/2017
WO WO-2017/180694 A1 10/2017
WO WO-2017/180711 A1 10/2017
WO WO-2017/180915 A2 10/2017
WO WO-2017/181107 A2 10/2017
WO WO-2017/181735 A2 10/2017
WO WO-2017/182468 A1 10/2017
WO WO-2017/184334 A1 10/2017
WO WO-2017/184768 A1 10/2017
WO WO-2017/184786 A1 10/2017
WO WO-2017/186550 A1 11/2017
WO WO-2017/189308 A1 11/2017
WO WO-2017/189336 A1 11/2017
WO WO-2017/190257 A1 11/2017
WO WO-2017/190664 A1 11/2017
WO WO-2017/191210 A1 11/2017
WO WO-2017/192172 A1 11/2017
WO WO-2017/192512 A2 11/2017
WO WO-2017/192544 A1 11/2017
WO WO-2017/192573 A1 11/2017
WO WO-2017/193029 A2 11/2017
WO WO-2017/193053 A1 11/2017
WO WO-2017/196768 A1 11/2017
WO WO-2017/197038 A1 11/2017
WO WO-2017/197238 A1 11/2017
WO WO-2017/197301 A1 11/2017

OTHER PUBLICATIONS

Supplementary European Search Report for Application No. EP 12845790.0, dated Oct. 12, 2015.
International Preliminary Report on Patentability for PCT/US2014/052231, dated Mar. 3, 2016.
International Preliminary Report on patentability for PCT/US2014/050283, dated Feb. 18, 2016.
International Preliminary Report on Patentability for PCT/US2014/054247, dated Mar. 17, 2016.
International Preliminary Report on Patentability for PCT/US2014/054291, dated Mar. 17, 2016.
International Preliminary Report on Patentability or PCT/US2014/054252, dated Mar. 17, 2016.
International Preliminary Report on Patentability for PCT/US2014/070038, dated Jun. 23, 2016.
International Search Report and Written Opinion for PCT/US2015/042770, dated Feb. 23, 2016.
International Preliminary Report on Patentability for PCT/US2015/042770, dated Dec. 19, 2016.
International Search Report and Written Opinion for PCT/US2015/058479, dated Feb. 11, 2016.
Invitation to Pay Additional Fees for PCT/US2016/058344, dated Mar. 1, 2017.
[No Author Listed], EMBL Accession No. Q99ZW2. Nov. 2012. 2 pages.
[No Author Listed], Invitrogen Lipofectamine™ 2000 product sheets, 2002. 2 pages.
[No Author Listed], Invitrogen Lipofectamine™ 2000 product sheets, 2005. 3 pages.
[No Author Listed], Invitrogen Lipofectamine™ LTX product sheets, 2011. 4 pages.
[No Author Listed], Thermo Fisher Scientific—How Cationic Lipid Mediated Transfection Works, retrieved from the internet Aug. 27, 2015. 2 pages.
Alexandrov et al., Signatures of mutational processes in human cancer. Nature. Aug. 22, 2013;500(7463):415-21. doi: 10.1038/nature12477. Epub Aug. 14, 2013.
Bulow et al., Multienzyme systems obtained by gene fusion. Trends Biotechnol. Jul. 1991;9(7):226-31.
Chichili et al., Linkers in the structural biology of protein-protein interactions. Protein Science. 2013;22:153-67.
Cho et al., Targeted genome engineering in human cells with the Cas9 RNA-guided endonuclease. Nat Biotechnol. Mar. 2013;31(3):230-2. doi: 10.1038/nbt.2507. Epub Jan. 29, 2013.
Eltoukhy et al., Nucleic acid-mediated intracellular protein delivery by lipid-like nanoparticles. Biomaterials. Aug. 2014;35(24):6454-61. doi: 10.1016/j.biomaterials.2014.04.014. Epub May 13, 2014.

(56) References Cited

OTHER PUBLICATIONS

Fonfara et al., Phylogeny of Cas9 determines functional exchangeability of dual-RNA and Cas9 among orthologous type II CRISPR-Cas systems. Nucleic Acids Res. Feb. 2014;42(4):2577-90. doi: 10.1093/nar/gkt1074. Epub Nov. 22, 2013.
Freshney, Culture of Animal Cells. A Manual of Basic Technique. Alan R. Liss, Inc. New York. 1983;4.
Gardlik et al., Vectors and delivery systems in gene therapy. Med Sci Monit. Apr. 2005;11(4):RA110-21. Epub Mar. 24, 2005.
Kim et al., Transcriptional repression by zinc finger peptides. Exploring the potential for applications in gene therapy. J Biol Chem. Nov. 21, 1997;272(47):29795-800.
Komor et al., Programmable editing of a target base in genomic DNA without double-stranded DNA cleavage. Nature. Apr. 20, 2016;533(7603):420-4. doi: 10.1038/nature17946.
Lee et al., Recognition of liposomes by cells: in vitro binding and endocytosis mediated by specific lipid headgroups and surface charge density. Biochim Biophys Acta. Jan. 31, 1992;1103(2):185-97.
Li et al., Current approaches for engineering proteins with diverse biological properties. Adv Exp Med Biol. 2007;620:18-33.
Nishida et al., Targeted nucleotide editing using hybrid prokaryotic and vertebrate adaptive immune systems. Science. Sep. 16, 2016;353(6305). pii: aaf8729. doi: 10.1126/science.aaf8729. Epub Aug. 4, 2016.
Shah et al., Kinetic control of one-pot trans-splicing reactions by using a wild-type and designed split intein. Angew Chem Int Ed Engl. Jul. 11, 2011;50(29):6511-5. doi: 10.1002/anie.201102909. Epub Jun. 8, 2011.
Sirk et al., Expanding the zinc-finger recombinase repertoire: directed evolution and mutational analysis of serine recombinase specificity determinants. Nucleic Acids Res. Apr. 2014;42(7):4755-66. doi: 10.1093/nar/gkt1389. Epub Jan. 21, 2014.
Sternberg et al., DNA interrogation by the CRISPR RNA-guided endonuclease Cas9. Nature.Mar. 6, 2014;507(7490):62-7. doi: 10.1038/nature13011. Epub Jan. 29, 2014.
Truong et al., Development of an intein-mediated split-Cas9 system for gene therapy. Nucleic Acids Res. Jul. 27, 2015;43(13):6450-8. doi: 10.1093/nar/gkv601. Epub Jun. 16, 2015.
Wang et al., Efficient delivery of genome-editing proteins using bioreducible lipid nanoparticles. Proc Natl Acad Sci U S A. Feb. 29, 2016. pii: 201520244. [Epub ahead of print].
Yang et al., Genome editing with targeted deaminases. BioRxiv. Preprint. First posted online Jul. 28, 2016.
U.S. Appl. No. 61/716,256, filed Oct. 19, 2012, Jinek et al.
U.S. Appl. No. 61/717,324, filed Oct. 23, 2012, Cho et al.
U.S. Appl. No. 61/734,256, filed Dec. 6, 2012, Chen et al.
U.S. Appl. No. 61/758,624, filed Jan. 30, 2013, Chen et al.
U.S. Appl. No. 61/761,046, filed Feb. 5, 2013, Knight et al.
U.S. Appl. No. 61/794,422, filed Mar. 15, 2013, Knight et al.
U.S. Appl. No. 61/803,599, filed Mar. 20, 2013, Kim et al.
U.S. Appl. No. 61/837,481, filed Jun. 20, 2013, Cho et al.
International Preliminary Report on Patentability for PCT/US2012/047778, dated Feb. 6, 2014.
International Search Report and Written Opinion for PCT/US2012/047778, dated May 30, 2013.
Partial Supplementary European Search Report for Application No. EP 12845790.0, dated Mar. 18, 2015.
International Search Report and Written Opinion for PCT/US2014/052231, dated Dec. 4, 2014.
International Search Report and Written Opinion for PCT/US2014/052231, dated Jan. 30, 2015.
International Search Report and Written Opinion for PCT/US2014/050283, dated Nov. 6, 2014.
International Search Report and Written Opinion for PCT/US2014/054247, dated Mar. 27, 2015.
Invitation to Pay Additional Fees for PCT/US2014/054291, dated Dec. 18, 2014.
International Search Report and Written Opinion for PCT/US2014/054291, dated Mar. 27, 2015.
International Search Report and Written Opinion for PCT/US2014/054252, dated Mar. 5, 2015.
International Search Report and Written Opinion for PCT/US2014/070038, dated Apr. 14, 2015.
International Search Report for PCT/US2013/032589, dated Jul. 26, 2013.
Adrian et al., Targeted SAINT-O-Somes for improved intracellular delivery of siRNA and cytotoxic drugs into endothelial cells. J Control Release. Jun. 15, 2010;144(3):341-9. doi: 10.1016/j.jconrel.2010.03.003. Epub Mar. 11, 2010.
Aguilera et al., Systemic in vivo distribution of activatable cell penetrating peptides is superior to that of cell penetrating peptides. Integr Biol (Camb). Jun. 2009;1(5-6):371-81. doi: 10.1039/b904878b. Epub May 11, 2009.
Akinc et al., A combinatorial library of lipid-like materials for delivery of RNAi therapeutics. Nat Biotechnol. May 2008;26(5):561-9. doi: 10.1038/nbt1402. Epub Apr. 27, 2008.
Allen et al., Liposomal drug delivery systems: from concept to clinical applications. Adv Drug Deliv Rev. Jan. 2013;65(1):36-48. doi: 10.1016/j.addr.2012.09.037. Epub Oct. 1, 2012.
Al-Taei et al., Intracellular traffic and fate of protein transduction domains HIV-1 TAT peptide and octaarginine. Implications for their utilization as drug delivery vectors. Bioconjug Chem. Jan.-Feb. 2006;17(1):90-100.
Barrangou et al., CRISPR provides acquired resistance against viruses in prokaryotes. Science. Mar. 23, 2007;315(5819):1709-12.
Barrangou, RNA-mediated programmable DNA cleavage. Nat Biotechnol. Sep. 2012;30(9):836-8. doi: 10.1038/nbt.2357.
Basha et al., Influence of cationic lipid composition on gene silencing properties of lipid nanoparticle formulations of siRNA in antigen-presenting cells. Mol Ther. Dec. 2011;19(12):2186-200. doi: 10.1038/mt.2011.190. Epub Oct. 4, 2011.
Bedell et al., In vivo genome editing using a high-efficiency TALEN system. Nature. Nov. 1, 2012;491(7422):114-8. Doi: 10.1038/nature11537. Epub Sep. 23, 2012.
Beumer et al., Efficient gene targeting in *Drosophila* with zinc-finger nucleases. Genetics. Apr. 2006;172(4):2391-403. Epub Feb. 1, 2006.
Bibikova et al., Targeted chromosomal cleavage and mutagenesis in *Drosophila* using zinc-finger nucleases. Genetics. Jul. 2002;161(3):1169-75.
Boch, TALEs of genome targeting. Nat Biotechnol. Feb. 2011;29(2):135-6. Doi: 10.1038/nbt.1767.
Boeckle et al., Melittin analogs with high lytic activity at endosomal pH enhance transfection with purified targeted PEI polyplexes. J Control Release. May 15, 2006;112(2):240-8. Epub Mar. 20, 2006.
Branden and Tooze, Introduction to Protein Structure. 1999; 2nd edition. Garland Science Publisher: 3-12.
Cade et al., Highly efficient generation of heritable zebrafish gene mutations using homo- and heterodimeric TALENs. Nucleic Acids Res. Sep. 2012;40(16):8001-10. Doi: 10.1093/nar/gks518. Epub Jun. 7, 2012.
Cameron, Recent advances in transgenic technology. Mol Biotechnol. Jun. 1997;7(3):253-65.
Caron et al., Intracellular delivery of a Tat-eGFP fusion protein into muscle cells. Mol Ther. Mar. 2001;3(3):310-8.
Carroll et al., Gene targeting in *Drosophila* and Caenorhabditis elegans with zinc-finger nucleases. Methods Mol Biol. 2008;435:63-77. doi: 10.1007/978-1-59745-232-8_5.
Carroll et al., Progress and prospects: zinc-finger nucleases as gene therapy agents. Gene Ther. Nov. 2008;15(22):1463-8. doi: 10.1038/gt.2008.145. Epub Sep. 11, 2008.
Carroll, A CRISPR approach to gene targeting. Mol Ther. Sep. 2012;20(9):1658-60. doi: 10.1038/mt.2012.171.
Cermak et al., Efficient design and assembly of custom TALEN and other TAL effector-based constructs for DNA targeting. Nucleic Acids Res. Jul. 2011;39(12):e82. Doi: 10.1093/nar/gkr218. Epub Apr. 14, 2011.
Chen et al., Fusion protein linkers: property, design and functionality. Adv Drug Deliv Rev. Oct. 2013;65(10):1357-69. doi:10.1016/j.addr.2012.09.039. Epub Sep. 29, 2012.
Chesnoy et al., Structure and function of lipid-DNA complexes for gene delivery. Annu Rev Biophys Biomol Struct. 2000;29:27-47.

(56) References Cited

OTHER PUBLICATIONS

Christian et al., Targeting DNA double-strand breaks with TAL effector nucleases. Genetics. Oct. 2010;186(2):757-61. Doi: 10.1534/genetics.110.120717. Epub Jul. 26, 2010.
Chung-Il et al., Artificial control of gene expression in mammalian cells by modulating RNA interference through aptamer-small molecule interaction. RNA. May 2006;12(5):710-6. Epub Apr. 10, 2006.
Chylinski et al., The tracrRNA and Cas9 families of type II CRISPR-Cas immunity systems. RNA Biol. May 2013;10(5):726-37. doi: 10.4161/rna.24321. Epub Apr. 5, 2013.
Colletier et al., Protein encapsulation in liposomes: efficiency depends on interactions between protein and phospholipid bilayer. BMC Biotechnol. May 10, 2002;2:9.
Cong et al., Multiplex genome engineering using CRISPR/Cas systems. Science. Feb. 15, 2013;339(6121):819-23. doi: 10.1126/science.1231143. Epub Jan. 3, 2013.
Cradick et al., CRISPR/Cas9 systems targeting β-globin and CCR5 genes have substantial off-target activity. Nucleic Acids Res. Nov. 1, 2013;41(20):9584-92. doi: 10.1093/nar/gkt714. Epub Aug. 11, 2013.
Cradick et al., Zinc-finger nucleases as a novel therapeutic strategy for targeting hepatitis B virus DNAs. Mol Ther. May 2010;18(5):947-54. Doi: 10.1038/mt.2010.20. Epub Feb. 16, 2010.
Cradick et al., ZFN-site searches genomes for zinc finger nuclease target sites and off-target sites. BMC Bioinformatics. May 13, 2011;12:152. doi: 10.1186/1471-2105-12-152.
Cronican et al., A class of human proteins that deliver functional proteins into mammalian cells in vitro and in vivo. Chem Biol. Jul. 29, 2011;18(7):833-8. doi: 10.1016/j.chembio1.2011.07.003.
Cronican et al., Potent delivery of functional proteins into mammalian cells in vitro and in vivo using a supercharged protein. ACS Chem Biol. Aug. 20, 2010;5(8):747-52. doi: 10.1021/cb1001153.
Cui et al., Targeted integration in rat and mouse embryos with zinc-finger nucleases. Nat Biotechnol. Jan. 2011;29(1):64-7. Doi: 10.1038/nbt.1731. Epub Dec. 12, 2010.
Dahlem et al., Simple methods for generating and detecting locus-specific mutations induced with TALENs in the zebrafish genome. PLoS Genet. 2012;8(8):e1002861. doi: 10.1371/journal.pgen.1002861. Epub Aug. 16, 2012.
Deltcheva et al., CRISPR RNA maturation by trans-encoded small RNA and host factor RNase III. Nature. Mar. 31, 2011;471(7340):602-7. doi: 10.1038/nature09886.
Dicarlo et al., Genome engineering in *Saccharomyces cerevisiae* using CRISPR-Cas systems. Nucleic Acids Res. Apr. 2013;41(7):4336-43. doi: 10.1093/nar/gkt135. Epub Mar. 4, 2013.
Ding et al., A TALEN genome-editing system for generating human stern cell-based disease models. Cell Stem Cell. Feb. 7, 2013;12(2):238-51. Doi: 10.1016/j.stem.2012.11.011. Epub Dec. 13, 2012.
Doyon et al., Heritable targeted gene disruption in zebrafish using designed zinc-finger nucleases. Nat Biotechnol. Jun. 2008;26(6):702-8. Doi: 10.1038/nbt1409. Epub May 25, 2008.
Esvelt et al., Orthogonal Cas9 proteins for RNA-guided gene regulation and editing. Nat Methods. Nov. 2013;10(11):1116-21. doi: 10.1038/nmeth.2681. Epub Sep. 29, 2013.
Fu et al., Improving CRISPR-Cas nuclease specificity using truncated guide RNAs. Nat Biotechnol. Mar. 2014;32(3):279-84. doi: 10.1038/nbt.2808. Epub Jan. 26, 2014.
Fu et al., High-frequency off-target mutagenesis induced by CRISPR-Cas nucleases in human cells. Nat Biotechnol. Sep. 2013;31(9):822-6. doi: 10.1038/nbt.2623. Epub Jun. 23, 2013.
Fuchs et al., Polyarginine as a multifunctional fusion tag. Protein Sci. Jun. 2005;14(6):1538-44.
Gaj et al., ZFN, TALEN, and CRISPR/Cas-based methods for genome engineering. Trends Biotechnol. Jul. 2013;31(7):397-405. doi: 10.1016/j.tibtech.2013.04.004. Epub May 9, 2013.
Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86. Epub Sep. 4, 2012. Supplementary materials included.
Gasiunas et al., RNA-dependent DNA endonuclease Cas9 of the CRISPR system: Holy Grail of genome editing? Trends Microbiol. Nov. 2013;21(11):562-7. doi: 10.1016/j.tim.2013.09.001. Epub Oct. 1, 2013.
Genbank Submission; NIH/NCBI, Accession No. J04623. Kita et al., Apr. 26, 1993. 2 pages.
Genbank Submission; NIH/NCBI, Accession No. NC_002737.1. Ferretti et al., Jun. 27, 2013. 1 page.
Genbank Submission; NIH/NCBI, Accession No. NC_015683.1. Trost et al., Jul. 6, 2013. 1 page.
Genbank Submission; NIH/NCBI, Accession No. NC_016782.1. Trost et al., Jun. 11, 2013. 1 page.
Genbank Submission; NIH/NCBI, Accession No. NC_016786.1. Trost et al., Aug. 28, 2013. 1 page.
Genbank Submission; NIH/NCBI, Accession No. NC_017053.1. Fittipaldi et al., Jul. 6, 2013. 1 page.
Genbank Submission; NIH/NCBI, Accession No. NC_017317.1. Trost et al., Jun. 11, 2013. 1 page.
Genbank Submission; NIH/NCBI, Accession No. NC_017861.1. Heidelberg et al., Jun. 11, 2013. 1 page.
Genbank Submission; NIH/NCBI, Accession No. NC_018010.1. Lucas et al., Jun. 11, 2013. 2 pages.
Genbank Submission; NIH/NCBI, Accession No. NC_018721.1. Feng et al., Jun. 11, 2013. 1 pages.
Genbank Submission; NIH/NCBI, Accession No. NC_021284.1. Ku et al., Jul. 12, 2013. 1 page.
Genbank Submission; NIH/NCBI, Accession No. NC_021314.1. Zhang et al., Jul. 15, 2013. 1 page.
Genbank Submission; NIH/NCBI, Accession No. NC_021846.1. Lo et al., Jul. 22, 2013. 1 page.
Genbank Submission; NIH/NCBI, Accession No. NP_472073.1. Glaser et al., Jun. 27, 2013. 2 pages.
Genbank Submission; NIH/NCBI, Accession No. P42212. Prasher et al., Mar. 19, 2014. 7 pages.
Genbank Submission; NIH/NCBI, Accession No. YP_002342100.1. Bernardini et al., Jun. 10, 2013. 2 pages.
Genbank Submission; NIH/NCBI, Accession No. YP_002344900.1. Gundogdu et al., Mar. 19, 2014. 2 pages.
Genbank Submission; NIH/NCBI, Accession No. YP_820832.1. Makarova et al., Aug. 27, 2013. 2 pages.
Gilbert et al., CRISPR-mediated modular RNA-guided regulation of transcription in eukaryotes. Cell. 2013 154(2):442-51.
Gilleron et al., Image-based analysis of lipid nanoparticle-mediated siRNA delivery, intracellular trafficking and endosomal escape. Nat Biotechnol. Jul. 2013;31(7):638-46. doi: 10.1038/nbt.2612. Epub Jun. 23, 2013.
Gordley et al., Evolution of programmable zinc finger-recombinases with activity in human cells. J Mol Biol. Mar. 30, 2007;367(3):802-13. Epub Jan. 12, 2007.
Guilinger et al., Fusion of catalytically inactive Cas9 to FokI nuclease improves the specificity of genome modification. Nat Biotechnol. Jun. 2014;32(6):577-82. doi: 10.1038/nbt.2909. Epub Apr. 25, 2014.
Guo et al., Directed evolution of an enhanced and highly efficient FokI cleavage domain for zinc finger nucleases. J Mol Biol. Jul. 2, 2010;400(1):96-107. doi: 10.1016/j.jmb.2010.04.060. Epub May 4, 2010.
Guo et al., Protein tolerance to random amino acid change. J Gene Med. Mar.-Apr. 2002;4(2):195-204.
Hale et al., RNA-guided RNA cleavage by a CRISPR RNA-Cas protein complex. Cell. Nov. 25, 2009;139(5):945-56. doi: 10.1016/j.ce11.2009.07.040.
Hasadsri et al., Functional protein delivery into neurons using polymeric nanoparticles. J Biol Chem. Mar. 13, 2009;284(11):6972-81. doi: 10.1074/jbc.M805956200. Epub Jan. 7, 2009.
Heitz et al., Twenty years of cell-penetrating peptides: from molecular mechanisms to therapeutics. Br J Pharmacol. May 2009;157(2):195-206. doi: 10.1111/j.1476-5381.2009.00057.x. Epub Mar. 20, 2009.

(56) References Cited

OTHER PUBLICATIONS

Hill et al., Functional analysis of conserved histidines in ADP-glucose pyrophosphorylase from *Escherichia coli*.Biochem Biophys Res Commun. Mar. 17, 1998;244(2):573-7.

Hope et al., Cationic lipids, phosphatidylethanolamine and the intracellular delivery of polymeric, nucleic acid-based drugs (review). Mol Membr Biol. Jan.-Mar. 1998;15(1):1-14.

Horvath et al., CRISPR/Cas, the immune system of bacteria and archaea. Science. Jan. 8, 2010;327(5962):167-70. doi: 10.1126/science.1179555.

Houdebine, The methods to generate transgenic animals and to control transgene expression. J Biotechnol. Sep. 25, 2002;98(2-3):145-60.

Hsu et al., DNA targeting specificity of RNA-guided Cas9 nucleases. Nat Biotechnol. Sep. 2013;31(9):827-32. doi: 10.1038/nbt.2647. Epub Jul. 21, 2013.

Huang et al., Heritable gene targeting in zebrafish using customized TALENs. Nat Biotechnol. Aug. 5, 2011;29(8):699-700. doi: 10.1038/nbt.1939.

Huang et al., Long-range pseudoknot interactions dictate the regulatory response in the tetrahydrofolate riboswitch. Proc Natl Acad Sci U S A. Sep. 6, 2011;108(36):14801-6. doi: 10.1073/pnas.1111701108. Epub Aug. 22, 2011.

Humbert et al., Targeted gene therapies: tools, applications, optimization. Crit Rev Biochem Mol Biol. May-Jun. 2012;47(3):264-81. doi: 10.3109/10409238.2012.658112.

Hurt et al., Highly specific zinc finger proteins obtained by directed domain shuffling and cell-based selection. Proc Natl Acad Sci U S A. Oct. 14, 2003;100(21):12271-6. Epub Oct. 3, 2003.

Hwang et al., Efficient genome editing in zebrafish using a CRISPR-Cas system. Nat Biotechnol. Mar. 2013;31(3):227-9. doi: 10.1038/nbt.2501. Epub Jan. 29, 2013.

Jamieson et al., Drug discovery with engineered zinc-finger proteins. Nat Rev Drug Discov. May 2003;2(5):361-8.

Jiang et al., RNA-guided editing of bacterial genomes using CRISPR-Cas systems. Nat Biotechnol. Mar. 2013;31(3):233-9. doi: 10.1038/nbt.2508. Epub Jan. 29, 2013.

Jinek et al., A programmable dual-RNA-guided DNA endonuclease in adaptive bacterial immunity. Science. Aug. 17, 2012;337(6096):816-21. doi: 10.1126/science.1225829. Epub Jun. 28, 2012.

Jinek et al., RNA-programmed genome editing in human cells. Elife. Jan. 29, 2013;2:e00471. doi: 10.7554/eLife.00471.

Jinek et al., Structures of Cas9 endonucleases reveal RNA-mediated conformational activation. Science. Mar. 14, 2014;343(6176):1247997. doi: 10.1126/science.1247997. Epub Feb. 6, 2014.

Jore et al., Structural basis for CRISPR RNA-guided DNA recognition by Cascade. Nat Struct Mol Biol. May 2011;18(5):529-36. doi: 10.1038/nsmb.2019. Epub Apr. 3, 2011.

Joung et al.,TALENs: a widely applicable technology for targeted genome editing. Nat Rev Mol Cell Biol. Jan. 2013;14(1):49-55. doi: 10.1038/nrm3486. Epub Nov. 21, 2012.

Kaiser et al., Gene therapy. Putting the fingers on gene repair. Science. Dec. 23, 2005;310(5756):1894-6.

Kandavelou et al., Targeted manipulation of mammalian genomes using designed zinc finger nucleases. Biochem Biophys Res Commun. Oct. 9, 2009;388(1):56-61. doi: 10.1016/j.bbrc.2009.07.112. Epub Jul. 25, 2009.

Kappel et al., Regulating gene expression in transgenic animals. Curr Opin Biotechnol. Oct. 1992;3(5):548-53.

Kim et al., A library of TAL effector nucleases spanning the human genome. Nat Biotechnol. Mar. 2013;31(3):251-8. Doi: 10.1038/nbt.2517. Epub Feb. 17, 2013.

Kim et al., Hybrid restriction enzymes: zinc finger fusions to Fok I cleavage domain. Proc Natl Acad Sci U S A. Feb. 6, 1996;93(3):1156-60.

Kim et al., TALENs and ZFNs are associated with different mutationsignatures. Nat Methods. Mar. 2013;10(3):185. doi: 10.1038/nmeth.2364. Epub Feb. 10, 2013.

Kim et al., Targeted genome editing in human cells with zinc finger nucleases constructed via modular assembly. Genome Res. Jul. 2009;19(7):1279-88. doi: 10.1101/gr.089417.108. Epub May 21, 2009.

Klauser et al., An engineered small RNA-mediated genetic switch based on a ribozyme expression platform. Nucleic Acids Res. May 1, 2013;41(10):5542-52. doi: 10.1093/nar/gkt253. Epub Apr. 12, 2013.

Klug et al., Zinc fingers: a novel protein fold for nucleic acid recognition. Cold Spring Harb Symp Quant Biol. 1987;52:473-82.

Krishna et al., Structural classification of zinc fingers: survey and summary. Nucleic Acids Res. Jan. 15, 2003;31(2):532-50.

Larson et al., CRISPR interference (CRISPRi) for sequence-specific control of gene expression. Nat Protoc. Nov. 2013;8(11):2180-96. doi: 10.1038/nprot.2013.132. Epub Oct. 17, 2013.

Lawrence et al., Supercharging proteins can impart unusual resilience. J Am Chem Soc. Aug. 22, 2007;129(33):10110-2. Epub Aug. 1, 2007.

Lazar et al., Transforming growth factor alpha: mutation of aspartic acid 47 and leucine 48 results in different biological activities. Mol Cell Biol. Mar. 1988;8(3):1247-52.

Lei et al., Efficient targeted gene disruption in Xenopus embryos using engineered transcription activator-like effector nucleases (TALENs). Proc Natl Acad Sci U S A. Oct. 23, 2012;109(43):17484-9. Doi: 10.1073/pnas.1215421109. Epub Oct. 8, 2012.

Lewis et al., A serum-resistant cytofectin for cellular delivery of antisense oligodeoxynucleotides and plasmid DNA. Proc Natl Acad Sci U S A. Apr. 16, 1996;93(8):3176-81.

Li et al., Modularly assembled designer TAL effector nucleases for targeted gene knockout and gene replacement in eukaryotes. Nucleic Acids Res. Aug. 2011;39(14):6315-25. doi: 10.1093/nar/gkr188. Epub Mar. 31, 2011.

Li et al., TAL nucleases (TALNs): hybrid proteins composed of TAL effectors and FokI DNA-cleavage domain. Nucleic Acids Res. Jan. 2011;39(1):359-72. doi: 10.1093/nar/gkq704. Epub Aug. 10, 2010.

Liu et al., Cell-penetrating peptide-mediated delivery of TALEN proteins via bioconjugation for genome engineering. PLoS One. Jan. 20, 2014;9(1):e85755. doi: 10.1371/journal.pone.0085755. eCollection 2014.

Liu et al., Design of polydactyl zinc-finger proteins for unique addressing within complex genomes. Proc Natl Acad Sci U S A. May 27, 1997;94(11):5525-30.

Liu et al., Fast Colorimetric Sensing of Adenosine and Cocaine Based on a General Sensor Design Involving Aptamers and Nanoparticles. Angew Chem. 2006;118(1):96-100.

Lombardo et al., Gene editing in human stem cells using zinc finger nucleases and integrase-defective lentiviral vector delivery. Nat Biotechnol. Nov. 2007;25(11):1298-306. Epub Oct. 28, 2007.

Lundberg et al., Delivery of short interfering RNA using endosomolytic cell-penetrating peptides. FASEB J. Sep. 2007;21(11):2664-71. Epub Apr. 26, 2007.

Maeder et al., CRISPR RNA-guided activation of endogenous human genes. Nat Methods. Oct. 2013;10(10):977-9. doi: 10.1038/nmeth.2598. Epub Jul. 25, 2013.

Maeder et al., Rapid "open-source" engineering of customized zinc-finger nucleases for highly efficient gene modification. Mol Cell. Jul. 25, 2008;31(2):294-301. doi:10.1016/j.molce1.2008.06.016.

Maeder et al., Robust, synergistic regulation of human gene expression using TALE activators. Nat Methods. Mar. 2013;10(3):243-5. doi: 10.1038/nmeth.2366. Epub Feb. 10, 2013.

Mahfouz et al., De novo-engineered transcription activator-like effector (TALE) hybrid nuclease with novel DNA binding specificity creates double-strand breaks. Proc Natl Acad Sci U S A. Feb. 8, 2011;108(6):2623-8. doi: 10.1073/pnas.1019533108. Epub Jan. 24, 2011.

Mali et al., Cas9 as a versatile tool for engineeringbiology. Nat Methods. Oct. 2013;10(10):957-63. doi: 10.1038/nmeth.2649.

Mali et al., CAS9 transcriptional activators for target specificity screening and paired nickases for cooperative genome engineering. Nat Biotechnol. Sep. 2013;31(9):833-8. doi: 10.1038/nbt.2675. Epub Aug. 1, 2013.

(56) References Cited

OTHER PUBLICATIONS

Mali et al., RNA-guided human genome engineering via Cas9. Science. Feb. 15, 2013;339(6121):823-6. doi: 10.1126/science.1232033. Epub Jan. 3, 2013.
Mani et al., Design, engineering, and characterization of zinc finger nucleases. Biochem Biophys Res Commun. Sep. 23, 2005;335(2):447-57.
McNaughton et al., Mammalian cell penetration, siRNA transfection, and DNA transfection by supercharged proteins. Proc Natl Acad Sci U S A. Apr. 14, 2009;106(15):6111-6. doi: 10.1073/pnas.0807883106. Epub Mar. 23, 2009.
Meng et al., Targeted gene inactivation in zebrafish using engineered zinc-finger nucleases. Nat Biotechnol. Jun. 2008;26(6):695-701. doi: 10.1038/nbt1398. Epub May 25, 2008.
Meyer et al., Breathing life into polycations: functionalization with pH-responsive endosomolytic peptides and polyethylene glycol enables siRNA delivery. J Am Chem Soc. Mar. 19, 2008;130(11):3272-3. doi: 10.1021/ja710344v. Epub Feb. 21, 2008.
Midoux et al., Chemical vectors for gene delivery: a current review on polymers, peptides and lipids containing histidine or imidazole as nucleic acids carriers. Br J Pharmacol. May 2009;157(2):166-78. doi: 10.1111/j.1476-5381.2009.00288.x.
Miller et al., A TALE nuclease architecture for efficient genome editing. Nat Biotechnol. Feb. 2011;29(2):143-8. doi:10.1038/nbt.1755. Epub Dec. 22, 2010.
Miller et al., An improved zinc-finger nuclease architecture for highly specific genome editing. Nat Biotechnol. Jul. 2007;25(7):778-85. Epub Jul. 1, 2007.
Moore et al., Improved somatic mutagenesis in zebrafish using transcription activator-like effector nucleases (TALENs). PloS One. 2012;7(5):e37877. Doi: 10.1371/journal.pone.0037877. Epub May 24, 2012.
Morris et al., A peptide carrier for the delivery of biologically active proteins into mammalian cells. Nat Biotechnol. Dec. 2001;19(12):1173-6.
Mullins et al., Transgenesis in nonmurine species. Hypertension. Oct. 1993;22(4):630-3.
Mussolino et al., A novel TALE nuclease scaffold enables high genome editing activity in combination with low toxicity. Nucleic Acids Res. Nov. 2011;39(21):9283-93. Doi: 10.1093/nar/gkr597. Epub Aug. 3, 2011.
Mussolino et al., TALE nucleases: tailored genome engineering made easy. Curr Opin Biotechnol. Oct. 2012;23(5):644-50. doi: 10.1016/j.copbio.2012.01.013. Epub Feb. 17, 2012.
Narayanan et al., Clamping down on weak terminal base pairs: oligonucleotides with molecular caps as fidelity-enhancing elements at the 5'- and 3'-terminal residues. Nucleic Acids Res. May 20, 2004;32(9):2901-11. Print 2004.
NCBI Reference Sequence: NM_002427.3. Wu et al., May 3, 2014. 5 pages.
Nishimasu et al., Crystal structure of Cas9 in complex with guide RNA and target DNA. Cell. Feb. 27, 2014;156(5):935-49. doi: 10.1016/j.cell.2014.02.001. Epub Feb. 13, 2014.
Nomura et al., Synthetic mammalian riboswitches based on guanine aptazyme. Chem Commun (Camb). Jul. 21, 2012;48(57):7215-7. doi: 10.1039/c2cc33140c. Epub Jun. 13, 2012.
O'Connell et al., Programmable RNA recognition and cleavage by CRISPR/Cas9. Nature. Sep. 28, 2014. doi: 10.1038/nature13769.
Osborn et al., TALEN-based gene correction for epidermolysis bullosa. Mol Ther. Jun. 2013;21(6):1151-9. doi: 10.1038/mt.2013.56. Epub Apr. 2, 2013.
Pan et al., Biological and biomedical applications of engineered nucleases. Mol Biotechnol. Sep. 2013;55(1):54-62. doi: 10.1007/s12033-012-9613-9.
Pattanayak et al., Determining the specificities of TALENs, Cas9, and other genome-editing enzymes. Methods Enzymol. 2014;546:47-78. doi: 10.1016/B978-0-12-801185-0.00003-9.
Pattanayak et al., High-throughput profiling of off-target DNA cleavage reveals RNA-programmed Cas9 nuclease specificity. Nat Biotechnol. Sep. 2013;31(9):839-43. doi: 10.1038/nbt.2673. Epub Aug. 11, 2013.
Pattanayak et al., Revealing off-target cleavage specificities of zinc-finger nucleases by in vitro selection. Nat Methods. Aug. 7, 2011;8(9):765-70. doi: 10.1038/nmeth.1670.
Pennisi et al., The CRISPR craze. Science. Aug. 23, 2013;341(6148):833-6. doi: 10.1126/science.341.6148.833.
Pennisi et al., The tale of the TALEs. Science. Dec. 14, 2012;338(6113):1408-11. doi: 10.1126/science.338.6113.1408.
Perez et al., Establishment of HIV-1 resistance in CD4+ T cells by genome editing using zinc-finger nucleases. Nat Biotechnol. Jul. 2008;26(7):808-16. Doi: 10.1038/nbt1410. Epub Jun. 29, 2008.
Perez-Pinera et al., Advances in targeted genome editing. Curr Opin Chem Biol. Aug. 2012;16(3-4):268-77. doi: 10.1016/j.cbpa.2012.06.007. Epub Jul. 20, 2012.
Perez-Pinera et al., RNA-guided gene activation by CRISPR-Cas9-based transcription factors. Nat Methods. Oct. 2013;10(10):973-6. doi: 10.1038/nmeth.2600. Epub Jul. 25, 2013.
Phillips, The challenge of gene therapy and DNA delivery. J Pharm Pharmacol. Sep. 2001;53(9):1169-74.
Porteus, Design and testing of zinc finger nucleases for use in mammalian cells. Methods Mol Biol. 2008;435:47-61. doi: 10.1007/978-1-59745-232-8_4.
Putney et al., Improving protein therapeutics with sustained-release formulations. Nat Biotechnol. Feb. 1998;16(2):153-7.
Qi et al., Repurposing CRISPR as an RNA-guided platform for sequence-specific control of gene expression. Cell. Feb. 28, 2013;152(5):1173-83. doi: 10.1016/j.cell.2013.02.022.
Qi et al., Engineering naturally occurring trans-acting non-coding RNAs to sense molecular signals. Nucleic Acids Res. Jul. 2012;40(12):5775-86. doi: 10.1093/nar/gks168. Epub Mar. 1, 2012.
Ramakrishna et al., Gene disruption by cell-penetrating peptide-mediated delivery of Cas9 protein and guide RNA. Genome Res. Jun. 2014;24(6):1020-7. doi: 10.1101/gr.171264.113. Epub Apr. 2, 2014.
Ramirez et al., Engineered zinc finger nickases induce homology-directed repair with reduced mutagenic effects. Nucleic Acids Res. Jul. 2012;40(12):5560-8. doi: 10.1093/nar/gks179. Epub Feb. 28, 2012.
Ran et al., Double nicking by RNA-guided CRISPR Cas9 for enhanced genome editing specificity. Cell. Sep. 12, 2013;154(6):1380-9. doi: 10.1016/j.cell.2013.08.021. Epub Aug. 29, 2013.
Samal et al., Cationic polymers and their therapeutic potential. Chem Soc Rev. Nov. 7, 2012;41(21):7147-94. doi: 10.1039/c2cs35094g. Epub Aug. 10, 2012.
Sander et al., CRISPR-Cas systems for editing, regulating and targeting genomes. Nat Biotechnol. Apr. 2014;32(4):347-55. doi: 10.1038/nbt.2842. Epub Mar. 2, 2014.
Sander et al., Targeted gene disruption in somatic zebrafish cells using engineered TALENs. Nat Biotechnol. Aug. 5, 2011;29(8):697-8. doi: 10.1038/nbt.1934.
Sang, Prospects for transgenesis in the chick. Mech Dev. Sep. 2004;121(9):1179-86.
Santiago et al., Targeted gene knockout in mammalian cells by using engineered zinc-finger nucleases. Proc Natl Acad Sci U S A. Apr. 15, 2008;105(15):5809-14. doi: 10.1073/pnas.0800940105. Epub Mar. 21, 2008.
Sapranauskas et al., The *Streptococcus thermophilus* CRISPR/Cas system provides immunity in *Escherichia coli*. Nucleic Acids Res. Nov. 2011;39(21):9275-82. doi: 10.1093/nar/gkr606. Epub Aug. 3, 2011.
Sashital et al., Mechanism of foreign DNA selection in a bacterial adaptive immune system. Mol Cell. Jun. 8, 2012;46(5):606-15. doi: 10.1016/j.molcel.2012.03.020. Epub Apr. 19, 2012.
Schriefer et al., Low pressure DNA shearing: a method for random DNA sequence analysis. Nucleic Acids Res. Dec. 25, 1990;18(24):7455-6.
Schwank et al., Functional repair of CFTR by CRISPR/Cas9 in intestinal stem cell organoids of cystic fibrosis patients. Cell Stem Cell. Dec. 5, 2013;13(6):653-8. doi:10.1016/j.stem.2013.11.002.

(56) References Cited

OTHER PUBLICATIONS

Schwarze et al., In vivo protein transduction: delivery of a biologically active protein into the mouse. Science. Sep. 3, 1999;285(5433):1569-72.
Sells et al., Delivery of protein into cells using polycationic liposomes. Biotechniques. Jul. 1995;19(1):72-6, 78.
Semenova et al., Interference by clustered regularly interspaced short palindromic repeat (CRISPR) RNA is governed by a seed sequence. Proc Natl Acad Sci U S A. Jun. 21, 2011;108(25):10098-103. doi: 10.1073/pnas.1104144108. Epub Jun. 6, 2011.
Semple et al., Rational design of cationic lipids for siRNA delivery. Nat Biotechnol. Feb. 2010;28(2):172-6. doi: 10.1038/nbt.1602. Epub Jan. 17, 2010.
Shalem et al., Genome-scale CRISPR-Cas9 knockout screening in human cells. Science. Jan. 3, 2014;343(6166):84-7. doi: 10.1126/science.1247005. Epub Dec. 12, 2013.
Sheridan, First CRISPR-Cas patent opens race to stake out intellectual property. Nat Biotechnol. 2014;32(7):599-601.
Siebert et al., An improved PCR method for walking in uncloned genomic DNA. Nucleic Acids Res. Mar. 25, 1995;23(6):1087-8.
Sun et al., Optimized TAL effector nucleases (TALENs) for use in treatment of sickle cell disease. Mol Biosyst. Apr. 2012;8(4):1255-63. doi: 10.1039/c2mb05461b. Epub Feb. 3, 2012.
Thompson et al., Cellular uptake mechanisms and endosomal trafficking of supercharged proteins. Chem Biol. Jul. 27, 2012;19(7):831-43. doi: 10.1016/j.chembio1.2012.06.014.
Thompson et al., Engineering and identifying supercharged proteins for macromolecule delivery into mammalian cells. Methods Enzymol. 2012;503:293-319. doi: 10.1016/B978-0-12-396962-0.00012-4.
Thorpe et al., Functional correction of episomal mutations with short DNA fragments and RNA-DNA oligonucleotides. J Gene Med. Mar.-Apr. 2002;4(2):195-204.
Tsai et al., Dimeric CRISPR RNA-guided FokI nucleases for highly specific genome editing. Nat Biotechnol. Jun. 2014;32(6):569-76. doi: 10.1038/nbt.2908. Epub Apr. 25, 2014.
Uniprot Submission; UniProt, Accession No. P01011. Last modified Jun. 11, 2014, version 2. 15 pages.
Uniprot Submission; UniProt, Accession No. P04264. Last modified Jun. 11, 2014, version 6. 15 pages.
Uniprot Submission; UniProt, Accession No. P04275. Last modified Jul. 9, 2014, version 107. 29 pages.
Urnov et al., Genome editing with engineered zinc finger nucleases. Nat Rev Genet. Sep. 2010;11(9):636-46. doi: 10.1038/nrg2842.
Urnov et al., Highly efficient endogenous human gene correction using designed zinc-finger nucleases. Nature. Jun. 2, 2005;435(7042):646-51. Epub Apr. 3, 2005.
Wacey et al., Disentangling the perturbational effects of amino acid substitutions in the DNA-binding domain of p53. Hum Genet. Jan. 1999;104(1):15-22.
Wadia et al., Modulation of cellular function by TAT mediated transduction of full length proteins. Curr Protein Pept Sci. Apr. 2003;4(2):97-104.
Wadia et al., Transducible TAT-HA fusogenic peptide enhances escape of TAT-fusion proteins after lipid raft macropinocytosis. Nat Med. Mar. 2004;10(3):310-5. Epub Feb. 8, 2004.
Wang et al., Genetic screens in human cells using the CRISPR-Cas9 system. Science. Jan. 3, 2014;343(6166):80-4. doi: 10.1126/science.1246981. Epub Dec. 12, 2013.
Wang et al., One-step generation of mice carrying mutations in multiple genes by CRISPR/Cas-mediated genome engineering. Cell. May 9, 2013;153(4):910-8. doi: 10.1016/j.ce11.2013.04.025. Epub May 2, 2013.
Wang et al., Targeted gene addition to a predetermined site in the human genome using a ZFN-based nicking enzyme. Genome Res. Jul. 2012;22(7):1316-26. doi: 10.1101/gr.122879.111. Epub Mar. 20, 2012.
Wiedenheft et al., RNA-guided genetic silencing systems in bacteria and archaea. Nature. Feb. 15, 2012;482(7385):331-8. doi: 10.1038/nature10886. Review.
Wood et al., Targeted genome editing across species using ZFNs and TALENs. Science. Jul. 15, 2011;333(6040):307. doi: 10.1126/science.1207773. Epub Jun. 23, 2011.
Wu et al., Correction of a genetic disease in mouse via use of CRISPR-Cas9. Cell Stem Cell. Dec. 5, 2013;13(6):659-62. doi: 10.1016/j.stem.2013.10.016.
Yin et al., Genome editing with Cas9 in adult mice corrects a disease mutation and phenotype. Nat Biotechnol. Jun. 2014;32(6):551-3. doi: 10.1038/nbt.2884. Epub Mar. 30, 2014.
Zelphati et al., Intracellular delivery of proteins with a new lipid-mediated delivery system. J Biol Chem. Sep. 14, 2001;276(37):35103-10. Epub Jul. 10, 2001.
Zhang et al., CRISPR/Cas9 for genome editing: progress, implications and challenges. Hum Mol Genet. Sep. 15, 2014;23(R1):R40-6. doi: 10.1093/hmg/ddu125. Epub Mar. 20, 2014.
Zhang et al., Efficient construction of sequence-specific TAL effectors for modulating mammalian transcription. Nat Biotechnol. Feb. 2011;29(2):149-53. doi: 10.1038/nbt.1775. Epub Jan. 19, 2011.
Zorko et al., Cell-penetrating peptides: mechanism and kinetics of cargo delivery. Adv Drug Deliv Rev. Feb. 28, 2005;57(4):529-45. Epub Jan. 22, 2005.
Zou et al., Gene targeting of a disease-related gene in human induced pluripotent stem and embryonic stem cells. Cell Stem Cell. Jul. 2, 2009;5(1):97-110. doi: 10.1016/j.stem.2009.05.023. Epub Jun. 18, 2009.
U.S. Appl. No. 14/913,458, filed Feb. 22, 2016, Liu et al.
U.S. Appl. No. 14/874,123, filed Oct. 2, 2015, Liu et al.
U.S. Appl. No. 14/911,117, filed Feb. 9, 2016, Liu et al.
U.S. Appl. No. 14/916,679, filed Mar. 4, 2016, Liu et al.
U.S. Appl. No. 14/916,681, filed Mar. 4, 2016, Liu et al.
U.S. Appl. No. 14/916,683, filed Mar. 4, 2016, Liu et al.
U.S. Appl. No. 15/103,608, filed Jun. 10, 2016, Liu et al.
U.S. Appl. No. 15/329,925, filed Jan. 27, 2017, Liu et al.
U.S. Appl. No. 15/331,852, filed Oct. 22, 2016, Liu et al.
Addgene Plasmid # 44246. pdCas9-humanized, 2017, Stanley Qi.
Addgene Plasmid # 73021. PCMV-BE3, 2017, David Liu.
Addgene Plasmid # 79620. pcDNA3.1_pCMV-nCas-PmCDA1-ugi pH1-gRNA(HPRT), 2017, Akihiko Kondo.
Anders et al., Structural basis of PAM-dependent target DNA recognition by the Cas9 endonuclease. Nature. Sep. 25, 2014;513(7519):569-73. doi: 10.1038/nature13579. Epub Jul. 27, 2014.
Barnes et al., Repair and genetic consequences of endogenous DNA base damage in mammalian cells. Annu Rev Genet. 2004;38:445-76.
Beale et al., Comparison of the differential context-dependence of DNA deamination by APOBEC enzymes: correlation with mutation spectra in vivo. J Mol Biol. Mar. 26, 2004;337(3):585-96.
Begley, Scientists unveil the 'most clever CRISPR gadget' so far. STAT, Apr. 20, 2016. https://www.statnews.com/2016/04/20/clever-crispr-advance-unveiled/.
Birling et al., Site-specific recombinases for manipulation of the mouse genome. Methods Mol Biol. 2009;561:245-63. doi: 10.1007/978-1-60327-019-9_16.
Bitinaite et al., FokI dimerization is required for DNA cleavage. Proc Natl Acad Sci U S A. Sep. 1, 1998;95(18):10570-5.
Borman, Improved route to single-base genome editing. Chemical & Engineering News, Apr. 25, 2016;94(17)p5. http://cen.acs.org/articles/94/i17/Improved-route-single-base-genome.html.
Britt et al., Re-engineering plant gene targeting. Trends Plant Sci. Feb. 2003;8(2):90-5.
Brusse et al., Spinocerebellar ataxia associated with a mutation in the fibroblast growth factor 14 gene (SCA27): A new phenotype. Mov Disord. Mar. 2006;21(3):396-401.
Buchholz et al., Alteration of Cre recombinase site specificity by substrate-linked protein evolution. Nat Biotechnol. Nov. 2001;19(11):1047-52.
Caldecott et al., Single-strand break repair and genetic disease. Nat Rev Genet. Aug. 2008;9(8):619-31. doi: 10.1038/nrg2380.
Chadwick et al., In Vivo Base Editing of PCSK9 (Proprotein Convertase Subtilisin/Kexin Type 9) as a Therapeutic Alternative to

(56) References Cited

OTHER PUBLICATIONS

Genome Editing. Arterioscler Thromb Vasc Biol. Sep. 2017;37(9):1741-1747. doi: 10.1161/ATVBAHA.117.309881. Epub Jul. 27, 2017.
Chaikind et al., A programmable Cas9-serine recombinase fusion protein that operates on DNA sequences in mammalian cells. Nucleic Acids Res. Nov. 16, 2016;44(20):9758-9770. Epub Aug. 11, 2016.
Chavez et al., Highly efficient Cas9-mediated transcriptional programming. Nat Methods. Apr. 2015;12(4):326-8. doi: 10.1038/nmeth.3312. Epub Mar. 2, 2015.
Chavez et al., Precise Cas9 targeting enables genomic mutation prevention. Jun. 14, 2016. doi:https://doi.org/10.1101/058974. [Preprint].
Chen et al., Structure of the DNA deaminase domain of the HIV-1 restriction factor APOBEC3G. Nature. Mar. 6, 2008;452(7183):116-9. doi: 10.1038/nature06638. Epub Feb. 20, 2008.
Chu et al., Increasing the efficiency of homology-directed repair for CRISPR-Cas9-induced precise gene editing in mammalian cells. Nat Biotech. Feb. 13, 2015;33:543-8.
Cox et al., Conditional gene expression in the mouse inner ear using Cre-IoxP. J Assoc Res Otolaryngol. Jun. 2012;13(3):295-322. doi: 10.1007/s10162-012-0324-5. Epub Apr. 24, 2012.
Cox et al., Therapeutic genome editing: prospects and challenges. Nat Med. Feb. 2015;21(2):121-31. doi: 10.1038/nm.3793.
Cunningham et al., Ensembl 2015. Nucleic Acids Res. Jan. 2015;43(Database issue):D662-9. doi: 10.1093/nar/gku1010. Epub Oct. 28, 2014.
Davis et al., Small molecule-triggered Cas9 protein with improved genome-editing specificity. Nat Chem Biol. May 2015;11(5):316-8. doi: 10.1038/nchembio.1793. Epub Apr. 6, 2015.
Dormiani et al., Long-term and efficient expression of human β-globin gene in a hematopoietic cell line using a new site-specific integrating non-viral system. Gene Ther. Aug. 2015;22(8):663-74. doi: 10.1038/gt.2015.30. Epub Apr. 1, 2015.
Doudna et al., Genome editing. The new frontier of genome engineering with CRISPR-Cas9. Science. Nov. 28, 2014;346(6213):1258096. doi: 10.1126/science.1258096.
Dunaime, Breakthrough method means CRISPR just got a lot more relevant to human health. The Verge. Apr. 20, 2016. http://www.theverge.com/2016/4/20/11450262/crispr-base-editing-single-nucleotides-dna-gene-liu-harvard.
Fung et al., Repair at single targeted DNA double-strand breaks in pluripotent and differentiated human cells. PLoS One. 2011;6(5):e20514. doi: 10.1371/journal.pone.0020514. Epub May 25, 2011.
Gaj et al., A comprehensive approach to zinc-finger recombinase customization enables genomic targeting in human cells. Nucleic Acids Res. Feb. 6, 2013;41(6):3937-46.
Gaj et al., Enhancing the specificity of recombinase-mediated genome engineering through dimer interface redesign. J Am Chem Soc. Apr. 2, 2014;136(13):5047-56. doi: 10.1021/ja4130059. Epub Mar. 20, 2014.
Gaj et al., Expanding the scope of site-specific recombinases for genetic and metabolic engineering. Biotechnol Bioeng. Jan. 2014;111(1):1-15. doi: 10.1002/bit.25096. Epub Sep. 13, 2013.
Gao et al., DNA-guided genome editing using the Natronobacterium gregoryi Argonaute. Nat Biotechnol. Jul. 2016;34(7):768-73. doi: 10.1038/nbt.3547. Epub May 2, 2016.
Gersbach et al., Directed evolution of recombinase specificity by split gene reassembly. Nucleic Acids Res. Jul. 2010;38(12):4198-206. doi: 10.1093/nar/gkq125. Epub Mar. 1, 2010.
Gersbach et al., Targeted plasmid integration into the human genome by an engineered zinc-finger recombinase. Nucleic Acids Res. Sep. 1, 2011;39(17):7868-78. doi: 10.1093/nar/gkr421. Epub Jun. 7, 2011.
Gonzalez et al., An iCRISPR platform for rapid, multiplexable, and inducible genome editing in human pluripotent stem cells. Cell Stem Cell. Aug. 7, 2014;15(2):215-26. doi: 10.1016/j.stem.2014.05.018. Epub Jun. 12, 2014.
Han, New CRISPR/Cas9-based Tech Edits Single Nucleotides Without Breaking DNA. Genome Web, Apr. 20, 2016. https://www.genomeweb.com/gene-silencinggene-editing/new-crisprcas9-based-tech-edits-single-nucleotides-without-breaking-dna.
Harris et al., RNA editing enzyme APOBEC1 and some of its homologs can act as DNA mutators. Mol Cell. Nov. 2002;10(5):1247-53.
Hess et al., Directed evolution using dCas9-targeted somatic hypermutation in mammalian cells. Nat Methods. Dec. 2016;13(12):1036-1042. doi: 10.1038/nmeth.4038. Epub Oct. 31, 2016.
Hilton et al., Enabling functional genomics with genome engineering. Genome Res. Oct. 2015;25(10)1442-55. doi: 10.1101/gr.190124.115.
Hondares et al., Peroxisome Proliferator-activated Receptor α (PPARα) Induces PPARγ Coactivator 1α (PGC-1α) Gene Expression and Contributes to Thermogenic Activation of Brown Fat. J Biol. Chem Oct. 2011; 286(50):43112-22. doi: 10.1074/jbc.M111.252775.
Hou et al., Efficient genome engineering in human pluripotent stem cells using Cas9 from Neisseria meningitidis. Proc Natl Acad Sci U S A. Sep. 24, 2013;110(39):15644-9. doi: 10.1073/pnas.1313587110. Epub Aug. 12, 2013.
International Preliminary Report on Patentability for PCT/US2015/058479, dated May 11, 2017.
International Search Report and Written Opinion for PCT/US2016/058344, dated Apr. 20, 2017.
International Search Report and Written Opinion for PCT/US2017/046144, dated Oct. 10, 2017.
Jiang et al., Structures of a CRISPR-Cas9 R-loop complex primed for DNA cleavage. Science. Feb. 19, 2016;351(6275):867-71. doi: 10.1126/science.aad8282. Epub Jan. 14, 2016.
Karpinsky et al., Directed evolution of a recombinase that excises the provirus of most HIV-1 primary isolates with high specificity. Nat Biotechnol. Apr. 2016;34(4):401-9. doi: 10.1038/nbt.3467. Epub Feb. 22, 2016.
Kellendonk et al., Regulation of Cre recombinase activity by the synthetic steroid RU 486. Nucleic Acids Res. Apr. 15, 1996;24(8):1404-11.
Kim et al., Genome-wide target specificities of CRISPR RNA-guided programmable deaminases. Nat Biotechnol. May 2017;35(5):475-480. doi: 10.1038/nbt.3852. Epub Apr. 10, 2017.
Kim et al., Highly efficient RNA-guided base editing in mouse embryos. Nat Biotechnol. May 2017;35(5):435-437. doi: 10.1038/nbt.3816. Epub Feb. 27, 2017.
Kim et al., Increasing the genome-targeting scope and precision of base editing with engineered Cas9-cytidine deaminase fusions. Nat Biotechnol. Apr. 2017;35(4):371-376. doi: 10.1038/nbt.3803. Epub Feb. 13, 2017.
Kim et al., The role of apolipoprotein E in Alzheimer's disease. Neuron. Aug. 13, 2009;63(3):287-303. doi: 10.1016/j.neuron.2009.06.026.
Kitamura et al., Uracil DNA glycosylase counteracts APOBEC3G-induced hypermutation of hepatitis B viral genomes: excision repair of covalently closed circular DNA. PLoS Pathog. 2013;9(5):e1003361. doi: 10.1371/journal.ppat.1003361. Epub May 16, 2013.
Kleinstiver et al., Broadening the targeting range of *Staphylococcus aureus* CRISPR-Cas9 by modifying PAM recognition. Nat Biotechnol. Dec. 2015;33(12):1293-1298. doi: 10.1038/nbt.3404. Epub Nov. 2, 2015.
Kleinstiver et al., Engineered CRISPR-Cas9 nucleases with altered PAM specificities. Nature. Jul. 23, 2015;523(7561):481-5. doi: 10.1038/nature14592. Epub Jun. 22, 2015.
Kleinstiver et al., High-fidelity CRISPR-Cas9 nucleases with no detectable genome-wide off-target effects. Nature. Jan. 28, 2016;529(7587):490-5. doi: 10.1038/nature16526. Epub Jan. 6, 2016.

(56) References Cited

OTHER PUBLICATIONS

Klippel et al., Isolation and characterization of unusual gin mutants. EMBO J. Dec. 1, 1988;7(12):3983-9.
Klippel et al., The DNA invertase Gin of phage Mu: formation of a covalent complex with DNA via a phosphoserine at amino acid position 9. EMBO J. Apr. 1988;7(4):1229-37.
Kuscu et al., CRISPR-STOP: gene silencing through base-editing-induced nonsense mutations. Nat Methods. Jul. 2017;14(7):710-712. doi: 10.1038/nmeth.4327. Epub Jun. 5, 2017.
Kuscu et al., Genome-wide analysis reveals characteristics of off-target sites bound by the Cas9 endonuclease. Nat Biotechnol. Jul. 2014;32(7):677-83. doi: 10.1038/nbt.2916. Epub May 18, 2014.
Landrum et al., ClinVar: public archive of interpretations of clinically relevant variants. Nucleic Acids Res. Jan. 4, 2016;44(D1):D862-8. doi: 10.1093/nar/gkv1222. Epub Nov. 17, 2015.
Ledford, Gene-editing hack yields pinpoint precision. Nature, Apr. 20, 2016. http://www.nature.com/news/gene-editing-hack-yields-pinpoint-precision-1.19773.
Lee et al., A chimeric thyroid hormone receptor constitutively bound to DNA requires retinoid X receptor for hormone-dependent transcriptional activation in yeast. Mol Endocrinol. Sep. 1994;8(9):1245-52.
Li et al., Generation of Targeted Point Mutations in Rice by a Modified CRISPR/Cas9 System. Mol Plant. Mar. 6, 2017;10(3):526-529. doi: 10.1016/j.molp.2016.12.001. Epub Dec. 8, 2016.
Li et al., Highly efficient and precise base editing in discarded human tripronuclear embryos. Protein Cell. Aug. 19, 2017. doi: 10.1007/s13238-017-0458-7. [Epub ahead of print].
Lin et al., Enhanced homology-directed human genome engineering by controlled timing of CRISPR/Cas9 delivery. Elife. Dec. 15, 2014;3:e04766. doi: 10.7554/eLife.04766.
Liu et al., Apolipoprotein E and Alzheimer disease: risk, mechanisms and therapy. Nat Rev Neurol. Feb. 2013;9(2):106-18. doi: 10.1038/nrneurol.2012.263. Epub Jan. 8, 2013.
Lu et al., Precise Editing of a Target Base in the Rice Genome Using a Modified CRISPR/Cas9 System. Mol Plant. Mar. 6, 2017;10(3):523-525. doi: 10.1016/j.molp.2016.11.013. Epub Dec. 6, 2016.
Lundquist et al., Site-directed mutagenesis and characterization of uracil-DNA glycosylase inhibitor protein. Role of specific carboxylic amino acids in complex formation with *Escherichia coli* uracil-DNA glycosylase. J Biol Chem. Aug. 22, 1997;272(34):21408-19.
Ma et al., Targeted AID-mediated mutagenesis (TAM) enables efficient genomic diversification in mammalian cells. Nature Methods. Oct. 2016;13:1029-35. doi:10.1038/nmeth.4027.
Marioni et al., DNA methylation age of blood predicts all-cause mortality in later life. Genome Biol. Jan. 30, 2015;16:25. doi: 10.1186/s13059-015-0584-6.
Maruyama et al., Increasing the efficiency of precise genome editing with CRISPR-Cas9 by inhibition of nonhomologous end joining. Nat Biotechnol. May 2015;33(5):538-42. doi: 10.1038/nbt.3190. Epub Mar. 23, 2015.
Mercer et al., Chimeric TALE recombinases with programmable DNA sequence specificity. Nucleic Acids Res. Nov. 2012;40(21):11163-72. doi: 10.1093/nar/gks875. Epub Sep. 26, 2012.
Minoche et al., Evaluation of genomic high-throughput sequencing data generated on Illumina HiSeq and genome analyzer systems. Genome Biol. Nov. 8, 2011;12(11):R112. doi: 10.1186/gb-2011-12-11-r112.
Mol et al., Crystal structure of human uracil-DNA glycosylase in complex with a protein inhibitor: protein mimicry of DNA. Cell. Sep. 8, 1995;82(5):701-8.
Offord, Advances in Genome Editing. The Scientist, Apr. 20, 2016. http://www.the-scientist.com/?articles.view/articleNo/45903/title/Advances-in-Genome-Editing/.
Parker et al., Admixture mapping identifies a quantitative trait locus associated with FEV1/FVC in the COPDGene Study. Genet Epidemiol. Nov. 2014;38(7):652-9. doi: 10.1002/gepi.21847. Epub Aug. 11, 2014.
Petolino et al., Editing Plant Genomes: a new era of crop improvement. Plant Biotechnol J. Feb. 2016;14(2):435-6. doi: 10.1111/pbi.12542.
Plasterk et al., DNA inversions in the chromosome of *Escherichia coli* and in bacteriophage Mu: relationship to other site-specific recombination systems. Proc Natl Acad Sci U S A. Sep. 1983;80(17):5355-8.
Pluciennik et al., PCNA function in the activation and strand direction of MutLα endonuclease in mismatch repair. Proc Natl Acad Sci U S A. Sep. 14, 2010;107(37):16066-71. doi: 10.1073/pnas.1010662107. Epub Aug. 16, 2010.
Prorocic et al., Zinc-finger recombinase activities in vitro. Nucleic Acids Res. Nov. 2011;39(21):9316-28. doi: 10.1093/nar/gkr652. Epub Aug. 17, 2011.
Prykhozhij et al., CRISPR multitargeter: a web tool to find common and unique CRISPR single guide RNA targets in a set of similar sequences. PLoS One. Mar. 5, 2015;10(3):e0119372. doi: 10.1371/journal.pone.0119372. eCollection 2015.
Putnam et al., Protein mimicry of DNA from crystal structures of the uracil-DNA glycosylase inhibitor protein and its complex with *Escherichia coil* uracil-DNA glycosylase. J Mol Biol. Mar. 26, 1999;287(2):331-46.
Ran et al., Genome engineering using the CRISPR-Cas9 system. Nat Protoc. Nov. 2013;8(11):2281-308. doi: 10.1038/nprot.2013.143. Epub Oct. 24, 2013.
Ran et al., In vivo genome editing using *Staphylococcus aureus* Cas9. Nature. Apr. 9, 2015;520(7546):186-91. dol: 10.1038/nature14299. Epub Apr. 1, 2015.
Rath et al., Fidelity of end joining in mammalian episomes and the impact of Metnase on joint processing. BMC Mol Biol. Mar. 22, 2014;15:6. doi: 10.1186/1471-2199-15-6.
Rebuzzini et al., New mammalian cellular systems to study mutations introduced at the break site by non-homologous end-joining. DNA Repair (Amst). May 2, 2005;4(5):546-55.
Rees et al., Improving the DNA specificity and applicability of base editing through protein engineering and protein delivery. Nat Commun. Jun. 6, 2017;8:15790. doi: 10.1038/ncomms15790.
Richardson et al., Enhancing homology-directed genome editing by catalytically active and inactive CRISPR-Cas9 using asymmetric donor DNA. Nat Biotechnol. Mar. 2016;34(3):339-44. doi: 10.1038/nbt.3481. Epub Jan. 20, 2016.
Rong et al., Homologous recombination in human embryonic stem cells using CRISPR/Cas9 nickase and a long DNA donor template. Protein Cell. Apr. 2014;5(4):258-60. doi: 10.1007/s13238-014-0032-5.
Rowland et al., Regulatory mutations in Sin recombinase support a structure-based model of the synaptosome. Mol Microbiol. Oct. 2009;74(2):282-98. doi: 10.1111/j.1365-2958.2009.06756.x. Epub Jun. 8, 2009.
Sadelain et al., Safe harbours for the integration of new DNA in the human genome. Nat Rev Cancer. Dec. 1, 2011;12(1):51-8. doi: 10.1038/nrc3179.
Sanjana et al., A transcription activator-like effector toolbox for genome engineering. Nat Protoc. Jan. 5, 2012;7(1):171-92. doi: 10.1038/nprot.2011.431.
Saraconi et al., The RNA editing enzyme APOBEC1 induces somatic mutations and a compatible mutational signature is present in esophageal adenocarcinomas. Genome Biol. Jul. 31, 2014;15(7):417. doi: 10.1186/s13059-014-0417-z.
Sclimenti et al., Directed evolution of a recombinase for improved genomic integration at a native human sequence. Nucleic Acids Res. Dec. 15, 2001;29(24):5044-51.
Seripa et al., The missing ApoE allele. Ann Hum Genet. Jul. 2007;71(Pt 4):496-500. Epub Jan. 22, 2007.
Shah et al., Target-specific variants of Flp recombinase mediate genome engineering reactions in mammalian cells. FEBS J. Sep. 2015;282(17):3323-33. doi: 10.1111/febs.13345. Epub Jul. 1, 2015.
Sharbeen et al., Ectopic restriction of DNA repair reveals that UNG2 excises AID-induced uracils predominantly or exclusively

(56) References Cited

OTHER PUBLICATIONS during G1 phase. J Exp Med. May 7, 2012;209(5):965-74. doi: 10.1084/jem.20112379. Epub Apr. 23, 2012.
Shimantani et al., Targeted base editing in rice and tomato using a CRISPR-Cas9 cytidine deaminase fusion. Nat Biotechnol. May 2017:35(5):441-443. doi: 10.1038/nbt.3833. Epub Mar. 27, 2017.
Shimojima et al., Spinocerebellar ataxias type 27 derived from a disruption of the fibroblast growth factor 14 gene with mimicking phenotype of paroxysmal non-kinesigenic dyskinesia. Brain Dev. Mar. 2012;34(3):230-3. doi: 10.1016/j.braindev.2011.04.014. Epub May 19, 2011.
Simonelli et al., Base excision repair intermediates are mutagenic in mammalian cells. Nucleic Acids Res. Aug. 2, 2005;33(14):4404-11. Print 2005.
Sjoblom et al., The consensus coding sequences of human breast and colorectal cancers. Science. Oct. 13, 2006;314(5797):268-74. Epub Sep. 7, 2006.
Slaymaker et al., Rationally engineered Cas9 nucleases with improved specificity. Science. Jan. 1, 2016;351(6268):84-8. doi: 10.1126/science.aad5227. Epub Dec. 1, 2015.
Smith et al., Expression of a dominant negative retinoic acid receptor γ in Xenopus embryos leads to partial resistance to retinoic acid. Roux Arch Dev Biol. Mar. 1994;203(5):254-265. doi: 10.1007/BF00360521.
Stenglein et al., APOBEC3 proteins mediate the clearance of foreign DNA from human cells. Nat Struct Mol Biol. Feb. 2010;17(2):222-9. doi: 10.1038/nsmb.1744. Epub Jan. 10, 2010.
Swarts et al., Argonaute of the archaeon Pyrococcus furiosus is a DNA-guided nuclease that targets cognate DNA. Nucleic Acids Res. May 26, 2015;43(10):5120-9. doi: 10.1093/nar/gkv415. Epub Apr. 29, 2015.
Swarts et al., DNA-guided DNA interference by a prokaryotic Argonaute. Nature. Mar. 13, 2014;507(7491):258-61. doi: 10.1038/nature12971. Epub Feb. 16, 2014.
Swarts et al., The evolutionary journey of Argonaute proteins. Nat Struct Mol Biol. Sep. 2014;21(9):743-53. doi: 10.1038/nsmb.2879.
Tagalakis et al., Lack of RNA-DNA oligonucleotide (chimeraplast) mutagenic activity in mouse embryos. Mol Reprod Dev. Jun. 2005;71(2):140-4.
Thyagarajan et al., Mammalian genomes contain active recombinase recognition sites. Gene. Feb. 22, 2000;244(1-2):47-54.
Thyagarajan et al., Site-specific genomic integration in mammalian cells mediated by phage phiC31 integrase. Mol Cell Biol. Jun. 2001;21(12):3926-34.
Tirumalai et al., Recognition of core-type DNA sites by lambda integrase. J Mol Biol. Jun. 12, 1998;279(3):513-27.
Tsai et al., GUIDE-seq enables genome-wide profiling of off-target cleavage by CRISPR-Cas nucleases. Nat Biotechnol. Feb. 2015;33(2):187-97. doi: 10.1038/nbt.3117. Epub Dec. 16, 2014.
Turan et al., Recombinase-mediated cassette exchange (RMCE)—a rapidly-expanding toolbox for targeted genomic modifications. Gene. Feb. 15, 2013;515(1):1-27. doi: 10.1016/j.gene.2012.11.016. Epub Nov. 29, 2012.
Turan et al., Recombinase-mediated cassette exchange (RMCE): traditional concepts and current challenges. J Mol Biol. Mar. 25, 2011;407(2):193-221. doi: 10.1016/j.jmb.2011.01.004. Epub Jan. 15, 2011.
UniProt Submission; UniProt, Accession No. P01011. Last modified Sep. 18, 2013, version 2. 15 pages.
Van Swieten et al., A mutation in the fibroblast growth factor 14 gene is associated with autosomal dominant cerebellar ataxia [corrected]. Am J Hum Genet. Jan. 2003;72(1):191-9. Epub Dec. 13, 2002.
Wang et al., Nucleation, propagation and cleavage of target RNAs in Ago silencing complexes. Nature. Oct. 8, 2009;461(7265):754-61. doi: 10.1038/nature08434.
Wang et al., Recombinase technology: applications and possibilities. Plant Cell Rep. Mar. 2011;30(3):267-85. doi: 10.1007/s00299-010-0938-1. Epub Oct. 24, 2010.
Wang et al., Uracil-DNA glycosylase inhibitor gene of bacteriophage PBS2 encodes a binding protein specific for uracil-DNA glycosylase. J Biol Chem. Jan. 15, 1989;264(2)1163-71.
Warren et al., A chimeric Cre recombinase with regulated directionality. Proc Natl Acad Sci U S A. Nov. 25, 2008;105(47):18278-83. doi: 10.1073/pnas.0809949105. Epub Nov. 14, 2008.
Warren et al., Mutations in the amino-terminal domain of lambda-integrase have differential effects on integrative and excisive recombination. Mol Microbiol. Feb. 2005;55(4):1104-12.
Wijnker et al., Managing meiotic recombination in plant breeding. Trends Plant Sci. Dec. 2008;13(12):640-6. doi: 10.1016/j.tplants.2008.09.004. Epub Oct. 22, 2008.
Wu et al., Genome-wide binding of the CRISPR endonuclease Cas9 in mammalian cells. Nat Biotechnol. Jul. 2014;32(7):670-6. doi: 10.1038/nbt.2889. Epub Apr. 20, 2014.
Xu et al., Sequence determinants of improved CRISPR sgRNA design. Genome Res. Aug. 2015;25(8):1147-57. doi: 10.1101/gr.191452.115. Epub Jun. 10, 2015.
Yuan et al., Tetrameric structure of a serine integrase catalytic domain. Structure. Aug. 6, 2008;16(8):1275-86. doi: 10.1016/j.str.2008.04.018.
Yuen et al., Control of transcription factor activity and osteoblast differentiation in mammalian cells using an evolved small-molecule-dependent intein. J Am Chem Soc. Jul. 12, 2006;128(27):8939-46.
Zetsche et al., A split-Cas9 architecture for inducible genome editing and transcription modulation. Nat Biotechnol. Feb. 2015;33(2):139-42. doi: 10.1038/nbt.3149.
Zetsche et al., Cpf1 is a single RNA-guided endonuclease of a class 2 CRISPR-Cas system. Cell. Oct. 22, 2015;163(3):759-71. doi: 10.1016/j.cell.2015.09.038. Epub Sep. 25, 2015.
Zhang et al., Comparison of non-canonical PAMs for CRISPR/Cas9-mediated DNA cleavage in human cells. Sci Rep. Jun. 2014;4:5405.
Zhang et al., Programmable base editing of zebrafish genome using a modified CRISPR-Cas9 system. Nat Commun. Jul. 25, 2017;8(1):118. doi: 10.1038/s41467-017-00175-6.
Zong et al., Precise base editing in rice, wheat and maize with a Cas9-cytidine deaminase fusion. Nat Biotechnol. May 2017;35(5):438-440. doi: 10.1038/nbt.3811. Epub Feb. 27, 2017.
Zuris et al., Cationic lipid-mediated delivery of proteins enables efficient protein-based genome editing in vitro and in vivo. Nat Biotechnol. 2015;33:73-80.
Application Serial No. PCT/US2015/058479, dated May 11, 2017, International Preliminary Report on Patentability.
Application Serial No. PCT/US2016/058344, dated Apr. 20, 2017, International Search Report and Written Opinion.
Application Serial No. PCT/US2017/046144, dated Oct. 10, 2017, International Search Report and Written Opinion.

* cited by examiner wild type GGGCGATGCCACCTACGGCAAGCTGACCCTGAAGTTCATCTGCACCACCGGCAAGCTGCCCGTGCCCTGGCCCACCCTCGTGACCACCCTGACCTACGGCGTGCAGTGCTTCAGCCGCTACCCCGACCACATG Deletions 12 GGGCGAT---------------------------------------------------------------------------------CGGCGTGCAGTGCTTCAGCCGCTACCCCGACCACATG 9 GGGCGATGCCACCTACGGCAAGCTGACCCTGAAGTTCATCTGCACCACCG-----------------------------------------------------------------------------CGACCACATG 8 GGGCGATGCCACCTACGGCAAGCTGACCCTGAAGTTCATCTGCACC--CGGCAAGCTGCCCGTGCCCTGGCCCACCCTCGTGACCACCCTGACCTACGGCGTGCAGTGCTTCAGCCGCTACCCCGACCACATG 7 GGGCGATGCCACCTACGGCAAGCTG------------------------------CCCGTGCCCTGGCCCACCCTCGTGACCACCCTGACCTACGGCGTGCAGTGCTTCAGCCGCTACCCCGACCACATG 6 GGGCGATGCCACCTACGGCAAGCTGACCCTGAAGTTCATCTGCACCAC--GCAAGCTGCCCGTGCCCTGGCCCACCCTCGTGACCACCCTGACCTACGGCGTGCAGTGCTTCAGCCGCTACCCCGACCACATG 4 GGGCGATGCCACCTACGGCAAGCTGACCCTGAAGTTCATCTGCACCACCGGCAAGCTGC--GTGCCCTGGCCCACCCTCGTGACCACCCTGACCTACGGCGTGCAGTGCTTCAGCCGCTACCCCGACCACATG 3 GGGCGATGCCACCTACGGCAAGCTGACCCTGAAGTTCATCTGCACCACCGGCAAGCTGCCCG--CCCTGGCCCACCCTCGTGACCACCCTGACCTACGGCGTGCAGTGCTTCAGCCGCTACCCCGACCACATG 3 GGGCGATGCCACCTACGGCAAGCTGACCCTGAAGTTCATCTG--------GCAAGCTGCCCGTGCCCTGGCCCACCCTCGTGACCACCCTGACCTACGGCGTGCAGTGCTTCAGCCGCTACCCCGACCACATG 2 GGGCGATGCCACCTACGGCAAGCTGACCCTGAAGTTCATCTGCACCACCGC-----------------------------------------------------GCAGTGCTTCAGCCGCTACCCCGACCACATG 2 GGGCGATGCCACCTACGGCAAGCTGACCCTGAAGTTCATCTGCACCACC--CAAGCTGCCCGTGCCCTGGCCCACCCTCGTGACCACCCTGACCTACGGCGTGCAGTGCTTCAGCCGCTACCCCGACCACATG Insertions 2 GGGCGATGCCACCTACGGCAAGCTGACCCTGAAGTTCATCTGCACCACCGATGCAAGCTGCCCGTGCCCTGGCCCACCCTCGTGACCACCCTGACCTACGGCGTGCAGTGCTTCAGCCGCTACCCCGACCACATG 1 GGGCGATGCCACCTACGGCAAGCTGACCCTGAAGTTCATCTGCACCACCGGCAAGCTGACCCTGAAGTTCATCTGCACCACCGGCAAGCTGCCCGTGCCCTGGCCCACCCTCGTGACCACCCTGACCTACGGCGT
GCAGTGCTTCAGCCGCTACCCCGACCACATG 1 GGGCGATGCCACCTACGGCAAGCTGACCCTGAAG--AAATGAAGAAATGAAGAAA-TGCCCGTGCCCTGGCCCACCCTCGTGACCACCCTGACCTACGGCGTGCAGTGCTTCAGCCGCTACCCCGACCACATG

FIG. 43A wild type GGCAGAAGCTGGAAGAGGAAGGGCCGGAGTCTGAGCAGAAGAAGAAGGGTTCCCACCATATCAACCGGTGGCGCATCGCC Deletions 58 GGCAGAAGCTGGAAGAGGAAGGGCCGGAGTCTGAGCAGAAGA---AGGGTTCCCACCATATCAACCGGTGGCGCATCGCC 8 GGCAGAAGCTGGAAGAGGAAGGGCCGGAGTCTGAGCAGAA--AGAAGGGTTCCCACCATATCAACCGGTGGCGCATCGCC 7 GGCAGAAGCTGGAAGAGGAAGGGCCGGAGTCTGAG-------AGAAGGGTTCCCACCATATCAACCGGTGGCGCATCGCC 6 GGCAGAAGCTGGAAGAGGAAGGGCCGGAGTCTGAGCAGA----GAAGGGTTCCCACCATATCAACCGGTGGCGCATCGCC 6 GGCAGAAGCTGGAAGAGGAAGGGCCGGAGTCTGAG---------AAGGGTTCCCACCATATCAACCGGTGGCGCATCGCC 5 GGCAGAAGCTGGAAGAGGAAGGGCCGGAGTCTGAGCAGAAGAA---------CCACCATATCAACCGGTGGCGCATCGCC 4 GGCAGAAGCTGGAAGAGGAAGGGCCGGAGTCT----------AGAAGGGTTCCCACCATATCAACCGGTGGCGCATCGCC 3 GGCAGAAGCTGGAAGAGGAAGGGCCGGAGTCTGAGCAGAAGAAGAAGGGTTC--ACCATATCAACCGGTGGCGCATCGCC 3 GGCAGAAGCTGGAAGAGGAAGGGCCGGAGTCTGAGCAGAAG------GGTTCCCACCATATCAACCGGTGGCGCATCGCC 3 GGCAGAAGCTGGAAGAGGAAGGGCCGGAGTCTGAGCAG---------GGTTCCCACCATATCAACCGGTGGCGCATCGCC Insertions 4 GGCAGAAGCTGGAAGAGGAAGGGCCGGAGTCTGAGCAGAAGA--CCATA-TCCCACCATATCAACCGGTGGCGCATCGCC 1 GGCAGAAGCTGGAAGAGGAAGGGCCGGAGTCTGAGCAGAAGA--CCATATCCA-ACCATATCAACCGGTGGCGCATCGCC 1 GGCAGAAGCTGGAAGAGGAAGGGCCGGAGTCTGAGCAGAAGAAGAAGAAGGGTTCCCACCATATCAACCGGTGGCGCATCGCC

FIG. 43B

FIG. 49A
FIG. 49B
Streptavidin
Biotin
Anionic carrier
Protein to be delivered
Biotin
Negatively supercharged streptavidin
Protein to be delivered

DELIVERY OF NEGATIVELY CHARGED PROTEINS USING CATIONIC LIPIDS

RELATED APPLICATION

This application is a continuation-in-part of and claims priority under 35 U.S.C. § 120 to U.S. patent application Ser. No. 14/462,189, filed Aug. 18, 2014, to U.S. patent application Ser. No. 14/462,163, filed Aug. 18, 2014, and to International Application, PCT/US2014/054247, filed Sep. 5, 2014, which claims priority under 35 U.S.C. § 365(c) to U.S. patent application Ser. No. 14/462,189, filed Aug. 18, 2014, and to U.S. patent application Ser. No. 14/462,163, filed Aug. 18, 2014, and also claims priority under 35 U.S.C. § 119(e) to U.S. provisional patent application, Ser. No. 61/874,746, filed Sep. 6, 2013, the entire contents of each of which are incorporated herein by reference.

GOVERNMENT SUPPORT

This invention was made with Government support under grant number GM095501 awarded by the National Institutes of Health. The Government has certain rights in the invention.

BACKGROUND OF THE INVENTION

Macromolecular delivery into mammalian cells is an attractive approach for cell manipulation, as it would allow modulation of gene expression and modification of the genome, which, in turn, would open new avenues for research and enable the therapeutic targeting of molecules currently viewed as "undruggable" by small molecules. In particular, recombinant nucleases targeting genes or alleles associated with disease have great potential as therapeutic agents. The current methods of macromolecular delivery include viral delivery of nucleic acid molecules, receptor-mediated delivery of nucleic acids or proteins, and the use of protein fusions with cell-penetrating peptides such as TAT, Arg9, or Penetratin for the delivery of proteins. Each of these delivery systems offers benefits for particular applications; in most cases, however, questions regarding efficacy, cytotoxicity, and ease of preparation remain. Easily prepared reagents capable of effectively delivering macromolecules (e.g., functional effector proteins) to a variety of cell lines without significant cytotoxicity or other adverse side effect remain of considerable concern.

Most proteins do not spontaneously enter mammalian cells and are thus naturally limited in their use as research tools and their potential as therapeutic agents. Techniques for the delivery of proteins into mammalian cells have been developed recently to address intracellular targets. These techniques include the use of lipid-based reagents (Zelphati et al., *J. Biol. Chem.* 276, 35103-35110, 2001), nanoparticles (Hasadsri et al., *J. Biol. Chem.*, 2009), vault ribonucleoprotein particles (Lai et al., *ACS Nano* 3, 691-699, 2009); genetic or chemical fusion to receptor ligands (Gabel et al., *J. Cell Biol.* 103, 1817-1827, 1986; Rizk et al., *Proc. Natl. Acad. Sci. U.S.A.* 106, 11011-11015, 2009); and fusion to cell-penetrating peptides (Wadia et al., *Curr. Protein Pept. Sci.* 4, 97-104, 2003; Zhou et al., *Cell Stem Cell* 4, 381-384, 2009). Perhaps the most common method for protein delivery is genetic fusion to protein transduction domains (PTDs) including the HIV-1 transactivator of transcription (Tat) peptide and polyarginine peptides. These cationic PTDs promote association with negatively charged cell-surface structures and subsequent endocytosis of exogenous proteins. Both Tat and polyarginine have been used to deliver a variety of macromolecules into cells both in vitro and in vivo (Wadia et al., *Curr. Protein Pept. Sci.* 4, 97-104, 2003; Zhou et al., *Cell Stem Cell* 4, 381-384, 2009; Myou et al., *J. Immunol.* 169, 2670-2676, 2002; Bae et al., *Clin. Exp. Immunol.* 157, 128-138, 2009; Schwarze et al., *Science* 285, 1569-1572, 1999). Despite these advances, intracellular targets remain difficult to affect using exogenous proteins, and even modest success can require toxic concentrations of the respective transduction agent due to the low efficiency with which proteins are functionally delivered into cells (Zhou et al., *Cell Stem Cell* 4, 381-384, 2009; Wang et al., *Nat. Biotechnol.* 26, 901-908, 2008). Therefore, there remains a need for better delivery systems for getting functional effector proteins into cells to target intracellular biomolecules.

SUMMARY OF THE INVENTION

The present disclosure provides systems, compositions, preparations, kits, and related methods for delivering proteins into cells using cationic polymers or cationic lipids. In some embodiments, the proteins to be delivered are negatively charged proteins, also referred to herein as anionic proteins, such as, for example, naturally occurring or engineered negatively charged proteins. In some embodiments, the proteins to be delivered are associated with a negatively charged protein, e.g., via covalent or non-covalent interactions, to form a protein complex. In some such embodiments, the complex comprising the protein to be delivered associated with the negatively charged proteins, e.g., a supernegatively charged protein or a naturally occurring negatively charged protein, has a net negative charge. In some embodiments, the proteins to be delivered bind a nucleic acid thus forming a protein:nucleic acid complex having a net negative charge.

Some aspects of this disclosure are based on the discovery that negatively charged proteins can be associated with cationic polymers or cationic lipids and that such protein: lipid complexes are efficiently delivered into cells. This technology can be applied to naturally negatively charged proteins (e.g., the proteins listed in tables 3-6, Sirt1 (−59, 86 kDa), PPARg (−13, 54 kDa), PRDM16 (−23, 140 kDa), PGC1a (−15, 91 kDa), TP53BP1 (−148, 213 kDa), Utrophin (−142, 394 kDa), Dystrophin (−89, 426 kDa), Bik (−17, 18 kDa), IκBα (−29, 35 kDa), Von Hippel-Lindau disease tumor suppressor (−18, 24 kDa), E3 ubiquitin ligases, metal-binding proteins, VP64 transcriptional activators, the anionic 3×FLAG peptide tag, and fusions thereof), to engineered supernegatively charged proteins (e.g., supernegatively charged GFP or streptavidin variants), to proteins that bind to nucleic acids and form negatively charged protein: nucleic acid complexes (e.g., Cas9 proteins, and variants and fusions thereof), or to protein fusions in which a protein to be delivered is associated with a negatively charged protein, e.g., a supernegatively charged protein as disclosed herein.

For example, in some embodiments, systems, compositions, preparations, kits, and related methods are provided for delivering proteins to cells, for example, functional effector proteins, such as, e.g., enzymes (e.g., oxidoreductases, transferases, hydrolases, lyases, isomerases, or ligases); transcriptional activators, transcriptional repressors, genome editing proteins, Cas9 proteins, TALEs, TALENs, nucleases, binding proteins (e.g., ligands, receptors, antibodies, antibody fragments; nucleic acid binding proteins, etc.); structural proteins; therapeutic proteins (e.g., tumor suppressor proteins, therapeutic enzymes, growth factors, growth factor receptors, transcription factors, proteases, etc.), as well as variants and fusions thereof. Additional suitable proteins that can be delivered to cells according to the inventive concepts disclosed herein will be apparent to the skilled artisan based on the present disclosure, and the disclosure is not limited in this respect. In some embodiments, the protein to be delivered is a functional effector protein, for example, an enzyme, a tumor suppressor protein, or a protein that binds a nucleic acid, and is delivered into cells using a supercharged protein (e.g., a negatively charged supercharged protein, also referred to herein as a supernegatively charged protein), and a cationic polymer or a cationic lipid. As described in greater detail herein, fusing or associating proteins to be delivered to a cell, for example, functional effector proteins (e.g., enzymes, tumor suppressor proteins, proteins that bind a nucleic acid, nucleases, transcriptional activators/repressors, Cas9 proteins including variants and fusions thereof, etc.) with charged proteins, e.g., super positively or supernegatively charged proteins, allows for delivery of the proteins to the interior of cells, for example, to affect gene expression or genomic modifications While delivery of proteins has proven effective for extracellular targets, their use to address intracellular targets is comparatively undeveloped due to the inability of most proteins to spontaneously enter mammalian cells. Enabling exogenous proteins to access intracellular targets is most commonly achieved by delivery of their encoding DNA sequences through chemical transfection, electroporation, or viral delivery. The introduction of exogenous DNA into cells, however, raises the possibility of permanent recombination into the genome, potential disruption of endogenous genes, and long-term exposure to the encoded agent. For some research or therapeutic applications, including genome editing applications that seek to effect a one-time, permanent modification of genomic DNA, the functional delivery of non-replicable protein agents may offer improved safety or broader applicability. Further, while the delivery of proteins using cationic compounds such as lipids and polymers has remained technically challenging and in many cases induces cellular toxicity, it was surprisingly found, using the compositions and methods provided herein, that proteins (e.g., functional effector proteins as described herein) can be delivered to cells with no or minimal toxicity with significant improvements in efficiency. For example, as described in Example 7, delivery of Cas9:gRNA complexes with cationic lipids is highly efficient (up to 80% modification of cultured human cells from a single treatment) and also induces higher genome modification specificity compared with plasmid transfection, typically resulting in >10-fold higher on-target:off-target DNA modification ratios in human cells.

Accordingly, in some aspects, the present disclosure provides systems, strategies, reagents, and methods for the delivery of charged proteins, such as, for example, naturally occurring negatively charged proteins, engineered supernegatively charged proteins, proteins that bind nucleic acids, or are associated, covalently or non-covalently, with a negatively charged protein, into cells using cationic lipids or cationic polymers. In some embodiments, the proteins to be delivered are functional effector proteins, for example, enzymes, tumor suppressor proteins, proteins that bind a nucleic acid, nucleases, transcriptional activators/repressors, Cas9 proteins including variants and fusions thereof, etc.

In some embodiments, a negatively charged protein, e.g., a naturally occurring negatively charged protein or an engineered supernegatively charged protein, is delivered to a cell or associated with a protein to be delivered in order to deliver the latter protein into the cell. In some embodiments, the supercharged protein has been engineered to exhibit an increase in its overall surface charge as compared to the corresponding unmodified protein. In some embodiments, the supercharged protein has been engineered to exhibit a decrease in its overall surface charge as compared to the corresponding unmodified protein. In other embodiments, the supercharged protein used in the context of this disclosure is a naturally occurring supercharged protein. In embodiments, in which the supercharged protein is associated with the protein to be delivered, the supercharged protein may be associated with the protein to be delivered through covalent or non-covalent interactions. In some embodiments, a protein that binds to a nucleic acid is delivered to a cell. In such embodiments, the protein:nucleic acid complex typically has a net negative charge. For example, without wishing to be bound by any particular theory, a Cas9 protein, variant, or fusion protein associated with a gRNA has net negative charged facilitating association with a cationic polymer or cationic lipid or with a positively supercharged protein. In certain embodiments, the negatively charged protein, protein complex, or protein: nucleic acid complex, is further associated with a cationic polymer or cationic lipid for delivery into a cell.

Examples of suitable engineered or naturally occurring supercharged proteins are described in Tables 3-6 of this application, and in international PCT patent application PCT/US07/70254, filed Jun. 1, 2007, published as WO 2007/143574 on Dec. 13, 2007; in international PCT application PCT/US09/041984, filed on Apr. 28, 2009, published as WO 2009/134808 on Nov. 5, 2009; and in international PCT application PCT/US10/001250, filed on Apr. 28, 2010, published as WO 2010/129023 on Nov. 11, 2010; the entire contents of each of which are incorporated herein by reference. In some embodiments, the negatively charged protein is Sirt1 (−59, 86 kDa), PPARg (−13, 54 kDa), PRDM16 (−23, 140 kDa), PGC1a (−15, 91 kDa), TP53BP1 (−148, 213 kDa), Utrophin (−142, 394 kDa), Dystrophin (−89, 426 kDa), Bik (−17, 18 kDa), IκBα (−29, 35 kDa), Von Hippel-Lindau disease tumor suppressor (−18, 24 kDa), an E3 ubiquitin ligase, or a metal-binding protein. Further examples of supercharged proteins for use in delivering nucleases to cells are described herein.

Examples of suitable functional effector proteins, for example, nucleases and RNA-programmable effector proteins, such as Cas9 proteins, for delivery using the inventive methods, compositions, and systems are described in U.S. Provisional Patent Application Ser. No. 61/868,846, filed Aug. 22, 2013, entitled "Engineered Transcription Activator-Like Effector (TALE) Domains and Uses Thereof," U.S. Provisional Patent Application, Ser. No. 61/874,609, filed Sep. 6, 2013, entitled "Cas9 Variants and Uses Thereof," U.S. Provisional Patent Application Ser. No. 61/874,682, filed Sep. 6, 2013, entitled "Switchable Cas9 Nucleases and Uses Thereof," U.S. Non-provisional application Ser. No. 14/320,519, filed Jun. 20, 2014, entitled "Engineered Transcription Activator-Like Effector (TALE) Domains and Uses Thereof," U.S. Non-provisional application Ser. No. 14/320,498, filed Jun. 30, 2014, entitled "Cas9-FokI Fusion Proteins And Uses Thereof," U.S. Non-provisional application Ser. No. 14/320,467, filed Jun. 30, 2014, entitled "Cas9-Recombinase Fusion Proteins And Uses Thereof," U.S. Non-provisional application Ser. No. 14/326,329, filed Jul. 8, 2014, entitled "Switchable gRNAs Comprising Aptamers," U.S. Non-provisional application Ser. No. 14/326,340, filed Jul. 8, 2014, entitled "mRNA-Sensing Switchable gRNAs,"

U.S. Non-provisional application Ser. No. 14/326,361, filed Jul. 8, 2014, entitled "Extended DNA-Sensing gRNAs," U.S. Non-provisional application Ser. No. 14/325,815, filed Jul. 8, 2014, entitled "Fusions Of Cas9 Domains And Nucleic Acid-Editing Domains," U.S. Non-provisional application Ser. No. 14/326,109, filed Jul. 8, 2014, entitled "Methods For Nucleic Acid Editing," U.S. Non-provisional application Ser. No. 14/326,140, filed Jul. 8, 2014, entitled "Methods For Correcting PI3K Point Mutations," U.S. Non-provisional application. Ser. No. 14/326,269, filed Jul. 9, 2014, entitled "Methods For Correcting Presenilin Point Mutations," U.S. Non-provisional application Ser. No. 14/326,290, filed Jul. 8, 2014, entitled "Methods For Correcting α-Antitrypsin Point Mutations," U.S. Non-provisional application Ser. No. 14/326,318, filed Jul. 8, 2014, entitled "Methods For Correcting Von Willebrand Factor Point Mutations," U.S. Non-provisional application Ser. No. 14/326,303, filed Jul. 8, 2014, entitled "Methods For Correcting Caspase-9 Point Mutations," and U.S. Provisional Application Ser. No. 62/030,943, entitled "Cas9 Proteins Including Ligand-Dependent Inteins," the entire contents of each of which are incorporated herein by reference.

In some embodiments, the supercharged protein, engineered or naturally occurring, is positively charged. In other embodiments, for example those involving delivery of certain effector proteins using cationic lipids and/or cationic polymers, the supercharged protein is negatively charged. In certain embodiments, a superpositively or supernegatively charged protein is non-covalently associated with a protein to be delivered, for example, an effector protein. Alternatively, a superpositively or supernegatively charged protein may be covalently bound to the protein to be delivered, for example, an effector protein. In some embodiments, the effector protein is fused to a supercharged protein. In certain embodiments, the resulting fusion protein comprises a linker, e.g., a cleavable linker, between the supercharged protein and the effector protein.

Some aspects of this disclosure provide compositions comprising a supercharged protein, e.g., a supernegatively charged protein, associated with a protein to be delivered, e.g., a functional effector protein (e.g., enzymes (e.g., oxidoreductases, transferases, hydrolases, lyases, isomerases, or ligases); transcriptional activators, transcriptional repressors, genome editing proteins, Cas9 proteins, TALEs, TALENs, nucleases, binding proteins (e.g., ligands, receptors, antibodies, antibody fragments; nucleic acid binding proteins, etc.); structural proteins; therapeutic proteins (e.g., tumor suppressor proteins, therapeutic enzymes, growth factors, growth factor receptors, transcription factors, proteases, etc.), as well as variants and fusions thereof). In some embodiments, the composition further comprises a cationic lipid. In some embodiments, the composition further comprises a cationic polymer. In some embodiments, the composition further comprises a buffer or excipient. In some embodiments, the supercharged protein has an overall positive charge that is greater than its corresponding unmodified protein and is in a quantity sufficient for and is formulated for delivery to and penetration into a cell. In other embodiments, for example those involving delivery of certain proteins using cationic lipids and/or cationic polymers, the supercharged protein has an overall negative charge that is greater than its corresponding unmodified protein. In some embodiments, the functional effector protein is a site-specific enzyme, e.g., a nuclease, Cas9 protein, recombinase, etc. In some embodiments, the Cas9 protein is a wild type Cas9 protein, a Cas9 nickase, or comprises a nuclease inactivated (dCas9) protein. In some embodiments, the Cas9 protein is a fusion protein comprising dCas9. In some embodiments, the fusion protein comprises a transcriptional activator (e.g., VP64), a transcriptional repressor (e.g., KRAB, SID) a nuclease domain (e.g., FokI), a recombinase domain (e.g., Hin, Gin, or Tn3), a deaminase (e.g., a cytidine deaminase or an adenosine deaminase) or an epigenetic modifier domain (e.g., TET1). In some embodiments involving nucleases, the nuclease is a TALE nuclease, a Cas9 nuclease, a Cas9 nickase, or a zinc finger nuclease. In some embodiments, the nuclease specifically binds and cleaves a nucleic acid sequence. In some embodiments, the targeted nucleic acid sequence is a sequence of a gene that is a therapeutic target, for example a gene that is desirable to inactivate in the treatment of a disease. In some embodiments, the targeted nucleic acid sequence is a PRDM16, PPARγ, VEGF-A, Oct-4, PI3K, presenilin, α-antitrypsin, von willebrand factor, or caspase-9 gene sequence.

In some embodiments, the functional effector protein is a transcription factor. In some embodiments, the functional effector protein is a TALE transcriptional activator or repressor. In some embodiments, the transcription factor, transcriptional activator, or transcriptional repressor specifically binds and activates or represses a gene. In some embodiments, the gene is a therapeutic target. In some embodiments, the functional effector protein is a TALE effector. In some embodiments, the supercharged protein is covalently bound to the functional effector protein, thus forming a fusion protein. In some embodiments, the supercharged protein is associated with the functional effector protein via a linker. In some embodiments, the linker is a cleavable linker. In some embodiments, the linker is a UV-cleavable linker or a linker that is cleaved by a lysosomal enzyme. In some embodiments, the supercharged protein is non-covalently associated with the functional effector protein, thus forming a complex. In some embodiments, the supercharged protein has an overall net positive charge. In other embodiments the supercharged protein has an overall net negative charge, and the protein(s) are associated with a cationic lipid. In other embodiments the supercharged protein has an overall net negative charge, and the protein(s) are associated with a cationic polymer. In some embodiments, the overall net positive charge is between about +5 and about +40, or the overall net negative charge is between about −5 and about −50. In some embodiments, the supercharged protein is more positively charged or is more negatively charged at physiological pH than its corresponding unmodified protein. In some embodiments, the corresponding unmodified protein is a naturally occurring protein. In some embodiments, the supercharged protein is at least +5 more positively or is at least −5 more negatively charged at physiological pH than its corresponding unmodified protein. In some embodiments, the supercharged protein is a fluorescent protein. In some embodiments, the supercharged protein is green fluorescent protein (GFP). In some embodiments, the supercharged protein is a superpositively charged GFP. In some embodiments, the supercharged protein is a superpositively charged GFP (+36 GFP) comprising at least 20 contiguous amino acid residues of the sequence:

(SEQ ID NO: 1)

```
GGASKGERLFRGKVPILVELKGDVNGHKFSVRGKGKGDATRGKLTLKFIC

TTGKLPVPWPTLVTTLTYGVQCFSRYPKHMKRHDFFKSAMPKGYVQERTI

SFKKDGKYKTRAEVKFEGRTLVNRIKLKGRDFKEKGNILGHKLRYNFNSH
```

-continued

KVYITADKRKNGIKAKFKIRHNVKDGSVQLADHYQQNTPIGRGPVLLPRN

HYLSTRSKLSKDPKEKRDHMVLLEFVTAAGIKHGRDERYK.

In some embodiments, the supercharged protein comprises the amino acid sequence set forth in SEQ ID NO: 1. In some embodiments, the supercharged protein consists of the amino acid sequence set forth in SEQ ID NO: 1. In some embodiments, the composition is a pharmaceutical composition. In some embodiments, the composition comprises a pharmaceutically acceptable excipient. In some embodiments, the composition is formulated for administration to a subject and comprises the supercharged protein and the functional effector protein in an amount effective for delivery to at least one cell of the subject. In some embodiments, the composition comprises the supercharged protein and the functional effector protein in an amount effective for inducing a measurable therapeutic effect after administration to a subject.

Some aspects of the disclosure provide compositions comprising a protein to be delivered associated with a nucleic acid, e.g., with an RNA or DNA, and a cationic lipid or a cationic polymer. It was surprisingly found that when a nucleic acid-binding protein, such as, for example, a Cas9 protein, is associated with a nucleic acid, the complex can be encapsulated by cationic lipids and effectively delivered to cells. In some embodiments, the net charge of the protein and the associated nucleic acid is negative. In some embodiments, the protein alone, i.e., without the associated nucleic acid, is not negatively charged or cannot efficiently be associated with or encapsulated into a cationic polymer or a cationic lipid. In some embodiments, the composition comprises a protein to be delivered associated with a negatively supercharged protein (e.g., a supernegatively charged GFP or a supernegatively charged streptavidin) and a cationic lipid or cationic polymer, which also provides for effective delivery to a cell. In some embodiments, the association between the protein to be delivered and the supernegatively charged protein is covalent. For example, in some embodiments, the protein to be delivered and the supernegatively charged protein form a fusion protein. In other embodiments, the association is non-covalent. For example, in some embodiments, the protein to be delivered is conjugated to a first binding agent (e.g., biotin), and the supernegatively charged protein is conjugated to a second binding agent (e.g., streptavidin) that binds the first binding agent. It will be appreciated that the disclosure is not limited to biotin: streptavidin. Additional suitable methods and binding agents (e.g., additional ligand/receptor pairs, or antibody/antigen pairs) will be apparent to the skilled artisan based on the instant disclosure. In some embodiments, the protein to be delivered is associated with the supernegatively charged protein via a linker, for example, via a cleavable linker. In some embodiments, the linker is cleaved under conditions present in endosomes of the cell into which the protein is to be delivered, thus facilitating endosomal escape of the protein.

Some aspects of the disclosure provide compositions comprising a Cas9 protein associated with a gRNA and a cationic lipid. It was surprisingly found that when a Cas9 protein is associated with a gRNA, the complex can be encapsulated by cationic lipids and effectively delivered to cells. This may be accomplished with or without a supercharged protein. In some embodiments, the composition comprises a Cas9 protein associated with a negatively supercharged protein (e.g., supernegatively charged GFP) and a cationic lipid, which also provides for successful delivery to a cell. In some embodiments, the composition exhibits low toxicity when delivered to a population of cells, for example, wherein at least 60%, at least 65%, at least 70%, at least 75%, at least 80%, at least 85%, at least 90%, at least 95%, or at least 99% of the cells are viable following administration of the composition. In some embodiments, the Cas9 protein is a wild type Cas9 protein, a Cas9 nickase, or comprises a nuclease inactivated (dCas9) protein. In some embodiments, the Cas9 protein is a fusion protein comprising dCas9. In some embodiments, the fusion protein comprises a transcriptional activator (e.g., VP64), a transcriptional repressor (e.g., KRAB, SID) a nuclease domain (e.g., FokI), a recombinase domain (e.g., Hin, Gin, or Tn3), a deaminase (e.g., a cytidine deaminase or an adenosine deaminase) or an epigenetic modifier domain (e.g., TET1).

Other aspects of the disclosure provide compositions comprising a Cas9 protein associated with a gRNA and a cationic polymer. As with cationic lipids, when a Cas9 protein is associated with a gRNA, the complex can associate with cationic polymers and be effectively delivered to cells. This may be accomplished with or without a supercharged protein. In some embodiments, the composition comprises a Cas9 protein associated with a negatively supercharged protein (e.g., supernegatively charged GFP) and a cationic polymer, which also provides for successful delivery to a cell. In some embodiments, the composition exhibits low toxicity when delivered to a population of cells, for example, wherein at least 60%, at least 65%, at least 70%, at least 75%, at least 80%, at least 85%, at least 90%, at least 95%, or at least 99% of the cells are viable following administration of the composition. In some embodiments, the Cas9 protein is a wild type Cas9 protein, a Cas9 nickase, or comprises a nuclease inactivated (dCas9) protein. In some embodiments, the Cas9 protein is a fusion protein comprising dCas9. In some embodiments, the fusion protein comprises a transcriptional activator (e.g., VP64), a transcriptional repressor (e.g., KRAB, SID) a nuclease domain (e.g., FokI), a recombinase domain (e.g., Hin, Gin, or Tn3), a deaminase (e.g., a cytidine deaminase or an adenosine deaminase) or an epigenetic modifier domain (e.g., LSD1, TET1).

Some aspects of this disclosure provide methods for administering a composition provided herein to a subject. In some embodiments, the method comprises administering a composition described herein to a subject, for example, a composition comprising a protein to be delivered and a cationic polymer or cationic lipid. In some embodiments, the subject is susceptible to, is suffering from, or is displaying one or more symptoms of a disease, disorder, or condition. In some embodiments, the composition is administered to the subject in an amount sufficient and under suitable conditions for at least one sign or symptom to be ameliorated as a result of the administration. In some embodiments, the protein to be delivered is a protein implicated or known to be involved in a disease, disorder, or condition, for example, a protein listed in any of Tables 4-6. In some embodiments, the step of administering is performed under conditions sufficient for the functional effector protein to penetrate a cell of the subject. In some embodiments, the disease, disorder, or condition is associated with abnormally elevated levels of an mRNA, a protein, or combination thereof. For example, in some embodiments, the disease, disorder, or condition is associated with abnormally low levels or reduced activity of the protein to be delivered, wherein the protein to be delivered is a protein listed in any of Tables 3-6. In some embodiments, the composition comprises a nuclease that specifically binds and cleaves a genomic sequence, for example, a normal or a pathogenic allele; a gene associated with susceptibility to, or onset or progression of, a disease; a gene encoding a pathogenic RNA or protein; or a gene encoding an RNA or protein that is expressed at abnormally high levels in diseased cells or tissue. In some embodiments, the step of administering comprises a route of administration selected from the group consisting of oral, intravenous, intramuscular, intra-arterial, subcutaneous, intraventricular, topical, inhalational, and mucosal delivery.

Some aspects of this disclosure provide methods for introducing a protein to be delivered into a cell. In some embodiments, the method comprises contacting the cell with a composition described herein, e.g., with a composition comprising the protein to be delivered and a cationic polymer or cationic lipid, under conditions suitable for the protein to enter the cell, thereby introducing the protein into the cell. In some embodiments, the protein to be delivered is a negatively charged protein, for example, a naturally negatively charged protein or an engineered supernegatively charged protein. In some embodiments, the protein to be delivered is associated with a nucleic acid. In some embodiments, the protein to be delivered is associated with a negatively charged protein. The association may be covalent or non-covalent.

For example, in some embodiments, the method comprises contacting the cell with a composition comprising a Cas9 protein and a cationic lipid and/or cationic polymer under conditions suitable for the Cas9 protein to enter the cell, thereby introducing the Cas9 protein into the cell. In some embodiments, the Cas9 protein enters the nucleus of the cell, for example the Cas9 protein is directed to the nucleus by including a nuclear localization signal (NLS) in the protein. In some embodiments, the method further comprises confirming that the functional effector protein (e.g., including Cas9) has penetrated the cell. In some embodiments, the cell is in a subject, and the contacting is done in vivo. In some embodiments, the subject is diagnosed with having or being at risk of developing a disease associated with an abnormal expression level of a gene, and wherein the functional effector protein (e.g., including Cas9) modulates the expression level of the gene. In some embodiments, the method further comprises detecting a change in the level of expression of the gene or detecting a therapeutic response in the subject. In some embodiments, the cell is a somatic cell. In some embodiments, the cell is contacted with the composition or the pharmaceutical composition in an amount, for a time, and under conditions sufficient to induce programming of the cell to a desired cell fate. In some embodiments, the method further comprises using the programmed cell in a cell replacement therapeutic approach. In some embodiments, the cell is a cell carrying a genomic allele associated with a disease and the functional effector protein specifically targets the allele. In some embodiments, the cell is contacted ex vivo and re-administered to the subject after successful targeting of the undesired allele by the functional effector protein.

Some aspects of this disclosure provide kits comprising a composition as described herein, for example, a composition comprising a supercharged protein associated with a functional effector protein. In some embodiments, the kits comprises a Cas9 protein and a supercharged protein. In some embodiments, the kits comprises a Cas9 protein and a cationic lipid. In some embodiments, the kits comprises a Cas9 protein and a cationic polymer. In some embodiments, the kit further comprises instructions for using the components included in the kit.

These and other aspects and embodiments of the invention, as well as various advantages and utilities will be more apparent with respect to the drawings and detailed description of the invention.

Definitions

As used herein and in the claims, the singular forms "a," "an," and "the" include the singular and the plural reference unless the context clearly indicates otherwise. Thus, for example, a reference to "an agent" includes a single agent and a plurality of agents.

The term "associated with" as used herein in the context of two or more moieties (e.g., proteins or protein domains) refers to the fact that the moieties are physically associated with or connected to one another, either directly or via one or more additional moieties that serve as a linking agent, to form a structure that is sufficiently stable so that the moieties remain physically associated under the conditions in which the structure is used, e.g., under physiological conditions. Supercharged proteins may be associated with functional effector proteins (e.g., enzymes (e.g., oxidoreductases, transferases, hydrolases, lyases, isomerases, or ligases); transcriptional activators, transcriptional repressors, genome editing proteins, Cas9 proteins, TALEs, TALENs, nucleases, binding proteins (e.g., ligands, receptors, antibodies, antibody fragments; nucleic acid binding proteins, etc.); structural proteins; therapeutic proteins (e.g., tumor suppressor proteins, therapeutic enzymes, growth factors, growth factor receptors, transcription factors, proteases, etc.), as well as variants and fusions thereof) through non-covalent interactions (e.g., electrostatic interactions). In certain embodiments, a supercharged protein may be associated with a functional effector protein through electrostatic interactions to form a complex. In some embodiments, a sufficient number of weaker interactions can provide sufficient stability for moieties to remain physically associated under a variety of different conditions. In certain embodiments, a supercharged protein is associated with a functional effector protein via a covalent bond (e.g., an amide bond). In some embodiments, a functional effector protein is associated with a supercharged protein directly by a peptide bond, or indirectly via a linker.

The term "Cas9" or "Cas9 nuclease" refers to an RNA-guided nuclease comprising a Cas9 protein, or a fragment thereof (e.g., a protein comprising an active or inactive DNA cleavage domain of Cas9 or a partially inactive DNA cleavage domain (e.g., a Cas9 "nickase"), and/or the gRNA binding domain of Cas9). In some embodiments, the term "Cas9" refers to a fusion protein comprising Cas9 or a fragment thereof.

In some embodiments, Cas9 refers to Cas9 from: *Corynebacterium ulcerans* (NCBI Refs: NC_015683.1, NC_017317.1); *Corynebacterium diphtheria* (NCBI Refs: NC_016782.1, NC_016786.1); *Spiroplasma syrphidicola* (NCBI Ref: NC_021284.1); *Prevotella intermedia* (NCBI Ref: NC_017861.1); *Spiroplasma taiwanense* (NCBI Ref: NC_021846.1); *Streptococcus iniae* (NCBI Ref: NC_021314.1); *Belliella baltica* (NCBI Ref: NC_018010.1); *Psychroflexus torquisl* (NCBI Ref: NC_018721.1); *Streptococcus thermophilus* (NCBI Ref: YP_820832.1); *Listeria innocua* (NCBI Ref: NP_472073.1); *Campylobacter jejuni* (NCBI Ref: YP_002344900.1); or *Neisseria. meningitidis* (NCBI Ref: YP_002342100.1).

The term "cationic lipid" refers to a lipid which has a cationic, or positive, charge at physiologic pH. Cationic lipids can take a variety of forms including, but not limited to, liposomes or micelles. Cationic lipids useful for certain aspects of the present disclosure are known in the art, and, generally comprise both polar and non-polar domains, bind to polyanions, such as nucleic acid molecules or negatively supercharged proteins, and are typically known to facilitate the delivery of nucleic acids into cells. Examples of useful cationic lipids include polyethylenimine, polyamidoamine (PAMAM) starburst dendrimers, Lipofectin (a combination of DOTMA and DOPE), Lipofectase, LIPOFECTAMINE® (e.g., LIPOFECTAMINE® 2000, LIPOFECTAMINE® 3000, LIPOFECTAMINE® RNAiMAX, LIPOFECTAMINE® LTX), SAINT-RED (Synvolux Therapeutics, Groningen Netherlands), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3β-[N—(N',N'-dimethylaminoethane)carbamoyl]cholesterol (DC-Chol), 2,3,-dioleyloxy-N-[2(sperminecarboxamido)ethyl]-N,N-dimethyl-1-propanaminium trifluoroacetate (DOSPA), 1,2-dimyristyloxypropyl-3-dimethyl-hydroxyethyl ammonium bromide; and dimethyldioctadecylammonium bromide (DDAB). Cationic lipids have been used in the art to deliver nucleic acid molecules to cells (see, e.g., U.S. Pat. Nos. 5,855,910; 5,851,548; 5,830,430; 5,780,053; 5,767,099; 8,569,256; 8,691,750; 8,748,667; 8,758,810; 8,759,104; 8,771,728; Lewis et al. 1996. Proc. Natl. Acad. Sci. USA 93:3176; Hope et al. 1998. Molecular Membrane Biology 15:1). In addition, other lipid compositions are also known in the art and include, e.g., those taught in U.S. Pat. No. 4,235,871; U.S. Pat. Nos. 4,501,728; 4,837,028; 4,737,323.

The term "cationic polymer," as used herein, refers to a polymer having a net positive charge. Cationic polymers are well known in the art, and include those described in Samal et al., Cationic polymers and their therapeutic potential. *Chem Soc Rev.* 2012 Nov. 7; 41(21):7147-94; in published U.S. patent applications U.S. 2014/0141487 A1, U.S. 2014/0141094 A1, U.S. 2014/0044793 A1, U.S. 2014/0018404 A1, U.S. 2014/0005269 A1, and U.S. 2013/0344117 A1; and in U.S. Pat. Nos. 8,709,466; 8,728,526; 8,759,103; and 8,790,664; the entire contents of each are incorporated herein by reference. Exemplary cationic polymers include, but are not limited to, polyallylamine (PAH); polyethyleneimine (PEI); poly(L-lysine) (PLL); poly(L-arginine) (PLA); polyvinylamine homo- or copolymer; a poly(vinylbenzyl-tri-$C_1$-$C_4$-alkylammonium salt); a polymer of an aliphatic or araliphatic dihalide and an aliphatic N,N,N',N'-tetra-$C_1$-$C_4$-alkyl-alkylenediamine; a poly(vinylpyridin) or poly(vinylpyridinium salt); a poly(N,N-diallyl-N,N-di-$C_1$-$C_4$-alkyl-ammoniumhalide); a homo- or copolymer of a quaternized di-$C_1$-$C_4$-alkyl-aminoethyl acrylate or methacrylate; POLYQUAD™; a polyaminoamide; and the like.

The term "click chemistry" refers to a chemical philosophy introduced by K. Barry Sharpless of The Scripps Research Institute, describing chemistry tailored to generate covalent bonds quickly and reliably by joining small units comprising reactive groups together. Click chemistry does not refer to a specific reaction, but to a concept including reactions that mimic reactions found in nature. See, e.g., Kolb, Finn and Sharpless *Angewandte Chemie International Edition* (2001) 40: 2004-2021; Evans, *Australian Journal of Chemistry* (2007) 60: 384-395, and Joerg Lahann, *Click Chemistry for Biotechnology and Materials Science,* 2009, John Wiley & Sons Ltd, ISBN 978-0-470-69970-6, the entire contents of each of which are incorporated herein by reference. In some embodiments, click chemistry reactions are modular, wide in scope, give high chemical yields, generate inoffensive byproducts, are stereospecific, exhibit a large thermodynamic driving force >84 kJ/mol to favor a reaction with a single reaction product, and/or can be carried out under physiological conditions. A distinct exothermic reaction makes a reactant "spring loaded". In some embodiments, a click chemistry reaction exhibits high atom economy, can be carried out under simple reaction conditions, use readily available starting materials and reagents, uses no toxic solvents or use a solvent that is benign or easily removed (preferably water), and/or provides simple product isolation by non-chromatographic methods (crystallization or distillation).

The term "deaminase" refers to an enzyme that catalyzes a deamination reaction. In some embodiments, the deaminase is a cytidine deaminase, catalyzing the hydrolytic deamination of cytidine or deoxycytidine to uracil or deoxyuracil, respectively.

The term "effective amount," as used herein, refers to an amount of a biologically active agent that is sufficient to elicit a desired biological response. For example, in some embodiments, an effective amount of a functional effector protein (e.g., nucleases, transcriptional activators/repressors, recombinases, Cas9 proteins including variants and fusions thereof, etc.) may refer to the amount of the protein that is sufficient to induce a detectable effect (e.g., cleavage of a target site, modification of a target site, modulation of gene expression, etc.). Such an effect may be detected in a suitable assay, e.g., in a cell-free assay, or in a target cell, tissue, or subject organism. As will be appreciated by the skilled artisan, the effective amount of an agent, e.g., a functional effector protein, may vary depending on various factors as, for example, on the desired biological response, the specific allele to be targeted, the genome, target site, cell, or tissue being targeted, and the supercharged protein being used.

The term "effector protein" refers to a protein that modulates a biological function of a cell when introduced into the cell, e.g., a modification of a nucleic acid molecule in the cell (such as a cleavage, deamination, recombination, etc.), or a modulation (e.g., increases or decreases) the expression or the expression level of a gene in the cell.

The term "engineered," as used herein refers to a protein molecule, complex, substance, or entity that has been designed, produced, prepared, synthesized, and/or manufactured by a human. Accordingly, an engineered product is a product that does not occur in nature. In some embodiments, an engineered protein or composition, e.g., an engineered supercharged protein associated with a functional effector protein, such as a nuclease, Cas9 protein (including variants and fusions thereof) is a supercharged protein that has been designed to meet particular requirements or to have particular desired features, e.g., to have a specified net charge, to specifically bind and/or cleave or modify a target sequence of interest, to have a specific minimal or maximal cleavage or enzymatic activity, and/or to have a specific stability.

The term "epigenetic modifier," as used herein, refers to a protein or catalytic domain thereof having enzymatic activity that results in the epigenetic modification of DNA, for example chromosomal DNA. Epigenetic modifications include, but are not limited to DNA methylation and demethylation; histone modifications including methylation and demethylation (e.g., mono-, di- and tri-methylation), histone acetylation and deacetylation, as well we histone ubiquitylation, phosphorylation, and sumoylation.

The term "functional protein" refers to a protein that is in a form in which it exhibits a property and/or activity by which it is characterized.

The term "fusion protein" refers to a protein comprising a plurality of heterologous proteins, protein domains, or peptides, e.g., a supercharged protein and a functional effector protein, associated with each other via a peptide linkage, thus forming a single amino acid sequence. In certain embodiments, a fusion protein is encoded by a gene.

The term "gene" has its meaning as understood in the art. It will be appreciated by those of ordinary skill in the art that the term "gene" may include gene regulatory sequences (e.g., promoters, enhancers, etc.) and/or intron sequences. It will further be appreciated that definitions of gene include references to nucleic acids that do not encode proteins but rather encode functional RNA molecules such as RNAi agents, ribozymes, tRNAs, etc. For the purpose of clarity it should be noted that, as used in the present application, the term "gene" generally refers to a portion of a nucleic acid that encodes a protein; the term may optionally encompass regulatory sequences, as will be clear from context to those of ordinary skill in the art. This definition is not intended to exclude application of the term "gene" to non-protein—coding expression units but rather to clarify that, in most cases, the term as used in this document refers to a protein-coding nucleic acid.

The term "isolated" refers to a molecule, complex, substance, or entity that has been (1) separated from at least some of the components with which it was associated when initially produced (whether in nature or in an experimental setting), and/or (2) produced, prepared, synthesized, and/or manufactured by a human. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The term "linker," as used herein, refers to a chemical group or a molecule linking two molecules or moieties, e.g., a supercharged protein and a nuclease. Typically, the linker is positioned between, or flanked by, two groups, molecules, or other moieties and connected to each one via a covalent bond, thus connecting the two. In some embodiments, the linker comprises an amino acid or a plurality of amino acids (e.g., a peptide or protein). In some embodiments, the linker is an organic molecule, group, polymer, or chemical moiety. In some embodiments, the linker is a cleavable linker, e.g., the linker comprises a bond that can be cleaved upon exposure to a cleaving activity, such as UV light or a hydrolytic enzyme, such as a lysosomal protease. In some embodiments, the linker is any stretch of amino acids having at least 1, at least 2, at least 3, at least 4, at least 5, at least 6, at least 7, at least 8, at least 9, at least 10, at least 15, at least 20, at least 25, at least 30, at least 40, at least 50, or more amino acids. In some embodiments, the peptide linker comprises repeats of the tri-peptide Gly-Gly-Ser, e.g., comprising the sequence $(GGS)_n$, wherein n represents at least 1, 2, 3, 4, 5, 6, 7, 8, 9, 10, or more repeats. In some embodiments, the linker comprises the sequence $(GGS)_6$ (SEQ ID NO:2). In some embodiments, the peptide linker is the 16 residue "XTEN" linker, or a variant thereof (See, e.g., Schellenberger et al. A recombinant polypeptide extends the in vivo half-life of peptides and proteins in a tunable manner. *Nat. Biotechnol.* 27, 1186-1190 (2009)). In some embodiments, the XTEN linker comprises the sequence SGSETPGTSESATPES (SEQ ID NO:3), SGSETPGTSESA (SEQ ID NO:4), or SGSETPGTSESATPEGGSGGS (SEQ ID NO:5). In some embodiments, the peptide linker is one or more selected from VPFLLEPDNINGKTC (SEQ ID NO:6), GSAGSAAGSGEF (SEQ ID NO:7), SIVAQLSRPDPA (SEQ ID NO:8), MKIIEQLPSA (SEQ ID NO:9), VRHKLKRVGS (SEQ ID NO:10), GHGTGSTGSGSS (SEQ ID NO:11), MSRPDPA (SEQ ID NO:12); or GGSM (SEQ ID NO:13).

The term "nuclease," as used herein, refers to an agent, for example, a protein or a small molecule, capable of cleaving a phosphodiester bond connecting nucleotide residues in a nucleic acid molecule. In some embodiments, a nuclease is a protein, e.g., an enzyme that can bind a nucleic acid molecule and cleave a phosphodiester bond connecting nucleotide residues within the nucleic acid molecule. A nuclease may be an endonuclease, cleaving a phosphodiester bond within a polynucleotide chain, or an exonuclease, cleaving a phosphodiester bond at the end of the polynucleotide chain. In some embodiments, a nuclease is a site-specific nuclease, binding and/or cleaving a specific phosphodiester bond within a specific nucleotide sequence, which is also referred to herein as the "recognition sequence," the "nuclease target site," or the "target site." In some embodiments, a nuclease recognizes a single stranded target site, while in other embodiments, a nuclease recognizes a double-stranded target site, for example, a double-stranded DNA target site. The target sites of many naturally occurring nucleases, for example, many naturally occurring DNA restriction nucleases, are well known to those of skill in the art. In many cases, a DNA nuclease, such as EcoRI, HindIII, or BamHI, recognize a palindromic, double-stranded DNA target site of 4 to 10 base pairs in length, and cut each of the two DNA strands at a specific position within the target site. Some endonucleases cut a double-stranded nucleic acid target site symmetrically, i.e., cutting both strands at the same position so that the ends comprise base-paired nucleotides, also referred to herein as blunt ends. Other endonucleases cut a double-stranded nucleic acid target site asymmetrically, i.e., cutting each strand at a different position so that the ends comprise unpaired nucleotides. Unpaired nucleotides at the end of a double-stranded DNA molecule are also referred to as "overhangs," e.g., as "5'-overhang" or as "3'-overhang," depending on whether the unpaired nucleotide(s) form(s) the 5' or the 3' end of the respective DNA strand. Double-stranded DNA molecule ends ending with unpaired nucleotide(s) are also referred to as sticky ends, as they can "stick to" other double-stranded DNA molecule ends comprising complementary unpaired nucleotide(s). A nuclease protein typically comprises a "binding domain" that mediates the interaction of the protein with the nucleic acid substrate, and a "cleavage domain" that catalyzes the cleavage of the phosphodiester bond within the nucleic acid backbone. In some embodiments, a nuclease protein can bind and cleave a nucleic acid molecule in a monomeric form, while, in other embodiments, a nuclease protein has to dimerize or multimerize in order to cleave a target nucleic acid molecule. Binding domains and cleavage domains of naturally occurring nucleases, as well as modular binding domains and cleavage domains that can be combined to create nucleases that bind specific target sites, are well known to those of skill in the art. For example, transcriptional activator like elements can be used as binding domains to specifically bind a desired target site, and fused or conjugated to a cleavage domain, for example, the cleavage domain of FokI, to create an engineered nuclease cleaving the desired target site.

The term "nucleic acid" and the term "nucleic acid molecule," as used interchangeably herein, refer to a compound comprising a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or including non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The term "pharmaceutical composition," as used herein, refers to a composition that can be administrated to a subject, for example, in the context of treatment of a disease or disorder. In some embodiments, a pharmaceutical composition comprises an active ingredient, e.g., a supercharged protein associated with a functional effector protein, such as a nuclease, or a nucleic acid encoding a supercharged protein and a functional effector protein, e.g., in the form of a fusion protein, and a pharmaceutically acceptable excipient.

The term "physiological pH" as used herein refers to a pH value that is found in a normal, non-pathologic cell or subject. In some embodiments, physiological pH is between pH 5-8. In some embodiments, physiological pH is pH 7-7.5, for example, pH 7.0, pH 7.1, pH 7.2, pH 7.3, pH 7.4, or pH 7.5. In some embodiments, physiological pH is pH 6.5-7.5. In some embodiments, physiological pH is pH 5, pH 5.5, pH 6, pH 6.5, pH 7, pH 7.5, or pH 8.

The term "prevention" or "prevent" refer to the prophylactic treatment of a subject who is at risk of developing a disease, disorder, or condition (e.g., at an elevated risk as compared to a control subject, or a control group of subject, or at an elevated risk as compared to the average risk of an age-matched and/or gender-matched subject), resulting in a decrease in the probability that the subject will develop the disease, disorder, or condition (as compared to the probability without prevention), and/or to the inhibition of further advancement of an already established disorder.

The term "proliferative disease," as used herein, refers to any disease in which cell or tissue homeostasis is disturbed in that a cell or cell population exhibits an abnormally elevated proliferation rate. Proliferative diseases include hyperproliferative diseases, such as pre-neoplastic hyperplastic conditions and neoplastic diseases. Neoplastic diseases are characterized by an abnormal proliferation of cells and include both benign and malignant neoplasias. Malignant neoplasms are also referred to as cancers.

The term "protein" is interchangeably used herein with the terms "peptide" and "polypeptide" and refers to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a TALE effector protein may comprise a nucleic acid binding domain and an effector domain, e.g., a nucleic acid cleavage domain or a transcriptional activator or repressor domain. In some embodiments, a protein comprises a proteinaceous part, e.g., an amino acid sequence constituting a nucleic acid binding domain, and an organic compound, e.g., a compound that can act as a nucleic acid cleavage agent.

The term "protein to be delivered," also sometimes referred to herein as "effector protein" or "functional effector protein," refers to a protein that is to be delivered to a target cell. The protein may be any type of protein, including, for example, enzymes (e.g., oxidoreductases, transferases, hydrolases, lyases, isomerases, or ligases); transcriptional activators, transcriptional repressors, genome editing proteins, Cas9 proteins, TALEs, TALENs, nucleases, binding proteins (e.g., ligands, receptors, antibodies, antibody fragments; nucleic acid binding proteins, etc.); structural proteins; therapeutic proteins (e.g., tumor suppressor proteins, therapeutic enzymes, growth factors, growth factor receptors, transcription factors, proteases, etc.), fluorescent proteins, as well as variants and fusions thereof.

The term "RNA-programmable nuclease," and "RNA-guided nuclease" are used interchangeably herein and refer to a nuclease that forms a complex with (e.g., binds or associates with) one or more RNA molecule that is not a target for cleavage. In some embodiments, an RNA-programmable nuclease, when in a complex with an RNA, may be referred to as a nuclease:RNA complex. RNA-programmable nucleases include Cas9. Typically, the bound RNA(s) is referred to as a guide RNA (gRNA). gRNAs can exist as a complex of two or more RNAs, or as a single RNA molecule. gRNAs that exist as a single RNA molecule may be referred to as single-guide RNAs (sgRNAs), though "gRNA" is used interchangeably to refer to guide RNAs that exist as either single molecules or as a complex of two or more molecules. Typically, gRNAs that exist as single RNA species comprise two domains: (1) a domain that shares homology to a target nucleic acid (e.g., and directs binding of a Cas9 complex to the target); and (2) a domain that binds a Cas9 protein. The gRNA comprises a nucleotide sequence that complements a target site, which mediates binding of the nuclease/RNA complex to said target site and providing the sequence specificity of the nuclease:RNA complex.

The term "recombinase," as used herein, refers to a site-specific enzyme that mediates the recombination of DNA between recombinase recognition sequences, which results in the excision, integration, inversion, or exchange (e.g., translocation) of DNA fragments between the recombinase recognition sequences. Recombinases can be classified into two distinct families: serine recombinases (e.g., resolvases and invertases) and tyrosine recombinases (e.g., integrases). Examples of serine recombinases include, without limitation, Hin, Gin, Tn3, β-six, CinH, ParA, γδ, Bxb1, ϕC31, TP901, TG1, φBT1, R4, φRV1, φFC1, MR11, A118, U153, and gp29. Examples of tyrosine recombinases include, without limitation, Cre, FLP, R, Lambda, HK101, HK022, and pSAM2. The serine and tyrosine recombinase names stem from the conserved nucleophilic amino acid residue that the recombinase uses to attack the DNA and which becomes covalently linked to the DNA during strand exchange. Recombinases have numerous applications, including the creation of gene knockouts/knock-ins and gene therapy applications. See, e.g., Brown et al., "Serine recombinases as tools for genome engineering." *Methods.* 2011; 53(4):372-9; Hirano et al., "Site-specific recombinases as tools for heterologous gene integration." *Appl. Microbiol. Biotechnol.* 2011; 92(2):227-39; Chavez and Calos, "Therapeutic applications of the ΦC31 integrase system." *Curr. Gene Ther.* 2011; 11(5):375-81; Turan and Bode, "Site-specific recombinases: from tag-and-target- to tag-and-exchange-based genomic modifications." *FASEB J.* 2011; 25(12):4088-107; Venken and Bellen, "Genome-wide manipulations of *Drosophila melanogaster* with transposons, Flp recombinase, and ΦC31 integrase." *Methods Mol. Biol.* 2012; 859:203-28; Murphy, "Phage recombinases and their applications." *Adv. Virus Res.* 2012; 83:367-414; Zhang et al., "Conditional gene manipulation: Cre-ating a new biological era." *J. Zhejiang Univ. Sci. B.* 2012; 13(7):511-24; Karpenshif and Bernstein, "From yeast to mammals: recent advances in genetic control of homologous recombination." *DNA Repair* (*Amst*). 2012; 1; 11(10):781-8; the entire contents of each are hereby incorporated by reference in their entirety. The recombinases provided herein are not meant to be exclusive examples of recombinases that can be used in embodiments of the invention. The methods and compositions of the invention can be expanded by mining databases for new orthogonal recombinases or designing synthetic recombinases with defined DNA specificities (See, e.g., Groth et al., "Phage integrases: biology and applications." *J. Mol. Biol.* 2004; 335, 667-678; Gordley et al., "Synthesis of programmable integrases." *Proc. Natl. Acad. Sci. USA.* 2009; 106, 5053-5058; the entire contents of each are hereby incorporated by reference in their entirety). Other examples of recombinases that are useful in the methods and compositions described herein are known to those of skill in the art, and any new recombinase that is discovered or generated is expected to be able to be used in the different embodiments of the invention. In some embodiments, a recombinase (or catalytic domain thereof) is fused to a Cas9 protein (e.g., dCas9).

The term "recombine," or "recombination," in the context of a nucleic acid modification (e.g., a genomic modification), is used to refer to the process by which two or more nucleic acid molecules, or two or more regions of a single nucleic acid molecule, are modified by the action of a recombinase protein. Recombination can result in, inter alia, the insertion, inversion, excision, or translocation of a nucleic acid sequence, e.g., in or between one or more nucleic acid molecules.

The term "subject," as used herein, refers to an individual organism. In some embodiments, the subject is a human of either sex at any stage of development. In some embodiments, the subject is a non-human mammal. In some embodiments, the subject is a non-human primate. In some embodiments, the subject is a rodent. In some embodiments, the subject is a laboratory animal, for example, a mouse, a rat, a gerbil, a guinea pig, a fish, a frog, or a fly. In some embodiments, the subject is a farm animal, for example, a sheep, a goat, a pig, or a cattle. In some embodiments, the subject is a companion animal, for example, a cat or a dog. In some embodiments, the subject is a vertebrate, an amphibian, a reptile, a fish, an insect, a fly, or a nematode. In some embodiments, the subject is genetically engineered, e.g., a genetically engineered non-human subject.

The term "supercharge" refers to any modification of a protein that results in the increase or decrease of the overall net charge of the protein. Modifications include, but are not limited to, alterations in amino acid sequence or addition of charged moieties (e.g., carboxylic acid groups, phosphate groups, sulfate groups, amino groups). Supercharging also refers to the association of an agent with a charged protein, naturally occurring or modified, to form a complex with increased or decreased charge relative to the agent alone.

The term "target site," as used herein in the context of functional effector proteins that bind a nucleic acid molecule, such as nucleases and transcriptional activators or repressors, refers to a sequence within a nucleic acid molecule that is bound and acted upon by the effector protein, e.g., cleaved by the nuclease or transcriptionally activated or repressed by the transcriptional activator or repressor, respectively. A target site may be single-stranded or double-stranded. In the context of RNA-guided (e.g., RNA-programmable) nucleases (e.g., Cas9), a target site typically comprises a nucleotide sequence that is complementary to the gRNA of the RNA-programmable nuclease, and a protospacer adjacent motif (PAM) at the 3' end adjacent to the gRNA-complementary sequence. For the RNA-guided nuclease Cas9 (or variants or fusions comprising having gRNA binding activity), the target site may be, in some embodiments, 20 base pairs plus a 3 base pair PAM (e.g., NNN, wherein N represents any nucleotide). Typically, the first nucleotide of a PAM can be any nucleotide, while the two downstream nucleotides are specified depending on the specific RNA-guided nuclease. Exemplary target sites for RNA-guided nucleases, such as Cas9, are known to those of skill in the art and include, without limitation, NNG, NGN, NAG, and NGG, wherein N represents any nucleotide. In addition, Cas9 nucleases from different species (e.g., *S. thermophilus* instead of *S. pyogenes*) recognizes a PAM that comprises the sequence NGGNG. Additional PAM sequences are known, including, but not limited to, NNAGAAW and NAAR (see, e.g., Esvelt and Wang, Molecular Systems Biology, 9:641 (2013), the entire contents of which are incorporated herein by reference). For example, the target site of an RNA-guided nuclease, such as, e.g., Cas9, may comprise the structure [NZ]-[PAM], where each N is, independently, any nucleotide, and Z is an integer between 1 and 50, inclusive. In some embodiments, Z is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, or at least 50. In some embodiments, Z is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, Z is 20. In some embodiments, "target site" may also refer to a sequence within a nucleic acid molecule that is bound but not cleaved by a nuclease. For example, certain embodiments described herein provide proteins comprising an inactive (or inactivated) Cas9 DNA cleavage domain. Such proteins (e.g., when also including a Cas9 RNA binding domain) are able to bind the target site specified by the gRNA, however because the DNA cleavage site is inactivated, the target site is not cleaved by the particular protein. However, such proteins as described herein are typically conjugated, fused, or bound by another protein (e.g., a nuclease, transcriptional activator, recombinase, deaminase, etc.) or molecule that mediates modification of the nucleic acid molecule. In some embodiments, the sequence actually cleaved will depend on the protein (e.g., nuclease) or molecule that mediates cleavage of the nucleic acid molecule, and in some cases, for example, will relate to the proximity or distance from which the inactivated Cas9 protein(s) is/are bound. In the context of nucleases that dimerize, for example, dimers of a protein comprising an inactive Cas9 (or a Cas9 RNA binding domain) and a DNA cleavage domain (e.g., FokI cleavage domain or an active Cas9 cleavage domain), a target sites typically comprises a left-half site (bound by one protein), a right-half site (bound by the second protein), and a spacer sequence between the half sites in which the cut is made. In some embodiments, either the left-half site or the right half-site (and not the spacer sequence) is cut. This structure ([left-half site]-[spacer sequence]-[right-half site]) is referred to herein as an LSR structure. In some embodiments, the left-half site and/or the right-half site correspond to an RNA-guided target site (e.g., a Cas9 target site). In some embodiments, either or both half-sites are shorter or longer than, e.g., a typical region targeted by Cas9, for example shorter or longer than 20 nucleotides. In some embodiments, the left and right half sites comprise different nucleic acid sequences. In some embodiments, the target site is a sequence comprising three (3) RNA-guided nuclease target site sequences, for example, three sequences corresponding to Cas9 target site sequences, in which the first and second, and second and third Cas9 target site sequences are separated by a spacer sequence. In some embodiments, the spacer sequence is at least 5, at least 6, at least 7, at least 8, at least 9, at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, at least 100, at least 125, at least 150, at least 175, at least 200, or at least 250 bp long.

The terms "transcriptional activator" and "transcriptional repressor" refer to an agent such as a protein (e.g., a transcription factor or fragment thereof), that binds a target nucleic acid sequence and causes an increase or decrease of the level of expression of a gene product associated with the target nucleic acid sequence, respectively. For example, if the target nucleic acid sequence is located within a regulatory region of a gene, a transcriptional activator causes an increase of the level of expression of a gene product encoded by the gene (conversely, a transcriptional repressor causes a decrease of the level of expression of a gene product encoded by the gene). The gene product can be an RNA transcribed from the gene (e.g., an mRNA) or a polypeptide translated from an mRNA transcribed from the gene. Typically an increase or decrease in the level of an mRNA results in an or decrease increase in the level of a polypeptide translated therefrom. The level of expression may be determined using standard techniques for measuring mRNA or protein.

The term "Transcriptional Activator-Like Effector," (TALE) as used herein, refers to effector proteins comprising a DNA binding domain, which contains a highly conserved 33-34 amino acid sequence comprising a highly variable two-amino acid motif (Repeat Variable Diresidue, RVD). The RVD motif determines binding specificity to a nucleic acid sequence, and can be engineered according to methods well known to those of skill in the art to specifically bind a desired DNA sequence (see, e.g., Miller, Jeffrey; et. al. (February 2011). "A TALE nuclease architecture for efficient genome editing". *Nature Biotechnology* 29 (2): 143-8; Zhang, Feng; et. al. (February 2011). "Efficient construction of sequence-specific TAL effectors for modulating mammalian transcription". *Nature Biotechnology* 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Boch, Jens (February 2011). "TALEs of genome targeting". *Nature Biotechnology* 29 (2): 135-6; Boch, Jens; et. al. (December 2009). "Breaking the Code of DNA Binding Specificity of TAL-Type III Effectors". *Science* 326 (5959): 1509-12; and Moscou, Matthew J.; Adam J. Bogdanove (December 2009). "A Simple Cipher Governs DNA Recognition by TAL Effectors". *Science* 326 (5959): 1501; the entire contents of each of which are incorporated herein by reference). The simple relationship between amino acid sequence and DNA recognition has allowed for the engineering of specific DNA binding domains by selecting a combination of repeat segments containing the appropriate RVDs. TALE effector proteins include, without limitation, TALE nucleases (TALENs) and TALE transcriptional activators and repressors.

The term "Transcriptional Activator-Like Element Nuclease," (TALEN) as used herein, refers to an artificial nuclease comprising a transcriptional activator like effector DNA binding domain to a DNA cleavage domain, for example, a FokI domain. A number of modular assembly schemes for generating engineered TALE constructs have been reported (Zhang, Feng; et. al. (February 2011). "Efficient construction of sequence-specific TAL effectors for modulating mammalian transcription". *Nature Biotechnology* 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". *Nucleic Acids Research*; Morbitzer, R.; Elsaesser, J.; Hausner, J.; Lahaye, T. (2011). "Assembly of custom TALE-type DNA binding domains by modular cloning". *Nucleic Acids Research*; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". *Nucleic Acids Research*.; Weber, E.; Gruetzner, R.; Werner, S.; Engler, C.; Marillonnet, S. (2011). Bendahmane, Mohammed. ed. "Assembly of Designer TAL Effectors by Golden Gate Cloning". *PLoS ONE* 6 (5): e19722; each of which is incorporated herein by reference).

The term "transcriptional repressor" refers to a transcription factor, e.g., a protein, that binds a target nucleic acid sequence and causes a reduction of the level of expression of a gene product associated with the target nucleic acid sequence. For example, if the target nucleic acid sequence is located within a regulatory region of a gene, a transcriptional repressor causes a reduction of the level of expression of a gene product encoded by the gene. The gene product can be an RNA transcribed from the gene (e.g., an mRNA) or a polypeptide translated from an mRNA transcribed from the gene. Typically a reduction in the level of an mRNA results in a reduction in the level of a polypeptide translated therefrom. The level of expression may be determined using standard techniques for measuring mRNA or protein.

The term "zinc finger nuclease," as used herein, refers to a nuclease comprising a nucleic acid cleavage domain conjugated to a binding domain that comprises a zinc finger array. In some embodiments, the cleavage domain is the cleavage domain of the type II restriction endonuclease FokI. Zinc finger nucleases can be designed to target virtually any desired sequence in a given nucleic acid molecule for cleavage, and the possibility to design zinc finger binding domains to bind unique sites in the context of complex genomes allows for targeted cleavage of a single genomic site in living cells, for example, to achieve a targeted genomic alteration of therapeutic value. Targeting a double-strand break to a desired genomic locus can be used to introduce frame-shift mutations into the coding sequence of a gene due to the error-prone nature of the non-homologous DNA repair pathway. Zinc finger nucleases can be generated to target a site of interest by methods well known to those of skill in the art. For example, zinc finger binding domains with a desired specificity can be designed by combining individual zinc finger motifs of known specificity. The structure of the zinc finger protein Zif268 bound to DNA has informed much of the work in this field and the concept of obtaining zinc fingers for each of the 64 possible base pair triplets and then mixing and matching these modular zinc fingers to design proteins with any desired sequence specificity has been described (Pavletich NP, Pabo Colo. (May 1991). "Zinc finger-DNA recognition: crystal structure of a Zif268-DNA complex at 2.1 A". *Science* 252 (5007): 809-17, the entire contents of which are incorporated herein). In some embodiments, separate zinc fingers that each recognizes a 3 base pair DNA sequence are combined to generate 3-, 4-, 5-, or 6-finger arrays that recognize target sites ranging from 9 base pairs to 18 base pairs in length. In some embodiments, longer arrays are contemplated. In other embodiments, 2-finger modules recognizing 6-8 nucleotides are combined to generate 4-, 6-, or 8-zinc finger arrays. In some embodiments, bacterial or phage display is employed to develop a zinc finger domain that recognizes a desired nucleic acid sequence, for example, a desired nuclease target site of 3-30 bp in length. Zinc finger nucleases, in some embodiments, comprise a zinc finger binding domain and a cleavage domain fused or otherwise conjugated to each other via a linker, for example, a polypeptide linker. The length of the linker determines the distance of the cut from the nucleic acid sequence bound by the zinc finger domain. If a shorter linker is used, the cleavage domain will cut the nucleic acid closer to the bound nucleic acid sequence, while a longer linker will result in a greater distance between the cut and the bound nucleic acid sequence. In some embodiments, the cleavage domain of a zinc finger nuclease has to dimerize in order to cut a bound nucleic acid. In some such embodiments, the dimer is a heterodimer of two monomers, each of which comprise a different zinc finger binding domain. For example, in some embodiments, the dimer may comprise one monomer comprising zinc finger domain A conjugated to a FokI cleavage domain, and one monomer comprising zinc finger domain B conjugated to a FokI cleavage domain. In this non-limiting example, zinc finger domain A binds a nucleic acid sequence on one side of the target site, zinc finger domain B binds a nucleic acid sequence on the other side of the target site, and the dimerize FokI domain cuts the nucleic acid in between the zinc finger domain binding sites.

The term "zinc finger," as used herein, refers to a small nucleic acid-binding protein structural motif characterized by a fold and the coordination of one or more zinc ions that stabilize the fold. Zinc fingers encompass a wide variety of differing protein structures (see, e.g., Klug A, Rhodes D (1987). "Zinc fingers: a novel protein fold for nucleic acid recognition". Cold Spring Harb. Symp. Quant. Biol. 52: 473-82, the entire contents of which are incorporated herein by reference). Zinc fingers can be designed to bind a specific sequence of nucleotides, and zinc finger arrays comprising fusions of a series of zinc fingers, can be designed to bind virtually any desired target sequence. Such zinc finger arrays can form a binding domain of a protein, for example, of a nuclease, e.g., if conjugated to a nucleic acid cleavage domain. Different types of zinc finger motifs are known to those of skill in the art, including, but not limited to, $Cys_2His_2$, Gag knuckle, Treble clef, Zinc ribbon, $Zn_2/Cys_6$, and TAZ2 domain-like motifs (see, e.g., Krishna S S, Majumdar I, Grishin N V (January 2003). "Structural classification of zinc fingers: survey and summary". *Nucleic Acids Res.* 31 (2): 532-50). Typically, a single zinc finger motif binds 3 or 4 nucleotides of a nucleic acid molecule. Accordingly, a zinc finger domain comprising 2 zinc finger motifs may bind 6-8 nucleotides, a zinc finger domain comprising 3 zinc finger motifs may bind 9-12 nucleotides, a zinc finger domain comprising 4 zinc finger motifs may bind 12-16 nucleotides, and so forth. Any suitable protein engineering technique can be employed to alter the DNA-binding specificity of zinc fingers and/or design novel zinc finger fusions to bind virtually any desired target sequence from 3-30 nucleotides in length (see, e.g., Pabo Colo., Peisach E, Grant R A (2001). "Design and selection of novel cys2His2 Zinc finger proteins". *Annual Review of Biochemistry* 70: 313-340; Jamieson A C, Miller J C, Pabo Colo. (2003). "Drug discovery with engineered zinc-finger proteins". *Nature Reviews Drug Discovery* 2 (5): 361-368; and Liu Q, Segal D J, Ghiara J B, Barbas C F (May 1997). "Design of polydactyl zinc-finger proteins for unique addressing within complex genomes". *Proc. Natl. Acad. Sci. U.S.A.* 94 (11); the entire contents of each of which are incorporated herein by reference). Fusions between engineered zinc finger arrays and protein domains that cleave a nucleic acid can be used to generate a "zinc finger nuclease." A zinc finger nuclease typically comprises a zinc finger domain that binds a specific target site within a nucleic acid molecule, and a nucleic acid cleavage domain that cuts the nucleic acid molecule within or in proximity to the target site bound by the binding domain. Typical engineered zinc finger nucleases comprise a binding domain having between 3 and 6 individual zinc finger motifs and binding target sites ranging from 9 base pairs to 18 base pairs in length. Longer target sites are particularly attractive in situations where it is desired to bind and cleave a target site that is unique in a given genome.

The terms "treatment," "treat," and "treating," refer to a clinical intervention aimed to reverse, alleviate, delay the onset of, or inhibit the progress of a disease or disorder, or one or more symptoms thereof, as described herein. As used herein, the terms "treatment," "treat," and "treating" refer to a clinical intervention aimed to reverse, alleviate, delay the onset of, or inhibit the progress of a disease or disorder, or one or more symptoms thereof, as described herein. In some embodiments, treatment may be administered after one or more symptoms have developed and/or after a disease has been diagnosed. In other embodiments, treatment may be administered in the absence of symptoms, e.g., to prevent or delay onset of a symptom or inhibit onset or progression of a disease. For example, treatment may be administered to a susceptible individual prior to the onset of symptoms (e.g., in light of a history of symptoms and/or in light of genetic or other susceptibility factors). Treatment may also be continued after symptoms have resolved, for example, to prevent or delay their recurrence.

BRIEF DESCRIPTION OF THE DRAWINGS

FIG. 27(A) shows that recombinases, transcriptional-activator-like effector (TALE) proteins, and Cas9 endonucleases bind nucleic acids and are natively cationic (net theoretical charges are shown in black) and are not efficiently encapsulated by cationic lipids. These proteins can be rendered highly anionic, however, by fusion to either a supernegatively charged protein such as (−30)GFP, or by complexation with polyanionic nucleic acids. FIG. 27(B) shows a schematic representing that cationic lipids commonly used to transfect DNA and RNA encapsulate the resulting highly anionic proteins or protein:nucleic acid complexes, mediating their delivery into mammalian cells.

In FIG. 28(A), the fusion of either highly cationic (+36)GFP or highly anionic (−30)GFP to Cre recombinase is shown. A HeLa reporter cell line that expresses DsRed upon Cre-mediated recombination was used to evaluate Cre delivery efficiency; (GGS)9 corresponds to SEQ ID NO: 252 and His6 corresponds to SEQ ID NO: 253. In FIG. 28(B) HeLa dsRed cells treated with 10 nM (−30)GFP-Cre and the cationic lipid RNAiMAX. Cells were visualized after incubation for 48 hours in media containing 10% fetal bovine serum (FBS). FIG. 28(C) shows the delivery of (+36)GFP-Cre in 10% FBS media or in serum-free media, and (−30)GFP-Cre with or without the cationic lipid RNAiMAX (0.8 μL) in full-serum media. FIG. 28(D) presents the effect of cationic lipid dose on functional (−30)GFP-Cre delivery efficacy after 48 hours in 275 μL media containing 10% FBS. FIG. 28(E) is a comparison of several commercially available cationic lipids and polymers for functional delivery efficacy of (−30)dGFP-Cre. FIG. 28(F) shows the RNAiMAX-mediated delivery of multiple anionic peptide or protein sequences fused to Cre. FIG. 28(G) shows RNAiMAX-mediated delivery of multiple anionic peptide or protein sequences fused to Cre. The net theoretical charge of the VP64 activation domain and the 3×FLAG tag is −22 and −7, respectively. All experiments were performed with 25 nM protein in 48-well plate format using 275 μL DMEM with 10% FBS and no antibiotics. Error bars reflect the standard deviation from three biological replicates performed on different days.

FIG. 29(A) shows the design of an 18.5-repeat TALE activator fused C-terminally to a VP64 activation domain and N-terminally to (−30)GFP and an NLS; (GGS)9 corresponds to SEQ ID NO: 252 and His6 corresponds to SEQ ID NO: 253. The overall net theoretical charge of the fusion is −43. FIG. 29(B) demonstrates the activation of NTF3 transcription by traditional transfection of plasmids encoding TALE-VP64 activators that target sites in the NTF3 gene, or by RNAiMAX cationic lipid-mediated delivery of the corresponding NTF3-targeting (−30)GFP-TALE-VP64 proteins. Gene expression levels were measured by qRT-PCR and are normalized to GAPDH expression levels. Incubation times for TALE activators by plasmid transfection and protein delivery were those found to give maximal increases in NTF3 mRNA levels. FIG. 29(C) shows the time course of TALE activation for protein delivery and plasmid transfection by measuring NTF3 mRNA levels and then normalizing each method to the highest activation value achieved over any time point for that method. Optimal protein (25-50 nM) and lipid dosage (1.5 μL RNAiMAX) was used for each delivery technique. Error bars reflect the standard deviation from three biological replicates performed on different days.

FIG. 30(A) demonstrates the cationic lipid-mediated delivery of Cas9 protein variants complexed with an EGFP-targeting sgRNA or a VEGF-targeting sgRNA to U2OS EGFP reporter cells. U2OS EGFP reporter cells were treated with 100 nM of the Cas9 protein variant shown, 0.8 μL of the cationic lipid shown, and either 50 nM of the sgRNA shown for Cas9 protein treatment, or 125 nM of the sgRNA shown for (+36)dGFP-NLS-Cas9 and (−30)dGFP-NLS-Cas9 treatment. The fraction of cells lacking EGFP expression was measured by flow cytometry. Plasmid DNA transfection of 750 ng Cas9 and 250 ng sgRNA expression plasmids using 0.8 μL Lipofectamine 2000 is shown as well. Results are compared to that of standard transfection of Cas9 and sgRNA expression plasmids. FIG. 30(B) shows the results of a T7 endonuclease I (T7EI) assay to measure the modification of EGFP from no treatment (lane 1), treatment with EGFP-targeting sgRNA alone (lane 2), Cas9 protein alone (lane 3), Cas9 protein+VEGF-targeting sgRNA+RNAiMAX (lane 4), DNA transfection of plasmids expressing Cas9 and EGFP-targeting sgRNA (lane 5), or Cas9 protein+EGFP-targeting sgRNA+RNAiMAX (lane 6). Indel efficiencies calculated by densitometry are shown below the gel image. FIG. 30(C) presents the results of a T7EI assay of genome modification at EGFP and three endogenous genes with a single delivery of Cas9 complexed with four sgRNAs and RNAiMAX. T7EI assay of simultaneous genome modification at EGFP and three endogenous genes in U2OS cells 48 hours after a single treatment of 100 nM Cas9 protein, 25 nM of each of the four sgRNAs shown (100 nM total sgRNA), and 0.8 μL RNAiMAX. Indel efficiencies calculated by densitometry are shown below the gel image. FIG. 30(D) shows the delivery of Cas9 D10A nickase and pairs of sgRNAs either by plasmid transfection or by RNAiMAX-mediated protein:RNA complex delivery. Delivery of Cas9 D10A nickase and pairs of sgRNAs either by plasmid transfection or by RNAiMAX-mediated protein:sgRNA complex delivery under conditions described in FIG. 30(A) with 50 nM EGFP-disrupting sgRNAs (25 nM each) for protein delivery, and 250 ng sgRNA-expressing plasmids (125 ng each) for DNA delivery. EGFP-disrupting sgRNAs GFP g1+GFP g5, or GFP g3+GFP g7, are expected to result in gene disruption, while GFP g5+GFP g7 target the same strand and are therefore expected to be non-functional. FIG. 30(E) shows the delivery of catalytically dead (dCas9)-VP64 transcriptional activators that target NTF3 either by plasmid transfection or RNAiMAX-mediated protein delivery. Delivery of both VEGF g3 and VEGF g5 sgRNAs served as a negative control for NTF3 gene activation. Error bars reflect the standard deviation from six biological replicates performed on different days.

In FIG. 31(A), a T7EI assay was performed for on-target modification of endogenous CLTA, EMX, and VEGF genes. In FIG. 31(B-D) the on-target:off-target DNA modification ratio resulting from Cas9:sgRNA for plasmid transfection or cationic lipid-mediated protein:sgRNA delivery is shown. The conditions for each treatment were adjusted to result in ~10% on-target cleavage, enabling a comparison of DNA cleavage specificity between the two delivery methods under conditions in which on-target gene modification efficiencies are comparable. P values are listed in Table 2. Each on- and off-target sample was sequenced once with >10,000 sequences analyzed per on-target sample and an average of >111,000 sequences analyzed per off-target sample (Table 2). All protein:sgRNA deliveries and plasmid transfections were performed in 24-well format using 1.6 μL RNAiMAX in 550 μL DMEM-FBS without antibiotics.

In FIG. 32(A), the scala media (cochlear duct) of P0 floxP-tdTomato mice (n=4) were injected with 0.3 μL of 23 μM (−30)GFP-Cre in 50% RNAiMAX or with RNAiMAX alone (control). After 5 days, tdTomato expression indicative of Cre-mediated recombination was visualized using immunohistology. Red=tdTomato; green=Myo7a; white=Sox2; blue=DAPI. Yellow brackets indicate the outer hair cell (OHC) layer. FIG. 32(B) shows that, ten days after (−30)GFP-Cre delivery, intact espin (Esp)-expressing stereocilia of tdTomato-positive outer hair cells were present (arrow), similar to stereocilia in control cochlea. Red=tdTomato; green=Esp; white=Sox2; blue=DAPI. FIG. 32(C) is identical to FIG. 32(A) except using Lipofectamine 2000 instead of RNAiMAX. (n=4). The upper and lower panels are images of mice cochlea at low and high magnification, respectively, detailing the efficiency of delivery as well as the effect on cochlear architecture and hair cell loss. FIG. 32(D) shows the results when the scala media (cochlear duct) of P2 Atoh1-GFP mice (n=3) were injected with 0.3 μL of 33 μM Cas9, 33 μM sgRNA in 50% RNAiMAX, 16.5 μM EGFP sgRNA in 50% RNAiMAX or Lipofectamine 2000. Cas9-mediated gene disruption results in the loss of GFP expression when visualized 10 days later. The upper panels show GFP signal only, while lower panels include additional immunohistological markers. Yellow boxes in the lower panels highlight hair cells that have lost GFP expression. Red=tdTomato; green=Myo7a; white/light blue=Sox2; blue=DAPI. All scale bars, shown in white, are 10 μm.

FIG. 33(A) shows the optimization of (−30)GFP-Cre delivery in BSR-TdTomato cells, a second reporter cell line used for measuring Cre recombination efficiency. FIG. 33(B) demonstrates the effect of RNAiMAX dosage on (−30)GFP-Cre recombination efficiency in HeLa dsRed reporter cells and toxicity as measured by FACS. HeLa cells were sorted by forward-scatter and side-scatter gating to identify live cells that retained normal morphology. FIG. 33(C) illustrates the relationship between net charge of the protein fused to Cre recombinase and cationic lipid-mediated functional Cre delivery efficiency. Cre recombinase fused to the domains listed at 25 nM were combined with 1.5 μL RNAiMAX and incubated with HeLa dsRed reporter cells. After 2 days, recombination efficiency was measured by FACS. FIG. 33(D) shows the optimization of Cre expression plasmid transfection in HeLa DsRed reporter cells by varying both plasmid dose and Lipofectamine 2000 dose and measuring the presence of DsRed fluorescent cells 48 hours after transfection by flow cytometry. Based on these results, 500 ng of Cre expression plasmid was chosen for 48-well format experiments using 275 μL of DMEM-FBS without antibiotics. FIG. 33(E) demonstrates the effect of RNAiMAX dosage on (−30)GFP-Cre recombination efficiency in HeLa dsRed reporter cells and corresponding toxicity as measured by flow cytometry using the TO-PRO-3 live/dead stain (Life Technologies). FIG. 33(F) shows the effect of Lipofectamine 2000 dosage on transfected Cre plasmid DsRed recombination efficiency and corresponding toxicity as measured by flow cytometry using the TO-PRO-3 live/dead stain. Error bars reflect the standard deviation from three biological replicates performed on different days.

FIG. 34(A) quantifies GFP fluorescence from cells treated with either (−30)GFP-Cre and RNAiMAX or (+36) GFP-Cre after washing cells with PBS+heparin (20 U/mL) to remove unbound protein. FIG. 34(B) shows the functional Cre recombinase delivery efficiency of (−30)GFP-Cre+1.5 μL RNAiMAX relative to Cre recombinase delivery efficiency arising from fusion with (+36)GFP. FIG. 34(C) provides a comparison of mCherry uptake by (−30)GFP-fusion+1.5 μM RNAiMAX treatment versus (+36)GFP fusion by measuring mean mCherry fluorescence of total cell population 48 hours after treatment and washing cells with PBS+heparin. FIG. 34(D) shows the total cellular GFP fluorescence of (−30)GFP-Cre or (+36)GFP-Cre in the presence or absence of RNAiMAX. Data shown reflect a single biological replicate.

FIG. 36(A) provides a schematic of EGFP disruption in U2OS cells by NHEJ induced by Cas9 double-stranded breaks. FIG. 36(B) shows the delivery of EGFP-targeting sgRNA or an off-target sgRNA complexed with (−30)dGFP-Cas9 using RNAiMAX along with a plasmid transfection positive control (orange). FIG. 36(C) provides confirmation that disruption of EGFP fluorescence is not a result of cellular toxicity by treating samples with the TO-PRO-3 live/dead stain (Life Technologies, Carlsbad Calif.) and analyzing the resulting cells by flow cytometry. FIG. 36(D) shows testing of the TO-PRO-3 stain by addition of a cell permeabilizing, but not completely membrane lysing, detergent (0.5% Tween).

In FIG. 37(A), cationic lipid-mediated delivery efficiency of two tested constructs shows that the more anionic (−30)dGFP-NLS-Cas9 facilitates more efficient delivery at low protein and sgRNA concentrations compared with native Cas9. FIG. 37(B) shows the delivery optimization of (−30)dGFP-NLS-Cas9 as a function of protein and sgRNA concentration. FIG. 37(C) shows the delivery of Cas9 protein without any fusions or tags as a function of protein and sgRNA concentration. FIG. 37(D) provides the optimal sgRNA to protein ratio for RNAiMAX-mediated delivery of (−30)dGFP-NLS-Cas9 and native Cas9. Error bars reflect standard deviation from three biological replicates performed on different days. All experiments were performed in a 48-well plate using a volume of 275 μL DMEM-FBS without antibiotics and EGFP gene disruption was measured by flow cytometry.

(FIG. 38(D)) 5 nM, (FIG. 38(E)) 12.5 nM, and (FIG. 38(F)) 25 nM, along with varying protein concentrations show in the graphs. Delivery was performed using 0.8 μL RNAiMAX in 48-well format using 275 μL DMEM-FBS without antibiotics and assayed by FACS 48 hours later for loss of EGFP fluorescence signal. Error bars (FIGS. 38(D-F)) reflect standard deviation from three biological replicates performed on different days.

In FIG. 39(A), EGFP gene disruption at different Cas9 protein concentrations and a constant dose of 100 nM EGFP sgRNA in U2OS EGFP reporter cells treated for 16 hours with either 0.8 μL of RNAiMAX or 0.8 μL Lipofectamine 2000. After 16 hours, media was removed and fresh media was added to cells until end point of assay 48-72 hours post protein delivery treatment. The live cell population was determined by FACS using TO-PRO-3 Live/Dead stain.

FIG. 39(B) shows the toxicity profile for Cas9:sgRNA delivery to U2OS cells as a function of Lipofectamine 2000 dose. FIG. 39(C) provides the toxicity profile for cells as a function of RNAiMAX dose. FIG. 39(D) shows the cellular toxicity for a broad range of Cas9:sgRNA treatments using 1:1 protein:sgRNA delivery conditions at optimal doses of RNAiMAX or Lipofectamine 2000 by TO-PRO-3 live/dead stain and flow cytometry. Dose of RNAiMAX and Lipofectamine 2000 were both 0.8 μL in a volume of 275 μL in a 48-well plate format. Error bars reflect standard deviation from three biological replicates performed on different days.

FIG. 40(A) shows HEK293T cells treated with dCas9-VP64 activator and either NTF3-targeting gRNA g2 or a mixture of all six NTF3-targeting sgRNAs for 16 hours and 0.8 μL RNAiMAX in 48-well plate format (275 μL final volume). NTF3 mRNA levels were determined by qRT-PCR and normalized to those of GAPDH. Total sgRNA concentrations are listed (each sgRNA is present at one-sixth of the listed total concentration). FIG. 40(B) shows the time course for NTF3 gene activation by protein:sgRNA delivery and plasmid transfection. NTF3 mRNA levels were measured at several time points using all six sgRNAs either from expression plasmids (in the case of the dCas9-VP64 activator plasmid transfection treatment), or as in vitro transcribed sgRNAs complexed with 100 nM dCas9-VP64 activator and cationic lipids (in the case of protein:sgRNA delivery). Error bars reflect standard deviation from six biological replicates performed on different days.

FIG. 41(A) shows the on-target and off-target indel frequencies for the CLTA gene. FIG. 41(B) provides the on-target and off-target indel frequencies for the EMX gene. FIG. 41(C) demonstrates the on-target and off-target indel frequencies for the VEGF gene. Each on- and off-target sample was sequenced once with >10,000 sequences analyzed per on-target sample and an average of >111,000 sequences analyzed per off-target sample (Table 2). Error bars reflect standard deviation from three biological replicates performed on different days.

FIG. 42(A) shows floating spheres treated with 100 nM Cas9 protein and 0.8 μL RNAiMAX but no sgRNA (control) retained strong GFP fluorescence (right), while those treated with 100 nM Cas9:sgRNA and 0.8 μL RNAiMAX exhibited decreased GFP fluorescence (left). Scale bars are 100 μm. FIG. 42(B) shows the control progenitor cells after cell attachment, and virtually all the control progenitor cells were GFP positive (right panels). Cas9:sgRNA treatment led to significant reduction in GFP expression (left panels) and many progenitor cells showed complete GFP knockdown (arrows) after cell attachment. Scale bars are 20 μm. FIG. 42(C) shows a T7EI assay on stem cells harvested after imaging confirm cleavage of GFP reporter. Similar gene target modification efficiencies were observed from cationic lipid-mediated Cas9:sgRNA delivery (24%) and from co-transfection of Cas9 and EGFP sgRNA plasmids (20%).

FIGS. 43A-B. Genome modification induced by cationic lipid-mediated protein delivery of Cas9 nuclease and sgRNA at endogenous loci in vivo. Approximately 10 days after injection of Cas9:sgRNA protein into Atoh1-GFP mice under identical conditions described in FIG. 32(D), ~15 mg of mouse hair cell tissue was dissected. 150 ng of isolated genomic DNA was prepared for high-throughput sequencing. FIG. 43(A) shows representative examples of genomic DNA sequences at the EGFP on-target locus that are modified following cationic lipid-mediated delivery of Cas9 and EGFP sgRNA in mouse hair cells. For each example shown, the unmodified genomic site is the first sequence, followed by the most abundant eight sequences containing deletions and three sequences containing insertions. The numbers before each sequence indicate sequencing counts. The sgRNA target sites are bold. Insertions and deletions are shown. PAM site is shown as well. FIG. 43(B) shows an identical analysis as in FIG. 42(A) for EMX on-target site in mouse hair cells. Indels shown here for both the EGFP and EMX genomic loci are from a single biological replicate chosen from a representative set of sequenced samples all showing similar indel profiles. The sequences shown in FIG. 43(A), from top to bottom, correspond to SEQ ID NOs: 223-236; and the sequences shown in FIG. 43(B), from top to bottom, correspond to SEQ ID NOs: 237-250.

FIG. 44(A) shows the optimization of transfection efficiency for Cas9 expression plasmid in U2OS EGFP reporter cell line was performed by varying both the amount of Cas9 plasmid and the dose of Lipofectamine 2000. Input sgRNA expression plasmid was held constant at 250 ng input DNA for all treatments. All treatments were performed in a 48-well plate with 275 μL DMEM-FBS without antibiotics. After 48 hours, cells were assayed for loss of EGFP by flow cytometry. FIG. 44(B) measures the toxicity of various Cas9 plasmid/Lipofectamine 2000 transfection conditions after 48 hours using TO-PRO-3 live/dead stain and quantifying cellular toxicity by flow cytometry. From FIG. 44(A) and FIG. 44(B) a Cas9 plasmid dose of 750 ng and a Lipofectamine 2000 dose of 0.8 μL were chosen as plasmid transfection conditions that resulted in maximal gene disruption for the remaining studies in this work. For FIG. 44(A) and FIG. 44(B), error bars reflect standard deviation from three biological replicates performed on different days.

FIG. 45(A) shows Cas9:sgRNA protein delivery optimization of HDR efficiency in a reporter cell line that expresses EGFP upon repair of a disrupted EGFP reporter gene[57] using cationic lipid-mediated protein delivery, a 2:1 ratio of T2 sgRNA:Cas9 protein, 1 μL Lipofectamine 2000, and variable amounts of ssODN donor template (see materials and methods below) performed as a single treatment. FIG. 45(B) shows optimization of plasmid transfection-mediated HDR using 700 ng Cas9 plasmid and 250 ng sgRNA plasmid with variable doses of Lipofectamine 2000 and ssODN donor template. FIG. 45(C) HDR efficiency comparison of cationic lipid-mediated protein: sgRNA delivery and plasmid DNA transfection at optimized conditions for both techniques using on-target (T2) and non-target (VEGF) sgRNAs. For FIG. 45(B-C), error bars reflect standard deviation of three independent biological replicates performed on different days.

FIG. 46(A) shows Indel modification frequencies measured by high-throughput sequencing for VEGF on- and off-target sites at varying doses of Cas9:sgRNA. FIG. 46(B) shows on-target:off-target specificity ratio at different Cas9: sgRNA concentrations. FIG. 46(C) shows a comparison of on-target:off target specificity ratio for protein delivery and plasmid transfection at VEGF off-target site #1 as a function of on-target indel modification frequency at a range of modification frequencies for both treatments (~1% to ~40% indel modification frequency). FIGS. 46(D, E, F) show the same as FIG. 46(C) for VEGF off-target sites #2, #3, and #4. Each on- and off-target sample was sequenced once with >10,000 sequences analyzed per on-target sample and an average of >111,000 sequences analyzed per off-target sample. All data shown were from a single biological replicate.

FIG. 48(A) shows flow cytometry plots showing Alexa647 fluorescence of cells treated with 50 nM Alexa647-conjugated Cas9 and 50 nM EGFP sgRNA, or of untreated cells. FIG. 48(B) U2OS EGFP reporter cells were treated with 50 nM Alexa647-conjugated Cas9 protein, 50 nM EGFP sgRNA, and 0.8 μL of Lipofectamine 2000. After a 4-hour incubation at 37° C., cells were washed extensively with PBS containing 20 U/mL of heparin to remove electrostatically-bound cationic lipid complexes, and then trypsinized. In a plate reader (Tecan M1000 Pro) with fluorescence excitation at 650 nm and emission at 665 nm, wells each containing 10,000 Cas9-Alexa647-treated cells were measured for whole population fluorescence. Standard curves were established by measuring the fluorescence of known quantities of Cas9-Alexa647 in either DMEM containing 10% FBS, or in a suspension of trypsinized U2OS cells at 10,000 cells per well, with protein either diluted directly, or pre-complexed with 0.8 μL Lipofectamine 2000 then diluted. A two-fold serial dilution starting from 50 pmol to 0.048 pmols was performed to generate the standard curve samples. Values for 0.048 pmol to 3.125 pmol are shown. The intersection of the dotted black lines shows the measured total Alexa647 fluorescence of 10,000 cells treated with 50 nM Alexa647-conjugated Cas9 and 50 nM EGFP sgRNA and washed as described above. 50 nM Cas9-Alexa647-treated cells showed a total cell-associated Alexa647-labeled protein signal of 0.5 pmol per well. This quantity represents 4% of the input protein in the Cas9-Alexa647:sgRNA treatment, and corresponds to $(6.02\times10^{23})*5.0\times10^{-13}$ moles Cas9-Alexa647/10,000 cells per well=$3\times10^{7}$ molecules of Cas9-Alexa647 per cell. Assuming a total protein content per cell of roughly $7.9\times10^{9}$ molecules (estimate from Molecular Cell Biology, Section 1.2, 4th edition), internalized Cas9-Alexa647 represented 0.4% of total cellular protein. All values shown are the average of three technical replicates.

FIGS. 49 A-B. Generation of exemplary negatively charged protein complexes comprising biotinylated proteins to be delivered.

DETAILED DESCRIPTION OF CERTAIN EMBODIMENTS OF THE INVENTION

Figure 1:
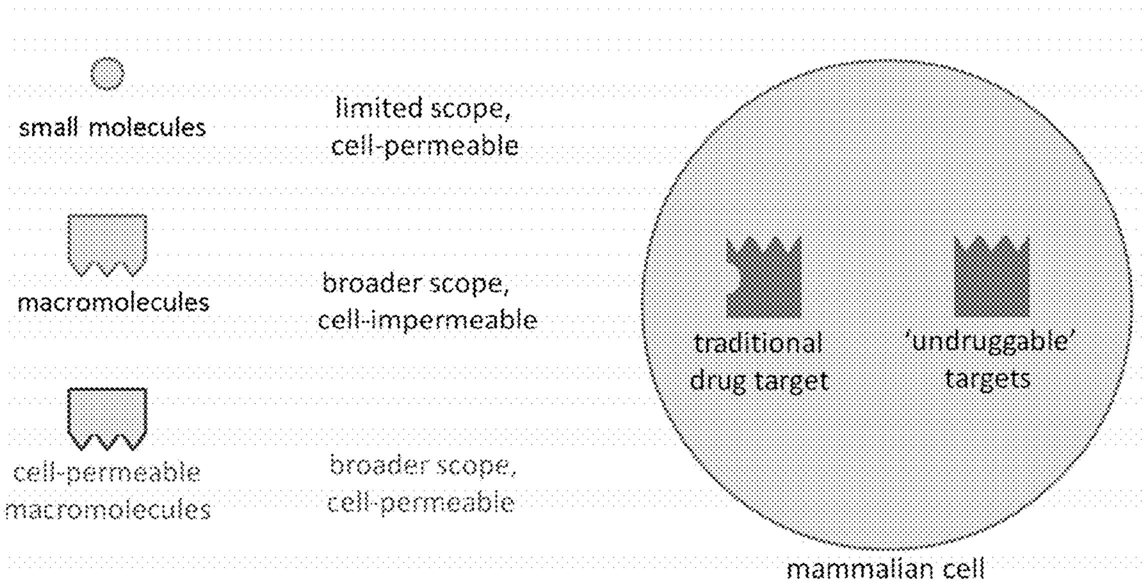
FIG. 1. Schematic of macromolecular delivery into mammalian cells.

The present invention provide complexes, compositions, preparations, kits, systems, and related methods for the delivery of proteins to cells using cationic polymers or cationic lipids. The inventive concepts can be applied to the delivery of proteins that are charged or uncharged, naturally occurring or engineered. Typically, the protein to be delivered is introduced into the interior of a cell, e.g., to cause a measurable biological effect or transformation in the cell. For example, in some embodiments, the biological effect comprises a therapeutic benefit to a subject in which the cell is found. The complexes, compositions, preparations, systems, kits, and related methods for delivery of proteins are thus useful for introducing proteins into a cell, e.g., in the context of manipulating the cell for a diagnostic, research, or therapeutic purpose. The compositions, preparations, systems, kits, and related methods for delivery of proteins provided herein exhibit improved efficacy and/or reduced cytotoxicity, and ease of preparation as compared to current technologies. They are also widely applicable to a variety of proteins. For example, the compositions, preparations, systems, kits, and related methods for delivery of negatively charged proteins provided herein are applicable to the exemplary proteins listed in any of Tables 3-6. The cationic polymer or cationic lipid-mediated delivery of proteins using the compositions, preparations, systems, kits, and related methods provided herein allows for the manipulation/modification of the host cell in vitro or in vivo while avoiding the use of more invasive delivery methods, such as viral delivery of vectors encoding proteins to be delivered.

Some aspects of this disclosure provide compositions comprising a protein to be delivered and a cationic polymer or lipid. In some embodiments, the protein to be delivered is an anionic protein, e.g., a protein exhibiting a negative net charge. In some embodiments, the protein to be delivered is associated with a nucleic acid. For example, in some such embodiments, the protein to be delivered is a nucleic acid-binding protein. One exemplary nucleic acid binding protein is Cas9 and its nucleic acid-binding variants. Other suitable nucleic acid-binding proteins are provided herein or will be apparent to those of skill in the art based on the present disclosure, which is not limited in this respect. In some embodiments, the protein to be delivered is associated with a supernegatively charged protein, wherein the net charge of the protein to be delivered and the supernegatively charged protein is negative.

In some embodiments, the inventive technology uses a supercharged protein to deliver a protein into a cell. In certain embodiments, the supercharged protein is an engineered protein. In some embodiments, the supercharged protein is a naturally occurring supercharged protein.

Some aspects of this invention are based on the recognition that negatively charged proteins or protein complexes, for example, supernegatively charged proteins, naturally occurring negatively charged proteins, proteins associated with nucleic acids, or fusion proteins with a net negative charge, can be associated with cationic polymers or cationic lipids, and that such protein:polymer or protein:lipid complexes are endocytosed by cells. Typically, proteins to be delivered are effectively taken up by cells together with the cationic polymer or lipid, are able to escape the cellular endosomes, and retain their biological function after cellular uptake.

In some embodiments, the protein to be delivered is a negatively charged protein, for example, a protein listed in any one of Tables 3-6. In some embodiments, the protein to be delivered is a functional effector protein (e.g., a nuclease, transcriptional activator/repressor, a recombinases, or a Cas9 protein, or variants or fusions thereof). In some embodiments, proteins to be delivered are useful as therapeutic agents, diagnostic agents, or research tools. In some embodiments, a protein to be delivered, such as, for example, an enzyme, transcription factor, or binding protein, may be therapeutically active, e.g., in that it modulates or ameliorates aberrant expression of a gene associated with a disease or disorder.

In some embodiments, methods are provided in which a cell is contacted with an inventive composition described herein to introduce the protein to be delivered into the cell. In some embodiments, an inventive composition is administered to a subject in need thereof to introduce a protein to be delivered into a cell within the subject, e.g., into a cell associated with a disease or disorder. Suitable cells and cell types and proteins for delivery according to some aspects of this disclosure are listed herein and include, but are not limited to, human cells, mammalian cells, T-cells, neurons, stem cells, progenitor cells, blood cells, fibroblasts, epithelial cells, neoplastic cells, and tumor cells. Additional suitable cells, cell types, and proteins will be apparent to those of skill in the art, and the disclosure is not limited in this respect.

Delivery of Negatively Charged Proteins or Protein Complexes

Some aspects of this disclosure provide compositions for delivering proteins to cells. In some embodiments, the protein to be delivered is itself negatively charged, or is associated with a negatively charged molecule, such as a nucleic acid molecule or a negatively charged protein (e.g., a supernegatively charged protein with a net charge of less than −5, less than −10, less than −20, less than −30, less than −40, less than −50, or less than −100), wherein the resulting complex (e.g., the protein:nucleic acid complex or the protein:protein complex) exhibits a net negative charge. Such negatively charged proteins or protein complexes can be contacted with a cationic polymer or a cationic lipid, resulting in compositions that are effectively taken up by cells via endocytosis. Accordingly, some aspects of this disclosure provide compositions comprising a protein to be delivered and a cationic polymer or cationic lipid.

In some embodiments, the protein to be delivered is negatively charged. In some embodiments, the protein to be delivered is associated with a negatively charged molecule (e.g., a negatively charged molecule with a net charge of less than −5, less than −10, less than −20, less than −30, less than −40, less than −50, or less than −100), for example, with a nucleic acid or with a supernegatively charged protein.

In some embodiments, the protein to be delivered is a naturally occurring negatively charged protein, or a negatively charged fragment thereof. In some embodiments, the protein to be delivered is a supernegatively charged protein or a negatively charged fragment thereof. In some embodiments, the fragment comprises a sequence of at least 10, at least 20, at least 30, at least 40, at least 50, at least 75, or at least 100 consecutive amino acids.

In some embodiments, in which the protein to be delivered is associated with a nucleic acid or with a negatively charged protein, the protein to be delivered is not negatively charged. In some such embodiments, the combined net charge of the protein to be delivered and of the nucleic acid is negative. In some embodiments, the combined net charge of the protein to be delivered and the associated supernegatively charged protein is negative. In some embodiments, the protein to be delivered is fused to a supernegatively charged protein thus forming a fusion protein.

In some embodiments, the net charge of the protein to be delivered, or the combined net charge of the protein to be delivered and the nucleic acid associated with the protein to be delivered, or the combined net charge of the protein to be delivered and the supernegatively charged protein associated with the protein to be delivered is less than −10, less than −20, less than −30, less than −40, less than −50, less than −60, less than −70, less than −80, less than −90, less than −100, less than −110, less than −120, less than −130, less than −140, less than −150, less than −160, less than −170, less than −180, less than −190, less than −200, less than −250, less than −300, or less than −400.

In some embodiments, the charge:molecular weight ratio of the protein to be delivered, or the combined charge: molecular weight ratio of the protein to be delivered and the nucleic acid associated with the protein to be delivered, or the combined charge:molecular weight ratio of the protein to be delivered and the supernegatively charged protein associated with the protein to be delivered is less than −0.03, less than −0.04, less than −0.05, less than −0.06, less than −0.07, less than −0.08, less than −0.09, less than −0.1, less than −0.2, less than −0.3, less than −0.4, less than −0.5, less than −0.6, less than −0.7, less than −0.8, less than −0.9, less than −1, less than −1.1, less than −1.2, less than −1.3, less than −1.4, less than −1.5, less than −1.6, less than −1.7, less than −1.8, less than −1.9, less than −2, less than −2.1, less than −2.2, less than −2.3, less than −2.4, less than −2.5, less than −2.6, less than −2.7, less than −2.8, less than −2.9, less than −3, less than −3.1, less than −3.2, less than −3.3, less than −3.4, less than −3.5, less than −3.6, less than −3.7, less than −3.8, less than −3.9, or less than −4.

In some embodiments, the protein to be delivered is a protein listed in Table 3. In some embodiments, the protein to be delivered is implicated in a disease or disorder. In some embodiments, the protein to be delivered is listed in any of Tables 4, 5, and 6. In some embodiments, the protein to be delivered is a tumor suppressor. In some embodiments, the protein to be delivered is listed in Table 6. In some embodiments, the protein to be delivered is Sirt1 (−59, 86 kDa), PPARg (−13, 54 kDa), PRDM16 (−23, 140 kDa), PGC1a (−15, 91 kDa), TP53BP1 (−148, 213 kDa), Utrophin (−142, 394 kDa), Dystrophin (−89, 426 kDa), Bik (net charge −17, 18 kDa), IκBα (−29, 35 kDa), Von Hippel-Lindau disease tumor suppressor (−18, 24 kDa), an E3 ubiquitin ligase, or a metal-binding protein.

In some embodiments, the supernegatively charged protein associated with the protein to be delivered comprises a 3×FLAG sequence, a VP64 sequence, or a supernegatively charged fluorescent protein or streptavidin. In some embodiments, the supernegatively charged protein comprises −7 GFP or −20 GFP, or a negatively charged fragment thereof. In some embodiments, the fragment comprises a sequence of at least 10, at least 20, at least 30, at least 40, at least 50, at least 75, or at least 100 consecutive amino acids.

In some embodiments, the protein to be delivered is associated with biotin thus forming a biotinylated version of the protein to be delivered. In some embodiments, the protein to be delivered is associated to the biotin via a linker. In some embodiments, the linker comprises a covalent bond generated via click chemistry, NHS ester chemistry, or maleimide chemistry. In some embodiments, the linker is a cleavable linker. In some embodiments, the linker is cleaved by a protease, an esterases, or by a reducing environment. In some embodiments, the linker is cleaved by an enzyme present in endosomes or under conditions present in endosomes. In some embodiments, the biotinylated protein to be delivered is associated with the supernegatively charged protein via non-covalent interaction. In some embodiments, the supernegatively charged protein is a supernegatively charged avidin or avidin variant, or a biotin-binding fragment thereof. In some embodiments, the supernegatively charged avidin or avidin variant is a supernegatively charged streptavidin or a biotin-binding fragment thereof. In some embodiments, the supernegatively charged protein is fused to an avidin or avidin variant. In some embodiments, the avidin or avidin variant is streptavidin, or a biotin-binding fragment thereof.

In some embodiments, the cationic polymer or the cationic lipid is suitable for delivery of an agent bound by the polymer or lipid to a cell. In some embodiments, the cationic lipid is selected from the group consisting of Lipofectamine® 2000, Lipofectamine® 3000, Lipofectamine® RNAiMAX, and Lipofectamine® LTX.

In some embodiments, the composition exhibits low toxicity when administered to a population of cells. In some embodiments, the at least 60%, at least 65%, at least 70%, at least 75%, at least 80%, at least 85%, at least 90%, at least 95%, or at least 99% of the cells are viable 24 hours after administration of an amount of the composition effective for delivery of the protein to be delivered into at least 1%, at least 2%, at least 5%, at least 10%, at least 20%, at least 25%, at least 30%, or at least 50% of the cells.

In some embodiments, the composition is a pharmaceutical composition. Some aspects of this disclosure provide compositions comprising (a) a protein to be delivered; and (b) a negatively charged molecule conjugated to the protein to be delivered resulting in a complex that is negatively charged. In some embodiments, the negatively charged molecule is a nucleic acid. In some embodiments, the negatively charged molecule is a negatively charged protein. In some embodiments, the negatively charged protein is a supernegatively charged protein, e.g., a supernegatively charged protein provided herein or otherwise known to those of skill in the art. In some embodiments, the supernegatively charged protein is a supernegatively charged fluorescent protein or a supernegatively charged streptavidin.

Some aspects of this disclosure provide methods for delivering a protein to be delivered to a cell, comprising contacting the cell with a composition provided herein. In some embodiments, the contacting is in vitro. In some embodiments, the contacting is in vivo.

Some aspects of this disclosure provide kits comprising a composition as provided herein or kits for carrying out a delivery method as provided herein.

Supercharged Proteins

Supercharged proteins for use in the present invention can be produced by changing non-conserved amino acids on the surface of a protein to more polar or charged amino acid residues. In certain embodiments, non-conserved amino acids on the surface of the protein are mutated into amino acids that are positively charged at physiological pH (pH ~7.4). The amino acid residues to be modified may be hydrophobic, hydrophilic, charged, or a combination thereof. Supercharged proteins can also be produced by the attachment of charged moieties to the protein in order to supercharge the protein. Supercharged proteins frequently are resistant to aggregation, have an increased ability to refold, resist improper folding, have improved solubility, and are generally more stable under a wide range of conditions, including denaturing conditions such as heat or the presence of a detergent.

Supercharged proteins suitable for use according to aspects of this disclosure are known in the art and include, without limitation, those supercharged proteins disclosed in international PCT patent application, PCT/US07/70254, filed Jun. 1, 2007, published as WO 2007/143574 on Dec. 13, 2007; in international PCT application, PCT/US09/041984, filed on Apr. 28, 2009, published as WO 2009/134808 on Nov. 5, 2009; and in international PCT application, PCT/US10/001250, filed on Apr. 28, 2010, published as WO 2010/129023 on Nov. 11, 2010; the entire contents of each of which are incorporated herein by reference. In some embodiments, the supercharged protein is an engineered supercharged protein. In some embodiments, the supercharged protein is a naturally occurring supercharged protein, e.g., a naturally supercharged protein disclosed in international PCT application, PCT/US10/001250, filed on Apr. 28, 2010, published as WO 2010/129023 on Nov. 11, 2010; each of which is incorporated herein by reference. In some embodiments, the supercharged protein, engineered or naturally occurring, exhibits a charge:molecular weight ratio of greater than 0.8, e.g., ≥0.85, ≥0.9, ≥0.95, ≥1, ≥1.1, ≥1.2, ≥1.3, ≥1.4, ≥1.5, ≥1.6, ≥1.7, ≥1.8, ≥1.9, ≥2, ≥2.5, ≥3, ≥4, ≥5, ≥6, ≥7, ≥8, or ≥10.

The supercharged protein employed may be derived from any species of plant, animal, and/or microorganism. In certain embodiments, the supercharged protein is a mammalian protein. In certain embodiments, the supercharged protein is a human protein. In certain embodiments, the protein is derived from an organism typically used in research. For example, the protein to be modified may be from a primate (e.g., ape, monkey), rodent (e.g., rabbit, hamster, gerbil), pig, dog, cat, fish (e.g., *Danio rerio*), nematode (e.g., *C. elegans*), yeast (e.g., *Saccharomyces cerevisiae*), or bacteria (e.g., *E. coli*). In certain embodiments, the protein is non-immunogenic. In certain embodiments, the protein is non-antigenic. In certain embodiments, the protein does not have inherent biological activity or has been modified to have no biological activity. In certain embodiments, the protein is chosen based on its targeting ability. In certain embodiments, the protein is a green fluorescent protein. In some embodiments, the supercharged protein is supercharged glutathione S-transferase (GST). In some embodiments, the supercharged protein is supercharged streptavidin.

In some embodiments, a supercharged protein is used that has been modified to increase the overall net charge, or to increase the total number of charged residues on the protein surface. In certain embodiments, the theoretical net charge of the supercharged protein is increased by at least +1, at least +2, at least +3, at least +4, at least +5, at least +10, at least +15, at least +20, at least +25, at least +30, at least +35, or at least +40 as compared to the unmodified protein. In certain embodiments, the theoretical net charge of the supercharged protein is at least +1, at least +2, at least +3, at least +4, at least +5, at least +10, at least +15, at least +20, at least +25, at least +30, at least +35, or at least +40 at physiological pH (i.e., −7.4).

In other embodiments, for example those involving use of cationic lipids and/or cationic polymers, a supercharged protein is used that has been modified to decrease the overall net charge, or to decrease the total number of charged residues on the protein surface. In certain embodiments, the theoretical net charge of the supercharged protein is decreased ("minus" or "negative" represented by '−') by at least −1, at least −2, at least −3, at least −4, at least −5, at least −10, at least −15, at least −20, at least −25, at least −30, at least −35, at least −40, at least −45, or at least −50 as compared to the unmodified protein. In certain embodiments, the theoretical net charge of the supercharged protein is at least −1, at least −2, at least −3, at least −4, at least −5, at least −10, at least −15, at least −20, at least −25, at least −30, at least −35, at least −40, at least −45, or at least −50.

While some exemplary supercharged proteins are described herein in order to exemplify the inventive technology, the disclosure is not limited in this respect. Those of skill in the art will be able to ascertain additional suitable supercharged proteins for delivering functional effector proteins to cells based on the instant disclosure. A number of naturally occurring proteins may be modified to generate suitable supercharged proteins. The desired modifications in such proteins may be accomplished using any techniques known in the art. Recombinant DNA techniques for introducing such changes in a protein sequence are well known in the art. In certain embodiments, the modifications are made by site-directed mutagenesis of the polynucleotide encoding the protein. Other techniques for introducing mutations are discussed in *Molecular Cloning: A Laboratory Manual,* 2nd Ed., ed. by Sambrook, Fritsch, and Maniatis (Cold Spring Harbor Laboratory Press: 1989); the treatise, *Methods in Enzymology* (Academic Press, Inc., N.Y.); Ausubel et al., *Current Protocols in Molecular Biology* (John Wiley & Sons, Inc., New York, 1999); each of which is incorporated herein by reference.

Supercharged proteins may be further modified. Proteins including supercharged proteins can be modified using techniques known to those of skill in the art. For example, supercharged proteins may be modified chemically or biologically. One or more amino acids may be added, deleted, or changed from the primary sequence. For example, a poly-histidine tag or other tag may be added to the supercharged protein to aid in the purification of the protein. Other peptides or proteins may be added onto the supercharged protein to alter the biological, biochemical, and/or biophysical properties of the protein. For example, an endosomolytic peptide may be added to the primary sequence of the supercharged protein, or a targeting peptide, may be added to the primary sequence of the supercharged protein. Other modifications of the supercharged protein include, but are not limited to, post-translational modifications (e.g., glycosylation, phosphorylation, acylation, lipidation, farnesylation, acetylation, proteolysis, etc.). In certain embodiments, the supercharged protein is modified to reduce its immunogenicity. In certain embodiments, the supercharged protein is modified to enhance its ability to deliver a functional effector protein (e.g., nucleases, transcriptional activators/repressors, recombinases, Cas9 proteins including variants and fusions thereof, etc.) to a cell. In certain embodiments, the supercharged protein is conjugated to a polymer. For example, the protein may be PEGylated by conjugating the protein to a polyethylene glycol (PEG) polymer. Other methods can be used to produce supercharged proteins without modification of the protein sequence. For example, moieties that alter the net charge can be attached to proteins (e.g., by chemical or enzymatic reactions) to provide surface charge to achieve supercharging. In certain embodiments, the method of modifying proteins described in Shaw et al., *Protein Science* 17:1446, 2008 is used to supercharge a protein that is used in the instantly disclosed inventive technology.

The design and creation of variants of several different supercharged proteins suitable for use with the instantly disclosed technology is described in international PCT patent application, PCT/US07/70254, filed Jun. 1, 2007, published as WO 2007/143574 on Dec. 13, 2007; in international PCT application, PCT/US09/041984, filed on Apr. 28, 2009, published as WO 2009/134808 on Nov. 5, 2009; and in international PCT application PCT/US10/001250, filed on Apr. 28, 2010, published as WO 2010/129023 on Nov. 11, 2010; the entire contents of each of which are incorporated herein by reference. Some of the disclosed supercharged proteins described therein have been shown to be more stable and to retain their biological function, e.g., their fluorescence in the case of fluorescent proteins. For example, a green fluorescent protein (GFP) from Aequorea victoria is described in GenBank Accession Number P42212, incorporated herein by reference. The amino acid sequence of this wild type GFP is as follows:

```
                                              (SEQ ID NO: 14)
MSKGEELFTGVVPILVELDGDVNGHKFSVSGEGEGDATYGKLTLKFICTT

GKLPVPWPTLVTTFSYGVQCFSRYPDHMKQHDFFKSAMPEGYVQERTIFF

KDDGNYKTRAEVKFEGDTLVNRIELKGIDFKEDGNILGHKLEYNYNSHNV

YIMADKQKNGIKVNFKIRHNIEDGSVQLADHYQQNTPIGDGPVLLPDNHY

LSTQSALSKDPNEKRDHMVLLEFVTAAGITHGMDELYK
```

Wild type GFP has a theoretical net charge of −7. Variants with a theoretical net charge of −29, −30, −25, +15, +25, +36, +48, and +49 have been reported, e.g., in in international PCT application PCT/US10/001250, filed on Apr. 28, 2010, published as WO 2010/129023 on Nov. 11, 2010, the entire contents of which are incorporated herein by reference. Even after heating the +36 GFP to 95° C., 100% of the variant protein is soluble and the protein retains ≥70% of its fluorescence.

Some aspects of this disclosure are based on the discovery that +36 GFP efficiently delivers functional effector proteins (e.g., nucleases, transcriptional activators/repressors, recombinases, Cas9 proteins including variants and fusions thereof, etc.) to target cells, and that the effector proteins so delivered retain their biological function. Therefore, GFP or other proteins with a net charge of at least +15, at least +25, at least +30, at least +35, or at least +40 are thought to be particularly useful for introducing functional effector proteins into a cell.

In some embodiments, particularly useful supercharged proteins are proteins that allow for a charge distribution or a surface charge density similar to that of +36 GFP. Further, in some embodiments, particularly useful supercharged proteins are proteins exhibiting a stable folded structure not easily perturbed by supercharging, thus allowing the supercharged protein to be well folded. In some embodiments, particularly useful supercharged proteins are proteins sharing a structural feature with a supercharged protein described herein or in international PCT patent application, PCT/US07/70254, filed Jun. 1, 2007, published as WO 2007/143574 on Dec. 13, 2007; in international PCT application, PCT/US09/041984, filed on Apr. 28, 2009, published as WO 2009/134808 on Nov. 5, 2009; and in international PCT application, PCT/US10/001250, filed on Apr. 28, 2010, published as WO 2010/129023 on Nov. 11, 2010; the entire contents of each of which are incorporated herein by reference; for example, a globular structure, or a β-barrel structure. Protein folding, protein fold structure stability and perturbation of protein folding by substitution of specific amino acids with differently charged amino acids, charge distribution, and surface charge density can be modeled in silico by methods and algorithms provided herein and others known to those of skill in the art. Accordingly, it will be apparent to those of skill in the art from no more than routine experimentation, whether a supercharged protein in question will be well folded. Thus, those of skill in the art will be able to identify from a given amino acid sequence whether a given supercharged protein will be useful for cellular delivery of a functional effector protein according to the technology described herein.

Some exemplary, suitable variants of GFP include, without limitation:

```
+15 GFP:
                                                       (SEQ ID NO: 15)
MGHHHHHHGGASKGERLFTGVVPILVELDGDVNGHKFSVRGEGEGDATRGKLTLKFICTTGKLPVPWPTLVTTLTYG

VQCFSRYPKHMKRHDFFKSAMPEGYVQERTISFKKDGTYKTRAEVKFEGRTLVNRIELKGRDFKEKGNILGHKLEYN

FNSHNVYITADKRKNGIKANFKIRHNVKDGSVQLADHYQQNTPIGRGPVLLPRNHYLSTRSALSKDPKEKRDHMVLL

EFVTAAGITHGMDELYK

+25 GFP:
                                                       (SEQ ID NO: 16)
MGHHHHHHGGASKGERLFTGVVPILVELDGDVNGHKFSVRGKGKGDATRGKLTLKFICTTGKLPVPWPTLVTTLTYG

VQCFSRYPKHMKRHDFFKSAMPKGYVQERTISFKKDGTYKTRAEVKFEGRTLVNRIKLKGRDFKEKGNILGHKLRYN

FNSHNVYITADKRKNGIKANFKIRHNVKDGSVQLADHYQQNTPIGRGPVLLPRNHYLSTRSALSKDPKEKRDHMVLL

EFVTAAGITHGMDELYK

+36 GFP:
                                                       (SEQ ID NO: 17)
MGHHHHHHGGASKGERLFRGKVPILVELKGDVNGHKFSVRGKGKGDATRGKLTLKFICTTGKLPVPWPTLVTTLTYG

VQCFSRYPKHMKRHDFFKSAMPKGYVQERTISFKKDGKYKTRAEVKFEGRTLVNRIKLKGRDFKEKGNILGHKLRYN

FNSHKVYITADKRKNGIKAKFKIRHNVKDGSVQLADHYQQNTPIGRGPVLLPRNHYLSTRSKLSKDPKEKRDHMVLL

EFVTAAGIKHGRDERYK

+42 GFP:
                                                       (SEQ ID NO: 18)
MGHHHHHHGGRSKGKRLFRGKVPILVELKGDVNGHKFSVRGKGKGDATRGKLTLKFICTTGKLPVPWPTLVTTLTYG

VQCFSRYPKHMKRHDFFKSAMPKGYVQERTISFKKDGKYKTRAEVKFEGRTLVNRIKLKGRDFKEKGNILGHKLRYN

FNSHKVYITADKRKNGIKAKFKIRHNVKDGSVQLADHYQQNTPIGRGPVLLPRKHYLSTRSKLSKDPKEKRDHMVLL

EFVTAAGIKHGRKERYK

+48 GFP:
                                                       (SEQ ID NO: 19)
MGHHHHHHGGRSKGKRLFRGKVPILVKLKGDVNGHKFSVRGKGKGDATRGKLTLKFICTTGKLPVPWPTLVTTLTYG

VQCFSRYPKHMKRHDFFKSAMPKGYVQERTISFKKDGKYKTRAEVKFKGRTLVNRIKLKGRDFKEKGNILGHKLRYN

FNSHKVYITADKRKNGIKAKFKIRHNVKDGSVQLAKHYQQNTPIGRGPVLLPRKHYLSTRSKLSKDPKEKRDHMVLL

EFVTAAGIKHGRKERYK

+49 GFP:
                                                       (SEQ ID NO: 20)
MGHHHHHHGGRSKGKRLFRGKVPILVKLKGDVNGHKFSVRGKGKGDATRGKLTLKFICTTGKLPVPWPTLVTTLTYG

VQCFSRYPKHMKRHDFFKSAMPKGYVQERTISFKKDGKYKTRAEVKFKGRTLVNRIKLKGRDFKEKGNILGHKLRYN
```

-continued

FNSHKVYITADKRKNGIKAKFKIRHNVKDGSVQLAKHYQQNTPIGRGPVLLPRKHYLSTRSKLSKDPKEKRDHMVLK

EFVTAAGIKHGRKERYK

-7 GFP:

(SEQ ID NO: 275)

MGHHHHHHGGASKGEELFTGVVPILVELDGDVNGHKFSVRGEGEGDATNGKLTLKFICTTGKLPVPWPTLVTTLTYG

VQCFSRYPDHMKQHDFFKSAMPEGYVQERTISFKDDGTYKTRAEVKFEGDTLVNRIELKGIDFKEDGNILGHKLEYN

FNSHNVYITADKQKNGIKANFKIRHNVEDGSVQLADHYQQNTPIGDGPVLLPDNHYLSTQSALSKDPNEKRDHMVLL

EFVTAAGITHGMDELYK

-25 GFP:

(SEQ ID NO: 276)

MGHHHHHHGGASKGEELFTGVVPILVELDGDVNGHEFSVRGEGEGDATEGELTLKFICTTGELPVPWPTLVTTLTYG

VQCFSRYPDHMKQHDFFKSAMPEGYVQERTISFKDDGTYKTRAEVKFEGDTLVNRIELKGIDFKEDGNILGHKLEYN

FNSHDVYITADKQENGIKAEFEIRHNVEDGSVQLADHYQQNTPIGDGPVLLPDDHYLSTESALSKDPNEDRDHMVLL

EFVTAAGIDHGMDELYK

-29 GFP:

(SEQ ID NO: 277)

MGHHHHHHGGASKGEELFDGEVPILVELDGDVNGHEFSVRGEGEGDATEGELTLKFICTTGELPVPWPTLVTTLTYG

VQCFSRYPDHMDQHDFFKSAMPEGYVQERTISFKDDGTYKTRAEVKFEGDTLVNRIELKGIDFKEDGNILGHKLEYN

FNSHDVYITADKQENGIKAEFEIRHNVEDGSVQLADHYQQNTPIGDGPVLLPDDHYLSTESALSKDPNEDRDHMVLL

EFVTAAGIDHGMDELYK (-)30 GFP:

(SEQ ID NO: 21)

MGHHHHHHGGASKGEELFDGVVPILVELDGDVNGHEFSVRGEGEGDATEGELTLKFICTTGELPVPWPTLVTTLTYG

VQCFSDYPDHMDQHDFFKSAMPEGYVQERTISFKDDGTYKTRAEVKFEGDTLVNRIELKGIDFKEDGNILGHKLEYN

FNSHDVYITADKQENGIKAEFEIRHNVEDGSVQLADHYQQNTPIGDGPVLLPDDHYLSTESALSKDPNEDRDHMVLL

EFVTAAGIDHGMDELYK

In some embodiments, a supercharged variant of streptavidin (SAV) is used for delivery of a protein to be delivered to a target cell. Such variants retain the capability of wild-type streptavidin to bind biotin. The amino acid sequence of wild-type streptavidin and of some exemplary useful streptavidin variants are provided below. Wild type streptavidin has a theoretical net charge of −4. The provided SAV variants with a theoretical net charge of −40 and +52 are soluble and bind biotin.

Wild type SAV:

(SEQ ID NO: 278)

AAEAGITGTWYNQLGSTFIVTAGADGALTGTYESAVGNAESRYVLTGRYD

SAPATDGSGTALGWTVAWKNNYRNAHSATTWSGQYVGGAEARINTQWLLT

SGTTEANAWKSTLVGHDTFTKVKPSAAS

-40 SAV:

(SEQ ID NO: 279)

MGHHHHHHGGAEAGITGTWYNQLGSTFIVTAGADGALTGTYESAVGDAES

EYVLTGRYDSAPATDGSGTALGWTVAWKNDYENAHSATTWSGQYVGGAEA

RINTQWLLTSGTTEADAWKSTLVGHDTFTKVEPSAAS

-continued

+52 SAV (SEQ ID NO: 280)

MGHHHHHHGGAKAGITGTWYNQLGSTFIVTAGAKGALTGTYESAVGNAKS

RYVLTGRYDSAPATKGSGTALGWTVAWKNKYRNAHSA1TWSGQYVGGAKA

RINTQWLLTSGTTKAKAWKSTLVGHDTFTKVKPSAAS

Additional suitable supercharged proteins and protein variants will be apparent to those of skill in the art. It will also be apparent to the skilled artisan that some of the sequences provided herein, e.g., some of the sequences provided immediately above, include an artificial tag, e.g., an N-terminal His6 tag, and that sequences without such a tag or with a different tag are also suitable.

In order to promote the biological function of the functional effector protein (e.g., nucleases, transcriptional activators/repressors, recombinases, Cas9 proteins including variants and fusions thereof, etc.) after delivery to a cell, it may be desirable to enhance endosomal escape of the functional effector protein after cellular uptake. A supercharged protein or a functional effector protein may be fused to or associated with a protein, peptide, or other entity known to enhance endosome degradation or lysis of the endosome. In certain embodiments, the peptide is hemagglutinin 2 (HA2) peptide which is known to enhance endosome degradation. In certain particular embodiments, HA2 peptide is fused to supercharged GFP (e.g., +36 GFP). In certain particular embodiments, the fused protein is of the sequence:

+36 GFP-HA2

(SEQ ID NO: 22)

MGHHHHHHGGASKGERLFRGKVPILVELKGDVNGHKFSVRGKGKGDATRG

KLTLKFICTTGKLPVPWPTLVTTLTYGVQCFSRYPKHMKRHDFFKSAMPK

GYVQERTISFKKDGKYKTRAEVKFEGRTLVNRIKLKGRDFKEKGNILGHK

LRYNFNSHKVYITADKRKNGIKAKFKIRHNVKDGSVQLADHYQQNTPIGR

GPVLLPRNHYLSTRSKLSKDPKEKRDHMVLLEFVTAAGIKHGRDERYKGS

AGSAAGSGEFGLFGAIAGFIENGWEGMIDG

In certain embodiments, the endosomolytic peptide is melittin peptide (GIGAVLKVLTTGLPALISWIKRKRQQ, SEQ ID NO: 23) (Meyer et al., *JACS* 130(11): 3272-3273, 2008; which is incorporated herein by reference). In certain embodiments, the melittin peptide is modified by one, two, three, four, or five amino acid substitutions, deletions, and/or additions. In certain embodiments, the melittin peptide is of the sequence: CIGAVLKVLTTGLPALISWIKRKRQQ (SEQ ID NO:24). In certain particular embodiments, the melittin peptide is fused to supercharged GFP (e.g., +36 GFP).

In certain embodiments, the endosomolytic peptide is penetratin peptide (RQIKIWFQNRRMKWKK-amide, SEQ ID NO:25), bovine PrP (1-30) peptide (MVKSKIGSWILVLFVAMWSDVGLCKKRPKP-amide, SEQ ID NO: 26), MPG$\Delta^{NLs}$ peptide (which lacks a functional nuclear localization sequence because of a K→S substitution) (GALFLGWLGAAGSTMGAPKSKRKV, SEQ ID NO:27), TP-10 peptide (AGYLLGKINLKALAALAKKIL-amide, SEQ ID NO:28), and/or EB1 peptide (LIRLWSHLIHIWFQNRRLKWKKK-amide, SEQ ID NO:29) (Lundberg et al., 2007, *FASEB J.* 21:2664; incorporated herein by reference). In certain embodiments, the penetratin, PrP (1-30), MPG, TP-10, and/or EB1 peptide is modified by one, two, three, four, or five amino acid substitutions, deletions, and/or additions. In certain particular embodiments, the PrP (1-30), MPG, TP-10, and/or EB1 peptide is fused to supercharged GFP (e.g., +36 GFP). In some embodiments, an Aurein peptide is fused to the supercharged protein.

Other peptides or proteins may also be fused to the supercharged protein or to a fusion protein comprising a supercharged protein and a functional effector protein (e.g., nucleases, transcriptional activators/repressors, recombinases, Cas9 proteins including variants and fusions thereof, etc.). For example, a targeting peptide may be fused to the supercharged protein in order to selectively deliver a functional effector protein to a particular cell type. Peptides or proteins that enhance cellular uptake of the functional effector protein may also be used. In certain embodiments, the peptide fused to the supercharged protein is a peptide hormone. In certain embodiments, the peptide fused to the supercharged protein is a peptide ligand.

The exemplary supercharged proteins described in detail herein are not meant to limit the disclosure, and one of skill in the art will appreciate that other supercharged proteins may be used for the cellular delivery of functional effector proteins (e.g., nucleases, transcriptional activators/repressors, recombinases, Cas9 proteins including variants and fusions thereof, etc.), including, but not limited to, other GFP-style fluorescent proteins. In certain embodiments, the supercharged protein is a supercharged version of blue fluorescent protein. In certain embodiments, the supercharged protein is a supercharged version of cyan fluorescent protein. In certain embodiments, the supercharged protein is a supercharged version of yellow fluorescent protein. Exemplary suitable fluorescent proteins include, but are not limited to, enhanced green fluorescent protein (EGFP), AcGFP, TurboGFP, Emerald, Azami Green, ZsGreen, EBFP, Sapphire, T-Sapphire, ECFP, mCFP, Cerulean, CyPet, AmCyan1, Midori-Ishi Cyan, mTFP1 (Teal), enhanced yellow fluorescent protein (EYFP), Topaz, Venus, mCitrine, YPet, PhiYFP, ZsYellow1, mBanana, Kusabira Orange, mOrange, dTomato, dTomato-Tandem, DsRed, DsRed2, DsRed-Express (T1), DsRed-Monomer, mTangerine, mStrawberry, AsRed2, mRFP1, JRed, mCherry, HcRedl, mRaspberry, HcRedl, HcRed-Tandem, mPlum, and AQ143.

Yet other proteins that may be supercharged and used, e.g., in the delivery of functional effector proteins as disclosed herein (e.g., nucleases, transcriptional activators/repressors, recombinases, Cas9 proteins including variants and fusions thereof, etc.), include histone components or histone-like proteins, high-mobility-group proteins (HMGs), enzymes (e.g., amylases, pectinases, hydrolases, proteases, glucose isomerase, lipases, phytases, alglucerase, imiglucerase, agalsidase beta, α-1-iduronidase, acid α-glucosidase, and iduronate-2-sulfatase, N-acetylgalactosamine-4-sulfatase.

Charged polymers other than proteins may also be used to deliver functional effector proteins. Additionally, as described in greater detail herein, cationic lipids and lipid-like materials as well as cationic polymers can also be used to deliver functional effector proteins. Suitable cationic lipids, lipid-like materials and cationic polymers are disclosed herein and additional suitable lipids and lipid-like materials are known to those of skill in the art (see, e.g., those described in Akinc et al., *Nature Biotechnology* 26, 561-569 (2008), the entire contents of which are incorporated herein by reference).

Delivery of Functional Effector Proteins Using Supercharged Proteins

The present invention provides systems and methods for the delivery of functional effector proteins (e.g., nucleases, transcriptional activators/repressors, recombinases, Cas9 proteins including variants and fusions thereof, etc.) to cells in vivo, ex vivo, or in vitro. Such systems and methods typically involve association of the functional effector protein with a supercharged protein to form a complex or a fusion protein, and delivery of the complex or fusion protein to a cell. In some embodiments, the functional effector protein to be delivered by the supercharged protein has therapeutic activity. In some embodiments, delivery of the complex or fusion protein to a cell involves administering the complex or fusion protein comprising a supercharged protein associated with a functional effector protein to a subject in need thereof.

In some embodiments, a functional effector protein (e.g., nucleases, transcriptional activators/repressors, recombinases, Cas9 proteins including variants and fusions thereof, etc.) by itself may not be able to enter a cell, but is able to enter a cell when associated with a supercharged protein, for example, via a covalent bond or a non-covalent interaction. In some embodiments, a composition is provided that includes a functional effector protein that is covalently bound to a supercharged protein. In some embodiments, the composition includes a functional effector protein fused to a supercharged protein via a peptide bond, for example, via direct fusion or via a peptide linker. In some embodiments, the composition includes a functional effector protein that is bound to a supercharged protein by non-covalent interaction. In some embodiments, a supercharged protein is utilized to allow a functional effector protein to enter a cell. In some embodiments, the functional effector protein delivered to the cell associated with a supercharged protein is separated from the supercharged protein after delivery to the cell, for example, by cleavage of a linker peptide by a cellular protease (e.g., an endosomal protease) or by dissociation of the functional effector protein from the supercharged protein in a specific cellular microenvironment, for example, in the endosome. In some embodiments, functional effector proteins delivered to a cell by a system or method provided by this disclosure have therapeutic activity.

In some embodiments, a functional effector protein (e.g., nucleases, transcriptional activators/repressors, recombinases, Cas9 proteins including variants and fusions thereof, etc.) is delivered to a cell in vivo, ex vivo, or in vitro by a system, composition, or method provided herein. In some embodiments, a functional effector protein is a protein able to carry out a biological function within the target cell, for example, an enzyme able to bind its substrate and to catalyze an enzymatic reaction in the target cell, e.g., a nuclease able to bind and cut a nucleic acid molecule within a target cell, or a transcription factor able to interact with the genome of a target cell and to activate or inhibit transcription of a target gene in the cell.

In some embodiments, a method for generating a fusion of a functional effector protein and a supercharged protein includes the generation of an expression nucleic acid construct containing the coding sequences of the functional protein and the supercharged protein, as well as, optionally, a peptide linker, in frame; the expression of such a recombinant fusion protein in a prokaryotic or eukaryotic cell in culture, the extraction and purification of the fusion protein of the fusion protein. In some embodiments, a nucleic acid construct is generated in the form of an expression vector, for example, a vector suitable for propagation in a bacterial host and for expression in a prokaryotic or eukaryotic cell.

In some embodiments, a vector suitable for fusion protein expression is generated by cloning of a nucleotide sequence coding for a functional effector protein to be delivered into a cloning vector including a nucleotide sequence coding for a supercharged protein under the control of a eukaryotic and/or a prokaryotic promoter, by a cloning approach that results in both coding sequences being in frame with each other. In some embodiments, the cloning vector includes a nucleotide sequence coding for a peptide linker between a nucleotide sequence coding for a supercharged protein and a restriction site useful for inserting a nucleotide sequence coding for a protein in frame with the linker and the supercharged protein. In some embodiments, the cloning vector further includes an additional sequence enhancing expression of a fusion protein in a prokaryotic or eukaryotic cell or facilitating purification of expressed fusion proteins from such cells, for example, a sequence stabilizing a transcript encoding the fusion protein, such as a poly-A signal, a spliceable intron, a sequence encoding an in-frame peptide or protein domain tag (e.g., an Arg-tag, calmodulin-binding peptide tag, cellulose-binding domain tag, DsbA tag, c-myc-tag, glutathione S-transferase tag, FLAG-tag, HAT-tag, His-tag, maltose-binding protein tag, NusA tag, S-tag, SBP-tag, Strep-tag, or thioredoxin tag), or a selection marker or reporter cassette allowing for identification of cells harboring and expressing the expression construct and/or quantifying the level of expression in such cells. Methods for cloning and expressing fusion proteins are well known to those in the art, see, for example Sambrook et al., *Molecular Cloning: A Laboratory Manual*, Volume 1-3, CSHL Press (1989); Gellissen et al., Production of recombinant proteins, Wiley-VCH, 2005.

In some embodiments, the functional effector protein is associated with a supercharged GFP, for example, +36 GFP or −30 GFP, for delivery to a target cell. The benefit of endosomal disruption in the delivery of macromolecules by supercharged proteins has been previously demonstrated (Wadia et al., *Nat. Med.* 10, 310-315, 2004) and in some embodiments, additional steps to effect enhanced endosomal escape, as provided herein or known in the art, are performed. Highly efficient protein internalization, when coupled with effective endosomal release, has the potential to minimize the requisite doses of exogenous protein agents, enhancing their potential as research tools and leads for therapeutic development.

In some embodiments, a composition comprising a functional effector protein associated with a supercharged protein is administered to a target cell after isolation and/or purification. Protein isolation methods and technologies are well known to those of skill in the art and include, for example, affinity chromatography or immunoprecipitation. The methods suitable for isolating and/or purifying a specific functional effector proteins, supercharged proteins, and/or fusion proteins will depend on the nature of the respective protein. For example, a His-tagged fusion protein can readily be isolated and purified via Ni or Co ion chromatography, while fusion proteins tagged with other peptides or domains or untagged fusion proteins can be purified by other well established methods.

Functional effector proteins suitable for delivery to a target cell in vivo, ex vivo, or in vitro, by a system or method provided herein will be apparent to those of skill in the art and include, for example, DNA-binding proteins, such as transcription factors and nucleases, as well as Cas9 proteins (including variants and fusions thereof).

In some embodiments, a method, composition, or system provided herein is used to deliver a therapeutic functional effector protein to a cell. Examples of therapeutic proteins include, but are not limited to, nucleases and Cas9 proteins (including variants and fusions thereof) targeting a genomic allele associated with a disease or disorder, and transcription factors activating a beneficial gene or repressing a pathogenic gene.

In some embodiments, Cas9 is fused to a supercharged protein for delivery to a cell. In some embodiments, the supercharged protein is positively charged. In some embodiments, the supercharged protein fused to Cas9 is (+36)GFP. In some embodiments, the fusion of Cas9 and (+36)GFP comprises the amino acid sequence of SEQ ID NO:30 (e.g., with or without a nuclear localization signal (NLS) and with or without a 6×His tag), or comprises an amino acid sequence that is at least 80%, at least 85%, at least 90%, at least 95%, at least 98%, or at least 99% identical to the amino acid sequence of SEQ ID NO:30 (e.g., with or without a nuclear localization signal (NLS) and with or without a 6×His tag). In some embodiments, the supercharged protein fused to Cas9 is (−30)GFP. In some embodiments, the fusion of Cas9 and (−30)GFP comprises the amino acid sequence of SEQ ID NO:31 (e.g., with or without a nuclear localization signal (NLS) and with or without a 6×His tag), or comprises an amino acid sequence that is at least 80%, at least 85%, at least 90%, at least 95%, at least 98%, or at least 99% identical to the amino acid sequence of SEQ ID NO:31 (e.g., with or without a nuclear localization signal (NLS) and with or without a 6×His tag).

Cas9-6xHis:

(SEQ ID NO: 260)

MDKKYSIGLAIGTNSVGWAVITDEYKVPSKKFKVLGNTDRHSIKKNLIGALLFDSGETAEATRLKRTARRR

YTRRKNRICYLQEIFSNEMAKVDDSLEHRLEESFLVEEDKKHERHPIFGNIVDEVAYHEKYPTIYHLRKKLV

DSTDKADLRLIYLALAHMIKFRGHFLIEGDLNPDNSDVDKLFIQLVQTYNQLFLENPINASGVDAKAILSAR

LSKSRRLENLIAQLPGEKKNGLFGNLIALSLGLTPNFKSNFDLAEDAKLQLSKDTYDDDLDNLLAQIGDQY

ADLFLAAKNLSDAILLSDILRVNTEITKAPLSASMIKRYDEHHQDLTLLKALVRQQLPEKYKEIFFDQSKNG

YAGYIDGGASQEEFYKFIKPILEKMDGTEELLVKLNREDLLRKQRTFDNGSIPHQIHLGELHAILRRQEDFYP

FLKDNREKIEKILTFRIPYYVGPLARGNSRFAWMTRKSEETITPWNFEEVVDKGASAQSFIERMTNFDKNLP

NEKVLPKHSLLYEYFTVYNELTKVKYVTEGMRKPAFLSGEQKKAIVDLLFKTNRKVTVKQLKEDYFKKIE

CFDSVETSGVEDRFNASLGTYHDLLKIIKDKDFLDNEENEDILEDIVLTLTLFEDREMIEERLKTYAHLFDDK

VMKQLKRRRYTGWGRLSRKLINGIRDKQSGKTILDFLKSDGFANRNFMQLIHDDSLTFKEDIQKAQVSGQG

DSLHEHIANLAGSPAIKKGILQTVKVVDELVKVMGRHKPENIVIEMARENQTTQKGQKNSRERMKRIEEGI

KELGSQILKEHPVENTQLQNEKLYLYYLQNGRDMYVDQELDINRLSDYDVDHIVPQSFLKDDSIDNKVLTR

SDKNRGKSDNVPSEEVVKKMKNYWRQLLNAKLITQRKFDNLTKAERGGLSELDKAGFIKRQLVETRQITK

HVAQILDSRMNTKYDENDKLIREVKVITLKSKLVSDFRKDFQFYKVREINNYHHAHDAYLNAVVGTALIK

KYPKLESEFVYGDYKVYDVRKMIAKSEQEIGKATAKYFFYSNIMNFFKTEITLANGEIRKRPLIETNGETGEI

VWDKGRDFATVRKVLSMPQVNIVKKTEVQTGGFSKESILPKRNSDKLIARKKDWDPKKYGGFDSPTVAYS

VLVVAKVEKGKSKKLKSVKELLGITIMERSSEEKNPIDFLEAKGYKEVKKDLIIKLPKYSLFELENGRKRML

ASAGELQKGNELALPSKYVNFLYLASHYEKLKGSPEDNEQKQLFVEQHKHYLDEIIEQISEFSKRVILADAN

LDKVLSAYNKHRDKPIREQAENIIHLFTLTNLGAPAAFKYFDTTIDRKRYTSTKEVLDATLIHQSITGLYETRI

DLSQLGGDHHHHHH (+36)dGFP-NLS-Cas9-6xHis (Y67S):

(SEQ ID NO: 30)

MGASKGERLFRGKVPILVELKGDVNGHKFSVRGKGKGDATRGKLTLKFICTTGKLPVPWPTLVTTLTSGV

QCFSRYPKHMKRHDFFKSAMPKGYVQERTISFKKDGKYKTRAEVKFEGRTLVNRIKLKGRDFKEKGNILG

HKLRYNFNSHKVYITADKRKNGIKAKFKIRHNVKDGSVQLADHYQQNTPIGRGPVLLPRNHYLSTRSKLS

KDPKEKRDHMVLLEFVTAAGIKHGRDERYKTGGSGGSGGSGGSGGSGGSGGSGGSGGTALALPKKKRKVM

DKKYSIGLDIGTNSVGWAVITDEYKVPSKKFKVLGNTDRHSIKKNLIGALLFDSGETAEATRLKRTARRR

YTRRKNRICYLQEIFSNEMAKVDDSFFHRLEESFLVEEDKKHERHPIFGNIVDEVAYHEKYPTIYHLRKK

LVDSTDKADLRLIYLALAHMIKFRGHFLIEGDLNPDNSDVDKLFIQLVQTYNQLFEENPINASGVDAKAI

LSARLSKSRRLENLIAQLPGEKKNGLFGNLIALSLGLTPNFKSNFDLAEDAKLQLSKDTYDDDLDNLLAQ

IGDQYADLFLAAKNLSDAILLSDILRVNTEITKAPLSASMIKRYDEHHQDLTLLKALVRQQLPEKYKEIF

FDQSKNGYAGYIDGGASQEEFYKFIKPILEKMDGTEELLVKLNREDLLRKQRTFDNGSIPHQIHLGELHA

ILRRQEDFYPFLKDNREKIEKILTFRIPYYVGPLARGNSRFAWMTRKSEETITPWNFEEVVDKGASAQSF

IERMTNFDKNLPNEKVLPKHSLLYEYFTVYNELTKVKYVTEGMRKPAFLSGEQKKAIVDLLFKTNRKVTV

KQLKEDYFKKIECFDSVEISGVEDRFNASLGTYHDLLKIIKDKDFLDNEENEDILEDIVLTLTLFEDREM

IEERLKTYAHLFDDKVMKQLKRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVMGRHKPENIVIEMARENQTTQ

KGQKNSRERMKRIEEGIKELGSQILKEHPVENTQLQNEKLYLYYLQNGRDMYVDQELDINRLSDYDVDHI

VPQSFLKDDSIDNKVLTRSDKNRGKSDNVPSEEVVKKMKNYWRQLLNAKLITQRKFDNLTKAERGGLSEL

DKAGFIKRQLVETRQITKHVAQILDSRMNTKYDENDKLIREVKVITLKSKLVSDFRKDFQFYKVREINNY

HHAHDAYLNAVVGTALIKKYPKLESEFVYGDYKVYDVRKMIAKSEQEIGKATAKYFFYSNIMNFFKTEIT

-continued

LANGEIRKRPLIETNGETGEIVWDKGRDFATVRKVLSMPQVNIVKKTEVQTGGFSKESILPKRNSDKLIA

RKKDWDPKKYGGFDSPTVAYSVLVVAKVEKGKSKKLKSVKELLGITIMERSSFEKNPIDFLEAKGYKEVK

KDLIIKLPKYSLFELENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGAPAAFKYFDTTI

DRKRYTSTKEVLDATLIHQSITGLYETRIDLSQLGGDHHHHHH (SEQ ID NO: 261)

ATGGGTGCTAGCAAAGGTGAACGTCTGTTTCGTGGTAAAGTACCGATCTTAGTGGAATTAAAGGGCGACGTGAACGG

TCATAAATTTAGCGTGCGCGGCAAAGGCAAAGGTGACGCTACCCGTGGTAAATTGACCCTGAAGTTTATTTGCACAA

CAGGCAAATTACCCGTTCCGTGGCCCACCTTAGTGACCACCCTGACCTCCGGCGTTCAGTGCTTCAGTCGTTACCCT

AAACATATGAAACGTCACGATTTTTTCAAATCAGCCATGCCTAAAGGATATGTTCAAGAGCGTACAATCAGCTTCAA

GAAGGATGGCAAATATAAAACGCGTGCGGAAGTGAAATTTGAAGGCCGCACATTAGTAAATCGTATCAAACTGAAAG

GTCGTGACTTCAAAGAAAAAGGCAACATTTTAGGCCATAAACTGCGTTATAACTTTAATTCTCATAAGGTGTATATT

ACGGCCGATAAACGCAAGAATGGTATCAAGGCAAAATTCAAAATTCGCCATAACGTGAAAGACGGCAGCGTTCAATT

AGCGGATCATTATCAACAAAACACGCCGATTGGTCGCGGGCCTGTACTGTTACCTCGCAACCACTACCTGAGCACCC

GTTCTAAACTGAGCAAAGATCCGAAAGAAAAACGCGATCACATGGTTCTGTTAGAATTCGTGACCGCTGCAGGCATT

AAGCACGGACGCGACGAACGCTACAAGACCGGTGGTAGCGGTGGTTCTGGTGGTTCTGGTGGTAGCGGCGGTAGCGG

TGGTAGCGGTGGTAGCGGTGGCAGCGGCGGTACCGCGCTCGCGCTGCCCAAGAAGAAGAGGAAGGTGATGGATAAGA

AATACTCAATAGGCTTAGATATCGGCACAAATAGCGTCGGATGGGCGGTGATCACTGATGAATATAAGGTTCCGTCT

AAAAAGTTCAAGGTTCTGGGAAATACAGACCGCCACAGTATCAAAAAAAATCTTATAGGGGCTCTTTTATTTGACAG

TGGAGAGACAGCGGAAGCGACTCGTCTCAAACGGACAGCTCGTAGAAGGTATACACGTCGGAAGAATCGTATTTGTT

ATCTACAGGAGATTTTTTCAAATGAGATGGCGAAAGTAGATGATAGTTTCTTTCATCGACTTGAAGAGTCTTTTTTG

GTGGAAGAAGACAAGAAGCATGAACGTCATCCTATTTTTGGAAATATAGTAGATGAAGTTGCTTATCATGAGAAATA

TCCAACTATCTATCATCTGCGAAAAAAATTGGTAGATTCTACTGATAAAGCGGATTTGCGCTTAATCTATTTGGCCT

TAGCGCATATGATTAAGTTTCGTGGTCATTTTTTGATTGAGGGAGATTTAAATCCTGATAATAGTGATGTGGACAAA

CTATTTATCCAGTTGGTACAAACCTACAATCAATTATTTGAAGAAAACCCTATTAACGCAAGTGGAGTAGATGCTAA

AGCGATTCTTTCTGCACGATTGAGTAAATCAAGACGATTAGAAAATCTCATTGCTCAGCTCCCCGGTGAGAAGAAAA

ATGGCTTATTTGGGAATCTCATTGCTTTGTCATTGGGTTTGACCCCTAATTTTAAATCAAATTTTGATTTGGCAGAA

GATGCTAAATTACAGCTTTCAAAAGATACTTACGATGATGATTTAGATAATTTATTGGCGCAAATTGGAGATCAATA

TGCTGATTTGTTTTTGGCAGCTAAGAATTTATCAGATGCTATTTTACTTTCAGATATCCTAAGAGTAAATACTGAAA

TAACTAAGGCTCCCCTATCAGCTTCAATGATTAAACGCTACGATGAACATCATCAAGACTTGACTCTTTTAAAAGCT

TTAGTTCGACAACAACTTCCAGAAAAGTATAAAGAAATCTTTTTTGATCAATCAAAAAACGGATATGCAGGTTATAT

TGATGGGGGAGCTAGCCAAGAAGAATTTTATAAATTTATCAAACCAATTTTAGAAAAAATGGATGGTACTGAGGAAT

TATTGGTGAAACTAAATCGTGAAGATTTGCTGCGCAAGCAACGGACCTTTGACAACGGCTCTATTCCCCATCAAATT

CACTTGGGTGAGCTGCATGCTATTTTGAGAAGACAAGAAGACTTTTATCCATTTTTAAAAGACAATCGTGAGAAGAT

TGAAAAAATCTTGACTTTTCGAATTCCTTATTATGTTGGTCCATTGGCGCGTGGCAATAGTCGTTTTGCATGGATGA

CTCGGAAGTCTGAAGAAACAATTACCCCATGGAATTTTGAAGAAGTTGTCGATAAAGGTGCTTCAGCTCAATCATTT

ATTGAACGCATGACAAACTTTGATAAAAATCTTCCAAATGAAAAAGTACTACCAAAACATAGTTTGCTTTATGAGTA

TTTTACGGTTTATAACGAATTGACAAAGGTCAAATATGTTACTGAAGGAATGCGAAAACCAGCATTTCTTTCAGGTG

AACAGAAGAAAGCCATTGTTGATTTACTCTTCAAAACAAATCGAAAAGTAACCGTTAAGCAATTAAAAGAAGATTAT

TTCAAAAAAATAGAATGTTTTGATAGTGTTGAAATTTCAGGAGTTGAAGATAGATTTAATGCTTCATTAGGTACCTA

CCATGATTTGCTAAAAATTATTAAAGATAAAGATTTTTTGGATAATGAAGAAAATGAAGATATCTTAGAGGATATTG

-continued

TTTTAACATTGACCTTATTTGAAGATAGGGAGATGATTGAGGAAAGACTTAAAACATATGCTCACCTCTTTGATGAT

AAGGTGATGAAACAGCTTAAACGTCGCCGTTATACTGGTTGGGGACGTTTGTCTCGAAAATTGATTAATGGTATTAG

GGATAAGCAATCTGGCAAAACAATATTAGATTTTTTGAAATCAGATGGTTTTGCCAATCGCAATTTTATGCAGCTGA

TCCATGATGATAGTTTGACATTTAAAGAAGACATTCAAAAAGCACAAGTGTCTGGACAAGGCGATAGTTTACATGAA

CATATTGCAAATTTAGCTGGTAGCCCTGCTATTAAAAAAGGTATTTTACAGACTGTAAAAGTTGTTGATGAATTGGT

CAAAGTAATGGGGCGGCATAAGCCAGAAAATATCGTTATTGAAATGGCACGTGAAAATCAGACAACTCAAAAGGGCC

AGAAAAATTCGCGAGAGCGTATGAAACGAATCGAAGAAGGTATCAAAGAATTAGGAAGTCAGATTCTTAAAGAGCAT

CCTGTTGAAAATACTCAATTGCAAAATGAAAAGCTCTATCTCTATTATCTCCAAAATGGAAGAGACATGTATGTGGA

CCAAGAATTAGATATTAATCGTTTAAGTGATTATGATGTCGATCACATTGTTCCACAAAGTTTCCTTAAAGACGATT

CAATAGACAATAAGGTCTTAACGCGTTCTGATAAAAATCGTGGTAAATCGGATAACGTTCCAAGTGAAGAAGTAGTC

AAAAAGATGAAAAACTATTGGAGACAACTTCTAAACGCCAAGTTAATCACTCAACGTAAGTTTGATAATTTAACGAA

AGCTGAACGTGGAGGTTTGAGTGAACTTGATAAAGCTGGTTTTATCAAACGCCAATTGGTTGAAACTCGCCAAATCA

CTAAGCATGTGGCACAAATTTTGGATAGTCGCATGAATACTAAATACGATGAAAATGATAAACTTATTCGAGAGGTT

AAAGTGATTACCTTAAAATCTAAATTAGTTTCTGACTTCCGAAAAGATTTCCAATTCTATAAAGTACGTGAGATTAA

CAATTACCATCATGCCCATGATGCGTATCTAAATGCCGTCGTTGGAACTGCTTTGATTAAGAAATATCCAAAACTTG

AATCGGAGTTTGTCTATGGTGATTATAAAGTTTATGATGTTCGTAAAATGATTGCTAAGTCTGAGCAAGAAATAGGC

AAAGCAACCGCAAAATATTTCTTTTACTCTAATATCATGAACTTCTTCAAAACAGAAATTACACTTGCAAATGGAGA

GATTCGCAAACGCCCTCTAATCGAAACTAATGGGGAAACTGGAGAAATTGTCTGGGATAAAGGGCGAGATTTTGCCA

CAGTGCGCAAAGTATTGTCCATGCCCCAAGTCAATATTGTCAAGAAAACAGAAGTACAGACAGGCGGATTCTCCAAG

GAGTCAATTTTACCAAAAAGAAATTCGGACAAGCTTATTGCTCGTAAAAAAGACTGGGATCCAAAAAAATATGGTGG

TTTTGATAGTCCAACGGTAGCTTATTCAGTCCTAGTGGTTGCTAAGGTGGAAAAAGGGAAATCGAAGAAGTTAAAAT

CCGTTAAAGAGTTACTAGGGATCACAATTATGGAAAGAAGTTCCTTTGAAAAAAATCCGATTGACTTTTTAGAAGCT

AAAGGATATAAGGAAGTTAAAAAAGACTTAATCATTAAACTACCTAAATATAGTCTTTTTGAGTTAGAAAACGGTCG

TAAACGGATGCTGGCTAGTGCCGGAGAATTACAAAAAGGAAATGAGCTGGCTCTGCCAAGCAAATATGTGAATTTTT

TATATTTAGCTAGTCATTATGAAAAGTTGAAGGGTAGTCCAGAAGATAACGAACAAAAACAATTGTTTGTGGAGCAG

CATAAGCATTATTTAGATGAGATTATTGAGCAAATCAGTGAATTTTCTAAGCGTGTTATTTTAGCAGATGCCAATTT

AGATAAAGTTCTTAGTGCATATAACAAACATAGAGACAAACCAATACGTGAACAAGCAGAAAATATTATTCATTTAT

TTACGTTGACGAATCTTGGAGCTCCCGCTGCTTTTAAATATTTTGATACAACAATTGATCGTAAACGATATACGTCT

ACAAAAGAAGTTTAGATGCCACTCTTATCCATCAATCCATCACTGGTCTTTATGAAACACGCATTGATTTGAGTCA

GCTAGGAGGTGACCATCACCACCACCATCAC (-30)dGFP-NLS-Cas9-6xHis (Y67S):

(SEQ ID NO: 31)

MGASKGEELFDGVVPILVELDGDVNGHEFSVRGEGEGDATEGELTLKFICTTGELPVPWPTLVTTLTSGV

QCFSDYPDHMDQHDFFKSAMPEGYVQERTISFKDDGTYKTRAEVKFEGDTLVNRIELKGIDFKEDGNILG

HKLEYNFNSHDVYITADKQENGIKAEFEIRHNVEDGSVQLADHYQQNTPIGDGPVLLPDDHYLSTESALS

KDPNEDRDHMVLLEFVTAAGIDHGMDELYKTGGSGGSGGSGGSGGSGGSGGSGGSGGTALALPKKKRKVM

DKKYSIGLDIGTNSVGWAVITDEYKVPSKKFKVLGNTDRHSIKKNLIGALLFDSGETAEATRLKRTARRR

YTRRKNRICYLQEIFSNEMAKVDDSFFHRLEESFLVEEDKKHERHPIFGNIVDEVAYHEKYPTIYHLRKK

LVDSTDKADLRLIYLALAHMIKFRGHFLIEGDLNPDNSDVDKLFIQLVQTYNQLFEENPINASGVDAKAI

LSARLSKSRRLENLIAQLPGEKKNGLFGNLIALSLGLTPNFKSNFDLAEDAKLQLSKDTYDDDLDNLLAQ

IGDQYADLFLAAKNLSDAILLSDILRVNTEITKAPLSASMIKRYDEHHQDLTLLKALVRQQLPEKYKEIF

-continued

FDQSKNGYAGYIDGGASQEEFYKFIKPILEKMDGTEELLVKLNREDLLRKQRTFDNGSIPHQIHLGELHA

ILRRQEDFYPFLKDNREKIEKILTFRIPYYVGPLARGNSRFAWMTRKSEETITPWNFEEVVDKGASAQSF

IERMTNFDKNLPNEKVLPKHSLLYEYFTVYNELTKVKYVTEGMRKPAFLSGEQKKAIVDLLFKTNRKVTV

KQLKEDYFKKIECFDSVEISGVEDRFNASLGTYHDLLKIIKDKDFLDNEENEDILEDIVLTLTLFEDREM

IEERLKTYAHLFDDKVMKQLKRRRYTGWGRLSRKLINGIRDKQSGKTILDFLKSDGFANRNFMQLIHDDS

LTFKEDIQKAQVSGQGDSLHEHIANLAGSPAIKKGILQTVKVVDELVKVMGRHKPENIVIEMARENQTTQ

KGQKNSRERMKRIEEGIKELGSQILKEHPVENTQLQNEKLYLYYLQNGRDMYVDQELDINRLSDYDVDHI

VPQSFLKDDSIDNKVLTRSDKNRGKSDNVPSEEVVKKMKNYWRQLLNAKLITQRKFDNLTKAERGGLSEL

DKAGFIKRQLVETRQITKHVAQILDSRMNTKYDENDKLIREVKVITLKSKLVSDFRKDFQFYKVREINNY

HHAHDAYLNAVVGTALIKKYPKLESEFVYGDYKVYDVRKMIAKSEQEIGKATAKYFFYSNIMNFFKTEIT

LANGEIRKRPLIETNGETGEIVWDKGRDFATVRKVLSMPQVNIVKKTEVQTGGFSKESILPKRNSDKLIA

RKKDWDPKKYGGFDSPTVAYSVLVVAKVEKGKSKKLKSVKELLGITIMERSSFEKNPIDFLEAKGYKEVK

KDLIIKLPKYSLFELENGRKRMLASAGELQKGNELALPSKYVNFLYLASHYEKLKGSPEDNEQKQLFVEQ

HKHYLDEIIEQISEFSKRVILADANLDKVLSAYNKHRDKPIREQAENIIHLFTLTNLGAPAAFKYFDTTI

DRKRYTSTKEVLDATLIHQSITGLYETRIDLSQLGGDHHHHHH (SEQ ID NO: 262)

ATGGGTGCTAGCAAAGGTGAAGAGCTGTTTGACGGTGTAGTACCGATCTTAGTGGAATTAGACGGCGACGTGAACGG

TCACGAATTTAGCGTGCGCGGCGAGGGCGAAGGTGACGCTACCGAGGGTGAATTGACCCTGAAGTTTATTTGCACAA

CAGGCGAATTACCCGTTCCGTGGCCCACCTTAGTGACCACCCTGACCICCGGCGTTCAGTGCTTCAGTGATTACCCA

GATCATATGGATCAACACGATTTTTTCAAATCAGCCATGCCTGAAGGATATGTTCAAGAGCGTACAATCAGCTTCAA

GGACGATGGCACCTATAAAACGCGTGCGGAAGTGAAATTTGAAGGCGACACATTAGTAAACCGTATCGAACTGAAAG

GTATCGACTTCAAAGAAGACGGCAACATTTTAGGCCATAAGCTGGAATATAACTTTAATTCTCATGACGTGTATATT

ACGGCCGATAAACAGGAAAACGGTATCAAGGCAGAATTTGAAATTCGCCATAACGTGGAGGACGGCAGCGTTCAATT

AGCGGATCATTATCAACAAAACACGCCGATTGGTGATGGGCCTGTACTGTTACCTGACGATCACTACCTGAGCACGG

AGTCAGCCCTGAGCAAAGATCCGAACGAAGACCGCGATCACATGGTTCTGTTAGAATTCGTGACCGCTGCAGGCATT

GATCATGGAATGGACGAGCTGTACAAGACCGGTGGTAGCGGTGGTTCTGGTGGTTCTGGTGGTAGCGGCGGTAGCGG

TGGTAGCGGTGGTAGCGGTGGCAGCGGCGGTACCGCGCTCGCGCTGCCCAAGAAGAAGAGGAAGGTGATGGATAAGA

AATACTCAATAGGCTTAGATATCGGCACAAATAGCGTCGGATGGGCGGTGATCACTGATGAATATAAGGTTCCGTCT

AAAAAGTTCAAGGTTCTGGGAAATACAGACCGCCACAGTATCAAAAAAAATCTTATAGGGGCTCTTTTATTTGACAG

TGGAGAGACAGCGGAAGCGACTCGTCTCAAACGGACAGCTCGTAGAAGGTATACACGTCGGAAGAATCGTATTTGTT

ATCTACAGGAGATTTTTTCAAATGAGATGGCGAAAGTAGATGATAGTTTCTTTCATCGACTTGAAGAGTCTTTTTTG

GTGGAAGAAGACAAGAAGCATGAACGTCATCCTATTTTTGGAAATATAGTAGATGAAGTTGCTTATCATGAGAAATA

TCCAACTATCTATCATCTGCGAAAAAAATTGGTAGATTCTACTGATAAAGCGGATTTGCGCTTAATCTATTTGGCCT

TAGCGCATATGATTAAGTTTCGTGGTCATTTTTTGATTGAGGGAGATTTAAATCCTGATAATAGTGATGTGGACAAA

CTATTTATCCAGTTGGTACAAACCTACAATCAATTATTTGAAGAAAACCCTATTAACGCAAGTGGAGTAGATGCTAA

AGCGATTCTTTCTGCACGATTGAGTAAATCAAGACGATTAGAAAATCTCATTGCTCAGCTCCCCGGTGAGAAGAAAA

ATGGCTTATTTGGGAATCTCATTGCTTTGTCATTGGGTTTGACCCCTAATTTTAAATCAAATTTTGATTTGGCAGAA

GATGCTAAATTACAGCTTTCAAAAGATACTTACGATGATGATTTAGATAATTTATTGGCGCAAATTGGAGATCAATA

TGCTGATTTGTTTTTGGCAGCTAAGAATTTATCAGATGCTATTTTACTTTCAGATATCCTAAGAGTAAATACTGAAA

TAACTAAGGCTCCCCTATCAGCTTCAATGATTAAACGCTACGATGAACATCATCAAGACTTGACTCTTTTAAAAGCT

TTAGTTCGACAACAACTTCCAGAAAAGTATAAAGAAATCTTTTTTGATCAATCAAAAAACGGATATGCAGGTTATAT

-continued

TGATGGGGGAGCTAGCCAAGAAGAATTTTATAAATTTATCAAACCAATTTTAGAAAAAATGGATGGTACTGAGGAAT

TATTGGTGAAACTAAATCGTGAAGATTTGCTGCGCAAGCAACGGACCTTTGACAACGGCTCTATTCCCCATCAAATT

CACTTGGGTGAGCTGCATGCTATTTTGAGAAGACAAGAAGACTTTTATCCATTTTTAAAAGACAATCGTGAGAAGAT

TGAAAAAATCTTGACTTTTCGAATTCCTTATTATGTTGGTCCATTGGCGCGTGGCAATAGTCGTTTTGCATGGATGA

CTCGGAAGTCTGAAGAAACAATTACCCCATGGAATTTTGAAGAAGTTGTCGATAAAGGTGCTTCAGCTCAATCATTT

ATTGAACGCATGACAAACTTTGATAAAAATCTTCCAAATGAAAAAGTACTACCAAAACATAGTTTGCTTTATGAGTA

TTTTACGGTTTATAACGAATTGACAAAGGTCAAATATGTTACTGAAGGAATGCGAAAACCAGCATTTCTTTCAGGTG

AACAGAAGAAAGCCATTGTTGATTTACTCTTCAAAACAAATCGAAAAGTAACCGTTAAGCAATTAAAAGAAGATTAT

TTCAAAAAAATAGAATGTTTTGATAGTGTTGAAATTTCAGGAGTTGAAGATAGATTTAATGCTTCATTAGGTACCTA

CCATGATTTGCTAAAAATTATTAAAGATAAAGATTTTTTGGATAATGAAGAAAATGAAGATATCTTAGAGGATATTG

TTTTAACATTGACCTTATTTGAAGATAGGGAGATGATTGAGGAAAGACTTAAAACATATGCTCACCTCTTTGATGAT

AAGGTGATGAAACAGCTTAAACGTCGCCGTTATACTGGTTGGGGACGTTTGTCTCGAAAATTGATTAATGGTATTAG

GGATAAGCAATCTGGCAAAACAATATTAGATTTTTTGAAATCAGATGGTTTTGCCAATCGCAATTTTATGCAGCTGA

TCCATGATGATAGTTTGACATTTAAAGAAGACATTCAAAAAGCACAAGTGTCTGGACAAGGCGATAGTTTACATGAA

CATATTGCAAATTTAGCTGGTAGCCCTGCTATTAAAAAAGGTATTTTACAGACTGTAAAAGTTGTTGATGAATTGGT

CAAAGTAATGGGGCGGCATAAGCCAGAAAATATCGTTATTGAAATGGCACGTGAAAATCAGACAACTCAAAAGGGCC

AGAAAAATTCGCGAGAGCGTATGAAACGAATCGAAGAAGGTATCAAAGAATTAGGAAGTCAGATTCTTAAAGAGCAT

CCTGTTGAAAATACTCAATTGCAAAATGAAAAGCTCTATCTCTATTATCTCCAAAATGGAAGAGACATGTATGTGGA

CCAAGAATTAGATATTAATCGTTTAAGTGATTATGATGTCGATCACATTGTTCCACAAAGTTTCCTTAAAGACGATT

CAATAGACAATAAGGTCTTAACGCGTTCTGATAAAAATCGTGGTAAATCGGATAACGTTCCAAGTGAAGAAGTAGTC

AAAAAGATGAAAAACTATTGGAGACAACTTCTAAACGCCAAGTTAATCACTCAACGTAAGTTTGATAATTTAACGAA

AGCTGAACGTGGAGGTTTGAGTGAACTTGATAAAGCTGGTTTTATCAAACGCCAATTGGTTGAAACTCGCCAAATCA

CTAAGCATGTGGCACAAATTTTGGATAGTCGCATGAATACTAAATACGATGAAAATGATAAACTTATTCGAGAGGTT

AAAGTGATTACCTTAAAATCTAAATTAGTTTCTGACTTCCGAAAAGATTTCCAATTCTATAAAGTACGTGAGATTAA

CAATTACCATCATGCCCATGATGCGTATCTAAATGCCGTCGTTGGAACTGCTTTGATTAAGAAATATCCAAAACTTG

AATCGGAGTTTGTCTATGGTGATTATAAAGTTTATGATGTTCGTAAAATGATTGCTAAGTCTGAGCAAGAAATAGGC

AAAGCAACCGCAAAATATTTCTTTTACTCTAATATCATGAACTTCTTCAAAACAGAAATTACACTTGCAAATGGAGA

GATTCGCAAACGCCCTCTAATCGAAACTAATGGGGAAACTGGAGAAATTGTCTGGGATAAAGGGCGAGATTTTGCCA

CAGTGCGCAAAGTATTGTCCATGCCCCAAGTCAATATTGTCAAGAAAACAGAAGTACAGACAGGCGGATTCTCCAAG

GAGTCAATTTTACCAAAAAGAAATTCGGACAAGCTTATTGCTCGTAAAAAAGACTGGGATCCAAAAAAATATGGTGG

TTTTGATAGTCCAACGGTAGCTTATTCAGTCCTAGTGGTTGCTAAGGTGGAAAAAGGGAAATCGAAGAAGTTAAAAT

CCGTTAAAGAGTTACTAGGGATCACAATTATGGAAAGAAGTTCCTTTGAAAAAAATCCGATTGACTTTTTAGAAGCT

AAAGGATATAAGGAAGTTAAAAAAGACTTAATCATTAAACTACCTAAATATAGTCTTTTTGAGTTAGAAAACGGTCG

TAAACGGATGCTGGCTAGTGCCGGAGAATTACAAAAAGGAAATGAGCTGGCTCTGCCAAGCAAATATGTGAATTTTT

TATATTTAGCTAGTCATTATGAAAAGTTGAAGGGTAGTCCAGAAGATAACGAACAAAAACAATTGTTTGTGGAGCAG

CATAAGCATTATTTAGATGAGATTATTGAGCAAATCAGTGAATTTTCTAAGCGTGTTATTTTAGCAGATGCCAATTT

AGATAAAGTTCTTAGTGCATATAACAAACATAGAGACAAACCAATACGTGAACAAGCAGAAAATATTATTCATTTAT

TTACGTTGACGAATCTTGGAGCTCCCGCTGCTTTTAAATATTTTGATACAACAATTGATCGTAAACGATATACGTCT

ACAAAAGAAGTTTTAGATGCCACTCTTATCCATCAATCCATCACTGGTCTTTATGAAACACGCATTGATTTGAGTCA

GCTAGGAGGTGACCATCACCACCACCATCAC

Compositions of Functional Effector Proteins and Cationic Lipids

Certain aspects of the disclosure relate to the use of cationic lipids for the delivery of effector proteins (e.g., nucleases, transcriptional activators/repressors, recombinases, Cas9 proteins including variants and fusions thereof, etc.), for example as opposed to delivering "naked" protein preparations. Surprisingly, existing liposomal delivery reagents that have been engineered for the delivery of nucleic acids such as DNA and RNA were found to effectively deliver certain effector proteins (e.g., Cas9 proteins including variants and fusions thereof) both in vitro and in vivo, as described herein. Nucleic acid delivery has benefited greatly from the development of liposomal reagents over the past two decades. Cationic liposomal formulations have enabled DNA and RNA transfection to become a routine technique in basic research and have even been used in clinical trials. The lipid bilayer of the liposome protects encapsulated nucleic acids from degradation and can prevent specific neutralization by antibodies that can bind naked preparations of the nucleic acids. Importantly, fusion of the liposome with the endosomal membrane during endosomal maturation can enable highly efficient endosomal escape of cationic lipid-delivered cargo. Other non-cationic, but reversibly ionizable, lipid nanoparticle formulations have enabled efficient encapsulation and delivery of nucleic acids, while avoiding non-specific electrostatic interactions and consequent sequestration. However, proteins are chemically diverse, and therefore unlike highly anionic nucleic acids, liposomal formulations have not been similarly successful for the efficient delivery of proteins. For example, while proteins can be encapsulated non-specifically and delivered by rehydrated lipids in vitro, the efficacy of encapsulation is dependent on protein concentration and is generally inefficient, and thus has not seen widespread application. Aspects of the present disclosure relate to the recognition that anionic proteins or protein complexes (including those proteins associated with nucleic acids) may be able to take advantage of the same electrostatics-driven encapsulation used by cationic liposomal reagents for nucleic acid delivery. While few proteins natively possess the density of negative charges found in the phosphate backbone of nucleic acids, translational fusion to, or non-covalent association with, an anionic carrier such as a negatively supercharged protein or a nucleic acid as described herein render the resulting effector protein or protein complex sufficiently anionic to drive efficient encapsulation of such protein cargoes by cationic liposomal reagents.

In some embodiments, association or fusion with an engineered supernegatively charged GFP is capable of driving efficient encapsulation and delivery of proteins into cultured mammalian cells by cationic lipids commonly used to transfect nucleic acids. This approach is effective even at low nanomolar protein concentrations and in the presence of serum, resulting in up to 1,000-fold more efficient functional protein delivery than protein delivery methods that use fusion to cationic peptides or proteins. As shown in the Examples, the efficacy of delivery depends, in some embodiments, on e.g., the theoretical net charge of the fusion tag, and that popular natively anionic peptide tags e.g., 3×FLAG and VP64, can likewise enable liposomal protein delivery.

The Examples further show that Cas9 nuclease protein associated with polyanionic guide RNAs (gRNA) can be efficiently delivered in functional form into mammalian cells by these common cationic liposomal formulations because, while not wishing to be bound by any particular theory, it is believed that the gRNA acts as a polyanionic mediator between the otherwise cationic Cas9 protein and the cationic lipids. Delivery of Cas9:gRNA complexes is not only highly efficient (e.g., up to 80% modification from a single treatment) but also results in markedly higher genome modification specificity compared with plasmid transfection, typically resulting in >10-fold higher on-target:off-target modification ratios, presumably due to the transient nature of the delivered Cas9:gRNA activity. In some embodiments, delivery of Cas9:gRNA complexes results in at least a 2-fold, 3-fold, 4-fold, 5-fold, 6-fold, 7-fold, 8-fold, 9-fold, 10-fold, 11-fold, 12-fold, 13-fold, 14-fold, 15-fold, 20-fold or 25-fold or higher on-target:off-target modification ratio. The Examples also demonstrate that this protein delivery approach can be effective in vivo, for example by delivering functional Cre recombinase and functional Cas9:gRNA complexes to hair cells in the inner ear of mice.

Accordingly, some aspects of the disclosure provide compositions comprising a Cas9 protein (e.g., as described herein; see e.g., Cas9 effector proteins below) and a cationic lipid capable of delivering the Cas9 protein to the interior of a cell. In some embodiments, the Cas9 protein is associated with a gRNA, which e.g., provides anionic charge to the complex thereby allowing the Cas9:gRNA complex to be encapsulated by the cationic lipids. In some embodiments, the Cas9 protein need not be associated with a gRNA for effective encapsulation by a cationic lipid, but instead is associated with a negatively supercharged protein, as described herein. In some embodiments where a Cas9 protein is associated with a negatively supercharged protein, the Cas9 protein is also associated with a gRNA. In some embodiments, the Cas9 protein is a wild type Cas9 protein, a fragment of a wild type Cas9 protein, or a variant of a wild type Cas9 protein. In some embodiments, the Cas9 protein comprises a dCas9 domain (e.g., as described herein). In some embodiments, the Cas9 protein is a fusion protein comprising a dCas9 domain (e.g., as described herein). In some embodiments, the Cas9 protein is a Cas9 nickase.

In other embodiments, compositions comprising an effector protein (e.g., other than a Cas9 protein) and a cationic lipid are provided which are capable of delivering the effector protein to the interior of a cell (e.g., to the nucleus of the cell). The effector protein is either naturally negatively charged, is modified to have a net overall negative charge, or is associated with a negatively supercharged protein, as described herein. In some embodiments, the effector protein is any effector protein described herein. In some embodiments, the effector protein is a recombinase, e.g., any recombinase described herein. In some embodiments, the recombinase is Cre recombinase. In some embodiments, the Cre recombinase comprises the amino acid sequence of SEQ ID NO:32 (e.g., with or without the 6×His tag). In some embodiments, the Cre recombinase comprises an amino acid sequence that is at least 80%, at least 85%, at least 90%, at least 95%, at least 98%, or at least 99% identical to the amino acid sequence of SEQ ID NO:32 (e.g., with or without the 6×His tag). In some embodiments, the Cre recombinase is fused to a supercharged protein (e.g., +36 GFP or −30 GFP). In some embodiments, the Cre recombinase fused to a supercharged protein comprises the amino acid sequence of SEQ ID NO:33 (e.g., with or without the 6×His tag) or SEQ ID NO:34 (e.g., with or without the 6×His tag), or comprises an amino acid sequence that is at least 80%, at least 85%, at least 90%, at least 95%, at least 98%, or at least 99% identical to the amino acid sequence of SEQ ID NO:33 or SEQ ID NO:34 (e.g., with or without the 6×His tag). In some embodiments, the effector protein is a TALE protein, (e.g., as described herein including those provided in the Examples). In some embodiments, the TALE protein comprises one or more of a VP64 transcriptional activator domain (e.g., SEQ ID NO:35). In some embodiments, the TALE protein with a VP64 transcriptional activator domain further comprises an amino acid sequence selected from the group consisting of SEQ ID NO:36-39 (e.g., with or without the 6×His tag). In some embodiments, the TALE protein with a VP64 transcriptional activator domain comprises an amino acid sequence that is at least 80%, at least 85%, at least 90%, at least 95%, at least 98%, or at least 99% identical to an amino acid sequence selected from the group consisting of SEQ ID NO:36-39 (e.g., with or without the 6×His tag). In some embodiments, the TALE effector protein comprises a (−30)GFP domain (e.g., SEQ ID NO:21 or SEQ ID NO:40), a N-terminal region of a TALE domain (e.g., SEQ ID NO:41), a variable repeat domain (e.g., an 18.5 mer repeat domain as provided in Maeder et al., "Robust, synergistic regulation of human gene expression using TALE activators." Nat. Methods. 2013; 10, 243-245), a C-terminal TALE domain (e.g., SEQ ID NO:42), a VP64 activation domain (e.g., SEQ ID NO:35), and optionally one or more linkers (e.g., GGS(9), SEQ ID NO: 252) between any domain and optionally a sequence tag (e.g., 6×His, SEQ ID NO:253).

While liposomal delivery of cargo such as DNA and RNA has been known to induce toxicity in targeted cells, it was found that the inventive compositions described herein deliver their cargo both in vitro and in vivo surprisingly with no or low toxicity. For example, in some embodiments, the compositions comprising a Cas9 protein or other effector proteins described herein exhibit low toxicity when administered to a population of cells (e.g., in vitro or in vivo). In some embodiments, at least 60%, at least 65%, at least 70%, at least 75%, at least 80%, at least 85%, at least 90%, at least 95%, or at least 99% of the cells in a population are viable following administration of an inventive composition comprising a Cas9 protein or other effector protein and cationic lipids. Methods for assessing the toxicity of a composition when administered to a population of cells are well known in the art and include those described in the Examples.

Cre-6xHis (6xHis tag underlined):

(SEQ ID NO: 32)

MASNLLTVHQNLPALPVDATSDEVRKNLMDMFRDRQAFSEHTWKMLLSVCRSWAAWCKLNNRKWFPAEPE

DVRDYLLYLQARGLAVKTIQQHLGQLNMLHRRSGLPRPSDSNAVSLVMRRIRKENVDAGERAKQALAFER

TDFDQVRSLMENSDRCQDIRNLAFLGIAYNTLLRIAEIARIRVKDISRTDGGRMLIHIGRTKTLVSTAGV

EKALSLGVTKLVERWISVSGVADDPNNYLFCRVRKNGVAAPSATSQLSTRALEGIFEATHRLIYGAKDDS

GQRYLAWSGHSARVGAARDMARAGVSIPEIMQAGGWTNVNIVMNYIRNLDSETGAMVRLLEDGDGGSHHH

HHH (SEQ ID NO: 263)

ATGGCGAGCAATTTACTGACCGTACACCAAAATTTGCCTGCATTGCCGGTCGATGCAACGAGTGATGA

GGTTCGCAAGAACCTGATGGACATGTTCAGGGATCGCCAGGCGTTTTCTGAGCATACCTGGAAAATGC

TTCTGTCCGTTTGCCGGTCGTGGGCGGCATGGTGCAAGTTGAATAACCGGAAATGGTTTCCCGCAGAA

CCTGAAGATGTTCGCGATTATCTTCTATATCTTCAGGCGCGCGGTCTGGCAGTAAAAACTATCCAGCAA

CATTTGGGCCAGCTAAACATGCTTCATCGTCGGTCCGGGCTGCCACGACCAAGTGACAGCAATGCTGT

TTCACTGGTTATGCGGCGTATCCGAAAAGAAAACGTTGATGCCGGTGAACGTGCAAAACAGGCTCTAG

CGTTCGAACGCACTGATTTCGACCAGGTTCGTTCACTCATGGAAAATAGCGATCGCTGCCAGGATATA

CGTAATCTGGCATTTCTGGGGATTGCTTATAACACCCTGTTACGTATAGCCGAAATTGCCAGGATCAGG

GTTAAAGATATCTCACGTACTGACGGTGGGAGAATGTTAATCCATATTGGCAGAACGAAAACGCTGGT

TAGCACCGCAGGTGTAGAGAAGGCACTTAGCCTGGGGGTAACTAAACTGGTCGAGCGATGGATTTCCG

TCTCTGGTGTAGCTGATGATCCGAATAACTACCTGTTTTGCCGGGTCAGAAAAAATGGTGTTGCCGCGC

CATCTGCCACCAGCCAGCTATCAACTCGCGCCCTGGAAGGGATTTTTGAAGCAACTCATCGATTGATTT

ACGGCGCTAAGGATGACTCTGGTCAGAGATACCTGGCCTGGTCTGGACACAGTGCCCGTGTCGGAGCC

GCGCGAGATATGGCCCGCGCTGGAGTTTCAATACCGGAGATCATGCAAGCTGGTGGCTGGACCAATGT

AAATATTGTCATGAACTATATCCGTAACCTGGATAGTGAAACAGGGGCAATGGTGCGCCTGCTGGAAG

ATGGCGACGGCGGATCCCATCACCACCACCATCAC (+36)GFP-Cre-6xHis (+36 GFP double-underlined;
6xHis tag underlined):

(SEQ ID NO: 33)

MGASKGERLFRGKVPILVELKGDVNGHKFSVRGKGKGDATRGKLTLKFICTTGKLPVPWPTLVTTLTYGV

QCFSRYPKHMKRHDFFKSAMPKGYVQERTISFKKDGKYKTRAEVKFEGRTLVNRIKLKGRDFKEKGNILG

HKLRYNFNSHKVYITADKRKNGIKAKFKIRHNVKDGSVQLADHYQQNTPIGRGPVLLPRNHYLSTRSKLS

-continued

KDPKEKRDHMVLLEFVTAAGIKHGRDERYKTGGSGGSGGSGGSGGSGGSGGSGGSGGTASNLLTVHQNLP

ALPVDATSDEVRKNLMDMFRDRQAFSEHTWKMLLSVCRSWAAWCKLNNRKWFPAEPEDVRDYLLYLQARG

LAVKTIQQHLGQLNMLHRRSGLPRPSDSNAVSLVMRRIRKENVDAGERAKQALAFERTDFDQVRSLMENS

DRCQDIRNLAFLGIAYNTLLRIAEIARIRVKDISRTDGGRMLIHIGRTKTLVSTAGVEKALSLGVTKLVE

RWISVSGVADDPNNYLFCRVRKNGVAAPSATSQLSTRALEGIFEATHRLIYGAKDDSGQRYLAWSGHSAR

VGAARDMARAGVSIPEIMQAGGWTNVNIVMNYIRNLDSETGAMVRLLEDGDGGSHHHHHH (-30)GFP-Cre-6xHis (-30 GFP double-underlined;
6xHis tag underlined):

(SEQ ID NO: 34)

MGASKGEELFDGVVPILVELDGDVNGHEFSVRGEGEGDATEGELTLKFICTTGELPVPWPTLVTTLTYGV

QCFSDYPDHMDQHDFFKSAMPEGYVQERTISFKDDGTYKTRAEVKFEGDTLVNRIELKGIDFKEDGNILG

HKLEYNFNSHDVYITADKQENGIKAEFEIRHNVEDGSVQLADHYQQNTPIGDGPVLLPDDHYLSTESALS

KDPNEDRDHMVLLEFVTAAGIDHGMDELYKTGGSGGSGGSGGSGGSGGSGGSGGSGGTASNLLTVHQNLP

ALPVDATSDEVRKNLMDMFRDRQAFSEHTWKMLLSVCRSWAAWCKLNNRKWFPAEPEDVRDYLLYLQARG

LAVKTIQQHLGQLNMLHRRSGLPRPSDSNAVSLVMRRIRKENVDAGERAKQALAFERTDFDQVRSLMENS

DRCQDIRNLAFLGIAYNTLLRIAEIARIRVKDISRTDGGRMLIHIGRTKTLVSTAGVEKALSLGVTKLVE

RWISVSGVADDPNNYLFCRVRKNGVAAPSATSQLSTRALEGIFEATHRLIYGAKDDSGQRYLAWSGHSAR

VGAARDMARAGVSIPEIMQAGGWTNVNIVMNYIRNLDSETGAMVRLLEDGDGGSHHHHHH (SEQ ID NO: 264)

ATGGGTGCTAGCAAAGGTGAAGAGCTGTTTGACGGTGTAGTACCGATCTTAGTGGAATTAGACGGCGA

CGTGAACGGTCACGAATTTAGCGTGCGCGGCGAGGGCGAAGGTGACGCTACCGAGGGTGAATTGACC

CTGAAGTTTATTTGCACAACAGGCGAATTACCCGTTCCGTGGCCCACCTTAGTGACCACCCTGACCTAT

GGCGTTCAGTGCTTCAGTGATTACCCAGATCATATGGATCAACACGATTTTTTCAAATCAGCCATGCCT

GAAGGATATGTTCAAGAGCGTACAATCAGCTTCAAGGACGATGGCACCTATAAAACGCGTGCGGAAG

TGAAATTTGAAGGCGACACATTAGTAAACCGTATCGAACTGAAAGGTATCGACTTCAAAGAAGACGG

CAACATTTTAGGCCATAAGCTGGAATATAACTTTAATTCTCATGACGTGTATATTACGGCCGATAAACA

GGAAAACGGTATCAAGGCAGAATTTGAAATTCGCCATAACGTGGAGGACGGCAGCGTTCAATTAGCG

GATCATTATCAACAAAACACGCCGATTGGTGATGGGCCTGTACTGTTACCTGACGATCACTACCTGAG

CACGGAGTCAGCCCTGAGCAAAGATCCGAACGAAGACCGCGATCACATGGTTCTGTTAGAATTCGTGA

CCGCTGCAGGCATTGATCATGGAATGGACGAGCTGTACAAGACCGGTGGTAGCGGTGGTTCTGGTGGT

TCTGGTGGTAGCGGCGGTAGCGGTGGTAGCGGTGGTAGCGGTGGCAGCGGCGGTACCGCGAGCAATT

TACTGACCGTACACCAAAATTTGCCTGCATTGCCGGTCGATGCAACGAGTGATGAGGTTCGCAAGAAC

CTGATGGACATGTTCAGGGATCGCCAGGCGTTTTCTGAGCATACCTGGAAAATGCTTCTGTCCGTTTGC

CGGTCGTGGGCGGCATGGTGCAAGTTGAATAACCGGAAATGGTTTCCCGCAGAACCTGAAGATGTTCG

CGATTATCTTCTATATCTTCAGGCGCGCGGTCTGGCAGTAAAAACTATCCAGCAACATTTGGGCCAGCT

AAACATGCTTCATCGTCGGTCCGGGCTGCCACGACCAAGTGACAGCAATGCTGTTTCACTGGTTATGC

GGCGTATCCGAAAAGAAAACGTTGATGCCGGTGAACGTGCAAAACAGGCTCTAGCGTTCGAACGCAC

TGATTTCGACCAGGTTCGTTCACTCATGGAAAATAGCGATCGCTGCCAGGATATACGTAATCTGGCATT

TCTGGGGATTGCTTATAACACCCTGTTACGTATAGCCGAAATTGCCAGGATCAGGGTTAAAGATATCT

CACGTACTGACGGTGGGAGAATGTTAATCCATATTGGCAGAACGAAAACGCTGGTTAGCACCGCAGGT

GTAGAGAAGGCACTTAGCCTGGGGGTAACTAAACTGGTCGAGCGATGGATTTCCGTCTCTGGTGTAGC

TGATGATCCGAATAACTACCTGTTTTGCCGGGTCAGAAAAAATGGTGTTGCCGCGCCATCTGCCACCA

-continued

GCCAGCTATCAACTCGCGCCCTGGAAGGGATTTTTGAAGCAACTCATCGATTGATTTACGGCGCTAAG

GATGACTCTGGTCAGAGATACCTGGCCTGGTCTGGACACAGTGCCCGTGTCGGAGCCGCGCGAGATAT

GGCCCGCGCTGGAGTTTCAATACCGGAGATCATGCAAGCTGGTGGCTGGACCAATGTAAATATTGTCA

TGAACTATATCCGTAACCTGGATAGTGAAACAGGGGCAATGGTGCGCCTGCTGGAAGATGGCGACGG

CGGATCCCATCACCACCACCATCAC (-7)GFP-Cre-6x His:

(SEQ ID NO: 265)

MGASKGEELFTGVVPILVELDGDVNGHKFSVRGEGEGDATNGKLTLKFICTTGKLPVPWPTLVTTLTYGV

QCFSRYPDHMKQHDFFKSAMPEGYVQERTISFKDDGTYKTRAEVKFEGDTLVNRIELKGIDFKEDGNILGH

KLEYNFNSHNVYITADKQKNGIKANFKIRHNVEDGSVQLADHYQQNTPIGDGPVLLPDNHYLSTQSALSKD

PNEKRDHMVLLEFVTAAGITHGMDELYKTGGSGGSGGSGGSGGSGGSGGSGGSGGTASNLLTVHQNLPAL

PVDATSDEVRKNLMDMFRDRQAFSEHTWKMLLSVCRSWAAWCKLNNRKWFPAEPEDVRDYLLYLQAR

GLAVKTIQQHLGQLNMLHRRSGLPRPSDSNAVSLVMRRIRKENVDAGERAKQALAFERTDFDQVRSLMEN

SDRCQDIRNLAFLGIAYNTLLRIAEIARIRVKDISRTDGGRMLIHIGRTKTLVSTAGVEKALSLGVTKLVERW

ISVSGVADDPNNYLFCRVRKNGVAAPSATSQLSTRALEGIFEATHRLIYGAKDDSGQRYLAWSGHSARVG

AARDMARAGVSIPEIMQAGGWTNVNIVMNYIRNLDSETGAMVRLLEDGDGGSHHHHHH (SEQ ID NO: 266)

ATGGGTGCTAGCAAAGGTGAAGAGCTGTTTACGGGTGTAGTACCGATCTTAGTGGAATTAGACGGCGA

CGTGAACGGTCACAAATTTAGCGTGCGCGGCGAAGGCGAAGGTGACGCTACCAATGGTAAATTGACC

CTGAAGTTTATTTGCACAACAGGCAAATTACCCGTTCCGTGGCCCACCTTAGTGACCACCCTGACCTAT

GGCGTTCAGTGCTTCAGTCGTTACCCAGATCATATGAAACAACACGATTTTTTCAAATCAGCCATGCCT

GAAGGATATGTTCAAGAGCGTACAATCAGCTTCAAGGACGATGGCACCTATAAAACGCGTGCGGAAG

TGAAATTTGAAGGCGACACATTAGTAAACCGTATCGAACTGAAAGGTATCGACTTCAAAGAAGACGG

CAACATTTTAGGCCATAAGCTGGAATATAACTTTAATTCTCATAACGTGTATATTACGGCCGATAAACA

GAAAAACGGTATCAAGGCAAATTTCAAAATTCGCCATAACGTGGAAGACGGCAGCGTTCAATTAGCG

GATCATTATCAACAAAACACGCCGATTGGTGACGGGCCTGTACTGTTACCTGACAACCACTACCTGAG

CACCCAGTCAGCACTGAGCAAAGATCCGAACGAAAAACGCGATCACATGGTTCTGTTAGAATTCGTGA

CCGCTGCAGGCATTACTCACGGAATGGACGAACTCTACAAGACCGGTGGTAGCGGTGGTTCTGGTGGT

TCTGGTGGTAGCGGCGGTAGCGGTGGTAGCGGTGGTAGCGGTGGCAGCGGCGGTACCGCGAGCAATT

TACTGACCGTACACCAAAATTTGCCTGCATTGCCGGTCGATGCAACGAGTGATGAGGTTCGCAAGAAC

CTGATGGACATGTTCAGGGATCGCCAGGCGTTTTCTGAGCATACCTGGAAAATGCTTCTGTCCGTTTGC

CGGTCGTGGGCGGCATGGTGCAAGTTGAATAACCGGAAATGGTTTCCCGCAGAACCTGAAGATGTTCG

CGATTATCTTCTATATCTTCAGGCGCGCGGTCTGGCAGTAAAAACTATCCAGCAACATTTGGGCCAGCT

AAACATGCTTCATCGTCGGTCCGGGCTGCCACGACCAAGTGACAGCAATGCTGTTTCACTGGTTATGC

GGCGTATCCGAAAAGAAAACGTTGATGCCGGTGAACGTGCAAAACAGGCTCTAGCGTTCGAACGCAC

TGATTTCGACCAGGTTCGTTCACTCATGGAAAATAGCGATCGCTGCCAGGATATACGTAATCTGGCATT

TCTGGGGATTGCTTATAACACCCTGTTACGTATAGCCGAAATTGCCAGGATCAGGGTTAAAGATATCT

CACGTACTGACGGTGGGAGAATGTTAATCCATATTGGCAGAACGAAAACGCTGGTTAGCACCGCAGGT

GTAGAGAAGGCACTTAGCCTGGGGGTAACTAAACTGGTCGAGCGATGGATTTCCGTCTCTGGTGTAGC

TGATGATCCGAATAACTACCTGTTTTGCCGGGTCAGAAAAAATGGTGTTGCCGCGCCATCTGCCACCA

GCCAGCTATCAACTCGCGCCCTGGAAGGGATTTTTGAAGCAACTCATCGATTGATTTACGGCGCTAAG

GATGACTCTGGTCAGAGATACCTGGCCTGGTCTGGACACAGTGCCCGTGTCGGAGCCGCGCGAGATAT

-continued

GGCCCGCGCTGGAGTTTCAATACCGGAGATCATGCAAGCTGGTGGCTGGACCAATGTAAATATTGTCA

TGAACTATATCCGTAACCTGGATAGTGAAACAGGGGCAATGGTGCGCCTGCTGGAAGATGGCGACGG

CGGATCCCATCACCACCACCATCAC (-20)GFP-Cre-6xHis:

(SEQ ID NO: 267)

MGASKGEELFTGVVPILVELDGDVNGHKFSVRGEGEGDATNGKLTLKFICTTGKLPVPWPTLVTTLTYGV

QCFSRYPDHMDQHDFFKSAMPEGYVQERTISFKDDGTYKTRAEVKFEGDTLVNRIELKGIDFKEDGNILGH

KLEYNFNSHDVYITADKQENGIKAEFEIRHNVEDGSVQLADHYQQNTPIGDGPVLLPDDHYLSTESALSKD

PNEDRDHMVLLEFVTAAGIDHGMDELYKTGGSGGSGGSGGSGGSGGSGGSGGSGGTASNLLTVHQNLPA

LPVDATSDEVRKNLMDMFRDRQAFSEHTWKMLLSVCRSWAAWCKLNNRKWFPAEPEDVRDYLLYLQAR

GLAVKTIQQHLGQLNMLHRRSGLPRPSDSNAVSLVMRRIRKENVDAGERAKQALAFERTDFDQVRSLMEN

SDRCQDIRNLAFLGIAYNTLLRIAEIARIRVKDISRTDGGRMLIHIGRTKTLVSTAGVEKALSLGVTKLVERW

ISVSGVADDPNNYLFCRVRKNGVAAPSATSQLSTRALEGIFEATHRLIYGAKDDSGQRYLAWSGHSARVG

AARDMARAGVSIPEIMQAGGWTNVNIVMNYIRNLDSETGAMVRLLEDGDGGSHHHHHH (SEQ ID NO:268)

ATGGGTGCTAGCAAAGGTGAAGAGCTGTTTACGGGTGTAGTACCGATCTTAGTGGAATTAGACGGCGA

CGTGAACGGTCACAAATTTAGCGTGCGCGGCGAAGGCGAAGGTGACGCTACCAATGGTAAATTGACC

CTGAAGTTTATTTGCACAACAGGCAAATTACCCGTTCCGTGGCCCACCTTAGTGACCACCCTGACCTAT

GGCGTTCAGTGCTTCAGTCGTTACCCAGATCATATGGATCAACACGATTTTTTCAAATCAGCCATGCCT

GAAGGATATGTTCAAGAGCGTACAATCAGCTTCAAGGACGATGGCACCTATAAAACGCGTGCGGAAG

TGAAATTTGAAGGCGACACATTAGTAAACCGTATCGAACTGAAAGGTATCGACTTCAAAGAAGACGG

CAACATTTTAGGCCATAAGCTGGAATATAACTTTAATTCTCATGACGTGTATATTACGGCCGATAAACA

GGAAAACGGTATCAAGGCAGAATTTGAAATTCGCCATAACGTGGAGGACGGCAGCGTTCAATTAGCG

GATCATTATCAACAAAACACGCCGATTGGTGATGGGCCTGTACTGTTACCTGACGATCACTACCTGAG

CACGGAGTCAGCCCTGAGCAAAGATCCGAACGAAGACCGCGATCACATGGTTCTGTTAGAATTCGTGA

CCGCTGCAGGCATTGATCATGGAATGGACGAGCTGTACAAGACCGGTGGTAGCGGTGGTTCTGGTGGT

TCTGGTGGTAGCGGCGGTAGCGGTGGTAGCGGTGGTAGCGGTGGCAGCGGCGGTACCGCGAGCAATT

TACTGACCGTACACCAAAATTTGCCTGCATTGCCGGTCGATGCAACGAGTGATGAGGTTCGCAAGAAC

CTGATGGACATGTTCAGGGATCGCCAGGCGTTTTCTGAGCATACCTGGAAAATGCTTCTGTCCGTTTGC

CGGTCGTGGGCGGCATGGTGCAAGTTGAATAACCGGAAATGGTTTCCCGCAGAACCTGAAGATGTTCG

CGATTATCTTCTATATCTTCAGGCGCGCGGTCTGGCAGTAAAAACTATCCAGCAACATTTGGGCCAGCT

AAACATGCTTCATCGTCGGTCCGGGCTGCCACGACCAAGTGACAGCAATGCTGTTTCACTGGTTATGC

GGCGTATCCGAAAAGAAAACGTTGATGCCGGTGAACGTGCAAAACAGGCTCTAGCGTTCGAACGCAC

TGATTTCGACCAGGTTCGTTCACTCATGGAAAATAGCGATCGCTGCCAGGATATACGTAATCTGGCATT

TCTGGGGATTGCTTATAACACCCTGTTACGTATAGCCGAAATTGCCAGGATCAGGGTTAAAGATATCT

CACGTACTGACGGTGGGAGAATGTTAATCCATATTGGCAGAACGAAAACGCTGGTTAGCACCGCAGGT

GTAGAGAAGGCACTTAGCCTGGGGGTAACTAAACTGGTCGAGCGATGGATTTCCGTCTCTGGTGTAGC

TGATGATCCGAATAACTACCTGTTTTGCCGGGTCAGAAAAAATGGTGTTGCCGCGCCATCTGCCACCA

GCCAGCTATCAACTCGCGCCCTGGAAGGGATTTTTGAAGCAACTCATCGATTGATTTACGGCGCTAAG

GATGACTCTGGTCAGAGATACCTGGCCTGGTCTGGACACAGTGCCCGTGTCGGAGCCGCGCGAGATAT

-continued

GGCCCGCGCTGGAGTTTCAATACCGGAGATCATGCAAGCTGGTGGCTGGACCAATGTAAATATTGTCA

TGAACTATATCCGTAACCTGGATAGTGAAACAGGGGCAATGGTGCGCCTGCTGGAAGATGGCGACGG

CGGATCCCATCACCACCACCATCAC (+36)GFP-PPARγ-TALE-2 (+36 GFP double-underlined;
6xHis tag underlined):

(SEQ ID NO: 36)

MGASKGERLFRGKVPILVELKGDVNGHKFSVRGKGKGDATRGKLTLKFICTTGKLPVPWPTLVTTLTYGV

QCFSRYPKHMKRHDFFKSAMPKGYVQERTISFKKDGKYKTRAEVKFEGRTLVNRIKLKGRDFKEKGNILG

HKLRYNFNSHKVYITADKRKNGIKAKFKIRHNVKDGSVQLADHYQQNTPIGRGPVLLPRNHYLSTRSKLS

KDPKEKRDHMVLLEFVTAAGIKHGRDERYKTGGSGGSGGSGGSGGSGGSGGSGGSGGTAPKKKRKVGIHR

GVPMVDLRTLGYSQQQQEKIKPKVRSTVAQHHEALVGHGFTHAHIVALSQHPAALGTVAVKYQDMIAALP

EATHEAIVGVGKQWSGARALEALLTVAGELRGPPLQLDTGQLLKIAKRGGVTAVEAVHAWRNALTGAPLN

LTPDQVVAIASNIGGKQALETVQRLLPVLCQDHGLTPEQVVAIASNIGGKQALETVQRLLPVLCQAHGLT

PDQVVAIASNGGGKQALETVQRLLPVLCQAHGLTPAQVVAIANNNGGKQALETVQRLLPVLCQDHGLTPD

QVVAIASNGGGKQALETVQRLLPVLCQDHGLTPEQVVAIASNIGGKQALETVQRLLPVLCQAHGLTPDQV

VAIASHDGGKQALETVQRLLPVLCQAHGLTPAQVVAIASHDGGKQALETVQRLLPVLCQDHGLTPDQVVA

IASNIGGKQALETVQRLLPVLCQDHGLTPEQVVAIASNIGGKQALETVQRLLPVLCQAHGLTPDQVVAIA

NNNGGKQALETVQRLLPVLCQAHGLTPAQVVAIASNGGGKQALETVQRLLPVLCQDHGLTPDQVVAIASH

DGGKQALETVQRLLPVLCQDHGLTPEQVVAIASNGGGKQALETVQRLLPVLCQAHGLTPDQVVAIASNGG

GKQALETVQRLLPVLCQAHGLTPAQVVAIANNNGGKQALETVQRLLPVLCQDHGLTPDQVVAIASHDGGK

QALETVQRLLPVLCQDHGLTPEQVVAIASHDGGKQALETVQRLLPVLCQAHGLTPEQVVAIASNIGGRPA

LESIVAQLSRPDPALAALTNDHLVALACLGGRPALDAVKKGLPHAPALIKRTNRRIPERTSHRVADHAQV

VRVLGFFQCHSHPAQAFDDAMTQFGMSGGGSGRADALDDFDLDMLGSDALDDFDLDMLGSDALDDFDLDM

LGSDALDDFDLDMLHHHHHH (+36)GFP-PRDM16_TALE-3(+36 GFP double-underlined;
6xHis tag underlined):

(SEQ ID NO: 37)

MGASKGERLFRGKVPILVELKGDVNGHKFSVRGKGKGDATRGKLTLKFICTTGKLPVPWPTLVTTLTYGV

QCFSRYPKHMKRHDFFKSAMPKGYVQERTISFKKDGKYKTRAEVKFEGRTLVNRIKLKGRDFKEKGNILG

HKLRYNFNSHKVYITADKRKNGIKAKFKIRHNVKDGSVQLADHYQQNTPIGRGPVLLPRNHYLSTRSKLS

KDPKEKRDHMVLLEFVTAAGIKHGRDERYKTGGSGGSGGSGGSGGSGGSGGSGGSGGTAPKKKRKVGIHR

GVPMVDLRTLGYSQQQQEKIKPKVRSTVAQHHEALVGHGFTHAHIVALSQHPAALGTVAVKYQDMIAALP

EATHEAIVGVGKQWSGARALEALLTVAGELRGPPLQLDTGQLLKIAKRGGVTAVEAVHAWRNALTGAPLN

LTPDQVVAIASNGGGKQALETVQRLLPVLCQDHGLTPEQVVAIANNNGGKQALETVQRLLPVLCQAHGLT

PDQVVAIANNNGGKQALETVQRLLPVLCQAHGLTPAQVVAIASHDGGKQALETVQRLLPVLCQDHGLTPD

QVVAIASHDGGKQALETVQRLLPVLCQDHGLTPEQVVAIASHDGGKQALETVQRLLPVLCQAHGLTPDQV

VAIASHDGGKQALETVQRLLPVLCQAHGLTPAQVVAIANNNGGKQALETVQRLLPVLCQDHGLTPDQVVA

IANNNGGKQALETVQRLLPVLCQDHGLTPEQVVAIASHDGGKQALETVQRLLPVLCQAHGLTPDQVVAIA

NNNGGKQALETVQRLLPVLCQAHGLTPAQVVAIASNIGGKQALETVQRLLPVLCQDHGLTPDQVVAIANN

NGGKQALETVQRLLPVLCQDHGLTPEQVVAIANNNGGKQALETVQRLLPVLCQAHGLTPDQVVAIANNNG

GKQALETVQRLLPVLCQAHGLTPAQVVAIANNNGGKQALETVQRLLPVLCQDHGLTPDQVVAIASNGGGK

-continued

QALETVQRLLPVLCQDHGLTPEQVVAIANNNGGKQALETVQRLLPVLCQAHGLTPEQVVAIASNGGGRPA

LESIVAQLSRPDPALAALTNDHLVALACLGGRPALDAVKKGLPHAPALIKRTNRRIPERTSHRVADHAQV

VRVLGFFQCHSHPAQAFDDAMTQFGMSGGGSGRADALDDFDLDMLGSDALDDFDLDMLGSDALDDFDLDM

LGSDALDDFDLDMLHHHHHH (-30)GFP-PPARγ-TALE-2 (-30 GFP double-underlined;
6xHis tag underlined):

(SEQ ID NO: 38)

MGASKGEELFDGVVPILVELDGDVNGHEFSVRGEGEGDATEGELTLKFICTTGELPVPWPTLVTTLTYGV

QCFSDYPDHMDQHDFFKSAMPEGYVQERTISFKDDGTYKTRAEVKFEGDTLVNRIELKGIDFKEDGNILG

HKLEYNFNSHDVYITADKQENGIKAEFEIRHNVEDGSVQLADHYQQNTPIGDGPVLLPDDHYLSTESALS

KDPNEDRDHMVLLEFVTAAGIDHGMDELYKAPKKKRKVGIHRGVPMVDLRTLGYSQQQQEKIKPKVRSTV

AQHHEALVGHGFTHAHIVALSQHPAALGTVAVKYQDMIAALPEATHEAIVGVGKQWSGARALEALLTVAG

ELRGPPLQLDTGQLLKIAKRGGVTAVEAVHAWRNALTGAPLNLTPDQVVAIASNIGGKQALETVQRLLPV

LCQDHGLTPEQVVAIASNIGGKQALETVQRLLPVLCQAHGLTPDQVVAIASNGGGKQALETVQRLLPVLC

QAHGLTPAQVVAIANNNGGKQALETVQRLLPVLCQDHGLTPDQVVAIASNGGGKQALETVQRLLPVLCQD

HGLTPEQVVAIASNIGGKQALETVQRLLPVLCQAHGLTPDQVVAIASHDGGKQALETVQRLLPVLCQAHG

LTPAQVVAIASHDGGKQALETVQRLLPVLCQDHGLTPDQVVAIASNIGGKQALETVQRLLPVLCQDHGLT

PEQVVAIASNIGGKQALETVQRLLPVLCQAHGLTPDQVVAIANNNGGKQALETVQRLLPVLCQAHGLTPA

QVVAIASNGGGKQALETVQRLLPVLCQDHGLTPDQVVAIASHDGGKQALETVQRLLPVLCQDHGLTPEQV

VAIASNGGGKQALETVQRLLPVLCQAHGLTPDQVVAIASNGGGKQALETVQRLLPVLCQAHGLTPAQVVA

IANNNGGKQALETVQRLLPVLCQDHGLTPDQVVAIASHDGGKQALETVQRLLPVLCQDHGLTPEQVVAIA

SHDGGKQALETVQRLLPVLCQAHGLTPEQVVAIASNIGGRPALESIVAQLSRPDPALAALTNDHLVALAC

LGGRPALDAVKKGLPHAPALIKRTNRRIPERTSHRVADHAQVVRVLGFFQCHSHPAQAFDDAMTQFGMSG

GGSGRADALDDFDLDMLGSDALDDFDLDMLGSDALDDFDLDMLGSDALDDFDLDMLHHHHHH (-30)GFP-PRDM16_TALE-3(-30 GFP double-underlined;
6xHis tag underlined):

(SEQ ID NO: 39)

MGASKGEELFDGVVPILVELDGDVNGHEFSVRGEGEGDATEGELTLKFICTTGELPVPWPTLVTTLTYGV

QCFSDYPDHMDQHDFFKSAMPEGYVQERTISFKDDGTYKTRAEVKFEGDTLVNRIELKGIDFKEDGNILG

HKLEYNFNSHDVYITADKQENGIKAEFEIRHNVEDGSVQLADHYQQNTPIGDGPVLLPDDHYLSTESALS

KDPNEDRDHMVLLEFVTAAGIDHGMDELYKAPKKKRKVGIHRGVPMVDLRTLGYSQQQQEKIKPKVRSTV

AQHHEALVGHGFTHAHIVALSQHPAALGTVAVKYQDMIAALPEATHEAIVGVGKQWSGARALEALLTVAG

ELRGPPLQLDTGQLLKIAKRGGVTAVEAVHAWRNALTGAPLNLTPDQVVAIASNGGGKQALETVQRLLPV

LCQDHGLTPEQVVAIANNNGGKQALETVQRLLPVLCQAHGLTPDQVVAIANNNGGKQALETVQRLLPVLC

QAHGLTPAQVVAIASHDGGKQALETVQRLLPVLCQDHGLTPDQVVAIASHDGGKQALETVQRLLPVLCQD

HGLTPEQVVAIASHDGGKQALETVQRLLPVLCQAHGLTPDQVVAIASHDGGKQALETVQRLLPVLCQAHG

LTPAQVVAIANNNGGKQALETVQRLLPVLCQDHGLTPDQVVAIANNNGGKQALETVQRLLPVLCQDHGLT

PEQVVAIASHDGGKQALETVQRLLPVLCQAHGLTPDQVVAIANNNGGKQALETVQRLLPVLCQAHGLTPA

QVVAIASNIGGKQALETVQRLLPVLCQDHGLTPDQVVAIANNNGGKQALETVQRLLPVLCQDHGLTPEQV

VAIANNNGGKQALETVQRLLPVLCQAHGLTPDQVVAIANNNGGKQALETVQRLLPVLCQAHGLTPAQVVA

IANNNGGKQALETVQRLLPVLCQDHGLTPDQVVAIASNGGGKQALETVQRLLPVLCQDHGLTPEQVVAIA

NNNGGKQALETVQRLLPVLCQAHGLTPEQVVAIASNGGGRPALESIVAQLSRPDPALAALTNDHLVALAC

LGGRPALDAVKKGLPHAPALIKRTNRRIPERTSHRVADHAQVVRVLGFFQCHSHPAQAFDDAMTQFGMSG

GGSGRADALDDFDLDMLGSDALDDFDLDMLGSDALDDFDLDMLGSDALDDFDLDMLHHHHHH

-continued (-30)GFP:

(SEQ ID NO: 40)

MGASKGEELFDGVVPILVELDGDVNGHEFSVRGEGEGDATEGELTLKFICTTGELPVPWPTLVTTLTYGV

QCFSDYPDHMDQHDFFKSAMPEGYVQERTISFKDDGTYKTRAEVKFEGDTLVNRIELKGIDFKEDGNILG

HKLEYNFNSHDVYITADKQENGIKAEFEIRHNVEDGSVQLADHYQQNTPIGDGPVLLPDDHYLSTESALS

KDPNEDRDHMVLLEFVTAAGIDHGMDELYK

N-terminal TALE domain:

(SEQ ID NO: 41)

APKKKRKVGIHRGVPMVDLRTLGYSQQQQEKIKPKVRSTVAQHHEALVGHGFTHAHIVALSQHPAALGTV

AVKYQDMIAALPEATHEAIVGVGKQWSGARALEALLTVAGELRGPPLQLDTGQLLKIAKRGGVTAVEAVH

AWRNALTGAPLNL

C-terminal TALE domain:

(SEQ ID NO: 42)

LESIVAQLSRPDPALAALTNDHLVALACLGGRPALDAVKKGLPHAPALIKRTNRRIPERTSHRVADHAQV

VRVLGFFQCHSHPAQAFDDAMTQFGMSGGGS

VP64 activation domain:

(SEQ ID NO: 35)

GRADALDDFDLDMLGSDALDDFDLDMLGSDALDDFDLDMLGSDALDDFDLDML

Compositions of Functional Effector Proteins and Cationic Polymers

Certain aspects of the disclosure relate to the use of cationic polymers for the delivery of effector proteins (e.g., nucleases, transcriptional activators/repressors, recombinases, Cas9 proteins including variants and fusions thereof, etc.), for example as opposed to delivering "naked" protein preparations. As with cationic lipids, aspects of the present disclosure relate to the recognition that anionic proteins or protein complexes (including those proteins associated with nucleic acids) can take advantage of electrostatics-driven encapsulation by and/or association with cationic polymers for delivery of functional effector proteins. While few proteins natively possess the density of negative charges found in the phosphate backbone of nucleic acids, translational fusion to, or non-covalent association with, an anionic carrier such as a negatively supercharged protein or a nucleic acid as described herein render the resulting effector protein or protein complex sufficiently anionic to drive efficient encapsulation/association of such protein cargoes by cationic polymers.

In some embodiments, association or fusion with an engineered supernegatively charged GFP is capable of driving efficient encapsulation/association and delivery of proteins into cultured mammalian cells by cationic polymers. In some embodiments, Cas9 protein associated with polyanionic guide RNAs (gRNA) can be efficiently delivered in functional form into mammalian cells using cationic polymers. Accordingly, in some embodiments, a composition comprising a Cas9 protein and a cationic polymer is provided, wherein the Cas9 protein is associated with a gRNA, and the composition is capable of delivering the Cas9 protein to the interior of a cell. In some embodiments, delivery of Cas9:gRNA complexes using cationic polymers results in at least a 2-fold, 3-fold, 4-fold, 5-fold, 6-fold, 7-fold, 8-fold, 9-fold, 10-fold, 11-fold, 12-fold, 13-fold, 14-fold, 15-fold, 20-fold or 25-fold or higher on-target:off-target modification ratio as compared with plasmid transfection of the Cas9 protein.

Accordingly, some aspects of the disclosure provide compositions comprising a Cas9 protein (e.g., as described herein; see e.g., Cas9 effector proteins below) and a cationic polymer capable of delivering the Cas9 protein to the interior of a cell. In some embodiments, the Cas9 protein is associated with a gRNA, which e.g., provides anionic charge to the complex thereby allowing the Cas9:gRNA complex to be encapsulated and/or associated with the cationic polymers. In some embodiments, the Cas9 protein need not be associated with a gRNA for effective encapsulation by and/or association with a cationic lipid, but instead is associated with a negatively supercharged protein, as described herein. In some embodiments where a Cas9 protein is associated with a negatively supercharged protein, the Cas9 protein is also associated with a gRNA. In some embodiments, the Cas9 protein is a wild type Cas9 protein, a fragment of a wild type Cas9 protein, or a variant of a wild type Cas9 protein. In some embodiments, the Cas9 protein comprises a dCas9 domain (e.g., as described herein). In some embodiments, the Cas9 protein is a fusion protein comprising a dCas9 domain (e.g., as described herein). In some embodiments, the Cas9 protein is a Cas9 nickase.

In other embodiments, compositions comprising an effector protein (e.g., other than a Cas9 protein) and a cationic polymer are provided which are capable of delivering the effector protein to the interior of a cell (e.g., to the nucleus of the cell). The effector protein is either naturally negatively charged, is modified to have a net overall negative charge, or is associated with a negatively supercharged protein, as described herein. In some embodiments, the effector protein is any effector protein described herein. In some embodiments, the effector protein is a recombinase, e.g., any recombinase described herein. In some embodiments, the recombinase is Cre recombinase. In some embodiments, the Cre recombinase comprises the amino acid sequence of SEQ ID NO:32 (e.g., with or without the 6×His tag). In some embodiments, the Cre recombinase comprises an amino acid sequence that is at least 80%, at least 85%, at least 90%, at least 95%, at least 98%, or at least 99% identical to the amino acid sequence of SEQ ID NO:32 (e.g., with or without the 6×His tag). In some embodiments, the Cre recombinase is fused to a supercharged protein (e.g., +36 GFP or −30 GFP). In some embodiments, the Cre recombinase fused to a supercharged protein comprises the amino acid sequence of SEQ ID NO:33 (e.g., with or without the 6×His tag) or SEQ ID NO:34 (e.g., with or without the 6×His tag), or comprises an amino acid sequence that is at least 80%, at least 85%, at least 90%, at least 95%, at least 98%, or at least 99% identical to the amino acid sequence of SEQ ID NO:33 or SEQ ID NO:34 (e.g., with or without the 6×His tag). In some embodiments, the effector protein is a TALE protein, (e.g., as described herein including those provided in the Examples). In some embodiments, the TALE protein comprises one or more of a VP64 transcriptional activator domain (e.g., SEQ ID NO:35). In some embodiments, the TALE protein with a VP64 transcriptional activator domain further comprises an amino acid sequence selected from the group consisting of SEQ ID NO:36-39 (e.g., with or without the 6×His tag). In some embodiments, the TALE protein with a VP64 transcriptional activator domain comprises an amino acid sequence that is at least 80%, at least 85%, at least 90%, at least 95%, at least 98%, or at least 99% identical to an amino acid sequence selected from the group consisting of SEQ ID NO:36-39 (e.g., with or without the 6×His tag). In some embodiments, the TALE effector protein comprises a (−30)GFP domain (e.g., SEQ ID NO:21 or SEQ ID NO:40), a N-terminal region of a TALE domain (e.g., SEQ ID NO:41), a variable repeat domain (e.g., an 18.5 mer repeat domain as provided in Maeder et al., "Robust, synergistic regulation of human gene expression using TALE activators." *Nat. Methods.* 2013; 10, 243-245), a C-terminal TALE domain (e.g., SEQ ID NO:42), a VP64 activation domain (e.g., SEQ ID NO:35), and optionally one or more linkers (e.g., GGS(9), SEQ ID NO: 252) between any domain and optionally a sequence tag (e.g., 6×His, SEQ ID NO: 253).

In some embodiments, the compositions comprising a Cas9 protein or other effector proteins described herein and a cationic polymer exhibit low toxicity when administered to a population of cells (e.g., in vitro or in vivo). In some embodiments, at least 60%, at least 65%, at least 70%, at least 75%, at least 80%, at least 85%, at least 90%, at least 95%, or at least 99% of the cells in a population are viable following administration of an inventive composition comprising a Cas9 protein or other effector protein and cationic polymers. Methods for assessing the toxicity of a composition when administered to a population of cells are well known in the art and include those described in the Examples.

Cas9 Effector Proteins

In some embodiments, effector proteins comprising a RNA-programmable protein (or fragment or variant thereof) is delivered to a target cell by a system or method provided herein. In some embodiments, an RNA-guided or RNA-programmable nuclease is delivered to a target cell by a system or method provided herein. In some embodiments, the RNA-programmable protein is a Cas9 nuclease, a Cas9 variant, or a fusion of a Cas9 protein, which is delivered to a target cell by a system or method provided herein.

In some embodiments, the RNA-programmable nuclease is a (CRISPR-associated system) Cas9 endonuclease, for example, Cas9 (Csn1) from *Streptococcus pyogenes* (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L. expand/collapse author list McLaughlin R. E., *Proc. Natl. Acad. Sci. U.S.A.* 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., *Nature* 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference. Because RNA-programmable nucleases (e.g., Cas9) use RNA:DNA hybridization to determine target DNA cleavage sites, these proteins are able to cleave, in principle, any sequence specified by the guide RNA. Methods of using RNA-programmable nucleases, such as Cas9, for site-specific cleavage (e.g., to modify a genome) are known in the art (see e.g., Cong, L. et al. Multiplex genome engineering using CRISPR/Cas systems. *Science* 339, 819-823 (2013); Mali, P. et al. RNA-guided human genome engineering via Cas9. *Science* 339, 823-826 (2013); Hwang, W. Y. et al. Efficient genome editing in zebrafish using a CRISPR-Cas system. *Nature biotechnology* 31, 227-229 (2013); Jinek, M. et al. RNA-programmed genome editing in human cells. eLife 2, e00471 (2013); Dicarlo, J. E. et al. Genome engineering in *Saccharomyces cerevisiae* using CRISPR-Cas systems. *Nucleic acids research* (2013); Jiang, W. et al. RNA-guided editing of bacterial genomes using CRISPR-Cas systems. *Nature biotechnology* 31, 233-239 (2013); the entire contents of each of which are incorporated herein by reference).

A Cas9 nuclease may also be referred to sometimes as a casn1 nuclease or a CRISPR (clustered regularly interspaced short palindromic repeat)-associated nuclease. CRISPR is an adaptive immune system that provides protection against mobile genetic elements (viruses, transposable elements and conjugative plasmids). CRISPR clusters contain spacers, sequences complementary to antecedent mobile elements, and target invading nucleic acids. CRISPR clusters are transcribed and processed into CRISPR RNA (crRNA). In type II CRISPR systems correct processing of pre-crRNA requires a trans-encoded small RNA (tracrRNA), endogenous ribonuclease 3 (rnc) and a Cas9 protein. The tracrRNA serves as a guide for ribonuclease 3-aided processing of pre-crRNA. Subsequently, Cas9/crRNA/tracrRNA endonucleolytically cleaves linear or circular dsDNA target complementary to the spacer. The target strand that is not complementary to the crRNA is first cut endonucleolytically, then trimmed 3'-5' exonucleolytically. In nature, DNA-binding and cleavage typically requires protein and both RNA. However, single guide RNAs ("sgRNA", or simply "gNRA") can be engineered so as to incorporate aspects of both the crRNA and tracrRNA into a single RNA species. See e.g., Jinek M., Chylinski K., Fonfara I., Hauer M., Doudna J. A., Charpentier E. *Science* 337:816-821(2012), the entire contents of which is hereby incorporated by reference. Cas9 recognizes a short motif in the CRISPR repeat sequences (the PAM or protospacer adjacent motif) to help distinguish self versus non-self. Cas9 nuclease sequences and structures are well known to those of skill in the art (see, e.g., "Complete genome sequence of an M1 strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L. expand/collapse author list McLaughlin R. E., *Proc. Natl. Acad. Sci. U.S.A.* 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., *Nature* 471:602-607(2011); and "A programmable dual-RNA-guided DNA endonuclease in adaptive bacterial immunity." Jinek M., Chylinski K., Fonfara I., Hauer M., Doudna J. A., Charpentier E. *Science* 337:816-821(2012), the entire contents of each of which are incorporated herein by reference).

Cas9 orthologs have been described in various species, including, but not limited to, *S. pyogenes* and *S. thermophilus*. Additional suitable Cas9 nucleases and sequences will be apparent to those of skill in the art based on this disclosure, and such Cas9 nucleases and sequences include Cas9 sequences from the organisms and loci disclosed in Chylinski, Rhun, and Charpentier, "The tracrRNA and Cas9 families of type II CRISPR-Cas immunity systems" (2013) *RNA Biology* 10:5, 726-737; the entire contents of which are incorporated herein by reference. In some embodiments, proteins comprising Cas9 proteins or fragments thereof are referred to as "Cas9 variants." A Cas9 variant shares homology to Cas9, or a fragment thereof. For example, a Cas9 variant is at least about 70% identical, at least about 80% identical, at least about 90% identical, at least about 95% identical, at least about 98% identical, at least about 99% identical, at least about 99.5% identical, or at least about 99.9% to wild type Cas9. In some embodiments, the Cas9 variant comprises a fragment of Cas9 (e.g., a gRNA binding domain or a DNA-cleavage domain, an N-terminal domain or a C-terminal domain, etc.), such that the fragment is at least about 70% identical, at least about 80% identical, at least about 90% identical, at least about 95% identical, at least about 98% identical, at least about 99% identical, at least about 99.5% identical, or at least about 99.9% to the corresponding fragment of wild type Cas9. In some embodiments, wild type Cas9 corresponds to Cas9 from *Streptococcus pyogenes* (NCBI Reference Sequence: NC_017053.1, SEQ ID NO:43 (nucleotide); SEQ ID NO:44 (amino acid)). In some embodiments, a Cas9 protein has an inactive (e.g., an inactivated) DNA cleavage domain. A nuclease-inactivated Cas9 protein may interchangeably be referred to as a "dCas9" protein (for nuclease "dead" Cas9). In some embodiments, dCas9 corresponds to, or comprises in part or in whole, the amino acid set forth as SEQ ID NO:45, below. In some embodiments, variants of dCas9 (e.g., variants of SEQ ID NO:45) are provided. For example, in some embodiments, variants having mutations other than D10A and H840A are provided, which result in nuclease inactivated Cas9 (dCas9). Such mutations, by way of example, include other amino acid substitutions at D10 and H840, or other substitutions within the nuclease domain of Cas9 (e.g., substitutions in the HNH nuclease subdomain and/or the RuvC1 subdomain). In some embodiments, variants or homologues of dCas9 (e.g., variants of SEQ ID NO:45) are provided which are at least about 70% identical, at least about 80% identical, at least about 90% identical, at least about 95% identical, at least about 98% identical, at least about 99% identical, at least about 99.5% identical, or at least about 99.9% to SEQ ID NO:45. In some embodiments, variants of dCas9 (e.g., variants of SEQ ID NO:45) are provided having amino acid sequences which are shorter, or longer than SEQ ID NO:45, by about 5 amino acids, by about 10 amino acids, by about 15 amino acids, by about 20 amino acids, by about 25 amino acids, by about 30 amino acids, by about 40 amino acids, by about 50 amino acids, by about 75 amino acids, by about 100 amino acids, or more. In some embodiments, Cas9 "nickases" are provided which comprise a mutation which inactivates a single nuclease domain in Cas9. Such nickases induce a single strand break in a target nucleic acid as opposed to a double strand break.

```
Cas9
                                                                 (SEQ ID NO: 43)
ATGGATAAGAAATACTCAATAGGCTTAGATATCGGCACAAATAGCGTCGGATGGGCGGTGATCACTGATGATTATAA

GGTTCCGTCTAAAAAGTTCAAGGTTCTGGGAAATACAGACCGCCACAGTATCAAAAAAAATCTTATAGGGGCTCTTT

TATTTGGCAGTGGAGAGACAGCGGAAGCGACTCGTCTCAAACGGACAGCTCGTAGAAGGTATACACGTCGGAAGAAT

CGTATTTGTTATCTACAGGAGATTTTTTCAAATGAGATGGCGAAAGTAGATGATAGTTTCTTTCATCGACTTGAAGA

GTCTTTTTTGGTGGAAGAAGACAAGAAGCATGAACGTCATCCTATTTTTGGAAATATAGTAGATGAAGTTGCTTATC

ATGAGAAATATCCAACTATCTATCATCTGCGAAAAAAATTGGCAGATTCTACTGATAAAGCGGATTTGCGCTTAATC

TATTTGGCCTTAGCGCATATGATTAAGTTTCGTGGTCATTTTTTGATTGAGGGAGATTTAAATCCTGATAATAGTGA

TGTGGACAAACTATTTATCCAGTTGGTACAAATCTACAATCAATTATTTGAAGAAAACCCTATTAACGCAAGTAGAG

TAGATGCTAAAGCGATTCTTTCTGCACGATTGAGTAAATCAAGACGATTAGAAAATCTCATTGCTCAGCTCCCCGGT

GAGAAGAGAAATGGCTTGTTTGGGAATCTCATTGCTTTGTCATTGGGATTGACCCCTAATTTTAAATCAAATTTTGA

TTTGGCAGAAGATGCTAAATTACAGCTTTCAAAAGATACTTACGATGATGATTTAGATAATTTATTGGCGCAAATTG

GAGATCAATATGCTGATTTGTTTTTGGCAGCTAAGAATTTATCAGATGCTATTTTACTTTCAGATATCCTAAGAGTA

AATAGTGAAATAACTAAGGCTCCCCTATCAGCTTCAATGATTAAGCGCTACGATGAACATCATCAAGACTTGACTCT

TTTAAAAGCTTTAGTTCGACAACAACTTCCAGAAAAGTATAAAGAAATCTTTTTTGATCAATCAAAAAACGGATATG

CAGGTTATATTGATGGGGGAGCTAGCCAAGAAGAATTTTATAAATTTATCAAACCAATTTTAGAAAAAATGGATGGT

ACTGAGGAATTATTGGTGAAACTAAATCGTGAAGATTTGCTGCGCAAGCAACGGACCTTTGACAACGGCTCTATTCC

CCATCAAATTCACTTGGGTGAGCTGCATGCTATTTTGAGAAGACAAGAAGACTTTTATCCATTTTTAAAAGACAATC

GTGAGAAGATTGAAAAAATCTTGACTTTTCGAATTCCTTATTATGTTGGTCCATTGGCGCGTGGCAATAGTCGTTTT

GCATGGATGACTCGGAAGTCTGAAGAAACAATTACCCCATGGAATTTTGAAGAAGTTGTCGATAAAGGTGCTTCAGC
```

-continued

TCAATCATTTATTGAACGCATGACAAACTTTGATAAAAATCTTCCAAATGAAAAAGTACTACCAAAACATAGTTTGC

TTTATGAGTATTTTACGGTTTATAACGAATTGACAAAGGTCAAATATGTTACTGAGGGAATGCGAAAACCAGCATTT

CTTTCAGGTGAACAGAAGAAAGCCATTGTTGATTTACTCTTCAAAACAAATCGAAAAGTAACCGTTAAGCAATTAAA

AGAAGATTATTTCAAAAAAATAGAATGTTTTGATAGTGTTGAAATTTCAGGAGTTGAAGATAGATTTAATGCTTCAT

TAGGCGCCTACCATGATTTGCTAAAAATTATTAAAGATAAAGATTTTTTGGATAATGAAGAAAATGAAGATATCTTA

GAGGATATTGTTTTAACATTGACCTTATTTGAAGATAGGGGGATGATTGAGGAAAGACTTAAAACATATGCTCACCT

CTTTGATGATAAGGTGATGAAACAGCTTAAACGTCGCCGTTATACTGGTTGGGGACGTTTGTCTCGAAAATTGATTA

ATGGTATTAGGGATAAGCAATCTGGCAAAACAATATTAGATTTTTTGAAATCAGATGGTTTTGCCAATCGCAATTTT

ATGCAGCTGATCCATGATGATAGTTTGACATTTAAAGAAGATATTCAAAAAGCACAGGTGTCTGGACAAGGCCATAG

TTTACATGAACAGATTGCTAACTTAGCTGGCAGTCCTGCTATTAAAAAAGGTATTTTACAGACTGTAAAAATTGTTG

ATGAACTGGTCAAAGTAATGGGGCATAAGCCAGAAAATATCGTTATTGAAATGGCACGTGAAAATCAGACAACTCAA

AAGGGCCAGAAAAATTCGCGAGAGCGTATGAAACGAATCGAAGAAGGTATCAAAGAATTAGGAAGTCAGATTCTTAA

AGAGCATCCTGTTGAAAATACTCAATTGCAAAATGAAAAGCTCTATCTCTATTATCTACAAAATGGAAGAGACATGT

ATGTGGACCAAGAATTAGATATTAATCGTTTAAGTGATTATGATGTCGATCACATTGTTCCACAAAGTTTCATTAAA

GACGATTCAATAGACAATAAGGTACTAACGCGTTCTGATAAAAATCGTGGTAAATCGGATAACGTTCCAAGTGAAGA

AGTAGTCAAAAAGATGAAAAACTATTGGAGACAACTTCTAAACGCCAAGTTAATCACTCAACGTAAGTTTGATAATT

TAACGAAAGCTGAACGTGGAGGTTTGAGTGAACTTGATAAAGCTGGTTTTATCAAACGCCAATTGGTTGAAACTCGC

CAAATCACTAAGCATGTGGCACAAATTTTGGATAGTCGCATGAATACTAAATACGATGAAAATGATAAACTTATTCG

AGAGGTTAAAGTGATTACCTTAAAATCTAAATTAGTTTCTGACTTCCGAAAAGATTTCCAATTCTATAAAGTACGTG

AGATTAACAATTACCATCATGCCCATGATGCGTATCTAAATGCCGTCGTTGGAACTGCTTTGATTAAGAAATATCCA

AAACTTGAATCGGAGTTTGTCTATGGTGATTATAAAGTTTATGATGTTCGTAAAATGATTGCTAAGTCTGAGCAAGA

AATAGGCAAAGCAACCGCAAAATATTTCTTTTACTCTAATATCATGAACTTCTTCAAAACAGAAATTACACTTGCAA

ATGGAGAGATTCGCAAACGCCCTCTAATCGAAACTAATGGGGAAACTGGAGAAATTGTCTGGGATAAAGGGCGAGAT

TTTGCCACAGTGCGCAAAGTATTGTCCATGCCCCAAGTCAATATTGTCAAGAAAACAGAAGTACAGACAGGCGGATT

CTCCAAGGAGTCAATTTTACCAAAAAGAAATTCGGACAAGCTTATTGCTCGTAAAAAAGACTGGGATCCAAAAAAAT

ATGGTGGTTTTGATAGTCCAACGGTAGCTTATTCAGTCCTAGTGGTTGCTAAGGTGGAAAAAGGGAAATCGAAGAAG

TTAAAATCCGTTAAAGAGTTACTAGGGATCACAATTATGGAAAGAAGTTCCTTTGAAAAAAATCCGATTGACTTTTT

AGAAGCTAAAGGATATAAGGAAGTTAAAAAAGACTTAATCATTAAACTACCTAAATATAGTCTTTTTGAGTTAGAAA

ACGGTCGTAAACGGATGCTGGCTAGTGCCGGAGAATTACAAAAAGGAAATGAGCTGGCTCTGCCAAGCAAATATGTG

AATTTTTTATATTTAGCTAGTCATTATGAAAAGTTGAAGGGTAGTCCAGAAGATAACGAACAAAAACAATTGTTTGT

GGAGCAGCATAAGCATTATTTAGATGAGATTATTGAGCAAATCAGTGAATTTTCTAAGCGTGTTATTTTAGCAGATG

CCAATTTAGATAAAGTTCTTAGTGCATATAACAAACATAGAGACAAACCAATACGTGAACAAGCAGAAAATATTATT

CATTTATTTACGTTGACGAATCTTGGAGCTCCCGCTGCTTTTAAATATTTTGATACAACAATTGATCGTAAACGATA

TACGTCTACAAAAGAAGTTTTAGATGCCACTCTTATCCATCAATCCATCACTGGTCTTTATGAAACACGCATTGATT

TGAGTCAGCTAGGAGGTGACTGA (SEQ ID NO: 44)

MDKKYSIGLAIGTNSVGWAVITDEYKVPSKKFKVLGNTDRHSIKKNLIGALLFDSGETAEATRLKRTARRRYTRRKN

RICYLQEIFSNEMAKVDDSFFHRLEESFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASGVDAKAILSARLSKSRRLENLIAQLPG

EKKNGLFGNLIALSLGLTPNFKSNFDLAEDAKLQLSKDTYDDDLDNLLAQIGDQYADLFLAAKNLSDAILLSDILRV

NTEITKAPLSASMIKRYDEHHQDLTLLKALVRQQLPEKYKEIFFDQSKNGYAGYIDGGASQEEFYKFIKPILEKMDG

-continued

TEELLVKLNREDLLRKQRTFDNGSIPHQIHLGELHAILRRQEDFYPFLKDNREKIEKILTFRIPYYVGPLARGNSRF

AWMTRKSEETITPWNFEEVVDKGASAQSFIERMTNFDKNLPNEKVLPKHSLLYEYFTVYNELTKVKYVTEGMRKPAF

LSGEQKKAIVDLLFKTNRKVTVKQLKEDYFKKIECFDSVEISGVEDRFNASLGTYHDLLKIIKDKDFLDNEENEDIL

EDIVLTLTLFEDREMIEERLKTYAHLFDDKVMKQLKRRRYTGWGRLSRKLINGIRDKQSGKTILDFLKSDGFANRNF

MQLIHDDSLTFKEDIQKAQVSGQGDSLHEHIANLAGSPAIKKGILQTVKVVDELVKVMGRHKPENIVIEMARENQTT

QKGQKNSRERMKRIEEGIKELGSQILKEHPVENTQLQNEKLYLYYLQNGRDMYVDQELDINRLSDYDVDHIVPQSFL

KDDSIDNKVLTRSDKNRGKSDNVPSEEVVKKMKNYWRQLLNAKLITQRKFDNLTKAERGGLSELDKAGFIKRQLVET

RQITKHVAQILDSRMNTKYDENDKLIREVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEITLANGEIRKRPLIETNGETGEIVWDKGR

DFATVRKVLSMPQVNIVKKTEVQTGGFSKESILPKRNSDKLIARKKDWDPKKYGGFDSPTVAYSVLVVAKVEKGKSK

KLKSVKELLGITIMERSSFEKNPIDFLEAKGYKEVKKDLIIKLPKYSLFELENGRKRMLASAGELQKGNELALPSKY

VNFLYLASHYEKLKGSPEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGD
(single underline: HNH domain; double underline: RuvC domain)

dCas9 (D10A and H840A):

(SEQ ID NO: 45)

MDKKYSIGLAIGTNSVGWAVITDEYKVPSKKFKVLGNTDRHSIKKNLIGALLFDSGETAEATRLKRTARRRYTRRKN

RICYLQEIFSNEMAKVDDSFFHRLEESFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASGVDAKAILSARLSKSRRLENLIAQLPG

EKKNGLFGNLIALSLGLTPNFKSNFDLAEDAKLQLSKDTYDDDLDNLLAQIGDQYADLFLAAKNLSDAILLSDILRV

NTEITKAPLSASMIKRYDEHHQDLTLLKALVRQQLPEKYKEIFFDQSKNGYAGYIDGGASQEEFYKFIKPILEKMDG

TEELLVKLNREDLLRKQRTFDNGSIPHQIHLGELHAILRRQEDFYPFLKDNREKIEKILTFRIPYYVGPLARGNSRF

AWMTRKSEETITPWNFEEVVDKGASAQSFIERMTNFDKNLPNEKVLPKHSLLYEYFTVYNELTKVKYVTEGMRKPAF

LSGEQKKAIVDLLFKTNRKVTVKQLKEDYFKKIECFDSVEISGVEDRFNASLGTYHDLLKIIKDKDFLDNEENEDIL

EDIVLTLTLFEDREMIEERLKTYAHLFDDKVMKQLKRRRYTGWGRLSRKLINGIRDKQSGKTILDFLKSDGFANRNF

MQLIHDDSLTFKEDIQKAQVSGQGDSLHEHIANLAGSPAIKKGILQTVKVVDELVKVMGRHKPENIVIEMARENQTT

QKGQKNSRERMKRIEEGIKELGSQILKEHPVENTQLQNEKLYLYYLQNGRDMYVDQELDINRLSDYDVDAIVPQSFL

KDDSIDNKVLTRSDKNRGKSDNVPSEEVVKKMKNYWRQLLNAKLITQRKFDNLTKAERGGLSELDKAGFIKRQLVET

RQITKHVAQILDSRMNTKYDENDKLIREVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEITLANGEIRKRPLIETNGETGEIVWDKGR

DFATVRKVLSMPQVNIVKKTEVQTGGFSKESILPKRNSDKLIARKKDWDPKKYGGFDSPTVAYSVLVVAKVEKGKSK

KLKSVKELLGITIMERSSFEKNPIDFLEAKGYKEVKKDLIIKLPKYSLFELENGRKRMLASAGELQKGNELALPSKY

VNFLYLASHYEKLKGSPEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGD
(single underline: HNH domain; double underline: RuvC domain)

Cas9 nickase (D10A):

(SEQ ID NO: 46)

MDKKYSIGLAIGTNSVGWAVITDEYKVPSKKFKVLGNTDRHSIKKNLIGALLFDSGETAEATRLKRTARRRYTRRKN

RICYLQEIFSNEMAKVDDSFFHRLEESFLVEEDKKHERHPIFGNIVDEVAYHEKYPTIYHLRKKLVDSTDKADLRLI

YLALAHMIKFRGHFLIEGDLNPDNSDVDKLFIQLVQTYNQLFEENPINASGVDAKAILSARLSKSRRLENLIAQLPG

EKKNGLFGNLIALSLGLTPNFKSNFDLAEDAKLQLSKDTYDDDLDNLLAQIGDQYADLFLAAKNLSDAILLSDILRV

NTEITKAPLSASMIKRYDEHHQDLTLLKALVRQQLPEKYKEIFFDQSKNGYAGYIDGGASQEEFYKFIKPILEKMDG

TEELLVKLNREDLLRKQRTFDNGSIPHQIHLGELHAILRRQEDFYPFLKDNREKIEKILTFRIPYYVGPLARGNSRF

AWMTRKSEETITPWNFEEVVDKGASAQSFIERMTNFDKNLPNEKVLPKHSLLYEYFTVYNELTKVKYVTEGMRKPAF

-continued

```
LSGEQKKAIVDLLFKTNRKVTVKQLKEDYFKKIECFDSVEISGVEDRFNASLGTYHDLLKIIKDKDFLDNEENEDIL

EDIVLTLTLFEDREMIEERLKTYAHLFDDKVMKQLKRRRYTGWGRLSRKLINGIRDKQSGKTILDFLKSDGFANRNF

MQLIHDDSLTFKEDIQKAQVSGQGDSLHEHIANLAGSPAIKKGILQTVKVVDELVKVMGRHKPENIVIEMARENQTT

QKGQKNSRERMKRIEEGIKELGSQILKEHPVENTQLQNEKLYLYYLQNGRDMYVDQELDINRLSDYDVDHIVPQSFL

KDDSIDNKVLTRSDKNRGKSDNVPSEEVVKKMKNYWRQLLNAKLITQRKFDNLTKAERGGLSELDKAGFIKRQLVET

RQITKHVAQILDSRMNTKYDENDKLIREVKVITLKSKLVSDFRKDFQFYKVREINNYHHAHDAYLNAVVGTALIKKY

PKLESEFVYGDYKVYDVRKMIAKSEQEIGKATAKYFFYSNIMNFFKTEITLANGEIRKRPLIETNGETGEIVWDKGR

DFATVRKVLSMPQVNIVKKTEVQTGGFSKESILPKRNSDKLIARKKDWDPKKYGGFDSPTVAYSVLVVAKVEKGKSK

KLKSVKELLGITIMERSSFEKNPIDFLEAKGYKEVKKDLIIKLPKYSLFELENGRKRMLASAGELQKGNELALPSKY

VNFLYLASHYEKLKGSPEDNEQKQLFVEQHKHYLDEIIEQISEFSKRVILADANLDKVLSAYNKHRDKPIREQAENI

IHLFTLTNLGAPAAFKYFDTTIDRKRYTSTKEVLDATLIHQSITGLYETRIDLSQLGGD
```

In some embodiments, fusion proteins comprising a Cas9 protein are provided for use in any of the compositions and methods described herein. In some embodiments, the fusion protein comprises a dCas9 protein (e.g., as described herein). In some embodiments, the fusion protein comprises a linker (e.g., as described herein) between dCas9 and one or more domains (e.g., enzymatic domains). In some embodiments, the fusion protein comprises dCas9 and a transcriptional activator domain, a transcriptional repressor domain, a recombinase domain, a gene editing domain (e.g., a deaminase domain), or an epigenetic modifier domain.

In some embodiments, the general architecture of exemplary fusion proteins provided herein comprises the structure:

[$NH_2$]-[enzymatic domain]-[dCas9]-[COOH] or

[$NH_2$]-[dCas9]-[enzymatic domain]-[COOH];

wherein $NH_2$ is the N-terminus of the fusion protein, COOH is the C-terminus of the fusion protein, and the enzymatic domain comprises a nuclease domain (e.g., FokI), a recombinase catalytic domain (e.g., Hin, Gin, or Tn3 recombinase domains), a nucleic acid-editing domain (e.g., a deaminase domain), a transcriptional activator domain (e.g., VP64, p65), a transcriptional repressor domain (e.g., KRAB, SID), or an epigenetic modifier (e.g., LSD1 histone demethylase, TET1 hydroxylase).

Additional features may be present, for example, one or more linker sequences between certain domains. Other exemplary features that may be present are localization sequences, such as nuclear localization sequences (NLS; e.g., MAPKKKRKVGIHRGVP (SEQ ID NO:47)); cytoplasmic localization sequences; export sequences, such as nuclear export sequences; or other localization sequences, as well as sequence tags that are useful for solubilization, purification, or detection of the fusion proteins. Suitable localization signal sequences and sequences of protein tags are provided herein and are known in the art, and include, but are not limited to, biotin carboxylase carrier protein (BCCP) tags, myc-tags, calmodulin-tags, FLAG-tags (e.g., 3×FLAG TAG: MDYKDHDGDYKDHDIDYKDDDDK (SEQ ID NO:48)), hemagglutinin (HA) tags, polyhistidine tags, also referred to as histidine tags or His-tags, maltose binding protein (MBP)-tags, nus-tags, glutathione-S-transferase (GST) tags, green fluorescent protein (GFP) tags, thioredoxin-tags, S-tags, Softags (e.g., Softag 1, Softag 3), strep-tags, biotin ligase tags, FlAsH tags, V5 tags, and SBP-tags. Additional suitable sequences will be apparent to those of skill in the art.

In some embodiments, the enzymatic domain comprises a nuclease or a catalytic domain thereof. For example, in some embodiments, the general architecture of exemplary ligand-dependent dCas9 fusion proteins with a nuclease domain comprises the structure:

[$NH_2$]-[NLS]-[dCas9]-[nuclease]-[COOH],

[$NH_2$]-[NLS]-[nuclease]-[dCas9]-[COOH],

[$NH_2$]-[dCas9]-[nuclease]-[COOH], or

[$NH_2$]-[nuclease]-[dCas9]-[COOH];

wherein NLS is a nuclear localization signal, $NH_2$ is the N-terminus of the fusion protein, and COOH is the C-terminus of the fusion protein. In some embodiments, a linker is inserted between the dCas9 and the nuclease domain. In some embodiments, a linker is inserted between the NLS and the nuclease and/or dCas9 domain. In some embodiments, the NLS is located C-terminal of the nuclease and/or the dCas9 domain. In some embodiments, the NLS is located between the nuclease and the dCas9 domain. Additional features, such as sequence tags, may also be present. In some aspects, the nuclease domain is a nuclease requiring dimerization (e.g., the coming together of two monomers of the nuclease) in order to cleave a target nucleic acid (e.g., DNA). In some embodiments, the nuclease domain is a monomer of the FokI DNA cleavage domain. The FokI DNA cleavage domain is known, and in some aspects corresponds to amino acids 388-583 of FokI (NCBI accession number J04623). In some embodiments, the FokI DNA cleavage domain corresponds to amino acids 300-583, 320-583, 340-583, or 360-583 of FokI. See also Wah et al., "Structure of FokI has implications for DNA cleavage" *Proc. Natl. Acad. Sci. USA.* 1998; 1; 95(18):10564-9; Li et al., "TAL nucleases (TALNs): hybrid proteins composed of TAL effectors and FokI DNA-cleavage domain" *Nucleic Acids Res.* 2011; 39(1):359-72; Kim et al., "Hybrid restriction enzymes: zinc finger fusions to Fok I cleavage domain" *Proc. Natl Acad. Sci. USA.* 1996; 93:1156-1160; the entire contents of each are herein incorporated by reference). In some embodiments, the FokI DNA cleavage domain corresponds to, or comprises in part or whole, the amino acid sequence set forth as SEQ ID NO:49. In some embodiments, the FokI DNA cleavage domain is a variant of FokI (e.g., a variant of SEQ ID NO:49), as described herein. Other exemplary compositions and methods of using dCas9-nuclease fusion proteins can be found in U.S. patent application Ser. No. 14/320,498; titled "Cas9-FokI fusion Proteins and Uses Thereof," filed Jun. 30, 2014; the entire contents of which are incorporated herein by reference.

FokI nuclease domain:

(SEQ ID NO: 49)

GSQLVKSELEEKKSELRHKLKYVPHEYIELIEIARNSTQDRILEMKVMEFFMKVYGYRGKHLGGSRKPDGAIYTVGS

PIDYGVIVDTKAYSGGYNLPIGQADEMQRYVEENQTRNKHINPNEWWKVYPSSVTEFKFLFVSGHFKGNYKAQLTRL

NHITNCNGAVLSVEELLIGGEMIKAGTLTLEEVRRKFNNGEINF fCas9 (e.g., dCas9-NLS-GGS3linker-FokI):

(SEQ ID NO: 50)

ATGGATAAAAAGTATTCTATTGGTTTAGCTATCGGCACTAATTCCGTTGGATGGGCTGTCATAACCGATGAATACAA

AGTACCTTCAAAGAAATTTAAGGTGTTGGGGAACACAGACCGTCATTCGATTAAAAAGAATCTTATCGGTGCCCTCC

TATTCGATAGTGGCGAAACGGCAGAGGCGACTCGCCTGAAACGAACCGCTCGGAGAAGGTATACACGTCGCAAGAAC

CGAATATGTTACTTACAAGAAATTTTTAGCAATGAGATGGCCAAAGTTGACGATTCTTTCTTTCACCGTTTGGAAGA

GTCCTTCCTTGTCGAAGAGGACAAGAAACATGAACGGCACCCCATCTTTGGAAACATAGTAGATGAGGTGGCATATC

ATGAAAAGTACCCAACGATTTATCACCTCAGAAAAAAGCTAGTTGACTCAACTGATAAAGCGGACCTGAGGTTAATC

TACTTGGCTCTTGCCCATATGATAAAGTTCCGTGGGCACTTTCTCATTGAGGGTGATCTAAATCCGGACAACTCGGA

TGTCGACAAACTGTTCATCCAGTTAGTACAAACCTATAATCAGTTGTTTGAAGAGAACCCTATAAATGCAAGTGGCG

TGGATGCGAAGGCTATTCTTAGCGCCCGCCTCTCTAAATCCCGACGGCTAGAAAACCTGATCGCACAATTACCCGGA

GAGAAGAAAAATGGGTTGTTCGGTAACCTTATAGCGCTCTCACTAGGCCTGACACCAAATTTTAAGTCGAACTTCGA

CTTAGCTGAAGATGCCAAATTGCAGCTTAGTAAGGACACGTACGATGACGATCTCGACAATCTACTGGCACAAATTG

GAGATCAGTATGCGGACTTATTTTTGGCTGCCAAAAACCTTAGCGATGCAATCCTCCTATCTGACATACTGAGAGTT

AATACTGAGATTACCAAGGCGCCGTTATCCGCTTCAATGATCAAAAGGTACGATGAACATCACCAAGACTTGACACT

TCTCAAGGCCCTAGTCCGTCAGCAACTGCCTGAGAAATATAAGGAAATATTCTTTGATCAGTCGAAAAACGGGTACG

CAGGTTATATTGACGGCGGAGCGAGTCAAGAGGAATTCTACAAGTTTATCAAACCCATATTAGAGAAGATGGATGGG

ACGGAAGAGTTGCTTGTAAAACTCAATCGCGAAGATCTACTGCGAAAGCAGCGGACTTTCGACAACGGTAGCATTCC

ACATCAAATCCACTTAGGCGAATTGCATGCTATACTTAGAAGGCAGGAGGATTTTTATCCGTTCCTCAAAGACAATC

GTGAAAAGATTGAGAAAATCCTAACCTTTCGCATACCTTACTATGTGGGACCCCTGGCCCGAGGGAACTCTCGGTTC

GCATGGATGACAAGAAAGTCCGAAGAAACGATTACTCCATGGAATTTTGAGGAAGTTGTCGATAAAGGTGCGTCAGC

TCAATCGTTCATCGAGAGGATGACCAACTTTGACAAGAATTTACCGAACGAAAAAGTATTGCCTAAGCACAGTTTAC

TTTACGAGTATTTCACAGTGTACAATGAACTCACGAAAGTTAAGTATGTCACTGAGGGCATGCGTAAACCCGCCTTT

CTAAGCGGAGAACAGAAGAAAGCAATAGTAGATCTGTTATTCAAGACCAACCGCAAAGTGACAGTTAAGCAATTGAA

AGAGGACTACTTTAAGAAAATTGAATGCTTCGATTCTGTCGAGATCTCCGGGGTAGAAGATCGATTTAATGCGTCAC

TTGGTACGTATCATGACCTCCTAAAGATAATTAAAGATAAGGACTTCCTGGATAACGAAGAGAATGAAGATATCTTA

GAAGATATAGTGTTGACTCTTACCCTCTTTGAAGATCGGGAAATGATTGAGGAAAGACTAAAAACATACGCTCACCT

GTTCGACGATAAGGTTATGAAACAGTTAAAGAGGCGTCGCTATACGGGCTGGGGACGATTGTCGCGGAAACTTATCA

ACGGGATAAGAGACAAGCAAAGTGGTAAAACTATTCTCGATTTTCTAAAGAGCGACGGCTTCGCCAATAGGAACTTT

ATGCAGCTGATCCATGATGACTCTTTAACCTTCAAAGAGGATATACAAAAGGCACAGGTTTCCGGACAAGGGGACTC

ATTGCACGAACATATTGCGAATCTTGCTGGTTCGCCAGCCATCAAAAAGGGCATACTCCAGACAGTCAAAGTAGTGG

ATGAGCTAGTTAAGGTCATGGGACGTCACAAACCGGAAAACATTGTAATCGAGATGGCACGCGAAAATCAAACGACT

CAGAAGGGGCAAAAAAACAGTCGAGAGCGGATGAAGAGAATAGAAGAGGGTATTAAAGAACTGGGCAGCCAGATCTT

AAAGGAGCATCCTGTGGAAAATACCCAATTGCAGAACGAGAAACTTTACCTCTATTACCTACAAAATGGAAGGGACA

TGTATGTTGATCAGGAACTGGACATAAACCGTTTATCTGATTACGACGTCGATGCCATTGTACCCCAATCCTTTTTG

AAGGACGATTCAATCGACAATAAAGTGCTTACACGCTCGGATAAGAACCGAGGGAAAAGTGACAATGTTCCAAGCGA

GGAAGTCGTAAAGAAAATGAAGAACTATTGGCGGCAGCTCCTAAATGCGAAACTGATAACGCAAAGAAAGTTCGATA

ACTTAACTAAAGCTGAGAGGGGTGGCTTGTCTGAACTTGACAAGGCCGGATTTATTAAACGTCAGCTCGTGGAAACC

-continued

CGCCAAATCACAAAGCATGTTGCACAGATACTAGATTCCCGAATGAATACGAAATACGACGAGAACGATAAGCTGAT

TCGGGAAGTCAAAGTAATCACTTTAAAGTCAAAATTGGTGTCGGACTTCAGAAAGGATTTTCAATTCTATAAAGTTA

GGGAGATAAATAACTACCACCATGCGCACGACGCTTATCTTAATGCCGTCGTAGGGACCGCACTCATTAAGAAATAC

CCGAAGCTAGAAAGTGAGTTTGTGTATGGTGATTACAAAGTTTATGACGTCCGTAAGATGATCGCGAAAAGCGAACA

GGAGATAGGCAAGGCTACAGCCAAATACTTCTTTTATTCTAACATTATGAATTTCTTTAAGACGGAAATCACTCTGG

CAAACGGAGAGATACGCAAACGACCTTTAATTGAAACCAATGGGGAGACAGGTGAAATCGTATGGGATAAGGGCCGG

GACTTCGCGACGGTGAGAAAAGTTTTGTCCATGCCCCAAGTCAACATAGTAAAGAAAACTGAGGTGCAGACCGGAGG

GTTTTCAAAGGAATCGATTCTTCCAAAAAGGAATAGTGATAAGCTCATCGCTCGTAAAAAGGACTGGGACCCGAAAA

AGTACGGTGGCTTCGATAGCCCTACAGTTGCCTATTCTGTCCTAGTAGTGGCAAAAGTTGAGAAGGGAAAATCCAAG

AAACTGAAGTCAGTCAAAGAATTATTGGGGATAACGATTATGGAGCGCTCGTCTTTTGAAAAGAACCCCATCGACTT

CCTTGAGGCGAAAGGTTACAAGGAAGTAAAAAAGGATCTCATAATTAAACTACCAAAGTATAGTCTGTTTGAGTTAG

AAAATGGCCGAAAACGGATGTTGGCTAGCGCCGGAGAGCTTCAAAAGGGGAACGAACTCGCACTACCGTCTAAATAC

GTGAATTTCCTGTATTTAGCGTCCCATTACGAGAAGTTGAAAGGTTCACCTGAAGATAACGAACAGAAGCAACTTTT

TGTTGAGCAGCACAAACATTATCTCGACGAAATCATAGAGCAAATTTCGGAATTCAGTAAGAGAGTCATCCTAGCTG

ATGCCAATCTGGACAAAGTATTAAGCGCATACAACAAGCACAGGGATAAACCCATACGTGAGCAGGCGGAAAATATT

ATCCATTTGTTTACTCTTACCAACCTCGGCGCTCCAGCCGCATTCAAGTATTTTGACACAACGATAGATCGCAAACG

ATACACTTCTACCAAGGAGGTGCTAGACGCGACACTGATTCACCAATCCATCACGGGATTATATGAAACTCGGATAG

ATTTGTCACAGCTTGGGGGTGACGGATCCCCCAAGAAGAAGAGGAAAGTCTCGAGCGACTACAAAGACCATGACGGT

GATTATAAAGATCATGACATCGATTACAAGGATGACGATGACAAGGCTGCAGGATCAGGTGGAAGTGGCGGCAGCGG

AGGTTCTGGATCCCAACTAGTCAAAAGTGAACTGGAGGAGAAGAAATCTGAACTTCGTCATAAATTGAAATATGTGC

CTCATGAATATATTGAATTAATTGAAATTGCCAGAAATTCCACTCAGGATAGAATTCTTGAAATGAAGGTAATGGAA

TTTTTTATGAAAGTTTATGGATATAGAGGTAAACATTTGGGTGGATCAAGGAAACCGGACGGAGCAATTTATACTGT

CGGATCTCCTATTGATTACGGTGTGATCGTGGATACTAAAGCTTATAGCGGAGGTTATAATCTGCCAATTGGCCAAG

CAGATGAAATGCAACGATATGTCGAAGAAAATCAAACACGAAACAAACATATCAACCCTAATGAATGGTGGAAAGTC

TATCCATCTTCTGTAACGGAATTTAAGTTTTTATTTGTGAGTGGTCACTTTAAAGGAAACTACAAAGCTCAGCTTAC

ACGATTAAATCATATCACTAATTGTAATGGAGCTGTTCTTAGTGTAGAAGAGCTTTTAATTGGTGGAGAAATGATTA

AAGCCGGCACATTAACCTTAGAGGAAGTCAGACGGAAATTTAATAACGGCGAGATAAACTTT fCas9 (e.g., NLS-dCas9-GGS3linker-FokI):

(SEQ ID NO: 51)

ATGGACTACAAAGACCATGACGGTGATTATAAAGATCATGACATCGATTACAAGGATGACGATGACAAGATGGCCCC

CAAGAAGAAGAGGAAGGTGGGCATTCACCGCGGGGTACCTATGGATAAAAAGTATTCTATTGGTTTAGCTATCGGCA

CTAATTCCGTTGGATGGGCTGTCATAACCGATGAATACAAAGTACCTTCAAAGAAATTTAAGGTGTTGGGGAACACA

GACCGTCATTCGATTAAAAAGAATCTTATCGGTGCCCTCCTATTCGATAGTGGCGAAACGGCAGAGGCGACTCGCCT

GAAACGAACCGCTCGGAGAAGGTATACACGTCGCAAGAACCGAATATGTTACTTACAAGAAATTTTTAGCAATGAGA

TGGCCAAAGTTGACGATTCTTTCTTTCACCGTTTGGAAGAGTCCTTCCTTGTCGAAGAGGACAAGAAACATGAACGG

CACCCCATCTTTGGAAACATAGTAGATGAGGTGGCATATCATGAAAAGTACCCAACGATTTATCACCTCAGAAAAA

GCTAGTTGACTCAACTGATAAAGCGGACCTGAGGTTAATCTACTTGGCTCTTGCCCATATGATAAAGTTCCGTGGGC

ACTTTCTCATTGAGGGTGATCTAAATCCGGACAACTCGGATGTCGACAAACTGTTCATCCAGTTAGTACAAACCTAT

AATCAGTTGTTTGAAGAGAACCCTATAAATGCAAGTGGCGTGGATGCGAAGGCTATTCTTAGCGCCCGCCTCTCTAA

ATCCCGACGGCTAGAAAACCTGATCGCACAATTACCCGGAGAGAAGAAAAATGGGTTGTTCGGTAACCTTATAGCGC

TCTCACTAGGCCTGACACCAAATTTTAAGTCGAACTTCGACTTAGCTGAAGATGCCAAATTGCAGCTTAGTAAGGAC

-continued

ACGTACGATGACGATCTCGACAATCTACTGGCACAAATTGGAGATCAGTATGCGGACTTATTTTTGGCTGCCAAAAA

CCTTAGCGATGCAATCCTCCTATCTGACATACTGAGAGTTAATACTGAGATTACCAAGGCGCCGTTATCCGCTTCAA

TGATCAAAAGGTACGATGAACATCACCAAGACTTGACACTTCTCAAGGCCCTAGTCCGTCAGCAACTGCCTGAGAAA

TATAAGGAAATATTCTTTGATCAGTCGAAAAACGGGTACGCAGGTTATATTGACGGCGGAGCGAGTCAAGAGGAATT

CTACAAGTTTATCAAACCCATATTAGAGAAGATGGATGGGACGGAAGAGTTGCTTGTAAAACTCAATCGCGAAGATC

TACTGCGAAAGCAGCGGACTTTCGACAACGGTAGCATTCCACATCAAATCCACTTAGGCGAATTGCATGCTATACTT

AGAAGGCAGGAGGATTTTTATCCGTTCCTCAAAGACAATCGTGAAAAGATTGAGAAAATCCTAACCTTTCGCATACC

TTACTATGTGGGACCCCTGGCCCGAGGGAACTCTCGGTTCGCATGGATGACAAGAAAGTCCGAAGAAACGATTACTC

CATGGAATTTTGAGGAAGTTGTCGATAAAGGTGCGTCAGCTCAATCGTTCATCGAGAGGATGACCAACTTTGACAAG

AATTTACCGAACGAAAAAGTATTGCCTAAGCACAGTTTACTTTACGAGTATTTCACAGTGTACAATGAACTCACGAA

AGTTAAGTATGTCACTGAGGGCATGCGTAAACCCGCCTTTCTAAGCGGAGAACAGAAGAAAGCAATAGTAGATCTGT

TATTCAAGACCAACCGCAAAGTGACAGTTAAGCAATTGAAAGAGGACTACTTTAAGAAAATTGAATGCTTCGATTCT

GTCGAGATCTCCGGGGTAGAAGATCGATTTAATGCGTCACTTGGTACGTATCATGACCTCCTAAAGATAATTAAAGA

TAAGGACTTCCTGGATAACGAAGAGAATGAAGATATCTTAGAAGATATAGTGTTGACTCTTACCCTCTTTGAAGATC

GGGAAATGATTGAGGAAAGACTAAAAACATACGCTCACCTGTTCGACGATAAGGTTATGAAACAGTTAAAGAGGCGT

CGCTATACGGGCTGGGGACGATTGTCGCGGAAACTTATCAACGGGATAAGAGACAAGCAAAGTGGTAAAACTATTCT

CGATTTTCTAAAGAGCGACGGCTTCGCCAATAGGAACTTTATGCAGCTGATCCATGATGACTCTTTAACCTTCAAAG

AGGATATACAAAAGGCACAGGTTTCCGGACAAGGGGACTCATTGCACGAACATATTGCGAATCTTGCTGGTTCGCCA

GCCATCAAAAAGGGCATACTCCAGACAGTCAAAGTAGTGGATGAGCTAGTTAAGGTCATGGGACGTCACAAACCGGA

AAACATTGTAATCGAGATGGCACGCGAAAATCAAACGACTCAGAAGGGGCAAAAAAACAGTCGAGAGCGGATGAAGA

GAATAGAAGAGGGTATTAAAGAACTGGGCAGCCAGATCTTAAAGGAGCATCCTGTGGAAAATACCCAATTGCAGAAC

GAGAAACTTTACCTCTATTACCTACAAAATGGAAGGGACATGTATGTTGATCAGGAACTGGACATAAACCGTTTATC

TGATTACGACGTCGATGCCATTGTACCCCAATCCTTTTTGAAGGACGATTCAATCGACAATAAAGTGCTTACACGCT

CGGATAAGAACCGAGGGAAAAGTGACAATGTTCCAAGCGAGGAAGTCGTAAAGAAAATGAAGAACTATTGGCGGCAG

CTCCTAAATGCGAAACTGATAACGCAAAGAAAGTTCGATAACTTAACTAAAGCTGAGAGGGGTGGCTTGTCTGAACT

TGACAAGGCCGGATTTATTAAACGTCAGCTCGTGGAAACCCGCCAAATCACAAAGCATGTTGCACAGATACTAGATT

CCCGAATGAATACGAAATACGACGAGAACGATAAGCTGATTCGGGAAGTCAAAGTAATCACTTTAAAGTCAAAATTG

GTGTCGGACTTCAGAAAGGATTTTCAATTCTATAAAGTTAGGGAGATAAATAACTACCACCATGCGCACGACGCTTA

TCTTAATGCCGTCGTAGGGACCGCACTCATTAAGAAATACCCGAAGCTAGAAAGTGAGTTTGTGTATGGTGATTACA

AAGTTTATGACGTCCGTAAGATGATCGCGAAAAGCGAACAGGAGATAGGCAAGGCTACAGCCAAATACTTCTTTTAT

TCTAACATTATGAATTTCTTTAAGACGGAAATCACTCTGGCAAACGGAGAGATACGCAAACGACCTTTAATTGAAAC

CAATGGGGAGACAGGTGAAATCGTATGGGATAAGGGCCGGGACTTCGCGACGGTGAGAAAAGTTTTGTCCATGCCCC

AAGTCAACATAGTAAAGAAAACTGAGGTGCAGACCGGAGGGTTTTCAAAGGAATCGATTCTTCCAAAAAGGAATAGT

GATAAGCTCATCGCTCGTAAAAAGGACTGGGACCCGAAAAAGTACGGTGGCTTCGATAGCCCTACAGTTGCCTATTC

TGTCCTAGTAGTGGCAAAAGTTGAGAAGGGAAAATCCAAGAAACTGAAGTCAGTCAAAGAATTATTGGGGATAACGA

TTATGGAGCGCTCGTCTTTTGAAAAGAACCCCATCGACTTCCTTGAGGCGAAAGGTTACAAGGAAGTAAAAAAGGAT

CTCATAATTAAACTACCAAAGTATAGTCTGTTTGAGTTAGAAAATGGCCGAAAACGGATGTTGGCTAGCGCCGGAGA

GCTTCAAAAGGGGAACGAACTCGCACTACCGTCTAAATACGTGAATTTCCTGTATTTAGCGTCCCATTACGAGAAGT

TGAAAGGTTCACCTGAAGATAACGAACAGAAGCAACTTTTTGTTGAGCAGCACAAACATTATCTCGACGAAATCATA

GAGCAAATTTCGGAATTCAGTAAGAGAGTCATCCTAGCTGATGCCAATCTGGACAAAGTATTAAGCGCATACAACAA

GCACAGGGATAAACCCATACGTGAGCAGGCGGAAAATATTATCCATTTGTTTACTCTTACCAACCTCGGCGCTCCAG

-continued

CCGCATTCAAGTATTTTGACACAACGATAGATCGCAAACGATACACTTCTACCAAGGAGGTGCTAGACGCGACACTG

ATTCACCAATCCATCACGGGATTATATGAAACTCGGATAGATTTGTCACAGCTTGGGGGTGACTCAGGTGGAAGTGG

CGGCAGCGGAGGTTCTGGATCCCAACTAGTCAAAAGTGAACTGGAGGAGAAGAAATCTGAACTTCGTCATAAATTGA

AATATGTGCCTCATGAATATATTGAATTAATTGAAATTGCCAGAAATTCCACTCAGGATAGAATTCTTGAAATGAAG

GTAATGGAATTTTTTATGAAAGTTTATGGATATAGAGGTAAACATTTGGGTGGATCAAGGAAACCGGACGGAGCAAT

TTATACTGTCGGATCTCCTATTGATTACGGTGTGATCGTGGATACTAAAGCTTATAGCGGAGGTTATAATCTGCCAA

TTGGCCAAGCAGATGAAATGCAACGATATGTCGAAGAAAATCAAACACGAAACAAACATATCAACCCTAATGAATGG

TGGAAAGTCTATCCATCTTCTGTAACGGAATTTAAGTTTTTATTTGTGAGTGGTCACTTTAAAGGAAACTACAAAGC

TCAGCTTACACGATTAAATCATATCACTAATTGTAATGGAGCTGTTCTTAGTGTAGAAGAGCTTTTAATTGGTGGAG

AAATGATTAAAGCCGGCACATTAACCTTAGAGGAAGTCAGACGGAAATTTAATAACGGCGAGATAAACTTT fCas9 (e.g., FokI-GGS3linker-dCas9-NLS):

(SEQ ID NO: 52)

ATGGGATCCCAACTAGTCAAAAGTGAACTGGAGGAGAAGAAATCTGAACTTCGTCATAAATTGAAATATGTGCCTCA

TGAATATATTGAATTAATTGAAATTGCCAGAAATTCCACTCAGGATAGAATTCTTGAAATGAAGGTAATGGAATTTT

TTATGAAAGTTTATGGATATAGAGGTAAACATTTGGGTGGATCAAGGAAACCGGACGGAGCAATTTATACTGTCGGA

TCTCCTATTGATTACGGTGTGATCGTGGATACTAAAGCTTATAGCGGAGGTTATAATCTGCCAATTGGCCAAGCAGA

TGAAATGCAACGATATGTCGAAGAAAATCAAACACGAAACAAACATATCAACCCTAATGAATGGTGGAAAGTCTATC

CATCTTCTGTAACGGAATTTAAGTTTTTATTTGTGAGTGGTCACTTTAAAGGAAACTACAAAGCTCAGCTTACACGA

TTAAATCATATCACTAATTGTAATGGAGCTGTTCTTAGTGTAGAAGAGCTTTTAATTGGTGGAGAAATGATTAAAGC

CGGCACATTAACCTTAGAGGAAGTCAGACGGAAATTTAATAACGGCGAGATAAACTTTGGCGGTAGTGGGGGATCTG

GGGGAAGTATGGATAAAAAGTATTCTATTGGTTTAGCTATCGGCACTAATTCCGTTGGATGGGCTGTCATAACCGAT

GAATACAAAGTACCTTCAAAGAAATTTAAGGTGTTGGGGAACACAGACCGTCATTCGATTAAAAAGAATCTTATCGG

TGCCCTCCTATTCGATAGTGGCGAAACGGCAGAGGCGACTCGCCTGAAACGAACCGCTCGGAGAAGGTATACACGTC

GCAAGAACCGAATATGTTACTTACAAGAAATTTTTAGCAATGAGATGGCCAAAGTTGACGATTCTTTCTTTCACCGT

TTGGAAGAGTCCTTCCTTGTCGAAGAGGACAAGAAACATGAACGGCACCCCATCTTTGGAAACATAGTAGATGAGGT

GGCATATCATGAAAAGTACCCAACGATTTATCACCTCAGAAAAAAGCTAGTTGACTCAACTGATAAAGCGGACCTGA

GGTTAATCTACTTGGCTCTTGCCCATATGATAAAGTTCCGTGGGCACTTTCTCATTGAGGGTGATCTAAATCCGGAC

AACTCGGATGTCGACAAACTGTTCATCCAGTTAGTACAAACCTATAATCAGTTGTTTGAAGAGAACCCTATAAATGC

AAGTGGCGTGGATGCGAAGGCTATTCTTAGCGCCCGCCTCTCTAAATCCCGACGGCTAGAAAACCTGATCGCACAAT

TACCCGGAGAGAAGAAAAATGGGTTGTTCGGTAACCTTATAGCGCTCTCACTAGGCCTGACACCAAATTTTAAGTCG

AACTTCGACTTAGCTGAAGATGCCAAATTGCAGCTTAGTAAGGACACGTACGATGACGATCTCGACAATCTACTGGC

ACAAATTGGAGATCAGTATGCGGACTTATTTTTGGCTGCCAAAAACCTTAGCGATGCAATCCTCCTATCTGACATAC

TGAGAGTTAATACTGAGATTACCAAGGCGCCGTTATCCGCTTCAATGATCAAAAGGTACGATGAACATCACCAAGAC

TTGACACTTCTCAAGGCCCTAGTCCGTCAGCAACTGCCTGAGAAATATAAGGAAATATTCTTTGATCAGTCGAAAAA

CGGGTACGCAGGTTATATTGACGGCGGAGCGAGTCAAGAGGAATTCTACAAGTTTATCAAACCCATATTAGAGAAGA

TGGATGGGACGGAAGAGTTGCTTGTAAAACTCAATCGCGAAGATCTACTGCGAAAGCAGCGGACTTTCGACAACGGT

AGCATTCCACATCAAATCCACTTAGGCGAATTGCATGCTATACTTAGAAGGCAGGAGGATTTTTATCCGTTCCTCAA

AGACAATCGTGAAAAGATTGAGAAAATCCTAACCTTTCGCATACCTTACTATGTGGGACCCCTGGCCCGAGGGAACT

CTCGGTTCGCATGGATGACAAGAAAGTCCGAAGAAACGATTACTCCATGGAATTTTGAGGAAGTTGTCGATAAAGGT

GCGTCAGCTCAATCGTTCATCGAGAGGATGACCAACTTTGACAAGAATTTACCGAACGAAAAAGTATTGCCTAAGCA

CAGTTTACTTTACGAGTATTTCACAGTGTACAATGAACTCACGAAAGTTAAGTATGTCACTGAGGGCATGCGTAAAC

-continued

CCGCCTTTCTAAGCGGAGAACAGAAGAAAGCAATAGTAGATCTGTTATTCAAGACCAACCGCAAAGTGACAGTTAAG

CAATTGAAAGAGGACTACTTTAAGAAAATTGAATGCTTCGATTCTGTCGAGATCTCCGGGGTAGAAGATCGATTTAA

TGCGTCACTTGGTACGTATCATGACCTCCTAAAGATAATTAAAGATAAGGACTTCCTGGATAACGAAGAGAATGAAG

ATATCTTAGAAGATATAGTGTTGACTCTTACCCTCTTTGAAGATCGGGAAATGATTGAGGAAAGACTAAAAACATAC

GCTCACCTGTTCGACGATAAGGTTATGAAACAGTTAAAGAGGCGTCGCTATACGGGCTGGGGACGATTGTCGCGGAA

ACTTATCAACGGGATAAGAGACAAGCAAAGTGGTAAAACTATTCTCGATTTTCTAAAGAGCGACGGCTTCGCCAATA

GGAACTTTATGCAGCTGATCCATGATGACTCTTTAACCTTCAAAGAGGATATACAAAAGGCACAGGTTTCCGGACAA

GGGGACTCATTGCACGAACATATTGCGAATCTTGCTGGTTCGCCAGCCATCAAAAAGGGCATACTCCAGACAGTCAA

AGTAGTGGATGAGCTAGTTAAGGTCATGGGACGTCACAAACCGGAAAACATTGTAATCGAGATGGCACGCGAAAATC

AAACGACTCAGAAGGGGCAAAAAAACAGTCGAGAGCGGATGAAGAGAATAGAAGAGGGTATTAAAGAACTGGGCAGC

CAGATCTTAAAGGAGCATCCTGTGGAAAATACCCAATTGCAGAACGAGAAACTTTACCTCTATTACCTACAAAATGG

AAGGGACATGTATGTTGATCAGGAACTGGACATAAACCGTTTATCTGATTACGACGTCGATGCCATTGTACCCCAAT

CCTTTTTGAAGGACGATTCAATCGACAATAAAGTGCTTACACGCTCGGATAAGAACCGAGGGAAAAGTGACAATGTT

CCAAGCGAGGAAGTCGTAAAGAAAATGAAGAACTATTGGCGGCAGCTCCTAAATGCGAAACTGATAACGCAAAGAAA

GTTCGATAACTTAACTAAAGCTGAGAGGGGTGGCTTGTCTGAACTTGACAAGGCCGGATTTATTAAACGTCAGCTCG

TGGAAACCCGCCAAATCACAAAGCATGTTGCACAGATACTAGATTCCCGAATGAATACGAAATACGACGAGAACGAT

AAGCTGATTCGGGAAGTCAAAGTAATCACTTTAAAGTCAAAATTGGTGTCGGACTTCAGAAAGGATTTTCAATTCTA

TAAAGTTAGGGAGATAAATAACTACCACCATGCGCACGACGCTTATCTTAATGCCGTCGTAGGGACCGCACTCATTA

AGAAATACCCGAAGCTAGAAAGTGAGTTTGTGTATGGTGATTACAAAGTTTATGACGTCCGTAAGATGATCGCGAAA

AGCGAACAGGAGATAGGCAAGGCTACAGCCAAATACTTCTTTTATTCTAACATTATGAATTTCTTTAAGACGGAAAT

CACTCTGGCAAACGGAGAGATACGCAAACGACCTTTAATTGAAACCAATGGGGAGACAGGTGAAATCGTATGGGATA

AGGGCCGGGACTTCGCGACGGTGAGAAAAGTTTTGTCCATGCCCCAAGTCAACATAGTAAAGAAAACTGAGGTGCAG

ACCGGAGGGTTTTCAAAGGAATCGATTCTTCCAAAAAGGAATAGTGATAAGCTCATCGCTCGTAAAAAGGACTGGGA

CCCGAAAAAGTACGGTGGCTTCGATAGCCCTACAGTTGCCTATTCTGTCCTAGTAGTGGCAAAAGTTGAGAAGGGAA

AATCCAAGAAACTGAAGTCAGTCAAAGAATTATTGGGGATAACGATTATGGAGCGCTCGTCTTTTGAAAAGAACCCC

ATCGACTTCCTTGAGGCGAAAGGTTACAAGGAAGTAAAAAAGGATCTCATAATTAAACTACCAAAGTATAGTCTGTT

TGAGTTAGAAAATGGCCGAAAACGGATGTTGGCTAGCGCCGGAGAGCTTCAAAAGGGGAACGAACTCGCACTACCGT

CTAAATACGTGAATTTCCTGTATTTAGCGTCCCATTACGAGAAGTTGAAAGGTTCACCTGAAGATAACGAACAGAAG

CAACTTTTTGTTGAGCAGCACAAACATTATCTCGACGAAATCATAGAGCAAATTTCGGAATTCAGTAAGAGAGTCAT

CCTAGCTGATGCCAATCTGGACAAAGTATTAAGCGCATACAACAAGCACAGGGATAAACCCATACGTGAGCAGGCGG

AAAATATTATCCATTTGTTTACTCTTACCAACCTCGGCGCTCCAGCCGCATTCAAGTATTTTGACACAACGATAGAT

CGCAAACGATACACTTCTACCAAGGAGGTGCTAGACGCGACACTGATTCACCAATCCATCACGGGATTATATGAAAC

TCGGATAGATTTGTCACAGCTTGGGGGTGACGGATCCCCCAAGAAGAAGAGGAAAGTCTCGAGCGACTACAAAGACC

ATGACGGTGATTATAAAGATCATGACATCGATTACAAGGATGACGATGACAAGGCTGCAGGA fCas9 (e.g., NLS-FokI-GGS3linker-dCas9):

(SEQ ID NO: 53)

ATGGACTACAAAGACCATGACGGTGATTATAAAGATCATGACATCGATTACAAGGATGACGATGACAAGATGGCCCC

CAAGAAGAAGAGGAAGGTGGGCATTCACCGCGGGGTACCTGGAGGTTCTATGGGATCCCAACTAGTCAAAAGTGAAC

TGGAGGAGAAGAAATCTGAACTTCGTCATAAATTGAAATATGTGCCTCATGAATATATTGAATTAATTGAAATTGCC

AGAAATTCCACTCAGGATAGAATTCTTGAAATGAAGGTAATGGAATTTTTTATGAAAGTTTATGGATATAGAGGTAA

ACATTTGGGTGGATCAAGGAAACCGGACGGAGCAATTTATACTGTCGGATCTCCTATTGATTACGGTGTGATCGTGG

ATACTAAAGCTTATAGCGGAGGTTATAATCTGCCAATTGGCCAAGCAGATGAAATGCAACGATATGTCGAAGAAAAT

-continued

CAAACACGAAACAAACATATCAACCCTAATGAATGGTGGAAAGTCTATCCATCTTCTGTAACGGAATTTAAGTTTTT

ATTTGTGAGTGGTCACTTTAAAGGAAACTACAAAGCTCAGCTTACACGATTAAATCATATCACTAATTGTAATGGAG

CTGTTCTTAGTGTAGAAGAGCTTTTAATTGGTGGAGAAATGATTAAAGCCGGCACATTAACCTTAGAGGAAGTCAGA

CGGAAATTTAATAACGGCGAGATAAACTTTGGCGGTAGTGGGGGATCTGGGGGAAGTATGGATAAAAAGTATTCTAT

TGGTTTAGCTATCGGCACTAATTCCGTTGGATGGGCTGTCATAACCGATGAATACAAAGTACCTTCAAAGAAATTTA

AGGTGTTGGGGAACACAGACCGTCATTCGATTAAAAAGAATCTTATCGGTGCCCTCCTATTCGATAGTGGCGAAACG

GCAGAGGCGACTCGCCTGAAACGAACCGCTCGGAGAAGGTATACACGTCGCAAGAACCGAATATGTTACTTACAAGA

AATTTTTAGCAATGAGATGGCCAAAGTTGACGATTCTTTCTTTCACCGTTTGGAAGAGTCCTTCCTTGTCGAAGAGG

ACAAGAAACATGAACGGCACCCCATCTTTGGAAACATAGTAGATGAGGTGGCATATCATGAAAAGTACCCAACGATT

TATCACCTCAGAAAAAAGCTAGTTGACTCAACTGATAAAGCGGACCTGAGGTTAATCTACTTGGCTCTTGCCCATAT

GATAAAGTTCCGTGGGCACTTTCTCATTGAGGGTGATCTAAATCCGGACAACTCGGATGTCGACAAACTGTTCATCC

AGTTAGTACAAACCTATAATCAGTTGTTTGAAGAGAACCCTATAAATGCAAGTGGCGTGGATGCGAAGGCTATTCTT

AGCGCCCGCCTCTCTAAATCCCGACGGCTAGAAAACCTGATCGCACAATTACCCGGAGAGAAGAAAAATGGGTTGTT

CGGTAACCTTATAGCGCTCTCACTAGGCCTGACACCAAATTTTAAGTCGAACTTCGACTTAGCTGAAGATGCCAAAT

TGCAGCTTAGTAAGGACACGTACGATGACGATCTCGACAATCTACTGGCACAAATTGGAGATCAGTATGCGGACTTA

TTTTTGGCTGCCAAAAACCTTAGCGATGCAATCCTCCTATCTGACATACTGAGAGTTAATACTGAGATTACCAAGGC

GCCGTTATCCGCTTCAATGATCAAAAGGTACGATGAACATCACCAAGACTTGACACTTCTCAAGGCCCTAGTCCGTC

AGCAACTGCCTGAGAAATATAAGGAAATATTCTTTGATCAGTCGAAAAACGGGTACGCAGGTTATATTGACGGCGGA

GCGAGTCAAGAGGAATTCTACAAGTTTATCAAACCCATATTAGAGAAGATGGATGGGACGGAAGAGTTGCTTGTAAA

ACTCAATCGCGAAGATCTACTGCGAAAGCAGCGGACTTTCGACAACGGTAGCATTCCACATCAAATCCACTTAGGCG

AATTGCATGCTATACTTAGAAGGCAGGAGGATTTTTATCCGTTCCTCAAAGACAATCGTGAAAAGATTGAGAAAATC

CTAACCTTTCGCATACCTTACTATGTGGGACCCCTGGCCCGAGGGAACTCTCGGTTCGCATGGATGACAAGAAAGTC

CGAAGAAACGATTACTCCATGGAATTTTGAGGAAGTTGTCGATAAAGGTGCGTCAGCTCAATCGTTCATCGAGAGGA

TGACCAACTTTGACAAGAATTTACCGAACGAAAAAGTATTGCCTAAGCACAGTTTACTTTACGAGTATTTCACAGTG

TACAATGAACTCACGAAAGTTAAGTATGTCACTGAGGGCATGCGTAAACCCGCCTTTCTAAGCGGAGAACAGAAGAA

AGCAATAGTAGATCTGTTATTCAAGACCAACCGCAAAGTGACAGTTAAGCAATTGAAAGAGGACTACTTTAAGAAAA

TTGAATGCTTCGATTCTGTCGAGATCTCCGGGGTAGAAGATCGATTTAATGCGTCACTTGGTACGTATCATGACCTC

CTAAAGATAATTAAAGATAAGGACTTCCTGGATAACGAAGAGAATGAAGATATCTTAGAAGATATAGTGTTGACTCT

TACCCTCTTTGAAGATCGGGAAATGATTGAGGAAAGACTAAAAACATACGCTCACCTGTTCGACGATAAGGTTATGA

AACAGTTAAAGAGGCGTCGCTATACGGGCTGGGGACGATTGTCGCGGAAACTTATCAACGGGATAAGAGACAAGCAA

AGTGGTAAAACTATTCTCGATTTTCTAAAGAGCGACGGCTTCGCCAATAGGAACTTTATGCAGCTGATCCATGATGA

CTCTTTAACCTTCAAAGAGGATATACAAAAGGCACAGGTTTCCGGACAAGGGGACTCATTGCACGAACATATTGCGA

ATCTTGCTGGTTCGCCAGCCATCAAAAAGGGCATACTCCAGACAGTCAAAGTAGTGGATGAGCTAGTTAAGGTCATG

GGACGTCACAAACCGGAAAACATTGTAATCGAGATGGCACGCGAAAATCAAACGACTCAGAAGGGGCAAAAAAACAG

TCGAGAGCGGATGAAGAGAATAGAAGAGGGTATTAAAGAACTGGGCAGCCAGATCTTAAAGGAGCATCCTGTGGAAA

ATACCCAATTGCAGAACGAGAAACTTTACCTCTATTACCTACAAAATGGAAGGGACATGTATGTTGATCAGGAACTG

GACATAAACCGTTTATCTGATTACGACGTCGATGCCATTGTACCCCAATCCTTTTTGAAGGACGATTCAATCGACAA

TAAAGTGCTTACACGCTCGGATAAGAACCGAGGGAAAAGTGACAATGTTCCAAGCGAGGAAGTCGTAAAGAAAATGA

AGAACTATTGGCGGCAGCTCCTAAATGCGAAACTGATAACGCAAAGAAAGTTCGATAACTTAACTAAAGCTGAGAGG

GGTGGCTTGTCTGAACTTGACAAGGCCGGATTTATTAAACGTCAGCTCGTGGAAACCCGCCAAATCACAAAGCATGT

-continued

TGCACAGATACTAGATTCCCGAATGAATACGAAATACGACGAGAACGATAAGCTGATTCGGGAAGTCAAAGTAATCA

CTTTAAAGTCAAAATTGGTGTCGGACTTCAGAAAGGATTTTCAATTCTATAAAGTTAGGGAGATAAATAACTACCAC

CATGCGCACGACGCTTATCTTAATGCCGTCGTAGGGACCGCACTCATTAAGAAATACCCGAAGCTAGAAAGTGAGTT

TGTGTATGGTGATTACAAAGTTTATGACGTCCGTAAGATGATCGCGAAAAGCGAACAGGAGATAGGCAAGGCTACAG

CCAAATACTTCTTTTATTCTAACATTATGAATTTCTTTAAGACGGAAATCACTCTGGCAAACGGAGAGATACGCAAA

CGACCTTTAATTGAAACCAATGGGGAGACAGGTGAAATCGTATGGGATAAGGGCCGGGACTTCGCGACGGTGAGAAA

AGTTTTGTCCATGCCCCAAGTCAACATAGTAAAGAAAACTGAGGTGCAGACCGGAGGGTTTTCAAAGGAATCGATTC

TTCCAAAAAGGAATAGTGATAAGCTCATCGCTCGTAAAAAGGACTGGGACCCGAAAAAGTACGGTGGCTTCGATAGC

CCTACAGTTGCCTATTCTGTCCTAGTAGTGGCAAAAGTTGAGAAGGGAAAATCCAAGAAACTGAAGTCAGTCAAAGA

ATTATTGGGGATAACGATTATGGAGCGCTCGTCTTTTGAAAAGAACCCCATCGACTTCCTTGAGGCGAAAGGTTACA

AGGAAGTAAAAAAGGATCTCATAATTAAACTACCAAAGTATAGTCTGTTTGAGTTAGAAAATGGCCGAAAACGGATG

TTGGCTAGCGCCGGAGAGCTTCAAAAGGGGAACGAACTCGCACTACCGTCTAAATACGTGAATTTCCTGTATTTAGC

GTCCCATTACGAGAAGTTGAAAGGTTCACCTGAAGATAACGAACAGAAGCAACTTTTTGTTGAGCAGCACAAACATT

ATCTCGACGAAATCATAGAGCAAATTTCGGAATTCAGTAAGAGAGTCATCCTAGCTGATGCCAATCTGGACAAAGTA

TTAAGCGCATACAACAAGCACAGGGATAAACCCATACGTGAGCAGGCGGAAAATATTATCCATTTGTTTACTCTTAC

CAACCTCGGCGCTCCAGCCGCATTCAAGTATTTTGACACAACGATAGATCGCAAACGATACACTTCTACCAAGGAGG

TGCTAGACGCGACACTGATTCACCAATCCATCACGGGATTATATGAAACTCGGATAGATTTGTCACAGCTTGGGGGT

GAC fCas9:

(SEQ ID NO: 54)

ATGGACTACAAAGACCATGACGGTGATTATAAAGATCATGACATCGATTACAAGGATGACGATGACAAGATGGCCCC

CAAGAAGAAGAGGAAGGTGGGCATTCACCGCGGGGTACCTGGAGGTTCTGGATCCCAACTAGTCAAAAGTGAACTGG

AGGAGAAGAAATCTGAACTTCGTCATAAATTGAAATATGTGCCTCATGAATATATTGAATTAATTGAAATTGCCAGA

AATTCCACTCAGGATAGAATTCTTGAAATGAAGGTAATGGAATTTTTTATGAAAGTTTATGGATATAGAGGTAAACA

TTTGGGTGGATCAAGGAAACCGGACGGAGCAATTTATACTGTCGGATCTCCTATTGATTACGGTGTGATCGTGGATA

CTAAAGCTTATAGCGGAGGTTATAATCTGCCAATTGGCCAAGCAGATGAAATGCAACGATATGTCGAAGAAAATCAA

ACACGAAACAAACATATCAACCCTAATGAATGGTGGAAAGTCTATCCATCTTCTGTAACGGAATTTAAGTTTTTATT

TGTGAGTGGTCACTTTAAAGGAAACTACAAAGCTCAGCTTACACGATTAAATCATATCACTAATTGTAATGGAGCTG

TTCTTAGTGTAGAAGAGCTTTTAATTGGTGGAGAAATGATTAAAGCCGGCACATTAACCTTAGAGGAAGTCAGACGG

AAATTTAATAACGGCGAGATAAACTTTAGCGGCAGCGAGACTCCCGGGACCTCAGAGTCCGCCACACCCGAAAGTGA

TAAAAAGTATTCTATTGGTTTAGCTATCGGCACTAATTCCGTTGGATGGGCTGTCATAACCGATGAATACAAAGTAC

CTTCAAAGAAATTTAAGGTGTTGGGGAACACAGACCGTCATTCGATTAAAAAGAATCTTATCGGTGCCCTCCTATTC

GATAGTGGCGAAACGGCAGAGGCGACTCGCCTGAAACGAACCGCTCGGAGAAGGTATACACGTCGCAAGAACCGAAT

ATGTTACTTACAAGAAATTTTTAGCAATGAGATGGCCAAAGTTGACGATTCTTTCTTTCACCGTTTGGAAGAGTCCT

TCCTTGTCGAAGAGGACAAGAAACATGAACGGCACCCCATCTTTGGAAACATAGTAGATGAGGTGGCATATCATGAA

AAGTACCCAACGATTTATCACCTCAGAAAAAAGCTAGTTGACTCAACTGATAAAGCGGACCTGAGGTTAATCTACTT

GGCTCTTGCCCATATGATAAAGTTCCGTGGGCACTTTCTCATTGAGGGTGATCTAAATCCGGACAACTCGGATGTCG

ACAAACTGTTCATCCAGTTAGTACAAACCTATAATCAGTTGTTTGAAGAGAACCCTATAAATGCAAGTGGCGTGGAT

GCGAAGGCTATTCTTAGCGCCCGCCTCTCTAAATCCCGACGGCTAGAAAACCTGATCGCACAATTACCCGGAGAGAA

GAAAAATGGGTTGTTCGGTAACCTTATAGCGCTCTCACTAGGCCTGACACCAAATTTTAAGTCGAACTTCGACTTAG

CTGAAGATGCCAAATTGCAGCTTAGTAAGGACACGTACGATGACGATCTCGACAATCTACTGGCACAAATTGGAGAT

CAGTATGCGGACTTATTTTTGGCTGCCAAAAACCTTAGCGATGCAATCCTCCTATCTGACATACTGAGAGTTAATAC

-continued

TGAGATTACCAAGGCGCCGTTATCCGCTTCAATGATCAAAAGGTACGATGAACATCACCAAGACTTGACACTTCTCA

AGGCCCTAGTCCGTCAGCAACTGCCTGAGAAATATAAGGAAATATTCTTTGATCAGTCGAAAAACGGGTACGCAGGT

TATATTGACGGCGGAGCGAGTCAAGAGGAATTCTACAAGTTTATCAAACCCATATTAGAGAAGATGGATGGGACGGA

AGAGTTGCTTGTAAAACTCAATCGCGAAGATCTACTGCGAAAGCAGCGGACTTTCGACAACGGTAGCATTCCACATC

AAATCCACTTAGGCGAATTGCATGCTATACTTAGAAGGCAGGAGGATTTTTATCCGTTCCTCAAAGACAATCGTGAA

AAGATTGAGAAAATCCTAACCTTTCGCATACCTTACTATGTGGGACCCCTGGCCCGAGGGAACTCTCGGTTCGCATG

GATGACAAGAAAGTCCGAAGAAACGATTACTCCATGGAATTTTGAGGAAGTTGTCGATAAAGGTGCGTCAGCTCAAT

CGTTCATCGAGAGGATGACCAACTTTGACAAGAATTTACCGAACGAAAAAGTATTGCCTAAGCACAGTTTACTTTAC

GAGTATTTCACAGTGTACAATGAACTCACGAAAGTTAAGTATGTCACTGAGGGCATGCGTAAACCCGCCTTTCTAAG

CGGAGAACAGAAGAAAGCAATAGTAGATCTGTTATTCAAGACCAACCGCAAAGTGACAGTTAAGCAATTGAAAGAGG

ACTACTTTAAGAAAATTGAATGCTTCGATTCTGTCGAGATCTCCGGGGTAGAAGATCGATTTAATGCGTCACTTGGT

ACGTATCATGACCTCCTAAAGATAATTAAAGATAAGGACTTCCTGGATAACGAAGAGAATGAAGATATCTTAGAAGA

TATAGTGTTGACTCTTACCCTCTTTGAAGATCGGGAAATGATTGAGGAAAGACTAAAAACATACGCTCACCTGTTCG

ACGATAAGGTTATGAAACAGTTAAAGAGGCGTCGCTATACGGGCTGGGGACGATTGTCGCGGAAACTTATCAACGGG

ATAAGAGACAAGCAAAGTGGTAAAACTATTCTCGATTTTCTAAAGAGCGACGGCTTCGCCAATAGGAACTTTATGCA

GCTGATCCATGATGACTCTTTAACCTTCAAAGAGGATATACAAAAGGCACAGGTTTCCGGACAAGGGGACTCATTGC

ACGAACATATTGCGAATCTTGCTGGTTCGCCAGCCATCAAAAAGGGCATACTCCAGACAGTCAAAGTAGTGGATGAG

CTAGTTAAGGTCATGGGACGTCACAAACCGGAAAACATTGTAATCGAGATGGCACGCGAAAATCAAACGACTCAGAA

GGGGCAAAAAAACAGTCGAGAGCGGATGAAGAGAATAGAAGAGGGTATTAAAGAACTGGGCAGCCAGATCTTAAAGG

AGCATCCTGTGGAAAATACCCAATTGCAGAACGAGAAACTTTACCTCTATTACCTACAAAATGGAAGGGACATGTAT

GTTGATCAGGAACTGGACATAAACCGTTTATCTGATTACGACGTCGATGCCATTGTACCCCAATCCTTTTTGAAGGA

CGATTCAATCGACAATAAAGTGCTTACACGCTCGGATAAGAACCGAGGGAAAAGTGACAATGTTCCAAGCGAGGAAG

TCGTAAAGAAAATGAAGAACTATTGGCGGCAGCTCCTAAATGCGAAACTGATAACGCAAAGAAAGTTCGATAACTTA

ACTAAAGCTGAGAGGGGTGGCTTGTCTGAACTTGACAAGGCCGGATTTATTAAACGTCAGCTCGTGGAAACCCGCCA

AATCACAAAGCATGTTGCACAGATACTAGATTCCCGAATGAATACGAAATACGACGAGAACGATAAGCTGATTCGGG

AAGTCAAAGTAATCACTTTAAAGTCAAAATTGGTGTCGGACTTCAGAAAGGATTTTCAATTCTATAAAGTTAGGGAG

ATAAATAACTACCACCATGCGCACGACGCTTATCTTAATGCCGTCGTAGGGACCGCACTCATTAAGAAATACCCGAA

GCTAGAAAGTGAGTTTGTGTATGGTGATTACAAAGTTTATGACGTCCGTAAGATGATCGCGAAAAGCGAACAGGAGA

TAGGCAAGGCTACAGCCAAATACTTCTTTTATTCTAACATTATGAATTTCTTTAAGACGGAAATCACTCTGGCAAAC

GGAGAGATACGCAAACGACCTTTAATTGAAACCAATGGGGAGACAGGTGAAATCGTATGGGATAAGGGCCGGGACTT

CGCGACGGTGAGAAAAGTTTTGTCCATGCCCCAAGTCAACATAGTAAAGAAAACTGAGGTGCAGACCGGAGGGTTTT

CAAAGGAATCGATTCTTCCAAAAAGGAATAGTGATAAGCTCATCGCTCGTAAAAAGGACTGGGACCCGAAAAAGTAC

GGTGGCTTCGATAGCCCTACAGTTGCCTATTCTGTCCTAGTAGTGGCAAAAGTTGAGAAGGGAAAATCCAAGAAACT

GAAGTCAGTCAAAGAATTATTGGGGATAACGATTATGGAGCGCTCGTCTTTTGAAAAGAACCCCATCGACTTCCTTG

AGGCGAAAGGTTACAAGGAAGTAAAAAAGGATCTCATAATTAAACTACCAAAGTATAGTCTGTTTGAGTTAGAAAAT

GGCCGAAAACGGATGTTGGCTAGCGCCGGAGAGCTTCAAAAGGGGAACGAACTCGCACTACCGTCTAAATACGTGAA

TTTCCTGTATTTAGCGTCCCATTACGAGAAGTTGAAAGGTTCACCTGAAGATAACGAACAGAAGCAACTTTTTGTTG

AGCAGCACAAACATTATCTCGACGAAATCATAGAGCAAATTTCGGAATTCAGTAAGAGAGTCATCCTAGCTGATGCC

-continued

AATCTGGACAAAGTATTAAGCGCATACAACAAGCACAGGGATAAACCCATACGTGAGCAGGCGGAAAATATTATCCA

TTTGTTTACTCTTACCAACCTCGGCGCTCCAGCCGCATTCAAGTATTTTGACACAACGATAGATCGCAAACGATACA

CTTCTACCAAGGAGGTGCTAGACGCGACACTGATTCACCAATCCATCACGGGATTATATGAAACTCGGATAGATTTG

TCACAGCTTGGGGGTGAC

In some embodiments, the enzymatic domain comprises a recombinase or catalytic domain thereof. For example, in some embodiments, the general architecture of exemplary ligand-dependent dCas9 fusion proteins with a recombinase domain comprises the structure:

[$NH_2$]-[NLS]-[dCas9]-[recombinase]-[COOH],

[$NH_2$]-[NLS]-[recombinase]-[dCas9]-[COOH],

[$NH_2$]-[dCas9]-[recombinase]-[COOH], or

[$NH_2$]-[recombinase]-[dCas9]-[COOH];

wherein NLS is a nuclear localization signal, $NH_2$ is the N-terminus of the fusion protein, and COOH is the C-terminus of the fusion protein. In some embodiments, a linker is inserted between the dCas9 and the recombinase domain. In some embodiments, a linker is inserted between the NLS and the recombinase and/or dCas9 domain. In some embodiments, the NLS is located C-terminal of the recombinase domain and/or the dCas9 domain. In some embodiments, the NLS is located between the recombinase domain and the dCas9 domain. Additional features, such as sequence tags, may also be present. By "catalytic domain of a recombinase," it is meant that a fusion protein includes a domain comprising an amino acid sequence of (e.g., derived from) a recombinase, such that the domain is sufficient to induce recombination when contacted with a target nucleic acid (either alone or with additional factors including other recombinase catalytic domains which may or may not form part of the fusion protein). In some embodiments, a catalytic domain of a recombinase does not include the DNA binding domain of the recombinase. In some embodiments, the catalytic domain of a recombinase includes part or all of a recombinase, e.g., the catalytic domain may include a recombinase domain and a DNA binding domain, or parts thereof, or the catalytic domain may include a recombinase domain and a DNA binding domain that is mutated or truncated to abolish DNA binding activity. Recombinases and catalytic domains of recombinases are known to those of skill in the art, and include, for example, those described herein. In some embodiments, the catalytic domain is derived from any recombinase. In some embodiments, the recombinase catalytic domain is a catalytic domain of aTn3 resolvase, a Hin recombinase, or a Gin recombinase. In some embodiments, the catalytic domain comprises a Tn3 resolvase (e.g., Stark Tn3 recombinase) that is encoded by a nucleotide sequence comprising, in part or in whole, SEQ ID NO:55, as provided below. In some embodiments, a Tn3 catalytic domain is encoded by a variant of SEQ ID NO:55. In some embodiments, a Tn3 catalytic domain is encoded by a polynucleotide (or a variant thereof) that encodes the polypeptide corresponding to SEQ ID NO:56. In some embodiments, the catalytic domain comprises a Hin recombinase that is encoded by a nucleotide sequence comprising, in part or in whole, SEQ ID NO:57, as provided below. In some embodiments, a Hin catalytic domain is encoded by a variant of SEQ ID NO:57. In some embodiments, a Hin catalytic domain is encoded by a polynucleotide (or a variant thereof) that encodes the polypeptide corresponding to SEQ ID NO:58. In some embodiments, the catalytic domain comprises a Gin recombinase (e.g., Gin beta recombinase) that is encoded by a nucleotide sequence comprising, in part or in whole, SEQ ID NO:59, as provided below. In some embodiments, a Gin catalytic domain is encoded by a variant of SEQ ID NO:59. In some embodiments, a Gin catalytic domain is encoded by a polynucleotide (or a variant thereof) that encodes the polypeptide corresponding to SEQ ID NO:60. Other exemplary compositions and methods of using dCas9-recombinase fusion proteins can be found in U.S. patent application Ser. No. 14/320,467; titled "Cas9 Variants and Uses Thereof," filed Jun. 30, 2014; the entire contents of which are incorporated herein by reference.

Stark Tn3 recombinase (nucleotide: SEQ ID NO: 55;
amino acid: SEQ ID NO: 56):

(SEQ ID NO: 55)

ATGGCCCTGTTTGGCTACGCACGCGTGTCTACCAGTCAACAGTCACTCGATTTGCAAGTGAGGGCTCTTAAAGATGC

CGGAGTGAAGGCAAACAGAATTTTTACTGATAAGGCCAGCGGAAGCAGCACAGACAGAGAGGGGCTGGATCTCCTGA

GAATGAAGGTAAAGGAGGGTGATGTGATCTTGGTCAAAAAATTGGATCGACTGGGGAGAGACACAGCTGATATGCTT

CAGCTTATTAAAGAGTTTGACGCTCAGGGTGTTGCCGTGAGGTTTATCGATGACGGCATCTCAACCGACTCCTACAT

TGGTCTTATGTTTGTGACAATTTTGTCCGCTGTGGCTCAGGCTGAGCGGAGAAGGATTCTCGAAAGGACGAATGAGG

GACGGCAAGCAGCTAAGTTGAAAGGTATCAAATTTGGCAGACGAAGG (SEQ ID NO: 56)

MALFGYARVSTSQQSLDLQVRALKDAGVKANRIFTDKASGSSTDREGLDLLRMKVKEGDVILVKKLDRLGRDTADML

QLIKEFDAQGVAVRFIDDGISTDSYIGLMFVTILSAVAQAERRRILERTNEGRQAAKLKGIKFGRRR

Hin Recombinase (nucleotide: SEQ ID NO: 57;
amino acid: SEQ ID NO: 58):

(SEQ ID NO: 57)

ATGGCAACCATTGGCTACATAAGGGTGTCTACCATCGACCAAAATATCGACCTGCAGCGCAACGCTCTGACATCCGC

CAACTGCGATCGGATCTTCGAGGATAGGATCAGTGGCAAGATCGCCAACCGGCCCGGTCTGAAGCGGGCTCTGAAGT

-continued

ACGTGAATAAGGGCGATACTCTGGTTGTGTGGAAGTTGGATCGCTTGGGTAGATCAGTGAAGAATCTCGTAGCCCTG

ATAAGCGAGCTGCACGAGAGGGGTGCACATTTCCATTCTCTGACCGATTCCATCGATACGTCTAGCGCCATGGGCCG

ATTCTTCTTTTACGTCATGTCCGCCCTCGCTGAAATGGAGCGCGAACTTATTGTTGAACGGACTTTGGCTGGACTGG

CAGCGGCTAGAGCACAGGGCCGACTTGGA (SEQ ID NO: 58)

MATIGYIRVSTIDQNIDLQRNALTSANCDRIFEDRISGKIANRPGLKRALKYVNKGDTLVVWKLDRLGRSVKNLVAL

ISELHERGAHFHSLTDSIDTSSAMGRFFFYVMSALAEMERELIVERTLAGLAAARAQGRLG

Gin beta recombinase (nucleotide: SEQ ID NO: 59;
amino acid: SEQ ID NO: 60):

(SEQ ID NO: 59)

ATGCTCATTGGCTATGTAAGGGTCAGCACCAATGACCAAAACACAGACTTGCAACGCAATGCTTTGGTTTGCGCCGG

ATGTGAACAGATATTTGAAGATAAACTGAGCGGCACTCGGACAGACAGACCTGGGCTTAAGAGAGCACTGAAAAGAC

TGCAGAAGGGGGACACCCTGGTCGTCTGGAAACTGGATCGCCTCGGACGCAGCATGAAACATCTGATTAGCCTGGTT

GGTGAGCTTAGGGAGAGAGGAATCAACTTCAGAAGCCTGACCGACTCCATCGACACCAGTAGCCCCATGGGACGATT

CTTCTTCTATGTGATGGGAGCACTTGCTGAGATGGAAAGAGAGCTTATTATCGAAAGAACTATGGCTGGTATCGCTG

CTGCCCGGAACAAAGGCAGACGGTTCGGCAGACCGCCGAAGAGCGGC (SEQ ID NO: 60)

MLIGYVRVSTNDQNTDLQRNALVCAGCEQIFEDKLSGTRTDRPGLKRALKRLQKGDTLVVWKLDRLGRSMKHLISLV

GELRERGINFRSLTDSIDTSSPMGRFFFYVMGALAEMERELIIERTMAGIAAARNKGRRFGRPPKSG

In some embodiments, the enzymatic domain comprises a deaminase or a catalytic domain thereof. For example, in some embodiments, the general architecture of exemplary dCas9 fusion proteins with a deaminase enzyme or domain comprises the structure:

[$NH_2$]-[NLS]-[Cas9]-[deaminase]-[COOH],

[$NH_2$]-[NLS][deaminase]-[Cas9]-[COOH],

[$NH_2$]-[Cas9]-[deaminase]-[COOH], or

[$NH_2$][deaminase]-[Cas9]-[COOH];

wherein NLS is a nuclear localization signal, $NH_2$ is the N-terminus of the fusion protein, and COOH is the C-terminus of the fusion protein. In some embodiments, a linker is inserted between the dCas9 and the deaminase domain. In some embodiments, a linker is inserted between the NLS and the deaminase and/or dCas9 domain. In some embodiments, the NLS is located C-terminal of the deaminase and/or the dCas9 domain. In some embodiments, the NLS is located between the deaminase domain and the dCas9 domain. Additional features, such as sequence tags, may also be present. One exemplary suitable type of nucleic acid-editing enzymes and domains are cytosine deaminases, for example, of the apolipoprotein B mRNA-editing complex (APOBEC) family of cytosine deaminase enzymes, including activation-induced cytidine deaminase (AID) and apolipoprotein B editing complex 3 (APOBEC3) enzyme. Another exemplary suitable type of nucleic acid-editing enzyme and domain thereof suitable for use in the present invention include adenosine deaminases. For example, an ADAT family adenosine deaminase can be fused to a dCas9 domain. Some exemplary suitable nucleic-acid editing enzymes and domains, e.g., deaminases and deaminase domains, that can be fused to dCas9 domains according to aspects of this disclosure are provided below. It will be understood that, in some embodiments, the active domain of the respective sequence can be used, e.g., the domain without a localizing signal (nuclear localizing signal, without nuclear export signal, cytoplasmic localizing signal). Other exemplary compositions and methods of using dCas9-nuclease fusion proteins can be found in U.S. patent application Ser. No. 14/325,815; titled "Fusions of Cas9 Domains and Nucleic Acid-Editing Domains," filed Jul. 8, 2014; the entire contents of which are incorporated herein by reference.

Human AID:

(SEQ ID NO: 61)

MDSLLMNRRKFLYQFKNVRWAKGRRETYLCYVVKRRDSATSFSLDFGYLRNKNGCHVELLFLRYISDWDLDPGRCYR

VTWFTSWSPCYDCARHVADFLRGNPNLSLRIFTARLYFCEDRKAEPEGLRRLHRAGVQIAIMTFKDYFYCWNTFVEN

HERTFKAWEGLHENSVRLSRQLRRILLPLYEVDDLRDAFRTLGL (underline: nuclear localization signal; double underline: nuclear export signal)

-continued

Mouse AID:

(SEQ ID NO: 62)

MDSLLMKQKKFLYHFKNVRWAKGRHETYLCYVVKRRDSATSCSLDFGHLRNKSGCHVELLFLRYISDWDLDPGRCYR

VTWFTSWSPCYDCARHVAEFLRWNPNLSLRIFTARLYFCEDRKAEPEGLRRLHRAGVQIGIMTFKDYFYCWNTFVEN

RERTFKAWEGLHENSVRLTRQLRRILLPLYEVDDLRDAFRMLGF (underline: nuclear localization signal; double underline: nuclear export signal)

Dog AID:

(SEQ ID NO: 63)

MDSLLMKQRKFLYHFKNVRWAKGRHETYLCYVVKRRDSATSFSLDFGHLRNKSGCHVELLFLRYISDWDLDPGRCYR

VTWFTSWSPCYDCARHVADFLRGYPNLSLRIFAARLYFCEDRKAEPEGLRRLHRAGVQIAIMTFKDYFYCWNTFVEN

REKTFKAWEGLHENSVRLSRQLRRILLPLYEVDDLRDAFRTLGL (underline: nuclear localization signal; double underline: nuclear export signal)

Bovine AID:

(SEQ ID NO: 64)

MDSLLKKQRQFLYQFKNVRWAKGRHETYLCYVVKRRDSPTSFSLDFGHLRNKAGCHVELLFLRYISDWDLDPGRCYR

VTWFTSWSPCYDCARHVADFLRGYPNLSLRIFTARLYFCDKERKAEPEGLRRLHRAGVQIAIMTFKDYFYCWNTFVE

NHERTFKAWEGLHENSVRLSRQLRRILLPLYEVDDLRDAFRTLGL (underline: nuclear localization signal; double underline: nuclear export signal)

Mouse APOBEC-3:

(SEQ ID NO: 65)

MGPFCLGCSHRKCYSPIRNLISQETFKFHFKNLGYAKGRKDTFLCYEVTRKDCDSPVSLHHGVFKNKDNIHAEICFL

YWFHDKVLKVLSPREEFKITWYMSWSPCFECAEQIVRFLATHHNLSLDIFSSRLYNVQDPETQQNLCRLVQEGAQVA

AMDLYEFKKCWKKFVDNGGRRFRPWKRLLTNFRYQDSKLQEILRPCYIPVPSSSSSTLSNICLTKGLPETRFCVEGR

RMDPLSEEEFYSQFYNQRVKHLCYYHRMKPYLCYQLEQFNGQAPLKGCLLSEKGKQHAEILFLDKIRSMELSQVTIT

CYLTWSPCPNCAWQLAAFKRDRPDLILHIYTSRLYFHWKRPFQKGLCSLWQSGILVDVMDLPQFTDCWTNFVNPKRP

FWPWKGLEIISRRTQRRLRRIKESWGLQDLVNDFGNLQLGPPMS (underline: nucleic acid editing domain)

Rat APOBEC-3:

(SEQ ID NO: 66)

MGPFCLGCSHRKCYSPIRNLISQETFKFHFKNLRYAIDRKDTFLCYEVTRKDCDSPVSLHHGVFKNKDNIHAEICFL

YWFHDKVLKVLSPREEFKITWYMSWSPCFECAEQVLRFLATHHNLSLDIFSSRLYNIRDPENQQNLCRLVQEGAQVA

AMDLYEFKKCWKKFVDNGGRRFRPWKKLLTNFRYQDSKLQEILRPCYIPVPSSSSSTLSNICLTKGLPETRFCVERR

RVHLLSEEEFYSQFYNQRVKHLCYYHGVKPYLCYQLEQFNGQAPLKGCLLSEKGKQHAEILFLDKIRSMELSQVIIT

CYLTWSPCPNCAWQLAAFKRDRPDLILHIYTSRLYFHWKRPFQKGLCSLWQSGILVDVMDLPQFTDCWTNFVNPKRP

FWPWKGLEIISRRTQRRLHRIKESWGLQDLVNDFGNLQLGPPMS (underline: nucleic acid editing domain)

Rhesus macaque APOBEC-3G:

(SEQ ID NO: 67)

MVEPMDPRTFVSNFNNRPILSGLNTVWLCCEVKTKDPSGPPLDAKIFQGKVYSKAKY*HPEMFLRWFHKWRQIHHDQ*

*EYKVTWYVSWSPCTRC*ANSVATFLAKDPKVTLTIFVARLYYFWKPDYQQALRILCQKRGGPHATMKIMNYNEFQDCW

NKFVDGRGKPFKPRNNLPKHYTLLQATLGELLRHLMDPGTFTSNFNNKPWVSGQHETYLCYKVERLHNDTWVPLNQH

RGFLRNQAPNIHGFPKGR*HAELCFLDLIPFWKLDGQQYRVTCFTSWSPCFSC*AQEMAKFISNNEHVSLCIFAARIYD

DQGRYQEGLRALHRDGAKIAMMNYSEFEYCWDTFVDRQGRPFQPWDGLDEHSQALSGRLRAI (bold italic: nucleic acid editing domain; underline: cytoplasmic localization signal)

Chimpanzee APOBEC-3G:

(SEQ ID NO: 68)

MKPHFRNPVERMYQDTFSDNFYNRPILSHRNTVWLCYEVKTKGPSRPPLDAKIFRGQVYSKLKYHPEMRFFHWFSKW

RKLHRDQEYEVTWYISWSPCTKCTRDVATFLAEDPKVTLTIFVARLYYFWDPDYQEALRSLCQKRDGPRATMKIMNY

-continued

DEFQHCWSKFVYSQRELFEPWNNLPKYYILLHIMLGEILRHSMDPPTFTSNFNNELWVRGRHETYLCYEVERLHNDT

WVLLNQRRGFLCNQAPHKHGFLEGRHAELCFLDVIPFWKLDLHQDYRVTCFTSWSPCFSCAQEMAKFISNNKHVSLC

IFAARIYDDQGRCQEGLRTLAKAGAKISIMTYSEFKHCWDTFVDHQGCPFQPWDGLEEHSQALSGRLRAILQNQGN
(underline: nucleic acid editing domain; double underline: cytoplasmic localization signal)

Green monkey APOBEC-3G:

(SEQ ID NO: 69)
MNPQIRNMVEQMEPDIFVYYFNNRPILSGRNTVWLCYEVKTKDPSGPPLDANIFQGKLYPEAKDHPEMKFLHWFRKW

RQLHRDQEYEVTWYVSWSPCTRCANSVATFLAEDPKVTLTIFVARLYYFWKPDYQQALRILCQERGGPHATMKIMNY

NEFQHCWNEFVDGQGKPFKPRKNLPKHYTLLHATLGELLRHVMDPGTFTSNFNNKPWVSGQRETYLCYKVERSHNDT

WVLLNQHRGFLRNQAPDRHGFPKGRHAELCFLDLIPFWKLDDQQYRVTCFTSWSPCFSCAQKMAKFISNNKHVSLCI

FAARIYDDQGRCQEGLRTLHRDGAKIAVMNYSEFEYCWDTFVDRQGRPFQPWDGLDEHSQALSGRLRAI
(underline: nucleic acid editing domain; double underline: cytoplasmic localization signal)

Human APOBEC-3G:

(SEQ ID NO: 70)
MKPHFRNTVERMYRDTFSYNFYNRPILSRRNTVWLCYEVKTKGPSRPPLDAKIFRGQVYSELKYHPEMRFFHWFSKW

RKLHRDQEYEVTWYISWSPCTKCTRDMATFLAEDPKVTLTIFVARLYYFWDPDYQEALRSLCQKRDGPRATMKIMNY

DEFQHCWSKFVYSQRELFEPWNNLPKYYILLHIMLGEILRHSMDPPTFTFNFNNEPWVRGRHETYLCYEVERMHNDT

WVLLNQRRGFLCNQAPHKHGFLEGRHAELCFLDVIPFWKLDLDQDYRVTCFTSWSPCFSCAQEMAKFISKNKHVSLC

IFTARIYDDQGRCQEGLRTLAEAGAKISIMTYSEFKHCWDTFVDHQGCPFQPWDGLDEHSQDLSGRLRAILQNQEN
(underline: nucleic acid editing domain; double underline: cytoplasmic localization signal)

Human APOBEC-3F:

(SEQ ID NO: 71)
MKPHFRNTVERMYRDTFSYNFYNRPILSRRNTVWLCYEVKTKGPSRPRLDAKIFRGQVYSQPEHHAEMCFLSWFCGN

QLPAYKCFQITWFVSWTPCPDCVAKLAEFLAEHPNVTLTISAARLYYYWERDYRRALCRLSQAGARVKIMDDEEFAY

CWENFVYSEGQPFMPWYKFDDNYAFLHRTLKEILRNPMEAMYPHIFYFHFKNLRKAYGRNESWLCFTMEVVKHHSPV

SWKRGVFRNQVDPETHCHAERCFLSWFCDDILSPNTNYEVTWYTSWSPCPECAGEVAEFLARHSNVNLTIFTARLYY

FWDTDYQEGLRSLSQEGASVEIMGYKDFKYCWENFVYNDDEPFKPWKGLKYNFLFLDSKLQEILE
(underline: nucleic acid editing domain)

Human APOBEC-3B:

(SEQ ID NO: 72)
MNPQIRNPMERMYRDTFYDNFENEPILYGRSYTWLCYEVKIKRGRSNLLWDTGVFRGQVYFKPQYHAEMCFLSWFCG

NQLPAYKCFQITWFVSWTPCPDCVAKLAEFLSEHPNVTLTISAARLYYYWERDYRRALCRLSQAGARVTIMDYEEFA

YCWENFVYNEGQQFMPWYKFDENYAFLHRTLKEILRYLMDPDTFTFNFNNDPLVLRRRQTYLCYEVERLDNGTWVLM

DQHMGFLCNEAKNLLCGFYGRHAELRFLDLVPSLQLDPAQIYRVTWFISWSPCFSWGCAGEVRAFLQENTHVRLRIF

AARIYDYDPLYKEALQMLRDAGAQVSIMTYDEFEYCWDTFVYRQGCPFQPWDGLEEHSQALSGRLRAILQNQGN
(underline: nucleic acid editing domain)

Human APOBEC-3C:

(SEQ ID NO: 73)
MNPQIRNPMKAMYPGTFYFQFKNLWEANDRNETWLCFTVEGIKRRSVVSWKTGVFRNQVDSETHCHAERCFLSWFCD

DILSPNTKYQVTWYTSWSPCPDCAGEVAEFLARHSNVNLTIFTARLYYFQYPCYQEGLRSLSQEGVAVEIMDYEDFK

YCWENFVYNDNEPFKPWKGLKTNFRLLKRRLRESLQ
(underline: nucleic acid editing domain)

Human APOBEC-3A:

(SEQ ID NO: 74)
MEASPASGPRHLMDPHIFTSNFNNGIGRHKTYLCYEVERLDNGTSVKMDQHRGFLHNQAKNLLCGFYGRHAELRFLD

LVPSLQLDPAQIYRVTWFISWSPCFSWGCAGEVRAFLQENTHVRLRIFAARIYDYDPLYKEALQMLRDAGAQVSIMT

YDEFKHCWDTFVDHQGCPFQPWDGLDEHSQALSGRLRAILQNQGN
(underline: nucleic acid editing domain)

-continued

Human APOBEC-3H:

(SEQ ID NO: 75)

MALLTAETFRLQFNNKRRLRRPYYPRKALLCYQLTPQNGSTPTRGYFENKKKCHAEICFINEIKSMGLDETQCYQVT

CYLTWSPCSSCAWELVDFIKAHDHLNLGIFASRLYYHWCKPQQKGLRLLCGSQVPVEVMGFPKFADCWENFVDHEKP

LSFNPYKMLEELDKNSRAIKRRLERIKIPGVRAQGRYMDILCDAEV (underline: nucleic acid editing domain)

Human APOBEC-3D:

(SEQ ID NO: 76)

MNPQIRNPMERMYRDTFYDNFENEPILYGRSYTWLCYEVKIKRGRSNLLWDTGVFRGPVLPKRQSNHRQEVYFRFEN

HAEMCFLSWFCGNRLPANRRFQITWFVSWNPCLPCVVKVTKFLAEHPNVTLTISAARLYYYRDRDWRWVLLRLHKAG

ARVKIMDYEDFAYCWENFVCNEGQPFMPWYKFDDNYASLHRTLKEILRNPMEAMYPHIFYFHFKNLLKACGRNESWL

CFTMEVTKHHSAVFRKRGVFRNQVDPETHCHAERCFLSWFCDDILSPNTNYEVTWYTSWSPCPECAGEVAEFLARHS

NVNLTIFTARLCYFWDTDYQEGLCSLSQEGASVKIMGYKDFVSCWKNFVYSDDEPFKPWKGLQTNFRLLKRRLREIL

Q (underline: nucleic acid editing domain)

Human APOBEC-1:

(SEQ ID NO: 77)

MTSEKGPSTGDPTLRRRIEPWEFDVFYDPRELRKEACLLYEIKWGMSRKIWRSSGKNTTNHVEVNFIKKFTSERDFH

PSMSCSITWFLSWSPCWECSQAIREFLSRHPGVTLVIYVARLFWHMDQQNRQGLRDLVNSGVTIQIMRASEYYHCWR

NFVNYPPGDEAHWPQYPPLWMMLYALELHCIILSLPPCLKISRRWQNHLTFFRLHLQNCHYQTIPPHILLATGLIHP

SVAWR

Mouse APOBEC-1:

(SEQ ID NO: 78)

MSSETGPVAVDPTLRRRIEPHEFEVFFDPRELRKETCLLYEINWGGRHSVWRHTSQNTSNHVEVNFLEKFTTERYFR

PNTRCSITWFLSWSPCGECSRAITEFLSRHPYVTLFIYIARLYHHTDQRNRQGLRDLISSGVTIQIMTEQEYCYCWR

NFVNYPPSNEAYWPRYPHLWVKLYVLELYCIILGLPPCLKILRRKQPQLTFFTITLQTCHYQRIPPHLLWATGLK

Rat APOBEC-1:

(SEQ ID NO: 79)

MSSETGPVAVDPTLRRRIEPHEFEVFFDPRELRKETCLLYEINWGGRHSIWRHTSQNTNKHVEVNFIEKFTTERYFC

PNTRCSITWFLSWSPCGECSRAITEFLSRYPHVTLFIYIARLYHHADPRNRQGLRDLISSGVTIQIMTEQESGYCWR

NFVNYSPSNEAHWPRYPHLWVRLYVLELYCIILGLPPCLNILRRKQPQLTFFTIALQSCHYQRLPPHILWATGLK

Human ADAT-2:

(SEQ ID NO: 80)

MEAKAAPKPAASGACSVSAEETEKWMEEAMHMAKEALENTEVPVGCLMVYNNEVVGKGRNEVNQTKNATRHAEMVAI

DQVLDWCRQSGKSPSEVFEHTVLYVTVEPCIMCAAALRLMKIPLVVYGCQNERFGGCGSVLNIASADLPNTGRPFQC

IPGYRAEEAVEMLKTFYKQENPNAPKSKVRKKECQKS

Mouse ADAT-2:

(SEQ ID NO: 81)

MEEKVESTTTPDGPCVVSVQETEKWMEEAMRMAKEALENIEVPVGCLMVYNNEVVGKGRNEVNQTKNATRHAEMVAI

DQVLDWCHQHGQSPSTVFEHTVLYVTVEPCIMCAAALRLMKIPLVVYGCQNERFGGCGSVLNIASADLPNTGRPFQC

IPGYRAEEAVELLKTFYKQENPNAPKSKVRKKDCQKS

Mouse ADAT-1:

(SEQ ID NO: 82)

MWTADEIAQLCYAHYNVRLPKQGKPEPNREWTLLAAVVKIQASANQACDIPEKEVQVTKEVVSMGTGTKCIGQSKMR

ESGDILNDSHAEIIARRSFQRYLLHQLHLAAVLKEDSIFVPGTQRGLWRLRPDLSFVFFSSHTPCGDASIIPMLEFE

EQPCCPVIRSWANNSPVQETENLEDSKDKRNCEDPASPVAKKMRLGTPARSLSNCVAHHGTQESGPVKPDVSSSDLT

KEEPDAANGIASGSFRVVDVYRTGAKCVPGETGDLREPGAAYHQVGLLRVKPGRGDRTCSMSCSDKMARWNVLGCQG

ALLMHFLEKPIYLSAVVIGKCPYSQEAMRRALTGRCEETLVLPRGFGVQELEIQQSGLLFEQSRCAVHRKRGDSPGR

-continued

LVPCGAAISWSAVPQQPLDVTANGFPQGTTKKEIGSPRARSRISKVELFRSFQKLLSSIADDEQPDSIRVTKKLDTY

QEYKDAASAYQEAWGALRRIQPFASWIRNPPDYHQFK
(underline: nucleic acid editing domain)

Human ADAT-1:

(SEQ ID NO: 83)
MWTADEIAQLCYEHYGIRLPKKGKPEPNHEWTLLAAVVKIQSPADKACDTPDKPVQVTKEVVSMGTGTKCIGQSKMR

KNGDILNDSHAEVIARRSFQRYLLHQLQLAATLKEDSIFVPGTQKGVWKLRRDLIFVFFSSHTPCGDASIIPMLEFE

DQPCCPVFRNWAHNSSVEASSNLEAPGNERKCEDPDSPVTKKMRLEPGTAAREVTNGAAHHQSFGKQKSGPISPGIH

SCDLTVEGLATVTRIAPGSAKVIDVYRTGAKCVPGEAGDSGKPGAAFHQVGLLRVKPGRGDRTRSMSCSDKMARWNV

LGCQGALLMHLLEEPIYLSAVVIGKCPYSQEAMQRALIGRCQNVSALPKGFGVQELKILQSDLLFEQSRSAVQAKRA

DSPGRLVPCGAAISWSAVPEQPLDVTANGFPQGTTKKTIGSLQARSQISKVELFRSFQKLLSRIARDKWPHSLRVQK

LDTYQEYKEAASSYQEAWSTLRKQVFGSWIRNPPDYHQFK
(underline: nucleic acid editing domain)

In some embodiments, the enzymatic domain comprises one or more of a transcriptional activator. For example, in some embodiments, the general architecture of exemplary dCas9 fusion proteins with a transcriptional activator domain comprises the structure:

[$NH_2$]-[NLS]-[Cas9]-[(transcriptional activator)$_n$]-[COOH],

[$NH_2$]-[NLS]-[(transcriptional activator)$_n$]-[Cas9]-[COOH],

[$NH_2$]-[Cas9]-[(transcriptional activator)$_n$]-[COOH], or

[$NH_2$]-[(transcriptional activator)$_n$]-[Cas9]-[COOH];

wherein NLS is a nuclear localization signal, $NH_2$ is the N-terminus of the fusion protein, and COOH is the C-terminus of the fusion protein. In some embodiments, the fusion proteins comprises one or more repeats of the transcriptional activator, for example wherein n=1-10 (e.g., n is 1, 2, 3, 4, 5, 6, 7, 8, 9, or 10). In some embodiments, n=1-20. In some embodiments, a linker is inserted between the dCas9 and the transcriptional activator domain. In some embodiments, a linker is inserted between the NLS and the transcriptional activator and/or dCas9 domain. In some embodiments, the NLS is located C-terminal of the transcriptional activator and/or the dCas9 domain. In some embodiments, the NLS is located between the transcriptional activator domain and the dCas9 domain. Additional features, such as sequence tags, may also be present. In some embodiments, the transcriptional activator is selected from the group consisting of VP64, (SEQ ID NO:84 or SEQ ID NO:35), VP16 (SEQ ID NO:85), and p65 (SEQ ID NO:86). In some embodiments, a dCas9-VP64 fusion protein comprises the amino acid sequence of SEQ ID NO:87 (e.g., with or without the 6×His tag) or comprises an amino acid sequence that is at least 80%, at least 85%, at least 90%, at least 95%, at least 98%, or at least 99% identical to the amino acid sequence of SEQ ID NO:87 (e.g., with or without the 6×His tag).

VP64

(SEQ ID NO: 84)
GSGRADALDDFDLDMLGSDALDDFDLDMLGSDALDDFDLDMLGSDALDDFDLDMLIN

VP16

(SEQ ID NO: 85)
APPTDVSLGDELHLDGEDVAMAHADALDDFDLDMLGDGDSPGPGFTPHDSAPYGALDMADFEFEQMFTDA

LGIDEYGGEFPGIRR p65:

(SEQ ID NO: 86)
PSGQISNQALALAPSSAPVLAQTMVPSSAMVPLAQPPAPAPVLTPGPPQSLSAPVPKSTQAGEGTLSEAL

LHLQFDADEDLGALLGNSTDPGVFTDLASVDNSEFQQLLNQGVSMSHSTAEPMLMEYPEAITRLVTGSQR

PPDPAPTPLGTSGLPNGLSGDEDFSSIADMDFSALLSQISSSGQ dCas9-VP64-6xHis:

(SEQ ID NO: 87)
MDKKYSIGLAIGTNSVGWAVITDEYKVPSKKFKVLGNTDRHSIKKNLIGALLFDSGETAEATRLKRTARR

RYTRRKNRICYLQEIFSNEMAKVDDSFFHRLEESFLVEEDKKHERHPIFGNIVDEVAYHEKYPTIYHLRK

KLVDSTDKADLRLIYLALAHMIKFRGHFLIEGDLNPDNSDVDKLFIQLVQTYNQLFEENPINASGVDAKA

ILSARLSKSRRLENLIAQLPGEKKNGLFGNLIALSLGLTPNFKSNFDLAEDAKLQLSKDTYDDDLDNLLA

QIGDQYADLFLAAKNLSDAILLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLRKQRTFDNGSIPHQIHLGELH

AILRRQEDFYPFLKDNREKIEKILTFRIPYYVGPLARGNSRFAWMTRKSEETITPWNFEEVVDKGASAQS

-continued

FIERMTNFDKNLPNEKVLPKHSLLYEYFTVYNELTKVKYVTEGMRKPAFLSGEQKKAIVDLLFKTNRKVT

VKQLKEDYFKKIECFDSVEISGVEDRFNASLGTYHDLLKIIKDKDFLDNEENEDILEDIVLTLTLFEDRE

MIEERLKTYAHLFDDKVMKQLKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKVMGRHKPENIVIEMARENQTT

QKGQKNSRERMKRIEEGIKELGSQILKEHPVENTQLQNEKLYLYYLQNGRDMYVDQELDINRLSDYDVDA

IVPQSFLKDDSIDNKVLTRSDKNRGKSDNVPSEEVVKKMKNYWRQLLNAKLITQRKFDNLTKAERGGLSE

LDKAGFIKRQLVETRQITKHVAQILDSRMNTKYDENDKLIREVKVITLKSKLVSDFRKDFQFYKVREINN

YHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLI

ARKKDWDPKKYGGFDSPTVAYSVLVVAKVEKGKSKKLKSVKELLGITIMERSSFEKNPIDFLEAKGYKEV

KKDLIIKLPKYSLFELENGRKRMLASAGELQKGNELALPSKYVNFLYLASHYEKLKGSPEDNEQKQLFVE

QHKHYLDEIIEQISEFSKRVILADANLDKVLSAYNKHRDKPIREQAENIIHLFTLTNLGAPAAFKYFDTT

IDRKRYTSTKEVLDATLIHQSITGLYETRIDLSQLGGDGSPKKKRKVSSDYKDHDGDYKDHDIDYKDDDD

KAAGGGGSGRADALDDFDLDMLGSDALDDFDLDMLGSDALDDFDLDMLGSDALDDFDLDMLHHHHHH (SEQ ID NO: 269)

ATGGATAAGAAATACTCAATAGGCTTAGCTATCGGCACAAATAGCGTCGGATGGGCGGTGATCACTGATG

AATATAAGGTTCCGTCTAAAAAGTTCAAGGTTCTGGGAAATACAGACCGCCACAGTATCAAAAAAAATCT

TATAGGGGCTCTTTTATTTGACAGTGGAGAGACAGCGGAAGCGACTCGTCTCAAACGGACAGCTCGTAGA

AGGTATACACGTCGGAAGAATCGTATTTGTTATCTACAGGAGATTTTTTCAAATGAGATGGCGAAAGTAG

ATGATAGTTTCTTTCATCGACTTGAAGAGTCTTTTTTGGTGGAAGAAGACAAGAAGCATGAACGTCATCC

TATTTTTGGAAATATAGTAGATGAAGTTGCTTATCATGAGAAATATCCAACTATCTATCATCTGCGAAAA

AAATTGGTAGATTCTACTGATAAAGCGGATTTGCGCTTAATCTATTTGGCCTTAGCGCATATGATTAAGT

TTCGTGGTCATTTTTTGATTGAGGGAGATTTAAATCCTGATAATAGTGATGTGGACAAACTATTTATCCA

GTTGGTACAAACCTACAATCAATTATTTGAAGAAAACCCTATTAACGCAAGTGGAGTAGATGCTAAAGCG

ATTCTTTCTGCACGATTGAGTAAATCAAGACGATTAGAAAATCTCATTGCTCAGCTCCCCGGTGAGAAGA

AAAATGGCTTATTTGGGAATCTCATTGCTTTGTCATTGGGTTTGACCCCTAATTTTAAATCAAATTTTGA

TTTGGCAGAAGATGCTAAATTACAGCTTTCAAAAGATACTTACGATGATGATTTAGATAATTTATTGGCG

CAAATTGGAGATCAATATGCTGATTTGTTTTTGGCAGCTAAGAATTTATCAGATGCTATTTTACTTTCAG

ATATCCTAAGAGTAAATACTGAAATAACTAAGGCTCCCCTATCAGCTTCAATGATTAAACGCTACGATGA

ACATCATCAAGACTTGACTCTTTTAAAAGCTTTAGTTCGACAACAACTTCCAGAAAAGTATAAAGAAATC

TTTTTTGATCAATCAAAAAACGGATATGCAGGTTATATTGATGGGGGAGCTAGCCAAGAAGAATTTTATA

AATTTATCAAACCAATTTTAGAAAAAATGGATGGTACTGAGGAATTATTGGTGAAACTAAATCGTGAAGA

TTTGCTGCGCAAGCAACGGACCTTTGACAACGGCTCTATTCCCCATCAAATTCACTTGGGTGAGCTGCAT

GCTATTTTGAGAAGACAAGAAGACTTTTATCCATTTTTAAAAGACAATCGTGAGAAGATTGAAAAAATCT

TGACTTTTCGAATTCCTTATTATGTTGGTCCATTGGCGCGTGGCAATAGTCGTTTTGCATGGATGACTCG

GAAGTCTGAAGAAACAATTACCCCATGGAATTTTGAAGAAGTTGTCGATAAAGGTGCTTCAGCTCAATCA

TTTATTGAACGCATGACAAACTTTGATAAAAATCTTCCAAATGAAAAAGTACTACCAAAACATAGTTTGC

TTTATGAGTATTTTACGGTTTATAACGAATTGACAAAGGTCAAATATGTTACTGAAGGAATGCGAAAACC

AGCATTTCTTTCAGGTGAACAGAAGAAAGCCATTGTTGATTTACTCTTCAAAACAAATCGAAAAGTAACC

GTTAAGCAATTAAAAGAAGATTATTTCAAAAAAATAGAATGTTTTGATAGTGTTGAAATTTCAGGAGTTG

AAGATAGATTTAATGCTTCATTAGGTACCTACCATGATTTGCTAAAAATTATTAAAGATAAAGATTTTTT

-continued

GGATAATGAAGAAAATGAAGATATCTTAGAGGATATTGTTTTAACATTGACCTTATTTGAAGATAGGGAG

ATGATTGAGGAAAGACTTAAAACATATGCTCACCTCTTTGATGATAAGGTGATGAAACAGCTTAAACGTC

GCCGTTATACTGGTTGGGGACGTTTGTCTCGAAAATTGATTAATGGTATTAGGGATAAGCAATCTGGCAA

AACAATATTAGATTTTTTGAAATCAGATGGTTTTGCCAATCGCAATTTTATGCAGCTGATCCATGATGAT

AGTTTGACATTTAAAGAAGACATTCAAAAAGCACAAGTGTCTGGACAAGGCGATAGTTTACATGAACATA

TTGCAAATTTAGCTGGTAGCCCTGCTATTAAAAAAGGTATTTTACAGACTGTAAAAGTTGTTGATGAATT

GGTCAAAGTAATGGGGCGGCATAAGCCAGAAAATATCGTTATTGAAATGGCACGTGAAAATCAGACAACT

CAAAAGGGCCAGAAAAATTCGCGAGAGCGTATGAAACGAATCGAAGAAGGTATCAAAGAATTAGGAAGTC

AGATTCTTAAAGAGCATCCTGTTGAAAATACTCAATTGCAAAATGAAAAGCTCTATCTCTATTATCTCCA

AAATGGAAGAGACATGTATGTGGACCAAGAATTAGATATTAATCGTTTAAGTGATTATGATGTCGATGCC

ATTGTTCCACAAAGTTTCCTTAAAGACGATTCAATAGACAATAAGGTCTTAACGCGTTCTGATAAAAATC

GTGGTAAATCGGATAACGTTCCAAGTGAAGAAGTAGTCAAAAAGATGAAAAACTATTGGAGACAACTTCT

AAACGCCAAGTTAATCACTCAACGTAAGTTTGATAATTTAACGAAAGCTGAACGTGGAGGTTTGAGTGAA

CTTGATAAAGCTGGTTTTATCAAACGCCAATTGGTTGAAACTCGCCAAATCACTAAGCATGTGGCACAAA

TTTTGGATAGTCGCATGAATACTAAATACGATGAAAATGATAAACTTATTCGAGAGGTTAAAGTGATTAC

CTTAAAATCTAAATTAGTTTCTGACTTCCGAAAAGATTTCCAATTCTATAAAGTACGTGAGATTAACAAT

TACCATCATGCCCATGATGCGTATCTAAATGCCGTCGTTGGAACTGCTTTGATTAAGAAATATCCAAAAC

TTGAATCGGAGTTTGTCTATGGTGATTATAAAGTTTATGATGTTCGTAAAATGATTGCTAAGTCTGAGCA

AGAAATAGGCAAAGCAACCGCAAAATATTTCTTTTACTCTAATATCATGAACTTCTTCAAAACAGAAATT

ACACTTGCAAATGGAGAGATTCGCAAACGCCCTCTAATCGAAACTAATGGGGAAACTGGAGAAATTGTCT

GGGATAAAGGGCGAGATTTTGCCACAGTGCGCAAAGTATTGTCCATGCCCCAAGTCAATATTGTCAAGAA

AACAGAAGTACAGACAGGCGGATTCTCCAAGGAGTCAATTTTACCAAAAAGAAATTCGGACAAGCTTATT

GCTCGTAAAAAAGACTGGGATCCAAAAAAATATGGTGGTTTTGATAGTCCAACGGTAGCTTATTCAGTCC

TAGTGGTTGCTAAGGTGGAAAAAGGGAAATCGAAGAAGTTAAAATCCGTTAAAGAGTTACTAGGGATCAC

AATTATGGAAAGAAGTTCCTTTGAAAAAAATCCGATTGACTTTTTAGAAGCTAAAGGATATAAGGAAGTT

AAAAAAGACTTAATCATTAAACTACCTAAATATAGTCTTTTTGAGTTAGAAAACGGTCGTAAACGGATGC

TGGCTAGTGCCGGAGAATTACAAAAAGGAAATGAGCTGGCTCTGCCAAGCAAATATGTGAATTTTTTATA

TTTAGCTAGTCATTATGAAAAGTTGAAGGGTAGTCCAGAAGATAACGAACAAAAACAATTGTTTGTGGAG

CAGCATAAGCATTATTTAGATGAGATTATTGAGCAAATCAGTGAATTTTCTAAGCGTGTTATTTTAGCAG

ATGCCAATTTAGATAAAGTTCTTAGTGCATATAACAAACATAGAGACAAACCAATACGTGAACAAGCAGA

AAATATTATTCATTTATTTACGTTGACGAATCTTGGAGCTCCCGCTGCTTTTAAATATTTTGATACAACA

ATTGATCGTAAACGATATACGTCTACAAAAGAAGTTTTAGATGCCACTCTTATCCATCAATCCATCACTG

GTCTTTATGAAACACGCATTGATTTGAGTCAGCTAGGAGGTGACGGTTCTCCCAAGAAGAAGAGGAAAGT

CTCGAGCGACTACAAAGACCATGACGGTGATTATAAAGATCATGACATCGATTACAAGGATGACGATGAC

AAGGCTGCAGGAGGCGGTGGAAGCGGGCGCGCCGACGCGCTGGACGATTTCGATCTCGACATGCTGGGTT

CTGATGCCCTCGATGACTTTGACCTGGATATGTTGGGAAGCGACGCATTGGATGACTTTGATCTGGACAT

GCTCGGCTCCGATGCTCTGGACGATTTCGATCTCGATATGTTACATCACCACCACCATCAC

Cas9-NLS-6xHis:

(SEQ ID NO: 270)

MDKKYSIGLAIGTNSVGWAVITDEYKVPSKKFKVLGNTDRHSIKKNLIGALLFDSGETAEATRLKRTARR

RYTRRKNRICYLQEIFSNEMAKVDDSFFHRLEESFLVEEDKKHERHPIFGNIVDEVAYHEKYPTIYHLRK

-continued

KLVDSTDKADLRLIYLALAHMIKFRGHFLIEGDLNPDNSDVDKLFIQLVQTYNQLFEENPINASGVDAKA

ILSARLSKSRRLENLIAQLPGEKKNGLFGNLIALSLGLTPNFKSNFDLAEDAKLQLSKDTYDDDLDNLLA

QIGDQYADLFLAAKNLSDAILLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLRKQRTFDNGSIPHQIHLGELH

AILRRQEDFYPFLKDNREKIEKILTFRIPYYVGPLARGNSRFAWMTRKSEETITPWNFEEVVDKGASAQS

FIERMTNFDKNLPNEKVLPKHSLLYEYFTVYNELTKVKYVTEGMRKPAFLSGEQKKAIVDLLFKTNRKVT

VKQLKEDYFKKIECFDSVEISGVEDRFNASLGTYHDLLKIIKDKDFLDNEENEDILEDIVLTLTLFEDRE

MIEERLKTYAHLFDDKVMKQLKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKVMGRHKPENIVIEMARENQTT

QKGQKNSRERMKRIEEGIKELGSQILKEHPVENTQLQNEKLYLYYLQNGRDMYVDQELDINRLSDYDVDH

IVPQSFLKDDSIDNKVLTRSDKNRGKSDNVPSEEVVKKMKNYWRQLLNAKLITQRKFDNLTKAERGGLSE

LDKAGFIKRQLVETRQITKHVAQILDSRMNTKYDENDKLIREVKVITLKSKLVSDFRKDFQFYKVREINN

YHHAHDAYLNAVVGTALIKKYPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEVQTGGFSKESILPKRNSDKLI

ARKKDWDPKKYGGFDSPTVAYSVLVVAKVEKGKSKKLKSVKELLGITIMERSSFEKNPIDFLEAKGYKEV

KKDLIIKLPKYSLFELENGRKRMLASAGELQKGNELALPSKYVNFLYLASHYEKLKGSPEDNEQKQLFVE

QHKHYLDEIIEQISEFSKRVILADANLDKVLSAYNKHRDKPIREQAENIIHLFTLTNLGAPAAFKYFDTT

IDRKRYTSTKEVLDATLIHQSITGLYETRIDLSQLGGDPKKKRKVMDKHHHHHH (SEQ ID NO: 271)

ATGGATAAGAAATACTCAATAGGCTTAGATATCGGCACAAATAGCGTCGGATGGGCGGTGATCACTGATG

AATATAAGGTTCCGTCTAAAAAGTTCAAGGTTCTGGGAAATACAGACCGCCACAGTATCAAAAAAAATCT

TATAGGGGCTCTTTTATTTGACAGTGGAGAGACAGCGGAAGCGACTCGTCTCAAACGGACAGCTCGTAGA

AGGTATACACGTCGGAAGAATCGTATTTGTTATCTACAGGAGATTTTTTCAAATGAGATGGCGAAAGTAG

ATGATAGTTTCTTTCATCGACTTGAAGAGTCTTTTTTGGTGGAAGAAGACAAGAAGCATGAACGTCATCC

TATTTTTGGAAATATAGTAGATGAAGTTGCTTATCATGAGAAATATCCAACTATCTATCATCTGCGAAAA

AAATTGGTAGATTCTACTGATAAAGCGGATTTGCGCTTAATCTATTTGGCCTTAGCGCATATGATTAAGT

TTCGTGGTCATTTTTTGATTGAGGGAGATTTAAATCCTGATAATAGTGATGTGGACAAACTATTTATCCA

GTTGGTACAAACCTACAATCAATTATTTGAAGAAAACCCTATTAACGCAAGTGGAGTAGATGCTAAAGCG

ATTCTTTCTGCACGATTGAGTAAATCAAGACGATTAGAAAATCTCATTGCTCAGCTCCCCGGTGAGAAGA

AAAATGGCTTATTTGGGAATCTCATTGCTTTGTCATTGGGTTTGACCCCTAATTTTAAATCAAATTTTGA

TTTGGCAGAAGATGCTAAATTACAGCTTTCAAAAGATACTTACGATGATGATTTAGATAATTTATTGGCG

CAAATTGGAGATCAATATGCTGATTTGTTTTTGGCAGCTAAGAATTTATCAGATGCTATTTTACTTTCAG

ATATCCTAAGAGTAAATACTGAAATAACTAAGGCTCCCCTATCAGCTTCAATGATTAAACGCTACGATGA

ACATCATCAAGACTTGACTCTTTTAAAAGCTTTAGTTCGACAACAACTTCCAGAAAAGTATAAAGAAATC

TTTTTTGATCAATCAAAAAACGGATATGCAGGTTATATTGATGGGGGAGCTAGCCAAGAAGAATTTTATA

AATTTATCAAACCAATTTTAGAAAAAATGGATGGTACTGAGGAATTATTGGTGAAACTAAATCGTGAAGA

TTTGCTGCGCAAGCAACGGACCTTTGACAACGGCTCTATTCCCCATCAAATTCACTTGGGTGAGCTGCAT

GCTATTTTGAGAAGACAAGAAGACTTTTATCCATTTTTAAAAGACAATCGTGAGAAGATTGAAAAAATCT

TGACTTTTCGAATTCCTTATTATGTTGGTCCATTGGCGCGTGGCAATAGTCGTTTTGCATGGATGACTCG

GAAGTCTGAAGAAACAATTACCCCATGGAATTTTGAAGAAGTTGTCGATAAAGGTGCTTCAGCTCAATCA

TTTATTGAACGCATGACAAACTTTGATAAAAATCTTCCAAATGAAAAAGTACTACCAAAACATAGTTTGC

-continued

TTTATGAGTATTTTACGGTTTATAACGAATTGACAAAGGTCAAATATGTTACTGAAGGAATGCGAAAACC

AGCATTTCTTTCAGGTGAACAGAAGAAAGCCATTGTTGATTTACTCTTCAAAACAAATCGAAAAGTAACC

GTTAAGCAATTAAAAGAAGATTATTTCAAAAAAATAGAATGTTTTGATAGTGTTGAAATTTCAGGAGTTG

AAGATAGATTTAATGCTTCATTAGGTACCTACCATGATTTGCTAAAAATTATTAAAGATAAAGATTTTTT

GGATAATGAAGAAAATGAAGATATCTTAGAGGATATTGTTTTAACATTGACCTTATTTGAAGATAGGGAG

ATGATTGAGGAAAGACTTAAAACATATGCTCACCTCTTTGATGATAAGGTGATGAAACAGCTTAAACGTC

GCCGTTATACTGGTTGGGGACGTTTGTCTCGAAAATTGATTAATGGTATTAGGGATAAGCAATCTGGCAA

AACAATATTAGATTTTTTGAAATCAGATGGTTTTGCCAATCGCAATTTTATGCAGCTGATCCATGATGAT

AGTTTGACATTTAAAGAAGACATTCAAAAAGCACAAGTGTCTGGACAAGGCGATAGTTTACATGAACATA

TTGCAAATTTAGCTGGTAGCCCTGCTATTAAAAAAGGTATTTTACAGACTGTAAAAGTTGTTGATGAATT

GGTCAAAGTAATGGGGCGGCATAAGCCAGAAAATATCGTTATTGAAATGGCACGTGAAAATCAGACAACT

CAAAAGGGCCAGAAAAATTCGCGAGAGCGTATGAAACGAATCGAAGAAGGTATCAAAGAATTAGGAAGTC

AGATTCTTAAAGAGCATCCTGTTGAAAATACTCAATTGCAAAATGAAAAGCTCTATCTCTATTATCTCCA

AAATGGAAGAGACATGTATGTGGACCAAGAATTAGATATTAATCGTTTAAGTGATTATGATGTCGATCAC

ATTGTTCCACAAAGTTTCCTTAAAGACGATTCAATAGACAATAAGGTCTTAACGCGTTCTGATAAAAATC

GTGGTAAATCGGATAACGTTCCAAGTGAAGAAGTAGTCAAAAAGATGAAAAACTATTGGAGACAACTTCT

AAACGCCAAGTTAATCACTCAACGTAAGTTTGATAATTTAACGAAAGCTGAACGTGGAGGTTTGAGTGAA

CTTGATAAAGCTGGTTTTATCAAACGCCAATTGGTTGAAACTCGCCAAATCACTAAGCATGTGGCACAAA

TTTTGGATAGTCGCATGAATACTAAATACGATGAAAATGATAAACTTATTCGAGAGGTTAAAGTGATTAC

CTTAAAATCTAAATTAGTTTCTGACTTCCGAAAAGATTTCCAATTCTATAAAGTACGTGAGATTAACAAT

TACCATCATGCCCATGATGCGTATCTAAATGCCGTCGTTGGAACTGCTTTGATTAAGAAATATCCAAAAC

TTGAATCGGAGTTTGTCTATGGTGATTATAAAGTTTATGATGTTCGTAAAATGATTGCTAAGTCTGAGCA

AGAAATAGGCAAAGCAACCGCAAAATATTTCTTTTACTCTAATATCATGAACTTCTTCAAAACAGAAATT

ACACTTGCAAATGGAGAGATTCGCAAACGCCCTCTAATCGAAACTAATGGGGAAACTGGAGAAATTGTCT

GGGATAAAGGGCGAGATTTTGCCACAGTGCGCAAAGTATTGTCCATGCCCCAAGTCAATATTGTCAAGAA

AACAGAAGTACAGACAGGCGGATTCTCCAAGGAGTCAATTTTACCAAAAAGAAATTCGGACAAGCTTATT

GCTCGTAAAAAAGACTGGGATCCAAAAAAATATGGTGGTTTTGATAGTCCAACGGTAGCTTATTCAGTCC

TAGTGGTTGCTAAGGTGGAAAAAGGGAAATCGAAGAAGTTAAAATCCGTTAAAGAGTTACTAGGGATCAC

AATTATGGAAAGAAGTTCCTTTGAAAAAAATCCGATTGACTTTTTAGAAGCTAAAGGATATAAGGAAGTT

AAAAAAGACTTAATCATTAAACTACCTAAATATAGTCTTTTTGAGTTAGAAAACGGTCGTAAACGGATGC

TGGCTAGTGCCGGAGAATTACAAAAAGGAAATGAGCTGGCTCTGCCAAGCAAATATGTGAATTTTTTATA

TTTAGCTAGTCATTATGAAAAGTTGAAGGGTAGTCCAGAAGATAACGAACAAAAACAATTGTTTGTGGAG

CAGCATAAGCATTATTTAGATGAGATTATTGAGCAAATCAGTGAATTTTCTAAGCGTGTTATTTTAGCAG

ATGCCAATTTAGATAAAGTTCTTAGTGCATATAACAAACATAGAGACAAACCAATACGTGAACAAGCAGA

AAATATTATTCATTTATTTACGTTGACGAATCTTGGAGCTCCCGCTGCTTTTAAATATTTTGATACAACA

ATTGATCGTAAACGATATACGTCTACAAAAGAAGTTTTAGATGCCACTCTTATCCATCAATCCATCACTG

GTCTTTATGAAACACGCATTGATTTGAGTCAGCTAGGAGGTGACCCCAAGAAGAAGAGGAAGGTGATGGA

TAAGCATCACCACCACCATCAC

NLS-Cas9-6xHis:

(SEQ ID NO: 272)

MPKKKRKVMDKKYSIGLAIGTNSVGWAVITDEYKVPSKKFKVLGNTDRHSIKKNLIGALLFDSGETAEAT

RLKRTARRRYTRRKNRICYLQEIFSNEMAKVDDSFFHRLEESFLVEEDKKHERHPIFGNIVDEVAYHEKY

-continued

```
PTIYHLRKKLVDSTDKADLRLIYLALAHMIKFRGHFLIEGDLNPDNSDVDKLFIQLVQTYNQLFEENPIN

ASGVDAKAILSARLSKSRRLENLIAQLPGEKKNGLFGNLIALSLGLTPNFKSNFDLAEDAKLQLSKDTYD

DDLDNLLAQIGDQYADLFLAAKNLSDAILLSDILRVNTEITKAPLSASMIKRYDEHHQDLTLLKALVRQQ

LPEKYKEIFFDQSKNGYAGYIDGGASQEEFYKFIKPILEKMDGTEELLVKLNREDLLRKQRTFDNGSIPH

QIHLGELHAILRRQEDFYPFLKDNREKIEKILTFRIPYYVGPLARGNSRFAWMTRKSEETITPWNFEEVV

DKGASAQSFIERMTNFDKNLPNEKVLPKHSLLYEYFTVYNELTKVKYVTEGMRKPAFLSGEQKKAIVDLL

FKTNRKVTVKQLKEDYFKKIECFDSVEISGVEDRFNASLGTYHDLLKIIKDKDFLDNEENEDILEDIVLT

LTLFEDREMIEERLKTYAHLFDDKVMKQLKRRRYTGWGRLSRKLINGIRDKQSGKTILDFLKSDGFANRN

FMQLIHDDSLTFKEDIQKAQVSGQGDSLHEHIANLAGSPAIKKGILQTVKVVDELVKVMGRHKPENIVIE

MARENQTTQKGQKNSRERMKRIEEGIKELGSQILKEHPVENTQLQNEKLYLYYLQNGRDMYVDQELDINR

LSDYDVDHIVPQSFLKDDSIDNKVLTRSDKNRGKSDNVPSEEVVKKMKNYWRQLLNAKLITQRKFDNLTK

AERGGLSELDKAGFIKRQLVETRQITKHVAQILDSRMNTKYDENDKLIREVKVITLKSKLVSDFRKDFQF

YKVREINNYHHAHDAYLNAVVGTALIKKYPKLESEFVYGDYKVYDVRKMIAKSEQEIGKATAKYFFYSNI

MNFFKTEITLANGEIRKRPLIETNGETGEIVWDKGRDFATVRKVLSMPQVNIVKKTEVQTGGFSKESILP

KRNSDKLIARKKDWDPKKYGGFDSPTVAYSVLVVAKVEKGKSKKLKSVKELLGITIMERSSFEKNPIDFL

EAKGYKEVKKDLIIKLPKYSLFELENGRKRMLASAGELQKGNELALPSKYVNFLYLASHYEKLKGSPEDN

EQKQLFVEQHKHYLDEIIEQISEFSKRVILADANLDKVLSAYNKHRDKPIREQAENIIHLFTLTNLGAPA

AFKYFDTTIDRKRYTSTKEVLDATLIHQSITGLYETRIDLSQLGGDHHHHHH
```

In some embodiments, the enzymatic domain comprises one or more of a transcriptional repressor. For example, in some embodiments, the general architecture of exemplary dCas9 fusion proteins with a transcriptional repressor domain comprises the structure:

$[NH_2]$-[NLS]-[Cas9]-[(transcriptional repressor)$_n$]-[COOH], $[NH_2]$-[NLS]-[(transcriptional repressor)$_n$]-[Cas9]-[COOH], $[NH_2]$-[Cas9]-[(transcriptional repressor)$_n$]-[COOH], or $[NH_2]$-[(transcriptional repressor)$_n$]-[Cas9]-[COOH];

wherein NLS is a nuclear localization signal, $NH_2$ is the N-terminus of the fusion protein, and COOH is the C-terminus of the fusion protein. In some embodiments, the fusion proteins comprises one or more repeats of the transcriptional repressor, for example wherein n=1-10 (e.g., n is 1, 2, 3, 4, 5, 6, 7, 8, 9, or 10). In some embodiments, n=1-20. In some embodiments, a linker is inserted between the dCas9 and the transcriptional repressor domain. In some embodiments, a linker is inserted between the NLS and the transcriptional repressor and/or dCas9 domain. In some embodiments, the NLS is located C-terminal of the transcriptional repressor and/or the dCas9 domain. In some embodiments, the NLS is located between the transcriptional repressor domain and the dCas9 domain. Additional features, such as sequence tags, may also be present. In some embodiments, the transcriptional repressor is selected from the group consisting of the KRAB (Krüppel associated box) domain of Kox1, SID (mSin3 interaction domain), the CS (Chromo Shadow) domain of HP1α, or the WRPW domain of Hes1. These and other repressor domains are known in the art, and in some embodiments correspond to those described in Urrutia, KRAB-containing zinc-finger repressor proteins. *Genome Biol.* 2003; 4(10):231; Gilbert et al. CRISPR-mediated modular RNA-guided regulation of transcription in eukaryotes. *Cell.* 2013; 154, 442-451; Konermann et al., Optical control of mammalian endogenous transcription and epigenetic states. *Nature.* 2013; 500, 472-476; and published U.S. patent application Ser. No. 14/105,017, published as U.S. 2014/0186958 A1, the entire contents of which are incorporated herein by reference. In some embodiments, the transcription repressor domain comprises one or more repeats (e.g., 2, 3, 4, 5, 6, 7, 8, 9, or 10 repeats) of a KRAB domain. In some embodiments, the KRAB domain comprises an amino acid sequence selected from the group consisting of SEQ ID NOs: 88-91. In some embodiments, the transcriptional repressor domains comprises one or more repeats of a SID protein. In some embodiments, the SID protein comprises an amino acid sequence set forth as SEQ ID NO:80. In some embodiments, the repressor domain comprises 2, 3, 4, 5, 6, 7, 8, 9, or 10 repeats of a SID protein (e.g., SEQ ID NO:92). In some embodiments, the repressor domain comprises four repeats of SID (e.g., SID4x; SEQ ID NO:93).

```
KRAB (human; GenBank: AAD20972.1)
                                         (SEQ ID NO: 88)
MNMFKEAVTFKDVAVAFTEEELGLLGPAQRKLYRDVMVENFRNLLSVGHP

PFKQDVSPIERNEQLWIMTTATRRQGNLDTLPVKALLLYDLAQT

KRAB protein domain, partial
(human; GenBank: CAB52478.1):
                                         (SEQ ID NO: 89)
EQVSFKDVCVDFTQEEWYLLDPAQKILYRDVILENYSNLVSVGYCITKPE

VIFKIEQGEEPWILEKGFPSQCHP

KRAB A domain, partial
(human; GenBank: AAB03530.1):
                                         (SEQ ID NO: 90)
EAVTFKDVAVVFTEEELGLLDPAQRKLYRDVMLENFRNLLSV
```

-continued

KRAB (mouse; C2H2 type domain containing protein; GenBank: CAM27971.1):

(SEQ ID NO: 91)
MDLVTYDDVHVNFTQDEWALLDPSQKSLYKGVMLETYKNLTAIGYIWEEH

TIEDHFQTSRSHGSNKKTH

SID repressor domain:

(SEQ ID NO: 92)
GSGMNIQMLLEAADYLERREREAEHGYASMLP

SID4x repressor domain:

(SEQ ID NO: 93)
GSGMNIQMLLEAADYLERREREAEHGYASMLPGSGMNIQMLLEAADYLER

REREAEHGYASMLPGSGMNIQMLLEAADYLERREREAEHGYASMLPGSGM

NIQMLLEAADYLERREREAEHGYASMLPSR

In some embodiments, the enzymatic domain comprises an epigenetic modifier or a catalytic domain thereof. For example, in some embodiments, the general architecture of exemplary dCas9 fusion proteins with an epigenetic modifier or domain comprises the structure:

[$NH_2$]-[NLS]-[Cas9]-[epigenetic modifier]-[COOH],

[$NH_2$]-[NLS]-[epigenetic modifier]-[Cas9]-[COOH],

[$NH_2$]-[Cas9]-[epigenetic modifier]-[COOH], or

[$NH_2$]-[epigenetic modifier]-[Cas9]-[COOH];

wherein NLS is a nuclear localization signal, $NH_2$ is the N-terminus of the fusion protein, and COOH is the C-terminus of the fusion protein. In some embodiments, a linker is inserted between the dCas9 and the epigenetic modifier domain. In some embodiments, a linker is inserted between the NLS and the epigenetic modifier and/or dCas9 domain. In some embodiments, the NLS is located C-terminal of the epigenetic modifier and/or the dCas9 domain. In some embodiments, the NLS is located between the epigenetic modifier domain and the dCas9 domain. Additional features, such as sequence tags, may also be present. Epigenetic modifiers are well known in the art, and typically catalyze DNA methylation (and demethylation) or histone modifications (e.g., histone methylation/demethylation, acetylation/deacetylation, ubiquitylation, phosphorylation, sumoylation, etc.). The presence of one more epigenetic modifications can affect the transcriptional activity of one or more genes, for example turning genes from an "on" state to an "off" state, and vice versa. Epigenetic modifiers include, but are not limited to, histone demethylase, histone methyltransferase, hydroxylase, histone deacetylase, and histone acetyltransferase. Exemplary epigenetic modifying proteins can be found in Konermann et al., Optical control of mammalian endogenous transcription and epigenetic states. *Nature.* 2013; 500, 472-476; Mendenhall et al., Locus-specific editing of histone modifications at endogenous enhancers. *Nat. Biotechnol.* 2013; 31, 1133-1136; and Maeder et al., Targeted DNA demethylation and activation of endogenous genes using programmable TALE-TET1 fusion proteins. *Nat. Biotechnol.* 2013; 31, 1137-1142; the entire contents of each are incorporated herein by reference. In some embodiments, the epigenetic modifier domain is LSD1 (Lysine (K)-specific demethylase 1A) histone demethylase, which in some embodiments, comprises in whole or in part, an amino acid sequence set forth as SEQ ID NO:94 or SEQ ID NO:95. In some embodiments, the epigenetic modifier domain is TET1 hydroxylase catalytic domain, which in some embodiments, comprises an amino acid sequence set forth as SEQ ID NO:96. In some embodiments, the epigenetic modifier is a histone deacetylase (HDAC) effector domain. In some embodiments, the HDAC effector domain comprises in whole in in part, an amino acid sequence corresponding to any of the HDAC effector proteins provided in Supplementary Table 2 of Konermann et al., Optical control of mammalian endogenous transcription and epigenetic states. *Nature.* 2013; 500, 472-476; SEQ ID NOs: 97-108. In some embodiments, the epigenetic modifier is a histone methyltransferase (HMT) effector domain. In some embodiments, the HMT effector domain comprises in whole in in part, an amino acid sequence corresponding to any of the HDAC effector proteins provided in Supplementary Table 3 of Konermann et al., Optical control of mammalian endogenous transcription and epigenetic states. *Nature.* 2013; 500, 472-476; SEQ ID NOs: 109-118.

LSD1, isoform a (human):

(SEQ ID NO: 94)
MLSGKKAAAAAAAAAAAATGTEAGPGTAGGSENGSEVAAQPAGLSGPAEVGPGAVGERTPRKKEPPRASP

PGGLAEPPGSAGPQAGPTVVPGSATPMETGIAETPEGRRTSRRKRAKVEYREMDESLANLSEDEYYSEEE

RNAKAEKEKKLPPPPPQAPPEEENESEPEEPSGQAGGLQDDSSGGYGDGQASGVEGAAFQSRLPHDRMTS

QEAACFPDIISGPQQTQKVFLFIRNRTLQLWLDNPKIQLTFEATLQQLEAPYNSDTVLVHRVHSYLERHG

LINFGIYKRIKPLPTKKTGKVIIIGSGVSGLAAARQLQSFGMDVTLLEARDRVGGRVATFRKGNYVADLG

AMVVTGLGGNPMAVVSKQVNMELAKIKQKCPLYEANGQADTVKVPKEKDEMVEQEFNRLLEATSYLSHQL

DFNVLNNKPVSLGQALEVVIQLQEKHVKDEQIEHWKKIVKTQEELKELLNKMVNLKEKIKELHQQYKEAS

EVKPPRDITAEFLVKSKHRDLTALCKEYDELAETQGKLEEKLQELEANPPSDVYLSSRDRQILDWHFANL

EFANATPLSTLSLKHWDQDDDFEFTGSHLTVRNGYSCVPVALAEGLDIKLNTAVRQVRYTASGCEVIAVN

TRSTSQTFIYKCDAVLCTLPLGVLKQQPPAVQFVPPLPEWKTSAVQRMGFGNLNKVVLCFDRVFWDPSVN

LFGHVGSTTASRGELFLFWNLYKAPILLALVAGEAAGIMENISDDVIVGRCLAILKGIFGSSAVPQPKET

VVSRWRADPWARGSYSYVAAGSSGNDYDLMAQPITPGPSIPGAPQPIPRLFFAGEHTIRNYPATVHGALL

SGLREAGRIADQFLGAMYTLPRQATPGVPAQQSPSM

-continued

LSD1, isoform b (human):

(SEQ ID NO: 95)

MLSGKKAAAAAAAAAAAATGTEAGPGTAGGSENGSEVAAQPAGLSGPAEVGPGAVGERTPRKKEPPRASP
PGGLAEPPGSAGPQAGPTVVPGSATPMETGIAETPEGRRTSRRKRAKVEYREMDESLANLSEDEYYSEEE
RNAKAEKEKKLPPPPPQAPPEEENESEPEEPSGVEGAAFQSRLPHDRMTSQEAACFPDIISGPQQTQKVF
LFIRNRTLQLWLDNPKIQLTFEATLQQLEAPYNSDTVLVHRVHSYLERHGLINFGIYKRIKPLPTKKTGK
VIIIGSGVSGLAAARQLQSFGMDVTLLEARDRVGGRVATFRKGNYVADLGAMVVTGLGGNPMAVVSKQVN
MELAKIKQKCPLYEANGQAVPKEKDEMVEQEFNRLLEATSYLSHQLDFNVLNNKPVSLGQALEVVIQLQE
KHVKDEQIEHWKKIVKTQEELKELLNKMVNLKEKIKELHQQYKEASEVKPPRDITAEFLVKSKHRDLTAL
CKEYDELAETQGKLEEKLQELEANPPSDVYLSSRDRQILDWHFANLEFANATPLSTLSLKHWDQDDDFEF
TGSHLTVRNGYSCVPVALAEGLDIKLNTAVRQVRYTASGCEVIAVNTRSTSQTFIYKCDAVLCTLPLGVL
KQQPPAVQFVPPLPEWKTSAVQRMGFGNLNKVVLCFDRVFWDPSVNLFGHVGSTTASRGELFLFWNLYKA
PILLALVAGEAAGIMENISDDVIVGRCLAILKGIFGSSAVPQPKETVVSRWRADPWARGSYSYVAAGSSG
NDYDLMAQPITPGPSIPGAPQPIPRLFFAGEHTIRNYPATVHGALLSGLREAGRIADQFLGAMYTLPRQA
TPGVPAQQSPSM

TET1 catalytic domain:

(SEQ ID NO: 96)

SIVAQLSRPDPALAALTNDHLVALACLGGRPALDAVKKGLPHAPALIKRTNRRIPERTSHRVADHAQVVR
VLGFFQCHSHPAQAFDDAMTQFGMSGGGSLPTCSCLDRVIQKDKGPYYTHLGAGPSVAAVREIMENRYGQ
KGNAIRIEIVVYTGKEGKSSHGCPIAKWVLRRSSDEEKVLCLVRQRTGHHCPTAVMVVLIMVWDGIPLPM
ADRLYTELTENLKSYNGHPTDRRCTLNENRTCTCQGIDPETCGASFSFGCSWSMYFNGCKFGRSPSPRRF
RIDPSSPLHEKNLEDNLQSLATRLAPIYKQYAPVAYQNQVEYENVARECRLGSKEGRPFSGVTACLDFCA
HPHRDIHNMNNGSTVVCTLTREDNRSLGVIPQDEQLHVLPLYKLSDTDEFGSKEGMEAKIKSGAIEVLAP
RRKKRTCFTQPVPRSGKKRAAMMTEVLAHKIRAVEKKPIPRIKRKNNSTTTNNSKPSSLPTLGSNTETVQ
PEVKSETEPHFILKSSDNTKTYSLMPSAPHPVKEASPGFSWSPKTASATPAPLKNDATASCGFSERSSTP
HCTMPSGRLSGANAAAADGPGISQLGEVAPLPTLSAPVMEPLINSEPSTGVTEPLTPHQPNHQPSFLTSP
QDLASSPMEEDEQHSEADEPPSDEPLSDDPLSPAEEKLPHIDEYWSDSEHIFLDANIGGVAIAPAHGSVL
IECARRELHATTPVEHPNRNHPTRLSLVFYQHKNLNKPQHGFELNKIKFEAKEAKNKKMKASEQKDQAAN
EGPEQSSEVNELNQIPSHKALTLTHDNVVTVSPYALTHVAGPYNHWV

HDAC effector domains:

HDAC8 (*X. laevis*):

(SEQ ID NO: 97)

ASSPKKKRKVEASMSRVVKPKVASMEEMAAFHTDAYLQHLHKVSEEGDNDDPETLEYGLGYDCPITEGIY
DYAAAVGGATLTAAEQLIEGKTRIAVNWPGGWHHAKKDEASGFCYLNDAVLGILKLREKFDRVLYVDMDL
HHGDGVEDAFSFTSKVMTVSLHKFSPGFFPGTGDVSDIGLGKGRYYSINVPLQDGIQDDKYYQICEGVLK
EVFTTFNPEAVVLQLGADTIAGDPMCSFNMTPEGIGKCLKYVLQWQLPTLILGGGGYHLPNTARCWTYLT
ALIVGRTLSSEIPDHEFFTEYGPDYVLEITPSCRPDRNDTQKVQEILQSIKGNLKRVVEF

RPD3 (*S. cerevisiae*):

(SEQ ID NO: 98)

ASSPKKKRKVEASRRVAYFYDADVGNYAYGAGHPMKPHRIRMAHSLIMNYGLYKKMEIYRAKPATKQEMC
QFHTDEYIDFLSRVTPDNLEMFKRESVKFNVGDDCPVFDGLYEYCSISGGGSMEGAARLNRGKCDVAVNY
AGGLHHAKKSEASGFCYLNDIVLGIIELLRYHPRVLYIDIDVHHGDGVEEAFYTTDRVMTCSFHKYGEFF
PGTGELRDIGVGAGKNYAVNVPLRDGIDDATYRSVFEPVIKKIMEWYQPSAVVLQCGGDSLSGDRLGCFN
LSMEGHANCVNYVKSFGIPMMVVGGGGYTMRNVARTWCFETGLLNNVVLDKDLPYEF

-continued

MesoLo4 (*M. loti*):

(SEQ ID NO: 99)

ASSPKKKRKVEASMPLQIVHHPDYDAGFATNHRFPMSKYPLLMEALRARGLASPDALNTTEPAPASWLKL

AHAADYVDQVISCSVPEKIEREIGFPVGPRVSLRAQLATGGTILAARLALRHGIACNTAGGSHHARRAQG

AGFCTFNDVAVASLVLLDEGAAQNILVVDLDVHQGDGTADILSDEPGVFTFSMHGERNYPVRKIASDLDI

ALPDGTGDAAYLRRLATILPELSARARWDIVFYNAGVDVHAEDRLGRLALSNGGLRARDEMVIGHFRALG

IPVCGVIGGGYSTDVPALASRHAILFEVASTYAEF

HDAC11 (human):

(SEQ ID NO: 100)

ASSPKKKRKVEASMLHTTQLYQHVPETRWPIVYSPRYNITFMGLEKLHPFDAGKWGKVINFLKEEKLLSD

SMLVEAREASEEDLLVVHTRRYLNELKWSFAVATITEIPPVIFLPNFLVQRKVLRPLRTQTGGTIMAGKL

AVERGWAINVGGGFHHCSSDRGGGFCAYADITLAIKFLFERVEGISRATIIDLDAHQGNGHERDFMDDKR

VYIMDVYNRHIYPGDRFAKQAIRRKVELEWGTEDDEYLDKVERNIKKSLQEHLPDVVVYNAGTDILEGDR

LGGLSISPAGIVKRDELVFRMVRGRRVPILMVTSGGYQKRTARIIADSILNLFGLGLIGPESPSVSAQNS

DTPLLPPAVPEF

HDT1 (*A. thaliana*):

(SEQ ID NO: 101)

ASSPKKKRKVEASMEFWGIEVKSGKPVTVTPEEGILIHVSQASLGECKNKKGEFVPLHVKVGNQNLVLGT

LSTENIPQLFCDLVFDKEFELSHTWGKGSVYFVGYKTPNIEPQGYSEEEEEEEEEVPAGNAAKAVAKPKA

KPAEVKPAVDDEEDESDSDGMDEDDSDGEDSEEEEPTPKKPASSKKRANETTPKAPVSAKKAKVAVTPQK

TDEKKKGGKAANQSEF

SIRT3 (human):

(SEQ ID NO: 102)

ASSPKKKRKVEASMVGAGISTPSGIPDFRSPGSGLYSNLQQYDLPYPEAIFELPFFFHNPKPFFTLAKEL

YPGNYKPNVTHYFLRLLHDKGLLLRLYTQNIDGLERVSGIPASKLVEAHGTFASATCTVCQRPFPGEDIR

ADVMADRVPRCPVCTGVVKPDIVFFGEPLPQRFLLHVVDFPMADLLLILGTSLEVEPFASLTEAVRSSVP

RLLINRDLVGPLAWHPRSRDVAQLGDVVHGVESLVELLGWTEEMRDLVQRETGKLDGPDKEF

HST2 (*S. cerevisiae*):

(SEQ ID NO: 103)

ASSPKKKRKVEASTEMSVRKIAAHMKSNPNAKVIFMVGAGISTSCGIPDFRSPGTGLYHNLARLKLPYPE

AVFDVDFFQSDPLPFYTLAKELYPGNFRPSKFHYLLKLFQDKDVLKRVYTQNIDTLERQAGVKDDLIIEA

HGSFAHCHCIGCGKVYPPQVFKSKLAEHPIKDFVKCDVCGELVKPAIVFFGEDLPDSFSETWLNDSEWLR

EKITTSGKHPQQPLVIVVGTSLAVYPFASLPEEIPRKVKRVLCNLETVGDFKANKRPTDLIVHQYSDEFA

EQLVEELGWQEDFEKILTAQGGMGEF

CobB (*E. coli* (K12)):

(SEQ ID NO: 104)

ASSPKKKRKVEASMEKPRVLVLTGAGISAESGIRTFRAADGLWEEHRVEDVATPEGFDRDPELVQAFYNA

RRRQLQQPEIQPNAAHLALAKLQDALGDRFLLVTQNIDNLHERAGNTNVIHMHGELLKVRCSQSGQVLDW

TGDVTPEDKCHCCQFPAPLRPHVVWFGEMPLGMDEIYMALSMADIFIAIGTSGHVYPAAGFVHEAKLHGA

HTVELNLEPSQVGNEFAEKYYGPASQVVPEFVEKLLKGLKAGSIAEF

HST2 (*C. albicans*):

(SEQ ID NO: 105)

ASSPKKKRKVEASMPSLDDILKPVAEAVKNGKKVTFFNGAGISTGAGIPDFRSPDTGLYANLAKLNLPFA

EAVFDIDFFKEDPKPFYTLAEELYPGNFAPTKFHHFIKLLQDQGSLKRVYTQNIDTLERLAGVEDKYIVE

AHGSFASNHCVDCHKEMTTETLKTYMKDKKIPSCQHCEGYVKPDIVFFGEGLPVKFFDLWEDDCEDVEVA

IVAGTSLTVFPFASLPGEVNKKCLRVLVNKEKVGTFKHEPRKSDIIALHDCDIVAERLCTLLGLDDKLNE

VYEKEKIKYSKAETKEIKMHEIEDKLKEEAHLKEDKHTTKVDKKEKQNDANDKELEQLIDKAKAEF

-continued

SIRT5 (human):
(SEQ ID NO: 106)
ASSPKKKRKVEASSSSMADFRKFFAKAKHIVIISGAGVSAESGVPTFRGAGGYWRKWQAQDLATPLAFAH

NPSRVWEFYHYRREVMGSKEPNAGHRAIAECETRLGKQGRRVVVITQNIDELHRKAGTKNLLEIHGSLFK

TRCTSCGVVAENYKSPICPALSGKGAPEPGTQDASIPVEKLPRCEEAGCGGLLRPHVVWFGENLDPAILE

EVDRELAHCDLCLVVGTSSVVYPAAMFAPQVAARGVPVAEFNTETTPATNRFRFHFQGPCGTTLPEALAC

HENETVSEF

Sir2A (*P. falciparum*):
(SEQ ID NO: 107)
ASSPKKKRKVEASMGNLMISFLKKDTQSITLEELAKIIKKCKHVVALTGSGTSAESNIPSFRGSSNSIWS

KYDPRIYGTIWGFWKYPEKIWEVIRDISSDYEIEINNGHVALSTLESLGYLKSVVTQNVDGLHEASGNTK

VISLHGNVFEAVCCTCNKIVKLNKIMLQKTSHFMHQLPPECPCGGIFKPNIILFGEVVSSDLLKEAEEEI

AKCDLLLVIGTSSTVSTATNLCHFACKKKKKIVEINISKTYITNKMSDYHVCAKFSELTKVANILKGSSE

KNKKIMEF

SIRT6 (human):
(SEQ ID NO: 108)
ASSPKKKRKVEASMSVNYAAGLSPYADKGKCGLPEIFDPPEELERKVWELARLVWQSSSVVFHTGAGIST

ASGIPDFRGPHGVWTMEERGLAPKFDTTFESARPTQTHMALVQLERVGLLRFLVSQNVDGLHVRSGFPRD

KLAELHGNMFVEECAKCKTQYVRDTVVGTMGLKATGRLCTVAKARGLRACRGELRDTILDWEDSLPDRDL

ALADEASRNADLSITLGTSLQIRPSGNLPLATKRRGGRLVIVNLQPTKHDRHADLRIHGYVDEVMTRLMK

HLGLEIPAWDGPRVLERALPPLEF

HMT effector domains:
NUE (*C. trachomatis*):
(SEQ ID NO: 109)
ASSPKKKRKVEASMTTNSTQDTLYLSLHGGIDSAIPYPVRRVEQLLQFSFLPELQFQNAAVKQRIQRLCY

REEKRLAVSSLAKWLGQLHKQRLRAPKNPPVAICWINSYVGYGVFARESIPAWSYIGEYTGILRRRQALW

LDENDYCFRYPVPRYSFRYFTIDSGMQGNVTRFINHSDNPNLEAIGAFENGIFHIIIRAIKDILPGEELC

YHYGPLYWKHRKKREEFVPQEEEF vSET (*P. bursaria chlorella* virus):
(SEQ ID NO: 110)
ASSPKKKRKVEASMFNDRVIVKKSPLGGYGVFARKSFEKGELVEECLCIVRHNDDWGTALEDYLFSRKNM

SAMALGFGAIFNHSKDPNARHELTAGLKRMRIFTIKPIAIGEEITISYGDDYWLSRPRLTQNEF

SUV39H1 (human):
(SEQ ID NO: 111)
ASSPKKKRKVEASNLKCVRILKQFHKDLERELLRRHHRSKTPRHLDPSLANYLVQKAKQRRALRRWEQEL

NAKRSHLGRITVENEVDLDGPPRAFVYINEYRVGEGITLNQVAVGCECQDCLWAPTGGCCPGASLHKFAY

NDQGQVRLRAGLPIYECNSRCRCGYDCPNRVVQKGIRYDLCIFRTDDGRGWGVRTLEKIRKNSFVMEYVG

EIITSEEAERRGQIYDRQGATYLFDLDYVEDVYTVDAAYYGNISHFVNHSCDPNLQVYNVFIDNLDERLP

RIAFFATRTIRAGEELTFDYNMQVDPVDMESTRMDSNFGLAGLPGSPKKRVRIECKCGTESCRKYLFEF

DIMS (*N. crassa*):
(SEQ ID NO: 112)
ASSPKKKRKVEASMEKAFRPHFFNHGKPDANPKEKKNCHWCQIRSFATHAQLPISIVNREDDAFLNPNFR

FIDHSIIGKNVPVADQSFRVGCSCASDEECMYSTCQCLDEMAPDSDEEADPYTRKKRFAYYSQGAKKGLL

RDRVLQSQEPIYECHQGCACSKDCPNRVVERGRTVPLQIFRTKDRGWGVKCPVNIKRGQFVDRYLGEIIT

SEEADRRRAESTIARRKDVYLFALDKFSDPDSLDPLLAGQPLEVDGEYMSGPTRFINHSCDPNMAIFARV

GDHADKHIHDLALFAIKDIPKGTELTFDYVNGLTGLESDAHDPSKISEMTKCLCGTAKCRGYLWEF

-continued

KYP (*A. thaliana*):
(SEQ ID NO: 113)
ASSPKKKRKVEASDISGGLEFKGIPATNRVDDSPVSPTSGFTYIKSLIIEPNVIIPKSSTGCNCRGSCTD

SKKCACAKLNGGNFPYVDLNDGRLIESRDVVFECGPHCGCGPKCVNRTSQKRLRFNLEVFRSAKKGWAVR

SWEYIPAGSPVCEYIGVVRRTADVDTISDNEYIFEIDCQQTMQGLGGRQRRLRDVAVPMNNGVSQSSEDE

NAPEFCIDAGSTGNFARFINHSCEPNLFVQCVLSSHQDIRLARVVLFAADNISPMQELTYDYGYALDSVH

EF

SUVR4 (*A. thaliana*):
(SEQ ID NO: 114)
ASSPKKKRKVEASQSAYLHVSLARISDEDCCANCKGNCLSADFPCTCARETSGEYAYTKEGLLKEKFLDT

CLKMKKEPDSFPKVYCKDCPLERDHDKGTYGKCDGHLIRKFIKECWRKCGCDMQCGNRVVQRGIRCQLQV

YFTQEGKGWGLRTLQDLPKGTFICEYIGEILTNTELYDRNVRSSSERHTYPVTLDADWGSEKDLKDEEAL

CLDATICGNVARFINHRCEDANMIDIPIEIETPDRHYYHIAFFTLRDVKAMDELTWDYMIDFNDKSHPVK

AFRCCCGSESCRDRKIKGSQGKSIERRKIVSAKKQQGSKEVSKKRKEF

Set4 (*C. elegans*):
(SEQ ID NO: 115)
ASSPKKKRKVEASMQLHEQIANISVTFNDIPRSDHSMTPTELCYFDDFATTLVVDSVLNFTTHKMSKKRR

YLYQDEYRTARTVMKTFREQRDWTNAIYGLLTLRSVSHFLSKLPPNKLFEFRDHIVRFLNMFILDSGYTI

QECKRYSQEGHQGAKLVSTGVWSRGDKIERLSGVVCLLSSEDEDSILAQEGSDFSVMYSTRKRCSTLWLG

PGAYINHDCRPTCEFVSHGSTAHIRVLRDMVPGDEITCFYGSEFFGPNNIDCECCTCEKNMNGAFSYLRG

NENAEPIISEKKTKYELRSRSEF

Set1 (*C. elegans*):
(SEQ ID NO: 116)
ASSPKKKRKVEASMKVAAKKLATSRMRKDRAAAASPSSDIENSENPSSLASHSSSSGRMTPSKNTRSRKG

VSVKDVSNHKITEFFQVRRSNRKTSKQISDEAKHALRDTVLKGTNERLLEVYKDVVKGRGIRTKVNFEKG

DFVVEYRGVMMEYSEAKVIEEQYSNDEEIGSYMYFFEHNNKKWCIDATKESPWKGRLINHSVLRPNLKTK

VVEIDGSHHLILVARRQIAQGEELLYDYGDRSAETIAKNPWLVNTEF

SETD8 (human)
(SEQ ID NO: 117)
ASSPKKKRKVEASSCDSTNAAIAKQALKKPIKGKQAPRKKAQGKTQQNRKLTDFYPVRRSSRKSKAELQS

EERKRIDELIESGKEEGMKIDLIDGKGRGVIATKQFSRGDFVVEYHGDLIEITDAKKREALYAQDPSTGC

YMYYFQYLSKTYCVDATRETNRLGRLINHSKCGNCQTKLHDIDGVPHLILIASRDIAAGEELLYDYGDRS

KASIEAFPWLKHEF

TgSET8 (*T. gondii*):
(SEQ ID NO: 118)
ASSPKKKRKVEASASRRTGEFLRDAQAPSRWLKRSKTGQDDGAFCLETWLAGAGDDAAGGERGRDREGAA

DKAKQREERRQKELEERFEEMKVEFEEKAQRMIARRAALTGEIYSDGKGSKKPRVPSLPENDDDALIEII

IDPEQGILKWPLSVMSIRQRTVIYQECLRRDLTACIHLTKVPGKGRAVFAADTILKDDFVVEYKGELCSE

REAREREQRYNRSKVPMGSFMFYFKNGSRMMAIDATDEKQDFGPARLINHSRRNPNMTPRAITLGDFNSE

PRLIFVARRNIEKGEELLVDYGERDPDVIKEHPWLNSEF

Those of skill in the art will understand that any of the exemplary Cas9 proteins, including the exemplary Cas9 nucleases, variants, and fusions thereof, e.g., described herein, can be delivered to cells using the instantly disclosed technology, and that the disclosure is not limited in this respect.

Nuclease Effector Proteins

TALE nucleases, or TALENs, are artificial nucleases comprising a transcriptional activator-like effector DNA binding domain associated with a DNA cleavage domain, for example, a FokI domain. A number of modular assembly schemes for generating engineered TALE constructs have been reported (Zhang, Feng; et. al. (February 2011). "Efficient construction of sequence-specific TAL effectors for modulating mammalian transcription". *Nature Biotechnology* 29 (2): 149-53; Geiβler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". *PLoS ONE* 6 (5): e19509; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". *Nucleic Acids Research*; Morbitzer, R.; Elsaesser, J.; Hausner, J.; Lahaye, T. (2011). "Assembly of custom TALE-type DNA binding domains by modular cloning". *Nucleic Acids Research*; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". *Nucleic Acids Research*.; Weber, E.; Gruetzner, R.; Werner, S.; Engler, C.; Marillonnet, S. (2011). Bendahmane, Mohammed. ed. "Assembly of Designer TAL Effectors by Golden Gate Cloning". *PLoS ONE* 6 (5): e19722; the entire contents of each of which are incorporated herein by reference). Those of skill in the art will understand that TALE nucleases can be engineered to target virtually any genomic sequence with high specificity, and that such engineered nucleases can be used in embodiments of the present technology to manipulate the genome of a cell, e.g., by delivering the respective TALEN via a method or strategy disclosed herein under circumstances suitable for the TALEN to bind and cleave its target sequence within the genome of the cell. In some embodiments, the delivered TALEN targets a gene or allele associated with a disease or disorder. In some embodiments, delivery of the TALEN to a subject confers a therapeutic benefit to the subject.

Zinc finger nucleases are a class of artificial nucleases that comprise a DNA cleavage domain and a zinc finger DNA binding domain. In some embodiments, the DNA cleavage domain is a non-specific DNA cleavage domain of a restriction endonuclease, for example, of FokI. In some embodiments, the DNA cleavage domain is a domain that only cleaves double-stranded DNA when dimerized with a second DNA cleavage domain of the same type. In some embodiments, the DNA cleavage domain is fused to the C-terminus of the zinc finger domain via a linker, for example, a peptide linker. In some embodiments, the zinc finger domain comprises between about 3 and about 6 zinc fingers and specifically recognizes and binds a target sequence of about 9-20 nucleotides in length. In some embodiments, a plurality of zinc finger nuclease molecules is delivered to a target cell by a system or method provided by this invention, with the zinc finger domain of one zinc finger nuclease molecule binding a target sequence in close proximity of the target sequence of a second zinc finger nuclease molecule. In some embodiments, the zinc finger domains of the zinc finger nuclease molecules binding target sequences in close proximity to each other are different. In some embodiments, a zinc finger nuclease molecule delivered to a cell by a system or method provided herein binds a target nucleic acid sequence in close proximity to the target sequence of another zinc finger nuclease molecule, so that the DNA cleavage domains of the molecules dimerize and cleave a DNA molecule at a site between the two target sequences.

In some embodiments, the genome of the target cell is edited by a nuclease delivered to the cell via a strategy or method disclosed herein, e.g., by a TALEN, or a zinc-finger nuclease, or a plurality or combination of such nucleases. In some embodiments, a single- or double-strand break is introduced at a specific site within the genome of a target cell by the nuclease, resulting in a disruption of the targeted genomic sequence. In some embodiments, the targeted genomic sequence is a nucleic acid sequence within the coding region of a gene. In some embodiments, the strand break introduced by the nuclease leads to a mutation within the target gene that impairs the expression of the encoded gene product. In some embodiments, a nucleic acid is co-delivered to the cell with the nuclease. In some embodiments, the nucleic acid comprises a sequence that is identical or homologous to a sequence adjacent to the nuclease target site. In some such embodiments, the strand break effected by the nuclease is repaired by the cellular DNA repair machinery to introduce all or part of the co-delivered nucleic acid into the cellular DNA at the break site, resulting in a targeted insertion of the co-delivered nucleic acid, or part thereof. In some embodiments, the insertion results in the disruption or repair of a pathogenic allele. In some embodiments, the insertion is detected by a suitable assay, e.g., a DNA sequencing assay, a southern blot assay, or an assay for a reporter gene encoded by the co-delivered nucleic acid, e.g., a fluorescent protein or resistance to an antibiotic. In some embodiments, the nucleic acid is co-delivered by association to a supercharged protein. In some embodiments, the supercharged protein is also associated to the functional effector protein, e.g., the nuclease. In some embodiments, the delivery of a nuclease to a target cell results in a clinically or therapeutically beneficial disruption of the function of a gene.

In some embodiments, cells from a subject are obtained and a nuclease or other effector protein is delivered to the cells by a system or method provided herein ex vivo. In some embodiments, the treated cells are selected for those cells in which a desired nuclease-mediated genomic editing event has been effected. In some embodiments, treated cells carrying a desired genomic mutation or alteration are returned to the subject they were obtained from.

Methods for engineering, generation, and isolation of nucleases targeting specific sequences, e.g., TALE, or zinc finger nucleases, and editing cellular genomes at specific target sequences, are well known in the art (see, e.g., Mani et al., *Biochemical and Biophysical Research Communications* 335:447-457, 2005; Perez et al., *Nature Biotechnology* 26:808-16, 2008; Kim et al., *Genome Research,* 19:1279-88, 2009; Urnov et al., *Nature* 435:646-51, 2005; Carroll et al., *Gene Therapy* 15:1463-68, 2005; Lombardo et al., *Nature Biotechnology* 25:1298-306, 2007; Kandavelou et al., *Biochemical and Biophysical Research Communications* 388: 56-61, 2009; and Hockemeyer et al., *Nature Biotechnology* 27(9):851-59, 2009, as well as the reference recited in the respective section for each nuclease). The skilled artisan will be able to ascertain suitable methods for use in the context of the present disclosure based on the guidance provided herein.

TALE Effector Proteins

In some embodiments, effector proteins comprising a TALE domain are delivered to a target cell by a system or method provided herein. In some embodiments, a TALE effector, e.g., an engineered TALE transcription factor comprising a TALE DNA binding domain and a heterologous transcriptional activator or repressor domain, is delivered to a cell by a system or method provided by aspects of this invention. In some embodiments, the TALE effector, e.g., a transcription factor, is delivered to a cell in an amount sufficient to activate or inhibit transcription of a target gene of the transcription factor within the cell. In some embodiments, a transcription factor is delivered in an amount and over a time period sufficient to effect a change in the phenotype of a target cell, for example, a change in cellular function, or a change in developmental potential. Exemplary TALE transcription factors are described herein, and the skilled artisan will be able to identify additional suitable TALE transcription factors based on the guidance provided herein and the knowledge of such TALE transcription factors in the art.

In some embodiments, a target cell, for example, a somatic cell, is contacted with a TALE transcription factor, or a combination of such factors, associated with a supercharged protein provided herein. In some embodiments the target cell is a primary somatic cell and is contacted in vitro or ex vivo with a TALE transcription factor associated with a supercharged protein. In some embodiments, the TALE transcription factor is associated with a positively charged supercharged protein, e.g., as described herein. In some embodiments, the TALE transcription factor is associated with a negatively charged supercharged proteins, e.g., as described herein. In some embodiments, the TALE transcription factor is associated with a cationic lipid and/or cationic polymer, e.g., as described herein. In some embodiments, the TALE transcription factor is associated with a negatively charged supercharged protein and a cationic lipid and/or cationic polymer, e.g., as described herein.

In some embodiments, a target cell is contacted, or repeatedly contacted, with a TALE transcription factor associated with a supercharged protein (and optionally a cationic lipid and/or cationic polymer) as provided herein, and a desired change in cellular phenotype or gene expression is detected. In some embodiments, a target cell is contacted repeatedly with a TALE transcription factor associated with a supercharged protein (and optionally a cationic lipid and/or cationic polymer) as provided herein until the formation of a desired cellular phenotype is detected. Methods for detecting cellular phenotypes and gene expression are well known to those in the art and include, for example, morphological analysis, and detection of marker gene expression by well-established methods such as immunohistochemistry, fluorescence activated cell sorting (FACS), or fluorescent microscopy. In some embodiments, a target cell is contacted with a TALE transcription factor associated with a supercharged protein as provided herein for a period of at least 3 hours, at least 6 hours, at least 12 hours, at least 1 day, at least 2 days, at least 3 days, at least 4 days, at least 5 days, at least 6 days, at least 7 days, at least 10-12 days, at least 12-15 days, at least 15-20 days, at least 20-25 days, at least 25-30 days, at least 30-40 days, at least 40-50 days, at least 50-60 days, at least 60-70, or at least 70-100 days.

In some embodiments, a target cell is contacted with a TALE transcription factor associated with a supercharged protein (and optionally a cationic lipid and/or cationic polymer) as provided herein in an amount and for a time period effective to program the cell towards a different cell state. As will be apparent to those of skill in the art, the amount necessary to program or re-program a cell will dependent on various factors, for example, on the cell type and the treatment schedule. In general, delivery of a TALE transcription factor to a target somatic cell by a system or method provided herein will be at a concentration below a concentration at which significant toxicity can be observed. The critical concentration will depend, for example, on the specific TALE transcription factor, the supercharged protein it is associated with, the type of association, and the type of cell being treated.

A useful concentration of a functional effector protein associated with a supercharged protein (and optionally a cationic lipid and/or cationic polymer) for delivery to a specific cell type can be established by those of skill in the art by routine experimentation. In some embodiments a target cell is contacted in vitro or ex vivo with a functional effector protein associated with a supercharged protein (and optionally a cationic lipid and/or cationic polymer) at a concentration of about 1 pM to about 1 μM. In some embodiments, a target cell is contacted in vitro or ex vivo with the functional effector protein associated to a supercharged protein at a concentration of about 1 pM, about 2.5 pM, about 5 pM, about 7.5 pM, about 10 pM, about 20 pM, about 25 pM, about 30 pM, about 40 pM, about 50 pM, about 60 pM, about 70 pM, about 75 pM, about 80 pM, about 90 pM, about 100 pM, about 200 pM, about 250 pM, about 300 pM, about 400 pM, about 500 pM, about 600 pM, about 700 pM, about 750 pM, about 800 pM, about 900 pM, about 1 nM, about 2 nM, about 3 nM, about 4 nM, about 5 nM, about 6 nM, about 7 nM, about 8 nM, about 9 nM, about 10 nM, about 20 nM, about 25 nM, about 30 nM, about 40 nM, about 50 nM, about 60 nm, about 70 nM, about 75 nM, about 80 nM, about 90 nM, about 100 nM, about 200 nM, about 250 nM, about 300 nM, about 400 nM, about 500 nM, about 600 nM, about 700 nM, about 750 nM, about 800 nM, about 900 nM, or about 1 μM. A useful time of exposure of the target cell to the functional effector protein, and, if necessary, incubation after administration in the absence of the functional effector protein, as well as a number of administration/incubation cycles useful to achieve a desired biological effect (e.g., change in gene transcription, cleavage of a target site by a delivered nuclease, etc.), or a desired cellular phenotype can also be established by those of skill in the art by routine experimentation.

In some embodiments, the target cell for delivery of a functional effector protein by a system or method provided herein, is a primary cell obtained by a biopsy from a subject. In some embodiments, the subject is diagnosed as having a disease. In some embodiments the disease is a degenerative disease characterized by diminished function of a specific cell type, for example, a neural cell. In some embodiments, a cell treated with a functional effector protein according to the strategies or methods disclosed herein, or the progeny of such a cell, is used in a cell-replacement therapeutic approach. In some embodiments, the treated cells are administered to the subject from which the somatic cell was obtained in an autologous cell replacement therapeutic approach.

In some embodiments, a functional effector protein, e.g., TALE transcription factor able to convert a cell from one differentiated state into another, is delivered to a target cell in vitro or in vivo by a system or method provided herein. Transcription factors that effect transdifferentiation are known in the art (see, e.g., Zhou et al., *Nature* 455:627-33, 2008). In some embodiments, a TALE transcription factor modulating the expression of PPARγ or PRDM16 are delivered to fibroblast cells by a system or method as provided by this invention. It is known in the art that expression these transcription factors is a pivotal step in the programming of fibroblasts towards a brown fat or white fat cell state. In some embodiments, a programmed brown fat cell is generated from a fibroblast obtained from a subject in need of brown fat cells, and is administered to the subject, e.g., used in a cell-replacement therapeutic approach involving the subject.

Formation of Complexes

The present invention provides complexes comprising supercharged proteins associated with one or more functional effector proteins to be delivered. In some embodiments, supercharged proteins are associated with one or more functional effector proteins to be delivered through non-covalent interactions. In some embodiments, supercharged proteins are associated with one or more functional effector proteins through electrostatic interactions. In certain embodiments, supercharged proteins have an overall net positive charge, and the functional effector proteins to be delivered have an overall net negative charge. In some embodiments, the complex further comprises a cationic lipid and/or cationic polymer. For example, in some embodiments, the supercharged protein of the complex is supernegatively charged, allowing for association with cationic lipids and/or polymers.

In certain embodiments, supercharged proteins are associated with one or more functional effector proteins to be delivered via covalent bond. For example, a supercharged protein may be fused to a functional effector protein to be delivered. Covalent attachment may be direct or indirect (e.g., through a linker). In some embodiments, a covalent attachment is mediated through one or more linkers. In some embodiments, the linker is a cleavable linker. In certain embodiments, the cleavable linker comprises an amide, ester, or disulfide bond. For example, the linker may be an amino acid sequence that is cleavable by a cellular enzyme. In certain embodiments, the enzyme is a protease. In other embodiments, the enzyme is an esterase. In some embodiments, the enzyme is one that is more highly expressed in certain cell types than in other cell types. For example, the enzyme may be one that is more highly expressed in tumor cells than in non-tumor cells. Exemplary linkers and enzymes that cleave those linkers are presented below.

Cleavable Linkers

| Linker Sequence | Enzyme(s) Targeting Linker |
|---|---|
| X[1]-AGVF-X (SEQ ID NO: 256) | lysosomal thiol proteinases (see, e.g., Duncan et al., 1982, *Biosci. Rep.*, 2: 1041-46; incorporated herein by reference) |
| X-GFLG-X (SEQ ID NO: 257) | lysosomal cysteine proteinases (see, e.g., Vasey et al., *Clin. Canc. Res.*, 1999, 5: 83-94; incorporated herein by reference) |
| X-FK-X | Cathepsin B - ubiquitous, overexpressed in many solid tumors, such as breast cancer (see, e.g., Dubowchik et al., 2002, *Bioconjugate Chem.*, 13: 855-69; incorporated herein by reference) |
| X-A*L-X | Cathepsin B - ubiquitous, overexpressed in many solid tumors, such as breast cancer (see, e.g., Trouet et al., 1982, *Proc. Natl. Acad. Sci.*, USA, 79: 626-29; incorporated herein by reference) |
| X-A*LA*L-X (SEQ ID NO: 258) | Cathepsin B - ubiquitous, overexpressed in many solid tumors (see, e.g., Schmid et al., 2007, *Bioconjugate Chem*, 18: 702-16; incorporated herein by reference) |
| X-AL*AL*A-X (SEQ ID NO: 259) | Cathepsin D - ubiquitous (see, e.g., Czerwinski et al., 1998, *Proc. Natl. Acad. Sci.*, USA, 95: 11520-25; incorporated herein by reference) |

[1]X denotes a supercharged protein or a functional effector protein to be delivered
*refers to observed cleavage site To give but one particular example, a +36 GFP may be associated with a functional effector protein to be delivered by a cleavable linker, such as ALAL (SEQ ID NO: 254), to generate +36 GFP-$(GGS)_4$-ALAL-$(GGS)_4$-[functional effector protein X] (SEQ ID NO: 255).

In certain embodiments, the functional effector protein to be delivered is contacted with the supercharged protein to form a complex. In some embodiments, formation of complexes is carried out at or around pH 7. In some embodiments, formation of complexes is carried out at about pH 5, about pH 6, about pH 7, about pH 8, or about pH 9. Formation of complexes is typically carried out at a pH that does not negatively affect the function of the supercharged protein and/or the functional effector protein. In some embodiments, formation of complexes is carried out at room temperature. In some embodiments, formation of complexes is carried out at or around 37° C. In some embodiments, formation of complexes is carried out below 4° C., at about 4° C., at about 10° C., at about 15° C., at about 20° C., at about 25° C., at about 30° C., at about 35° C., at about 37° C., at about 40° C., or higher than 40° C. Formation of complexes is typically carried out at a temperature that does not negatively affect the function of the supercharged protein and/or functional effector protein. In some embodiments, formation of complexes is carried out in serum-free medium. In some embodiments, formation of complexes is carried out in the presence of $CO_2$ (e.g., about 1%, about 2%, about 3%, about 4%, about 5%, about 6%, or more).

In some embodiments, formation of complexes is carried out using concentrations of functional effector protein of about 100 nM. In some embodiments, formation of complexes is carried out using concentrations of functional effector protein of about 25 nM, about 50 nM, about 75 nM, about 90 nM, about 100 nM, about 110 nM, about 125 nM, about 150 nM, about 175 nM, or about 200 nM. In some embodiments, formation of complexes is carried out using concentrations of supercharged protein of about 40 nM. In some embodiments, formation of complexes is carried out using concentrations of supercharged protein of about 10 nM, about 20 nM, about 30 nM, about 40 nM, about 50 nM, about 60 nM, about 70 nM, about 80 nM, about 90 nM, or about 100 nM.

In some embodiments, formation of complexes is carried out under conditions of excess functional effector protein. In some embodiments, formation of complexes is carried out with ratios of functional effector protein:supercharged protein of about 20:1, about 10:1, about 9:1, about 8:1, about 7:1, about 6:1, about 5:1, about 4:1, about 3:1, about 2:1, or about 1:1. In some embodiments, formation of complexes is carried out with ratios of functional effector protein:supercharged protein of about 3:1. In some embodiments, formation of complexes is carried out with ratios of supercharged protein: functional effector protein of about 20:1, about 10:1, about 9:1, about 8:1, about 7:1, about 6:1, about 5:1, about 4:1, about 3:1, about 2:1, or about 1:1.

In some embodiments, formation of complexes is carried out by mixing supercharged protein with functional effector protein, and agitating the mixture (e.g., by inversion). In some embodiments, formation of complexes is carried out by mixing supercharged protein with functional effector protein, and allowing the mixture to sit still. In some embodiments, the formation of the complex is carried out in the presence of a pharmaceutically acceptable carrier or excipient. In some embodiments, the complex is further combined with a pharmaceutically acceptable carrier or excipient. Exemplary excipients or carriers include water, solvents, lipids, proteins, peptides, endosomolytic agents (e.g., chloroquine, pyrene butyric acid), small molecules, carbohydrates, buffers, natural polymers, synthetic polymers (e.g., PLGA, polyurethane, polyesters, polycaprolactone, polyphosphazenes), pharmaceutical agents, etc.

In some embodiments, complexes comprising supercharged protein and functional effector protein may migrate more slowly in gel electrophoresis assays than either the supercharged protein alone or the functional effector protein alone.

Applications

The present invention provides compositions comprising supercharged proteins, naturally occurring or engineered, associated with functional effector proteins (e.g., nucleases, transcriptional activators/repressors, recombinases, Cas9 proteins including variants and fusions thereof, etc.) to be delivered to a cell, as well as methods of using such compositions and uses of such compositions. In certain embodiments, compositions are provided comprising a Cas9 protein (e.g., wherein the Cas9 protein is associated with a gRNA) and a cationic lipid. In certain embodiments, compositions are provided comprising a Cas9 protein (e.g., wherein the Cas9 protein is associated with a gRNA) and a cationic polymer. The inventive compositions may be used to treat or prevent any disease that can benefit, e.g., from the delivery of an agent to a cell. The inventive compositions may also be used to transfect or treat cells for research purposes.

In some embodiments, compositions in accordance with the invention may be used for research purposes, e.g., to efficiently deliver functional effector proteins to cells in a research context. In some embodiments, compositions in accordance with the present invention may be used for therapeutic purposes. In some embodiments, compositions in accordance with the present invention may be used for treatment of any of a variety of diseases, disorders, and/or conditions, including, but not limited to, one or more of the following: autoimmune disorders (e.g., diabetes, lupus, multiple sclerosis, psoriasis, rheumatoid arthritis); inflammatory disorders (e.g., arthritis, pelvic inflammatory disease); infectious diseases (e.g., viral infections (e.g., HIV, HCV, RSV), bacterial infections, fungal infections, sepsis); neurological disorders (e.g. Alzheimer's disease, Huntington's disease; autism; Duchenne muscular dystrophy); cardiovascular disorders (e.g. atherosclerosis, hypercholesterolemia, thrombosis, clotting disorders, angiogenic disorders such as macular degeneration); proliferative disorders (e.g. cancer, benign neoplasms); respiratory disorders (e.g. chronic obstructive pulmonary disease); digestive disorders (e.g. inflammatory bowel disease, ulcers); musculoskeletal disorders (e.g. fibromyalgia, arthritis); endocrine, metabolic, and nutritional disorders (e.g. diabetes, osteoporosis); urological disorders (e.g. renal disease); psychological disorders (e.g. depression, schizophrenia); skin disorders (e.g. wounds, eczema); blood and lymphatic disorders (e.g. anemia, hemophilia); etc.

Compositions of the invention may be used in a clinical setting. For example, a supercharged protein may be associated with a functional effector protein that can be used for therapeutic applications. Such functional effector protein may be, for example, nucleases or transcriptional activators. Other compositions comprising a Cas9 protein and a cationic lipid may also be used for therapeutic applications.

In some embodiments, the supercharged protein or functional effector protein associated with a supercharged protein includes a detectable label. These molecules can be used in detection, imaging, disease staging, diagnosis, or patient selection. Suitable labels include fluorescent, chemiluminescent, enzymatic labels, colorimetric, phosphorescent, density-based labels, e.g., labels based on electron density, and in general contrast agents, and/or radioactive labels.

Pharmaceutical Compositions

The present invention provides compositions comprising supercharged proteins associated with at least one functional effector protein to be delivered, and in some embodiments are encapsulated by cationic lipids. Other compositions comprising a Cas9 protein and a cationic lipid are provided. Thus, the present invention provides pharmaceutical compositions comprising one or more supercharged proteins associated with a functional effector protein, and/or one or more functional effector proteins associated with a cationic lipid and/or cationic polymer, and one or more pharmaceutically acceptable excipients. Pharmaceutical compositions may optionally comprise one or more additional therapeutically active substances. In accordance with some embodiments, a method of administering pharmaceutical compositions comprising one or more supercharged proteins associated with a functional effector protein to be delivered to a subject in need thereof is provided. In some embodiments, compositions are administered to humans. For the purposes of the present disclosure, the phrase "active ingredient" generally refers to a Cas9 protein and/or supercharged protein associated with a functional effector protein, or to the functional effector protein to be delivered as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions is contemplated include, but are not limited to, humans and/or other primates; mammals, including commercially relevant mammals such as cattle, pigs, horses, sheep, cats, dogs, mice, and/or rats; and/or birds, including commercially relevant birds such as chickens, ducks, geese, and/or turkeys.

Formulations of the pharmaceutical compositions described herein may be prepared by any method known or hereafter developed in the art of pharmacology. In general, such preparatory methods include the step of bringing the active ingredient into association with an excipient and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's *The Science and Practice of Pharmacy,* 21$^{st}$ Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and/or combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and/or combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum® [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween®20), polyoxyethylene sorbitan (Tween®60), polyoxyethylene sorbitan monooleate [Tween®80], sorbitan monopalmitate [Span®40], sorbitan monostearate [Span®60], sorbitan tristearate [Span®65], glyceryl monooleate, sorbitan monooleate [Span®80]), polyoxyethylene esters (e.g. polyoxyethylene monostearate [Myrj®45], polyoxyethylene hydrogenated castor oil, polyethoxylated castor oil, polyoxymethylene stearate, and Solutol®), sucrose fatty acid esters, polyethylene glycol fatty acid esters (e.g. Cremophor®), polyoxyethylene ethers, (e.g. polyoxyethylene lauryl ether (Brij®30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic®F 68, Poloxamer®188, cetrimonium bromide, cetylpyridinium chloride, benzalkonium chloride, docusate sodium, etc. and/or combinations thereof.

Exemplary binding agents include, but are not limited to, starch (e.g. cornstarch and starch paste); gelatin; sugars (e.g. sucrose, glucose, dextrose, dextrin, molasses, lactose, lactitol, mannitol,); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum®), and larch arabogalactan); alginates; polyethylene oxide; polyethylene glycol; inorganic calcium salts; silicic acid; polymethacrylates; waxes; water; alcohol; etc.; and combinations thereof.

Exemplary preservatives may include, but are not limited to, antioxidants, chelating agents, antimicrobial preservatives, antifungal preservatives, alcohol preservatives, acidic preservatives, and/or other preservatives. Exemplary antioxidants include, but are not limited to, alpha tocopherol, ascorbic acid, ascorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and/or sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and/or trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and/or thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and/or sorbic acid. Exemplary alcohol preservatives include, but are not limited to, ethanol, polyethylene glycol, phenol, phenolic compounds, bisphenol, chlorobutanol, hydroxybenzoate, and/or phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and/or phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus®, Phenonip®, methylparaben, Germall®115, Germaben®II, Neolone™, Kathon™, and/or Euxyl®.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and/or combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and/or combinations thereof.

Liquid dosage forms for oral and parenteral administration include, but are not limited to, pharmaceutically acceptable emulsions, microemulsions, solutions, suspensions, syrups, and/or elixirs. In addition to active ingredients, liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, oral compositions can include adjuvants such as wetting agents, emulsifying and suspending agents, sweetening, flavoring, and/or perfuming agents. In certain embodiments for parenteral administration, compositions are mixed with solubilizing agents such as Cremophor®, alcohols, oils, modified oils, glycols, polysorbates, cyclodextrins, polymers, and/or combinations thereof.

Injectable preparations, for example, sterile injectable aqueous or oleaginous suspensions may be formulated according to the known art using suitable dispersing agents, wetting agents, and/or suspending agents. Sterile injectable preparations may be sterile injectable solutions, suspensions, and/or emulsions in nontoxic parenterally acceptable diluents and/or solvents, for example, as a solution in 1,3-butanediol. Among the acceptable vehicles and solvents that may be employed are water, Ringer's solution, U.S.P., and isotonic sodium chloride solution. Sterile, fixed oils are conventionally employed as a solvent or suspending medium. For this purpose any bland fixed oil can be employed including synthetic mono- or diglycerides. Fatty acids such as oleic acid can be used in the preparation of injectables.

Injectable formulations can be sterilized, for example, by filtration through a bacterial-retaining filter, and/or by incorporating sterilizing agents in the form of sterile solid compositions which can be dissolved or dispersed in sterile water or other sterile injectable medium prior to use.

In order to prolong the effect of an active ingredient, it is often desirable to slow the absorption of the active ingredient from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are prepared by entrapping the drug in liposomes or microemulsions which are compatible with body tissues.

Compositions for rectal or vaginal administration are typically suppositories which can be prepared by mixing compositions with suitable non-irritating excipients such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, an active ingredient is mixed with at least one inert, pharmaceutically acceptable excipient such as sodium citrate or dicalcium phosphate and/or fillers or extenders (e.g. starches, lactose, sucrose, glucose, mannitol, and silicic acid), binders (e.g. carboxymethylcellulose, alginates, gelatin, polyvinylpyrrolidinone, sucrose, and acacia), humectants (e.g. glycerol), disintegrating agents (e.g. agar, calcium carbonate, potato or tapioca starch, alginic acid, certain silicates, and sodium carbonate), solution retarding agents (e.g. paraffin), absorption accelerators (e.g. quaternary ammonium compounds), wetting agents (e.g. cetyl alcohol and glycerol monostearate), absorbents (e.g. kaolin and bentonite clay), and lubricants (e.g. talc, calcium stearate, magnesium stearate, solid polyethylene glycols, sodium lauryl sulfate), and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. Solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polyethylene glycols and the like.

Dosage forms for topical and/or transdermal administration of a composition may include ointments, pastes, creams, lotions, gels, powders, solutions, sprays, inhalants and/or patches. Generally, an active ingredient is admixed under sterile conditions with a pharmaceutically acceptable excipient and/or any needed preservatives and/or buffers as may be required. Additionally, the present invention contemplates the use of transdermal patches, which often have the added advantage of providing controlled delivery of a compound to the body. Such dosage forms may be prepared, for example, by dissolving and/or dispensing the compound in the proper medium. Alternatively or additionally, rate may be controlled by either providing a rate controlling membrane and/or by dispersing the compound in a polymer matrix and/or gel.

Suitable devices for use in delivering intradermal pharmaceutical compositions described herein include short needle devices. Intradermal compositions may be administered by devices which limit the effective penetration length of a needle into the skin and functional equivalents thereof. Jet injection devices which deliver liquid compositions to the dermis via a liquid jet injector and/or via a needle which pierces the stratum corneum and produces a jet which reaches the dermis are suitable. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of active ingredient may be as high as the solubility limit of the active ingredient in the solvent. Formulations for topical administration may further comprise one or more of the additional ingredients described herein.

A pharmaceutical composition may be prepared, packaged, and/or sold in a formulation suitable for pulmonary administration via the buccal cavity. Such a formulation may comprise dry particles which comprise the active ingredient and which have a diameter in the range from about 0.5 nm to about 7 nm or from about 1 nm to about 6 nm. Such compositions are conveniently in the form of dry powders for administration using a device comprising a dry powder reservoir to which a stream of propellant may be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nm and at least 95% of the particles by number have a diameter less than 7 nm. Alternatively, at least 95% of the particles by weight have a diameter greater than 1 nm and at least 90% of the particles by number have a diameter less than 6 nm. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50% to 99.9% (w/w) of the composition, and active ingredient may constitute 0.1% to 20% (w/w) of the composition. A propellant may further comprise additional ingredients such as a liquid non-ionic and/or solid anionic surfactant and/or a solid diluent (which may have a particle size of the same order as particles comprising the active ingredient).

Pharmaceutical compositions formulated for pulmonary delivery may provide an active ingredient in the form of droplets of a solution and/or suspension. Such formulations may be prepared, packaged, and/or sold as aqueous and/or dilute alcoholic solutions and/or suspensions, optionally sterile, comprising active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. Droplets provided by this route of administration may have an average diameter in the range from about 0.1 nm to about 200 nm.

Formulations described herein as being useful for pulmonary delivery are useful for intranasal delivery of a pharmaceutical composition. Another formulation suitable for intranasal administration is a coarse powder comprising the active ingredient and having an average particle from about 0.2 μm to 500 μm. Such a formulation is administered in the manner in which snuff is taken, i.e. by rapid inhalation through the nasal passage from a container of the powder held close to the nose.

Formulations suitable for nasal administration may, for example, comprise from about as little as 0.1% (w/w) and as much as 100% (w/w) of active ingredient, and may comprise one or more of the additional ingredients described herein. A pharmaceutical composition may be prepared, packaged, and/or sold in a formulation suitable for buccal administration. Such formulations may, for example, be in the form of tablets and/or lozenges made using conventional methods, and may, for example, 0.1% to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising active ingredient. Such powdered, aerosolized, and/or aerosolized formulations, when dispersed, may have an average particle and/or droplet size in the range from about 0.1 nm to about 200 nm, and may further comprise one or more of any additional ingredients described herein.

A pharmaceutical composition may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of any additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005 (incorporated herein by reference).

Administration

The present invention provides methods comprising administering compositions of supercharged proteins associated with functional effector proteins to a subject in need thereof. In some embodiments, methods of administering compositions comprising other functional effector proteins (e.g., a Cas9 protein) and cationic lipid and/or cationic polymers are provided. Such compositions may be administered to a subject using any amount and any route of administration effective for preventing, treating, diagnosing, or imaging a disease, disorder, and/or condition. The exact amount required will vary from subject to subject, depending on the species, age, and general condition of the subject, the severity of the disease, the particular composition, its mode of administration, its mode of activity, and the like. Compositions in accordance with the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective, prophylactially effective, or appropriate imaging dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

Compositions of supercharged proteins associated with functional effector proteins to be delivered as well as compositions comprising e.g., a Cas9 protein and cationic lipid may be administered by any route. In some embodiments, such compositions are administered by one or more of a variety of routes, including oral, intravenous, intramuscular, intra-arterial, intramedullary, intrathecal, subcutaneous, intraventricular, transdermal, interdermal, rectal, intravaginal, intraperitoneal, topical (e.g., by powders, ointments, creams, gels, lotions, and/or drops), mucosal, nasal, buccal, enteral, vitreal, intratumoral, sublingual; by intratracheal instillation, bronchial instillation, and/or inhalation; as an oral spray, nasal spray, and/or aerosol, and/or through a portal vein catheter. In some embodiments, supercharged proteins or complexes, and/or pharmaceutical, prophylactic, diagnostic, or imaging compositions thereof, are administered by systemic intravenous injection. In specific embodiments, supercharged proteins or complexes and/or pharmaceutical, prophylactic, diagnostic, or imaging compositions thereof may be administered intravenously and/or orally. In specific embodiments, such compositions may be administered in a way which allows the functional effector protein to cross the blood-brain barrier, vascular barrier, or other epithelial barrier.

In certain embodiments, compositions in accordance with the invention may be administered at dosage levels sufficient to deliver an amount of functional effector protein of from about 0.0001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic, diagnostic, prophylactic, or imaging effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

Compositions comprising supercharged proteins associated with functional effector proteins may be administered in combination with one or more other therapeutic, prophylactic, diagnostic, or imaging agents. By "in combination with," it is not intended to imply that the agents must be administered at the same time and/or formulated for delivery together, although these methods of delivery are within the scope of the invention. Compositions can be administered concurrently with, prior to, or subsequent to, one or more other desired therapeutics or medical procedures. In general, each agent will be administered at a dose and/or on a time schedule determined for that agent. In some embodiments, the invention encompasses the delivery of pharmaceutical, prophylactic, diagnostic, or imaging compositions in combination with agents that may improve their bioavailability, reduce and/or modify their metabolism, inhibit their excretion, and/or modify their distribution within the body.

Kits

The invention provides a variety of kits for conveniently and/or effectively carrying out methods of the present invention. Typically kits will comprise sufficient amounts and/or numbers of components to allow a user to perform multiple treatments of a subject(s) and/or to perform multiple experiments. In some embodiments, kits comprise one or more of (i) a supercharged protein, as described herein; (ii) a functional effector protein to be delivered; (ii) a cationic lipid and/or cationic polymer; and (iv) instructions for formulating a composition comprising the functional protein associated to the supercharged protein. In some embodiments, the kits comprise a Cas9 protein and a cationic lipid. In some embodiments, kits comprise a nucleic acid encoding for the supercharged protein and/or the functional protein to be delivered. In some embodiments, the kit comprises a cloning vector encoding a supercharged protein and a cloning site allowing the in-frame cloning of a functional effector protein to generate a fusion protein. In some embodiments, kits comprise a pharmaceutical composition provided herein comprising a supercharged protein associated with a functional effector protein; a syringe, needle, or applicator for administration of the pharmaceutical composition to a subject; and instructions for administration of the pharmaceutical composition to the subject.

These and other aspects of the present invention will be further appreciated upon consideration of the following Examples, which are intended to illustrate certain particular embodiments of the invention but are not intended to limit its scope, as defined by the claims.

EXAMPLES

Example 1: Delivery of TALE Activators Fused to Supercharged GFP

A major target for reprogramming fibroblast cell fate towards brown or white adipocyte cell fate lies in the switch from White Adipose Tissue (WAT) to Brown Adipose Tissue (BAT), which is governed by expression of PRDM16 and PPARγ. Robust TALE transcriptional activators fused to a +36 GFP were engineered that target PPARγ and PRDM16 genomic sequences in fibroblasts. Fusion proteins were purified using a heparin column and/or an SEC and gels show a single band at 130 kD The modulation of expression and effect on cellular phenotype after delivery of the TALE activators was compared to the modulation after viral delivery of a PPARγ cDNA followed by 7-day treatment with adipogenesis cocktail. It was observed that adipocytes formed upon treatment with +36 GFP TALEPRDM16 fusion. Expression of white adipose tissue marker genes was detected after delivery of supercharged PRDM16 TALE activators.

A one-time supercharged protein-mediated delivery of a TALE activator for PPARγ was found to induce expression of white-fat genes and to differentiate fibroblasts into white-fat cells. Supercharged protein-mediated delivery of both a PPARγ and PRDM16 TALE activator induced the differentiation of fat cells with increased expression of brown-fat markers such as PRDM16, cox8b, elovl3, and cidea as well as a small increase in thermogenic gene expression markers PGC1a and UCP1.

An Aurein peptide was fused to the N-terminus of the +36 GFP-TALE-activator fusion protein. Delivery of Aurein +36 GFP TALE purified by heparin column was observed by detecting fluorescence in nucleus of the treated cells.

Figure 2:
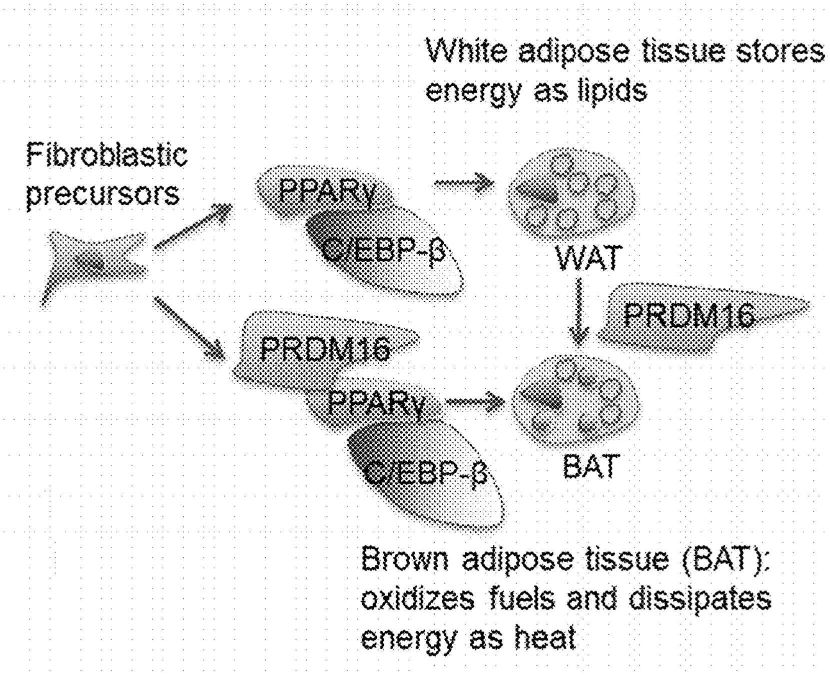
FIG. 2. Programming adipocyte cell fate: the switch from White Adipose Tissue (WAT) to Brown Adipose Tissue (BAT).
Figure 3:
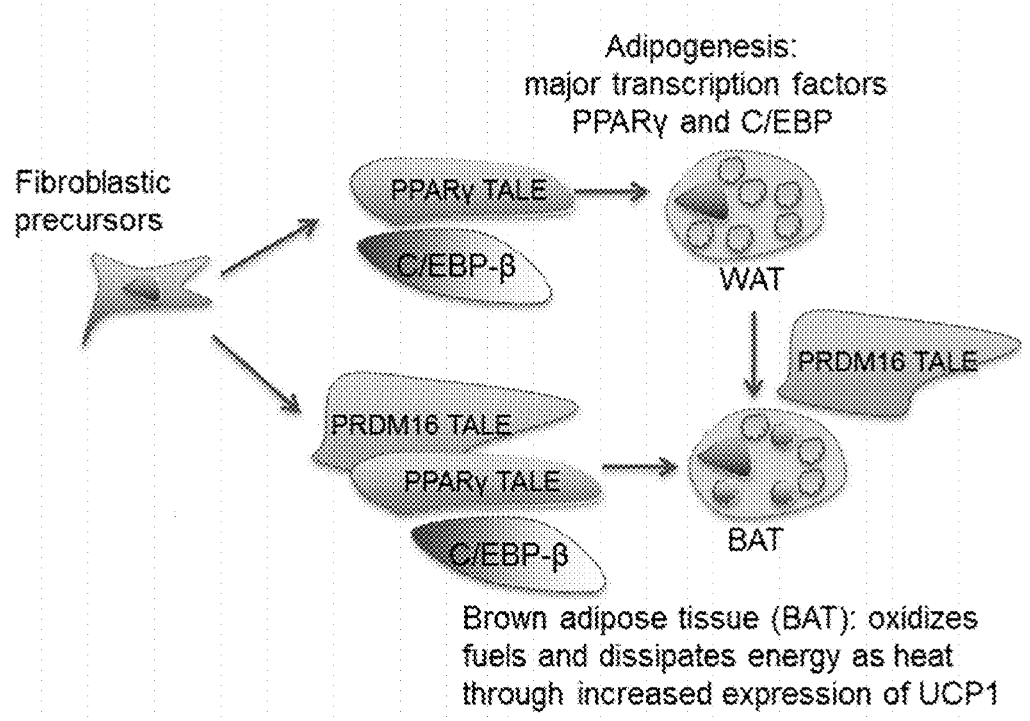
FIG. 3. Using supercharged delivery platforms to deliver TALE activators programmed to target PPARγ or PRDM16.
Figure 4:
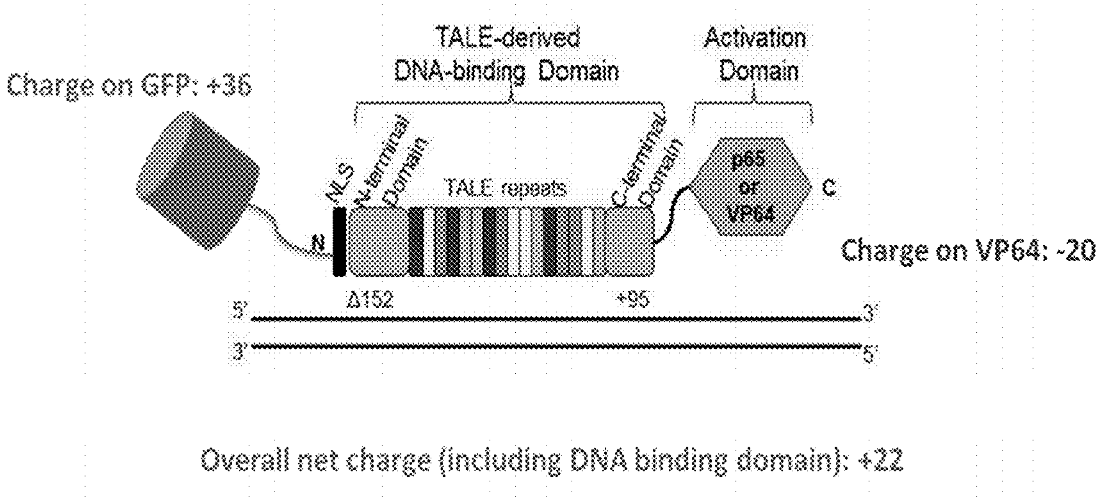
FIG. 4. Schematic of a fusion protein comprising a +36 GFP fusion, an 18.5 mer TALE domain, and a VP64 activation domain.
Figure 5:
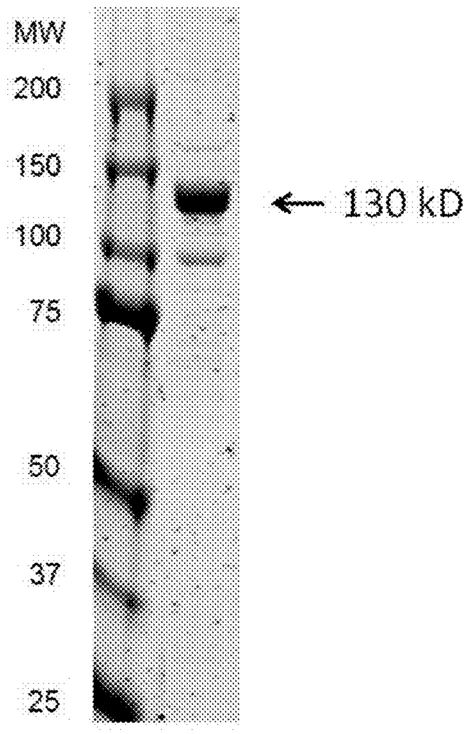
FIG. 5. Expression and purification of the +36 GFP-TALE activator-fusion protein.
Figure 6:
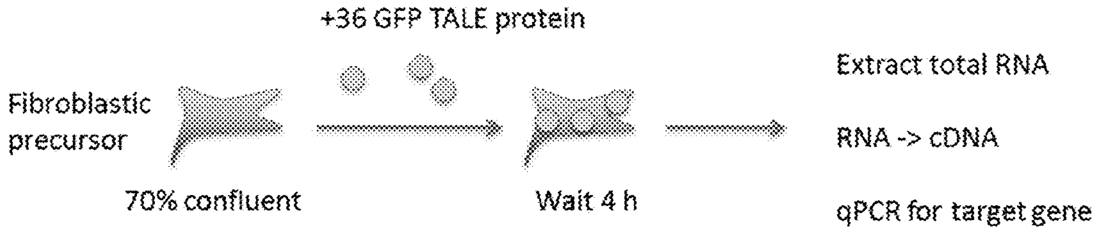
FIG. 6. Testing for activation of fat cell regulator genes upon delivery of +36 GFP PPARγ and PRDM16 TALE activator fusion proteins.

FIG. 1 shows a schematic of macromolecular delivery into mammalian cells. FIG. 2 shows an overview of the switch from White Adipose Tissue (WAT) to Brown Adipose Tissue (BAT). FIG. 3 shows a schematic of supercharged delivery platforms to deliver TALE activators programmed to target PPARγ or PRDM16. FIG. 4 shows a schematic of a fusion protein comprising a +36 GFP fusion, an 18.5 mer TALE domain, and a VP64 activation domain. FIG. 5 shows expression and purification of the +36 GFP-TALE activator-fusion protein. FIG. 6 shows testing assays for activation of fat cell regulator genes upon delivery of +36 GFP PPARγ and PRDM16 TALE activator fusion proteins.

Figure 7:
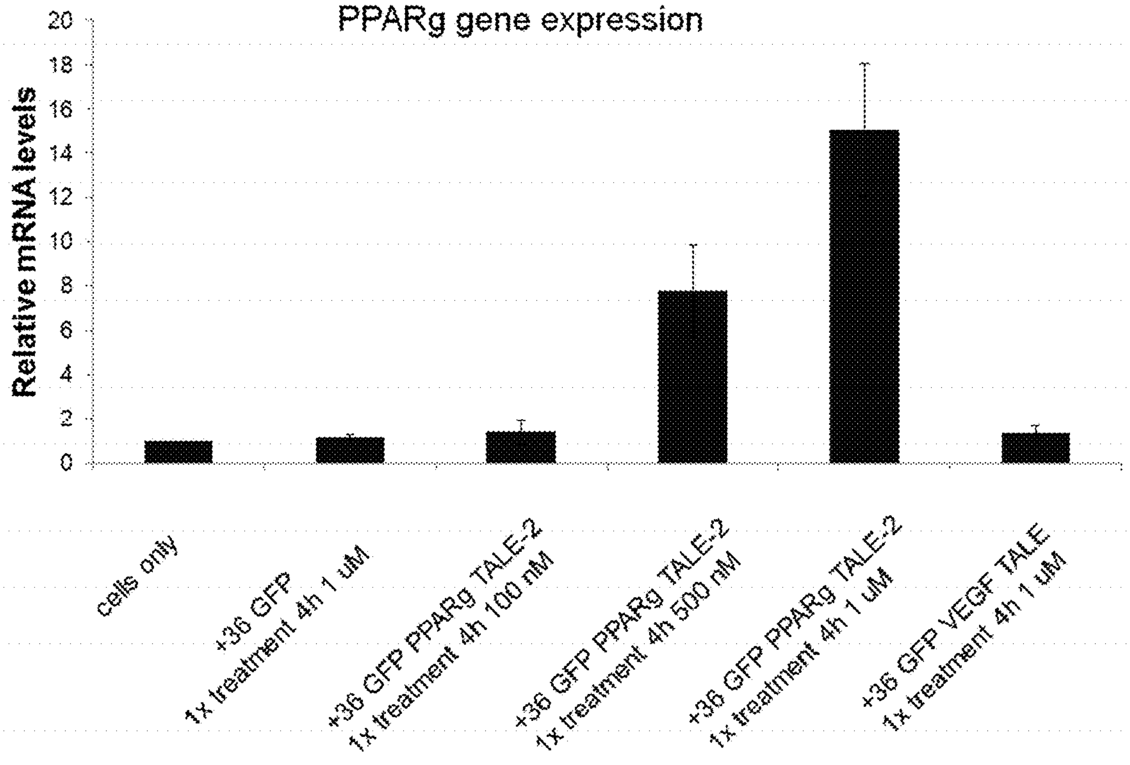
FIG. 7. Delivery efficacy of +36 GFP TALE activator fusion proteins at different concentrations.
Figure 8:
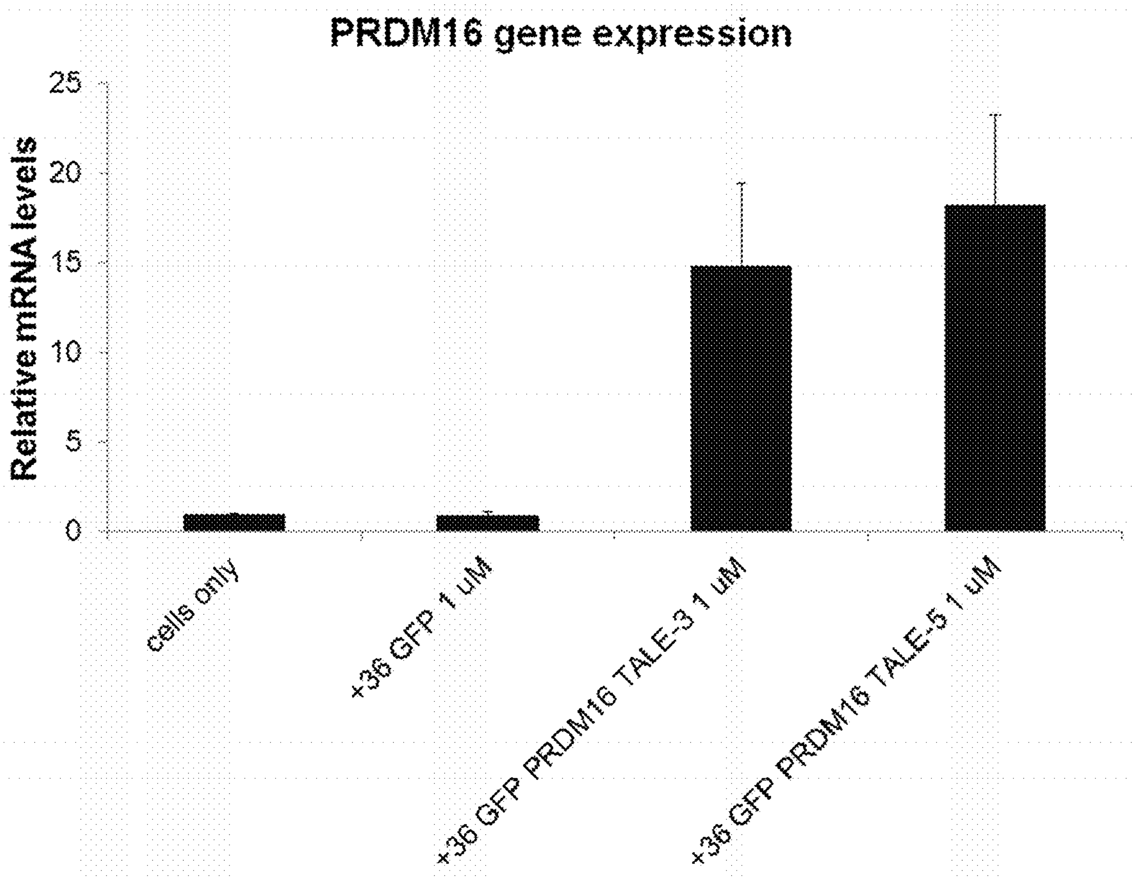
FIG. 8. Comparison of delivery efficacy of two different +36 GFP-PRDM16 TALE fusion proteins in NIH 3T3 cells.
Figure 9:
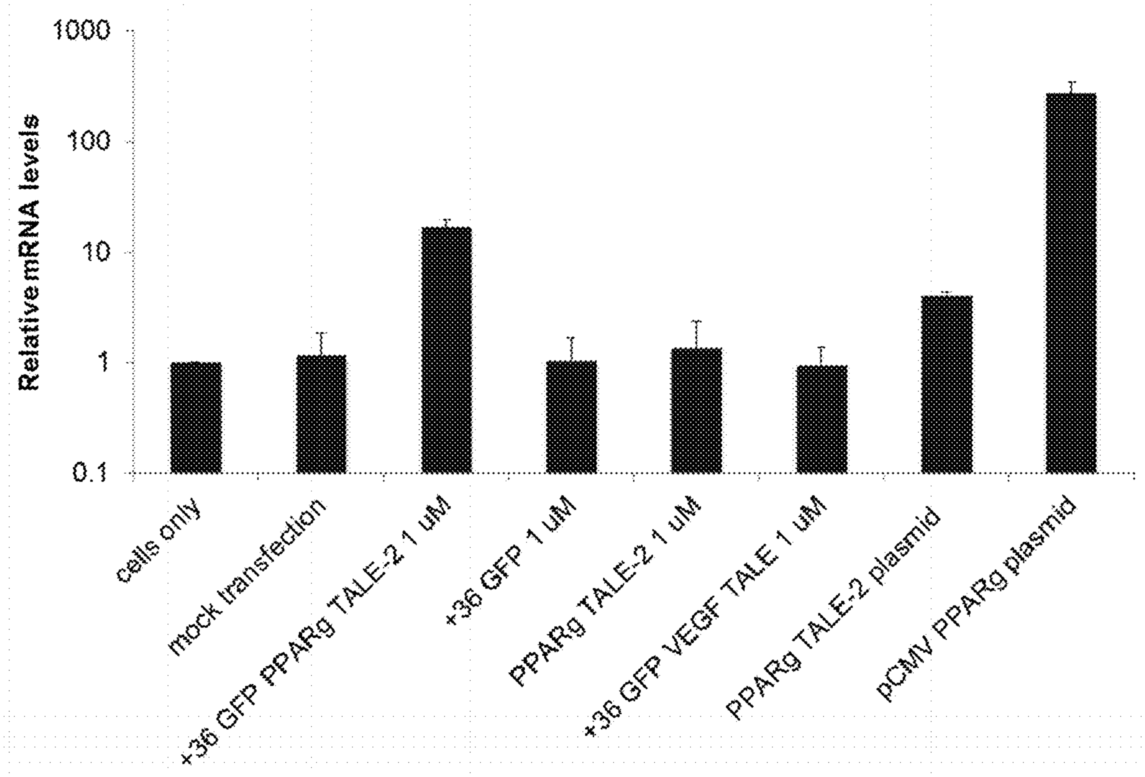
FIG. 9. PPARγ gene expression after delivery of PPARγ-TALE activator fusion and comparison to various controls.
Figure 10:
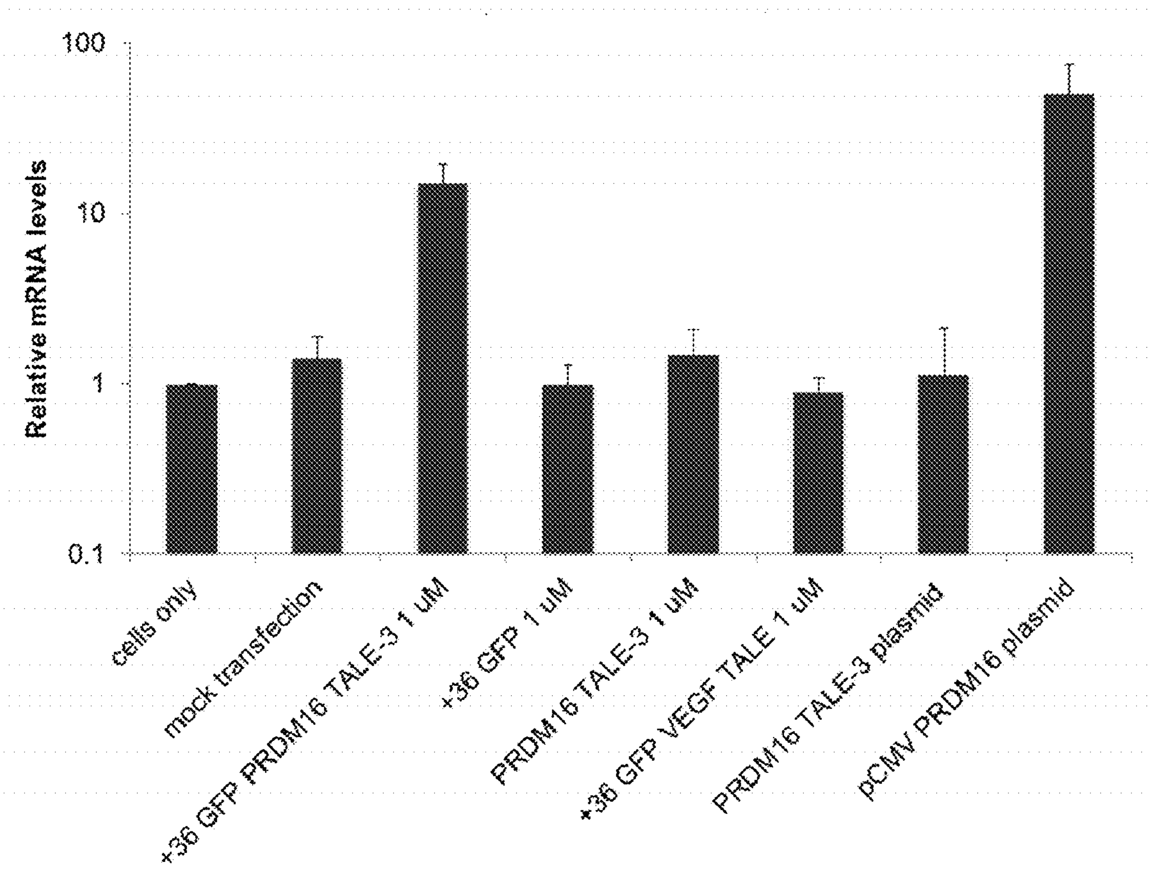
FIG. 10. PRDM16 gene expression after delivery of RDM16-TALE activator fusion and comparison to various controls.
Figure 11:
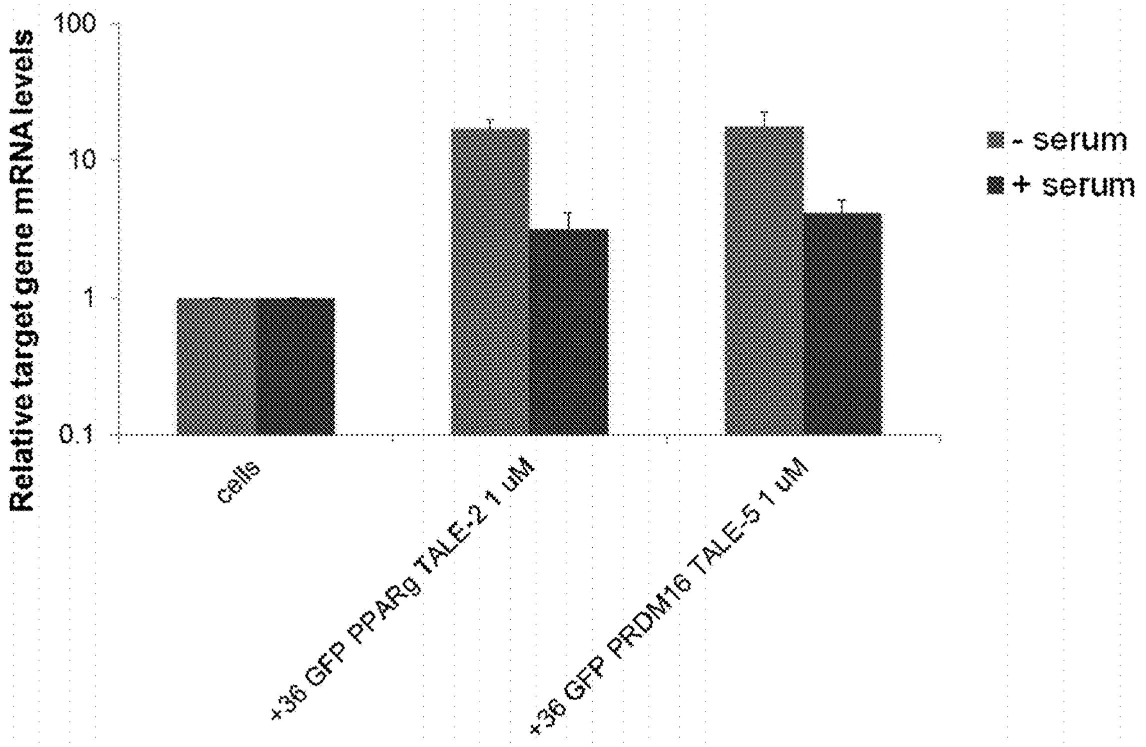
FIG. 11. Moderate TALE activity is observed in the presence of serum.

FIG. 7 shows delivery efficacy of +36 GFP TALE activator fusion proteins at different concentrations. FIG. 8 shows a comparison of delivery efficacy of two different +36 GFP-PRDM16 TALE fusion proteins in NIH 3T3 cells. FIG. 9 shows PPARγ gene expression after delivery of PPARγ-TALE activator fusion and comparison to various controls. FIG. 10 shows PRDM16 gene expression after delivery of RDM16-TALE activator fusion and comparison to various controls. FIG. 11 shows moderate TALE activity observed in the presence of serum.

Figure 12:
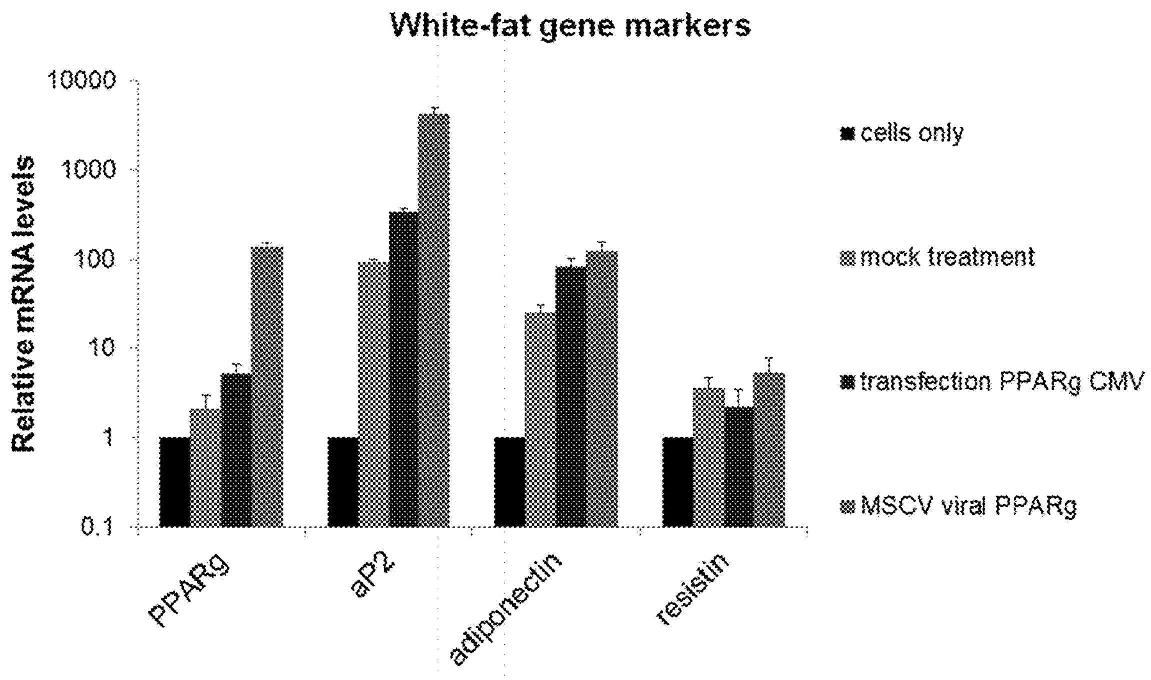
FIG. 12. Validation of viral delivery of PPARγ followed by 7-day treatment with adipogenesis cocktail.
Figure 13:
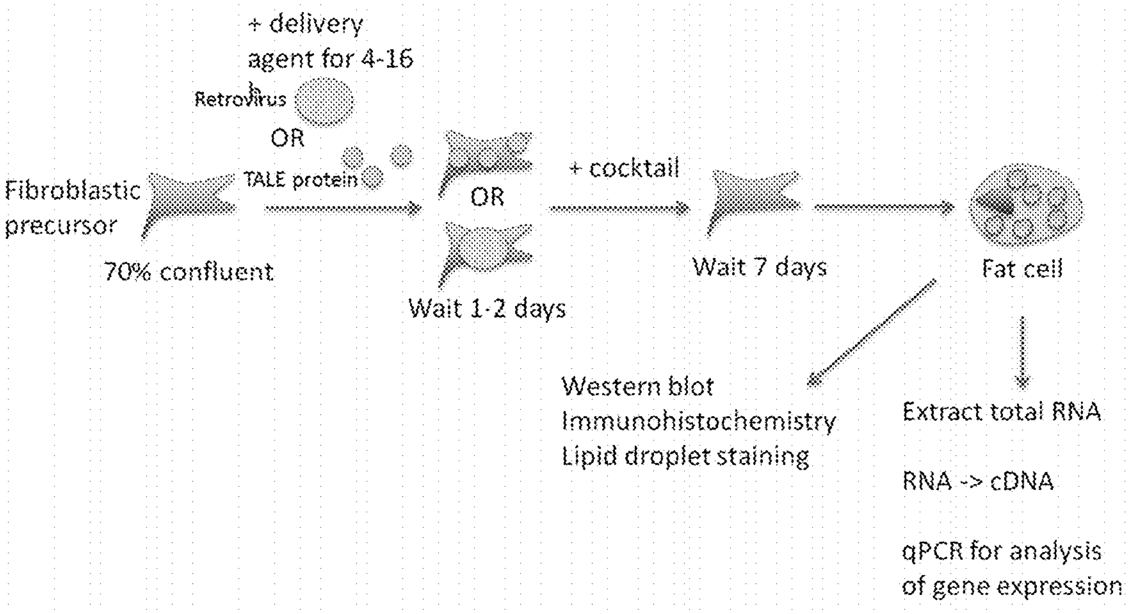
FIG. 13. Schematic of an assay for programming fibroblasts into WAT and BAT.
Figure 14:
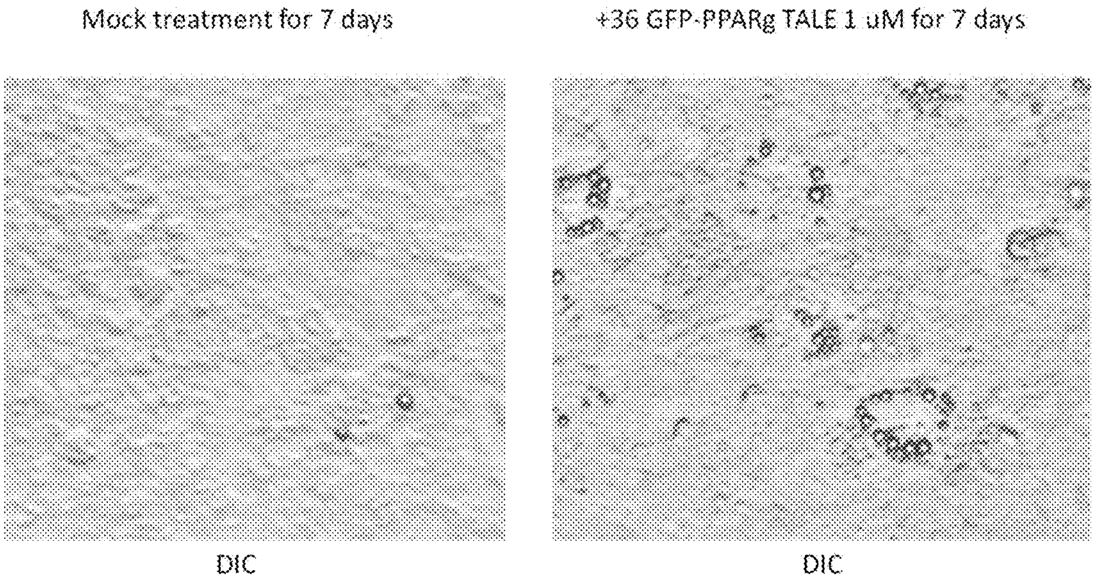
FIG. 14. Adipocyte formation observed upon treatment with +36 GFP TALE activator fusion protein.
Figure 15:
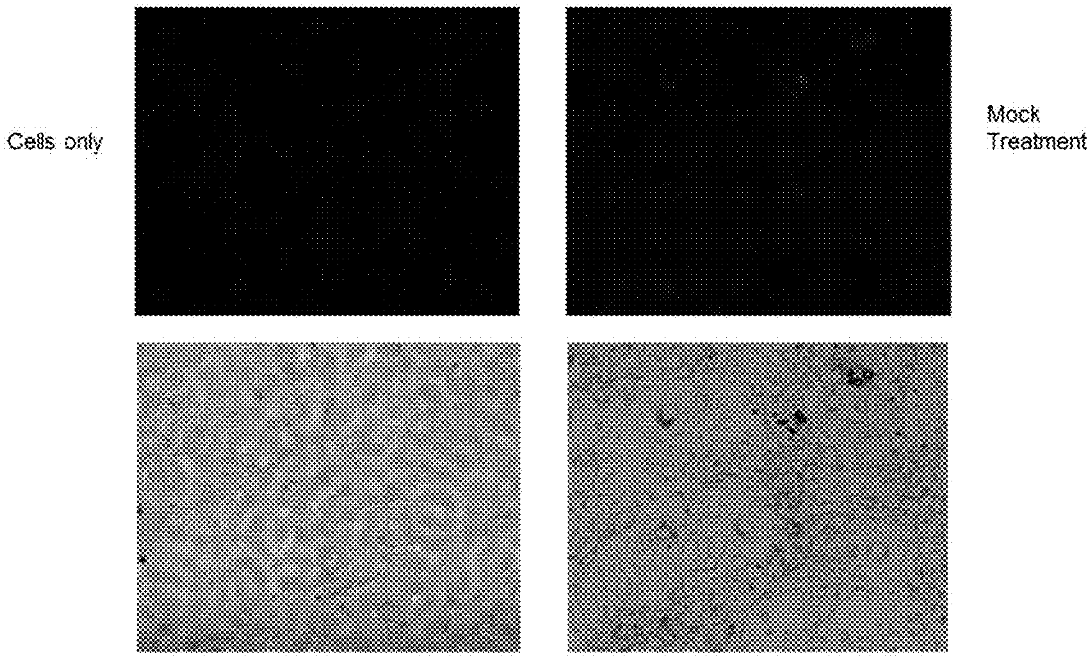
FIG. 15. Staining of various treatments after 7 days with LipidTOX red shows formation of adipocytes after viral delivery as well as after delivery of supercharged PPARγ TALE activator fusion protein.
Figure 16:
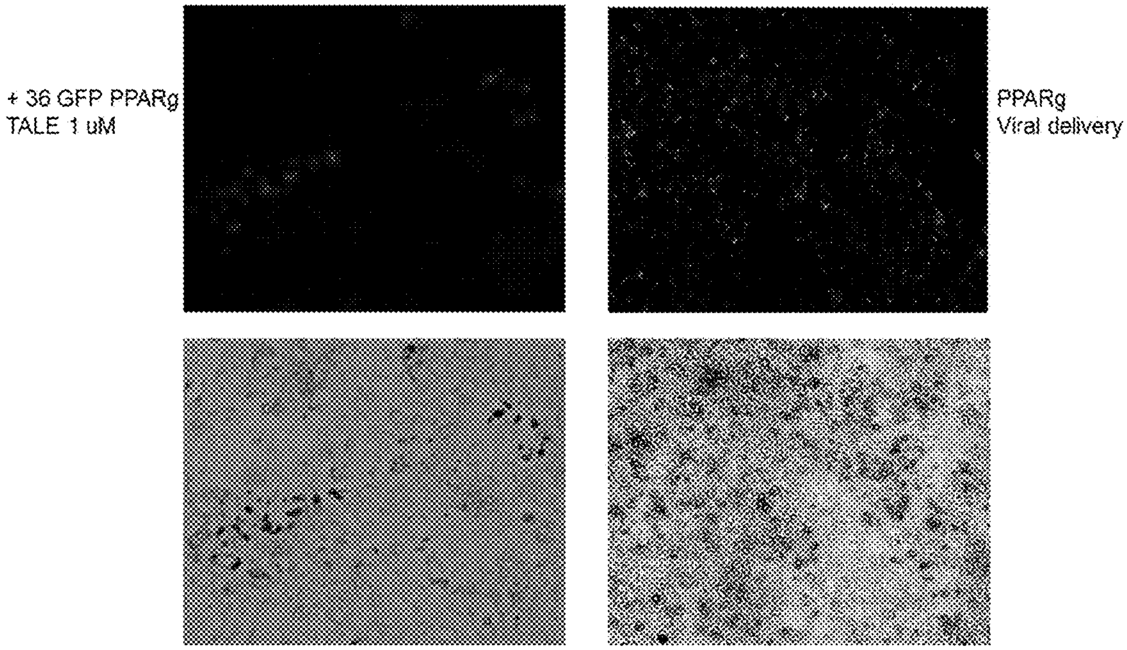
FIG. 16. Staining of various treatments after 7 days with LipidTOX red shows formation of adipocytes after viral delivery as well as after delivery of supercharged PPARγ TALE activator fusion protein.
Figure 17:
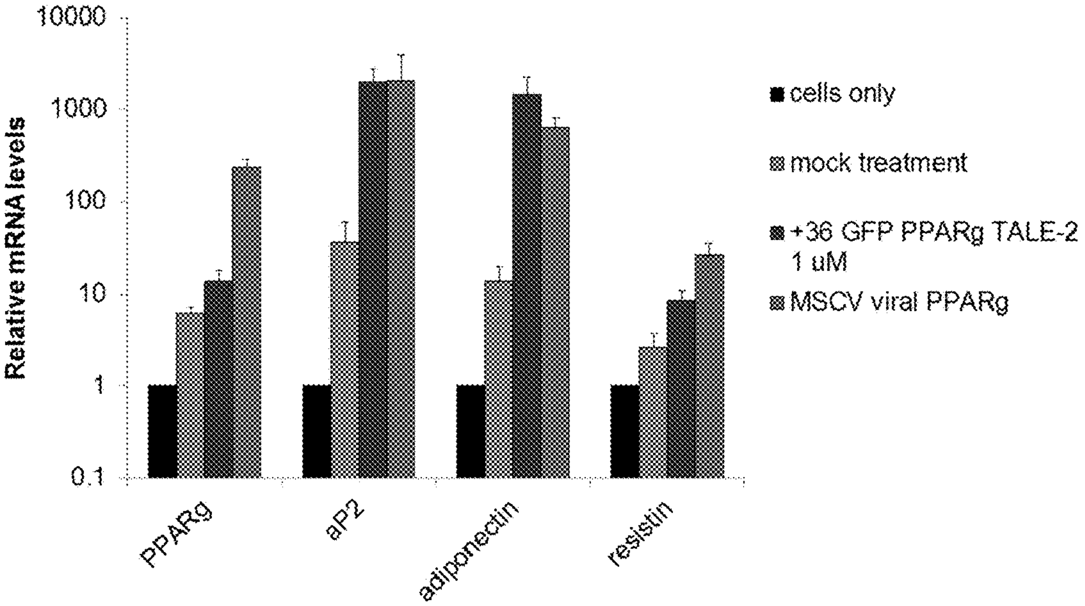
FIG. 17. Expression of WAT biomarker genes after viral delivery as well as after delivery of supercharged PPARγ TALE activator fusion protein.

FIG. 12 shows a validation of viral delivery of PPARγ followed by 7-day treatment with adipogenesis cocktail. FIG. 13 shows a schematic of an assay for programming fibroblasts into WAT and BAT. FIG. 14 shows adipocyte formation observed upon treatment with +36 GFP TALE activator fusion protein. FIG. 15 shows staining of various treatments after 7 days with LipidTOX red, demonstrating formation of adipocytes after viral delivery as well as after delivery of supercharged PPARγ TALE activator fusion protein. FIG. 16 shows staining of cells after various treatments after 7 days with LipidTOX red, demonstrating formation of adipocytes after viral delivery as well as after delivery of supercharged PPARγ TALE activator fusion protein. FIG. 17 shows expression of WAT biomarker genes after viral delivery as well as after delivery of supercharged PPARγ TALE activator fusion protein.

Example 2: In Vivo Delivery of TALE Activators Fused to Supercharged GFP

NIH 3T3 cells were grown to 70-90% confluence and treated with 1 μM or between 0.5-5 μM of +36 GFP PPARγ TALE and/or +36 GFP PRDM16 TALE fusion protein in DMEM without serum. A serum-free medium was chosen, because serum can decrease the effectiveness of protein-based delivery. Cells were incubated with the respective fusion protein solution for 4 hours before the media was removed and full DMEM containing serum was added back to cells. Control cells were infected with a viral construct encoding PPARγ or PRDM16 in order to serve as a positive control for expression of WAT and BAT genes according to known protocols (see, e.g., Seale et al. 2008 *Nature* 454, 961-967, the entire contents of which are incorporated herein by reference). Once all cells reached 100% confluence an adipogenesis cocktail containing isobutylmethylxanthine, insulin, rosiglitazone, dexamethosone, T3, and indomethacin was added to the cells and replaced 48 hours later with a form of the cocktail containing only insulin, T3, and rosiglitazone. At 48 hours after this second replacement of cocktail another dosage of T3, insulin, and rosiglitazone was added to the cells. The next day, which is now one week from the start of the experiment, cells were harvested with TRIzol, total RNA was extracted, and qRT-PCR was performed to measure gene expression levels of PPARγ, PRDM16, and other brown fat marker genes such as UCP1, PGC1a, Elovl3, and Cidea.

Figure 18:
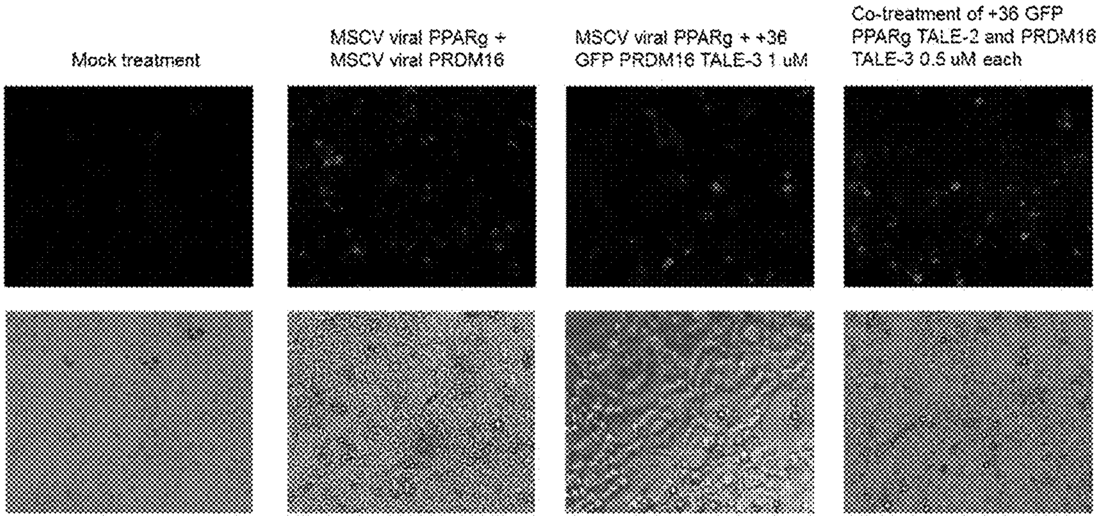
FIG. 18. Delivery of supercharged PRDM16 TALE activator fusion proteins to induce brown-fat adipocytes in vivo. Robust adipocyte formation was observed after viral delivery of PPARγ and PRDM16 and also after delivery of supercharged TALE activator protein fusions.
Figure 19:
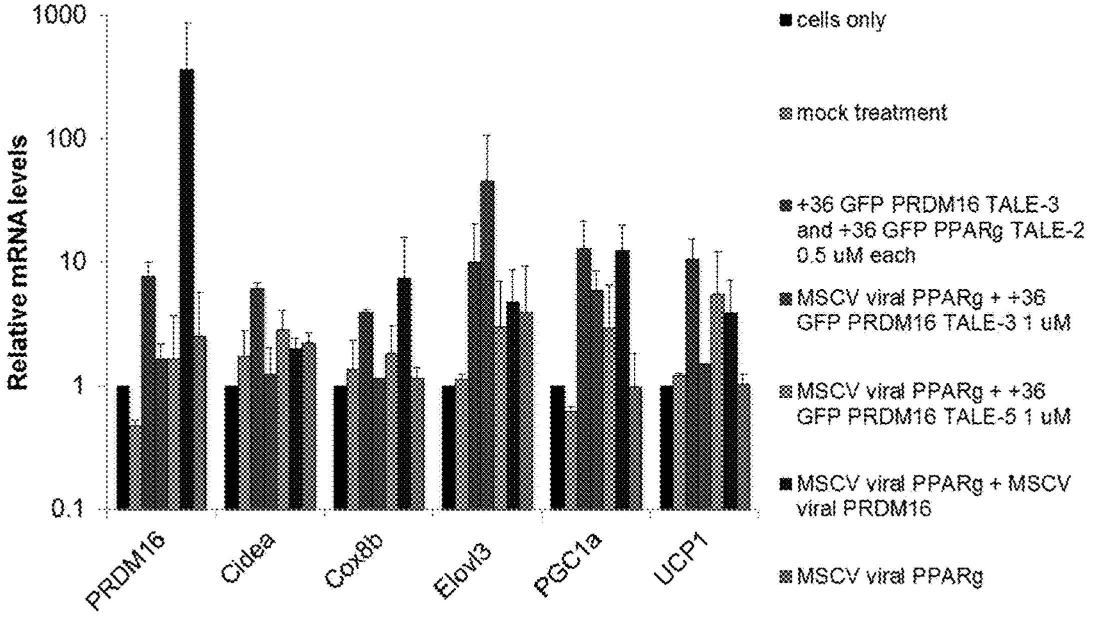
FIG. 19. Comparison of TALE/TALE, viral/TALE, and viral/viral-induced expression of brown fat markers by expression of PPARγ and PRDM16.
Figure 20:
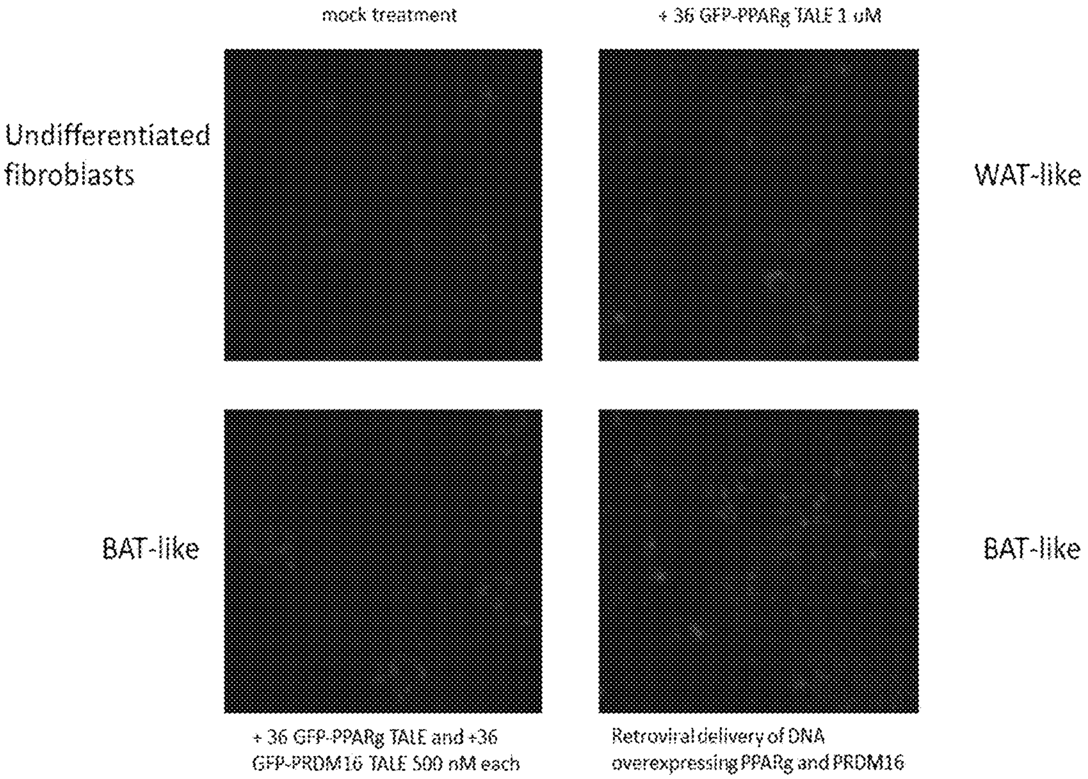
FIG. 20. RT-qPCR assessments are consistent with fat cell differentiation observed by LipidTOX staining.

FIG. 18 shows delivery of supercharged PRDM16 TALE activator fusion proteins to induce brown-fat adipocytes in vivo. Robust adipocyte formation was observed after viral delivery of PPARγ and PRDM16 and also after delivery of supercharged TALE activator protein fusions. FIG. 19 shows a comparison of supercharged (TALE) and viral delivery of PPARγ and PRDM16 to cells. The figure shows TALE/TALE, viral/TALE, and viral/viral-induced expression of brown fat markers by expression of PPARγ and PRDM16. FIG. 20 shows RT-qPCR assessments consistent with fat cell differentiation, which were also observed by LipidTOX staining.

Example 3: Delivery of TALE Activators Complexed with Supercharged GFP

Figure 21:
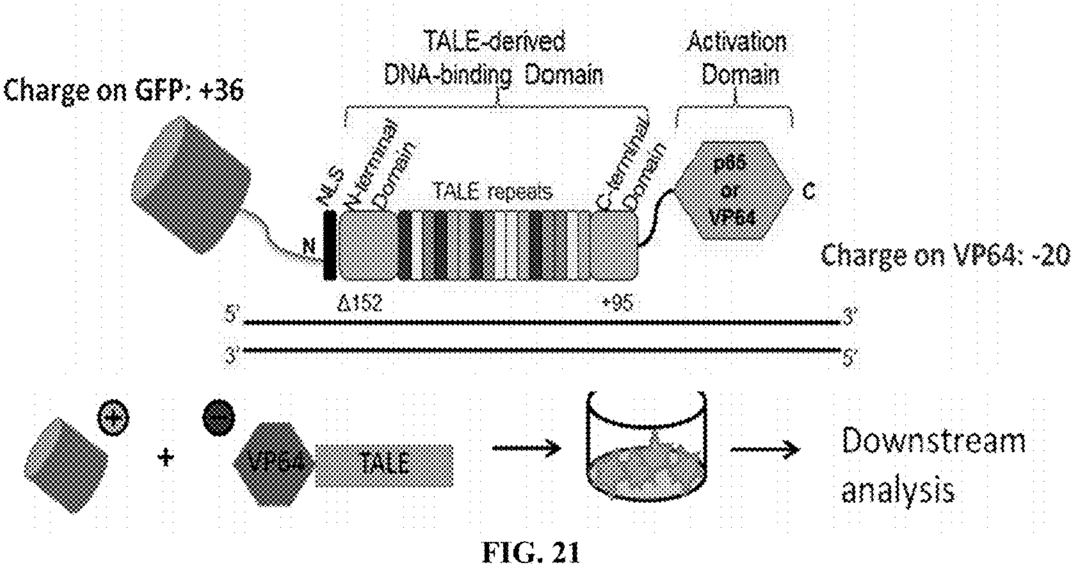
FIG. 21. Delivery of functional TALE activator fusion proteins as complexes with +36 GFP improves TALE activator activity after delivery.
Figure 22:
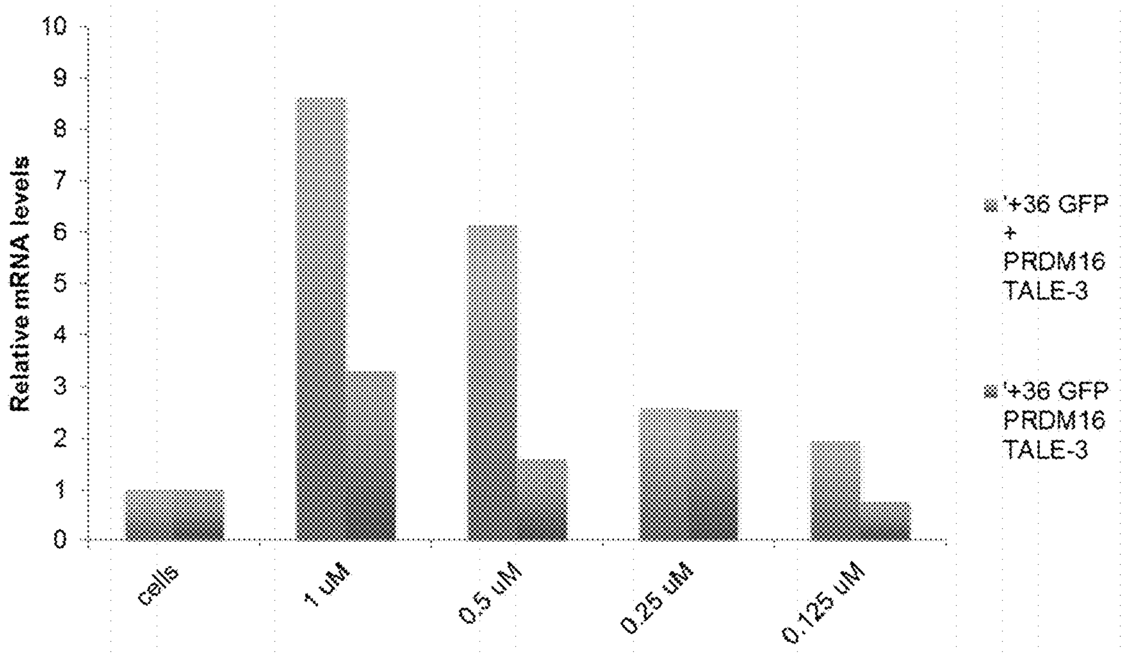
FIG. 22. PRDM16 gene expression after TALE activator fusion delivery either as a fusion (+36GFP PRDM16 TALE-3) or a complex (+36GFP+PRDM16 TALE-3) with +36GFP. Delivery of complexes tends to increase TALE activator activity.

In order to improve delivery efficacy, protein complexes in which the functional protein was non-covalently associated with the supercharged protein were generated and administered to cells. FIG. 21. shows that delivery of functional TALE activator fusion proteins as complexes with +36 GFP improves TALE activator activity after delivery. FIG. 22 shows PRDM16 gene expression after TALE activator fusion delivery either as a fusion (+36 GFP PRDM16 TALE-3) or a complex (+36 GFP+PRDM16 TALE-3) with +36 GFP. It was observed that delivery of complexes tended to increase TALE activator activity.

Example 4: Effect of Aurein Fusions on Delivery Efficacy

Figure 23:
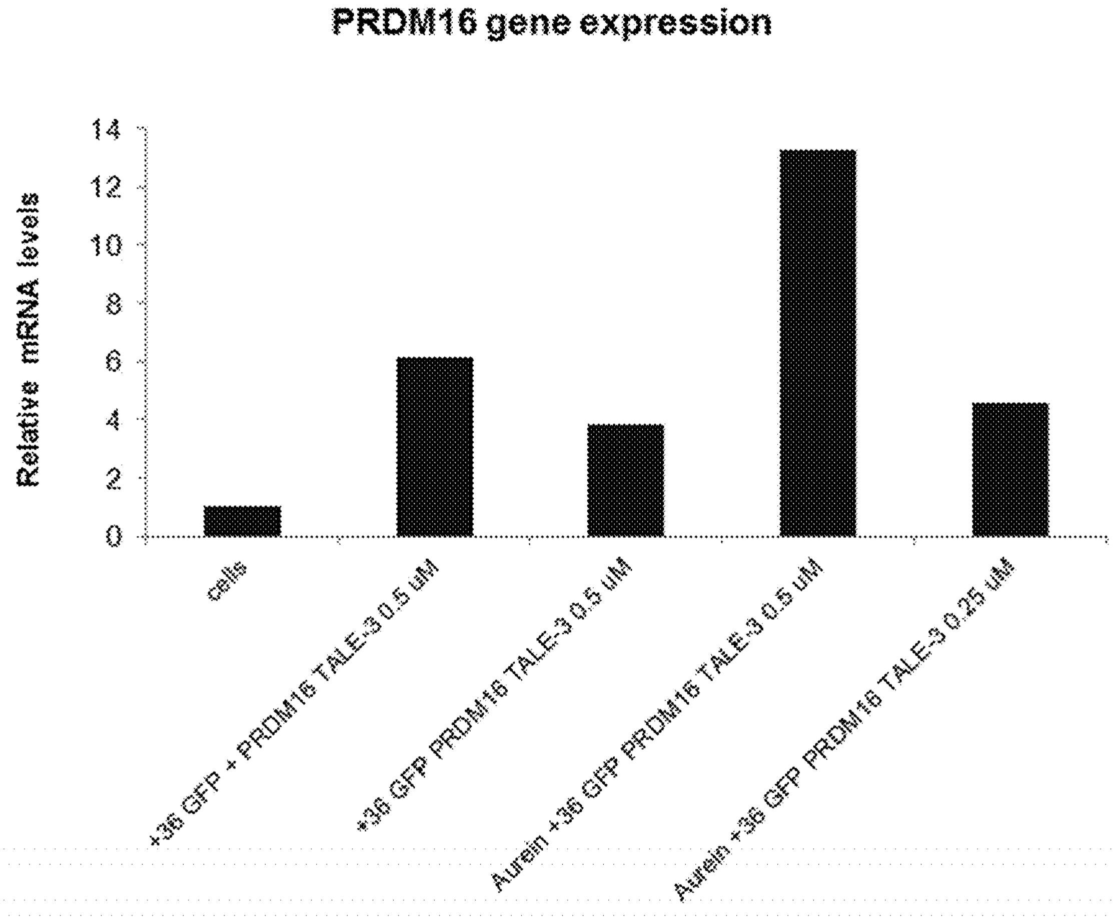
FIG. 23. Effect of Aurein peptide fusion to +36GFP on PRDM16 gene expression after TALE activator fusion delivery (either as a fusion or a complex with +36GFP).

FIG. 23 shows the effect of an N-terminal Aurein peptide fusion to +36 GFP on PRDM16 gene expression after TALE activator fusion delivery (either as a fusion or a complex with +36 GFP). The Aurein peptide was fused to the N-terminus of the GFP-TALE construct via a GGS(9) (SEQ ID NO: 252) linker, resulting in an Aurein peptide-GGS(9) linker-(+)36 GFP protein-GGS(9) linker –PRDM16 TALE-3 fusion protein. The protein was purified using size exclusion chromatography.

Figure 24:
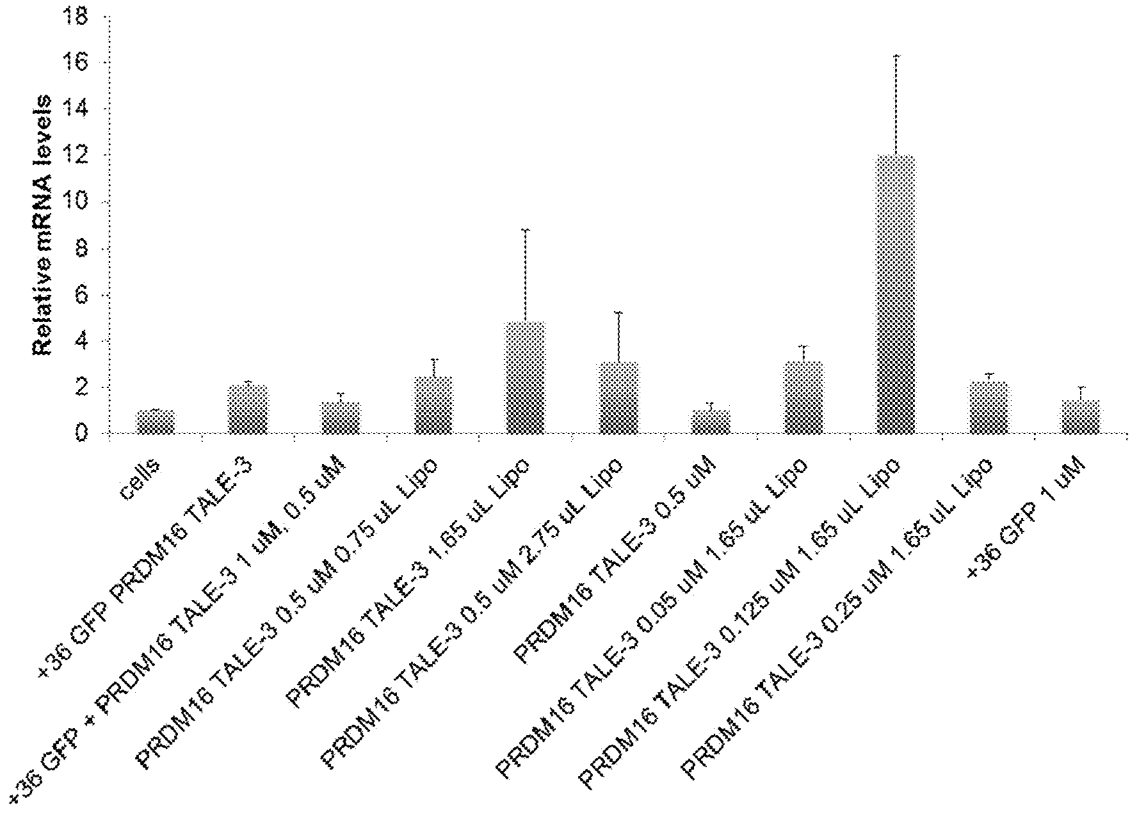
FIG. 24. PRDM16 gene expression after TALE activator fusion delivery either as a fusion (+36GFP PRDM16 TALE-3) or a complex (+36GFP+PRDM16 TALE-3) with Lipofectamine LTX.

Example 5: Delivery of TALE Activators Complexed with Supercharged GFP or Cationic Lipids FIG. 24 shows PRDM16 gene expression after TALE PRDM16 activator protein delivery either as a fusion with +36 GFP (+36 GFP PRDM16 TALE-3), a complex with +36 GFP (+36 GFP+PRDM16 TALE-3), or a complex with Lipofectamine LTX, for which an increase in gene expression was observed.

Example 6: Delivery of Cas9 Fused to Supercharged GFP

Figure 25:
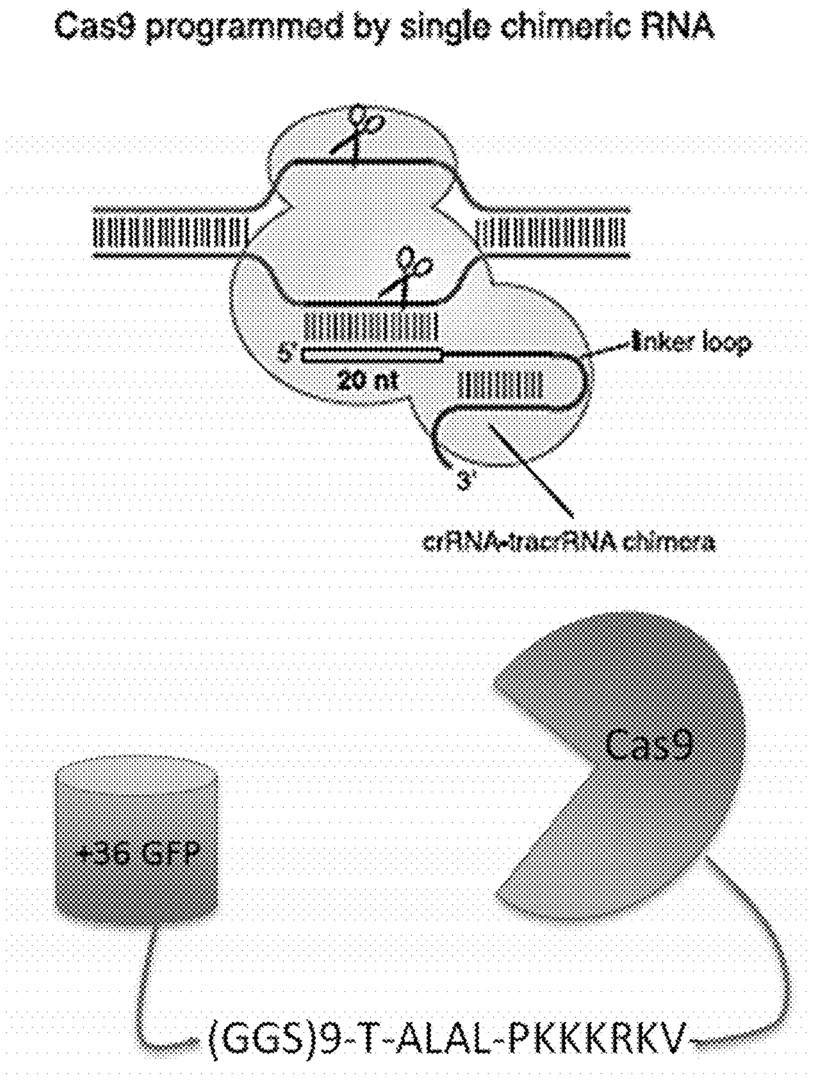
FIG. 25. Delivery of supercharged fusion proteins or complexes with Cas9 into mammalian cells. (GGS)9-T-ALAL-PKKKRKV corresponds to SEQ ID NO: 251.
Figure 26:
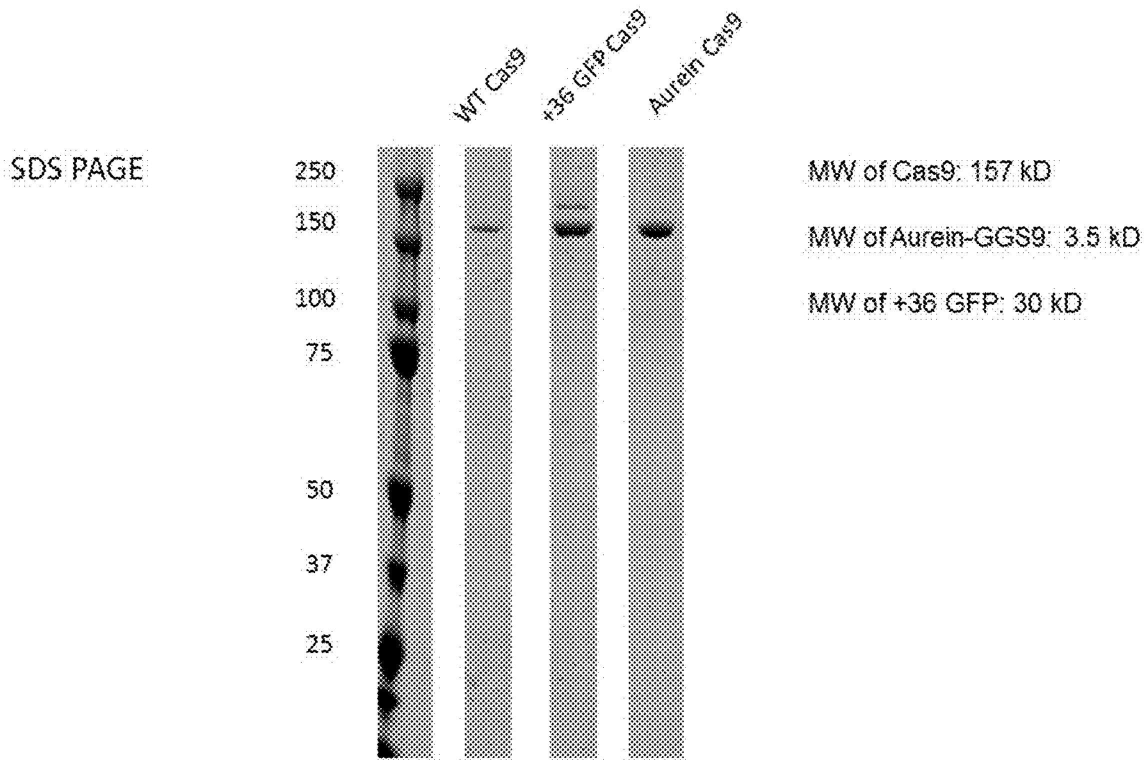
FIG. 26. Purification of wild-type Cas9 protein and Cas9 fusion proteins with +36GFP and Aurein-GGS9.

Supercharged delivery of Cas9 into mammalian cells would allow the application of powerful RNA-programmable nuclease technology in cells without the drawbacks of prior delivery methods. To this end, a Cas9 fusion with +36 GFP was generated, using an ALAL linker. FIG. 25 shows a schematic of the supercharged fusion protein with Cas9. FIG. 26 shows the purification of wild-type Cas9 protein and Cas9 fusion proteins with +36 GFP and Aurein-GGS9. The fusion protein is administered to cells in the same manner as the TALE activator fusion proteins above. The Cas9, once delivered to the cells, binds and cleaves its target site in the cellular genome. Nuclease activity in the target cells is detected via a suitable assay, e.g., via southern blot or sequencing assay.

Example 7: Efficient Delivery of Genome Editing Proteins In Vitro and In Vivo Efficient intracellular delivery of proteins to the nucleus or cytoplasm is needed to fully realize the potential of protein therapeutics including genome-editing agents. Current methods of protein delivery often suffer from low tolerance for serum proteins, poor endosomal escape, and limited in vivo efficacy. As demonstrated in this Example, common cationic lipid reagents originally developed for nucleic acid transfection can potently deliver proteins that are fused to negatively supercharged proteins, that contain natural anionic domains, or that natively bind to anionic nucleic acids. This approach mediates the functional delivery of Cre recombinase, TALE- and Cas9-based transcriptional activators, and Cas9:sgRNA nuclease complexes into cultured human cells at low nanomolar concentrations in media containing 10% serum. Lipid-based delivery can be >1,000-fold more potent than cationic protein delivery strategies. Delivery of Cas9:sgRNA complexes resulted in genome modification efficiencies as high as 80% with substantially higher specificity compared to standard DNA transfection, likely due to the transient nature of delivered Cas9:sgRNA complexes. This approach also mediated efficient delivery of Cre recombinase and Cas9:sgRNA complexes into the mouse inner ear in vivo, achieving up to 90% Cre-mediated recombination and 20% Cas9-mediated genome modification in the targeted hair-cell population.

Example 8: Delivery of Biotinylated Proteins to Cells

Figure 49A:
FIG. 49A shows an exemplary embodiment, in which a biotinylated protein to be delivered is complexed with an anionic carrier, e.g., a negatively charged fluorescent protein, such as −30GFP, an anionic naturally occurring protein, an anionic peptide, or a synthetic anionic polymer. The anionic carrier is conjugated to streptavidin and contacted with the biotinylated protein to be delivered. Biotin can be linked to the protein to be delivered in any suitable manner, for example, chemically, e.g., via click chemistry, NHS ester, or maleimide, or enzymatically. The linkage of biotin to the protein to be delivered and/or the linkage of streptavidin to the anionic carrier may be permanent or cleavable, e.g., by cellular proteases, esterases, or by a reducing cellular environment.
Figure 49B:
FIG. 49B shows an exemplary embodiment, in which a biotinylated protein to be delivered is complexed with an anionic streptavidin variant, e.g., with a negatively supercharged streptavidin variant, such as, for example, −40SAV. The anionic streptavidin variant is contacted with the biotinylated protein to be delivered. Biotin can be linked to the protein to be delivered in any suitable manner, for example, chemically, e.g., via click chemistry, NHS ester, or maleimide, or enzymatically. The linkage of biotin to the protein to be delivered may be permanent or cleavable, e.g., by cellular proteases, esterases, or by a reducing cellular environment. The protein complexes illustrated in FIG. 49A-B can be contacted with a cationic polymer or a cationic lipid for cellular delivery.

Efficient intracellular delivery of proteins to the nucleus or cytoplasm is effected by providing a protein to be delivered in a biotinylated form, complexing it with a negatively supercharged streptavidin (−40SAV), contacting the resulting negatively charged protein complex with a cationic lipid, and contacting cells with the resulting composition. Methods for generating complexes of biotinylated proteins to be delivered and anionic carriers, e.g., a negatively supercharged streptavidin or a negatively charged protein conjugated to streptavidin are illustrated in FIG. 49. A protein to be delivered, for example, a genome-editing protein, is associated to biotin via a linker, for example using click chemistry, NHS ester chemistry, or maleimide chemistry. The linker comprises a cleavage site that is cleaved by an endosomal protease present in endosomes of the cell into which the protein is to be delivered. The biotinylated form of the protein to be delivered is conjugated to a supernegatively charged streptavidin variant, for example, to a supernegatively charged streptavidin variant disclosed in International Application international PCT application PCT/US09/041984, filed on Apr. 28, 2009, published as WO 2009/134808 on Nov. 5, 2009, the entire contents of which are incorporated herein by reference. The biotinylated protein associated with the supernegatively charged streptavidin is contacted with a cationic lipid, e.g., with Lipofectamine®, and the resulting composition is contacted with the cells into which the protein is to be delivered. The composition is used at a concentration at which the cells exhibit less than 5% mortality 24 hours after being contacted with the composition. The protein to be delivered is subsequently observed in at least 10% of the target cells.

Materials and Methods

Construction of Cas9, Cre, and TALE Fusion and sgRNA Expression Plasmids.

Sequences of all constructs used in this paper are listed below or provided elsewhere in the specification. All protein constructs were generated from previously reported plasmids for protein of interest cloned into a pET29a expression plasmid.

Expression and Purification of *S. pyogenes* Cas9 and Other Proteins.

*E. coli* BL21 STAR (DE3) competent cells (Life Technologies) were transformed with pMJ806[47] encoding the *S. pyogenes* Cas9 fused to an N-terminal 10×His-tag/maltose binding protein. The resulting expression strain was inoculated in Luria-Bertani (LB) broth containing 100 μg/mL of ampicillin at 37° C. overnight. The cells were diluted 1:100 into the same growth medium and grown at 37° C. to $OD_{600}$=~0.6. The culture was incubated at 20° C. for 30 min, and isopropyl β-D-1-thiogalactopyranoside (IPTG) was added at 0.5 mM to induce Cas9 expression. After approximately 16 hours, the cells were collected by centrifugation at 8,000 g and resuspended in lysis buffer (50 mM tris (hydroxymethyl)-aminomethane (Tris)-HCl, pH 8.0, 1 M NaCl, 20% glycerol, 10 mM tris(2-carboxyethyl)phosphine (TCEP)). The cells were lysed by sonication (1 sec pulse-on, 1 sec pulse-off for 15 minutes total at 6 W output) and the soluble lysate was obtained by centrifugation at 20,000 g for 30 minutes.

The cell lysate was incubated with His-Pur nickel-nitrilo-acetic acid (nickel-NTA) resin (Thermo Scientific) at 4° C. for 30 minutes to capture His-tagged Cas9. The resin was transferred to a 20-mL column and washed with 20 column volumes of lysis buffer. Cas9 was eluted in 50 mM Tris-HCl (pH 8), 0.1 M NaCl, 20% glycerol, 10 mM TCEP, and 300 mM imidazole, and concentrated by Amicon ultra centrifugal filter (Millipore, 100-kDa molecular weight cut-off) to ~50 mg/mL. The 6×His tag and maltose-binding protein were removed by TEV protease treatment at 4° C. for 20 hours and captured by a second Ni-affinity purification step. The eluent, containing Cas9, was injected into a HiTrap SP HP column (GE Healthcare) in purification buffer containing 50 mM Tris-HCl (pH 8), 0.1 M NaCl, 20% glycerol, and 10 mM TCEP. Cas9 was eluted with purification buffer containing a linear NaCl gradient from 0.1 M to 1 M over five column volumes. The eluted fractions containing Cas9 were concentrated down to a concentration of 200 μM as quantified by Bicinchoninic acid assay (BCA) (Pierce Biotechnology), snap-frozen in liquid nitrogen, and stored in aliquots at −80° C. All other proteins were purified by this method but without TEV cleavage step and proteins containing (−30) GFP were purified by anion exchange using a Hi-Trap Q HP anion exchange column (GE Healthcare) using the same purification protocol.

In Vitro Transcription of sgRNAs.

Linear DNA fragments containing the T7 promoter binding site followed by the 20-bp sgRNA target sequence were transcribed in vitro using the T7 High Yield RNA Synthesis Kit (NEB) according to the manufacturer's instructions. In vitro transcribed RNA was precipitated with ethanol and purified by gel electrophoresis on a Criterion 10% polyacrylamide TBE-Urea gel (Bio-Rad). Excised gel fragments were extracted in 420 μL of 300 mM NaCl overnight on a rocking surface at 4° C. Gel-purified sgRNA was precipitated with ethanol and redissolved in water and sgRNA concentration was finally quantified by UV absorbance and snap-frozen at −80° C.

Plasmid Transfection.

Plasmid DNA was transfected using Lipofectamine 2000 (Life Technologies) according the manufacturer's protocol. For TALE activator plasmids, 300 ng of DNA was transfected, and for the activator synergy experiments 60 ng of each of five plasmids was pooled and transfected. For Cas9 nuclease delivery experiments, linear DNA PCR products expressing sgRNAs were used in transfection experiments targeting genomic sites in CLTA, EMX, VEGF, and GFP (sgRNA GFP g1, GFP g3, GFP g5, and GFP g7 for nickase studies). Linear DNA PCR products were generated using plasmid containing the U6 promoter as template and forward primers bearing the U6 promoter upstream sequence and reverse primers containing U6 downstream sequence followed by the sgRNA sequence (20-bp sequence unique to each target plus constant sgRNA backbone architecture sequence). sgRNAs expressed from linear DNA templates contained at least two 5' guanosines to match in vitro transcribed sgRNAs that required these bases for T7 transcription. Primer sequences and PCR conditions are listed below. For dCas9 activator experiments, 700 ng of Cas9 or dCas9-VP64 plasmid DNA was co-transfected with 250 ng of the appropriate sgRNA expression plasmid. For activator synergy experiments 50 ng of DNA from each of the six sgRNA was pooled and co-transfected with 700 ng of dCas9-VP64 plasmid.

Delivery of Transcription Factor Proteins Complexed with Cationic Lipids in Cell Culture.

A more in-depth description of the delivery of genome-editing proteins both in vitro and in vivo can be found below. Briefly, cultured cells were plated in 48-well format (250 μL volume) in Dulbecco's Modified Eagle's Media plus GlutaMAX (Life Technologies, Carlsbad, Calif.) with 10% FBS ("full serum media") and antibiotics at a cell density necessary to reach ~70% confluence the next day. Full serum media was replaced with the same media but containing no antibiotics one hour before delivery. Delivery of Cre and TALE proteins was performed by combining 1 nM to 1 μM protein (in 275 μL final volume) with 0.2-2.5 μL of commercially available cationic lipids in 25 μL OPTIMEM media (Life Technologies, Carlsbad, Calif.) according to the manufacturer's protocol for normal plasmid transfection, including incubation time. For Cas9 delivery in vitro, transcribed sgRNA was incubated with Cas9 protein for 5 min before complexing with the cationic lipid reagent. 25 μL lipid complexes in OPTIMEM media were added to cells and media was replaced 12-16 hours later fresh media unless otherwise noted. Cells were assayed for recombination 48 hours after delivery, for gene activation either 4 (TALE) or 12-16 hours (dCas9-VP64) after delivery, and for gene modification (Cas9) 48 and 72 hours after delivery.

T7 Endonuclease I Assay to Detect Genomic Modifications.

U2OS-EGFP cells or HEK293T cells were transfected with Cas9 expression and sgRNA expression plasmids or linear DNA PCR products as described above or treated with only Cas9 protein, only in vitro transcribed sgRNA, or only RNAiMAX. Genomic DNA was isolated from cells 2 days after transfection using the DNAdvance Kit (Agencourt) following the manufacturer's instructions. 200 ng of genomic DNA was used as template in PCR reactions to amplify the targeted genomic loci with flanking survey primer pairs specified below. PCR products were purified with a QIAquick PCR Purification Kit (Qiagen) and quantified with Quant-iT™ PicoGreen® dsDNA Kit (Life Technologies). 250 ng of purified PCR DNA was combined with 2 μL of NEBuffer 2 (NEB) in a total volume of 19 μL and denatured then re-annealed with thermocycling at 95° C. for 5 minutes, 95 to 85° C. at 2° C./s; 85 to 20° C. at 0.2° C./s. The re-annealed DNA was incubated with 1 μl of T7 Endonuclease I (10 U/μl, NEB) at 37° C. for 15 minutes. 10 μL of 50% glycerol was added to the T7 Endonuclease reaction and 12 μL was analyzed on a 5% TBE 18-well Criterion PAGE gel (Bio-Rad) electrophoresed for 30 minutes at 200 V, then stained with 1×SYBR Gold (Life Technologies) for 30 min. Cas9-induced cleavage bands and the uncleaved band were visualized on an AlphaImager HP (Alpha Innotech) and quantified using ImageJ software[54]. The peak intensities of the cleaved bands were divided by the total intensity of all bands (uncleaved+cleaved bands) to determine the fraction cleaved which was used to estimate gene modification levels as previously described.[46] For each sample, transfections and subsequent modification measurements were performed in triplicate on different days.

Stem Cell Culture and Delivery.

Mouse embryonic stem cell (ES) line Tau-GFP containing a permanent GFP gene insertion was cultured in DMEM with 15% FBS (Gibco), 100 mM MEM nonessential amino acids (Gibco), 0.55 mM 2-mercaptoethanol (Sigma), and leukemia inhibitory factor (1,000 units/ml; Chemicon). After 5 days floating spheres were formed that exhibited GFP fluorescence. Complexes of Cas9:sgRNA and RNAiMAX were added to the culture containing the floating spheres for 16 hours. After Cas9:sgRNA treatment, the cells were cultured in the above media for 3 days. The floating spheres were treated with trypsin for 5 minutes then passed through a 70 inn filter to collect single cells. The cells were cultured on laminin-coated slides in DMEM/F12 (1:1) supplemented with 1×N2, 1×B27, penicillin-streptomycin (100 μg/mL; Life Technologies) and 10% FBS for two days before labeling. Immunohistochemistry was performed using an anti-GFP antibody (#ab13970, Abcam) to assess GFP expression. To quantify the number of GFP-negative cells, we counted the total number of GFP-positive and GFP-negative cells from three representative visual fields at 20× magnification, and calculated the average efficiency. Three independent experiments were performed for each condition.

Microinjection of Proteins to Mouse Inner Ear.

P0 floxP-tdTomato mice (The Jackson Laboratory) were used for (−30)GFP-Cre injection and P2 Atoh1-GFP mice (courtesy of Dr. J. Johnson, Southwestern Medical Center, University of Texas) were used for Cas9:sgRNA injection. Animals were used under protocols approved by the Massachusetts Eye & Ear Infirmary (IACUC) committee. Mice were anesthetized by lowering their temperature on ice. Cochleostomies were performed by making an incision behind the ear to expose the cochlea. Glass micropipettes held by a micromanipulator were used to deliver the complex into the scala media, which allows access to inner ear hair cells. For delivery of (−30)GFP-Cre, 3 μL of 45 μM protein was mixed with 3 μL of either RNAiMAX or Lipofectamine 2000 and incubated at room temperature for 30 minutes prior to injection. Four mice were injected per treatment group. For delivery of Cas9:sgRNA complexes, 1 μL of 200 μM Cas9 protein was mixed with 2 μL of 100 μM sgRNA and incubated for 5 minutes at room temperature before mixing with 3 μL of either RNAiMAX or Lipofectamine 2000 and incubating for an additional 30 minutes prior to injection. Three mice were injected per treatment group. The total delivery volume for every injection was 0.3 μL per cochlea and the release was controlled by a micromanipulator at the speed of 3 nL/sec.

Immunohistochemistry and Quantification.

5-10 days after injection, the mice were sacrificed and cochlea were harvested by standard protocols.[55] For immunohistochemistry, antibodies against hair-cell markers (Myo7a and Esp) and supporting cells (Sox2) were used following a previously described protocol.[55] To quantify the number of tdTomato positive cells after (−30)GFP-Cre or GFP negative cells after Cas9:sgRNA delivery, we counted the total number of outer hair cells in a region spanning 200 μm around the site of injection in the base turn of the cochlea. The efficiency of (−30)GFP-Cre-induced recombination or Cas9:sgRNA-induced genome modification was calculated as the percentage of outer hair cells that expressed tdTomato or that lost GFP expression.

High-Throughput DNA Sequencing of Genome Modifications.

HEK293T cells were either transfected with Cas9 and sgRNA expression plasmids or linear DNA PCR products or treated with 50 nM Cas9 protein, 125 nM or 250 nM purified sgRNA, and cationic lipids as described earlier for Cas9 protein delivery to U2OS-EGFP reporter cells. For plasmid-based transfection experiments, 700 ng of Cas9 expression plasmid plus 250 ng of sgRNA plasmid or 50 ng of a linear DNA PCR product expressing sgRNA for targeting either the EMX1, CLTA2, or VEGF locus were transfected with Lipofectamine 2000 (Life Technologies) and cells were isolated 2 days later. For protein delivery experiments in vivo, ~30 mg of mouse tissue was isolated as previously described[55] from anesthetized mice and genomic DNA was extracted using the Agencourt DNAAdvance Genomic DNA Isolation Kit (Beckman Coulter). For cell culture experiments genomic DNA was isolated as described above. 150 ng of genomic DNA was used as template to amplify by PCR the on-target and off-target genomic sites with flanking HTS primer pairs specified below. Relative amounts of crude PCR products were quantified by gel electrophoresis and samples treated with different sgRNA pairs or Cas9 nuclease types were separately pooled in equimolar concentrations before purification with the QIAquick PCR Purification Kit (Qiagen). Approximately 150 ng of pooled DNA was electrophoresed using a 5% TBE 18-well Criterion PAGE gel (BioRad) for 30 min at 200 V and DNAs ~125 bp to ~300 bp in length were isolated and purified by QIAquick PCR Purification Kit (Qiagen). Purified DNA was amplified by PCR with primers containing sequencing adapters, purified, and sequenced on a MiSeq high-throughput DNA sequencer (Illumina) as previously described.[47]

Quantification of Cas9 Protein Uptake.

We used Alexa Fluor 647 C2 Maleimide (Life Technologies) to fluorescently label Cas9 protein on surface cysteines. A 10 mM stock solution of Alexa 647 was prepared in anhydrous DMSO (Sigma). In a 0.4 mL reaction, 10 nmol of purified Cas9 protein and 200 nmol of Alexa 647 maleimide were combined in buffer conditions used for Cas9 protein storage. The labeling reaction was incubated at 4° C. for 16 hours. At the end of the reaction, excess unconjugated Alexa 647 was removed by re-purifying the labeled Cas9 protein by cation exchange chromatography as described above. To measure the amount of protein delivered into treated cells, 20,000 cells were plated in the wells of a 48-well plate 1 day prior to treatment. On the day of treatment, 50 nM of Alexa 647-labeled Cas9 (Cas9-Alexa 647) and 50 nM of EGFP sgRNA were prepared for delivery using 0.8 μL of Lipofectamine 2000 as described above, and applied to the cells. After 4 hours, Cas9-Alexa 647:sgRNA Lipofectamine-containing media was removed, and cells were washed three times with 500 μL of PBS containing 20 U/mL heparin. The cells were trypsinized and prepared for counting and flow cytometry as described above. Cas9-Alexa 647 uptake was measured by flow cytometry, while 10,000 cells of the treated population were transferred to a black, flat-bottomed, opaque 96-well plate. Standard curves of Cas9-Alexa 647 were prepared by complexing 50 pmol of the Cas9-Alexa 647 protein with Lipofectamine 2000 exactly as described for Cas9-Alexa 647 delivery, followed by serial 2-fold dilutions in DMEM with 10% FBS containing 10,000 U2OS cells per well in the 96-well plate. The effect of U2OS cells or complexation with Lipofectamine 2000 on Alexa 647 fluorescence was determined by preparing three additional Cas9-Alexa 647 standard curves: (i) with Lipofectamine 2000 in media lacking U2OS cells, (ii) without Lipofectamine 2000 in media containing U2OS cells, and (iii) without Lipofectamine 2000 in media lacking U2OS cells.

Data Analysis

Illumina sequencing reads were filtered and parsed with scripts written in Unix Bash as outlined below. Sample sizes for sequencing experiments were maximized (within practical experimental considerations) to ensure greatest power to detect effects. Statistical analyses for Cas9-modified genomic sites (Table 2) were performed as previously described[56] with multiple comparison correction using the Bonferroni method.

All scripts (DNA Sequence-Processing Algorithms) were written in bash and described in detail previously.[16]

The following is a list of upstream and downstream flanking sequences for each genomic target site.

| Target Site | Downstream genomic sequence | Upstream genomic sequence |
|---|---|---|
| EMX_On | GGCCTGCTTCGTGGCAATGC (SEQ ID NO: 119) | ACCTGGGCCAGGGAGGGAGG (SEQ ID NO: 120) |
| EMX_Off1 | CTCACTTAGACTTTCTCTCC (SEQ ID NO: 121) | CTCGGAGTCTAGCTCCTGCA (SEQ ID NO: 122) |

-continued

| Target Site | Downstream genomic sequence | Upstream genomic sequence |
|---|---|---|
| EMX_ Off2 | TGGCCCCAGTCTCTCTTC (SEQ ID NO: 123) | TACAGCCTCTGAACAGCTCCCG (SEQ ID NO: 124) |
| EMX_ Off3 | TGACTTGGCCTTTGTAGGAA (SEQ ID NO: 125) | GAGGCTACTGAAACATAAGT (SEQ ID NO: 126) |
| EMX_ Off4 | TGCTACCTGTACATCTGCACC (SEQ ID NO: 127) | ATCAATGATTGGGCATTTC (SEQ ID NO: 128) |
| VEG_ On | ACTCCAGTCCCAAATATGTAAC (SEQ ID NO: 129) | TAGGGGGCGCTCGGCCAC (SEQ ID NO: 130) |
| VEG_ Off1 | CTGAGTCAACTGTAAGCATTGGC (SEQ ID NO: 131) | CAGGTGCAGTGATTCAT (SEQ ID NO: 132) |
| VEG_ Off2 | TCGTGTCATCTTGTTTGTGC (SEQ ID NO: 133) | GGCAGAGCCCAGCGGACACT (SEQ ID NO: 134) |
| VEG_ Off3 | CAAGGTGAGCCTGGGTCTGT (SEQ ID NO: 135) | ATCACTGCCCAAGAAGTGCA (SEQ ID NO: 136) |
| VEG_ Off4 | TTGTAGGATGTTTAGCAGCA (SEQ ID NO: 137) | ACTTGCTCTCTTTAGAGAAC (SEQ ID NO: 138) |
| CLT2_ On | CTCAAGCAGGCCCCGCTGGT (SEQ ID NO: 139) | TTTTGGACCAAACCTTTTTG (SEQ ID NO: 140) |
| CLT2_ Off1 | TGAGGTTATTTGTCCATTGT (SEQ ID NO: 141) | TAAGGGGAGTATTTACACCA (SEQ ID NO: 142) |
| CLT2_ Off2 | TCAAGAGCAGAAAATGTGAC (SEQ ID NO: 143) | CTTGCAGGGACCTTCTGATT (SEQ ID NO: 144) |
| CLT2_ Off3 | TGTGTGTAGGACTAAACTCTGA (SEQ ID NO: 145) | TAGCAGTATGACCTTGGG (SEQ ID NO: 146) |
| EGFP | AGCGTGTCCGGCGAGGGCGA (SEQ ID NO: 147) | AGCGTGTCCGGCGAGGGCGA (SEQ ID NO: 148) |
| MusEMX | CAGAATCGGAGGACAAAATAACGAAGCAAAC (SEQ ID NO: 149) | CAGGCCAACGGGGAGGACA (SEQ ID NO: 150) |

Primers Used for Generating PCR Products to Serve as Substrates for T7 Transcription of sgRNAs.

T7_gRNA-Rev was used in all cases. DNA template used was EGFP sgRNA plasmid as noted above. NTF3 and VEGF sgRNAs for dCas9-VP64 activator experiments were reported previously (Maeder et al., CRISPR RNA-guided activation of endogenous human genes. *Nat. Methods.* 2013; 10, 977-979). The T2 sgRNA target was previously reported[11]. All oligonucleotides were purchased from Integrated DNA Technologies.

T7_EGFP1-Fwd
(SEQ ID NO: 151)
TAA TAC GAC TCA CTA TA GGGCACGGGCAGCTTGCCGG

T7-GFP g1-Fwd
(SEQ ID NO: 152)
TAA TAC GAC TCA CTA TA GGCCTCGAACTTCACCTCGGCG

GAAAGGACGAAACACC

T7-GFP g5-Fwd
(SEQ ID NO: 153)
TAA TAC GAC TCA CTA TA GGCTGAAGGGCATCGACTTCA

GAAAGGACGAAACACC

-continued

T7-GFP g3-Fwd
(SEQ ID NO: 154)
TAA TAC GAC TCA CTA TA GGCAGCTCGATGCGGTTCACCA

GAAAGGACGAAACACC

T7-GFP g7-Fwd
(SEQ ID NO: 155)
TAA TAC GAC TCA CTA TA GGCAAGGAGGACGGCAACATCC

GAAAGGACGAAACACC

T7-EMX-Fwd
(SEQ ID NO: 156)
TAA TAC GAC TCA CTA TA GGAGTCCGAGCAGAAGAAGAA

GAAAGGACGAAACACC

T7-VEG-Fwd
(SEQ ID NO: 157)
TAA TAC GAC TCA CTA TA GGGGTGGGGGGAGTTTGCTCC

GAAAGGACGAAACACC

T7-CLT2-Fwd
(SEQ ID NO: 158)
TAA TAC GAC TCA CTA TA GGCAGATGTAGTGTTTCCACA

GAAAGGACGAAACACC

T7-T2 HDR-Fwd
(SEQ ID NO: 273)
TAA TAC GAC TCA CTA TA GGGGCCACTAGGGACAGGAT

GAAAGGACGAAACACC

T7_gRNA-Rev
(SEQ ID NO: 159)
AAAAAAAGCACCGACTCGGTG

Sequence of Single-Stranded Oligonucleotide Donor Template (ssODN) Used in HDR Studies.

(SEQ ID NO: 274)
CGACCACATGAAGCAGCACGACTTCTTCAAGTCCGCCATGCCCGAAGGCT

ACGTCCAGGAGCGCACCATCTTCTTCAAGGACGACGGCAACTACAAGACC

CGCGCCGAGGTGAAGTTCGAGGGCGACACCCTGGTGAACCGCATCGAGCT

GAAGGGCATCGACTTCAAGGAGGACGGCAACATCCTGGGGCACAAGCTGG

Primers for Generating Linear DNA PCR Product for Transfection.

PCR extension at (72° C., 3 min) on plasmid containing U6 promoter as template with PCR_sgRNA-fwd1, PCR_sgRNA-rev2 and appropriate PCR_sgRNA primers listed below.

PCR_gRNA-fwd1
(SEQ ID NO: 160)
CTGTACAAAAAAGCAGGCTTTA

PCR_gRNA-rev2
(SEQ ID NO: 161)
AAAAAAAGCACCGACTCGGTGCCACTTTTTCAAGTTGATAACGG

ACTAGCCTTATTTTAACTTGCTATTTCTAGCTCTAAAAC

PCR-G-GFP1
(SEQ ID NO: 162)
GAAAGGACGAAACACC

GGCCTCGAACTTCACCTCGGCGGTTTTAGAGCTAGAAATAGCAA

-continued

PCR-G-GFP3
(SEQ ID NO: 163)
GAAAGGACGAAACACC

GGCAGCTCGATGCGGTTCACCAGTTTTAGAGCTAGAAATAGCAA

PCR-G-GFP5
(SEQ ID NO: 164)
GAAAGGACGAAACACC

GGCTGAAGGGCATCGACTTCAGTTTTAGAGCTAGAAATAGCAA

PCR-G-GFP7
(SEQ ID NO: 165)
GAAAGGACGAAACACC

GGCAAGGAGGACGGCAACATCCGTTTTAGAGCTAGAAATAGCAA

PCR-G-CLT2
(SEQ ID NO: 166)
GAAAGGACGAAACACC

GGCAGATGTAGTGTTTCCACAGTTTTAGAGCTAGAAATAGCAA

PCR-G-EMX
(SEQ ID NO: 167)
GAAAGGACGAAACACC

GGAGTCCGAGCAGAAGAAGAAGTTTTAGAGCTAGAAATAGCAA

PCR-G-VEG
(SEQ ID NO: 168)
GAAAGGACGAAACACC

GGGGTGGGGGGAGTTTGCTCCGTTTTAGAGCTAGAAATAGCAA

Primers for Performing T7 Endonuclease I DNA Cleavage Assay.

| | | |
|---|---|---|
| Survey_GFP-fwd | TACGGCAAGCTGACCCTGAA | (SEQ ID NO: 169) |
| Survey_GFP-rev | GTCCATGCCGAGAGTGATCC | (SEQ ID NO: 170) |
| Survey_CLTA-fwd | GCCAGGGGCTGTTATCTTGG | (SEQ ID NO: 171) |
| Survey_CLTA-rev | ATGCACAGAAGCACAGGTTGA | (SEQ ID NO: 172) |
| Survey_EMX-fwd | CTGTGTCCTCTTCCTGCCCT | (SEQ ID NO: 173) |
| Survey_EMX-rev | CTCTCCGAGGAGAAGGCCAA | (SEQ ID NO: 174) |
| Survey_VEGF-fwd | CCACACAGCTTCCCGTTCTC | (SEQ ID NO: 175) |
| Survey_VEGF-rev | GAGAGCCGTTCCCTCTTTGC | (SEQ ID NO: 176) |

Primers for High-Throughput Sequencing of on-Target and Off-Target Sites in Human Genome.

HTS_EMX_ON-fwd
(SEQ ID NO: 177)
CACTCTTTCCCTACACGACGCTCTTCCGATCT

CCTCCCCATTGGCCTGCTTC

HTS_EMX_Off1-fwd
(SEQ ID NO: 178)
CACTCTTTCCCTACACGACGCTCTTCCGATCT

TCGTCCTGCTCTCACTTAGAC

-continued

HTS_EMX_Off2-fwd
(SEQ ID NO: 179)
CACTCTTTCCCTACACGACGCTCTTCCGATCT

TTTTGTGGCTTGGCCCCAGT

HTS_EMX_Off3-fwd
(SEQ ID NO: 180)
CACTCTTTCCCTACACGACGCTCTTCCGATCT

TGCAGTCTCATGACTTGGCCT

HTS_EMX_Off4-fwd
(SEQ ID NO: 181)
CACTCTTTCCCTACACGACGCTCTTCCGATCT

TTCTGAGGGCTGCTACCTGT

HTS_VEFG_ON-fwd
(SEQ ID NO: 182)
CACTCTTTCCCTACACGACGCTCTTCCGATCT

ACATGAAGCAACTCCAGTCCCA

HTS_VEGF_Off1-fwd
(SEQ ID NO: 183)
CACTCTTTCCCTACACGACGCTCTTCCGATCT

AGCAGACCCACTGAGTCAACTG

HTS_VEGF_Off2-fwd
(SEQ ID NO: 184)
CACTCTTTCCCTACACGACGCTCTTCCGATCT

CCCGCCACAGTCGTGTCAT

HTS_VEGF_Off3-fwd
(SEQ ID NO: 185)
CACTCTTTCCCTACACGACGCTCTTCCGATCT

CGCCCCGGTACAAGGTGA

HTS_VEGF_Off4-fwd
(SEQ ID NO: 186)
CACTCTTTCCCTACACGACGCTCTTCCGATCT

GTACCGTACATTGTAGGATGTTT

HTS_CLTA2_ON-fwd
(SEQ ID NO: 187)
CACTCTTTCCCTACACGACGCTCTTCCGATCT

CCTCATCTCCCTCAAGCAGGC

HTS_CLTA2_Off1-fwd
(SEQ ID NO: 188)
CACTCTTTCCCTACACGACGCTCTTCCGATCT

ATTCTGCTCTTGAGGTTATTTGT

HTS_CLTA2_Off2-fwd
(SEQ ID NO: 189)
CACTCTTTCCCTACACGACGCTCTTCCGATCT

CACCTCTGCCTCAAGAGCAGAAAA

HTS_CLTA2_Off3-fwd
(SEQ ID NO: 190)
CACTCTTTCCCTACACGACGCTCTTCCGATCT

TGTGTGTGTGTGTGTGTAGGACT

HTS_EMX_ON-rev
(SEQ ID NO: 191)
GGAGTTCAGACGTGTGCTCTTCCGATCT

TCATCTGTGCCCCTCCCTCC

-continued

Figure 27A:
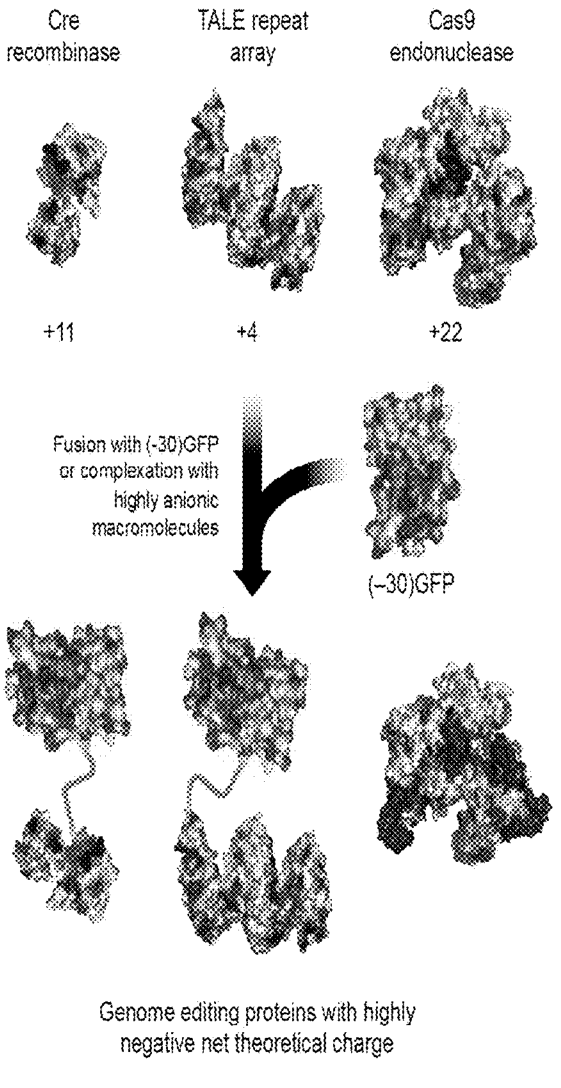
FIG. 27A-B. A strategy for delivering proteins into mammalian cells by fusion or non-covalent association with polyanionic macromolecules and encapsulation with cationic lipids is shown.

HTS_EMX_Off1-rev
(SEQ ID NO: 192)
GGAGTTCAGACGTGTGCTCTTCCGATCT
CGAGAAGGAGGTGCAGGAG HTS_EMX_Off2-rev
(SEQ ID NO: 193)
GGAGTTCAGACGTGTGCTCTTCCGATCT
CGGGAGCTGTTCAGAGGCTG HTS_EMX_Off3-rev
(SEQ ID NO: 194)
GGAGTTCAGACGTGTGCTCTTCCGATCT
CTCACCTGGGCGAGAAAGGT HTS_EMX_Off4-rev
(SEQ ID NO: 195)
GGAGTTCAGACGTGTGCTCTTCCGATCT
AAAACTCAAAGAAATGCCCAATCA HTS_VEFG_ON-rev
(SEQ ID NO: 196)
GGAGTTCAGACGTGTGCTCTTCCGATCT
AGACGCTGCTCGCTCCATTC HTS_VEGF_Off1-rev
(SEQ ID NO: 197)
GGAGTTCAGACGTGTGCTCTTCCGATCT
ACAGGCATGAATCACTGCACCT HTS_VEGF_Off2-rev
(SEQ ID NO: 198)
GGAGTTCAGACGTGTGCTCTTCCGATCT
GCGGCAACTTCAGACAACCGA HTS_VEGF_Off3-rev
(SEQ ID NO: 199)
GGAGTTCAGACGTGTGCTCTTCCGATCT
GACCCAGGGGCACCAGTT HTS_VEGF_Off4-rev
(SEQ ID NO: 200)
GGAGTTCAGACGTGTGCTCTTCCGATCT
CTGCCTTCATTGCTTAAAAGTGGAT HTS_CLTA2_ON-rev
(SEQ ID NO: 201)
GGAGTTCAGACGTGTGCTCTTCCGATCT
ACAGTTGAAGGAAGGAAACATGC HTS_CLTA2_Off1-rev
(SEQ ID NO: 202)
GGAGTTCAGACGTGTGCTCTTCCGATCT
GCTGCATTTGCCCATTTCCA HTS_CLTA2_Off2-rev
(SEQ ID NO: 203)
GGAGTTCAGACGTGTGCTCTTCCGATCT
GTTGGGGGAGGAGGAGCTTAT HTS_CLTA2_Off3-rev
(SEQ ID NO: 204)
GGAGTTCAGACGTGTGCTCTTCCGATCT
CTAAGAGCTATAAGGGCAAATGACT -continued HTS_EGFP-fwd
(SEQ ID NO: 205)
CACTCTTTCCCTACACGACGCTCTTCCGATCTNNNN
ACGTAAACGGCCACAAGTTC HTS_EGFP-rev
(SEQ ID NO: 206)
GGAGTTCAGACGTGTGCTCTTCCGATCT
GTCGTCCTTGAAGAAGATGGTG HTS_MusEMX_ON-fwd
(SEQ ID NO: 207)
CACTCTTTCCCTACACGACGCTCTTCCGATCT
CCAGGTGAAGGTGTGGTTCCAG HTS_MusEMX_ON-rev
(SEQ ID NO: 208)
GGAGTTCAGACGTGTGCTCTTCCGATCT
CCCCTAGTCATTGGAGGTGAC Results Highly Efficient Delivery of Cre Recombinase Fused to a Supernegatively Charged Protein It was speculated that imparting the highly anionic electrostatic properties of nucleic acids to genome-editing proteins may enable their efficient delivery into mammalian cells using cationic lipids (FIG. 27(A)). For proteins of interest that are not natively highly negatively charged, it was thought that fusion with a natural or engineered supernegatively charged protein[17] would impart a polyanionic character. For nucleic acid-binding proteins, it was speculated that simple complexation with native DNA or RNA substrates might provide sufficient anionic character to support cationic lipid-based delivery (FIG. 27(A)).

Figure 27B:
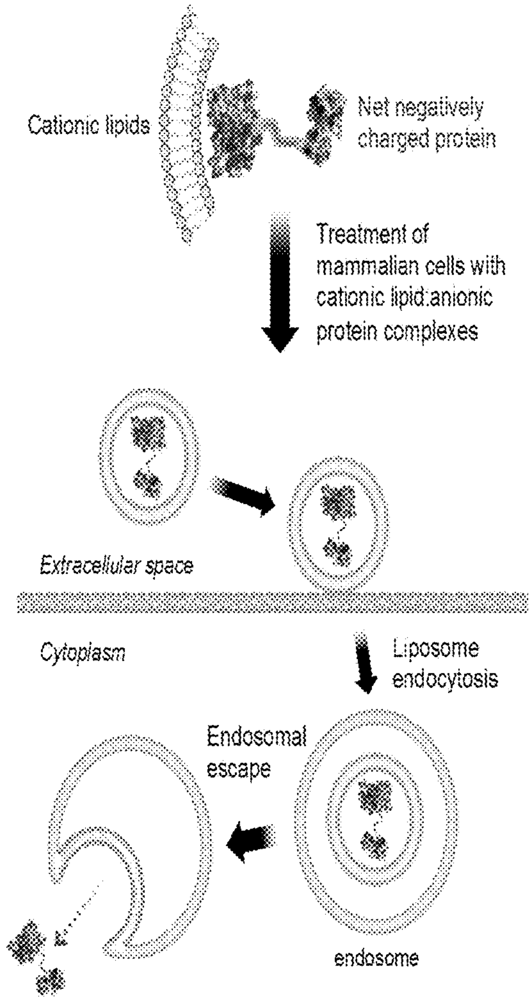
Figure 28A:
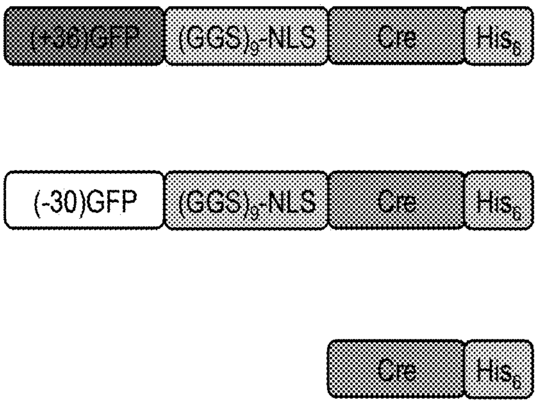
FIG. 28A-G. Delivery of Cre recombinase to cultured human cells.
Figure 28B:
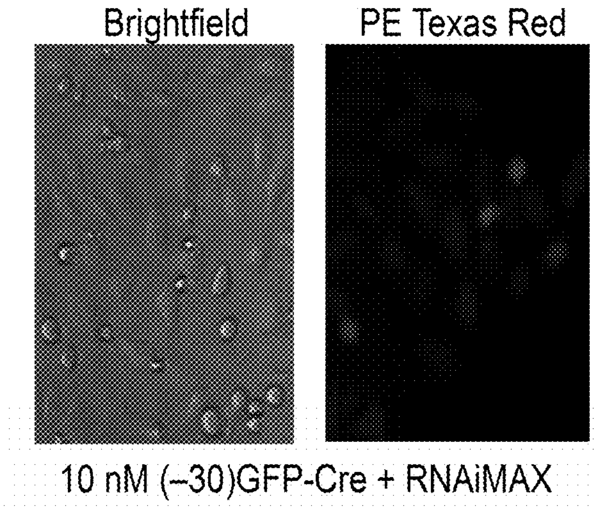

It was first tested whether the engineered supernegatively charged GFP variant,[35] (−30)GFP, could mediate encapsulation and delivery of fused protein cargo (FIG. 27(B)). (−30)GFP was fused to Cre recombinase and several commercially available cationic lipids were tested for their ability to functionally deliver the fusion into HeLa cells that only express DsRed upon Cre-mediated recombination (FIG. 28(A)). Delivery of 10 nM (−30)GFP-Cre complexed with 1.5 μL Lipofectamine RNAiMAX (hereafter referred to as "RNAiMAX", Life Technologies, Carlsbad Calif.) in media containing 10% fetal bovine serum (FBS) led to strong DsRed fluorescence signal among treated cells. Fluorescence-activated cell sorting (FACS) revealed that 48 hours after treatment 52% of cells expressed DsRed consistent with Cre recombination (FIG. 28(B)).

Figure 28C:
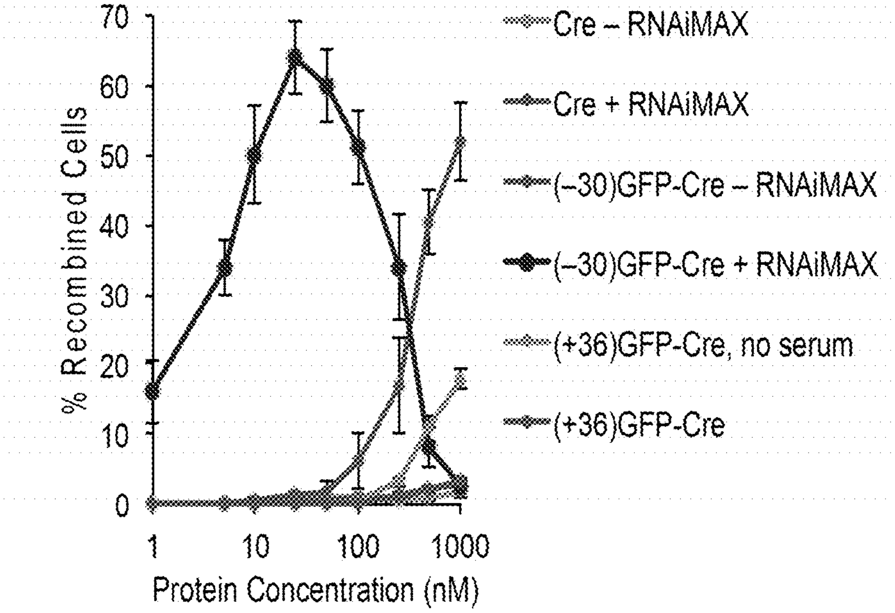
Figure 33A:
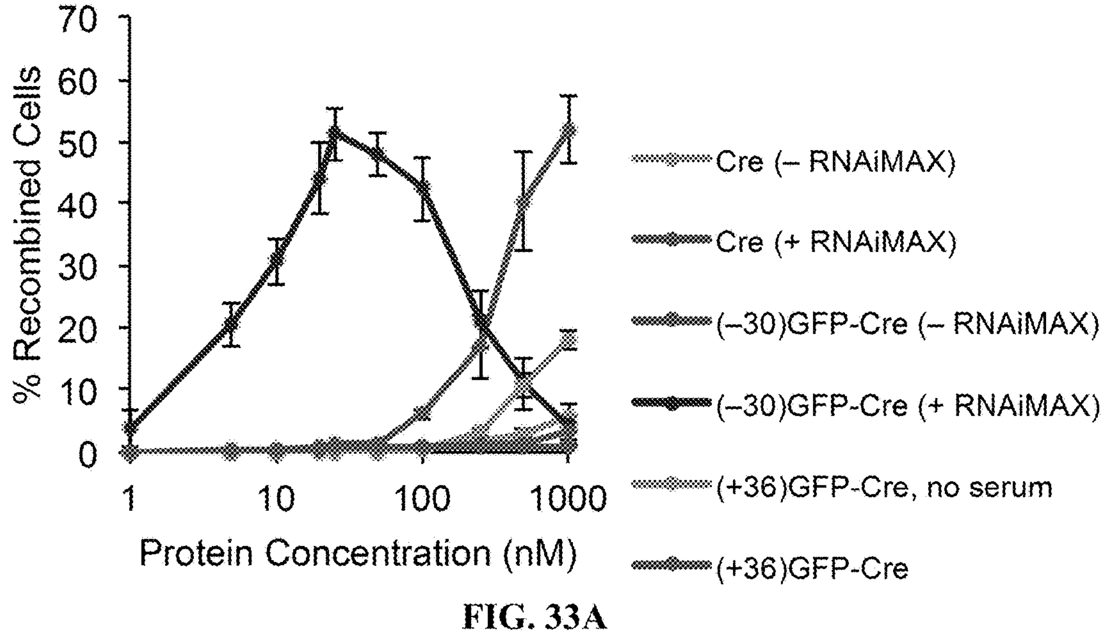
FIG. 33A-F. Optimization of cationic lipid-mediated delivery of Cre recombinase and comparison to delivery using (+36)GFP-Cre and plasmid transfection.
Figure 33B:
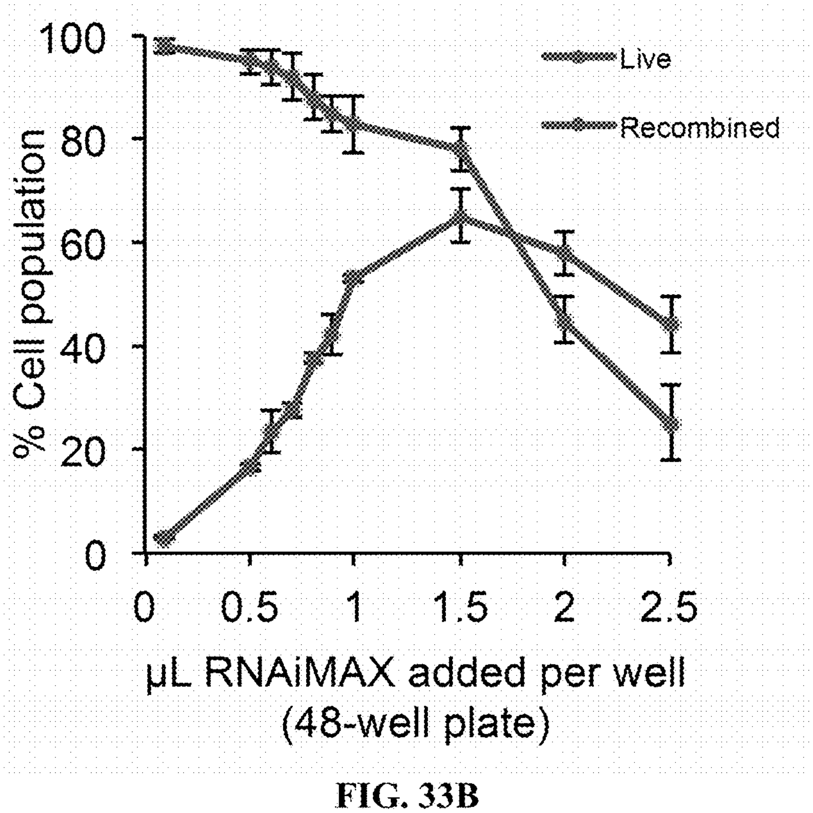

Optimization resulted in recombination efficiencies of 65% using 25 nM (−30)GFP-Cre complexed with 1.5 μL RNAiMAX in 250 μL of media containing 10% FBS (FIG. 28(C)). The potency of lipid-mediated anionic Cre delivery is notable compared to that of cationic protein-mediated delivery. Only 1 nM (−30)GFP-Cre with cationic lipid was needed to result in 15-20% recombined cells, whereas 1 μM (+36)GFP-Cre was required to achieve this extent of recombination, representing a 1,000-fold difference in delivery potency (FIG. 28(C)). Nearly identical results were observed in a second Cre reporter cell line (BSR TdTomato) (FIG. 33(A)). Increasing the amount of cationic lipid increased toxicity (FIG. 33(B)) and it was found that 1.5 μL RNAiMAX per 250 μL sample maximized recombination efficiency while inducing minimal cell toxicity. Under these conditions, cationic lipids did not increase the delivery potency of neutral or cationic Cre recombinase fusions (FIG.

Figure 28D:
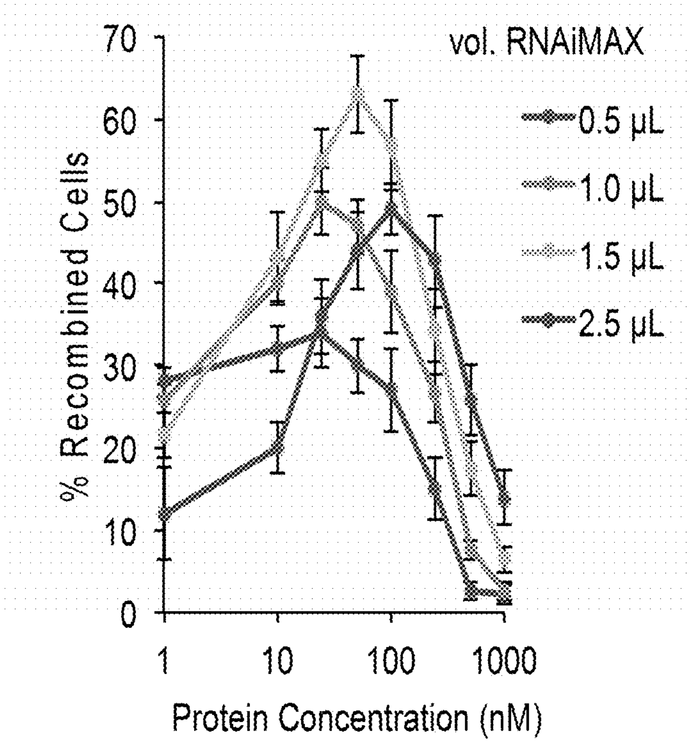
Figure 33C:
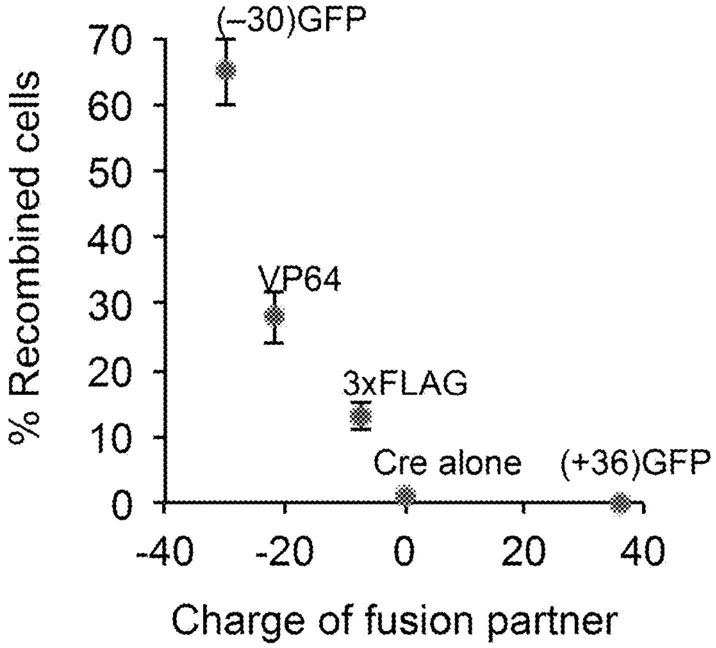
Figure 33D:
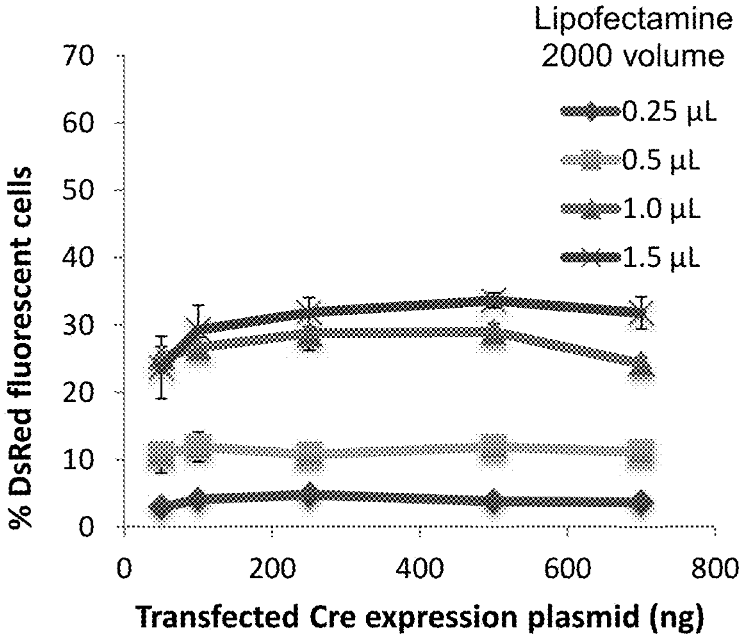
Figure 33E:
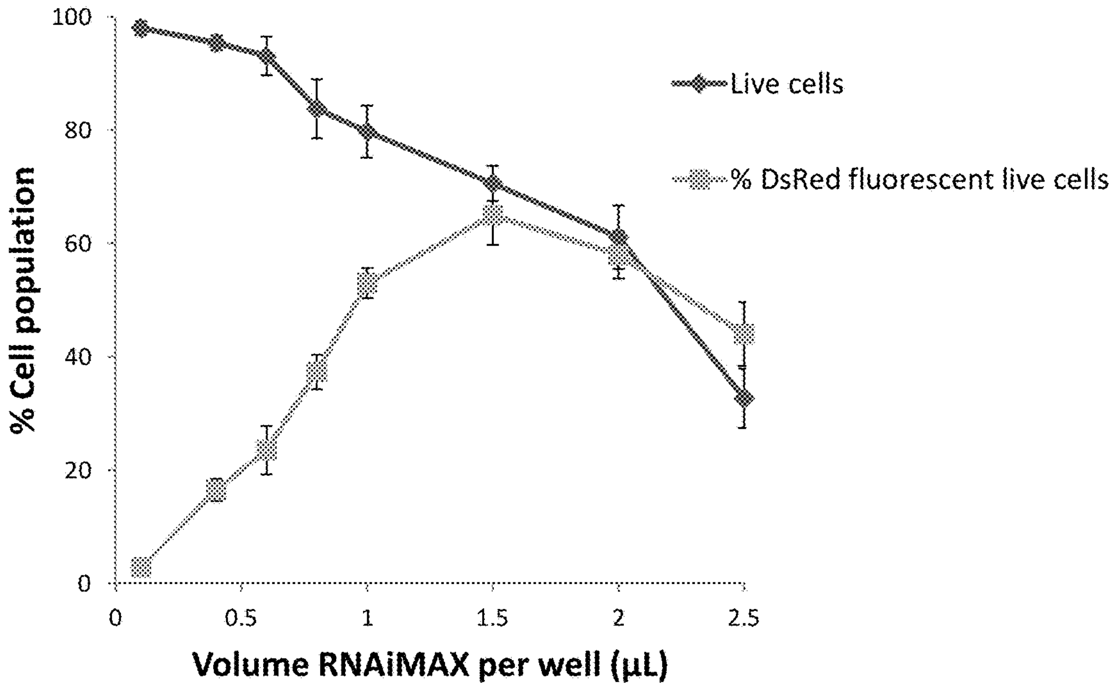
Figure 33F:
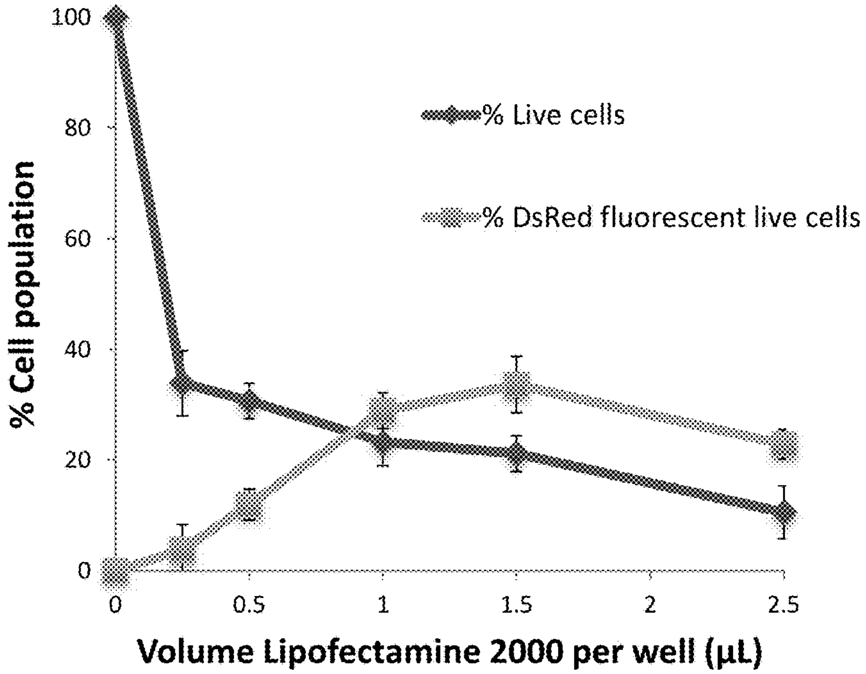
Figure 34A:
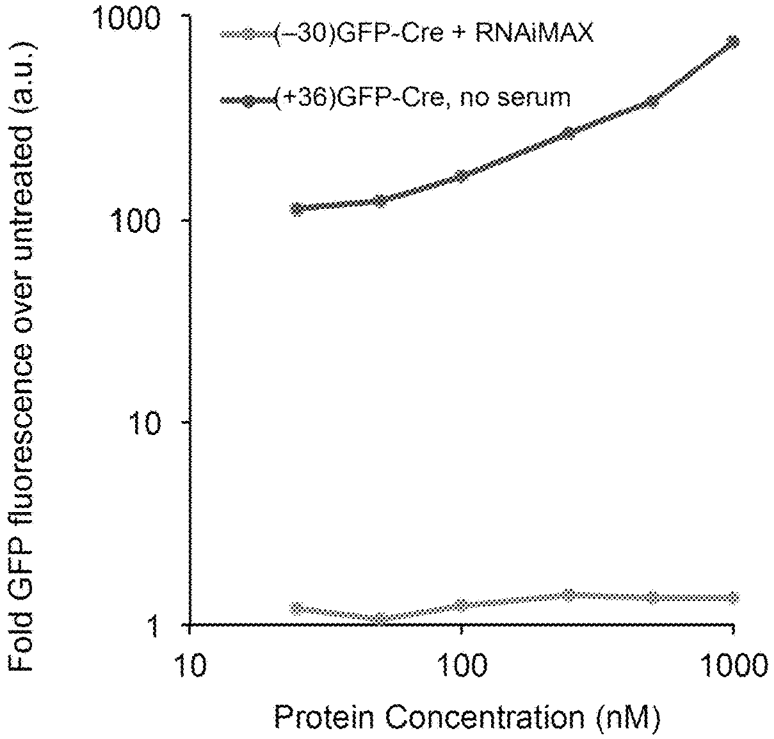
FIGS. 34A-D. Protein uptake by cationic lipid-mediated delivery versus superpositively charged cationic protein delivery.
Figure 34B:
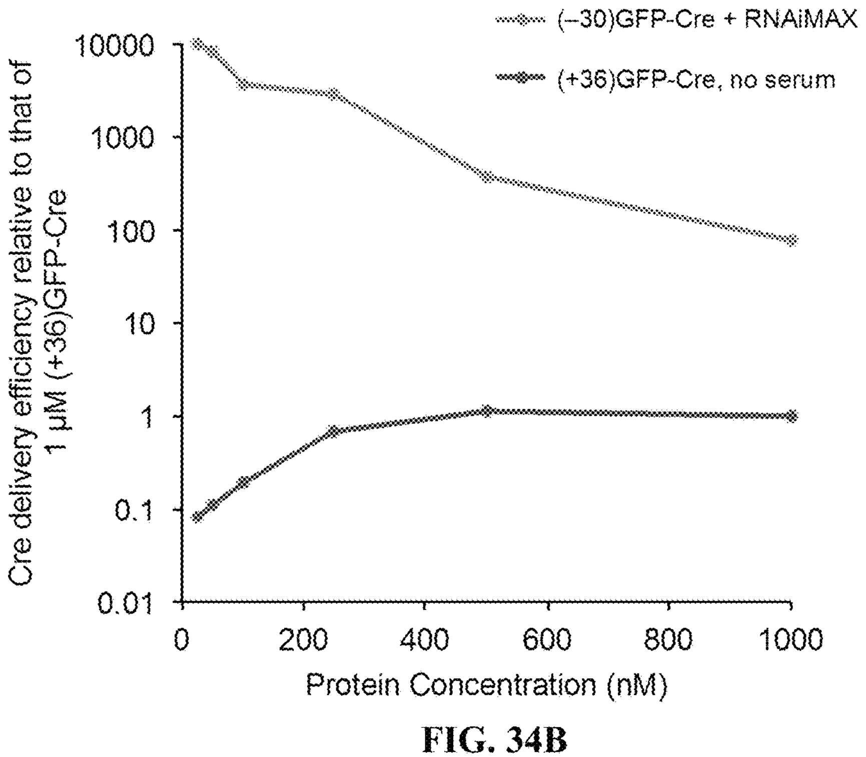
Figure 34C:
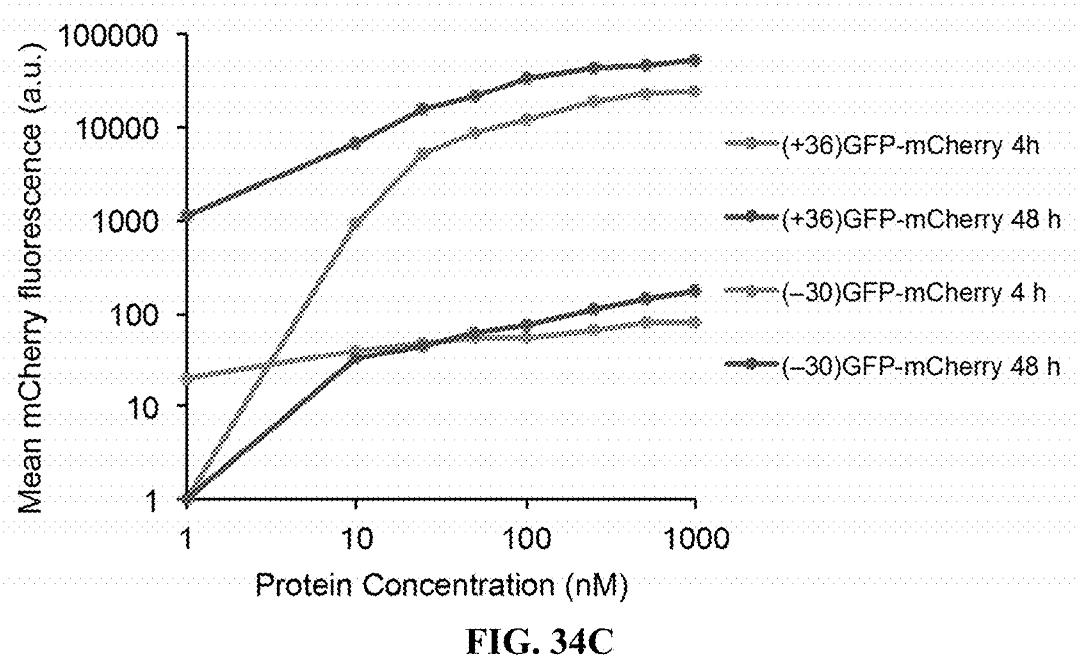
Figure 34D:
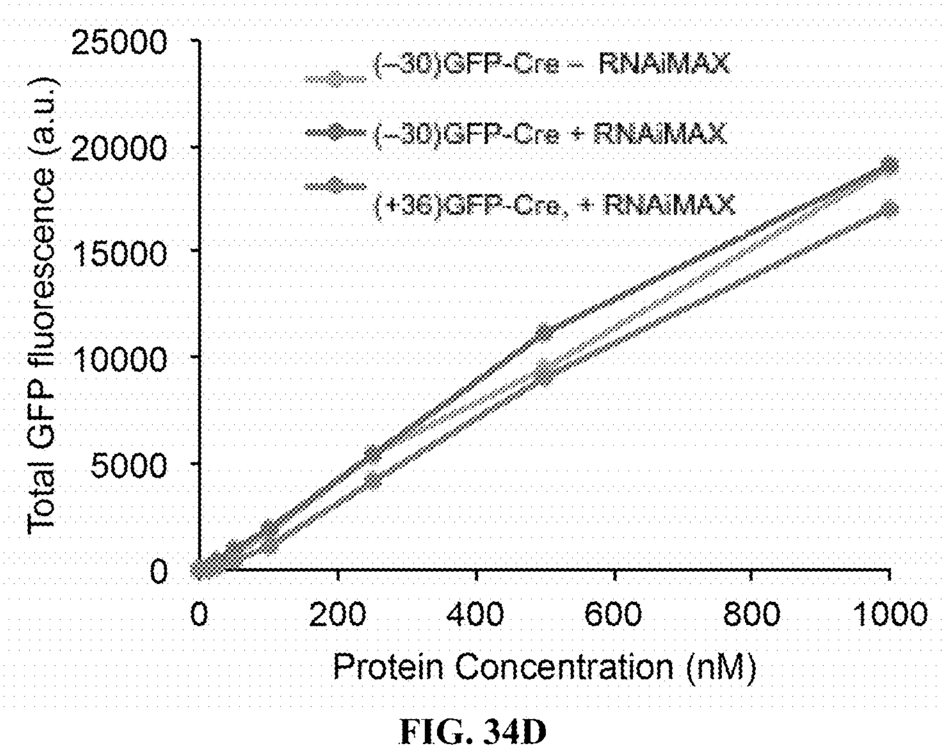

28(C) and FIG. 33(C)), indicating that the strongly negative charge of (−30)GFP-Cre was required to participate in cationic lipid-mediated delivery. It was also observed that increasing the amount of cationic lipid increased the concentration of protein required for maximal recombination, consistent with a model in which deliverable proteins are complexed with specific stoichiometries of cationic lipids (FIG. 28(D)). These observations collectively indicate that cationic lipids can mediate the potent delivery of polyanionic proteins into mammalian cells even in the presence of serum.

To determine if the higher potency of cationic lipid-mediated (−30)GFP-Cre delivery relative to cationic protein-mediated delivery arises from more total protein uptake by cells, or from a higher fraction of functional, non-endosomal protein molecules that enter cells, flow cytometry was used to measure GFP fluorescence of cells treated with either (+36)GFP-Cre or liposomal (−30)GFP-Cre under their respective optimal Cre delivery conditions. Comparison of cellular fluorescence and recombination efficiency reveals that lipid-mediated functional delivery of (−30)GFP-Cre is 9,800-fold more potent per amount of endocytosed protein than delivery of (+36)GFP-Cre (FIG. 34). Taken together, these results suggest that the unusually high potency of lipid-mediated delivery of anionic proteins does not arise from unusually high protein uptake in each cell, but rather from post-endocytosis processes that likely include endosomal escape into the cytoplasm and the avoidance of lysosomal protein degradation.

Figure 28E:
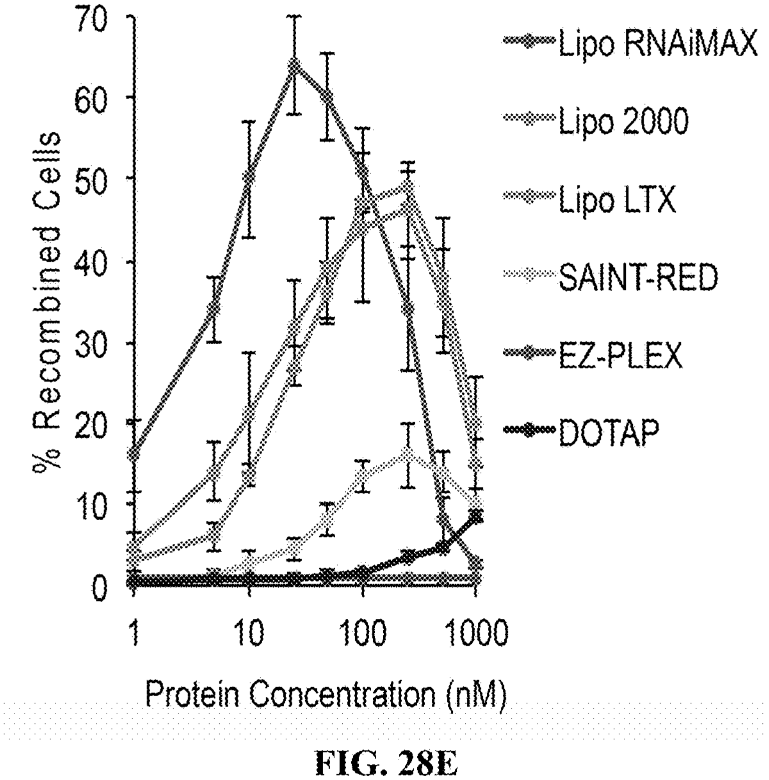

To test whether the ability to deliver polyanionic proteins is dependent on proprietary components in RNAiMAX or if other cationic lipids are capable of mediating similarly potent delivery, several other transfection reagents designed to deliver nucleic acids were tested (FIG. 28(E)). While RNAiMAX remained the most effective functional delivery agent for (−30)GFP-Cre, other cationic lipid formulations also resulted in potent delivery. Lipofectamine 2000 and Lipofectamine LTX (Life Technologies, Carlsbad Calif.), two plasmid transfection reagents based on cationic lipid formulations,[21] and SAINT-Red (Synvolux Therapeutics, Groningen Netherlands), an siRNA delivery formulation containing a synthetic pyridium-containing cationic lipid, all resulted in strong functional (−30)GFP-Cre delivery over a range of concentrations (FIG. 28(E)). In contrast, strong deliveries with the cationic lipid DOTAP (Roche Diagnostics, Indianapolis Ind.) or the peptide-based nucleic acid delivery agent EZ-PLEX (Ascension Bio, Tampa Fla.) were not observed (FIG. 28(E)). These observations collectively indicate that several (but not all) cationic lipids are able to encapsulate and deliver negatively charged proteins into human cells.

It was speculated that it should be possible to use cationic lipids to deliver polyanionic proteins other than (−30)GFP. Engineered polyanionic protein domains commonly used in biomedical research include the VP64 activation domain (−22 net theoretical charge) widely used in fusions with engineered zinc finger arrays, TALE repeat arrays, or dCas9 for transcriptional activation, and 3×FLAG (−7 net theoretical charge), an epitope tag used for protein purification and visualization (FIG. 28(F)). It was observed that both VP64 and 3×FLAG enhance functional delivery of Cre recombinase with cationic lipids, though not as effectively as (−30) GFP, likely due to their lower overall negative charge (FIG. 33(C)). These observations demonstrate that unusually negatively charged proteins beyond (−30)GFP can mediate efficient cationic lipid-based delivery into mammalian cells. Protein delivery efficacy by cationic lipids is predominantly a function of total negative charge, and does not require a particular distribution of anionic residues.

Comparison of Recombination Efficiency and Cellular Toxicity for Liposomal Protein Delivery of (−30)GFP-Cre Versus Optimized Plasmid DNA Transfection We optimized plasmid transfection of HeLa reporter cells across a range of plasmid and Lipofectamine 2000 doses, and found that transfection efficiency in this cell line yielded a maximum of 33% DsRed fluorescent cells (FIG. 27(B)). These findings suggest that cationic lipid-based (−30)GFP-Cre protein delivery can result in more functional Cre recombinase activity than well-established plasmid DNA transfection methods.

As nucleic acid transfection by cationic lipids is to known to induce cellular toxicity,[1] we also characterized the toxicity of cationic lipid-mediated (−30)GFP-Cre protein delivery and compared the results with those of plasmid transfection methods (FIGS. 27(B-C)). Cells undergoing protein delivery or plasmid transfection were analyzed for cell survival by flow cytometry using the TO-PRO-3 live/dead cell stain (Life Technologies). While increasing the amount of RNAiMAX predictably increased toxicity (FIG. 27(B)), the use of 1.5 μL RNAiMAX per 275 μL sample maximized recombination efficiency (>50% DsRed-positive live cells) while inducing minimal cell toxicity (>80% live cells, FIG. 27(C)). In contrast, all efficacious plasmid DNA delivery conditions tested exhibited much greater toxicity (FIG. 27(D)), with fewer than 40% of cells surviving plasmid transfection under any condition that resulted in >5% DsRed-positive live cells. These results indicate that optimized cationic lipid-mediated delivery of anionic Cre recombinase achieves substantially greater delivered Cre activity with much lower toxicity than optimized plasmid DNA transfection.

Delivery Efficacy of Various Anionic Proteins Fused to Cre

Figure 28F:
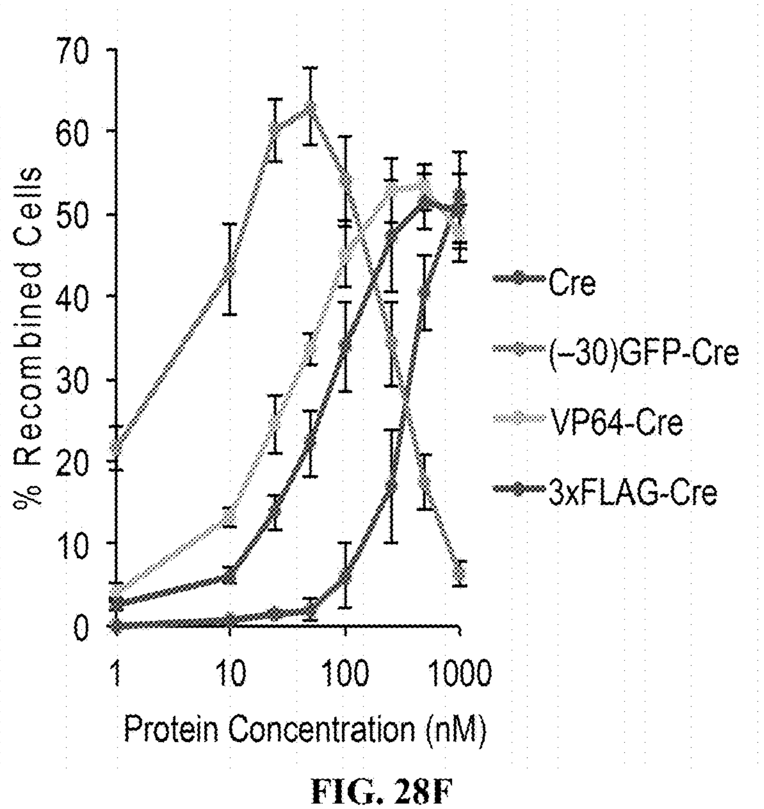
Figure 28G:
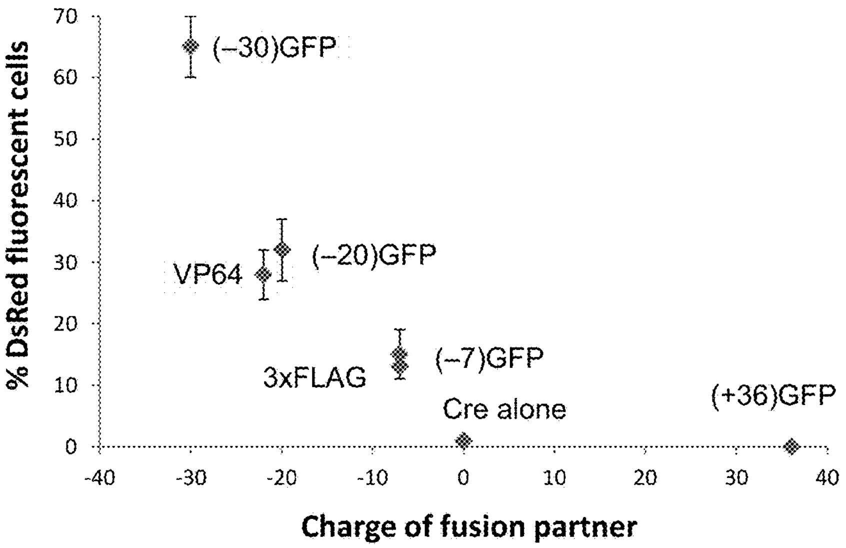

We observed that both VP64 and 3×FLAG enhance functional delivery of Cre recombinase with cationic lipids, though not as effectively as (−30)GFP, likely due to their lower overall negative charge (FIG. 28(F)). To further probe the relationship between net anionic charge and protein delivery efficiency, we generated two new anionic GFP-Cre fusions of comparable charge as 3×FLAG-Cre and VP64-Cre using (−7)GFP and (−20)GFP, respectively. The (−7) GFP-Cre and (−20)GFP-Cre fusions showed nearly identical protein delivery efficacy as their like-charged anionic peptide-tagged counterparts (FIG. 28(F)), suggesting that the efficacy of delivery by cationic lipids is predominantly a function of the total negative charge, and not the distribution or density of charged residues.

Functional Delivery of TALE Activator Proteins

Figure 29A:
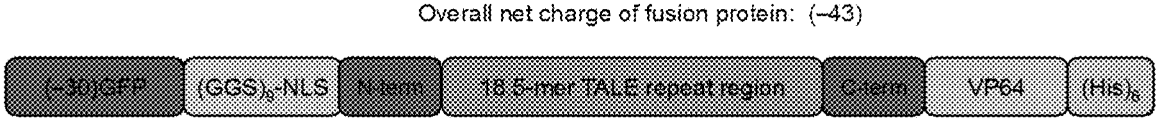
FIG. 29A-C. Delivery of TALE transcriptional activators into cultured human cells.
Figure 29B:
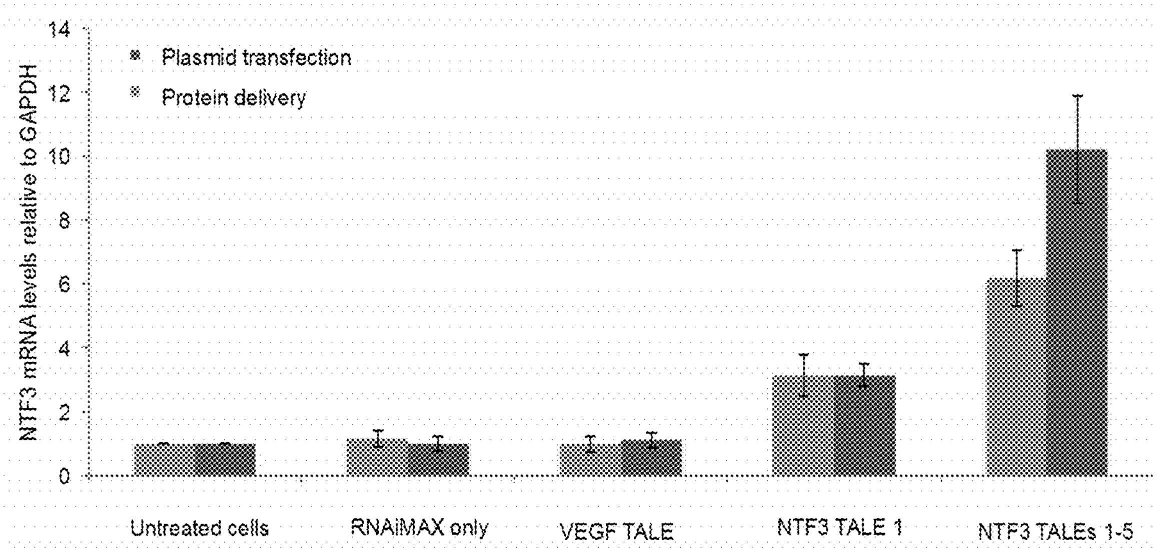

The lipid-mediated delivery of TALE-VP64 transcriptional activators (approximately +4 theoretical net charge, depending on TALE variant used) into cultured human cells was tested. While modestly effective cleavage of endogenous genes by delivered TALEN proteins has been demonstrated in mammalian cells in the absence of serum using cationic peptides such as $Arg_9$,[36] the delivery of TALE-based transcription factor proteins has not yet been reported, and no effective delivery of TALE proteins in serum has been previously described to our knowledge. The gene for neurotrophin-3 (NTF3), a neural growth factor that has been associated with neurodegenerative diseases, was targeted.[37] A previously described NTF3-targetting TALE-VP64[38] was fused to (−30)GFP (FIG. 29(A)) and treated HEK293T cells with 25 nM (−30)GFP-NTF3 TALE1-VP64 and RNAiMAX under the conditions optimized for Cre delivery. Gene expression levels of NTF3 4 hours after treatment were 3.5-fold higher in cells treated with 25 nM (−30)GFP-NTF3 TALE-VP64 and RNAiMAX than untreated cells, cells treated with RNAiMAX only, or cells treated with a VEGF-targeting TALE transcriptional activator (FIG. 29(B)). Comparable levels of NTF3 expression were observed 48 hours after transfection of plasmids encoding the same NTF3-targeting TALE-VP64 (FIG. 29(B)).

Figure 29C:
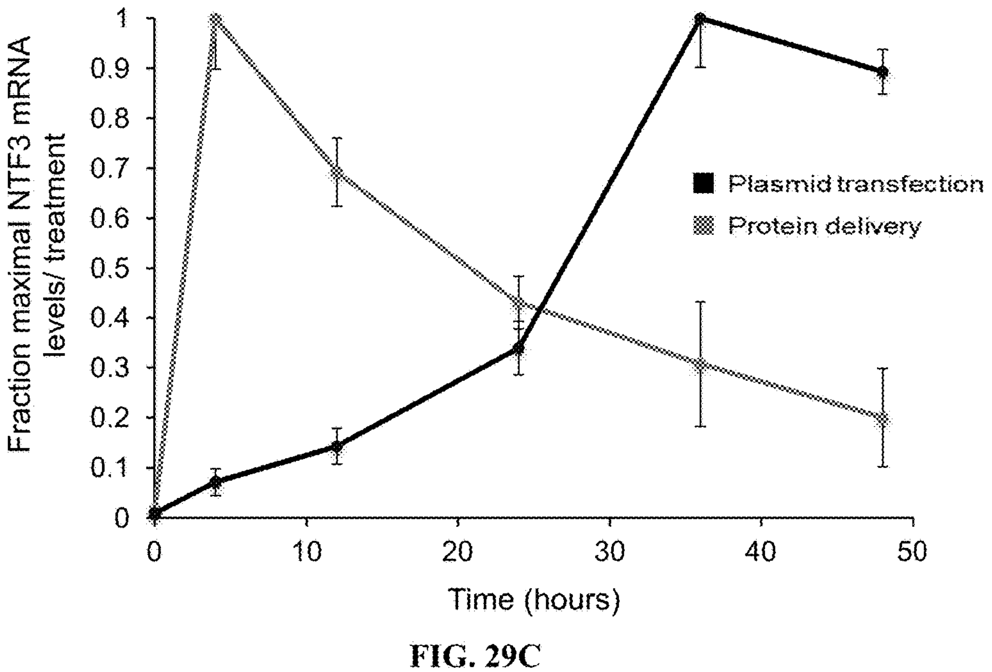
Figure 35:
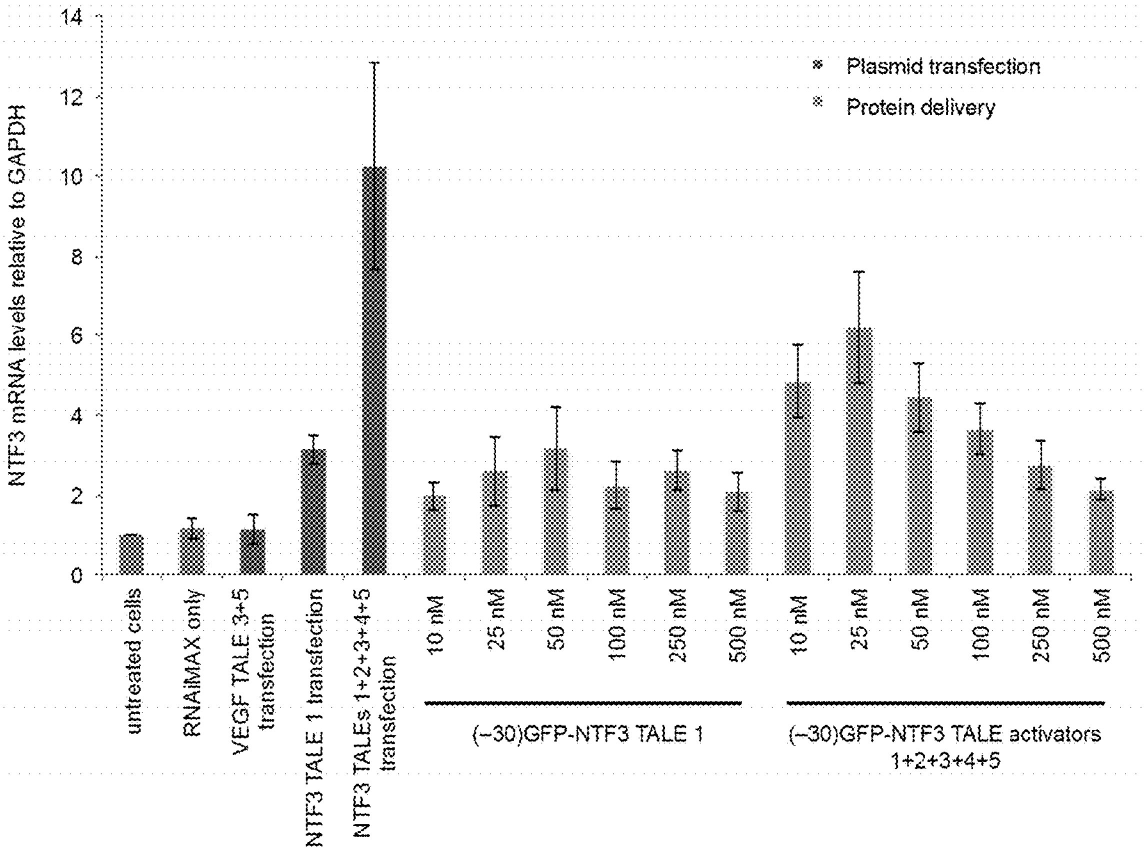
FIG. 35. Delivery optimization of TALE activators designed to target the NTF3 gene. HEK293T cells were treated with either NTF3 TALE plasmid by transfection of by liposomal delivery of NTF3 TALE proteins. Cells were harvested after empirically determined optimal incubation time for both treatments and analyzed by qRT-PCR for mRNA levels of NTF3. Optimal protein (25-50 nM) and lipid dosage (1.5 μL RNAiMAX) was chosen for comparison of two delivery techniques in FIG. 29B. All protein-delivery and transfection experiments were performed in a 48-well plate with 275 μL DMEM-FBS without antibiotics. Error bars reflect the standard deviation from six biological replicates performed on different days.

Since the synergistic expression of multiple TALE activators targeting different sites on the same gene has been shown to augment gene activation,[38] five distinct NTF3-targeting TALE activators fused to (−30)GFP using RNAiMAX were simultaneously delivered. Protein-lipid complexes were prepared as above by adding the five (−30)GFP-NTF3-TALE-VP64 proteins at 5 nM each, for a total of 25 nM protein. A 7-fold increase in NTF3 expression was observed after a 4-hour incubation (FIG. 29(B) and FIG. 35), while plasmid co-transfection of all five NTF3 TALE activators, followed by a 48-hour incubation, resulted in a 10-fold increase in NTF3 expression levels (FIG. 29(B)). To characterize TALE activity over time using these two methods, NTF3 mRNA levels were measured over a 48-hour period following protein or DNA delivery. TALE activator activity following protein delivery peaks ~4 hours post-treatment and falls over the next 44 hours (FIG. 29(C)), whereas plasmid DNA transfection required ~24 hours to show above-background levels of NTF3 activation, which plateaued at ~36-48 hours (FIG. 29(C)). These findings demonstrate that TALE activator proteins can be delivered using cationic lipids to transiently activate gene expression in human cells. While not limited to such embodiments, this capability may prove especially valuable for proteins that effect a one-time permanent change in cell state or cell fate when transiently expressed.[39]

Highly Efficient Delivery of Cas9:sgRNA Protein:RNA Complexes into Human Cells

Figure 36A:
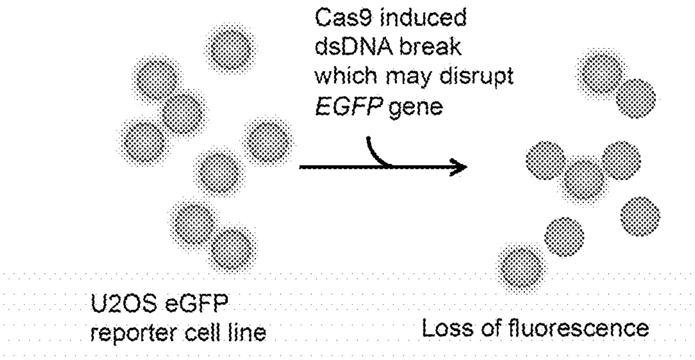
FIGS. 36A-D. Determination of gene disruption frequency of an EGFP reporter gene by delivery of Cas9:sgRNA and analyzing by flow cytometry.

Given the potent lipid-mediated delivery of polyanionic Cre and TALE activator protein variants in full-serum media, it was speculated that CRISPR-Cas9:sgRNA complexes, either as fusions with (−30)GFP or as native polyanionic Cas9:guide RNA complexes, might also be delivered into human cells using this approach. Using a well-established Cas9-induced gene disruption assay,[40] specific sites within a genomic EGFP reporter gene in human U2OS cells were targeted (FIG. 36(A)). On-target Cas9 cleavage induces non-homologous end joining (NHEJ) in EGFP and the loss of cell fluorescence. To avoid interference from the fluorescence of (−30)GFP, a Y67S mutation was introduced into (−30)GFP to eliminate its fluorescence, and designated this non-fluorescent variant as (−30)dGFP.

Figure 30A:
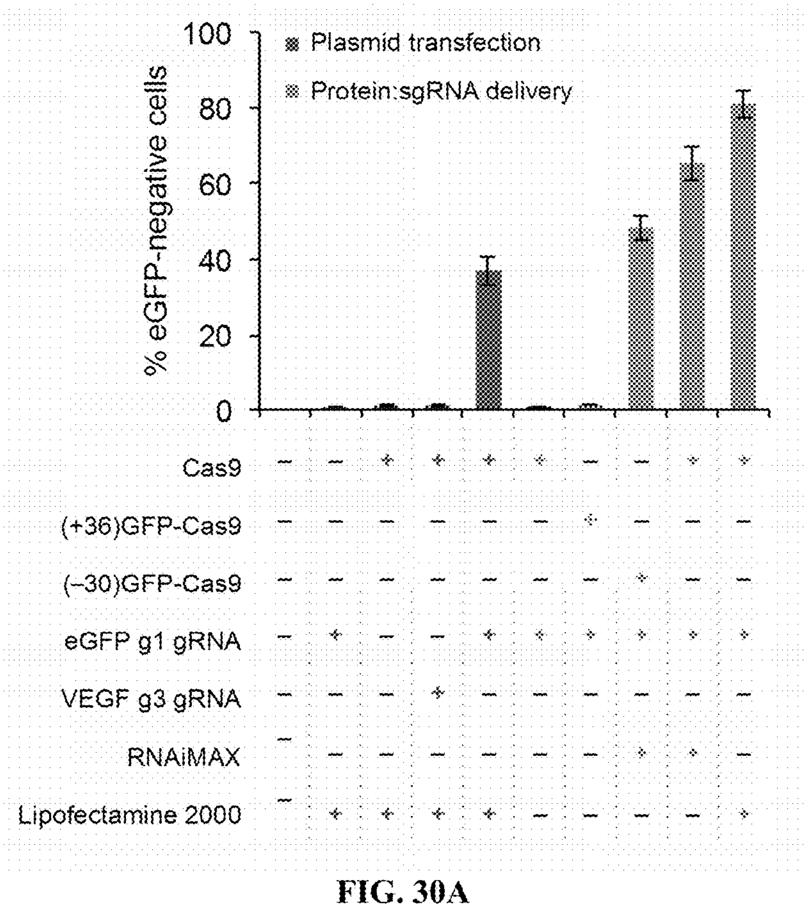
FIG. 30A-E. Delivery of Cas9:sgRNA, Cas9 D10A nickase, and dCas9-VP64 transcriptional activators to cultured human cells.
Figure 31A:
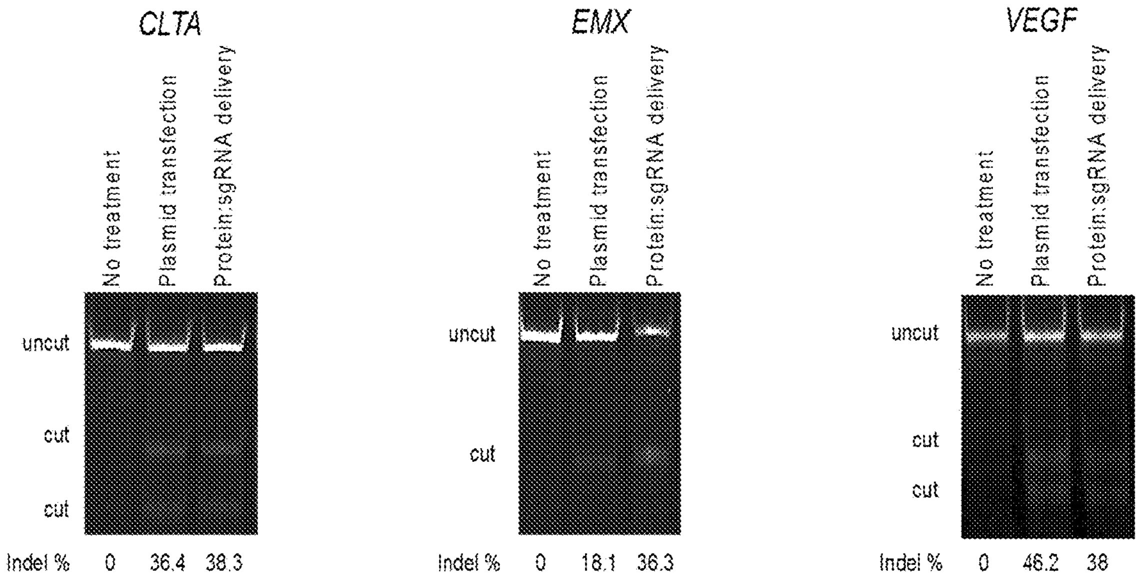
FIG. 31A-D. The DNA sequence specificity of Cas9-mediated endogenous gene cleavage in cultured human cells by plasmid transfection or by cationic lipid-mediated protein:sgRNA delivery is shown.
Figure 31B:
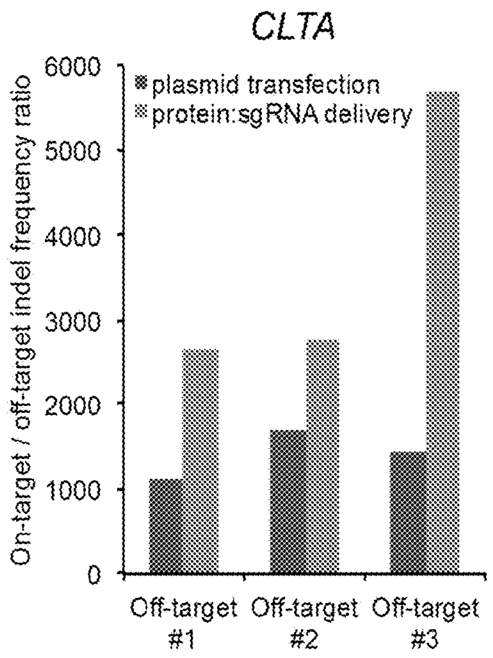
Figure 31C:
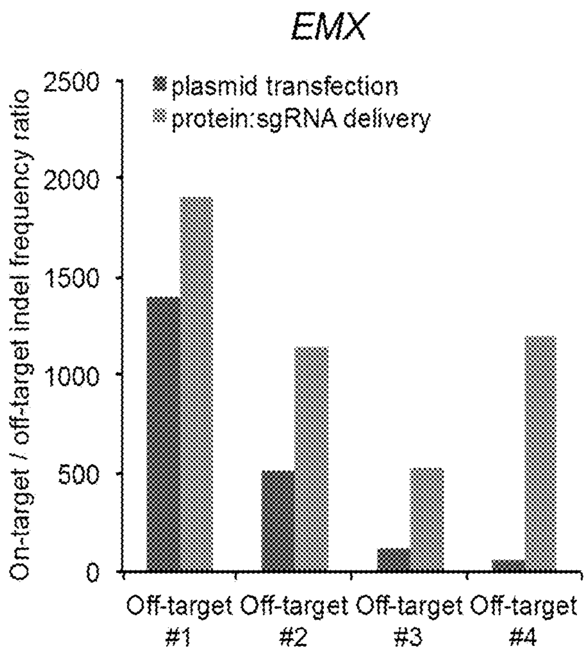
Figure 31D:
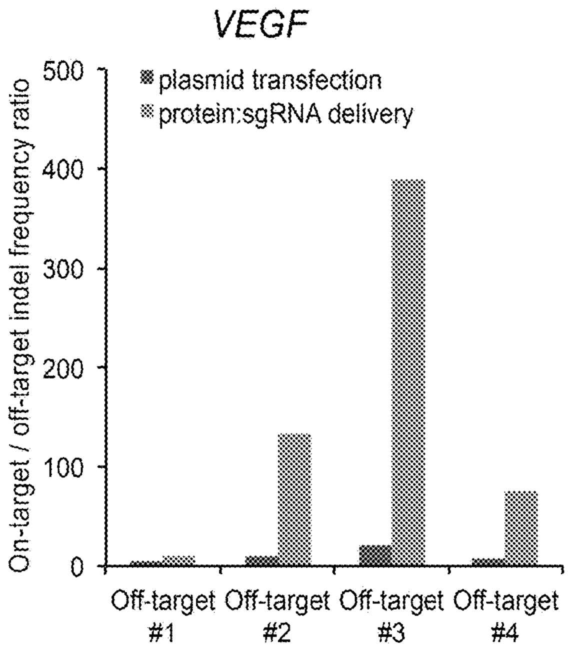
Figure 36B:
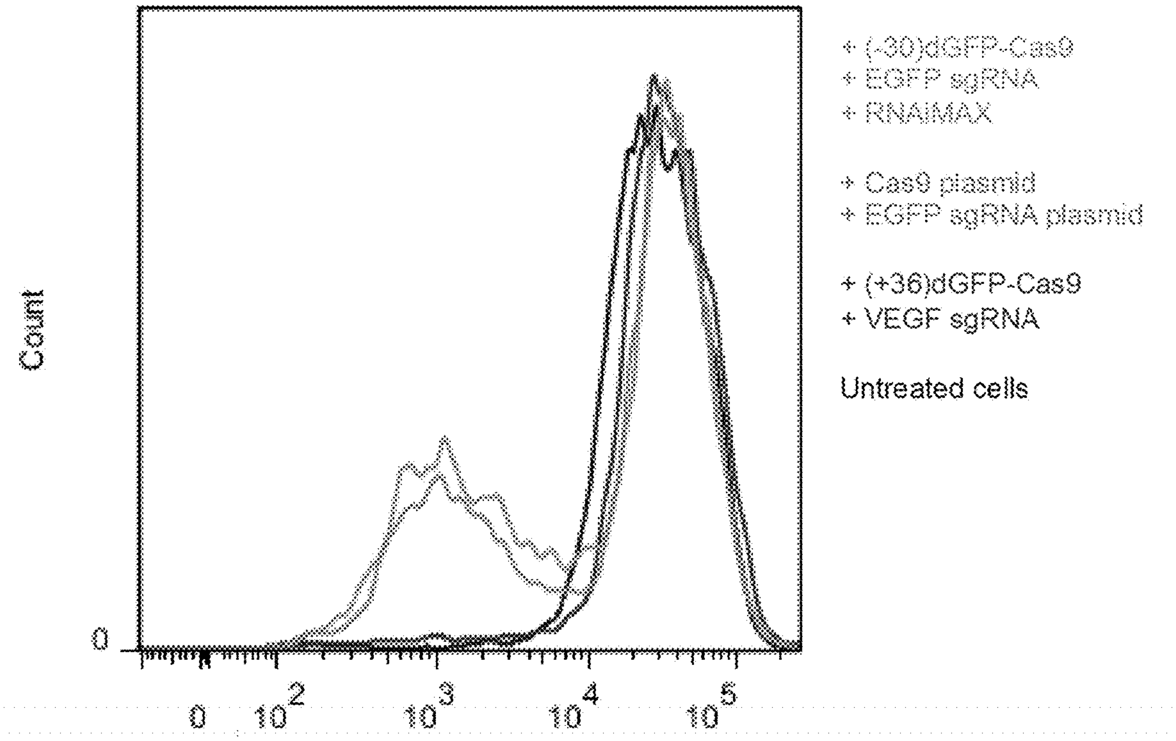
Figure 36C:
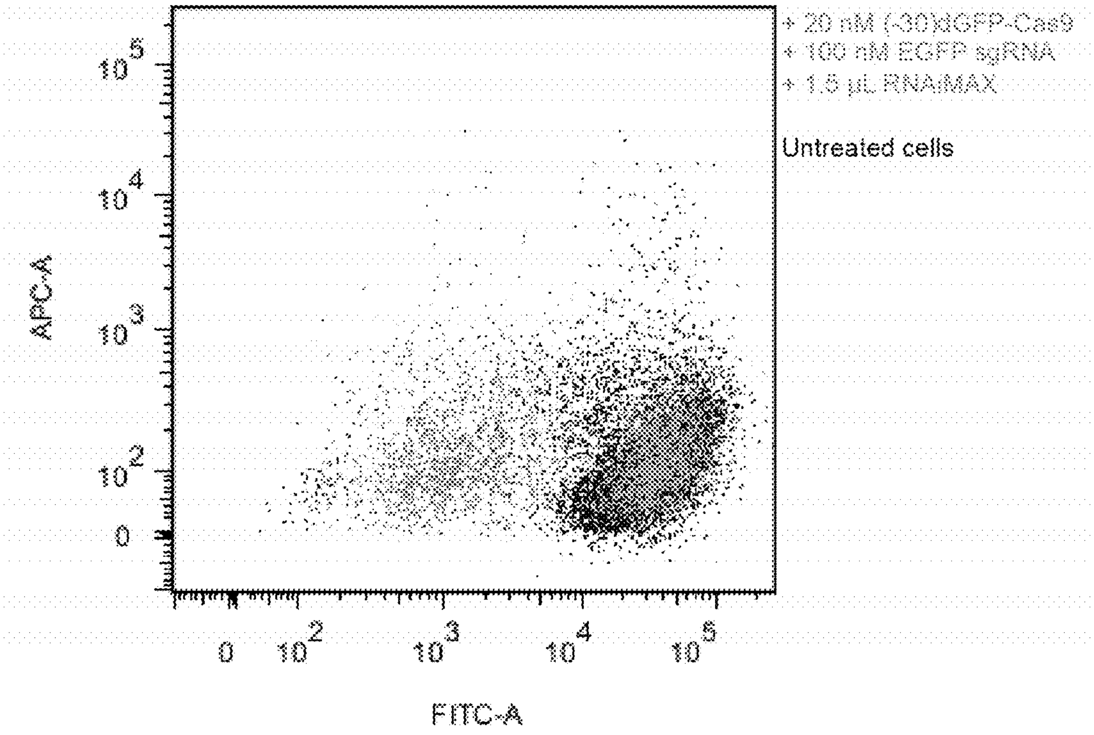
Figure 36D:
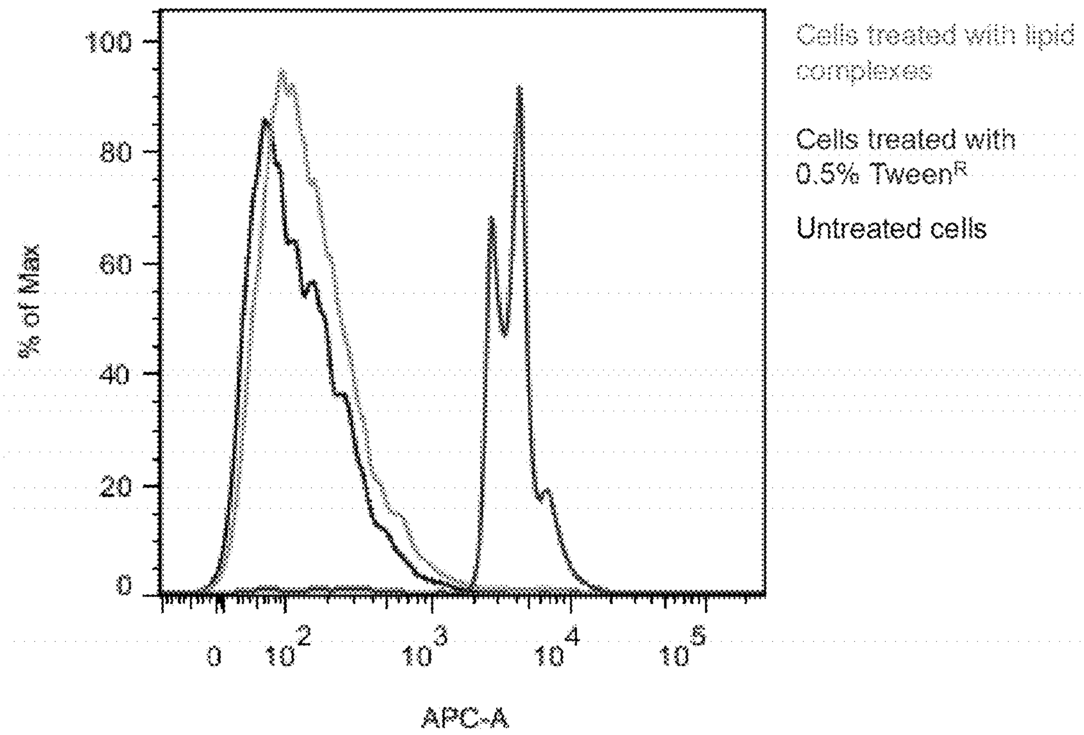

Treatment of U2OS reporter cells with 25 nM (−30)dGFP-NLS-Cas9 and 50 nM EGFP-targeting sgRNA with RNAiMAX in media containing 10% FBS showed loss of EGFP expression in 48% of cells (FIG. 30(A)). Cotransfection of plasmids expressing Cas9 or sgRNA resulted in similar EGFP loss in 37% of cells (FIG. 30(A)). No significant EGFP disruption was observed upon transfection of plasmids encoding EGFP sgRNA alone, Cas9 alone, or cotransfection of plasmids encoding Cas9 and an sgRNA designed to target a VEGF locus (FIG. 30(A), FIG. 36(B)). It was confirmed that the robust disruption of EGFP was not a result of cellular toxicity (FIGS. 36(C)-(D)). It was also observed that treatment of cells with (+36)dGFP-NLS-Cas9 and sgRNA in the presence of 10% FBS serum did not lead to efficient gene disruption (FIG. 30(A)), suggesting that cationic-peptide based methods of delivery for Cas9 and sgRNA are not effective perhaps due to interference of gRNA:Cas9 complex formation or nuclease function by superpositively charged proteins.[41] Together, these results establish that cationic lipid-mediated delivery of (−30)dGFP-NLS-Cas9:sgRNA complexes can result in efficient sgRNA-dependent target gene disruption in human cells. Cas9 and sgRNA in the presence of 10% FBS did not lead to efficient gene disruption (FIG. 30(A)), suggesting that cationic-protein based methods of delivery for Cas9 and sgRNA may not be effective, perhaps due to interference of Cas9:sgRNA complex formation or nuclease function by cationic proteins,[41] consistent with a recent study describing the delivery of Cas9 protein with an oligoarginine peptide tag which achieved only moderate levels of gene disruption.[58] Optimization of plasmid transfection conditions did not yield higher than 40% EGFP disruption (FIG. 30(A) and FIG. 31(A)), and the transfection conditions required to achieve this level of gene disruption resulted in high levels of cellular toxicity (FIG. 31(B)). Together, these results establish that cationic lipid-mediated delivery of (−30)dGFP-NLS-Cas9:sgRNA complexes can result in efficient sgRNA-dependent target gene disruption in human cells with minimal toxicity, unlike cationic peptide-based protein delivery or plasmid DNA transfection methods.

Polyanionic sgRNA is Necessary and Sufficient for Efficient Lipid-Mediated Cas9 Delivery Since the complex of native Cas9 protein (+22 net theoretical charge) and an sgRNA (~103 anionic phosphate groups) should be overall highly anionic, next it was tested if native Cas9:sgRNA complexes without fusion to polyanionic proteins can be delivered into human cells using cationic lipids. Treatment of U2OS EGFP reporter cells with 100 nM Cas9, 100 nM EGFP sgRNA, and 0.8 μL RNAiMAX resulted in 65% disruption of the EGFP reporter gene (FIG. 30(A)). Treatment of cells with Cas9 protein and sgRNA, but without RNAiMAX, resulted in no loss of GFP fluorescence (FIG. 30(A)). These observations suggest that sgRNA alone, even in the absence of a supernegatively charged fusion protein, can provide the highly anionic character needed to mediate cationic lipid-based delivery of Cas9.

Figure 39A:
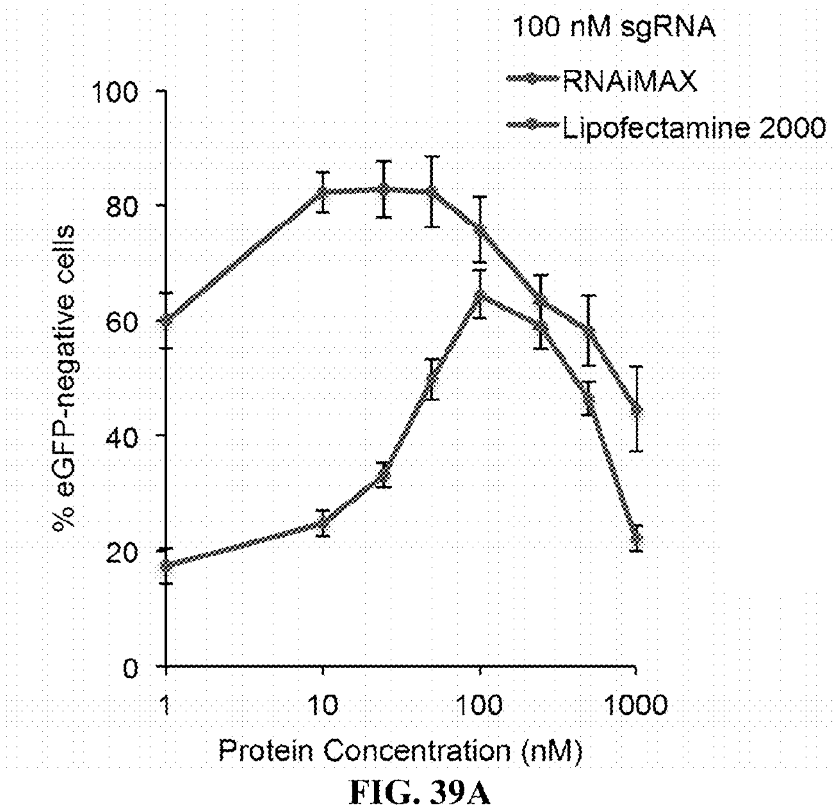
FIGS. 39A-D. Effects of RNAiMAX and Lipofectamine 2000 on Cas9:sgRNA delivery efficiency and cellular toxicity.
Figure 39B:
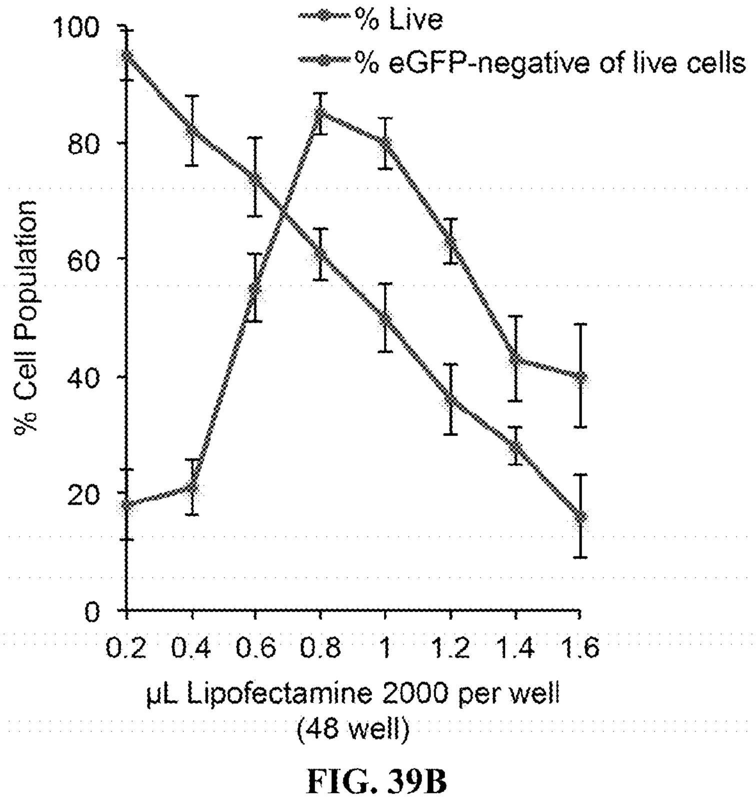
Figure 39C:
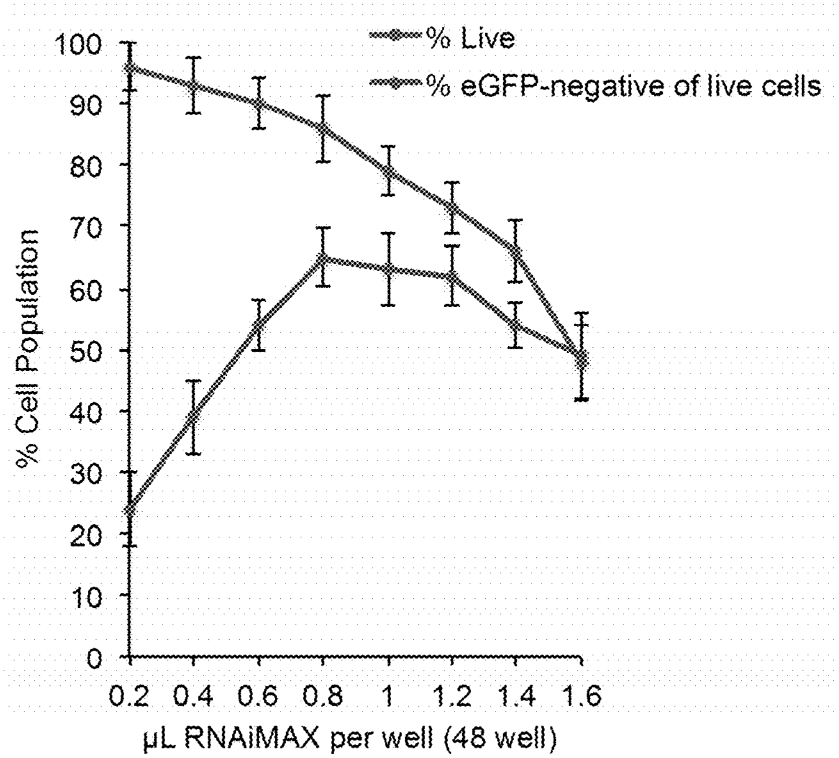
Figure 39D:
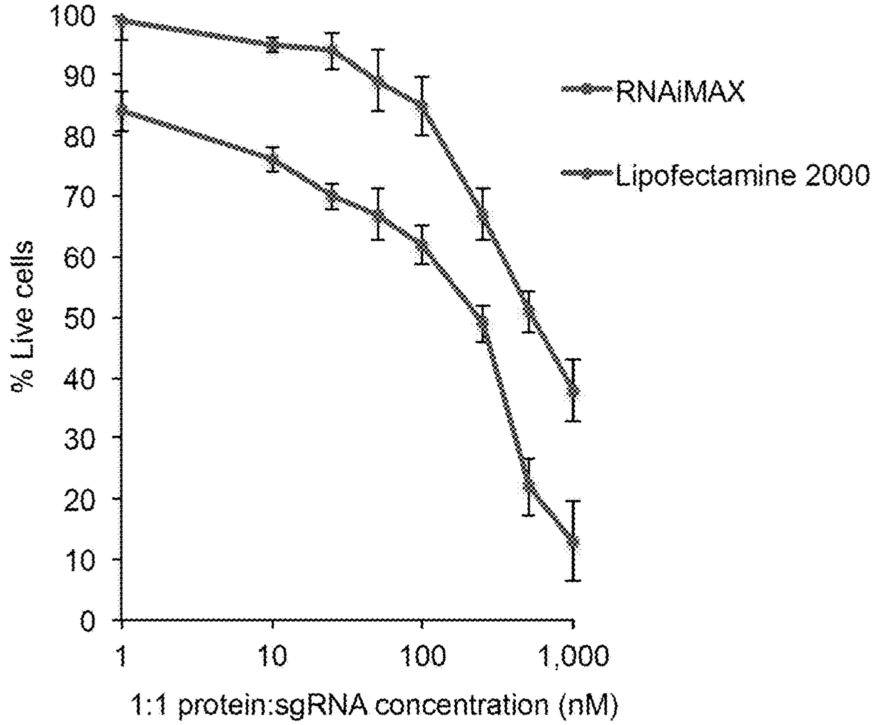

Treatment of U2OS EGFP reporter cells with 100 nM Cas9, 50 nM EGFP sgRNA, and 0.8 μL RNAiMAX resulted in 65% disruption of the EGFP reporter gene (FIG. 30(A)). These observations suggest that sgRNA alone, even in the absence of a supernegatively charged fusion protein, can provide the highly anionic character needed to mediate cationic lipid-based delivery of Cas9. We evaluated several different Cas9 constructs over a broad range of conditions (FIGS. 37(A-D), FIGS. 38(D-F) and results herein) and lipid formulations (FIG. 39(A) and results herein) for their effect on EGFP disruption and observed that up to 80% targeted gene disruption resulted from Cas9:sgRNA complexed with Lipofectamine 2000 (FIG. 30(A)). Due to the modestly higher toxicity of Lipofectamine 2000 compared to RNAiMAX across a range of doses (FIGS. 39(B-D) and results herein), we continued using RNAiMAX for cell culture studies unless otherwise noted.

Figure 37A:
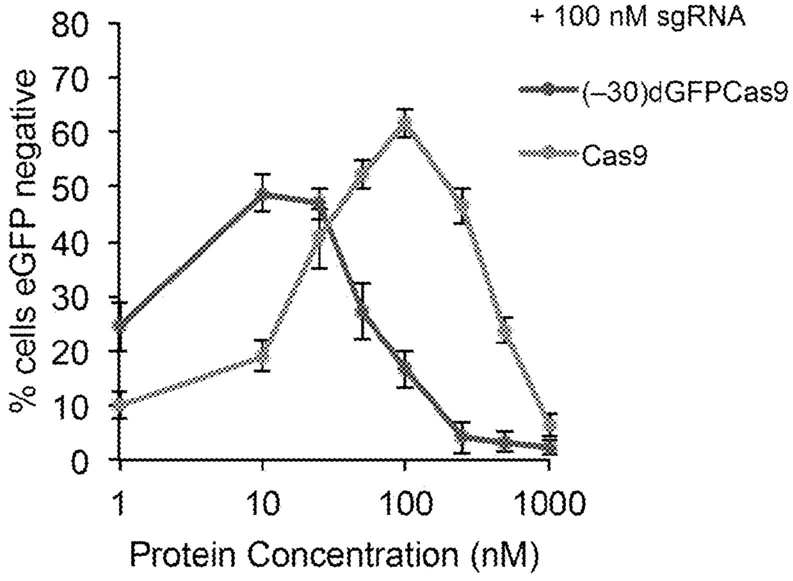
FIGS. 37A-D. Optimization of Cas9:sgRNA functional delivery.
Figure 37B:
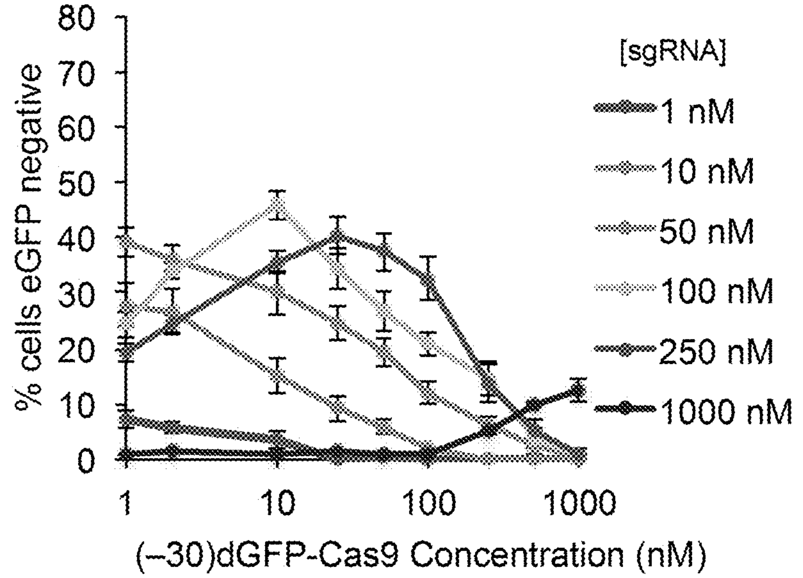
Figure 37C:
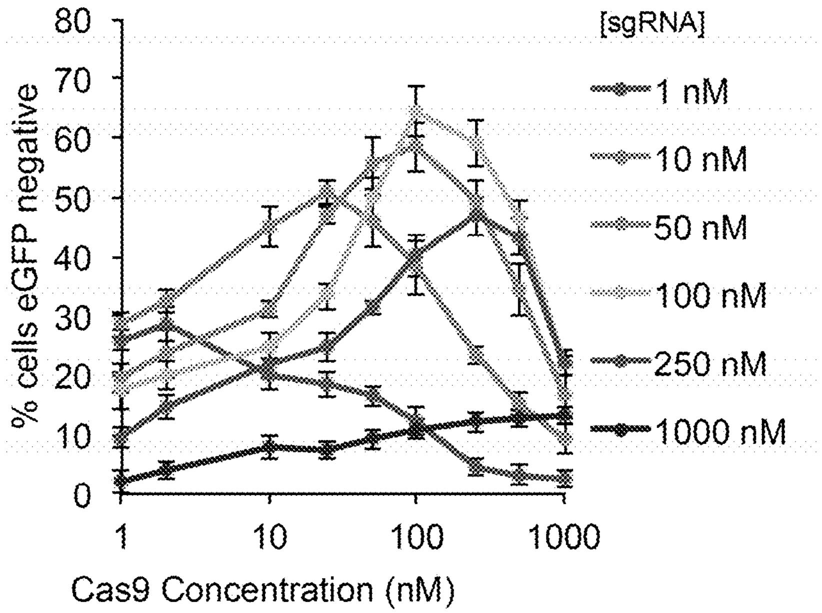

Comparison of gene disruption efficiency arising from the cationic lipid-mediated delivery of (−30)dGFP-NLS-Cas9:sgRNA versus Cas9:sgRNA revealed that at low doses (−30)dGFP-NLS-Cas9 results in more efficient gene disruption than native Cas9 (FIG. 37(A)), it is outperformed by native Cas9 at higher concentrations, as well as at the respective optimal protein:sgRNA dose of either protein (FIGS. 37(B)-37(C)). These results further establish that sgRNA can supply sufficient negative charge to support cationic lipid-based delivery of complexed Cas9 protein.

Figure 37D:
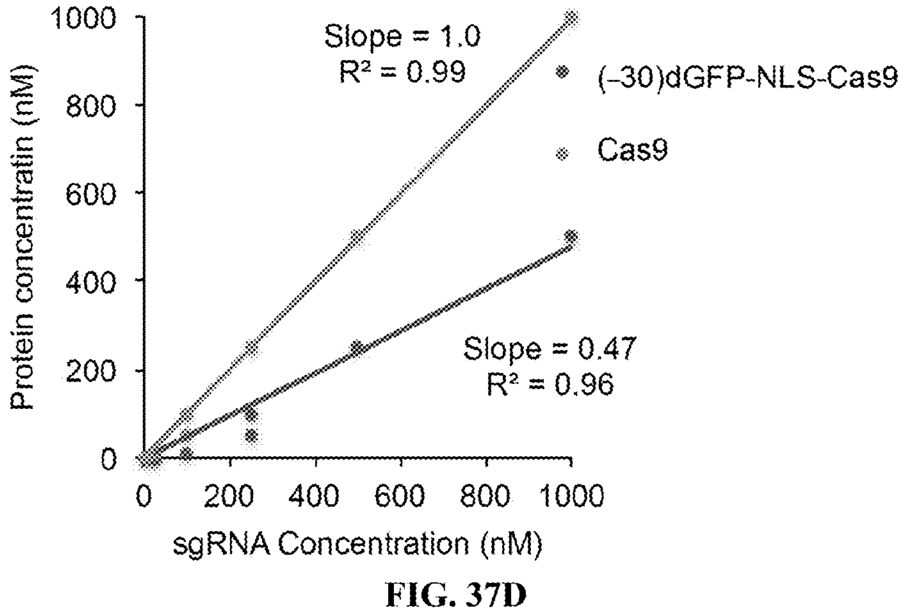
Figure 38A:
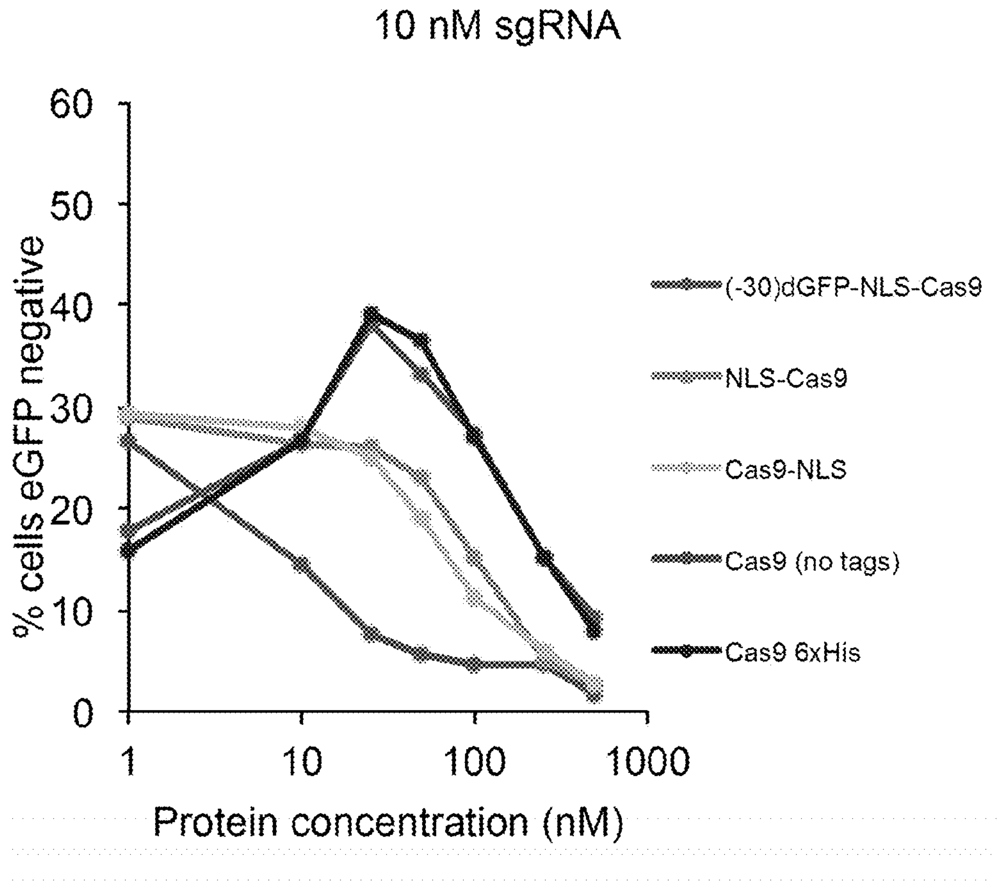
FIGS. 38A-F. Effect of an N- or C-terminal NLS, an N-terminal (−30)dGFP fusion, or a C-terminal His-tag on functional Cas9 delivery as a function of both sgRNA and Cas9 concentration. EGFP gene disruption was measured at three fixed sgRNA concentrations: 10 nM (FIG. 38(A)), 25 nM (FIG. 38(B)), and 50 nM (FIG. 38(C)), along with varying protein concentrations show in the graphs. EGFP gene disruption in U2OS EGFP reporter cell line was measured at three additional fixed sgRNA concentrations.
Figure 38B:
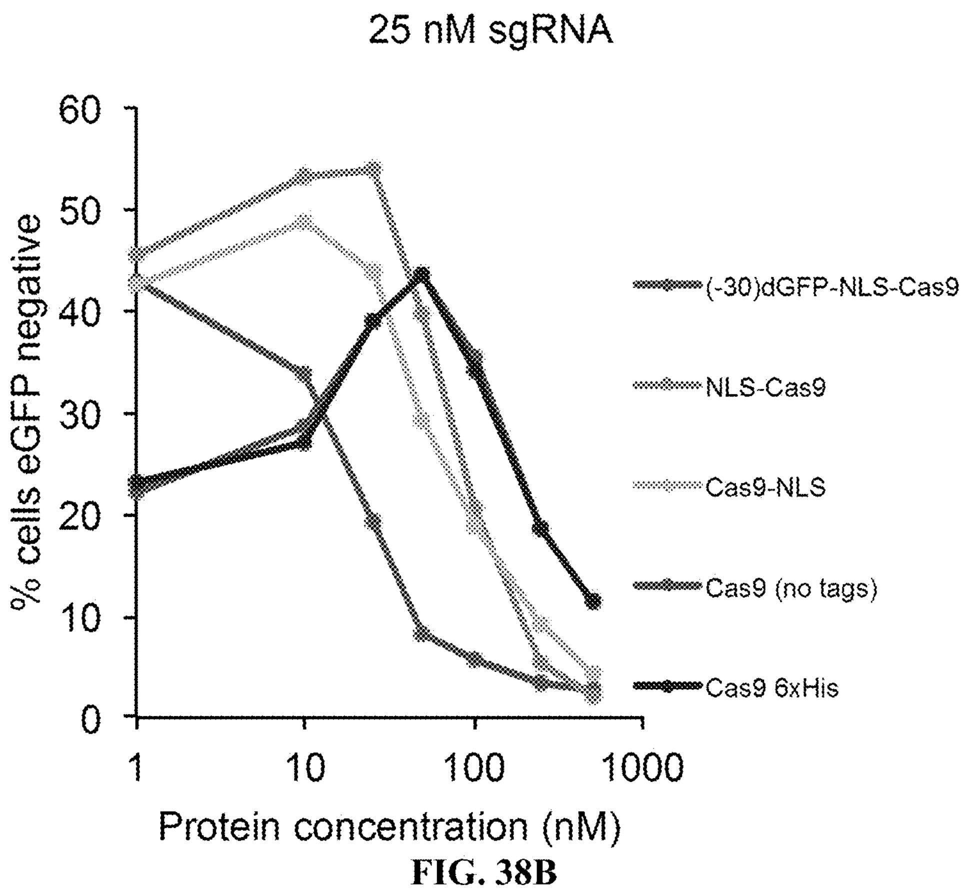
Figure 38C:
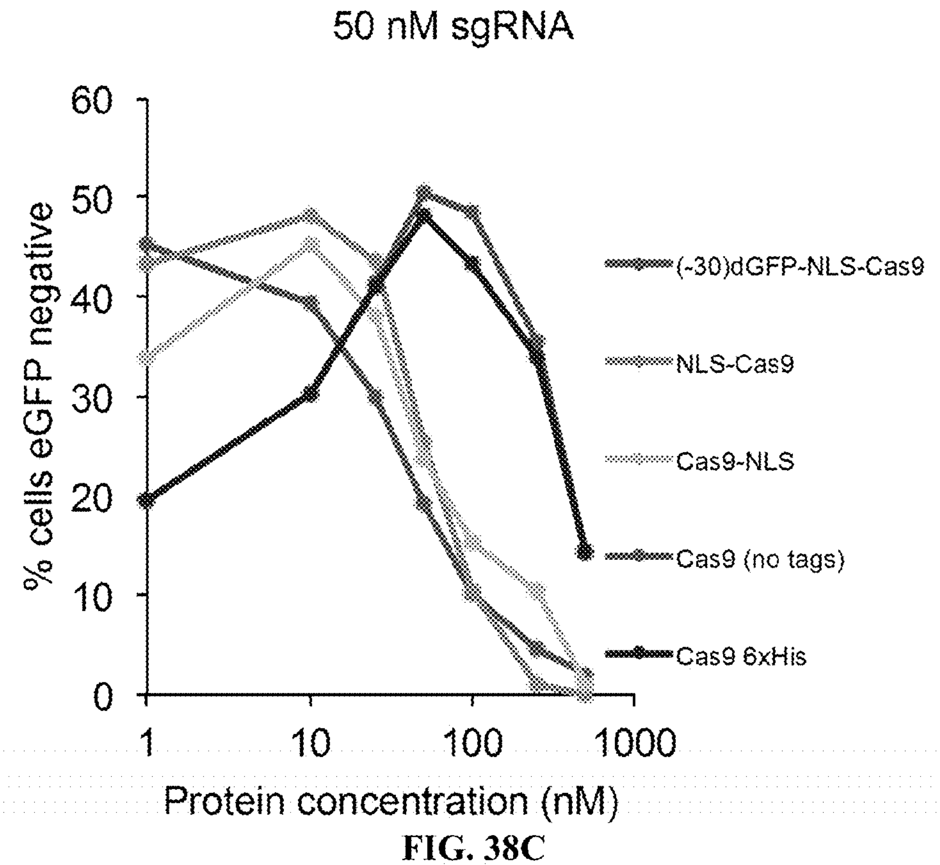
Figure 38D:
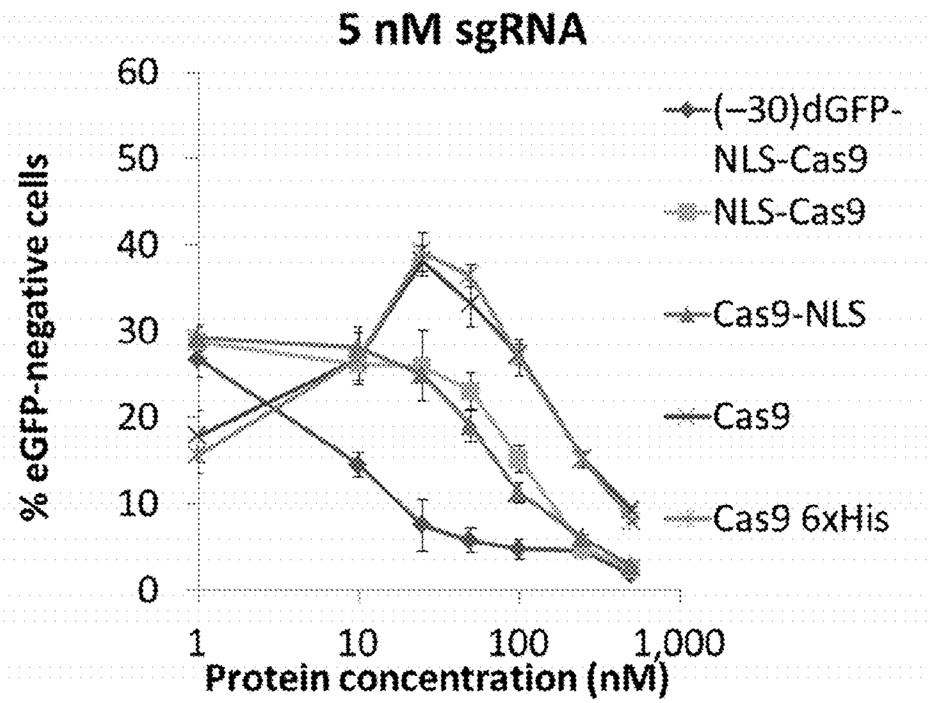
Figure 38E:
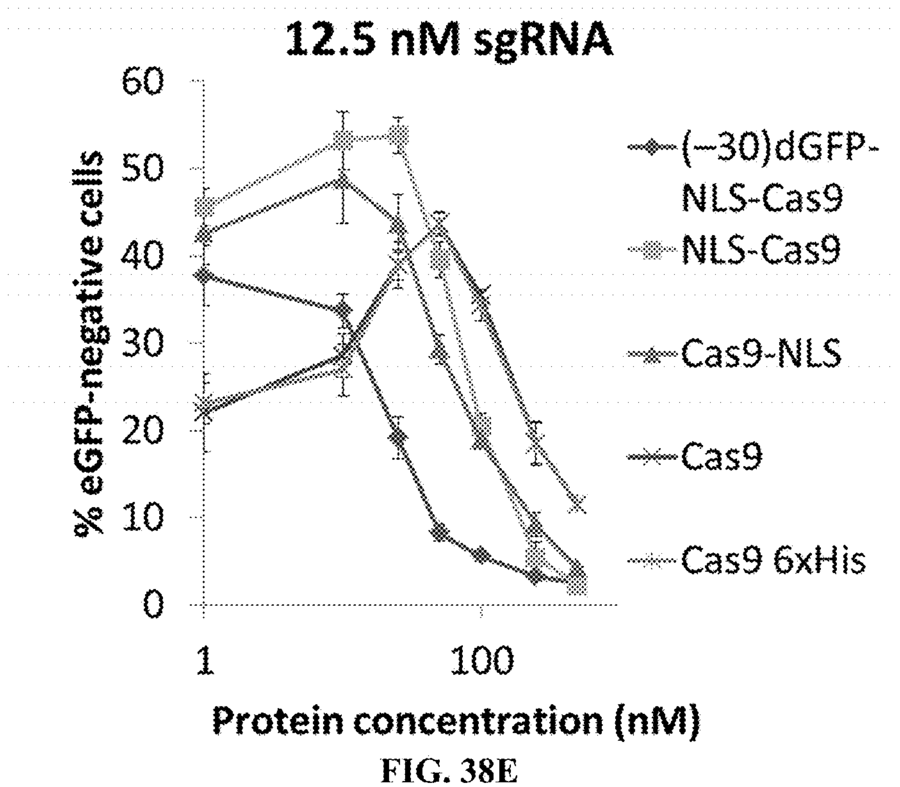
Figure 38F:
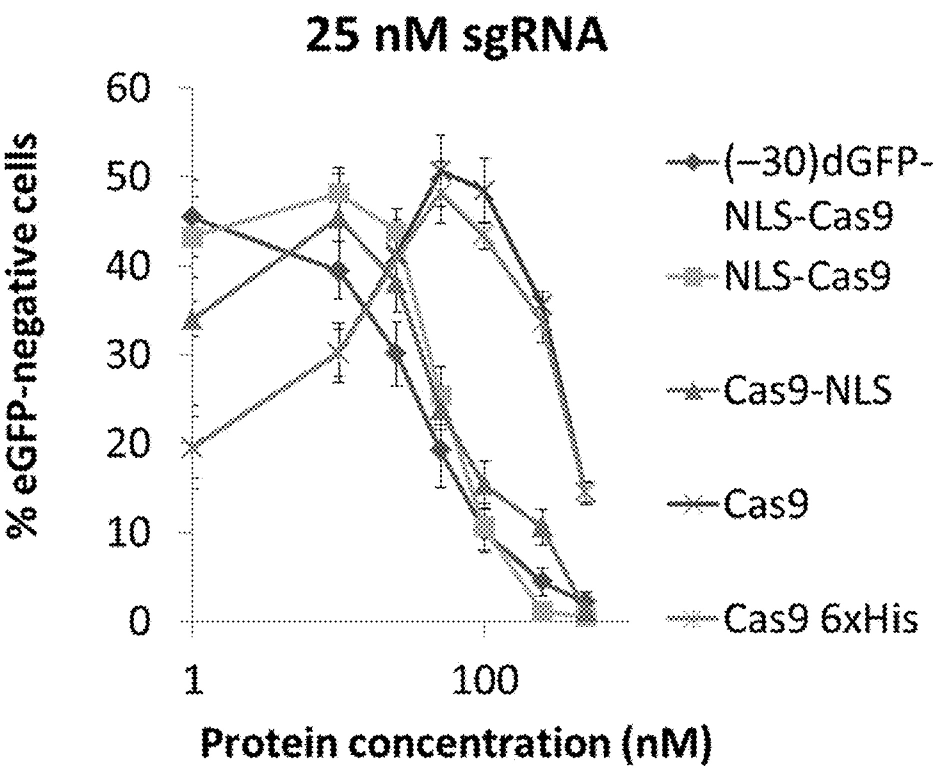

It was also observed that while overall less protein was required for optimal delivery of (−30)dGFP-NLS-Cas9 than Cas9, a higher sgRNA:protein ratio was required for maximal (−30)dGFP-NLS-Cas9-mediated EGFP gene disruption than for native Cas9-mediated gene disruption (FIG. 37(D)). It was speculated that more equivalents of sgRNA are needed to complex with (−30)dGFP-NLS-Cas9 since fused (−30)dGFP may electrostatically interfere with Cas9:sgRNA complexation. As the ideal protein dose for (−30)dGFP-NLS-Cas9 mediated EGFP gene disruption is 10-fold lower than that of wild-type Cas9, the results also suggest that (−30)dGFP-Cas9 is better encapsulated by cationic liposomes than Cas9:sgRNA due to its higher overall negative charge, but this charge magnitude may interfere with Cas9: sgRNA interactions, necessitating more sgRNA per protein and potentially reducing total delivered Cas9 activity. In addition, NLS-Cas9 and Cas9-NLS proteins were generated and tested, and it was observed that while the presence of an NLS in (−30)dGFP-NLS-Cas9 could at least partially explain differences in delivery efficacy at very low concentrations, Cas9, NLS-Cas9, and Cas9-NLS all result in higher efficiency of EGFP disruption than (−30)dGFP-NLS-Cas9 at 25 nM or higher concentrations (FIGS. 38(A)-(C)) the reduction in activity due to the presence of the large anionic fusion partner to Cas9 compromises its overall performance.

Cas9:sgRNA delivery with cationic lipid formulations other than RNAiMAX was also tested. Delivery with Lipofectamine 2000 was notably more efficient than with RNAiMAX, resulting in up to 80% Cas9-mediated gene disruption (FIG. 39(A)), and maintaining high efficiency (60% gene disruption) even at 1 nM protein (FIG. 39(A)). However, due to the somewhat higher toxicity of Lipofectamine 2000 compared to RNAiMAX under cell culture conditions (FIGS. 33(B)-C)), RNAiMAX was used for all subsequent cell culture studies.

Figure 30B:
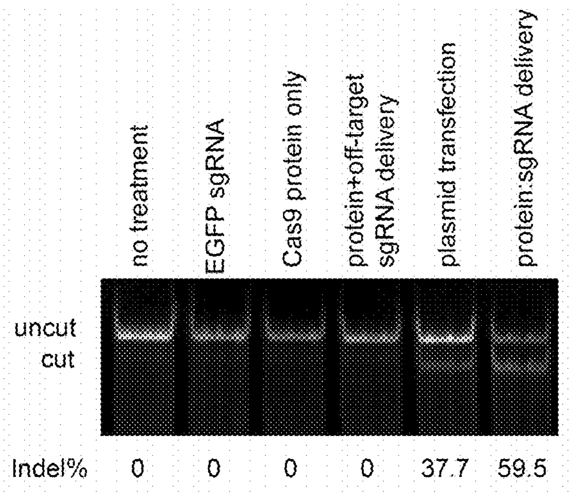

To verify that EGFP disruption arose from genome modification and not only from Cas9 binding,[42] the T7 endonuclease I (T7EI) assay[43] was used to detect and quantify the frequency of Cas9-mediated genomic insertion/deletion mutations (indels) at the target EGFP locus (FIG. 30(B)). The T7EI assay results showed that only those cells treated with both Cas9 and EGFP sgRNA plasmids, or Cas9 protein and purified EGFP sgRNA, contained indels at the target site 48 hours after treatment. Taken together, these findings establish that active Cas9:sgRNA complexes can be potently delivered into human cells with cationic lipids in a manner dependent on the negative charge provided by the sgRNA.

Figure 30C:
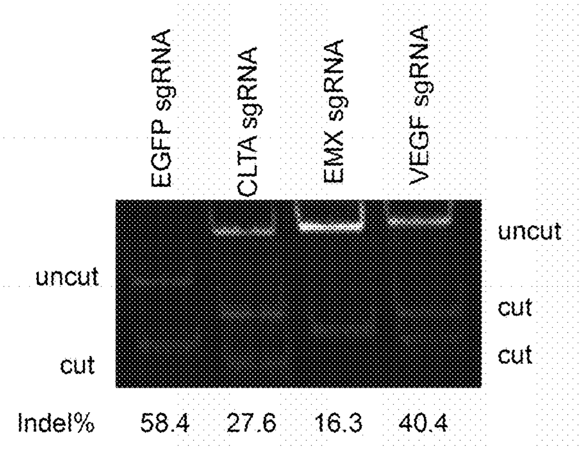

U2OS EGFP reporter cells were also treated with a single lipid-mediated delivery treatment of Cas9 complexed with a mixture of four gRNAs targeting EGFP, CLTA, EMX, and VEGF. This treatment resulted in efficient disruption of all four targets, with cleavage efficiencies of 58%, 28%, 16%, and 40%, respectively, as measured by T7E1 cleavage assay. These high gene disruption efficiencies from a single delivery of 50 nM Cas9 and 25 nM of each sgRNA (100 nM total sgRNA) demonstrate that lipid-mediated Cas9:sgRNA delivery can support efficient multiplexed genome editing (FIG. 30(C)).

Figure 44A:
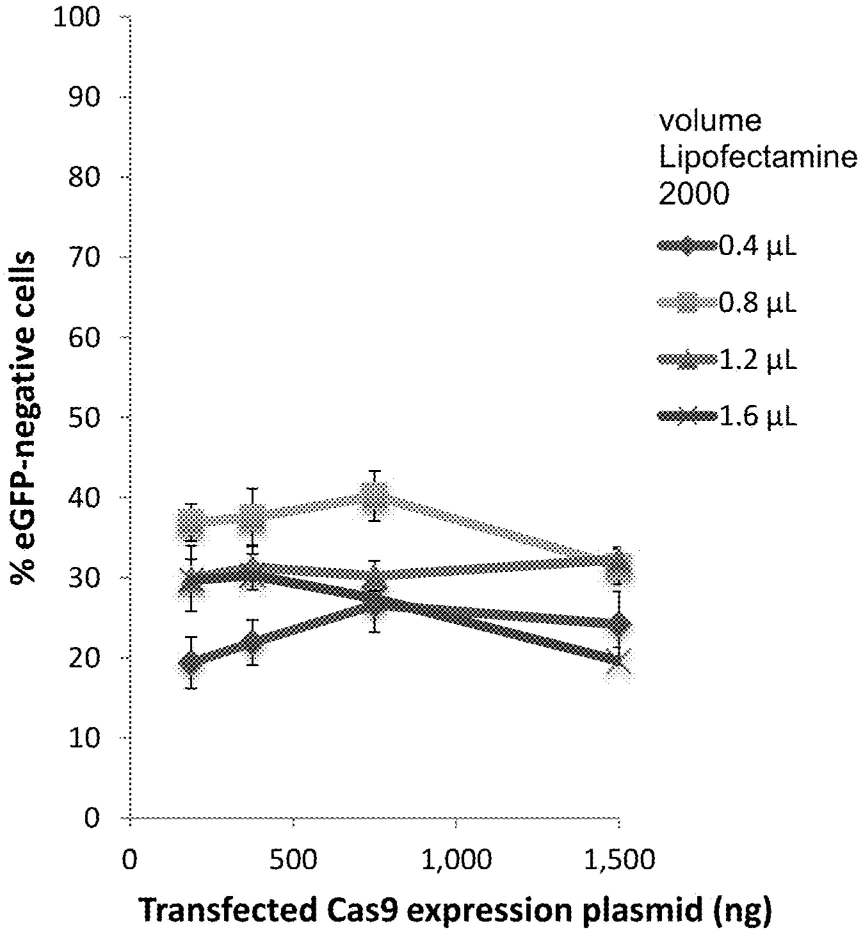
FIGS. 44A-B. Optimization of Cas9 plasmid transfection conditions and measurement of cellular toxicity at different doses of Lipofectamine 2000 is depicted.
Figure 44B:
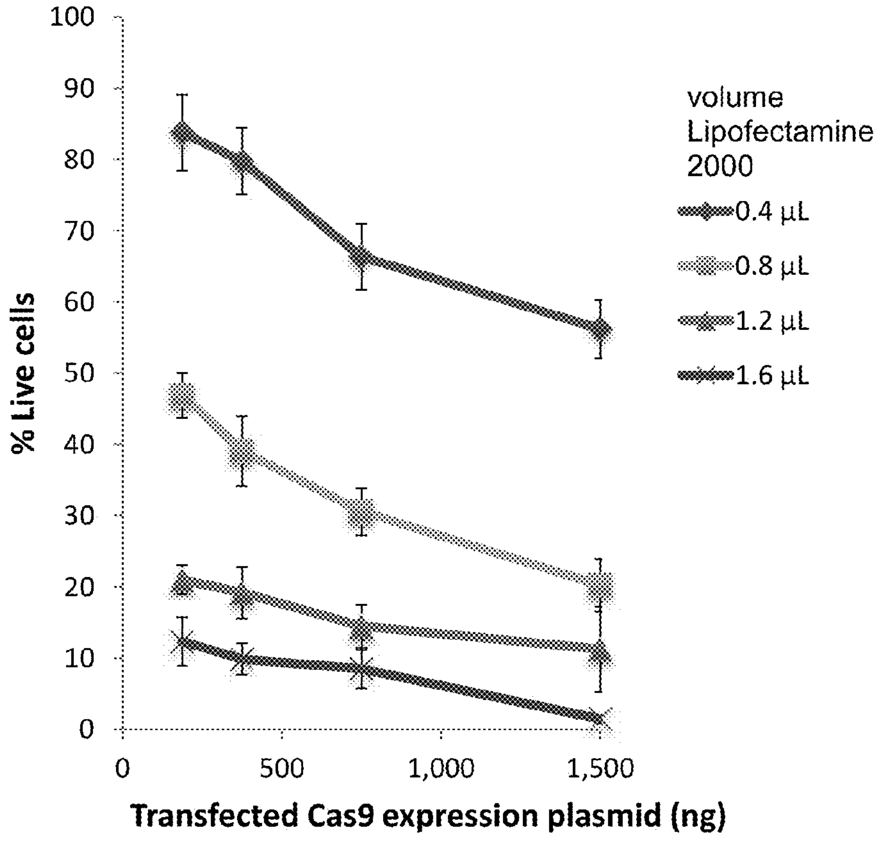
Figure 45A:
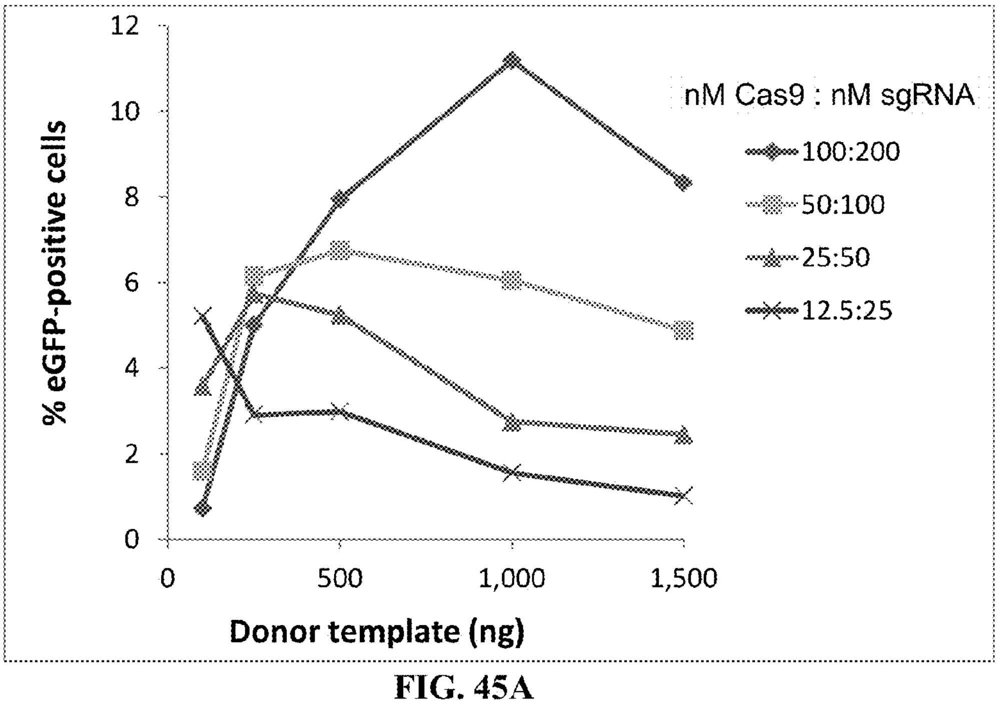
FIGS. 45A-C. Optimization and comparison of homology-directed repair (HDR) efficiency for Cas9:sgRNA delivery by cationic lipids and plasmid transfection is shown.
Figure 45B:
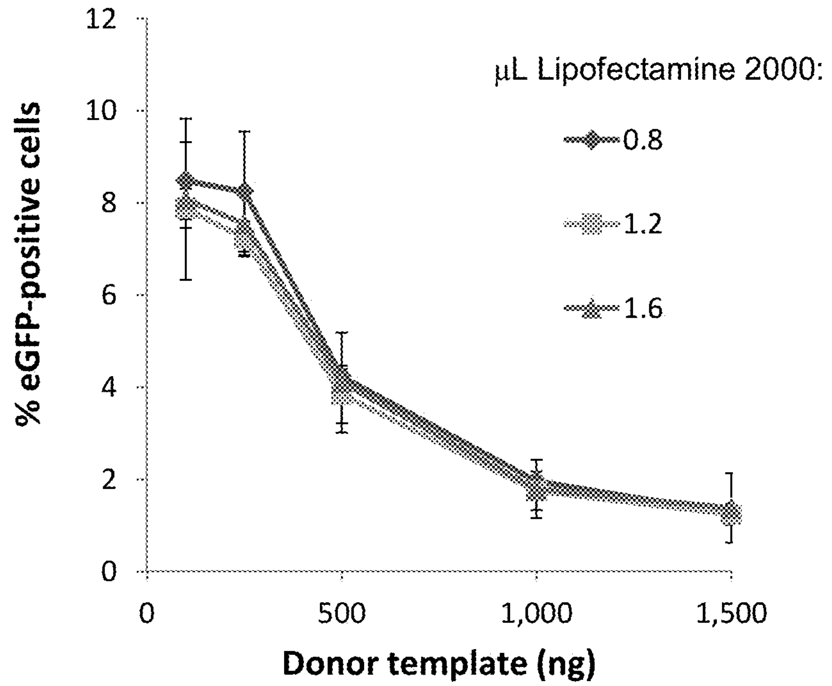
Figure 45C:
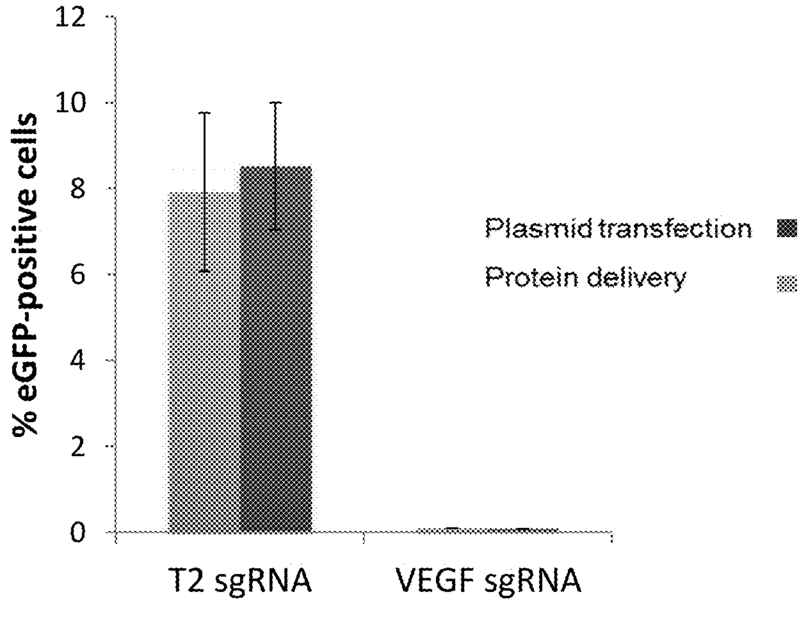
Figure 46A:
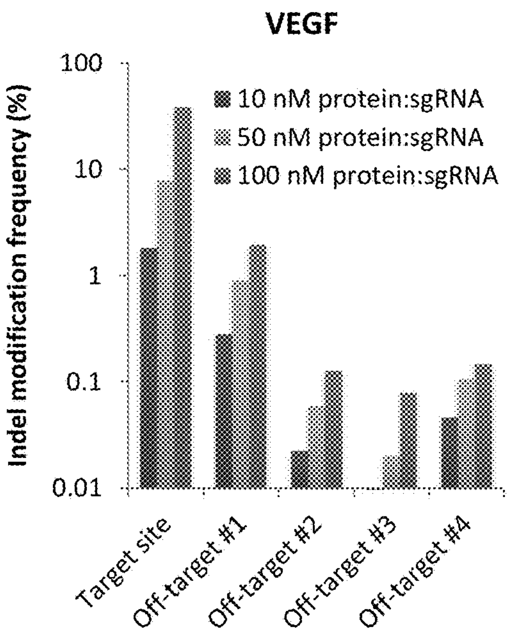
FIGS. 46A-F. Concentration dependence of on-target and off-target indel modification frequencies for Cas9 plasmid transfection or lipid-mediated protein:sgRNA delivery is shown.
Figure 46B:
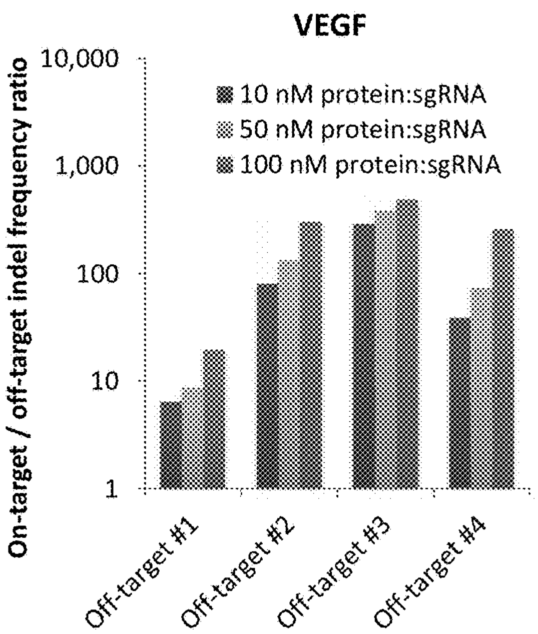
Figure 46C:
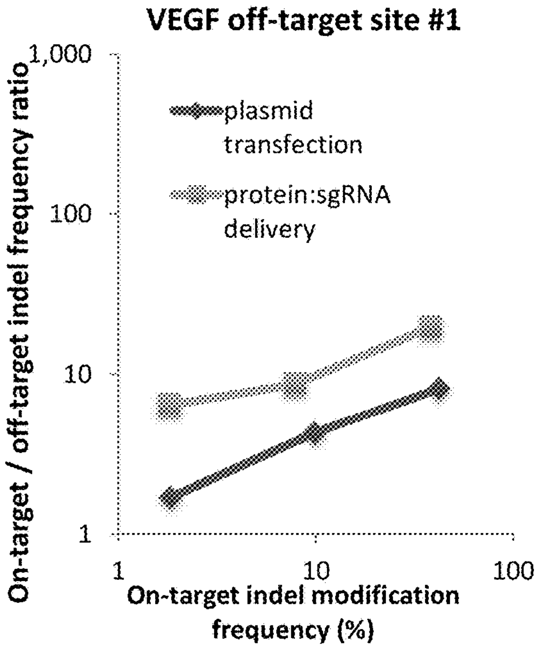
Figure 46D:
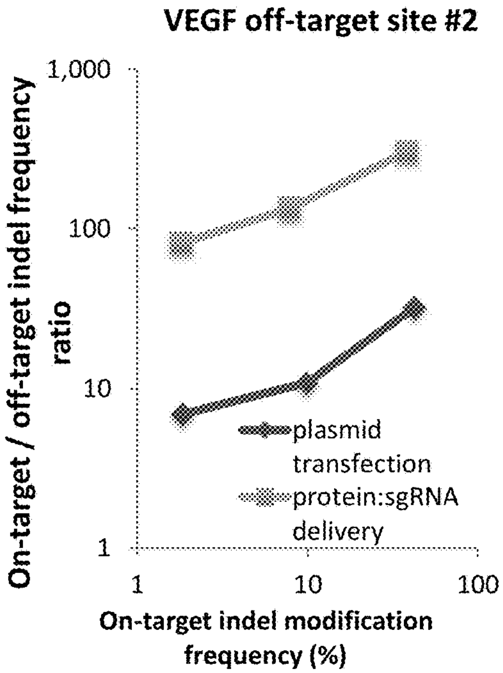
Figure 46E:
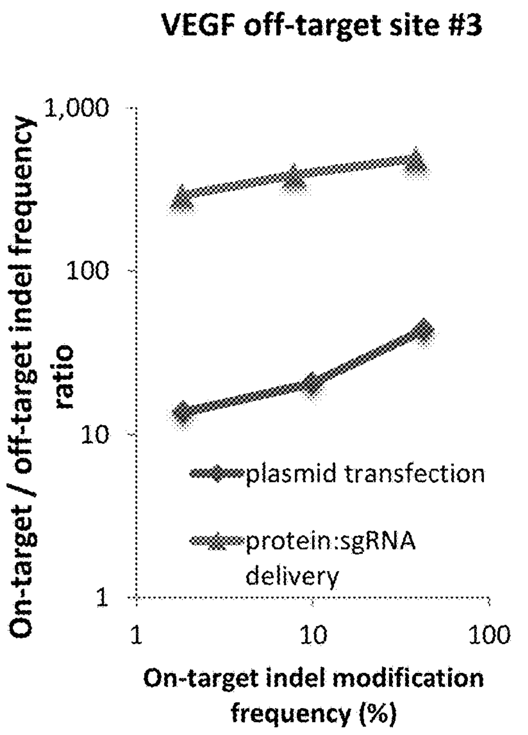
Figure 46F:
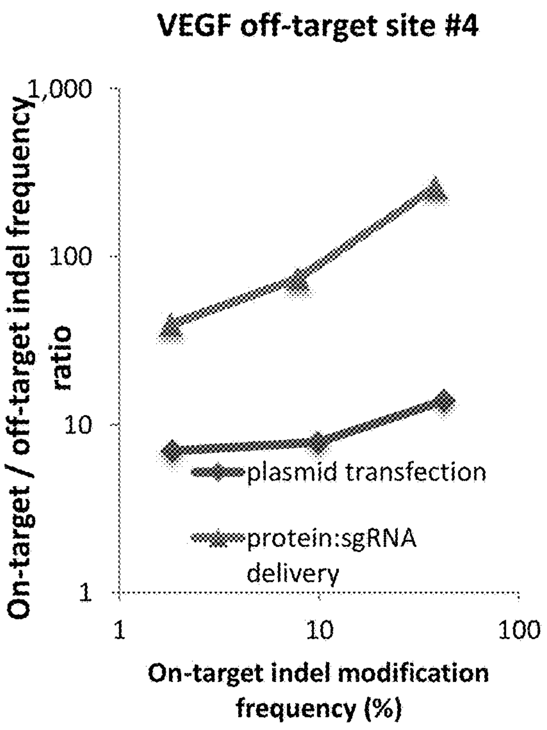

We also tested whether delivered Cas9 nuclease:sgRNA complexes are capable of effecting homology-directed repair (HDR) using an EGFP-repair reporter cell line.[57] We combined Cas9 and EGFP-targeting sgRNA, mixed the resulting protein:RNA complexes with varying concentrations of single-stranded DNA oligonucleotide (ssODN) donor template, and delivered the Cas9:sgRNA+ssODN mixture using Lipofectamine 2000 (FIG. 44(A)). Cas9: sgRNA delivery achieved EGFP HDR frequencies of −8-11%, similar to that of optimized plasmid transfection-based HDR (FIGS. 44(B-C)), and consistent with previous reports using the same reporter cell line, suggesting that cationic lipid-based delivery of Cas9:sgRNA is a viable approach to efficient HDR.

Figure 30D:
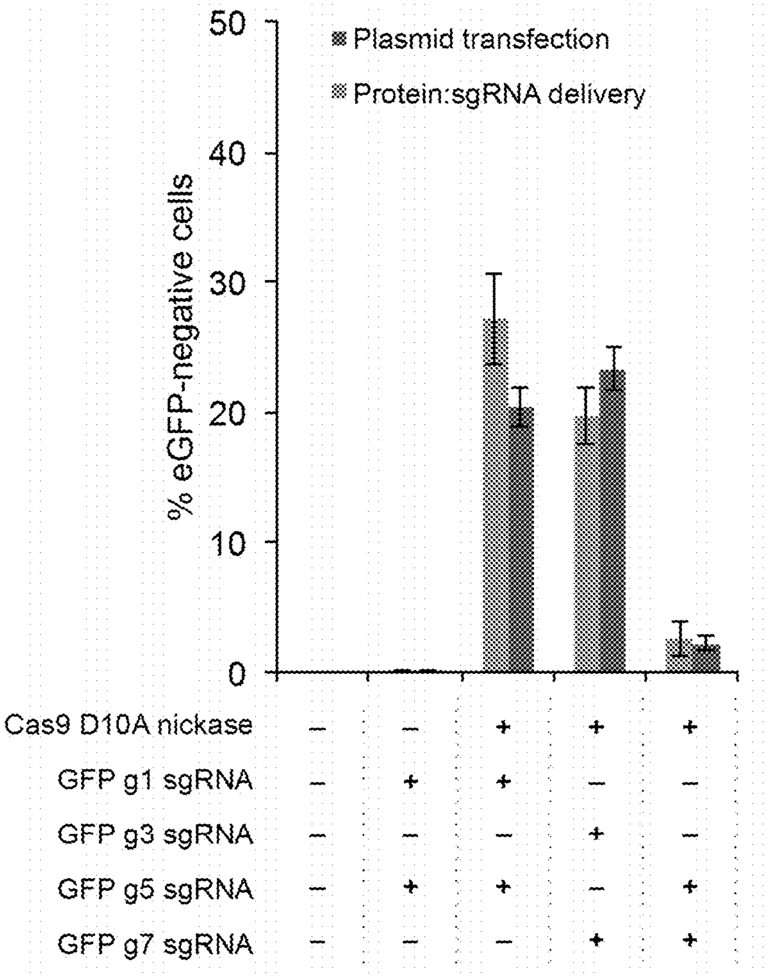
Figure 30E:
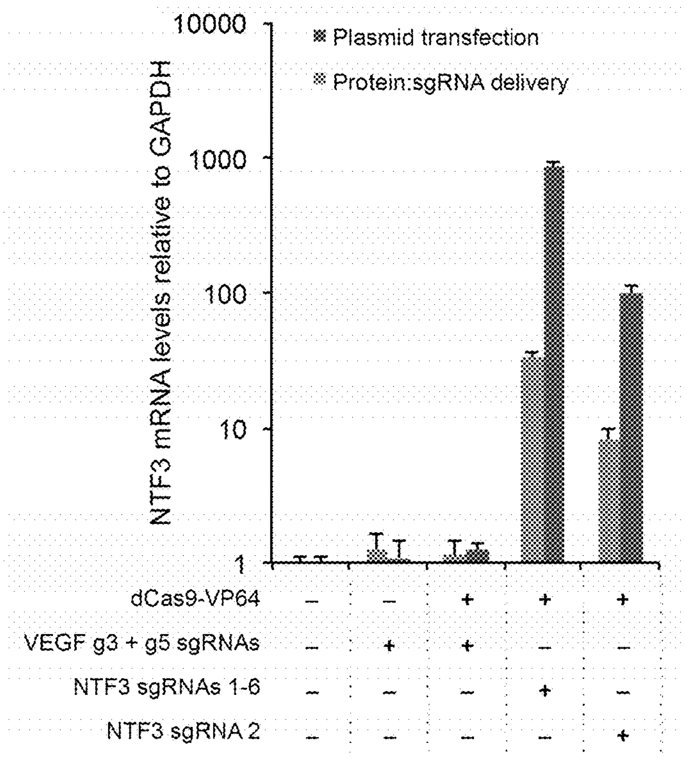
Figure 40A:
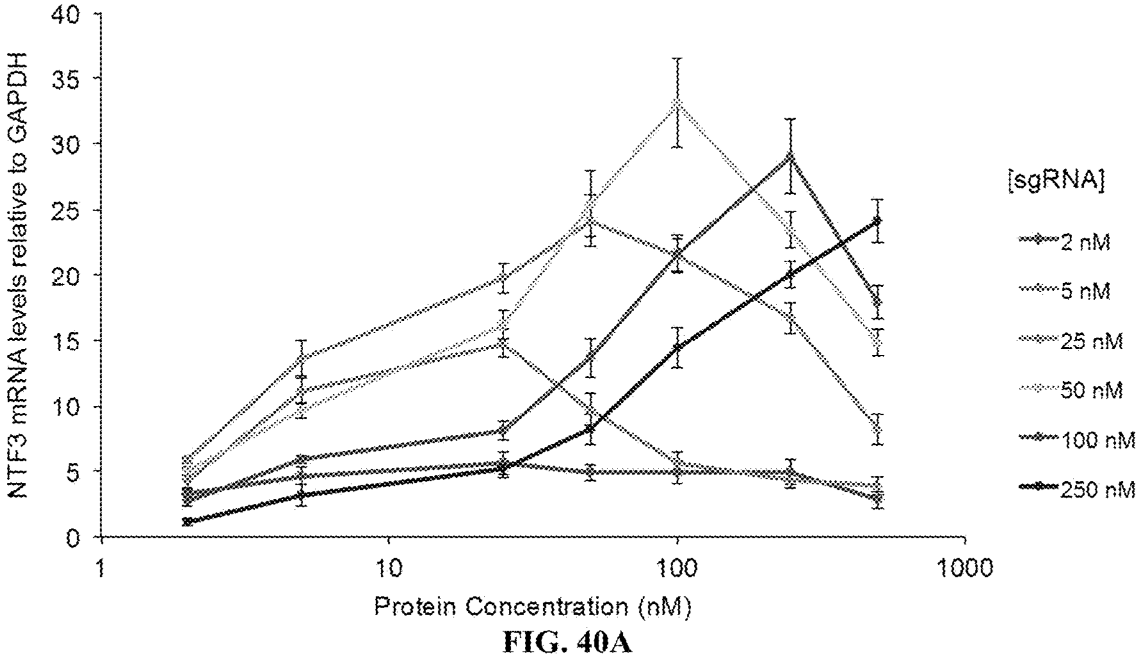
FIGS. 40A-B. Optimization of dCas9-VP64 delivery targeting the NTF3 gene at varying concentrations of protein and sgRNA.

Next we determined whether cationic lipid-based protein delivery could be applied to deliver other Cas9-derived genome engineering tools such as Cas9 nickases[44] and Cas9-based transcriptional activators.[45] We measured gene disruption efficiency in U2OS EGFP reporter cells resulting from delivery of Cas9 D10A nickase (FIG. 30(D) and results herein) and achieved results similar to previous reports using plasmid transfection.[46] Delivery of dCas9-VP64 activators either by plasmid transfection or RNAiMAX-mediated protein delivery resulted in strong (≥~10-fold) activation of NTF3 transcription (FIG. 30(E) and FIG. 40(A)). As observed above with TALE activators (FIG. 29(C)), dCas9-VP64 protein delivery resulted in fast-acting and transient transcriptional activation compared to DNA delivery (FIG. 40(B) and results herein). These results collectively indicate that both Cas9 nickases and Cas9 transcriptional activators can also be delivered effectively by cationic lipid-mediated protein: sgRNA complex delivery.

Functional Delivery of Cas9 Nickases and dCas9 Activators

Next, whether cationic lipid-based protein delivery could be extended to deliver other Cas9-derived genome engineering tools such as Cas9 nickases[44] and Cas9-based transcriptional activators was tested.[45] Gene disruption efficiency in U2OS EGFP reporter cells resulting from delivery of Cas9 D10A nickase was measured, either by cotransfection of nickase and appropriate paired EGFP-targeting sgRNA plasmids, or as purified protein complexed with pairs of EGFP sgRNAs using RNAiMAX (FIG. 30(D)). Both plasmid and cationic lipid-mediated protein:RNA delivery of dual Cas9 nickases resulted in EGFP disruption with similar efficiencies (FIG. 30(D)) only in the presence of sgRNA pairs targeting opposite strands, (sgRNA pairs g1+g5, and g3+g7), but not with sgRNA pairs targeting the same strand (sgRNA pair g5+g7) (FIG. 30(D)), consistent with previous reports of Cas9 nickase cleavage requirements.[46]

The NTF3 transcriptional activation efficiencies in HEK293T cells resulting from either plasmid transfection or direct protein:sgRNA complex delivery of dCas9 fused to a VP64 activation domain were also compared.[45] Delivery of dCas9-VP64 activators either by plasmid transfection or RNAiMAX-mediated protein delivery resulted in strong (≥~10-fold) activation of NTF3 transcription (FIG. 30(E) and FIG. 40). Transcriptional activation levels resulting from plasmid transfection were more potent than activation resulting from protein delivery at optimal assay times for each delivery method (FIG. 30(E)), potentially due to the sustained expression both Cas9 activator protein and sgRNA from the plasmids compared to the transient, single dose of purified protein and RNA. While the above results indicate that such factors do not limit the potency of irreversible genome modification by delivered Cas9 nuclease and nickase proteins (FIGS. 40(A) and 40(D)), the low dose and transient nature of the delivered protein may more strongly limit potency of dynamic processes such as transcriptional activation. Nevertheless, these results collectively indicate that both Cas9 nickases and Cas9 transcriptional activators can also be delivered effectively by cationic lipid-mediated protein: sgRNA complex delivery.

Comparison of Lipofectamine 2000 and RNAiMAX for Cas9 Delivery Efficiency and Toxicity We tested Cas9:sgRNA delivery with cationic lipid formulations other than RNAiMAX. EGFP disruption with Lipofectamine 2000 was notably more efficient than with RNAiMAX, resulting in up to 80% Cas9-mediated gene disruption (FIG. 39(A)), and maintaining high efficiency (60% gene disruption) even at 1 nM protein (FIG. 39(A)). However, due to the somewhat higher toxicity of Lipofectamine 2000 (FIG. 39(B)) for protein:sgRNA delivery compared to that of RNAiMAX (FIG. 39(C)) under cell culture conditions, we continued to use RNAiMAX for subsequent cell culture studies. We also observed that increasing the dosage of Cas9:sgRNA increased toxicity at constant amounts of either RNAiMAX or Lipofectamine 2000 (FIG. 39(D)).

Cas9:sgRNA Delivery Modifies Genomes with Greater Specificity than DNA Transfection DNA-free delivery of functional Cas9:sgRNA complexes circumvents risks associated with viral or other gene delivery methods and has the potential to improve the specificity of genome modification by avoiding the unnecessary expression of genome-editing agent after the target locus is modified. Transient delivery of functional Cas9:sgRNA protein: RNA complexes circumvents risks associated with viral or other gene delivery methods and has the potential to improve the specificity of genome editing by minimizing the opportunity of agents to modify off-target substrates after the target locus is modified, or to reverse on-target modification. To test if the described approach can disrupt endogenous genes in human cells, genomic loci in the EMX1, CLTA2, and VEGF genes were targeted due to their potential biomedical relevance and their use in previous studies[40,46,47] of Cas9 off-target cleavage activity. Cationic lipid-mediated delivery of Cas9:sgRNA complexes into HEK293T cells resulted in robust cleavage of all three human genes with efficiencies comparable to or greater than those of plasmid transfection methods as revealed by the T7EI assay using the same Cas9:sgRNA delivery conditions previously optimized for U2OS cells (FIG. 31(A)).

Figure 41A:
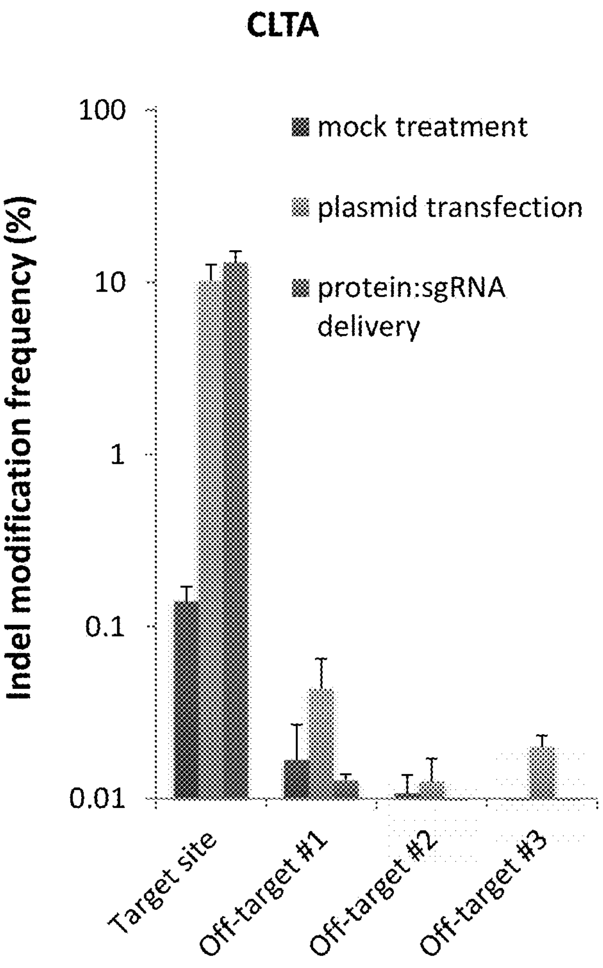
FIGS. 41A-C. Indel frequencies, measured by high-throughput sequencing, of several human genes treated either by a mock treatment, by transfection of Cas9 plasmid and sgRNA linear DNA PCR product, or by cationic lipid-mediated protein:sgRNA delivery are depicted. Mock treatment involved cationic lipid-mediated protein: sgRNA delivery of EGFP-targeting sgRNA instead of one of the three human gene-targeting sgRNAs.
Figure 41B:
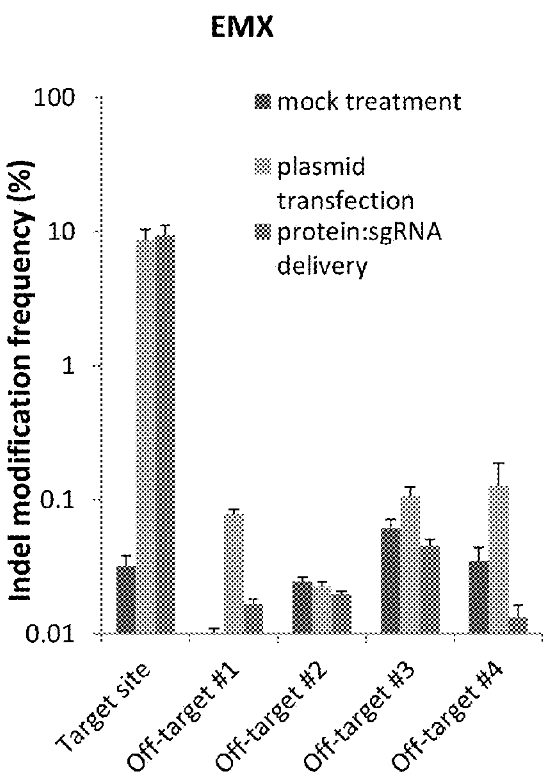
Figure 41C:
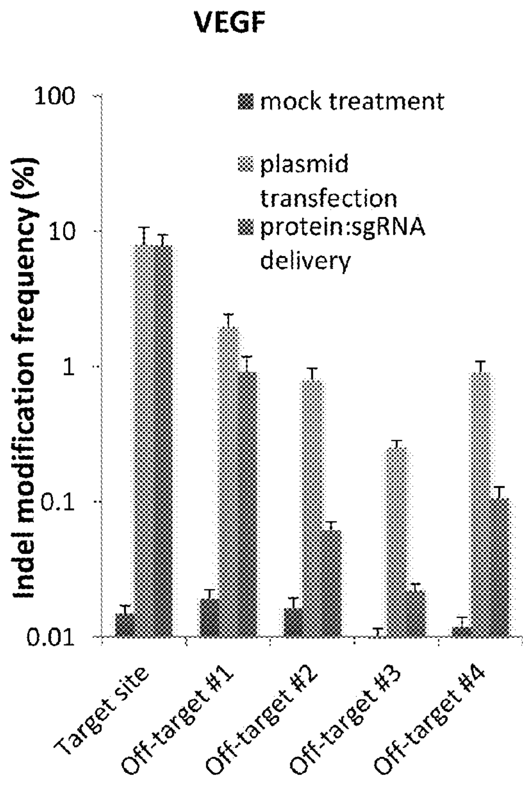

To compare the endogenous gene modification specificity of plasmid versus protein:RNA delivery methods for Cas9, the on-target locus was amplified as well as several known off-target sites (Table 1) from genomic DNA isolated from HEK293 cells treated either by transfection of Cas9 and sgRNA expression plasmids, or by RNAiMAX-mediated Cas9:sgRNA complex delivery under conditions that resulted in comparable on-target modification efficiencies. The indel frequencies at the three on-target and 11 off-target sites were assayed by high-throughput DNA sequencing (Table 2). For all three target genes, the frequency of on-target DNA modification resulting from either plasmid or protein:sgRNA delivery was approximately 10%±2% (FIG. 41), enabling the comparison of off-target modification under conditions that result in very similar on-target modification efficiencies. Importantly, the frequency of off-target genome modification for all 11 off-target sites was lower from protein:sgRNA delivery compared with plasmid delivery (FIGS. 41(A-C)), and as a result the ratio of on-target to off-target modification ratio for all sites tested was up to 19-fold higher for protein:sgRNA delivery than for plasmid delivery (FIGS. 31(B-D)).

Figure 47:
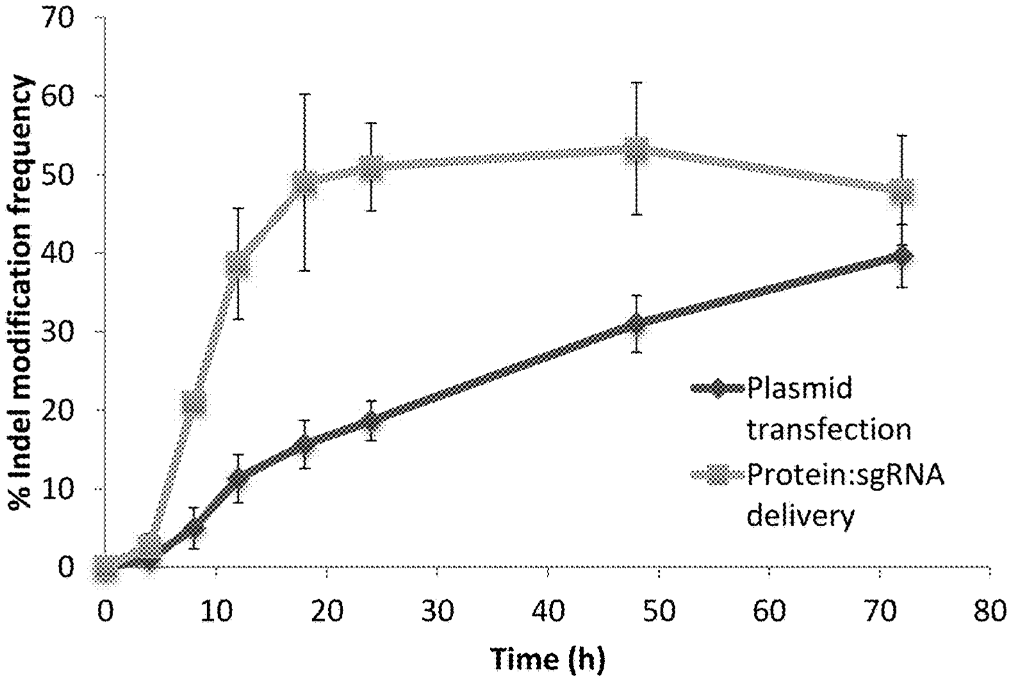
FIG. 47. A time course of Cas9 nuclease activity from protein:sgRNA delivery and plasmid transfection is shown. U2OS EGFP reporter cells were treated with either 50 nM Cas9 protein and 50 nM sgRNA and 0.8 μL Lipofectamine 2000 in 275 μL DMEM-FBS without antibiotics, or transfected with 750 ng Cas9 expression plasmid and 250 ng EGFP sgRNA expression plasmid for 2 hours. Media was either removed and samples collected after another 2 hours, or replaced with fresh DMEM-FBS without delivery agents and collected at later time points, as shown. Samples were analyzed for indels in the EGFP gene using a Surveyor T7E1 cleavage assay. Bands were quantified by ImageJ software. Error bars reflect standard deviation from three biological replicates performed on different days.
Figure 48A:
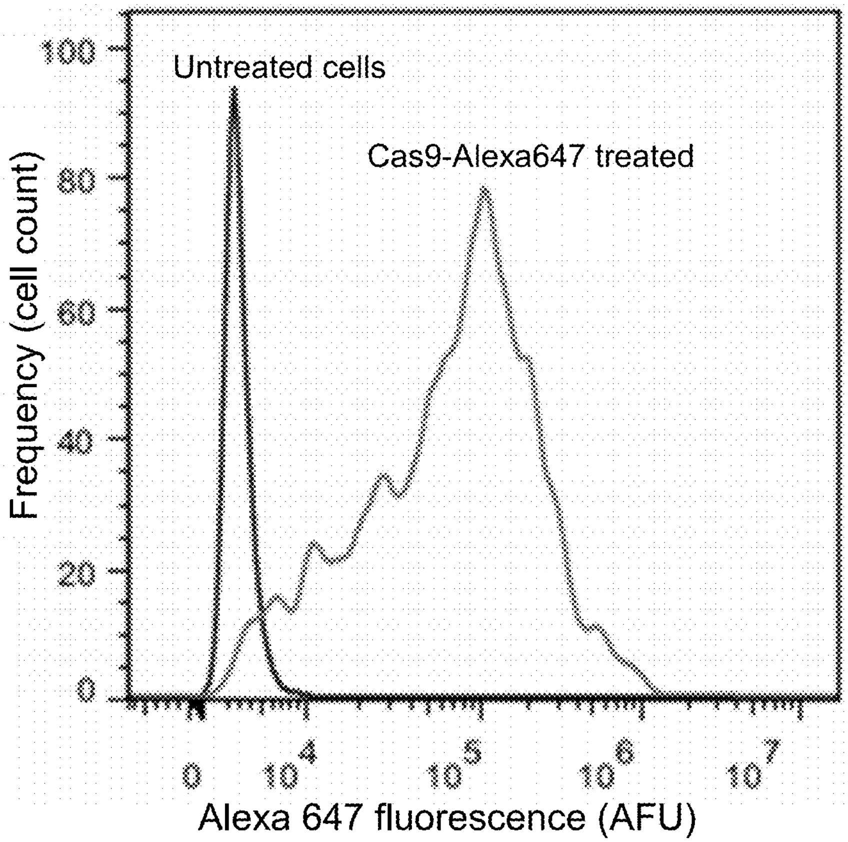
FIGS. 48A-B. Quantification of Cas9 protein uptake into U2OS EGFP reporter cells is shown.
Figure 48B:
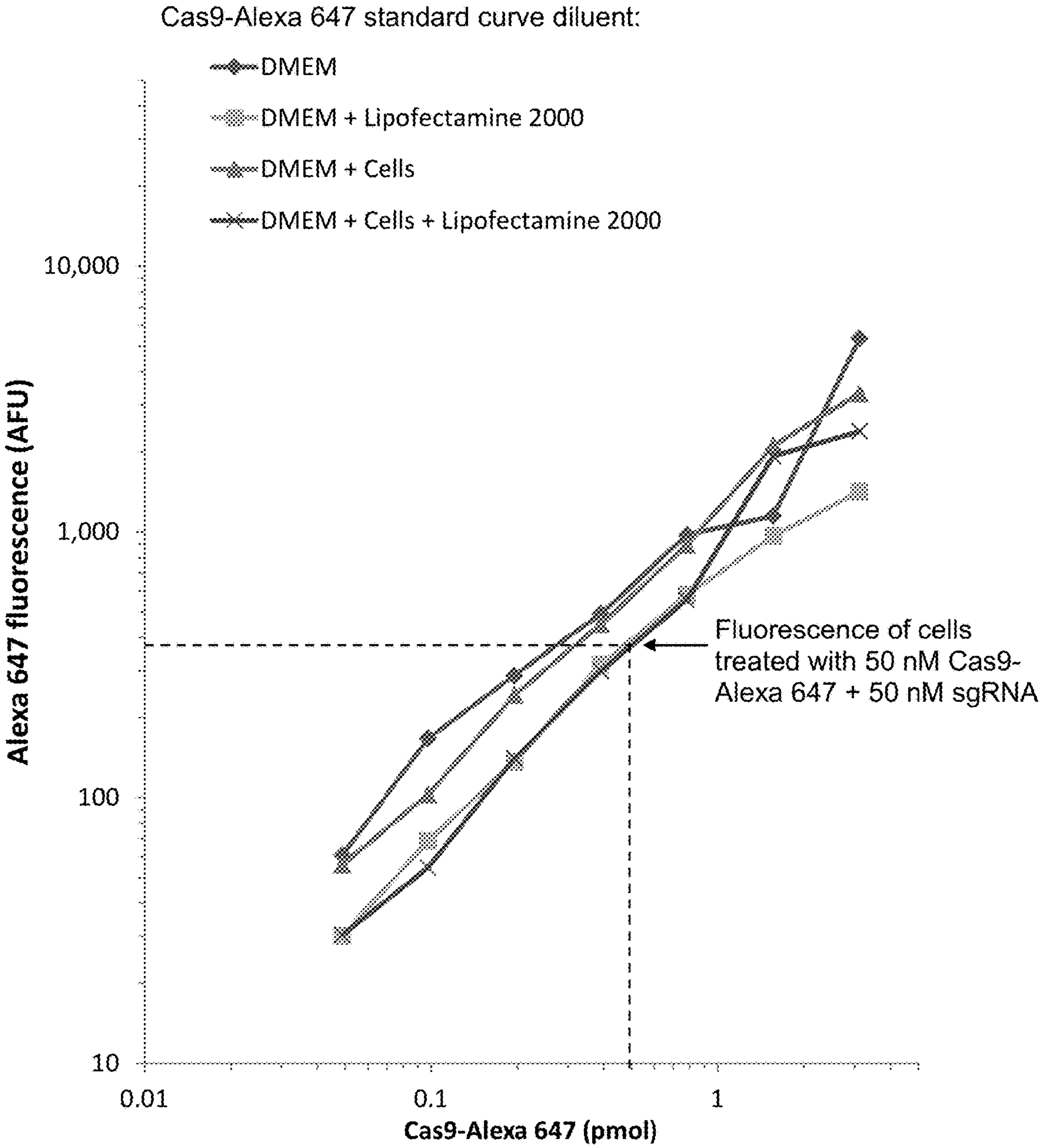

We also observed that the increase in specificity for Cas9 protein delivery relative to DNA transfection persists across a wide range of on-target cleavage efficiencies (~1%, ~10%, and ~40%) (FIG. 46 and results herein). This increase in specificity using protein delivery is consistent with the transient nature of the delivered protein:sgRNA complexes compared to plasmid transfection (FIG. 47 and results herein). We also measured the amount of protein internalized by cells using our cationic lipid-based protein delivery approach and determined that ~4% of the total protein used in the treatment was internalized by cells (FIG. 48 and results herein). We note that the majority of this protein likely exists within endosomes and may not be available to effect genome modification.[18,59]

We tested whether the observed increase in specificity for Cas9 protein delivery holds at different cleavage efficiencies, focusing on the VEGF on-target and its four known off-target sites. We tuned Cas9-mediated on-target modification rates over a broad range by scaling the amount of Cas9: sgRNA delivered by plasmid transfection and liposomal protein delivery, resulting in conditions that yield low (~1%), moderate (~10%), and high (~40%) on-target DNA modification. We observed that across all levels of on-target modification, Cas9:sgRNA delivery always resulted in substantially (typically ~10-fold) higher on:off-target modification ratios than comparable Cas9 plasmid DNA transfections (FIG. 46). This increase in specificity can likely be explained by the transient nature of the delivered protein:sgRNA complexes (FIG. 47) as well as the quality of the sgRNA complexed with the Cas9 protein compared to that of the endogenously produced sgRNA transcripts. There is the potential for degraded or otherwise modified sgRNAs to interact with the Cas9 protein and allow it to mediate unintended and unpredictable genome modifications. We also note that RNA pol III transcription has an error rate of $\sim 10^{-5}$, while published T7 RNAP error rates may be up to 10-times lower. In a given 20-base spacer target sequence, there would be one incorrect version per every 5,000 transcripts versus one in every 50,000 for our pre-complex sgRNAs. Such differences may further account for the observed increases in specificity.

DNA modification specificity was higher for protein: sgRNA delivery than for plasmid delivery at loci with high levels of off-target modification (such as the four VEGF off-target sites, for which plasmid delivery yielded average on-target:off-target modification ratios between 4- and 20-fold but protein:RNA delivery yielded average on-target: off-target modification ratios between 9- and 400-fold) as well as for loci with lower levels of off-target modification (such as the three EMX off-target loci, for which plasmid delivery yielded average on-target:off-target modification ratios as low as 64-fold but protein:RNA delivery yielded average on-target:off-target modification ratios of 500- to 2,000-fold). Taken together, these results indicate that the delivery of Cas9:sgRNA complexes using cationic lipids can effect target gene modification at high efficiency and with substantially greater specificity than the delivery of DNA expressing Cas9 and sgRNA.

Figure 40B:
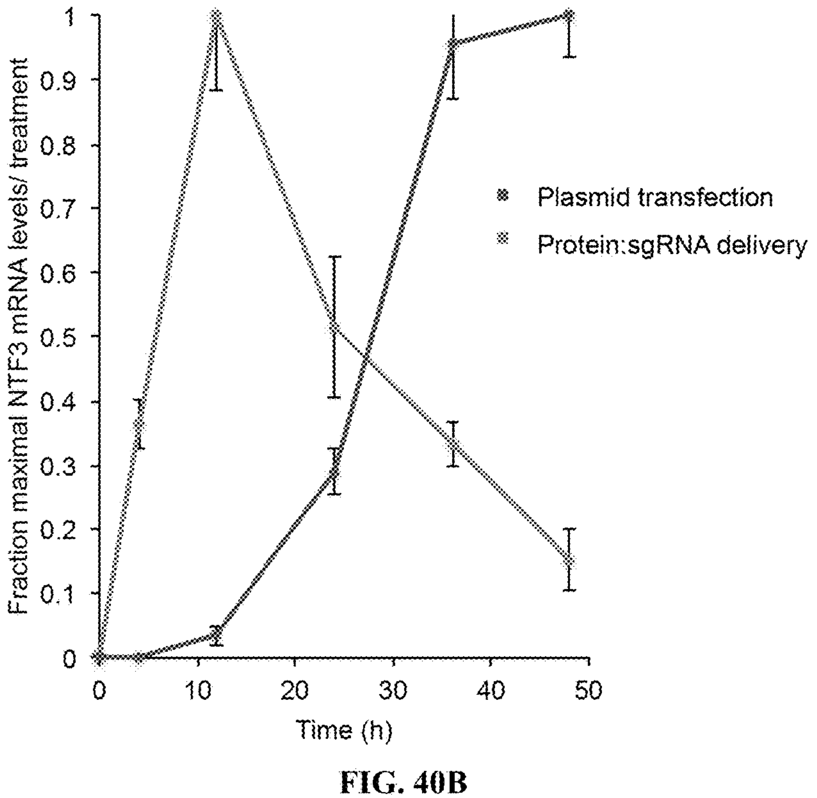

Time Course of Gene Disruption from Cas9:sgRNA Delivery Versus Plasmid DNA Transfection The remarkable increases in Cas9 specificity for protein: sgRNA delivery is likely a result of the transient nature of the delivered protein that was directly observed with both TALE-activator and dCas9-activator delivery (FIG. 35(A) and FIG. 40(B)). We performed a time course experiment that measured indel modification rate by Surveyor assay from protein:sgRNA or plasmid DNA delivery over the course of 72 hours post-treatment (FIG. 47). Whereas indel formation in U2OS EGFP reporter cells following Cas9 plasmid transfection continued to increase 72 hours after DNA delivery, protein:sgRNA delivery leads to near-maximal indel modification between 12 and 24 hours after treatment (FIG. 47). Together, these results suggest that protein:sgRNA delivery rapidly achieves a transient dose of Cas9:sgRNA activity that mediates efficient genome modification and is degraded before off-target modifications can accumulate to the extent that arises from long-term expression.

Quantification of Total Cas9 Protein Uptake into Cells

Finally, we quantitated the amount of protein internalized by cells using our cationic lipid-based protein delivery approach. We labeled Cas9 protein with Alexa 647 and delivered it to U2OS cells at 50 nM with 100 nM sgRNA. After 4 hours, cells were washed extensively to remove bound protein and trypsinized. Cellular Alexa 647 fluorescence was measured and compared to that of a standard curve of known Cas9-Alexa 647 amounts in the presence of an identical composition of media, cells, and lipid. Nearly all treated cells were found to have internalized the Cas9-Alexa 647 protein (FIG. 48(A)), and 4% of the total protein used in the treatment was internalized by cells (FIG. 48(A)). Comparison with the standard curve suggests that ~$3\times10^7$ molecules of Cas9-Alexa 647 entered each cell, corresponding to 0.4% of total cellular protein.[60] We note, however, that the majority of this protein is likely sequestered within endosomes and may not be immediately available to effect genome modification.[18,59]

Delivery of Cas9:sgRNA into Mouse Embryonic Stem Cells

Figure 42A:
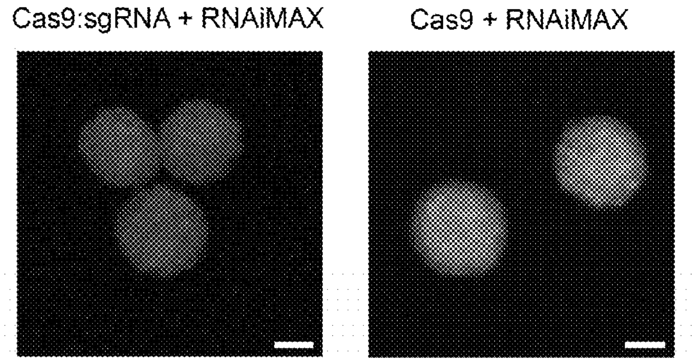
FIGS. 42A-C. Delivery of Cas9 endonuclease to mouse embryonic stem cells.
Figure 42B:
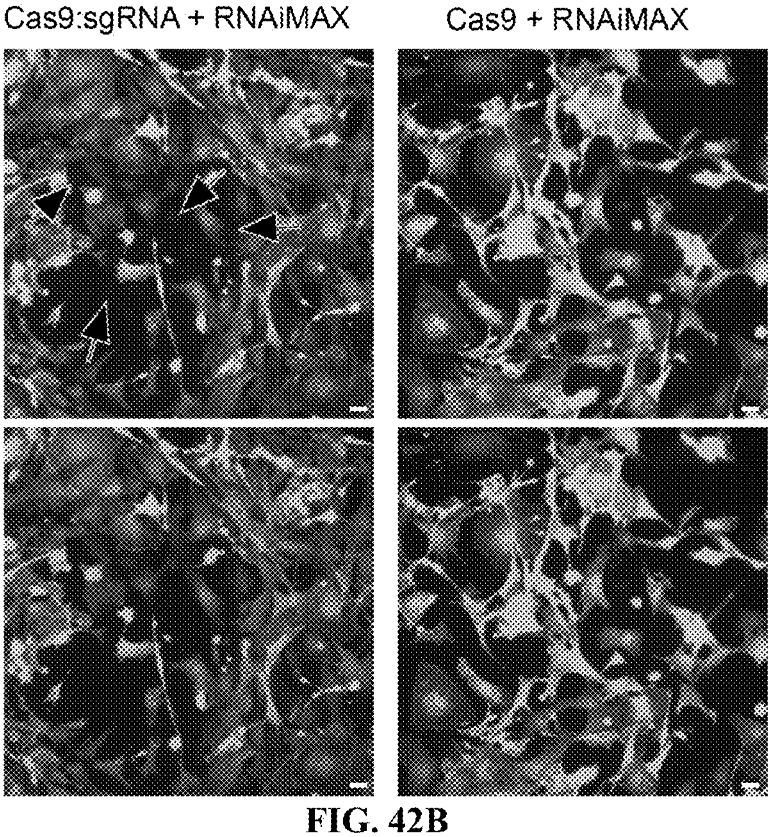
Figure 42C:
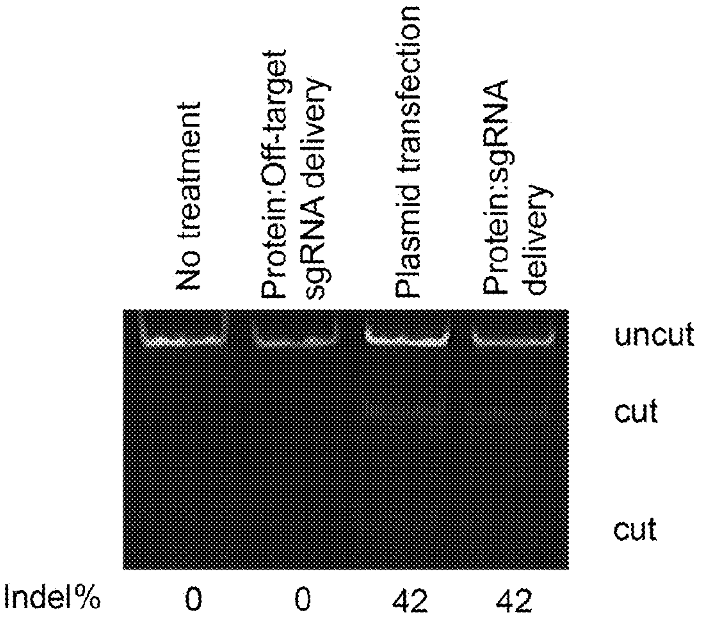

The rapid, potent, and transient cationic lipid-mediated delivery of Cas9:sgRNA to effect genome editing could be especially useful in stem cells, where Cas9 off-target activity over the course of multiple cell divisions could lead to both unwanted mutations, and mosaicism. To test the effectiveness of Cas9:sgRNA delivery in stem cells, we treated mouse embryonic stem cells expressing Tau-EGFP[48] with Cas9 and an EGFP-targeting sgRNA. Under standard stem-cell culture conditions, EGFP-positive floating spheres were formed. We treated these floating spheres with Cas9:sgRNA complexed with Lipofectamine 2000, or with Cas9 and Lipofectamine 2000 without sgRNA as a control. Three days post-treatment, we observed a reduction in GFP fluorescence in the Cas9:sgRNA-treated spheres compared to the control samples (FIG. 42(A)). The treated spheres were dissociated, and the cells were allowed to attach to a laminin-coated dish and differentiate into progenitor cells. Immunohistochemistry using an anti-GFP antibody confirmed knockdown of EGFP expression in the cells of Cas9:sgRNA treated samples, with many nuclei lacking any apparent EGFP. In contrast, all cells derived from control spheres were EGFP positive (FIG. 42(B)). Genomic DNA harvested from Cas9:sgRNA-treated cells was subjected to T7EI assay, resulting in clear evidence of indels at the Tau-EGFP locus (FIG. 42(C)). From this assay we calculated an indel frequency of 24% from cationic lipid-mediated Cas9:sgRNA delivery and 20% from DNA transfection. No target modification was detected in control samples lacking Cas9:sgRNA or containing Cas9 and an unrelated gRNA. These findings demonstrate that cationic lipid-mediated Cas9:sgRNA delivery can effect efficient gene disruption in mouse embryonic stem cells.

Delivery of Cas9:sgRNA into Mouse Embryonic Stem Cells

The potent and transient cationic lipid-mediated delivery of Cas9:sgRNA to effect efficient, permanent, and highly specific gene editing could be especially useful in stem cells. To test this possibility, mouse embryonic stem cells expressing Tau-EGFP[48] were treated with Cas9 and an EGFP-targeting sgRNA. Under standard stem-cell culture conditions, EGFP-positive floating spheres were formed. The floating spheres were treated with Cas9:sgRNA complexed with RNAiMAX, or with Cas9 and RNAiMAX without sgRNA as a control. Three days post-treatment, a reduction in GFP fluorescence in the Cas9:sgRNA-treated spheres compared to the control samples was observed (FIG. 42(A)). The treated spheres were dissociated, and the cells were allowed to attach to a gelatin-coated dish and differentiate into progenitor cells. Immunohistochemistry using an anti-GFP antibody confirmed knockdown of EGFP expression in the cells of Cas9:sgRNA treated samples, with many nuclei lacking any apparent EGFP. In contrast, all cells derived from control spheres were EGFP positive (FIG. 42(B)). Genomic DNA harvested from Cas9:sgRNA-treated cells was subjected to T7EI assay, resulting in clear evidence of indels at the Tau-EGFP locus (FIG. 42(C)). From this assay, an indel frequency of 42% was calculated from both cationic lipid-mediated Cas9:sgRNA delivery and transfection of Cas9 and sgRNA DNA. No target modification was detected in control samples lacking Cas9:sgRNA or containing Cas9 and an unrelated gRNA. These findings demonstrate that cationic lipid-mediated Cas9: sgRNA delivery can effect highly efficient gene disruption in mouse embryonic stem cells.

In Vivo Cationic Lipid-Mediated Delivery of Cre Recombinase and Cas9:sgRNA

The high-efficiency delivery of functional genome-editing proteins in vivo enables a wide range of applications including non-viral therapeutic genome editing to correct genetic diseases. To evaluate the protein delivery method described above in a living mammal, delivery to the mouse inner ear was chosen, due to its confined space, well-characterized inner ear cell types, and the existence of genetic deafness mouse models that may enable future hearing recovery studies. The in vivo deliveries of two types of proteins into the mouse inner year were attempted. First, the delivery of (−30)GFP-Cre protein was tested to assess the targeting of inner ear cell types and the efficiency of functional protein delivery. Second, the delivery of Cas9:sgRNA complexes to the inner ear were evaluated to determine if cationic lipid-mediated protein:gRNA complex delivery can support CRISPR-based gene editing in vivo.

It has been previously shown that (+36)GFP-Cre can be delivered to mouse retina,[16] although the protein resulted in only modest levels of recombinant conversion suggestive of inefficient in vivo delivery. For our initial inner ear delivery trials, (−30)GFP-Cre was complexed with RNAiMAX and the complex was injected into the cochlea of postnatal day 1 (P1) reporter mice with a genomically integrated floxed-STOP tdTomato reporter. As with the previously described in vitro Cre reporter cell line, functional delivery of Cre to the inner ear cells, followed by endosomal escape, nuclear localization, and Cre-mediated recombination results in expression of tdTomato. After injection, the cochleas were harvested for immunolabeling with inner ear cell markers for co-localization with tdTomato. RNAiMAX injection alone was used as control. Five days following injection of (−30)GFP-Cre and RNAiMAX, cochlear outer hair cells, the auditory sensory cells that detect sound, showed strong tdTomato signal that co-localized with the hair cell marker myosin VIIa (Myo7a), demonstrating functional Cre delivery to hair cells (FIGS. 32(A)-(B)). No tdTomato expression was detected in control cochleas (FIG. 32(A)). The tdTomato signal was concentrated in the region of the injection site at the basal turn of the cochlea. On average 33±3% of outer hair cells were tdTomato positive at the base of the cochlea ($P<0.001$; mean±SEM, $n=4$) and intact sterocilia were observed indicative of healthy hair cells (FIG. 32(B)). We also tested delivery using Lipofectamine 2000 due to its higher potency in vitro (FIG. 39(A)) and observed dramatically higher recombination efficiency: 91±5% outer hair cells in cochleas treated with (−30)GFP-Cre+Lipofectamine 2000 were tdTomato positive (FIG. 32(C)). In comparison to control samples, some outer hair cell loss was observed (FIG. 42(C)), consistent with our previous observation of higher cell toxicity of Lipofectamine 2000, although overall cochlear architecture was preserved.

To further determine the effect of cationic lipid-mediated (−30)GFP-Cre protein delivery on targeted cells, hair cell stereocilia, a delicate structure that is essential for hearing, were examined 10 days post-injection. TdTomato positive outer hair cells had typical stereocilia structure as imaged by espin expression, similar to control stereocilia (FIG. 32(B)). No tdTomato expression was detected in control cochleas. These observations indicate that cationic lipid-mediated delivery of (−30)GFP-Cre protein effects recombination in cochlear outer hair cells without apparently affecting hair cell architecture.

Because target volume, protein dose, and sgRNA dose in vivo are different than in cell culture experiments, the above experiments were repeated under different delivery conditions. Delivery using Lipofectamine 2000 was tested due to its higher potency in vitro (FIG. 39(A)) and dramatically higher recombination efficiency was observed: over 90% outer hair cells in cochleas treated with (−30)GFP-Cre+ Lipofectamine 2000 were tdTomato positive (FIG. 32(C)). In comparison to control samples, some outer hair cell loss was observed (FIG. 32(C)), consistent with the previous observation of the higher cell toxicity of Lipofectamine 2000, although the overall cochlear architecture was preserved.

To test the effectiveness of Cas9:sgRNA delivery in vivo, Cas9 and sgRNA targeting EGFP were combined with RNAiMAX and the resulting complexes were injected into postnatal day 2 (P2) transgenic Atoh1-GFP mouse cochlea in which all hair cells express GFP under the control of a hair cell-specific enhancer for transcription factor Atoh1.[49] Using this model, Cas9:sgRNA-mediated disruption of EGFP results in loss of EGFP fluorescence in outer hair cells. Ten days after injection of Cas9:sgRNA with cationic lipid, the absence of GFP was observed in 13% of outer hair cells near the injection site. In contrast, control cochlea injected with Cas9 protein and RNAiMAX without any sgRNA showed no loss of EGFP signal (FIG. 32(D)). The outer hair cells of cochlea injected with Cas9:sgRNA RNAiMAX complexes appeared to be otherwise unaffected, with stereotypical expression of Myo7a and healthy nuclei, consistent with minimal hair cell toxicity (FIG. 32(D)). High-throughput DNA sequencing of genomic DNA isolated from cochlea tissue samples revealed indels consistent with GFP target gene disruption in the treated samples, but not in the control samples that lacked sgRNA (FIG. 43(A)). In addition, the inner ear in vivo delivery of Cas9:sgRNA using an sgRNA that targets the EMX gene was repeated and indels in the EMX gene in treated animals, but not control animals were similarly observed (FIG. 43(B)).

After validating Cas9:sgRNA delivery in reporter cells (FIGS. 30(A-E)), and in neuron-derived mouse embryonic stem cells (FIG. 42 and results herein), we tested Cas9:sgRNA delivery in vivo. Cas9 and sgRNA targeting EGFP were combined with RNAiMAX and the resulting complexes were injected into postnatal day 2 (P2) transgenic Atoh1-GFP mouse cochlea in which all hair cells express GFP under the control of a hair cell-specific enhancer for transcription factor Atoh1.[49] Using this model, Cas9:sgRNA-mediated disruption of Atoh1-GFP results in loss of GFP fluorescence in outer hair cells. Ten days after injection of Cas9:sgRNA with cationic lipid, we observed the absence of GFP in 13% of outer hair cells near the injection site. In contrast, control cochlea injected with Cas9 protein and RNAiMAX without any sgRNA showed no loss of EGFP signal (FIG. 32(D)). The outer hair cells of cochlea injected with Cas9:sgRNA RNAiMAX complexes appeared to be otherwise unaffected, with stereotypical expression of Myo7a and healthy nuclei, consistent with minimal hair cell toxicity (FIG. 32(D)). High-throughput DNA sequencing of genomic DNA isolated from cochlea tissue samples revealed indels consistent with GFP target gene disruption in the treated samples, but not in the control samples that lacked sgRNA (FIG. 43(A)). In addition, we repeated inner ear in vivo delivery of Cas9:sgRNA using an sgRNA that targets the EMX gene and similarly observed indels in the EMX gene in treated animals, but not control animals (FIG. 43(B)).).

Figure 32A:
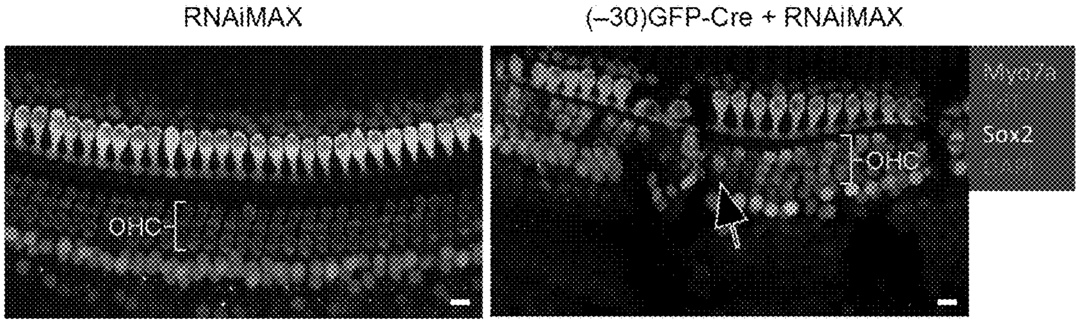
FIGS. 32A-D. The in vivo delivery of Cre recombinase and Cas9:sgRNA complexes to hair cells in the mouse inner ear is shown.
Figure 32B:
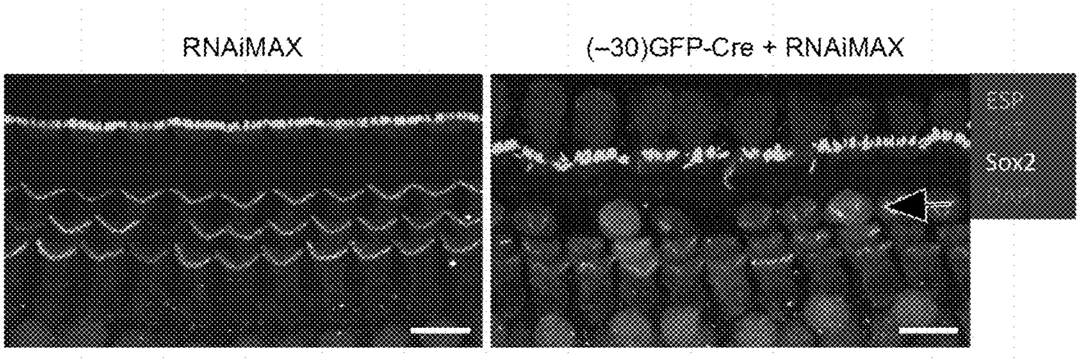
Figure 32C:
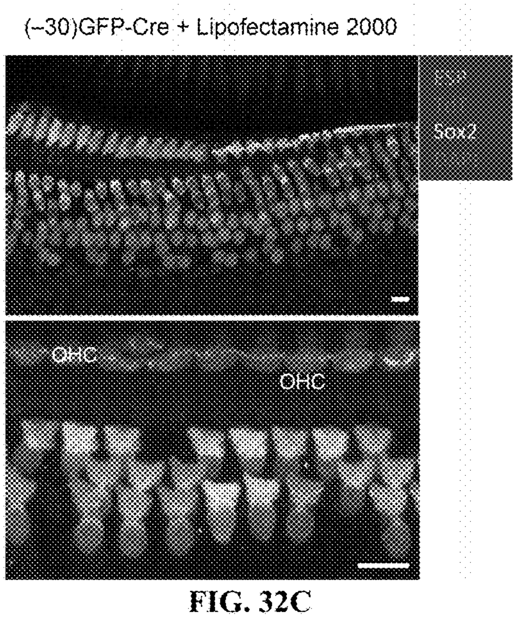
Figure 32D:
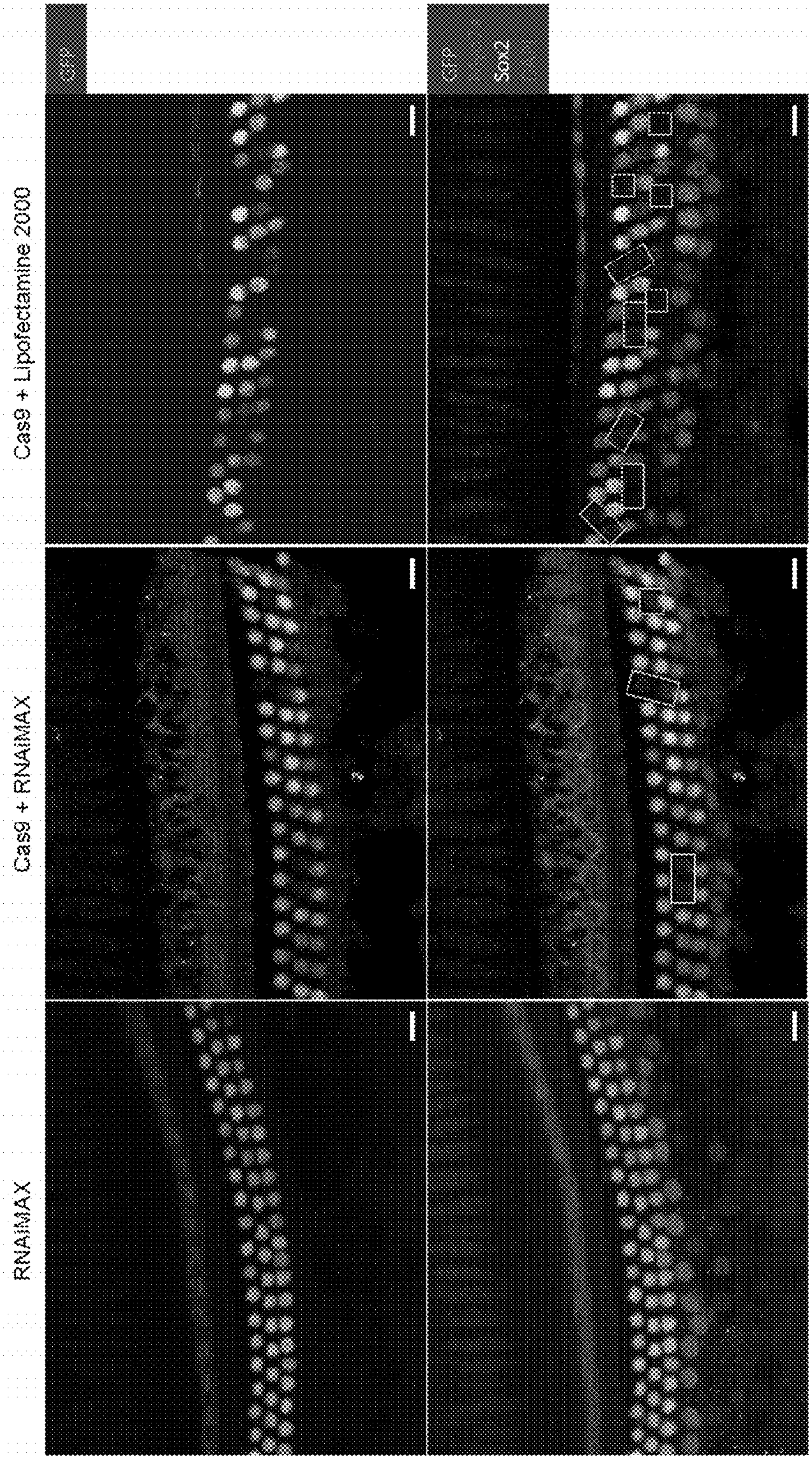

As (−30)GFP-Cre complexed with Lipofectamine 2000 resulted in more efficient modification of the target hair cell population than (−30)GFP-Cre complexed with RNAiMAX (FIGS. 32(A) and 32(C)), its use on Cas9:sgRNA delivery to Atoh1-GFP cochlea was tested as above. Loss of GFP expression was observed in 20%±3% of outer hair cells near the injection site after 10 days, whereas all outer hair cells maintained strong GFP expression in control cochlea injected with Cas9 and Lipofectamine 2000 but no sgRNA (FIG. 32(D)). In contrast to modest hair cell loss observed following Lipofectamine 2000 delivery of (−30)GFP-Cre (FIG. 32(C)), outer hair cells targeted by Cas9:sgRNA exhibited no obvious toxicity or structural alteration (FIG. 32(D)).

As with (−30)GFP-Cre, virus-free, cationic lipid-mediated delivery of Cas9:sgRNA into the mouse inner ear successfully modified a specific genomic locus in the outer hair cell population, leading to loss of target gene expression. Nearly half of all types of genetic deafness arise from hair cell loss or dysfunction,[50] the results presented herein suggest a potential strategy based on the delivery of Cas9:sgRNA complexes to genetically modify these cells to effect hearing recovery. These findings suggest that cationic lipid-mediated delivery of genome-editing proteins can serve as a powerful tool and a potential in vivo strategy for the treatment of genetic disease.

Determination of Protein Delivery Efficacy for (−30)GFP-Cre

To determine if the higher potency of liposome-mediated (−30)GFP-Cre delivery compared with that of cationic protein delivery arises from more total protein uptake by cells or from a higher fraction of functional, non-endosomal protein molecules taken up by the cells, flow cytometry was used to measure GFP fluorescence of cells treated with either (+36)GFP-Cre or liposomal (−30)GFP-Cre under their respective optimal Cre delivery conditions. Cell fluorescence reports total endocytosed (−30)GFP-Cre or (+36) GFP-Cre regardless of endosomal or non-endosomal localization.[1] Lipid-mediated protein delivery resulted in surprisingly small increases in total protein uptake (FIG. 34(A)), despite the high efficiency of lipid-mediated functional Cre delivery. While (+36)GFP-Cre treatment increased cellular GFP fluorescence by up to three orders of magnitude in a dose-dependent manner (FIG. 34(A)), consistent with previous reports,[1,2] liposomal (−30)GFP-Cre treatment induced at most 5-fold increases in cellular GFP fluorescence (FIG. 34(A)). Comparison of cellular fluorescence and recombination efficiency reveals that lipid-mediated functional delivery of (−30)GFP-Cre is 9,800-fold more potent per amount of endocytosed protein than delivery of (+36)GFP-Cre (FIG. 34(B)).

To test if complexation of anionic (−30)GFP with cationic lipids interferes with GFP fluorescence and thus masks the true amount of cargo that enters the cell mCherry, which is fluorescent but not highly anionic, was fused to either (−30)GFP or (+36)GFP and delivered both protein fusions to HeLa cells. After washing away protein that may have adhered to cell surface but did not enter the cell with PBS+heparin (20 U/mL), the cells were analyzed by FACS for mCherry fluorescence 4 hours and 24 hours after treatment. It was observed that lipid-mediated delivery of (−30) GFP-fused mCherry results in only slight increases in cellular mCherry fluorescence, whereas mCherry fluorescence upon delivery of (+36)GFP-mCherry was generally ≥100-fold higher (FIG. 34(C)) suggesting that fusion to (−30)GFP does not cause substantial amounts of protein cargo to enter the cell. Moreover, addition of lipids to (−30)GFP-Cre did not measurably alter the GFP fluorescence signal (FIG. 34(D)), despite the fact that cationic lipids and anionic (−30)GFP clearly interact. Taken together, these results suggest that the unusually high potency of lipid-mediated delivery of anionic proteins does not arise from unusually high protein uptake in each cell, but rather from post-endocytosis processes that likely include avoidance of protein degradation and endosomal escape into the cytoplasm.

Sensitivity Limit of Off-Target Cleavage Assays

The sensitivity of the high-throughput sequencing method for detecting genomic off-target cleavage is limited by the amount genomic DNA (gDNA) input into the PCR amplification of each genomic target site. A 1 ng sample of human gDNA represents only approximately 330 unique genomes, and thus only approximately 330 unique copies of each genomic site are present. PCR amplification for each genomic target was performed on a total of 150 ng of input gDNA, which provides amplicons derived from at most 50,000, unique gDNA copies, respectively. Therefore, the high-throughput sequencing assay cannot detect rare genome modification events that occur at a frequency of less than 1 in 50,000 (0.002%). This limit is noted in Table 2.

Taken together, these findings suggest that cationic lipid-mediated delivery of genome-editing proteins can serve as a powerful tool and an in vivo strategy for the treatment of genetic disease.

CONCLUSIONS

Efficient intracellular protein delivery in vitro and especially in vivo has been a persistent challenge in biomedical research and protein therapeutics. While delivery using cationic peptides and proteins has been widely studied for over two decades, sensitivity to serum proteins, neutralization by antibodies, degradation by extracellular and intracellular proteases, and poor endosomal escape post-internalization have limited the scope of protein delivery applications using that approach.

In the current Example, a general strategy for protein delivery that makes use of anionic protein complexation with cationic liposomes is demonstrated. This method was used to deliver diverse protein classes, including the Cre tyrosine recombinase, TALE transcriptional activators, and Cas9 nucleases, nickases, and transcriptional activators (FIG. 27(A)) to cultured cell lines, stem cell colonies, and therapeutically relevant in vivo sites within the mouse inner ear. The described approach is highly efficient, producing modification rates on par with established nucleic acid transfection methods in cell culture, and enabling Cre recombinase and Cas9-mediated genome modification rates of up to 90% and 20%, respectively, within the inner ear hair cell population of live mice (FIGS. 32(C)-(D)). For Cas9 nuclease delivery, this approach also typically results in >10-fold more specific genome modification than traditional plasmid transfection (FIGS. 32(B-D)), likely due to the transient window of Cas9 activity to which each genome is exposed (FIG. 47) compared to DNA delivery methods, consistent with previous reports.[61] These results also suggest that it may be possible to use cationic lipids to efficiently deliver other nucleic acid-binding proteins, including transcription factors that induce therapeutically relevant changes in cell fate, by complexing them with nucleic acids.

Cationic lipid-based anionic protein delivery outperforms a potent cationic protein delivery fusion partner, (+36)GFP, by up to 9,800-fold per amount of endocytosed protein, inducing more efficient modification of treated cells with orders of magnitude lower doses of protein (FIGS. 28(C) 34). For Cas9 nuclease delivery, this approach also results in >10-fold more specific genome modification than traditional plasmid transfection (FIGS. 31(B)-(D)), likely due to the transient window of Cas9 activity to which each genome is exposed compared to DNA delivery methods, consistent with previous reports.[51]

The described approach is simple to implement, requiring only the purified deliverable protein and the use of popular commercial nucleic acid transfection reagents (FIG. 27(B)). Rendering a given protein amenable to this approach requires simple translational fusion to a highly anionic partner, such as (−30)GFP (FIG. 27(A)), and is even effective with common translational fusion tags including the VP64 activation domain, and the 3×FLAG affinity tag (FIG. 28(F) and FIG. 33(C)). In certain cases, as with the Cas9 protein, pre-complexation with a cognate nucleic acid (sgRNA in this case) is sufficient (FIG. 30(A)), as the partially exposed bound nucleic acid likely provides sufficient anionic charge to mediate complexation with cationic lipids.

Others groups have reported the in vivo delivery of Cas9 expression constructs in DNA or mRNA form.[52,53] The present Example demonstrates that protein delivery is a viable approach to in vivo genome editing. These results also demonstrate that cationic lipids can efficiently deliver other proteins in vitro and in vivo, including natively anionic proteins or proteins that can be fused or bound to polyanionic macromolecules.

TABLE 1

| | |
|---|---|
| EMX_On | GAGTCCGAGCAGAAGAAGAAGGG (SEQ ID NO: 209) |
| EMX_Off1 | GAG**g**CCGAGCAGAAGAA**ag**ACGG (SEQ ID NO: 210) |
| EMX_Off2 | GAGTCC**t**AGCAG**g**AGAAGAAG**a**G (SEQ ID NO: 211) |
| EMX_Off3 | GAGTC**ta**AGCAGAAGAAGAAG**a**G (SEQ ID NO: 212) |
| EMX_Off4 | GAGT**ta**GAGCAGAAGAAGAAAGG (SEQ ID NO: 213) |
| VEGF_On | GGGTGGGGGGAGTTTGCTCCTGG (SEQ ID NO: 214) |
| VEGF_Off1 | GG**a**TGG**a**GGGAGTTTGCTCCTGG (SEQ ID NO: 215) |
| VEGF_Off2 | GGG**a**GGG**t**GGAGTTTGCTCCTGG (SEQ ID NO: 216) |

TABLE 1-continued

| | |
|---|---|
| VEGF_Off3 | **c**GG**g**GG**a**GGGAGTTTGCTCCTGG (SEQ ID NO: 217) |
| VEGF_Off4 | GGG**ga**GGGG**a**AGTTTGCTCCTGG (SEQ ID NO: 218) |
| CLTA_On | GCAGATGTAGTGTTTCCACAGGG (SEQ ID NO: 219) |
| CLTA_Off1 | **a**CA**a**ATGTAGT**a**TTTCCACAGGG (SEQ ID NO: 220) |
| CLTA_Off2 | **c**CAGATGTAGT**a**TT**c**CCACAGGG (SEQ ID NO: 221) |
| CLTA_Off3 | **ct**AGATG**a**AGTG**c**TTCCACATGG (SEQ ID NO: 222) |

Table 1. On-target and known off-target substrates of Cas9: sgRNAs that target sites in EMX, VEGF, and CLTA. A list of genomic on-target and off-targets sites of the EMX, VEGF, and CLTA are shown with mutations from the on-target sequence shown in lower case and bold. PAMs are shown in underline.

TABLE 2

Table 2. Indel frequencies, P values, and on-target:off-target cleavage specificity ratios for EMX, CLTA, and VEGF on-target sites and 11 known off-target sites.

| | Mock treatment | Plasmid transfection | Protein:sgRNA delivery |
|---|---|---|---|
| CLTA Sites | | | |
| CLTA_On | | | |
| Indels | 14 | 1228 | 1498 |
| Total | 10000 | 10000 | 10000 |
| Modified (%) | 0.140 | 12.280 | 14.980 |
| P-value | | <1.0E−300 | <1.0E−300 |
| On:off specificity | 1 | 1 | 1 |
| CLTA_Off1 | | | |
| Indels | 7 | 29 | 14 |
| Total | 41518 | 205204 | 125370 |
| Modified (%) | 0.017 | 0.014 | 0.011 |
| P-value | | 6.6E−01 | 4.5E−01 |
| On:off specificity | | 869 | 1341 |
| CLTA_Off2 | | | |
| Indels | 5 | 11 | 8 |
| Total | 25338 | 83944 | 54409 |
| Modified (%) | 0.020 | 0.013 | 0.015 |
| P-value | | 5.5E−01 | 5.7E−01 |
| On:off specificity | | 937 | 1019 |
| CLTA_Off3 | | | |
| Indels | 6 | 22 | 8 |
| Total | 41633 | 189886 | 76863 |
| Modified (%) | 0.014 | 0.012 | 0.010 |
| P-value | | 6.2E−01 | 5.8E−01 |
| On:off specificity | | 1060 | 1439 |
| EMX Sites | | | |
| EMX_On | | | |
| Indels | 3 | 930 | 1140 |
| Total | 10000 | 10000 | 10000 |
| Modified (%) | | 0.030 | 9.300 |
| P-value | | 1.6E−264 | <1.0E−300 |
| On:off specificity | 1 | 1 | 1 |
| EMX_Off1 | | | |
| Indels | 0 | 6 | 6 |
| Total | 24623 | 90935 | 100778 |
| Modified (%) | | <0.002 | 0.007 |
| P-value | | 3.5E−01 | 6.1E−01 |
| On:off specificity | | 1409 | 1915 |
| EMX_Off2 | | | |
| Indels | 16 | 53 | 38 |
| Total | 36061 | 204068 | 130084 |
| Modified (%) | | 0.044 | 0.026 |
| P-value | | 6.4E−02 | 1.8E−01 |
| On:off specificity | | 358 | 390 |
| EMX_Off3 | | | |
| Indels | 20 | 147 | 44 |
| Total | 32575 | 157848 | 110878 |
| Modified (%) | | 0.061 | 0.093 |
| P-value | | 8.1E−02 | 1.3E−01 |
| On:off specificity | | 100 | 287 |
| EMX_Off4 | | | |
| Indels | 16 | 141 | 23 |
| Total | 45548 | 86586 | 73451 |
| Modified (%) | | 0.035 | 0.163 |
| P-value | | 2.8E−12 | 7.4E−01 |
| On:off specificity | | 57 | 364 |
| VEGF Sites | | | |
| VEGF_On | | | |
| Indels | 1 | 989 | 785 |
| Total | | 10000 | 10000 |
| Modified (%) | 0.010 | 9.890 | 7.850 |
| P-value | | 1.5E−285 | 5.7E−228 |
| On:off specificity | 1 | 1 | 1 |
| VEGF_Off1 | | | |
| Indels | 4 | 4240 | 602 |
| Total | | 38625 | 184554 |
| Modified (%) | 0.010 | 2.297 | 0.394 |
| P-value | | <1.0E−300 | 3.7E−52 |
| On:off specificity | | 4 | 20 |
| VEGF_Off2 | | | |
| Indels | 5 | 727 | 18 |
| Total | | 30301 | 79164 |
| Modified (%) | 0.017 | 0.918 | <0.002 |
| P-value | | 4.7E−93 | 1.3E−04 |
| On:off specificity | | 11 | 3925 |
| VEGF_Off3 | | | |
| Indels | 2 | 536 | 21 |
| Total | | 26379 | 110902 |
| Modified (%) | 0.008 | 0.483 | 0.022 |
| P-value | | 2.0E−46 | 2.0E−01 |
| On:off specificity | | 20 | 352 |
| VEGF_Off4 | | | |
| Indels | 0 | 1531 | 45 |
| Total | | 26012 | 122403 |

CLTA sites: Total: total number of sequence counts; only the first 10,000 sequences were analyzed for the on-target site sequences. Modified: number of indels divided by total number of sequences as percentages. Upper limits of potential modification were calculated for sites with no observed indels by assuming there is less than one indel then dividing by the total sequence count to arrive at an upper limit modification percentage, or taking the theoretical limit of detection (1/49,500; see Results above), whichever value was larger. P-values: for mock treatment, Cas9 plasmid transfection, and liposomal Cas9 protein:sgRNA delivery, P-values were calculated as using a two-sided Fisher's exact test between each CLTA-targeted treatment sample (either DNA transfection or protein:sgRNA delivery) versus the control sample (mock treatment) treated with Cas9 protein and an sgRNA targeting EGFP. On:off specificity is the ratio of on-target to off-target genomic modification frequency for each site.

EMX sites shows the experimental and analytic methods of CLTA analysis applied to EMX target sites.

VEGF sites shows the experimental and analytic methods of CLTA analysis as applied to VEGF target sites. Indel numbers in the mock treatment control were subtracted from both plasmid transfection and protein:sgRNA delivery indel numbers for determining total number of indels and for calculating on-target:off-target ratios in FIG. 31 in the main text and also for FIG. 41.

TABLE 3

Exemplary naturally occurring negatively supercharged proteins.

Q8WXI7 (MUC16; 2, 353, −426, −0.18)
Q8WXG9 (GPR98; 693, −412, −0.59)
Q8WUY3 (PRUNE2; 341, −348, −1.02)
Q8WZ42 (TTN; 3, 816, −344, −0.09)
P13611 (VCAN; 373, −322, −0.86)
Q03001 (DST; 861, −316, −0.36)
Q8NF91 (SYNE1; 1, 011, −315, −0.31)
Q8N3K9 (CMYA5; 449, −312, −0.69)
Q8IWN7 (RP1L1; 261 , −278, −1.06)
Q8WXH0 (SYNE2; 796, −271, −0.34)
P16112 (ACAN; 250, −269, −1.07)
Q9NZW4 (DSPP; 131, −266, −2.02)
Q9UPN3 (MACF1; 838, −263, −0.31)
Q14517 (FAT1; 506, −256, −0.50)
Q685J3 (MUC17; 452, −255, −0.56)
P98164 (LRP2; 522, −243, −0.46)
Q8TDW7 (FAT3; 506, −237, −0.46)
Q99996 (AKAP9; 454, −233, −0.51)
Q6V0I7 (FAT4; 543, −230, −0.42)
Q02952 (AKAP12; 191 , −226, −1.18)
Q9UKN1 (MUC12; 558, −226, −0.40)
Q9H251 (CDH23; 369, −223, −0.60)
Q01484 (ANK2; 434, −212, −0.48)
P21817 (RYR1; 565, −207, −0.36)
Q14789 (GOLGB1; 376, −205, −0.54)
Q6V1P9 (DCHS2; 322, −202, −0.62)
Q9NYQ8 (FAT2; 479, −199, −0.41)
P48681 (NES; 177, −199, −1.12)
Q9NZR2 (LRP1B; 515, −196, −0.38)
Q9Y6R7 (FCGBP; 572, −184, −0.32)
O95359 (TACC2; 309, −183, −0.59)
Q9NU22 (MDN1; 633, −180, −0.28)
Q07954 (LRP1; 505, −178, −0.35)
Q7Z6Z7 (HUWE1; 482, −173, −0.35)
Q5VST9 (OBSCN; 868, −173, −0.19)
P78559 (MAP1A; 305, −170, −0.55)
P46821 (MAP1B; 271, −169, −0.62)
P49454 (CENPF; 368, −169, −0.45)
Q86XX4 (FRAS1; 443, −168, −0.37)
Q8NFC6 (BOD1L1; 330, −162, −0.49)
Q96JQ0 (DCHS1; 346, −162, −0.46)
O94854 (KIAA0754; 135, −162, −1.19)
E2RYF6 (MUC22; 173, −161, −0.92)
O15069 (NACAD; 161, −160, −0.99)
Q5SZK8 (FREM2; 351, −158, −0.44)
Q8IVF2 (AHNAK2; 617, −157, −0.25)
P23327 (HRC; 80, −157, −1.95)
Q8IWU2 (LMTK2; 165, −156, −0.94)
P02549 (SPTA1; 280, −153, −0.54)
O14686 (KMT2D; 593, −148, −0.24)
Q12888 (TP53BP1; 214, −148, −0.69)
Q9BV73 (CEP250; 281, −144, −0.51)
P22105 (TNXB; 464, −144, −0.31)
O95613 (PCNT; 378, −142, −0.37)
P46939 (UTRN; 394, −142, −0.35)
P23471 (PTPRZ1; 255, −139, −0.54)
Q0VD83 (APOBR; 115, −138, −1.20)
Q96QF7 (ACRC; 76, −81, −1.06)
Q3BBV1 (NBPF20; 109, −81, −0.74)
Q2M2H8 (0; 278, −81, −0.29)
Q02224 (CENPE; 316, −81, −0.25)
Q14028 (CNGB1; 140, −80, −0.57)
Q6ZNL6 (FGD5; 160, −80, −0.50)
Q9Y2I1 (NISCH; 167, −80, −0.48)
Q9Y4B6 (VPRBP; 169, −80, −0.47)
Q9BTT0 (ANP32E; 31, −80, −2.60)
Q8N3D4 (EHBP1L1; 162, −80, −0.49)
Q9UM47 (NOTCH3; 244, −80, −0.32)
Q86UQ4 (ABCA13; 576, −80, −0.13)
Q7Z408 (CSMD2; 380, −79, −0.20)
Q32MZ4 (LRRFIP1; 89, −79, −0.88)
Q96T23 (RSF1; 164, −79, −0.48)
P35442 (THBS2; 130, −79, −0.60)
Q9UKA4 (AKAP11; 211 , −78, −0.37)
Q5JTC6 (AMER1; 124, −78, −0.62)
Q9P2D7 (DNAH1; 494, −78, −0.15)
O60229 (KALRN; 340, −78, −0.22)
Q9H094 (NBPF3; 73, −78, −1.06)
Q8N4C6 (NIN; 243, −138, −0.56)
Q13023 (AKAP6; 257, −137, −0.53)
P35556 (FBN2; 315, −137, −0.43)
Q5JRA6 (MIA3; 214, −136, −0.63)
Q15413 (RYR3; 552, −135, −0.24)
Q75N90 (FBN3; 300, −134, −0.44)
O60494 (CUBN; 399, −133, −0.33)
P35555 (FBN1; 312, −132, −0.42)
Q70CQ2 (USP34; 404, −131, −0.32)
Q8NDA2 (HMCN2; 543, −128, −0.23)
P12270 (TPR; 267, −127, −0.47)
Q3T8J9 (GON4L; 249, −126, −0.50)
P46531 (NOTCH1; 273, −125, −0.45)
A2VEC9 (SSPO; 548, −125, −0.22)
Q8IZL8 (PELP1; 120, −122, −1.01)
O43719 (HTATSF1; 86, −122, −1.42)
Q92736 (RYR2; 565, −119, −0.21)
Q12802 (AKAP13; 308, −118, −0.38)
Q9NR09 (BIRC6; 530, −118, −0.22)
P11137 (MAP2; 200, −118, −0.59)
Q04721 (NOTCH2; 265, −117, −0.44)
P49321 (NASP; 85, −115, −1.34)
Q7Z5P9 (MUC19; 598, −115, −0.19)
A6H8Y1 (BDP1; 294, −114, −0.38)
Q9H0E9 (BRD8; 135, −114, −0.84)
P24821 (TNC; 241, −114, −0.47)
B4DH59 (NBPF26; 104, −114, −1.09)
P58107 (EPPK1; 556, −113, −0.20)
Q5H9T9 (FSCB; 88, −113, −1.28)
Q4G0P3 (HYDIN; 576, −113, −0.19)
Q13813 (SPTAN1; 285, −113, −0.39)
Q96JN2 (CCDC136; 134, −112, −0.83)
Q7KZ85 (SUPT6H; 199, −112, −0.56)
Q5RHP9 (ERICH3; 168, −111, −0.65)
P08519 (LPA; 501, −111, −0.22)
Q15751 (HERC1; 532, −111, −0.20)
Q9HAW4 (CLSPN; 151, −110, −0.72)
Q86TD4 (SRL; 101, −109, −1.08)
P11277 (SPTB; 246, −107, −0.43)
Q5TCS8 (AK9; 221, −106, −0.47)
Q9NQC3 (RTN4; 130, −106, −0.81)
Q5JY77 (GPRASP1; 157, −105, −0.66)
Q9UPS6 (SETD1B; 213, −104, −0.48)
Q4LDE5 (SVEP1; 390, −104, −0.26)
Q8WVC0 (LEO1; 75, −103, −1.36)
Q15154 (PCM1; 229, −103, −0.45)
Q9HCU4 (CELSR2; 317, −102, −0.32)
Q5T4S7 (UBR4; 574, −102, −0.17)
O94915 (FRYL; 340, −101, −0.29)
Q13316 (DMP1; 56, −101, −1.81)
Q9BZV3 (IMPG2; 139, −100, −0.72)
P0C091 (FREM3; 238, −100, −0.41)
Q6ZMQ8 (AATK; 145, −98, −0.67)
Q69YN4 (KIAA1429; 202, −98, −0.48)
Q3BBV0 (NBPF1; 139, −98, −0.70)
Q3ZCN5 (OTOGL; 262, −98, −0.37)
P07942 (LAMB1; 198, −98, −0.49)
Q9NZ53 (PODXL2; 65, −73, −1.12)
O15061 (SYNM; 173, −73, −0.42)
Q5RGN0 (NBPF24; 90, −73, −0.80)
Q7Z6I6 (ARHGAP30; 119, −73, −0.61)
Q9C0D2 (KIAA1731; 295, −73, −0.24)
Q9Y2F5 (ICE1; 248, −72, −0.29)
Q8N108 (MIER1; 58, −72, −1.24)
A6NKG5 (RTL1; 155, −72, −0.46)
Q93008 (USP9X; 292, −72, −0.24)
O00507 (USP9Y; 291, −72, −0.24)
A5YM69 (ARHGEF35; 53, −71, −1.33)
P31415 (CASQ1; 45, −71, −1.57)
Q96JQ2 (CLMN; 112, −71, −0.63)
Q96QU1 (PCDH15; 216, −71, −0.32)
Q96JI7 (SPG11; 279, −71, −0.25)
P38398 (BRCA1; 208, −70, −0.33)
O95153 (BZRAP1; 200, −70, −0.34)
Q9Y222 (DMTF1; 84, −70, −0.82)
Q5TBA9 (FRY; 339, −70, −0.20)
Q96Q04 (LMTK3; 154, −70, −0.45)
Q14160 (SCRIB; 175, −70, −0.40)
Q8NI35 (INADL; 196, −97, −0.49)
Q5TI25 (NBPF14; 106, −97, −0.91)
Q8TCU4 (ALMS1; 461, −96, −0.20)
Q86TB3 (ALPK2; 237, −95, −0.40)
Q9Y4E1 (FAM21C; 145, −95, −0.65)
O43164 (PJA2; 78, −95, −1.21)
Q9P1V8 (SAMD15; 77, −95, −1.23)
Q92628 (KIAA0232; 155, −95, −0.61)
O75970 (MPDZ; 222, −94, −0.42)
Q7Z3T8 (ZFYVE16; 169, −94, −0.55)
Q641Q2 (FAM21A; 147, −94, −0.63)
P78509 (RELN; 388, −94, −0.24)
Q8IWT3 (CUL9; 281, −93, −0.33)
Q9NYC9 (DNAH9; 512, −93, −0.18)
Q96ST2 (IWS1; 92, −93, −1.01)
P21675 (TAF1; 213, −93, −0.43)
Q5VU43 (PDE4DIP; 265, −92, −0.34)
Q9P2P6 (STARD9; 516, −92, −0.17)
Q01082 (SPTBN1; 275, −90, −0.32)
Q15643 (TRIP11; 228, −90, −0.39)
Q6ULP2 (AFTPH; 102, −89, −0.87)
Q9BYE9 (CDHR2; 142, −89, −0.62)
Q9UGM3 (DMBT1; 261, −89, −0.34)
Q8IVF4 (DNAH10; 515, −89, −0.17)
P04275 (VWF; 309, −89, −0.28)
P11532 (DMD; 427, −89, −0.20)
Q86WI1 (PKHD1L1; 466, −89, −0.19)
Q9UFH2 (DNAH17; 512, −88, −0.17)
Q13387 (MAPK8IP2; 88, −88, −1.00)
O60732 (MAGEC1; 124, −88, −0.71)
Q96NY7 (CLIC6; 73, −87, −1.19)
Q5T1H1 (EYS; 351, −87, −0.24)
Q63HN8 (RNF213; 591, −87, −0.14)
Q5SNT6 (FAM21B; 137, −87, −0.63)
Q13439 (GOLGA4; 261, −87, −0.33)
Q8IWJ2 (GCC2; 196, −86, −0.43)
Q09666 (AHNAK; 629, −85, −0.13)
Q6VMQ6 (ATF7IP; 136, −85, −0.62)
Q01538 (MYT1; 122, −85, −0.69)
Q9C0C2 (TNKS1BP1; 182, −85, −0.46)
Q86TY3 (C14orf37; 84, −85, −1.00)
Q8NG31 (CASC5; 265, −84, −0.31)
O00461 (GOLIM4; 82, −83, −1.01)
O75096 (LRP4; 212, −83, −0.39)
Q15149 (PLEC; 532, −83, −0.15)
P98160 (HSPG2; 469, −83, −0.17)
O95714 (HERC2; 527, −83, −0.15)
Q7Z407 (CSMD3; 406, −82, −0.20)
Q6UVK1 (CSPG4; 251, −82, −0.32)
Q9BQS8 (FYCO1; 167, −82, −0.49)
Q9ULT8 (HECTD1; 289, −82, −0.28)
P50851 (LRBA; 319, −82, −0.25)
Q3BBV2 (NBPF8; 99, −82, −0.82)
Q9GZU2 (PEG3; 181, −82, −0.45)
Q96PZ7 (CSMD1; 389, −81, −0.20)
Q5TD94 (RSPH4A; 81 , −81 , −1.00)
Q9H0K4 (RSPH6A; 81 , −81 , −1.00)
Q2M3C7 (SPHKAP; 186, −66, −0.35)
A6NDB9 (PALM3; 72, −66, −0.92)
Q96R06 (SPAG5; 134, −66, −0.49)
Q5UIP0 (RIF1; 274, −66, −0.24)
Q9Y485 (DMXL1; 338, −65, −0.19)
Q96RW7 (HMCN1; 613, −65, −0.10)
Q8NFP9 (NBEA; 328, −65, −0.19)
O43157 (PLXNB1; 232, −65, −0.27)
Q96S38 (RPS6KC1; 119, −65, −0.54)
O15027 (SEC16A; 234, −65, −0.27)
O15047 (SETD1A; 186, −65, −0.34)
P49747 (COMP; 83, −65, −0.78)
P82279 (CRB1; 154, −65, −0.42)
O75962 (TRIO; 347, −65, −0.18)
Q5CZC0 (FSIP2; 781, −65, −0.08)
Q06481 (APLP2; 87, −64, −0.73)
P05067 (APP; 87, −64, −0.73)
Q96GW7 (BCAN; 99, −64, −0.64)
O75369 (FLNB; 278, −64, −0.23)
P42858 (HTT; 348, −64, −0.18)
P11047 (LAMC1; 178, −64, −0.36)

TABLE 3-continued

Exemplary naturally occurring negatively supercharged proteins.

Q9Y2I6 (NINL; 156, −78, −0.49)
Q9UPN7 (PPP6R1; 97, −78, −0.80)
Q5H9R7 (PPP6R3; 98, −78, −0.79)
Q6P3W6 (NBPF10; 96, −78, −0.80)
Q14767 (LTBP2; 195, −77, −0.39)
Q9UL68 (MYT1L; 133, −77, −0.57)
Q9BXP8 (PAPPA2; 199, −77, −0.38)
O75154 (RAB11FIP3; 82, −77, −0.93)
Q5T011 (SZT2; 378, −77, −0.20)
O43149 (ZZEF1; 331, −77, −0.23)
Q5QJ38 (TCHHL1; 99, −76, −0.76)
Q96DX7 (TRIM44; 38, −76, −1.97)
P07476 (IVL; 68, −76, −1.10)
P98095 (FBLN2; 127, −76, −0.60)
Q8IWZ3 (ANKHD1; 269, −75, −0.27)
O94985 (CLSTN1; 110, −75, −0.68)
Q7Z7A1 (CNTRL; 269, −75, −0.27)
Q16643 (DBN1; 71, −75, −1.04)
O15355 (PPM1G; 59, −75, −1.26)
Q9H2G4 (TSPYL2; 79, −75, −0.94)
Q6PJW8 (CNST; 80, −74, −0.92)
O60309 (LRRC37A3; 181, −74, −0.40)
Q02817 (MUC2; 540, −74, −0.13)
Q86UW6 (N4BP2; 199, −74, −0.37)
Q6ZRI0 (OTOG; 315, −74, −0.23)
Q96RG2 (PASK; 143, −74, −0.51)
P49746 (THBS3; 104, −74, −0.71)
Q15911 (ZFHX3; 404, −74, −0.18)
H0YM25 (GOLGA6L22; 108, −74, −0.68)
Q92752 (TNR; 150, −74, −0.49)
O60522 (TDRD6; 237, −74, −0.31)
A6NC98 (CCDC88B; 165, −73, −0.44)
Q8TDJ6 (DMXL2; 340, −73, −0.21)
Q8WXX0 (DNAH7; 461, −73, −0.15)
Q86SJ6 (DSG4; 114, −73, −0.64)
O95373 (IPO7; 120, −73, −0.61)
P82094 (TMF1; 123, −61, −0.49)
Q8N660 (NBPF15; 78, −61, −0.78)
Q5SXJ2 (NBPF16; 78, −61, −0.78)
P35499 (SCN4A; 208, −61, −0.29)
P16157 (ANK1; 206, −60, −0.29)
P0C7V8 (DCAF8L2; 71, −60, −0.84)
Q9Y6X4 (FAM169A; 75, −60, −0.80)
A1L4K1 (FSD2; 85, −60, −0.70)
Q9ULW6 (NAP1L2; 53, −60, −1.14)
O75170 (PPP6R2; 105, −60, −0.57)
Q9NWF9 (RNF216; 99, −60, −0.60)
Q9H2G2 (SLK; 143, −60, −0.42)
O95071 (UBR5; 309, −60, −0.19)
P19338 (NCL; 77, −60, −0.78)
Q96M32 (AK7; 83, −60, −0.72)
Q5VXU9 (C9orf84; 165, −60, −0.36)
Q02410 (APBA1; 93, −59, −0.63)
P27797 (CALR; 48, −59, −1.22)
P22223 (CDH3; 91, −59, −0.64)
Q9P225 (DNAH2; 508, −59, −0.11)
Q9P2D6 (FAM135A; 170, −59, −0.34)
Q5VWN6 (FAM208B; 269, −59, −0.21)
Q5SYB0 (FRMPD1; 173, −59, −0.34)
Q9UBN7 (HDAC6; 131, −59, −0.44)
Q92824 (PCSK5; 207, −59, −0.28)
Q96EB6 (SIRT1; 82, −59, −0.72)
Q9UBS9 (SUCO; 139, −59, −0.42)
Q6ZS81 (WDFY4; 354, −59, −0.16)
O14958 (CASQ2; 46, −59, −1.27)
Q96MT7 (WDR52; 112, −59, −0.52)
P10745 (RBP3; 135, −59, −0.43)
Q2TAZ0 (ATG2A; 213, −58, −0.27)
Q96KC9 (CABS1; 43, −58, −1.34)
A2RUR9 (CCDC144A; 165, −58, −0.35)
O94986 (CEP152; 196, −58, −0.29)
Q14315 (FLNC; 291, −58, −0.19)
Q8TEX9 (IPO4; 119, −58, −0.48)
Q5T7N2 (L1TD1; 99, −58, −0.58)
O75197 (LRP5; 179, −58, −0.32)
Q9BZA7 (PCDH11X; 148, −58, −0.39)
Q68CZ1 (RPGRIP1L; 151, −58, −0.38)
Q7Z7G8 (VPS13B; 449, −58, −0.12)
Q8IWB6 (TEX14; 168, −70, −0.41)
Q96PC5 (MIA2; 62, −70, −1.13)
Q14112 (NID2; 151, −70, −0.46)
Q9BZQ8 (FAM129A; 103, −69, −0.66)
Q5H8C1 (FREM1; 244, −69, −0.28)
Q2LD37 (KIAA1109; 555, −69, −0.12)
A6NMS7 (LRRC37A; 188, −69, −0.36)
P07197 (NEFM; 102, −69, −0.67)
Q92834 (RPGR; 113, −69, −0.60)
Q92673 (SORL1; 248, −69, −0.27)
P37275 (ZEB1; 124, −69, −0.55)
Q14515 (SPARCL1; 75, −69, −0.91)
Q86T75 (NBPF11; 99, −69, −0.69)
Q96K76 (USP47; 157, −69, −0.43)
A6NM11 (LRRC37A2; 188, −69, −0.36)
O95405 (ZFYVE9; 156, −68, −0.43)
Q3BBW0 (NBPF9; 100, −68, −0.68)
O43847 (NRD1; 132, −68, −0.51)
Q92688 (ANP32B; 29, −67, −2.32)
Q96BY7 (ATG2B; 233, −67, −0.28)
Q9NYQ6 (CELSR1; 329, −67, −0.20)
Q8TE73 (DNAH5; 529, −67, −0.12)
Q9C0G6 (DNAH6; 476, −67, −0.14)
Q96M86 (DNHD1; 534, −67, −0.12)
P42566 (EPS15; 99, −67, −0.67)
Q9Y4D8 (HECTD4; 439, −67, −0.15)
Q16821 (PPP1R3A; 126, −67, −0.53)
Q8TF05 (PPP4R1; 107, −67, −0.62)
Q76I76 (SSH2; 158, −67, −0.42)
P07996 (THBS1; 129, −67, −0.51)
Q9C0A1 (ZFHX2; 274, −67, −0.24)
Q05DH4 (FAM160A1; 117, −67, −0.57)
Q8IZX4 (TAF1L; 207, −67, −0.32)
Q562E7 (WDR81; 212, −67, −0.31)
Q9UPV0 (CEP164; 164, −66, −0.40)
P14314 (PRKCSH; 59, −66, −1.11)
Q53GL7 (PARP10; 110, −57, −0.51)
P20908 (COL5A1; 184, −57, −0.31)
Q8IVV2 (LOXHD1; 222, −57, −0.25)
P35580 (MYH10; 229, −57, −0.24)
P12259 (F5; 252, −57, −0.22)
Q96JB1 (DNAH8; 515, −57, −0.11)
P49418 (AMPH; 76, −56, −0.73)
Q12774 (ARHGEF5; 177, −56, −0.31)
Q8WYN3 (CSRNP3; 65, −56, −0.86)
Q6XZF7 (DNMBP; 177, −56, −0.31)
Q15029 (EFTUD2; 109, −56, −0.51)
P02751 (FN1; 263, −56, −0.21)
Q14C86 (GAPVD1; 165, −56, −0.33)
P25391 (LAMA1; 337, −56, −0.16)
Q99698 (LYST; 429, −56, −0.13)
O14594 (NCAN; 143, −56, −0.39)
Q8IUM7 (NPAS4; 87, −56, −0.64)
O95197 (RTN3; 113, −56, −0.49)
Q9C093 (SPEF2; 210, −56, −0.26)
Q9C0C9 (UBE2O; 141, −56, −0.39)
Q9C0G0 (ZNF407; 247, −56, −0.22)
P98155 (VLDLR; 96, −56, −0.58)
O60518 (RANBP6; 125, −56, −0.44)
P39059 (COL15A1; 142, −56, −0.39)
O75443 (TECTA; 240, −56, −0.23)
O14525 (ASTN1; 145, −55, −0.37)
P14625 (HSP90B1; 92, −55, −0.59)
Q14676 (MDC1; 227, −55, −0.24)
Q7RTP6 (MICAL3; 224, −55, −0.24)
Q6PFW1 (PPIP5K1; 160, −55, −0.34)
O60437 (PPL; 205, −55, −0.26)
Q9BXT8 (RNF17; 185, −55, −0.29)
P56715 (RP1; 241, −55, −0.22)
P0DME0 (SETSIP; 35, −55, −1.57)
A4UGR9 (XIRP2; 382, −55, −0.14)
Q99689 (FEZ1; 45, −55, −1.21)
Q8TBY9 (WDR66; 130, −55, −0.42)
Q99767 (APBA2; 83, −54, −0.65)
P12830 (CDH1; 97, −54, −0.55)
Q9UJ99 (CDH22; 89, −54, −0.60)
Q5VT06 (CEP350; 351, −54, −0.15)
P21333 (FLNA; 281, −54, −0.19)
O75147 (OBSL1; 207, −64, −0.30)
O75807 (PPP1R15A; 73, −64, −0.87)
Q9BYH1 (SEZ6L; 112, −64, −0.57)
Q9H254 (SPTBN4; 289, −64, −0.22)
Q7Z3K6 (MIER3; 61, −64, −1.04)
P07199 (CENPB; 65, −64, −0.98)
Q6ZMV5 (SMEK3P; 96, −64, −0.66)
A6NFI3 (ZNF316; 108, −64, −0.59)
Q86UP3 (ZFHX4; 394, −64, −0.16)
Q12955 (ANK3; 480, −64, −0.13)
Q9NYF5 (FAM13B; 105, −63, −0.60)
O00410 (IPO5; 124, −63, −0.50)
Q99466 (NOTCH4; 210, −63, −0.30)
P35443 (THBS4; 106, −63, −0.59)
Q14DG7 (TMEM132B; 119, −63, −0.52)
Q9BXT5 (TEX15; 315, −63, −0.19)
Q96DT5 (DNAH11; 521 , −63, −0.12)
P39687 (ANP32A; 29, −62, −2.16)
Q4LE39 (ARID4B; 148, −62, −0.41)
Q8NEP3 (DNAAF1; 80, −62, −0.77)
Q76N89 (HECW1; 180, −62, −0.34)
Q9P2P5 (HECW2; 176, −62, −0.35)
Q96P70 (IPO9; 116, −62, −0.53)
Q14643 (ITPR1; 314, −62, −0.19)
Q8NEZ4 (KMT2C; 541, −62, −0.11)
A2RRP1 (NBAS; 269, −62, −0.23)
O60271 (SPAG9; 146, −62, −0.42)
Q9UPW8 (UNC13A; 193, −62, −0.32)
Q9HCK1 (ZDBF2; 266, −62, −0.23)
P27824 (CANX; 68, −62, −0.91)
A8MZA4 (GOLGA6L6; 94, −62, −0.65)
Q8TF21 (ANKRD24; 124, −61, −0.49)
P29374 (ARID4A; 143, −61, −0.42)
Q96SN8 (CDK5RAP2; 215, −61, −0.28)
Q8IWE5 (PLEKHM2; 113, −61, −0.54)
Q8TDY2 (RB1CC1; 183, −61, −0.33)
Q8IUX7 (AEBP1; 131, −53, −0.40)
P05060 (CHGB; 78, −53, −0.67)
Q99715 (COL12A1; 333, −53, −0.15)
Q49AJ0 (FAM135B; 156, −53, −0.34)
Q8NBR6 (FAM63B; 67, −53, −0.78)
Q58FF7 (HSP90AB3P; 68, −53, −0.77)
P21815 (IBSP; 35, −53, −1.50)
Q92794 (KAT6A; 225, −53, −0.23)
O60333 (KIF1B; 204, −53, −0.25)
Q14596 (NBR1; 107, −53, −0.49)
Q9P2E7 (PCDH10; 113, −53, −0.46)
Q7Z442 (PKD1L2; 273, −53, −0.19)
Q86YN6 (PPARGC1 B; 113, −53, −0.46)
Q6GYQ0 (RALGAPA1; 230, −53, −0.23)
O15020 (SPTBN2; 271, −53, −0.19)
Q6ZRS2 (SRCAP; 344, −53, −0.15)
Q01105 (SET; 33, −53, −1.58)
Q5SWA1 (PPP1R15B; 79, −53, −0.66)
P01266 (TG; 305, −53, −0.17)
Q9NZN5 (ARHGEF12; 173, −52, −0.30)
Q4G0X9 (CCDC40; 130, −52, −0.39)
Q9NR16 (CD163L1; 159, −52, −0.32)
Q9BZQ6 (EDEM3; 105, −52, −0.49)
Q6PRD1 (GPR179; 257, −52, −0.20)
Q9H1H9 (KIF13A; 202, −52, −0.25)
Q9Y4W2 (LAS1L; 83, −52, −0.62)
Q14114 (LRP8; 106, −52, −0.49)
O00566 (MPHOSPH10; 79, −52, −0.65)
Q9HC84 (MUC5B; 596, −52, −0.08)
Q9UKK3 (PARP4; 193, −52, −0.26)
O60721 (SLC24A1; 121, −52, −0.42)
Q9P2D8 (UNC79; 295, −52, −0.17)
Q5THJ4 (VPS13D; 492, −52, −0.10)
Q9C0E2 (XPO4; 130, −52, −0.39)
O15085 (ARHGEF11; 168, −51 , −0.30)
Q9Y6J0 (CABIN1; 246, −51, −0.20)
Q9HBT6 (CDH20; 89, −51, −0.57)
P30622 (CLIP1; 162, −51, −0.31)
Q05707 (COL14A1; 194, −51, −0.26)
O95196 (CSPG5; 60, −51, −0.84)
P0C2W7 (CT47B1; 31, −51, −1.62)
Q9Y2J2 (EPB41L3; 121, −51, −0.42)

TABLE 3-continued

Exemplary naturally occurring negatively supercharged proteins.

O75581 (LRP6; 180, −58, −0.32)
Q9P2G1 (ANKIB1; 122, −57, −0.46)
Q5TH69 (ARFGEF3; 241, −57, −0.23)
Q9Y5Q5 (CORIN; 116, −57, −0.48)
Q14204 (DYNC1H1; 532, −57, −0.10)
Q5W0A0 (ERICH6B; 82, −57, −0.69)
Q8N3X1 (FNBP4; 110, −57, −0.51)
Q92538 (GBF1; 206, −57, −0.27)
Q9UHV7 (MED13; 239, −57, −0.23)
Q8N7H5 (PAF1; 60, −57, −0.95)
Q9BZA8 (PCDH11Y; 147, −57, −0.38)
Q9HCL0 (PCDH18; 126, −57, −0.45)
P09619 (PDGFRB; 124, −57, −0.45)
O60216 (RAD21; 72, −57, −0.79)
O14967 (CLGN; 70, −57, −0.81)
Q5T7N3 (KANK4; 107, −50, −0.46)
Q9UPT6 (MAPK8IP3; 147, −50, −0.33)
Q8N344 (MIER2; 60, −50, −0.83)
Q96PX1 (RNF157; 74, −50, −0.67)
Q96RS0 (TGS1; 97, −50, −0.51)
H0YKK7 (GOLGA6L19; 64, −50, −0.77)
Q96M43 (NBPF4; 72, −50, −0.69)
Q5VWK0 (NBPF6; 72, −50, −0.69)
Q6ZRS4 (CCDC129; 115, −50, −0.43)
Q8WUM0 (NUP133; 129, −50, −0.38)
Q9H159 (CDH19; 87, −49, −0.56)
Q5TB80 (CEP162; 162, −49, −0.30)
P28715 (ERCC5; 133, −49, −0.36)
Q14974 (KPNB1; 97, −49, −0.50)
P07196 (NEFL; 62, −49, −0.79)
Q9ULJ8 (PPP1R9A; 123, −49, −0.39)
Q15276 (RABEP1; 99, −49, −0.49)
P49792 (RANBP2; 358, −49, −0.13)
Q14257 (RCN2; 37, −49, −1.32)
Q96Q15 (SMG1; 411, −49, −0.11)
Q9UKZ4 (TENM1; 305, −49, −0.16)
Q9UNS1 (TIMELESS; 139, −49, −0.35)
Q96A61 (TRIM52; 35, −49, −1.41)
O60763 (USO1; 108, −49, −0.45)
O43379 (WDR62; 166, −49, −0.29)
Q68DK2 (ZFYVE26; 285, −49, −0.17)
P10645 (CHGA; 51, −49, −0.96)
O15240 (VGF; 67, −49, −0.72)
Q8NEM2 (SHCBP1; 76, −49, −0.64)
Q12797 (ASPH; 86, −49, −0.57)
Q5VZP5 (DUSP27; 130, −49, −0.37)
Q9UJ98 (STAG3; 139, −49, −0.35)
Q08378 (GOLGA3; 167, −49, −0.29)
Q8IWV7 (UBR1; 200, −49, −0.24)
Q9UKX3 (MYH13; 224, −49, −0.21)
Q9Y493 (ZAN; 306, −49, −0.16)
Q9BXK5 (BCL2L13; 53, −48, −0.91)
Q9P1Z2 (CALCOCO1; 77, −48, −0.62)
P12107 (COL11A1; 181 , −48, −0.26)
Q9UER7 (DAXX; 81, −48, −0.58)
Q96RT1 (ERBB2IP; 158, −48, −0.30)
P48551 (IFNAR2; 58, −48, −0.83)
O15397 (IPO8; 120, −48, −0.40)
Q14678 (KANK1; 147, −48, −0.32)
Q8WYB5 (KAT6B; 231, −48, −0.20)
P50748 (KNTC1; 251, −48, −0.19)
Q6ZNJ1 (NBEAL2; 303, −48, −0.15)
P14543 (NID1; 136, −48, −0.35)
Q9BYW2 (SETD2; 288, −48, −0.16)
P32418 (SLC8A1; 109, −48, −0.44)
Q6IN85 (SMEK1; 95, −48, −0.50)
Q5MIZ7 (SMEK2; 97, −48, −0.49)
O75643 (SNRNP200; 245, −48, −0.19)
P18583 (SON; 264, −48, −0.18)
O75410 (TACC1; 88, −48, −0.54)
Q13685 (AAMP; 47, −48, −1.02)
P52739 (ZNF131; 71, −48, −0.67)
Q86UP0 (CDH24; 88, −43, −0.49)
Q9BQT9 (CLSTN3; 106, −43, −0.40)
P55884 (EIF3B; 92, −43, −0.46)
Q04637 (EIF4G1; 175, −43, −0.24)
Q2NKX8 (ERCC6L; 141, −43, −0.30)
Q8NB25 (FAM184A; 133, −43, −0.32)
Q6ZWJ8 (KCP; 160, −54, −0.33)
O43451 (MGAM; 210, −54, −0.25)
Q02505 (MUC3A; 266, −54, −0.20)
P55209 (NAP1L1; 45, −54, −1.19)
Q14494 (NFE2L1; 85, −54, −0.63)
Q9Y6V0 (PCLO; 553, −54, −0.09)
P50542 (PEX5; 71, −54, −0.76)
P08F94 (PKHD1; 447, −54, −0.12)
Q16799 (RTN1; 84, −54, −0.64)
P28290 (SSFA2; 138, −54, −0.39)
O00267 (SUPT5H; 121, −54, −0.44)
Q9Y4G6 (TLN2; 272, −54, −0.19)
Q6ZSY5 (PPP1R3F; 83, −54, −0.65)
P55286 (CDH8; 88, −54, −0.61)
Q96QE4 (LRRC37B; 106, −54, −0.51)
P55287 (CDH11; 88, −48, −0.54)
P14410 (SI; 209, −48, −0.22)
Q14839 (CHD4; 218, −48, −0.22)
Q9UPS8 (ANKRD26; 196, −47, −0.23)
P19022 (CDH2; 100, −47, −0.47)
O15078 (CEP290; 290, −47, −0.16)
Q9P2D1 (CHD7; 336, −47, −0.13)
Q9HCE0 (EPG5; 292, −47, −0.16)
Q9UK61 (FAM208A; 189, −47, −0.24)
Q5T1M5 (FKBP15; 134, −47, −0.35)
Q16236 (NFE2L2; 68, −47, −0.69)
Q12769 (NUP160; 162, −47, −0.28)
Q9HC10 (OTOF; 227, −47, −0.20)
P16234 (PDGFRA; 123, −47, −0.38)
A6NGW2 (STRCP1; 192, −47, −0.24)
Q5H9L4 (TAF7L; 53, −47, −0.89)
O94972 (TRIM37; 108, −47, −0.43)
Q8N3P4 (VPS8; 162, −47, −0.29)
Q9NZT2 (OGFR; 73, −47, −0.64)
P78362 (SRPK2; 78, −47, −0.60)
Q3MJ40 (CCDC144B; 83, −47, −0.56)
P55283 (CDH4; 100, −47, −0.46)
Q9Y5G9 (PCDHGA4; 101, −47, −0.46)
Q9Y5G8 (PCDHGA5; 101, −47, −0.46)
Q9Y5G6 (PCDHGA7; 102, −47, −0.46)
Q8N2S1 (LTBP4; 173, −47, −0.27)
O60303 (KIAA0556; 181, −47, −0.25)
Q7RTU9 (STRC; 193, −47, −0.24)
P13535 (MYH8; 223, −47, −0.21)
P12882 (MYH1; 223, −47, −0.21)
P35579 (MYH9; 227, −47, −0.20)
H7BZ55 (0; 248, −47, −0.18)
Q8IZF6 (GPR112; 333, −47, −0.14)
Q92667 (AKAP1; 97, −46, −0.47)
Q9H4D0 (CLSTN2; 107, −46, −0.42)
Q5JQC4 (CT47A1; 30, −46, −1.52)
Q6ZR08 (DNAH12; 357, −46, −0.12)
Q5JWR5 (DOPEY1; 277, −46, −0.16)
Q8NCM8 (DYNC2H1; 493, −46, −0.09)
Q96KQ7 (EHMT2; 132, −46, −0.34)
Q8IWE2 (FAM114A1; 61 , −46, −0.75)
A1Z1Q3 (MACROD2; 50, −46, −0.91)
Q71F56 (MED13L; 243, −46, −0.18)
Q14980 (NUMA1; 238, −46, −0.19)
Q8WY54 (PPM1E; 85, −46, −0.54)
Q96SB3 (PPP1R9B; 89, −46, −0.51)
Q6UXD5 (SEZ6L2; 98, −46, −0.47)
P10451 (SPP1; 35, −46, −1.29)
Q9NY15 (STAB1; 275, −46, −0.16)
Q66K14 (TBC1D9B; 141 , −46, −0.32)
Q92973 (TNPO1; 102, −46, −0.44)
Q8N3L3 (TXLNB; 77, −46, −0.60)
Q9UPU5 (USP24; 294, −46, −0.15)
Q7Z5K2 (WAPAL; 133, −46, −0.34)
Q58FF6 (HSP90AB4P; 58, −46, −0.78)
D6RB28 (GOLGA6L18; 63, −46, −0.73)
Q5IJ48 (CRB2; 134, −46, −0.34)
Q8IYF3 (TEX11; 108, −42, −0.38)
P00450 (CP; 122, −42, −0.34)
O43432 (EIF4G3; 177, −42, −0.23)
Q14524 (SCN5A; 227, −42, −0.18)
Q14573 (ITPR3; 304, −42, −0.13)
Q14571 (ITPR2; 308, −42, −0.13)
Q14CM0 (FRMPD4; 144, −51, −0.35)
P54257 (HAP1; 76, −51, −0.67)
Q16659 (MAPK6; 83, −51, −0.61)
P35749 (MYH11; 227, −51, −0.22)
Q06190 (PPP2R3A; 130, −51, −0.39)
Q9NRC6 (SPTBN5; 417, −51, −0.12)
A6NEF3 (GOLGA6L4; 68, −51, −0.75)
Q08379 (GOLGA2; 113, −51, −0.45)
O43423 (ANP32C; 27, −50, −1.86)
Q8N1W1 (ARHGEF28; 192, −50, −0.26)
O75309 (CDH16; 90, −50, −0.55)
Q14999 (CUL7; 191, −50, −0.26)
Q9UPY3 (DICER1; 219, −50, −0.22)
O75923 (DYSF; 237, −50, −0.21)
Q8NC44 (FAM134A; 58, −50, −0.86)
Q5T9S5 (CCDC18; 169, −46, −0.27)
P11055 (MYH3; 224, −46, −0.20)
Q5TZA2 (CROCC; 229, −45, −0.19)
A6NGE4 (DCAF8L1; 67, −45, −0.66)
Q8TD57 (DNAH3; 471, −45, −0.09)
Q6PGQ1 (DRICH1; 25, −45, −1.79)
P11717 (IGF2R; 274, −45, −0.16)
O60502 (MGEA5; 103, −45, −0.43)
P13533 (MYH6; 224, −45, −0.20)
Q13018 (PLA2R1; 169, −45, −0.26)
Q9NY27 (PPP4R2; 47, −45, −0.95)
Q8NDX1 (PSD4; 116, −45, −0.38)
P13521 (SCG2; 71, −45, −0.63)
Q6ZT12 (UBR3; 212, −45, −0.21)
Q9UHP3 (USP25; 122, −45, −0.36)
Q96RL7 (VPS13A; 360, −45, −0.12)
Q9BUR4 (WRAP53; 59, −45, −0.75)
Q8N8U3 (ZCCHC5; 53, −45, −0.85)
Q9GZS0 (DNAI2; 69, −45, −0.65)
Q9Y5Q9 (GTF3C3; 101, −45, −0.44)
O14787 (TNPO2; 101, −45, −0.44)
Q08174 (PCDH1; 115, −45, −0.39)
Q96KN7 (RPGRIP1; 147, −45, −0.30)
Q14766 (LTBP1; 187, −45, −0.24)
Q9Y623 (MYH4; 223, −45, −0.20)
Q8NB66 (UNC13C; 251, −45, −0.17)
Q9Y6D6 (ARFGEF1; 209, −44, −0.21)
Q8IW35 (CEP97; 97, −44, −0.45)
Q8TD26 (CHD6; 305, −44, −0.14)
P54105 (CLNS1A; 26, −44, −1.67)
P53675 (CLTCL1; 187, −44, −0.23)
Q16531 (DDB1; 127, −44, −0.34)
Q96F46 (IL17RA; 96, −44, −0.45)
Q8N201 (INTS1; 244, −44, −0.18)
Q9NPG4 (PCDH12; 129, −44, −0.34)
O14917 (PCDH17; 126, −44, −0.34)
Q9UN71 (PCDHGB4; 100, −44, −0.44)
P06454 (PTMA; 12, −44, −3.60)
Q5HYW3 (RGAG4; 65, −44, −0.67)
Q15393 (SF3B3; 136, −44, −0.32)
Q9BXU1 (STK31; 116, −44, −0.38)
Q9H7C4 (SYNC; 55, −44, −0.79)
O95759 (TBC1D8; 131, −44, −0.33)
Q96RU2 (USP28; 122, −44, −0.35)
Q93009 (USP7; 128, −44, −0.34)
Q96ER3 (SAAL1; 54, −44, −0.82)
Q9H069 (LRRC48; 61, −44, −0.72)
P55289 (CDH12; 88, −44, −0.49)
Q9ULB4 (CDH9; 89, −44, −0.49)
P08048 (ZFY; 91, −44, −0.48)
Q9P260 (KIAA1468; 135, −44, −0.32)
A4FU69 (EFCAB5; 173, −44, −0.25)
Q13219 (PAPPA; 181, −44, −0.24)
Q8N7Z5 (ANKRD31; 211, −44, −0.20)
Q9H1A4 (ANAPC1; 217, −43, −0.19)
O15013 (ARHGEF10; 152, −43, −0.28)
Q9NW68 (BSDC1; 47, −43, −0.91)
P57103 (SLC8A3; 103, −40, −0.38)
Q8WXE9 (STON2; 101, −40, −0.39)
Q9Y6A5 (TACC3; 90, −40, −0.44)
Q6N022 (TENM4; 308, −40, −0.12)
Q9Y4E8 (USP15; 112, −40, −0.35)
Q86YA3 (ZGRF1; 237, −40, −0.16)

TABLE 3-continued

Exemplary naturally occurring negatively supercharged proteins.

Q8IYD8 (FANCM; 232, −43, −0.18)
Q17R60 (IMPG1; 89, −43, −0.48)
P41229 (KDM5C; 176, −43, −0.24)
Q9UQF2 (MAPK8IP1; 78, −43, −0.55)
Q7Z406 (MYH14; 228, −43, −0.18)
Q9UKX2 (MYH2; 223, −43, −0.19)
Q6ZS30 (NBEAL1; 307, −43, −0.13)
Q6IBW4 (NCAPH2; 68, −43, −0.63)
Q9H5I5 (PIEZO2; 318, −43, −0.13)
Q86YS3 (RAB11FIP4; 72, −43, −0.59)
Q2NKQ1 (SGSM1; 130, −43, −0.33)
Q8N3U4 (STAG2; 141, −43, −0.30)
Q8N1F8 (STK11IP; 121, −43, −0.35)
Q9UMZ2 (SYNRG; 141, −43, −0.30)
Q6YHU6 (THADA; 220, −43, −0.19)
P98073 (TMPRSS15; 113, −43, −0.38)
Q8IWV8 (UBR2; 201, −43, −0.21)
Q9HCC9 (ZFYVE28; 96, −43, −0.44)
Q13438 (OS9; 76, −43, −0.56)
Q9Y5H3 (PCDHGA10; 101, −43, −0.42)
Q9Y5H1 (PCDHGA2; 101, −43, −0.42)
Q8N6L0 (CCDC155; 63, −42, −0.66)
Q9P219 (CCDC88C; 228, −42, −0.18)
P16070 (CD44; 82, −42, −0.51)
Q02413 (DSG1; 114, −42, −0.36)
Q14126 (DSG2; 122, −42, −0.34)
Q86X53 (ERICH1; 49, −42, −0.85)
Q9H501 (ESF1; 99, −42, −0.42)
P14317 (HCLS1; 54, −42, −0.77)
P82970 (HMGN5; 32, −42, −1.33)
Q1KMD3 (HNRNPUL2; 85, −42, −0.49)
Q5VYJ5 (MALRD1; 164, −42, −0.25)
Q6ZN16 (MAP3K15; 147, −42, −0.28)
P12883 (MYH7; 223, −42, −0.18)
P27815 (PDE4A; 98, −42, −0.42)
Q7Z5L2 (R3HCC1L; 88, −42, −0.47)
Q9H2M9 (RAB3GAP2; 156, −42, −0.26)
P46060 (RANGAP1; 64, −42, −0.66)
Q9H446 (RWDD1; 28, −42, −1.50)
Q92543 (SNX19; 109, −42, −0.38)
Q8WVM7 (STAG1; 144, −42, −0.29)
Q6ZT07 (TBC1D9; 143, −42, −0.29)
Q9H1E5 (TMX4; 39, −42, −1.07)
Q8WV44 (TRIM41; 72, −42, −0.58)
P45974 (USP5; 96, −42, −0.43)
Q5MJ10 (SPANXN2; 20, −42, −2.10)
A6NEY3 (GOLGA6L3; 56, −42, −0.75)
Q7Z6P3 (RAB44; 78, −42, −0.54)
Q6NZY4 (ZCCHC8; 79, −42, −0.53)
P17010 (ZFX; 91, −42, −0.46)
Q9Y5G1 (PCDHGB3; 101, −42, −0.41)
Q8TC90 (CCER1; 46, −38, −0.81)
Q9NYQ7 (CELSR3; 358, −38, −0.10)
Q8TDI0 (CHD5; 223, −38, −0.17)
Q6P2E9 (EDC4; 152, −38, −0.25)
Q15075 (EEA1; 162, −38, −0.23)
Q6P6B1 (ERICH5; 40, −38, −0.95)
Q9UNN5 (FAF1; 74, −38, −0.51)
P49327 (FASN; 273, −38, −0.13)
Q9UK22 (FBXO2; 33, −38, −1.14)
Q9BQQ3 (GORASP1; 46, −38, −0.81)
Q9BQS7 (HEPH; 130, −38, −0.29)
Q9UPZ3 (HPS5; 127, −38, −0.29)
Q9UG01 (IFT172; 198, −38, −0.19)
Q9NQT8 (KIF13B; 203, −38, −0.18)
Q99683 (MAP3K5; 155, −38, −0.24)
O75095 (MEGF6; 161, −38, −0.23)
Q9UBG0 (MRC2; 167, −38, −0.22)
Q9Y4A8 (NFE2L3; 76, −38, −0.49)
Q92621 (NUP205; 228, −38, −0.16)
Q9Y5H5 (PCDHA9; 102, −38, −0.37)
O60330 (PCDHGA12; 101, −38, −0.37)
Q6P2P2 (PRMT9; 95, −38, −0.40)
Q13200 (PSMD2; 100, −38, −0.37)
Q86WV1 (SKAP1; 41, −38, −0.91)
O15040 (TECPR2; 154, −38, −0.24)
Q13610 (PWP1; 56, −38, −0.68)
P30203 (CD6; 72, −38, −0.52)
Q9P1Z9 (CCDC180; 191, −41, −0.21)
Q9HCK8 (CHD8; 291, −41, −0.14)
P24386 (CHM; 73, −41, −0.55)
Q00610 (CLTC; 192, −41, −0.21)
Q9Y5B0 (CTDP1; 104, −41, −0.39)
Q5JWF2 (GNAS; 111, −41, −0.36)
P07900 (HSP90AA1; 85, −41, −0.48)
Q9BVV6 (KIAA0586; 169, −41, −0.24)
P24043 (LAMA2; 344, −41, −0.11)
Q9UBF1 (MAGEC2; 41, −41, −0.99)
Q13615 (MTMR3; 134, −41, −0.30)
P13591 (NCAM1; 95, −41, −0.43)
Q15003 (NCAPH; 83, −41, −0.49)
O94916 (NFAT5; 166, −41, −0.24)
Q6ZVD8 (PHLPP2; 147, −41, −0.27)
Q5THK1 (PRR14L; 237, −41, −0.17)
Q07283 (TCHH; 254, −41, −0.16)
Q96RT7 (TUBGCP6; 200, −41, −0.20)
Q14139 (UBE4A; 123, −41, −0.33)
Q9HAU5 (UPF2; 148, −41, −0.27)
Q9H321 (VCX3B; 27, −41, −1.52)
Q702N8 (XIRP1; 199, −41, −0.20)
Q8N7Z2 (GOLGA6L1; 77, −41, −0.53)
O00418 (EEF2K; 82, −41, −0.49)
P01130 (LDLR; 95, −41, −0.42)
Q9Y5G7 (PCDHGA6; 101, −41, −0.40)
Q9Y5H4 (PCDHGA1; 101, −41, −0.40)
Q9Y5F6 (PCDHGC5; 102, −41, −0.40)
O43707 (ACTN4; 105, −41, −0.39)
Q8N2E2 (VWDE; 177, −41, −0.23)
P60006 (ANAPC15; 14, −40, −2.80)
Q9UNK9 (ANGEL1; 75, −40, −0.53)
Q9C0F0 (ASXL3; 242, −40, −0.16)
P55291 (CDH15; 89, −40, −0.44)
Q9ULB5 (CDH7; 87, −40, −0.45)
Q9P2I0 (CPSF2; 88, −40, −0.45)
Q96S65 (CSRNP1; 64, −40, −0.62)
Q7L7V1 (DHX32; 84, −40, −0.47)
O95905 (ECD; 73, −40, −0.54)
Q9H9B1 (EHMT1; 141, −40, −0.28)
Q5W0V3 (FAM160B1; 87, −40, −0.46)
Q4V328 (GRIPAP1; 96, −40, −0.41)
Q9BXL5 (HEMGN; 55, −40, −0.72)
P08238 (HSP90AB1; 83, −40, −0.48)
Q96RY7 (IFT140; 165, −40, −0.24)
Q9BY66 (KDM5D; 174, −40, −0.22)
Q96Q89 (KIF20B; 211, −40, −0.18)
Q6A162 (KRT40; 48, −40, −0.83)
Q9Y2K3 (MYH15; 225, −40, −0.17)
Q9HD67 (MYO10; 237, −40, −0.16)
Q8TAB3 (PCDH19; 126, −40, −0.31)
Q86WI3 (NLRC5; 205, −37, −0.18)
Q8N6Y1 (PCDH20; 105, −37, −0.35)
Q9UN67 (PCDHB10; 88, −37, −0.42)
Q9UN66 (PCDHB8; 88, −37, −0.42)
Q08499 (PDE4D; 91, −37, −0.40)
Q07864 (POLE; 262, −37, −0.14)
Q15262 (PTPRK; 162, −37, −0.22)
Q2PPJ7 (RALGAPA2; 211, −37, −0.17)
Q09028 (RBBP4; 48, −37, −0.77)
Q15424 (SAFB; 103, −37, −0.36)
O60279 (SUSD5; 68, −37, −0.54)
Q8WVT3 (TRAPPC12; 79, −37, −0.46)
Q2M329 (CCDC96; 63, −37, −0.59)
Q9BQI7 (PSD2; 85, −37, −0.43)
Q9Y5G3 (PCDHGB1; 100, −37, −0.36)
P35606 (COPB2; 102, −37, −0.36)
O43491 (EPB41L2; 113, −37, −0.32)
O75976 (CPD; 153, −37, −0.24)
O00763 (ACACB; 277, −36, −0.13)
Q9Y4K1 (AIM1; 189, −36, −0.19)
O75179 (ANKRD17; 274, −36, −0.13)
Q6ZP65 (CCDC64; 65, −36, −0.55)
Q9HBB8 (CDHR5; 88, −36, −0.40)
Q9UQ88 (CDK11A; 91, −36, −0.39)
P26374 (CHML; 74, −36, −0.48)
Q9NZV1 (CRIM1; 114, −36, −0.31)
Q8NEL9 (DDHD1; 100, −36, −0.35)
O43852 (CALU; 37, −40, −1.07)
P0C7A2 (FAM153B; 44, −40, −0.91)
Q00987 (MDM2; 55, −40, −0.72)
Q92681 (RSC1A1; 67, −40, −0.59)
Q0VDD7 (C19orf57; 70, −40, −0.57)
Q9Y5F1 (PCDHB12; 87, −40, −0.46)
P19838 (NFKB1; 105, −40, −0.37)
O00291 (HIP1; 116, −40, −0.34)
Q6ZRK6 (CCDC73; 124, −40, −0.32)
Q9HC56 (PCDH9; 136, −40, −0.29)
Q6Q759 (SPAG17; 252, −40, −0.15)
Q9NY61 (AATF; 63, −39, −0.61)
Q13085 (ACACA; 266, −39, −0.14)
Q8N4S0 (CCDC82; 64, −39, −0.60)
Q8IUR6 (CREBRF; 72, −39, −0.54)
Q9Y6B2 (EID1; 21, −39, −1.86)
Q7L0X2 (ERICH6; 75, −39, −0.51)
Q6H9L7 (ISM2; 64, −39, −0.61)
Q92845 (KIFAP3; 91, −39, −0.42)
Q6UXC1 (MAMDC4; 131, −39, −0.29)
O60462 (NRP2; 105, −39, −0.37)
Q9UN73 (PCDHA6; 103, −39, −0.37)
Q12923 (PTPN13; 277, −39, −0.14)
Q9H5N1 (RABEP2; 64, −39, −0.61)
Q9Y3P9 (RABGAP1; 122, −39, −0.32)
O15034 (RIMBP2; 116, −39, −0.33)
P08922 (ROS1; 264, −39, −0.14)
Q8IZE3 (SCYL3; 83, −39, −0.47)
Q8IY92 (SLX4; 200, −39, −0.19)
Q9BYV6 (TRIM55; 60, −39, −0.64)
Q9NYU2 (UGGT1; 177, −39, −0.22)
P51784 (USP11; 110, −39, −0.35)
Q8IZQ1 (WDFY3; 395, −39, −0.09)
Q96B54 (ZNF428; 20, −39, −1.90)
A1L162 (ERICH2; 18, −39, −2.20)
P55822 (SH3BGR; 26, −39, −1.49)
Q96F63 (CCDC97; 39, −39, −1.00)
P10912 (GHR; 72, −39, −0.54)
Q9Y5E8 (PCDHB15; 86, −39, −0.45)
O00408 (PDE2A; 106, −39, −0.36)
Q53EL9 (SEZ6; 107, −39, −0.36)
Q7Z3S7 (CACNA2D4; 128, −39, −0.30)
Q5KSL6 (DGKK; 142, −39, −0.27)
Q9UQP3 (TNN; 144, −39, −0.27)
Q9UKP4 (ADAMTS7; 184, −39, −0.21)
Q9UMZ3 (PTPRQ; 261, −39, −0.14)
P98161 (PKD1; 463, −39, −0.08)
O75445 (USH2A; 576, −39, −0.06)
Q9Y2D5 (AKAP2; 95, −38, −0.40)
O96018 (APBA3; 61, −38, −0.61)
Q8IYA2 (CCDC144CP; 143, −38, −0.26)
Q5T481 (RBM20; 134, −36, −0.26)
Q8NHU2 (C20orf26; 141, −36, −0.25)
Q9H7P9 (PLEKHG2; 148, −36, −0.24)
Q6IE36 (OVOS2; 161, −36, −0.22)
P78363 (ABCA4; 256, −35, −0.13)
Q5T1B0 (AXDND1; 118, −35, −0.29)
O60566 (BUB1B; 120, −35, −0.29)
O60840 (CACNA1F; 221, −35, −0.15)
Q9ULU8 (CADPS; 153, −35, −0.22)
Q0VF96 (CGNL1; 149, −35, −0.23)
Q86UF2 (CTAGE6; 88, −35, −0.39)
Q8WYA6 (CTNNBL1; 65, −35, −0.53)
P32926 (DSG3; 108, −35, −0.32)
O60344 (ECE2; 100, −35, −0.35)
Q13144 (EIF2B5; 80, −35, −0.43)
Q8TF40 (FNIP1; 131, −35, −0.26)
P29083 (GTF2E1; 49, −35, −0.70)
Q92539 (LPIN2; 99, −35, −0.35)
Q96PY6 (NEK1; 143, −35, −0.24)
Q8N543 (OGFOD1; 63, −35, −0.55)
Q9NWQ8 (PAG1; 47, −35, −0.74)
Q9Y5F0 (PCDHB13; 88, −35, −0.39)
Q07343 (PDE4B; 83, −35, −0.41)
Q6P1J6 (PLB1; 163, −35, −0.21)
Q6WKZ4 (RAB11FIP1; 137, −35, −0.25)
Q16576 (RBBP7; 48, −35, −0.73)
Q8WYR4 (RSPH1; 35, −35, −0.99)

TABLE 3-continued

Exemplary naturally occurring negatively supercharged proteins.

Q9Y5F2 (PCDHB11; 87, −38, −0.43)
P55285 (CDH6; 88, −38, −0.43)
Q9Y6N8 (CDH10; 88, −38, −0.42)
Q96D09 (GPRASP2; 94, −38, −0.40)
Q9Y5H0 (PCDHGA3; 101, −38, −0.37)
Q9Y5H2 (PCDHGA11; 102, −38, −0.37)
Q9Y5H8 (PCDHA3; 102, −38, −0.37)
P12814 (ACTN1; 103, −38, −0.36)
A1L4H1 (SSC5D; 166, −38, −0.22)
Q9NZ56 (FMN2; 180, −38, −0.21)
P16144 (ITGB4; 202, −38, −0.18)
O00213 (APBB1; 77, −37, −0.47)
Q9H1I8 (ASCC2; 86, −37, −0.42)
O75952 (CABYR; 53, −37, −0.70)
Q8N163 (CCAR2; 103, −37, −0.35)
Q13634 (CDH18; 88, −37, −0.42)
Q9H175 (CSRNP2; 60, −37, −0.62)
Q58WW2 (DCAF6; 96, −37, −0.38)
Q9Y3R5 (DOPEY2; 258, −37, −0.14)
O14576 (DYNC1I1; 73, −37, −0.50)
Q9Y6C2 (EMILIN1; 107, −37, −0.34)
Q9UNN4 (GTF2A1L; 52, −37, −0.70)
Q969F1 (GTF3C6; 24, −37, −1.53)
O95163 (IKBKAP; 150, −37, −0.24)
P24394 (IL4R; 90, −37, −0.41)
Q9UI26 (IPO11; 113, −37, −0.32)
P09848 (LCT; 219, −37, −0.16)
A7E2Y1 (MYH7B; 221, −37, −0.16)
Q99733 (NAP1L4; 43, −37, −0.86)
Q96JN8 (NEURL4; 167, −37, −0.22)
Q8WZ55 (BSND; 35, −34, −0.96)
Q16790 (CA9; 50, −34, −0.68)
O75155 (CAND2; 135, −34, −0.25)
P17655 (CAPN2; 80, −34, −0.42)
Q86VB7 (CD163; 125, −34, −0.27)
O15320 (CTAGE5; 91, −34, −0.37)
O14529 (CUX2; 162, −34, −0.21)
Q13409 (DYNC1I2; 71, −34, −0.47)
Q9P2K8 (EIF2AK4; 187, −34, −0.18)
P52655 (GTF2A1; 42, −34, −0.81)
Q03933 (HSF2; 60, −34, −0.56)
Q14568 (HSP90AA2; 39, −34, −0.86)
P32019 (INPP5B; 113, −34, −0.30)
O94829 (IPO13; 108, −34, −0.31)
P20701 (ITGAL; 129, −34, −0.26)
Q53EV4 (LRRC23; 40, −34, −0.85)
Q9C099 (LRRCC1; 120, −34, −0.28)
Q96JM4 (LRRIQ1; 199, −34, −0.17)
Q96GA3 (LTV1; 55, −34, −0.61)
P43363 (MAGEA10; 41, −34, −0.83)
P49736 (MCM2; 102, −34, −0.33)
Q96NT1 (NAP1L5; 20, −34, −1.73)
Q9Y4C0 (NRXN3; 181, −34, −0.18)
Q9Y5I2 (PCDHA10; 103, −34, −0.33)
Q9Y5E1 (PCDHB9; 87, −34, −0.39)
Q58EX7 (PLEKHG4; 131, −34, −0.25)
Q9ULL4 (PLXNB3; 207, −34, −0.16)
Q9HAZ2 (PRDM16; 140, −34, −0.24)
Q96D15 (RCN3; 37, −34, −0.90)
Q9BWU0 (SLC4A1AP; 89, −34, −0.38)
Q13033 (STRN3; 87, −34, −0.38)
Q9Y5L0 (TNPO3; 104, −34, −0.32)
P48553 (TRAPPC10; 142, −34, −0.23)
Q96RT8 (TUBGCP5; 118, −34, −0.28)
Q86VQ3 (TXNDC2; 60, −34, −0.56)
P41226 (UBA7; 112, −34, −0.30)
O94763 (URI1; 60, −34, −0.56)
O75717 (WDHD1; 126, −34, −0.26)
P0C2Y1 (NBPF7; 48, −34, −0.70)
Q9H6Z4 (RANBP3; 60, −34, −0.56)
Q9Y692 (GMEB1; 63, −34, −0.54)
P54829 (PTPN5; 64, −34, −0.53)
B2RXH4 (BTBD18; 78, −34, −0.43)
Q86UA1 (PRPF39; 78, −34, −0.43)
Q5H9M0 (MUM1L1; 79, −34, −0.43)
O14867 (BACH1; 82, −34, −0.41)
O43815 (STRN; 86, −34, −0.39)
Q9Y5E4 (PCDHB5; 86, −34, −0.39)
Q8NDI1 (EHBP1; 140, −36, −0.25)
Q9NZJ5 (EIF2AK3; 125, −36, −0.28)
O60841 (EIF5B; 139, −36, −0.25)
Q7Z2Y8 (GVINP1; 279, −36, −0.12)
Q9NQC8 (IFT46; 34, −36, −1.04)
Q86UP2 (KTN1; 156, −36, −0.23)
P55268 (LAMB2; 196, −36, −0.18)
A6NHM9 (MOXD2P; 56, −36, −0.63)
Q86W25 (NLRP13; 119, −36, −0.30)
P07237 (P4HB; 57, −36, −0.63)
Q08493 (PDE4C; 80, −36, −0.45)
P35913 (PDE6B; 98, −36, −0.36)
P40855 (PEX19; 33, −36, −1.09)
O15067 (PFAS; 145, −36, −0.24)
Q15042 (RAB3GAP1; 111, −36, −0.32)
Q9NRP7 (STK36; 144, −36, −0.25)
O14795 (UNC13B; 181, −36, −0.19)
Q8NDM7 (WDR96; 192, −36, −0.18)
Q8TBC5 (ZSCAN18; 55, −36, −0.65)
Q49AR2 (C5orf22; 50, −36, −0.72)
Q9H6L5 (FAM134B; 55, −36, −0.65)
Q6PI26 (SHQ1; 65, −36, −0.55)
Q9UJC3 (HOOK1; 85, −36, −0.42)
Q8IV76 (PASD1; 87, −36, −0.41)
Q9Y5E9 (PCDHB14; 88, −36, −0.41)
Q9Y5G4 (PCDHGA9; 102, −36, −0.35)
Q9UN74 (PCDHA4; 102, −36, −0.35)
P57740 (NUP107; 106, −36, −0.33)
Q68DQ2 (CRYBG3; 116, −36, −0.30)
P01133 (EGF; 134, −36, −0.26)
Q96JB5 (CDK5RAP3; 57, −33, −0.57)
O00533 (CHL1; 135, −33, −0.24)
P33076 (CIITA; 124, −33, −0.26)
Q2KHT3 (CLEC16A; 118, −33, −0.28)
Q9NVR5 (DNAAF2; 91, −33, −0.36)
Q9UBC2 (EPS15L1; 94, −33, −0.35)
Q86XD5 (FAM131B; 36, −33, −0.92)
Q9Y4F9 (FAM65B; 119, −33, −0.27)
Q16665 (HIF1A; 93, −33, −0.35)
Q96DU7 (ITPKC; 75, −33, −0.43)
Q32P28 (LEPRE1; 83, −33, −0.39)
Q92791 (LEPREL4; 50, −33, −0.65)
O94898 (LRIG2; 119, −33, −0.27)
Q8IXH7 (NELFCD; 66, −33, −0.49)
O60500 (NPHS1; 135, −33, −0.24)
P80303 (NUCB2; 50, −33, −0.65)
Q9BTK6 (PAGR1; 28, −33, −1.19)
O60245 (PCDH7; 116, −33, −0.28)
Q9Y5I0 (PCDHA13; 102, −33, −0.32)
Q9UN72 (PCDHA7; 101, −33, −0.32)
O75864 (PPP1R37; 75, −33, −0.44)
Q9BRK5 (SDF4; 42, −33, −0.78)
Q9UPR5 (SLC8A2; 100, −33, −0.32)
Q9NRL3 (STRN4; 81, −33, −0.40)
Q96A49 (SYAP1; 40, −33, −0.82)
Q86VP1 (TAX1BP1; 91, −33, −0.36)
Q9NYB0 (TERF2IP; 44, −33, −0.74)
Q8NFQ8 (TOR1AIP2; 51, −33, −0.64)
Q9Y3S1 (WNK2; 243, −33, −0.13)
O60784 (TOM1; 54, −33, −0.61)
A6NI86 (GOLGA6L10; 55, −33, −0.59)
P20810 (CAST; 77, −33, −0.43)
Q9Y5E6 (PCDHB3; 87, −33, −0.38)
Q9Y5E3 (PCDHB6; 87, −33, −0.37)
Q8NDB2 (BANK1; 89, −33, −0.36)
Q12864 (CDH17; 92, −33, −0.35)
Q9Y5F9 (PCDHGB6; 101, −33, −0.32)
P35609 (ACTN2; 104, −33, −0.31)
Q9H158 (PCDHAC1; 104, −33, −0.31)
Q8N8A2 (ANKRD44; 108, −33, −0.30)
Q9Y219 (JAG2; 133, −33, −0.24)
A4D0S4 (LAMB4; 194, −33, −0.17)
Q99102 (MUC4; 232, −33, −0.14)
O15084 (ANKRD28; 113, −32, −0.28)
Q10567 (AP1B1; 105, −32, −0.30)
Q86WG3 (ATCAY; 42, −32, −0.75)
P51587 (BRCA2; 384, −32, −0.08)
Q9P0X4 (CACNA1I; 245, −32, −0.13)
Q8WTS6 (SETD7; 41, −35, −0.85)
Q92922 (SMARCC1; 123, −35, −0.28)
Q8TAQ2 (SMARCC2; 133, −35, −0.26)
Q8WWQ8 (STAB2; 277, −35, −0.12)
Q9P273 (TENM3; 301, −35, −0.11)
Q9Y490 (TLN1; 270, −35, −0.12)
O60296 (TRAK2; 101, −35, −0.34)
Q6BDS2 (UHRF1BP1; 159, −35, −0.21)
Q96DT7 (ZBTB10; 95, −35, −0.36)
A1YPR0 (ZBTB7C; 69, −35, −0.50)
Q8TCN5 (ZNF507; 106, −35, −0.33)
Q8IY42 (C4orf19; 34, −35, −1.03)
A8MU46 (SMTNL1; 49, −35, −0.71)
Q8N0Z9 (VSIG10; 59, −35, −0.59)
Q8NG66 (NEK11; 74, −35, −0.47)
Q96TA0 (PCDHB18; 80, −35, −0.43)
Q14872 (MTF1; 81, −35, −0.43)
Q9Y5E7 (PCDHB2; 87, −35, −0.40)
Q9Y5G2 (PCDHGB2; 101, −35, −0.34)
Q9Y5F8 (PCDHGB7; 101, −35, −0.34)
Q9Y5H6 (PCDHA8; 103, −35, −0.33)
Q8TEV9 (SMCR8; 105, −35, −0.33)
P38570 (ITGAE; 130, −35, −0.26)
Q9NVE5 (USP40; 140, −35, −0.24)
Q99707 (MTR; 141, −35, −0.24)
Q13576 (IQGAP2; 181, −35, −0.19)
P27708 (CAD; 243, −35, −0.14)
Q9P2R3 (ANKFY1; 128, −34, −0.26)
Q2M1Z3 (ARHGAP31; 157, −34, −0.21)
Q9Y4X5 (ARIH1; 64, −34, −0.53)
Q86V87 (FAM160B2; 82, −32, −0.38)
Q9BXW9 (FANCD2; 166, −32, −0.19)
O75420 (GIGYF1; 115, −32, −0.27)
Q6Y7W6 (GIGYF2; 150, −32, −0.21)
Q9BQ67 (GRWD1; 49, −32, −0.64)
Q9Y4L1 (HYOU1; 111, −32, −0.28)
Q27J81 (INF2; 136, −32, −0.23)
P08514 (ITGA2B; 113, −32, −0.28)
Q8TD91 (MAGEC3; 72, −32, −0.44)
Q9H8L6 (MMRN2; 104, −32, −0.30)
Q9Y4B5 (MTCL1; 210, −32, −0.15)
Q9NYA4 (MTMR4; 133, −32, −0.23)
Q8N307 (MUC20; 72, −32, −0.44)
Q92614 (MYO18A; 233, −32, −0.13)
O75113 (N4BP1; 100, −32, −0.31)
Q9ULI1 (NWD2; 197, −32, −0.16)
Q504Q3 (PAN2; 135, −32, −0.23)
Q96AQ6 (PBXIP1; 81, −32, −0.39)
Q9Y5G5 (PCDHGA8; 101, −32, −0.31)
Q9NQM4 (PIH1D3; 24, −32, −1.32)
O15031 (PLXNB2; 205, −32, −0.15)
Q9NVM4 (PRMT7; 78, −32, −0.40)
Q12913 (PTPRJ; 146, −32, −0.21)
Q8IZ41 (RASEF; 83, −32, −0.38)
Q9ULF5 (SLC39A10; 94, −32, −0.33)
P02730 (SLC4A1; 102, −32, −0.31)
Q5TCY1 (TTBK1; 143, −32, −0.22)
Q05086 (UBE3A; 101, −32, −0.31)
O60287 (URB1; 254, −32, −0.12)
Q9UFB7 (ZBTB47; 83, −32, −0.38)
Q5BKZ1 (ZNF326; 66, −32, −0.48)
Q9UID6 (ZNF639; 56, −32, −0.57)
O75312 (ZPR1; 51, −32, −0.62)
Q9UHY8 (FEZ2; 40, −32, −0.80)
Q8N9T8 (KRI1; 83, −32, −0.38)
Q9UN75 (PCDHA12; 102, −32, −0.31)
Q99460 (PSMD1; 106, −32, −0.30)
Q5VV43 (KIAA0319; 118, −32, −0.27)
O14976 (GAK; 143, −32, −0.22)
Q9H4Z2 (ZNF335; 145, −32, −0.22)
Q8N1P7 (AIM1L; 69, −31, −0.45)
O43823 (AKAP8; 76, −31, −0.40)
Q96PE2 (ARHGEF17; 222, −31, −0.13)
Q8TER5 (ARHGEF40; 165, −31, −0.18)
Q9NT62 (ATG3; 36, −31, −0.86)
Q8TC20 (CAGE1; 90, −31, −0.34)
Q9UKL3 (CASP8AP2; 223, −31, −0.13)
Q3V6T2 (CCDC88A; 216, −31, −0.14)

TABLE 3-continued

Exemplary naturally occurring negatively supercharged proteins.

Q9BRC7 (PLCD4; 88, −34, −0.38)
Q9HBM0 (VEZT; 89, −34, −0.38)
Q9BYV9 (BACH2; 93, −34, −0.36)
Q9Y5G0 (PCDHGB5; 100, −34, −0.34)
Q9Y5I3 (PCDHA1; 103, −34, −0.33)
Q9HCM3 (KIAA1549; 211, −34, −0.16)
Q8IZ07 (ANKRD13A; 68, −33, −0.48)
Q6TDU7 (CASC1; 83, −33, −0.39)
Q96A33 (CCDC47; 56, −33, −0.59)
Q8IX15 (HOMEZ; 61, −31, −0.50)
Q9BYX4 (IFIH1; 117, −31, −0.26)
Q9HBE5 (IL21R; 59, −31, −0.52)
P52732 (KIF11; 119, −31, −0.26)
P43362 (MAGEA9; 35, −31, −0.88)
Q99435 (NELL2; 91, −31, −0.33)
Q9P2S2 (NRXN2; 185, −31, −0.16)
Q02818 (NUCB1; 54, −31, −0.57)
P08575 (PTPRC; 147, −31, −0.21)
Q9HD43 (PTPRH; 122, −31, −0.25)
P0DJD0 (RGPD1; 197, −31, −0.15)
Q12765 (SCRN1; 46, −31, −0.66)
Q9H4L7 (SMARCAD1; 117, −31, −0.26)
Q24JP5 (TMEM132A; 110, −31, −0.28)
Q2TAA8 (TSNAXIP1; 77, −31, −0.40)
A0JNW5 (UHRF1BP1L; 164, −31, −0.18)
Q8N2C7 (UNC80; 363, −31, −0.08)
O60315 (ZEB2; 136, −31, −0.22)
P09871 (C1S; 77, −31, −0.40)
Q86VS8 (HOOK3; 83, −31, −0.37)
P33151 (CDH5; 88, −31, −0.35)
Q8IX94 (CTAGE4; 88, −31, −0.35)
Q9Y5H9 (PCDHA2; 102, −31, −0.30)
B5ME19 (EIF3CL; 105, −31, −0.29)
Q6ZU35 (KIAA1211; 137, −31, −0.22)
Q9NS15 (LTBP3; 139, −31, −0.22)
P39060 (COL18A1; 178, −31, −0.17)
Q13129 (RLF; 218, −31, −0.14)
Q8N302 (AGGF1; 81, −30, −0.37)
Q8NEU8 (APPL2; 74, −30, −0.40)
A7KAX9 (ARHGAP32; 231, −30, −0.13)
Q9HCE6 (ARHGEF10L; 140, −30, −0.21)
O43313 (ATMIN; 88, −30, −0.33)
P46379 (BAG6; 119, −30, −0.25)
O43497 (CACNA1G; 262, −30, −0.11)
Q99674 (CGREF1; 32, −30, −0.94)
Q8N137 (CNTROB; 101, −30, −0.29)
Q9UBP4 (DKK3; 38, −30, −0.78)
Q9Y238 (DLEC1; 196, −30, −0.15)
Q99613 (EIF3C; 105, −30, −0.28)
Q13683 (ITGA7; 129, −30, −0.23)
P22459 (KCNA4; 73, −30, −0.40)
Q9NS87 (KIF15; 160, −30, −0.18)
Q9Y561 (LRP12; 95, −30, −0.31)
Q8WXG6 (MADD; 183, −30, −0.16)
Q7Z3U7 (MON2; 190, −30, −0.15)
Q86XG9 (NBPF5P; 41, −30, −0.73)
Q92823 (NRCAM; 144, −30, −0.20)
Q86Y26 (NUTM1; 120, −30, −0.24)
Q8N573 (OXR1; 98, −30, −0.30)
Q9UPQ7 (PDZRN3; 120, −30, −0.25)
O94880 (PHF14; 100, −30, −0.29)
Q6ZUJ8 (PIK3AP1; 90, −30, −0.33)
Q5R372 (RABGAP1L; 93, −30, −0.32)
Q8TEU7 (RAPGEF6; 179, −30, −0.16)
Q52MB2 (CCDC184; 20, −28, −1.36)
O95400 (CD2BP2; 38, −28, −0.74)
Q9Y5S2 (CDC42BPB; 194, −28, −0.14)
Q8N129 (CNPY4; 28, −28, −0.98)
Q8WYK1 (CNTNAP5; 146, −28, −0.19)
Q9UKF6 (CPSF3; 77, −28, −0.36)
Q02487 (DSC2; 100, −28, −0.28)
Q9H4G0 (EPB41L1; 99, −28, −0.28)
Q6UXB0 (FAM131A; 36, −28, −0.77)
Q9H8M7 (FAM188A; 50, −28, −0.56)
Q8TB52 (FBXO30; 82, −28, −0.34)
O95302 (FKBP9; 63, −28, −0.44)
Q9NYA3 (GOLGA6A; 80, −28, −0.35)
Q96I76 (GPATCH3; 59, −28, −0.47)
Q5T0F9 (CC2D1B; 94, −32, −0.33)
Q96AJ1 (CLUAP1; 48, −32, −0.66)
O75153 (CLUH; 147, −32, −0.21)
Q96PW8 (CSPG4P5; 49, −32, −0.65)
A4D2H0 (CTAGE15; 88, −32, −0.36)
Q5TAQ9 (DCAF8; 67, −32, −0.47)
Q09013 (DMPK; 69, −32, −0.46)
Q96EV8 (DTNBP1; 39, −32, −0.81)
P04626 (ERBB2; 138, −32, −0.23)
Q9Y6Y8 (SEC23IP; 111, −30, −0.27)
Q9UBV2 (SEL1L; 89, −30, −0.33)
Q86VW0 (SESTD1; 79, −30, −0.37)
Q14BN4 (SLMAP; 95, −30, −0.31)
Q96LK8 (SPATA32; 42, −30, −0.70)
Q92783 (STAM; 59, −30, −0.50)
Q9NT68 (TENM2; 308, −30, −0.09)
Q96FV9 (THOC1; 76, −30, −0.39)
Q9Y6L7 (TLL2; 114, −30, −0.26)
Q12899 (TRIM26; 62, −30, −0.48)
Q92995 (USP13; 97, −30, −0.30)
Q9H4A3 (WNK1; 251, −30, −0.11)
Q9BYP7 (WNK3; 198, −30, −0.15)
Q86T24 (ZBTB33; 74, −30, −0.40)
P20962 (PTMS; 12, −30, −2.60)
Q9BQE6 (C11orf48; 32, −30, −0.95)
Q96CW6 (SLC7A6OS; 35, −30, −0.85)
Q8IZU1 (FAM9A; 37, −30, −0.80)
Q9NZA1 (CLIC5; 47, −30, −0.64)
Q9BY79 (MFRP; 62, −30, −0.48)
Q9HA65 (TBC1D17; 73, −30, −0.41)
Q12934 (BFSP1; 75, −30, −0.40)
Q8TE96 (DQX1; 79, −30, −0.37)
Q32M88 (ATHL1; 81, −30, −0.37)
A4FU28 (CTAGE9; 88, −30, −0.34)
P49754 (VPS41; 99, −30, −0.30)
Q6ZP82 (CCDC141; 101, −30, −0.29)
Q6ZP01 (RBM44; 118, −30, −0.25)
Q6IE37 (OVOS1; 134, −30, −0.22)
Q13464 (ROCK1; 158, −30, −0.18)
Q16363 (LAMA4; 203, −30, −0.14)
Q9ULX6 (AKAP8L; 72, −29, −0.40)
Q9Y6D5 (ARFGEF2; 202, −29, −0.14)
Q8TD16 (BICD2; 94, −29, −0.31)
Q6PGQ7 (BORA; 61, −29, −0.47)
Q6PJG6 (BRAT1; 88, −29, −0.32)
Q8IY82 (CCDC135; 103, −29, −0.28)
Q9HCU0 (CD248; 81, −29, −0.35)
Q969H4 (CNKSR1; 80, −29, −0.36)
Q9NQ92 (COPRS; 20, −29, −1.44)
Q6UXH1 (CRELD2; 38, −29, −0.75)
Q6V1X1 (DPP8; 103, −29, −0.28)
Q08554 (DSC1; 100, −29, −0.29)
P11171 (EPB41; 97, −29, −0.29)
Q9UKA1 (FBXL5; 79, −29, −0.36)
A9Z1Z3 (FER1L4; 201, −29, −0.14)
Q2V2M9 (FHOD3; 159, −29, −0.18)
Q9UJ14 (GGT7; 70, −29, −0.41)
Q9UHF4 (IL20RA; 62, −29, −0.46)
Q68E01 (INTS3; 118, −29, −0.24)
P17301 (ITGA2; 129, −29, −0.22)
Q96EK5 (KIAA1279; 72, −29, −0.40)
Q12756 (KIF1A; 191, −29, −0.15)
O00629 (KPNA4; 58, −29, −0.50)
Q9HBX8 (LGR6; 104, −29, −0.27)
P33241 (LSP1; 37, −29, −0.77)
P29966 (MARCKS; 32, −29, −0.91)
Q8N4P2 (TTC30B; 76, −28, −0.36)
Q86WT1 (TTC30A; 76, −28, −0.36)
Q7Z304 (MAMDC2; 78, −28, −0.36)
A6NDK9 (GOLGA6C; 80, −28, −0.35)
Q9Y5E2 (PCDHB7; 87, −28, −0.32)
Q92805 (GOLGA1; 88, −28, −0.31)
Q9H1K0 (ZFYVE20; 89, −28, −0.31)
P23508 (MCC; 93, −28, −0.30)
Q5JSH3 (WDR44; 101, −28, −0.27)
Q08043 (ACTN3; 103, −28, −0.27)
O14983 (ATP2A1; 110, −28, −0.25)
P0CG39 (POTEJ; 117, −28, −0.23)
P55290 (CDH13; 78, −31, −0.39)
P21127 (CDK11B; 93, −31, −0.33)
Q96JK2 (DCAF5; 104, −31, −0.29)
O60610 (DIAPH1; 141, −31, −0.21)
Q0VG06 (FAAP100; 93, −31, −0.33)
Q9NRY5 (FAM114A2; 55, −31, −0.55)
Q9UHL3 (FAM153A; 35, −31, −0.89)
Q8N5J2 (FAM63A; 52, −31, −0.59)
P23142 (FBLN1; 77, −31, −0.40)
O60318 (MCM3AP; 218, −29, −0.13)
A6BM72 (MEGF11; 111, −29, −0.26)
Q9NZM1 (MYOF; 235, −29, −0.12)
Q12968 (NFATC3; 116, −29, −0.25)
P25963 (NFKBIA; 36, −29, −0.81)
Q15653 (NFKBIB; 38, −29, −0.76)
Q8N427 (NME8; 67, −29, −0.43)
Q96RS6 (NUDCD1; 67, −29, −0.43)
Q96CV9 (OPTN; 66, −29, −0.43)
P13667 (PDIA4; 73, −29, −0.39)
Q6ZMN7 (PDZRN4; 117, −29, −0.24)
O60346 (PHLPP1; 185, −29, −0.15)
Q8NG27 (PJA1; 71, −29, −0.40)
Q96KN3 (PKNOX2; 52, −29, −0.55)
Q9ULL1 (PLEKHG1; 155, −29, −0.18)
O75145 (PPFIA3; 133, −29, −0.21)
O75688 (PPM1B; 53, −29, −0.55)
Q9Y4B4 (RAD54L2; 163, −29, −0.17)
P0DJD1 (RGPD2; 197, −29, −0.14)
Q9Y6N7 (ROBO1; 181, −29, −0.16)
O75563 (SKAP2; 41, −29, −0.70)
O60641 (SNAP91; 93, −29, −0.31)
Q13342 (SP140; 98, −29, −0.29)
Q69YQ0 (SPECC1L; 125, −29, −0.23)
P07204 (THBD; 60, −29, −0.48)
P63316 (TNNC1; 18, −29, −1.57)
Q9P2K2 (TXNDC16; 94, −29, −0.30)
Q9P2H5 (USP35; 113, −29, −0.25)
Q6AWC2 (WWC2; 134, −29, −0.21)
P52747 (ZNF143; 69, −29, −0.42)
O95125 (ZNF202; 75, −29, −0.38)
P02585 (TNNC2; 18, −29, −1.60)
A6NNZ2 (0; 50, −29, −0.58)
P19235 (EPOR; 55, −29, −0.52)
Q2M3C6 (C15orf27; 58, −29, −0.49)
C9JE40 (PATL2; 61, −29, −0.47)
Q53GT1 (KLHL22; 72, −29, −0.40)
P0CG23 (ZNF853; 75, −29, −0.38)
Q9Y5E5 (PCDHB4; 87, −29, −0.33)
P0CG41 (CTAGE8; 88, −29, −0.32)
Q14566 (MCM6; 93, −29, −0.31)
Q60I27 (ALS2CL; 108, −29, −0.26)
O43592 (XPOT; 110, −29, −0.26)
P69849 (NOMO3; 134, −29, −0.21)
Q5JPE7 (NOMO2; 139, −29, −0.20)
Q14203 (DCTN1; 142, −29, −0.20)
O15118 (NPC1; 142, −29, −0.20)
Q9Y5Y9 (SCN10A; 221, −29, −0.13)
Q7Z591 (AKNA; 155, −28, −0.18)
Q96QP1 (ALPK1; 139, −28, −0.20)
Q9UJX6 (ANAPC2; 94, −28, −0.29)
O14727 (APAF1; 142, −28, −0.19)
Q6ZUM4 (ARHGAP27; 98, −28, −0.28)
O75129 (ASTN2; 148, −28, −0.18)
P30530 (AXL; 98, −28, −0.28)
O14977 (AZIN1; 50, −28, −0.56)
Q5VU97 (CACHD1; 142, −28, −0.19)
Q7Z6M4 (MTERF4; 44, −27, −0.61)
Q14764 (MVP; 99, −27, −0.27)
O75592 (MYCBP2; 510, −27, −0.05)
P08138 (NGFR; 45, −27, −0.59)
Q99650 (OSMR; 111, −27, −0.24)
Q16549 (PCSK7; 86, −27, −0.31)
Q6P996 (PDXDC1; 87, −27, −0.31)
P19174 (PLCG1; 149, −27, −0.18)
Q86W92 (PPFIBP1; 114, −27, −0.23)
Q9UD71 (PPP1R1B; 23, −27, −1.17)
Q92932 (PTPRN2; 111, −27, −0.24)
Q92692 (PVRL2; 58, −27, −0.46)

TABLE 3-continued

Exemplary naturally occurring negatively supercharged proteins.

Q9UHW5 (GPN3; 33, −28, −0.85)
Q5TGJ6 (HDGFL1; 27, −28, −1.02)
Q9NQG7 (HPS4; 77, −28, −0.36)
Q9NQC1 (JADE2; 87, −28, −0.32)
Q7Z3Y9 (KRT26; 52, −28, −0.53)
Q16626 (MEA1; 20, −28, −1.40)
Q14149 (MORC3; 107, −28, −0.26)
Q13075 (NAIP; 160, −28, −0.17)
O15259 (NPHP1; 83, −28, −0.33)
Q9UHY1 (NRBP1; 60, −28, −0.46)
Q02509 (OC90; 53, −28, −0.52)
Q9Y5I1 (PCDHA11; 103, −28, −0.27)
Q9NRJ7 (PCDHB16; 85, −28, −0.32)
Q9UN70 (PCDHGC3; 101, −28, −0.27)
P16499 (PDE6A; 100, −28, −0.28)
Q13087 (PDIA2; 58, −28, −0.48)
O00562 (PITPNM1; 135, −28, −0.20)
P47712 (PLA2G4A; 85, −28, −0.32)
Q9P212 (PLCE1; 259, −28, −0.10)
P09884 (POLA1; 166, −28, −0.16)
O14974 (PPP1R12A; 115, −28, −0.24)
Q9UKN5 (PRDM4; 88, −28, −0.31)
Q7Z3J3 (RGPD4; 197, −28, −0.14)
P35498 (SCN1A; 229, −28, −0.12)
Q92563 (SPOCK2; 47, −28, −0.59)
O60284 (ST18; 115, −28, −0.24)
Q9Y2W6 (TDRKH; 62, −28, −0.45)
P07951 (TPM2; 33, −28, −0.85)
O43156 (TTI1; 122, −28, −0.22)
Q14166 (TTLL12; 74, −28, −0.37)
Q5BVD1 (TTMP; 24, −28, −1.15)
Q96QK1 (VPS35; 92, −28, −0.30)
Q96J92 (WNK4; 135, −28, −0.20)
Q8NA77 (TEX19; 18, −28, −1.51)
Q86VG3 (C11orf74; 25, −28, −1.10)
P06753 (TPM3; 33, −28, −0.84)
Q6PD74 (AAGAB; 35, −28, −0.80)
Q14242 (SELPLG; 43, −28, −0.64)
Q53HC9 (TSSC1; 44, −28, −0.64)
P55081 (MFAP1; 52, −28, −0.53)
Q96HR8 (NAF1; 54, −28, −0.52)
P15260 (IFNGR1; 54, −28, −0.51)
Q5TF58 (IFFO2; 57, −28, −0.48)
Q96MR6 (WDR65; 145, −27, −0.18)
Q8TE82 (SH3TC1; 147, −27, −0.18)
P06213 (INSR; 156, −27, −0.17)
P12821 (ACE; 150, −26, −0.17)
Q92625 (ANKS1A; 123, −26, −0.21)
P63010 (AP2B1; 105, −26, −0.24)
O60306 (AQR; 171, −26, −0.15)
O00499 (BIN1; 65, −26, −0.40)
O14981 (BTAF1; 207, −26, −0.12)
Q01850 (CDR2; 52, −26, −0.50)
Q76N32 (CEP68; 81, −26, −0.32)
Q5VXU3 (CHIC1; 26, −26, −1.01)
O14578 (CIT; 231, −26, −0.11)
P83436 (COG7; 86, −26, −0.30)
Q8NA03 (FSIP1; 66, −26, −0.39)
A6NDN3 (GOLGA6B; 80, −26, −0.32)
Q8IYU2 (HACE1; 102, −26, −0.25)
Q92619 (HMHA1; 125, −26, −0.20)
Q58FF8 (HSP90AB2P; 44, −26, −0.58)
Q92598 (HSPH1; 97, −26, −0.26)
Q9NWB7 (IFT57; 49, −26, −0.52)
Q6UXK2 (ISLR2; 79, −26, −0.32)
P78504 (JAG1; 134, −26, −0.19)
Q12767 (KIAA0195; 151, −26, −0.17)
Q9P2E2 (KIF17; 115, −26, −0.22)
Q12840 (KIF5A; 117, −26, −0.22)
Q76NI1 (KNDC1; 191, −26, −0.13)
O76015 (KRT38; 50, −26, −0.51)
Q5S007 (LRRK2; 286, −26, −0.09)
P43364 (MAGEA11; 48, −26, −0.54)
Q9UDY8 (MALT1; 92, −26, −0.28)
O00462 (MANBA; 101, −26, −0.25)
Q9Y6R4 (MAP3K4; 182, −26, −0.14)
P48740 (MASP1; 79, −26, −0.32)
Q7Z7M0 (MEGF8; 303, −26, −0.08)
Q13370 (PDE3B; 124, −28, −0.22)
Q5T0N1 (TTC18; 126, −28, −0.22)
Q9UPM8 (AP4E1; 127, −28, −0.21)
Q7Z6G8 (ANKS1B; 138, −28, −0.20)
O75334 (PPFIA2; 143, −28, −0.19)
P54296 (MYOM2; 165, −28, −0.16)
Q7Z2Y5 (NRK; 178, −28, −0.15)
Q6ZU64 (CCDC108; 217, −28, −0.12)
Q86VV8 (RTTN; 249, −28, −0.11)
A8K2U0 (A2ML1; 161, −27, −0.16)
Q9H3P7 (ACBD3; 61, −27, −0.44)
Q8N4X5 (AFAP1L2; 91, −27, −0.29)
Q96Q42 (ALS2; 184, −27, −0.14)
Q8IW19 (APLF; 57, −27, −0.47)
Q96P48 (ARAP1; 162, −27, −0.16)
Q99856 (ARID3A; 63, −27, −0.42)
Q9NWV8 (BABAM1; 37, −27, −0.73)
Q9P287 (BCCIP; 36, −27, −0.75)
Q12830 (BPTF; 338, −27, −0.07)
P54289 (CACNA2D1; 125, −27, −0.21)
Q86VP6 (CAND1; 136, −27, −0.19)
Q5VVM6 (CCDC30; 91, −27, −0.29)
Q7Z6B0 (CCDC91; 50, −27, −0.54)
Q66GS9 (CEP135; 133, −27, −0.20)
Q9P2M7 (CGN; 136, −27, −0.19)
Q9Y678 (COPG1; 98, −27, −0.27)
Q9BSW2 (CRACR2A; 46, −27, −0.59)
Q16832 (DDR2; 97, −27, −0.27)
P98153 (DGCR2; 61, −27, −0.44)
Q8NFT8 (DNER; 78, −27, −0.34)
Q8IUD2 (ERC1; 128, −27, −0.21)
Q9UK99 (FBXO3; 55, −27, −0.49)
Q2WGJ9 (FER1L6; 209, −27, −0.12)
Q53EP0 (FNDC3B; 133, −27, −0.20)
Q02153 (GUCY1B3; 71, −27, −0.38)
Q9UQL6 (HDAC5; 122, −27, −0.22)
Q9H583 (HEATR1; 242, −27, −0.11)
P34932 (HSPA4; 94, −27, −0.28)
Q0D2I5 (IFFO1; 62, −27, −0.43)
P35968 (KDR; 152, −27, −0.17)
Q9Y468 (L3MBTL1; 84, −27, −0.32)
Q9Y2L9 (LRCH1; 81, −27, −0.33)
P43357 (MAGEA3; 35, −27, −0.77)
O15151 (MDM4; 55, −27, −0.49)
Q5U5Q3 (MEX3C; 69, −27, −0.38)
Q14C87 (TMEM132D; 122, −26, −0.21)
O14545 (TRAFD1; 65, −26, −0.40)
Q92574 (TSC1; 130, −26, −0.20)
Q15714 (TSC22D1; 110, −26, −0.23)
Q13107 (USP4; 109, −26, −0.23)
Q709C8 (VPS13C; 422, −26, −0.06)
Q9P253 (VPS18; 110, −26, −0.23)
Q15061 (WDR43; 75, −26, −0.34)
O94967 (WDR47; 102, −26, −0.25)
O14980 (XPO1; 123, −26, −0.21)
Q9NUA8 (ZBTB40; 138, −26, −0.18)
Q9UPT8 (ZC3H4; 140, −26, −0.18)
O43561 (LAT; 28, −26, −0.93)
P51861 (CDR1; 31, −26, −0.83)
Q9BVW5 (TIPIN; 35, −26, −0.75)
P54725 (RAD23A; 40, −26, −0.65)
Q6ZS10 (CLEC17A; 43, −26, −0.60)
Q4V339 (CBWD6; 44, −26, −0.59)
Q5JTY5 (CBWD3; 44, −26, −0.59)
Q5RIA9 (CBWD5; 44, −26, −0.58)
Q8IZM8 (ZNF654; 66, −26, −0.39)
Q96ED9 (HOOK2; 83, −26, −0.31)
Q96CN9 (GCC1; 88, −26, −0.29)
Q9H9E3 (COG4; 89, −26, −0.29)
Q96CN4 (EVI5L; 91, −26, −0.28)
Q03167 (TGFBR3; 93, −26, −0.27)
Q9Y5F7 (PCDHGC4; 101, −26, −0.25)
Q8IYH5 (ZZZ3; 102, −26, −0.25)
Q92888 (ARHGEF1; 102, −26, −0.25)
Q6IEE7 (TMEM132E; 107, −26, −0.24)
Q9Y5I4 (PCDHAC2; 109, −26, −0.23)
Q96G01 (BICD1; 111, −26, −0.23)
P13637 (ATP1A3; 112, −26, −0.23)
O95072 (REC8; 63, −27, −0.43)
Q9H9A7 (RMI1; 70, −27, −0.38)
Q9UBS8 (RNF14; 54, −27, −0.50)
Q99250 (SCN2A; 228, −27, −0.11)
Q96JE7 (SEC16B; 117, −27, −0.23)
Q6P5W5 (SLC39A4; 68, −27, −0.39)
Q969G3 (SMARCE1; 47, −27, −0.57)
P09486 (SPARC; 35, −27, −0.77)
Q8TE77 (SSH3; 73, −27, −0.36)
O75886 (STAM2; 58, −27, −0.46)
Q8NE28 (STKLD1; 76, −27, −0.35)
Q9Y5B9 (SUPT16H; 120, −27, −0.22)
Q9NUY8 (TBC1D23; 78, −27, −0.34)
Q96HA7 (TONSL; 151, −27, −0.17)
P09493 (TPM1; 33, −27, −0.82)
A6NMA1 (TRPC5OS; 12, −27, −2.19)
Q712K3 (UBE2R2; 27, −27, −0.99)
Q8N806 (UBR7; 48, −27, −0.56)
Q9H320 (VCX; 22, −27, −1.21)
O95365 (ZBTB7A; 61, −27, −0.43)
Q9ULD5 (ZNF777; 85, −27, −0.31)
Q96B23 (C18orf25; 43, −27, −0.62)
O15379 (HDAC3; 49, −27, −0.55)
Q9H074 (PAIP1; 54, −27, −0.50)
Q8NAP8 (ZBTB8B; 54, −27, −0.49)
O15488 (GYG2; 55, −27, −0.48)
Q6ZVM7 (TOM1L2; 56, −27, −0.48)
Q9BQ31 (KCNS3; 56, −27, −0.48)
Q9UK59 (DBR1; 62, −27, −0.43)
Q6ZVT6 (C3orf67; 76, −27, −0.35)
P0CG33 (GOLGA6D; 80, −27, −0.33)
Q02447 (SP3; 82, −27, −0.32)
Q9NY33 (DPP3; 83, −27, −0.32)
Q68BL8 (OLFML2B; 84, −27, −0.32)
P18564 (ITGB6; 86, −27, −0.31)
Q05209 (PTPN12; 88, −27, −0.30)
Q9Y5F3 (PCDHB1; 90, −27, −0.29)
Q5K4E3 (PRSS36; 92, −27, −0.29)
P52790 (HK3; 99, −27, −0.27)
Q8IWG1 (WDR63; 103, −27, −0.26)
Q13474 (DRP2; 108, −27, −0.25)
Q8NB46 (ANKRD52; 115, −27, −0.23)
P53708 (ITGA8; 117, −27, −0.22)
Q14432 (PDE3A; 125, −27, −0.21)
Q7RTW8 (OTOA; 129, −27, −0.21)
Q6IA86 (ELP2; 93, −25, −0.27)
Q8TAM6 (ERMN; 33, −25, −0.76)
P78312 (FAM193A; 140, −25, −0.17)
A6H8Z2 (FAM221B; 45, −25, −0.55)
Q969H0 (FBXW7; 80, −25, −0.31)
O95684 (FGFR1OP; 43, −25, −0.58)
P35916 (FLT4; 153, −25, −0.16)
Q9C0B1 (FTO; 58, −25, −0.42)
Q06547 (GABPB1; 42, −25, −0.58)
E2RYF7 (HCG22; 26, −25, −0.95)
O94992 (HEXIM1; 41, −25, −0.61)
Q8TDY8 (IGDCC4; 134, −25, −0.18)
O75164 (KDM4A; 121, −25, −0.20)
Q2M2Z5 (KIZ; 75, −25, −0.33)
O00505 (KPNA3; 58, −25, −0.43)
P19012 (KRT15; 49, −25, −0.50)
Q9UIQ6 (LNPEP; 117, −25, −0.21)
O94822 (LTN1; 201, −25, −0.12)
P20916 (MAG; 69, −25, −0.36)
P43356 (MAGEA2; 35, −25, −0.71)
P43360 (MAGEA6; 35, −25, −0.71)
Q8TD90 (MAGEE2; 60, −25, −0.41)
Q9BUU2 (METTL22; 44, −25, −0.56)
P84157 (MXRA7; 21, −25, −1.16)
Q15746 (MYLK; 211, −25, −0.11)
Q9BPX3 (NCAPG; 114, −25, −0.21)
Q96PU5 (NEDD4L; 112, −25, −0.22)
Q92832 (NELL1; 90, −25, −0.27)
Q96MN2 (NLRP4; 113, −25, −0.22)
Q92636 (NSMAF; 104, −25, −0.23)
O75694 (NUP155; 155, −25, −0.16)
Q9ULW8 (PADI3; 75, −25, −0.33)
Q9BPZ3 (PAIP2; 15, −25, −1.66)

TABLE 3-continued

Exemplary naturally occurring negatively supercharged proteins.

Q12866 (MERTK; 110, −26, −0.23)
Q8TDB4 (MGARP; 25, −26, −1.02)
O60291 (MGRN1; 61, −26, −0.42)
P98088 (MUC5AC; 527, −26, −0.04)
Q8NI08 (NCOA7; 106, −26, −0.24)
Q15155 (NOM01; 134, −26, −0.19)
Q14207 (NPAT; 154, −26, −0.16)
Q9ULB1 (NRXN1; 162, −26, −0.16)
P52948 (NUP98; 198, −26, −0.13)
Q9NP74 (PALMD; 63, −26, −0.41)
Q6QHF9 (PAOX; 70, −26, −0.36)
A2A3N6 (PIPSL; 95, −26, −0.27)
O75051 (PLXNA2; 211, −26, −0.12)
Q9NYI0 (PSD3; 116, −26, −0.22)
Q9H4I0 (RAD21L1; 63, −26, −0.41)
Q15293 (RCN1; 39, −26, −0.66)
A6NKT7 (RGPD3; 197, −26, −0.13)
Q5EBL4 (RILPL1; 47, −26, −0.55)
O75116 (ROCK2; 161, −26, −0.16)
Q15459 (SF3A1; 89, −26, −0.29)
Q15477 (SKIV2L; 138, −26, −0.18)
Q9HBR0 (SLC38A10; 120, −26, −0.21)
Q13509 (TUBB3; 50, −25, −0.49)
P04350 (TUBB4A; 50, −25, −0.50)
P68371 (TUBB4B; 50, −25, −0.50)
P22314 (UBA1; 118, −25, −0.21)
Q9BSL1 (UBAC1; 45, −25, −0.55)
O94888 (UBXN7; 55, −25, −0.45)
Q8NFA0 (USP32; 182, −25, −0.13)
O43298 (ZBTB43; 53, −25, −0.47)
Q9BT43 (POLR3GL; 25, −25, −0.98)
P26436 (ACRV1; 28, −25, −0.88)
P67936 (TPM4; 29, −25, −0.87)
Q5TZF3 (ANKRD45; 32, −25, −0.78)
P57768 (SNX16; 39, −25, −0.63)
Q9H6Y2 (WDR55; 42, −25, −0.59)
Q8IUF1 (CBWD2; 44, −25, −0.56)
Q9BRT8 (CBWD1; 44, −25, −0.56)
Q9NQL2 (RRAGD; 46, −25, −0.54)
Q3ZCM7 (TUBB8; 50, −25, −0.50)
Q9BUF5 (TUBB6; 50, −25, −0.50)
Q9BVA1 (TUBB2B; 50, −25, −0.50)
Q8IYS4 (C16orf71; 56, −25, −0.44)
P30154 (PPP2R1B; 66, −25, −0.37)
P16471 (PRLR; 70, −25, −0.35)
Q969S8 (HDAC10; 71, −25, −0.34)
P21980 (TGM2; 77, −25, −0.32)
Q99567 (NUP88; 84, −25, −0.29)
P55072 (VCP; 89, −25, −0.27)
Q6NUQ1 (RINT1; 91, −25, −0.27)
A8MT70 (ZBBX; 91, −25, −0.27)
Q86XP0 (PLA2G4D; 92, −25, −0.27)
Q9NSG2 (C1orf112; 97, −25, −0.25)
P52630 (STAT2; 98, −25, −0.25)
Q12959 (DLG1; 100, −25, −0.24)
P10253 (GAA; 105, −25, −0.23)
Q9P107 (GMIP; 107, −25, −0.23)
P49588 (AARS; 107, −25, −0.23)
P12109 (COL6A1; 109, −25, −0.23)
Q07075 (ENPEP; 109, −25, −0.22)
P57678 (GEMIN4; 120, −25, −0.20)
Q8IZS8 (CACNA2D3; 123, −25, −0.20)
Q13349 (ITGAD; 127, −25, −0.19)
Q9Y6N6 (LAMC3; 171, −25, −0.14)
Q7Z5N4 (SDK1; 242, −25, −0.10)
P04114 (APOB; 516, −25, −0.04)
O00468 (AGRN; 217, −24, −0.11)
Q9UPW5 (AGTPBP1; 138, −24, −0.17)
P15144 (ANPEP; 110, −24, −0.21)
Q8NFD5 (ARID1B; 236, −24, −0.10)
Q16515 (ASIC2; 58, −24, −0.41)
Q8IXJ9 (ASXL1; 165, −24, −0.14)
Q04656 (ATP7A; 163, −24, −0.14)
Q9H3M9 (ATXN3L; 41, −24, −0.58)
Q14457 (BECN1; 52, −24, −0.46)
Q8NDZ0 (BEND2; 88, −24, −0.27)
Q13137 (CALCOCO2; 52, −24, −0.45)
P62158 (CALM1; 17, −24, −1.42)
Q13367 (AP3B2; 119, −26, −0.21)
Q8NG08 (HELB; 123, −26, −0.21)
Q0IIM8 (TBC1D8B; 129, −26, −0.20)
Q9H195 (MUC3B; 131, −26, −0.19)
P08069 (IGF1R; 155, −26, −0.16)
Q9ULJ7 (ANKRD50; 156, −25, −0.16)
Q9HCE9 (ANO8; 136, −25, −0.18)
Q6Q4G3 (AQPEP; 113, −25, −0.22)
P16615 (ATP2A2; 115, −25, −0.21)
Q3SYG4 (BBS9; 99, −25, −0.25)
P56945 (BCAR1; 93, −25, −0.26)
Q5T5X7 (BEND3; 94, −25, −0.26)
Q92994 (BRF1; 74, −25, −0.33)
Q6YHK3 (CD109; 162, −25, −0.15)
Q6DT37 (CDC42BPG; 172, −25, −0.14)
Q14CN2 (CLCA4; 101, −25, −0.24)
Q9Y5P4 (COL4A3BP; 71, −25, −0.35)
Q96BA8 (CREB3L1; 57, −25, −0.43)
P55060 (CSE1L; 110, −25, −0.22)
P35222 (CTNNB1; 85, −25, −0.29)
O94830 (DDHD2; 81, −25, −0.30)
Q96HP0 (DOCK6; 230, −25, −0.10)
Q96MC2 (DRC1; 87, −25, −0.28)
O95967 (EFEMP2; 49, −25, −0.50)
Q14444 (CAPRIN1; 78, −24, −0.30)
Q9BXL7 (CARD11; 133, −24, −0.18)
Q9BXL6 (CARD14; 113, −24, −0.21)
Q96G28 (CCDC104; 39, −24, −0.60)
A1A5D9 (CCDC64B; 57, −24, −0.42)
O75794 (CDC123; 39, −24, −0.61)
O75419 (CDC45; 66, −24, −0.36)
Q03701 (CEBPZ; 121, −24, −0.19)
Q92496 (CFHR4; 65, −24, −0.36)
Q96JB2 (COG3; 94, −24, −0.25)
Q8IZJ3 (CPAMD8; 207, −24, −0.11)
Q9NQ79 (CRTAC; 71, −24, −0.33)
P32927 (CSF2RB; 97, −24, −0.24)
Q66K89 (E4F1; 83, −24, −0.28)
Q9BSJ8 (ESYT1; 123, −24, −0.19)
Q6ZS17 (FAM65A; 132, −24, −0.18)
Q86WN1 (FCHSD1; 77, −24, −0.31)
Q14318 (FKBP8; 45, −24, −0.53)
P36888 (FLT3; 113, −24, −0.21)
Q9NQX3 (GPHN; 80, −24, −0.30)
Q9C091 (GREB1L; 214, −24, −0.11)
Q99871 (HAUS7; 41, −24, −0.58)
Q86XA9 (HEATR5A; 222, −24, −0.10)
Q8IU57 (IFNLR1; 58, −24, −0.41)
Q8N6C5 (IGSF1; 149, −24, −0.16)
Q9ULD6 (INTU; 106, −24, −0.22)
Q6NY19 (KANK3; 88, −24, −0.27)
O76014 (KRT37; 50, −24, −0.48)
P32004 (L1CAM; 140, −24, −0.17)
Q8IVL5 (LEPREL1; 81, −24, −0.29)
Q9HAR2 (LPHN3; 162, −24, −0.14)
Q9BTT6 (LRRC1; 59, −24, −0.40)
P43365 (MAGEA12; 35, −24, −0.68)
Q9HCI5 (MAGEE1; 103, −24, −0.23)
Q86UL8 (MAGI2; 159, −24, −0.15)
O00339 (MATN2; 107, −24, −0.22)
Q9Y6F6 (MRVI1; 96, −24, −0.24)
Q8NFW9 (MYRIP; 96, −24, −0.25)
Q99457 (NAP1L3; 58, −24, −0.41)
Q8TD19 (NEK9; 107, −24, −0.22)
P06748 (NPM1; 33, −24, −0.73)
O75459 (PAGE1; 16, −24, −1.48)
Q9Y5H7 (PCDHA5; 102, −24, −0.23)
A6NKB5 (PCNXL2; 237, −24, −0.10)
Q13371 (PDCL; 34, −24, −0.70)
P51160 (PDE6C; 99, −24, −0.24)
Q9Y2I7 (PIKFYVE; 237, −24, −0.10)
O60331 (PIP5K1C; 73, −24, −0.32)
Q00G26 (PLIN5; 51, −24, −0.47)
Q13136 (PPFIA1; 136, −24, −0.17)
Q96LW4 (PRIMPOL; 64, −24, −0.37)
O43422 (PRKRIR; 88, −24, −0.27)
O60678 (PRMT3; 60, −24, −0.40)
P55036 (PSMD4; 41, −24, −0.58)
O15534 (PER1; 136, −25, −0.18)
Q96JS3 (PGBD1; 93, −25, −0.27)
P46020 (PHKA1; 137, −25, −0.18)
Q6S8J3 (POTEE; 121, −25, −0.20)
A5A3E0 (POTEF; 121, −25, −0.20)
Q9Y5P8 (PPP2R3B; 65, −25, −0.38)
Q8TCU6 (PREX1; 186, −25, −0.13)
P49810 (PSEN2; 50, −25, −0.49)
P23470 (PTPRG; 162, −25, −0.15)
Q16827 (PTPRO; 138, −25, −0.18)
P08195 (SLC3A2; 68, −25, −0.36)
Q9NWM0 (SMOX; 62, −25, −0.40)
Q6GMV2 (SMYD5; 47, −25, −0.52)
Q9BQ16 (SPOCK3; 49, −25, −0.50)
Q5VX71 (SUSD4; 54, −25, −0.46)
Q496J9 (SV2C; 82, −25, −0.30)
Q15542 (TAF5; 87, −25, −0.28)
Q8IWB9 (TEX2; 125, −25, −0.19)
Q9UBB9 (TFIP11; 97, −25, −0.25)
Q6PL24 (TMED8; 36, −25, −0.69)
Q9UPV9 (TRAK1; 106, −25, −0.23)
O15050 (TRANK1; 336, −25, −0.07)
P07437 (TUBB; 50, −25, −0.50)
Q13885 (TUBB2A; 50, −25, −0.50)
Q8WXD2 (SCG3; 53, −24, −0.45)
Q9NY46 (SCN3A; 226, −24, −0.10)
Q9UHV2 (SERTAD1; 25, −24, −0.97)
Q14140 (SERTAD2; 34, −24, −0.70)
Q9NRF2 (SH2B1; 79, −24, −0.30)
Q8TF17 (SH3TC2; 145, −24, −0.16)
Q9ULL8 (SHROOM4; 165, −24, −0.14)
Q9BZZ2 (SIGLEC1; 183, −24, −0.13)
Q2VWA4 (SKOR2; 104, −24, −0.23)
P04920 (SLC4A2; 137, −24, −0.17)
O00193 (SMAP; 20, −24, −1.18)
Q9UPR3 (SMG5; 114, −24, −0.21)
P43307 (SSR1; 32, −24, −0.74)
Q15468 (STIL; 143, −24, −0.16)
Q17RD7 (SYT16; 72, −24, −0.33)
Q8IUC6 (TICAM1; 76, −24, −0.31)
O43897 (TLL1; 115, −24, −0.20)
Q96JJ7 (TMX3; 52, −24, −0.46)
Q71U36 (TUBA1A; 50, −24, −0.47)
P68366 (TUBA4A; 50, −24, −0.48)
Q9NY65 (TUBA8; 50, −24, −0.47)
A0AVT1 (UBA6; 118, −24, −0.20)
Q14694 (USP10; 87, −24, −0.27)
Q5W0Q7 (USPL1; 120, −24, −0.19)
Q86XK7 (VSIG1; 42, −24, −0.57)
Q9HAV4 (XPO5; 136, −24, −0.17)
Q14966 (ZNF638; 221, −24, −0.10)
Q969E8 (TSR2; 21, −24, −1.14)
P68363 (TUBA1B; 50, −24, −0.47)
Q9UIR0 (BTNL2; 50, −24, −0.47)
Q9P0W5 (SCHIP1; 53, −24, −0.44)
Q99456 (KRT12; 54, −24, −0.44)
Q6ZN18 (AEBP2; 54, −24, −0.44)
Q9HAU8 (RNPEPL1; 56, −24, −0.43)
Q9Y6I3 (EPN1; 60, −24, −0.39)
P15391 (CD19; 61, −24, −0.39)
Q8NEB7 (ACRBP; 61, −24, −0.39)
O75553 (DAB1; 64, −24, −0.37)
P30153 (PPP2R1A; 65, −24, −0.36)
O94769 (ECM2; 80, −24, −0.30)
P50747 (HLCS; 81, −24, −0.29)
Q9C0B2 (KIAA1751; 87, −24, −0.27)
Q68DD2 (PLA2G4F; 95, −24, −0.25)
O95206 (PCDH8; 113, −24, −0.21)
P0CG38 (POTEI; 121, −24, −0.19)
P42702 (LIFR; 124, −24, −0.19)
Q16720 (ATP2B3; 134, −24, −0.17)
P29144 (TPP2; 138, −24, −0.17)
Q9UPP5 (KIAA1107; 156, −24, −0.15)
Q8TEQ6 (GEMIN5; 169, −24, −0.14)
Q9H9F9 (ACTR5; 68, −23, −0.33)
Q9UJX5 (ANAPC4; 92, −23, −0.24)
P13798 (APEH; 81, −23, −0.28)
Q6PL18 (ATAD2; 159, −23, −0.14)

TABLE 3-continued

Exemplary naturally occurring negatively supercharged proteins.

A6NHC0 (CAPN8; 79, −24, −0.30)
Q86YS7 (C2CD5; 110, −23, −0.20)
Q86UW7 (CADPS2; 148, −23, −0.15)
Q8IX12 (CCAR1; 133, −23, −0.17)
O95273 (CCNDBP1; 40, −23, −0.57)
A6H8M9 (CDHR4; 86, −23, −0.26)
Q4KMG0 (CDON; 139, −23, −0.16)
Q8TEP8 (CEP192; 213, −23, −0.10)
Q9UEE9 (CFDP1; 34, −23, −0.68)
Q10570 (CPSF1; 161, −23, −0.14)
Q14247 (CTTN; 62, −23, −0.37)
Q96QB1 (DLC1; 171, −23, −0.13)
Q01094 (E2F1; 47, −23, −0.49)
Q96EK7 (FAM120B; 104, −23, −0.22)
O15360 (FANCA; 163, −23, −0.14)
Q6PIJ6 (FBXO38; 134, −23, −0.17)
Q13045 (FLII; 145, −23, −0.15)
Q06546 (GABPA; 51, −23, −0.44)
Q14697 (GANAB; 107, −23, −0.21)
Q9BTY7 (HGH1; 42, −23, −0.54)
Q8WZA9 (IRGQ; 63, −23, −0.36)
P78415 (IRX3; 52, −23, −0.44)
P08648 (ITGA5; 115, −23, −0.20)
P05106 (ITGB3; 87, −23, −0.26)
Q4ADV7 (KIAA1432; 159, −23, −0.14)
Q96L93 (KIF16B; 152, −23, −0.15)
Q2TBA0 (KLHL40; 69, −23, −0.33)
Q8IWV1 (LAX1; 44, −23, −0.52)
P20700 (LMNB1; 66, −23, −0.34)
P31152 (MAPK4; 66, −23, −0.34)
P55196 (MLLT4; 207, −23, −0.11)
Q7Z745 (MROH2B; 181, −23, −0.12)
Q8N987 (NECAB1; 41, −23, −0.56)
Q86XW9 (NME9; 37, −23, −0.62)
O14786 (NRP1; 103, −23, −0.22)
P16435 (POR; 77, −23, −0.29)
P49593 (PPM1F; 50, −23, −0.46)
Q3YEC7 (RABL6; 80, −23, −0.28)
Q15291 (RBBP5; 59, −23, −0.38)
O14593 (RFXANK; 28, −23, −0.81)
Q96BU1 (S100PBP; 46, −23, −0.50)
Q14151 (SAFB2; 107, −23, −0.21)
P18827 (SDC1; 32, −23, −0.70)
Q86SQ7 (SDCCAG8; 83, −23, −0.27)
Q9UGP8 (SEC63; 88, −23, −0.26)
Q9Y2K2 (SIK3; 140, −23, −0.16)
Q9UMX1 (SUFU; 54, −23, −0.42)
O94864 (SUPT7L; 46, −23, −0.49)
Q9C0B7 (TANGO6; 121, −23, −0.19)
Q9BTW9 (TBCD; 133, −23, −0.17)
Q7Z6L1 (TECPR1; 130, −23, −0.17)
Q07157 (TJP1; 195, −23, −0.11)
Q969Q1 (TRIM63; 40, −23, −0.57)
Q9BQE3 (TUBA1C; 50, −23, −0.46)
Q13748 (TUBA3C; 50, −23, −0.46)
Q8TEY7 (USP33; 107, −23, −0.21)
Q8NEZ3 (WDR19; 152, −23, −0.15)
P49750 (YLPM1; 220, −23, −0.10)
Q9NZ09 (UBAP1; 55, −22, −0.39)
Q6UXZ4 (UNC5D; 106, −22, −0.20)
O94966 (USP19; 146, −22, −0.15)
Q9Y2K6 (USP20; 102, −22, −0.21)
Q9Y334 (VWA7; 96, −22, −0.22)
Q96SY0 (VWA9; 57, −22, −0.38)
Q14191 (WRN; 162, −22, −0.13)
Q13105 (ZBTB17; 88, −22, −0.25)
O15156 (ZBTB7B; 58, −22, −0.37)
Q9H4I2 (ZHX3; 105, −22, −0.21)
P17040 (ZSCAN20; 118, −22, −0.18)
Q8N402 (0; 27, −22, −0.81)
P0C7M4 (RHOXF2B; 32, −22, −0.69)
Q9UN42 (ATP1B4; 42, −22, −0.52)
P0DJD9 (PGA5; 42, −22, −0.52)
Q16254 (E2F4; 44, −22, −0.50)
P31323 (PRKAR2B; 46, −22, −0.47)
O60268 (KIAA0513; 47, −22, −0.47)
Q9NP70 (AMBN; 48, −22, −0.45)
Q6PEY2 (TUBA3E; 50, −22, −0.44)
P10586 (PTPRF; 213, −24, −0.11)
Q9BWH6 (RPAP1; 153, −24, −0.15)
Q15020 (SART3; 110, −24, −0.21)
Q99592 (ZBTB18; 58, −23, −0.39)
Q9NRM2 (ZNF277; 53, −23, −0.43)
Q2M1K9 (ZNF423; 145, −23, −0.15)
P36508 (ZNF76; 62, −23, −0.37)
O15318 (POLR3G; 26, −23, −0.88)
P09496 (CLTA; 27, −23, −0.84)
Q9H063 (MAF1; 29, −23, −0.79)
P45379 (TNNT2; 36, −23, −0.64)
P0DJD7 (PGA4; 42, −23, −0.54)
Q8WVN8 (UBE2Q2; 43, −23, −0.53)
O95393 (BMP10; 48, −23, −0.47)
Q969R8 (ITFG2; 49, −23, −0.46)
Q49A92 (C8orf34; 50, −23, −0.45)
Q15846 (CLUL1; 54, −23, −0.42)
P16389 (KCNA2; 57, −23, −0.40)
Q14181 (POLA2; 66, −23, −0.34)
P52306 (RAP1GDS1; 66, −23, −0.34)
P07911 (UMOD; 70, −23, −0.32)
Q9H347 (UBQLN3; 71, −23, −0.32)
A0MZ66 (KIAA1598; 72, −23, −0.32)
Q8N309 (LRRC43; 73, −23, −0.31)
Q7Z4Q2 (HEATR3; 75, −23, −0.30)
P42898 (MTHFR; 75, −23, −0.30)
Q8IYI6 (EXOC8; 82, −23, −0.28)
Q16819 (MEP1A; 84, −23, −0.27)
Q99523 (SORT1; 92, −23, −0.24)
Q06033 (ITIH3; 100, −23, −0.23)
Q4G0T1 (0; 109, −23, −0.21)
P05023 (ATP1A1; 113, −23, −0.20)
Q8N961 (ABTB2; 114, −23, −0.20)
Q8N0W3 (FUK; 118, −23, −0.19)
P27816 (MAP4; 121, −23, −0.19)
Q5DID0 (UMODL1; 144, −23, −0.15)
P31629 (HIVEP2; 269, −23, −0.08)
Q13315 (ATM; 351, −23, −0.06)
P01023 (A2M; 163, −22, −0.13)
P78536 (ADAM17; 93, −22, −0.23)
P24588 (AKAP5; 47, −22, −0.46)
Q6ZW76 (ANKS3; 72, −22, −0.30)
Q8N8V4 (ANKS4B; 47, −22, −0.47)
Q9UKG1 (APPL1; 80, −22, −0.27)
O75143 (ATG13; 57, −22, −0.38)
P46100 (ATRX; 283, −22, −0.07)
P54252 (ATXN3; 42, −22, −0.52)
O75363 (BCAS1; 62, −22, −0.35)
Q9NSY1 (BMP2K; 129, −22, −0.17)
Q9H8G2 (CAAP1; 38, −22, −0.57)
Q9NY47 (CACNA2D2; 130, −22, −0.16)
O14815 (CAPN9; 79, −22, −0.27)
Q9Y2G2 (CARD8; 49, −22, −0.44)
Q13042 (CDC16; 72, −22, −0.30)
Q96JP9 (CDHR1; 94, −22, −0.23)
Q8N4Q1 (CHCHD4; 16, −22, −1.37)
Q96HD1 (CRELD1; 45, −22, −0.48)
Q9NQC7 (CYLD; 107, −22, −0.20)
Q9UJU6 (DBNL; 48, −22, −0.45)
Q68CQ4 (DIEXF; 87, −22, −0.25)
Q5ZPR3 (CD276; 57, −21, −0.36)
P49427 (CDC34; 27, −21, −0.78)
Q5VT25 (CDC42BPA; 197, −21, −0.10)
Q6P2H3 (CEP85; 86, −21, −0.24)
O76071 (CIAO1; 38, −21, −0.55)
P35523 (CLCN1; 109, −21, −0.19)
Q96KN2 (CNDP1; 57, −21, −0.37)
O43889 (CREB3; 44, −21, −0.47)
Q8IUI8 (CRLF3; 50, −21, −0.42)
Q8IYB7 (DIS3L2; 99, −21, −0.21)
O75165 (DNAJC13; 254, −21, −0.08)
Q96N67 (DOCK7; 243, −21, −0.08)
Q86YF9 (DZIP1; 99, −21, −0.21)
O43281 (EFS; 59, −21, −0.35)
Q8TE02 (ELP5; 35, −21, −0.60)
Q96DN0 (ERP27; 30, −21, −0.68)
Q9BS26 (ERP44; 47, −21, −0.44)
Q96AQ9 (FAM131C; 30, −21, −0.69)
Q9UIF8 (BAZ2B; 240, −23, −0.09)
Q6W2J9 (BCOR; 192, −23, −0.11)
A8MW95 (BECN1P1; 48, −23, −0.47)
P78352 (DLG4; 80, −22, −0.27)
Q9BU89 (DOHH; 33, −22, −0.66)
Q7Z2Z2 (EFTUD1; 125, −22, −0.17)
Q99645 (EPYC; 37, −22, −0.60)
P21860 (ERBB3; 148, −22, −0.14)
Q9UBX5 (FBLN5; 50, −22, −0.43)
Q5VW36 (FOCAD; 200, −22, −0.10)
Q8TDT2 (GPR152; 51, −22, −0.43)
P57764 (GSDMD; 53, −22, −0.41)
P51858 (HDGF; 27, −22, −0.82)
Q9BQA5 (HINFP; 60, −22, −0.36)
Q00613 (HSF1; 57, −22, −0.38)
P11021 (HSPA5; 72, −22, −0.30)
O75054 (IGSF3; 135, −22, −0.16)
Q13651 (IL10RA; 63, −22, −0.34)
Q5VZ66 (JAKMIP3; 99, −22, −0.22)
Q8NAB2 (KBTBD3; 69, −22, −0.31)
Q9BQK8 (LPIN3; 94, −22, −0.23)
Q6UXM1 (LRIG3; 123, −22, −0.17)
O60449 (LY75; 198, −22, −0.11)
P80192 (MAP3K9; 122, −22, −0.18)
Q9UHC7 (MKRN1; 53, −22, −0.41)
Q96JB8 (MPP4; 73, −22, −0.30)
Q04912 (MST1R; 152, −22, −0.14)
Q8N3F0 (MTURN; 15, −22, −1.47)
Q5VVJ2 (MYSM1; 95, −22, −0.23)
Q9BW27 (NUP85; 75, −22, −0.29)
Q8WWZ8 (OIT3; 60, −22, −0.36)
Q99983 (OMD; 49, −22, −0.44)
Q9BYE7 (PCGF6; 39, −22, −0.56)
P46019 (PHKA2; 138, −22, −0.15)
Q9P215 (POGK; 69, −22, −0.31)
O60237 (PPP1R12B; 110, −22, −0.19)
Q15435 (PPP1R7; 42, −22, −0.52)
Q9P1A2 (PPP4R1L; 46, −22, −0.47)
P55345 (PRMT2; 49, −22, −0.44)
Q96NY8 (PVRL4; 55, −22, −0.39)
Q99666 (RGPD5; 199, −22, −0.11)
Q9BQY4 (RHOXF2; 32, −22, −0.69)
Q96TC7 (RMDN3; 52, −22, −0.42)
P13489 (RNH1; 50, −22, −0.44)
Q96T51 (RUFY1; 80, −22, −0.27)
Q9NZJ4 (SACS; 521, −22, −0.04)
Q9Y467 (SALL2; 105, −22, −0.20)
Q12874 (SF3A3; 59, −22, −0.37)
Q13435 (SF3B2; 100, −22, −0.21)
P60896 (SHFM1; 8, −22, −2.65)
Q8N196 (SIX5; 75, −22, −0.29)
P48751 (SLC4A3; 136, −22, −0.16)
O60749 (SNX2; 58, −22, −0.37)
Q13043 (STK4; 56, −22, −0.39)
Q4ZIN3 (TMEM259; 68, −22, −0.32)
Q96A56 (TP53INP1; 27, −22, −0.80)
O75157 (TSC22D2; 79, −22, −0.27)
Q96J42 (TXNDC15; 40, −22, −0.55)
Q9UBT2 (UBA2; 71, −22, −0.30)
Q9GZZ9 (UBA5; 45, −22, −0.49)
O94885 (SASH1; 137, −21, −0.15)
O60239 (SH3BP5; 50, −21, −0.41)
Q15043 (SLC39A14; 54, −21, −0.38)
Q5BKX6 (SLC45A4; 84, −21, −0.25)
Q92966 (SNAPC3; 47, −21, −0.44)
Q13501 (SQSTM1; 48, −21, −0.44)
Q92502 (STARD8; 113, −21, −0.18)
Q13188 (STK3; 56, −21, −0.37)
Q7L1I2 (SV2B; 77, −21, −0.27)
Q96GX1 (TCTN2; 77, −21, −0.27)
Q13263 (TRIM28; 89, −21, −0.23)
A6NGJ6 (TRIM64; 52, −21, −0.40)
Q99614 (TTC1; 34, −21, −0.62)
Q96AY4 (TTC28; 271, −21, −0.07)
Q96RL1 (UIMC1; 80, −21, −0.26)
Q86UV5 (USP48; 119, −21, −0.17)
Q7Z7L7 (ZER1; 88, −21, −0.23)
Q9Y4E5 (ZNF451; 121, −21, −0.17)

TABLE 3-continued

Exemplary naturally occurring negatively supercharged proteins.

Q86VR2 (FAM134C; 51, −22, −0.42)
Q16656 (NRF1; 54, −22, −0.41)
Q9UNF0 (PACSIN2; 56, −22, −0.39)
Q8N4U5 (TCP11L2; 58, −22, −0.37)
Q9Y3X0 (CCDC9; 60, −22, −0.36)
Q9NPQ8 (RIC8A; 60, −22, −0.36)
P14784 (IL2RB; 61, −22, −0.35)
A2RU67 (KIAA1467; 67, −22, −0.32)
P51693 (APLP1; 72, −22, −0.30)
O00187 (MASP2; 76, −22, −0.29)
Q96MT8 (CEP63; 81, −22, −0.27)
Q8TBP0 (TBC1D16; 86, −22, −0.25)
Q96D71 (REPS1; 87, −22, −0.25)
P26010 (ITGB7; 87, −22, −0.25)
Q8IXH8 (CDH26; 95, −22, −0.23)
P52789 (HK2; 102, −22, −0.21)
Q8TET4 (GANC; 104, −22, −0.21)
Q6ZVH7 (ESPNL; 108, −22, −0.20)
Q13563 (PKD2; 110, −22, −0.20)
Q6ZN30 (BNC2; 122, −22, −0.17)
Q15111 (PLCL1; 123, −22, −0.17)
Q96AE7 (TTC17; 130, −22, −0.16)
Q96C45 (ULK4; 142, −22, −0.15)
O43933 (PEX1; 143, −22, −0.15)
Q8IZU2 (WDR17; 148, −22, −0.14)
Q9BXX3 (ANKRD30A; 159, −22, −0.13)
Q13009 (TIAM1; 178, −22, −0.12)
Q02388 (COL7A1; 295, −22, −0.07)
Q9H799 (C5orf42; 362, −22, −0.06)
Q5T8D3 (ACBD5; 60, −21, −0.34)
Q9BYF1 (ACE2; 92, −21, −0.22)
O95376 (ARIH2; 58, −21, −0.36)
Q8NHH9 (ATL2; 66, −21, −0.31)
O94812 (BAIAP3; 132, −21, −0.15)
Q8N9N5 (BANP; 56, −21, −0.37)
Q9UBW5 (BIN2; 62, −21, −0.33)
P35219 (CA8; 33, −21, −0.63)
Q14790 (CASP8; 55, −20, −0.36)
P41180 (CASR; 121, −20, −0.16)
Q9ULG6 (CCPG1; 87, −20, −0.22)
Q6ZTQ4 (CDHR3; 98, −20, −0.20)
Q70SY1 (CREB3L2; 57, −20, −0.34)
Q99062 (CSF3R; 92, −20, −0.21)
Q9BQY9 (DBNDD2; 28, −20, −0.72)
O00273 (DFFA; 37, −20, −0.54)
Q0VDD8 (DNAH14; 400, −20, −0.05)
Q9BV94 (EDEM2; 65, −20, −0.30)
Q3B7T1 (EDRF1; 139, −20, −0.14)
Q9HC35 (EML4; 109, −20, −0.18)
Q8TC92 (ENOX1; 73, −20, −0.27)
Q86VI1 (EXOC3L1; 82, −20, −0.24)
A1A519 (FAM170A; 37, −20, −0.53)
Q9ULE4 (FAM184B; 121, −20, −0.16)
Q6UN15 (FIP1L1; 67, −20, −0.30)
Q92949 (FOXJ1; 45, −20, −0.44)
Q0D2H9 (GOLGA8DP; 48, −20, −0.41)
Q08AF8 (GOLGA8F;; 48, −20, −0.41)
Q9NPB8 (GPCPD1; 76, −20, −0.26)
Q9HCN4 (GPN1; 42, −20, −0.47)
Q86UP8 (GTF2IRD2; 107, −20, −0.18)
Q15034 (HERC3; 117, −20, −0.17)
Q5GLZ8 (HERC4; 119, −20, −0.16)
O14879 (IFIT3; 56, −20, −0.35)
P14616 (INSRR; 144, −20, −0.13)
Q8TB96 (ITFG1; 68, −20, −0.29)
Q9UKP3 (ITGB1BP2; 38, −20, −0.52)
Q7Z5Y7 (KCTD20; 47, −20, −0.42)
O94889 (KLHL18; 64, −20, −0.31)
Q9UJP4 (KLHL21; 67, −20, −0.30)
O76009 (KRT33A; 46, −20, −0.43)
O76013 (KRT36; 52, −20, −0.38)
O43283 (MAP3K13; 108, −20, −0.18)
Q8IWI9 (MGA; 332, −20, −0.06)
Q13434 (MKRN4P; 53, −20, −0.37)
A6NES4 (MROH2A; 193, −20, −0.10)
O15394 (NCAM2; 93, −20, −0.21)
Q14934 (NFATC4; 95, −20, −0.20)
Q00653 (NFKB2; 97, −20, −0.20)
A6NMN3 (FAM170B; 32, −21, −0.65)
Q8N128 (FAM177A1; 24, −21, −0.88)
Q96AY3 (FKBP10; 64, −21, −0.32)
Q8N475 (FSTL5; 96, −21, −0.21)
Q8IYD1 (GSPT2; 69, −21, −0.30)
O00165 (HAX1; 32, −21, −0.66)
Q9ULI3 (HEG1; 147, −21, −0.14)
Q9H0H0 (INTS2; 134, −21, −0.15)
Q63ZY3 (KANK2; 91, −21, −0.23)
Q92806 (KCNJ9; 44, −21, −0.47)
Q7Z3Y8 (KRT27; 50, −21, −0.42)
Q14532 (KRT32; 50, −21, −0.41)
O95751 (LDOC1; 17, −21, −1.23)
Q15334 (LLGL1; 115, −21, −0.18)
P42704 (LRPPRC; 158, −21, −0.13)
P43358 (MAGEA4; 35, −21, −0.60)
P43361 (MAGEA8; 35, −21, −0.59)
Q6ZSS7 (MFSD6; 88, −21, −0.23)
P40692 (MLH1; 85, −21, −0.24)
Q99550 (MPHOSPH9; 133, −21, −0.15)
Q9UQQ1 (NAALADL1; 81, −21, −0.26)
Q5TAG4 (NBPF12; 31, −21, −0.67)
Q92859 (NEO1; 160, −21, −0.13)
Q9NX02 (NLRP2; 121, −21, −0.17)
P55786 (NPEPPS; 103, −21, −0.20)
Q9ULR5 (PAIP2B; 14, −21, −1.47)
Q01064 (PDE1B; 61, −21, −0.34)
O76074 (PDE5A; 100, −21, −0.21)
O15055 (PER2; 137, −21, −0.15)
Q8IYB4 (PEX5L; 70, −21, −0.30)
Q96JA3 (PLEKHA8; 58, −21, −0.36)
Q8IUK5 (PLXDC1; 56, −21, −0.37)
Q9UL42 (PNMA2; 42, −21, −0.50)
P48147 (PREP; 81, −21, −0.26)
P41743 (PRKCI; 68, −21, −0.30)
P07602 (PSAP; 58, −21, −0.36)
Q13905 (RAPGEF1; 121, −21, −0.17)
Q9UKA8 (RCAN3; 27, −21, −0.76)
O43567 (RNF13; 43, −21, −0.49)
O75056 (SDC3; 45, −20, −0.43)
Q99574 (SERPINI1; 46, −20, −0.43)
Q9Y6P5 (SESN1; 57, −20, −0.35)
Q96HU1 (SGSM3; 85, −20, −0.23)
Q8N1H7 (SIX6OS1; 68, −20, −0.29)
Q6U841 (SLC4A10; 126, −20, −0.15)
Q8TBB6 (SLC7A14; 84, −20, −0.23)
A6NFE2 (SMCO2; 39, −20, −0.50)
Q9BXP5 (SRRT; 101, −20, −0.19)
Q8NFI4 (ST13P5; 41, −20, −0.48)
Q5T4T6 (SYCP2L; 94, −20, −0.21)
Q15545 (TAF7; 40, −20, −0.49)
Q9BQ87 (TBL1Y; 57, −20, −0.35)
O94842 (TOX4; 66, −20, −0.30)
O95361 (TRIM16; 64, −20, −0.31)
Q8NB14 (USP38; 117, −20, −0.17)
P19320 (VCAM1; 81, −20, −0.24)
Q9NNX9 (VCX3A; 20, −20, −0.99)
Q8IWA0 (WDR75; 94, −20, −0.21)
Q9NQW7 (XPNPEP1; 70, −20, −0.28)
P25490 (YY1; 45, −20, −0.44)
Q8TF50 (ZNF526; 74, −20, −0.27)
A7E2V4 (ZSWIM8; 197, −20, −0.10)
Q5MJ09 (SPANXN3; 16, −20, −1.28)
Q9HCU9 (BRMS1; 28, −20, −0.70)
P06870 (KLK1; 29, −20, −0.69)
I3L3R5 (CCER2; 30, −20, −0.65)
Q7Z6L0 (PRRT2; 35, −20, −0.57)
Q86YD5 (LDLRAD3; 37, −20, −0.53)
Q5PSV4 (BRMS1L; 38, −20, −0.53)
Q53T59 (HS1BP3; 43, −20, −0.46)
Q9UNH6 (SNX7; 45, −20, −0.44)
Q96C92 (SDCCAG3; 48, −20, −0.41)
Q8TAK5 (GABPB2; 49, −20, −0.41)
P35557 (GCK; 52, −20, −0.38)
P45452 (MMP13; 54, −20, −0.37)
Q16322 (KCNA10; 58, −20, −0.34)
P55259 (GP2; 59, −20, −0.33)
Q9Y6K8 (AK5; 63, −20, −0.31)
Q96IT1 (ZNF496; 67, −21, −0.31)
Q9H9R9 (DBNDD1; 17, −21, −1.23)
Q8IVU9 (C10orf107; 24, −21, −0.87)
P17677 (GAP43; 25, −21, −0.84)
Q6ZRP0 (PRR23C; 28, −21, −0.75)
Q9NZQ9 (TMOD4; 39, −21, −0.53)
Q4G1C9 (GLIPR1L2; 40, −21, −0.52)
O75381 (PEX14; 41, −21, −0.50)
P0DJD8 (PGA3; 42, −21, −0.50)
Q8NFH3 (NUP43; 42, −21, −0.49)
Q8IXS6 (PALM2; 42, −21, −0.49)
Q9HB90 (RRAGC; 44, −21, −0.47)
P49354 (FNTA; 44, −21, −0.47)
O95810 (SDPR; 47, −21, −0.44)
Q9H4B7 (TUBB1; 50, −21, −0.41)
P16870 (CPE; 53, −21, −0.39)
Q8WWU5 (TCP11; 56, −21, −0.37)
Q13596 (SNX1; 59, −21, −0.35)
Q8N239 (KLHL34; 71, −21, −0.29)
Q8N9W4 (GOLGA6L2; 79, −21, −0.26)
Q0ZGT2 (NEXN; 81, −21, −0.26)
Q8N5V2 (NGEF; 82, −21, −0.25)
Q9UMQ6 (CAPN11; 84, −21, −0.24)
P0C869 (PLA2G4B; 88, −21, −0.23)
P57737 (CORO7; 101, −21, −0.20)
P40189 (IL6ST; 104, −21, −0.20)
Q9HBJ7 (USP29; 104, −21, −0.20)
Q93084 (ATP2A3; 114, −21, −0.18)
Q13797 (ITGA9; 114, −21, −0.18)
Q711Q0 (C10orf71; 156, −21, −0.13)
Q9H0J4 (QRICH2; 181, −21, −0.11)
Q9H6A9 (PCNXL3; 222, −21, −0.09)
Q63HQ0 (AP1AR; 34, −20, −0.58)
Q13017 (ARHGAP5; 172, −20, −0.11)
Q9Y2Y0 (ARL2BP; 19, −20, −1.06)
P20020 (ATP2B1; 139, −20, −0.14)
Q14692 (BMS1; 146, −20, −0.13)
Q96Q07 (BTBD9; 69, −20, −0.28)
O14936 (CASK; 105, −20, −0.19)
O60337 (MARCH6; 103, −19, −0.18)
Q969K4 (ABTB1; 54, −19, −0.35)
Q9GZN1 (ACTR6; 46, −19, −0.41)
Q8WYP5 (AHCTF1; 252, −19, −0.07)
O75891 (ALDH1L1; 99, −19, −0.19)
Q8N6M6 (AOPEP; 94, −19, −0.20)
Q2VPB7 (AP5B1; 94, −19, −0.20)
Q9Y294 (ASF1A; 23, −19, −0.82)
Q9Y4P1 (ATG4B; 44, −19, −0.42)
Q01814 (ATP2B2; 137, −19, −0.13)
P61421 (ATP6V0D1; 40, −19, −0.47)
P80723 (BASP1; 23, −19, −0.83)
Q13873 (BMPR2; 115, −19, −0.16)
Q12982 (BNIP2; 36, −19, −0.52)
Q96KV6 (BTN2A3P; 66, −19, −0.28)
O43683 (BUB1; 122, −19, −0.15)
Q8IWF9 (CCDC83; 49, −19, −0.38)
Q9BSQ5 (CCM2; 49, −19, −0.38)
Q8IX05 (CD302; 26, −19, −0.72)
Q9BS16 (CENPK; 32, −19, −0.60)
Q6ZU80 (CEP128; 128, −19, −0.14)
Q13111 (CHAF1A; 107, −19, −0.17)
Q9UHC6 (CNTNAP2; 148, −19, −0.12)
P53618 (COPB1; 107, −19, −0.17)
Q8N6G5 (CSGALNACT2; 63, −19, −0.30)
P39880 (CUX1; 164, −19, −0.11)
O75398 (DEAF1; 59, −19, −0.32)
Q5F1R6 (DNAJC21; 62, −19, −0.30)
Q86TI2 (DPP9; 98, −19, −0.19)
Q9HA90 (EFCC1; 66, −19, −0.28)
Q9UHY7 (ENOPH1; 29, −19, −0.65)
Q15303 (ERBB4; 147, −19, −0.12)
O75460 (ERN1; 110, −19, −0.17)
Q8N3Y1 (FBXW8; 67, −19, −0.28)
O94868 (FCHSD2; 84, −19, −0.22)
P22607 (FGFR3; 88, −19, −0.21)
O43524 (FOXO3; 71, −19, −0.26)
Q6MZW2 (FSTL4; 93, −19, −0.20)
Q9H8Y8 (GORASP2; 47, −19, −0.40)

TABLE 3-continued

Exemplary naturally occurring negatively supercharged proteins.

Q8N2Q7 (NLGN1; 94, −20, −0.21)
Q8NFZ3 (NLGN4Y; 92, −20, −0.21)
Q96SU4 (OSBPL9; 83, −20, −0.24)
Q9Y5B6 (PAXBP1; 105, −20, −0.19)
Q6UXB8 (PI16; 49, −20, −0.40)
Q9P0L9 (PKD2L1; 92, −20, −0.21)
Q13401 (PMS2P3; 19, −20, −1.06)
P61218 (POLR2F; 14, −20, −1.38)
Q9BZL4 (PPP1R12C; 85, −20, −0.23)
Q9NQV6 (PRDM10; 130, −20, −0.15)
Q9Y6C5 (PTCH2; 131, −20, −0.15)
Q15185 (PTGES3; 19, −20, −1.06)
Q15269 (PWP2; 102, −20, −0.19)
Q9P0K7 (RAI14; 110, −20, −0.18)
P78332 (RBM6; 129, −20, −0.15)
O14715 (RGPD8; 199, −20, −0.10)
Q13753 (LAMC2; 131, −19, −0.14)
Q03252 (LMNB2; 68, −19, −0.28)
Q7Z4F1 (LRP10; 76, −19, −0.24)
P10911 (MCF2; 108, −19, −0.17)
Q86YR7 (MCF2L2; 127, −19, −0.14)
Q99687 (MEIS3; 41, −19, −0.46)
Q96T76 (MMS19; 113, −19, −0.16)
Q96JA4 (MS4A14; 77, −19, −0.24)
Q32MK0 (MYLK3; 88, −19, −0.21)
Q13562 (NEUROD1; 40, −19, −0.47)
Q8N0W4 (NLGN4X; 92, −19, −0.20)
Q5SRE5 (NUP188; 196, −19, −0.09)
Q8N1F7 (NUP93; 93, −19, −0.20)
Q6DKJ4 (NXN; 48, −19, −0.39)
O75665 (OFD1; 117, −19, −0.16)
Q9BXW6 (OSBPL1A; 108, −19, −0.17)
O75781 (PALM; 42, −19, −0.45)
Q6UWI2 (PARM1; 32, −19, −0.58)
Q8NEN9 (PDZD8; 129, −19, −0.14)
P55347 (PKNOX1; 48, −19, −0.39)
Q8ND90 (PNMA1; 40, −19, −0.47)
Q9Y535 (POLR3H; 23, −19, −0.82)
P41236 (PPP1R2; 23, −19, −0.82)
Q96MT3 (PRICKLE1; 94, −19, −0.20)
Q05513 (PRKCZ; 68, −19, −0.28)
P26022 (PTX3; 42, −19, −0.45)
P20742 (PZP; 164, −19, −0.11)
Q12967 (RALGDS; 101, −19, −0.18)
P47736 (RAP1GAP; 73, −19, −0.25)
O75901 (RASSF9; 50, −19, −0.37)
P98175 (RBM10; 104, −19, −0.18)
O95199 (RCBTB2; 60, −19, −0.31)
O00237 (RNF103; 79, −19, −0.23)
Q5VTR2 (RNF20; 114, −19, −0.16)
Q8N2Y8 (RUSC2; 161, −19, −0.11)
Q9UQD0 (SCN8A; 225, −19, −0.08)
Q9NZV5 (SEPN1; 66, −19, −0.28)
Q15047 (SETDB1; 143, −19, −0.13)
Q9H2J7 (SLC6A15; 82, −19, −0.23)
Q9HBV2 (SPACA1; 32, −19, −0.59)
Q8NBT2 (SPC24; 22, −19, −0.84)
Q8WYL5 (SSH1; 116, −19, −0.16)
Q7L0J3 (SV2A; 83, −19, −0.22)
Q9BZK7 (TBL1XR1; 56, −19, −0.34)
Q8N1K5 (THEMIS; 73, −19, −0.25)
Q9Y6Q6 (TNFRSF11A; 66, −19, −0.28)
O75674 (TOM1L1; 53, −19, −0.35)
Q7Z7E8 (UBE2Q1; 46, −19, −0.41)
O95185 (UNC5C; 103, −19, −0.18)
Q9NX94 (WBP1L; 38, −19, −0.50)
Q96S15 (WDR24; 102, −19, −0.18)
Q8IX03 (WWC1; 125, −19, −0.15)
P13010 (XRCC5; 83, −19, −0.22)
O15060 (ZBTB39; 79, −19, −0.24)
Q86UZ6 (ZBTB46; 64, −19, −0.29)
Q8IWT0 (ZBTB8OS; 19, −19, −0.97)
Q8WW38 (ZFPM2; 128, −19, −0.14)
Q03112 (MECOM; 118, −18, −0.15)
O75121 (MFAP3L; 45, −18, −0.39)
P08582 (MFI2; 80, −18, −0.22)
Q969V6 (MKL1; 99, −18, −0.18)
Q9BV36 (MLPH; 66, −18, −0.27)
Q5TAA0 (TTC22; 63, −20, −0.31)
Q8WXK1 (ASB15; 66, −20, −0.30)
Q6TGC4 (PADI6; 78, −20, −0.25)
O94782 (USP1; 88, −20, −0.22)
O75366 (AVIL; 92, −20, −0.21)
Q6P3X3 (TTC27; 97, −20, −0.20)
Q9UBF2 (COPG2; 98, −20, −0.20)
P19021 (PAM; 108, −20, −0.18)
Q92622 (KIAA0226; 109, −20, −0.18)
Q8N283 (ANKRD35; 110, −20, −0.18)
Q8TBY8 (PMFBP1; 119, −20, −0.16)
P49796 (RGS3; 132, −20, −0.15)
Q10571 (MN1; 136, −20, −0.14)
O14841 (OPLAH; 137, −20, −0.14)
Q01970 (PLCB3; 139, −20, −0.14)
Q5VTT5 (MYOM3; 162, −20, −0.12)
P23468 (PTPRD; 215, −20, −0.09)
Q13332 (PTPRS; 217, −20, −0.09)
P17022 (ZNF18; 62, −19, −0.30)
P27482 (CALML3; 17, −19, −1.12)
Q99750 (MDFI; 25, −19, −0.75)
A6NLC5 (C3orf70; 28, −19, −0.68)
P62258 (YWHAE; 29, −19, −0.65)
B4DZS4 (TCP11X1; 35, −19, −0.54)
Q8N5Z5 (KCTD17; 36, −19, −0.53)
Q96IW2 (SHD; 38, −19, −0.49)
Q13426 (XRCC4; 38, −19, −0.49)
A8K0S8 (MEIS3P2; 39, −19, −0.48)
Q9BRP1 (PDCD2L; 39, −19, −0.48)
Q9BUA3 (C11orf84; 41, −19, −0.46)
Q969K3 (RNF34; 42, −19, −0.45)
Q5H9J9 (TCP11X2; 46, −19, −0.40)
P35716 (SOX11; 47, −19, −0.40)
P21128 (ENDOU; 47, −19, −0.40)
A6NEM1 (GOLGA6L9; 49, −19, −0.38)
Q86TP1 (PRUNE; 50, −19, −0.37)
A6NFL8 (GOLGA6L20; 50, −19, −0.37)
A6NI03 (TRIM64B; 52, −19, −0.36)
P08670 (VIM; 54, −19, −0.35)
Q96QS3 (ARX; 58, −19, −0.32)
P17658 (KCNA6; 59, −19, −0.32)
Q96M34 (C3orf30; 60, −19, −0.31)
Q8WTU2 (SRCRB4D; 61, −19, −0.31)
Q6ZS11 (RINL; 62, −19, −0.30)
Q99504 (EYA3; 63, −19, −0.30)
Q8NBE8 (KLHL23; 64, −19, −0.29)
Q96MW5 (COG8; 68, −19, −0.27)
Q8NAN2 (FAM73A; 71, −19, −0.26)
Q9UN88 (GABRQ; 72, −19, −0.26)
Q8NBF2 (NHLRC2; 79, −19, −0.23)
Q8TC07 (TBC1D15; 79, −19, −0.23)
Q04446 (GBE1; 80, −19, −0.23)
Q9UIU6 (SIX4; 83, −19, −0.22)
O60568 (PLOD3; 85, −19, −0.22)
P25205 (MCM3; 91, −19, −0.20)
O60658 (PDE8A; 93, −19, −0.20)
Q5VTH9 (WDR78; 95, −19, −0.20)
P18858 (LIG1; 102, −19, −0.18)
Q6EKJ0 (GTF2IRD2B; 107, −19, −0.17)
Q12860 (CNTN1; 113, −19, −0.16)
P18206 (VCL; 124, −19, −0.15)
Q149M9 (NWD1; 175, −19, −0.10)
P12111 (COL6A3; 344, −19, −0.05)
Q9UKV3 (ACIN1; 152, −18, −0.11)
Q9UP79 (ADAMTS8; 96, −18, −0.18)
Q3LIE5 (ADPRM; 40, −18, −0.45)
P02771 (AFP; 69, −18, −0.26)
Q9Y3D8 (AK6; 20, −18, −0.89)
P09917 (ALOX5; 78, −18, −0.23)
P08133 (ANXA6; 76, −18, −0.23)
Q9NRY4 (ARHGAP35; 171, −18, −0.10)
O14497 (ARID1A; 242, −18, −0.07)
Q8N8L6 (ARL10; 27, −18, −0.65)
O43681 (ASNA1; 39, −18, −0.46)
P18848 (ATF4; 39, −18, −0.46)
Q6ZRG5 (0; 24, −18, −0.74)
P40337 (VHL; 24, −18, −0.74)
Q8WVE0 (N6AMT2; 25, −18, −0.73)
Q4ZG55 (GREB1; 216, −19, −0.08)
P43080 (GUCA1A; 23, −19, −0.82)
Q13547 (HDAC1; 55, −19, −0.34)
Q58FF3 (HSP90B2P; 46, −19, −0.41)
P22304 (IDS; 62, −19, −0.30)
O14498 (ISLR; 46, −19, −0.41)
P06756 (ITGAV; 116, −19, −0.16)
P05556 (ITGB1; 88, −19, −0.21)
Q9Y6Y0 (IVNS1ABP; 72, −19, −0.26)
Q9NVX7 (KBTBD4; 58, −19, −0.32)
Q7Z4S6 (KIF21A; 187, −19, −0.10)
Q53G59 (KLHL12; 63, −19, −0.30)
P52294 (KPNA1; 60, −19, −0.31)
O60684 (KPNA6; 60, −19, −0.31)
Q7Z3Z0 (KRT25; 49, −19, −0.38)
Q14525 (KRT33B; 46, −19, −0.41)
O15230 (LAMA5; 400, −19, −0.04)
Q07021 (C1QBP; 31, −18, −0.57)
P01024 (C3; 187, −18, −0.09)
Q8TD86 (CALML6; 21, −18, −0.86)
Q8N187 (CARF; 81, −18, −0.22)
Q8TBZ0 (CCDC110; 97, −18, −0.18)
Q16543 (CDC37; 44, −18, −0.40)
Q3L8U1 (CHD9; 326, −18, −0.05)
Q9Y240 (CLEC11A; 36, −18, −0.50)
Q9UFF9 (CNOT8; 34, −18, −0.53)
Q68CJ9 (CREB3L3; 49, −18, −0.36)
P26232 (CTNNA2; 105, −18, −0.17)
Q9H467 (CUEDC2; 32, −18, −0.56)
Q13948 (CUX1; 77, −18, −0.23)
Q96SD1 (DCLRE1C; 78, −18, −0.22)
Q8TF46 (DIS3L; 121, −18, −0.14)
Q8IZD9 (DOCK3; 233, −18, −0.07)
P24534 (EEF1B2; 25, −18, −0.72)
Q99814 (EPAS1; 96, −18, −0.18)
Q15375 (EPHA7; 112, −18, −0.16)
A6NGS2 (ERICH4; 14, −18, −1.24)
P43268 (ETV4; 54, −18, −0.33)
P41161 (ETV5; 58, −18, −0.31)
O60447 (EVI5; 93, −18, −0.19)
Q8NE31 (FAM13C; 66, −18, −0.27)
Q96IP4 (FAM46A; 50, −18, −0.36)
O95466 (FMNL1; 122, −18, −0.14)
P01100 (FOS; 41, −18, −0.44)
O95257 (GADD45G; 17, −18, −1.05)
Q9HCG7 (GBA2; 105, −18, −0.17)
Q92990 (GLMN; 68, −18, −0.26)
Q8TBA6 (GOLGA5; 83, −18, −0.21)
Q8NBJ4 (GOLM1; 45, −18, −0.39)
Q9HD26 (GOPC; 51, −18, −0.35)
Q68CZ6 (HAUS3; 70, −18, −0.25)
Q7Z4H7 (HAUS6; 109, −18, −0.16)
Q8IV36 (HID1; 89, −18, −0.20)
P28067 (HLA-DMA; 29, −18, −0.61)
Q96EW2 (HSPBAP1; 55, −18, −0.32)
Q8NDH6 (ICA1L; 54, −18, −0.33)
Q9Y366 (IFT52; 50, −18, −0.36)
P42701 (IL12RB1; 73, −18, −0.24)
P46940 (IQGAP1; 189, −18, −0.09)
Q96I82 (KAZALD1; 33, −18, −0.54)
Q8IZA0 (KIAA0319L; 116, −18, −0.15)
Q8TCG1 (KIAA1524; 102, −18, −0.17)
Q9ULH0 (KIDINS220; 197, −18, −0.09)
O60282 (KIF5C; 109, −18, −0.16)
Q15323 (KRT31; 47, −18, −0.38)
Q92764 (KRT35; 50, −18, −0.35)
A4D1U4 (LCHN; 51, −18, −0.34)
Q9BXB1 (LGR4; 104, −18, −0.17)
Q38SD2 (LRRK1; 225, −18, −0.07)
Q9NTJ4 (MAN2C1; 116, −18, −0.15)
Q12851 (MAP4K2; 92, −18, −0.19)
Q96GX5 (MASTL; 97, −18, −0.18)
O15068 (MCF2L; 128, −18, −0.14)
Q9BTE3 (MCMBP; 73, −18, −0.24)
Q8N944 (AMER3; 90, −17, −0.18)
Q9H9E1 (ANKRA2; 34, −17, −0.49)
Q8WVL7 (ANKRD49; 27, −17, −0.62)
Q7Z5R6 (APBB1IP; 73, −17, −0.23)

TABLE 3-continued

Exemplary naturally occurring negatively supercharged proteins.

P49959 (MRE11A; 81, −18, −0.22)
Q96HT8 (MRFAP1L1; 15, −18, −1.21)
Q9H3R2 (MUC13; 55, −18, −0.32)
Q13564 (NAE1; 60, −18, −0.29)
O14777 (NDC80; 74, −18, −0.24)
Q9Y3T9 (NOC2L; 85, −18, −0.21)
O94818 (NOL4; 71, −18, −0.25)
Q96MY1 (NOL4L; 47, −18, −0.38)
Q9UNZ2 (NSFL1C; 41, −18, −0.44)
Q8TEM1 (NUP210; 205, −18, −0.08)
Q96FW1 (OTUB1; 31, −18, −0.57)
Q5JRK9 (PAGE2B; 12, −18, −1.49)
Q86YC2 (PALB2; 131, −18, −0.13)
Q63HM2 (PCNXL4; 133, −18, −0.13)
Q53EL6 (PDCD4; 52, −18, −0.34)
Q9P2J9 (PDP2; 60, −18, −0.30)
Q5T2W1 (PDZK1; 57, −18, −0.31)
Q9Y4G2 (PLEKHM1; 117, −18, −0.15)
Q9UNA4 (POLI; 83, −18, −0.21)
P35813 (PPM1A; 42, −18, −0.42)
P13861 (PRKAR2A; 46, −18, −0.39)
Q14699 (RFTN1; 63, −18, −0.28)
Q8IXI1 (RHOT2; 68, −18, −0.26)
Q7Z5B4 (RIC3; 41, −18, −0.43)
O14730 (RIOK3; 59, −18, −0.30)
O75298 (RTN2; 59, −18, −0.30)
Q9UHR5 (SAP30BP; 34, −18, −0.53)
Q93073 (SECISBP2L; 122, −18, −0.14)
P58004 (SESN2; 54, −18, −0.33)
P31947 (SFN; 28, −18, −0.64)
O43147 (SGSM2; 113, −18, −0.15)
Q9H0K1 (SIK2; 104, −18, −0.17)
Q9P2F8 (SIPA1L2; 190, −18, −0.09)
P63208 (SKP1; 19, −18, −0.96)
Q13433 (SLC39A6; 85, −18, −0.21)
Q9Y3F4 (STRAP; 38, −18, −0.46)
Q8IYJ3 (SYTL1; 62, −18, −0.29)
Q3MII6 (TBC1D25; 76, −18, −0.23)
Q13445 (TMED1; 25, −18, −0.71)
Q9C0H2 (TTYH3; 58, −18, −0.31)
Q8IZJ1 (UNC5B; 104, −18, −0.17)
Q8N6Y0 (USHBP1; 76, −18, −0.23)
Q96QU8 (XPO6; 129, −18, −0.13)
Q96MU7 (YTHDC1; 85, −18, −0.21)
Q05516 (ZBTB16; 74, −18, −0.24)
Q9UBW7 (ZMYM2; 155, −18, −0.11)
Q9UDV7 (ZNF282; 74, −18, −0.24)
Q9UGI0 (ZRANB1; 81, −18, −0.22)
P07919 (UQCRH; 11, −18, −1.67)
Q13068 (GAGE4; 13, −18, −1.39)
P31431 (SDC4; 22, −18, −0.83)
Q5H9L2 (TCEAL5; 23, −18, −0.77)
Q58FG1 (HSP90AA4P; 48, −17, −0.35)
O95757 (HSPA4L; 95, −17, −0.17)
Q96FT9 (IFT43; 24, −17, −0.72)
Q96HW7 (INTS4; 108, −17, −0.15)
Q9UPP2 (IQSEC3; 128, −17, −0.13)
O95965 (ITGBL1; 54, −17, −0.31)
P29375 (KDM5A; 192, −17, −0.08)
O60662 (KLHL41; 68, −17, −0.24)
Q2M2I5 (KRT24; 55, −17, −0.30)
O76011 (KRT34; 49, −17, −0.34)
Q6UX15 (LAYN; 43, −17, −0.39)
O60711 (LPXN; 43, −17, −0.39)
P43355 (MAGEA1; 34, −17, −0.49)
P43243 (MATR3; 95, −17, −0.17)
Q8NI22 (MCFD2; 16, −17, −1.03)
O14770 (MEIS2; 52, −17, −0.32)
Q6WCQ1 (MPRIP; 117, −17, −0.14)
Q5JR59 (MTUS2; 150, −17, −0.11)
Q5SSG8 (MUC21; 54, −17, −0.31)
Q9Y6X6 (MYO16; 206, −17, −0.08)
Q09161 (NCBP1; 92, −17, −0.18)
P25208 (NFYB; 23, −17, −0.74)
P59047 (NLRP5; 134, −17, −0.12)
Q16620 (NTRK2; 92, −17, −0.18)
Q8IVD9 (NUDCD3; 41, −17, −0.41)
Q9H1M0 (NUP62CL; 21, −17, −0.81)
P15374 (UCHL3; 26, −18, −0.68)
Q8WUU8 (TMEM174; 26, −18, −0.68)
A4D2B0 (MBLAC1; 27, −18, −0.66)
A6NEV1 (PRR23A; 28, −18, −0.63)
Q9H6K1 (C6orf106; 33, −18, −0.54)
Q9Y5U2 (TSSC4; 34, −18, −0.52)
Q9P2X3 (IMPACT; 36, −18, −0.49)
P55082 (MFAP3; 40, −18, −0.44)
Q9UGV2 (NDRG3; 41, −18, −0.43)
Q53QW1 (C2orf57; 42, −18, −0.43)
Q5TDH0 (DDI2; 45, −18, −0.40)
Q9HAS0 (C17orf75; 45, −18, −0.40)
Q9NXR5 (ANKRD10; 45, −18, −0.40)
Q9BSE4 (HERPUD2; 45, −18, −0.39)
Q9NWX5 (ASB6; 47, −18, −0.38)
P09104 (ENO2; 47, −18, −0.38)
Q9H313 (TTYH1; 49, −18, −0.36)
P78396 (CCNA1; 52, −18, −0.34)
P15036 (ETS2; 53, −18, −0.33)
Q09470 (KCNA1; 56, −18, −0.31)
Q01113 (IL9R; 57, −18, −0.31)
Q9Y5P3 (RAI2; 57, −18, −0.31)
Q13705 (ACVR2B; 58, −18, −0.31)
P06239 (LCK; 58, −18, −0.31)
Q2L4Q9 (PRSS53; 58, −18, −0.30)
Q6ZTN6 (ANKRD13D; 58, −18, −0.30)
P09603 (CSF1; 60, −18, −0.29)
P06865 (HEXA; 61, −18, −0.29)
Q6ZWJ1 (STXBP4; 62, −18, −0.29)
Q9H5J0 (ZBTB3; 62, −18, −0.29)
P32519 (ELF1; 67, −18, −0.26)
O95677 (EYA4; 70, −18, −0.25)
Q9H6X5 (C19orf44; 71, −18, −0.25)
Q5VWK5 (IL23R; 72, −18, −0.25)
Q8WVZ9 (KBTBD7; 77, −18, −0.23)
Q8N3R9 (MPP5; 77, −18, −0.23)
Q16820 (MEP1B; 80, −18, −0.22)
Q9BXC9 (BBS2; 80, −18, −0.22)
Q9NVR0 (KLHL11; 80, −18, −0.22)
Q9UP52 (TFR2; 89, −18, −0.20)
Q6XPR3 (RPTN; 91, −18, −0.19)
A2RTX5 (TARSL2; 93, −18, −0.19)
Q5T447 (HECTD3; 97, −18, −0.18)
Q8ND30 (PPFIBP2; 99, −18, −0.18)
O15327 (INPP4B; 105, −18, −0.17)
Q17RG1 (KCTD19; 105, −18, −0.17)
Q9H0M0 (WWP1; 105, −18, −0.17)
Q70J99 (UNC13D; 123, −18, −0.14)
Q5JYT7 (KIAA1755; 131, −18, −0.13)
Q5TEA3 (C20orf194; 132, −18, −0.13)
Q2VIQ3 (KIF4B; 140, −18, −0.12)
P41252 (IARS; 144, −18, −0.12)
Q9BXX2 (ANKRD30B; 158, −18, −0.11)
Q9BZC7 (ABCA2; 270, −17, −0.06)
Q8N0X2 (SPAG16; 71, −17, −0.24)
Q9UEE5 (STK17A; 47, −17, −0.36)
Q9ULQ0 (STRIP2; 95, −17, −0.17)
Q92797 (SYMPK; 141, −17, −0.12)
A6NDD5 (SYNDIG1L; 26, −17, −0.65)
Q6ZMZ3 (SYNE3; 112, −17, −0.15)
Q5QJ74 (TBCEL; 48, −17, −0.35)
Q9Y4R8 (TELO2; 92, −17, −0.18)
Q9Y6I9 (TEX264; 34, −17, −0.49)
P22735 (TGM1; 90, −17, −0.18)
Q9UIK5 (TMEFF2; 41, −17, −0.41)
Q96PN7 (TRERF1; 132, −17, −0.12)
Q9BYV2 (TRIM54; 40, −17, −0.42)
Q8N9V2 (TRIML1; 53, −17, −0.32)
Q06418 (TYRO3; 97, −17, −0.17)
Q6NUM6 (TYW1B; 77, −17, −0.22)
Q96S82 (UBL7; 41, −17, −0.41)
Q9Y6N9 (USH1C; 62, −17, −0.27)
Q9HCJ6 (VAT1L; 46, −17, −0.37)
Q9H7D7 (WDR26; 72, −17, −0.23)
Q9HAD4 (WDR41; 52, −17, −0.32)
Q9Y2K1 (ZBTB1; 82, −17, −0.20)
Q8N5A5 (ZGPAT; 57, −17, −0.29)
Q96K83 (ZNF521; 148, −17, −0.11)
Q8TDY4 (ASAP3; 99, −17, −0.17)
Q9UBL3 (ASH2L; 69, −17, −0.24)
Q8WYN0 (ATG4A; 45, −17, −0.37)
P50993 (ATP1A2; 112, −17, −0.15)
Q8NBF6 (AVL9; 72, −17, −0.23)
Q9UIF9 (BAZ2A; 211, −17, −0.08)
Q9H165 (BCL11A; 91, −17, −0.18)
Q9BUH8 (BEGAIN; 65, −17, −0.26)
Q13323 (BIK; 18, −17, −0.94)
Q14137 (BOP1; 84, −17, −0.20)
P59827 (BPIFB4; 65, −17, −0.26)
O00478 (BTN3A3; 65, −17, −0.26)
Q9BV29 (C15orf57; 21, −17, −0.82)
P01031 (C5; 188, −17, −0.09)
Q86V35 (CABP7; 24, −17, −0.69)
Q01668 (CACNA1D; 245, −17, −0.06)
Q9BY67 (CADM1; 49, −17, −0.35)
P05937 (CALB1; 30, −17, −0.56)
A5YM72 (CARNS1; 88, −17, −0.19)
Q9Y3C0 (CCDC53; 21, −17, −0.80)
Q9H3Q1 (CDC42EP4; 38, −17, −0.44)
Q6UY09 (CEACAM20; 65, −17, −0.26)
Q9BY43 (CHMP4A; 25, −17, −0.67)
O75838 (CIB2; 22, −17, −0.78)
Q9UIV1 (CNOT7; 33, −17, −0.51)
Q9Y2V7 (COG6; 73, −17, −0.23)
P07333 (CSF1R; 108, −17, −0.15)
O60716 (CTNND1; 108, −17, −0.15)
P35638 (DDIT3; 19, −17, −0.88)
Q8IV53 (DENND1C; 87, −17, −0.19)
O75140 (DEPDC5; 181, −17, −0.09)
Q92620 (DHX38; 141, −17, −0.12)
Q9BVC3 (DSCC1; 45, −17, −0.37)
Q56P03 (EAPP; 33, −17, −0.51)
Q9UNE0 (EDAR; 49, −17, −0.34)
O75822 (EIF3J; 29, −17, −0.58)
O95834 (EML2; 71, −17, −0.24)
P34910 (EVI2B; 49, −17, −0.34)
Q8TAG9 (EXOC6; 94, −17, −0.18)
Q6PEV8 (FAM199X; 43, −17, −0.39)
Q5TGI0 (FAXC; 47, −17, −0.36)
Q9BSK4 (FEM1A; 74, −17, −0.23)
P21802 (FGFR2; 92, −17, −0.18)
Q75LS8 (FKBP9P1; 16, −17, −1.09)
Q9UN86 (G3BP2; 54, −17, −0.31)
O75293 (GADD45B; 18, −17, −0.95)
A1L429 (GAGE12B;; 13, −17, −1.31)
Q9UEU5 (GAGE2D;; 13, −17, −1.33)
Q96PP8 (GBP5; 67, −17, −0.25)
P16383 (GCFC2; 89, −17, −0.19)
P36915 (GNL1; 69, −17, −0.24)
P80108 (GPLD1; 92, −17, −0.18)
P15170 (GSPT1; 56, −17, −0.30)
O14641 (DVL2; 79, −17, −0.21)
P48380 (RFX3; 84, −17, −0.20)
Q9UGT4 (SUSD2; 90, −17, −0.18)
P02671 (FGA; 95, −17, −0.17)
Q3MJ16 (PLA2G4E; 98, −17, −0.17)
P86452 (ZBED6; 110, −17, −0.15)
Q8N398 (VWA5B2; 133, −17, −0.12)
Q9NZM4 (GLTSCR1; 158, −17, −0.10)
Q5T5Y3 (CAMSAP1; 178, −17, −0.09)
Q5JTZ9 (AARS2; 107, −16, −0.14)
Q96P50 (ACAP3; 92, −16, −0.17)
P35611 (ADD1; 81, −16, −0.19)
Q9BRR6 (ADPGK; 54, −16, −0.29)
Q9NX46 (ADPRHL2; 39, −16, −0.41)
P35573 (AGL; 175, −16, −0.09)
Q96B36 (AKT1S1; 27, −16, −0.58)
O00203 (AP3B1; 121, −16, −0.13)
P98171 (ARHGAP4; 105, −16, −0.15)
P78348 (ASIC1; 60, −16, −0.26)
Q9HBG4 (ATP6V0A4; 96, −16, −0.16)
Q8WXE1 (ATRIP; 86, −16, −0.18)
Q9UBB4 (ATXN10; 53, −16, −0.29)
Q8IWZ6 (BBS7; 80, −16, −0.19)
P50895 (BCAM; 67, −16, −0.23)
Q9C0K0 (BCL11B; 96, −16, −0.16)

TABLE 3-continued

Exemplary naturally occurring negatively supercharged proteins.

A6NDY0 (PABPN1L; 30, −17, −0.55)
Q9BY11 (PACSIN1; 51, −17, −0.33)
Q9Y2J8 (PADI2; 76, −17, −0.22)
Q7Z2X7 (PAGE2; 12, −17, −1.40)
P29120 (PCSK1; 84, −17, −0.20)
Q15084 (PDIA6; 48, −17, −0.35)
Q9NQ66 (PLCB1; 139, −17, −0.12)
O95397 (PLEKHA8P1; 44, −17, −0.39)
O94827 (PLEKHG5; 117, −17, −0.14)
O00592 (PODXL; 59, −17, −0.28)
P19387 (POLR2C; 31, −17, −0.54)
P27169 (PON1; 40, −17, −0.42)
O75335 (PPFIA4; 134, −17, −0.12)
Q96I34 (PPP1R16A; 58, −17, −0.29)
P53611 (RABGGTB; 37, −17, −0.46)
Q15311 (RALBP1; 76, −17, −0.22)
Q9Y4G8 (RAPGEF2; 167, −17, −0.10)
Q99708 (RBBP8; 102, −17, −0.16)
Q5W0B1 (RNF219; 81, −17, −0.20)
Q9NYV6 (RRN3; 74, −17, −0.22)
Q96DX4 (RSPRY1; 64, −17, −0.26)
Q9NXZ1 (SAGE1; 99, −17, −0.17)
P0C264 (SBK3; 38, −17, −0.44)
Q9Y2G9 (SBNO2; 150, −17, −0.11)
Q14108 (SCARB2; 54, −17, −0.31)
Q16586 (SGCA; 43, −17, −0.39)
Q9HC58 (SLC24A3; 72, −17, −0.23)
Q92504 (SLC39A7; 50, −17, −0.33)
Q07837 (SLC3A1; 79, −17, −0.21)
O75093 (SLIT1; 168, −17, −0.10)
O94964 (SOGA1; 160, −17, −0.10)
P11362 (FGFR1; 92, −16, −0.17)
Q96RU3 (FNBP1; 71, −16, −0.22)
Q6PJQ5 (FOXR2; 36, −16, −0.44)
Q13283 (G3BP1; 52, −16, −0.30)
P24522 (GADD45A; 18, −16, −0.87)
Q4V321 (GAGE13; 13, −16, −1.24)
Q13066 (GAGE2B; 13, −16, −1.25)
O76087 (GAGE7; 13, −16, −1.23)
Q9Y2T3 (GDA; 51, −16, −0.31)
Q9NZ52 (GGA3; 78, −16, −0.20)
Q6P9H5 (GIMAP6; 33, −16, −0.48)
O43424 (GRID2; 113, −16, −0.14)
Q9C0E4 (GRIP2; 113, −16, −0.14)
Q8TAX9 (GSDMB; 47, −16, −0.34)
Q9Y2N7 (HIF3A; 72, −16, −0.22)
P01906 (HLA-DQA2; 28, −16, −0.57)
Q92902 (HPS1; 79, −16, −0.20)
Q9HBG6 (IFT122; 142, −16, −0.11)
B1AKI9 (ISM1; 52, −16, −0.30)
Q8IWB1 (ITPRIP; 62, −16, −0.25)
Q9UNX9 (KCNJ14; 48, −16, −0.33)
Q8IV33 (KIAA0825; 148, −16, −0.10)
A8MWY0 (KIAA1324L; 114, −16, −0.14)
Q9UH77 (KLHL3; 65, −16, −0.24)
P13645 (KRT10; 59, −16, −0.27)
Q7Z3Y7 (KRT28; 51, −16, −0.31)
Q08380 (LGALS3BP; 65, −16, −0.24)
Q1L5Z9 (LONRF2; 84, −16, −0.19)
O95490 (LPHN2; 163, −16, −0.09)
Q6T4P5 (LPPR3; 76, −16, −0.21)
Q9HBG7 (LY9; 72, −16, −0.22)
Q13164 (MAPK7; 88, −16, −0.18)
Q15528 (MED22; 22, −16, −0.72)
Q8TDZ2 (MICAL1; 118, −16, −0.13)
P08253 (MMP2; 74, −16, −0.21)
P22897 (MRC1; 166, −16, −0.09)
Q9BUK6 (MSTO1; 62, −16, −0.25)
Q13765 (NACA; 23, −16, −0.68)
Q9BTE0 (NAT9; 23, −16, −0.68)
Q9UBB6 (NCDN; 79, −16, −0.20)
Q9NZQ3 (NCKIPSD; 79, −16, −0.20)
Q15788 (NCOA1; 157, −16, −0.10)
P46934 (NEDD4; 149, −16, −0.10)
O60524 (NEMF; 123, −16, −0.13)
Q9NZ94 (NLGN3; 94, −16, −0.17)
Q8WX94 (NLRP7; 112, −16, −0.14)
Q9NXX6 (NSMCE4A; 44, −16, −0.36)
Q13070 (GAGE6; 13, −17, −1.31)
Q13069 (GAGE5; 13, −17, −1.31)
Q13067 (GAGE3; 13, −17, −1.31)
Q8WWF1 (C1orf54; 15, −17, −1.13)
O75607 (NPM3; 19, −17, −0.87)
Q96PQ5 (PPP1R2P1; 23, −17, −0.74)
P09497 (CLTB; 25, −17, −0.67)
A8MT33 (SYCE1L; 27, −17, −0.62)
Q8N4E4 (PDCL2; 28, −17, −0.60)
P12004 (PCNA; 29, −17, −0.59)
Q96HH4 (TMEM169; 34, −17, −0.50)
Q96FV0 (LRRC46; 35, −17, −0.48)
Q9NRS6 (SNX15; 38, −17, −0.44)
Q14012 (CAMK1; 41, −17, −0.41)
Q9H756 (LRRC19; 42, −17, −0.40)
P20142 (PGC; 42, −17, −0.40)
Q8N831 (TSPYL6; 46, −17, −0.37)
Q14209 (E2F2; 48, −17, −0.35)
Q9Y664 (KPTN; 48, −17, −0.35)
Q96N77 (ZNF641; 50, −17, −0.34)
P13646 (KRT13; 50, −17, −0.34)
Q8TBK2 (SETD6; 53, −17, −0.31)
Q7RTX7 (CATSPER4; 54, −17, −0.31)
A6NK89 (RASSF10; 57, −17, −0.29)
Q92696 (RABGGTA; 65, −17, −0.26)
Q07065 (CKAP4; 66, −17, −0.25)
O95671 (ASMTL; 69, −17, −0.24)
A6NJ88 (0; 69, −17, −0.24)
P04844 (RPN2; 69, −17, −0.24)
Q9UJY5 (GGA1; 70, −17, −0.24)
Q96M63 (CCDC114; 75, −17, −0.22)
Q7RTS9 (DYM; 76, −17, −0.22)
P52888 (THOP1; 79, −17, −0.21)
P43686 (PSMC4; 47, −16, −0.33)
Q14761 (PTPRCAP; 21, −16, −0.75)
P28827 (PTPRM; 164, −16, −0.09)
Q9H4A4 (RNPEP; 73, −16, −0.22)
Q7LG56 (RRM2B; 41, −16, −0.39)
O75995 (SASH3; 42, −16, −0.38)
Q9Y6U3 (SCIN; 80, −16, −0.19)
P16581 (SELE; 67, −16, −0.24)
Q9UJW9 (SERTAD3; 22, −16, −0.73)
Q2Y0W8 (SLC4A8; 123, −16, −0.13)
Q969T3 (SNX21; 41, −16, −0.38)
O94768 (STK17B; 42, −16, −0.37)
Q15431 (SYCP1; 114, −16, −0.14)
Q9H7V2 (SYNDIG1; 29, −16, −0.56)
Q15750 (TAB1; 55, −16, −0.29)
O95551 (TDP2; 41, −16, −0.39)
Q5JTD0 (TJAP1; 62, −16, −0.25)
Q4V9L6 (TMEM119; 29, −16, −0.54)
Q13625 (TP53BP2; 126, −16, −0.12)
P36406 (TRIM23; 64, −16, −0.24)
Q9NQ86 (TRIM36; 83, −16, −0.19)
Q9Y5S1 (TRPV2; 86, −16, −0.18)
Q9H6E5 (TUT1; 94, −16, −0.17)
P17480 (UBTF; 89, −16, −0.17)
Q9P1Q0 (VPS54; 111, −16, −0.14)
Q9BQA1 (WDR77; 37, −16, −0.43)
Q96S55 (WRNIP1; 72, −16, −0.22)
P46937 (YAP1; 54, −16, −0.29)
Q9HC78 (ZBTB20; 81, −16, −0.19)
O15062 (ZBTB5; 74, −16, −0.21)
Q9UQR1 (ZNF148; 89, −16, −0.17)
P21754 (ZP3; 47, −16, −0.34)
A6NER3 (GAGE12J; 13, −16, −1.24)
P0CL80 (GAGE12F; 13, −16, −1.23)
P0CL81 (GAGE12G; 13, −16, −1.23)
P0CL82 (GAGE12I; 13, −16, −1.23)
Q5T4I8 (C6orf52; 17, −16, −0.92)
Q9BU02 (THTPA; 26, −16, −0.62)
A6NDR6 (MEIS3P1; 30, −16, −0.52)
Q9BR61 (ACBD6; 31, −16, −0.51)
Q8NF67 (0; 31, −16, −0.51)
Q7L4S7 (ARMCX6; 33, −16, −0.48)
Q8WTX7 (GATSL3; 36, −16, −0.44)
Q15165 (PON2; 39, −16, −0.40)
P52788 (SMS; 41, −16, −0.38)
Q7Z569 (BRAP; 67, −16, −0.23)
Q05682 (CALD1; 93, −16, −0.17)
Q9NZT1 (CALML5; 16, −16, −1.00)
P20807 (CAPN3; 94, −16, −0.16)
Q9BWT7 (CARD10; 116, −16, −0.13)
Q6ZRH7 (CATSPERG; 133, −16, −0.12)
Q96JG6 (CCDC132; 111, −16, −0.14)
P0C7W6 (CCDC172; 31, −16, −0.51)
Q7Z3E2 (CCDC186; 104, −16, −0.15)
Q99467 (CD180; 74, −16, −0.21)
Q9NPY3 (CD93; 69, −16, −0.23)
P19835 (CEL; 79, −16, −0.20)
Q8N960 (CEP120; 113, −16, −0.14)
O15182 (CETN3; 20, −16, −0.81)
Q9ULV3 (CIZ1; 100, −16, −0.15)
Q96S66 (CLCC1; 62, −16, −0.25)
Q9C0A0 (CNTNAP4; 145, −16, −0.11)
Q13561 (DCTN2; 44, −16, −0.36)
Q6IQ26 (DENND5A; 147, −16, −0.10)
Q8WYQ5 (DGCR8; 86, −16, −0.18)
Q96F81 (DISP1; 171, −16, −0.09)
P27487 (DPP4; 88, −16, −0.18)
Q16828 (DUSP6; 42, −16, −0.37)
Q12805 (EFEMP1; 55, −16, −0.29)
Q9BQI3 (EIF2AK1; 71, −16, −0.22)
P56537 (EIF6; 27, −16, −0.60)
Q16206 (ENOX2; 70, −16, −0.22)
P14921 (ETS1; 50, −16, −0.31)
Q8IXR5 (FAM178B; 94, −16, −0.17)
O94952 (FBXO21; 72, −16, −0.22)
Q5JSP0 (FGD3; 79, −16, −0.20)
Q96M96 (FGD4; 87, −16, −0.18)
Q8WVB3 (HEXDC; 54, −16, −0.29)
Q495W5 (FUT11; 56, −16, −0.28)
O15131 (KPNA5; 60, −16, −0.26)
P43251 (BTD; 61, −16, −0.26)
P35527 (KRT9; 62, −16, −0.25)
Q0D2K2 (KLHL30; 64, −16, −0.25)
P37173 (TGFBR2; 65, −16, −0.24)
Q0VAK6 (LMOD3; 65, −16, −0.24)
Q8WVV4 (POF1B; 68, −16, −0.23)
Q14651 (PLS1; 70, −16, −0.22)
F8WBI6 (GOLGA8N; 72, −16, −0.22)
C9JLR9 (C11orf95; 73, −16, −0.21)
Q96SB4 (SRPK1; 74, −16, −0.21)
Q2M243 (CCDC27; 75, −16, −0.21)
P20591 (MX1; 76, −16, −0.21)
Q96NG3 (TTC25; 77, −16, −0.20)
Q6P9F0 (CCDC62; 78, −16, −0.20)
Q9Y6B7 (AP4B1; 83, −16, −0.19)
Q2TAL8 (QRICH1; 86, −16, −0.18)
Q9Y4K0 (LOXL2; 87, −16, −0.18)
P51692 (STAT5B; 90, −16, −0.17)
Q86Y56 (HEATR2; 94, −16, −0.17)
Q96M69 (LRGUK; 94, −16, −0.17)
Q658Y4 (FAM91A1; 94, −16, −0.17)
Q9H5Y7 (SLITRK6; 95, −16, −0.16)
P42658 (DPP6; 98, −16, −0.16)
Q9UKY1 (ZHX1; 98, −16, −0.16)
Q92953 (KCNB2; 103, −16, −0.15)
Q969F9 (HPS3; 114, −16, −0.14)
Q8N3T6 (TMEM132C; 122, −16, −0.13)
Q9BXT4 (TDRD1; 132, −16, −0.12)
Q86XP1 (DGKH; 135, −16, −0.11)
Q5TIA1 (MEI1; 141, −16, −0.11)
P13942 (COL11A2; 172, −16, −0.09)
Q6T4R5 (NHS; 179, −16, −0.08)
Q8NF50 (DOCK8; 239, −16, −0.06)
Q99965 (ADAM2; 82, −15, −0.18)
Q8TC27 (ADAM32; 88, −15, −0.17)
P35612 (ADD2; 81, −15, −0.18)
P35869 (AHR; 96, −15, −0.15)
Q7LC44 (ARC; 45, −15, −0.33)
O43307 (ARHGEF9; 61, −15, −0.24)
Q7Z3E5 (ARMC9; 92, −15, −0.16)
Q8N3C0 (ASCC3; 251, −15, −0.05)
Q86U10 (ASPG; 61, −15, −0.24)
P06576 (ATP5B; 57, −15, −0.26)

TABLE 3-continued

Exemplary naturally occurring negatively supercharged proteins.

Q9NXG6 (P4HTM; 57, −16, −0.28)
Q9BVG4 (PBDC1; 26, −16, −0.61)
Q96KB5 (PBK; 36, −16, −0.44)
Q9H2J4 (PDCL3; 28, −16, −0.57)
Q86TG7 (PEG10; 80, −16, −0.19)
P12955 (PEPD; 55, −16, −0.29)
O00264 (PGRMC1; 22, −16, −0.73)
Q92576 (PHF3; 229, −16, −0.06)
Q9UBF8 (PI4KB; 91, −16, −0.17)
Q8WXW3 (PIBF1; 90, −16, −0.17)
Q6TFL3 (CCDC171; 153, −15, −0.09)
P50990 (CCT8; 60, −15, −0.25)
Q7L3B6 (CDC37L1; 39, −15, −0.38)
Q8NHQ1 (CEP70; 70, −15, −0.21)
Q9H444 (CHMP4B; 25, −15, −0.60)
Q96Q77 (CIB3; 22, −15, −0.68)
P12277 (CKB; 43, −15, −0.35)
A8TX70 (COL6A5; 290, −15, −0.05)
Q8N4Y2 (CRACR2B; 45, −15, −0.33)
Q9Y4D2 (DAGLA; 115, −15, −0.13)
P53355 (DAPK1; 160, −15, −0.09)
O60443 (DFNA5; 55, −15, −0.27)
Q9NRI5 (DISC1; 94, −15, −0.16)
Q155Q3 (DIXDC1; 77, −15, −0.19)
Q14574 (DSC3; 100, −15, −0.15)
Q8WWB3 (DYDC1; 21, −15, −0.71)
P29692 (EEF1D; 31, −15, −0.48)
Q96JJ3 (ELMO2; 83, −15, −0.18)
Q9NZ08 (ERAP1; 107, −15, −0.13)
Q9H790 (EXO5; 42, −15, −0.35)
Q96TA1 (FAM129B; 84, −15, −0.17)
O60320 (FAM189A1; 57, −15, −0.26)
O15287 (FANCG; 69, −15, −0.21)
P98174 (FGD1; 107, −15, −0.14)
P98177 (FOXO4; 54, −15, −0.27)
Q6NT46 (GAGE2A; 13, −15, −1.17)
Q9H2C0 (GAN; 68, −15, −0.22)
P31150 (GDI1; 51, −15, −0.29)
Q9H3C7 (GGNBP2; 79, −15, −0.18)
Q9UKD1 (GMEB2; 56, −15, −0.26)
Q9H9Y4 (GPN2; 35, −15, −0.43)
P13807 (GYS1; 84, −15, −0.17)
Q7Z353 (HDX; 77, −15, −0.19)
Q15011 (HERPUD1; 44, −15, −0.34)
O75146 (HIP1R; 119, −15, −0.12)
P20036 (HLA-DPA1; 29, −15, −0.51)
Q01581 (HMGCS1; 57, −15, −0.26)
P20823 (HNF1A; 67, −15, −0.22)
P52597 (HNRNPF; 46, −15, −0.32)
P78318 (IGBP1; 39, −15, −0.38)
O14920 (IKBKB; 87, −15, −0.17)
Q8NAC3 (IL17RC; 86, −15, −0.17)
P01584 (IL1B; 31, −15, −0.48)
Q9Y573 (IPP; 65, −15, −0.22)
Q6NXR0 (IRGC; 50, −15, −0.29)
O75578 (ITGA10; 128, −15, −0.11)
Q3ZCT8 (KBTBD12; 71, −15, −0.21)
Q8IY47 (KBTBD2; 71, −15, −0.21)
P48051 (KCNJ6; 48, −15, −0.30)
Q9H714 (KIAA0226L; 73, −15, −0.20)
Q96J84 (KIRREL; 84, −15, −0.17)
Q9NXS3 (KLHL28; 64, −15, −0.23)
P08779 (KRT16; 51, −15, −0.29)
P13796 (LCP1; 70, −15, −0.21)
P48357 (LEPR; 132, −15, −0.11)
Q5JTD7 (LRRC73; 33, −15, −0.44)
Q0VAA2 (LRRC74; 55, −15, −0.27)
A6NEC2 (NPEPPSL1; 54, −15, −0.27)
P04217 (A1BG; 54, −15, −0.27)
Q8IVJ1 (SLC41A1; 55, −15, −0.27)
Q92769 (HDAC2; 55, −15, −0.27)
O95497 (VNN1; 57, −15, −0.26)
Q9NUJ3 (TCP11L1; 57, −15, −0.26)
P55895 (RAG2; 59, −15, −0.25)
Q6DD88 (ATL3; 61, −15, −0.24)
P54750 (PDE1A; 61, −15, −0.24)
Q9BVS4 (RIOK2; 63, −15, −0.23)
Q1MX18 (INSC; 63, −15, −0.23)
Q16621 (NFE2; 41, −16, −0.38)
P54727 (RAD23B; 43, −16, −0.37)
P14091 (CTSE; 43, −16, −0.36)
Q8IZ63 (PRR22; 44, −16, −0.36)
Q99932 (SPAG8; 45, −16, −0.35)
Q9BXU3 (TEX13A; 46, −16, −0.35)
Q04695 (KRT17; 48, −16, −0.33)
P48165 (GJA8; 48, −16, −0.33)
Q6P531 (GGT6; 51, −16, −0.31)
Q9H993 (C6orf211; 51, −16, −0.31)
A6NLI5 (TRIM64C; 51, −16, −0.31)
Q5R3I4 (TTC38; 53, −16, −0.30)
P57077 (MAP3K7CL; 27, −15, −0.55)
Q86XN8 (MEX3D; 65, −15, −0.23)
Q96C03 (MIEF2; 49, −15, −0.30)
Q13064 (MKRN3; 56, −15, −0.26)
P09238 (MMP10; 54, −15, −0.27)
Q8NDA8 (MROH1; 181, −15, −0.08)
Q00872 (MYBPC1; 128, −15, −0.11)
P12525 (MYCLP1; 41, −15, −0.36)
Q9BZK3 (NACAP1; 23, −15, −0.64)
Q15021 (NCAPD2; 157, −15, −0.09)
Q7Z6G3 (NECAB2; 43, −15, −0.34)
Q8NFZ4 (NLGN2; 91, −15, −0.16)
Q9C000 (NLRP1; 166, −15, −0.09)
Q7RTR0 (NLRP9; 113, −15, −0.13)
P0CE71 (OCM2; 12, −15, −1.23)
Q9ULD0 (OGDHL; 114, −15, −0.13)
O15460 (P4HA2; 61, −15, −0.24)
Q96GU1 (PAGE5; 14, −15, −1.06)
O75914 (PAK3; 62, −15, −0.24)
Q9ULE6 (PALD1; 97, −15, −0.15)
Q8NCN5 (PDPR; 99, −15, −0.15)
Q76G19 (PDZD4; 86, −15, −0.17)
A8MUH7 (PDZK1P1; 44, −15, −0.34)
Q5SV97 (PERM1; 81, −15, −0.18)
Q8TDX9 (PKD1L1; 315, −15, −0.04)
A1L390 (PLEKHG3; 134, −15, −0.11)
Q96PX9 (PLEKHG4B; 140, −15, −0.10)
Q8IYS1 (PM20D2; 48, −15, −0.31)
Q9UBK2 (PPARGC1A; 91, −15, −0.16)
Q969Q6 (PPP2R3C; 53, −15, −0.28)
P60510 (PPP4C; 35, −15, −0.42)
Q92733 (PRCC; 52, −15, −0.28)
P41219 (PRPH; 54, −15, −0.27)
P49768 (PSEN1; 53, −15, −0.28)
Q14997 (PSME4; 211, −15, −0.07)
Q92565 (RAPGEF5; 68, −15, −0.22)
Q96EP0 (RNF31; 120, −15, −0.12)
O75150 (RNF40; 114, −15, −0.13)
Q92766 (RREB1; 181, −15, −0.08)
P55735 (SEC13; 36, −15, −0.42)
P01009 (SERPINA1; 47, −15, −0.32)
Q9UHJ3 (SFMBT1; 98, −15, −0.15)
Q96EQ0 (SGTB; 33, −15, −0.44)
Q9H173 (SIL1; 52, −15, −0.28)
P55011 (SLC12A2; 131, −15, −0.11)
Q504Y0 (SLC39A12; 77, −15, −0.19)
Q695T7 (SLC6A19; 71, −15, −0.21)
Q92485 (SMPDL3B; 51, −15, −0.29)
O75971 (SNAPC5; 11, −15, −1.32)
Q96RF0 (SNX18; 69, −15, −0.21)
Q9Y5X1 (SNX9; 67, −15, −0.22)
Q96EA4 (SPDL1; 70, −15, −0.21)
O43295 (SRGAP3; 125, −15, −0.12)
Q13586 (STIM1; 77, −15, −0.19)
Q9UH65 (SWAP70; 69, −15, −0.21)
O75529 (TAF5L; 66, −15, −0.22)
O60347 (TBC1D12; 86, −15, −0.17)
P35613 (BSG; 42, −14, −0.33)
Q9BUW7 (C9orf16; 9, −14, −1.54)
Q86V15 (CASZ1; 190, −14, −0.07)
Q9P2K1 (CC2D2A; 186, −14, −0.07)
Q8N998 (CCDC89; 44, −14, −0.31)
P41002 (CCNF; 88, −14, −0.15)
P48643 (CCT5; 60, −14, −0.23)
Q9BXL8 (CDCA4; 26, −14, −0.53)
Q86X02 (CDR2L; 53, −14, −0.26)
Q96A70 (AZIN2; 50, −15, −0.30)
Q9NRL2 (BAZ1A; 179, −15, −0.08)
Q6ZW61 (BBS12; 79, −15, −0.18)
Q7L3V2 (BOP; 39, −15, −0.38)
Q9H8M2 (BRD9; 67, −15, −0.22)
Q9NP86 (CABP5; 20, −15, −0.75)
Q13936 (CACNA1C; 249, −15, −0.06)
Q13698 (CACNA1S; 212, −15, −0.07)
Q9BXU9 (CALN1; 25, −15, −0.60)
Q6P4E1 (CASC4; 49, −15, −0.30)
Q7Z7H3 (CATIP; 44, −15, −0.34)
Q8WUA7 (TBC1D22A; 59, −15, −0.25)
Q969E4 (TCEAL3; 23, −15, −0.66)
Q96BS2 (TESC; 25, −15, −0.60)
Q12800 (TFCP2; 57, −15, −0.26)
P19532 (TFE3; 62, −15, −0.24)
Q68CZ2 (TNS3; 155, −15, −0.09)
Q96Q05 (TRAPPC9; 129, −15, −0.11)
Q9C019 (TRIM15; 52, −15, −0.28)
Q9BZW7 (TSGA10; 81, −15, −0.18)
Q9H0U9 (TSPYL1; 49, −15, −0.30)
Q9ULT0 (TTC7A; 96, −15, −0.15)
Q5T124 (UBXN11; 57, −15, −0.26)
Q08AM6 (VAC14; 88, −15, −0.17)
Q9P2L0 (WDR35; 134, −15, −0.11)
O95785 (WIZ; 179, −15, −0.08)
Q9HCS7 (XAB2; 100, −15, −0.14)
Q9UIA9 (XPO7; 124, −15, −0.12)
O43829 (ZBTB14; 51, −15, −0.29)
Q8WU90 (ZC3H15; 49, −15, −0.30)
Q9BRR0 (ZKSCAN3; 61, −15, −0.24)
Q9Y462 (ZNF711; 86, −15, −0.17)
Q9BXV9 (C14orf142; 11, −15, −1.38)
A6NGK3 (GAGE10; 13, −15, −1.18)
Q4V326 (GAGE2E; 13, −15, −1.17)
A6NDE8 (GAGE12H; 13, −15, −1.16)
Q16143 (SNCB; 14, −15, −1.04)
Q13065 (GAGE1; 16, −15, −0.96)
Q0D2K3 (RIPPLY1; 16, −15, −0.91)
Q7Z7G2 (CPLX4; 18, −15, −0.81)
Q7Z4R8 (C6orf120; 21, −15, −0.72)
A0PJX0 (CIB4; 22, −15, −0.68)
Q9NVP2 (ASF1B; 22, −15, −0.66)
Q6NXS1 (PPP1R2P3; 23, −15, −0.65)
P28066 (PSMA5; 26, −15, −0.56)
Q6IC83 (C22orf42; 28, −15, −0.54)
Q6ZRT6 (PRR23B; 28, −15, −0.53)
P61981 (YWHAG; 28, −15, −0.52)
Q2T9L4 (C15orf59; 32, −15, −0.46)
Q9GZS3 (WDR61; 34, −15, −0.44)
Q6NSI1 (ANKRD26P1; 35, −15, −0.42)
P0CV99 (TSPY4; 36, −15, −0.41)
P0CW01 (TSPY10; 36, −15, −0.41)
A8MV65 (VGLL3; 36, −15, −0.41)
Q7Z7C7 (STRA8; 37, −15, −0.40)
Q5VVX9 (UBE2U; 38, −15, −0.39)
Q9NQS1 (AVEN; 39, −15, −0.38)
Q9NYL9 (TMOD3; 40, −15, −0.37)
Q7Z465 (BNIPL; 40, −15, −0.37)
P08727 (KRT19; 44, −15, −0.34)
Q5H9B9 (BMP2KL; 46, −15, −0.32)
P49356 (FNTB; 49, −15, −0.30)
P55010 (EIF5; 49, −15, −0.30)
O95264 (HTR3B; 50, −15, −0.29)
P11926 (ODC1; 51, −15, −0.29)
Q9NWZ3 (IRAK4; 52, −15, −0.29)
O14896 (IRF6; 53, −15, −0.28)
P17661 (DES; 54, −15, −0.28)
Q9BZI1 (IRX2; 49, −14, −0.28)
P13612 (ITGA4; 115, −14, −0.12)
P14923 (JUP; 82, −14, −0.17)
Q9UGL1 (KDM5B; 176, −14, −0.07)
Q6A163 (KRT39; 56, −14, −0.25)
Q96JM7 (L3MBTL3; 88, −14, −0.15)
Q8NHL6 (LILRB1; 71, −14, −0.19)
Q9C0E8 (LNP; 48, −14, −0.29)
A6NDA9 (LRIT2; 60, −14, −0.23)
Q6UWE0 (LRSAM1; 84, −14, −0.16)

TABLE 3-continued

Exemplary naturally occurring negatively supercharged proteins.

O95460 (MATN4; 68, −15, −0.21)
Q6JEL2 (KLHL10; 69, −15, −0.21)
Q8N9H9 (C1orf127; 70, −15, −0.21)
Q53F19 (C17orf85; 71, −15, −0.21)
P13797 (PLS3; 71, −15, −0.21)
I6L899 (GOLGA8R; 71, −15, −0.20)
A6NCC3 (GOLGA8O; 72, −15, −0.20)
Q96PP9 (GBP4; 73, −15, −0.20)
O15296 (ALOX15B; 76, −15, −0.19)
Q6ZSI9 (CAPN12; 81, −15, −0.18)
O43506 (ADAM20; 82, −15, −0.18)
Q9NVE7 (PANK4; 86, −15, −0.17)
P42892 (ECE1; 87, −15, −0.17)
P18084 (ITGB5; 88, −15, −0.17)
Q9NXL2 (ARHGEF38; 89, −15, −0.16)
P42226 (STAT6; 94, −15, −0.15)
O00206 (TLR4; 96, −15, −0.15)
Q15700 (DLG2; 98, −15, −0.15)
Q68CR7 (LRRC66; 98, −15, −0.15)
Q9UI47 (CTNNA3; 100, −15, −0.15)
P43246 (MSH2; 105, −15, −0.14)
P12110 (COL6A2; 109, −15, −0.13)
P20648 (ATP4A; 114, −15, −0.13)
Q9BX69 (CARD6; 116, −15, −0.12)
O15294 (OGT; 117, −15, −0.12)
P14735 (IDE; 118, −15, −0.12)
Q9Y3R0 (GRIP1; 122, −15, −0.12)
Q9UKP5 (ADAMTS6; 125, −15, −0.11)
P56199 (ITGA1; 131, −15, −0.11)
Q00722 (PLCB2; 134, −15, −0.11)
O75747 (PIK3C2G; 166, −15, −0.09)
Q5QGS0 (KIAA2022; 168, −15, −0.08)
Q9H2U9 (ADAM7; 86, −14, −0.16)
Q9NZN9 (AIPL1; 44, −14, −0.31)
Q8NAG6 (ANKLE1; 67, −14, −0.20)
Q6UB98 (ANKRD12; 236, −14, −0.05)
Q16853 (AOC3; 85, −14, −0.16)
Q92870 (APBB2; 83, −14, −0.16)
P07306 (ASGR1; 33, −14, −0.42)
Q9ULI0 (ATAD2B; 165, −14, −0.08)
Q7Z3C6 (ATG9A; 94, −14, −0.14)
P38606 (ATP6V1A; 68, −14, −0.20)
P35670 (ATP7B; 157, −14, −0.08)
P56817 (BACE1; 56, −14, −0.25)
O95429 (BAG4; 50, −14, −0.28)
P46736 (BRCC3; 36, −14, −0.38)
Q9Y4L5 (RNF115; 34, −14, −0.41)
Q9ULK6 (RNF150; 48, −14, −0.29)
Q9P0P0 (RNF181; 18, −14, −0.78)
Q6ZMZ0 (RNF19B; 78, −14, −0.17)
Q9UK32 (RPS6KA6; 84, −14, −0.16)
P08865 (RPSA; 33, −14, −0.42)
Q86UC2 (RSPH3; 64, −14, −0.21)
Q9BVN2 (RUSC1; 96, −14, −0.14)
O43765 (SGTA; 34, −14, −0.41)
Q8IX90 (SKA3; 46, −14, −0.30)
Q9UP95 (SLC12A4; 121, −14, −0.11)
Q96RN1 (SLC26A8; 109, −14, −0.12)
Q9Y6M7 (SLC4A7; 136, −14, −0.10)
A6NLE4 (SMIM23; 18, −14, −0.76)
P60880 (SNAP25; 23, −14, −0.60)
Q8IUI4 (SNX29P2; 27, −14, −0.51)
Q5TF21 (SOGA3; 103, −14, −0.13)
Q9UPU3 (SORCS3; 136, −14, −0.10)
Q8NB90 (SPATA5; 98, −14, −0.14)
P50502 (ST13; 41, −14, −0.33)
Q8IZP2 (ST13P4; 27, −14, −0.51)
O95210 (STBD1; 39, −14, −0.35)
Q9Y6Q2 (STON1; 83, −14, −0.16)
O60499 (STX10; 28, −14, −0.49)
Q15544 (TAF11; 23, −14, −0.60)
Q9UPU7 (TBC1D2B; 110, −14, −0.12)
Q96NH3 (TBC1D32; 145, −14, −0.09)
Q8TEA7 (TBCK; 101, −14, −0.13)
A7MCY6 (TBKBP1; 68, −14, −0.20)
Q9BXS4 (TMEM59; 36, −14, −0.38)
Q9BSE2 (TMEM79; 44, −14, −0.32)
Q71RG4 (TMUB2; 34, −14, −0.41)
Q9P209 (CEP72; 72, −14, −0.19)
Q5T4B2 (CERCAM; 68, −14, −0.20)
O00748 (CES2; 62, −14, −0.22)
A5YKK6 (CNOT1; 267, −14, −0.05)
O75175 (CNOT3; 82, −14, −0.17)
Q9Y2B0 (CNPY2; 21, −14, −0.67)
A8K830 (COLCA2; 17, −14, −0.83)
Q5KU26 (COLEC12; 82, −14, −0.17)
P61201 (COPS2; 52, −14, −0.27)
P15085 (CPA1; 47, −14, −0.29)
Q9HC73 (CRLF2; 42, −14, −0.33)
Q9UBG3 (CRNN; 54, −14, −0.26)
P61962 (DCAF7; 39, −14, −0.35)
Q8N9W5 (DNAAF3; 59, −14, −0.23)
Q92874 (DNASE1L2; 33, −14, −0.42)
Q96FX2 (DPH3; 9, −14, −1.51)
Q9H4G8 (DPH3P1; 9, −14, −1.60)
A6NNW6 (ENO4; 69, −14, −0.20)
O14638 (ENPP3; 100, −14, −0.13)
Q9Y6X5 (ENPP4; 52, −14, −0.27)
Q9UJA9 (ENPP5; 55, −14, −0.25)
P29317 (EPHA2; 108, −14, −0.12)
Q9NQ60 (EQTN; 33, −14, −0.42)
Q06265 (EXOSC9; 49, −14, −0.28)
O94988 (FAM13A; 117, −14, −0.11)
Q5VUB5 (FAM171A1; 98, −14, −0.14)
P02679 (FGG; 52, −14, −0.27)
Q02790 (FKBP4; 52, −14, −0.27)
Q8NFG4 (FLCN; 64, −14, −0.21)
Q16676 (FOXD1; 46, −14, −0.30)
O15353 (FOXN1; 69, −14, −0.20)
Q68DX3 (FRMPD2; 144, −14, −0.09)
P09958 (FURIN; 87, −14, −0.16)
P48506 (GCLC; 73, −14, −0.19)
Q9NWU2 (GID8; 27, −14, −0.52)
Q9BRT9 (GINS4; 26, −14, −0.53)
P19087 (GNAT2; 40, −14, −0.34)
Q3KR37 (GRAMD1B; 85, −14, −0.16)
Q9P0R6 (GSKIP; 16, −14, −0.89)
Q96MB7 (HARBI1; 39, −14, −0.35)
Q9BY41 (HDAC8; 42, −14, −0.33)
O75330 (HMMR; 84, −14, −0.16)
Q9NZL4 (HSPBP1; 39, −14, −0.35)
Q14627 (IL13RA2; 44, −14, −0.31)
Q14116 (IL18; 22, −14, −0.62)
Q6UWB1 (IL27RA; 69, −14, −0.20)
Q16352 (INA; 55, −14, −0.25)
O15357 (INPPL1; 139, −14, −0.10)
P63104 (YWHAZ; 28, −14, −0.50)
P27348 (YWHAQ; 28, −14, −0.50)
P31946 (YWHAB; 28, −14, −0.49)
Q8IWD4 (CCDC117; 31, −14, −0.45)
Q92537 (KIAA0247; 32, −14, −0.43)
A6NDU8 (C5orf51; 34, −14, −0.41)
O14579 (COPE; 34, −14, −0.40)
P0CW00 (TSPY8; 35, −14, −0.39)
Q99795 (GPA33; 36, −14, −0.39)
A8MYB1 (TMCO5B; 36, −14, −0.39)
A6NNH0 (GATSL1; 36, −14, −0.38)
A2A368 (MAGEB16; 36, −14, −0.38)
Q9H6J7 (C11orf49; 37, −14, −0.37)
B7ZBB8 (PPP1R3G; 38, −14, −0.36)
P46597 (ASMT; 38, −14, −0.36)
Q15166 (PON3; 40, −14, −0.35)
Q13477 (MADCAM1; 40, −14, −0.34)
Q8N8Y2 (ATP6V0D2; 40, −14, −0.34)
Q6AI12 (ANKRD40; 41, −14, −0.34)
Q6ZQY2 (0; 42, −14, −0.33)
P04220 (0; 43, −14, −0.32)
Q96G97 (BSCL2; 44, −14, −0.31)
Q9Y614 (ACTL7B; 45, −14, −0.30)
P06727 (APOA4; 45, −14, −0.30)
Q13515 (BFSP2; 46, −14, −0.30)
Q14653 (IRF3; 47, −14, −0.29)
Q0VDG4 (SCRN3; 49, −14, −0.28)
Q5VWJ9 (SNX30; 50, −14, −0.28)
P02533 (KRT14; 52, −14, −0.27)
P00740 (F9; 52, −14, −0.27)
Q9Y6D9 (MAD1L1; 83, −14, −0.16)
Q12852 (MAP3K12; 93, −14, −0.15)
P41279 (MAP3K8; 53, −14, −0.26)
O60336 (MAPKBP1; 164, −14, −0.08)
Q9NPJ6 (MED4; 30, −14, −0.47)
Q5VZV1 (METTL21C; 30, −14, −0.47)
Q9ULH7 (MKL2; 118, −14, −0.11)
Q6NVV0 (MKRN9P; 4, −14, −3.67)
Q6UVY6 (MOXD1; 70, −14, −0.20)
Q9P289 (MST4; 47, −14, −0.30)
P04198 (MYCN; 50, −14, −0.28)
Q9Y2A7 (NCKAP1; 129, −14, −0.10)
Q92597 (NDRG1; 43, −14, −0.32)
Q9UN36 (NDRG2; 41, −14, −0.34)
Q86W24 (NLRP14; 125, −14, −0.11)
Q9H8H0 (NOL11; 81, −14, −0.17)
Q86YC3 (NRROS; 76, −14, −0.18)
P49902 (NT5C2; 65, −14, −0.21)
P0CE72 (OCM; 12, −14, −1.14)
Q969R2 (OSBP2; 101, −14, −0.13)
Q6ZW49 (PAXIP1; 121, −14, −0.11)
Q9NQP4 (PFDN4; 15, −14, −0.91)
Q8NDX5 (PHC3; 106, −14, −0.13)
P42356 (PI4KA; 231, −14, −0.06)
Q9NRD5 (PICK1; 47, −14, −0.30)
Q5SXH7 (PLEKHS1; 52, −14, −0.27)
Q9HCM2 (PLXNA4; 212, −14, −0.06)
P54317 (PNLIPRP2; 52, −14, −0.26)
O15160 (POLR1C; 39, −14, −0.35)
Q6NYC8 (PPP1R18; 68, −14, −0.20)
P16298 (PPP3CB; 59, −14, −0.23)
Q5VV67 (PPRC1; 178, −14, −0.07)
Q4J6C6 (PREPL; 84, −14, −0.16)
Q15139 (PRKD1; 102, −14, −0.13)
P78527 (PRKDC; 469, −14, −0.02)
P07225 (PROS1; 75, −14, −0.18)
Q14289 (PTK2B; 116, −14, −0.12)
Q9H3S7 (PTPN23; 179, −14, −0.07)
Q9UHX1 (PUF60; 60, −14, −0.23)
O60671 (RAD1; 32, −14, −0.43)
P20936 (RASA1; 116, −14, −0.12)
Q13127 (REST; 122, −14, −0.11)
Q52LD8 (RFTN2; 56, −14, −0.25)
Q8HWS3 (RFX6; 102, −14, −0.13)
Q8NET4 (RGAG1; 144, −14, −0.09)
Q13546 (RIPK1; 76, −14, −0.18)
P12271 (RLBP1; 36, −14, −0.38)
A6ND36 (FAM83G; 91, −14, −0.15)
Q8WUH2 (TGFBRAP1; 97, −14, −0.14)
Q2TAC2 (CCDC57; 103, −14, −0.13)
Q86W56 (PARG; 111, −14, −0.12)
Q8N9B5 (JMY; 111, −14, −0.12)
Q9UQ52 (CNTN6; 114, −14, −0.12)
A6QL63 (BTBD11; 121, −14, −0.11)
Q5M9N0 (CCDC158; 127, −14, −0.11)
Q6MZM0 (HEPHL1; 132, −14, −0.10)
O95487 (SEC24B; 137, −14, −0.10)
Q07889 (SOS1; 152, −14, −0.09)
Q8WWZ4 (ABCA10; 176, −14, −0.07)
A6NJZ7 (RIMBP3C; 181, −14, −0.07)
A6NNM3 (RIMBP3B; 181, −14, −0.07)
A6NMZ7 (COL6A6; 247, −14, −0.05)
Q8IUG5 (MYO18B; 285, −14, −0.04)
P15924 (DSP; 332, −14, −0.04)
P68133 (ACTA1; 42, −13, −0.30)
P62736 (ACTA2; 42, −13, −0.30)
P68032 (ACTC1; 42, −13, −0.30)
Q8TDY3 (ACTRT2; 42, −13, −0.31)
P27037 (ACVR2A; 58, −13, −0.22)
P43652 (AFM; 69, −13, −0.18)
P02765 (AHSG; 39, −13, −0.33)
Q9NP73 (ALG13; 126, −13, −0.10)
P18054 (ALOX12; 76, −13, −0.17)
Q9UKV5 (AMFR; 73, −13, −0.17)
Q16671 (AMHR2; 63, −13, −0.20)
Q9UJ72 (ANXA10; 37, −13, −0.34)
P08758 (ANXA5; 36, −13, −0.36)
Q8N9N2 (ASCC1; 46, −13, −0.28)

TABLE 3-continued

Exemplary naturally occurring negatively supercharged proteins.

O95271 (TNKS; 142, −14, −0.09)
Q59H18 (TNNI3K; 93, −14, −0.15)
Q9Y2L5 (TRAPPC8; 161, −14, −0.08)
Q15642 (TRIP10; 68, −14, −0.20)
Q9NX07 (TRNAU1AP; 32, −14, −0.43)
Q6PKC3 (TXNDC11; 111, −14, −0.12)
Q9UMX0 (UBQLN1; 63, −14, −0.22)
Q86T82 (USP37; 110, −14, −0.12)
Q8N1B4 (VPS52; 82, −14, −0.17)
Q6UX27 (VSTM1; 26, −14, −0.53)
Q96DN2 (VWCE; 100, −14, −0.14)
Q6R2W3 (ZBED9; 152, −14, −0.09)
Q8N680 (ZBTB2; 57, −14, −0.24)
Q9NWS9 (ZNF446; 49, −14, −0.28)
Q96NB3 (ZNF830; 42, −14, −0.33)
Q8WXC6 (MYEOV2; 6, −14, −2.25)
P04271 (S100B; 11, −14, −1.30)
Q9NNZ6 (PRM3; 11, −14, −1.24)
P60660 (MYL6; 17, −14, −0.82)
Q6ZWK4 (C1orf186; 19, −14, −0.72)
P62256 (UBE2H; 21, −14, −0.67)
B2RUY7 (VWC2L; 25, −14, −0.56)
Q8IXP5 (C11orf53; 25, −14, −0.55)
Q9UNT1 (RABL2B; 26, −14, −0.53)
Q9UBK7 (RABL2A; 26, −14, −0.53)
Q96RT6 (CTAGE1; 85, −13, −0.15)
Q96HY6 (DDRGK1; 36, −13, −0.36)
Q13838 (DDX39B; 49, −13, −0.26)
O00548 (DLL1; 78, −13, −0.16)
Q6P3W2 (DNAJC24; 17, −13, −0.76)
P24855 (DNASE1; 31, −13, −0.41)
Q92608 (DOCK2; 212, −13, −0.06)
Q8N608 (DPP10; 91, −13, −0.14)
Q9HAV5 (EDA2R; 33, −13, −0.39)
P05198 (EIF2S1; 36, −13, −0.35)
Q99607 (ELF4; 71, −13, −0.18)
Q92556 (ELMO1; 84, −13, −0.15)
Q7L775 (EPM2AIP1; 70, −13, −0.18)
Q96HE7 (ERO1L; 54, −13, −0.23)
P50549 (ETV1; 55, −13, −0.23)
Q8NHP7 (EXD1; 58, −13, −0.22)
Q96A65 (EXOC4; 110, −13, −0.11)
Q9Y2D4 (EXOC6B; 94, −13, −0.13)
Q96CS3 (FAF2; 53, −13, −0.24)
Q8TCP9 (FAM200A; 66, −13, −0.19)
P0C7Q3 (FAM58BP; 29, −13, −0.45)
Q96KN4 (FAM84A; 32, −13, −0.40)
Q9HB96 (FANCE; 59, −13, −0.22)
Q7L513 (FCRLA; 39, −13, −0.33)
P09769 (FGR; 59, −13, −0.21)
Q4L180 (FILIP1L; 130, −13, −0.09)
P53539 (FOSB; 36, −13, −0.36)
Q14393 (GAS6; 80, −13, −0.16)
Q8N8V2 (GBP7; 73, −13, −0.17)
Q96QA5 (GSDMA; 49, −13, −0.26)
Q9Y5Z4 (HEBP2; 23, −13, −0.56)
Q5T8I9 (HENMT1; 45, −13, −0.29)
P01903 (HLA-DRA; 29, −13, −0.45)
P13747 (HLA-E; 40, −13, −0.32)
O60812 (HNRNPCL1; 32, −13, −0.40)
Q00839 (HNRNPU; 91, −13, −0.14)
Q86YM7 (HOMER1; 40, −13, −0.32)
P0CW71 (HSMCR30; 33, −13, −0.39)
P11142 (HSPA8; 71, −13, −0.18)
Q96LB3 (IFT74; 69, −13, −0.18)
Q08334 (IL10RB; 37, −13, −0.35)
Q01344 (IL5RA; 48, −13, −0.27)
Q12905 (ILF2; 43, −13, −0.30)
Q9UKX5 (ITGA11; 133, −13, −0.09)
Q6GPH6 (ITPRIPL1; 63, −13, −0.20)
Q96AA8 (JAKMIP2; 95, −13, −0.13)
Q9P0J7 (KCMF1; 42, −13, −0.30)
P48544 (KCNJ5; 48, −13, −0.27)
Q8NC54 (KCT2; 29, −13, −0.44)
Q9H3R0 (KDM4C; 120, −13, −0.10)
Q8N371 (KDM8; 47, −13, −0.27)
Q9NSK0 (KLC4; 69, −13, −0.18)
Q9NR64 (KLHL1; 83, −13, −0.15)
P15289 (ARSA; 54, −14, −0.26)
Q9Y4I5 (MTL5; 55, −14, −0.25)
Q8NA56 (TTC29; 55, −14, −0.25)
Q9NXN4 (GDAP2; 56, −14, −0.24)
Q8NCR0 (B3GALNT2; 57, −14, −0.24)
P09923 (ALPI; 57, −14, −0.24)
Q8WUA2 (PPIL4; 57, −14, −0.24)
Q8TBB5 (KLHDC4; 58, −14, −0.24)
O75191 (XYLB; 58, −14, −0.23)
P32942 (ICAM3; 60, −14, −0.23)
Q15822 (CHRNA2; 60, −14, −0.23)
P51687 (SUOX; 60, −14, −0.23)
H3BUK9 (POTEB2; 62, −14, −0.22)
O95741 (CPNE6; 62, −14, −0.22)
Q96A19 (CCDC102A; 63, −14, −0.22)
A6NN90 (C2orf81; 63, −14, −0.22)
Q9NQ89 (C12orf4; 64, −14, −0.21)
Q9NY59 (SMPD3; 71, −14, −0.19)
Q9H089 (LSG1; 75, −14, −0.18)
Q13480 (GAB1; 77, −14, −0.18)
Q9H892 (TTC12; 79, −14, −0.17)
Q8IWA4 (MFN1; 84, −14, −0.16)
Q9UL63 (MKLN1; 85, −14, −0.16)
O75843 (AP1G2; 87, −14, −0.16)
P42224 (STAT1; 87, −14, −0.16)
Q58DX5 (NAALADL2; 89, −14, −0.15)
O43264 (ZW10; 89, −14, −0.15)
P36776 (LONP1; 106, −13, −0.12)
Q8N386 (LRRC25; 33, −13, −0.39)
Q14392 (LRRC32; 72, −13, −0.18)
Q6UXK5 (LRRN1; 81, −13, −0.16)
P36941 (LTBR; 47, −13, −0.27)
Q96LR2 (LURAP1; 26, −13, −0.50)
P49641 (MAN2A2; 131, −13, −0.09)
Q15555 (MAPRE2; 37, −13, −0.35)
P49006 (MARCKSL1; 20, −13, −0.66)
Q495T6 (MMEL1; 89, −13, −0.14)
Q99549 (MPHOSPH8; 97, −13, −0.13)
P42345 (MTOR; 289, −13, −0.04)
Q8N387 (MUC15; 36, −13, −0.35)
P01106 (MYC; 49, −13, −0.26)
Q92802 (N4BP2L2; 67, −13, −0.19)
Q5TF39 (NAGLT1; 56, −13, −0.23)
P41271 (NBL1; 19, −13, −0.66)
Q15596 (NCOA2; 159, −13, −0.08)
Q9HC29 (NOD2; 115, −13, −0.11)
Q7Z494 (NPHP3; 151, −13, −0.08)
Q16288 (NTRK3; 94, −13, −0.13)
Q9H1E3 (NUCKS1; 27, −13, −0.47)
Q5VV17 (OTUD1; 51, −13, −0.25)
Q01804 (OTUD4; 124, −13, −0.10)
Q86U42 (PABPN1; 33, −13, −0.39)
Q9BYG5 (PARD6B; 41, −13, −0.31)
Q16342 (PDCD2; 39, −13, −0.33)
Q5VY43 (PEAR1; 111, −13, −0.11)
O95394 (PGM3; 60, −13, −0.21)
Q9H814 (PHAX; 44, −13, −0.29)
P40967 (PMEL; 70, −13, −0.18)
Q9H5K3 (POMK; 40, −13, −0.32)
P37231 (PPARG; 58, −13, −0.22)
Q9Y2Y8 (PRG3; 25, −13, −0.51)
Q9UGI9 (PRKAG3; 54, −13, −0.23)
Q99873 (PRMT1; 42, −13, −0.31)
Q96LA8 (PRMT6; 42, −13, −0.30)
Q8N271 (PROM2; 92, −13, −0.14)
P17980 (PSMC3; 49, −13, −0.26)
Q16401 (PSMD5; 56, −13, −0.23)
Q5TGL8 (PXDC1; 27, −13, −0.48)
Q9BYM8 (RBCK1; 58, −13, −0.22)
Q96EV2 (RBM33; 130, −13, −0.10)
Q2KHR2 (RFX7; 147, −13, −0.08)
O15211 (RGL2; 84, −13, −0.15)
Q05823 (RNASEL; 84, −13, −0.15)
Q5VTB9 (RNF220; 63, −13, −0.20)
Q9HCK4 (ROBO2; 151, −13, −0.08)
Q01974 (ROR2; 105, −13, −0.12)
Q7L099 (RUFY3; 53, −13, −0.24)
Q59EK9 (RUNDC3A; 50, −13, −0.26)
Q6ZU67 (BEND4; 58, −13, −0.22)
Q9ULD4 (BRPF3; 136, −13, −0.09)
Q13410 (BTN1A1; 59, −13, −0.22)
Q8N5S9 (CAMKK1; 56, −13, −0.23)
Q08AD1 (CAMSAP2; 168, −13, −0.07)
P07384 (CAPN1; 82, −13, −0.15)
Q6UXS9 (CASP12; 39, −13, −0.33)
P83916 (CBX1; 21, −13, −0.60)
Q8WV48 (CCDC107; 31, −13, −0.42)
Q9NUG4 (CCM2L; 62, −13, −0.20)
P24385 (CCND1; 34, −13, −0.38)
Q96SF2 (CCT8L2; 59, −13, −0.21)
O43866 (CD5L; 38, −13, −0.34)
Q8N8E3 (CEP112; 113, −13, −0.11)
Q9Y592 (CEP83; 82, −13, −0.15)
Q6UWW8 (CES3; 62, −13, −0.20)
Q96EP1 (CHFR; 73, −13, −0.17)
Q9Y259 (CHKB; 45, −13, −0.28)
P11230 (CHRNB1; 57, −13, −0.22)
Q04844 (CHRNE; 55, −13, −0.23)
Q99828 (CIB1; 22, −13, −0.59)
Q9H2X3 (CLEC4M; 45, −13, −0.28)
Q96SW2 (CRBN; 51, −13, −0.25)
Q8TEY5 (CREB3L4; 43, −13, −0.29)
Q6UUV9 (CRTC1; 67, −13, −0.19)
O75534 (CSDE1; 89, −13, −0.14)
O43304 (SEC14L5; 79, −13, −0.16)
Q9UIV8 (SERPINB13; 44, −13, −0.29)
O75830 (SERPINI2; 46, −13, −0.28)
P58005 (SESN3; 57, −13, −0.22)
O14492 (SH2B2; 68, −13, −0.19)
Q99962 (SH3GL2; 40, −13, −0.32)
Q8IXJ6 (SIRT2; 43, −13, −0.30)
Q86UW2 (SLC51B; 14, −13, −0.90)
Q8TEQ0 (SNX29; 91, −13, −0.14)
O15370 (SOX12; 34, −13, −0.38)
Q15506 (SPA17; 17, −13, −0.74)
Q8N0X7 (SPG20; 73, −13, −0.17)
O95772 (STARD3NL; 27, −13, −0.48)
Q5VSL9 (STRIP1; 96, −13, −0.13)
Q8N205 (SYNE4; 44, −13, −0.29)
P15923 (TCF3; 68, −13, −0.19)
A2RU30 (TESPA1; 59, −13, −0.21)
Q5TEJ8 (THEMIS2; 72, −13, −0.18)
P51854 (TKTL1; 65, −13, −0.19)
Q6P9B6 (TLDC1; 51, −13, −0.25)
Q9Y2Y6 (TMEM98; 25, −13, −0.52)
P28289 (TMOD1; 41, −13, −0.32)
O14763 (TNFRSF10B; 48, −13, −0.27)
O14798 (TNFRSF10C; 27, −13, −0.47)
Q9H2S6 (TNMD; 37, −13, −0.35)
Q9NS69 (TOMM22; 16, −13, −0.83)
Q9Y4K3 (TRAF6; 60, −13, −0.21)
O43280 (TREH; 67, −13, −0.19)
Q9UPN9 (TRIM33; 123, −13, −0.10)
Q8WW01 (TSEN15; 19, −13, −0.69)
Q9UJT2 (TSKS; 65, −13, −0.19)
Q9BSA4 (TTYH2; 59, −13, −0.22)
Q9UGJ1 (TUBGCP4; 76, −13, −0.17)
Q8NBS9 (TXNDC5; 48, −13, −0.27)
O43396 (TXNL1; 32, −13, −0.40)
P17643 (TYRP1; 61, −13, −0.21)
Q8TCY9 (URGCP; 105, −13, −0.12)
Q2YD98 (UVSSA; 81, −13, −0.16)
Q9H867 (VCPKMT; 26, −13, −0.50)
Q9Y4E6 (WDR7; 164, −13, −0.07)
Q9ULE0 (WWC3; 123, −13, −0.10)
Q9GZV5 (WWTR1; 44, −13, −0.29)
Q04917 (YWHAH; 28, −13, −0.46)
Q14202 (ZMYM3; 152, −13, −0.08)
Q8TD17 (ZNF398; 71, −13, −0.18)
Q86VK4 (ZNF410; 52, −13, −0.24)
O43309 (ZSCAN12; 70, −13, −0.18)
Q9BS18 (ANAPC13; 9, −13, −1.52)
A6NHS1 (0; 10, −13, −1.27)
Q53QV2 (LBH; 12, −13, −1.06)
Q92748 (THRSP; 17, −13, −0.78)
E9PB15 (PTGES3L; 19, −13, −0.68)

TABLE 3-continued

Exemplary naturally occurring negatively supercharged proteins.

Q96NJ5 (KLHL32; 70, −13, −0.18)
P52292 (KPNA2; 58, −13, −0.22)
Q9GZY6 (LAT2; 27, −13, −0.48)
O75473 (LGR5; 100, −13, −0.13)
Q9HAE3 (EFCAB1; 24, −13, −0.53)
P20396 (TRH; 27, −13, −0.47)
A6NLX3 (SPDYE4; 28, −13, −0.46)
P20941 (PDC; 28, −13, −0.46)
Q6ZMS7 (ZNF783; 31, −13, −0.41)
Q8WVE6 (TMEM171; 35, −13, −0.37)
P0CV98 (TSPY3; 35, −13, −0.37)
P62714 (PPP2CB; 36, −13, −0.36)
P0C870 (JMJD7; 36, −13, −0.36)
A6NHX0 (GATSL2; 36, −13, −0.36)
Q8NFH4 (NUP37; 37, −13, −0.35)
Q9HBI0 (PARVG; 37, −13, −0.34)
Q9Y266 (NUDC; 38, −13, −0.33)
Q16589 (CCNG2; 39, −13, −0.33)
Q9NTX7 (RNF146; 39, −13, −0.33)
Q9Y2Z0 (SUGT1; 41, −13, −0.31)
Q99638 (RAD9A; 43, −13, −0.30)
O00470 (MEIS1; 43, −13, −0.30)
Q96K31 (C8orf76; 43, −13, −0.30)
Q9NNX1 (TUFT1; 44, −13, −0.29)
P17050 (NAGA; 47, −13, −0.27)
Q9GZL7 (WDR12; 48, −13, −0.27)
Q5VXM1 (CDCP2; 49, −13, −0.26)
Q9UIF3 (TEKT2; 50, −13, −0.26)
P14136 (GFAP; 50, −13, −0.26)
A6NHL2 (TUBAL3; 50, −13, −0.26)
Q9BX59 (TAPBPL; 50, −13, −0.25)
Q8N594 (MPND; 51, −13, −0.25)
Q9NRH3 (TUBG2; 51, −13, −0.25)
P49005 (POLD2; 51, −13, −0.25)
Q8TD10 (MIPOL1; 52, −13, −0.25)
P16871 (IL7R; 52, −13, −0.25)
Q92569 (PIK3R3; 54, −13, −0.23)
Q96NZ1 (FOXN4; 55, −13, −0.23)
Q8WU10 (PYROXD1; 56, −13, −0.23)
I3L273 (GFY; 56, −13, −0.23)
O60381 (HBP1; 58, −13, −0.22)
Q9NVN3 (RIC8B; 59, −13, −0.22)
Q9NW07 (ZNF358; 59, −13, −0.21)
Q9H6K5 (0; 60, −13, −0.21)
P14679 (TYR; 60, −13, −0.21)
Q96JW4 (SLC41A2; 62, −13, −0.20)
P02748 (C9; 63, −13, −0.20)
P49023 (PXN; 65, −13, −0.20)
Q8IV77 (CNGA4; 66, −13, −0.19)
Q9H900 (ZWILCH; 67, −13, −0.19)
Q5TGY1 (TMCO4; 68, −13, −0.19)
Q04864 (REL; 69, −13, −0.18)
O43187 (IRAK2; 69, −13, −0.18)
P00734 (F2; 70, −13, −0.18)
A7E2F4 (GOLGA8A; 70, −13, −0.18)
A6PW82 (CXorf30; 72, −13, −0.18)
Q8N1W2 (ZNF710; 74, −13, −0.17)
Q3SXY7 (LRIT3; 75, −13, −0.17)
Q9Y216 (MTMR7; 76, −13, −0.17)
P00736 (C1R; 80, −13, −0.16)
Q9UBK8 (MTRR; 80, −13, −0.16)
O95239 (KIF4A; 140, −12, −0.08)
Q8N7A1 (KLHDC1; 47, −12, −0.25)
Q8N4N3 (KLHL36; 70, −12, −0.17)
Q9Y5K2 (KLK4; 27, −12, −0.44)
Q9BQD3 (KXD1; 20, −12, −0.61)
Q8IVL6 (LEPREL2; 82, −12, −0.14)
Q99538 (LGMN; 49, −12, −0.24)
Q8NG48 (LINS; 86, −12, −0.13)
Q8N448 (LNX2; 76, −12, −0.15)
O94910 (LPHN1; 163, −12, −0.07)
Q12912 (LRMP; 62, −12, −0.19)
P09960 (LTA4H; 69, −12, −0.17)
Q16539 (MAPK14; 41, −12, −0.29)
P45984 (MAPK9; 48, −12, −0.24)
P43121 (MCAM; 72, −12, −0.16)
Q13503 (MED21; 16, −12, −0.77)
Q9H1U4 (MEGF9; 63, −12, −0.19)
Q9NSI8 (SAMSN1; 42, −13, −0.31)
O95248 (SBF1; 208, −13, −0.06)
Q6UWP8 (SBSN; 61, −13, −0.21)
Q14162 (SCARF1; 87, −13, −0.14)
Q9NY72 (SCN3B; 25, −13, −0.52)
Q9NQ36 (SCUBE2; 110, −13, −0.11)
O43196 (MSH5; 93, −13, −0.13)
Q9Y6H5 (SNCAIP; 100, −13, −0.12)
Q9UDR5 (AASS; 102, −13, −0.12)
Q0P6D6 (CCDC15; 110, −13, −0.11)
O15197 (EPHB6; 111, −13, −0.11)
Q9BXX0 (EMILIN2; 116, −13, −0.11)
Q8IXT5 (RBM12B; 118, −13, −0.11)
Q9NNW5 (WDR6; 122, −13, −0.10)
Q3MJ13 (WDR72; 123, −13, −0.10)
Q6ZWH5 (NEK10; 133, −13, −0.09)
Q9BXT6 (MOV10L1; 135, −13, −0.09)
P02452 (COL1A1; 139, −13, −0.09)
P16885 (PLCG2; 148, −13, −0.08)
Q9UHC9 (NPC1L1; 149, −13, −0.08)
Q07890 (SOS2; 153, −13, −0.08)
Q86V21 (AACS; 75, −12, −0.15)
O95477 (ABCA1; 254, −12, −0.04)
Q9P2A4 (ABI3; 39, −12, −0.30)
Q9NR19 (ACSS2; 79, −12, −0.15)
P63261 (ACTG1; 42, −12, −0.28)
P63267 (ACTG2; 42, −12, −0.28)
Q86TH1 (ADAMTSL2; 105, −12, −0.11)
Q9UEY8 (ADD3; 79, −12, −0.15)
O75969 (AKAP3; 95, −12, −0.12)
Q9UJX3 (ANAPC7; 67, −12, −0.17)
Q9GZV1 (ANKRD2; 40, −12, −0.30)
Q53RT3 (ASPRV1; 37, −12, −0.32)
Q8WWH4 (ASZ1; 53, −12, −0.22)
P15313 (ATP6V1B1; 57, −12, −0.21)
P54687 (BCAT1; 43, −12, −0.27)
Q5TBC7 (BCL2L15; 18, −12, −0.67)
Q13489 (BIRC3; 68, −12, −0.17)
O75808 (CAPN15; 117, −12, −0.10)
Q68D86 (CCDC102B; 60, −12, −0.19)
Q05D60 (CCDC67; 71, −12, −0.16)
Q8TD31 (CCHCR1; 89, −12, −0.13)
Q8WWL7 (CCNB3; 158, −12, −0.07)
P14209 (CD99; 19, −12, −0.63)
Q9BXF3 (CECR2; 164, −12, −0.07)
Q9C0F1 (CEP44; 44, −12, −0.27)
P08603 (CFH; 139, −12, −0.08)
Q9NZZ3 (CHMP5; 25, −12, −0.48)
Q9NRU3 (CNNM1; 104, −12, −0.11)
Q6P4Q7 (CNNM4; 87, −12, −0.13)
Q53SF7 (COBLL1; 132, −12, −0.09)
Q8IYK4 (COLGALT2; 73, −12, −0.16)
Q7L5N1 (COPS6; 36, −12, −0.33)
Q99829 (CPNE1; 59, −12, −0.20)
P17927 (CR1; 224, −12, −0.05)
O75718 (CRTAP; 47, −12, −0.25)
Q14894 (CRYM; 34, −12, −0.35)
O95825 (CRYZL1; 39, −12, −0.31)
Q6PD62 (CTR9; 134, −12, −0.08)
Q6UX04 (CWC27; 54, −12, −0.22)
P00167 (CYB5A; 15, −12, −0.78)
P98082 (DAB2; 82, −12, −0.14)
O00148 (DDX39A; 49, −12, −0.24)
Q3KNS1 (PTCHD3; 87, −12, −0.13)
Q05397 (PTK2; 119, −12, −0.10)
Q92729 (PTPRU; 162, −12, −0.07)
Q9NP90 (RAB9B; 23, −12, −0.52)
Q7Z6M1 (RABEPK; 41, −12, −0.29)
Q86X10 (RALGAPB; 167, −12, −0.07)
Q9Y4C8 (RBM19; 107, −12, −0.11)
P53805 (RCAN1; 28, −12, −0.42)
Q6JBY9 (RCSD1; 45, −12, −0.26)
Q6PCD5 (RFWD3; 85, −12, −0.14)
Q9NZL6 (RGL1; 87, −12, −0.13)
Q9BYZ6 (RHOBTB2; 83, −12, −0.14)
Q96NA2 (RILP; 44, −12, −0.27)
Q5TAB7 (RIPPLY2; 14, −12, −0.86)
Q6F5E8 (RLTPR; 155, −12, −0.07)
Q6P9G4 (TMEM154; 20, −13, −0.63)
Q8IYI0 (C20orf196; 23, −13, −0.56)
O75496 (GMNN; 24, −13, −0.55)
Q8WWG9 (KCNE4; 24, −13, −0.54)
Q9NPB3 (CABP2; 24, −13, −0.53)
Q9NQI0 (DDX4; 79, −12, −0.15)
Q9H4E7 (DEF6; 74, −12, −0.16)
Q5VZ89 (DENND4C; 187, −12, −0.06)
Q9BSY9 (DESI2; 21, −12, −0.55)
O95424 (DEXI; 10, −12, −1.15)
P49366 (DHPS; 41, −12, −0.29)
Q7Z6W7 (DNAJB7; 35, −12, −0.33)
Q96CJ1 (EAF2; 29, −12, −0.41)
P00533 (EGFR; 134, −12, −0.08)
Q13347 (EIF3I; 37, −12, −0.32)
Q9UBQ5 (EIF3K; 25, −12, −0.47)
Q8TE68 (EPS8L1; 80, −12, −0.14)
Q6P179 (ERAP2; 110, −12, −0.10)
Q9Y282 (ERGIC3; 43, −12, −0.27)
Q96DZ1 (ERLEC1; 55, −12, −0.21)
Q8N693 (ESX1; 44, −12, −0.27)
Q9NV70 (EXOC1; 102, −12, −0.11)
O60645 (EXOC3; 87, −12, −0.13)
Q17RC7 (EXOC3L4; 80, −12, −0.15)
Q15024 (EXOSC7; 32, −12, −0.37)
O43909 (EXTL3; 105, −12, −0.11)
P00488 (F13A1; 83, −12, −0.14)
Q8IW50 (FAM219A; 20, −12, −0.58)
Q96KN1 (FAM84B; 34, −12, −0.34)
Q00597 (FANCC; 63, −12, −0.18)
Q969U6 (FBXW5; 64, −12, −0.18)
Q9UK73 (FEM1B; 70, −12, −0.17)
Q9Y613 (FHOD1; 127, −12, −0.09)
Q14254 (FLOT2; 47, −12, −0.25)
O15409 (FOXP2; 80, −12, −0.15)
A2A2Y4 (FRMD3; 69, −12, −0.17)
Q9H227 (GBA3; 54, −12, −0.22)
Q9NU53 (GINM1; 37, −12, −0.32)
Q9Y625 (GPC6; 63, −12, −0.19)
Q8IV16 (GPIHBP1; 20, −12, −0.60)
P81274 (GPSM2; 77, −12, −0.15)
A4D1B5 (GSAP; 98, −12, −0.12)
Q9UMX6 (GUCA1B; 23, −12, −0.51)
Q9UKV0 (HDAC9; 111, −12, −0.10)
Q96JB3 (HIC2; 66, −12, −0.18)
P30511 (HLA-F; 39, −12, −0.30)
P07910 (HNRNPC; 34, −12, −0.35)
Q9UMF0 (ICAM5; 97, −12, −0.12)
Q9Y6K9 (IKBKG; 48, −12, −0.24)
Q13422 (IKZF1; 58, −12, −0.20)
Q6UXL0 (IL20RB; 35, −12, −0.34)
Q9NV88 (INTS9; 74, −12, −0.16)
Q9ULR0 (ISY1; 33, −12, −0.36)
Q9H0X4 (ITFG3; 60, −12, −0.20)
Q9Y287 (ITM2B; 30, −12, −0.39)
Q15046 (KARS; 68, −12, −0.17)
Q8NFY9 (KBTBD8; 69, −12, −0.17)
Q9NS61 (KCNIP2; 31, −12, −0.38)
P63252 (KCNJ2; 48, −12, −0.24)
Q14667 (KIAA0100; 254, −12, −0.04)
A2VDJ0 (KIAA0922; 179, −12, −0.06)
Q5T5P2 (KIAA1217; 214, −12, −0.05)
Q9Y5K5 (UCHL5; 38, −12, −0.31)
Q9H3U1 (UNC45A; 103, −12, −0.11)
Q15853 (USF2; 37, −12, −0.32)
P54578 (USP14; 56, −12, −0.21)
Q8NEZ2 (VPS37A; 44, −12, −0.27)
Q5VIR6 (VPS53; 80, −12, −0.15)
Q6P4I2 (WDR73; 42, −12, −0.28)
Q96KV7 (WDR90; 187, −12, −0.06)
Q15007 (WTAP; 44, −12, −0.27)
Q8IZ13 (ZBED8; 68, −12, −0.17)
O15209 (ZBTB22; 66, −12, −0.18)
Q5VYS8 (ZCCHC6; 171, −12, −0.07)
P17028 (ZNF24; 42, −12, −0.28)
Q05996 (ZP2; 82, −12, −0.14)
Q3MJ62 (ZSCAN23; 45, −12, −0.26)
Q96AP4 (ZUFSP; 66, −12, −0.18)

TABLE 3-continued

Exemplary naturally occurring negatively supercharged proteins.

P50579 (METAP2; 53, −12, −0.22)
Q9H3L0 (MMADHC; 33, −12, −0.36)
P08473 (MME; 86, −12, −0.14)
P14780 (MMP9; 78, −12, −0.15)
Q9Y605 (MRFAP1; 15, −12, −0.81)
P21757 (MSR1; 50, −12, −0.24)
P00403 (MT-CO2; 26, −12, −0.46)
P19105 (MYL12A; 20, −12, −0.60)
P24844 (MYL9; 20, −12, −0.60)
Q9BSU3 (NAA11; 26, −12, −0.46)
Q96RE7 (NACC1; 57, −12, −0.20)
P55160 (NCKAP1L; 128, −12, −0.09)
O75376 (NCOR1; 270, −12, −0.04)
Q8WX92 (NELFB; 66, −12, −0.18)
Q96P20 (NLRP3; 118, −12, −0.10)
Q8IXF0 (NPAS3; 101, −12, −0.11)
Q8TAT6 (NPLOC4; 68, −12, −0.17)
Q9Y2I2 (NTNG1; 61, −12, −0.19)
P04629 (NTRK1; 87, −12, −0.13)
Q9Y5A7 (NUB1; 71, −12, −0.17)
P53384 (NUBP1; 35, −12, −0.34)
Q9BRQ3 (NUDT22; 33, −12, −0.36)
Q9UKK9 (NUDT5; 24, −12, −0.49)
Q5SWX8 (ODR4; 51, −12, −0.23)
O95428 (PAPLN; 138, −12, −0.08)
Q8NBP7 (PCSK9; 74, −12, −0.16)
O95263 (PDE8B; 99, −12, −0.12)
Q9HB75 (PIDD1; 100, −12, −0.12)
Q9NWS0 (PIH1D1; 32, −12, −0.37)
P27986 (PIK3R1; 84, −12, −0.14)
Q16513 (PKN2; 112, −12, −0.10)
Q8TD55 (PLEKHO2; 53, −12, −0.22)
O60664 (PLIN3; 47, −12, −0.25)
P29590 (PML; 98, −12, −0.12)
Q9NRF9 (POLE3; 17, −12, −0.71)
Q08209 (PPP3CA; 59, −12, −0.20)
Q13976 (PRKG1; 76, −12, −0.15)
O14744 (PRMT5; 73, −12, −0.16)
Q9UIG4 (PSORS1C2; 15, −12, −0.79)
Q13635 (PTCH1; 161, −12, −0.07)
Q8N9M5 (TMEM102; 54, −12, −0.22)
Q05084 (ICA1; 55, −12, −0.21)
Q96P66 (GPR101; 57, −12, −0.21)
Q8WU20 (FRS2; 57, −12, −0.21)
Q495B1 (ANKDD1A; 58, −12, −0.20)
Q9Y575 (ASB3; 58, −12, −0.20)
P32456 (GBP2; 67, −12, −0.17)
Q9H0I9 (TKTL2; 68, −12, −0.17)
P09172 (DBH; 69, −12, −0.17)
Q8WZ60 (KLHL6; 70, −12, −0.17)
P33908 (MAN1A1; 73, −12, −0.16)
Q9UHV5 (RAPGEFL1; 73, −12, −0.16)
Q9BVL4 (SELO; 73, −12, −0.16)
O43572 (AKAP10; 74, −12, −0.16)
O43895 (XPNPEP2; 76, −12, −0.15)
Q9UKJ8 (ADAM21; 81, −12, −0.14)
Q8NA54 (IQUB; 93, −12, −0.12)
P56192 (MARS; 101, −12, −0.11)
Q9HCR9 (PDE11A; 105, −12, −0.11)
P22670 (RFX1; 105, −12, −0.11)
Q6ZNA4 (RNF111; 109, −12, −0.11)
Q9H2T7 (RANBP17; 124, −12, −0.09)
P11498 (PC; 130, −12, −0.09)
Q6ZUT9 (DENND5B; 145, −12, −0.08)
O95425 (SVIL; 248, −12, −0.04)
Q92599 (SEPT8; 56, −11, −0.19)
Q96GR2 (ACSBG1; 81, −11, −0.13)
O96019 (ACTL6A; 47, −11, −0.23)
O94805 (ACTL6B; 47, −11, −0.23)
O60266 (ADCY3; 129, −11, −0.08)
Q16186 (ADRM1; 42, −11, −0.26)
P31749 (AKT1; 56, −11, −0.19)
P02768 (ALB; 69, −11, −0.15)
Q400G9 (AMZ1; 55, −11, −0.20)
Q6UB99 (ANKRD11; 298, −11, −0.03)
Q96NW4 (ANKRD27; 117, −11, −0.09)
Q9NQ90 (ANO2; 114, −11, −0.09)
P10275 (AR; 99, −11, −0.11)
Q9Y3C5 (RNF11; 17, −12, −0.68)
Q6ZRF8 (RNF207; 71, −12, −0.16)
P31350 (RRM2; 45, −12, −0.26)
P0C263 (SBK2; 38, −12, −0.31)
Q96NL6 (SCLT1; 81, −12, −0.14)
P01011 (SERPINA3; 48, −12, −0.25)
P07988 (SFTPB; 42, −12, −0.28)
Q7L8J4 (SH3BP5L; 43, −12, −0.27)
A4FU49 (SH3D21; 71, −12, −0.17)
Q2M3G4 (SHROOM1; 91, −12, −0.13)
Q8NDZ2 (SIMC1; 97, −12, −0.12)
Q96FS4 (SIPA1; 112, −12, −0.10)
Q8IVB4 (SLC9A9; 73, −12, −0.16)
Q9H3E2 (SNX25; 98, −12, −0.12)
Q96KW9 (SPACA7; 21, −12, −0.55)
Q7Z6B7 (SRGAP1; 124, −12, −0.09)
O75044 (SRGAP2; 121, −12, −0.09)
P42229 (STAT5A; 91, −12, −0.13)
Q16623 (STX1A; 33, −12, −0.36)
P61266 (STX1B; 33, −12, −0.36)
Q9NX95 (SYBU; 72, −12, −0.16)
Q9BYX2 (TBC1D2; 105, −12, −0.11)
Q9BQ70 (TCF25; 77, −12, −0.15)
P20061 (TCN1; 48, −12, −0.24)
Q587J7 (TDRD12; 133, −12, −0.09)
O14948 (TFEC; 39, −12, −0.30)
Q86XR7 (TICAM2; 27, −12, −0.44)
Q9BX73 (TM2D2; 23, −12, −0.52)
Q9Y3A6 (TMED5; 26, −12, −0.46)
Q9NRS4 (TMPRSS4; 48, −12, −0.24)
P28908 (TNFRSF8; 64, −12, −0.18)
Q96F44 (TRIM11; 53, −12, −0.22)
P14373 (TRIM27; 58, −12, −0.20)
Q9BSJ1 (TRIM51; 52, −12, −0.22)
Q8N7C3 (TRIML2; 44, −12, −0.27)
Q7Z4N2 (TRPM1; 182, −12, −0.06)
Q01534 (TSPY1; 35, −12, −0.34)
A6NKD2 (TSPY2; 35, −12, −0.34)
Q9GZX9 (TWSG1; 25, −12, −0.47)
Q8TBC4 (UBA3; 52, −12, −0.23)
Q9H832 (UBE2Z; 38, −12, −0.31)
O95155 (UBE4B; 146, −12, −0.08)
Q9Y4F5 (CEP170B; 172, −11, −0.06)
O96017 (CHEK2; 61, −11, −0.18)
Q8IUN9 (CLEC10A; 35, −11, −0.31)
Q9UDT6 (CLIP2; 116, −11, −0.09)
Q96KP4 (CNDP2; 53, −11, −0.20)
Q8NE01 (CNNM3; 76, −11, −0.14)
Q9BV87 (CNPPD1; 45, −11, −0.24)
Q9P232 (CNTN3; 113, −11, −0.09)
Q9BT78 (COPS4; 46, −11, −0.23)
Q6QEF8 (CORO6; 53, −11, −0.20)
P22792 (CPN2; 61, −11, −0.18)
Q9HCH3 (CPNE5; 66, −11, −0.16)
Q9H3G5 (CPVL; 54, −11, −0.20)
Q9NS37 (CREBZF; 37, −11, −0.29)
Q86T23 (CROCCP2; 12, −11, −0.88)
O43739 (CYTH3; 46, −11, −0.23)
Q9NPI6 (DCP1A; 63, −11, −0.17)
Q9P1A6 (DLGAP2; 118, −11, −0.09)
Q5QJE6 (DNTTIP2; 84, −11, −0.13)
Q9BQC3 (DPH2; 52, −11, −0.21)
P21918 (DRD5; 53, −11, −0.20)
Q6XUX3 (DSTYK; 105, −11, −0.10)
Q92997 (DVL3; 78, −11, −0.14)
O00716 (E2F3; 49, −11, −0.22)
P49770 (EIF2B2; 39, −11, −0.28)
Q7L2H7 (EIF3M; 43, −11, −0.25)
Q5MY95 (ENTPD8; 54, −11, −0.20)
P21709 (EPHA1; 108, −11, −0.10)
Q9NVM1 (EVA1B; 18, −11, −0.59)
Q96EL1 (FAM212A; 31, −11, −0.35)
P06734 (FCER2; 36, −11, −0.30)
P07332 (FES; 93, −11, −0.11)
Q9P278 (FNIP2; 122, −11, −0.09)
Q9H334 (FOXP1; 75, −11, −0.14)
Q8IVH2 (FOXP4; 73, −11, −0.14)
Q9BZ68 (FRMD8P1; 41, −11, −0.26)
A6NLX4 (TMEM210; 16, −12, −0.77)
P52434 (POLR2H; 17, −12, −0.69)
Q16082 (HSPB2; 20, −12, −0.59)
Q9UMX2 (OAZ3; 21, −12, −0.56)
Q9BQE9 (BCL7B; 22, −12, −0.54)
P43487 (RANBP1; 23, −12, −0.51)
Q07699 (SCN1B; 25, −12, −0.48)
Q6P0A1 (FAM180B; 25, −12, −0.47)
Q96MW1 (CCDC43; 25, −12, −0.47)
Q9Y235 (APOBEC2; 26, −12, −0.46)
O43752 (STX6; 29, −12, −0.41)
Q6ZUJ4 (C3orf62; 30, −12, −0.39)
Q5VT99 (LRRC38; 32, −12, −0.37)
Q6ZW13 (C16orf86; 34, −12, −0.35)
Q9HAI6 (CXorf21; 34, −12, −0.35)
O15162 (PLSCR1; 35, −12, −0.34)
Q13287 (NMI; 35, −12, −0.34)
Q9BV68 (RNF126; 36, −12, −0.33)
P67775 (PPP2CA; 36, −12, −0.33)
Q15329 (E2F5; 38, −12, −0.31)
A6NIE6 (RRN3P2; 38, −12, −0.31)
A6NJJ6 (C19orf67; 40, −12, −0.30)
A6NED2 (RCCD1; 40, −12, −0.29)
F5GYI3 (UBAP1L; 41, −12, −0.29)
P60709 (ACTB; 42, −12, −0.28)
P0CW26 (PNMA6C; 44, −12, −0.27)
P0CZ20 (PNMA6D; 44, −12, −0.27)
P49441 (INPP1; 44, −12, −0.27)
P22891 (PROZ; 45, −12, −0.26)
Q5VWP2 (FAM46C; 45, −12, −0.26)
Q9UPV7 (KIAA1045; 45, −12, −0.26)
Q499Z3 (SLFNL1; 46, −12, −0.26)
Q5T4F4 (ZFYVE27; 46, −12, −0.26)
Q96P63 (SERPINB12; 46, −12, −0.25)
Q9NVG8 (TBC1D13; 47, −12, −0.25)
Q96FV2 (SCRN2; 47, −12, −0.25)
B7U540 (KCNJ18; 49, −12, −0.24)
Q8NCJ5 (SPRYD3; 50, −12, −0.24)
P04070 (PROC; 52, −12, −0.23)
Q9H9V9 (JMJD4; 52, −12, −0.22)
Q9ULV5 (HSF4; 53, −12, −0.22)
Q9UKT9 (IKZF3; 58, −11, −0.18)
P01583 (IL1A; 31, −11, −0.35)
Q9NZN1 (IL1RAPL1; 80, −11, −0.13)
Q9NPH2 (ISYNA1; 61, −11, −0.18)
Q96N16 (JAKMIP1; 73, −11, −0.15)
P22001 (KCNA3; 64, −11, −0.17)
Q14500 (KCNJ12; 49, −11, −0.22)
Q14145 (KEAP1; 70, −11, −0.15)
P33176 (KIF5B; 110, −11, −0.10)
Q9P2K6 (KLHL42; 57, −11, −0.19)
Q9P2G9 (KLHL8; 69, −11, −0.15)
P05783 (KRT18; 48, −11, −0.22)
Q9UPQ0 (LIMCH1; 122, −11, −0.09)
Q96NW7 (LRRC7; 173, −11, −0.06)
P48449 (LSS; 83, −11, −0.13)
Q8N653 (LZTR1; 95, −11, −0.11)
Q7Z434 (MAVS; 57, −11, −0.19)
Q93074 (MED12; 243, −11, −0.04)
Q86XA0 (METTL23; 21, −11, −0.51)
Q86U44 (METTL3; 64, −11, −0.17)
Q9HBH9 (MKNK2; 52, −11, −0.21)
Q9ULZ9 (MMP17; 67, −11, −0.16)
Q96G30 (MRAP2; 24, −11, −0.46)
Q9H579 (MROH8; 55, −11, −0.20)
Q8NCY6 (MSANTD4; 41, −11, −0.26)
Q9C0I1 (MTMR12; 86, −11, −0.12)
O14950 (MYL12B; 20, −11, −0.55)
Q8IZQ8 (MYOCD; 102, −11, −0.10)
Q86TC9 (MYPN; 145, −11, −0.07)
Q14CX7 (NAA25; 112, −11, −0.09)
Q9H009 (NACA2; 23, −11, −0.47)
P54920 (NAPA; 33, −11, −0.33)
Q9H115 (NAPB; 34, −11, −0.32)
Q13772 (NCOA4; 70, −11, −0.15)
Q68D85 (NCR3LG1; 51, −11, −0.21)
Q92542 (NCSTN; 78, −11, −0.14)
Q14511 (NEDD9; 93, −11, −0.11)

TABLE 3-continued

Exemplary naturally occurring negatively supercharged proteins.

Q15052 (ARHGEF6; 87, −11, −0.12)
O43150 (ASAP2; 112, −11, −0.09)
Q9NVM9 (ASUN; 80, −11, −0.13)
Q96DT6 (ATG4C; 52, −11, −0.20)
Q9H1Y0 (ATG5; 32, −11, −0.33)
P98196 (ATP11A; 130, −11, −0.08)
Q9H7F0 (ATP13A3; 138, −11, −0.07)
O75185 (ATP2C2; 103, −11, −0.10)
Q93050 (ATP6V0A1; 96, −11, −0.11)
Q07817 (BCL2L1; 26, −11, −0.42)
Q8NFU1 (BEST2; 57, −11, −0.19)
Q9NUP1 (BLOC1S4; 23, −11, −0.47)
Q86Y37 (CACUL1; 41, −11, −0.26)
Q8N3J6 (CADM2; 48, −11, −0.23)
P22676 (CALB2; 32, −11, −0.34)
P22681 (CBL; 100, −11, −0.11)
Q5TID7 (CCDC181; 60, −11, −0.18)
P06731 (CEACAM5; 77, −11, −0.14)
Q9HC77 (CENPJ; 153, −11, −0.07)
P63098 (PPP3R1; 19, −11, −0.56)
Q96LZ3 (PPP3R2; 20, −11, −0.56)
Q8NI37 (PPTC7; 33, −11, −0.33)
O43586 (PSTPIP1; 48, −11, −0.23)
Q7RTS3 (PTF1A; 35, −11, −0.31)
Q14671 (PUM1; 126, −11, −0.08)
Q9HD47 (RANGRF; 20, −11, −0.53)
Q8WZA2 (RAPGEF4; 116, −11, −0.09)
Q04206 (RELA; 60, −11, −0.18)
P07949 (RET; 124, −11, −0.08)
Q6ZWI9 (RFPL4B; 30, −11, −0.36)
Q9H4X1 (RGCC; 15, −11, −0.75)
Q8IXI2 (RHOT1; 71, −11, −0.15)
Q9UFD9 (RIMBP3; 181, −11, −0.06)
Q5XPI4 (RNF123; 149, −11, −0.07)
Q9H6Y7 (RNF167; 38, −11, −0.28)
Q86UA6 (RPAIN; 25, −11, −0.44)
P05386 (RPLP1; 12, −11, −0.95)
P23297 (S100A1; 11, −11, −1.04)
Q9UBE0 (SAE1; 38, −11, −0.28)
Q96KG9 (SCYL1; 90, −11, −0.12)
P34741 (SDC2; 22, −11, −0.49)
Q92503 (SEC14L1; 81, −11, −0.13)
Q9BQF6 (SENP7; 120, −11, −0.09)
P35237 (SERPINB6; 43, −11, −0.25)
Q99961 (SH3GL1; 41, −11, −0.26)
Q9BRV8 (SIKE1; 24, −11, −0.46)
P42285 (SKIV2L2; 118, −11, −0.09)
A0AV02 (SLC12A8; 78, −11, −0.14)
P36021 (SLC16A2; 60, −11, −0.18)
Q9UI40 (SLC24A2; 74, −11, −0.14)
Q9Y6M5 (SLC30A1; 55, −11, −0.19)
Q9BRI3 (SLC30A2; 35, −11, −0.31)
Q9NQ40 (SLC52A3; 51, −11, −0.21)
Q9GZV3 (SLC5A7; 63, −11, −0.17)
Q96T83 (SLC9A7; 80, −11, −0.13)
O15079 (SNPH; 54, −11, −0.20)
Q8IUW3 (SPATA2L; 46, −11, −0.23)
Q9P0W8 (SPATA7; 68, −11, −0.16)
Q9Y5Y6 (ST14; 95, −11, −0.11)
Q9Y6E0 (STK24; 49, −11, −0.22)
Q9P2W9 (STX18; 39, −11, −0.28)
Q13277 (STX3; 33, −11, −0.33)
O00204 (SULT2B1; 41, −11, −0.26)
Q8N103 (TAGAP; 81, −11, −0.13)
O60907 (TBL1X; 62, −11, −0.17)
Q9UL17 (TBX21; 58, −11, −0.18)
O43493 (TGOLN2; 51, −11, −0.21)
Q9NR97 (TLR8; 120, −11, −0.09)
Q96DC7 (TMCO6; 54, −11, −0.20)
Q8IV31 (TMEM139; 24, −11, −0.46)
Q9H3N1 (TMX1; 32, −11, −0.34)
Q9NS68 (TNFRSF19; 46, −11, −0.23)
Q16473 (TNXA; 34, −11, −0.32)
Q92547 (TOPBP1; 171, −11, −0.06)
Q9H497 (TOR3A; 46, −11, −0.23)
Q9UDY6 (TRIM10; 55, −11, −0.19)
O15234 (CASC3; 76, −10, −0.13)
P20273 (CD22; 95, −10, −0.10)
P02794 (FTH1; 21, −11, −0.51)
Q7L5D6 (GET4; 37, −11, −0.30)
O76003 (GLRX3; 37, −11, −0.29)
Q6AI39 (GLTSCR1L; 115, −11, −0.09)
P04899 (GNAI2; 40, −11, −0.27)
O95467 (GNAS; 28, −11, −0.39)
P11488 (GNAT1; 40, −11, −0.27)
Q8N954 (GPATCH11; 30, −11, −0.36)
Q8IZF2 (GPR116; 149, −11, −0.07)
Q13224 (GRIN2B; 166, −11, −0.06)
Q9BYG8 (GSDMC; 58, −11, −0.19)
P46976 (GYG1; 39, −11, −0.27)
P56524 (HDAC4; 119, −11, −0.09)
Q8TDG4 (HELQ; 124, −11, −0.08)
O14964 (HGS; 86, −11, −0.12)
P14652 (HOXB2; 38, −11, −0.29)
Q0VDF9 (HSPA14; 55, −11, −0.20)
P08107 (HSPA1A; 70, −11, −0.15)
Q9Y547 (HSPB11; 16, −11, −0.67)
Q5VY09 (IER5; 34, −11, −0.32)
Q9UKS7 (IKZF2; 60, −11, −0.18)
Q9C035 (TRIM5; 56, −11, −0.19)
Q9NZQ8 (TRPM5; 131, −11, −0.08)
Q9NQA5 (TRPV5; 83, −11, −0.13)
Q99576 (TSC22D3; 15, −11, −0.74)
O95801 (TTC4; 45, −11, −0.24)
Q9NRR5 (UBQLN4; 64, −11, −0.17)
Q8TAS1 (UHMK1; 47, −11, −0.23)
P09327 (VIL1; 93, −11, −0.11)
O95876 (WDPCP; 85, −11, −0.12)
P0C1S8 (WEE2; 63, −11, −0.17)
Q8WTP9 (XAGE3; 12, −11, −0.89)
Q969M3 (YIPF5; 28, −11, −0.39)
Q8N8F6 (YIPF7; 31, −11, −0.35)
O15391 (YY2; 41, −11, −0.26)
O96006 (ZBED1; 78, −11, −0.14)
O75132 (ZBED4; 130, −11, −0.08)
O75800 (ZMYND10; 50, −11, −0.21)
Q969S3 (ZNF622; 54, −11, −0.20)
A8K0R7 (ZNF839; 87, −11, −0.12)
P0DL12 (SMIM17; 13, −11, −0.82)
O15514 (POLR2D; 16, −11, −0.67)
Q01658 (DR1; 19, −11, −0.56)
P13693 (TPT1; 20, −11, −0.56)
Q8IXQ3 (C9orf40; 21, −11, −0.52)
O14990 (PPP1R2P9; 23, −11, −0.48)
A0PJX2 (TLDC2; 24, −11, −0.46)
Q5GAN6 (RNASE10; 24, −11, −0.45)
Q86SE8 (NPM2; 24, −11, −0.45)
P55327 (TPD52; 24, −11, −0.45)
Q9P1T7 (MDFIC; 26, −11, −0.42)
Q9BZJ3 (TPSD1; 27, −11, −0.41)
Q9H3S4 (TPK1; 27, −11, −0.40)
P20851 (C4BPB; 28, −11, −0.38)
O14618 (CCS; 29, −11, −0.37)
P57796 (CABP4; 30, −11, −0.36)
P30279 (CCND2; 33, −11, −0.33)
Q8IWE4 (DCUN1D3; 34, −11, −0.32)
P29017 (CD1C; 38, −11, −0.29)
Q8N140 (EID3; 38, −11, −0.28)
Q6N063 (OGFOD2; 39, −11, −0.28)
Q9UNM6 (PSMD1 3; 43, −11, −0.25)
P0C5W0 (PNMA6B; 44, −11, −0.24)
P0CW24 (PNMA6A; 44, −11, −0.24)
Q03154 (ACY1; 46, −11, −0.23)
P35900 (KRT20; 48, −11, −0.22)
A8MYZ6 (FOXO6; 51, −11, −0.21)
Q8WUX9 (CHMP7; 51, −11, −0.21)
Q5SQS7 (SH2D4B; 51, −11, −0.21)
Q9Y2T4 (PPP2R2C; 52, −11, −0.21)
O95219 (SNX4; 52, −11, −0.21)
Q8IYU4 (UBQLNL; 53, −11, −0.20)
P02774 (GC; 53, −11, −0.20)
P41586 (ADCYAP1R1; 53, −11, −0.20)
Q6NXE6 (ARMC6; 54, −11, −0.20)
Q9BR76 (CORO1B; 54, −11, −0.20)
Q8NCB2 (CAMKV; 54, −11, −0.20)
P11597 (CETP; 55, −11, −0.20)
P12036 (NEFH; 112, −11, −0.09)
Q9BYH8 (NFKBIZ; 78, −11, −0.14)
P16066 (NPR1; 119, −11, −0.09)
P13056 (NR2C1; 67, −11, −0.16)
Q9NSY0 (NRBP2; 58, −11, −0.19)
Q96CM4 (NXNL1; 24, −11, −0.45)
A1E959 (ODAM; 31, −11, −0.35)
Q86WS3 (OOSP2; 18, −11, −0.61)
P13674 (P4HA1; 61, −11, −0.18)
Q86U86 (PBRM1; 193, −11, −0.05)
P35558 (PCK1; 69, −11, −0.15)
Q86YL7 (PDPN; 17, −11, −0.65)
Q9H792 (PEAK1; 193, −11, −0.05)
Q13608 (PEX6; 104, −11, −0.10)
O00628 (PEX7; 36, −11, −0.30)
Q16512 (PKN1; 104, −11, −0.10)
Q9Y263 (PLAA; 87, −11, −0.12)
Q6UX71 (PLXDC2; 60, −11, −0.18)
Q9UIW2 (PLXNA1; 211, −11, −0.05)
P54315 (PNLIPRP1; 52, −11, −0.21)
Q9NY84 (VNN3; 56, −11, −0.19)
Q6ZNG9 (KRBA2; 56, −11, −0.19)
O15123 (ANGPT2; 57, −11, −0.19)
Q9H972 (C14orf93; 59, −11, −0.18)
Q96C11 (FGGY; 60, −11, −0.18)
Q6P5Q4 (LMOD2; 62, −11, −0.17)
Q8IYJ1 (CPNE9; 62, −11, −0.17)
Q9BRS2 (RIOK1; 66, −11, −0.16)
Q9H201 (EPN3; 68, −11, −0.16)
P04843 (RPN1; 69, −11, −0.16)
Q8NE63 (HIPK4; 69, −11, −0.15)
P51168 (SCNN1B; 73, −11, −0.15)
Q86V97 (KBTBD6; 76, −11, −0.14)
Q5T2E6 (C10orf76; 79, −11, −0.13)
O75074 (LRP3; 83, −11, −0.13)
Q01826 (SATB1; 86, −11, −0.12)
Q96II8 (LRCH3; 86, −11, −0.12)
Q9Y233 (PDE10A; 88, −11, −0.12)
P51790 (CLCN3; 91, −11, −0.12)
Q5W041 (ARMC3; 96, −11, −0.11)
Q12979 (ABR; 98, −11, −0.11)
Q96EN8 (MOCOS; 98, −11, −0.11)
Q9H6U6 (BCAS3; 101, −11, −0.10)
Q96J02 (ITCH; 103, −11, −0.10)
Q9UNX4 (WDR3; 106, −11, −0.10)
O95786 (DDX58; 107, −11, −0.10)
Q9UFE4 (CCDC39; 110, −11, −0.10)
Q02218 (OGDH; 116, −11, −0.09)
Q17R98 (ZNF827; 119, −11, −0.09)
P31327 (CPS1; 165, −11, −0.06)
O14646 (CHD1; 197, −11, −0.05)
Q4AC94 (C2CD3; 260, −11, −0.04)
O43236 (SEPT4; 55, −10, −0.18)
P00813 (ADA; 41, −10, −0.24)
Q8NDY3 (ADPRHL1; 40, −10, −0.24)
Q96MA6 (AK8; 55, −10, −0.18)
Q9Y243 (AKT3; 56, −10, −0.17)
P05187 (ALPP; 58, −10, −0.17)
P10696 (ALPPL2; 57, −10, −0.17)
Q9P2S6 (ANKMY1; 106, −10, −0.09)
Q07960 (ARHGAP1; 50, −10, −0.19)
Q9UNA1 (ARHGAP26; 92, −10, −0.10)
Q52LW3 (ARHGAP29; 142, −10, −0.07)
P52566 (ARHGDIB; 23, −10, −0.43)
P07307 (ASGR2; 35, −10, −0.28)
O95352 (ATG7; 78, −10, −0.12)
Q8WXF7 (ATL1; 64, −10, −0.15)
P54707 (ATP12A; 116, −10, −0.08)
Q4VNC1 (ATP13A4; 134, −10, −0.07)
P0C7T5 (ATXN1L; 73, −10, −0.13)
Q9Y5Z0 (BACE2; 56, −10, −0.17)
Q5H9J7 (BEX5; 13, −10, −0.79)
Q96CA5 (BIRC7; 33, −10, −0.30)
O60238 (BNIP3L; 24, −10, −0.41)
Q9NPI1 (BRD7; 74, −10, −0.13)
Q9H6R7 (C2orf44; 79, −10, −0.12)
P54284 (CACNB3; 55, −10, −0.18)
Q9NPP4 (NLRC4; 116, −10, −0.08)

TABLE 3-continued

Exemplary naturally occurring negatively supercharged proteins.

Q9NPF0 (CD320; 29, −10, −0.34)
P11912 (CD79A; 25, −10, −0.39)
Q96L14 (CEP170P1; 33, −10, −0.30)
Q6NT32 (CES5A; 64, −10, −0.15)
Q12798 (CETN1; 20, −10, −0.51)
Q99675 (CGRRF1; 38, −10, −0.26)
Q99653 (CHP1; 22, −10, −0.44)
P02708 (CHRNA1; 55, −10, −0.18)
O15111 (CHUK; 85, −10, −0.11)
Q99966 (CITED1; 20, −10, −0.50)
Q96MX0 (CMTM3; 20, −10, −0.50)
Q8WXI2 (CNKSR2; 118, −10, −0.08)
Q9H8M5 (CNNM2; 97, −10, −0.10)
P61923 (COPZ1; 20, −10, −0.49)
Q96SM3 (CPXM1; 82, −10, −0.12)
Q8IX95 (CTAGE3P; 18, −10, −0.55)
O43310 (CTIF; 68, −10, −0.14)
P17812 (CTPS1; 67, −10, −0.14)
P07711 (CTSL; 38, −10, −0.26)
Q7L576 (CYFIP1; 145, −10, −0.06)
Q15438 (CYTH1; 46, −10, −0.21)
P43146 (DCC; 158, −10, −0.06)
Q96HY7 (DHTKD1; 103, −10, −0.09)
Q9H3Z4 (DNAJC5; 22, −10, −0.45)
P49184 (DNASE1L1; 34, −10, −0.29)
Q96BY6 (DOCK10; 250, −10, −0.04)
Q8N350 (DOS; 76, −10, −0.13)
Q7L8W6 (DPH6; 30, −10, −0.32)
Q9BTV6 (DPH7; 51, −10, −0.19)
Q8IY85 (EFCAB13; 110, −10, −0.09)
Q14156 (EFR3A; 93, −10, −0.10)
O00303 (EIF3F; 38, −10, −0.26)
Q14240 (EIF4A2; 46, −10, −0.21)
O15083 (ERC2; 111, −10, −0.09)
Q8WUF8 (FAM172A; 48, −10, −0.20)
Q8N9W8 (FAM71D; 47, −10, −0.21)
Q7L4E1 (FAM73B; 66, −10, −0.15)
Q9NVI1 (FANCI; 149, −10, −0.06)
Q9UKT6 (FBXL21; 49, −10, −0.20)
Q96LA6 (FCRL1; 47, −10, −0.21)
Q9NSA1 (FGF21; 22, −10, −0.44)
Q9UIM3 (FKBPL; 38, −10, −0.26)
Q8IVF7 (FMNL3; 117, −10, −0.08)
Q8TBE3 (FNDC9; 25, −10, −0.39)
Q9BZ67 (FRMD8; 51, −10, −0.19)
Q969S9 (GFM2; 87, −10, −0.11)
Q14390 (GGTLC2; 24, −10, −0.42)
Q9Y223 (GNE; 79, −10, −0.12)
Q8IXQ4 (GPALPP1; 38, −10, −0.26)
Q86YR5 (GPSM1; 75, −10, −0.13)
Q9ULK0 (GRID1; 112, −10, −0.08)
Q14520 (HABP2; 63, −10, −0.15)
O14929 (HAT1; 50, −10, −0.20)
Q00341 (HDLBP; 141, −10, −0.07)
Q9NWT6 (HIF1AN; 40, −10, −0.24)
Q9P246 (STIM2; 84, −10, −0.11)
Q9BR01 (SULT4A1; 33, −10, −0.30)
Q92844 (TANK; 48, −10, −0.20)
Q86TI0 (TBC1D1; 133, −10, −0.07)
Q92609 (TBC1D5; 89, −10, −0.11)
Q9BY14 (TEX101; 27, −10, −0.37)
P19484 (TFEB; 53, −10, −0.18)
P07101 (TH; 59, −10, −0.17)
Q7Z3E1 (TIPARP; 76, −10, −0.13)
Q9BXR5 (TLR10; 95, −10, −0.10)
O60602 (TLR5; 98, −10, −0.10)
Q9NZR1 (TMOD2; 40, −10, −0.25)
Q9UPQ9 (TNRC6B; 194, −10, −0.05)
O14773 (TPP1; 61, −10, −0.16)
A5PLN9 (TRAPPC13; 47, −10, −0.21)
O15016 (TRIM66; 135, −10, −0.07)
P23258 (TUBG1; 51, −10, −0.19)
Q9NZI7 (UBP1; 60, −10, −0.16)
Q04323 (UBXN1; 33, −10, −0.30)
Q9NYU1 (UGGT2; 175, −10, −0.05)
Q92900 (UPF1; 124, −10, −0.08)
Q9NQZ2 (UTP3; 55, −10, −0.18)
Q92558 (WASF1; 62, −10, −0.16)
P30460 (HLA-B; 40, −10, −0.24)
P03989 (HLA-B; 40, −10, −0.24)
P30499 (HLA-C; 41, −10, −0.24)
P17693 (HLA-G; 38, −10, −0.26)
P30519 (HMOX2; 36, −10, −0.27)
O43364 (HOXA2; 41, −10, −0.24)
P48723 (HSPA13; 52, −10, −0.19)
P17066 (HSPA6; 71, −10, −0.14)
P13284 (IFI30; 28, −10, −0.35)
P17181 (IFNAR1; 64, −10, −0.15)
Q9H7X7 (IFT22; 21, −10, −0.47)
P08833 (IGFBP1; 28, −10, −0.35)
Q9UPX0 (IGSF9B; 147, −10, −0.06)
Q8N6P7 (IL22RA1; 63, −10, −0.15)
P78414 (IRX1; 50, −10, −0.20)
P20702 (ITGAX; 128, −10, −0.07)
P19827 (ITIH1; 101, −10, −0.09)
Q9Y2W7 (KCNIP3; 29, −10, −0.34)
P48050 (KCNJ4; 50, −10, −0.20)
Q9ULS6 (KCNS2; 54, −10, −0.18)
Q6UXG2 (KIAA1324; 111, −10, −0.08)
Q2M1P5 (KIF7; 151, −10, −0.06)
Q07866 (KLC1; 65, −10, −0.15)
Q96M94 (KLHL15; 70, −10, −0.14)
Q9H0H3 (KLHL25; 66, −10, −0.15)
Q9P2J3 (KLHL9; 69, −10, −0.14)
P01042 (KNG1; 72, −10, −0.13)
Q6GTX8 (LAIR1; 31, −10, −0.31)
Q5VSP4 (LCN1P1; 18, −10, −0.55)
P0C866 (LINC00869; 31, −10, −0.32)
P58215 (LOXL3; 83, −10, −0.12)
Q14693 (LPIN1; 99, −10, −0.10)
Q5VUJ6 (LRCH2; 85, −10, −0.11)
Q8IV03 (LURAP1L; 25, −10, −0.40)
Q15759 (MAPK11; 41, −10, −0.24)
O43513 (MED7; 27, −10, −0.36)
Q96KG7 (MEGF10; 122, −10, −0.08)
Q96AZ1 (METTL21B; 25, −10, −0.40)
Q9BRT3 (MIEN1; 12, −10, −0.80)
Q9UGB7 (MIOX; 33, −10, −0.30)
Q14165 (MLEC; 32, −10, −0.31)
Q9BVC4 (MLST8; 36, −10, −0.27)
P08254 (MMP3; 54, −10, −0.18)
Q96BY2 (MOAP1; 40, −10, −0.25)
Q86VX9 (MON1A; 62, −10, −0.16)
Q7L1V2 (MON1B; 59, −10, −0.16)
P40238 (MPL; 71, −10, −0.14)
Q9NZW5 (MPP6; 61, −10, −0.16)
Q8NCE2 (MTMR14; 72, −10, −0.13)
P12524 (MYCL; 40, −10, −0.24)
P41227 (NAA10; 26, −10, −0.37)
Q147X3 (NAA30; 39, −10, −0.25)
Q6IQ20 (NAPEPLD; 46, −10, −0.21)
Q86XI2 (NCAPG2; 131, −10, −0.07)
Q9NXR1 (NDE1; 39, −10, −0.25)
Q9GZM8 (NDEL1; 38, −10, −0.26)
Q9NV92 (NDFIP2; 36, −10, −0.27)
Q9BV99 (LRRC61; 28, −10, −0.35)
A6NM15 (CBWD7; 28, −10, −0.35)
Q92530 (PSMF1; 30, −10, −0.33)
P21964 (COMT; 30, −10, −0.33)
P27707 (DCK; 31, −10, −0.32)
Q6ZRC1 (C4orf50; 31, −10, −0.32)
O95229 (ZWINT; 31, −10, −0.31)
O75663 (TIPRL; 31, −10, −0.31)
Q9UPY8 (MAPRE3; 32, −10, −0.31)
O95983 (MBD3; 33, −10, −0.30)
Q96MP8 (KCTD7; 33, −10, −0.30)
P50135 (HNMT; 33, −10, −0.30)
Q96NL1 (TMEM74; 33, −10, −0.29)
A8MZ36 (EVPLL; 34, −10, −0.29)
Q6ZSA7 (LRRC55; 34, −10, −0.29)
Q9NQ48 (LZTFL1; 35, −10, −0.28)
Q96AB6 (NTAN1; 35, −10, −0.28)
A6NI79 (CCDC69; 35, −10, −0.28)
Q6IPT4 (CYB5RL; 36, −10, −0.27)
Q8TC99 (FNDC8; 36, −10, −0.27)
Q16651 (PRSS8; 36, −10, −0.27)
Q9NWW6 (NMRK1; 23, −10, −0.43)
O75052 (NOS1AP; 56, −10, −0.17)
P17342 (NPR3; 60, −10, −0.16)
Q01968 (OCRL; 104, −10, −0.09)
Q9ULJ1 (ODF2L; 74, −10, −0.13)
Q9H1P3 (OSBPL2; 55, −10, −0.18)
Q96BN8 (OTULIN; 40, −10, −0.24)
O95453 (PARN; 73, −10, −0.13)
Q96RV3 (PCNX; 259, −10, −0.03)
P16519 (PCSK2; 71, −10, −0.14)
Q6P474 (PDXDC2P; 52, −10, −0.19)
P56645 (PER3; 132, −10, −0.07)
O15173 (PGRMC2; 24, −10, −0.41)
Q96FE7 (PIK3IP1; 28, −10, −0.35)
Q9GZP4 (PITHD1; 24, −10, −0.41)
Q5JRX3 (PITRM1; 117, −10, −0.08)
P54277 (PMS1; 106, −10, −0.09)
Q9NVU0 (POLR3E; 80, −10, −0.12)
Q9HBU9 (POPDC2; 40, −10, −0.24)
Q6S8J7 (POTEA; 56, −10, −0.17)
Q16633 (POU2AF1; 27, −10, −0.36)
Q96T49 (PPP1R16B; 64, −10, −0.15)
Q15257 (PPP2R4; 41, −10, −0.24)
P0C7W0 (PRR29; 21, −10, −0.48)
P07478 (PRSS2; 26, −10, −0.37)
P28065 (PSMB9; 23, −10, −0.42)
Q96EY7 (PTCD3; 79, −10, −0.12)
Q9P2B2 (PTGFRN; 99, −10, −0.10)
Q4JDL3 (PTPN20A;; 48, −10, −0.20)
O14522 (PTPRT; 162, −10, −0.06)
Q8NC74 (RBBP8NL; 71, −10, −0.13)
Q8NDN9 (RCBTB1; 58, −10, −0.17)
Q8WZ73 (RFFL; 41, −10, −0.24)
Q969X0 (RILPL2; 24, −10, −0.41)
Q8WYP3 (RIN2; 100, −10, −0.09)
Q06587 (RING1; 42, −10, −0.23)
Q8WU17 (RNF139; 76, −10, −0.13)
Q8WZ75 (ROBO4; 107, −10, −0.09)
Q96C34 (RUNDC1; 68, −10, −0.14)
Q86WG5 (SBF2; 208, −10, −0.04)
Q8WU76 (SCFD2; 75, −10, −0.13)
Q9GZR1 (SENP6; 126, −10, −0.07)
P50452 (SERPINB8; 43, −10, −0.23)
Q86TU7 (SETD3; 67, −10, −0.14)
Q8IWL2 (SFTPA1; 26, −10, −0.38)
Q99963 (SH3GL3; 39, −10, −0.25)
Q13796 (SHROOM2; 176, −10, −0.05)
P84550 (SKOR1; 100, −10, −0.10)
Q8IZD6 (SLC22A15; 61, −10, −0.16)
Q9C0K1 (SLC39A8; 50, −10, −0.20)
Q9H1V8 (SLC6A17; 81, −10, −0.12)
Q96PX8 (SLITRK1; 78, −10, −0.12)
Q9NTJ3 (SMC4; 147, −10, −0.06)
Q9UH36 (SRRD; 39, −10, −0.25)
Q9NP77 (SSU72; 23, −10, −0.44)
O95630 (STAMBP; 48, −10, −0.20)
Q96LT7 (C9orf72; 54, −10, −0.18)
Q5SR56 (HIATL1; 55, −10, −0.18)
Q13568 (IRF5; 56, −10, −0.17)
Q5I0G3 (MDH1B; 59, −10, −0.17)
Q86V42 (FAM124A; 60, −10, −0.16)
Q8N5T2 (TBC1D19; 60, −10, −0.16)
Q13153 (PAK1; 61, −10, −0.16)
Q96FN4 (CPNE2; 61, −10, −0.16)
Q01201 (RELB; 62, −10, −0.16)
Q9H257 (CARD9; 62, −10, −0.16)
Q9H808 (TLE6; 63, −10, −0.15)
Q99502 (EYA1; 65, −10, −0.15)
O75083 (WDR1; 66, −10, −0.15)
Q6ZV50 (RFX8; 66, −10, −0.15)
Q6L8Q7 (PDE12; 67, −10, −0.14)
P22303 (ACHE; 68, −10, −0.14)
O76083 (PDE9A; 68, −10, −0.14)
P51114 (FXR1; 70, −10, −0.14)
Q8N3J3 (C17orf53; 70, −10, −0.14)
P54652 (HSPA2; 70, −10, −0.14)
P07359 (GP1BA; 72, −10, −0.13)
Q6ZN66 (GBP6; 72, −10, −0.13)

TABLE 3-continued

Exemplary naturally occurring negatively supercharged proteins.

C4AMC7 (WASH3P; 50, −10, −0.20)
Q9NQA3 (WASH6P; 48, −10, −0.20)
O75554 (WBP4; 43, −10, −0.23)
Q96FK6 (WDR89; 43, −10, −0.23)
Q8TEU8 (WFIKKN2; 64, −10, −0.15)
Q9NRH1 (YAE1D1; 25, −10, −0.39)
P24278 (ZBTB25; 49, −10, −0.20)
Q8NCN2 (ZBTB34; 56, −10, −0.18)
Q86WB0 (ZC3HC1; 55, −10, −0.18)
O15015 (ZNF646; 201, −10, −0.04)
Q9NWK9 (ZNHIT6; 54, −10, −0.18)
Q96GX2 (ATXN7L3B; 11, −10, −0.92)
Q504U0 (C4orf46; 12, −10, −0.84)
Q17R26 (ZNF300P1; 16, −10, −0.63)
Q9H5X1 (FAM96A; 18, −10, −0.54)
P60604 (UBE2G2; 19, −10, −0.53)
Q8N9N8 (EIF1AD; 19, −10, −0.52)
Q8IZT9 (FAM9C; 19, −10, −0.52)
Q96LC9 (BMF; 21, −10, −0.48)
Q68D20 (PMS2CL; 21, −10, −0.47)
Q9BUN5 (CCDC28B; 22, −10, −0.45)
Q8N0U2 (TMEM61; 22, −10, −0.45)
A8MWL6 (0; 25, −10, −0.40)
Q5VZI3 (C9orf91; 38, −10, −0.26)
Q6ZSR9 (0; 38, −10, −0.26)
A6NGH7 (CCDC160; 38, −10, −0.26)
O75695 (RP2; 40, −10, −0.25)
P09471 (GNAO1; 40, −10, −0.24)
Q504Y3 (ZCWPW2; 41, −10, −0.24)
E9PGG2 (ANHX; 42, −10, −0.23)
Q562R1 (ACTBL2; 42, −10, −0.23)
Q8N9B4 (ANKRD42; 43, −10, −0.23)
Q8WTU0 (DDI1; 44, −10, −0.22)
Q9HB65 (ELL3; 45, −10, −0.22)
Q96EP9 (SLC10A4; 47, −10, −0.21)
P48052 (CPA2; 47, −10, −0.21)
P47972 (NPTX2; 47, −10, −0.21)
Q6NT76 (HMBOX1; 47, −10, −0.21)
Q6NW40 (RGMB; 48, −10, −0.21)
Q9UKS6 (PACSIN3; 48, −10, −0.20)
Q96LV5 (INTS4L1; 49, −10, −0.20)
P06280 (GLA; 49, −10, −0.20)
Q2T9F4 (INTS4L2; 49, −10, −0.20)
Q86YG4 (NT5DC4; 49, −10, −0.20)
C9JR72 (KBTBD13; 49, −10, −0.20)
P04180 (LCAT; 50, −10, −0.20)
Q8WW24 (TEKT4; 51, −10, −0.19)
P04004 (VTN; 54, −10, −0.18)
Q9NW82 (WDR70; 73, −10, −0.13)
Q8NCG7 (DAGLB; 74, −10, −0.13)
P05160 (F13B; 76, −10, −0.13)
O96005 (CLPTM1; 76, −10, −0.13)
Q5VTL7 (FNDC7; 78, −10, −0.12)
Q9NUQ8 (ABCF3; 80, −10, −0.12)
Q04725 (TLE2; 80, −10, −0.12)
O00459 (PIK3R2; 82, −10, −0.12)
P51178 (PLCD1; 86, −10, −0.11)
P06396 (GSN; 86, −10, −0.11)
O43290 (SART1; 90, −10, −0.11)
Q9UKN8 (GTF3C4; 92, −10, −0.10)
Q8TB24 (RIN3; 108, −10, −0.09)
Q8IWY4 (SCUBE1; 108, −10, −0.09)
P57679 (EVC; 112, −10, −0.08)
Q05469 (LIPE; 117, −10, −0.08)
O94779 (CNTN5; 121, −10, −0.08)
Q9NRM1 (ENAM; 129, −10, −0.07)
Q14896 (MYBPC3; 141, −10, −0.07)
P05997 (COL5A2; 145, −10, −0.06)
Q8TER0 (SNED1; 152, −10, −0.06)
Q9UHC1 (MLH3; 164, −10, −0.06)

Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

TABLE 4

Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

Q8WXG9 (GPR98; 693, −412, −0.59)
P13611 (VCAN; 373, −322, −0.86)
Q03001 (DST; 861, −316, −0.36)
Q8NF91 (SYNE1; 1, 011, −315, −0.31)
Q8IWN7 (Q8IWN7; 261, −278, −1.06)
Q8WXH0 (SYNE2; 796, −271, −0.34)
P16112 (ACAN; 250, −269, −1.07)
Q9NZW4 (Q9NZW4; 131, −266, −2.02)
P98164 (P98164; 522, −243, −0.46)
Q99996 (AKAP9; 454, −233, −0.51)
Q6V0I7 (FAT4; 543, −230, −0.42)
Q9H251 (CDH23; 369, −223, −0.60)
Q01484 (Q01484; 434, −212, −0.48)
P21817 (RYR1; 565, −207, −0.36)
Q7Z6Z7 (HUWE1; 482, −173, −0.35)
Q5VST9 (OBSCN; 868, −173, −0.19)
Q86XX4 (FRAS1; 443, −168, −0.37)
Q96JQ0 (DCHS1; 346, −162, −0.46)
Q5SZK8 (Q5SZK8; 351, −158, −0.44)
P02549 (SPTA1; 280, −153, −0.54)
O14686 (KMT2D; 593, −148, −0.24)
Q12888 (Q12888; 214, −148, −0.69)
P22105 (TNXB; 464, −144, −0.31)
O95613 (PCNT; 378, −142, −0.37)
Q8N4C6 (NIN; 243, −138, −0.56)
P35556 (P35556; 315, −137, −0.43)
O60494 (CUBN; 399, −133, −0.33)
P35555 (FBN1; 312, −132, −0.42)
P12270 (P12270; 267, −127, −0.47)
P46531 (NOTCH1; 273, −125, −0.45)
Q92736 (Q92736; 565, −119, −0.21)
Q04721 (Q04721; 265, −117, −0.44)
P24821 (TNC; 241, −114, −0.47)
Q4G0P3 (HYDIN; 576, −113, −0.19)
Q13813 (SPTAN1; 285, −113, −0.39)
P11277 (SPTB; 246, −107, −0.43)
Q15154 (Q15154; 229, −103, −0.45)
O94915 (FRYL; 340, −101, −0.29)
Q13316 (Q13316; 56, −101, −1.81)

TABLE 4-continued

Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

Q9BZV3 (IMPG2; 139, −100, −0.72)
Q3ZCN5 (OTOGL; 262, −98, −0.37)
P07942 (P07942; 198, −98, −0.49)
Q8TCU4 (ALMS1; 461, −96, −0.20)
O75970 (MPDZ; 222, −94, −0.42)
P78509 (P78509; 388, −94, −0.24)
P21675 (TAF1; 213, −93, −0.43)
Q5VU43 (PDE4DIP; 265, −92, −0.34)
Q15643 (TRIP11; 228, −90, −0.39)
Q9UGM3 (DMBT1; 261, −89, −0.34)
P04275 (VWF; 309, −89, −0.28)
P11532 (P11532; 427, −89, −0.20)
Q5T1H1 (EYS; 351, −87, −0.24)
Q63HN8 (RNF213; 591, −87, −0.14)
Q8NG31 (CASC5; 265, −84, −0.31)
O75096 (LRP4; 212, −83, −0.39)
Q15149 (PLEC; 532, −83, −0.15)
O95714 (O95714; 527, −83, −0.15)
P98160 (P98160; 469, −83, −0.17)
Q9BQS8 (FYCO1; 167, −82, −0.49)
P50851 (LRBA; 319, −82, −0.25)
Q5TD94 (RSPH4A; 81, −81, −1.00)
Q14028 (CNGB1; 140, −80, −0.57)
Q9UM47 (Q9UM47; 244, −80, −0.32)
P35442 (THBS2; 130, −79, −0.60)
Q5JTC6 (AMER1; 124, −78, −0.62)
O60229 (KALRN; 340, −78, −0.22)
Q14767 (LTBP2; 195, −77, −0.39)
Q5T011 (SZT2; 378, −77, −0.20)
Q7Z7A1 (CNTRL; 269, −75, −0.27)
Q6ZRI0 (OTOG; 315, −74, −0.23)
Q86SJ6 (DSG4; 114, −73, −0.64)
Q93008 (USP9X; 292, −72, −0.24)
O00507 (USP9Y; 291, −72, −0.24)
Q96QU1 (PCDH15; 216, −71, −0.32)
Q96JI7 (SPG11; 279, −71, −0.25)
P38398 (BRCA1; 208, −70, −0.33)
Q14160 (SCRIB; 175, −70, −0.40)
Q5H8C1 (FREM1; 244, −69, −0.28)

TABLE 4-continued

Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

Q92834 (RPGR; 113, −69, −0.60)
Q92673 (SORL1; 248, −69, −0.27)
P37275 (ZEB1; 124, −69, −0.55)
Q9NYQ6 (CELSR1; 329, −67, −0.20)
Q8TE73 (DNAH5; 529, −67, −0.12)
P42566 (EPS15; 99, −67, −0.67)
Q16821 (PPP1R3A; 126, −67, −0.53)
Q562E7 (Q562E7; 212, −67, −0.31)
Q9UPV0 (CEP164; 164, −66, −0.40)
P14314 (PRKCSH; 59, −66, −1.11)
Q96RW7 (HMCN1; 613, −65, −0.10)
P49747 (P49747; 83, −65, −0.78)
P82279 (P82279; 154, −65, −0.42)
P05067 (APP; 87, −64, −0.73)
O75369 (FLNB; 278, −64, −0.23)
P42858 (HTT; 348, −64, −0.18)
O75147 (OBSL1; 207, −64, −0.30)
Q86UP3 (Q86UP3; 394, −64, −0.16)
Q12955 (Q12955; 480, −64, −0.13)
Q96DT5 (Q96DT5; 521, −63, −0.12)
Q8NEP3 (DNAAF1; 80, −62, −0.77)
Q14643 (ITPR1; 314, −62, −0.19)
A2RRP1 (NBAS; 269, −62, −0.23)
Q96SN8 (CDK5RAP2; 215, −61, −0.28)
P35499 (P35499; 208, −61, −0.29)
P16157 (ANK1; 206, −60, −0.29)
Q9NWF9 (RNF216; 99, −60, −0.60)
P22223 (CDH3; 91, −59, −0.64)
Q9UBN7 (HDAC6; 131, −59, −0.44)
P10745 (P10745; 135, −59, −0.43)
O14958 (O14958; 46, −59, −1.27)
O94986 (CEP152; 196, −58, −0.29)
Q14315 (FLNC; 291, −58, −0.19)
O75197 (LRP5; 179, −58, −0.32)
Q68CZ1 (RPGRIP1L; 151, −58, −0.38)
Q7Z7G8 (VPS13B; 449, −58, −0.12)
O75581 (O75581; 180, −58, −0.32)
Q9Y5Q5 (CORIN; 116, −57, −0.48)
Q14204 (DYNC1H1; 532, −57, −0.10)
Q9BZA8 (PCDH11Y; 147, −57, −0.38)
P09619 (PDGFRB; 124, −57, −0.45)
O60216 (RAD21; 72, −57, −0.79)
Q8IVV2 (Q8IVV2; 222, −57, −0.25)
P20908 (P20908; 184, −57, −0.31)
P12259 (P12259; 252, −57, −0.22)
Q15029 (EFTUD2; 109, −56, −0.51)
P02751 (FN1; 263, −56, −0.21)
Q99698 (LYST; 429, −56, −0.13)
P98155 (P98155; 96, −56, −0.58)
O75443 (O75443; 240, −56, −0.23)
P56715 (RP1; 241, −55, −0.22)
P12830 (CDH1; 97, −54, −0.55)
P21333 (FLNA; 281, −54, −0.19)
P50542 (PEX5; 71, −54, −0.76)
P08F94 (PKHD1; 447, −54, −0.12)
Q92794 (KAT6A; 225, −53, −0.23)
O60333 (KIF1B; 204, −53, −0.25)
O15020 (SPTBN2; 271, −53, −0.19)
Q6ZRS2 (SRCAP; 344, −53, −0.15)
Q01105 (Q01105; 33, −53, −1.58)
P01266 (P01266; 305, −53, −0.17)
Q9NZN5 (ARHGEF12; 173, −52, −0.30)
Q4G0X9 (CCDC40; 130, −52, −0.39)
Q6PRD1 (GPR179; 257, −52, −0.20)
Q14114 (LRP8; 106, −52, −0.49)
Q9HC84 (MUC5B; 596, −52, −0.08)
O60721 (SLC24A1; 121, −52, −0.42)
P35749 (MYH11; 227, −51, −0.22)
Q14999 (CUL7; 191, −50, −0.26)
Q9UPY3 (DICER1; 219, −50, −0.22)
O75923 (DYSF; 237, −50, −0.21)
P28715 (ERCC5; 133, −49, −0.36)
P07196 (NEFL; 62, −49, −0.79)

TABLE 4-continued

Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

P49792 (RANBP2; 358, −49, −0.13)
O43379 (WDR62; 166, −49, −0.29)
Q68DK2 (ZFYVE26; 285, −49, −0.17)
Q8IWV7 (Q8IWV7; 200, −49, −0.24)
P12107 (COL11A1; 181, −48, −0.26)
Q14678 (KANK1; 147, −48, −0.32)
Q8WYB5 (KAT6B; 231, −48, −0.20)
Q6ZNJ1 (NBEAL2; 303, −48, −0.15)
Q9BYW2 (SETD2; 288, −48, −0.16)
O75643 (SNRNP200; 245, −48, −0.19)
P14410 (P14410; 209, −48, −0.22)
P55287 (P55287; 88, −48, −0.54)
O15078 (CEP290; 290, −47, −0.16)
Q9P2D1 (CHD7; 336, −47, −0.13)
Q9HCE0 (EPG5; 292, −47, −0.16)
Q9HC10 (OTOF; 227, −47, −0.20)
P16234 (PDGFRA; 123, −47, −0.38)
O94972 (TRIM37; 108, −47, −0.43)
P13535 (P13535; 223, −47, −0.21)
Q7RTU9 (Q7RTU9; 193, −47, −0.24)
P35579 (P35579; 227, −47, −0.20)
Q8N2S1 (Q8N2S1; 173, −47, −0.27)
Q8NCM8 (DYNC2H1; 493, −46, −0.09)
Q71F56 (MED13L; 243, −46, −0.18)
P11055 (P11055; 224, −46, −0.20)
P13533 (MYH6; 224, −45, −0.20)
Q96RL7 (VPS13A; 360, −45, −0.12)
Q9BUR4 (WRAP53; 59, −45, −0.75)
Q9GZS0 (Q9GZS0; 69, −45, −0.65)
Q96KN7 (Q96KN7; 147, −45, −0.30)
Q8TD26 (CHD6; 305, −44, −0.14)
Q96F46 (IL17RA; 96, −44, −0.45)
O15013 (ARHGEF10; 152, −43, −0.28)
Q04637 (EIF4G1; 175, −43, −0.24)
Q8IYD8 (FANCM; 232, −43, −0.18)
P41229 (KDM5C; 176, −43, −0.24)
Q9UQF2 (MAPK8IP1; 78, −43, −0.55)
Q7Z406 (MYH14; 228, −43, −0.18)
Q9UKX2 (MYH2; 223, −43, −0.19)
Q9H5I5 (PIEZO2; 318, −43, −0.13)
Q6YHU6 (THADA; 220, −43, −0.19)
P98073 (TMPRSS15; 113, −43, −0.38)
Q9P219 (CCDC88C; 228, −42, −0.18)
Q02413 (DSG1; 114, −42, −0.36)
Q14126 (DSG2; 122, −42, −0.34)
P12883 (MYH7; 223, −42, −0.18)
Q9H2M9 (RAB3GAP2; 156, −42, −0.26)
P00450 (P00450; 122, −42, −0.34)
Q14524 (Q14524; 227, −42, −0.18)
Q9HCK8 (CHD8; 291, −41, −0.14)
P24386 (CHM; 73, −41, −0.55)
Q9Y5B0 (CTDP1; 104, −41, −0.39)
Q5JWF2 (GNAS; 111, −41, −0.36)
P24043 (LAMA2; 344, −41, −0.11)
Q96RT7 (TUBGCP6; 200, −41, −0.20)
P01130 (P01130; 95, −41, −0.42)
O43707 (O43707; 105, −41, −0.39)
Q9C0F0 (ASXL3; 242, −40, −0.16)
P55291 (CDH15; 89, −40, −0.44)
Q9H9B1 (EHMT1; 141, −40, −0.28)
Q96RY7 (IFT140; 165, −40, −0.24)
Q8TAB3 (PCDH19; 126, −40, −0.31)
O00291 (O00291; 116, −40, −0.34)
Q00987 (Q00987; 55, −40, −0.72)
Q13085 (ACACA; 266, −39, −0.14)
P08922 (ROS1; 264, −39, −0.14)
Q8IY92 (SLX4; 200, −39, −0.19)
Q9UMZ3 (Q9UMZ3; 261, −39, −0.14)
P10912 (P10912; 72, −39, −0.54)
P98161 (P98161; 463, −39, −0.08)
Q7Z3S7 (Q7Z3S7; 128, −39, −0.30)
O75445 (O75445; 576, −39, −0.06)
Q8TDI0 (CHD5; 223, −38, −0.17)

TABLE 4-continued

Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

Q9UPZ3 (HPS5; 127, −38, −0.29)
Q9UG01 (IFT172; 198, −38, −0.19)
O15040 (TECPR2; 154, −38, −0.24)
P12814 (P12814; 103, −38, −0.36)
P16144 (P16144; 202, −38, −0.18)
O95163 (IKBKAP; 150, −37, −0.24)
P09848 (LCT; 219, −37, −0.16)
Q08499 (PDE4D; 91, −37, −0.40)
Q07864 (POLE; 262, −37, −0.14)
Q8NEL9 (DDHD1; 100, −36, −0.35)
Q8NDI1 (EHBP1; 140, −36, −0.25)
Q9NZJ5 (EIF2AK3; 125, −36, −0.28)
P55268 (LAMB2; 196, −36, −0.18)
P35913 (PDE6B; 98, −36, −0.36)
P40855 (PEX19; 33, −36, −1.09)
Q15042 (RAB3GAP1; 111, −36, −0.32)
Q5T481 (Q5T481; 134, −36, −0.26)
P01133 (P01133; 134, −36, −0.26)
Q9H6L5 (Q9H6L5; 55, −36, −0.65)
P78363 (ABCA4; 256, −35, −0.13)
O60566 (BUB1B; 120, −35, −0.29)
O60840 (CACNA1F; 221, −35, −0.15)
Q0VF96 (CGNL1; 149, −35, −0.23)
Q13144 (EIF2B5; 80, −35, −0.43)
Q92539 (LPIN2; 99, −35, −0.35)
Q96PY6 (NEK1; 143, −35, −0.24)
Q8WYR4 (RSPH1; 35, −35, −0.99)
Q9P273 (TENM3; 301, −35, −0.11)
Q99707 (Q99707; 141, −35, −0.24)
Q2M1Z3 (ARHGAP31; 157, −34, −0.21)
Q8WZ55 (BSND; 35, −34, −0.96)
O15320 (CTAGE5; 91, −34, −0.37)
Q9P2K8 (EIF2AK4; 187, −34, −0.18)
Q9HAZ2 (PRDM16; 140, −34, −0.24)
Q9HCM3 (Q9HCM3; 211, −34, −0.16)
P33076 (CIITA; 124, −33, −0.26)
Q2KHT3 (CLEC16A; 118, −33, −0.28)
Q9NVR5 (DNAAF2; 91, −33, −0.36)
Q96DU7 (ITPKC; 75, −33, −0.43)
Q32P28 (LEPRE1; 83, −33, −0.39)
O94898 (LRIG2; 119, −33, −0.27)
O60500 (NPHS1; 135, −33, −0.24)
P35609 (P35609; 104, −33, −0.31)
Q8NDB2 (Q8NDB2; 89, −33, −0.36)
Q86WG3 (ATCAY; 42, −32, −0.75)
P51587 (BRCA2; 384, −32, −0.08)
Q09013 (DMPK; 69, −32, −0.46)
Q96EV8 (DTNBP1; 39, −32, −0.81)
P04626 (ERBB2; 138, −32, −0.23)
Q9BXW9 (FANCD2; 166, −32, −0.19)
Q6Y7W6 (GIGYF2; 150, −32, −0.21)
Q27J81 (INF2; 136, −32, −0.23)
P08514 (ITGA2B; 113, −32, −0.28)
P02730 (SLC4A1; 102, −32, −0.31)
Q05086 (UBE3A; 101, −32, −0.31)
Q5VV43 (Q5VV43; 118, −32, −0.27)
Q9H4Z2 (Q9H4Z2; 145, −32, −0.22)
O60610 (DIAPH1; 141, −31, −0.21)
P23142 (FBLN1; 77, −31, −0.40)
Q9BYX4 (IFIH1; 117, −31, −0.26)
Q9HBE5 (IL21R; 59, −31, −0.52)
P52732 (KIF11; 119, −31, −0.26)
P08575 (PTPRC; 147, −31, −0.21)
Q9H4L7 (SMARCAD1; 117, −31, −0.26)
O60315 (ZEB2; 136, −31, −0.22)
P09871 (P09871; 77, −31, −0.40)
P39060 (P39060; 178, −31, −0.17)
Q9NS15 (Q9NS15; 139, −31, −0.22)
Q8N302 (AGGF1; 81, −30, −0.37)
Q8NEU8 (APPL2; 74, −30, −0.40)
Q9Y238 (DLEC1; 196, −30, −0.15)
Q13683 (ITGA7; 129, −30, −0.23)
Q86Y26 (NUTM1; 120, −30, −0.24)
Q9H4A3 (WNK1; 251, −30, −0.11)
Q16363 (Q16363; 203, −30, −0.14)
Q12934 (Q12934; 75, −30, −0.40)
Q9BY79 (Q9BY79; 62, −30, −0.48)
Q9Y6D5 (ARFGEF2; 202, −29, −0.14)
Q8TD16 (BICD2; 94, −29, −0.31)
Q6PJG6 (BRAT1; 88, −29, −0.32)
P11171 (EPB41; 97, −29, −0.29)
Q96EK5 (KIAA1279; 72, −29, −0.40)
Q12756 (KIF1A; 191, −29, −0.15)
P25963 (NFKBIA; 36, −29, −0.81)
Q8N427 (NME8; 67, −29, −0.43)
Q96CV9 (OPTN; 66, −29, −0.43)
Q69YQ0 (SPECC1L; 125, −29, −0.23)
P07204 (THBD; 60, −29, −0.48)
P63316 (TNNC1; 18, −29, −1.57)
Q9Y5Y9 (Q9Y5Y9; 221, −29, −0.13)
P19235 (P19235; 55, −29, −0.52)
Q14203 (Q14203; 142, −29, −0.20)
O15118 (O15118; 142, −29, −0.20)
P30530 (AXL; 98, −28, −0.28)
Q02487 (DSC2; 100, −28, −0.28)
Q9H4G0 (EPB41L1; 99, −28, −0.28)
Q9NQG7 (HPS4; 77, −28, −0.36)
O15259 (NPHP1; 83, −28, −0.33)
P16499 (PDE6A; 100, −28, −0.28)
P47712 (PLA2G4A; 85, −28, −0.32)
Q9P212 (PLCE1; 259, −28, −0.10)
P35498 (SCN1A; 229, −28, −0.12)
P07951 (TPM2; 33, −28, −0.85)
Q96QK1 (VPS35; 92, −28, −0.30)
Q96J92 (WNK4; 135, −28, −0.20)
O14983 (O14983; 110, −28, −0.25)
Q9UPM8 (Q9UPM8; 127, −28, −0.21)
Q6PD74 (Q6PD74; 35, −28, −0.80)
P15260 (P15260; 54, −28, −0.51)
P06753 (P06753; 33, −28, −0.84)
Q86VV8 (Q86VV8; 249, −28, −0.11)
Q96Q42 (ALS2; 184, −27, −0.14)
Q66GS9 (CEP135; 133, −27, −0.20)
Q16832 (DDR2; 97, −27, −0.27)
Q8IUD2 (ERC1; 128, −27, −0.21)
P35968 (KDR; 152, −27, −0.17)
Q5U5Q3 (MEX3C; 69, −27, −0.38)
Q99650 (OSMR; 111, −27, −0.24)
Q99250 (SCN2A; 228, −27, −0.11)
Q6P5W5 (SLC39A4; 68, −27, −0.39)
Q969G3 (SMARCE1; 47, −27, −0.57)
P09493 (TPM1; 33, −27, −0.82)
Q7RTW8 (Q7RTW8; 129, −27, −0.21)
P06213 (P06213; 156, −27, −0.17)
P53708 (P53708; 117, −27, −0.22)
Q96MR6 (Q96MR6; 145, −27, −0.18)
P12821 (ACE; 150, −26, −0.17)
O00499 (BIN1; 65, −26, −0.40)
P83436 (COG7; 86, −26, −0.30)
Q8IYU2 (HACE1; 102, −26, −0.25)
P78504 (JAG1; 134, −26, −0.19)
Q12840 (KIF5A; 117, −26, −0.22)
Q5S007 (LRRK2; 286, −26, −0.09)
Q9UDY8 (MALT1; 92, −26, −0.28)
O00462 (MANBA; 101, −26, −0.25)
P48740 (MASP1; 79, −26, −0.32)
Q7Z7M0 (MEGF8; 303, −26, −0.08)
Q12866 (MERTK; 110, −26, −0.23)
P52948 (NUP98; 198, −26, −0.13)
Q15477 (SKIV2L; 138, −26, −0.18)
Q92574 (TSC1; 130, −26, −0.20)
Q9H9E3 (Q9H9E3; 89, −26, −0.29)
P13637 (P13637; 112, −26, −0.23)
P08069 (P08069; 155, −26, −0.16)
Q6IEE7 (Q6IEE7; 107, −26, −0.24)
P16615 (ATP2A2; 115, −25, −0.21)

TABLE 4-continued

Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

Q3SYG4 (BBS9; 99, −25, −0.25)
P35222 (CTNNB1; 85, −25, −0.29)
O94830 (DDHD2; 81, −25, −0.30)
Q96HP0 (DOCK6; 230, −25, −0.10)
Q96MC2 (DRC1; 87, −25, −0.28)
O95967 (EFEMP2; 49, −25, −0.50)
O95684 (FGFR1OP; 43, −25, −0.58)
P35916 (FLT4; 153, −25, −0.16)
Q9C0B1 (FTO; 58, −25, −0.42)
Q15746 (MYLK; 211, −25, −0.11)
P46020 (PHKA1; 137, −25, −0.18)
P49810 (PSEN2; 50, −25, −0.49)
Q16827 (PTPRO; 138, −25, −0.18)
Q13885 (TUBB2A; 50, −25, −0.50)
Q13509 (TUBB3; 50, −25, −0.49)
P04350 (TUBB4A; 50, −25, −0.50)
P22314 (UBA1; 118, −25, −0.21)
P12109 (P12109; 109, −25, −0.23)
P49588 (P49588; 107, −25, −0.23)
Q9Y6N6 (Q9Y6N6; 171, −25, −0.14)
P10253 (P10253; 105, −25, −0.23)
P04114 (P04114; 516, −25, −0.04)
P55072 (P55072; 89, −25, −0.27)
P16471 (P16471; 70, −25, −0.35)
Q9BVA1 (Q9BVA1; 50, −25, −0.50)
O00468 (AGRN; 217, −24, −0.11)
Q8NFD5 (ARID1B; 236, −24, −0.10)
Q8IXJ9 (ASXL1; 165, −24, −0.14)
Q04656 (ATP7A; 163, −24, −0.14)
P62158 (CALM1; 17, −24, −1.42)
Q9BXL7 (CARD11; 133, −24, −0.18)
Q9BXL6 (CARD14; 113, −24, −0.21)
P32927 (CSF2RB; 97, −24, −0.24)
P36888 (FLT3; 113, −24, −0.21)
Q9NQX3 (GPHN; 80, −24, −0.30)
Q8N6C5 (IGSF1; 149, −24, −0.16)
P32004 (L1CAM; 140, −24, −0.17)
Q8IVL5 (LEPREL1; 81, −24, −0.29)
P06748 (NPM1; 33, −24, −0.73)
P51160 (PDE6C; 99, −24, −0.24)
Q9Y2I7 (PIKFYVE; 237, −24, −0.10)
O60331 (PIP5K1C; 73, −24, −0.32)
Q96LW4 (PRIMPOL; 64, −24, −0.37)
Q15020 (SART3; 110, −24, −0.21)
Q8TF17 (SH3TC2; 145, −24, −0.16)
Q9ULL8 (SHROOM4; 165, −24, −0.14)
Q15468 (STIL; 143, −24, −0.16)
Q8IUC6 (TICAM1; 76, −24, −0.31)
O43897 (TLL1; 115, −24, −0.20)
Q71U36 (TUBA1A; 50, −24, −0.47)
Q9NY65 (TUBA8; 50, −24, −0.47)
Q99456 (Q99456; 54, −24, −0.44)
P50747 (P50747; 81, −24, −0.29)
P15391 (P15391; 61, −24, −0.39)
Q9UIR0 (Q9UIR0; 50, −24, −0.47)
Q16720 (Q16720; 134, −24, −0.17)
P42702 (P42702; 124, −24, −0.19)
Q6W2J9 (BCOR; 192, −23, −0.11)
Q4KMG0 (CDON; 139, −23, −0.16)
O15360 (FANCA; 163, −23, −0.14)
Q6PIJ6 (FBXO38; 134, −23, −0.17)
P05106 (ITGB3; 87, −23, −0.26)
Q2TBA0 (KLHL40; 69, −23, −0.33)
P20700 (LMNB1; 66, −23, −0.34)
P55196 (MLLT4; 207, −23, −0.11)
P16435 (POR; 77, −23, −0.29)
O14593 (RFXANK; 28, −23, −0.81)
Q86SQ7 (SDCCAG8; 83, −23, −0.27)
Q9UGP8 (SEC63; 88, −23, −0.26)
Q9UMX1 (SUFU; 54, −23, −0.42)
Q8NEZ3 (WDR19; 152, −23, −0.15)
Q99592 (ZBTB18; 58, −23, −0.39)
Q2M1K9 (ZNF423; 145, −23, −0.15)

TABLE 4-continued

Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

Q13315 (Q13315; 351, −23, −0.06)
P45379 (P45379; 36, −23, −0.64)
P07911 (P07911; 70, −23, −0.32)
P42898 (P42898; 75, −23, −0.30)
Q99523 (Q99523; 92, −23, −0.24)
P78536 (ADAM17; 93, −22, −0.23)
P46100 (ATRX; 283, −22, −0.07)
P54252 (ATXN3; 42, −22, −0.52)
Q96JP9 (CDHR1; 94, −22, −0.23)
Q96HD1 (CRELD1; 45, −22, −0.48)
Q9NQC7 (CYLD; 107, −22, −0.20)
P21860 (ERBB3; 148, −22, −0.14)
Q9UBX5 (FBLN5; 50, −22, −0.43)
P11021 (HSPA5; 72, −22, −0.30)
Q13651 (IL10RA; 63, −22, −0.34)
P80192 (MAP3K9; 122, −22, −0.18)
P46019 (PHKA2; 138, −22, −0.15)
Q96NY8 (PVRL4; 55, −22, −0.39)
Q9NZJ4 (SACS; 521, −22, −0.04)
Q8N196 (SIX5; 75, −22, −0.29)
Q13043 (STK4; 56, −22, −0.39)
Q14191 (WRN; 162, −22, −0.13)
Q9H799 (Q9H799; 362, −22, −0.06)
O00187 (O00187; 76, −22, −0.29)
Q02388 (Q02388; 295, −22, −0.07)
O43933 (O43933; 143, −22, −0.15)
Q13563 (Q13563; 110, −22, −0.20)
Q96MT8 (Q96MT8; 81, −22, −0.27)
P35219 (CA8; 33, −21, −0.63)
P35523 (CLCN1; 109, −21, −0.19)
Q8IYB7 (DIS3L2; 99, −21, −0.21)
Q96AY3 (FKBP10; 64, −21, −0.32)
O00165 (HAX1; 32, −21, −0.66)
P42704 (LRPPRC; 158, −21, −0.13)
P40692 (MLH1; 85, −21, −0.24)
O15055 (PER2; 137, −21, −0.15)
P07602 (PSAP; 58, −21, −0.36)
Q13501 (SQSTM1; 48, −21, −0.44)
Q96GX1 (TCTN2; 77, −21, −0.27)
Q0ZGT2 (Q0ZGT2; 81, −21, −0.26)
Q9H4B7 (Q9H4B7; 50, −21, −0.41)
O75381 (O75381; 41, −21, −0.50)
Q9Y2Y0 (ARL2BP; 19, −20, −1.06)
Q96Q07 (BTBD9; 69, −20, −0.28)
O14936 (CASK; 105, −20, −0.19)
Q14790 (CASP8; 55, −20, −0.36)
P41180 (CASR; 121, −20, −0.16)
Q70SY1 (CREB3L2; 57, −20, −0.34)
Q99062 (CSF3R; 92, −20, −0.21)
Q6UN15 (FIP1L1; 67, −20, −0.30)
Q92949 (FOXJ1; 45, −20, −0.44)
Q86UP8 (GTF2IRD2; 107, −20, −0.18)
Q00653 (NFKB2; 97, −20, −0.20)
Q9Y6C5 (PTCH2; 131, −20, −0.15)
Q99574 (SERPINI1; 46, −20, −0.43)
Q8TBB6 (SLC7A14; 84, −20, −0.23)
O14841 (O14841; 137, −20, −0.14)
Q7Z6L0 (Q7Z6L0; 35, −20, −0.57)
P35557 (P35557; 52, −20, −0.38)
Q10571 (Q10571; 136, −20, −0.14)
Q92622 (Q92622; 109, −20, −0.18)
P45452 (P45452; 54, −20, −0.37)
Q13873 (BMPR2; 115, −19, −0.16)
Q9BSQ5 (CCM2; 49, −19, −0.38)
Q9BS16 (CENPK; 32, −19, −0.60)
Q9UHC6 (CNTNAP2; 148, −19, −0.12)
Q15303 (ERBB4; 147, −19, −0.12)
P22607 (FGFR3; 88, −19, −0.21)
O43524 (FOX03; 71, −19, −0.26)
P43080 (GUCA1A; 23, −19, −0.82)
P22304 (IDS; 62, −19, −0.30)
Q7Z4S6 (KIF21A; 187, −19, −0.10)
Q13753 (LAMC2; 131, −19, −0.14)

TABLE 4-continued

Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

Q03252 (LMNB2; 68, −19, −0.28)
P10911 (MCF2; 108, −19, −0.17)
Q86YR7 (MCF2L2; 127, −19, −0.14)
Q13562 (NEUROD1; 40, −19, −0.47)
Q8N0W4 (NLGN4X; 92, −19, −0.20)
Q5SRE5 (NUP188; 196, −19, −0.09)
O75665 (OFD1; 117, −19, −0.16)
Q96MT3 (PRICKLE1; 94, −19, −0.20)
P98175 (RBM10; 104, −19, −0.18)
Q9UQD0 (SCN8A; 225, −19, −0.08)
Q9NZV5 (SEPN1; 66, −19, −0.28)
Q9Y6Q6 (TNFRSF11A; 66, −19, −0.28)
Q8WW38 (ZFPM2; 128, −19, −0.14)
P12111 (P12111; 344, −19, −0.05)
P18206 (P18206; 124, −19, −0.15)
P08670 (P08670; 54, −19, −0.35)
Q12860 (Q12860; 113, −19, −0.16)
Q96MW5 (Q96MW5; 68, −19, −0.27)
Q04446 (Q04446; 80, −19, −0.23)
Q96QS3 (Q96QS3; 58, −19, −0.32)
O60568 (O60568; 85, −19, −0.22)
Q6EKJ0 (Q6EKJ0; 107, −19, −0.17)
O14497 (ARID1A; 242, −18, −0.07)
P01024 (C3; 187, −18, −0.09)
Q9H467 (CUEDC2; 32, −18, −0.56)
Q96SD1 (DCLRE1C; 78, −18, −0.22)
Q8IZD9 (DOCK3; 233, −18, −0.07)
Q99814 (EPAS1; 96, −18, −0.18)
O60447 (EVI5; 93, −18, −0.19)
Q9HCG7 (GBA2; 105, −18, −0.17)
Q92990 (GLMN; 68, −18, −0.26)
Q8TBA6 (GOLGA5; 83, −18, −0.21)
Q9HD26 (GOPC; 51, −18, −0.35)
Q96EW2 (HSPBAP1; 55, −18, −0.32)
P42701 (IL12RB1; 73, −18, −0.24)
O60282 (KIF5C; 109, −18, −0.16)
Q9BXB1 (LGR4; 104, −18, −0.17)
Q96GX5 (MASTL; 97, −18, −0.18)
Q03112 (MECOM; 118, −18, −0.15)
Q969V6 (MKL1; 99, −18, −0.18)
Q9BV36 (MLPH; 66, −18, −0.27)
P49959 (MRE11A; 81, −18, −0.22)
Q86YC2 (PALB2; 131, −18, −0.13)
Q9Y4G2 (PLEKHM1; 117, −18, −0.15)
O75298 (RTN2; 59, −18, −0.30)
Q05516 (ZBTB16; 74, −18, −0.24)
Q9UBW7 (ZMYM2; 155, −18, −0.11)
Q9BXC9 (Q9BXC9; 80, −18, −0.22)
O95677 (O95677; 70, −18, −0.25)
Q09470 (Q09470; 56, −18, −0.31)
Q70J99 (Q70J99; 123, −18, −0.14)
P06865 (P06865; 61, −18, −0.29)
Q9UP52 (Q9UP52; 89, −18, −0.20)
Q13705 (Q13705; 58, −18, −0.31)
Q5VWK5 (Q5VWK5; 72, −18, −0.25)
P06239 (P06239; 58, −18, −0.31)
P09603 (P09603; 60, −18, −0.29)
P40337 (P40337; 24, −18, −0.74)
P50993 (ATP1A2; 112, −17, −0.15)
Q9H165 (BCL11A; 91, −17, −0.18)
P01031 (C5; 188, −17, −0.09)
Q01668 (CACNA1D; 245, −17, −0.06)
O75838 (CIB2; 22, −17, −0.78)
Q9Y2V7 (COG6; 73, −17, −0.23)
P07333 (CSF1R; 108, −17, −0.15)
P35638 (DDIT3; 19, −17, −0.88)
O75140 (DEPDC5; 181, −17, −0.09)
Q9UNE0 (EDAR; 49, −17, −0.34)
P21802 (FGFR2; 92, −17, −0.18)
Q96FT9 (IFT43; 24, −17, −0.72)
P43243 (MATR3; 95, −17, −0.17)
Q8NI22 (MCFD2; 16, −17, −1.03)
Q16620 (NTRK2; 92, −17, −0.18)

TABLE 4-continued

Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

P29120 (PCSK1; 84, −17, −0.20)
Q9NQ66 (PLCB1; 139, −17, −0.12)
O94827 (PLEKHG5; 117, −17, −0.14)
P27169 (PON1; 40, −17, −0.42)
Q99708 (RBBP8; 102, −17, −0.16)
Q14108 (SCARB2; 54, −17, −0.31)
Q16586 (SGCA; 43, −17, −0.39)
Q07837 (SLC3A1; 79, −17, −0.21)
P22735 (TGM1; 90, −17, −0.18)
Q9Y6N9 (USH1C; 62, −17, −0.27)
Q96K83 (ZNF521; 148, −17, −0.11)
Q96M63 (Q96M63; 75, −17, −0.22)
P02671 (P02671; 95, −17, −0.17)
Q7RTS9 (Q7RTS9; 76, −17, −0.22)
Q9Y664 (Q9Y664; 48, −17, −0.35)
P13646 (P13646; 50, −17, −0.34)
Q5JTZ9 (AARS2; 107, −16, −0.14)
P35573 (AGL; 175, −16, −0.09)
O00203 (AP3B1; 121, −16, −0.13)
Q9HBG4 (ATP6V0A4; 96, −16, −0.16)
Q9UBB4 (ATXN10; 53, −16, −0.29)
Q8IWZ6 (BBS7; 80, −16, −0.19)
P20807 (CAPN3; 94, −16, −0.16)
P19835 (CEL; 79, −16, −0.20)
Q9ULV3 (CIZ1; 100, −16, −0.15)
Q16828 (DUSP6; 42, −16, −0.37)
Q12805 (EFEMP1; 55, −16, −0.29)
Q96M96 (FGD4; 87, −16, −0.18)
P11362 (FGFR1; 92, −16, −0.17)
Q96RU3 (FNBP1; 71, −16, −0.22)
Q92902 (HPS1; 79, −16, −0.20)
Q9HBG6 (IFT122; 142, −16, −0.11)
Q9UH77 (KLHL3; 65, −16, −0.24)
P13645 (KRT10; 59, −16, −0.27)
P08253 (MMP2; 74, −16, −0.21)
Q9NZQ3 (NCKIPSD; 79, −16, −0.20)
Q15788 (NCOA1; 157, −16, −0.10)
Q9NZ94 (NLGN3; 94, −16, −0.17)
Q8WX94 (NLRP7; 112, −16, −0.14)
P12955 (PEPD; 55, −16, −0.29)
Q7LG56 (RRM2B; 41, −16, −0.39)
P46937 (YAP1; 54, −16, −0.29)
P43251 (P43251; 61, −16, −0.26)
P48165 (P48165; 48, −16, −0.33)
Q9Y6B7 (Q9Y6B7; 83, −16, −0.19)
Q86Y56 (Q86Y56; 94, −16, −0.17)
Q9H5Y7 (Q9H5Y7; 95, −16, −0.16)
P42658 (P42658; 98, −16, −0.16)
P51692 (P51692; 90, −16, −0.17)
P37173 (P37173; 65, −16, −0.24)
Q969F9 (Q969F9; 114, −16, −0.14)
Q8NF50 (Q8NF50; 239, −16, −0.06)
P35527 (P35527; 62, −16, −0.25)
Q6T4R5 (Q6T4R5; 179, −16, −0.08)
C9JLR9 (C9JLR9; 73, −16, −0.21)
Q04695 (Q04695; 48, −16, −0.33)
Q8WVV4 (Q8WVV4; 68, −16, −0.23)
P13942 (P13942; 172, −16, −0.09)
P52788 (P52788; 41, −16, −0.38)
O43307 (ARHGEF9; 61, −15, −0.24)
Q6ZW61 (BBS12; 79, −15, −0.18)
Q13936 (CACNA1C; 249, −15, −0.06)
Q13698 (CACNA1S; 212, −15, −0.07)
Q9H444 (CHMP4B; 25, −15, −0.60)
A8TX70 (COL6A5; 290, −15, −0.05)
Q9Y4D2 (DAGLA; 115, −15, −0.13)
O60443 (DFNA5; 55, −15, −0.27)
Q9NRI5 (DISC1; 94, −15, −0.16)
Q14574 (DSC3; 100, −15, −0.15)
O15287 (FANCG; 69, −15, −0.21)
P98174 (FGD1; 107, −15, −0.14)
P98177 (FOX04; 54, −15, −0.27)
Q9H2C0 (GAN; 68, −15, −0.22)

TABLE 4-continued

Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

P31150 (GDI1; 51, −15, −0.29)
P13807 (GYS1; 84, −15, −0.17)
P20823 (HNF1A; 67, −15, −0.22)
P78318 (IGBP1; 39, −15, −0.38)
O14920 (IKBKB; 87, −15, −0.17)
P08779 (KRT16; 51, −15, −0.29)
P13796 (LCP1; 70, −15, −0.21)
P48357 (LEPR; 132, −15, −0.11)
Q13064 (MKRN3; 56, −15, −0.26)
Q00872 (MYBPC1; 128, −15, −0.11)
Q9C000 (NLRP1; 166, −15, −0.09)
O75914 (PAK3; 62, −15, −0.24)
Q92733 (PRCC; 52, −15, −0.28)
P49768 (PSEN1; 53, −15, −0.28)
P01009 (SERPINA1; 47, −15, −0.32)
Q9H173 (SIL1; 52, −15, −0.28)
Q695T7 (SLC6A19; 71, −15, −0.21)
O43295 (SRGAP3; 125, −15, −0.12)
Q13586 (STIM1; 77, −15, −0.19)
P19532 (TFE3; 62, −15, −0.24)
Q96Q05 (TRAPPC9; 129, −15, −0.11)
Q9H0U9 (TSPYL1; 49, −15, −0.30)
Q9ULT0 (TTC7A; 96, −15, −0.15)
Q9P2L0 (WDR35; 134, −15, −0.11)
Q9Y462 (ZNF711; 86, −15, −0.17)
Q9UI47 (Q9UI47; 100, −15, −0.15)
P12110 (P12110; 109, −15, −0.13)
P55895 (P55895; 59, −15, −0.25)
Q9Y3R0 (Q9Y3R0; 122, −15, −0.12)
P43246 (P43246; 105, −15, −0.14)
P42892 (P42892; 87, −15, −0.17)
O00206 (O00206; 96, −15, −0.15)
Q5QGS0 (Q5QGS0; 168, −15, −0.08)
P17661 (P17661; 54, −15, −0.28)
Q6DD88 (Q6DD88; 61, −15, −0.24)
O15294 (O15294; 117, −15, −0.12)
P13797 (P13797; 71, −15, −0.21)
Q9NWZ3 (Q9NWZ3; 52, −15, −0.29)
Q6JEL2 (Q6JEL2; 69, −15, −0.21)
O14896 (O14896; 53, −15, −0.28)
Q9H2U9 (ADAM7; 86, −14, −0.16)
Q9NZN9 (AIPL1; 44, −14, −0.31)
P35670 (ATP7B; 157, −14, −0.08)
P46736 (BRCC3; 36, −14, −0.38)
Q9P2K1 (CC2D2A; 186, −14, −0.07)
P48643 (CCT5; 60, −14, −0.23)
Q8N9W5 (DNAAF3; 59, −14, −0.23)
P29317 (EPHA2; 108, −14, −0.12)
P02679 (FGG; 52, −14, −0.27)
Q8NFG4 (FLCN; 64, −14, −0.21)
O15353 (FOXN1; 69, −14, −0.20)
P48506 (GCLC; 73, −14, −0.19)
P19087 (GNAT2; 40, −14, −0.34)
Q9BY41 (HDAC8; 42, −14, −0.33)
O15357 (INPPL1; 139, −14, −0.10)
P14923 (JUP; 82, −14, −0.17)
Q6UWE0 (LRSAM1; 84, −14, −0.16)
Q9Y6D9 (MAD1L1; 83, −14, −0.16)
Q9ULH7 (MKL2; 118, −14, −0.11)
P04198 (MYCN; 50, −14, −0.28)
Q92597 (NDRG1; 43, −14, −0.32)
P49902 (NT5C2; 65, −14, −0.21)
O15160 (POLR1C; 39, −14, −0.35)
Q4J6C6 (PREPL; 84, −14, −0.16)
P07225 (PROS1; 75, −14, −0.18)
Q14289 (PTK2B; 116, −14, −0.12)
Q9UHX1 (PUF60; 60, −14, −0.23)
P20936 (RASA1; 116, −14, −0.12)
Q8HWS3 (RFX6; 102, −14, −0.13)
P12271 (RLBP1; 36, −14, −0.38)
Q96RN1 (SLC26A8; 109, −14, −0.12)
Q9BSE2 (TMEM79; 44, −14, −0.32)
Q13515 (Q13515; 46, −14, −0.30)

TABLE 4-continued

Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

Q96G97 (Q96G97; 44, −14, −0.31)
P02533 (P02533; 52, −14, −0.27)
Q15822 (Q15822; 60, −14, −0.23)
Q07889 (Q07889; 152, −14, −0.09)
P00740 (P00740; 52, −14, −0.27)
P51687 (P51687; 60, −14, −0.23)
P15924 (P15924; 332, −14, −0.04)
P15289 (P15289; 54, −14, −0.26)
Q8NCR0 (Q8NCR0; 57, −14, −0.24)
P42224 (P42224; 87, −14, −0.16)
P68133 (ACTA1; 42, −13, −0.30)
P62736 (ACTA2; 42, −13, −0.30)
P68032 (ACTC1; 42, −13, −0.30)
Q9NP73 (ALG13; 126, −13, −0.10)
P18054 (ALOX12; 76, −13, −0.17)
Q16671 (AMHR2; 63, −13, −0.20)
P08758 (ANXA5; 36, −13, −0.36)
Q8N9N2 (ASCC1; 46, −13, −0.28)
Q08AD1 (CAMSAP2; 168, −13, −0.07)
P24385 (CCND1; 34, −13, −0.38)
P11230 (CHRNB1; 57, −13, −0.22)
Q04844 (CHRNE; 55, −13, −0.23)
Q96SW2 (CRBN; 51, −13, −0.25)
Q6UUV9 (CRTC1; 67, −13, −0.19)
P24855 (DNASE1; 31, −13, −0.41)
Q8N608 (DPP10; 91, −13, −0.14)
Q99607 (ELF4; 71, −13, −0.18)
P50549 (ETV1; 55, −13, −0.23)
Q9HB96 (FANCE; 59, −13, −0.22)
P09769 (FGR; 59, −13, −0.21)
Q08334 (IL10RB; 37, −13, −0.35)
P48544 (KCNJ5; 48, −13, −0.27)
Q9GZY6 (LAT2; 27, −13, −0.48)
P01106 (MYC; 49, −13, −0.26)
Q15596 (NCOA2; 159, −13, −0.08)
Q9HC29 (NOD2; 115, −13, −0.11)
Q7Z494 (NPHP3; 151, −13, −0.08)
Q86U42 (PABPN1; 33, −13, −0.39)
Q9H5K3 (POMK; 40, −13, −0.32)
P37231 (PPARG; 58, −13, −0.22)
Q05823 (RNASEL; 84, −13, −0.15)
Q9HCK4 (ROB02; 151, −13, −0.08)
Q01974 (ROR2; 105, −13, −0.12)
O95248 (SBF1; 208, −13, −0.06)
Q9NY72 (SCN3B; 25, −13, −0.52)
Q8N0X7 (SPG20; 73, −13, −0.17)
Q8N205 (SYNE4; 44, −13, −0.29)
P15923 (TCF3; 68, −13, −0.19)
O14763 (TNFRSF10B; 48, −13, −0.27)
O43280 (TREH; 67, −13, −0.19)
Q9UPN9 (TRIM33; 123, −13, −0.10)
P17643 (TYRP1; 61, −13, −0.21)
Q2YD98 (UVSSA; 81, −13, −0.16)
Q14202 (ZMYM3; 152, −13, −0.08)
P14679 (P14679; 60, −13, −0.21)
P14136 (P14136; 50, −13, −0.26)
Q3MJ13 (Q3MJ13; 123, −13, −0.10)
P02452 (P02452; 139, −13, −0.09)
P02748 (P02748; 63, −13, −0.20)
Q9NPB3 (Q9NPB3; 24, −13, −0.53)
P00734 (P00734; 70, −13, −0.18)
P16885 (P16885; 148, −13, −0.08)
Q9UBK8 (Q9UBK8; 80, −13, −0.16)
Q9UDR5 (Q9UDR5; 102, −13, −0.12)
Q3SXY7 (Q3SXY7; 75, −13, −0.17)
Q8TD10 (Q8TD10; 52, −13, −0.25)
Q9NTX7 (Q9NTX7; 39, −13, −0.33)
Q9Y6H5 (Q9Y6H5; 100, −13, −0.12)
O00470 (O00470; 43, −13, −0.30)
P17050 (P17050; 47, −13, −0.27)
P16871 (P16871; 52, −13, −0.25)
O95477 (ABCA1; 254, −12, −0.04)
P63261 (ACTG1; 42, −12, −0.28)

TABLE 4-continued

Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

Q86TH1 (ADAMTSL2; 105, −12, −0.11)
P15313 (ATP6V1B1; 57, −12, −0.21)
Q13489 (BIRC3; 68, −12, −0.17)
P08603 (CFH; 139, −12, −0.08)
Q6P4Q7 (CNNM4; 87, −12, −0.13)
O75718 (CRTAP; 47, −12, −0.25)
P00167 (CYB5A; 15, −12, −0.78)
P00533 (EGFR; 134, −12, −0.08)
P00488 (F13A1; 83, −12, −0.14)
Q00597 (FANCC; 63, −12, −0.18)
O15409 (FOXP2; 80, −12, −0.15)
Q9Y625 (GPC6; 63, −12, −0.19)
P81274 (GPSM2; 77, −12, −0.15)
Q9UMX6 (GUCA1B; 23, −12, −0.51)
Q9UKV0 (HDAC9; 111, −12, −0.10)
Q9Y6K9 (IKBKG; 48, −12, −0.24)
Q13422 (IKZF1; 58, −12, −0.20)
Q9Y287 (ITM2B; 30, −12, −0.39)
Q15046 (KARS; 68, −12, −0.17)
P63252 (KCNJ2; 48, −12, −0.24)
Q9Y5K2 (KLK4; 27, −12, −0.44)
Q8NG48 (LINS; 86, −12, −0.13)
Q9H3L0 (MMADHC; 33, −12, −0.36)
P14780 (MMP9; 78, −12, −0.15)
P21757 (MSR1; 50, −12, −0.24)
P00403 (MT-C02; 26, −12, −0.46)
Q96P20 (NLRP3; 118, −12, −0.10)
Q8IXF0 (NPAS3; 101, −12, −0.11)
P04629 (NTRK1; 87, −12, −0.13)
Q8NBP7 (PCSK9; 74, −12, −0.16)
O95263 (PDE8B; 99, −12, −0.12)
P27986 (PIK3R1; 84, −12, −0.14)
P29590 (PML; 98, −12, −0.12)
Q13976 (PRKG1; 76, −12, −0.15)
Q13635 (PTCH1; 161, −12, −0.07)
Q05397 (PTK2; 119, −12, −0.10)
P07988 (SFTPB; 42, −12, −0.28)
Q8IVB4 (SLC9A9; 73, −12, −0.16)
O75044 (SRGAP2; 121, −12, −0.09)
Q16623 (STX1A; 33, −12, −0.36)
P14373 (TRIM27; 58, −12, −0.20)
Q7Z4N2 (TRPM1; 182, −12, −0.06)
Q01534 (TSPY1; 35, −12, −0.34)
Q8NEZ2 (VPS37A; 44, −12, −0.27)
Q9ULV5 (Q9ULV5; 53, −12, −0.22)
P09172 (P09172; 69, −12, −0.17)
P60709 (P60709; 42, −12, −0.28)
Q07699 (Q07699; 25, −12, −0.48)
P56192 (P56192; 101, −12, −0.11)
Q9BQE9 (Q9BQE9; 22, −12, −0.54)
Q9HCR9 (Q9HCR9; 105, −12, −0.11)
P11498 (P11498; 130, −12, −0.09)
Q5T4F4 (Q5T4F4; 46, −12, −0.26)
O43572 (O43572; 74, −12, −0.16)
P04070 (P04070; 52, −12, −0.23)
B7U540 (B7U540; 49, −12, −0.24)
P31749 (AKT1; 56, −11, −0.19)
P02768 (ALB; 69, −11, −0.15)
Q6UB99 (ANKRD11; 298, −11, −0.03)
P10275 (AR; 99, −11, −0.11)
Q15052 (ARHGEF6; 87, −11, −0.12)
P22681 (CBL; 100, −11, −0.11)
Q9HC77 (CENPJ; 153, −11, −0.07)
O96017 (CHEK2; 61, −11, −0.18)
Q9UDT6 (CLIP2; 116, −11, −0.09)
P21918 (DRD5; 53, −11, −0.20)
P49770 (EIF2B2; 39, −11, −0.28)
P07332 (FES; 93, −11, −0.11)
Q9H334 (FOXP1; 75, −11, −0.14)
P02794 (FTH1; 21, −11, −0.51)
O95467 (GNAS; 28, −11, −0.39)
P11488 (GNAT1; 40, −11, −0.27)
Q13224 (GRIN2B; 166, −11, −0.06)
P46976 (GYG1; 39, −11, −0.27)
P56524 (HDAC4; 119, −11, −0.09)
Q9NZN1 (IL1RAPL1; 80, −11, −0.13)
P05783 (KRT18; 48, −11, −0.22)
Q8N653 (LZTR1; 95, −11, −0.11)
Q93074 (MED12; 243, −11, −0.04)
Q96G30 (MRAP2; 24, −11, −0.46)
Q86TC9 (MYPN; 145, −11, −0.07)
Q13772 (NCOA4; 70, −11, −0.15)
Q92542 (NCSTN; 78, −11, −0.14)
P12036 (NEFH; 112, −11, −0.09)
Q86U86 (PBRM1; 193, −11, −0.05)
P35558 (PCK1; 69, −11, −0.15)
Q13608 (PEX6; 104, −11, −0.10)
O00628 (PEX7; 36, −11, −0.30)
O43586 (PSTPIP1; 48, −11, −0.23)
Q7RTS3 (PTF1A; 35, −11, −0.31)
Q04206 (RELA; 60, −11, −0.18)
P07949 (RET; 124, −11, −0.08)
P35237 (SERPINB6; 43, −11, −0.25)
Q99961 (SH3GL1; 41, −11, −0.26)
A0AV02 (SLC12A8; 78, −11, −0.14)
P36021 (SLC16A2; 60, −11, −0.18)
Q9BRI3 (SLC30A2; 35, −11, −0.31)
Q9NQ40 (SLC52A3; 51, −11, −0.21)
Q9GZV3 (SLC5A7; 63, −11, −0.17)
Q9P0W8 (SPATA7; 68, −11, −0.16)
Q9Y5Y6 (ST14; 95, −11, −0.11)
Q9UL17 (TBX21; 58, −11, −0.18)
P09327 (VIL1; 93, −11, −0.11)
O95876 (WDPCP; 85, −11, −0.12)
O75800 (ZMYND10; 50, −11, −0.21)
Q03154 (Q03154; 46, −11, −0.23)
Q96C11 (Q96C11; 60, −11, −0.18)
P31327 (P31327; 165, −11, −0.06)
Q9UFE4 (Q9UFE4; 110, −11, −0.10)
P11597 (P11597; 55, −11, −0.20)
P57796 (P57796; 30, −11, −0.36)
Q9H6U6 (Q9H6U6; 101, −11, −0.10)
Q4AC94 (Q4AC94; 260, −11, −0.04)
P51168 (P51168; 73, −11, −0.15)
Q96J02 (Q96J02; 103, −11, −0.10)
Q9H3S4 (Q9H3S4; 27, −11, −0.40)
Q96EN8 (Q96EN8; 98, −11, −0.11)
P00813 (ADA; 41, −10, −0.24)
Q9Y243 (AKT3; 56, −10, −0.17)
Q9UNA1 (ARHGAP26; 92, −10, −0.10)
Q8WXF7 (ATL1; 64, −10, −0.15)
Q4VNC1 (ATP13A4; 134, −10, −0.07)
Q9NPF0 (CD320; 29, −10, −0.34)
P11912 (CD79A; 25, −10, −0.39)
P02708 (CHRNA1; 55, −10, −0.18)
O15111 (CHUK; 85, −10, −0.11)
Q9H8M5 (CNNM2; 97, −10, −0.10)
P43146 (DCC; 158, −10, −0.06)
Q96HY7 (DHTKD1; 103, −10, −0.09)
Q9H3Z4 (DNAJC5; 22, −10, −0.45)
Q9NVI1 (FANCI; 149, −10, −0.06)
Q9Y223 (GNE; 79, −10, −0.12)
P03989 (HLA-B; 40, −10, −0.24)
O43364 (HOXA2; 41, −10, −0.24)
Q2M1P5 (KIF7; 151, −10, −0.06)
P01042 (KNG1; 72, −10, −0.13)
Q14693 (LPIN1; 99, −10, −0.10)
Q96KG7 (MEGF10; 122, −10, −0.08)
P08254 (MMP3; 54, −10, −0.18)
P40238 (MPL; 71, −10, −0.14)
Q8NCE2 (MTMR14; 72, −10, −0.13)
P41227 (NAA10; 26, −10, −0.37)
Q9NXR1 (NDE1; 39, −10, −0.25)
Q01968 (OCRL; 104, −10, −0.09)
Q16633 (POU2AF1; 27, −10, −0.36)
Q8WYP3 (RIN2; 100, −10, −0.09)

TABLE 4-continued

| Exemplary naturally occurring negatively supercharged proteins that are involved in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided. |
|---|
| **Q8WU17** (RNF139; 76, −10, −0.13) |
| **Q86WG5** (SBF2; 208, −10, −0.04) |
| **Q8IWL2** (SFTPA1; 26, −10, −0.38) |
| **Q96PX8** (SLITRK1; 78, −10, −0.12) |
| **O95630** (STAMBP; 48, −10, −0.20) |
| **P07101** (TH; 59, −10, −0.17) |
| **O60602** (TLR5; 98, −10, −0.10) |
| **O14773** (TPP1; 61, −10, −0.16) |
| **P23258** (TUBG1; 51, −10, −0.19) |
| **Q9NRM1** (Q9NRM1; 129, −10, −0.07) |
| **P06396** (P06396; 86, −10, −0.11) |
| **Q9BUN5** (Q9BUN5; 22, −10, −0.45) |
| **Q9NQ48** (Q9NQ48; 35, −10, −0.28) |
| **Q99502** (Q99502; 65, −10, −0.15) |
| **Q9H257** (Q9H257; 62, −10, −0.16) |
| **Q14896** (Q14896; 141, −10, −0.07) |
| **P05997** (P05997; 145, −10, −0.06) |
| **P57679** (P57679; 112, −10, −0.08) |
| **Q96MP8** (Q96MP8; 33, −10, −0.30) |
| **P09471** (P09471; 40, −10, −0.24) |
| **P06280** (P06280; 49, −10, −0.20) |
| **P05160** (P05160; 76, −10, −0.13) |
| **Q96LT7** (Q96LT7; 54, −10, −0.18) |
| **Q9UHC1** (Q9UHC1; 164, −10, −0.06) |
| **Q13568** (Q13568; 56, −10, −0.17) |
| **P04180** (P04180; 50, −10, −0.20) |
| **O00459** (O00459; 82, −10, −0.12) |
| **P51178** (P51178; 86, −10, −0.11) |
| **C9JR72** (C9JR72; 49, −10, −0.20) |
| **P07359** (P07359; 72, −10, −0.13) |
| **O75695** (O75695; 40, −10, −0.25) |

TABLE 5

| Exemplary naturally occurring negatively supercharged proteins, a deficiency or recessive allele of which is implicated in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided. |
|---|
| **Q03001** (DST; 861, −316, −0.36) |
| **Q8NF91** (SYNE1; 1, 011, −315, −0.31) |
| **P98164** (P98164; 522, −243, −0.46) |
| **Q6V0I7** (FAT4; 543, −230, −0.42) |
| **Q9H251** (CDH23; 369, −223, −0.60) |
| **P21817** (RYR1; 565, −207, −0.36) |
| **Q7Z6Z7** (HUWE1; 482, −173, −0.35) |
| **Q96JQ0** (DCHS1; 346, −162, −0.46) |
| **P02549** (SPTA1; 280, −153, −0.54) |
| **P22105** (TNXB; 464, −144, −0.31) |
| **Q8N4C6** (NIN; 243, −138, −0.56) |
| **O60494** (CUBN; 399, −133, −0.33) |
| **Q4G0P3** (HYDIN; 576, −113, −0.19) |
| **Q13316** (Q13316; 56, −101, −1.81) |
| **Q3ZCN5** (OTOGL; 262, −98, −0.37) |
| **P07942** (P07942; 198, −98, −0.49) |
| **Q8TCU4** (ALMS1; 461, −96, −0.20) |
| **O75970** (MPDZ; 222, −94, −0.42) |
| **P04275** (VWF; 309, −89, −0.28) |
| **P11532** (P11532; 427, −89, −0.20) |
| **Q8NG31** (CASC5; 265, −84, −0.31) |
| **Q15149** (PLEC; 532, −83, −0.15) |
| **O95714** (O95714; 527, −83, −0.15) |
| **P98160** (P98160; 469, −83, −0.17) |
| **P50851** (LRBA; 319, −82, −0.25) |
| **Q14767** (LTBP2; 195, −77, −0.39) |
| **Q5T011** (SZT2; 378, −77, −0.20) |
| **Q6ZRI0** (OTOG; 315, −74, −0.23) |

TABLE 5-continued

| Exemplary naturally occurring negatively supercharged proteins, a deficiency or recessive allele of which is implicated in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided. |
|---|
| **Q93008** (USP9X; 292, −72, −0.24) |
| **Q96QU1** (PCDH15; 216, −71, −0.32) |
| **Q96JI7** (SPG11; 279, −71, −0.25) |
| **Q8TE73** (DNAH5; 529, −67, −0.12) |
| **Q9UPV0** (CEP164; 164, −66, −0.40) |
| **P82279** (P82279; 154, −65, −0.42) |
| **O75147** (OBSL1; 207, −64, −0.30) |
| **Q12955** (Q12955; 480, −64, −0.13) |
| **Q96DT5** (Q96DT5; 521, −63, −0.12) |
| **A2RRP1** (NBAS; 269, −62, −0.23) |
| **Q96SN8** (CDK5RAP2; 215, −61, −0.28) |
| **P16157** (ANK1; 206, −60, −0.29) |
| **Q9NWF9** (RNF216; 99, −60, −0.60) |
| **P22223** (CDH3; 91, −59, −0.64) |
| **O94986** (CEP152; 196, −58, −0.29) |
| **O75197** (LRP5; 179, −58, −0.32) |
| **Q7Z7G8** (VPS13B; 449, −58, −0.12) |
| **Q8IVV2** (Q8IVV2; 222, −57, −0.25) |
| **P12259** (P12259; 252, −57, −0.22) |
| **Q99698** (LYST; 429, −56, −0.13) |
| **O75443** (O75443; 240, −56, −0.23) |
| **P08F94** (PKHD1; 447, −54, −0.12) |
| **O15020** (SPTBN2; 271, −53, −0.19) |
| **Q6PRD1** (GPR179; 257, −52, −0.20) |
| **O60721** (SLC24A1; 121, −52, −0.42) |
| **Q14999** (CUL7; 191, −50, −0.26) |
| **O75923** (DYSF; 237, −50, −0.21) |
| **P28715** (ERCC5; 133, −49, −0.36) |
| **O43379** (WDR62; 166, −49, −0.29) |
| **Q68DK2** (ZFYVE26; 285, −49, −0.17) |
| **Q6ZNJ1** (NBEAL2; 303, −48, −0.15) |
| **P14410** (P14410; 209, −48, −0.22) |
| **O15078** (CEP290; 290, −47, −0.16) |
| **Q9P2D1** (CHD7; 336, −47, −0.13) |
| **Q9HCE0** (EPG5; 292, −47, −0.16) |
| **Q9HC10** (OTOF; 227, −47, −0.20) |
| **O94972** (TRIM37; 108, −47, −0.43) |
| **Q7RTU9** (Q7RTU9; 193, −47, −0.24) |
| **Q8NCM8** (DYNC2H1; 493, −46, −0.09) |
| **Q96RL7** (VPS13A; 360, −45, −0.12) |
| **Q9BUR4** (WRAP53; 59, −45, −0.75) |
| **Q96F46** (IL17RA; 96, −44, −0.45) |
| **P98073** (TMPRSS15; 113, −43, −0.38) |
| **Q9P219** (CCDC88C; 228, −42, −0.18) |
| **Q9H2M9** (RAB3GAP2; 156, −42, −0.26) |
| **P00450** (P00450; 122, −42, −0.34) |
| **P24386** (CHM; 73, −41, −0.55) |
| **Q9Y5B0** (CTDP1; 104, −41, −0.39) |
| **Q96RT7** (TUBGCP6; 200, −41, −0.20) |
| **Q96RY7** (IFT140; 165, −40, −0.24) |
| **Q13085** (ACACA; 266, −39, −0.14) |
| **Q9UMZ3** (Q9UMZ3; 261, −39, −0.14) |
| **Q9UPZ3** (HPS5; 127, −38, −0.29) |
| **Q9UG01** (IFT172; 198, −38, −0.19) |
| **O15040** (TECPR2; 154, −38, −0.24) |
| **P16144** (P16144; 202, −38, −0.18) |
| **P09848** (LCT; 219, −37, −0.16) |
| **Q07864** (POLE; 262, −37, −0.14) |
| **Q8NEL9** (DDHD1; 100, −36, −0.35) |
| **Q9NZJ5** (EIF2AK3; 125, −36, −0.28) |
| **Q9H6L5** (Q9H6L5; 55, −36, −0.65) |
| **P78363** (ABCA4; 256, −35, −0.13) |
| **Q92539** (LPIN2; 99, −35, −0.35) |
| **Q96PY6** (NEK1; 143, −35, −0.24) |
| **Q99707** (Q99707; 141, −35, −0.24) |
| **Q8WZ55** (BSND; 35, −34, −0.96) |
| **Q9P2K8** (EIF2AK4; 187, −34, −0.18) |
| **P33076** (CIITA; 124, −33, −0.26) |
| **O94898** (LRIG2; 119, −33, −0.27) |
| **Q96EV8** (DTNBP1; 39, −32, −0.81) |
| **Q9H4Z2** (Q9H4Z2; 145, −32, −0.22) |
| **Q9HBE5** (IL21R; 59, −31, −0.52) |

TABLE 5-continued

Exemplary naturally occurring negatively supercharged proteins, a deficiency or recessive allele of which is implicated in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

P08575 (PTPRC; 147, −31, −0.21)
P09871 (P09871; 77, −31, −0.40)
Q13683 (ITGA7; 129, −30, −0.23)
Q9H4A3 (WNK1; 251, −30, −0.11)
Q9BY79 (Q9BY79; 62, −30, −0.48)
Q9Y6D5 (ARFGEF2; 202, −29, −0.14)
P11171 (EPB41; 97, −29, −0.29)
Q12756 (KIF1A; 191, −29, −0.15)
P25963 (NFKBIA; 36, −29, −0.81)
Q9NQG7 (HPS4; 77, −28, −0.36)
O15259 (NPHP1; 83, −28, −0.33)
P47712 (PLA2G4A; 85, −28, −0.32)
P15260 (P15260; 54, −28, −0.51)
P06753 (P06753; 33, −28, −0.84)
Q66GS9 (CEP135; 133, −27, −0.20)
Q6P5W5 (SLC39A4; 68, −27, −0.39)
Q7RTW8 (Q7RTW8; 129, −27, −0.21)
P06213 (P06213; 156, −27, −0.17)
P12821 (ACE; 150, −26, −0.17)
P83436 (COG7; 86, −26, −0.30)
Q9UDY8 (MALT1; 92, −26, −0.28)
O00462 (MANBA; 101, −26, −0.25)
Q7Z7M0 (MEGF8; 303, −26, −0.08)
Q15477 (SKIV2L; 138, −26, −0.18)
Q9H9E3 (Q9H9E3; 89, −26, −0.29)
Q3SYG4 (BBS9; 99, −25, −0.25)
O94830 (DDHD2; 81, −25, −0.30)
O95967 (EFEMP2; 49, −25, −0.50)
Q04656 (ATP7A; 163, −24, −0.14)
Q9BXL7 (CARD11; 133, −24, −0.18)
Q9NQX3 (GPHN; 80, −24, −0.30)
P32004 (L1CAM; 140, −24, −0.17)
O60331 (PIP5K1C; 73, −24, −0.32)
Q8TF17 (SH3TC2; 145, −24, −0.16)
Q15468 (STIL; 143, −24, −0.16)
P50747 (P50747; 81, −24, −0.29)
P15391 (P15391; 61, −24, −0.39)
P42702 (P42702; 124, −24, −0.19)
P16435 (POR; 77, −23, −0.29)
O14593 (RFXANK; 28, −23, −0.81)
Q8NEZ3 (WDR19; 152, −23, −0.15)
Q2M1K9 (ZNF423; 145, −23, −0.15)
Q13315 (Q13315; 351, −23, −0.06)
P42898 (P42898; 75, −23, −0.30)
P21860 (ERBB3; 148, −22, −0.14)
Q9UBX5 (FBLN5; 50, −22, −0.43)
Q13043 (STK4; 56, −22, −0.39)
Q14191 (WRN; 162, −22, −0.13)
O00187 (O00187; 76, −22, −0.29)
Q02388 (Q02388; 295, −22, −0.07)
O43933 (O43933; 143, −22, −0.15)
Q96MT8 (Q96MT8; 81, −22, −0.27)
P35523 (CLCN1; 109, −21, −0.19)
Q8IYB7 (DIS3L2; 99, −21, −0.21)
Q96AY3 (FKBP10; 64, −21, −0.32)
O00165 (HAX1; 32, −21, −0.66)
P42704 (LRPPRC; 158, −21, −0.13)
P40692 (MLH1; 85, −21, −0.24)
P07602 (PSAP; 58, −21, −0.36)
Q14790 (CASP8; 55, −20, −0.36)
Q00653 (NFKB2; 97, −20, −0.20)
O14841 (O14841; 137, −20, −0.14)
Q92622 (Q92622; 109, −20, −0.18)
Q03252 (LMNB2; 68, −19, −0.28)
Q96MT3 (PRICKLE1; 94, −19, −0.20)
Q9Y6Q6 (TNFRSF11A; 66, −19, −0.28)
Q8WW38 (ZFPM2; 128, −19, −0.14)
Q12860 (Q12860; 113, −19, −0.16)
Q96MW5 (Q96MW5; 68, −19, −0.27)
Q96QS3 (Q96QS3; 58, −19, −0.32)
O60568 (O60568; 85, −19, −0.22)
P01024 (C3; 187, −18, −0.09)

TABLE 5-continued

Exemplary naturally occurring negatively supercharged proteins, a deficiency or recessive allele of which is implicated in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

Q96SD1 (DCLRE1C; 78, −18, −0.22)
Q9HCG7 (GBA2; 105, −18, −0.17)
P42701 (IL12RB1; 73, −18, −0.24)
Q9BV36 (MLPH; 66, −18, −0.27)
P49959 (MRE11A; 81, −18, −0.22)
Q9Y4G2 (PLEKHM1; 117, −18, −0.15)
Q9BXC9 (Q9BXC9; 80, −18, −0.22)
P06865 (P06865; 61, −18, −0.29)
P40337 (P40337; 24, −18, −0.74)
P01031 (C5; 188, −17, −0.09)
O75838 (CIB2; 22, −17, −0.78)
Q9Y2V7 (COG6; 73, −17, −0.23)
Q9UNE0 (EDAR; 49, −17, −0.34)
Q8NI22 (MCFD2; 16, −17, −1.03)
P29120 (PCSK1; 84, −17, −0.20)
O94827 (PLEKHG5; 117, −17, −0.14)
Q99708 (RBBP8; 102, −17, −0.16)
Q14108 (SCARB2; 54, −17, −0.31)
Q16586 (SGCA; 43, −17, −0.39)
Q07837 (SLC3A1; 79, −17, −0.21)
P22735 (TGM1; 90, −17, −0.18)
Q9Y6N9 (USH1C; 62, −17, −0.27)
P02671 (P02671; 95, −17, −0.17)
Q7RTS9 (Q7RTS9; 76, −17, −0.22)
Q9Y664 (Q9Y664; 48, −17, −0.35)
Q5JTZ9 (AARS2; 107, −16, −0.14)
O00203 (AP3B1; 121, −16, −0.13)
Q9HBG4 (ATP6V0A4; 96, −16, −0.16)
Q8IWZ6 (BBS7; 80, −16, −0.19)
P20807 (CAPN3; 94, −16, −0.16)
Q16828 (DUSP6; 42, −16, −0.37)
Q96M96 (FGD4; 87, −16, −0.18)
P11362 (FGFR1; 92, −16, −0.17)
Q92902 (HPS1; 79, −16, −0.20)
Q9UH77 (KLHL3; 65, −16, −0.24)
P08253 (MMP2; 74, −16, −0.21)
P12955 (PEPD; 55, −16, −0.29)
P43251 (P43251; 61, −16, −0.26)
Q9H5Y7 (Q9H5Y7; 95, −16, −0.16)
P51692 (P51692; 90, −16, −0.17)
Q969F9 (Q969F9; 114, −16, −0.14)
Q8NF50 (Q8NF50; 239, −16, −0.06)
P13942 (P13942; 172, −16, −0.09)
P52788 (P52788; 41, −16, −0.38)
Q6ZW61 (BBS12; 79, −15, −0.18)
Q13936 (CACNA1C; 249, −15, −0.06)
Q9H2C0 (GAN; 68, −15, −0.22)
P31150 (GDI1; 51, −15, −0.29)
O14920 (IKBKB; 87, −15, −0.17)
P48357 (LEPR; 132, −15, −0.11)
Q00872 (MYBPC1; 128, −15, −0.11)
O75914 (PAK3; 62, −15, −0.24)
P01009 (SERPINA1; 47, −15, −0.32)
Q9H173 (SIL1; 52, −15, −0.28)
Q695T7 (SLC6A19; 71, −15, −0.21)
Q13586 (STIM1; 77, −15, −0.19)
Q96Q05 (TRAPPC9; 129, −15, −0.11)
Q9HOU9 (TSPYL1; 49, −15, −0.30)
Q9ULT0 (TTC7A; 96, −15, −0.15)
Q9P2L0 (WDR35; 134, −15, −0.11)
P12110 (P12110; 109, −15, −0.13)
P55895 (P55895; 59, −15, −0.25)
Q9NWZ3 (Q9NWZ3; 52, −15, −0.29)
P35670 (ATP7B; 157, −14, −0.08)
P48643 (CCT5; 60, −14, −0.23)
P02679 (FGG; 52, −14, −0.27)
Q8NFG4 (FLCN; 64, −14, −0.21)
O15353 (FOXN1; 69, −14, −0.20)
P48506 (GCLC; 73, −14, −0.19)
P14923 (JUP; 82, −14, −0.17)
Q92597 (NDRG1; 43, −14, −0.32)
P49902 (NT5C2; 65, −14, −0.21)

TABLE 5-continued

Exemplary naturally occurring negatively supercharged proteins, a deficiency or recessive allele of which is implicated in diseases, disorders, or conditions. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

Q4J6C6 (PREPL; 84, −14, −0.16)
P07225 (PROS1; 75, −14, −0.18)
P12271 (RLBP1; 36, −14, −0.38)
Q96G97 (Q96G97; 44, −14, −0.31)
P02533 (P02533; 52, −14, −0.27)
P00740 (P00740; 52, −14, −0.27)
P51687 (P51687; 60, −14, −0.23)
P15924 (P15924; 332, −14, −0.04)
P15289 (P15289; 54, −14, −0.26)
Q8NCR0 (Q8NCR0; 57, −14, −0.24)
P42224 (P42224; 87, −14, −0.16)
Q9NP73 (ALG13; 126, −13, −0.10)
P11230 (CHRNB1; 57, −13, −0.22)
Q04844 (CHRNE; 55, −13, −0.23)
Q96SW2 (CRBN; 51, −13, −0.25)
Q7Z494 (NPHP3; 151, −13, −0.08)
Q9H5K3 (POMK; 40, −13, −0.32)
Q01974 (ROR2; 105, −13, −0.12)
O95248 (SBF1; 208, −13, −0.06)
Q8NOX7 (SPG20; 73, −13, −0.17)
Q8N205 (SYNE4; 44, −13, −0.29)
O43280 (TREH; 67, −13, −0.19)
P17643 (TYRP1; 61, −13, −0.21)
Q2YD98 (UVSSA; 81, −13, −0.16)
P14679 (P14679; 60, −13, −0.21)
P02748 (P02748; 63, −13, −0.20)
Q9NPB3 (Q9NPB3; 24, −13, −0.53)
P00734 (P00734; 70, −13, −0.18)
P16885 (P16885; 148, −13, −0.08)
Q9UBK8 (Q9UBK8; 80, −13, −0.16)
Q9UDR5 (Q9UDR5; 102, −13, −0.12)
Q3SXY7 (Q3SXY7; 75, −13, −0.17)
P17050 (P17050; 47, −13, −0.27)
P16871 (P16871; 52, −13, −0.25)
O95477 (ABCA1; 254, −12, −0.04)
Q86TH1 (ADAMTSL2; 105, −12, −0.11)
P15313 (ATP6V1B1; 57, −12, −0.21)
P08603 (CFH; 139, −12, −0.08)
O75718 (CRTAP; 47, −12, −0.25)
P00488 (F13A1; 83, −12, −0.14)
Q9Y625 (GPC6; 63, −12, −0.19)
P81274 (GPSM2; 77, −12, −0.15)
Q9Y6K9 (IKBKG; 48, −12, −0.24)
Q15046 (KARS; 68, −12, −0.17)
Q8NG48 (LINS; 86, −12, −0.13)
P00403 (MT-CO2; 26, −12, −0.46)
P04629 (NTRK1; 87, −12, −0.13)
P27986 (PIK3R1; 84, −12, −0.14)
Q8NEZ2 (VPS37A; 44, −12, −0.27)
P09172 (P09172; 69, −12, −0.17)
P11498 (P11498; 130, −12, −0.09)
P04070 (P04070; 52, −12, −0.23)
P10275 (AR; 99, −11, −0.11)
Q15052 (ARHGEF6; 87, −11, −0.12)
Q9HC77 (CENPJ; 153, −11, −0.07)
Q9NZN1 (IL1RAPL1; 80, −11, −0.13)
P35558 (PCK1; 69, −11, −0.15)
P07949 (RET; 124, −11, −0.08)
P35237 (SERPINB6; 43, −11, −0.25)
P36021 (SLC16A2; 60, −11, −0.18)
Q9BRI3 (SLC30A2; 35, −11, −0.31)
Q9P0W8 (SPATA7; 68, −11, −0.16)
Q9Y5Y6 (ST14; 95, −11, −0.11)
O95876 (WDPCP; 85, −11, −0.12)
Q03154 (Q03154; 46, −11, −0.23)
P31327 (P31327; 165, −11, −0.06)
P51168 (P51168; 73, −11, −0.15)
Q9H3S4 (Q9H3S4; 27, −11, −0.40)
Q96EN8 (Q96EN8; 98, −11, −0.11)
P00813 (ADA; 41, −10, −0.24)
P11912 (CD79A; 25, −10, −0.39)
Q9Y223 (GNE; 79, −10, −0.12)
Q2M1P5 (KIF7; 151, −10, −0.06)
P01042 (KNG1; 72, −10, −0.13)
Q14693 (LPIN1; 99, −10, −0.10)
Q96KG7 (MEGF10; 122, −10, −0.08)
P41227 (NAA10; 26, −10, −0.37)
Q86WG5 (SBF2; 208, −10, −0.04)
P07101 (TH; 59, −10, −0.17)
O14773 (TPP1; 61, −10, −0.16)
Q9NRM1 (Q9NRM1; 129, −10, −0.07)
Q9BUN5 (Q9BUN5; 22, −10, −0.45)
Q9NQ48 (Q9NQ48; 35, −10, −0.28)
Q9H257 (Q9H257; 62, −10, −0.16)
P57679 (P57679; 112, −10, −0.08)
Q96MP8 (Q96MP8; 33, −10, −0.30)
P05160 (P05160; 76, −10, −0.13)
P04180 (P04180; 50, −10, −0.20)

TABLE 6

Exemplary naturally occurring negatively supercharged tumor suppressor proteins that are suitable for delivery to malignant cells. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided.

O95359 (TACC2; 309, −183, −0.59)
Q12888 (TP53BP1; 214, −148, −0.69)
Q9UGM3 (DMBT1; 261, −89, −0.34)
P38398 (BRCA1; 208, −70, −0.33)
P39687 (ANP32A; 29, −62, −2.16)
O95071 (UBR5; 309, −60, −0.19)
Q9Y2J2 (EPB41L3; 121, −51, −0.42)
Q14678 (KANK1; 147, −48, −0.32)
Q6ZVD8 (PHLPP2; 147, −41, −0.27)
Q8TDI0 (CHD5; 223, −38, −0.17)
A1YPR0 (ZBTB7C; 69, −35, −0.50)
O94763 (URI1; 60, −34, −0.56)
P23142 (FBLN1; 77, −31, −0.40)
Q9Y238 (DLEC1; 196, −30, −0.15)
Q9Y561 (LRP12; 95, −30, −0.31)
Q9HBX8 (LGR6; 104, −29, −0.27)
O60346 (PHLPP1; 185, −29, −0.15)
P23508 (MCC; 93, −28, −0.30)
O00499 (BIN1; 65, −26, −0.40)
Q92574 (TSC1; 130, −26, −0.20)
Q66K89 (E4F1; 83, −24, −0.28)
Q13315 (ATM; 351, −23, −0.06)
Q5VW36 (FOCAD; 200, −22, −0.10)
Q96A56 (TP53INP1; 27, −22, −0.80)
O43889 (CREB3; 44, −21, −0.47)
O94885 (SASH1; 137, −21, −0.15)
Q10571 (MN1; 136, −20, −0.14)
Q9NRY4 (ARHGAP35; 171, −18, −0.10)
Q53EL6 (PDCD4; 52, −18, −0.34)
P40337 (VHL; 24, −18, −0.74)
Q9BY67 (CADM1; 49, −17, −0.35)
Q5JR59 (MTUS2; 150, −17, −0.11)
Q8N5A5 (ZGPAT; 57, −17, −0.29)
Q9NZM4 (GLTSCR1; 158, −17, −0.10)
Q9C0K0 (BCL11B; 96, −16, −0.16)
Q13625 (TP53BP2; 126, −16, −0.12)
O60443 (DFNA5; 55, −15, −0.27)
O15287 (FANCG; 69, −15, −0.21)
Q8NFG4 (FLCN; 64, −14, −0.21)
Q92597 (NDRG1; 43, −14, −0.32)
Q9UN36 (NDRG2; 41, −14, −0.34)
P50502 (ST13; 41, −14, −0.33)
Q96EP1 (CHFR; 73, −13, −0.17)

TABLE 6-continued

| Exemplary naturally occurring negatively supercharged tumor suppressor proteins that are suitable for delivery to malignant cells. Proteins listed have a negative net charge of −10 or less. For each protein, a unique Uniprot identifier is provided in bold. In parentheses, an exemplary name of the gene encoding the respective protein as well as its molecular weight, charge, and molecular weight:charge ratio are provided. |
|---|
| **P41271** (NBL1; 19, −13, −0.66) |
| **Q8IXJ6** (SIRT2; 43, −13, −0.30) |
| **P98082** (DAB2; 82, −12, −0.14) |
| **Q96CJ1** (EAF2; 29, −12, −0.41) |
| **O43909** (EXTL3; 105, −12, −0.11) |
| **A2A2Y4** (FRMD3; 69, −12, −0.17) |
| **Q9HB75** (PIDD1; 100, −12, −0.12) |
| **Q13635** (PTCH1; 161, −12, −0.07) |

REFERENCES

1. Putney, S. D. & Burke, P. A. Improving protein therapeutics with sustained-release formulations. *Nat. Biotechnol.* 16, 153-157 (1998).
2. Mullen, L. et al. Latent cytokines for targeted therapy of inflammatory disorders. *Expert Opin. Drug Deliv.* 11, 101-110 (2014).
3. Song, E. et al. Antibody mediated in vivo delivery of small interfering RNAs via cell-surface receptors. *Nat. Biotechnol.* 23, 709-717 (2005).
4. Leader, B., Baca, Q. J. & Golan, D. E. Protein therapeutics: a summary and pharmacological classification. *Nat. Rev. Drug Discov.* 7, 21-39 (2008).
5. Hartung, S. D. et al. Correction of Metabolic, Craniofacial, and Neurologic Abnormalities in MPS I Mice Treated at Birth with Adeno-associated Virus Vector Transducing the Human α-L-Iduronidase Gene. *Mol. Ther.* 9, 866-875 (2004).
6. Wang, J. et al. Neutralizing antibodies to therapeutic enzymes: considerations for testing, prevention and treatment. *Nat. Biotechnol.* 26, 901-908 (2008).
7. Urnov, F. D., Rebar, E. J., Holmes, M. C., Zhang, H. S. & Gregory, P. D. Genome editing with engineered zinc finger nucleases. *Nat. Rev. Genet.* 11, 636-646 (2010).
8. Sander, J. D. & Joung, J. K. CRISPR-Cas systems for editing, regulating and targeting genomes. *Nat. Biotechnol.* 32, 347-355 (2014).
9. Gaj, T., Gersbach, C. A. & Barbas, C. F. ZFN, TALEN, and CRISPR/Cas-based methods for genome engineering. *Trends Biotechnol.* 31, 397-405 (2013).
10. Midoux, P., Pichon, C., Yaouanc, J.-J. & Jaffrès, P.-A. Chemical vectors for gene delivery: a current review on polymers, peptides and lipids containing histidine or imidazole as nucleic acids carriers. *Br. J. Pharmacol.* 157, 166-178 (2009).
11. Bodles-Brakhop, A. M., Heller, R. & Draghia-Akli, R. Electroporation for the Delivery of DNA-based Vaccines and Immunotherapeutics: Current Clinical Developments. *Mol. Ther.* 17, 585-592 (2009).
12. Kay, M. A., Glorioso, J. C. & Naldini, L. Viral vectors for gene therapy: the art of turning infectious agents into vehicles of therapeutics. *Nat. Med.* 7, 33-40 (2001).
13. Zangi, L. et al. Modified mRNA directs the fate of heart progenitor cells and induces vascular regeneration after myocardial infarction. *Nat. Biotechnol.* 31, 898-907 (2013).
14. Wadia, J. S., Stan, R. V. & Dowdy, S. F. Transducible TAT-HA fusogenic peptide enhances escape of TAT-fusion proteins after lipid raft macropinocytosis. *Nat. Med.* 10, 310-315 (2004).
15. Daniels, D. S. & Schepartz, A. Intrinsically cell-permeable miniature proteins based on a minimal cationic PPII motif. *J. Am. Chem. Soc.* 129, 14578-14579 (2007).
16. Cronican, J. J. et al. Potent delivery of functional proteins into Mammalian cells in vitro and in vivo using a supercharged protein. *ACS Chem. Biol.* 5, 747-752 (2010).
17. Thompson, D. B., Cronican, J. J. & Liu, D. R. Engineering and identifying supercharged proteins for macromolecule delivery into mammalian cells. *Methods Enzymol.* 503, 293-319 (2012).
18. Thompson, D. B., Villaseñor, R., Dorr, B. M., Zerial, M. & Liu, D. R. Cellular uptake mechanisms and endosomal trafficking of supercharged proteins. *Chem. Biol.* 19, 831-843 (2012).
19. Heitz, F., Morris, M. C. & Divita, G. Twenty years of cell-penetrating peptides: from molecular mechanisms to therapeutics. *Br. J. Pharmacol.* 157, 195-206 (2009).
20. Caron, N. J. et al. Intracellular delivery of a Tat-eGFP fusion protein into muscle cells. *Mol. Ther. J. Am. Soc. Gene Ther.* 3, 310-318 (2001).
21. Chesnoy, S. & Huang, L. Structure and function of lipid-DNA complexes for gene delivery. *Annu. Rev. Biophys. Biomol. Struct.* 29, 27-47 (2000).
22. Al-Taei, S. et al. Intracellular traffic and fate of protein transduction domains HIV-1 TAT peptide and octaarginine. Implications for their utilization as drug delivery vectors. *Bioconjug. Chem.* 17, 90-100 (2006).
23. Shete, H. K., Prabhu, R. H. & Patravale, V. B. Endosomal escape: a bottleneck in intracellular delivery. *J. Nanosci. Nanotechnol.* 14, 460-474 (2014).
24. Aguilera, T. A., Olson, E. S., Timmers, M. M., Jiang, T. & Tsien, R. Y. Systemic in vivo distribution of activatable cell penetrating peptides is superior to that of cell penetrating peptides. *Integr. Biol. Quant. Biosci. Nano Macro* 1, 371-381 (2009).
25. Coelho, T. et al. Safety and efficacy of RNAi therapy for transthyretin amyloidosis. *N. Engl. J. Med.* 369, 819-829 (2013).
26. Judge, A. D., Bola, G., Lee, A. C. H. & MacLachlan, I. Design of noninflammatory synthetic siRNA mediating potent gene silencing in vivo. *Mol. Ther. J. Am. Soc. Gene Ther.* 13, 494-505 (2006).
27. Basha, G. et al. Influence of cationic lipid composition on gene silencing properties of lipid nanoparticle formulations of siRNA in antigen-presenting cells. *Mol. Ther. J. Am. Soc. Gene Ther.* 19, 2186-2200 (2011).
28. Semple, S. C. et al. Rational design of cationic lipids for siRNA delivery. *Nat. Biotechnol.* 28, 172-176 (2010).
29. Boeckle, S., Fahrmeir, J., Roedl, W., Ogris, M. & Wagner, E. Melittin analogs with high lytic activity at endosomal pH enhance transfection with purified targeted PEI polyplexes. *J. Control. Release Off. J. Control. Release Soc.* 112, 240-248 (2006).
30. Allen, T. M. & Cullis, P. R. Liposomal drug delivery systems: from concept to clinical applications. *Adv. Drug Deliv. Rev.* 65, 36-48 (2013).
31. Zelphati, O. et al. Intracellular delivery of proteins with a new lipid-mediated delivery system. *J. Biol. Chem.* 276, 35103-35110 (2001).
32. Adrian, J. E. et al. Targeted SAINT-O-Somes for improved intracellular delivery of siRNA and cytotoxic drugs into endothelial cells. *J. Control. Release Off. J. Control. Release Soc.* 144, 341-349 (2010).

33. Morris, M. C., Depollier, J., Mery, J., Heitz, F. & Divita, G. A peptide carrier for the delivery of biologically active proteins into mammalian cells. *Nat. Biotechnol.* 19, 1173-1176 (2001).
34. Colletier, J.-P., Chaize, B., Winterhalter, M. & Fournier, D. Protein encapsulation in liposomes: efficiency depends on interactions between protein and phospholipid bilayer. *BMC Biotechnol.* 2, 9 (2002).
35. Lawrence, M. S., Phillips, K. J. & Liu, D. R. Supercharging proteins can impart unusual resilience. *J. Am. Chem. Soc.* 129, 10110-10112 (2007).
36. Liu, J., Gaj, T., Patterson, J. T., Sirk, S. J. & Barbas I I I, C. F. Cell-Penetrating Peptide-Mediated Delivery of TALEN Proteins via Bioconjugation for Genome Engineering. *PLoS ONE* 9, e85755 (2014).
37. Tessarollo, L., Vogel, K. S., Palko, M. E., Reid, S. W. & Parada, L. F. Targeted mutation in the neurotrophin-3 gene results in loss of muscle sensory neurons. *Proc. Natl. Acad. Sci. U.S.A.* 91, 11844-11848 (1994).
38. Maeder, M. L. et al. Robust, synergistic regulation of human gene expression using TALE activators. *Nat. Methods* 10, 243-245 (2013).
39. Jopling, C., Boue, S. & Belmonte, J. C. I. Dedifferentiation, transdifferentiation and reprogramming: three routes to regeneration. *Nat. Rev. Mol. Cell Biol.* 12, 79-89 (2011).
40. Fu, Y., Sander, J. D., Reyon, D., Cascio, V. M. & Joung, J. K. Improving CRISPR-Cas nuclease specificity using truncated guide RNAs. *Nat. Biotechnol.* 32, 279-284 (2014).
41. McNaughton, B. R., Cronican, J. J., Thompson, D. B. & Liu, D. R. Mammalian cell penetration, siRNA transfection, and DNA transfection by supercharged proteins. *Proc. Natl. Acad. Sci. U.S.A.* 106, 6111-6116 (2009).
42. Qi, L. S. et al. Repurposing CRISPR as an RNA-Guided Platform for Sequence-Specific Control of Gene Expression. *Cell* 152, 1173-1183 (2013).
43. Guschin, D. Y. et al. A rapid and general assay for monitoring endogenous gene modification. *Methods Mol. Biol. Clifton N.J.* 649, 247-256 (2010).
44. Ran, F. A. et al. Double nicking by RNA-guided CRISPR Cas9 for enhanced genome editing specificity. *Cell* 154, 1380-1389 (2013).
45. Maeder, M. L. et al. CRISPR RNA-guided activation of endogenous human genes. *Nat. Methods* 10, 977-979 (2013).
46. Guilinger, J. P., Thompson, D. B. & Liu, D. R. Fusion of catalytically inactive Cas9 to FokI nuclease improves the specificity of genome modification. *Nat. Biotechnol.* 32, 577-582 (2014).
47. Pattanayak, V. et al. High-throughput profiling of off-target DNA cleavage reveals RNA-programmed Cas9 nuclease specificity. *Nat. Biotechnol.* 31, 839-843 (2013).
48. Li, H. et al. Differentiation of neurons from neural precursors generated in floating spheres from embryonic stem cells. *BMC Neurosci.* 10, 122 (2009).
49. Lumpkin, E. A. et al. Mathl-driven GFP expression in the developing nervous system of transgenic mice. *Gene Expr. Patterns GEP* 3, 389-395 (2003).
50. Van Camp, G. & Smith, R. Hereditary Hearing Loss. at <http://hereditaryhearingloss.org>
51. Kim, S., Kim, D., Cho, S. W., Kim, J. & Kim, J.-S. Highly efficient RNA-guided genome editing in human cells via delivery of purified Cas9 ribonucleoproteins. *Genome Res.* 24, 1012-1019 (2014).
52. Yin, H. et al. Genome editing with Cas9 in adult mice corrects a disease mutation and phenotype. *Nat. Biotechnol.* 32, 551-553 (2014).
53. Wang, H. et al. One-step generation of mice carrying mutations in multiple genes by CRISPR/Cas-mediated genome engineering. *Cell* 153, 910-918 (2013).
54. Schneider, C. A., Rasband, W. S. & Eliceiri, K. W. NIH Image to ImageJ: 25 years of image analysis. *Nat. Methods* 9, 671-675 (2012).
55. Sage, C. et al. Proliferation of functional hair cells in vivo in the absence of the retinoblastoma protein. *Science* 307, 1114-1118 (2005).
56. Sander, J. D. et al. In silico abstraction of zinc finger nuclease cleavage profiles reveals an expanded landscape of off-target sites. *Nucleic Acids Res.* 41, e181 (2013).
57. Mali, P. et al. RNA-guided human genome engineering via Cas9. Science 339, 823-826 (2013)
58. Ramakrishna, S. et al. Gene disruption by cell-penetrating peptide-mediated delivery of Cas9 protein and guide RNA. Genome Res. 24, 1020-1027 (2014).
59. Gilleron, J. et al. Image-based analysis of lipid nanoparticle-mediated siRNA delivery, intracellular trafficking and endosomal escape. Nat. Biotechnol. 31, 638-646 (2013).
60. Lodish, H. et al. Molecular Cell Biology. (W. H. Freeman, 2000).
61. Sojung Kim, D. K. Highly efficient RNA-guided genome editing in human cells via delivery of purified Cas9 ribonucleoproteins. Genome Res. (2014). doi:10.1101/gr.171322.113

EQUIVALENTS AND SCOPE

Those skilled in the art will recognize, or be able to ascertain using no more than routine experimentation, many equivalents to the specific embodiments, described herein. The scope of the present invention is not intended to be limited to the above Description, but rather is as set forth in the appended claims.

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any supercharged protein; any nucleic acid; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

What is claimed is:

1. A composition for delivering a protein into a cell, the composition comprising:

(a) a biotinylated protein to be delivered to a cell, wherein the protein is associated with a supernegatively charged streptavidin (SAV), or a biotin-binding fragment thereof, resulting in a complex that is negatively charged; and (b) a cationic polymer or a cationic lipid.

2. The composition of claim 1, wherein the complex has a net charge of less than −5, less than −10, less than −20, less than −30, less than −40, less than −50, less than −60, less than −70, less than −80, less than −90, less than −100, less than −110, less than −120, less than −130, less than −140, less than −150, less than −160, less than −170, less than −180, less than −190, less than −200, less than −250, less than −300, or less than −400.

3. The composition of claim 1, wherein the complex has a charge:molecular weight ratio of less than −0.03, less than −0.04, less than −0.05, less than −0.06, less than −0.07, less than −0.08, less than −0.09, less than −0.1, less than −0.2, less than −0.3, less than −0.4, less than −0.5, less than −0.6, less than −0.7, less than −0.8, less than −0.9, less than −1, less than −1.1, less than −1.2, less than −1.3, less than −1.4, less than −1.5, less than −1.6, less than −1.7, less than −1.8, less than −1.9, less than −2, less than −2.1, less than −2.2, less than −2.3, less than −2.4, less than −2.5, less than −2.6, less than −2.7, less than −2.8, less than −2.9, less than −3, less than −3.1, less than −3.2, less than −3.3, less than −3.4, less than −3.5, less than −3.6, less than −3.7, less than −3.8, less than −3.9, or less than −4.

4. The composition of claim 1, wherein the biotinylated protein to be delivered is a protein listed in any of Tables 3, 4, 5, and 6.

5. The composition of claim 1, wherein the biotinylated protein to be delivered is implicated in a disease or disorder.

6. The composition of claim 1, wherein the biotinylated protein to be delivered is Sirt1, PPARγ, PRDM16, PGC1a, TP53BP1, Utrophin, Dystrophin, Bik, IκBα, Von Hippel-Lindau disease tumor suppressor, or an E3 ubiquitin ligase.

7. The composition of claim 1, wherein the supernegatively charged streptavidin (SAV) comprises −40 SAV, or a negatively charged fragment thereof.

8. The composition of claim 1, wherein the biotinylated protein to be delivered is associated with the supernegatively charged streptavidin (SAV) via a non-covalent interaction.

9. The composition of claim 1, wherein the composition comprises a cationic lipid.

10. The composition of claim 9, wherein the cationic lipid is selected from the group consisting of Lipofectamine® 2000, Lipofectamine® 3000, Lipofectamine® RNAiMAX, and Lipofectamine®LTX.

11. The composition of claim 1, wherein the composition is a pharmaceutical composition.

12. A method for delivering a protein to be delivered to a cell, comprising contacting the cell with the composition of claim 1.

13. The composition of claim 1, wherein the biotinylated protein to be delivered is a nuclease.

14. The composition of claim 1, wherein the biotinylated protein to be delivered is a recombinase.

15. The composition of claim 1, wherein the biotinylated protein to be delivered is a Cas9 or a variant thereof.

16. The composition of claim 1, wherein the biotinylated protein to be delivered is a metal-binding protein.

17. The composition of claim 1, wherein the biotinylated protein to be delivered is associated to the biotin via a linker.

18. The composition of claim 17, wherein the linker comprises a covalent bond generated via click chemistry, NHS ester chemistry, or maleimide chemistry.

19. The composition of claim 1, wherein the composition exhibits low toxicity when administered to a population of cells.

20. The composition of claim 19, wherein at least 60%, at least 65%, at least 70%, at least 75%, at least 80%, at least 85%, at least 90%, at least 95%, or at least 99% of the cells are viable 24 hours after administration of an amount of the composition effective for delivery of the protein to be delivered into at least 1% of the cells.

21. The composition of claim 1, wherein the biotinylated protein is associated with a nucleic acid.

22. The composition of claim 21, wherein the nucleic acid is DNA.

23. The composition of claim 21, wherein the nucleic acid is RNA.

24. The method of claim 12, wherein the contacting is in vitro.

25. The method of claim 12, wherein the contacting is in vivo.

26. The composition of claim 1, wherein the biotinylated protein to be delivered is a fusion protein comprising a catalytically-inactive Cas9 (dCas9) fused to a functional effector protein.

27. The composition of claim 26, wherein the dCas9 protein is fused to a transcriptional activator, a transcriptional repressor, a nuclease domain, a recombinase domain, a deaminase, or an epigenetic modifier domain.

28. The composition of claim 17, wherein the linker is a cleavable linker cleaved by a protease, a esterase, or by a reducing environment.

29. The composition of claim 17, wherein the linker is a cleavable linker cleaved by an enzyme present in endosomes or under conditions present in endosomes.

* * * * *

SEQUENCE LISTING

```
<160> NUMBER OF SEQ ID NOS: 280

<210> SEQ ID NO 1
<211> LENGTH: 240
<212> TYPE: PRT
<213> ORGANISM: Artificial Sequence
<220> FEATURE:
<223> OTHER INFORMATION: Synthetic Polypeptide

<400> SEQUENCE: 1

Gly Gly Ala Ser Lys Gly Glu Arg Leu Phe Arg Gly Lys Val Pro Ile
1               5                   10                  15

Leu Val Glu Leu Lys Gly Asp Val Asn Gly His Lys Phe Ser Val Arg
            20                  25                  30

Gly Lys Gly Lys Gly Asp Ala Thr Arg Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Tyr Gly Val Gln Cys Phe Ser Arg Tyr Pro Lys His Met
65                  70                  75                  80

Lys Arg His Asp Phe Phe Lys Ser Ala Met Pro Lys Gly Tyr Val Gln
                85                  90                  95

Glu Arg Thr Ile Ser Phe Lys Lys Asp Gly Lys Tyr Lys Thr Arg Ala
            100                 105                 110

Glu Val Lys Phe Glu Gly Arg Thr Leu Val Asn Arg Ile Lys Leu Lys
        115                 120                 125

Gly Arg Asp Phe Lys Glu Lys Gly Asn Ile Leu Gly His Lys Leu Arg
    130                 135                 140

Tyr Asn Phe Asn Ser His Lys Val Tyr Ile Thr Ala Asp Lys Arg Lys
145                 150                 155                 160

Asn Gly Ile Lys Ala Lys Phe Lys Ile Arg His Asn Val Lys Asp Gly
                165                 170                 175

Ser Val Gln Leu Ala Asp His Tyr Gln Gln Asn Thr Pro Ile Gly Arg
            180                 185                 190

Gly Pro Val Leu Leu Pro Arg Asn His Tyr Leu Ser Thr Arg Ser Lys
```

```
        195                 200                 205

Leu Ser Lys Asp Pro Lys Glu Lys Arg Asp His Met Val Leu Leu Glu
    210                 215                 220

Phe Val Thr Ala Ala Gly Ile Lys His Gly Arg Asp Glu Arg Tyr Lys
225                 230                 235                 240


<210> SEQ ID NO 2
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 2

Gly Gly Ser Gly Gly Ser Gly Gly Ser Gly Gly Ser Gly Gly Ser Gly
1               5                   10                  15

Gly Ser


<210> SEQ ID NO 3
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 3

Ser Gly Ser Glu Thr Pro Gly Thr Ser Glu Ser Ala Thr Pro Glu Ser
1               5                   10                  15


<210> SEQ ID NO 4
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 4

Ser Gly Ser Glu Thr Pro Gly Thr Ser Glu Ser Ala
1               5                   10


<210> SEQ ID NO 5
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 5

Ser Gly Ser Glu Thr Pro Gly Thr Ser Glu Ser Ala Thr Pro Glu Gly
1               5                   10                  15

Gly Ser Gly Gly Ser
            20


<210> SEQ ID NO 6
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 6

Val Pro Phe Leu Leu Glu Pro Asp Asn Ile Asn Gly Lys Thr Cys
1               5                   10                  15
```

-continued

<210> SEQ ID NO 7
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 7

```
Gly Ser Ala Gly Ser Ala Ala Gly Ser Gly Glu Phe
1               5                   10
```

<210> SEQ ID NO 8
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 8

```
Ser Ile Val Ala Gln Leu Ser Arg Pro Asp Pro Ala
1               5                   10
```

<210> SEQ ID NO 9
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 9

```
Met Lys Ile Ile Glu Gln Leu Pro Ser Ala
1               5                   10
```

<210> SEQ ID NO 10
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 10

```
Val Arg His Lys Leu Lys Arg Val Gly Ser
1               5                   10
```

<210> SEQ ID NO 11
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 11

```
Gly His Gly Thr Gly Ser Thr Gly Ser Gly Ser Ser
1               5                   10
```

<210> SEQ ID NO 12
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 12

```
Met Ser Arg Pro Asp Pro Ala
1               5
```

<210> SEQ ID NO 13

<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 13

Gly Gly Ser Met
1

<210> SEQ ID NO 14
<211> LENGTH: 238
<212> TYPE: PRT
<213> ORGANISM: Aequorea victoria

<400> SEQUENCE: 14

Met Ser Lys Gly Glu Glu Leu Phe Thr Gly Val Val Pro Ile Leu Val
1 5 10 15

Glu Leu Asp Gly Asp Val Asn Gly His Lys Phe Ser Val Ser Gly Glu
20 25 30

Gly Glu Gly Asp Ala Thr Tyr Gly Lys Leu Thr Leu Lys Phe Ile Cys
35 40 45

Thr Thr Gly Lys Leu Pro Val Pro Trp Pro Thr Leu Val Thr Thr Phe
50 55 60

Ser Tyr Gly Val Gln Cys Phe Ser Arg Tyr Pro Asp His Met Lys Gln
65 70 75 80

His Asp Phe Phe Lys Ser Ala Met Pro Glu Gly Tyr Val Gln Glu Arg
85 90 95

Thr Ile Phe Phe Lys Asp Asp Gly Asn Tyr Lys Thr Arg Ala Glu Val
100 105 110

Lys Phe Glu Gly Asp Thr Leu Val Asn Arg Ile Glu Leu Lys Gly Ile
115 120 125

Asp Phe Lys Glu Asp Gly Asn Ile Leu Gly His Lys Leu Glu Tyr Asn
130 135 140

Tyr Asn Ser His Asn Val Tyr Ile Met Ala Asp Lys Gln Lys Asn Gly
145 150 155 160

Ile Lys Val Asn Phe Lys Ile Arg His Asn Ile Glu Asp Gly Ser Val
165 170 175

Gln Leu Ala Asp His Tyr Gln Gln Asn Thr Pro Ile Gly Asp Gly Pro
180 185 190

Val Leu Leu Pro Asp Asn His Tyr Leu Ser Thr Gln Ser Ala Leu Ser
195 200 205

Lys Asp Pro Asn Glu Lys Arg Asp His Met Val Leu Leu Glu Phe Val
210 215 220

Thr Ala Ala Gly Ile Thr His Gly Met Asp Glu Leu Tyr Lys
225 230 235

<210> SEQ ID NO 15
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 15

Met Gly His His His His His His Gly Gly Ala Ser Lys Gly Glu Arg
1 5 10 15

Leu Phe Thr Gly Val Val Pro Ile Leu Val Glu Leu Asp Gly Asp Val
20 25 30

Asn Gly His Lys Phe Ser Val Arg Gly Glu Gly Glu Gly Asp Ala Thr
35 40 45

Arg Gly Lys Leu Thr Leu Lys Phe Ile Cys Thr Thr Gly Lys Leu Pro
50 55 60

Val Pro Trp Pro Thr Leu Val Thr Thr Leu Thr Tyr Gly Val Gln Cys
65 70 75 80

Phe Ser Arg Tyr Pro Lys His Met Lys Arg His Asp Phe Phe Lys Ser
85 90 95

Ala Met Pro Glu Gly Tyr Val Gln Glu Arg Thr Ile Ser Phe Lys Lys
100 105 110

Asp Gly Thr Tyr Lys Thr Arg Ala Glu Val Lys Phe Glu Gly Arg Thr
115 120 125

Leu Val Asn Arg Ile Glu Leu Lys Gly Arg Asp Phe Lys Glu Lys Gly
130 135 140

Asn Ile Leu Gly His Lys Leu Glu Tyr Asn Phe Asn Ser His Asn Val
145 150 155 160

Tyr Ile Thr Ala Asp Lys Arg Lys Asn Gly Ile Lys Ala Asn Phe Lys
165 170 175

Ile Arg His Asn Val Lys Asp Gly Ser Val Gln Leu Ala Asp His Tyr
180 185 190

Gln Gln Asn Thr Pro Ile Gly Arg Gly Pro Val Leu Leu Pro Arg Asn
195 200 205

His Tyr Leu Ser Thr Arg Ser Ala Leu Ser Lys Asp Pro Lys Glu Lys
210 215 220

Arg Asp His Met Val Leu Leu Glu Phe Val Thr Ala Ala Gly Ile Thr
225 230 235 240

His Gly Met Asp Glu Leu Tyr Lys
245

<210> SEQ ID NO 16
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 16

Met Gly His His His His His His Gly Gly Ala Ser Lys Gly Glu Arg
1 5 10 15

Leu Phe Thr Gly Val Val Pro Ile Leu Val Glu Leu Asp Gly Asp Val
20 25 30

Asn Gly His Lys Phe Ser Val Arg Gly Lys Gly Lys Gly Asp Ala Thr
35 40 45

Arg Gly Lys Leu Thr Leu Lys Phe Ile Cys Thr Thr Gly Lys Leu Pro
50 55 60

Val Pro Trp Pro Thr Leu Val Thr Thr Leu Thr Tyr Gly Val Gln Cys
65 70 75 80

Phe Ser Arg Tyr Pro Lys His Met Lys Arg His Asp Phe Phe Lys Ser
85 90 95

Ala Met Pro Lys Gly Tyr Val Gln Glu Arg Thr Ile Ser Phe Lys Lys
100 105 110

Asp Gly Thr Tyr Lys Thr Arg Ala Glu Val Lys Phe Glu Gly Arg Thr
115 120 125

Leu Val Asn Arg Ile Lys Leu Lys Gly Arg Asp Phe Lys Glu Lys Gly
130 135 140

Asn Ile Leu Gly His Lys Leu Arg Tyr Asn Phe Asn Ser His Asn Val
145 150 155 160

Tyr Ile Thr Ala Asp Lys Arg Lys Asn Gly Ile Lys Ala Asn Phe Lys
165 170 175

Ile Arg His Asn Val Lys Asp Gly Ser Val Gln Leu Ala Asp His Tyr
180 185 190

Gln Gln Asn Thr Pro Ile Gly Arg Gly Pro Val Leu Leu Pro Arg Asn
195 200 205

His Tyr Leu Ser Thr Arg Ser Ala Leu Ser Lys Asp Pro Lys Glu Lys
210 215 220

Arg Asp His Met Val Leu Leu Glu Phe Val Thr Ala Ala Gly Ile Thr
225 230 235 240

His Gly Met Asp Glu Leu Tyr Lys
245

<210> SEQ ID NO 17
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 17

Met Gly His His His His His His Gly Gly Ala Ser Lys Gly Glu Arg
1 5 10 15

Leu Phe Arg Gly Lys Val Pro Ile Leu Val Glu Leu Lys Gly Asp Val
20 25 30

Asn Gly His Lys Phe Ser Val Arg Gly Lys Gly Lys Gly Asp Ala Thr
35 40 45

Arg Gly Lys Leu Thr Leu Lys Phe Ile Cys Thr Thr Gly Lys Leu Pro
50 55 60

Val Pro Trp Pro Thr Leu Val Thr Thr Leu Thr Tyr Gly Val Gln Cys
65 70 75 80

Phe Ser Arg Tyr Pro Lys His Met Lys Arg His Asp Phe Phe Lys Ser
85 90 95

Ala Met Pro Lys Gly Tyr Val Gln Glu Arg Thr Ile Ser Phe Lys Lys
100 105 110

Asp Gly Lys Tyr Lys Thr Arg Ala Glu Val Lys Phe Glu Gly Arg Thr
115 120 125

Leu Val Asn Arg Ile Lys Leu Lys Gly Arg Asp Phe Lys Glu Lys Gly
130 135 140

Asn Ile Leu Gly His Lys Leu Arg Tyr Asn Phe Asn Ser His Lys Val
145 150 155 160

Tyr Ile Thr Ala Asp Lys Arg Lys Asn Gly Ile Lys Ala Lys Phe Lys
165 170 175

Ile Arg His Asn Val Lys Asp Gly Ser Val Gln Leu Ala Asp His Tyr
180 185 190

Gln Gln Asn Thr Pro Ile Gly Arg Gly Pro Val Leu Leu Pro Arg Asn
195 200 205

His Tyr Leu Ser Thr Arg Ser Lys Leu Ser Lys Asp Pro Lys Glu Lys
210 215 220

Arg Asp His Met Val Leu Leu Glu Phe Val Thr Ala Ala Gly Ile Lys
225 230 235 240

His Gly Arg Asp Glu Arg Tyr Lys
245

<210> SEQ ID NO 18
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 18

```
Met Gly His His His His His His Gly Gly Arg Ser Lys Gly Lys Arg
1               5                   10                  15

Leu Phe Arg Gly Lys Val Pro Ile Leu Val Glu Leu Lys Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Lys
        195                 200                 205

His Tyr Leu Ser Thr Arg Ser Lys Leu Ser Lys Asp Pro Lys Glu Lys
    210                 215                 220

Arg Asp His Met Val Leu Leu Glu Phe Val Thr Ala Ala Gly Ile Lys
225                 230                 235                 240

His Gly Arg Lys Glu Arg Tyr Lys
                245
```

<210> SEQ ID NO 19
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 19

```
Met Gly His His His His His His Gly Gly Arg Ser Lys Gly Lys Arg
1               5                   10                  15

Leu Phe Arg Gly Lys Val Pro Ile Leu Val Lys Leu Lys Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
```

```
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Lys Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Lys His Tyr
            180                 185                 190

Gln Gln Asn Thr Pro Ile Gly Arg Gly Pro Val Leu Leu Pro Arg Lys
        195                 200                 205

His Tyr Leu Ser Thr Arg Ser Lys Leu Ser Lys Asp Pro Lys Glu Lys
    210                 215                 220

Arg Asp His Met Val Leu Leu Glu Phe Val Thr Ala Ala Gly Ile Lys
225                 230                 235                 240

His Gly Arg Lys Glu Arg Tyr Lys
                245


<210> SEQ ID NO 20
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 20

Met Gly His His His His His His Gly Gly Arg Ser Lys Gly Lys Arg
1               5                   10                  15

Leu Phe Arg Gly Lys Val Pro Ile Leu Val Lys Leu Lys Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Lys Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
```

```
                165                 170                 175

Ile Arg His Asn Val Lys Asp Gly Ser Val Gln Leu Ala Lys His Tyr
            180                 185                 190

Gln Gln Asn Thr Pro Ile Gly Arg Gly Pro Val Leu Leu Pro Arg Lys
        195                 200                 205

His Tyr Leu Ser Thr Arg Ser Lys Leu Ser Lys Asp Pro Lys Glu Lys
    210                 215                 220

Arg Asp His Met Val Leu Lys Glu Phe Val Thr Ala Ala Gly Ile Lys
225                 230                 235                 240

His Gly Arg Lys Glu Arg Tyr Lys
                245


<210> SEQ ID NO 21
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 21

Met Gly His His His His His His Gly Gly Ala Ser Lys Gly Glu Glu
1               5                   10                  15

Leu Phe Asp Gly Val Val Pro Ile Leu Val Glu Leu Asp Gly Asp Val
            20                  25                  30

Asn Gly His Glu Phe Ser Val Arg Gly Glu Gly Glu Gly Asp Ala Thr
        35                  40                  45

Glu Gly Glu Leu Thr Leu Lys Phe Ile Cys Thr Thr Gly Glu Leu Pro
    50                  55                  60

Val Pro Trp Pro Thr Leu Val Thr Thr Leu Thr Tyr Gly Val Gln Cys
65                  70                  75                  80

Phe Ser Asp Tyr Pro Asp His Met Asp Gln His Asp Phe Phe Lys Ser
                85                  90                  95

Ala Met Pro Glu Gly Tyr Val Gln Glu Arg Thr Ile Ser Phe Lys Asp
            100                 105                 110

Asp Gly Thr Tyr Lys Thr Arg Ala Glu Val Lys Phe Glu Gly Asp Thr
        115                 120                 125

Leu Val Asn Arg Ile Glu Leu Lys Gly Ile Asp Phe Lys Glu Asp Gly
    130                 135                 140

Asn Ile Leu Gly His Lys Leu Glu Tyr Asn Phe Asn Ser His Asp Val
145                 150                 155                 160

Tyr Ile Thr Ala Asp Lys Gln Glu Asn Gly Ile Lys Ala Glu Phe Glu
                165                 170                 175

Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asp
        195                 200                 205

His Tyr Leu Ser Thr Glu Ser Ala Leu Ser Lys Asp Pro Asn Glu Asp
    210                 215                 220

Arg Asp His Met Val Leu Leu Glu Phe Val Thr Ala Ala Gly Ile Asp
225                 230                 235                 240

His Gly Met Asp Glu Leu Tyr Lys
                245


<210> SEQ ID NO 22
<211> LENGTH: 280
<212> TYPE: PRT
```

<213> ORGANISM: Artificial Sequence
<220> FEATURE:
<223> OTHER INFORMATION: Synthetic Polypeptide

<400> SEQUENCE: 22

```
Met Gly His His His His His His Gly Gly Ala Ser Lys Gly Glu Arg
1               5                   10                  15

Leu Phe Arg Gly Lys Val Pro Ile Leu Val Glu Leu Lys Gly Asp Val
            20                  25                  30

Asn Gly His Lys Phe Ser Val Arg Gly Lys Gly Lys Gly Asp Ala Thr
        35                  40                  45

Arg Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Lys His Met Lys Arg His Asp Phe Phe Lys Ser
                85                  90                  95

Ala Met Pro Lys Gly Tyr Val Gln Glu Arg Thr Ile Ser Phe Lys Lys
            100                 105                 110

Asp Gly Lys Tyr Lys Thr Arg Ala Glu Val Lys Phe Glu Gly Arg Thr
        115                 120                 125

Leu Val Asn Arg Ile Lys Leu Lys Gly Arg Asp Phe Lys Glu Lys Gly
    130                 135                 140

Asn Ile Leu Gly His Lys Leu Arg Tyr Asn Phe Asn Ser His Lys Val
145                 150                 155                 160

Tyr Ile Thr Ala Asp Lys Arg Lys Asn Gly Ile Lys Ala Lys Phe Lys
                165                 170                 175

Ile Arg His Asn Val Lys Asp Gly Ser Val Gln Leu Ala Asp His Tyr
            180                 185                 190

Gln Gln Asn Thr Pro Ile Gly Arg Gly Pro Val Leu Leu Pro Arg Asn
        195                 200                 205

His Tyr Leu Ser Thr Arg Ser Lys Leu Ser Lys Asp Pro Lys Glu Lys
    210                 215                 220

Arg Asp His Met Val Leu Leu Glu Phe Val Thr Ala Ala Gly Ile Lys
225                 230                 235                 240

His Gly Arg Asp Glu Arg Tyr Lys Gly Ser Ala Gly Ser Ala Ala Gly
                245                 250                 255

Ser Gly Glu Phe Gly Leu Phe Gly Ala Ile Ala Gly Phe Ile Glu Asn
            260                 265                 270

Gly Trp Glu Gly Met Ile Asp Gly
        275                 280
```

<210> SEQ ID NO 23
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 23

```
Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25
```

<210> SEQ ID NO 24
<211> LENGTH: 26

<212> TYPE: PRT
<213> ORGANISM: Artificial Sequence
<220> FEATURE:
<223> OTHER INFORMATION: Synthetic Polypeptide

<400> SEQUENCE: 24

Cys Ile Gly Ala Val Leu Lys Val Leu Thr Thr Gly Leu Pro Ala Leu
1 5 10 15

Ile Ser Trp Ile Lys Arg Lys Arg Gln Gln
20 25

<210> SEQ ID NO 25
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 25

Arg Gln Ile Lys Ile Trp Phe Gln Asn Arg Arg Met Lys Trp Lys Lys
1 5 10 15

<210> SEQ ID NO 26
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 26

Met Val Lys Ser Lys Ile Gly Ser Trp Ile Leu Val Leu Phe Val Ala
1 5 10 15

Met Trp Ser Asp Val Gly Leu Cys Lys Lys Arg Pro Lys Pro
20 25 30

<210> SEQ ID NO 27
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 27

Gly Ala Leu Phe Leu Gly Trp Leu Gly Ala Ala Gly Ser Thr Met Gly
1 5 10 15

Ala Pro Lys Ser Lys Arg Lys Val
20

<210> SEQ ID NO 28
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 28

Ala Gly Tyr Leu Leu Gly Lys Ile Asn Leu Lys Ala Leu Ala Ala Leu
1 5 10 15

Ala Lys Lys Ile Leu
20

<210> SEQ ID NO 29
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 29

Leu Ile Arg Leu Trp Ser His Leu Ile His Ile Trp Phe Gln Asn Arg
1               5                   10                  15

Arg Leu Lys Trp Lys Lys Lys
            20

<210> SEQ ID NO 30
<211> LENGTH: 1653
<212> TYPE: PRT
<213> ORGANISM: Artificial Sequence
<220> FEATURE:
<223> OTHER INFORMATION: Synthetic Polypeptide

<400> SEQUENCE: 30

Met Gly Ala Ser Lys Gly Glu Arg Leu Phe Arg Gly Lys Val Pro Ile
1               5                   10                  15

Leu Val Glu Leu Lys Gly Asp Val Asn Gly His Lys Phe Ser Val Arg
            20                  25                  30

Gly Lys Gly Lys Gly Asp Ala Thr Arg Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Ser Gly Val Gln Cys Phe Ser Arg Tyr Pro Lys His Met
65                  70                  75                  80

Lys Arg His Asp Phe Phe Lys Ser Ala Met Pro Lys Gly Tyr Val Gln
                85                  90                  95

Glu Arg Thr Ile Ser Phe Lys Lys Asp Gly Lys Tyr Lys Thr Arg Ala
            100                 105                 110

Glu Val Lys Phe Glu Gly Arg Thr Leu Val Asn Arg Ile Lys Leu Lys
        115                 120                 125

Gly Arg Asp Phe Lys Glu Lys Gly Asn Ile Leu Gly His Lys Leu Arg
    130                 135                 140

Tyr Asn Phe Asn Ser His Lys Val Tyr Ile Thr Ala Asp Lys Arg Lys
145                 150                 155                 160

Asn Gly Ile Lys Ala Lys Phe Lys Ile Arg His Asn Val Lys Asp Gly
                165                 170                 175

Ser Val Gln Leu Ala Asp His Tyr Gln Gln Asn Thr Pro Ile Gly Arg
            180                 185                 190

Gly Pro Val Leu Leu Pro Arg Asn His Tyr Leu Ser Thr Arg Ser Lys
        195                 200                 205

Leu Ser Lys Asp Pro Lys Glu Lys Arg Asp His Met Val Leu Leu Glu
    210                 215                 220

Phe Val Thr Ala Ala Gly Ile Lys His Gly Arg Asp Glu Arg Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Leu Ala Leu
            260                 265                 270

Pro Lys Lys Lys Arg Lys Val Met Asp Lys Lys Tyr Ser Ile Gly Leu
        275                 280                 285

Asp Ile Gly Thr Asn Ser Val Gly Trp Ala Val Ile Thr Asp Glu Tyr
    290                 295                 300

Lys Val Pro Ser Lys Lys Phe Lys Val Leu Gly Asn Thr Asp Arg His

-continued

```
305                 310                 315                 320

Ser Ile Lys Lys Asn Leu Ile Gly Ala Leu Leu Phe Asp Ser Gly Glu
                325                 330                 335

Thr Ala Glu Ala Thr Arg Leu Lys Arg Thr Ala Arg Arg Arg Tyr Thr
            340                 345                 350

Arg Arg Lys Asn Arg Ile Cys Tyr Leu Gln Glu Ile Phe Ser Asn Glu
        355                 360                 365

Met Ala Lys Val Asp Asp Ser Phe Phe His Arg Leu Glu Glu Ser Phe
    370                 375                 380

Leu Val Glu Glu Asp Lys Lys His Glu Arg His Pro Ile Phe Gly Asn
385                 390                 395                 400

Ile Val Asp Glu Val Ala Tyr His Glu Lys Tyr Pro Thr Ile Tyr His
                405                 410                 415

Leu Arg Lys Lys Leu Val Asp Ser Thr Asp Lys Ala Asp Leu Arg Leu
            420                 425                 430

Ile Tyr Leu Ala Leu Ala His Met Ile Lys Phe Arg Gly His Phe Leu
        435                 440                 445

Ile Glu Gly Asp Leu Asn Pro Asp Asn Ser Asp Val Asp Lys Leu Phe
    450                 455                 460

Ile Gln Leu Val Gln Thr Tyr Asn Gln Leu Phe Glu Glu Asn Pro Ile
465                 470                 475                 480

Asn Ala Ser Gly Val Asp Ala Lys Ala Ile Leu Ser Ala Arg Leu Ser
                485                 490                 495

Lys Ser Arg Arg Leu Glu Asn Leu Ile Ala Gln Leu Pro Gly Glu Lys
            500                 505                 510

Lys Asn Gly Leu Phe Gly Asn Leu Ile Ala Leu Ser Leu Gly Leu Thr
        515                 520                 525

Pro Asn Phe Lys Ser Asn Phe Asp Leu Ala Glu Asp Ala Lys Leu Gln
    530                 535                 540

Leu Ser Lys Asp Thr Tyr Asp Asp Asp Leu Asp Asn Leu Leu Ala Gln
545                 550                 555                 560

Ile Gly Asp Gln Tyr Ala Asp Leu Phe Leu Ala Ala Lys Asn Leu Ser
                565                 570                 575

Asp Ala Ile Leu Leu Ser Asp Ile Leu Arg Val Asn Thr Glu Ile Thr
            580                 585                 590

Lys Ala Pro Leu Ser Ala Ser Met Ile Lys Arg Tyr Asp Glu His His
        595                 600                 605

Gln Asp Leu Thr Leu Leu Lys Ala Leu Val Arg Gln Gln Leu Pro Glu
    610                 615                 620

Lys Tyr Lys Glu Ile Phe Phe Asp Gln Ser Lys Asn Gly Tyr Ala Gly
625                 630                 635                 640

Tyr Ile Asp Gly Gly Ala Ser Gln Glu Glu Phe Tyr Lys Phe Ile Lys
                645                 650                 655

Pro Ile Leu Glu Lys Met Asp Gly Thr Glu Glu Leu Leu Val Lys Leu
            660                 665                 670

Asn Arg Glu Asp Leu Leu Arg Lys Gln Arg Thr Phe Asp Asn Gly Ser
        675                 680                 685

Ile Pro His Gln Ile His Leu Gly Glu Leu His Ala Ile Leu Arg Arg
    690                 695                 700

Gln Glu Asp Phe Tyr Pro Phe Leu Lys Asp Asn Arg Glu Lys Ile Glu
705                 710                 715                 720

Lys Ile Leu Thr Phe Arg Ile Pro Tyr Tyr Val Gly Pro Leu Ala Arg
                725                 730                 735
```

Gly Asn Ser Arg Phe Ala Trp Met Thr Arg Lys Ser Glu Glu Thr Ile
740 745 750

Thr Pro Trp Asn Phe Glu Glu Val Val Asp Lys Gly Ala Ser Ala Gln
755 760 765

Ser Phe Ile Glu Arg Met Thr Asn Phe Asp Lys Asn Leu Pro Asn Glu
770 775 780

Lys Val Leu Pro Lys His Ser Leu Leu Tyr Glu Tyr Phe Thr Val Tyr
785 790 795 800

Asn Glu Leu Thr Lys Val Lys Tyr Val Thr Glu Gly Met Arg Lys Pro
805 810 815

Ala Phe Leu Ser Gly Glu Gln Lys Lys Ala Ile Val Asp Leu Leu Phe
820 825 830

Lys Thr Asn Arg Lys Val Thr Val Lys Gln Leu Lys Glu Asp Tyr Phe
835 840 845

Lys Lys Ile Glu Cys Phe Asp Ser Val Glu Ile Ser Gly Val Glu Asp
850 855 860

Arg Phe Asn Ala Ser Leu Gly Thr Tyr His Asp Leu Leu Lys Ile Ile
865 870 875 880

Lys Asp Lys Asp Phe Leu Asp Asn Glu Glu Asn Glu Asp Ile Leu Glu
885 890 895

Asp Ile Val Leu Thr Leu Thr Leu Phe Glu Asp Arg Glu Met Ile Glu
900 905 910

Glu Arg Leu Lys Thr Tyr Ala His Leu Phe Asp Asp Lys Val Met Lys
915 920 925

Gln Leu Lys Arg Arg Arg Tyr Thr Gly Trp Gly Arg Leu Ser Arg Lys
930 935 940

Leu Ile Asn Gly Ile Arg Asp Lys Gln Ser Gly Lys Thr Ile Leu Asp
945 950 955 960

Phe Leu Lys Ser Asp Gly Phe Ala Asn Arg Asn Phe Met Gln Leu Ile
965 970 975

His Asp Asp Ser Leu Thr Phe Lys Glu Asp Ile Gln Lys Ala Gln Val
980 985 990

Ser Gly Gln Gly Asp Ser Leu His Glu His Ile Ala Asn Leu Ala Gly
995 1000 1005

Ser Pro Ala Ile Lys Lys Gly Ile Leu Gln Thr Val Lys Val Val
1010 1015 1020

Asp Glu Leu Val Lys Val Met Gly Arg His Lys Pro Glu Asn Ile
1025 1030 1035

Val Ile Glu Met Ala Arg Glu Asn Gln Thr Thr Gln Lys Gly Gln
1040 1045 1050

Lys Asn Ser Arg Glu Arg Met Lys Arg Ile Glu Glu Gly Ile Lys
1055 1060 1065

Glu Leu Gly Ser Gln Ile Leu Lys Glu His Pro Val Glu Asn Thr
1070 1075 1080

Gln Leu Gln Asn Glu Lys Leu Tyr Leu Tyr Tyr Leu Gln Asn Gly
1085 1090 1095

Arg Asp Met Tyr Val Asp Gln Glu Leu Asp Ile Asn Arg Leu Ser
1100 1105 1110

Asp Tyr Asp Val Asp His Ile Val Pro Gln Ser Phe Leu Lys Asp
1115 1120 1125

Asp Ser Ile Asp Asn Lys Val Leu Thr Arg Ser Asp Lys Asn Arg
1130 1135 1140

Gly Lys Ser Asp Asn Val Pro Ser Glu Glu Val Val Lys Lys Met
1145 1150 1155

Lys Asn Tyr Trp Arg Gln Leu Leu Asn Ala Lys Leu Ile Thr Gln
1160 1165 1170

Arg Lys Phe Asp Asn Leu Thr Lys Ala Glu Arg Gly Gly Leu Ser
1175 1180 1185

Glu Leu Asp Lys Ala Gly Phe Ile Lys Arg Gln Leu Val Glu Thr
1190 1195 1200

Arg Gln Ile Thr Lys His Val Ala Gln Ile Leu Asp Ser Arg Met
1205 1210 1215

Asn Thr Lys Tyr Asp Glu Asn Asp Lys Leu Ile Arg Glu Val Lys
1220 1225 1230

Val Ile Thr Leu Lys Ser Lys Leu Val Ser Asp Phe Arg Lys Asp
1235 1240 1245

Phe Gln Phe Tyr Lys Val Arg Glu Ile Asn Asn Tyr His His Ala
1250 1255 1260

His Asp Ala Tyr Leu Asn Ala Val Val Gly Thr Ala Leu Ile Lys
1265 1270 1275

Lys Tyr Pro Lys Leu Glu Ser Glu Phe Val Tyr Gly Asp Tyr Lys
1280 1285 1290

Val Tyr Asp Val Arg Lys Met Ile Ala Lys Ser Glu Gln Glu Ile
1295 1300 1305

Gly Lys Ala Thr Ala Lys Tyr Phe Phe Tyr Ser Asn Ile Met Asn
1310 1315 1320

Phe Phe Lys Thr Glu Ile Thr Leu Ala Asn Gly Glu Ile Arg Lys
1325 1330 1335

Arg Pro Leu Ile Glu Thr Asn Gly Glu Thr Gly Glu Ile Val Trp
1340 1345 1350

Asp Lys Gly Arg Asp Phe Ala Thr Val Arg Lys Val Leu Ser Met
1355 1360 1365

Pro Gln Val Asn Ile Val Lys Lys Thr Glu Val Gln Thr Gly Gly
1370 1375 1380

Phe Ser Lys Glu Ser Ile Leu Pro Lys Arg Asn Ser Asp Lys Leu
1385 1390 1395

Ile Ala Arg Lys Lys Asp Trp Asp Pro Lys Lys Tyr Gly Gly Phe
1400 1405 1410

Asp Ser Pro Thr Val Ala Tyr Ser Val Leu Val Val Ala Lys Val
1415 1420 1425

Glu Lys Gly Lys Ser Lys Lys Leu Lys Ser Val Lys Glu Leu Leu
1430 1435 1440

Gly Ile Thr Ile Met Glu Arg Ser Ser Phe Glu Lys Asn Pro Ile
1445 1450 1455

Asp Phe Leu Glu Ala Lys Gly Tyr Lys Glu Val Lys Lys Asp Leu
1460 1465 1470

Ile Ile Lys Leu Pro Lys Tyr Ser Leu Phe Glu Leu Glu Asn Gly
1475 1480 1485

Arg Lys Arg Met Leu Ala Ser Ala Gly Glu Leu Gln Lys Gly Asn
1490 1495 1500

Glu Leu Ala Leu Pro Ser Lys Tyr Val Asn Phe Leu Tyr Leu Ala
1505 1510 1515

Ser His Tyr Glu Lys Leu Lys Gly Ser Pro Glu Asp Asn Glu Gln
1520 1525 1530

Lys Gln Leu Phe Val Glu Gln His Lys His Tyr Leu Asp Glu Ile

```
    1535                1540                1545

Ile Glu  Gln Ile Ser Glu Phe  Ser Lys Arg Val Ile  Leu Ala Asp
    1550                1555                1560

Ala Asn  Leu Asp Lys Val Leu  Ser Ala Tyr Asn Lys  His Arg Asp
    1565                1570                1575

Lys Pro  Ile Arg Glu Gln Ala  Glu Asn Ile Ile His  Leu Phe Thr
    1580                1585                1590

Leu Thr  Asn Leu Gly Ala Pro  Ala Ala Phe Lys Tyr  Phe Asp Thr
    1595                1600                1605

Thr Ile  Asp Arg Lys Arg Tyr  Thr Ser Thr Lys Glu  Val Leu Asp
    1610                1615                1620

Ala Thr  Leu Ile His Gln Ser  Ile Thr Gly Leu Tyr  Glu Thr Arg
    1625                1630                1635

Ile Asp  Leu Ser Gln Leu Gly  Gly Asp His His His  His His His
    1640                1645                1650


<210> SEQ ID NO 31
<211> LENGTH: 1653
<212> TYPE: PRT
<213> ORGANISM: Artificial Sequence
<220> FEATURE:
<223> OTHER INFORMATION: Synthetic Polypeptide

<400> SEQUENCE: 31

Met Gly Ala Ser Lys Gly Glu Glu Leu Phe Asp Gly Val Val Pro Ile
1               5                   10                  15

Leu Val Glu Leu Asp Gly Asp Val Asn Gly His Glu Phe Ser Val Arg
            20                  25                  30

Gly Glu Gly Glu Gly Asp Ala Thr Glu Gly Glu Leu Thr Leu Lys Phe
        35                  40                  45

Ile Cys Thr Thr Gly Glu Leu Pro Val Pro Trp Pro Thr Leu Val Thr
    50                  55                  60

Thr Leu Thr Ser Gly Val Gln Cys Phe Ser Asp Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
        195                 200                 205

Leu Ser Lys Asp Pro Asn Glu Asp Arg Asp His Met Val Leu Leu Glu
    210                 215                 220

Phe Val Thr Ala Ala Gly Ile Asp His Gly Met Asp Glu Leu Tyr Lys
225                 230                 235                 240

Thr Gly Gly Ser Gly Gly Ser Gly Gly Ser Gly Gly Ser Gly Gly Ser
```

-continued

```
                245                 250                 255

Gly Gly Ser Gly Gly Ser Gly Gly Ser Gly Gly Thr Ala Leu Ala Leu
            260                 265                 270

Pro Lys Lys Lys Arg Lys Val Met Asp Lys Lys Tyr Ser Ile Gly Leu
        275                 280                 285

Asp Ile Gly Thr Asn Ser Val Gly Trp Ala Val Ile Thr Asp Glu Tyr
    290                 295                 300

Lys Val Pro Ser Lys Lys Phe Lys Val Leu Gly Asn Thr Asp Arg His
305                 310                 315                 320

Ser Ile Lys Lys Asn Leu Ile Gly Ala Leu Leu Phe Asp Ser Gly Glu
                325                 330                 335

Thr Ala Glu Ala Thr Arg Leu Lys Arg Thr Ala Arg Arg Arg Tyr Thr
            340                 345                 350

Arg Arg Lys Asn Arg Ile Cys Tyr Leu Gln Glu Ile Phe Ser Asn Glu
        355                 360                 365

Met Ala Lys Val Asp Asp Ser Phe Phe His Arg Leu Glu Glu Ser Phe
    370                 375                 380

Leu Val Glu Glu Asp Lys Lys His Glu Arg His Pro Ile Phe Gly Asn
385                 390                 395                 400

Ile Val Asp Glu Val Ala Tyr His Glu Lys Tyr Pro Thr Ile Tyr His
                405                 410                 415

Leu Arg Lys Lys Leu Val Asp Ser Thr Asp Lys Ala Asp Leu Arg Leu
            420                 425                 430

Ile Tyr Leu Ala Leu Ala His Met Ile Lys Phe Arg Gly His Phe Leu
        435                 440                 445

Ile Glu Gly Asp Leu Asn Pro Asp Asn Ser Asp Val Asp Lys Leu Phe
    450                 455                 460

Ile Gln Leu Val Gln Thr Tyr Asn Gln Leu Phe Glu Glu Asn Pro Ile
465                 470                 475                 480

Asn Ala Ser Gly Val Asp Ala Lys Ala Ile Leu Ser Ala Arg Leu Ser
                485                 490                 495

Lys Ser Arg Arg Leu Glu Asn Leu Ile Ala Gln Leu Pro Gly Glu Lys
            500                 505                 510

Lys Asn Gly Leu Phe Gly Asn Leu Ile Ala Leu Ser Leu Gly Leu Thr
        515                 520                 525

Pro Asn Phe Lys Ser Asn Phe Asp Leu Ala Glu Asp Ala Lys Leu Gln
    530                 535                 540

Leu Ser Lys Asp Thr Tyr Asp Asp Asp Leu Asp Asn Leu Leu Ala Gln
545                 550                 555                 560

Ile Gly Asp Gln Tyr Ala Asp Leu Phe Leu Ala Ala Lys Asn Leu Ser
                565                 570                 575

Asp Ala Ile Leu Leu Ser Asp Ile Leu Arg Val Asn Thr Glu Ile Thr
            580                 585                 590

Lys Ala Pro Leu Ser Ala Ser Met Ile Lys Arg Tyr Asp Glu His His
        595                 600                 605

Gln Asp Leu Thr Leu Leu Lys Ala Leu Val Arg Gln Gln Leu Pro Glu
    610                 615                 620

Lys Tyr Lys Glu Ile Phe Phe Asp Gln Ser Lys Asn Gly Tyr Ala Gly
625                 630                 635                 640

Tyr Ile Asp Gly Gly Ala Ser Gln Glu Glu Phe Tyr Lys Phe Ile Lys
                645                 650                 655

Pro Ile Leu Glu Lys Met Asp Gly Thr Glu Glu Leu Leu Val Lys Leu
            660                 665                 670
```

```
Asn Arg Glu Asp Leu Leu Arg Lys Gln Arg Thr Phe Asp Asn Gly Ser
        675                 680                 685

Ile Pro His Gln Ile His Leu Gly Glu Leu His Ala Ile Leu Arg Arg
    690                 695                 700

Gln Glu Asp Phe Tyr Pro Phe Leu Lys Asp Asn Arg Glu Lys Ile Glu
705                 710                 715                 720

Lys Ile Leu Thr Phe Arg Ile Pro Tyr Tyr Val Gly Pro Leu Ala Arg
                725                 730                 735

Gly Asn Ser Arg Phe Ala Trp Met Thr Arg Lys Ser Glu Glu Thr Ile
            740                 745                 750

Thr Pro Trp Asn Phe Glu Glu Val Val Asp Lys Gly Ala Ser Ala Gln
        755                 760                 765

Ser Phe Ile Glu Arg Met Thr Asn Phe Asp Lys Asn Leu Pro Asn Glu
    770                 775                 780

Lys Val Leu Pro Lys His Ser Leu Leu Tyr Glu Tyr Phe Thr Val Tyr
785                 790                 795                 800

Asn Glu Leu Thr Lys Val Lys Tyr Val Thr Glu Gly Met Arg Lys Pro
                805                 810                 815

Ala Phe Leu Ser Gly Glu Gln Lys Lys Ala Ile Val Asp Leu Leu Phe
            820                 825                 830

Lys Thr Asn Arg Lys Val Thr Val Lys Gln Leu Lys Glu Asp Tyr Phe
        835                 840                 845

Lys Lys Ile Glu Cys Phe Asp Ser Val Glu Ile Ser Gly Val Glu Asp
    850                 855                 860

Arg Phe Asn Ala Ser Leu Gly Thr Tyr His Asp Leu Leu Lys Ile Ile
865                 870                 875                 880

Lys Asp Lys Asp Phe Leu Asp Asn Glu Glu Asn Glu Asp Ile Leu Glu
                885                 890                 895

Asp Ile Val Leu Thr Leu Thr Leu Phe Glu Asp Arg Glu Met Ile Glu
            900                 905                 910

Glu Arg Leu Lys Thr Tyr Ala His Leu Phe Asp Asp Lys Val Met Lys
        915                 920                 925

Gln Leu Lys Arg Arg Arg Tyr Thr Gly Trp Gly Arg Leu Ser Arg Lys
    930                 935                 940

Leu Ile Asn Gly Ile Arg Asp Lys Gln Ser Gly Lys Thr Ile Leu Asp
945                 950                 955                 960

Phe Leu Lys Ser Asp Gly Phe Ala Asn Arg Asn Phe Met Gln Leu Ile
                965                 970                 975

His Asp Asp Ser Leu Thr Phe Lys Glu Asp Ile Gln Lys Ala Gln Val
            980                 985                 990

Ser Gly Gln Gly Asp Ser Leu His  Glu His Ile Ala Asn  Leu Ala Gly
        995                 1000                1005

Ser Pro  Ala Ile Lys Lys Gly  Ile Leu Gln Thr Val  Lys Val Val
    1010                1015                1020

Asp Glu  Leu Val Lys Val Met  Gly Arg His Lys Pro  Glu Asn Ile
    1025                1030                1035

Val Ile  Glu Met Ala Arg Glu  Asn Gln Thr Thr Gln  Lys Gly Gln
    1040                1045                1050

Lys Asn  Ser Arg Glu Arg Met  Lys Arg Ile Glu Glu  Gly Ile Lys
    1055                1060                1065

Glu Leu  Gly Ser Gln Ile Leu  Lys Glu His Pro Val  Glu Asn Thr
    1070                1075                1080
```

-continued

```
Gln Leu  Gln Asn Glu Lys Leu  Tyr Leu Tyr Tyr Leu  Gln Asn Gly
    1085                 1090                 1095

Arg Asp  Met Tyr Val Asp Gln  Glu Leu Asp Ile Asn  Arg Leu Ser
    1100                 1105                 1110

Asp Tyr  Asp Val Asp His Ile  Val Pro Gln Ser Phe  Leu Lys Asp
    1115                 1120                 1125

Asp Ser  Ile Asp Asn Lys Val  Leu Thr Arg Ser Asp  Lys Asn Arg
    1130                 1135                 1140

Gly Lys  Ser Asp Asn Val Pro  Ser Glu Glu Val Val  Lys Lys Met
    1145                 1150                 1155

Lys Asn  Tyr Trp Arg Gln Leu  Leu Asn Ala Lys Leu  Ile Thr Gln
    1160                 1165                 1170

Arg Lys  Phe Asp Asn Leu Thr  Lys Ala Glu Arg Gly  Gly Leu Ser
    1175                 1180                 1185

Glu Leu  Asp Lys Ala Gly Phe  Ile Lys Arg Gln Leu  Val Glu Thr
    1190                 1195                 1200

Arg Gln  Ile Thr Lys His Val  Ala Gln Ile Leu Asp  Ser Arg Met
    1205                 1210                 1215

Asn Thr  Lys Tyr Asp Glu Asn  Asp Lys Leu Ile Arg  Glu Val Lys
    1220                 1225                 1230

Val Ile  Thr Leu Lys Ser Lys  Leu Val Ser Asp Phe  Arg Lys Asp
    1235                 1240                 1245

Phe Gln  Phe Tyr Lys Val Arg  Glu Ile Asn Asn Tyr  His His Ala
    1250                 1255                 1260

His Asp  Ala Tyr Leu Asn Ala  Val Val Gly Thr Ala  Leu Ile Lys
    1265                 1270                 1275

Lys Tyr  Pro Lys Leu Glu Ser  Glu Phe Val Tyr Gly  Asp Tyr Lys
    1280                 1285                 1290

Val Tyr  Asp Val Arg Lys Met  Ile Ala Lys Ser Glu  Gln Glu Ile
    1295                 1300                 1305

Gly Lys  Ala Thr Ala Lys Tyr  Phe Phe Tyr Ser Asn  Ile Met Asn
    1310                 1315                 1320

Phe Phe  Lys Thr Glu Ile Thr  Leu Ala Asn Gly Glu  Ile Arg Lys
    1325                 1330                 1335

Arg Pro  Leu Ile Glu Thr Asn  Gly Glu Thr Gly Glu  Ile Val Trp
    1340                 1345                 1350

Asp Lys  Gly Arg Asp Phe Ala  Thr Val Arg Lys Val  Leu Ser Met
    1355                 1360                 1365

Pro Gln  Val Asn Ile Val Lys  Lys Thr Glu Val Gln  Thr Gly Gly
    1370                 1375                 1380

Phe Ser  Lys Glu Ser Ile Leu  Pro Lys Arg Asn Ser  Asp Lys Leu
    1385                 1390                 1395

Ile Ala  Arg Lys Lys Asp Trp  Asp Pro Lys Lys Tyr  Gly Gly Phe
    1400                 1405                 1410

Asp Ser  Pro Thr Val Ala Tyr  Ser Val Leu Val Val  Ala Lys Val
    1415                 1420                 1425

Glu Lys  Gly Lys Ser Lys Lys  Leu Lys Ser Val Lys  Glu Leu Leu
    1430                 1435                 1440

Gly Ile  Thr Ile Met Glu Arg  Ser Ser Phe Glu Lys  Asn Pro Ile
    1445                 1450                 1455

Asp Phe  Leu Glu Ala Lys Gly  Tyr Lys Glu Val Lys  Lys Asp Leu
    1460                 1465                 1470

Ile Ile  Lys Leu Pro Lys Tyr  Ser Leu Phe Glu Leu  Glu Asn Gly
```

1475 1480 1485

Arg Lys Arg Met Leu Ala Ser Ala Gly Glu Leu Gln Lys Gly Asn
1490 1495 1500

Glu Leu Ala Leu Pro Ser Lys Tyr Val Asn Phe Leu Tyr Leu Ala
1505 1510 1515

Ser His Tyr Glu Lys Leu Lys Gly Ser Pro Glu Asp Asn Glu Gln
1520 1525 1530

Lys Gln Leu Phe Val Glu Gln His Lys His Tyr Leu Asp Glu Ile
1535 1540 1545

Ile Glu Gln Ile Ser Glu Phe Ser Lys Arg Val Ile Leu Ala Asp
1550 1555 1560

Ala Asn Leu Asp Lys Val Leu Ser Ala Tyr Asn Lys His Arg Asp
1565 1570 1575

Lys Pro Ile Arg Glu Gln Ala Glu Asn Ile Ile His Leu Phe Thr
1580 1585 1590

Leu Thr Asn Leu Gly Ala Pro Ala Ala Phe Lys Tyr Phe Asp Thr
1595 1600 1605

Thr Ile Asp Arg Lys Arg Tyr Thr Ser Thr Lys Glu Val Leu Asp
1610 1615 1620

Ala Thr Leu Ile His Gln Ser Ile Thr Gly Leu Tyr Glu Thr Arg
1625 1630 1635

Ile Asp Leu Ser Gln Leu Gly Gly Asp His His His His His His
1640 1645 1650

<210> SEQ ID NO 32
<211> LENGTH: 353
<212> TYPE: PRT
<213> ORGANISM: Artificial Sequence
<220> FEATURE:
<223> OTHER INFORMATION: Synthetic Polypeptide

<400> SEQUENCE: 32

Met Ala Ser Asn Leu Leu Thr Val His Gln Asn Leu Pro Ala Leu Pro
1 5 10 15

Val Asp Ala Thr Ser Asp Glu Val Arg Lys Asn Leu Met Asp Met Phe
20 25 30

Arg Asp Arg Gln Ala Phe Ser Glu His Thr Trp Lys Met Leu Leu Ser
35 40 45

Val Cys Arg Ser Trp Ala Ala Trp Cys Lys Leu Asn Asn Arg Lys Trp
50 55 60

Phe Pro Ala Glu Pro Glu Asp Val Arg Asp Tyr Leu Leu Tyr Leu Gln
65 70 75 80

Ala Arg Gly Leu Ala Val Lys Thr Ile Gln Gln His Leu Gly Gln Leu
85 90 95

Asn Met Leu His Arg Arg Ser Gly Leu Pro Arg Pro Ser Asp Ser Asn
100 105 110

Ala Val Ser Leu Val Met Arg Arg Ile Arg Lys Glu Asn Val Asp Ala
115 120 125

Gly Glu Arg Ala Lys Gln Ala Leu Ala Phe Glu Arg Thr Asp Phe Asp
130 135 140

Gln Val Arg Ser Leu Met Glu Asn Ser Asp Arg Cys Gln Asp Ile Arg
145 150 155 160

Asn Leu Ala Phe Leu Gly Ile Ala Tyr Asn Thr Leu Leu Arg Ile Ala
165 170 175

Glu Ile Ala Arg Ile Arg Val Lys Asp Ile Ser Arg Thr Asp Gly Gly

-continued

```
            180                 185                 190

Arg Met Leu Ile His Ile Gly Arg Thr Lys Thr Leu Val Ser Thr Ala
        195                 200                 205

Gly Val Glu Lys Ala Leu Ser Leu Gly Val Thr Lys Leu Val Glu Arg
    210                 215                 220

Trp Ile Ser Val Ser Gly Val Ala Asp Asp Pro Asn Asn Tyr Leu Phe
225                 230                 235                 240

Cys Arg Val Arg Lys Asn Gly Val Ala Ala Pro Ser Ala Thr Ser Gln
                245                 250                 255

Leu Ser Thr Arg Ala Leu Glu Gly Ile Phe Glu Ala Thr His Arg Leu
            260                 265                 270

Ile Tyr Gly Ala Lys Asp Asp Ser Gly Gln Arg Tyr Leu Ala Trp Ser
        275                 280                 285

Gly His Ser Ala Arg Val Gly Ala Ala Arg Asp Met Ala Arg Ala Gly
    290                 295                 300

Val Ser Ile Pro Glu Ile Met Gln Ala Gly Gly Trp Thr Asn Val Asn
305                 310                 315                 320

Ile Val Met Asn Tyr Ile Arg Asn Leu Asp Ser Glu Thr Gly Ala Met
                325                 330                 335

Val Arg Leu Leu Glu Asp Gly Asp Gly Gly Ser His His His His His
            340                 345                 350

His


<210> SEQ ID NO 33
<211> LENGTH: 620
<212> TYPE: PRT
<213> ORGANISM: Artificial Sequence
<220> FEATURE:
<223> OTHER INFORMATION: Synthetic Polypeptide

<400> SEQUENCE: 33

Met Gly Ala Ser Lys Gly Glu Arg Leu Phe Arg Gly Lys Val Pro Ile
1               5                   10                  15

Leu Val Glu Leu Lys Gly Asp Val Asn Gly His Lys Phe Ser Val Arg
            20                  25                  30

Gly Lys Gly Lys Gly Asp Ala Thr Arg Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Tyr Gly Val Gln Cys Phe Ser Arg Tyr Pro Lys His Met
65                  70                  75                  80

Lys Arg His Asp Phe Phe Lys Ser Ala Met Pro Lys Gly Tyr Val Gln
                85                  90                  95

Glu Arg Thr Ile Ser Phe Lys Lys Asp Gly Lys Tyr Lys Thr Arg Ala
            100                 105                 110

Glu Val Lys Phe Glu Gly Arg Thr Leu Val Asn Arg Ile Lys Leu Lys
        115                 120                 125

Gly Arg Asp Phe Lys Glu Lys Gly Asn Ile Leu Gly His Lys Leu Arg
    130                 135                 140

Tyr Asn Phe Asn Ser His Lys Val Tyr Ile Thr Ala Asp Lys Arg Lys
145                 150                 155                 160

Asn Gly Ile Lys Ala Lys Phe Lys Ile Arg His Asn Val Lys Asp Gly
                165                 170                 175

Ser Val Gln Leu Ala Asp His Tyr Gln Gln Asn Thr Pro Ile Gly Arg
            180                 185                 190
```

```
Gly Pro Val Leu Leu Pro Arg Asn His Tyr Leu Ser Thr Arg Ser Lys
        195                 200                 205

Leu Ser Lys Asp Pro Lys Glu Lys Arg Asp His Met Val Leu Leu Glu
    210                 215                 220

Phe Val Thr Ala Ala Gly Ile Lys His Gly Arg Asp Glu Arg Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Ser Asn Leu
            260                 265                 270

Leu Thr Val His Gln Asn Leu Pro Ala Leu Pro Val Asp Ala Thr Ser
        275                 280                 285

Asp Glu Val Arg Lys Asn Leu Met Asp Met Phe Arg Asp Arg Gln Ala
    290                 295                 300

Phe Ser Glu His Thr Trp Lys Met Leu Leu Ser Val Cys Arg Ser Trp
305                 310                 315                 320

Ala Ala Trp Cys Lys Leu Asn Asn Arg Lys Trp Phe Pro Ala Glu Pro
                325                 330                 335

Glu Asp Val Arg Asp Tyr Leu Leu Tyr Leu Gln Ala Arg Gly Leu Ala
            340                 345                 350

Val Lys Thr Ile Gln Gln His Leu Gly Gln Leu Asn Met Leu His Arg
        355                 360                 365

Arg Ser Gly Leu Pro Arg Pro Ser Asp Ser Asn Ala Val Ser Leu Val
    370                 375                 380

Met Arg Arg Ile Arg Lys Glu Asn Val Asp Ala Gly Glu Arg Ala Lys
385                 390                 395                 400

Gln Ala Leu Ala Phe Glu Arg Thr Asp Phe Asp Gln Val Arg Ser Leu
                405                 410                 415

Met Glu Asn Ser Asp Arg Cys Gln Asp Ile Arg Asn Leu Ala Phe Leu
            420                 425                 430

Gly Ile Ala Tyr Asn Thr Leu Leu Arg Ile Ala Glu Ile Ala Arg Ile
        435                 440                 445

Arg Val Lys Asp Ile Ser Arg Thr Asp Gly Gly Arg Met Leu Ile His
    450                 455                 460

Ile Gly Arg Thr Lys Thr Leu Val Ser Thr Ala Gly Val Glu Lys Ala
465                 470                 475                 480

Leu Ser Leu Gly Val Thr Lys Leu Val Glu Arg Trp Ile Ser Val Ser
                485                 490                 495

Gly Val Ala Asp Asp Pro Asn Asn Tyr Leu Phe Cys Arg Val Arg Lys
            500                 505                 510

Asn Gly Val Ala Ala Pro Ser Ala Thr Ser Gln Leu Ser Thr Arg Ala
        515                 520                 525

Leu Glu Gly Ile Phe Glu Ala Thr His Arg Leu Ile Tyr Gly Ala Lys
    530                 535                 540

Asp Asp Ser Gly Gln Arg Tyr Leu Ala Trp Ser Gly His Ser Ala Arg
545                 550                 555                 560

Val Gly Ala Ala Arg Asp Met Ala Arg Ala Gly Val Ser Ile Pro Glu
                565                 570                 575

Ile Met Gln Ala Gly Gly Trp Thr Asn Val Asn Ile Val Met Asn Tyr
            580                 585                 590

Ile Arg Asn Leu Asp Ser Glu Thr Gly Ala Met Val Arg Leu Leu Glu
        595                 600                 605
```

Asp Gly Asp Gly Gly Ser His His His His His His
610 615 620

<210> SEQ ID NO 34
<211> LENGTH: 620
<212> TYPE: PRT
<213> ORGANISM: Artificial Sequence
<220> FEATURE:
<223> OTHER INFORMATION: Synthetic Polypeptide

<400> SEQUENCE: 34

Met Gly Ala Ser Lys Gly Glu Glu Leu Phe Asp Gly Val Val Pro Ile
1 5 10 15

Leu Val Glu Leu Asp Gly Asp Val Asn Gly His Glu Phe Ser Val Arg
20 25 30

Gly Glu Gly Glu Gly Asp Ala Thr Glu Gly Glu Leu Thr Leu Lys Phe
35 40 45

Ile Cys Thr Thr Gly Glu Leu Pro Val Pro Trp Pro Thr Leu Val Thr
50 55 60

Thr Leu Thr Tyr Gly Val Gln Cys Phe Ser Asp Tyr Pro Asp His Met
65 70 75 80

Asp Gln His Asp Phe Phe Lys Ser Ala Met Pro Glu Gly Tyr Val Gln
85 90 95

Glu Arg Thr Ile Ser Phe Lys Asp Asp Gly Thr Tyr Lys Thr Arg Ala
100 105 110

Glu Val Lys Phe Glu Gly Asp Thr Leu Val Asn Arg Ile Glu Leu Lys
115 120 125

Gly Ile Asp Phe Lys Glu Asp Gly Asn Ile Leu Gly His Lys Leu Glu
130 135 140

Tyr Asn Phe Asn Ser His Asp Val Tyr Ile Thr Ala Asp Lys Gln Glu
145 150 155 160

Asn Gly Ile Lys Ala Glu Phe Glu Ile Arg His Asn Val Glu Asp Gly
165 170 175

Ser Val Gln Leu Ala Asp His Tyr Gln Gln Asn Thr Pro Ile Gly Asp
180 185 190

Gly Pro Val Leu Leu Pro Asp Asp His Tyr Leu Ser Thr Glu Ser Ala
195 200 205

Leu Ser Lys Asp Pro Asn Glu Asp Arg Asp His Met Val Leu Leu Glu
210 215 220

Phe Val Thr Ala Ala Gly Ile Asp His Gly Met Asp Glu Leu Tyr Lys
225 230 235 240

Thr Gly Gly Ser Gly Gly Ser Gly Gly Ser Gly Gly Ser Gly Gly Ser
245 250 255

Gly Gly Ser Gly Gly Ser Gly Gly Ser Gly Gly Thr Ala Ser Asn Leu
260 265 270

Leu Thr Val His Gln Asn Leu Pro Ala Leu Pro Val Asp Ala Thr Ser
275 280 285

Asp Glu Val Arg Lys Asn Leu Met Asp Met Phe Arg Asp Arg Gln Ala
290 295 300

Phe Ser Glu His Thr Trp Lys Met Leu Leu Ser Val Cys Arg Ser Trp
305 310 315 320

Ala Ala Trp Cys Lys Leu Asn Asn Arg Lys Trp Phe Pro Ala Glu Pro
325 330 335

Glu Asp Val Arg Asp Tyr Leu Leu Tyr Leu Gln Ala Arg Gly Leu Ala
340 345 350

Val Lys Thr Ile Gln Gln His Leu Gly Gln Leu Asn Met Leu His Arg
355 360 365

Arg Ser Gly Leu Pro Arg Pro Ser Asp Ser Asn Ala Val Ser Leu Val
370 375 380

Met Arg Arg Ile Arg Lys Glu Asn Val Asp Ala Gly Glu Arg Ala Lys
385 390 395 400

Gln Ala Leu Ala Phe Glu Arg Thr Asp Phe Asp Gln Val Arg Ser Leu
405 410 415

Met Glu Asn Ser Asp Arg Cys Gln Asp Ile Arg Asn Leu Ala Phe Leu
420 425 430

Gly Ile Ala Tyr Asn Thr Leu Leu Arg Ile Ala Glu Ile Ala Arg Ile
435 440 445

Arg Val Lys Asp Ile Ser Arg Thr Asp Gly Gly Arg Met Leu Ile His
450 455 460

Ile Gly Arg Thr Lys Thr Leu Val Ser Thr Ala Gly Val Glu Lys Ala
465 470 475 480

Leu Ser Leu Gly Val Thr Lys Leu Val Glu Arg Trp Ile Ser Val Ser
485 490 495

Gly Val Ala Asp Asp Pro Asn Asn Tyr Leu Phe Cys Arg Val Arg Lys
500 505 510

Asn Gly Val Ala Ala Pro Ser Ala Thr Ser Gln Leu Ser Thr Arg Ala
515 520 525

Leu Glu Gly Ile Phe Glu Ala Thr His Arg Leu Ile Tyr Gly Ala Lys
530 535 540

Asp Asp Ser Gly Gln Arg Tyr Leu Ala Trp Ser Gly His Ser Ala Arg
545 550 555 560

Val Gly Ala Ala Arg Asp Met Ala Arg Ala Gly Val Ser Ile Pro Glu
565 570 575

Ile Met Gln Ala Gly Gly Trp Thr Asn Val Asn Ile Val Met Asn Tyr
580 585 590

Ile Arg Asn Leu Asp Ser Glu Thr Gly Ala Met Val Arg Leu Leu Glu
595 600 605

Asp Gly Asp Gly Gly Ser His His His His His His
610 615 620

<210> SEQ ID NO 35
<211> LENGTH: 53
<212> TYPE: PRT
<213> ORGANISM: Artificial Sequence
<220> FEATURE:
<223> OTHER INFORMATION: Synthetic Polypeptide

<400> SEQUENCE: 35

Gly Arg Ala Asp Ala Leu Asp Asp Phe Asp Leu Asp Met Leu Gly Ser
1 5 10 15

Asp Ala Leu Asp Asp Phe Asp Leu Asp Met Leu Gly Ser Asp Ala Leu
20 25 30

Asp Asp Phe Asp Leu Asp Met Leu Gly Ser Asp Ala Leu Asp Asp Phe
35 40 45

Asp Leu Asp Met Leu
50

<210> SEQ ID NO 36
<211> LENGTH: 1210
<212> TYPE: PRT
<213> ORGANISM: Artificial Sequence
<220> FEATURE:

<223> OTHER INFORMATION: Synthetic Polypeptide

<400> SEQUENCE: 36

Met Gly Ala Ser Lys Gly Glu Arg Leu Phe Arg Gly Lys Val Pro Ile
1 5 10 15

Leu Val Glu Leu Lys Gly Asp Val Asn Gly His Lys Phe Ser Val Arg
20 25 30

Gly Lys Gly Lys Gly Asp Ala Thr Arg Gly Lys Leu Thr Leu Lys Phe
35 40 45

Ile Cys Thr Thr Gly Lys Leu Pro Val Pro Trp Pro Thr Leu Val Thr
50 55 60

Thr Leu Thr Tyr Gly Val Gln Cys Phe Ser Arg Tyr Pro Lys His Met
65 70 75 80

Lys Arg His Asp Phe Phe Lys Ser Ala Met Pro Lys Gly Tyr Val Gln
85 90 95

Glu Arg Thr Ile Ser Phe Lys Lys Asp Gly Lys Tyr Lys Thr Arg Ala
100 105 110

Glu Val Lys Phe Glu Gly Arg Thr Leu Val Asn Arg Ile Lys Leu Lys
115 120 125

Gly Arg Asp Phe Lys Glu Lys Gly Asn Ile Leu Gly His Lys Leu Arg
130 135 140

Tyr Asn Phe Asn Ser His Lys Val Tyr Ile Thr Ala Asp Lys Arg Lys
145 150 155 160

Asn Gly Ile Lys Ala Lys Phe Lys Ile Arg His Asn Val Lys Asp Gly
165 170 175

Ser Val Gln Leu Ala Asp His Tyr Gln Gln Asn Thr Pro Ile Gly Arg
180 185 190

Gly Pro Val Leu Leu Pro Arg Asn His Tyr Leu Ser Thr Arg Ser Lys
195 200 205

Leu Ser Lys Asp Pro Lys Glu Lys Arg Asp His Met Val Leu Leu Glu
210 215 220

Phe Val Thr Ala Ala Gly Ile Lys His Gly Arg Asp Glu Arg Tyr Lys
225 230 235 240

Thr Gly Gly Ser Gly Gly Ser Gly Gly Ser Gly Gly Ser Gly Gly Ser
245 250 255

Gly Gly Ser Gly Gly Ser Gly Gly Ser Gly Gly Thr Ala Pro Lys Lys
260 265 270

Lys Arg Lys Val Gly Ile His Arg Gly Val Pro Met Val Asp Leu Arg
275 280 285

Thr Leu Gly Tyr Ser Gln Gln Gln Gln Glu Lys Ile Lys Pro Lys Val
290 295 300

Arg Ser Thr Val Ala Gln His His Glu Ala Leu Val Gly His Gly Phe
305 310 315 320

Thr His Ala His Ile Val Ala Leu Ser Gln His Pro Ala Ala Leu Gly
325 330 335

Thr Val Ala Val Lys Tyr Gln Asp Met Ile Ala Ala Leu Pro Glu Ala
340 345 350

Thr His Glu Ala Ile Val Gly Val Gly Lys Gln Trp Ser Gly Ala Arg
355 360 365

Ala Leu Glu Ala Leu Leu Thr Val Ala Gly Glu Leu Arg Gly Pro Pro
370 375 380

Leu Gln Leu Asp Thr Gly Gln Leu Leu Lys Ile Ala Lys Arg Gly Gly
385 390 395 400

-continued

```
Val Thr Ala Val Glu Ala Val His Ala Trp Arg Asn Ala Leu Thr Gly
                405                 410                 415

Ala Pro Leu Asn Leu Thr Pro Asp Gln Val Val Ala Ile Ala Ser Asn
            420                 425                 430

Ile Gly Gly Lys Gln Ala Leu Glu Thr Val Gln Arg Leu Leu Pro Val
        435                 440                 445

Leu Cys Gln Asp His Gly Leu Thr Pro Glu Gln Val Val Ala Ile Ala
    450                 455                 460

Ser Asn Ile Gly Gly Lys Gln Ala Leu Glu Thr Val Gln Arg Leu Leu
465                 470                 475                 480

Pro Val Leu Cys Gln Ala His Gly Leu Thr Pro Asp Gln Val Val Ala
                485                 490                 495

Ile Ala Ser Asn Gly Gly Gly Lys Gln Ala Leu Glu Thr Val Gln Arg
            500                 505                 510

Leu Leu Pro Val Leu Cys Gln Ala His Gly Leu Thr Pro Ala Gln Val
        515                 520                 525

Val Ala Ile Ala Asn Asn Asn Gly Gly Lys Gln Ala Leu Glu Thr Val
    530                 535                 540

Gln Arg Leu Leu Pro Val Leu Cys Gln Asp His Gly Leu Thr Pro Asp
545                 550                 555                 560

Gln Val Val Ala Ile Ala Ser Asn Gly Gly Gly Lys Gln Ala Leu Glu
                565                 570                 575

Thr Val Gln Arg Leu Leu Pro Val Leu Cys Gln Asp His Gly Leu Thr
            580                 585                 590

Pro Glu Gln Val Val Ala Ile Ala Ser Asn Ile Gly Gly Lys Gln Ala
        595                 600                 605

Leu Glu Thr Val Gln Arg Leu Leu Pro Val Leu Cys Gln Ala His Gly
    610                 615                 620

Leu Thr Pro Asp Gln Val Val Ala Ile Ala Ser His Asp Gly Gly Lys
625                 630                 635                 640

Gln Ala Leu Glu Thr Val Gln Arg Leu Leu Pro Val Leu Cys Gln Ala
                645                 650                 655

His Gly Leu Thr Pro Ala Gln Val Val Ala Ile Ala Ser His Asp Gly
            660                 665                 670

Gly Lys Gln Ala Leu Glu Thr Val Gln Arg Leu Leu Pro Val Leu Cys
        675                 680                 685

Gln Asp His Gly Leu Thr Pro Asp Gln Val Val Ala Ile Ala Ser Asn
    690                 695                 700

Ile Gly Gly Lys Gln Ala Leu Glu Thr Val Gln Arg Leu Leu Pro Val
705                 710                 715                 720

Leu Cys Gln Asp His Gly Leu Thr Pro Glu Gln Val Val Ala Ile Ala
                725                 730                 735

Ser Asn Ile Gly Gly Lys Gln Ala Leu Glu Thr Val Gln Arg Leu Leu
            740                 745                 750

Pro Val Leu Cys Gln Ala His Gly Leu Thr Pro Asp Gln Val Val Ala
        755                 760                 765

Ile Ala Asn Asn Asn Gly Gly Lys Gln Ala Leu Glu Thr Val Gln Arg
    770                 775                 780

Leu Leu Pro Val Leu Cys Gln Ala His Gly Leu Thr Pro Ala Gln Val
785                 790                 795                 800

Val Ala Ile Ala Ser Asn Gly Gly Gly Lys Gln Ala Leu Glu Thr Val
                805                 810                 815

Gln Arg Leu Leu Pro Val Leu Cys Gln Asp His Gly Leu Thr Pro Asp
```

```
            820                 825                 830

Gln Val Val Ala Ile Ala Ser His Asp Gly Gly Lys Gln Ala Leu Glu
        835                 840                 845

Thr Val Gln Arg Leu Leu Pro Val Leu Cys Gln Asp His Gly Leu Thr
    850                 855                 860

Pro Glu Gln Val Val Ala Ile Ala Ser Asn Gly Gly Gly Lys Gln Ala
865                 870                 875                 880

Leu Glu Thr Val Gln Arg Leu Leu Pro Val Leu Cys Gln Ala His Gly
                885                 890                 895

Leu Thr Pro Asp Gln Val Val Ala Ile Ala Ser Asn Gly Gly Gly Lys
            900                 905                 910

Gln Ala Leu Glu Thr Val Gln Arg Leu Leu Pro Val Leu Cys Gln Ala
        915                 920                 925

His Gly Leu Thr Pro Ala Gln Val Val Ala Ile Ala Asn Asn Asn Gly
    930                 935                 940

Gly Lys Gln Ala Leu Glu Thr Val Gln Arg Leu Leu Pro Val Leu Cys
945                 950                 955                 960

Gln Asp His Gly Leu Thr Pro Asp Gln Val Val Ala Ile Ala Ser His
                965                 970                 975

Asp Gly Gly Lys Gln Ala Leu Glu Thr Val Gln Arg Leu Leu Pro Val
            980                 985                 990

Leu Cys Gln Asp His Gly Leu Thr  Pro Glu Gln Val Val  Ala Ile Ala
        995                 1000                1005

Ser His  Asp Gly Gly Lys Gln  Ala Leu Glu Thr Val  Gln Arg Leu
    1010                1015                1020

Leu Pro  Val Leu Cys Gln Ala  His Gly Leu Thr Pro  Glu Gln Val
    1025                1030                1035

Val Ala  Ile Ala Ser Asn Ile  Gly Gly Arg Pro Ala  Leu Glu Ser
    1040                1045                1050

Ile Val  Ala Gln Leu Ser Arg  Pro Asp Pro Ala Leu  Ala Ala Leu
    1055                1060                1065

Thr Asn  Asp His Leu Val Ala  Leu Ala Cys Leu Gly  Gly Arg Pro
    1070                1075                1080

Ala Leu  Asp Ala Val Lys Lys  Gly Leu Pro His Ala  Pro Ala Leu
    1085                1090                1095

Ile Lys  Arg Thr Asn Arg Arg  Ile Pro Glu Arg Thr  Ser His Arg
    1100                1105                1110

Val Ala  Asp His Ala Gln Val  Val Arg Val Leu Gly  Phe Phe Gln
    1115                1120                1125

Cys His  Ser His Pro Ala Gln  Ala Phe Asp Asp Ala  Met Thr Gln
    1130                1135                1140

Phe Gly  Met Ser Gly Gly Gly  Ser Gly Arg Ala Asp  Ala Leu Asp
    1145                1150                1155

Asp Phe  Asp Leu Asp Met Leu  Gly Ser Asp Ala Leu  Asp Asp Phe
    1160                1165                1170

Asp Leu  Asp Met Leu Gly Ser  Asp Ala Leu Asp Asp  Phe Asp Leu
    1175                1180                1185

Asp Met  Leu Gly Ser Asp Ala  Leu Asp Asp Phe Asp  Leu Asp Met
    1190                1195                1200

Leu His  His His His His His
    1205                1210
```

<210> SEQ ID NO 37

<211> LENGTH: 1210
<212> TYPE: PRT
<213> ORGANISM: Artificial Sequence
<220> FEATURE:
<223> OTHER INFORMATION: Synthetic Polypeptide

<400> SEQUENCE: 37

Met Gly Ala Ser Lys Gly Glu Arg Leu Phe Arg Gly Lys Val Pro Ile
1 5 10 15

Leu Val Glu Leu Lys Gly Asp Val Asn Gly His Lys Phe Ser Val Arg
20 25 30

Gly Lys Gly Lys Gly Asp Ala Thr Arg Gly Lys Leu Thr Leu Lys Phe
35 40 45

Ile Cys Thr Thr Gly Lys Leu Pro Val Pro Trp Pro Thr Leu Val Thr
50 55 60

Thr Leu Thr Tyr Gly Val Gln Cys Phe Ser Arg Tyr Pro Lys His Met
65 70 75 80

Lys Arg His Asp Phe Phe Lys Ser Ala Met Pro Lys Gly Tyr Val Gln
85 90 95

Glu Arg Thr Ile Ser Phe Lys Lys Asp Gly Lys Tyr Lys Thr Arg Ala
100 105 110

Glu Val Lys Phe Glu Gly Arg Thr Leu Val Asn Arg Ile Lys Leu Lys
115 120 125

Gly Arg Asp Phe Lys Glu Lys Gly Asn Ile Leu Gly His Lys Leu Arg
130 135 140

Tyr Asn Phe Asn Ser His Lys Val Tyr Ile Thr Ala Asp Lys Arg Lys
145 150 155 160

Asn Gly Ile Lys Ala Lys Phe Lys Ile Arg His Asn Val Lys Asp Gly
165 170 175

Ser Val Gln Leu Ala Asp His Tyr Gln Gln Asn Thr Pro Ile Gly Arg
180 185 190

Gly Pro Val Leu Leu Pro Arg Asn His Tyr Leu Ser Thr Arg Ser Lys
195 200 205

Leu Ser Lys Asp Pro Lys Glu Lys Arg Asp His Met Val Leu Leu Glu
210 215 220

Phe Val Thr Ala Ala Gly Ile Lys His Gly Arg Asp Glu Arg Tyr Lys
225 230 235 240

Thr Gly Gly Ser Gly Gly Ser Gly Gly Ser Gly Gly Ser Gly Gly Ser
245 250 255

Gly Gly Ser Gly Gly Ser Gly Gly Ser Gly Gly Thr Ala Pro Lys Lys
260 265 270

Lys Arg Lys Val Gly Ile His Arg Gly Val Pro Met Val Asp Leu Arg
275 280 285

Thr Leu Gly Tyr Ser Gln Gln Gln Gln Glu Lys Ile Lys Pro Lys Val
290 295 300

Arg Ser Thr Val Ala Gln His His Glu Ala Leu Val Gly His Gly Phe
305 310 315 320

Thr His Ala His Ile Val Ala Leu Ser Gln His Pro Ala Ala Leu Gly
325 330 335

Thr Val Ala Val Lys Tyr Gln Asp Met Ile Ala Ala Leu Pro Glu Ala
340 345 350

Thr His Glu Ala Ile Val Gly Val Gly Lys Gln Trp Ser Gly Ala Arg
355 360 365

Ala Leu Glu Ala Leu Leu Thr Val Ala Gly Glu Leu Arg Gly Pro Pro
370 375 380

-continued

```
Leu Gln Leu Asp Thr Gly Gln Leu Leu Lys Ile Ala Lys Arg Gly Gly
385                 390                 395                 400

Val Thr Ala Val Glu Ala Val His Ala Trp Arg Asn Ala Leu Thr Gly
                405                 410                 415

Ala Pro Leu Asn Leu Thr Pro Asp Gln Val Val Ala Ile Ala Ser Asn
            420                 425                 430

Gly Gly Gly Lys Gln Ala Leu Glu Thr Val Gln Arg Leu Leu Pro Val
        435                 440                 445

Leu Cys Gln Asp His Gly Leu Thr Pro Glu Gln Val Val Ala Ile Ala
    450                 455                 460

Asn Asn Asn Gly Gly Lys Gln Ala Leu Glu Thr Val Gln Arg Leu Leu
465                 470                 475                 480

Pro Val Leu Cys Gln Ala His Gly Leu Thr Pro Asp Gln Val Val Ala
                485                 490                 495

Ile Ala Asn Asn Asn Gly Gly Lys Gln Ala Leu Glu Thr Val Gln Arg
            500                 505                 510

Leu Leu Pro Val Leu Cys Gln Ala His Gly Leu Thr Pro Ala Gln Val
        515                 520                 525

Val Ala Ile Ala Ser His Asp Gly Gly Lys Gln Ala Leu Glu Thr Val
    530                 535                 540

Gln Arg Leu Leu Pro Val Leu Cys Gln Asp His Gly Leu Thr Pro Asp
545                 550                 555                 560

Gln Val Val Ala Ile Ala Ser His Asp Gly Gly Lys Gln Ala Leu Glu
                565                 570                 575

Thr Val Gln Arg Leu Leu Pro Val Leu Cys Gln Asp His Gly Leu Thr
            580                 585                 590

Pro Glu Gln Val Val Ala Ile Ala Ser His Asp Gly Gly Lys Gln Ala
        595                 600                 605

Leu Glu Thr Val Gln Arg Leu Leu Pro Val Leu Cys Gln Ala His Gly
    610                 615                 620

Leu Thr Pro Asp Gln Val Val Ala Ile Ala Ser His Asp Gly Gly Lys
625                 630                 635                 640

Gln Ala Leu Glu Thr Val Gln Arg Leu Leu Pro Val Leu Cys Gln Ala
                645                 650                 655

His Gly Leu Thr Pro Ala Gln Val Val Ala Ile Ala Asn Asn Asn Gly
            660                 665                 670

Gly Lys Gln Ala Leu Glu Thr Val Gln Arg Leu Leu Pro Val Leu Cys
        675                 680                 685

Gln Asp His Gly Leu Thr Pro Asp Gln Val Val Ala Ile Ala Asn Asn
    690                 695                 700

Asn Gly Gly Lys Gln Ala Leu Glu Thr Val Gln Arg Leu Leu Pro Val
705                 710                 715                 720

Leu Cys Gln Asp His Gly Leu Thr Pro Glu Gln Val Val Ala Ile Ala
                725                 730                 735

Ser His Asp Gly Gly Lys Gln Ala Leu Glu Thr Val Gln Arg Leu Leu
            740                 745                 750

Pro Val Leu Cys Gln Ala His Gly Leu Thr Pro Asp Gln Val Val Ala
        755                 760                 765

Ile Ala Asn Asn Asn Gly Gly Lys Gln Ala Leu Glu Thr Val Gln Arg
    770                 775                 780

Leu Leu Pro Val Leu Cys Gln Ala His Gly Leu Thr Pro Ala Gln Val
785                 790                 795                 800
```

-continued

```
Val Ala Ile Ala Ser Asn Ile Gly Gly Lys Gln Ala Leu Glu Thr Val
                805                 810                 815

Gln Arg Leu Leu Pro Val Leu Cys Gln Asp His Gly Leu Thr Pro Asp
            820                 825                 830

Gln Val Val Ala Ile Ala Asn Asn Asn Gly Gly Lys Gln Ala Leu Glu
        835                 840                 845

Thr Val Gln Arg Leu Leu Pro Val Leu Cys Gln Asp His Gly Leu Thr
    850                 855                 860

Pro Glu Gln Val Val Ala Ile Ala Asn Asn Asn Gly Gly Lys Gln Ala
865                 870                 875                 880

Leu Glu Thr Val Gln Arg Leu Leu Pro Val Leu Cys Gln Ala His Gly
                885                 890                 895

Leu Thr Pro Asp Gln Val Val Ala Ile Ala Asn Asn Asn Gly Gly Lys
            900                 905                 910

Gln Ala Leu Glu Thr Val Gln Arg Leu Leu Pro Val Leu Cys Gln Ala
        915                 920                 925

His Gly Leu Thr Pro Ala Gln Val Val Ala Ile Ala Asn Asn Asn Gly
    930                 935                 940

Gly Lys Gln Ala Leu Glu Thr Val Gln Arg Leu Leu Pro Val Leu Cys
945                 950                 955                 960

Gln Asp His Gly Leu Thr Pro Asp Gln Val Val Ala Ile Ala Ser Asn
                965                 970                 975

Gly Gly Gly Lys Gln Ala Leu Glu Thr Val Gln Arg Leu Leu Pro Val
            980                 985                 990

Leu Cys Gln Asp His Gly Leu Thr  Pro Glu Gln Val Val  Ala Ile Ala
        995                 1000                1005

Asn Asn  Asn Gly Gly Lys Gln  Ala Leu Glu Thr Val  Gln Arg Leu
    1010                1015                1020

Leu Pro  Val Leu Cys Gln Ala  His Gly Leu Thr Pro  Glu Gln Val
    1025                1030                1035

Val Ala  Ile Ala Ser Asn Gly  Gly Gly Arg Pro Ala  Leu Glu Ser
    1040                1045                1050

Ile Val  Ala Gln Leu Ser Arg  Pro Asp Pro Ala Leu  Ala Ala Leu
    1055                1060                1065

Thr Asn  Asp His Leu Val Ala  Leu Ala Cys Leu Gly  Gly Arg Pro
    1070                1075                1080

Ala Leu  Asp Ala Val Lys Lys  Gly Leu Pro His Ala  Pro Ala Leu
    1085                1090                1095

Ile Lys  Arg Thr Asn Arg Arg  Ile Pro Glu Arg Thr  Ser His Arg
    1100                1105                1110

Val Ala  Asp His Ala Gln Val  Val Arg Val Leu Gly  Phe Phe Gln
    1115                1120                1125

Cys His  Ser His Pro Ala Gln  Ala Phe Asp Asp Ala  Met Thr Gln
    1130                1135                1140

Phe Gly  Met Ser Gly Gly Gly  Ser Gly Arg Ala Asp  Ala Leu Asp
    1145                1150                1155

Asp Phe  Asp Leu Asp Met Leu  Gly Ser Asp Ala Leu  Asp Asp Phe
    1160                1165                1170

Asp Leu  Asp Met Leu Gly Ser  Asp Ala Leu Asp Asp  Phe Asp Leu
    1175                1180                1185

Asp Met  Leu Gly Ser Asp Ala  Leu Asp Asp Phe Asp  Leu Asp Met
    1190                1195                1200

Leu His  His His His His His
```

```
    1205                1210


<210> SEQ ID NO 38
<211> LENGTH: 1182
<212> TYPE: PRT
<213> ORGANISM: Artificial Sequence
<220> FEATURE:
<223> OTHER INFORMATION: Synthetic Polypeptide

<400> SEQUENCE: 38

Met Gly Ala Ser Lys Gly Glu Glu Leu Phe Asp Gly Val Val Pro Ile
1               5                   10                  15

Leu Val Glu Leu Asp Gly Asp Val Asn Gly His Glu Phe Ser Val Arg
            20                  25                  30

Gly Glu Gly Glu Gly Asp Ala Thr Glu Gly Glu Leu Thr Leu Lys Phe
        35                  40                  45

Ile Cys Thr Thr Gly Glu Leu Pro Val Pro Trp Pro Thr Leu Val Thr
    50                  55                  60

Thr Leu Thr Tyr Gly Val Gln Cys Phe Ser Asp Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
        195                 200                 205

Leu Ser Lys Asp Pro Asn Glu Asp Arg Asp His Met Val Leu Leu Glu
    210                 215                 220

Phe Val Thr Ala Ala Gly Ile Asp His Gly Met Asp Glu Leu Tyr Lys
225                 230                 235                 240

Ala Pro Lys Lys Lys Arg Lys Val Gly Ile His Arg Gly Val Pro Met
                245                 250                 255

Val Asp Leu Arg Thr Leu Gly Tyr Ser Gln Gln Gln Gln Glu Lys Ile
            260                 265                 270

Lys Pro Lys Val Arg Ser Thr Val Ala Gln His His Glu Ala Leu Val
        275                 280                 285

Gly His Gly Phe Thr His Ala His Ile Val Ala Leu Ser Gln His Pro
    290                 295                 300

Ala Ala Leu Gly Thr Val Ala Val Lys Tyr Gln Asp Met Ile Ala Ala
305                 310                 315                 320

Leu Pro Glu Ala Thr His Glu Ala Ile Val Gly Val Gly Lys Gln Trp
                325                 330                 335

Ser Gly Ala Arg Ala Leu Glu Ala Leu Leu Thr Val Ala Gly Glu Leu
            340                 345                 350

Arg Gly Pro Pro Leu Gln Leu Asp Thr Gly Gln Leu Leu Lys Ile Ala
```

```
        355                 360                 365

Lys Arg Gly Gly Val Thr Ala Val Glu Ala Val His Ala Trp Arg Asn
    370                 375                 380

Ala Leu Thr Gly Ala Pro Leu Asn Leu Thr Pro Asp Gln Val Val Ala
385                 390                 395                 400

Ile Ala Ser Asn Ile Gly Gly Lys Gln Ala Leu Glu Thr Val Gln Arg
                405                 410                 415

Leu Leu Pro Val Leu Cys Gln Asp His Gly Leu Thr Pro Glu Gln Val
            420                 425                 430

Val Ala Ile Ala Ser Asn Ile Gly Gly Lys Gln Ala Leu Glu Thr Val
        435                 440                 445

Gln Arg Leu Leu Pro Val Leu Cys Gln Ala His Gly Leu Thr Pro Asp
    450                 455                 460

Gln Val Val Ala Ile Ala Ser Asn Gly Gly Gly Lys Gln Ala Leu Glu
465                 470                 475                 480

Thr Val Gln Arg Leu Leu Pro Val Leu Cys Gln Ala His Gly Leu Thr
                485                 490                 495

Pro Ala Gln Val Val Ala Ile Ala Asn Asn Asn Gly Gly Lys Gln Ala
            500                 505                 510

Leu Glu Thr Val Gln Arg Leu Leu Pro Val Leu Cys Gln Asp His Gly
        515                 520                 525

Leu Thr Pro Asp Gln Val Val Ala Ile Ala Ser Asn Gly Gly Gly Lys
    530                 535                 540

Gln Ala Leu Glu Thr Val Gln Arg Leu Leu Pro Val Leu Cys Gln Asp
545                 550                 555                 560

His Gly Leu Thr Pro Glu Gln Val Val Ala Ile Ala Ser Asn Ile Gly
                565                 570                 575

Gly Lys Gln Ala Leu Glu Thr Val Gln Arg Leu Leu Pro Val Leu Cys
            580                 585                 590

Gln Ala His Gly Leu Thr Pro Asp Gln Val Val Ala Ile Ala Ser His
        595                 600                 605

Asp Gly Gly Lys Gln Ala Leu Glu Thr Val Gln Arg Leu Leu Pro Val
    610                 615                 620

Leu Cys Gln Ala His Gly Leu Thr Pro Ala Gln Val Val Ala Ile Ala
625                 630                 635                 640

Ser His Asp Gly Gly Lys Gln Ala Leu Glu Thr Val Gln Arg Leu Leu
                645                 650                 655

Pro Val Leu Cys Gln Asp His Gly Leu Thr Pro Asp Gln Val Val Ala
            660                 665                 670

Ile Ala Ser Asn Ile Gly Gly Lys Gln Ala Leu Glu Thr Val Gln Arg
        675                 680                 685

Leu Leu Pro Val Leu Cys Gln Asp His Gly Leu Thr Pro Glu Gln Val
    690                 695                 700

Val Ala Ile Ala Ser Asn Ile Gly Gly Lys Gln Ala Leu Glu Thr Val
705                 710                 715                 720

Gln Arg Leu Leu Pro Val Leu Cys Gln Ala His Gly Leu Thr Pro Asp
                725                 730                 735

Gln Val Val Ala Ile Ala Asn Asn Asn Gly Gly Lys Gln Ala Leu Glu
            740                 745                 750

Thr Val Gln Arg Leu Leu Pro Val Leu Cys Gln Ala His Gly Leu Thr
        755                 760                 765

Pro Ala Gln Val Val Ala Ile Ala Ser Asn Gly Gly Gly Lys Gln Ala
    770                 775                 780
```

Leu Glu Thr Val Gln Arg Leu Leu Pro Val Leu Cys Gln Asp His Gly
785 790 795 800

Leu Thr Pro Asp Gln Val Val Ala Ile Ala Ser His Asp Gly Gly Lys
805 810 815

Gln Ala Leu Glu Thr Val Gln Arg Leu Leu Pro Val Leu Cys Gln Asp
820 825 830

His Gly Leu Thr Pro Glu Gln Val Val Ala Ile Ala Ser Asn Gly Gly
835 840 845

Gly Lys Gln Ala Leu Glu Thr Val Gln Arg Leu Leu Pro Val Leu Cys
850 855 860

Gln Ala His Gly Leu Thr Pro Asp Gln Val Val Ala Ile Ala Ser Asn
865 870 875 880

Gly Gly Gly Lys Gln Ala Leu Glu Thr Val Gln Arg Leu Leu Pro Val
885 890 895

Leu Cys Gln Ala His Gly Leu Thr Pro Ala Gln Val Val Ala Ile Ala
900 905 910

Asn Asn Asn Gly Gly Lys Gln Ala Leu Glu Thr Val Gln Arg Leu Leu
915 920 925

Pro Val Leu Cys Gln Asp His Gly Leu Thr Pro Asp Gln Val Val Ala
930 935 940

Ile Ala Ser His Asp Gly Gly Lys Gln Ala Leu Glu Thr Val Gln Arg
945 950 955 960

Leu Leu Pro Val Leu Cys Gln Asp His Gly Leu Thr Pro Glu Gln Val
965 970 975

Val Ala Ile Ala Ser His Asp Gly Gly Lys Gln Ala Leu Glu Thr Val
980 985 990

Gln Arg Leu Leu Pro Val Leu Cys Gln Ala His Gly Leu Thr Pro Glu
995 1000 1005

Gln Val Val Ala Ile Ala Ser Asn Ile Gly Gly Arg Pro Ala Leu
1010 1015 1020

Glu Ser Ile Val Ala Gln Leu Ser Arg Pro Asp Pro Ala Leu Ala
1025 1030 1035

Ala Leu Thr Asn Asp His Leu Val Ala Leu Ala Cys Leu Gly Gly
1040 1045 1050

Arg Pro Ala Leu Asp Ala Val Lys Lys Gly Leu Pro His Ala Pro
1055 1060 1065

Ala Leu Ile Lys Arg Thr Asn Arg Arg Ile Pro Glu Arg Thr Ser
1070 1075 1080

His Arg Val Ala Asp His Ala Gln Val Val Arg Val Leu Gly Phe
1085 1090 1095

Phe Gln Cys His Ser His Pro Ala Gln Ala Phe Asp Asp Ala Met
1100 1105 1110

Thr Gln Phe Gly Met Ser Gly Gly Gly Ser Gly Arg Ala Asp Ala
1115 1120 1125

Leu Asp Asp Phe Asp Leu Asp Met Leu Gly Ser Asp Ala Leu Asp
1130 1135 1140

Asp Phe Asp Leu Asp Met Leu Gly Ser Asp Ala Leu Asp Asp Phe
1145 1150 1155

Asp Leu Asp Met Leu Gly Ser Asp Ala Leu Asp Asp Phe Asp Leu
1160 1165 1170

Asp Met Leu His His His His His His
1175 1180

<210> SEQ ID NO 39
<211> LENGTH: 1182
<212> TYPE: PRT
<213> ORGANISM: Artificial Sequence
<220> FEATURE:
<223> OTHER INFORMATION: Synthetic Polypeptide

<400> SEQUENCE: 39

Met Gly Ala Ser Lys Gly Glu Glu Leu Phe Asp Gly Val Val Pro Ile
1 5 10 15

Leu Val Glu Leu Asp Gly Asp Val Asn Gly His Glu Phe Ser Val Arg
20 25 30

Gly Glu Gly Glu Gly Asp Ala Thr Glu Gly Glu Leu Thr Leu Lys Phe
35 40 45

Ile Cys Thr Thr Gly Glu Leu Pro Val Pro Trp Pro Thr Leu Val Thr
50 55 60

Thr Leu Thr Tyr Gly Val Gln Cys Phe Ser Asp Tyr Pro Asp His Met
65 70 75 80

Asp Gln His Asp Phe Phe Lys Ser Ala Met Pro Glu Gly Tyr Val Gln
85 90 95

Glu Arg Thr Ile Ser Phe Lys Asp Asp Gly Thr Tyr Lys Thr Arg Ala
100 105 110

Glu Val Lys Phe Glu Gly Asp Thr Leu Val Asn Arg Ile Glu Leu Lys
115 120 125

Gly Ile Asp Phe Lys Glu Asp Gly Asn Ile Leu Gly His Lys Leu Glu
130 135 140

Tyr Asn Phe Asn Ser His Asp Val Tyr Ile Thr Ala Asp Lys Gln Glu
145 150 155 160

Asn Gly Ile Lys Ala Glu Phe Glu Ile Arg His Asn Val Glu Asp Gly
165 170 175

Ser Val Gln Leu Ala Asp His Tyr Gln Gln Asn Thr Pro Ile Gly Asp
180 185 190

Gly Pro Val Leu Leu Pro Asp Asp His Tyr Leu Ser Thr Glu Ser Ala
195 200 205

Leu Ser Lys Asp Pro Asn Glu Asp Arg Asp His Met Val Leu Leu Glu
210 215 220

Phe Val Thr Ala Ala Gly Ile Asp His Gly Met Asp Glu Leu Tyr Lys
225 230 235 240

Ala Pro Lys Lys Lys Arg Lys Val Gly Ile His Arg Gly Val Pro Met
245 250 255

Val Asp Leu Arg Thr Leu Gly Tyr Ser Gln Gln Gln Gln Glu Lys Ile
260 265 270

Lys Pro Lys Val Arg Ser Thr Val Ala Gln His His Glu Ala Leu Val
275 280 285

Gly His Gly Phe Thr His Ala His Ile Val Ala Leu Ser Gln His Pro
290 295 300

Ala Ala Leu Gly Thr Val Ala Val Lys Tyr Gln Asp Met Ile Ala Ala
305 310 315 320

Leu Pro Glu Ala Thr His Glu Ala Ile Val Gly Val Gly Lys Gln Trp
325 330 335

Ser Gly Ala Arg Ala Leu Glu Ala Leu Leu Thr Val Ala Gly Glu Leu
340 345 350

Arg Gly Pro Pro Leu Gln Leu Asp Thr Gly Gln Leu Leu Lys Ile Ala
355 360 365

-continued

```
Lys Arg Gly Gly Val Thr Ala Val Glu Ala Val His Ala Trp Arg Asn
    370                 375                 380

Ala Leu Thr Gly Ala Pro Leu Asn Leu Thr Pro Asp Gln Val Val Ala
385                 390                 395                 400

Ile Ala Ser Asn Gly Gly Gly Lys Gln Ala Leu Glu Thr Val Gln Arg
                405                 410                 415

Leu Leu Pro Val Leu Cys Gln Asp His Gly Leu Thr Pro Glu Gln Val
            420                 425                 430

Val Ala Ile Ala Asn Asn Asn Gly Gly Lys Gln Ala Leu Glu Thr Val
        435                 440                 445

Gln Arg Leu Leu Pro Val Leu Cys Gln Ala His Gly Leu Thr Pro Asp
    450                 455                 460

Gln Val Val Ala Ile Ala Asn Asn Asn Gly Gly Lys Gln Ala Leu Glu
465                 470                 475                 480

Thr Val Gln Arg Leu Leu Pro Val Leu Cys Gln Ala His Gly Leu Thr
                485                 490                 495

Pro Ala Gln Val Val Ala Ile Ala Ser His Asp Gly Gly Lys Gln Ala
            500                 505                 510

Leu Glu Thr Val Gln Arg Leu Leu Pro Val Leu Cys Gln Asp His Gly
        515                 520                 525

Leu Thr Pro Asp Gln Val Val Ala Ile Ala Ser His Asp Gly Gly Lys
    530                 535                 540

Gln Ala Leu Glu Thr Val Gln Arg Leu Leu Pro Val Leu Cys Gln Asp
545                 550                 555                 560

His Gly Leu Thr Pro Glu Gln Val Val Ala Ile Ala Ser His Asp Gly
                565                 570                 575

Gly Lys Gln Ala Leu Glu Thr Val Gln Arg Leu Leu Pro Val Leu Cys
            580                 585                 590

Gln Ala His Gly Leu Thr Pro Asp Gln Val Val Ala Ile Ala Ser His
        595                 600                 605

Asp Gly Gly Lys Gln Ala Leu Glu Thr Val Gln Arg Leu Leu Pro Val
    610                 615                 620

Leu Cys Gln Ala His Gly Leu Thr Pro Ala Gln Val Val Ala Ile Ala
625                 630                 635                 640

Asn Asn Asn Gly Gly Lys Gln Ala Leu Glu Thr Val Gln Arg Leu Leu
                645                 650                 655

Pro Val Leu Cys Gln Asp His Gly Leu Thr Pro Asp Gln Val Val Ala
            660                 665                 670

Ile Ala Asn Asn Asn Gly Gly Lys Gln Ala Leu Glu Thr Val Gln Arg
        675                 680                 685

Leu Leu Pro Val Leu Cys Gln Asp His Gly Leu Thr Pro Glu Gln Val
    690                 695                 700

Val Ala Ile Ala Ser His Asp Gly Gly Lys Gln Ala Leu Glu Thr Val
705                 710                 715                 720

Gln Arg Leu Leu Pro Val Leu Cys Gln Ala His Gly Leu Thr Pro Asp
                725                 730                 735

Gln Val Val Ala Ile Ala Asn Asn Asn Gly Gly Lys Gln Ala Leu Glu
            740                 745                 750

Thr Val Gln Arg Leu Leu Pro Val Leu Cys Gln Ala His Gly Leu Thr
        755                 760                 765

Pro Ala Gln Val Val Ala Ile Ala Ser Asn Ile Gly Gly Lys Gln Ala
    770                 775                 780

Leu Glu Thr Val Gln Arg Leu Leu Pro Val Leu Cys Gln Asp His Gly
```

```
785                 790                 795                 800

Leu Thr Pro Asp Gln Val Val Ala Ile Ala Asn Asn Asn Gly Gly Lys
                805                 810                 815

Gln Ala Leu Glu Thr Val Gln Arg Leu Leu Pro Val Leu Cys Gln Asp
            820                 825                 830

His Gly Leu Thr Pro Glu Gln Val Val Ala Ile Ala Asn Asn Asn Gly
        835                 840                 845

Gly Lys Gln Ala Leu Glu Thr Val Gln Arg Leu Leu Pro Val Leu Cys
    850                 855                 860

Gln Ala His Gly Leu Thr Pro Asp Gln Val Val Ala Ile Ala Asn Asn
865                 870                 875                 880

Asn Gly Gly Lys Gln Ala Leu Glu Thr Val Gln Arg Leu Leu Pro Val
                885                 890                 895

Leu Cys Gln Ala His Gly Leu Thr Pro Ala Gln Val Val Ala Ile Ala
            900                 905                 910

Asn Asn Asn Gly Gly Lys Gln Ala Leu Glu Thr Val Gln Arg Leu Leu
        915                 920                 925

Pro Val Leu Cys Gln Asp His Gly Leu Thr Pro Asp Gln Val Val Ala
    930                 935                 940

Ile Ala Ser Asn Gly Gly Gly Lys Gln Ala Leu Glu Thr Val Gln Arg
945                 950                 955                 960

Leu Leu Pro Val Leu Cys Gln Asp His Gly Leu Thr Pro Glu Gln Val
                965                 970                 975

Val Ala Ile Ala Asn Asn Asn Gly Gly Lys Gln Ala Leu Glu Thr Val
            980                 985                 990

Gln Arg Leu Leu Pro Val Leu Cys  Gln Ala His Gly Leu  Thr Pro Glu
        995                 1000                1005

Gln Val  Val Ala Ile Ala Ser  Asn Gly Gly Gly Arg  Pro Ala Leu
    1010                1015                1020

Glu Ser  Ile Val Ala Gln Leu  Ser Arg Pro Asp Pro  Ala Leu Ala
    1025                1030                1035

Ala Leu  Thr Asn Asp His Leu  Val Ala Leu Ala Cys  Leu Gly Gly
    1040                1045                1050

Arg Pro  Ala Leu Asp Ala Val  Lys Lys Gly Leu Pro  His Ala Pro
    1055                1060                1065

Ala Leu  Ile Lys Arg Thr Asn  Arg Arg Ile Pro Glu  Arg Thr Ser
    1070                1075                1080

His Arg  Val Ala Asp His Ala  Gln Val Val Arg Val  Leu Gly Phe
    1085                1090                1095

Phe Gln  Cys His Ser His Pro  Ala Gln Ala Phe Asp  Asp Ala Met
    1100                1105                1110

Thr Gln  Phe Gly Met Ser Gly  Gly Gly Ser Gly Arg  Ala Asp Ala
    1115                1120                1125

Leu Asp  Asp Phe Asp Leu Asp  Met Leu Gly Ser Asp  Ala Leu Asp
    1130                1135                1140

Asp Phe  Asp Leu Asp Met Leu  Gly Ser Asp Ala Leu  Asp Asp Phe
    1145                1150                1155

Asp Leu  Asp Met Leu Gly Ser  Asp Ala Leu Asp Asp  Phe Asp Leu
    1160                1165                1170

Asp Met  Leu His His His His  His His
    1175                1180
```

<210> SEQ ID NO 40

<211> LENGTH: 240
<212> TYPE: PRT
<213> ORGANISM: Artificial Sequence
<220> FEATURE:
<223> OTHER INFORMATION: Synthetic Polypeptide

<400> SEQUENCE: 40

```
Met Gly Ala Ser Lys Gly Glu Glu Leu Phe Asp Gly Val Val Pro Ile
1               5                   10                  15

Leu Val Glu Leu Asp Gly Asp Val Asn Gly His Glu Phe Ser Val Arg
            20                  25                  30

Gly Glu Gly Glu Gly Asp Ala Thr Glu Gly Glu Leu Thr Leu Lys Phe
        35                  40                  45

Ile Cys Thr Thr Gly Glu Leu Pro Val Pro Trp Pro Thr Leu Val Thr
    50                  55                  60

Thr Leu Thr Tyr Gly Val Gln Cys Phe Ser Asp Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
        195                 200                 205

Leu Ser Lys Asp Pro Asn Glu Asp Arg Asp His Met Val Leu Leu Glu
    210                 215                 220

Phe Val Thr Ala Ala Gly Ile Asp His Gly Met Asp Glu Leu Tyr Lys
225                 230                 235                 240
```

<210> SEQ ID NO 41
<211> LENGTH: 153
<212> TYPE: PRT
<213> ORGANISM: Artificial Sequence
<220> FEATURE:
<223> OTHER INFORMATION: Synthetic Polypeptide

<400> SEQUENCE: 41

```
Ala Pro Lys Lys Lys Arg Lys Val Gly Ile His Arg Gly Val Pro Met
1               5                   10                  15

Val Asp Leu Arg Thr Leu Gly Tyr Ser Gln Gln Gln Gln Glu Lys Ile
            20                  25                  30

Lys Pro Lys Val Arg Ser Thr Val Ala Gln His His Glu Ala Leu Val
        35                  40                  45

Gly His Gly Phe Thr His Ala His Ile Val Ala Leu Ser Gln His Pro
    50                  55                  60

Ala Ala Leu Gly Thr Val Ala Val Lys Tyr Gln Asp Met Ile Ala Ala
65                  70                  75                  80

Leu Pro Glu Ala Thr His Glu Ala Ile Val Gly Val Gly Lys Gln Trp
```

```
                85                  90                  95

Ser Gly Ala Arg Ala Leu Glu Ala Leu Leu Thr Val Ala Gly Glu Leu
            100                 105                 110

Arg Gly Pro Pro Leu Gln Leu Asp Thr Gly Gln Leu Leu Lys Ile Ala
        115                 120                 125

Lys Arg Gly Gly Val Thr Ala Val Glu Ala Val His Ala Trp Arg Asn
    130                 135                 140

Ala Leu Thr Gly Ala Pro Leu Asn Leu
145                 150


<210> SEQ ID NO 42
<211> LENGTH: 99
<212> TYPE: PRT
<213> ORGANISM: Artificial Sequence
<220> FEATURE:
<223> OTHER INFORMATION: Synthetic Polypeptide

<400> SEQUENCE: 42

Leu Glu Ser Ile Val Ala Gln Leu Ser Arg Pro Asp Pro Ala Leu Ala
1               5                   10                  15

Ala Leu Thr Asn Asp His Leu Val Ala Leu Ala Cys Leu Gly Gly Arg
            20                  25                  30

Pro Ala Leu Asp Ala Val Lys Lys Gly Leu Pro His Ala Pro Ala Leu
        35                  40                  45

Ile Lys Arg Thr Asn Arg Arg Ile Pro Glu Arg Thr Ser His Arg Val
    50                  55                  60

Ala Asp His Ala Gln Val Val Arg Val Leu Gly Phe Phe Gln Cys His
65                  70                  75                  80

Ser His Pro Ala Gln Ala Phe Asp Asp Ala Met Thr Gln Phe Gly Met
                85                  90                  95

Ser Gly Gly


<210> SEQ ID NO 43
<211> LENGTH: 4104
<212> TYPE: DNA
<213> ORGANISM: Streptococcus pyogenes

<400> SEQUENCE: 43

atggataaga aatactcaat aggcttagat atcggcacaa atagcgtcgg atgggcggtg      60

atcactgatg attataaggt tccgtctaaa aagttcaagg ttctgggaaa tacagaccgc     120

cacagtatca aaaaaaatct tataggggct cttttatttg gcagtggaga gacagcggaa     180

gcgactcgtc tcaaacggac agctcgtaga aggtatacac gtcggaagaa tcgtatttgt     240

tatctacagg agatttttc aaatgagatg gcgaaagtag atgatagttt ctttcatcga      300

cttgaagagt cttttttggt ggaagaagac aagaagcatg aacgtcatcc tatttttgga     360

aatatagtag atgaagttgc ttatcatgag aaatatccaa ctatctatca tctgcgaaaa     420

aaattggcag attctactga taaagcggat ttgcgcttaa tctatttggc cttagcgcat     480

atgattaagt ttcgtggtca tttttttgatt gagggagatt taaatcctga taatagtgat     540

gtggacaaac tatttatcca gttggtacaa atctacaatc aattatttga agaaaaccct     600

attaacgcaa gtagagtaga tgctaaagcg attctttctg cacgattgag taaatcaaga     660

cgattagaaa atctcattgc tcagctcccc ggtgagaaga gaaatggctt gtttgggaat     720

ctcattgctt tgtcattggg attgacccct aattttaaat caaattttga tttggcagaa     780

gatgctaaat tacagctttc aaaagatact tacgatgatg atttagataa tttattggcg     840
```

caaattggag atcaatatgc tgatttgttt ttggcagcta agaatttatc agatgctatt 900
ttactttcag atatcctaag agtaaatagt gaaataacta aggctcccct atcagcttca 960
atgattaagc gctacgatga acatcatcaa gacttgactc ttttaaaagc tttagttcga 1020
caacaacttc cagaaaagta taaagaaatc ttttttgatc aatcaaaaaa cggatatgca 1080
ggttatattg atgggggagc tagccaagaa gaattttata aatttatcaa accaatttta 1140
gaaaaaatgg atggtactga ggaattattg gtgaaactaa atcgtgaaga tttgctgcgc 1200
aagcaacgga cctttgacaa cggctctatt ccccatcaaa ttcacttggg tgagctgcat 1260
gctattttga gaagacaaga agacttttat ccatttttaa aagacaatcg tgagaagatt 1320
gaaaaaatct tgacttttcg aattccttat tatgttggtc cattggcgcg tggcaatagt 1380
cgttttgcat ggatgactcg gaagtctgaa gaaacaatta ccccatggaa ttttgaagaa 1440
gttgtcgata aaggtgcttc agctcaatca tttattgaac gcatgacaaa ctttgataaa 1500
aatcttccaa atgaaaaagt actaccaaaa catagtttgc tttatgagta ttttacggtt 1560
tataacgaat tgacaaaggt caaatatgtt actgagggaa tgcgaaaacc agcatttctt 1620
tcaggtgaac agaagaaagc cattgttgat ttactcttca aaacaaatcg aaaagtaacc 1680
gttaagcaat taaaagaaga ttatttcaaa aaaatagaat gttttgatag tgttgaaatt 1740
tcaggagttg aagatagatt taatgcttca ttaggcgcct accatgattt gctaaaaatt 1800
attaaagata aagatttttt ggataatgaa gaaaatgaag atatcttaga ggatattgtt 1860
ttaacattga ccttatttga agatagggg atgattgagg aaagacttaa aacatatgct 1920
cacctctttg atgataaggt gatgaaacag cttaaacgtc gccgttatac tggttgggga 1980
cgtttgtctc gaaaattgat taatggtatt agggataagc aatctggcaa aacaatatta 2040
gatttttga aatcagatgg ttttgccaat cgcaatttta tgcagctgat ccatgatgat 2100
agtttgacat ttaaagaaga tattcaaaaa gcacaggtgt ctggacaagg ccatagttta 2160
catgaacaga ttgctaactt agctggcagt cctgctatta aaaaaggtat tttacagact 2220
gtaaaaattg ttgatgaact ggtcaaagta atggggcata agccagaaaa tatcgttatt 2280
gaaatggcac gtgaaaatca gacaactcaa aagggccaga aaaattcgcg agagcgtatg 2340
aaacgaatcg aagaaggtat caaagaatta ggaagtcaga ttcttaaaga gcatcctgtt 2400
gaaaatactc aattgcaaaa tgaaaagctc tatctctatt atctacaaaa tggaagagac 2460
atgtatgtgg accaagaatt agatattaat cgtttaagtg attatgatgt cgatcacatt 2520
gttccacaaa gtttcattaa agacgattca atagacaata aggtactaac gcgttctgat 2580
aaaaatcgtg gtaaatcgga taacgttcca agtgaagaag tagtcaaaaa gatgaaaaac 2640
tattggagac aacttctaaa cgccaagtta atcactcaac gtaagtttga taatttaacg 2700
aaagctgaac gtggaggttt gagtgaactt gataaagctg gttttatcaa acgccaattg 2760
gttgaaactc gccaaatcac taagcatgtg gcacaaattt tggatagtcg catgaatact 2820
aaatacgatg aaaatgataa acttattcga gaggttaaag tgattacctt aaaatctaaa 2880
ttagtttctg acttccgaaa agatttccaa ttctataaag tacgtgagat taacaattac 2940
catcatgccc atgatgcgta tctaaatgcc gtcgttggaa ctgctttgat taagaaatat 3000
ccaaaacttg aatcggagtt tgtctatggt gattataaag tttatgatgt tcgtaaaatg 3060
attgctaagt ctgagcaaga aataggcaaa gcaaccgcaa aatatttctt ttactctaat 3120
atcatgaact tcttcaaaac agaaattaca cttgcaaatg gagagattcg caaacgccct 3180

```
ctaatcgaaa ctaatgggga aactggagaa attgtctggg ataaagggcg agattttgcc   3240

acagtgcgca aagtattgtc catgccccaa gtcaatattg tcaagaaaac agaagtacag   3300

acaggcggat tctccaagga gtcaatttta ccaaaaagaa attcggacaa gcttattgct   3360

cgtaaaaaag actgggatcc aaaaaaatat ggtggttttg atagtccaac ggtagcttat   3420

tcagtcctag tggttgctaa ggtggaaaaa gggaaatcga agaagttaaa atccgttaaa   3480

gagttactag ggatcacaat tatggaaaga agttcctttg aaaaaaatcc gattgacttt   3540

ttagaagcta aaggatataa ggaagttaaa aaagacttaa tcattaaact acctaaatat   3600

agtctttttg agttagaaaa cggtcgtaaa cggatgctgg ctagtgccgg agaattacaa   3660

aaaggaaatg agctggctct gccaagcaaa tatgtgaatt ttttatattt agctagtcat   3720

tatgaaaagt tgaagggtag tccagaagat aacgaacaaa aacaattgtt tgtggagcag   3780

cataagcatt atttagatga gattattgag caaatcagtg aattttctaa gcgtgttatt   3840

ttagcagatg ccaatttaga taaagttctt agtgcatata acaaacatag agacaaacca   3900

atacgtgaac aagcagaaaa tattattcat ttatttacgt tgacgaatct tggagctccc   3960

gctgctttta aatattttga tacaacaatt gatcgtaaac gatatacgtc tacaaaagaa   4020

gttttagatg ccactcttat ccatcaatcc atcactggtc tttatgaaac acgcattgat   4080

ttgagtcagc taggaggtga ctga                                          4104
```

<210> SEQ ID NO 44
<211> LENGTH: 1368
<212> TYPE: PRT
<213> ORGANISM: Streptococcus pyogenes

<400> SEQUENCE: 44

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205
```

```
Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
```

-continued

```
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                 1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050
```

-continued

```
Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 45
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 45

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30
```

-continued

```
Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445
```

-continued

```
Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
```

-continued

```
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275
```

Arg Val Ile Leu Ala Asp Ala Asn Leu Asp Lys Val Leu Ser Ala
1280 1285 1290

Tyr Asn Lys His Arg Asp Lys Pro Ile Arg Glu Gln Ala Glu Asn
1295 1300 1305

Ile Ile His Leu Phe Thr Leu Thr Asn Leu Gly Ala Pro Ala Ala
1310 1315 1320

Phe Lys Tyr Phe Asp Thr Thr Ile Asp Arg Lys Arg Tyr Thr Ser
1325 1330 1335

Thr Lys Glu Val Leu Asp Ala Thr Leu Ile His Gln Ser Ile Thr
1340 1345 1350

Gly Leu Tyr Glu Thr Arg Ile Asp Leu Ser Gln Leu Gly Gly Asp
1355 1360 1365

<210> SEQ ID NO 46
<211> LENGTH: 1368
<212> TYPE: PRT
<213> ORGANISM: Artificial Sequence
<220> FEATURE:
<223> OTHER INFORMATION: Synthetic Polypeptide

<400> SEQUENCE: 46

Met Asp Lys Lys Tyr Ser Ile Gly Leu Ala Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

Asp Leu Ala Glu Asp Ala Lys Leu Gln Leu Ser Lys Asp Thr Tyr Asp
260 265 270

-continued

```
Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685
```

-continued

```
Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
```

```
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365


<210> SEQ ID NO 47
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 47

Met Ala Pro Lys Lys Lys Arg Lys Val Gly Ile His Arg Gly Val Pro
1               5                   10                  15


<210> SEQ ID NO 48
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 48

Met Asp Tyr Lys Asp His Asp Gly Asp Tyr Lys Asp His Asp Ile Asp
1               5                   10                  15
```

```
Tyr Lys Asp Asp Asp Asp Lys
            20


<210> SEQ ID NO 49
<211> LENGTH: 198
<212> TYPE: PRT
<213> ORGANISM: Artificial Sequence
<220> FEATURE:
<223> OTHER INFORMATION: Synthetic Polypeptide

<400> SEQUENCE: 49

Gly Ser Gln Leu Val Lys Ser Glu Leu Glu Glu Lys Lys Ser Glu Leu
1               5                   10                  15

Arg His Lys Leu Lys Tyr Val Pro His Glu Tyr Ile Glu Leu Ile Glu
            20                  25                  30

Ile Ala Arg Asn Ser Thr Gln Asp Arg Ile Leu Glu Met Lys Val Met
        35                  40                  45

Glu Phe Phe Met Lys Val Tyr Gly Tyr Arg Gly Lys His Leu Gly Gly
    50                  55                  60

Ser Arg Lys Pro Asp Gly Ala Ile Tyr Thr Val Gly Ser Pro Ile Asp
65                  70                  75                  80

Tyr Gly Val Ile Val Asp Thr Lys Ala Tyr Ser Gly Gly Tyr Asn Leu
                85                  90                  95

Pro Ile Gly Gln Ala Asp Glu Met Gln Arg Tyr Val Glu Glu Asn Gln
            100                 105                 110

Thr Arg Asn Lys His Ile Asn Pro Asn Glu Trp Trp Lys Val Tyr Pro
        115                 120                 125

Ser Ser Val Thr Glu Phe Lys Phe Leu Phe Val Ser Gly His Phe Lys
    130                 135                 140

Gly Asn Tyr Lys Ala Gln Leu Thr Arg Leu Asn His Ile Thr Asn Cys
145                 150                 155                 160

Asn Gly Ala Val Leu Ser Val Glu Glu Leu Leu Ile Gly Gly Glu Met
                165                 170                 175

Ile Lys Ala Gly Thr Leu Thr Leu Glu Glu Val Arg Arg Lys Phe Asn
            180                 185                 190

Asn Gly Glu Ile Asn Phe
        195


<210> SEQ ID NO 50
<211> LENGTH: 4836
<212> TYPE: DNA
<213> ORGANISM: Artificial Sequence
<220> FEATURE:
<223> OTHER INFORMATION: Synthetic Polynucleotide

<400> SEQUENCE: 50

atggataaaa agtattctat tggtttagct atcggcacta attccgttgg atgggctgtc      60

ataaccgatg aatacaaagt accttcaaag aaatttaagg tgttggggaa cacagaccgt     120

cattcgatta aaaagaatct tatcggtgcc ctcctattcg atagtggcga aacggcagag     180

gcgactcgcc tgaaacgaac cgctcggaga aggtatacac gtcgcaagaa ccgaatatgt     240

tacttacaag aaatttttag caatgagatg gccaaagttg acgattcttt ctttcaccgt     300

ttggaagagt ccttccttgt cgaagaggac aagaaacatg aacggcaccc catctttgga     360

aacatagtag atgaggtggc atatcatgaa aagtacccaa cgatttatca cctcagaaaa     420

aagctagttg actcaactga taaagcggac ctgaggttaa tctacttggc tcttgcccat     480

atgataaagt tccgtgggca ctttctcatt gagggtgatc taaatccgga caactcggat     540
```

-continued

```
gtcgacaaac tgttcatcca gttagtacaa acctataatc agttgtttga agagaaccct    600
ataaatgcaa gtggcgtgga tgcgaaggct attcttagcg cccgcctctc taaatcccga    660
cggctagaaa acctgatcgc acaattaccc ggagagaaga aaaatgggtt gttcggtaac    720
cttatagcgc tctcactagg cctgacacca aattttaagt cgaacttcga cttagctgaa    780
gatgccaaat tgcagcttag taaggacacg tacgatgacg atctcgacaa tctactggca    840
caaattggag atcagtatgc ggacttattt ttggctgcca aaaaccttag cgatgcaatc    900
ctcctatctg acatactgag agttaatact gagattacca aggcgccgtt atccgcttca    960
atgatcaaaa ggtacgatga acatcaccaa gacttgacac ttctcaaggc cctagtccgt   1020
cagcaactgc ctgagaaata taaggaaata ttctttgatc agtcgaaaaa cgggtacgca   1080
ggttatattg acggcggagc gagtcaagag gaattctaca agtttatcaa acccatatta   1140
gagaagatgg atgggacgga agagttgctt gtaaaactca atcgcgaaga tctactgcga   1200
aagcagcgga ctttcgacaa cggtagcatt ccacatcaaa tccacttagg cgaattgcat   1260
gctatactta gaaggcagga ggatttttat ccgttcctca aagacaatcg tgaaaagatt   1320
gagaaaatcc taacctttcg cataccttac tatgtgggac ccctggcccg agggaactct   1380
cggttcgcat ggatgacaag aaagtccgaa gaaacgatta ctccatggaa ttttgaggaa   1440
gttgtcgata aaggtgcgtc agctcaatcg ttcatcgaga ggatgaccaa ctttgacaag   1500
aatttaccga acgaaaaagt attgcctaag cacagtttac tttacgagta tttcacagtg   1560
tacaatgaac tcacgaaagt taagtatgtc actgagggca tgcgtaaacc cgcctttcta   1620
agcggagaac agaagaaagc aatagtagat ctgttattca agaccaaccg caaagtgaca   1680
gttaagcaat tgaaagagga ctactttaag aaaattgaat gcttcgattc tgtcgagatc   1740
tccggggtag aagatcgatt taatgcgtca cttggtacgt atcatgacct cctaaagata   1800
attaaagata aggacttcct ggataacgaa gagaatgaag atatcttaga agatatagtg   1860
ttgactctta ccctctttga agatcgggaa atgattgagg aaagactaaa aacatacgct   1920
cacctgttcg acgataaggt tatgaaacag ttaaagaggc gtcgctatac gggctgggga   1980
cgattgtcgc ggaaacttat caacgggata agagacaagc aaagtggtaa aactattctc   2040
gattttctaa agagcgacgg cttcgccaat aggaacttta tgcagctgat ccatgatgac   2100
tctttaacct tcaaagagga tatacaaaag gcacaggttt ccggacaagg ggactcattg   2160
cacgaacata ttgcgaatct tgctggttcg ccagccatca aaaagggcat actccagaca   2220
gtcaaagtag tggatgagct agttaaggtc atgggacgtc acaaaccgga aaacattgta   2280
atcgagatgg cacgcgaaaa tcaaacgact cagaaggggc aaaaaaacag tcgagagcgg   2340
atgaagagaa tagaagaggg tattaaagaa ctgggcagcc agatcttaaa ggagcatcct   2400
gtggaaaata cccaattgca gaacgagaaa ctttacctct attacctaca aaatggaagg   2460
gacatgtatg ttgatcagga actggacata aaccgtttat ctgattacga cgtcgatgcc   2520
attgtacccc aatccttttt gaaggacgat tcaatcgaca ataaagtgct tacacgctcg   2580
gataagaacc gagggaaaag tgacaatgtt ccaagcgagg aagtcgtaaa gaaaatgaag   2640
aactattggc ggcagctcct aaatgcgaaa ctgataacgc aaagaaagtt cgataactta   2700
actaaagctg agaggggtgg cttgtctgaa cttgacaagg ccggatttat taaacgtcag   2760
ctcgtggaaa cccgccaaat cacaaagcat gttgcacaga tactagattc ccgaatgaat   2820
acgaaatacg acgagaacga taagctgatt cgggaagtca aagtaatcac tttaaagtca   2880
```

-continued

```
aaattggtgt cggacttcag aaaggatttt caattctata aagttaggga gataaataac   2940

taccaccatg cgcacgacgc ttatcttaat gccgtcgtag ggaccgcact cattaagaaa   3000

tacccgaagc tagaaagtga gtttgtgtat ggtgattaca aagtttatga cgtccgtaag   3060

atgatcgcga aaagcgaaca ggagataggc aaggctacag ccaaatactt cttttattct   3120

aacattatga atttctttaa gacggaaatc actctggcaa acggagagat acgcaaacga   3180

cctttaattg aaaccaatgg ggagacaggt gaaatcgtat gggataaggg ccgggacttc   3240

gcgacggtga gaaaagtttt gtccatgccc caagtcaaca tagtaaagaa aactgaggtg   3300

cagaccggag ggttttcaaa ggaatcgatt cttccaaaaa ggaatagtga taagctcatc   3360

gctcgtaaaa aggactggga cccgaaaaag tacggtggct tcgatagccc tacagttgcc   3420

tattctgtcc tagtagtggc aaaagttgag aagggaaaat ccaagaaact gaagtcagtc   3480

aaagaattat tggggataac gattatggag cgctcgtctt ttgaaaagaa ccccatcgac   3540

ttccttgagg cgaaaggtta caaggaagta aaaaaggatc tcataattaa actaccaaag   3600

tatagtctgt ttgagttaga aaatggccga aaacggatgt tggctagcgc cggagagctt   3660

caaaagggga acgaactcgc actaccgtct aaatacgtga atttcctgta tttagcgtcc   3720

cattacgaga agttgaaagg ttcacctgaa gataacgaac agaagcaact tttgttgag    3780

cagcacaaac attatctcga cgaaatcata gagcaaattt cggaattcag taagagagtc   3840

atcctagctg atgccaatct ggacaaagta ttaagcgcat acaacaagca cagggataaa   3900

cccatacgtg agcaggcgga aaatattatc catttgttta ctcttaccaa cctcggcgct   3960

ccagccgcat tcaagtattt tgacacaacg atagatcgca aacgatacac ttctaccaag   4020

gaggtgctag acgcgacact gattcaccaa tccatcacgg gattatatga aactcggata   4080

gatttgtcac agcttggggg tgacggatcc cccaagaaga agaggaaagt ctcgagcgac   4140

tacaaagacc atgacggtga ttataaagat catgacatcg attacaagga tgacgatgac   4200

aaggctgcag gatcaggtgg aagtggcggc agcggaggtt ctggatccca actagtcaaa   4260

agtgaactgg aggagaagaa atctgaactt cgtcataaat tgaaatatgt gcctcatgaa   4320

tatattgaat taattgaaat tgccagaaat tccactcagg atagaattct tgaaatgaag   4380

gtaatggaat tttttatgaa agtttatgga tatagaggta aacatttggg tggatcaagg   4440

aaaccggacg gagcaattta tactgtcgga tctcctattg attacggtgt gatcgtggat   4500

actaaagctt atagcggagg ttataatctg ccaattggcc aagcagatga aatgcaacga   4560

tatgtcgaag aaaatcaaac acgaaacaaa catatcaacc ctaatgaatg gtggaaagtc   4620

tatccatctt ctgtaacgga atttaagttt ttatttgtga gtggtcactt taaaggaaac   4680

tacaaagctc agcttacacg attaaatcat atcactaatt gtaatggagc tgttcttagt   4740

gtagaagagc ttttaattgg tggagaaatg attaaagccg gcacattaac cttagaggaa   4800

gtcagacgga aatttaataa cggcgagata aacttt                             4836
```

```
<210> SEQ ID NO 51
<211> LENGTH: 4845
<212> TYPE: DNA
<213> ORGANISM: Artificial Sequence
<220> FEATURE:
<223> OTHER INFORMATION: Synthetic Polynucleotide

<400> SEQUENCE: 51

atggactaca aagaccatga cggtgattat aaagatcatg acatcgatta caaggatgac     60

gatgacaaga tggcccccaa gaagaagagg aaggtgggca ttcaccgcgg ggtacctatg    120
```

gataaaaagt attctattgg tttagctatc ggcactaatt ccgttggatg ggctgtcata 180
accgatgaat acaaagtacc ttcaaagaaa tttaaggtgt tggggaacac agaccgtcat 240
tcgattaaaa agaatcttat cggtgccctc ctattcgata gtggcgaaac ggcagaggcg 300
actcgcctga aacgaaccgc tcggagaagg tatacacgtc gcaagaaccg aatatgttac 360
ttacaagaaa tttttagcaa tgagatggcc aaagttgacg attctttctt tcaccgtttg 420
gaagagtcct tccttgtcga agaggacaag aaacatgaac ggcaccccat ctttggaaac 480
atagtagatg aggtggcata tcatgaaaag tacccaacga tttatcacct cagaaaaaag 540
ctagttgact caactgataa agcggacctg aggttaatct acttggctct tgcccatatg 600
ataaagttcc gtgggcactt tctcattgag ggtgatctaa atccggacaa ctcggatgtc 660
gacaaactgt tcatccagtt agtacaaacc tataatcagt tgtttgaaga gaaccctata 720
aatgcaagtg gcgtggatgc gaaggctatt cttagcgccc gcctctctaa atcccgacgg 780
ctagaaaacc tgatcgcaca attacccgga gagaagaaaa atgggttgtt cggtaacctt 840
atagcgctct cactaggcct gacaccaaat tttaagtcga acttcgactt agctgaagat 900
gccaaattgc agcttagtaa ggacacgtac gatgacgatc tcgacaatct actggcacaa 960
attggagatc agtatgcgga cttatttttg gctgccaaaa accttagcga tgcaatcctc 1020
ctatctgaca tactgagagt taatactgag attaccaagg cgccgttatc cgcttcaatg 1080
atcaaaaggt acgatgaaca tcaccaagac ttgacacttc tcaaggccct agtccgtcag 1140
caactgcctg agaaatataa ggaaatattc tttgatcagt cgaaaaacgg gtacgcaggt 1200
tatattgacg gcggagcgag tcaagaggaa ttctacaagt ttatcaaacc catattagag 1260
aagatggatg ggacggaaga gttgcttgta aaactcaatc gcgaagatct actgcgaaag 1320
cagcggactt tcgacaacgg tagcattcca catcaaatcc acttaggcga attgcatgct 1380
atacttagaa ggcaggagga tttttatccg ttcctcaaag acaatcgtga aaagattgag 1440
aaaatcctaa cctttcgcat accttactat gtgggacccc tggcccgagg gaactctcgg 1500
ttcgcatgga tgacaagaaa gtccgaagaa acgattactc catggaattt tgaggaagtt 1560
gtcgataaag gtgcgtcagc tcaatcgttc atcgagagga tgaccaactt tgacaagaat 1620
ttaccgaacg aaaaagtatt gcctaagcac agtttacttt acgagtattt cacagtgtac 1680
aatgaactca cgaaagttaa gtatgtcact gagggcatgc gtaaacccgc ctttctaagc 1740
ggagaacaga agaaagcaat agtagatctg ttattcaaga ccaaccgcaa agtgacagtt 1800
aagcaattga aagaggacta ctttaagaaa attgaatgct tcgattctgt cgagatctcc 1860
ggggtagaag atcgatttaa tgcgtcactt ggtacgtatc atgacctcct aaagataatt 1920
aaagataagg acttcctgga taacgaagag aatgaagata tcttagaaga tatagtgttg 1980
actcttaccc tctttgaaga tcgggaaatg attgaggaaa gactaaaaac atacgctcac 2040
ctgttcgacg ataaggttat gaaacagtta aagaggcgtc gctatacggg ctggggacga 2100
ttgtcgcgga aacttatcaa cgggataaga gacaagcaaa gtggtaaaac tattctcgat 2160
tttctaaaga gcgacggctt cgccaatagg aactttatgc agctgatcca tgatgactct 2220
ttaaccttca aagaggatat acaaaaggca caggtttccg gacaagggga ctcattgcac 2280
gaacatattg cgaatcttgc tggttcgcca gccatcaaaa agggcatact ccagacagtc 2340
aaagtagtgg atgagctagt taaggtcatg ggacgtcaca aaccggaaaa cattgtaatc 2400
gagatggcac gcgaaaatca aacgactcag aaggggcaaa aaaacagtcg agagcggatg 2460

-continued

```
aagagaatag aagagggtat taaagaactg ggcagccaga tcttaaagga gcatcctgtg   2520
gaaaataccc aattgcagaa cgagaaactt tacctctatt acctacaaaa tggaagggac   2580
atgtatgttg atcaggaact ggacataaac cgtttatctg attacgacgt cgatgccatt   2640
gtaccccaat ccttttttgaa ggacgattca atcgacaata aagtgcttac acgctcggat   2700
aagaaccgag ggaaaagtga caatgttcca agcgaggaag tcgtaaagaa aatgaagaac   2760
tattggcggc agctcctaaa tgcgaaactg ataacgcaaa gaaagttcga taacttaact   2820
aaagctgaga ggggtggctt gtctgaactt gacaaggccg gatttattaa acgtcagctc   2880
gtggaaaccc gccaaatcac aaagcatgtt gcacagatac tagattcccg aatgaatacg   2940
aaatacgacg agaacgataa gctgattcgg gaagtcaaag taatcacttt aaagtcaaaa   3000
ttggtgtcgg acttcagaaa ggattttcaa ttctataaag ttagggagat aaataactac   3060
caccatgcgc acgacgctta tcttaatgcc gtcgtaggga ccgcactcat taagaaatac   3120
ccgaagctag aaagtgagtt tgtgtatggt gattacaaag tttatgacgt ccgtaagatg   3180
atcgcgaaaa gcgaacagga gataggcaag gctacagcca aatacttctt ttattctaac   3240
attatgaatt tctttaagac ggaaatcact ctggcaaacg gagagatacg caaacgacct   3300
ttaattgaaa ccaatgggga gacaggtgaa atcgtatggg ataagggccg ggacttcgcg   3360
acggtgagaa aagttttgtc catgccccaa gtcaacatag taaagaaaac tgaggtgcag   3420
accggagggt tttcaaagga atcgattctt ccaaaaagga atagtgataa gctcatcgct   3480
cgtaaaaagg actgggaccc gaaaaagtac ggtggcttcg atagccctac agttgcctat   3540
tctgtcctag tagtggcaaa agttgagaag ggaaaatcca agaaactgaa gtcagtcaaa   3600
gaattattgg ggataacgat tatggagcgc tcgtcttttg aaaagaaccc catcgacttc   3660
cttgaggcga aaggttacaa ggaagtaaaa aaggatctca taattaaact accaaagtat   3720
agtctgtttg agttagaaaa tggccgaaaa cggatgttgg ctagcgccgg agagcttcaa   3780
aaggggaacg aactcgcact accgtctaaa tacgtgaatt tcctgtattt agcgtcccat   3840
tacgagaagt tgaaaggttc acctgaagat aacgaacaga agcaactttt tgttgagcag   3900
cacaaacatt atctcgacga aatcatagag caaatttcgg aattcagtaa gagagtcatc   3960
ctagctgatg ccaatctgga caaagtatta agcgcataca acaagcacag ggataaaccc   4020
atacgtgagc aggcggaaaa tattatccat ttgtttactc ttaccaacct cggcgctcca   4080
gccgcattca agtattttga cacaacgata gatcgcaaac gatacacttc taccaaggag   4140
gtgctagacg cgacactgat tcaccaatcc atcacgggat tatatgaaac tcggatagat   4200
ttgtcacagc ttgggggtga ctcaggtgga agtggcggca gcggaggttc tggatcccaa   4260
ctagtcaaaa gtgaactgga ggagaagaaa tctgaacttc gtcataaatt gaaatatgtg   4320
cctcatgaat atattgaatt aattgaaatt gccagaaatt ccactcagga tagaattctt   4380
gaaatgaagg taatggaatt ttttatgaaa gtttatggat atagaggtaa acatttgggt   4440
ggatcaagga aaccggacgg agcaatttat actgtcggat ctcctattga ttacggtgtg   4500
atcgtggata ctaaagctta tagcggaggt tataatctgc caattggcca agcagatgaa   4560
atgcaacgat atgtcgaaga aaatcaaaca cgaaacaaac atatcaaccc taatgaatgg   4620
tggaaagtct atccatcttc tgtaacggaa tttaagtttt tatttgtgag tggtcacttt   4680
aaaggaaact acaaagctca gcttacacga ttaaatcata tcactaattg taatggagct   4740
gttcttagtg tagaagagct tttaattggt ggagaaatga ttaaagccgg cacattaacc   4800
ttagaggaag tcagacggaa atttaataac ggcgagataa acttt                   4845
```

<210> SEQ ID NO 52
<211> LENGTH: 4836
<212> TYPE: DNA
<213> ORGANISM: Artificial Sequence
<220> FEATURE:
<223> OTHER INFORMATION: Synthetic Polynucleotide

<400> SEQUENCE: 52
atgggatccc aactagtcaa aagtgaactg gaggagaaga aatctgaact tcgtcataaa 60
ttgaaatatg tgcctcatga atatattgaa ttaattgaaa ttgccagaaa ttccactcag 120
gatagaattc ttgaaatgaa ggtaatggaa ttttttatga aagtttatgg atatagaggt 180
aaacatttgg gtggatcaag gaaaccggac ggagcaattt atactgtcgg atctcctatt 240
gattacggtg tgatcgtgga tactaaagct tatagcggag gttataatct gccaattggc 300
caagcagatg aaatgcaacg atatgtcgaa gaaaatcaaa cacgaaacaa acatatcaac 360
cctaatgaat ggtggaaagt ctatccatct tctgtaacgg aatttaagtt tttatttgtg 420
agtggtcact ttaaaggaaa ctacaaagct cagcttacac gattaaatca tatcactaat 480
tgtaatggag ctgttcttag tgtagaagag cttttaattg gtggagaaat gattaaagcc 540
ggcacattaa ccttagagga agtcagacgg aaatttaata acggcgagat aaactttggc 600
ggtagtgggg gatctggggg aagtatggat aaaaagtatt ctattggttt agctatcggc 660
actaattccg ttggatgggc tgtcataacc gatgaataca aagtaccttc aaagaaattt 720
aaggtgttgg ggaacacaga ccgtcattcg attaaaaaga atcttatcgg tgccctccta 780
ttcgatagtg gcgaaacggc agaggcgact cgcctgaaac gaaccgctcg gagaaggtat 840
acacgtcgca agaaccgaat atgttactta caagaaattt ttagcaatga gatggccaaa 900
gttgacgatt ctttctttca ccgtttggaa gagtccttcc ttgtcgaaga ggacaagaaa 960
catgaacggc accccatctt tggaaacata gtagatgagg tggcatatca tgaaaagtac 1020
ccaacgattt atcacctcag aaaaaagcta gttgactcaa ctgataaagc ggacctgagg 1080
ttaatctact tggctcttgc ccatatgata aagttccgtg ggcactttct cattgagggt 1140
gatctaaatc cggacaactc ggatgtcgac aaactgttca tccagttagt acaaacctat 1200
aatcagttgt ttgaagagaa ccctataaat gcaagtggcg tggatgcgaa ggctattctt 1260
agcgcccgcc tctctaaatc ccgacggcta gaaaacctga tcgcacaatt acccggagag 1320
aagaaaaatg ggttgttcgg taaccttata gcgctctcac taggcctgac accaaatttt 1380
aagtcgaact tcgacttagc tgaagatgcc aaattgcagc ttagtaagga cacgtacgat 1440
gacgatctcg acaatctact ggcacaaatt ggagatcagt atgcggactt atttttggct 1500
gccaaaaacc ttagcgatgc aatcctccta tctgacatac tgagagttaa tactgagatt 1560
accaaggcgc cgttatccgc ttcaatgatc aaaaggtacg atgaacatca ccaagacttg 1620
acacttctca aggccctagt ccgtcagcaa ctgcctgaga aatataagga aatattcttt 1680
gatcagtcga aaaacgggta cgcaggttat attgacggcg gagcgagtca agaggaattc 1740
tacaagttta tcaaacccat attagagaag atggatggga cggaagagtt gcttgtaaaa 1800
ctcaatcgcg aagatctact gcgaaagcag cggactttcg acaacggtag cattccacat 1860
caaatccact taggcgaatt gcatgctata cttagaaggc aggaggattt ttatccgttc 1920
ctcaaagaca atcgtgaaaa gattgagaaa atcctaacct ttcgcatacc ttactatgtg 1980
ggacccctgg cccgagggaa ctctcggttc gcatggatga caagaaagtc cgaagaaacg 2040

```
attactccat ggaattttga ggaagttgtc gataaaggtg cgtcagctca atcgttcatc   2100
gagaggatga ccaactttga caagaattta ccgaacgaaa aagtattgcc taagcacagt   2160
ttactttacg agtatttcac agtgtacaat gaactcacga aagttaagta tgtcactgag   2220
ggcatgcgta aacccgcctt tctaagcgga gaacagaaga aagcaatagt agatctgtta   2280
ttcaagacca accgcaaagt gacagttaag caattgaaag aggactactt taagaaaatt   2340
gaatgcttcg attctgtcga gatctccggg gtagaagatc gatttaatgc gtcacttggt   2400
acgtatcatg acctcctaaa gataattaaa gataaggact tcctggataa cgaagagaat   2460
gaagatatct tagaagatat agtgttgact cttaccctct ttgaagatcg ggaaatgatt   2520
gaggaaagac taaaaacata cgctcacctg ttcgacgata aggttatgaa acagttaaag   2580
aggcgtcgct atacgggctg ggacgattg tcgcggaaac ttatcaacgg gataagagac    2640
aagcaaagtg gtaaaactat tctcgatttt ctaaagagcg acggcttcgc caataggaac   2700
tttatgcagc tgatccatga tgactcttta accttcaaag aggatataca aaaggcacag   2760
gtttccggac aaggggactc attgcacgaa catattgcga atcttgctgg ttcgccagcc   2820
atcaaaaagg gcatactcca gacagtcaaa gtagtggatg agctagttaa ggtcatggga   2880
cgtcacaaac cggaaaacat tgtaatcgag atggcacgcg aaaatcaaac gactcagaag   2940
gggcaaaaaa acagtcgaga gcggatgaag agaatagaag agggtattaa agaactgggc   3000
agccagatct taaaggagca tcctgtggaa aatacccaat tgcagaacga gaaactttac   3060
ctctattacc tacaaaatgg aagggacatg tatgttgatc aggaactgga cataaaccgt   3120
ttatctgatt acgacgtcga tgccattgta ccccaatcct tttgaagga cgattcaatc    3180
gacaataaag tgcttacacg ctcggataag aaccgaggga aaagtgacaa tgttccaagc   3240
gaggaagtcg taaagaaaat gaagaactat tggcggcagc tcctaaatgc gaaactgata   3300
acgcaaagaa agttcgataa cttaactaaa gctgagaggg gtggcttgtc tgaacttgac   3360
aaggccggat ttattaaacg tcagctcgtg gaaacccgcc aaatcacaaa gcatgttgca   3420
cagatactag attcccgaat gaatacgaaa tacgacgaga acgataagct gattcgggaa   3480
gtcaaagtaa tcactttaaa gtcaaaattg gtgtcggact tcagaaagga ttttcaattc   3540
tataaagtta gggagataaa taactaccac catgcgcacg acgcttatct taatgccgtc   3600
gtagggaccg cactcattaa gaaatacccg aagctagaaa gtgagtttgt gtatggtgat   3660
tacaaagttt atgacgtccg taagatgatc gcgaaaagcg aacaggagat aggcaaggct   3720
acagccaaat acttctttta ttctaacatt atgaatttct ttaagacgga aatcactctg   3780
gcaaacggag agatacgcaa acgaccttta attgaaacca atggggagac aggtgaaatc   3840
gtatgggata agggccggga cttcgcgacg gtgagaaaag ttttgtccat gccccaagtc   3900
aacatagtaa agaaaactga ggtgcagacc ggagggtttt caaaggaatc gattcttcca   3960
aaaaggaata gtgataagct catcgctcgt aaaaaggact gggacccgaa aaagtacggt   4020
ggcttcgata gccctacagt tgcctattct gtcctagtag tggcaaaagt tgagaaggga   4080
aaatccaaga aactgaagtc agtcaaagaa ttattgggga taacgattat ggagcgctcg   4140
tcttttgaaa agaaccccat cgacttcctt gaggcgaaag gttacaagga agtaaaaaag   4200
gatctcataa ttaaactacc aaagtatagt ctgtttgagt tagaaaatgg ccgaaaacgg   4260
atgttggcta gcgccggaga gcttcaaaag gggaacgaac tcgcactacc gtctaaatac   4320
gtgaatttcc tgtatttagc gtcccattac gagaagttga aaggttcacc tgaagataac   4380
gaacagaagc aacttttgt tgagcagcac aaacattatc tcgacgaaat catagagcaa    4440
```

-continued atttcggaat tcagtaagag agtcatccta gctgatgcca atctggacaa agtattaagc 4500
gcatacaaca agcacaggga taaacccata cgtgagcagg cggaaaatat tatccatttg 4560
tttactctta ccaacctcgg cgctccagcc gcattcaagt attttgacac aacgatagat 4620
cgcaaacgat acacttctac caaggaggtg ctagacgcga cactgattca ccaatccatc 4680
acgggattat atgaaactcg gatagatttg tcacagcttg ggggtgacgg atcccccaag 4740
aagaagagga aagtctcgag cgactacaaa gaccatgacg gtgattataa agatcatgac 4800
atcgattaca aggatgacga tgacaaggct gcagga 4836

<210> SEQ ID NO 53
<211> LENGTH: 4854
<212> TYPE: DNA
<213> ORGANISM: Artificial Sequence
<220> FEATURE:
<223> OTHER INFORMATION: Synthetic Polynucleotide

<400> SEQUENCE: 53
atggactaca aagaccatga cggtgattat aaagatcatg acatcgatta caaggatgac 60
gatgacaaga tggcccccaa gaagaagagg aaggtgggca ttcaccgcgg ggtacctgga 120
ggttctatgg gatcccaact agtcaaaagt gaactggagg agaagaaatc tgaacttcgt 180
cataaattga aatatgtgcc tcatgaatat attgaattaa ttgaaattgc cagaaattcc 240
actcaggata gaattcttga aatgaaggta atggaatttt ttatgaaagt ttatggatat 300
agaggtaaac atttgggtgg atcaaggaaa ccggacggag caatttatac tgtcggatct 360
cctattgatt acggtgtgat cgtggatact aaagcttata gcggaggtta taatctgcca 420
attggccaag cagatgaaat gcaacgatat gtcgaagaaa atcaaacacg aaacaaacat 480
atcaacccta atgaatggtg gaaagtctat ccatcttctg taacggaatt taagttttta 540
tttgtgagtg gtcactttaa aggaaactac aaagctcagc ttacacgatt aaatcatatc 600
actaattgta atggagctgt tcttagtgta gaagagcttt taattggtgg agaaatgatt 660
aaagccggca cattaacctt agaggaagtc agacggaaat ttaataacgg cgagataaac 720
tttggcggta gtgggggatc tgggggaagt atggataaaa agtattctat tggtttagct 780
atcggcacta attccgttgg atgggctgtc ataaccgatg aatacaaagt accttcaaag 840
aaatttaagg tgttggggaa cacagaccgt cattcgatta aaaagaatct tatcggtgcc 900
ctcctattcg atagtggcga aacggcagag gcgactcgcc tgaaacgaac cgctcggaga 960
aggtatacac gtcgcaagaa ccgaatatgt tacttacaag aaatttttag caatgagatg 1020
gccaaagttg acgattcttt ctttcaccgt ttggaagagt ccttccttgt cgaagaggac 1080
aagaaacatg aacggcaccc catctttgga aacatagtag atgaggtggc atatcatgaa 1140
aagtacccaa cgatttatca cctcagaaaa aagctagttg actcaactga taaagcggac 1200
ctgaggttaa tctacttggc tcttgcccat atgataaagt tccgtgggca ctttctcatt 1260
gagggtgatc taaatccgga caactcggat gtcgacaaac tgttcatcca gttagtacaa 1320
acctataatc agttgtttga agagaaccct ataaatgcaa gtggcgtgga tgcgaaggct 1380
attcttagcg cccgcctctc taaatcccga cggctagaaa acctgatcgc acaattaccc 1440
ggagagaaga aaaatgggtt gttcggtaac cttatagcgc tctcactagg cctgacacca 1500
aattttaagt cgaacttcga cttagctgaa gatgccaaat tgcagcttag taaggacacg 1560
tacgatgacg atctcgacaa tctactggca caaattggag atcagtatgc ggacttattt 1620

-continued

```
ttggctgcca aaaaccttag cgatgcaatc ctcctatctg acatactgag agttaatact   1680
gagattacca aggcgccgtt atccgcttca atgatcaaaa ggtacgatga acatcaccaa   1740
gacttgacac ttctcaaggc cctagtccgt cagcaactgc ctgagaaata taaggaaata   1800
ttctttgatc agtcgaaaaa cgggtacgca ggttatattg acggcggagc gagtcaagag   1860
gaattctaca agtttatcaa acccatatta gagaagatgg atgggacgga agagttgctt   1920
gtaaaactca atcgcgaaga tctactgcga aagcagcgga ctttcgacaa cggtagcatt   1980
ccacatcaaa tccacttagg cgaattgcat gctatactta gaaggcagga ggatttttat   2040
ccgttcctca aagacaatcg tgaaaagatt gagaaaatcc taacctttcg cataccttac   2100
tatgtgggac ccctggcccg agggaactct cggttcgcat ggatgacaag aaagtccgaa   2160
gaaacgatta ctccatggaa ttttgaggaa gttgtcgata aaggtgcgtc agctcaatcg   2220
ttcatcgaga ggatgaccaa ctttgacaag aatttaccga acgaaaaagt attgcctaag   2280
cacagtttac tttacgagta tttcacagtg tacaatgaac tcacgaaagt taagtatgtc   2340
actgagggca tgcgtaaacc cgcctttcta agcggagaac agaagaaagc aatagtagat   2400
ctgttattca agaccaaccg caaagtgaca gttaagcaat tgaaagagga ctactttaag   2460
aaaattgaat gcttcgattc tgtcgagatc tccggggtag aagatcgatt taatgcgtca   2520
cttggtacgt atcatgacct cctaaagata attaaagata aggacttcct ggataacgaa   2580
gagaatgaag atatcttaga agatatagtg ttgactctta ccctctttga agatcgggaa   2640
atgattgagg aaagactaaa aacatacgct cacctgttcg acgataaggt tatgaaacag   2700
ttaaagaggc gtcgctatac gggctgggga cgattgtcgc ggaaacttat caacgggata   2760
agagacaagc aaagtggtaa aactattctc gattttctaa agagcgacgg cttcgccaat   2820
aggaacttta tgcagctgat ccatgatgac tctttaacct tcaaagagga tatacaaaag   2880
gcacaggttt ccggacaagg ggactcattg cacgaacata ttgcgaatct tgctggttcg   2940
ccagccatca aaaagggcat actccagaca gtcaaagtag tggatgagct agttaaggtc   3000
atgggacgtc acaaaccgga aaacattgta atcgagatgg cacgcgaaaa tcaaacgact   3060
cagaaggggc aaaaaaacag tcgagagcgg atgaagagaa tagaagaggg tattaaagaa   3120
ctgggcagcc agatcttaaa ggagcatcct gtggaaaata cccaattgca gaacgagaaa   3180
ctttacctct attacctaca aaatggaagg gacatgtatg ttgatcagga actggacata   3240
aaccgtttat ctgattacga cgtcgatgcc attgtacccc aatccttttt gaaggacgat   3300
tcaatcgaca ataaagtgct tacacgctcg gataagaacc gagggaaaag tgacaatgtt   3360
ccaagcgagg aagtcgtaaa gaaaatgaag aactattggc ggcagctcct aaatgcgaaa   3420
ctgataacgc aaagaaagtt cgataactta actaaagctg agaggggtgg cttgtctgaa   3480
cttgacaagg ccggatttat taaacgtcag ctcgtggaaa cccgccaaat cacaaagcat   3540
gttgcacaga tactagattc ccgaatgaat acgaaatacg acgagaacga taagctgatt   3600
cgggaagtca aagtaatcac tttaaagtca aaattggtgt cggacttcag aaaggatttt   3660
caattctata aagttaggga gataaataac taccaccatg cgcacgacgc ttatcttaat   3720
gccgtcgtag ggaccgcact cattaagaaa tacccgaagc tagaaagtga gtttgtgtat   3780
ggtgattaca aagtttatga cgtccgtaag atgatcgcga aaagcgaaca ggagataggc   3840
aaggctacag ccaaatactt cttttattct aacattatga atttctttaa gacggaaatc   3900
actctggcaa acggagagat acgcaaacga cctttaattg aaaccaatgg ggagacaggt   3960
gaaatcgtat gggataaggg ccgggacttc gcgacggtga gaaaagtttt gtccatgccc   4020
```

-continued caagtcaaca tagtaaagaa aactgaggtg cagaccggag ggttttcaaa ggaatcgatt 4080
cttccaaaaa ggaatagtga taagctcatc gctcgtaaaa aggactggga cccgaaaaag 4140
tacggtggct tcgatagccc tacagttgcc tattctgtcc tagtagtggc aaaagttgag 4200
aagggaaaat ccaagaaact gaagtcagtc aaagaattat tggggataac gattatggag 4260
cgctcgtctt ttgaaaagaa ccccatcgac ttccttgagg cgaaaggtta caaggaagta 4320
aaaaaggatc tcataattaa actaccaaag tatagtctgt ttgagttaga aaatggccga 4380
aaacggatgt tggctagcgc cggagagctt caaaagggga acgaactcgc actaccgtct 4440
aaatacgtga atttcctgta tttagcgtcc cattacgaga agttgaaagg ttcacctgaa 4500
gataacgaac agaagcaact tttgttgag cagcacaaac attatctcga cgaaatcata 4560
gagcaaattt cggaattcag taagagagtc atcctagctg atgccaatct ggacaaagta 4620
ttaagcgcat acaacaagca cagggataaa cccatacgtg agcaggcgga aaatattatc 4680
catttgttta ctcttaccaa cctcggcgct ccagccgcat tcaagtattt tgacacaacg 4740
atagatcgca aacgatacac ttctaccaag gaggtgctag acgcgacact gattcaccaa 4800
tccatcacgg gattatatga aactcggata gatttgtcac agcttggggg tgac 4854

<210> SEQ ID NO 54
<211> LENGTH: 4869
<212> TYPE: DNA
<213> ORGANISM: Artificial Sequence
<220> FEATURE:
<223> OTHER INFORMATION: Synthetic Polynucleotide

<400> SEQUENCE: 54
atggactaca aagaccatga cggtgattat aaagatcatg acatcgatta caaggatgac 60
gatgacaaga tggcccccaa gaagaagagg aaggtgggca ttcaccgcgg ggtacctgga 120
ggttctggat cccaactagt caaaagtgaa ctggaggaga agaaatctga acttcgtcat 180
aaattgaaat atgtgcctca tgaatatatt gaattaattg aaattgccag aaattccact 240
caggatagaa ttcttgaaat gaaggtaatg gaatttttta tgaaagttta tggatataga 300
ggtaaacatt tgggtggatc aaggaaaccg gacggagcaa tttatactgt cggatctcct 360
attgattacg gtgtgatcgt ggatactaaa gcttatagcg gaggttataa tctgccaatt 420
ggccaagcag atgaaatgca acgatatgtc gaagaaaatc aaacacgaaa caaacatatc 480
aaccctaatg aatggtggaa agtctatcca tcttctgtaa cggaatttaa gtttttattt 540
gtgagtggtc actttaaagg aaactacaaa gctcagctta cacgattaaa tcatatcact 600
aattgtaatg gagctgttct tagtgtagaa gagcttttaa ttggtggaga aatgattaaa 660
gccggcacat taaccttaga ggaagtcaga cggaaattta ataacggcga gataaacttt 720
agcggcagcg agactcccgg gacctcagag tccgccacac ccgaaagtga taaaaagtat 780
tctattggtt tagctatcgg cactaattcc gttggatggg ctgtcataac cgatgaatac 840
aaagtacctt caaagaaatt taaggtgttg gggaacacag accgtcattc gattaaaaag 900
aatcttatcg gtgccctcct attcgatagt ggcgaaacgg cagaggcgac tcgcctgaaa 960
cgaaccgctc ggagaaggta tacacgtcgc aagaaccgaa tatgttactt acaagaaatt 1020
tttagcaatg agatggccaa agttgacgat tctttctttc accgtttgga agagtccttc 1080
cttgtcgaag aggacaagaa acatgaacgg caccccatct ttggaaacat agtagatgag 1140
gtggcatatc atgaaaagta cccaacgatt tatcacctca gaaaaaagct agttgactca 1200

-continued

```
actgataaag cggacctgag gttaatctac ttggctcttg cccatatgat aaagttccgt   1260
gggcactttc tcattgaggg tgatctaaat ccggacaact cggatgtcga caaactgttc   1320
atccagttag tacaaaccta taatcagttg tttgaagaga accctataaa tgcaagtggc   1380
gtggatgcga aggctattct tagcgcccgc ctctctaaat cccgacggct agaaaacctg   1440
atcgcacaat tacccggaga gaagaaaaat gggttgttcg gtaaccttat agcgctctca   1500
ctaggcctga caccaaattt taagtcgaac ttcgacttag ctgaagatgc caaattgcag   1560
cttagtaagg acacgtacga tgacgatctc gacaatctac tggcacaaat tggagatcag   1620
tatgcggact tatttttggc tgccaaaaac cttagcgatg caatcctcct atctgacata   1680
ctgagagtta atactgagat taccaaggcg ccgttatccg cttcaatgat caaaaggtac   1740
gatgaacatc accaagactt gacacttctc aaggccctag tccgtcagca actgcctgag   1800
aaatataagg aaatattctt tgatcagtcg aaaaacgggt acgcaggtta tattgacggc   1860
ggagcgagtc aagaggaatt ctacaagttt atcaaaccca tattagagaa gatggatggg   1920
acggaagagt tgcttgtaaa actcaatcgc gaagatctac tgcgaaagca gcggactttc   1980
gacaacggta gcattccaca tcaaatccac ttaggcgaat tgcatgctat acttagaagg   2040
caggaggatt tttatccgtt cctcaaagac aatcgtgaaa agattgagaa aatcctaacc   2100
tttcgcatac cttactatgt gggacccctg gcccgaggga actctcggtt cgcatggatg   2160
acaagaaagt ccgaagaaac gattactcca tggaattttg aggaagttgt cgataaaggt   2220
gcgtcagctc aatcgttcat cgagaggatg accaactttg acaagaattt accgaacgaa   2280
aaagtattgc ctaagcacag tttactttac gagtatttca cagtgtacaa tgaactcacg   2340
aaagttaagt atgtcactga gggcatgcgt aaacccgcct ttctaagcgg agaacagaag   2400
aaagcaatag tagatctgtt attcaagacc aaccgcaaag tgacagttaa gcaattgaaa   2460
gaggactact ttaagaaaat tgaatgcttc gattctgtcg agatctccgg ggtagaagat   2520
cgatttaatg cgtcacttgg tacgtatcat gacctcctaa agataattaa agataaggac   2580
ttcctggata acgaagagaa tgaagatatc ttagaagata tagtgttgac tcttaccctc   2640
tttgaagatc gggaaatgat tgaggaaaga ctaaaaacat acgctcacct gttcgacgat   2700
aaggttatga aacagttaaa gaggcgtcgc tatacgggct ggggacgatt gtcgcggaaa   2760
cttatcaacg ggataagaga caagcaaagt ggtaaaacta ttctcgattt tctaaagagc   2820
gacggcttcg ccaataggaa ctttatgcag ctgatccatg atgactcttt aaccttcaaa   2880
gaggatatac aaaaggcaca ggtttccgga caaggggact cattgcacga acatattgcg   2940
aatcttgctg gttcgccagc catcaaaaag ggcatactcc agacagtcaa agtagtggat   3000
gagctagtta aggtcatggg acgtcacaaa ccggaaaaca ttgtaatcga gatggcacgc   3060
gaaaatcaaa cgactcagaa ggggcaaaaa aacagtcgag agcggatgaa gagaatagaa   3120
gagggtatta aagaactggg cagccagatc ttaaaggagc atcctgtgga aaatacccaa   3180
ttgcagaacg agaaacttta cctctattac ctacaaaatg gaagggacat gtatgttgat   3240
caggaactgg acataaaccg tttatctgat tacgacgtcg atgccattgt accccaatcc   3300
tttttgaagg acgattcaat cgacaataaa gtgcttacac gctcggataa gaaccgaggg   3360
aaaagtgaca atgttccaag cgaggaagtc gtaaagaaaa tgaagaacta ttggcggcag   3420
ctcctaaatg cgaaactgat aacgcaaaga aagttcgata acttaactaa agctgagagg   3480
ggtggcttgt ctgaacttga caaggccgga tttattaaac gtcagctcgt ggaaacccgc   3540
caaatcacaa agcatgttgc acagatacta gattcccgaa tgaatacgaa atacgacgag   3600
```

aacgataagc tgattcggga agtcaaagta atcactttaa agtcaaaatt ggtgtcggac 3660
ttcagaaagg attttcaatt ctataaagtt agggagataa ataactacca ccatgcgcac 3720
gacgcttatc ttaatgccgt cgtagggacc gcactcatta agaaataccc gaagctagaa 3780
agtgagtttg tgtatggtga ttacaaagtt tatgacgtcc gtaagatgat cgcgaaaagc 3840
gaacaggaga taggcaaggc tacagccaaa tacttctttt attctaacat tatgaatttc 3900
tttaagacgg aaatcactct ggcaaacgga gagatacgca aacgaccttt aattgaaacc 3960
aatggggaga caggtgaaat cgtatgggat aagggccggg acttcgcgac ggtgagaaaa 4020
gttttgtcca tgccccaagt caacatagta aagaaaactg aggtgcagac cggagggttt 4080
tcaaaggaat cgattcttcc aaaaaggaat agtgataagc tcatcgctcg taaaaaggac 4140
tgggacccga aaaagtacgg tggcttcgat agccctacag ttgcctattc tgtcctagta 4200
gtggcaaaag ttgagaaggg aaaatccaag aaactgaagt cagtcaaaga attattgggg 4260
ataacgatta tggagcgctc gtcttttgaa aagaacccca tcgacttcct tgaggcgaaa 4320
ggttacaagg aagtaaaaaa ggatctcata attaaactac caaagtatag tctgtttgag 4380
ttagaaaatg gccgaaaacg gatgttggct agcgccggag agcttcaaaa ggggaacgaa 4440
ctcgcactac cgtctaaata cgtgaatttc ctgtatttag cgtcccatta cgagaagttg 4500
aaaggttcac ctgaagataa cgaacagaag caactttttg ttgagcagca caaacattat 4560
ctcgacgaaa tcatagagca aatttcggaa ttcagtaaga gagtcatcct agctgatgcc 4620
aatctggaca aagtattaag cgcatacaac aagcacaggg ataaacccat acgtgagcag 4680
gcggaaaata ttatccattt gtttactctt accaacctcg gcgctccagc cgcattcaag 4740
tattttgaca caacgataga tcgcaaacga tacacttcta ccaaggaggt gctagacgcg 4800
acactgattc accaatccat cacgggatta tatgaaactc ggatagattt gtcacagctt 4860
gggggtgac 4869

<210> SEQ ID NO 55
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 55
atggccctgt ttggctacgc acgcgtgtct accagtcaac agtcactcga tttgcaagtg 60
agggctctta aagatgccgg agtgaaggca aacagaattt ttactgataa ggccagcgga 120
agcagcacag acagagaggg gctggatctc ctgagaatga aggtaaagga gggtgatgtg 180
atcttggtca aaaaattgga tcgactgggg agagacacag ctgatatgct tcagcttatt 240
aaagagtttg acgctcaggg tgttgccgtg aggtttatcg atgacggcat ctcaaccgac 300
tcctacattg gtcttatgtt tgtgacaatt ttgtccgctg tggctcaggc tgagcggaga 360
aggattctcg aaaggacgaa tgagggacgg caagcagcta agttgaaagg tatcaaattt 420
ggcagacgaa gg 432

<210> SEQ ID NO 56
<211> LENGTH: 144
<212> TYPE: PRT
<213> ORGANISM: Artificial Sequence
<220> FEATURE:
<223> OTHER INFORMATION: Synthetic Polypeptide

<400> SEQUENCE: 56

Met Ala Leu Phe Gly Tyr Ala Arg Val Ser Thr Ser Gln Gln Ser Leu
1 5 10 15

Asp Leu Gln Val Arg Ala Leu Lys Asp Ala Gly Val Lys Ala Asn Arg
20 25 30

Ile Phe Thr Asp Lys Ala Ser Gly Ser Ser Thr Asp Arg Glu Gly Leu
35 40 45

Asp Leu Leu Arg Met Lys Val Lys Glu Gly Asp Val Ile Leu Val Lys
50 55 60

Lys Leu Asp Arg Leu Gly Arg Asp Thr Ala Asp Met Leu Gln Leu Ile
65 70 75 80

Lys Glu Phe Asp Ala Gln Gly Val Ala Val Arg Phe Ile Asp Asp Gly
85 90 95

Ile Ser Thr Asp Ser Tyr Ile Gly Leu Met Phe Val Thr Ile Leu Ser
100 105 110

Ala Val Ala Gln Ala Glu Arg Arg Arg Ile Leu Glu Arg Thr Asn Glu
115 120 125

Gly Arg Gln Ala Ala Lys Leu Lys Gly Ile Lys Phe Gly Arg Arg Arg
130 135 140

<210> SEQ ID NO 57
<211> LENGTH: 414
<212> TYPE: DNA
<213> ORGANISM: Artificial Sequence
<220> FEATURE:
<223> OTHER INFORMATION: Synthetic Polynucleotide

<400> SEQUENCE: 57
atggcaacca ttggctacat aagggtgtct accatcgacc aaaatatcga cctgcagcgc 60
aacgctctga catccgccaa ctgcgatcgg atcttcgagg ataggatcag tggcaagatc 120
gccaaccggc ccggtctgaa gcgggctctg aagtacgtga ataagggcga tactctggtt 180
gtgtggaagt tggatcgctt gggtagatca gtgaagaatc tcgtagccct gataagcgag 240
ctgcacgaga ggggtgcaca tttccattct ctgaccgatt ccatcgatac gtctagcgcc 300
atgggccgat tcttctttta cgtcatgtcc gccctcgctg aaatggagcg cgaacttatt 360
gttgaacgga ctttggctgg actggcagcg gctagagcac agggccgact tgga 414

<210> SEQ ID NO 58
<211> LENGTH: 138
<212> TYPE: PRT
<213> ORGANISM: Artificial Sequence
<220> FEATURE:
<223> OTHER INFORMATION: Synthetic Polypeptide

<400> SEQUENCE: 58

Met Ala Thr Ile Gly Tyr Ile Arg Val Ser Thr Ile Asp Gln Asn Ile
1 5 10 15

Asp Leu Gln Arg Asn Ala Leu Thr Ser Ala Asn Cys Asp Arg Ile Phe
20 25 30

Glu Asp Arg Ile Ser Gly Lys Ile Ala Asn Arg Pro Gly Leu Lys Arg
35 40 45

Ala Leu Lys Tyr Val Asn Lys Gly Asp Thr Leu Val Val Trp Lys Leu
50 55 60

Asp Arg Leu Gly Arg Ser Val Lys Asn Leu Val Ala Leu Ile Ser Glu
65 70 75 80

Leu His Glu Arg Gly Ala His Phe His Ser Leu Thr Asp Ser Ile Asp

```
                85                  90                  95

Thr Ser Ser Ala Met Gly Arg Phe Phe Phe Tyr Val Met Ser Ala Leu
            100                 105                 110

Ala Glu Met Glu Arg Glu Leu Ile Val Glu Arg Thr Leu Ala Gly Leu
        115                 120                 125

Ala Ala Ala Arg Ala Gln Gly Arg Leu Gly
    130                 135
```

<210> SEQ ID NO 59
<211> LENGTH: 432
<212> TYPE: DNA
<213> ORGANISM: Artificial Sequence
<220> FEATURE:
<223> OTHER INFORMATION: Synthetic Polynucleotide

<400> SEQUENCE: 59

```
atgctcattg gctatgtaag ggtcagcacc aatgaccaaa acacagactt gcaacgcaat      60

gctttggttt gcgccggatg tgaacagata tttgaagata aactgagcgg cactcggaca     120

gacagacctg ggcttaagag agcactgaaa agactgcaga agggggacac cctggtcgtc     180

tggaaactgg atcgcctcgg acgcagcatg aaacatctga ttagcctggt tggtgagctt     240

agggagagag gaatcaactt cagaagcctg accgactcca tcgacaccag tagcccccatg     300

ggacgattct tcttctatgt gatgggagca cttgctgaga tggaaagaga gcttattatc     360

gaaagaacta tggctggtat cgctgctgcc cggaacaaag gcagacggtt cggcagaccg     420

ccgaagagcg gc                                                         432
```

<210> SEQ ID NO 60
<211> LENGTH: 144
<212> TYPE: PRT
<213> ORGANISM: Artificial Sequence
<220> FEATURE:
<223> OTHER INFORMATION: Synthetic Polypeptide

<400> SEQUENCE: 60

```
Met Leu Ile Gly Tyr Val Arg Val Ser Thr Asn Asp Gln Asn Thr Asp
1               5                   10                  15

Leu Gln Arg Asn Ala Leu Val Cys Ala Gly Cys Glu Gln Ile Phe Glu
            20                  25                  30

Asp Lys Leu Ser Gly Thr Arg Thr Asp Arg Pro Gly Leu Lys Arg Ala
        35                  40                  45

Leu Lys Arg Leu Gln Lys Gly Asp Thr Leu Val Val Trp Lys Leu Asp
    50                  55                  60

Arg Leu Gly Arg Ser Met Lys His Leu Ile Ser Leu Val Gly Glu Leu
65                  70                  75                  80

Arg Glu Arg Gly Ile Asn Phe Arg Ser Leu Thr Asp Ser Ile Asp Thr
                85                  90                  95

Ser Ser Pro Met Gly Arg Phe Phe Phe Tyr Val Met Gly Ala Leu Ala
            100                 105                 110

Glu Met Glu Arg Glu Leu Ile Ile Glu Arg Thr Met Ala Gly Ile Ala
        115                 120                 125

Ala Ala Arg Asn Lys Gly Arg Arg Phe Gly Arg Pro Pro Lys Ser Gly
    130                 135                 140
```

<210> SEQ ID NO 61
<211> LENGTH: 198
<212> TYPE: PRT
<213> ORGANISM: Homo sapiens

<400> SEQUENCE: 61

```
Met Asp Ser Leu Leu Met Asn Arg Arg Lys Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Leu Gly Leu
        195
```

<210> SEQ ID NO 62
<211> LENGTH: 198
<212> TYPE: PRT
<213> ORGANISM: Mus musculus

<400> SEQUENCE: 62

```
Met Asp Ser Leu Leu Met Lys Gln Lys Lys Phe Leu Tyr His Phe Lys
1               5                   10                  15

Asn Val Arg Trp Ala Lys Gly Arg His Glu Thr Tyr Leu Cys Tyr Val
            20                  25                  30

Val Lys Arg Arg Asp Ser Ala Thr Ser Cys Ser Leu Asp Phe Gly His
        35                  40                  45

Leu Arg Asn Lys Ser Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Thr Ser Trp Ser Pro Cys Tyr Asp Cys Ala Arg His Val Ala Glu
                85                  90                  95

Phe Leu Arg Trp Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Gly Ile Met Thr Phe Lys Asp Tyr
    130                 135                 140

Phe Tyr Cys Trp Asn Thr Phe Val Glu Asn Arg Glu Arg Thr Phe Lys
145                 150                 155                 160
```

Ala Trp Glu Gly Leu His Glu Asn Ser Val Arg Leu Thr Arg Gln Leu
165 170 175

Arg Arg Ile Leu Leu Pro Leu Tyr Glu Val Asp Asp Leu Arg Asp Ala
180 185 190

Phe Arg Met Leu Gly Phe
195

<210> SEQ ID NO 63
<211> LENGTH: 198
<212> TYPE: PRT
<213> ORGANISM: Canis lupus

<400> SEQUENCE: 63

Met Asp Ser Leu Leu Met Lys Gln Arg Lys Phe Leu Tyr His Phe Lys
1 5 10 15

Asn Val Arg Trp Ala Lys Gly Arg His Glu Thr Tyr Leu Cys Tyr Val
20 25 30

Val Lys Arg Arg Asp Ser Ala Thr Ser Phe Ser Leu Asp Phe Gly His
35 40 45

Leu Arg Asn Lys Ser Gly Cys His Val Glu Leu Leu Phe Leu Arg Tyr
50 55 60

Ile Ser Asp Trp Asp Leu Asp Pro Gly Arg Cys Tyr Arg Val Thr Trp
65 70 75 80

Phe Thr Ser Trp Ser Pro Cys Tyr Asp Cys Ala Arg His Val Ala Asp
85 90 95

Phe Leu Arg Gly Tyr Pro Asn Leu Ser Leu Arg Ile Phe Ala Ala Arg
100 105 110

Leu Tyr Phe Cys Glu Asp Arg Lys Ala Glu Pro Glu Gly Leu Arg Arg
115 120 125

Leu His Arg Ala Gly Val Gln Ile Ala Ile Met Thr Phe Lys Asp Tyr
130 135 140

Phe Tyr Cys Trp Asn Thr Phe Val Glu Asn Arg Glu Lys Thr Phe Lys
145 150 155 160

Ala Trp Glu Gly Leu His Glu Asn Ser Val Arg Leu Ser Arg Gln Leu
165 170 175

Arg Arg Ile Leu Leu Pro Leu Tyr Glu Val Asp Asp Leu Arg Asp Ala
180 185 190

Phe Arg Thr Leu Gly Leu
195

<210> SEQ ID NO 64
<211> LENGTH: 199
<212> TYPE: PRT
<213> ORGANISM: Bos taurus

<400> SEQUENCE: 64

Met Asp Ser Leu Leu Lys Lys Gln Arg Gln Phe Leu Tyr Gln Phe Lys
1 5 10 15

Asn Val Arg Trp Ala Lys Gly Arg His Glu Thr Tyr Leu Cys Tyr Val
20 25 30

Val Lys Arg Arg Asp Ser Pro Thr Ser Phe Ser Leu Asp Phe Gly His
35 40 45

Leu Arg Asn Lys Ala Gly Cys His Val Glu Leu Leu Phe Leu Arg Tyr
50 55 60

Ile Ser Asp Trp Asp Leu Asp Pro Gly Arg Cys Tyr Arg Val Thr Trp
65 70 75 80

```
Phe Thr Ser Trp Ser Pro Cys Tyr Asp Cys Ala Arg His Val Ala Asp
                85                  90                  95

Phe Leu Arg Gly Tyr Pro Asn Leu Ser Leu Arg Ile Phe Thr Ala Arg
            100                 105                 110

Leu Tyr Phe Cys Asp Lys Glu Arg Lys Ala Glu Pro Glu Gly Leu Arg
        115                 120                 125

Arg Leu His Arg Ala Gly Val Gln Ile Ala Ile Met Thr Phe Lys Asp
    130                 135                 140

Tyr Phe Tyr Cys Trp Asn Thr Phe Val Glu Asn His Glu Arg Thr Phe
145                 150                 155                 160

Lys Ala Trp Glu Gly Leu His Glu Asn Ser Val Arg Leu Ser Arg Gln
                165                 170                 175

Leu Arg Arg Ile Leu Leu Pro Leu Tyr Glu Val Asp Asp Leu Arg Asp
            180                 185                 190

Ala Phe Arg Thr Leu Gly Leu
        195


<210> SEQ ID NO 65
<211> LENGTH: 429
<212> TYPE: PRT
<213> ORGANISM: Mus musculus

<400> SEQUENCE: 65

Met Gly Pro Phe Cys Leu Gly Cys Ser His Arg Lys Cys Tyr Ser Pro
1               5                   10                  15

Ile Arg Asn Leu Ile Ser Gln Glu Thr Phe Lys Phe His Phe Lys Asn
            20                  25                  30

Leu Gly Tyr Ala Lys Gly Arg Lys Asp Thr Phe Leu Cys Tyr Glu Val
        35                  40                  45

Thr Arg Lys Asp Cys Asp Ser Pro Val Ser Leu His His Gly Val Phe
    50                  55                  60

Lys Asn Lys Asp Asn Ile His Ala Glu Ile Cys Phe Leu Tyr Trp Phe
65                  70                  75                  80

His Asp Lys Val Leu Lys Val Leu Ser Pro Arg Glu Glu Phe Lys Ile
                85                  90                  95

Thr Trp Tyr Met Ser Trp Ser Pro Cys Phe Glu Cys Ala Glu Gln Ile
            100                 105                 110

Val Arg Phe Leu Ala Thr His His Asn Leu Ser Leu Asp Ile Phe Ser
        115                 120                 125

Ser Arg Leu Tyr Asn Val Gln Asp Pro Glu Thr Gln Gln Asn Leu Cys
    130                 135                 140

Arg Leu Val Gln Glu Gly Ala Gln Val Ala Ala Met Asp Leu Tyr Glu
145                 150                 155                 160

Phe Lys Lys Cys Trp Lys Lys Phe Val Asp Asn Gly Gly Arg Arg Phe
                165                 170                 175

Arg Pro Trp Lys Arg Leu Leu Thr Asn Phe Arg Tyr Gln Asp Ser Lys
            180                 185                 190

Leu Gln Glu Ile Leu Arg Pro Cys Tyr Ile Pro Val Pro Ser Ser Ser
        195                 200                 205

Ser Ser Thr Leu Ser Asn Ile Cys Leu Thr Lys Gly Leu Pro Glu Thr
    210                 215                 220

Arg Phe Cys Val Glu Gly Arg Arg Met Asp Pro Leu Ser Glu Glu Glu
225                 230                 235                 240

Phe Tyr Ser Gln Phe Tyr Asn Gln Arg Val Lys His Leu Cys Tyr Tyr
```

245 250 255

His Arg Met Lys Pro Tyr Leu Cys Tyr Gln Leu Glu Gln Phe Asn Gly
260 265 270

Gln Ala Pro Leu Lys Gly Cys Leu Leu Ser Glu Lys Gly Lys Gln His
275 280 285

Ala Glu Ile Leu Phe Leu Asp Lys Ile Arg Ser Met Glu Leu Ser Gln
290 295 300

Val Thr Ile Thr Cys Tyr Leu Thr Trp Ser Pro Cys Pro Asn Cys Ala
305 310 315 320

Trp Gln Leu Ala Ala Phe Lys Arg Asp Arg Pro Asp Leu Ile Leu His
325 330 335

Ile Tyr Thr Ser Arg Leu Tyr Phe His Trp Lys Arg Pro Phe Gln Lys
340 345 350

Gly Leu Cys Ser Leu Trp Gln Ser Gly Ile Leu Val Asp Val Met Asp
355 360 365

Leu Pro Gln Phe Thr Asp Cys Trp Thr Asn Phe Val Asn Pro Lys Arg
370 375 380

Pro Phe Trp Pro Trp Lys Gly Leu Glu Ile Ile Ser Arg Arg Thr Gln
385 390 395 400

Arg Arg Leu Arg Arg Ile Lys Glu Ser Trp Gly Leu Gln Asp Leu Val
405 410 415

Asn Asp Phe Gly Asn Leu Gln Leu Gly Pro Pro Met Ser
420 425

<210> SEQ ID NO 66
<211> LENGTH: 429
<212> TYPE: PRT
<213> ORGANISM: Rattus norvegicus

<400> SEQUENCE: 66

Met Gly Pro Phe Cys Leu Gly Cys Ser His Arg Lys Cys Tyr Ser Pro
1 5 10 15

Ile Arg Asn Leu Ile Ser Gln Glu Thr Phe Lys Phe His Phe Lys Asn
20 25 30

Leu Arg Tyr Ala Ile Asp Arg Lys Asp Thr Phe Leu Cys Tyr Glu Val
35 40 45

Thr Arg Lys Asp Cys Asp Ser Pro Val Ser Leu His His Gly Val Phe
50 55 60

Lys Asn Lys Asp Asn Ile His Ala Glu Ile Cys Phe Leu Tyr Trp Phe
65 70 75 80

His Asp Lys Val Leu Lys Val Leu Ser Pro Arg Glu Glu Phe Lys Ile
85 90 95

Thr Trp Tyr Met Ser Trp Ser Pro Cys Phe Glu Cys Ala Glu Gln Val
100 105 110

Leu Arg Phe Leu Ala Thr His His Asn Leu Ser Leu Asp Ile Phe Ser
115 120 125

Ser Arg Leu Tyr Asn Ile Arg Asp Pro Glu Asn Gln Gln Asn Leu Cys
130 135 140

Arg Leu Val Gln Glu Gly Ala Gln Val Ala Ala Met Asp Leu Tyr Glu
145 150 155 160

Phe Lys Lys Cys Trp Lys Lys Phe Val Asp Asn Gly Gly Arg Arg Phe
165 170 175

Arg Pro Trp Lys Lys Leu Leu Thr Asn Phe Arg Tyr Gln Asp Ser Lys
180 185 190

Leu Gln Glu Ile Leu Arg Pro Cys Tyr Ile Pro Val Pro Ser Ser Ser
195 200 205

Ser Ser Thr Leu Ser Asn Ile Cys Leu Thr Lys Gly Leu Pro Glu Thr
210 215 220

Arg Phe Cys Val Glu Arg Arg Arg Val His Leu Leu Ser Glu Glu Glu
225 230 235 240

Phe Tyr Ser Gln Phe Tyr Asn Gln Arg Val Lys His Leu Cys Tyr Tyr
245 250 255

His Gly Val Lys Pro Tyr Leu Cys Tyr Gln Leu Glu Gln Phe Asn Gly
260 265 270

Gln Ala Pro Leu Lys Gly Cys Leu Leu Ser Glu Lys Gly Lys Gln His
275 280 285

Ala Glu Ile Leu Phe Leu Asp Lys Ile Arg Ser Met Glu Leu Ser Gln
290 295 300

Val Ile Ile Thr Cys Tyr Leu Thr Trp Ser Pro Cys Pro Asn Cys Ala
305 310 315 320

Trp Gln Leu Ala Ala Phe Lys Arg Asp Arg Pro Asp Leu Ile Leu His
325 330 335

Ile Tyr Thr Ser Arg Leu Tyr Phe His Trp Lys Arg Pro Phe Gln Lys
340 345 350

Gly Leu Cys Ser Leu Trp Gln Ser Gly Ile Leu Val Asp Val Met Asp
355 360 365

Leu Pro Gln Phe Thr Asp Cys Trp Thr Asn Phe Val Asn Pro Lys Arg
370 375 380

Pro Phe Trp Pro Trp Lys Gly Leu Glu Ile Ile Ser Arg Arg Thr Gln
385 390 395 400

Arg Arg Leu His Arg Ile Lys Glu Ser Trp Gly Leu Gln Asp Leu Val
405 410 415

Asn Asp Phe Gly Asn Leu Gln Leu Gly Pro Pro Met Ser
420 425

<210> SEQ ID NO 67
<211> LENGTH: 370
<212> TYPE: PRT
<213> ORGANISM: Macaca mulatta

<400> SEQUENCE: 67

Met Val Glu Pro Met Asp Pro Arg Thr Phe Val Ser Asn Phe Asn Asn
1 5 10 15

Arg Pro Ile Leu Ser Gly Leu Asn Thr Val Trp Leu Cys Cys Glu Val
20 25 30

Lys Thr Lys Asp Pro Ser Gly Pro Pro Leu Asp Ala Lys Ile Phe Gln
35 40 45

Gly Lys Val Tyr Ser Lys Ala Lys Tyr His Pro Glu Met Arg Phe Leu
50 55 60

Arg Trp Phe His Lys Trp Arg Gln Leu His His Asp Gln Glu Tyr Lys
65 70 75 80

Val Thr Trp Tyr Val Ser Trp Ser Pro Cys Thr Arg Cys Ala Asn Ser
85 90 95

Val Ala Thr Phe Leu Ala Lys Asp Pro Lys Val Thr Leu Thr Ile Phe
100 105 110

Val Ala Arg Leu Tyr Tyr Phe Trp Lys Pro Asp Tyr Gln Gln Ala Leu
115 120 125

Arg Ile Leu Cys Gln Lys Arg Gly Gly Pro His Ala Thr Met Lys Ile
130 135 140

Met Asn Tyr Asn Glu Phe Gln Asp Cys Trp Asn Lys Phe Val Asp Gly
145 150 155 160

Arg Gly Lys Pro Phe Lys Pro Arg Asn Asn Leu Pro Lys His Tyr Thr
165 170 175

Leu Leu Gln Ala Thr Leu Gly Glu Leu Leu Arg His Leu Met Asp Pro
180 185 190

Gly Thr Phe Thr Ser Asn Phe Asn Asn Lys Pro Trp Val Ser Gly Gln
195 200 205

His Glu Thr Tyr Leu Cys Tyr Lys Val Glu Arg Leu His Asn Asp Thr
210 215 220

Trp Val Pro Leu Asn Gln His Arg Gly Phe Leu Arg Asn Gln Ala Pro
225 230 235 240

Asn Ile His Gly Phe Pro Lys Gly Arg His Ala Glu Leu Cys Phe Leu
245 250 255

Asp Leu Ile Pro Phe Trp Lys Leu Asp Gly Gln Gln Tyr Arg Val Thr
260 265 270

Cys Phe Thr Ser Trp Ser Pro Cys Phe Ser Cys Ala Gln Glu Met Ala
275 280 285

Lys Phe Ile Ser Asn Asn Glu His Val Ser Leu Cys Ile Phe Ala Ala
290 295 300

Arg Ile Tyr Asp Asp Gln Gly Arg Tyr Gln Glu Gly Leu Arg Ala Leu
305 310 315 320

His Arg Asp Gly Ala Lys Ile Ala Met Met Asn Tyr Ser Glu Phe Glu
325 330 335

Tyr Cys Trp Asp Thr Phe Val Asp Arg Gln Gly Arg Pro Phe Gln Pro
340 345 350

Trp Asp Gly Leu Asp Glu His Ser Gln Ala Leu Ser Gly Arg Leu Arg
355 360 365

Ala Ile
370

<210> SEQ ID NO 68
<211> LENGTH: 384
<212> TYPE: PRT
<213> ORGANISM: Pan troglodytes

<400> SEQUENCE: 68

Met Lys Pro His Phe Arg Asn Pro Val Glu Arg Met Tyr Gln Asp Thr
1 5 10 15

Phe Ser Asp Asn Phe Tyr Asn Arg Pro Ile Leu Ser His Arg Asn Thr
20 25 30

Val Trp Leu Cys Tyr Glu Val Lys Thr Lys Gly Pro Ser Arg Pro Pro
35 40 45

Leu Asp Ala Lys Ile Phe Arg Gly Gln Val Tyr Ser Lys Leu Lys Tyr
50 55 60

His Pro Glu Met Arg Phe Phe His Trp Phe Ser Lys Trp Arg Lys Leu
65 70 75 80

His Arg Asp Gln Glu Tyr Glu Val Thr Trp Tyr Ile Ser Trp Ser Pro
85 90 95

Cys Thr Lys Cys Thr Arg Asp Val Ala Thr Phe Leu Ala Glu Asp Pro
100 105 110

Lys Val Thr Leu Thr Ile Phe Val Ala Arg Leu Tyr Tyr Phe Trp Asp
115 120 125

Pro Asp Tyr Gln Glu Ala Leu Arg Ser Leu Cys Gln Lys Arg Asp Gly

```
    130                 135                 140

Pro Arg Ala Thr Met Lys Ile Met Asn Tyr Asp Glu Phe Gln His Cys
145                 150                 155                 160

Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
            180                 185                 190

Leu Arg His Ser Met Asp Pro Pro Thr Phe Thr Ser Asn Phe Asn Asn
        195                 200                 205

Glu Leu Trp Val Arg Gly Arg His Glu Thr Tyr Leu Cys Tyr Glu Val
    210                 215                 220

Glu Arg Leu His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
            260                 265                 270

Leu His Gln Asp Tyr Arg Val Thr Cys Phe Thr Ser Trp Ser Pro Cys
        275                 280                 285

Phe Ser Cys Ala Gln Glu Met Ala Lys Phe Ile Ser Asn Asn Lys His
    290                 295                 300

Val Ser Leu Cys Ile Phe Ala Ala Arg Ile Tyr Asp Asp Gln Gly Arg
305                 310                 315                 320

Cys Gln Glu Gly Leu Arg Thr Leu Ala Lys Ala Gly Ala Lys Ile Ser
                325                 330                 335

Ile Met Thr Tyr Ser Glu Phe Lys His Cys Trp Asp Thr Phe Val Asp
            340                 345                 350

His Gln Gly Cys Pro Phe Gln Pro Trp Asp Gly Leu Glu Glu His Ser
        355                 360                 365

Gln Ala Leu Ser Gly Arg Leu Arg Ala Ile Leu Gln Asn Gln Gly Asn
    370                 375                 380


<210> SEQ ID NO 69
<211> LENGTH: 377
<212> TYPE: PRT
<213> ORGANISM: Chlorocebus sabaeus

<400> SEQUENCE: 69

Met Asn Pro Gln Ile Arg Asn Met Val Glu Gln Met Glu Pro Asp Ile
1               5                   10                  15

Phe Val Tyr Tyr Phe Asn Asn Arg Pro Ile Leu Ser Gly Arg Asn Thr
            20                  25                  30

Val Trp Leu Cys Tyr Glu Val Lys Thr Lys Asp Pro Ser Gly Pro Pro
        35                  40                  45

Leu Asp Ala Asn Ile Phe Gln Gly Lys Leu Tyr Pro Glu Ala Lys Asp
    50                  55                  60

His Pro Glu Met Lys Phe Leu His Trp Phe Arg Lys Trp Arg Gln Leu
65                  70                  75                  80

His Arg Asp Gln Glu Tyr Glu Val Thr Trp Tyr Val Ser Trp Ser Pro
                85                  90                  95

Cys Thr Arg Cys Ala Asn Ser Val Ala Thr Phe Leu Ala Glu Asp Pro
            100                 105                 110

Lys Val Thr Leu Thr Ile Phe Val Ala Arg Leu Tyr Tyr Phe Trp Lys
        115                 120                 125
```

```
Pro Asp Tyr Gln Gln Ala Leu Arg Ile Leu Cys Gln Glu Arg Gly Gly
    130                 135                 140

Pro His Ala Thr Met Lys Ile Met Asn Tyr Asn Glu Phe Gln His Cys
145                 150                 155                 160

Trp Asn Glu Phe Val Asp Gly Gln Gly Lys Pro Phe Lys Pro Arg Lys
                165                 170                 175

Asn Leu Pro Lys His Tyr Thr Leu Leu His Ala Thr Leu Gly Glu Leu
            180                 185                 190

Leu Arg His Val Met Asp Pro Gly Thr Phe Thr Ser Asn Phe Asn Asn
        195                 200                 205

Lys Pro Trp Val Ser Gly Gln Arg Glu Thr Tyr Leu Cys Tyr Lys Val
    210                 215                 220

Glu Arg Ser His Asn Asp Thr Trp Val Leu Leu Asn Gln His Arg Gly
225                 230                 235                 240

Phe Leu Arg Asn Gln Ala Pro Asp Arg His Gly Phe Pro Lys Gly Arg
                245                 250                 255

His Ala Glu Leu Cys Phe Leu Asp Leu Ile Pro Phe Trp Lys Leu Asp
            260                 265                 270

Asp Gln Gln Tyr Arg Val Thr Cys Phe Thr Ser Trp Ser Pro Cys Phe
        275                 280                 285

Ser Cys Ala Gln Lys Met Ala Lys Phe Ile Ser Asn Asn Lys His Val
    290                 295                 300

Ser Leu Cys Ile Phe Ala Ala Arg Ile Tyr Asp Asp Gln Gly Arg Cys
305                 310                 315                 320

Gln Glu Gly Leu Arg Thr Leu His Arg Asp Gly Ala Lys Ile Ala Val
                325                 330                 335

Met Asn Tyr Ser Glu Phe Glu Tyr Cys Trp Asp Thr Phe Val Asp Arg
            340                 345                 350

Gln Gly Arg Pro Phe Gln Pro Trp Asp Gly Leu Asp Glu His Ser Gln
        355                 360                 365

Ala Leu Ser Gly Arg Leu Arg Ala Ile
    370                 375


<210> SEQ ID NO 70
<211> LENGTH: 384
<212> TYPE: PRT
<213> ORGANISM: Homo sapiens

<400> SEQUENCE: 70

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Pro
        35                  40                  45

Leu Asp Ala Lys Ile Phe Arg Gly Gln Val Tyr Ser Glu Leu Lys Tyr
    50                  55                  60

His Pro Glu Met Arg Phe Phe His Trp Phe Ser Lys Trp Arg Lys Leu
65                  70                  75                  80

His Arg Asp Gln Glu Tyr Glu Val Thr Trp Tyr Ile Ser Trp Ser Pro
                85                  90                  95

Cys Thr Lys Cys Thr Arg Asp Met Ala Thr Phe Leu Ala Glu Asp Pro
            100                 105                 110

Lys Val Thr Leu Thr Ile Phe Val Ala Arg Leu Tyr Tyr Phe Trp Asp
        115                 120                 125
```

```
Pro Asp Tyr Gln Glu Ala Leu Arg Ser Leu Cys Gln Lys Arg Asp Gly
    130                 135                 140

Pro Arg Ala Thr Met Lys Ile Met Asn Tyr Asp Glu Phe Gln His Cys
145                 150                 155                 160

Trp Ser Lys Phe Val Tyr Ser Gln Arg Glu Leu Phe Glu Pro Trp Asn
                165                 170                 175

Asn Leu Pro Lys Tyr Tyr Ile Leu Leu His Ile Met Leu Gly Glu Ile
            180                 185                 190

Leu Arg His Ser Met Asp Pro Pro Thr Phe Thr Phe Asn Phe Asn Asn
        195                 200                 205

Glu Pro Trp Val Arg Gly Arg His Glu Thr Tyr Leu Cys Tyr Glu Val
    210                 215                 220

Glu Arg Met His Asn Asp Thr Trp Val Leu Leu Asn Gln Arg Arg Gly
225                 230                 235                 240

Phe Leu Cys Asn Gln Ala Pro His Lys His Gly Phe Leu Glu Gly Arg
                245                 250                 255

His Ala Glu Leu Cys Phe Leu Asp Val Ile Pro Phe Trp Lys Leu Asp
            260                 265                 270

Leu Asp Gln Asp Tyr Arg Val Thr Cys Phe Thr Ser Trp Ser Pro Cys
        275                 280                 285

Phe Ser Cys Ala Gln Glu Met Ala Lys Phe Ile Ser Lys Asn Lys His
    290                 295                 300

Val Ser Leu Cys Ile Phe Thr Ala Arg Ile Tyr Asp Asp Gln Gly Arg
305                 310                 315                 320

Cys Gln Glu Gly Leu Arg Thr Leu Ala Glu Ala Gly Ala Lys Ile Ser
                325                 330                 335

Ile Met Thr Tyr Ser Glu Phe Lys His Cys Trp Asp Thr Phe Val Asp
            340                 345                 350

His Gln Gly Cys Pro Phe Gln Pro Trp Asp Gly Leu Asp Glu His Ser
        355                 360                 365

Gln Asp Leu Ser Gly Arg Leu Arg Ala Ile Leu Gln Asn Gln Glu Asn
    370                 375                 380


<210> SEQ ID NO 71
<211> LENGTH: 373
<212> TYPE: PRT
<213> ORGANISM: Homo sapiens

<400> SEQUENCE: 71

Met Lys Pro His Phe Arg Asn Thr Val Glu Arg Met Tyr Arg Asp Thr
1               5                   10                  15

Phe Ser Tyr Asn Phe Tyr Asn Arg Pro Ile Leu Ser Arg Arg Asn Thr
            20                  25                  30

Val Trp Leu Cys Tyr Glu Val Lys Thr Lys Gly Pro Ser Arg Pro Arg
        35                  40                  45

Leu Asp Ala Lys Ile Phe Arg Gly Gln Val Tyr Ser Gln Pro Glu His
    50                  55                  60

His Ala Glu Met Cys Phe Leu Ser Trp Phe Cys Gly Asn Gln Leu Pro
65                  70                  75                  80

Ala Tyr Lys Cys Phe Gln Ile Thr Trp Phe Val Ser Trp Thr Pro Cys
                85                  90                  95

Pro Asp Cys Val Ala Lys Leu Ala Glu Phe Leu Ala Glu His Pro Asn
            100                 105                 110

Val Thr Leu Thr Ile Ser Ala Ala Arg Leu Tyr Tyr Tyr Trp Glu Arg
```

```
        115                 120                 125

Asp Tyr Arg Arg Ala Leu Cys Arg Leu Ser Gln Ala Gly Ala Arg Val
    130                 135                 140

Lys Ile Met Asp Asp Glu Glu Phe Ala Tyr Cys Trp Glu Asn Phe Val
145                 150                 155                 160

Tyr Ser Glu Gly Gln Pro Phe Met Pro Trp Tyr Lys Phe Asp Asp Asn
                165                 170                 175

Tyr Ala Phe Leu His Arg Thr Leu Lys Glu Ile Leu Arg Asn Pro Met
            180                 185                 190

Glu Ala Met Tyr Pro His Ile Phe Tyr Phe His Phe Lys Asn Leu Arg
        195                 200                 205

Lys Ala Tyr Gly Arg Asn Glu Ser Trp Leu Cys Phe Thr Met Glu Val
    210                 215                 220

Val Lys His His Ser Pro Val Ser Trp Lys Arg Gly Val Phe Arg Asn
225                 230                 235                 240

Gln Val Asp Pro Glu Thr His Cys His Ala Glu Arg Cys Phe Leu Ser
                245                 250                 255

Trp Phe Cys Asp Asp Ile Leu Ser Pro Asn Thr Asn Tyr Glu Val Thr
            260                 265                 270

Trp Tyr Thr Ser Trp Ser Pro Cys Pro Glu Cys Ala Gly Glu Val Ala
        275                 280                 285

Glu Phe Leu Ala Arg His Ser Asn Val Asn Leu Thr Ile Phe Thr Ala
    290                 295                 300

Arg Leu Tyr Tyr Phe Trp Asp Thr Asp Tyr Gln Glu Gly Leu Arg Ser
305                 310                 315                 320

Leu Ser Gln Glu Gly Ala Ser Val Glu Ile Met Gly Tyr Lys Asp Phe
                325                 330                 335

Lys Tyr Cys Trp Glu Asn Phe Val Tyr Asn Asp Asp Glu Pro Phe Lys
            340                 345                 350

Pro Trp Lys Gly Leu Lys Tyr Asn Phe Leu Phe Leu Asp Ser Lys Leu
        355                 360                 365

Gln Glu Ile Leu Glu
    370


<210> SEQ ID NO 72
<211> LENGTH: 382
<212> TYPE: PRT
<213> ORGANISM: Homo sapiens

<400> SEQUENCE: 72

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
        35                  40                  45

Leu Trp Asp Thr Gly Val Phe Arg Gly Gln Val Tyr Phe Lys Pro Gln
    50                  55                  60

Tyr His Ala Glu Met Cys Phe Leu Ser Trp Phe Cys Gly Asn Gln Leu
65                  70                  75                  80

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
            100                 105                 110
```

```
Asn Val Thr Leu Thr Ile Ser Ala Ala Arg Leu Tyr Tyr Tyr Trp Glu
        115                 120                 125

Arg Asp Tyr Arg Arg Ala Leu Cys Arg Leu Ser Gln Ala Gly Ala Arg
    130                 135                 140

Val Thr Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
            180                 185                 190

Met Asp Pro Asp Thr Phe Thr Phe Asn Phe Asn Asn Asp Pro Leu Val
        195                 200                 205

Leu Arg Arg Arg Gln Thr Tyr Leu Cys Tyr Glu Val Glu Arg Leu Asp
    210                 215                 220

Asn Gly Thr Trp Val Leu Met Asp Gln His Met Gly Phe Leu Cys Asn
225                 230                 235                 240

Glu Ala Lys Asn Leu Leu Cys Gly Phe Tyr Gly Arg His Ala Glu Leu
                245                 250                 255

Arg Phe Leu Asp Leu Val Pro Ser Leu Gln Leu Asp Pro Ala Gln Ile
            260                 265                 270

Tyr Arg Val Thr Trp Phe Ile Ser Trp Ser Pro Cys Phe Ser Trp Gly
        275                 280                 285

Cys Ala Gly Glu Val Arg Ala Phe Leu Gln Glu Asn Thr His Val Arg
    290                 295                 300

Leu Arg Ile Phe Ala Ala Arg Ile Tyr Asp Tyr Asp Pro Leu Tyr Lys
305                 310                 315                 320

Glu Ala Leu Gln Met Leu Arg Asp Ala Gly Ala Gln Val Ser Ile Met
                325                 330                 335

Thr Tyr Asp Glu Phe Glu Tyr Cys Trp Asp Thr Phe Val Tyr Arg Gln
            340                 345                 350

Gly Cys Pro Phe Gln Pro Trp Asp Gly Leu Glu Glu His Ser Gln Ala
        355                 360                 365

Leu Ser Gly Arg Leu Arg Ala Ile Leu Gln Asn Gln Gly Asn
    370                 375                 380


<210> SEQ ID NO 73
<211> LENGTH: 190
<212> TYPE: PRT
<213> ORGANISM: Homo sapiens

<400> SEQUENCE: 73

Met Asn Pro Gln Ile Arg Asn Pro Met Lys Ala Met Tyr Pro Gly Thr
1               5                   10                  15

Phe Tyr Phe Gln Phe Lys Asn Leu Trp Glu Ala Asn Asp Arg Asn Glu
            20                  25                  30

Thr Trp Leu Cys Phe Thr Val Glu Gly Ile Lys Arg Arg Ser Val Val
        35                  40                  45

Ser Trp Lys Thr Gly Val Phe Arg Asn Gln Val Asp Ser Glu Thr His
    50                  55                  60

Cys His Ala Glu Arg Cys Phe Leu Ser Trp Phe Cys Asp Asp Ile Leu
65                  70                  75                  80

Ser Pro Asn Thr Lys Tyr Gln Val Thr Trp Tyr Thr Ser Trp Ser Pro
                85                  90                  95

Cys Pro Asp Cys Ala Gly Glu Val Ala Glu Phe Leu Ala Arg His Ser
            100                 105                 110
```

Asn Val Asn Leu Thr Ile Phe Thr Ala Arg Leu Tyr Tyr Phe Gln Tyr
        115                 120                 125

Pro Cys Tyr Gln Glu Gly Leu Arg Ser Leu Ser Gln Glu Gly Val Ala
    130                 135                 140

Val Glu Ile Met Asp Tyr Glu Asp Phe Lys Tyr Cys Trp Glu Asn Phe
145                 150                 155                 160

Val Tyr Asn Asp Asn Glu Pro Phe Lys Pro Trp Lys Gly Leu Lys Thr
                165                 170                 175

Asn Phe Arg Leu Leu Lys Arg Arg Leu Arg Glu Ser Leu Gln
            180                 185                 190

<210> SEQ ID NO 74
<211> LENGTH: 199
<212> TYPE: PRT
<213> ORGANISM: Homo sapiens

<400> SEQUENCE: 74

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 75
<211> LENGTH: 200
<212> TYPE: PRT
<213> ORGANISM: Homo sapiens

<400> SEQUENCE: 75

Met Ala Leu Leu Thr Ala Glu Thr Phe Arg Leu Gln Phe Asn Asn Lys
1               5                   10                  15

Arg Arg Leu Arg Arg Pro Tyr Tyr Pro Arg Lys Ala Leu Leu Cys Tyr
            20                  25                  30

Gln Leu Thr Pro Gln Asn Gly Ser Thr Pro Thr Arg Gly Tyr Phe Glu
        35                  40                  45

```
Asn Lys Lys Lys Cys His Ala Glu Ile Cys Phe Ile Asn Glu Ile Lys
    50                  55                  60

Ser Met Gly Leu Asp Glu Thr Gln Cys Tyr Gln Val Thr Cys Tyr Leu
65                  70                  75                  80

Thr Trp Ser Pro Cys Ser Ser Cys Ala Trp Glu Leu Val Asp Phe Ile
                85                  90                  95

Lys Ala His Asp His Leu Asn Leu Gly Ile Phe Ala Ser Arg Leu Tyr
            100                 105                 110

Tyr His Trp Cys Lys Pro Gln Gln Lys Gly Leu Arg Leu Leu Cys Gly
        115                 120                 125

Ser Gln Val Pro Val Glu Val Met Gly Phe Pro Lys Phe Ala Asp Cys
    130                 135                 140

Trp Glu Asn Phe Val Asp His Glu Lys Pro Leu Ser Phe Asn Pro Tyr
145                 150                 155                 160

Lys Met Leu Glu Glu Leu Asp Lys Asn Ser Arg Ala Ile Lys Arg Arg
                165                 170                 175

Leu Glu Arg Ile Lys Ile Pro Gly Val Arg Ala Gln Gly Arg Tyr Met
            180                 185                 190

Asp Ile Leu Cys Asp Ala Glu Val
        195                 200


<210> SEQ ID NO 76
<211> LENGTH: 386
<212> TYPE: PRT
<213> ORGANISM: Homo sapiens

<400> SEQUENCE: 76

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
        35                  40                  45

Leu Trp Asp Thr Gly Val Phe Arg Gly Pro Val Leu Pro Lys Arg Gln
    50                  55                  60

Ser Asn His Arg Gln Glu Val Tyr Phe Arg Phe Glu Asn His Ala Glu
65                  70                  75                  80

Met Cys Phe Leu Ser Trp Phe Cys Gly Asn Arg Leu Pro Ala Asn Arg
                85                  90                  95

Arg Phe Gln Ile Thr Trp Phe Val Ser Trp Asn Pro Cys Leu Pro Cys
            100                 105                 110

Val Val Lys Val Thr Lys Phe Leu Ala Glu His Pro Asn Val Thr Leu
        115                 120                 125

Thr Ile Ser Ala Ala Arg Leu Tyr Tyr Tyr Arg Asp Arg Asp Trp Arg
    130                 135                 140

Trp Val Leu Leu Arg Leu His Lys Ala Gly Ala Arg Val Lys Ile Met
145                 150                 155                 160

Asp Tyr Glu Asp Phe Ala Tyr Cys Trp Glu Asn Phe Val Cys Asn Glu
                165                 170                 175

Gly Gln Pro Phe Met Pro Trp Tyr Lys Phe Asp Asp Asn Tyr Ala Ser
            180                 185                 190

Leu His Arg Thr Leu Lys Glu Ile Leu Arg Asn Pro Met Glu Ala Met
        195                 200                 205

Tyr Pro His Ile Phe Tyr Phe His Phe Lys Asn Leu Leu Lys Ala Cys
```

```
    210                 215                 220

Gly Arg Asn Glu Ser Trp Leu Cys Phe Thr Met Glu Val Thr Lys His
225                 230                 235                 240

His Ser Ala Val Phe Arg Lys Arg Gly Val Phe Arg Asn Gln Val Asp
                245                 250                 255

Pro Glu Thr His Cys His Ala Glu Arg Cys Phe Leu Ser Trp Phe Cys
            260                 265                 270

Asp Asp Ile Leu Ser Pro Asn Thr Asn Tyr Glu Val Thr Trp Tyr Thr
        275                 280                 285

Ser Trp Ser Pro Cys Pro Glu Cys Ala Gly Glu Val Ala Glu Phe Leu
    290                 295                 300

Ala Arg His Ser Asn Val Asn Leu Thr Ile Phe Thr Ala Arg Leu Cys
305                 310                 315                 320

Tyr Phe Trp Asp Thr Asp Tyr Gln Glu Gly Leu Cys Ser Leu Ser Gln
                325                 330                 335

Glu Gly Ala Ser Val Lys Ile Met Gly Tyr Lys Asp Phe Val Ser Cys
            340                 345                 350

Trp Lys Asn Phe Val Tyr Ser Asp Asp Glu Pro Phe Lys Pro Trp Lys
        355                 360                 365

Gly Leu Gln Thr Asn Phe Arg Leu Leu Lys Arg Arg Leu Arg Glu Ile
    370                 375                 380

Leu Gln
385


<210> SEQ ID NO 77
<211> LENGTH: 236
<212> TYPE: PRT
<213> ORGANISM: Homo sapiens

<400> SEQUENCE: 77

Met Thr Ser Glu Lys Gly Pro Ser Thr Gly Asp Pro Thr Leu Arg Arg
1               5                   10                  15

Arg Ile Glu Pro Trp Glu Phe Asp Val Phe Tyr Asp Pro Arg Glu Leu
            20                  25                  30

Arg Lys Glu Ala Cys Leu Leu Tyr Glu Ile Lys Trp Gly Met Ser Arg
        35                  40                  45

Lys Ile Trp Arg Ser Ser Gly Lys Asn Thr Thr Asn His Val Glu Val
    50                  55                  60

Asn Phe Ile Lys Lys Phe Thr Ser Glu Arg Asp Phe His Pro Ser Met
65                  70                  75                  80

Ser Cys Ser Ile Thr Trp Phe Leu Ser Trp Ser Pro Cys Trp Glu Cys
                85                  90                  95

Ser Gln Ala Ile Arg Glu Phe Leu Ser Arg His Pro Gly Val Thr Leu
            100                 105                 110

Val Ile Tyr Val Ala Arg Leu Phe Trp His Met Asp Gln Gln Asn Arg
        115                 120                 125

Gln Gly Leu Arg Asp Leu Val Asn Ser Gly Val Thr Ile Gln Ile Met
    130                 135                 140

Arg Ala Ser Glu Tyr Tyr His Cys Trp Arg Asn Phe Val Asn Tyr Pro
145                 150                 155                 160

Pro Gly Asp Glu Ala His Trp Pro Gln Tyr Pro Pro Leu Trp Met Met
                165                 170                 175

Leu Tyr Ala Leu Glu Leu His Cys Ile Ile Leu Ser Leu Pro Pro Cys
            180                 185                 190
```

Leu Lys Ile Ser Arg Arg Trp Gln Asn His Leu Thr Phe Phe Arg Leu
195 200 205

His Leu Gln Asn Cys His Tyr Gln Thr Ile Pro Pro His Ile Leu Leu
210 215 220

Ala Thr Gly Leu Ile His Pro Ser Val Ala Trp Arg
225 230 235

<210> SEQ ID NO 78
<211> LENGTH: 229
<212> TYPE: PRT
<213> ORGANISM: Mus musculus

<400> SEQUENCE: 78

Met Ser Ser Glu Thr Gly Pro Val Ala Val Asp Pro Thr Leu Arg Arg
1 5 10 15

Arg Ile Glu Pro His Glu Phe Glu Val Phe Phe Asp Pro Arg Glu Leu
20 25 30

Arg Lys Glu Thr Cys Leu Leu Tyr Glu Ile Asn Trp Gly Gly Arg His
35 40 45

Ser Val Trp Arg His Thr Ser Gln Asn Thr Ser Asn His Val Glu Val
50 55 60

Asn Phe Leu Glu Lys Phe Thr Thr Glu Arg Tyr Phe Arg Pro Asn Thr
65 70 75 80

Arg Cys Ser Ile Thr Trp Phe Leu Ser Trp Ser Pro Cys Gly Glu Cys
85 90 95

Ser Arg Ala Ile Thr Glu Phe Leu Ser Arg His Pro Tyr Val Thr Leu
100 105 110

Phe Ile Tyr Ile Ala Arg Leu Tyr His His Thr Asp Gln Arg Asn Arg
115 120 125

Gln Gly Leu Arg Asp Leu Ile Ser Ser Gly Val Thr Ile Gln Ile Met
130 135 140

Thr Glu Gln Glu Tyr Cys Tyr Cys Trp Arg Asn Phe Val Asn Tyr Pro
145 150 155 160

Pro Ser Asn Glu Ala Tyr Trp Pro Arg Tyr Pro His Leu Trp Val Lys
165 170 175

Leu Tyr Val Leu Glu Leu Tyr Cys Ile Ile Leu Gly Leu Pro Pro Cys
180 185 190

Leu Lys Ile Leu Arg Arg Lys Gln Pro Gln Leu Thr Phe Phe Thr Ile
195 200 205

Thr Leu Gln Thr Cys His Tyr Gln Arg Ile Pro Pro His Leu Leu Trp
210 215 220

Ala Thr Gly Leu Lys
225

<210> SEQ ID NO 79
<211> LENGTH: 229
<212> TYPE: PRT
<213> ORGANISM: Rattus norvegicus

<400> SEQUENCE: 79

Met Ser Ser Glu Thr Gly Pro Val Ala Val Asp Pro Thr Leu Arg Arg
1 5 10 15

Arg Ile Glu Pro His Glu Phe Glu Val Phe Phe Asp Pro Arg Glu Leu
20 25 30

Arg Lys Glu Thr Cys Leu Leu Tyr Glu Ile Asn Trp Gly Gly Arg His
35 40 45

-continued

Ser Ile Trp Arg His Thr Ser Gln Asn Thr Asn Lys His Val Glu Val
    50                  55                  60

Asn Phe Ile Glu Lys Phe Thr Thr Glu Arg Tyr Phe Cys Pro Asn Thr
65                  70                  75                  80

Arg Cys Ser Ile Thr Trp Phe Leu Ser Trp Ser Pro Cys Gly Glu Cys
                85                  90                  95

Ser Arg Ala Ile Thr Glu Phe Leu Ser Arg Tyr Pro His Val Thr Leu
            100                 105                 110

Phe Ile Tyr Ile Ala Arg Leu Tyr His His Ala Asp Pro Arg Asn Arg
        115                 120                 125

Gln Gly Leu Arg Asp Leu Ile Ser Ser Gly Val Thr Ile Gln Ile Met
    130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
        195                 200                 205

Ala Leu Gln Ser Cys His Tyr Gln Arg Leu Pro Pro His Ile Leu Trp
    210                 215                 220

Ala Thr Gly Leu Lys
225

<210> SEQ ID NO 80
<211> LENGTH: 191
<212> TYPE: PRT
<213> ORGANISM: Homo sapiens

<400> SEQUENCE: 80

Met Glu Ala Lys Ala Ala Pro Lys Pro Ala Ala Ser Gly Ala Cys Ser
1               5                   10                  15

Val Ser Ala Glu Glu Thr Glu Lys Trp Met Glu Glu Ala Met His Met
            20                  25                  30

Ala Lys Glu Ala Leu Glu Asn Thr Glu Val Pro Val Gly Cys Leu Met
        35                  40                  45

Val Tyr Asn Asn Glu Val Val Gly Lys Gly Arg Asn Glu Val Asn Gln
    50                  55                  60

Thr Lys Asn Ala Thr Arg His Ala Glu Met Val Ala Ile Asp Gln Val
65                  70                  75                  80

Leu Asp Trp Cys Arg Gln Ser Gly Lys Ser Pro Ser Glu Val Phe Glu
                85                  90                  95

His Thr Val Leu Tyr Val Thr Val Glu Pro Cys Ile Met Cys Ala Ala
            100                 105                 110

Ala Leu Arg Leu Met Lys Ile Pro Leu Val Val Tyr Gly Cys Gln Asn
        115                 120                 125

Glu Arg Phe Gly Gly Cys Gly Ser Val Leu Asn Ile Ala Ser Ala Asp
    130                 135                 140

Leu Pro Asn Thr Gly Arg Pro Phe Gln Cys Ile Pro Gly Tyr Arg Ala
145                 150                 155                 160

Glu Glu Ala Val Glu Met Leu Lys Thr Phe Tyr Lys Gln Glu Asn Pro
                165                 170                 175

Asn Ala Pro Lys Ser Lys Val Arg Lys Lys Glu Cys Gln Lys Ser
            180                 185                 190

<210> SEQ ID NO 81
<211> LENGTH: 191
<212> TYPE: PRT
<213> ORGANISM: Mus musculus

<400> SEQUENCE: 81

Met Glu Glu Lys Val Glu Ser Thr Thr Thr Pro Asp Gly Pro Cys Val
1 5 10 15

Val Ser Val Gln Glu Thr Glu Lys Trp Met Glu Glu Ala Met Arg Met
20 25 30

Ala Lys Glu Ala Leu Glu Asn Ile Glu Val Pro Val Gly Cys Leu Met
35 40 45

Val Tyr Asn Asn Glu Val Val Gly Lys Gly Arg Asn Glu Val Asn Gln
50 55 60

Thr Lys Asn Ala Thr Arg His Ala Glu Met Val Ala Ile Asp Gln Val
65 70 75 80

Leu Asp Trp Cys His Gln His Gly Gln Ser Pro Ser Thr Val Phe Glu
85 90 95

His Thr Val Leu Tyr Val Thr Val Glu Pro Cys Ile Met Cys Ala Ala
100 105 110

Ala Leu Arg Leu Met Lys Ile Pro Leu Val Val Tyr Gly Cys Gln Asn
115 120 125

Glu Arg Phe Gly Gly Cys Gly Ser Val Leu Asn Ile Ala Ser Ala Asp
130 135 140

Leu Pro Asn Thr Gly Arg Pro Phe Gln Cys Ile Pro Gly Tyr Arg Ala
145 150 155 160

Glu Glu Ala Val Glu Leu Leu Lys Thr Phe Tyr Lys Gln Glu Asn Pro
165 170 175

Asn Ala Pro Lys Ser Lys Val Arg Lys Lys Asp Cys Gln Lys Ser
180 185 190

<210> SEQ ID NO 82
<211> LENGTH: 499
<212> TYPE: PRT
<213> ORGANISM: Mus musculus

<400> SEQUENCE: 82

Met Trp Thr Ala Asp Glu Ile Ala Gln Leu Cys Tyr Ala His Tyr Asn
1 5 10 15

Val Arg Leu Pro Lys Gln Gly Lys Pro Glu Pro Asn Arg Glu Trp Thr
20 25 30

Leu Leu Ala Ala Val Val Lys Ile Gln Ala Ser Ala Asn Gln Ala Cys
35 40 45

Asp Ile Pro Glu Lys Glu Val Gln Val Thr Lys Glu Val Val Ser Met
50 55 60

Gly Thr Gly Thr Lys Cys Ile Gly Gln Ser Lys Met Arg Glu Ser Gly
65 70 75 80

Asp Ile Leu Asn Asp Ser His Ala Glu Ile Ile Ala Arg Arg Ser Phe
85 90 95

Gln Arg Tyr Leu Leu His Gln Leu His Leu Ala Ala Val Leu Lys Glu
100 105 110

Asp Ser Ile Phe Val Pro Gly Thr Gln Arg Gly Leu Trp Arg Leu Arg
115 120 125

Pro Asp Leu Ser Phe Val Phe Phe Ser Ser His Thr Pro Cys Gly Asp
130 135 140

Ala Ser Ile Ile Pro Met Leu Glu Phe Glu Glu Gln Pro Cys Cys Pro
145 150 155 160

Val Ile Arg Ser Trp Ala Asn Asn Ser Pro Val Gln Glu Thr Glu Asn
165 170 175

Leu Glu Asp Ser Lys Asp Lys Arg Asn Cys Glu Asp Pro Ala Ser Pro
180 185 190

Val Ala Lys Lys Met Arg Leu Gly Thr Pro Ala Arg Ser Leu Ser Asn
195 200 205

Cys Val Ala His His Gly Thr Gln Glu Ser Gly Pro Val Lys Pro Asp
210 215 220

Val Ser Ser Ser Asp Leu Thr Lys Glu Glu Pro Asp Ala Ala Asn Gly
225 230 235 240

Ile Ala Ser Gly Ser Phe Arg Val Val Asp Val Tyr Arg Thr Gly Ala
245 250 255

Lys Cys Val Pro Gly Glu Thr Gly Asp Leu Arg Glu Pro Gly Ala Ala
260 265 270

Tyr His Gln Val Gly Leu Leu Arg Val Lys Pro Gly Arg Gly Asp Arg
275 280 285

Thr Cys Ser Met Ser Cys Ser Asp Lys Met Ala Arg Trp Asn Val Leu
290 295 300

Gly Cys Gln Gly Ala Leu Leu Met His Phe Leu Glu Lys Pro Ile Tyr
305 310 315 320

Leu Ser Ala Val Val Ile Gly Lys Cys Pro Tyr Ser Gln Glu Ala Met
325 330 335

Arg Arg Ala Leu Thr Gly Arg Cys Glu Glu Thr Leu Val Leu Pro Arg
340 345 350

Gly Phe Gly Val Gln Glu Leu Glu Ile Gln Gln Ser Gly Leu Leu Phe
355 360 365

Glu Gln Ser Arg Cys Ala Val His Arg Lys Arg Gly Asp Ser Pro Gly
370 375 380

Arg Leu Val Pro Cys Gly Ala Ala Ile Ser Trp Ser Ala Val Pro Gln
385 390 395 400

Gln Pro Leu Asp Val Thr Ala Asn Gly Phe Pro Gln Gly Thr Thr Lys
405 410 415

Lys Glu Ile Gly Ser Pro Arg Ala Arg Ser Arg Ile Ser Lys Val Glu
420 425 430

Leu Phe Arg Ser Phe Gln Lys Leu Leu Ser Ser Ile Ala Asp Asp Glu
435 440 445

Gln Pro Asp Ser Ile Arg Val Thr Lys Lys Leu Asp Thr Tyr Gln Glu
450 455 460

Tyr Lys Asp Ala Ala Ser Ala Tyr Gln Glu Ala Trp Gly Ala Leu Arg
465 470 475 480

Arg Ile Gln Pro Phe Ala Ser Trp Ile Arg Asn Pro Pro Asp Tyr His
485 490 495

Gln Phe Lys

<210> SEQ ID NO 83
<211> LENGTH: 502
<212> TYPE: PRT
<213> ORGANISM: Homo sapiens

<400> SEQUENCE: 83

Met Trp Thr Ala Asp Glu Ile Ala Gln Leu Cys Tyr Glu His Tyr Gly
1 5 10 15

-continued

```
Ile Arg Leu Pro Lys Lys Gly Lys Pro Glu Pro Asn His Glu Trp Thr
            20                  25                  30

Leu Leu Ala Ala Val Val Lys Ile Gln Ser Pro Ala Asp Lys Ala Cys
        35                  40                  45

Asp Thr Pro Asp Lys Pro Val Gln Val Thr Lys Glu Val Val Ser Met
    50                  55                  60

Gly Thr Gly Thr Lys Cys Ile Gly Gln Ser Lys Met Arg Lys Asn Gly
65                  70                  75                  80

Asp Ile Leu Asn Asp Ser His Ala Glu Val Ile Ala Arg Arg Ser Phe
                85                  90                  95

Gln Arg Tyr Leu Leu His Gln Leu Gln Leu Ala Ala Thr Leu Lys Glu
            100                 105                 110

Asp Ser Ile Phe Val Pro Gly Thr Gln Lys Gly Val Trp Lys Leu Arg
        115                 120                 125

Arg Asp Leu Ile Phe Val Phe Phe Ser Ser His Thr Pro Cys Gly Asp
    130                 135                 140

Ala Ser Ile Ile Pro Met Leu Glu Phe Glu Asp Gln Pro Cys Cys Pro
145                 150                 155                 160

Val Phe Arg Asn Trp Ala His Asn Ser Ser Val Glu Ala Ser Ser Asn
                165                 170                 175

Leu Glu Ala Pro Gly Asn Glu Arg Lys Cys Glu Asp Pro Asp Ser Pro
            180                 185                 190

Val Thr Lys Lys Met Arg Leu Glu Pro Gly Thr Ala Ala Arg Glu Val
        195                 200                 205

Thr Asn Gly Ala Ala His His Gln Ser Phe Gly Lys Gln Lys Ser Gly
    210                 215                 220

Pro Ile Ser Pro Gly Ile His Ser Cys Asp Leu Thr Val Glu Gly Leu
225                 230                 235                 240

Ala Thr Val Thr Arg Ile Ala Pro Gly Ser Ala Lys Val Ile Asp Val
                245                 250                 255

Tyr Arg Thr Gly Ala Lys Cys Val Pro Gly Glu Ala Gly Asp Ser Gly
            260                 265                 270

Lys Pro Gly Ala Ala Phe His Gln Val Gly Leu Leu Arg Val Lys Pro
        275                 280                 285

Gly Arg Gly Asp Arg Thr Arg Ser Met Ser Cys Ser Asp Lys Met Ala
    290                 295                 300

Arg Trp Asn Val Leu Gly Cys Gln Gly Ala Leu Leu Met His Leu Leu
305                 310                 315                 320

Glu Glu Pro Ile Tyr Leu Ser Ala Val Val Ile Gly Lys Cys Pro Tyr
                325                 330                 335

Ser Gln Glu Ala Met Gln Arg Ala Leu Ile Gly Arg Cys Gln Asn Val
            340                 345                 350

Ser Ala Leu Pro Lys Gly Phe Gly Val Gln Glu Leu Lys Ile Leu Gln
        355                 360                 365

Ser Asp Leu Leu Phe Glu Gln Ser Arg Ser Ala Val Gln Ala Lys Arg
    370                 375                 380

Ala Asp Ser Pro Gly Arg Leu Val Pro Cys Gly Ala Ala Ile Ser Trp
385                 390                 395                 400

Ser Ala Val Pro Glu Gln Pro Leu Asp Val Thr Ala Asn Gly Phe Pro
                405                 410                 415

Gln Gly Thr Thr Lys Lys Thr Ile Gly Ser Leu Gln Ala Arg Ser Gln
            420                 425                 430
```

```
Ile Ser Lys Val Glu Leu Phe Arg Ser Phe Gln Lys Leu Leu Ser Arg
        435                 440                 445

Ile Ala Arg Asp Lys Trp Pro His Ser Leu Arg Val Gln Lys Leu Asp
    450                 455                 460

Thr Tyr Gln Glu Tyr Lys Glu Ala Ala Ser Ser Tyr Gln Glu Ala Trp
465                 470                 475                 480

Ser Thr Leu Arg Lys Gln Val Phe Gly Ser Trp Ile Arg Asn Pro Pro
                485                 490                 495

Asp Tyr His Gln Phe Lys
            500


<210> SEQ ID NO 84
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 84

Gly Ser Gly Arg Ala Asp Ala Leu Asp Asp Phe Asp Leu Asp Met Leu
1               5                   10                  15

Gly Ser Asp Ala Leu Asp Asp Phe Asp Leu Asp Met Leu Gly Ser Asp
            20                  25                  30

Ala Leu Asp Asp Phe Asp Leu Asp Met Leu Gly Ser Asp Ala Leu Asp
        35                  40                  45

Asp Phe Asp Leu Asp Met Leu Ile Asn
    50                  55


<210> SEQ ID NO 85
<211> LENGTH: 85
<212> TYPE: PRT
<213> ORGANISM: Artificial Sequence
<220> FEATURE:
<223> OTHER INFORMATION: Synthetic Polypeptide

<400> SEQUENCE: 85

Ala Pro Pro Thr Asp Val Ser Leu Gly Asp Glu Leu His Leu Asp Gly
1               5                   10                  15

Glu Asp Val Ala Met Ala His Ala Asp Ala Leu Asp Asp Phe Asp Leu
            20                  25                  30

Asp Met Leu Gly Asp Gly Asp Ser Pro Gly Pro Gly Phe Thr Pro His
        35                  40                  45

Asp Ser Ala Pro Tyr Gly Ala Leu Asp Met Ala Asp Phe Glu Phe Glu
    50                  55                  60

Gln Met Phe Thr Asp Ala Leu Gly Ile Asp Glu Tyr Gly Gly Glu Phe
65                  70                  75                  80

Pro Gly Ile Arg Arg
                85


<210> SEQ ID NO 86
<211> LENGTH: 184
<212> TYPE: PRT
<213> ORGANISM: Artificial Sequence
<220> FEATURE:
<223> OTHER INFORMATION: Synthetic Polypeptide

<400> SEQUENCE: 86

Pro Ser Gly Gln Ile Ser Asn Gln Ala Leu Ala Leu Ala Pro Ser Ser
1               5                   10                  15

Ala Pro Val Leu Ala Gln Thr Met Val Pro Ser Ser Ala Met Val Pro
```

20 25 30

Leu Ala Gln Pro Pro Ala Pro Ala Pro Val Leu Thr Pro Gly Pro Pro
35 40 45

Gln Ser Leu Ser Ala Pro Val Pro Lys Ser Thr Gln Ala Gly Glu Gly
50 55 60

Thr Leu Ser Glu Ala Leu Leu His Leu Gln Phe Asp Ala Asp Glu Asp
65 70 75 80

Leu Gly Ala Leu Leu Gly Asn Ser Thr Asp Pro Gly Val Phe Thr Asp
85 90 95

Leu Ala Ser Val Asp Asn Ser Glu Phe Gln Gln Leu Leu Asn Gln Gly
100 105 110

Val Ser Met Ser His Ser Thr Ala Glu Pro Met Leu Met Glu Tyr Pro
115 120 125

Glu Ala Ile Thr Arg Leu Val Thr Gly Ser Gln Arg Pro Pro Asp Pro
130 135 140

Ala Pro Thr Pro Leu Gly Thr Ser Gly Leu Pro Asn Gly Leu Ser Gly
145 150 155 160

Asp Glu Asp Phe Ser Ser Ile Ala Asp Met Asp Phe Ser Ala Leu Leu
165 170 175

Ser Gln Ile Ser Ser Ser Gly Gln
180

<210> SEQ ID NO 87
<211> LENGTH: 1467
<212> TYPE: PRT
<213> ORGANISM: Artificial Sequence
<220> FEATURE:
<223> OTHER INFORMATION: Synthetic Polypeptide

<400> SEQUENCE: 87

Met Asp Lys Lys Tyr Ser Ile Gly Leu Ala Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala

```
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620
```

Leu Phe Glu Asp Arg Glu Met Ile Glu Glu Arg Leu Lys Thr Tyr Ala
625 630 635 640

His Leu Phe Asp Asp Lys Val Met Lys Gln Leu Lys Arg Arg Arg Tyr
645 650 655

Thr Gly Trp Gly Arg Leu Ser Arg Lys Leu Ile Asn Gly Ile Arg Asp
660 665 670

Lys Gln Ser Gly Lys Thr Ile Leu Asp Phe Leu Lys Ser Asp Gly Phe
675 680 685

Ala Asn Arg Asn Phe Met Gln Leu Ile His Asp Asp Ser Leu Thr Phe
690 695 700

Lys Glu Asp Ile Gln Lys Ala Gln Val Ser Gly Gln Gly Asp Ser Leu
705 710 715 720

His Glu His Ile Ala Asn Leu Ala Gly Ser Pro Ala Ile Lys Lys Gly
725 730 735

Ile Leu Gln Thr Val Lys Val Val Asp Glu Leu Val Lys Val Met Gly
740 745 750

Arg His Lys Pro Glu Asn Ile Val Ile Glu Met Ala Arg Glu Asn Gln
755 760 765

Thr Thr Gln Lys Gly Gln Lys Asn Ser Arg Glu Arg Met Lys Arg Ile
770 775 780

Glu Glu Gly Ile Lys Glu Leu Gly Ser Gln Ile Leu Lys Glu His Pro
785 790 795 800

Val Glu Asn Thr Gln Leu Gln Asn Glu Lys Leu Tyr Leu Tyr Tyr Leu
805 810 815

Gln Asn Gly Arg Asp Met Tyr Val Asp Gln Glu Leu Asp Ile Asn Arg
820 825 830

Leu Ser Asp Tyr Asp Val Asp Ala Ile Val Pro Gln Ser Phe Leu Lys
835 840 845

Asp Asp Ser Ile Asp Asn Lys Val Leu Thr Arg Ser Asp Lys Asn Arg
850 855 860

Gly Lys Ser Asp Asn Val Pro Ser Glu Glu Val Val Lys Lys Met Lys
865 870 875 880

Asn Tyr Trp Arg Gln Leu Leu Asn Ala Lys Leu Ile Thr Gln Arg Lys
885 890 895

Phe Asp Asn Leu Thr Lys Ala Glu Arg Gly Gly Leu Ser Glu Leu Asp
900 905 910

Lys Ala Gly Phe Ile Lys Arg Gln Leu Val Glu Thr Arg Gln Ile Thr
915 920 925

Lys His Val Ala Gln Ile Leu Asp Ser Arg Met Asn Thr Lys Tyr Asp
930 935 940

Glu Asn Asp Lys Leu Ile Arg Glu Val Lys Val Ile Thr Leu Lys Ser
945 950 955 960

Lys Leu Val Ser Asp Phe Arg Lys Asp Phe Gln Phe Tyr Lys Val Arg
965 970 975

Glu Ile Asn Asn Tyr His His Ala His Asp Ala Tyr Leu Asn Ala Val
980 985 990

Val Gly Thr Ala Leu Ile Lys Lys Tyr Pro Lys Leu Glu Ser Glu Phe
995 1000 1005

Val Tyr Gly Asp Tyr Lys Val Tyr Asp Val Arg Lys Met Ile Ala
1010 1015 1020

Lys Ser Glu Gln Glu Ile Gly Lys Ala Thr Ala Lys Tyr Phe Phe
1025 1030 1035

```
Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365

Gly Ser  Pro Lys Lys Lys Arg  Lys Val Ser Ser Asp  Tyr Lys Asp
    1370                 1375                 1380

His Asp  Gly Asp Tyr Lys Asp  His Asp Ile Asp Tyr  Lys Asp Asp
    1385                 1390                 1395

Asp Asp  Lys Ala Ala Gly Gly  Gly Gly Ser Gly Arg  Ala Asp Ala
    1400                 1405                 1410

Leu Asp  Asp Phe Asp Leu Asp  Met Leu Gly Ser Asp  Ala Leu Asp
    1415                 1420                 1425

Asp Phe  Asp Leu Asp Met Leu  Gly Ser Asp Ala Leu  Asp Asp Phe
```

1430 1435 1440

Asp Leu Asp Met Leu Gly Ser Asp Ala Leu Asp Asp Phe Asp Leu
1445 1450 1455

Asp Met Leu His His His His His His
1460 1465

<210> SEQ ID NO 88
<211> LENGTH: 94
<212> TYPE: PRT
<213> ORGANISM: Homo sapiens

<400> SEQUENCE: 88

Met Asn Met Phe Lys Glu Ala Val Thr Phe Lys Asp Val Ala Val Ala
1 5 10 15

Phe Thr Glu Glu Glu Leu Gly Leu Leu Gly Pro Ala Gln Arg Lys Leu
20 25 30

Tyr Arg Asp Val Met Val Glu Asn Phe Arg Asn Leu Leu Ser Val Gly
35 40 45

His Pro Pro Phe Lys Gln Asp Val Ser Pro Ile Glu Arg Asn Glu Gln
50 55 60

Leu Trp Ile Met Thr Thr Ala Thr Arg Arg Gln Gly Asn Leu Asp Thr
65 70 75 80

Leu Pro Val Lys Ala Leu Leu Leu Tyr Asp Leu Ala Gln Thr
85 90

<210> SEQ ID NO 89
<211> LENGTH: 74
<212> TYPE: PRT
<213> ORGANISM: Homo sapiens

<400> SEQUENCE: 89

Glu Gln Val Ser Phe Lys Asp Val Cys Val Asp Phe Thr Gln Glu Glu
1 5 10 15

Trp Tyr Leu Leu Asp Pro Ala Gln Lys Ile Leu Tyr Arg Asp Val Ile
20 25 30

Leu Glu Asn Tyr Ser Asn Leu Val Ser Val Gly Tyr Cys Ile Thr Lys
35 40 45

Pro Glu Val Ile Phe Lys Ile Glu Gln Gly Glu Glu Pro Trp Ile Leu
50 55 60

Glu Lys Gly Phe Pro Ser Gln Cys His Pro
65 70

<210> SEQ ID NO 90
<211> LENGTH: 42
<212> TYPE: PRT
<213> ORGANISM: Homo sapiens

<400> SEQUENCE: 90

Glu Ala Val Thr Phe Lys Asp Val Ala Val Val Phe Thr Glu Glu Glu
1 5 10 15

Leu Gly Leu Leu Asp Pro Ala Gln Arg Lys Leu Tyr Arg Asp Val Met
20 25 30

Leu Glu Asn Phe Arg Asn Leu Leu Ser Val
35 40

<210> SEQ ID NO 91
<211> LENGTH: 69
<212> TYPE: PRT
<213> ORGANISM: Mus musculus

<400> SEQUENCE: 91

Met Asp Leu Val Thr Tyr Asp Asp Val His Val Asn Phe Thr Gln Asp
1 5 10 15

Glu Trp Ala Leu Leu Asp Pro Ser Gln Lys Ser Leu Tyr Lys Gly Val
20 25 30

Met Leu Glu Thr Tyr Lys Asn Leu Thr Ala Ile Gly Tyr Ile Trp Glu
35 40 45

Glu His Thr Ile Glu Asp His Phe Gln Thr Ser Arg Ser His Gly Ser
50 55 60

Asn Lys Lys Thr His
65

<210> SEQ ID NO 92
<211> LENGTH: 32
<212> TYPE: PRT
<213> ORGANISM: Artificial Sequence
<220> FEATURE:
<223> OTHER INFORMATION: Synthetic Polypeptide

<400> SEQUENCE: 92

Gly Ser Gly Met Asn Ile Gln Met Leu Leu Glu Ala Ala Asp Tyr Leu
1 5 10 15

Glu Arg Arg Glu Arg Glu Ala Glu His Gly Tyr Ala Ser Met Leu Pro
20 25 30

<210> SEQ ID NO 93
<211> LENGTH: 130
<212> TYPE: PRT
<213> ORGANISM: Artificial Sequence
<220> FEATURE:
<223> OTHER INFORMATION: Synthetic Polypeptide

<400> SEQUENCE: 93

Gly Ser Gly Met Asn Ile Gln Met Leu Leu Glu Ala Ala Asp Tyr Leu
1 5 10 15

Glu Arg Arg Glu Arg Glu Ala Glu His Gly Tyr Ala Ser Met Leu Pro
20 25 30

Gly Ser Gly Met Asn Ile Gln Met Leu Leu Glu Ala Ala Asp Tyr Leu
35 40 45

Glu Arg Arg Glu Arg Glu Ala Glu His Gly Tyr Ala Ser Met Leu Pro
50 55 60

Gly Ser Gly Met Asn Ile Gln Met Leu Leu Glu Ala Ala Asp Tyr Leu
65 70 75 80

Glu Arg Arg Glu Arg Glu Ala Glu His Gly Tyr Ala Ser Met Leu Pro
85 90 95

Gly Ser Gly Met Asn Ile Gln Met Leu Leu Glu Ala Ala Asp Tyr Leu
100 105 110

Glu Arg Arg Glu Arg Glu Ala Glu His Gly Tyr Ala Ser Met Leu Pro
115 120 125

Ser Arg
130

<210> SEQ ID NO 94
<211> LENGTH: 876
<212> TYPE: PRT
<213> ORGANISM: Homo sapiens

<400> SEQUENCE: 94

-continued

```
Met Leu Ser Gly Lys Lys Ala Ala Ala Ala Ala Ala Ala Ala Ala Ala
1               5                   10                  15

Ala Ala Thr Gly Thr Glu Ala Gly Pro Gly Thr Ala Gly Gly Ser Glu
            20                  25                  30

Asn Gly Ser Glu Val Ala Ala Gln Pro Ala Gly Leu Ser Gly Pro Ala
        35                  40                  45

Glu Val Gly Pro Gly Ala Val Gly Glu Arg Thr Pro Arg Lys Lys Glu
    50                  55                  60

Pro Pro Arg Ala Ser Pro Pro Gly Gly Leu Ala Glu Pro Pro Gly Ser
65                  70                  75                  80

Ala Gly Pro Gln Ala Gly Pro Thr Val Val Pro Gly Ser Ala Thr Pro
                85                  90                  95

Met Glu Thr Gly Ile Ala Glu Thr Pro Glu Gly Arg Arg Thr Ser Arg
            100                 105                 110

Arg Lys Arg Ala Lys Val Glu Tyr Arg Glu Met Asp Glu Ser Leu Ala
        115                 120                 125

Asn Leu Ser Glu Asp Glu Tyr Tyr Ser Glu Glu Glu Arg Asn Ala Lys
    130                 135                 140

Ala Glu Lys Glu Lys Lys Leu Pro Pro Pro Pro Pro Gln Ala Pro Pro
145                 150                 155                 160

Glu Glu Glu Asn Glu Ser Glu Pro Glu Glu Pro Ser Gly Gln Ala Gly
                165                 170                 175

Gly Leu Gln Asp Asp Ser Ser Gly Gly Tyr Gly Asp Gly Gln Ala Ser
            180                 185                 190

Gly Val Glu Gly Ala Ala Phe Gln Ser Arg Leu Pro His Asp Arg Met
        195                 200                 205

Thr Ser Gln Glu Ala Ala Cys Phe Pro Asp Ile Ile Ser Gly Pro Gln
    210                 215                 220

Gln Thr Gln Lys Val Phe Leu Phe Ile Arg Asn Arg Thr Leu Gln Leu
225                 230                 235                 240

Trp Leu Asp Asn Pro Lys Ile Gln Leu Thr Phe Glu Ala Thr Leu Gln
                245                 250                 255

Gln Leu Glu Ala Pro Tyr Asn Ser Asp Thr Val Leu Val His Arg Val
            260                 265                 270

His Ser Tyr Leu Glu Arg His Gly Leu Ile Asn Phe Gly Ile Tyr Lys
        275                 280                 285

Arg Ile Lys Pro Leu Pro Thr Lys Lys Thr Gly Lys Val Ile Ile Ile
    290                 295                 300

Gly Ser Gly Val Ser Gly Leu Ala Ala Ala Arg Gln Leu Gln Ser Phe
305                 310                 315                 320

Gly Met Asp Val Thr Leu Leu Glu Ala Arg Asp Arg Val Gly Gly Arg
                325                 330                 335

Val Ala Thr Phe Arg Lys Gly Asn Tyr Val Ala Asp Leu Gly Ala Met
            340                 345                 350

Val Val Thr Gly Leu Gly Gly Asn Pro Met Ala Val Val Ser Lys Gln
        355                 360                 365

Val Asn Met Glu Leu Ala Lys Ile Lys Gln Lys Cys Pro Leu Tyr Glu
    370                 375                 380

Ala Asn Gly Gln Ala Asp Thr Val Lys Val Pro Lys Glu Lys Asp Glu
385                 390                 395                 400

Met Val Glu Gln Glu Phe Asn Arg Leu Leu Glu Ala Thr Ser Tyr Leu
                405                 410                 415

Ser His Gln Leu Asp Phe Asn Val Leu Asn Asn Lys Pro Val Ser Leu
```

```
            420                 425                 430

Gly Gln Ala Leu Glu Val Val Ile Gln Leu Gln Glu Lys His Val Lys
        435                 440                 445

Asp Glu Gln Ile Glu His Trp Lys Lys Ile Val Lys Thr Gln Glu Glu
    450                 455                 460

Leu Lys Glu Leu Leu Asn Lys Met Val Asn Leu Lys Glu Lys Ile Lys
465                 470                 475                 480

Glu Leu His Gln Gln Tyr Lys Glu Ala Ser Glu Val Lys Pro Pro Arg
                485                 490                 495

Asp Ile Thr Ala Glu Phe Leu Val Lys Ser Lys His Arg Asp Leu Thr
            500                 505                 510

Ala Leu Cys Lys Glu Tyr Asp Glu Leu Ala Glu Thr Gln Gly Lys Leu
        515                 520                 525

Glu Glu Lys Leu Gln Glu Leu Glu Ala Asn Pro Pro Ser Asp Val Tyr
    530                 535                 540

Leu Ser Ser Arg Asp Arg Gln Ile Leu Asp Trp His Phe Ala Asn Leu
545                 550                 555                 560

Glu Phe Ala Asn Ala Thr Pro Leu Ser Thr Leu Ser Leu Lys His Trp
                565                 570                 575

Asp Gln Asp Asp Asp Phe Glu Phe Thr Gly Ser His Leu Thr Val Arg
            580                 585                 590

Asn Gly Tyr Ser Cys Val Pro Val Ala Leu Ala Glu Gly Leu Asp Ile
        595                 600                 605

Lys Leu Asn Thr Ala Val Arg Gln Val Arg Tyr Thr Ala Ser Gly Cys
    610                 615                 620

Glu Val Ile Ala Val Asn Thr Arg Ser Thr Ser Gln Thr Phe Ile Tyr
625                 630                 635                 640

Lys Cys Asp Ala Val Leu Cys Thr Leu Pro Leu Gly Val Leu Lys Gln
                645                 650                 655

Gln Pro Pro Ala Val Gln Phe Val Pro Pro Leu Pro Glu Trp Lys Thr
            660                 665                 670

Ser Ala Val Gln Arg Met Gly Phe Gly Asn Leu Asn Lys Val Val Leu
        675                 680                 685

Cys Phe Asp Arg Val Phe Trp Asp Pro Ser Val Asn Leu Phe Gly His
    690                 695                 700

Val Gly Ser Thr Thr Ala Ser Arg Gly Glu Leu Phe Leu Phe Trp Asn
705                 710                 715                 720

Leu Tyr Lys Ala Pro Ile Leu Leu Ala Leu Val Ala Gly Glu Ala Ala
                725                 730                 735

Gly Ile Met Glu Asn Ile Ser Asp Asp Val Ile Val Gly Arg Cys Leu
            740                 745                 750

Ala Ile Leu Lys Gly Ile Phe Gly Ser Ser Ala Val Pro Gln Pro Lys
        755                 760                 765

Glu Thr Val Val Ser Arg Trp Arg Ala Asp Pro Trp Ala Arg Gly Ser
    770                 775                 780

Tyr Ser Tyr Val Ala Ala Gly Ser Ser Gly Asn Asp Tyr Asp Leu Met
785                 790                 795                 800

Ala Gln Pro Ile Thr Pro Gly Pro Ser Ile Pro Gly Ala Pro Gln Pro
                805                 810                 815

Ile Pro Arg Leu Phe Phe Ala Gly Glu His Thr Ile Arg Asn Tyr Pro
            820                 825                 830

Ala Thr Val His Gly Ala Leu Leu Ser Gly Leu Arg Glu Ala Gly Arg
        835                 840                 845
```

Ile Ala Asp Gln Phe Leu Gly Ala Met Tyr Thr Leu Pro Arg Gln Ala
850 855 860

Thr Pro Gly Val Pro Ala Gln Gln Ser Pro Ser Met
865 870 875

<210> SEQ ID NO 95
<211> LENGTH: 852
<212> TYPE: PRT
<213> ORGANISM: Homo sapiens

<400> SEQUENCE: 95

Met Leu Ser Gly Lys Lys Ala Ala Ala Ala Ala Ala Ala Ala Ala Ala
1 5 10 15

Ala Ala Thr Gly Thr Glu Ala Gly Pro Gly Thr Ala Gly Gly Ser Glu
20 25 30

Asn Gly Ser Glu Val Ala Ala Gln Pro Ala Gly Leu Ser Gly Pro Ala
35 40 45

Glu Val Gly Pro Gly Ala Val Gly Glu Arg Thr Pro Arg Lys Lys Glu
50 55 60

Pro Pro Arg Ala Ser Pro Pro Gly Gly Leu Ala Glu Pro Pro Gly Ser
65 70 75 80

Ala Gly Pro Gln Ala Gly Pro Thr Val Val Pro Gly Ser Ala Thr Pro
85 90 95

Met Glu Thr Gly Ile Ala Glu Thr Pro Glu Gly Arg Arg Thr Ser Arg
100 105 110

Arg Lys Arg Ala Lys Val Glu Tyr Arg Glu Met Asp Glu Ser Leu Ala
115 120 125

Asn Leu Ser Glu Asp Glu Tyr Tyr Ser Glu Glu Glu Arg Asn Ala Lys
130 135 140

Ala Glu Lys Glu Lys Lys Leu Pro Pro Pro Pro Pro Gln Ala Pro Pro
145 150 155 160

Glu Glu Glu Asn Glu Ser Glu Pro Glu Glu Pro Ser Gly Val Glu Gly
165 170 175

Ala Ala Phe Gln Ser Arg Leu Pro His Asp Arg Met Thr Ser Gln Glu
180 185 190

Ala Ala Cys Phe Pro Asp Ile Ile Ser Gly Pro Gln Gln Thr Gln Lys
195 200 205

Val Phe Leu Phe Ile Arg Asn Arg Thr Leu Gln Leu Trp Leu Asp Asn
210 215 220

Pro Lys Ile Gln Leu Thr Phe Glu Ala Thr Leu Gln Gln Leu Glu Ala
225 230 235 240

Pro Tyr Asn Ser Asp Thr Val Leu Val His Arg Val His Ser Tyr Leu
245 250 255

Glu Arg His Gly Leu Ile Asn Phe Gly Ile Tyr Lys Arg Ile Lys Pro
260 265 270

Leu Pro Thr Lys Lys Thr Gly Lys Val Ile Ile Ile Gly Ser Gly Val
275 280 285

Ser Gly Leu Ala Ala Ala Arg Gln Leu Gln Ser Phe Gly Met Asp Val
290 295 300

Thr Leu Leu Glu Ala Arg Asp Arg Val Gly Gly Arg Val Ala Thr Phe
305 310 315 320

Arg Lys Gly Asn Tyr Val Ala Asp Leu Gly Ala Met Val Val Thr Gly
325 330 335

Leu Gly Gly Asn Pro Met Ala Val Val Ser Lys Gln Val Asn Met Glu

```
            340                 345                 350

Leu Ala Lys Ile Lys Gln Lys Cys Pro Leu Tyr Glu Ala Asn Gly Gln
        355                 360                 365

Ala Val Pro Lys Glu Lys Asp Glu Met Val Glu Gln Glu Phe Asn Arg
    370                 375                 380

Leu Leu Glu Ala Thr Ser Tyr Leu Ser His Gln Leu Asp Phe Asn Val
385                 390                 395                 400

Leu Asn Asn Lys Pro Val Ser Leu Gly Gln Ala Leu Glu Val Val Ile
                405                 410                 415

Gln Leu Gln Glu Lys His Val Lys Asp Glu Gln Ile Glu His Trp Lys
            420                 425                 430

Lys Ile Val Lys Thr Gln Glu Glu Leu Lys Glu Leu Leu Asn Lys Met
        435                 440                 445

Val Asn Leu Lys Glu Lys Ile Lys Glu Leu His Gln Gln Tyr Lys Glu
    450                 455                 460

Ala Ser Glu Val Lys Pro Pro Arg Asp Ile Thr Ala Glu Phe Leu Val
465                 470                 475                 480

Lys Ser Lys His Arg Asp Leu Thr Ala Leu Cys Lys Glu Tyr Asp Glu
                485                 490                 495

Leu Ala Glu Thr Gln Gly Lys Leu Glu Glu Lys Leu Gln Glu Leu Glu
            500                 505                 510

Ala Asn Pro Pro Ser Asp Val Tyr Leu Ser Ser Arg Asp Arg Gln Ile
        515                 520                 525

Leu Asp Trp His Phe Ala Asn Leu Glu Phe Ala Asn Ala Thr Pro Leu
    530                 535                 540

Ser Thr Leu Ser Leu Lys His Trp Asp Gln Asp Asp Asp Phe Glu Phe
545                 550                 555                 560

Thr Gly Ser His Leu Thr Val Arg Asn Gly Tyr Ser Cys Val Pro Val
                565                 570                 575

Ala Leu Ala Glu Gly Leu Asp Ile Lys Leu Asn Thr Ala Val Arg Gln
            580                 585                 590

Val Arg Tyr Thr Ala Ser Gly Cys Glu Val Ile Ala Val Asn Thr Arg
        595                 600                 605

Ser Thr Ser Gln Thr Phe Ile Tyr Lys Cys Asp Ala Val Leu Cys Thr
    610                 615                 620

Leu Pro Leu Gly Val Leu Lys Gln Gln Pro Pro Ala Val Gln Phe Val
625                 630                 635                 640

Pro Pro Leu Pro Glu Trp Lys Thr Ser Ala Val Gln Arg Met Gly Phe
                645                 650                 655

Gly Asn Leu Asn Lys Val Val Leu Cys Phe Asp Arg Val Phe Trp Asp
            660                 665                 670

Pro Ser Val Asn Leu Phe Gly His Val Gly Ser Thr Thr Ala Ser Arg
        675                 680                 685

Gly Glu Leu Phe Leu Phe Trp Asn Leu Tyr Lys Ala Pro Ile Leu Leu
    690                 695                 700

Ala Leu Val Ala Gly Glu Ala Ala Gly Ile Met Glu Asn Ile Ser Asp
705                 710                 715                 720

Asp Val Ile Val Gly Arg Cys Leu Ala Ile Leu Lys Gly Ile Phe Gly
                725                 730                 735

Ser Ser Ala Val Pro Gln Pro Lys Glu Thr Val Val Ser Arg Trp Arg
            740                 745                 750

Ala Asp Pro Trp Ala Arg Gly Ser Tyr Ser Tyr Val Ala Ala Gly Ser
        755                 760                 765
```

Ser Gly Asn Asp Tyr Asp Leu Met Ala Gln Pro Ile Thr Pro Gly Pro
    770                 775                 780

Ser Ile Pro Gly Ala Pro Gln Pro Ile Pro Arg Leu Phe Phe Ala Gly
785                 790                 795                 800

Glu His Thr Ile Arg Asn Tyr Pro Ala Thr Val His Gly Ala Leu Leu
                805                 810                 815

Ser Gly Leu Arg Glu Ala Gly Arg Ile Ala Asp Gln Phe Leu Gly Ala
            820                 825                 830

Met Tyr Thr Leu Pro Arg Gln Ala Thr Pro Gly Val Pro Ala Gln Gln
        835                 840                 845

Ser Pro Ser Met
    850

<210> SEQ ID NO 96
<211> LENGTH: 817
<212> TYPE: PRT
<213> ORGANISM: Artificial Sequence
<220> FEATURE:
<223> OTHER INFORMATION: Synthetic Polypeptide

<400> SEQUENCE: 96

Ser Ile Val Ala Gln Leu Ser Arg Pro Asp Pro Ala Leu Ala Ala Leu
1               5                   10                  15

Thr Asn Asp His Leu Val Ala Leu Ala Cys Leu Gly Gly Arg Pro Ala
            20                  25                  30

Leu Asp Ala Val Lys Lys Gly Leu Pro His Ala Pro Ala Leu Ile Lys
        35                  40                  45

Arg Thr Asn Arg Arg Ile Pro Glu Arg Thr Ser His Arg Val Ala Asp
    50                  55                  60

His Ala Gln Val Val Arg Val Leu Gly Phe Phe Gln Cys His Ser His
65                  70                  75                  80

Pro Ala Gln Ala Phe Asp Asp Ala Met Thr Gln Phe Gly Met Ser Gly
                85                  90                  95

Gly Gly Ser Leu Pro Thr Cys Ser Cys Leu Asp Arg Val Ile Gln Lys
            100                 105                 110

Asp Lys Gly Pro Tyr Tyr Thr His Leu Gly Ala Gly Pro Ser Val Ala
        115                 120                 125

Ala Val Arg Glu Ile Met Glu Asn Arg Tyr Gly Gln Lys Gly Asn Ala
    130                 135                 140

Ile Arg Ile Glu Ile Val Val Tyr Thr Gly Lys Glu Gly Lys Ser Ser
145                 150                 155                 160

His Gly Cys Pro Ile Ala Lys Trp Val Leu Arg Arg Ser Ser Asp Glu
                165                 170                 175

Glu Lys Val Leu Cys Leu Val Arg Gln Arg Thr Gly His His Cys Pro
            180                 185                 190

Thr Ala Val Met Val Val Leu Ile Met Val Trp Asp Gly Ile Pro Leu
        195                 200                 205

Pro Met Ala Asp Arg Leu Tyr Thr Glu Leu Thr Glu Asn Leu Lys Ser
    210                 215                 220

Tyr Asn Gly His Pro Thr Asp Arg Arg Cys Thr Leu Asn Glu Asn Arg
225                 230                 235                 240

Thr Cys Thr Cys Gln Gly Ile Asp Pro Glu Thr Cys Gly Ala Ser Phe
                245                 250                 255

Ser Phe Gly Cys Ser Trp Ser Met Tyr Phe Asn Gly Cys Lys Phe Gly
            260                 265                 270

-continued

```
Arg Ser Pro Ser Pro Arg Arg Phe Arg Ile Asp Pro Ser Ser Pro Leu
        275                 280                 285

His Glu Lys Asn Leu Glu Asp Asn Leu Gln Ser Leu Ala Thr Arg Leu
    290                 295                 300

Ala Pro Ile Tyr Lys Gln Tyr Ala Pro Val Ala Tyr Gln Asn Gln Val
305                 310                 315                 320

Glu Tyr Glu Asn Val Ala Arg Glu Cys Arg Leu Gly Ser Lys Glu Gly
                325                 330                 335

Arg Pro Phe Ser Gly Val Thr Ala Cys Leu Asp Phe Cys Ala His Pro
            340                 345                 350

His Arg Asp Ile His Asn Met Asn Asn Gly Ser Thr Val Val Cys Thr
        355                 360                 365

Leu Thr Arg Glu Asp Asn Arg Ser Leu Gly Val Ile Pro Gln Asp Glu
    370                 375                 380

Gln Leu His Val Leu Pro Leu Tyr Lys Leu Ser Asp Thr Asp Glu Phe
385                 390                 395                 400

Gly Ser Lys Glu Gly Met Glu Ala Lys Ile Lys Ser Gly Ala Ile Glu
                405                 410                 415

Val Leu Ala Pro Arg Arg Lys Lys Arg Thr Cys Phe Thr Gln Pro Val
            420                 425                 430

Pro Arg Ser Gly Lys Lys Arg Ala Ala Met Met Thr Glu Val Leu Ala
        435                 440                 445

His Lys Ile Arg Ala Val Glu Lys Lys Pro Ile Pro Arg Ile Lys Arg
    450                 455                 460

Lys Asn Asn Ser Thr Thr Thr Asn Asn Ser Lys Pro Ser Ser Leu Pro
465                 470                 475                 480

Thr Leu Gly Ser Asn Thr Glu Thr Val Gln Pro Glu Val Lys Ser Glu
                485                 490                 495

Thr Glu Pro His Phe Ile Leu Lys Ser Ser Asp Asn Thr Lys Thr Tyr
            500                 505                 510

Ser Leu Met Pro Ser Ala Pro His Pro Val Lys Glu Ala Ser Pro Gly
        515                 520                 525

Phe Ser Trp Ser Pro Lys Thr Ala Ser Ala Thr Pro Ala Pro Leu Lys
    530                 535                 540

Asn Asp Ala Thr Ala Ser Cys Gly Phe Ser Glu Arg Ser Ser Thr Pro
545                 550                 555                 560

His Cys Thr Met Pro Ser Gly Arg Leu Ser Gly Ala Asn Ala Ala Ala
                565                 570                 575

Ala Asp Gly Pro Gly Ile Ser Gln Leu Gly Glu Val Ala Pro Leu Pro
            580                 585                 590

Thr Leu Ser Ala Pro Val Met Glu Pro Leu Ile Asn Ser Glu Pro Ser
        595                 600                 605

Thr Gly Val Thr Glu Pro Leu Thr Pro His Gln Pro Asn His Gln Pro
    610                 615                 620

Ser Phe Leu Thr Ser Pro Gln Asp Leu Ala Ser Ser Pro Met Glu Glu
625                 630                 635                 640

Asp Glu Gln His Ser Glu Ala Asp Glu Pro Pro Ser Asp Glu Pro Leu
                645                 650                 655

Ser Asp Asp Pro Leu Ser Pro Ala Glu Glu Lys Leu Pro His Ile Asp
            660                 665                 670

Glu Tyr Trp Ser Asp Ser Glu His Ile Phe Leu Asp Ala Asn Ile Gly
        675                 680                 685
```

Gly Val Ala Ile Ala Pro Ala His Gly Ser Val Leu Ile Glu Cys Ala
690 695 700

Arg Arg Glu Leu His Ala Thr Thr Pro Val Glu His Pro Asn Arg Asn
705 710 715 720

His Pro Thr Arg Leu Ser Leu Val Phe Tyr Gln His Lys Asn Leu Asn
725 730 735

Lys Pro Gln His Gly Phe Glu Leu Asn Lys Ile Lys Phe Glu Ala Lys
740 745 750

Glu Ala Lys Asn Lys Lys Met Lys Ala Ser Glu Gln Lys Asp Gln Ala
755 760 765

Ala Asn Glu Gly Pro Glu Gln Ser Ser Glu Val Asn Glu Leu Asn Gln
770 775 780

Ile Pro Ser His Lys Ala Leu Thr Leu Thr His Asp Asn Val Val Thr
785 790 795 800

Val Ser Pro Tyr Ala Leu Thr His Val Ala Gly Pro Tyr Asn His Trp
805 810 815

Val

<210> SEQ ID NO 97
<211> LENGTH: 340
<212> TYPE: PRT
<213> ORGANISM: X. laevis

<400> SEQUENCE: 97

Ala Ser Ser Pro Lys Lys Lys Arg Lys Val Glu Ala Ser Met Ser Arg
1 5 10 15

Val Val Lys Pro Lys Val Ala Ser Met Glu Glu Met Ala Ala Phe His
20 25 30

Thr Asp Ala Tyr Leu Gln His Leu His Lys Val Ser Glu Glu Gly Asp
35 40 45

Asn Asp Asp Pro Glu Thr Leu Glu Tyr Gly Leu Gly Tyr Asp Cys Pro
50 55 60

Ile Thr Glu Gly Ile Tyr Asp Tyr Ala Ala Ala Val Gly Gly Ala Thr
65 70 75 80

Leu Thr Ala Ala Glu Gln Leu Ile Glu Gly Lys Thr Arg Ile Ala Val
85 90 95

Asn Trp Pro Gly Gly Trp His His Ala Lys Lys Asp Glu Ala Ser Gly
100 105 110

Phe Cys Tyr Leu Asn Asp Ala Val Leu Gly Ile Leu Lys Leu Arg Glu
115 120 125

Lys Phe Asp Arg Val Leu Tyr Val Asp Met Asp Leu His His Gly Asp
130 135 140

Gly Val Glu Asp Ala Phe Ser Phe Thr Ser Lys Val Met Thr Val Ser
145 150 155 160

Leu His Lys Phe Ser Pro Gly Phe Phe Pro Gly Thr Gly Asp Val Ser
165 170 175

Asp Ile Gly Leu Gly Lys Gly Arg Tyr Tyr Ser Ile Asn Val Pro Leu
180 185 190

Gln Asp Gly Ile Gln Asp Asp Lys Tyr Tyr Gln Ile Cys Glu Gly Val
195 200 205

Leu Lys Glu Val Phe Thr Thr Phe Asn Pro Glu Ala Val Val Leu Gln
210 215 220

Leu Gly Ala Asp Thr Ile Ala Gly Asp Pro Met Cys Ser Phe Asn Met
225 230 235 240

```
Thr Pro Glu Gly Ile Gly Lys Cys Leu Lys Tyr Val Leu Gln Trp Gln
                245                 250                 255

Leu Pro Thr Leu Ile Leu Gly Gly Gly Gly Tyr His Leu Pro Asn Thr
            260                 265                 270

Ala Arg Cys Trp Thr Tyr Leu Thr Ala Leu Ile Val Gly Arg Thr Leu
        275                 280                 285

Ser Ser Glu Ile Pro Asp His Glu Phe Phe Thr Glu Tyr Gly Pro Asp
    290                 295                 300

Tyr Val Leu Glu Ile Thr Pro Ser Cys Arg Pro Asp Arg Asn Asp Thr
305                 310                 315                 320

Gln Lys Val Gln Glu Ile Leu Gln Ser Ile Lys Gly Asn Leu Lys Arg
                325                 330                 335

Val Val Glu Phe
            340


<210> SEQ ID NO 98
<211> LENGTH: 331
<212> TYPE: PRT
<213> ORGANISM: S. cerevisiae

<400> SEQUENCE: 98

Ala Ser Ser Pro Lys Lys Lys Arg Lys Val Glu Ala Ser Arg Arg Val
1               5                   10                  15

Ala Tyr Phe Tyr Asp Ala Asp Val Gly Asn Tyr Ala Tyr Gly Ala Gly
            20                  25                  30

His Pro Met Lys Pro His Arg Ile Arg Met Ala His Ser Leu Ile Met
        35                  40                  45

Asn Tyr Gly Leu Tyr Lys Lys Met Glu Ile Tyr Arg Ala Lys Pro Ala
    50                  55                  60

Thr Lys Gln Glu Met Cys Gln Phe His Thr Asp Glu Tyr Ile Asp Phe
65                  70                  75                  80

Leu Ser Arg Val Thr Pro Asp Asn Leu Glu Met Phe Lys Arg Glu Ser
                85                  90                  95

Val Lys Phe Asn Val Gly Asp Asp Cys Pro Val Phe Asp Gly Leu Tyr
            100                 105                 110

Glu Tyr Cys Ser Ile Ser Gly Gly Gly Ser Met Glu Gly Ala Ala Arg
        115                 120                 125

Leu Asn Arg Gly Lys Cys Asp Val Ala Val Asn Tyr Ala Gly Gly Leu
    130                 135                 140

His His Ala Lys Lys Ser Glu Ala Ser Gly Phe Cys Tyr Leu Asn Asp
145                 150                 155                 160

Ile Val Leu Gly Ile Ile Glu Leu Leu Arg Tyr His Pro Arg Val Leu
                165                 170                 175

Tyr Ile Asp Ile Asp Val His His Gly Asp Gly Val Glu Glu Ala Phe
            180                 185                 190

Tyr Thr Thr Asp Arg Val Met Thr Cys Ser Phe His Lys Tyr Gly Glu
        195                 200                 205

Phe Phe Pro Gly Thr Gly Glu Leu Arg Asp Ile Gly Val Gly Ala Gly
    210                 215                 220

Lys Asn Tyr Ala Val Asn Val Pro Leu Arg Asp Gly Ile Asp Asp Ala
225                 230                 235                 240

Thr Tyr Arg Ser Val Phe Glu Pro Val Ile Lys Lys Ile Met Glu Trp
                245                 250                 255

Tyr Gln Pro Ser Ala Val Val Leu Gln Cys Gly Gly Asp Ser Leu Ser
            260                 265                 270
```

```
Gly Asp Arg Leu Gly Cys Phe Asn Leu Ser Met Glu Gly His Ala Asn
        275                 280                 285

Cys Val Asn Tyr Val Lys Ser Phe Gly Ile Pro Met Met Val Val Gly
    290                 295                 300

Gly Gly Gly Tyr Thr Met Arg Asn Val Ala Arg Thr Trp Cys Phe Glu
305                 310                 315                 320

Thr Gly Leu Leu Asn Asn Val Val Leu Asp Lys
                325                 330


<210> SEQ ID NO 99
<211> LENGTH: 315
<212> TYPE: PRT
<213> ORGANISM: M. loti

<400> SEQUENCE: 99

Ala Ser Ser Pro Lys Lys Lys Arg Lys Val Glu Ala Ser Met Pro Leu
1               5                   10                  15

Gln Ile Val His His Pro Asp Tyr Asp Ala Gly Phe Ala Thr Asn His
            20                  25                  30

Arg Phe Pro Met Ser Lys Tyr Pro Leu Leu Met Glu Ala Leu Arg Ala
        35                  40                  45

Arg Gly Leu Ala Ser Pro Asp Ala Leu Asn Thr Thr Glu Pro Ala Pro
    50                  55                  60

Ala Ser Trp Leu Lys Leu Ala His Ala Ala Asp Tyr Val Asp Gln Val
65                  70                  75                  80

Ile Ser Cys Ser Val Pro Glu Lys Ile Glu Arg Glu Ile Gly Phe Pro
                85                  90                  95

Val Gly Pro Arg Val Ser Leu Arg Ala Gln Leu Ala Thr Gly Gly Thr
            100                 105                 110

Ile Leu Ala Ala Arg Leu Ala Leu Arg His Gly Ile Ala Cys Asn Thr
        115                 120                 125

Ala Gly Gly Ser His His Ala Arg Arg Ala Gln Gly Ala Gly Phe Cys
    130                 135                 140

Thr Phe Asn Asp Val Ala Val Ala Ser Leu Val Leu Leu Asp Glu Gly
145                 150                 155                 160

Ala Ala Gln Asn Ile Leu Val Val Asp Leu Asp Val His Gln Gly Asp
                165                 170                 175

Gly Thr Ala Asp Ile Leu Ser Asp Glu Pro Gly Val Phe Thr Phe Ser
            180                 185                 190

Met His Gly Glu Arg Asn Tyr Pro Val Arg Lys Ile Ala Ser Asp Leu
        195                 200                 205

Asp Ile Ala Leu Pro Asp Gly Thr Gly Asp Ala Ala Tyr Leu Arg Arg
    210                 215                 220

Leu Ala Thr Ile Leu Pro Glu Leu Ser Ala Arg Ala Arg Trp Asp Ile
225                 230                 235                 240

Val Phe Tyr Asn Ala Gly Val Asp Val His Ala Glu Asp Arg Leu Gly
                245                 250                 255

Arg Leu Ala Leu Ser Asn Gly Gly Leu Arg Ala Arg Asp Glu Met Val
            260                 265                 270

Ile Gly His Phe Arg Ala Leu Gly Ile Pro Val Cys Gly Val Ile Gly
        275                 280                 285

Gly Gly Tyr Ser Thr Asp Val Pro Ala Leu Ala Ser Arg His Ala Ile
    290                 295                 300

Leu Phe Glu Val Ala Ser Thr Tyr Ala Glu Phe
```

305 310 315

<210> SEQ ID NO 100
<211> LENGTH: 362
<212> TYPE: PRT
<213> ORGANISM: Homo sapiens

<400> SEQUENCE: 100

Ala Ser Ser Pro Lys Lys Lys Arg Lys Val Glu Ala Ser Met Leu His
1 5 10 15

Thr Thr Gln Leu Tyr Gln His Val Pro Glu Thr Arg Trp Pro Ile Val
20 25 30

Tyr Ser Pro Arg Tyr Asn Ile Thr Phe Met Gly Leu Glu Lys Leu His
35 40 45

Pro Phe Asp Ala Gly Lys Trp Gly Lys Val Ile Asn Phe Leu Lys Glu
50 55 60

Glu Lys Leu Leu Ser Asp Ser Met Leu Val Glu Ala Arg Glu Ala Ser
65 70 75 80

Glu Glu Asp Leu Leu Val Val His Thr Arg Arg Tyr Leu Asn Glu Leu
85 90 95

Lys Trp Ser Phe Ala Val Ala Thr Ile Thr Glu Ile Pro Pro Val Ile
100 105 110

Phe Leu Pro Asn Phe Leu Val Gln Arg Lys Val Leu Arg Pro Leu Arg
115 120 125

Thr Gln Thr Gly Gly Thr Ile Met Ala Gly Lys Leu Ala Val Glu Arg
130 135 140

Gly Trp Ala Ile Asn Val Gly Gly Gly Phe His His Cys Ser Ser Asp
145 150 155 160

Arg Gly Gly Gly Phe Cys Ala Tyr Ala Asp Ile Thr Leu Ala Ile Lys
165 170 175

Phe Leu Phe Glu Arg Val Glu Gly Ile Ser Arg Ala Thr Ile Ile Asp
180 185 190

Leu Asp Ala His Gln Gly Asn Gly His Glu Arg Asp Phe Met Asp Asp
195 200 205

Lys Arg Val Tyr Ile Met Asp Val Tyr Asn Arg His Ile Tyr Pro Gly
210 215 220

Asp Arg Phe Ala Lys Gln Ala Ile Arg Arg Lys Val Glu Leu Glu Trp
225 230 235 240

Gly Thr Glu Asp Asp Glu Tyr Leu Asp Lys Val Glu Arg Asn Ile Lys
245 250 255

Lys Ser Leu Gln Glu His Leu Pro Asp Val Val Val Tyr Asn Ala Gly
260 265 270

Thr Asp Ile Leu Glu Gly Asp Arg Leu Gly Gly Leu Ser Ile Ser Pro
275 280 285

Ala Gly Ile Val Lys Arg Asp Glu Leu Val Phe Arg Met Val Arg Gly
290 295 300

Arg Arg Val Pro Ile Leu Met Val Thr Ser Gly Gly Tyr Gln Lys Arg
305 310 315 320

Thr Ala Arg Ile Ile Ala Asp Ser Ile Leu Asn Leu Phe Gly Leu Gly
325 330 335

Leu Ile Gly Pro Glu Ser Pro Ser Val Ser Ala Gln Asn Ser Asp Thr
340 345 350

Pro Leu Leu Pro Pro Ala Val Pro Glu Phe
355 360

<210> SEQ ID NO 101
<211> LENGTH: 226
<212> TYPE: PRT
<213> ORGANISM: A. thaliana

<400> SEQUENCE: 101

```
Ala Ser Ser Pro Lys Lys Lys Arg Lys Val Glu Ala Ser Met Glu Phe
1               5                   10                  15

Trp Gly Ile Glu Val Lys Ser Gly Lys Pro Val Thr Val Thr Pro Glu
            20                  25                  30

Glu Gly Ile Leu Ile His Val Ser Gln Ala Ser Leu Gly Glu Cys Lys
        35                  40                  45

Asn Lys Lys Gly Glu Phe Val Pro Leu His Val Lys Val Gly Asn Gln
    50                  55                  60

Asn Leu Val Leu Gly Thr Leu Ser Thr Glu Asn Ile Pro Gln Leu Phe
65                  70                  75                  80

Cys Asp Leu Val Phe Asp Lys Glu Phe Glu Leu Ser His Thr Trp Gly
                85                  90                  95

Lys Gly Ser Val Tyr Phe Val Gly Tyr Lys Thr Pro Asn Ile Glu Pro
            100                 105                 110

Gln Gly Tyr Ser Glu Glu Glu Glu Glu Glu Glu Glu Glu Val Pro Ala
        115                 120                 125

Gly Asn Ala Ala Lys Ala Val Ala Lys Pro Lys Ala Lys Pro Ala Glu
    130                 135                 140

Val Lys Pro Ala Val Asp Asp Glu Glu Asp Glu Ser Asp Ser Asp Gly
145                 150                 155                 160

Met Asp Glu Asp Asp Ser Asp Gly Glu Asp Ser Glu Glu Glu Glu Pro
                165                 170                 175

Thr Pro Lys Lys Pro Ala Ser Ser Lys Lys Arg Ala Asn Glu Thr Thr
            180                 185                 190

Pro Lys Ala Pro Val Ser Ala Lys Lys Ala Lys Val Ala Val Thr Pro
        195                 200                 205

Gln Lys Thr Asp Glu Lys Lys Lys Gly Gly Lys Ala Ala Asn Gln Ser
    210                 215                 220

Glu Phe
225
```

<210> SEQ ID NO 102
<211> LENGTH: 272
<212> TYPE: PRT
<213> ORGANISM: Homo sapiens

<400> SEQUENCE: 102

```
Ala Ser Ser Pro Lys Lys Lys Arg Lys Val Glu Ala Ser Met Val Gly
1               5                   10                  15

Ala Gly Ile Ser Thr Pro Ser Gly Ile Pro Asp Phe Arg Ser Pro Gly
            20                  25                  30

Ser Gly Leu Tyr Ser Asn Leu Gln Gln Tyr Asp Leu Pro Tyr Pro Glu
        35                  40                  45

Ala Ile Phe Glu Leu Pro Phe Phe Phe His Asn Pro Lys Pro Phe Phe
    50                  55                  60

Thr Leu Ala Lys Glu Leu Tyr Pro Gly Asn Tyr Lys Pro Asn Val Thr
65                  70                  75                  80

His Tyr Phe Leu Arg Leu Leu His Asp Lys Gly Leu Leu Leu Arg Leu
                85                  90                  95
```

```
Tyr Thr Gln Asn Ile Asp Gly Leu Glu Arg Val Ser Gly Ile Pro Ala
            100                 105                 110

Ser Lys Leu Val Glu Ala His Gly Thr Phe Ala Ser Ala Thr Cys Thr
        115                 120                 125

Val Cys Gln Arg Pro Phe Pro Gly Glu Asp Ile Arg Ala Asp Val Met
    130                 135                 140

Ala Asp Arg Val Pro Arg Cys Pro Val Cys Thr Gly Val Val Lys Pro
145                 150                 155                 160

Asp Ile Val Phe Phe Gly Glu Pro Leu Pro Gln Arg Phe Leu Leu His
                165                 170                 175

Val Val Asp Phe Pro Met Ala Asp Leu Leu Leu Ile Leu Gly Thr Ser
            180                 185                 190

Leu Glu Val Glu Pro Phe Ala Ser Leu Thr Glu Ala Val Arg Ser Ser
        195                 200                 205

Val Pro Arg Leu Leu Ile Asn Arg Asp Leu Val Gly Pro Leu Ala Trp
    210                 215                 220

His Pro Arg Ser Arg Asp Val Ala Gln Leu Gly Asp Val Val His Gly
225                 230                 235                 240

Val Glu Ser Leu Val Glu Leu Leu Gly Trp Thr Glu Glu Met Arg Asp
                245                 250                 255

Leu Val Gln Arg Glu Thr Gly Lys Leu Asp Gly Pro Asp Lys Glu Phe
            260                 265                 270


<210> SEQ ID NO 103
<211> LENGTH: 306
<212> TYPE: PRT
<213> ORGANISM: S. cerevisiae

<400> SEQUENCE: 103

Ala Ser Ser Pro Lys Lys Lys Arg Lys Val Glu Ala Ser Thr Glu Met
1               5                   10                  15

Ser Val Arg Lys Ile Ala Ala His Met Lys Ser Asn Pro Asn Ala Lys
            20                  25                  30

Val Ile Phe Met Val Gly Ala Gly Ile Ser Thr Ser Cys Gly Ile Pro
        35                  40                  45

Asp Phe Arg Ser Pro Gly Thr Gly Leu Tyr His Asn Leu Ala Arg Leu
    50                  55                  60

Lys Leu Pro Tyr Pro Glu Ala Val Phe Asp Val Asp Phe Phe Gln Ser
65                  70                  75                  80

Asp Pro Leu Pro Phe Tyr Thr Leu Ala Lys Glu Leu Tyr Pro Gly Asn
                85                  90                  95

Phe Arg Pro Ser Lys Phe His Tyr Leu Leu Lys Leu Phe Gln Asp Lys
            100                 105                 110

Asp Val Leu Lys Arg Val Tyr Thr Gln Asn Ile Asp Thr Leu Glu Arg
        115                 120                 125

Gln Ala Gly Val Lys Asp Asp Leu Ile Ile Glu Ala His Gly Ser Phe
    130                 135                 140

Ala His Cys His Cys Ile Gly Cys Gly Lys Val Tyr Pro Pro Gln Val
145                 150                 155                 160

Phe Lys Ser Lys Leu Ala Glu His Pro Ile Lys Asp Phe Val Lys Cys
                165                 170                 175

Asp Val Cys Gly Glu Leu Val Lys Pro Ala Ile Val Phe Phe Gly Glu
            180                 185                 190

Asp Leu Pro Asp Ser Phe Ser Glu Thr Trp Leu Asn Asp Ser Glu Trp
        195                 200                 205
```

```
Leu Arg Glu Lys Ile Thr Thr Ser Gly Lys His Pro Gln Gln Pro Leu
    210                 215                 220

Val Ile Val Val Gly Thr Ser Leu Ala Val Tyr Pro Phe Ala Ser Leu
225                 230                 235                 240

Pro Glu Glu Ile Pro Arg Lys Val Lys Arg Val Leu Cys Asn Leu Glu
                245                 250                 255

Thr Val Gly Asp Phe Lys Ala Asn Lys Arg Pro Thr Asp Leu Ile Val
            260                 265                 270

His Gln Tyr Ser Asp Glu Phe Ala Glu Gln Leu Val Glu Glu Leu Gly
        275                 280                 285

Trp Gln Glu Asp Phe Glu Lys Ile Leu Thr Ala Gln Gly Gly Met Gly
    290                 295                 300

Glu Phe
305


<210> SEQ ID NO 104
<211> LENGTH: 257
<212> TYPE: PRT
<213> ORGANISM: E. coli

<400> SEQUENCE: 104

Ala Ser Ser Pro Lys Lys Lys Arg Lys Val Glu Ala Ser Met Glu Lys
1               5                   10                  15

Pro Arg Val Leu Val Leu Thr Gly Ala Gly Ile Ser Ala Glu Ser Gly
            20                  25                  30

Ile Arg Thr Phe Arg Ala Ala Asp Gly Leu Trp Glu Glu His Arg Val
        35                  40                  45

Glu Asp Val Ala Thr Pro Glu Gly Phe Asp Arg Asp Pro Glu Leu Val
    50                  55                  60

Gln Ala Phe Tyr Asn Ala Arg Arg Arg Gln Leu Gln Gln Pro Glu Ile
65                  70                  75                  80

Gln Pro Asn Ala Ala His Leu Ala Leu Ala Lys Leu Gln Asp Ala Leu
                85                  90                  95

Gly Asp Arg Phe Leu Leu Val Thr Gln Asn Ile Asp Asn Leu His Glu
            100                 105                 110

Arg Ala Gly Asn Thr Asn Val Ile His Met His Gly Glu Leu Leu Lys
        115                 120                 125

Val Arg Cys Ser Gln Ser Gly Gln Val Leu Asp Trp Thr Gly Asp Val
    130                 135                 140

Thr Pro Glu Asp Lys Cys His Cys Cys Gln Phe Pro Ala Pro Leu Arg
145                 150                 155                 160

Pro His Val Val Trp Phe Gly Glu Met Pro Leu Gly Met Asp Glu Ile
                165                 170                 175

Tyr Met Ala Leu Ser Met Ala Asp Ile Phe Ile Ala Ile Gly Thr Ser
            180                 185                 190

Gly His Val Tyr Pro Ala Ala Gly Phe Val His Glu Ala Lys Leu His
        195                 200                 205

Gly Ala His Thr Val Glu Leu Asn Leu Glu Pro Ser Gln Val Gly Asn
    210                 215                 220

Glu Phe Ala Glu Lys Tyr Tyr Gly Pro Ala Ser Gln Val Val Pro Glu
225                 230                 235                 240

Phe Val Glu Lys Leu Leu Lys Gly Leu Lys Ala Gly Ser Ile Ala Glu
                245                 250                 255

Phe
```

<210> SEQ ID NO 105
<211> LENGTH: 346
<212> TYPE: PRT
<213> ORGANISM: C. albicans

<400> SEQUENCE: 105

```
Ala Ser Ser Pro Lys Lys Lys Arg Lys Val Glu Ala Ser Met Pro Ser
1               5                   10                  15

Leu Asp Asp Ile Leu Lys Pro Val Ala Glu Ala Val Lys Asn Gly Lys
            20                  25                  30

Lys Val Thr Phe Phe Asn Gly Ala Gly Ile Ser Thr Gly Ala Gly Ile
        35                  40                  45

Pro Asp Phe Arg Ser Pro Asp Thr Gly Leu Tyr Ala Asn Leu Ala Lys
    50                  55                  60

Leu Asn Leu Pro Phe Ala Glu Ala Val Phe Asp Ile Asp Phe Phe Lys
65                  70                  75                  80

Glu Asp Pro Lys Pro Phe Tyr Thr Leu Ala Glu Glu Leu Tyr Pro Gly
                85                  90                  95

Asn Phe Ala Pro Thr Lys Phe His His Phe Ile Lys Leu Leu Gln Asp
            100                 105                 110

Gln Gly Ser Leu Lys Arg Val Tyr Thr Gln Asn Ile Asp Thr Leu Glu
        115                 120                 125

Arg Leu Ala Gly Val Glu Asp Lys Tyr Ile Val Glu Ala His Gly Ser
    130                 135                 140

Phe Ala Ser Asn His Cys Val Asp Cys His Lys Glu Met Thr Thr Glu
145                 150                 155                 160

Thr Leu Lys Thr Tyr Met Lys Asp Lys Lys Ile Pro Ser Cys Gln His
                165                 170                 175

Cys Glu Gly Tyr Val Lys Pro Asp Ile Val Phe Phe Gly Glu Gly Leu
            180                 185                 190

Pro Val Lys Phe Phe Asp Leu Trp Glu Asp Asp Cys Glu Asp Val Glu
        195                 200                 205

Val Ala Ile Val Ala Gly Thr Ser Leu Thr Val Phe Pro Phe Ala Ser
    210                 215                 220

Leu Pro Gly Glu Val Asn Lys Lys Cys Leu Arg Val Leu Val Asn Lys
225                 230                 235                 240

Glu Lys Val Gly Thr Phe Lys His Glu Pro Arg Lys Ser Asp Ile Ile
                245                 250                 255

Ala Leu His Asp Cys Asp Ile Val Ala Glu Arg Leu Cys Thr Leu Leu
            260                 265                 270

Gly Leu Asp Asp Lys Leu Asn Glu Val Tyr Glu Lys Glu Lys Ile Lys
        275                 280                 285

Tyr Ser Lys Ala Glu Thr Lys Glu Ile Lys Met His Glu Ile Glu Asp
    290                 295                 300

Lys Leu Lys Glu Glu Ala His Leu Lys Glu Asp Lys His Thr Thr Lys
305                 310                 315                 320

Val Asp Lys Lys Glu Lys Gln Asn Asp Ala Asn Asp Lys Glu Leu Glu
                325                 330                 335

Gln Leu Ile Asp Lys Ala Lys Ala Glu Phe
            340                 345
```

<210> SEQ ID NO 106
<211> LENGTH: 289
<212> TYPE: PRT

<213> ORGANISM: Homo sapiens

<400> SEQUENCE: 106

Ala Ser Ser Pro Lys Lys Lys Arg Lys Val Glu Ala Ser Ser Ser Ser
1 5 10 15

Met Ala Asp Phe Arg Lys Phe Phe Ala Lys Ala Lys His Ile Val Ile
20 25 30

Ile Ser Gly Ala Gly Val Ser Ala Glu Ser Gly Val Pro Thr Phe Arg
35 40 45

Gly Ala Gly Gly Tyr Trp Arg Lys Trp Gln Ala Gln Asp Leu Ala Thr
50 55 60

Pro Leu Ala Phe Ala His Asn Pro Ser Arg Val Trp Glu Phe Tyr His
65 70 75 80

Tyr Arg Arg Glu Val Met Gly Ser Lys Glu Pro Asn Ala Gly His Arg
85 90 95

Ala Ile Ala Glu Cys Glu Thr Arg Leu Gly Lys Gln Gly Arg Arg Val
100 105 110

Val Val Ile Thr Gln Asn Ile Asp Glu Leu His Arg Lys Ala Gly Thr
115 120 125

Lys Asn Leu Leu Glu Ile His Gly Ser Leu Phe Lys Thr Arg Cys Thr
130 135 140

Ser Cys Gly Val Val Ala Glu Asn Tyr Lys Ser Pro Ile Cys Pro Ala
145 150 155 160

Leu Ser Gly Lys Gly Ala Pro Glu Pro Gly Thr Gln Asp Ala Ser Ile
165 170 175

Pro Val Glu Lys Leu Pro Arg Cys Glu Glu Ala Gly Cys Gly Gly Leu
180 185 190

Leu Arg Pro His Val Val Trp Phe Gly Glu Asn Leu Asp Pro Ala Ile
195 200 205

Leu Glu Glu Val Asp Arg Glu Leu Ala His Cys Asp Leu Cys Leu Val
210 215 220

Val Gly Thr Ser Ser Val Val Tyr Pro Ala Ala Met Phe Ala Pro Gln
225 230 235 240

Val Ala Ala Arg Gly Val Pro Val Ala Glu Phe Asn Thr Glu Thr Thr
245 250 255

Pro Ala Thr Asn Arg Phe Arg Phe His Phe Gln Gly Pro Cys Gly Thr
260 265 270

Thr Leu Pro Glu Ala Leu Ala Cys His Glu Asn Glu Thr Val Ser Glu
275 280 285

Phe

<210> SEQ ID NO 107
<211> LENGTH: 288
<212> TYPE: PRT
<213> ORGANISM: P. falciparum

<400> SEQUENCE: 107

Ala Ser Ser Pro Lys Lys Lys Arg Lys Val Glu Ala Ser Met Gly Asn
1 5 10 15

Leu Met Ile Ser Phe Leu Lys Lys Asp Thr Gln Ser Ile Thr Leu Glu
20 25 30

Glu Leu Ala Lys Ile Ile Lys Lys Cys Lys His Val Val Ala Leu Thr
35 40 45

Gly Ser Gly Thr Ser Ala Glu Ser Asn Ile Pro Ser Phe Arg Gly Ser
50 55 60

```
Ser Asn Ser Ile Trp Ser Lys Tyr Asp Pro Arg Ile Tyr Gly Thr Ile
65                  70                  75                  80

Trp Gly Phe Trp Lys Tyr Pro Glu Lys Ile Trp Glu Val Ile Arg Asp
                85                  90                  95

Ile Ser Ser Asp Tyr Glu Ile Glu Ile Asn Asn Gly His Val Ala Leu
            100                 105                 110

Ser Thr Leu Glu Ser Leu Gly Tyr Leu Lys Ser Val Val Thr Gln Asn
        115                 120                 125

Val Asp Gly Leu His Glu Ala Ser Gly Asn Thr Lys Val Ile Ser Leu
    130                 135                 140

His Gly Asn Val Phe Glu Ala Val Cys Cys Thr Cys Asn Lys Ile Val
145                 150                 155                 160

Lys Leu Asn Lys Ile Met Leu Gln Lys Thr Ser His Phe Met His Gln
                165                 170                 175

Leu Pro Pro Glu Cys Pro Cys Gly Gly Ile Phe Lys Pro Asn Ile Ile
            180                 185                 190

Leu Phe Gly Glu Val Val Ser Ser Asp Leu Leu Lys Glu Ala Glu Glu
        195                 200                 205

Glu Ile Ala Lys Cys Asp Leu Leu Leu Val Ile Gly Thr Ser Ser Thr
    210                 215                 220

Val Ser Thr Ala Thr Asn Leu Cys His Phe Ala Cys Lys Lys Lys Lys
225                 230                 235                 240

Lys Ile Val Glu Ile Asn Ile Ser Lys Thr Tyr Ile Thr Asn Lys Met
                245                 250                 255

Ser Asp Tyr His Val Cys Ala Lys Phe Ser Glu Leu Thr Lys Val Ala
            260                 265                 270

Asn Ile Leu Lys Gly Ser Ser Glu Lys Asn Lys Lys Ile Met Glu Phe
        275                 280                 285


<210> SEQ ID NO 108
<211> LENGTH: 304
<212> TYPE: PRT
<213> ORGANISM: Homo sapiens

<400> SEQUENCE: 108

Ala Ser Ser Pro Lys Lys Lys Arg Lys Val Glu Ala Ser Met Ser Val
1               5                   10                  15

Asn Tyr Ala Ala Gly Leu Ser Pro Tyr Ala Asp Lys Gly Lys Cys Gly
            20                  25                  30

Leu Pro Glu Ile Phe Asp Pro Pro Glu Glu Leu Glu Arg Lys Val Trp
        35                  40                  45

Glu Leu Ala Arg Leu Val Trp Gln Ser Ser Ser Val Val Phe His Thr
    50                  55                  60

Gly Ala Gly Ile Ser Thr Ala Ser Gly Ile Pro Asp Phe Arg Gly Pro
65                  70                  75                  80

His Gly Val Trp Thr Met Glu Glu Arg Gly Leu Ala Pro Lys Phe Asp
                85                  90                  95

Thr Thr Phe Glu Ser Ala Arg Pro Thr Gln Thr His Met Ala Leu Val
            100                 105                 110

Gln Leu Glu Arg Val Gly Leu Leu Arg Phe Leu Val Ser Gln Asn Val
        115                 120                 125

Asp Gly Leu His Val Arg Ser Gly Phe Pro Arg Asp Lys Leu Ala Glu
    130                 135                 140

Leu His Gly Asn Met Phe Val Glu Glu Cys Ala Lys Cys Lys Thr Gln
```

145 150 155 160

Tyr Val Arg Asp Thr Val Val Gly Thr Met Gly Leu Lys Ala Thr Gly
165 170 175

Arg Leu Cys Thr Val Ala Lys Ala Arg Gly Leu Arg Ala Cys Arg Gly
180 185 190

Glu Leu Arg Asp Thr Ile Leu Asp Trp Glu Asp Ser Leu Pro Asp Arg
195 200 205

Asp Leu Ala Leu Ala Asp Glu Ala Ser Arg Asn Ala Asp Leu Ser Ile
210 215 220

Thr Leu Gly Thr Ser Leu Gln Ile Arg Pro Ser Gly Asn Leu Pro Leu
225 230 235 240

Ala Thr Lys Arg Arg Gly Gly Arg Leu Val Ile Val Asn Leu Gln Pro
245 250 255

Thr Lys His Asp Arg His Ala Asp Leu Arg Ile His Gly Tyr Val Asp
260 265 270

Glu Val Met Thr Arg Leu Met Lys His Leu Gly Leu Glu Ile Pro Ala
275 280 285

Trp Asp Gly Pro Arg Val Leu Glu Arg Ala Leu Pro Pro Leu Glu Phe
290 295 300

<210> SEQ ID NO 109
<211> LENGTH: 234
<212> TYPE: PRT
<213> ORGANISM: C. trachomatis

<400> SEQUENCE: 109

Ala Ser Ser Pro Lys Lys Lys Arg Lys Val Glu Ala Ser Met Thr Thr
1 5 10 15

Asn Ser Thr Gln Asp Thr Leu Tyr Leu Ser Leu His Gly Gly Ile Asp
20 25 30

Ser Ala Ile Pro Tyr Pro Val Arg Arg Val Glu Gln Leu Leu Gln Phe
35 40 45

Ser Phe Leu Pro Glu Leu Gln Phe Gln Asn Ala Ala Val Lys Gln Arg
50 55 60

Ile Gln Arg Leu Cys Tyr Arg Glu Glu Lys Arg Leu Ala Val Ser Ser
65 70 75 80

Leu Ala Lys Trp Leu Gly Gln Leu His Lys Gln Arg Leu Arg Ala Pro
85 90 95

Lys Asn Pro Pro Val Ala Ile Cys Trp Ile Asn Ser Tyr Val Gly Tyr
100 105 110

Gly Val Phe Ala Arg Glu Ser Ile Pro Ala Trp Ser Tyr Ile Gly Glu
115 120 125

Tyr Thr Gly Ile Leu Arg Arg Arg Gln Ala Leu Trp Leu Asp Glu Asn
130 135 140

Asp Tyr Cys Phe Arg Tyr Pro Val Pro Arg Tyr Ser Phe Arg Tyr Phe
145 150 155 160

Thr Ile Asp Ser Gly Met Gln Gly Asn Val Thr Arg Phe Ile Asn His
165 170 175

Ser Asp Asn Pro Asn Leu Glu Ala Ile Gly Ala Phe Glu Asn Gly Ile
180 185 190

Phe His Ile Ile Ile Arg Ala Ile Lys Asp Ile Leu Pro Gly Glu Glu
195 200 205

Leu Cys Tyr His Tyr Gly Pro Leu Tyr Trp Lys His Arg Lys Lys Arg
210 215 220

Glu Glu Phe Val Pro Gln Glu Glu Glu Phe
225 230

<210> SEQ ID NO 110
<211> LENGTH: 134
<212> TYPE: PRT
<213> ORGANISM: P. bursaria chlorella virus

<400> SEQUENCE: 110

Ala Ser Ser Pro Lys Lys Lys Arg Lys Val Glu Ala Ser Met Phe Asn
1 5 10 15

Asp Arg Val Ile Val Lys Lys Ser Pro Leu Gly Gly Tyr Gly Val Phe
20 25 30

Ala Arg Lys Ser Phe Glu Lys Gly Glu Leu Val Glu Glu Cys Leu Cys
35 40 45

Ile Val Arg His Asn Asp Asp Trp Gly Thr Ala Leu Glu Asp Tyr Leu
50 55 60

Phe Ser Arg Lys Asn Met Ser Ala Met Ala Leu Gly Phe Gly Ala Ile
65 70 75 80

Phe Asn His Ser Lys Asp Pro Asn Ala Arg His Glu Leu Thr Ala Gly
85 90 95

Leu Lys Arg Met Arg Ile Phe Thr Ile Lys Pro Ile Ala Ile Gly Glu
100 105 110

Glu Ile Thr Ile Ser Tyr Gly Asp Asp Tyr Trp Leu Ser Arg Pro Arg
115 120 125

Leu Thr Gln Asn Glu Phe
130

<210> SEQ ID NO 111
<211> LENGTH: 349
<212> TYPE: PRT
<213> ORGANISM: Homo sapiens

<400> SEQUENCE: 111

Ala Ser Ser Pro Lys Lys Lys Arg Lys Val Glu Ala Ser Asn Leu Lys
1 5 10 15

Cys Val Arg Ile Leu Lys Gln Phe His Lys Asp Leu Glu Arg Glu Leu
20 25 30

Leu Arg Arg His His Arg Ser Lys Thr Pro Arg His Leu Asp Pro Ser
35 40 45

Leu Ala Asn Tyr Leu Val Gln Lys Ala Lys Gln Arg Arg Ala Leu Arg
50 55 60

Arg Trp Glu Gln Glu Leu Asn Ala Lys Arg Ser His Leu Gly Arg Ile
65 70 75 80

Thr Val Glu Asn Glu Val Asp Leu Asp Gly Pro Pro Arg Ala Phe Val
85 90 95

Tyr Ile Asn Glu Tyr Arg Val Gly Glu Gly Ile Thr Leu Asn Gln Val
100 105 110

Ala Val Gly Cys Glu Cys Gln Asp Cys Leu Trp Ala Pro Thr Gly Gly
115 120 125

Cys Cys Pro Gly Ala Ser Leu His Lys Phe Ala Tyr Asn Asp Gln Gly
130 135 140

Gln Val Arg Leu Arg Ala Gly Leu Pro Ile Tyr Glu Cys Asn Ser Arg
145 150 155 160

Cys Arg Cys Gly Tyr Asp Cys Pro Asn Arg Val Val Gln Lys Gly Ile
165 170 175

```
Arg Tyr Asp Leu Cys Ile Phe Arg Thr Asp Asp Gly Arg Gly Trp Gly
            180                 185                 190

Val Arg Thr Leu Glu Lys Ile Arg Lys Asn Ser Phe Val Met Glu Tyr
        195                 200                 205

Val Gly Glu Ile Ile Thr Ser Glu Glu Ala Glu Arg Arg Gly Gln Ile
    210                 215                 220

Tyr Asp Arg Gln Gly Ala Thr Tyr Leu Phe Asp Leu Asp Tyr Val Glu
225                 230                 235                 240

Asp Val Tyr Thr Val Asp Ala Ala Tyr Tyr Gly Asn Ile Ser His Phe
                245                 250                 255

Val Asn His Ser Cys Asp Pro Asn Leu Gln Val Tyr Asn Val Phe Ile
            260                 265                 270

Asp Asn Leu Asp Glu Arg Leu Pro Arg Ile Ala Phe Phe Ala Thr Arg
        275                 280                 285

Thr Ile Arg Ala Gly Glu Glu Leu Thr Phe Asp Tyr Asn Met Gln Val
    290                 295                 300

Asp Pro Val Asp Met Glu Ser Thr Arg Met Asp Ser Asn Phe Gly Leu
305                 310                 315                 320

Ala Gly Leu Pro Gly Ser Pro Lys Lys Arg Val Arg Ile Glu Cys Lys
                325                 330                 335

Cys Gly Thr Glu Ser Cys Arg Lys Tyr Leu Phe Glu Phe
            340                 345


<210> SEQ ID NO 112
<211> LENGTH: 346
<212> TYPE: PRT
<213> ORGANISM: N. crassa

<400> SEQUENCE: 112

Ala Ser Ser Pro Lys Lys Lys Arg Lys Val Glu Ala Ser Met Glu Lys
1               5                   10                  15

Ala Phe Arg Pro His Phe Phe Asn His Gly Lys Pro Asp Ala Asn Pro
            20                  25                  30

Lys Glu Lys Lys Asn Cys His Trp Cys Gln Ile Arg Ser Phe Ala Thr
        35                  40                  45

His Ala Gln Leu Pro Ile Ser Ile Val Asn Arg Glu Asp Asp Ala Phe
    50                  55                  60

Leu Asn Pro Asn Phe Arg Phe Ile Asp His Ser Ile Ile Gly Lys Asn
65                  70                  75                  80

Val Pro Val Ala Asp Gln Ser Phe Arg Val Gly Cys Ser Cys Ala Ser
                85                  90                  95

Asp Glu Glu Cys Met Tyr Ser Thr Cys Gln Cys Leu Asp Glu Met Ala
            100                 105                 110

Pro Asp Ser Asp Glu Glu Ala Asp Pro Tyr Thr Arg Lys Lys Arg Phe
        115                 120                 125

Ala Tyr Tyr Ser Gln Gly Ala Lys Lys Gly Leu Leu Arg Asp Arg Val
    130                 135                 140

Leu Gln Ser Gln Glu Pro Ile Tyr Glu Cys His Gln Gly Cys Ala Cys
145                 150                 155                 160

Ser Lys Asp Cys Pro Asn Arg Val Val Glu Arg Gly Arg Thr Val Pro
                165                 170                 175

Leu Gln Ile Phe Arg Thr Lys Asp Arg Gly Trp Gly Val Lys Cys Pro
            180                 185                 190

Val Asn Ile Lys Arg Gly Gln Phe Val Asp Arg Tyr Leu Gly Glu Ile
        195                 200                 205
```

```
Ile Thr Ser Glu Glu Ala Asp Arg Arg Arg Ala Glu Ser Thr Ile Ala
    210                 215                 220

Arg Arg Lys Asp Val Tyr Leu Phe Ala Leu Asp Lys Phe Ser Asp Pro
225                 230                 235                 240

Asp Ser Leu Asp Pro Leu Leu Ala Gly Gln Pro Leu Glu Val Asp Gly
                245                 250                 255

Glu Tyr Met Ser Gly Pro Thr Arg Phe Ile Asn His Ser Cys Asp Pro
            260                 265                 270

Asn Met Ala Ile Phe Ala Arg Val Gly Asp His Ala Asp Lys His Ile
        275                 280                 285

His Asp Leu Ala Leu Phe Ala Ile Lys Asp Ile Pro Lys Gly Thr Glu
    290                 295                 300

Leu Thr Phe Asp Tyr Val Asn Gly Leu Thr Gly Leu Glu Ser Asp Ala
305                 310                 315                 320

His Asp Pro Ser Lys Ile Ser Glu Met Thr Lys Cys Leu Cys Gly Thr
                325                 330                 335

Ala Lys Cys Arg Gly Tyr Leu Trp Glu Phe
            340                 345


<210> SEQ ID NO 113
<211> LENGTH: 282
<212> TYPE: PRT
<213> ORGANISM: A. thaliana

<400> SEQUENCE: 113

Ala Ser Ser Pro Lys Lys Lys Arg Lys Val Glu Ala Ser Asp Ile Ser
1               5                   10                  15

Gly Gly Leu Glu Phe Lys Gly Ile Pro Ala Thr Asn Arg Val Asp Asp
            20                  25                  30

Ser Pro Val Ser Pro Thr Ser Gly Phe Thr Tyr Ile Lys Ser Leu Ile
        35                  40                  45

Ile Glu Pro Asn Val Ile Ile Pro Lys Ser Ser Thr Gly Cys Asn Cys
    50                  55                  60

Arg Gly Ser Cys Thr Asp Ser Lys Lys Cys Ala Cys Ala Lys Leu Asn
65                  70                  75                  80

Gly Gly Asn Phe Pro Tyr Val Asp Leu Asn Asp Gly Arg Leu Ile Glu
                85                  90                  95

Ser Arg Asp Val Val Phe Glu Cys Gly Pro His Cys Gly Cys Gly Pro
            100                 105                 110

Lys Cys Val Asn Arg Thr Ser Gln Lys Arg Leu Arg Phe Asn Leu Glu
        115                 120                 125

Val Phe Arg Ser Ala Lys Lys Gly Trp Ala Val Arg Ser Trp Glu Tyr
    130                 135                 140

Ile Pro Ala Gly Ser Pro Val Cys Glu Tyr Ile Gly Val Val Arg Arg
145                 150                 155                 160

Thr Ala Asp Val Asp Thr Ile Ser Asp Asn Glu Tyr Ile Phe Glu Ile
                165                 170                 175

Asp Cys Gln Gln Thr Met Gln Gly Leu Gly Gly Arg Gln Arg Arg Leu
            180                 185                 190

Arg Asp Val Ala Val Pro Met Asn Asn Gly Val Ser Gln Ser Ser Glu
        195                 200                 205

Asp Glu Asn Ala Pro Glu Phe Cys Ile Asp Ala Gly Ser Thr Gly Asn
    210                 215                 220

Phe Ala Arg Phe Ile Asn His Ser Cys Glu Pro Asn Leu Phe Val Gln
```

```
225                 230                 235                 240

Cys Val Leu Ser Ser His Gln Asp Ile Arg Leu Ala Arg Val Val Leu
                245                 250                 255

Phe Ala Ala Asp Asn Ile Ser Pro Met Gln Glu Leu Thr Tyr Asp Tyr
            260                 265                 270

Gly Tyr Ala Leu Asp Ser Val His Glu Phe
        275                 280


<210> SEQ ID NO 114
<211> LENGTH: 328
<212> TYPE: PRT
<213> ORGANISM: A. thaliana

<400> SEQUENCE: 114

Ala Ser Ser Pro Lys Lys Lys Arg Lys Val Glu Ala Ser Gln Ser Ala
1               5                   10                  15

Tyr Leu His Val Ser Leu Ala Arg Ile Ser Asp Glu Asp Cys Cys Ala
            20                  25                  30

Asn Cys Lys Gly Asn Cys Leu Ser Ala Asp Phe Pro Cys Thr Cys Ala
        35                  40                  45

Arg Glu Thr Ser Gly Glu Tyr Ala Tyr Thr Lys Glu Gly Leu Leu Lys
    50                  55                  60

Glu Lys Phe Leu Asp Thr Cys Leu Lys Met Lys Lys Glu Pro Asp Ser
65                  70                  75                  80

Phe Pro Lys Val Tyr Cys Lys Asp Cys Pro Leu Glu Arg Asp His Asp
                85                  90                  95

Lys Gly Thr Tyr Gly Lys Cys Asp Gly His Leu Ile Arg Lys Phe Ile
            100                 105                 110

Lys Glu Cys Trp Arg Lys Cys Gly Cys Asp Met Gln Cys Gly Asn Arg
        115                 120                 125

Val Val Gln Arg Gly Ile Arg Cys Gln Leu Gln Val Tyr Phe Thr Gln
    130                 135                 140

Glu Gly Lys Gly Trp Gly Leu Arg Thr Leu Gln Asp Leu Pro Lys Gly
145                 150                 155                 160

Thr Phe Ile Cys Glu Tyr Ile Gly Glu Ile Leu Thr Asn Thr Glu Leu
                165                 170                 175

Tyr Asp Arg Asn Val Arg Ser Ser Ser Glu Arg His Thr Tyr Pro Val
            180                 185                 190

Thr Leu Asp Ala Asp Trp Gly Ser Glu Lys Asp Leu Lys Asp Glu Glu
        195                 200                 205

Ala Leu Cys Leu Asp Ala Thr Ile Cys Gly Asn Val Ala Arg Phe Ile
    210                 215                 220

Asn His Arg Cys Glu Asp Ala Asn Met Ile Asp Ile Pro Ile Glu Ile
225                 230                 235                 240

Glu Thr Pro Asp Arg His Tyr Tyr His Ile Ala Phe Phe Thr Leu Arg
                245                 250                 255

Asp Val Lys Ala Met Asp Glu Leu Thr Trp Asp Tyr Met Ile Asp Phe
            260                 265                 270

Asn Asp Lys Ser His Pro Val Lys Ala Phe Arg Cys Cys Cys Gly Ser
        275                 280                 285

Glu Ser Cys Arg Asp Arg Lys Ile Lys Gly Ser Gln Gly Lys Ser Ile
    290                 295                 300

Glu Arg Arg Lys Ile Val Ser Ala Lys Lys Gln Gln Gly Ser Lys Glu
305                 310                 315                 320
```

```
Val Ser Lys Lys Arg Lys Glu Phe
                325


<210> SEQ ID NO 115
<211> LENGTH: 303
<212> TYPE: PRT
<213> ORGANISM: C. elegans

<400> SEQUENCE: 115

Ala Ser Ser Pro Lys Lys Lys Arg Lys Val Glu Ala Ser Met Gln Leu
1               5                   10                  15

His Glu Gln Ile Ala Asn Ile Ser Val Thr Phe Asn Asp Ile Pro Arg
            20                  25                  30

Ser Asp His Ser Met Thr Pro Thr Glu Leu Cys Tyr Phe Asp Asp Phe
        35                  40                  45

Ala Thr Thr Leu Val Val Asp Ser Val Leu Asn Phe Thr Thr His Lys
    50                  55                  60

Met Ser Lys Lys Arg Arg Tyr Leu Tyr Gln Asp Glu Tyr Arg Thr Ala
65                  70                  75                  80

Arg Thr Val Met Lys Thr Phe Arg Glu Gln Arg Asp Trp Thr Asn Ala
                85                  90                  95

Ile Tyr Gly Leu Leu Thr Leu Arg Ser Val Ser His Phe Leu Ser Lys
            100                 105                 110

Leu Pro Pro Asn Lys Leu Phe Glu Phe Arg Asp His Ile Val Arg Phe
        115                 120                 125

Leu Asn Met Phe Ile Leu Asp Ser Gly Tyr Thr Ile Gln Glu Cys Lys
    130                 135                 140

Arg Tyr Ser Gln Glu Gly His Gln Gly Ala Lys Leu Val Ser Thr Gly
145                 150                 155                 160

Val Trp Ser Arg Gly Asp Lys Ile Glu Arg Leu Ser Gly Val Val Cys
                165                 170                 175

Leu Leu Ser Ser Glu Asp Glu Asp Ser Ile Leu Ala Gln Glu Gly Ser
            180                 185                 190

Asp Phe Ser Val Met Tyr Ser Thr Arg Lys Arg Cys Ser Thr Leu Trp
        195                 200                 205

Leu Gly Pro Gly Ala Tyr Ile Asn His Asp Cys Arg Pro Thr Cys Glu
    210                 215                 220

Phe Val Ser His Gly Ser Thr Ala His Ile Arg Val Leu Arg Asp Met
225                 230                 235                 240

Val Pro Gly Asp Glu Ile Thr Cys Phe Tyr Gly Ser Glu Phe Phe Gly
                245                 250                 255

Pro Asn Asn Ile Asp Cys Glu Cys Cys Thr Cys Glu Lys Asn Met Asn
            260                 265                 270

Gly Ala Phe Ser Tyr Leu Arg Gly Asn Glu Asn Ala Glu Pro Ile Ile
        275                 280                 285

Ser Glu Lys Lys Thr Lys Tyr Glu Leu Arg Ser Arg Ser Glu Phe
    290                 295                 300


<210> SEQ ID NO 116
<211> LENGTH: 257
<212> TYPE: PRT
<213> ORGANISM: C. elegans

<400> SEQUENCE: 116

Ala Ser Ser Pro Lys Lys Lys Arg Lys Val Glu Ala Ser Met Lys Val
1               5                   10                  15
```

```
Ala Ala Lys Lys Leu Ala Thr Ser Arg Met Arg Lys Asp Arg Ala Ala
            20                  25                  30

Ala Ala Ser Pro Ser Ser Asp Ile Glu Asn Ser Glu Asn Pro Ser Ser
        35                  40                  45

Leu Ala Ser His Ser Ser Ser Ser Gly Arg Met Thr Pro Ser Lys Asn
    50                  55                  60

Thr Arg Ser Arg Lys Gly Val Ser Val Lys Asp Val Ser Asn His Lys
65                  70                  75                  80

Ile Thr Glu Phe Phe Gln Val Arg Arg Ser Asn Arg Lys Thr Ser Lys
                85                  90                  95

Gln Ile Ser Asp Glu Ala Lys His Ala Leu Arg Asp Thr Val Leu Lys
            100                 105                 110

Gly Thr Asn Glu Arg Leu Leu Glu Val Tyr Lys Asp Val Val Lys Gly
        115                 120                 125

Arg Gly Ile Arg Thr Lys Val Asn Phe Glu Lys Gly Asp Phe Val Val
    130                 135                 140

Glu Tyr Arg Gly Val Met Met Glu Tyr Ser Glu Ala Lys Val Ile Glu
145                 150                 155                 160

Glu Gln Tyr Ser Asn Asp Glu Glu Ile Gly Ser Tyr Met Tyr Phe Phe
                165                 170                 175

Glu His Asn Asn Lys Lys Trp Cys Ile Asp Ala Thr Lys Glu Ser Pro
            180                 185                 190

Trp Lys Gly Arg Leu Ile Asn His Ser Val Leu Arg Pro Asn Leu Lys
        195                 200                 205

Thr Lys Val Val Glu Ile Asp Gly Ser His His Leu Ile Leu Val Ala
    210                 215                 220

Arg Arg Gln Ile Ala Gln Gly Glu Glu Leu Leu Tyr Asp Tyr Gly Asp
225                 230                 235                 240

Arg Ser Ala Glu Thr Ile Ala Lys Asn Pro Trp Leu Val Asn Thr Glu
                245                 250                 255

Phe


<210> SEQ ID NO 117
<211> LENGTH: 224
<212> TYPE: PRT
<213> ORGANISM: Homo sapiens

<400> SEQUENCE: 117

Ala Ser Ser Pro Lys Lys Lys Arg Lys Val Glu Ala Ser Ser Cys Asp
1               5                   10                  15

Ser Thr Asn Ala Ala Ile Ala Lys Gln Ala Leu Lys Lys Pro Ile Lys
            20                  25                  30

Gly Lys Gln Ala Pro Arg Lys Lys Ala Gln Gly Lys Thr Gln Gln Asn
        35                  40                  45

Arg Lys Leu Thr Asp Phe Tyr Pro Val Arg Arg Ser Ser Arg Lys Ser
    50                  55                  60

Lys Ala Glu Leu Gln Ser Glu Glu Arg Lys Arg Ile Asp Glu Leu Ile
65                  70                  75                  80

Glu Ser Gly Lys Glu Glu Gly Met Lys Ile Asp Leu Ile Asp Gly Lys
                85                  90                  95

Gly Arg Gly Val Ile Ala Thr Lys Gln Phe Ser Arg Gly Asp Phe Val
            100                 105                 110

Val Glu Tyr His Gly Asp Leu Ile Glu Ile Thr Asp Ala Lys Lys Arg
        115                 120                 125
```

```
Glu Ala Leu Tyr Ala Gln Asp Pro Ser Thr Gly Cys Tyr Met Tyr Tyr
    130                 135                 140

Phe Gln Tyr Leu Ser Lys Thr Tyr Cys Val Asp Ala Thr Arg Glu Thr
145                 150                 155                 160

Asn Arg Leu Gly Arg Leu Ile Asn His Ser Lys Cys Gly Asn Cys Gln
                165                 170                 175

Thr Lys Leu His Asp Ile Asp Gly Val Pro His Leu Ile Leu Ile Ala
            180                 185                 190

Ser Arg Asp Ile Ala Ala Gly Glu Glu Leu Leu Tyr Asp Tyr Gly Asp
        195                 200                 205

Arg Ser Lys Ala Ser Ile Glu Ala Phe Pro Trp Leu Lys His Glu Phe
    210                 215                 220


<210> SEQ ID NO 118
<211> LENGTH: 319
<212> TYPE: PRT
<213> ORGANISM: T. gondii

<400> SEQUENCE: 118

Ala Ser Ser Pro Lys Lys Lys Arg Lys Val Glu Ala Ser Ala Ser Arg
1               5                   10                  15

Arg Thr Gly Glu Phe Leu Arg Asp Ala Gln Ala Pro Ser Arg Trp Leu
            20                  25                  30

Lys Arg Ser Lys Thr Gly Gln Asp Asp Gly Ala Phe Cys Leu Glu Thr
        35                  40                  45

Trp Leu Ala Gly Ala Gly Asp Asp Ala Ala Gly Gly Glu Arg Gly Arg
    50                  55                  60

Asp Arg Glu Gly Ala Ala Asp Lys Ala Lys Gln Arg Glu Glu Arg Arg
65                  70                  75                  80

Gln Lys Glu Leu Glu Glu Arg Phe Glu Glu Met Lys Val Glu Phe Glu
                85                  90                  95

Glu Lys Ala Gln Arg Met Ile Ala Arg Arg Ala Ala Leu Thr Gly Glu
            100                 105                 110

Ile Tyr Ser Asp Gly Lys Gly Ser Lys Lys Pro Arg Val Pro Ser Leu
        115                 120                 125

Pro Glu Asn Asp Asp Asp Ala Leu Ile Glu Ile Ile Ile Asp Pro Glu
    130                 135                 140

Gln Gly Ile Leu Lys Trp Pro Leu Ser Val Met Ser Ile Arg Gln Arg
145                 150                 155                 160

Thr Val Ile Tyr Gln Glu Cys Leu Arg Arg Asp Leu Thr Ala Cys Ile
                165                 170                 175

His Leu Thr Lys Val Pro Gly Lys Gly Arg Ala Val Phe Ala Ala Asp
            180                 185                 190

Thr Ile Leu Lys Asp Asp Phe Val Val Glu Tyr Lys Gly Glu Leu Cys
        195                 200                 205

Ser Glu Arg Glu Ala Arg Glu Arg Glu Gln Arg Tyr Asn Arg Ser Lys
    210                 215                 220

Val Pro Met Gly Ser Phe Met Phe Tyr Phe Lys Asn Gly Ser Arg Met
225                 230                 235                 240

Met Ala Ile Asp Ala Thr Asp Glu Lys Gln Asp Phe Gly Pro Ala Arg
                245                 250                 255

Leu Ile Asn His Ser Arg Arg Asn Pro Asn Met Thr Pro Arg Ala Ile
            260                 265                 270

Thr Leu Gly Asp Phe Asn Ser Glu Pro Arg Leu Ile Phe Val Ala Arg
        275                 280                 285
```

```
Arg Asn Ile Glu Lys Gly Glu Glu Leu Leu Val Asp Tyr Gly Glu Arg
    290                 295                 300

Asp Pro Asp Val Ile Lys Glu His Pro Trp Leu Asn Ser Glu Phe
305                 310                 315


<210> SEQ ID NO 119
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 119

ggcctgcttc gtggcaatgc                                                  20


<210> SEQ ID NO 120
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 120

acctgggcca gggagggagg                                                  20


<210> SEQ ID NO 121
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 121

ctcacttaga ctttctctcc                                                  20


<210> SEQ ID NO 122
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 122

ctcggagtct agctcctgca                                                  20


<210> SEQ ID NO 123
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 123

tggccccagt ctctcttcta                                                  20


<210> SEQ ID NO 124
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 124

cagcctctga acagctcccg                                                  20
```

<210> SEQ ID NO 125
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 125
tgacttggcc tttgtaggaa 20

<210> SEQ ID NO 126
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 126
gaggctactg aaacataagt 20

<210> SEQ ID NO 127
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 127
tgctacctgt acatctgcac 20

<210> SEQ ID NO 128
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 128
catcaatgat tgggcatttc 20

<210> SEQ ID NO 129
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 129
actccagtcc caaatatgta 20

<210> SEQ ID NO 130
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 130
actagggggc gctcggccac 20

<210> SEQ ID NO 131
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 131
ctgagtcaac tgtaagcatt 20

<210> SEQ ID NO 132
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 132
ggccaggtgc agtgattcat 20

<210> SEQ ID NO 133
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 133
tcgtgtcatc ttgtttgtgc 20

<210> SEQ ID NO 134
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 134
ggcagagccc agcggacact 20

<210> SEQ ID NO 135
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 135
caaggtgagc ctgggtctgt 20

<210> SEQ ID NO 136
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 136
atcactgccc aagaagtgca 20

<210> SEQ ID NO 137
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 137
ttgtaggatg tttagcagca 20

<210> SEQ ID NO 138

<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 138
acttgctctc tttagagaac 20

<210> SEQ ID NO 139
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 139
ctcaagcagg ccccgctggt 20

<210> SEQ ID NO 140
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 140
ttttggacca aacctttttg 20

<210> SEQ ID NO 141
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 141
tgaggttatt tgtccattgt 20

<210> SEQ ID NO 142
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 142
taaggggagt atttacacca 20

<210> SEQ ID NO 143
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 143
tcaagagcag aaaatgtgac 20

<210> SEQ ID NO 144
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 144

-continued cttgcaggga ccttctgatt 20

<210> SEQ ID NO 145
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 145
tgtgtgtagg actaaactct 20

<210> SEQ ID NO 146
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 146
gatagcagta tgaccttggg 20

<210> SEQ ID NO 147
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 147
agcgtgtccg gcgagggcga 20

<210> SEQ ID NO 148
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 148
agcgtgtccg gcgagggcga 20

<210> SEQ ID NO 149
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 149
cagaatcgga ggacaaaata caaac 25

<210> SEQ ID NO 150
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 150
acgaagcagg ccaacgggga ggaca 25

<210> SEQ ID NO 151
<211> LENGTH: 37
<212> TYPE: DNA

<213> ORGANISM: Artificial Sequence
<220> FEATURE:
<223> OTHER INFORMATION: Synthetic Polynucleotide

<400> SEQUENCE: 151
taatacgact cactataggg cacgggcagc ttgccgg 37

<210> SEQ ID NO 152
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 152
taatacgact cactataggc ctcgaacttc acctcggcgg aaaggacgaa acacc 55

<210> SEQ ID NO 153
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 153
taatacgact cactataggc tgaagggcat cgacttcaga aaggacgaaa cacc 54

<210> SEQ ID NO 154
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 154
taatacgact cactataggc agctcgatgc ggttcaccag aaaggacgaa acacc 55

<210> SEQ ID NO 155
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 155
taatacgact cactataggc aaggaggacg gcaacatccg aaaggacgaa acacc 55

<210> SEQ ID NO 156
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 156
taatacgact cactatagga gtccgagcag aagaagaaga aaggacgaaa cacc 54

<210> SEQ ID NO 157
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 157
taatacgact cactatagggg gtggggggag tttgctccga aaggacgaaa cacc 54

<210> SEQ ID NO 158
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 158
taatacgact cactataggc agatgtagtg tttccacaga aaggacgaaa cacc 54

<210> SEQ ID NO 159
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 159
aaaaaaagca ccgactcggt g 21

<210> SEQ ID NO 160
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 160
ctgtacaaaa aagcaggctt ta 22

<210> SEQ ID NO 161
<211> LENGTH: 83
<212> TYPE: DNA
<213> ORGANISM: Artificial Sequence
<220> FEATURE:
<223> OTHER INFORMATION: Synthetic Polynucleotide

<400> SEQUENCE: 161
aaaaaaagca ccgactcggt gccacttttt caagttgata acggactagc cttattttaa 60
cttgctattt ctagctctaa aac 83

<210> SEQ ID NO 162
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 162
gaaaggacga aacaccggcc tcgaacttca cctcggcggt tttagagcta gaaatagcaa 60

<210> SEQ ID NO 163
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 163
gaaaggacga aacaccggca gctcgatgcg gttcaccagt tttagagcta gaaatagcaa 60

<210> SEQ ID NO 164
<211> LENGTH: 59
<212> TYPE: DNA

<213> ORGANISM: Artificial Sequence
<220> FEATURE:
<223> OTHER INFORMATION: Synthetic Polynucleotide

<400> SEQUENCE: 164
gaaaggacga aacaccggct gaagggcatc gacttcagtt ttagagctag aaatagcaa 59

<210> SEQ ID NO 165
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 165
gaaaggacga aacaccggca aggaggacgg caacatccgt tttagagcta gaaatagcaa 60

<210> SEQ ID NO 166
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 166
gaaaggacga aacaccggca gatgtagtgt ttccacagtt ttagagctag aaatagcaa 59

<210> SEQ ID NO 167
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 167
gaaaggacga aacaccggag tccgagcaga agaagaagtt ttagagctag aaatagcaa 59

<210> SEQ ID NO 168
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 168
gaaaggacga aacaccgggg tggggggagt ttgctccgtt ttagagctag aaatagcaa 59

<210> SEQ ID NO 169
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 169
tacggcaagc tgaccctgaa 20

<210> SEQ ID NO 170
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 170
gtccatgccg agagtgatcc 20

<210> SEQ ID NO 171
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 171
gccaggggct gttatcttgg 20

<210> SEQ ID NO 172
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 172
atgcacagaa gcacaggttg a 21

<210> SEQ ID NO 173
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 173
ctgtgtcctc ttcctgccct 20

<210> SEQ ID NO 174
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 174
ctctccgagg agaaggccaa 20

<210> SEQ ID NO 175
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 175
ccacacagct tcccgttctc 20

<210> SEQ ID NO 176
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 176
gagagccgtt ccctctttgc 20

<210> SEQ ID NO 177
<211> LENGTH: 52
<212> TYPE: DNA
<213> ORGANISM: Artificial Sequence
<220> FEATURE:

<223> OTHER INFORMATION: Synthetic Polynucleotide

<400> SEQUENCE: 177
cactctttcc ctacacgacg ctcttccgat ctcctcccca ttggcctgct tc 52

<210> SEQ ID NO 178
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 178
cactctttcc ctacacgacg ctcttccgat cttcgtcctg ctctcactta gac 53

<210> SEQ ID NO 179
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 179
cactctttcc ctacacgacg ctcttccgat ctttttgtgg cttggcccca gt 52

<210> SEQ ID NO 180
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 180
cactctttcc ctacacgacg ctcttccgat cttgcagtct catgacttgg cct 53

<210> SEQ ID NO 181
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 181
cactctttcc ctacacgacg ctcttccgat ctttctgagg gctgctacct gt 52

<210> SEQ ID NO 182
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 182
cactctttcc ctacacgacg ctcttccgat ctacatgaag caactccagt ccca 54

<210> SEQ ID NO 183
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 183
cactctttcc ctacacgacg ctcttccgat ctagcagacc cactgagtca actg 54

-continued

<210> SEQ ID NO 184
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 184
cactctttcc ctacacgacg ctcttccgat ctcccgccac agtcgtgtca t 51

<210> SEQ ID NO 185
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 185
cactctttcc ctacacgacg ctcttccgat ctcgccccgg tacaaggtga 50

<210> SEQ ID NO 186
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 186
cactctttcc ctacacgacg ctcttccgat ctgtaccgta cattgtagga tgttt 55

<210> SEQ ID NO 187
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 187
cactctttcc ctacacgacg ctcttccgat ctcctcatct ccctcaagca ggc 53

<210> SEQ ID NO 188
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 188
cactctttcc ctacacgacg ctcttccgat ctattctgct cttgaggtta tttgt 55

<210> SEQ ID NO 189
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 189
cactctttcc ctacacgacg ctcttccgat ctcacctctg cctcaagagc agaaaa 56

<210> SEQ ID NO 190
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 190
cactctttcc ctacacgacg ctcttccgat cttgtgtgtg tgtgtgtgta ggact 55

<210> SEQ ID NO 191
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 191
ggagttcaga cgtgtgctct tccgatcttc atctgtgccc ctccctcc 48

<210> SEQ ID NO 192
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 192
ggagttcaga cgtgtgctct tccgatctcg agaaggaggt gcaggag 47

<210> SEQ ID NO 193
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 193
ggagttcaga cgtgtgctct tccgatctcg ggagctgttc agaggctg 48

<210> SEQ ID NO 194
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 194
ggagttcaga cgtgtgctct tccgatctct cacctgggcg agaaaggt 48

<210> SEQ ID NO 195
<211> LENGTH: 52
<212> TYPE: DNA
<213> ORGANISM: Artificial Sequence
<220> FEATURE:
<223> OTHER INFORMATION: Synthetic Polynucleotide

<400> SEQUENCE: 195
ggagttcaga cgtgtgctct tccgatctaa aactcaaaga aatgcccaat ca 52

<210> SEQ ID NO 196
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 196
ggagttcaga cgtgtgctct tccgatctag acgctgctcg ctccattc 48

<210> SEQ ID NO 197
<211> LENGTH: 50

<212> TYPE: DNA
<213> ORGANISM: Artificial Sequence
<220> FEATURE:
<223> OTHER INFORMATION: Synthetic Polynucleotide

<400> SEQUENCE: 197
ggagttcaga cgtgtgctct tccgatctac aggcatgaat cactgcacct 50

<210> SEQ ID NO 198
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 198
ggagttcaga cgtgtgctct tccgatctgc ggcaacttca gacaaccga 49

<210> SEQ ID NO 199
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 199
ggagttcaga cgtgtgctct tccgatctga cccaggggca ccagtt 46

<210> SEQ ID NO 200
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 200
ggagttcaga cgtgtgctct tccgatctct gccttcattg cttaaaagtg gat 53

<210> SEQ ID NO 201
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 201
ggagttcaga cgtgtgctct tccgatctac agttgaagga aggaaacatg c 51

<210> SEQ ID NO 202
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 202
ggagttcaga cgtgtgctct tccgatctgc tgcatttgcc catttcca 48

<210> SEQ ID NO 203
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 203

-continued ggagttcaga cgtgtgctct tccgatctgt tgggggagga ggagcttat 49

<210> SEQ ID NO 204
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 204
ggagttcaga cgtgtgctct tccgatctct aagagctata agggcaaatg act 53

<210> SEQ ID NO 205
<211> LENGTH: 56
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (33)..(36)
<223> OTHER INFORMATION: n is a, c, g, or t

<400> SEQUENCE: 205
cactctttcc ctacacgacg ctcttccgat ctnnnnacgt aaacggccac aagttc 56

<210> SEQ ID NO 206
<211> LENGTH: 50
<212> TYPE: DNA
<213> ORGANISM: Artificial Sequence
<220> FEATURE:
<223> OTHER INFORMATION: Synthetic Polynucleotide

<400> SEQUENCE: 206
ggagttcaga cgtgtgctct tccgatctgt cgtccttgaa gaagatggtg 50

<210> SEQ ID NO 207
<211> LENGTH: 54
<212> TYPE: DNA
<213> ORGANISM: Artificial Sequence
<220> FEATURE:
<223> OTHER INFORMATION: Synthetic Polynucleotide

<400> SEQUENCE: 207
cactctttcc ctacacgacg ctcttccgat ctccaggtga aggtgtggtt ccag 54

<210> SEQ ID NO 208
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 208
ggagttcaga cgtgtgctct tccgatctcc cctagtcatt ggaggtgac 49

<210> SEQ ID NO 209
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 209
gagtccgagc agaagaagaa ggg 23

<210> SEQ ID NO 210
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 210
gaggccgagc agaagaaaga cgg 23

<210> SEQ ID NO 211
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 211
gagtcctagc aggagaagaa gag 23

<210> SEQ ID NO 212
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 212
gagtctaagc agaagaagaa gag 23

<210> SEQ ID NO 213
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 213
gagttagagc agaagaagaa agg 23

<210> SEQ ID NO 214
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 214
gggtgggggg agtttgctcc tgg 23

<210> SEQ ID NO 215
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 215
ggatggaggg agtttgctcc tgg 23

<210> SEQ ID NO 216
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 216
gggagggtgg agtttgctcc tgg 23

<210> SEQ ID NO 217
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 217
cgggggaggg agtttgctcc tgg 23

<210> SEQ ID NO 218
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 218
ggggagggga agtttgctcc tgg 23

<210> SEQ ID NO 219
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 219
gcagatgtag tgtttccaca ggg 23

<210> SEQ ID NO 220
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 220
acaaatgtag tatttccaca ggg 23

<210> SEQ ID NO 221
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 221
ccagatgtag tattcccaca ggg 23

<210> SEQ ID NO 222
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 222
ctagatgaag tgcttccaca tgg 23

<210> SEQ ID NO 223
<211> LENGTH: 133

<212> TYPE: DNA
<213> ORGANISM: Artificial Sequence
<220> FEATURE:
<223> OTHER INFORMATION: Synthetic Polynucleotide

<400> SEQUENCE: 223
gggcgatgcc acctacggca agctgaccct gaagttcatc tgcaccaccg gcaagctgcc 60
cgtgccctgg cccaccctcg tgaccaccct gacctacggc gtgcagtgct tcagccgcta 120
ccccgaccac atg 133

<210> SEQ ID NO 224
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 224
gggcgatcgg cgtgcagtgc ttcagccgct accccgacca catg 44

<210> SEQ ID NO 225
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 225
gggcgatgcc acctacggca agctgaccct gaagttcatc tgcaccaccg cgaccacatg 60

<210> SEQ ID NO 226
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 226
gggcgatgcc acctacggca agctgaccct gaagttcatc tgcacccggc aagctgcccg 60
tgccctggcc caccctcgtg accaccctga cctacggcgt gcagtgcttc agccgctacc 120
ccgaccacat g 131

<210> SEQ ID NO 227
<211> LENGTH: 100
<212> TYPE: DNA
<213> ORGANISM: Artificial Sequence
<220> FEATURE:
<223> OTHER INFORMATION: Synthetic Polynucleotide

<400> SEQUENCE: 227
gggcgatgcc acctacggca agctgcccgt gccctggccc accctcgtga ccaccctgac 60
ctacggcgtg cagtgcttca gccgctaccc cgaccacatg 100

<210> SEQ ID NO 228
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 228
gggcgatgcc acctacggca agctgaccct gaagttcatc tgcaccacgc aagctgcccg 60

-continued

```
tgccctggcc caccctcgtg accaccctga cctacggcgt gcagtgcttc agccgctacc    120

ccgaccacat g                                                         131


<210> SEQ ID NO 229
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 229

gggcgatgcc acctacggca agctgaccct gaagttcatc tgcaccaccg gcaagctgcg     60

tgccctggcc caccctcgtg accaccctga cctacggcgt gcagtgcttc agccgctacc    120

ccgaccacat g                                                         131


<210> SEQ ID NO 230
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 230

gggcgatgcc acctacggca agctgaccct gaagttcatc tgcaccaccg gcaagctgcc     60

cgccctggcc caccctcgtg accaccctga cctacggcgt gcagtgcttc agccgctacc    120

ccgaccacat g                                                         131


<210> SEQ ID NO 231
<211> LENGTH: 125
<212> TYPE: DNA
<213> ORGANISM: Artificial Sequence
<220> FEATURE:
<223> OTHER INFORMATION: Synthetic Polynucleotide

<400> SEQUENCE: 231

gggcgatgcc acctacggca agctgaccct gaagttcatc tggcaagctg cccgtgccct     60

ggcccaccct cgtgaccacc ctgacctacg gcgtgcagtg cttcagccgc taccccgacc    120

acatg                                                                125


<210> SEQ ID NO 232
<211> LENGTH: 82
<212> TYPE: DNA
<213> ORGANISM: Artificial Sequence
<220> FEATURE:
<223> OTHER INFORMATION: Synthetic Polynucleotide

<400> SEQUENCE: 232

gggcgatgcc acctacggca agctgaccct gaagttcatc tgcaccaccg cgcagtgctt     60

cagccgctac cccgaccaca tg                                              82


<210> SEQ ID NO 233
<211> LENGTH: 131
<212> TYPE: DNA
<213> ORGANISM: Artificial Sequence
<220> FEATURE:
<223> OTHER INFORMATION: Synthetic Polynucleotide

<400> SEQUENCE: 233

gggcgatgcc acctacggca agctgaccct gaagttcatc tgcaccaccc aagctgcccg     60

tgccctggcc caccctcgtg accaccctga cctacggcgt gcagtgcttc agccgctacc    120
```

ccgaccacat g 131

<210> SEQ ID NO 234
<211> LENGTH: 135
<212> TYPE: DNA
<213> ORGANISM: Artificial Sequence
<220> FEATURE:
<223> OTHER INFORMATION: Synthetic Polynucleotide

<400> SEQUENCE: 234
gggcgatgcc acctacggca agctgaccct gaagttcatc tgcaccaccg atgcaagctg 60
cccgtgccct ggcccaccct cgtgaccacc ctgacctacg gcgtgcagtg cttcagccgc 120
taccccgacc acatg 135

<210> SEQ ID NO 235
<211> LENGTH: 166
<212> TYPE: DNA
<213> ORGANISM: Artificial Sequence
<220> FEATURE:
<223> OTHER INFORMATION: Synthetic Polynucleotide

<400> SEQUENCE: 235
gggcgatgcc acctacggca agctgaccct gaagttcatc tgcaccaccg gcaagctgac 60
cctgaagttc atctgcacca ccggcaagct gcccgtgccc tggcccaccc tcgtgaccac 120
cctgacctac ggcgtgcagt gcttcagccg ctaccccgac cacatg 166

<210> SEQ ID NO 236
<211> LENGTH: 130
<212> TYPE: DNA
<213> ORGANISM: Artificial Sequence
<220> FEATURE:
<223> OTHER INFORMATION: Synthetic Polynucleotide

<400> SEQUENCE: 236
gggcgatgcc acctacggca agctgaccct gaagaaatga agaaatgaag aaatgcccgt 60
gccctggccc accctcgtga ccaccctgac ctacggcgtg cagtgcttca gccgctaccc 120
cgaccacatg 130

<210> SEQ ID NO 237
<211> LENGTH: 80
<212> TYPE: DNA
<213> ORGANISM: Artificial Sequence
<220> FEATURE:
<223> OTHER INFORMATION: Synthetic Polynucleotide

<400> SEQUENCE: 237
ggcagaagct ggaagaggaa gggccggagt ctgagcagaa gaagaagggt tcccaccata 60
tcaaccggtg gcgcatcgcc 80

<210> SEQ ID NO 238
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 238
ggcagaagct ggaagaggaa gggccggagt ctgagcagaa gaagggttcc caccatatca 60
accggtggcg catcgcc 77

<210> SEQ ID NO 239
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 239
ggcagaagct ggaagaggaa gggccggagt ctgagcagaa agaagggttc ccaccatatc 60
aaccggtggc gcatcgcc 78

<210> SEQ ID NO 240
<211> LENGTH: 73
<212> TYPE: DNA
<213> ORGANISM: Artificial Sequence
<220> FEATURE:
<223> OTHER INFORMATION: Synthetic Polynucleotide

<400> SEQUENCE: 240
ggcagaagct ggaagaggaa gggccggagt ctgagagaag ggttcccacc atatcaaccg 60
gtggcgcatc gcc 73

<210> SEQ ID NO 241
<211> LENGTH: 76
<212> TYPE: DNA
<213> ORGANISM: Artificial Sequence
<220> FEATURE:
<223> OTHER INFORMATION: Synthetic Polynucleotide

<400> SEQUENCE: 241
ggcagaagct ggaagaggaa gggccggagt ctgagcagag aagggttccc accatatcaa 60
ccggtggcgc atcgcc 76

<210> SEQ ID NO 242
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 242
ggcagaagct ggaagaggaa gggccggagt ctgagaaggg ttcccaccat atcaaccggt 60
ggcgcatcgc c 71

<210> SEQ ID NO 243
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 243
ggcagaagct ggaagaggaa gggccggagt ctgagcagaa gaaccaccat atcaaccggt 60
ggcgcatcgc c 71

<210> SEQ ID NO 244
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 244
ggcagaagct ggaagaggaa gggccggagt ctagaagggt tcccaccata tcaaccggtg 60
gcgcatcgcc 70

<210> SEQ ID NO 245
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 245
ggcagaagct ggaagaggaa gggccggagt ctgagcagaa gaagaagggt tcaccatatc 60
aaccggtggc gcatcgcc 78

<210> SEQ ID NO 246
<211> LENGTH: 74
<212> TYPE: DNA
<213> ORGANISM: Artificial Sequence
<220> FEATURE:
<223> OTHER INFORMATION: Synthetic Polynucleotide

<400> SEQUENCE: 246
ggcagaagct ggaagaggaa gggccggagt ctgagcagaa gggttcccac catatcaacc 60
ggtggcgcat cgcc 74

<210> SEQ ID NO 247
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 247
ggcagaagct ggaagaggaa gggccggagt ctgagcaggg ttcccaccat atcaaccggt 60
ggcgcatcgc c 71

<210> SEQ ID NO 248
<211> LENGTH: 77
<212> TYPE: DNA
<213> ORGANISM: Artificial Sequence
<220> FEATURE:
<223> OTHER INFORMATION: Synthetic Polynucleotide

<400> SEQUENCE: 248
ggcagaagct ggaagaggaa gggccggagt ctgagcagaa gaccatatcc caccatatca 60
accggtggcg catcgcc 77

<210> SEQ ID NO 249
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 249
ggcagaagct ggaagaggaa gggccggagt ctgagcagaa gaccatatcc aaccatatcc 60
caccatatca accggtggcg catcgcc 87

<210> SEQ ID NO 250
<211> LENGTH: 93
<212> TYPE: DNA

<213> ORGANISM: Artificial Sequence
<220> FEATURE:
<223> OTHER INFORMATION: Synthetic Polynucleotide

<400> SEQUENCE: 250
ggcagaagct ggaagaggaa gggccggagt ctgagcagaa gaagaagaag ggttcccacc 60
atatcccacc atatcaaccg gtggcgcatc gcc 93

<210> SEQ ID NO 251
<211> LENGTH: 39
<212> TYPE: PRT
<213> ORGANISM: Artificial Sequence
<220> FEATURE:
<223> OTHER INFORMATION: Synthetic Polypeptide

<400> SEQUENCE: 251

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser Thr Ala Leu Ala Leu
20 25 30

Pro Lys Lys Lys Arg Lys Val
35

<210> SEQ ID NO 252
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 252

Gly Gly Ser Gly Gly Ser Gly Gly Ser Gly Gly Ser Gly Gly Ser Gly
1 5 10 15

Gly Ser Gly Gly Ser Gly Gly Ser Gly Gly Ser
20 25

<210> SEQ ID NO 253
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 253

His His His His His His
1 5

<210> SEQ ID NO 254
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 254

Ala Leu Ala Leu
1

<210> SEQ ID NO 255
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 255

Gly Gly Ser Gly Gly Ser Gly Gly Ser Gly Gly Ser Ala Leu Ala Leu
1               5                   10                  15

Gly Gly Ser Gly Gly Ser Gly Gly Ser Gly Gly Ser
            20                  25

<210> SEQ ID NO 256
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 256

Xaa Ala Gly Val Phe Xaa
1               5

<210> SEQ ID NO 257
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 257

Xaa Gly Phe Leu Gly Xaa
1               5

<210> SEQ ID NO 258
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 258

Xaa Ala Leu Ala Leu Xaa
1               5

<210> SEQ ID NO 259
<211> LENGTH: 7
<212> TYPE: PRT
<213> ORGANISM: Artificial Sequence
<220> FEATURE:
<223> OTHER INFORMATION: Synthetic Polypeptide
<220> FEATURE:

```
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 259

Xaa Ala Leu Ala Leu Ala Xaa
1               5


<210> SEQ ID NO 260
<211> LENGTH: 1374
<212> TYPE: PRT
<213> ORGANISM: Artificial Sequence
<220> FEATURE:
<223> OTHER INFORMATION: Synthetic Polypeptide

<400> SEQUENCE: 260

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300
```

Ile Leu Arg Val Asn Thr Glu Ile Thr Lys Ala Pro Leu Ser Ala Ser
305 310 315 320

Met Ile Lys Arg Tyr Asp Glu His His Gln Asp Leu Thr Leu Leu Lys
325 330 335

Ala Leu Val Arg Gln Gln Leu Pro Glu Lys Tyr Lys Glu Ile Phe Phe
340 345 350

Asp Gln Ser Lys Asn Gly Tyr Ala Gly Tyr Ile Asp Gly Gly Ala Ser
355 360 365

Gln Glu Glu Phe Tyr Lys Phe Ile Lys Pro Ile Leu Glu Lys Met Asp
370 375 380

Gly Thr Glu Glu Leu Leu Val Lys Leu Asn Arg Glu Asp Leu Leu Arg
385 390 395 400

Lys Gln Arg Thr Phe Asp Asn Gly Ser Ile Pro His Gln Ile His Leu
405 410 415

Gly Glu Leu His Ala Ile Leu Arg Arg Gln Glu Asp Phe Tyr Pro Phe
420 425 430

Leu Lys Asp Asn Arg Glu Lys Ile Glu Lys Ile Leu Thr Phe Arg Ile
435 440 445

Pro Tyr Tyr Val Gly Pro Leu Ala Arg Gly Asn Ser Arg Phe Ala Trp
450 455 460

Met Thr Arg Lys Ser Glu Glu Thr Ile Thr Pro Trp Asn Phe Glu Glu
465 470 475 480

Val Val Asp Lys Gly Ala Ser Ala Gln Ser Phe Ile Glu Arg Met Thr
485 490 495

Asn Phe Asp Lys Asn Leu Pro Asn Glu Lys Val Leu Pro Lys His Ser
500 505 510

Leu Leu Tyr Glu Tyr Phe Thr Val Tyr Asn Glu Leu Thr Lys Val Lys
515 520 525

Tyr Val Thr Glu Gly Met Arg Lys Pro Ala Phe Leu Ser Gly Glu Gln
530 535 540

Lys Lys Ala Ile Val Asp Leu Leu Phe Lys Thr Asn Arg Lys Val Thr
545 550 555 560

Val Lys Gln Leu Lys Glu Asp Tyr Phe Lys Lys Ile Glu Cys Phe Asp
565 570 575

Ser Val Glu Ile Ser Gly Val Glu Asp Arg Phe Asn Ala Ser Leu Gly
580 585 590

Thr Tyr His Asp Leu Leu Lys Ile Ile Lys Asp Lys Asp Phe Leu Asp
595 600 605

Asn Glu Glu Asn Glu Asp Ile Leu Glu Asp Ile Val Leu Thr Leu Thr
610 615 620

Leu Phe Glu Asp Arg Glu Met Ile Glu Glu Arg Leu Lys Thr Tyr Ala
625 630 635 640

His Leu Phe Asp Asp Lys Val Met Lys Gln Leu Lys Arg Arg Arg Tyr
645 650 655

Thr Gly Trp Gly Arg Leu Ser Arg Lys Leu Ile Asn Gly Ile Arg Asp
660 665 670

Lys Gln Ser Gly Lys Thr Ile Leu Asp Phe Leu Lys Ser Asp Gly Phe
675 680 685

Ala Asn Arg Asn Phe Met Gln Leu Ile His Asp Asp Ser Leu Thr Phe
690 695 700

Lys Glu Asp Ile Gln Lys Ala Gln Val Ser Gly Gln Gly Asp Ser Leu
705 710 715 720

-continued

```
His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
```

```
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365

His His  His His His His
    1370
```

```
<210> SEQ ID NO 261
<211> LENGTH: 4959
<212> TYPE: DNA
<213> ORGANISM: Artificial Sequence
<220> FEATURE:
<223> OTHER INFORMATION: Synthetic Polynucleotide

<400> SEQUENCE: 261

atgggtgcta gcaaaggtga acgtctgttt cgtggtaaag taccgatctt agtggaatta     60

aagggcgacg tgaacggtca taaatttagc gtgcgcggca aaggcaaagg tgacgctacc    120

cgtggtaaat tgaccctgaa gtttatttgc acaacaggca aattacccgt tccgtggccc    180

accttagtga ccaccctgac ctccggcgtt cagtgcttca gtcgttaccc taaacatatg    240

aaacgtcacg attttttcaa atcagccatg cctaaaggat atgttcaaga gcgtacaatc    300

agcttcaaga aggatggcaa atataaaacg cgtgcggaag tgaaatttga aggccgcaca    360

ttagtaaatc gtatcaaact gaaaggtcgt gacttcaaag aaaaaggcaa cattttaggc    420

cataaactgc gttataactt taattctcat aaggtgtata ttacggccga taaacgcaag    480

aatggtatca aggcaaaatt caaaattcgc cataacgtga aagacggcag cgttcaatta    540

gcggatcatt atcaacaaaa cacgccgatt ggtcgcgggc ctgtactgtt acctcgcaac    600
```

-continued

```
cactacctga gcacccgttc taaactgagc aaagatccga aagaaaaacg cgatcacatg    660
gttctgttag aattcgtgac cgctgcaggc attaagcacg gacgcgacga acgctacaag    720
accggtggta gcggtggttc tggtggttct ggtggtagcg gcggtagcgg tggtagcggt    780
ggtagcggtg gcagcggcgg taccgcgctc gcgctgccca agaagaagag gaaggtgatg    840
gataagaaat actcaatagg cttagatatc ggcacaaata gcgtcggatg ggcggtgatc    900
actgatgaat ataaggttcc gtctaaaaag ttcaaggttc tgggaaatac agaccgccac    960
agtatcaaaa aaaatcttat aggggctctt ttatttgaca gtggagagac agcggaagcg   1020
actcgtctca aacggacagc tcgtagaagg tatacacgtc ggaagaatcg tatttgttat   1080
ctacaggaga tttttcaaa tgagatggcg aaagtagatg atagtttctt tcatcgactt    1140
gaagagtctt ttttggtgga agaagacaag aagcatgaac gtcatcctat ttttggaaat   1200
atagtagatg aagttgctta tcatgagaaa tatccaacta tctatcatct gcgaaaaaaa   1260
ttggtagatt ctactgataa agcggatttg cgcttaatct atttggcctt agcgcatatg   1320
attaagtttc gtggtcattt tttgattgag ggagatttaa atcctgataa tagtgatgtg   1380
gacaaactat ttatccagtt ggtacaaacc tacaatcaat tatttgaaga aaaccctatt   1440
aacgcaagtg gagtagatgc taaagcgatt ctttctgcac gattgagtaa atcaagacga   1500
ttagaaaatc tcattgctca gctccccggt gagaagaaaa atggcttatt tgggaatctc   1560
attgctttgt cattgggttt gacccctaat tttaaatcaa attttgattt ggcagaagat   1620
gctaaattac agctttcaaa agatacttac gatgatgatt tagataattt attggcgcaa   1680
attggagatc aatatgctga tttgtttttg gcagctaaga atttatcaga tgctatttta   1740
ctttcagata tcctaagagt aaatactgaa ataactaagg ctcccctatc agcttcaatg   1800
attaaacgct acgatgaaca tcatcaagac ttgactcttt taaaagcttt agttcgacaa   1860
caacttccag aaaagtataa agaaatcttt tttgatcaat caaaaaacgg atatgcaggt   1920
tatattgatg gggagctag ccaagaagaa ttttataaat ttatcaaacc aattttagaa    1980
aaaatggatg gtactgagga attattggtg aaactaaatc gtgaagattt gctgcgcaag   2040
caacggacct ttgacaacgg ctctattccc catcaaattc acttgggtga gctgcatgct   2100
attttgagaa gacaagaaga cttttatcca tttttaaaag acaatcgtga gaagattgaa   2160
aaaatcttga cttttcgaat tccttattat gttggtccat tggcgcgtgg caatagtcgt   2220
tttgcatgga tgactcggaa gtctgaagaa acaattaccc catggaattt tgaagaagtt   2280
gtcgataaag gtgcttcagc tcaatcattt attgaacgca tgacaaactt tgataaaaat   2340
cttccaaatg aaaaagtact accaaaacat agtttgcttt atgagtattt tacggtttat   2400
aacgaattga caaaggtcaa atatgttact gaaggaatgc gaaaaccagc atttctttca   2460
ggtgaacaga agaaagccat tgttgattta ctcttcaaaa caaatcgaaa agtaaccgtt   2520
aagcaattaa aagaagatta tttcaaaaaa atagaatgtt ttgatagtgt tgaaatttca   2580
ggagttgaag atagatttaa tgcttcatta ggtacctacc atgatttgct aaaaattatt   2640
aaagataaag atttttgga taatgaagaa aatgaagata tcttagagga tattgtttta    2700
acattgacct tatttgaaga tagggagatg attgaggaaa gacttaaaac atatgctcac   2760
ctctttgatg ataaggtgat gaaacagctt aaacgtcgcc gttatactgg ttggggacgt   2820
ttgtctcgaa aattgattaa tggtattagg gataagcaat ctggcaaaac aatattagat   2880
tttttgaaat cagatggttt tgccaatcgc aattttatgc agctgatcca tgatgatagt   2940
```

-continued

```
ttgacattta aagaagacat tcaaaaagca caagtgtctg gacaaggcga tagtttacat   3000

gaacatattg caaatttagc tggtagccct gctattaaaa aaggtatttt acagactgta   3060

aaagttgttg atgaattggt caaagtaatg gggcggcata agccagaaaa tatcgttatt   3120

gaaatggcac gtgaaaatca gacaactcaa aagggccaga aaaattcgcg agagcgtatg   3180

aaacgaatcg aagaaggtat caaagaatta ggaagtcaga ttcttaaaga gcatcctgtt   3240

gaaaatactc aattgcaaaa tgaaaagctc tatctctatt atctccaaaa tggaagagac   3300

atgtatgtgg accaagaatt agatattaat cgtttaagtg attatgatgt cgatcacatt   3360

gttccacaaa gtttccttaa agacgattca atagacaata aggtcttaac gcgttctgat   3420

aaaaatcgtg gtaaatcgga taacgttcca agtgaagaag tagtcaaaaa gatgaaaaac   3480

tattggagac aacttctaaa cgccaagtta atcactcaac gtaagtttga taatttaacg   3540

aaagctgaac gtggaggttt gagtgaactt gataaagctg gttttatcaa acgccaattg   3600

gttgaaactc gccaaatcac taagcatgtg gcacaaattt tggatagtcg catgaatact   3660

aaatacgatg aaaatgataa acttattcga gaggttaaag tgattacctt aaaatctaaa   3720

ttagtttctg acttccgaaa agatttccaa ttctataaag tacgtgagat taacaattac   3780

catcatgccc atgatgcgta tctaaatgcc gtcgttggaa ctgctttgat taagaaatat   3840

ccaaaacttg aatcggagtt tgtctatggt gattataaag tttatgatgt tcgtaaaatg   3900

attgctaagt ctgagcaaga aataggcaaa gcaaccgcaa aatatttctt ttactctaat   3960

atcatgaact tcttcaaaac agaaattaca cttgcaaatg gagagattcg caaacgccct   4020

ctaatcgaaa ctaatgggga aactggagaa attgtctggg ataaagggcg agattttgcc   4080

acagtgcgca aagtattgtc catgccccaa gtcaatattg tcaagaaaac agaagtacag   4140

acaggcggat tctccaagga gtcaatttta ccaaaaagaa attcggacaa gcttattgct   4200

cgtaaaaaag actgggatcc aaaaaaatat ggtggttttg atagtccaac ggtagcttat   4260

tcagtcctag tggttgctaa ggtggaaaaa gggaaatcga agaagttaaa atccgttaaa   4320

gagttactag ggatcacaat tatggaaaga agttcctttg aaaaaaatcc gattgacttt   4380

ttagaagcta aaggatataa ggaagttaaa aaagacttaa tcattaaact acctaaatat   4440

agtctttttg agttagaaaa cggtcgtaaa cggatgctgg ctagtgccgg agaattacaa   4500

aaaggaaatg agctggctct gccaagcaaa tatgtgaatt ttttatattt agctagtcat   4560

tatgaaaagt tgaagggtag tccagaagat aacgaacaaa aacaattgtt tgtggagcag   4620

cataagcatt atttagatga gattattgag caaatcagtg aattttctaa gcgtgttatt   4680

ttagcagatg ccaatttaga taaagttctt agtgcatata acaaacatag agacaaacca   4740

atacgtgaac aagcagaaaa tattattcat ttatttacgt tgacgaatct tggagctccc   4800

gctgctttta aatattttga tacaacaatt gatcgtaaac gatatacgtc tacaaaagaa   4860

gttttagatg ccactcttat ccatcaatcc atcactggtc tttatgaaac acgcattgat   4920

ttgagtcagc taggaggtga ccatcaccac caccatcac                         4959
```

<210> SEQ ID NO 262
<211> LENGTH: 4959
<212> TYPE: DNA
<213> ORGANISM: Artificial Sequence
<220> FEATURE:
<223> OTHER INFORMATION: Synthetic Polynucleotide

<400> SEQUENCE: 262

```
atgggtgcta gcaaaggtga agagctgttt gacggtgtag taccgatctt agtggaatta     60
```

gacggcgacg tgaacggtca cgaatttagc gtgcgcggcg agggcgaagg tgacgctacc 120
gagggtgaat tgaccctgaa gtttatttgc acaacaggcg aattacccgt tccgtggccc 180
accttagtga ccaccctgac ctccggcgtt cagtgcttca gtgattaccc agatcatatg 240
gatcaacacg attttttcaa atcagccatg cctgaaggat atgttcaaga gcgtacaatc 300
agcttcaagg acgatggcac ctataaaacg cgtgcggaag tgaaatttga aggcgacaca 360
ttagtaaacc gtatcgaact gaaaggtatc gacttcaaag aagacggcaa cattttaggc 420
cataagctgg aatataactt taattctcat gacgtgtata ttacggccga taaacaggaa 480
aacggtatca aggcagaatt tgaaattcgc cataacgtgg aggacggcag cgttcaatta 540
gcggatcatt atcaacaaaa cacgccgatt ggtgatgggc ctgtactgtt acctgacgat 600
cactacctga gcacggagtc agccctgagc aaagatccga acgaagaccg cgatcacatg 660
gttctgttag aattcgtgac cgctgcaggc attgatcatg gaatggacga gctgtacaag 720
accggtggta gcggtggttc tggtggttct ggtggtagcg gcggtagcgg tggtagcggt 780
ggtagcggtg gcagcggcgg taccgcgctc gcgctgccca agaagaagag gaaggtgatg 840
gataagaaat actcaatagg cttagatatc ggcacaaata gcgtcggatg ggcggtgatc 900
actgatgaat ataaggttcc gtctaaaaag ttcaaggttc tgggaaatac agaccgccac 960
agtatcaaaa aaaatcttat aggggctctt ttatttgaca gtggagagac agcggaagcg 1020
actcgtctca aacggacagc tcgtagaagg tatacacgtc ggaagaatcg tatttgttat 1080
ctacaggaga tttttcaaa tgagatggcg aaagtagatg atagtttctt tcatcgactt 1140
gaagagtctt ttttggtgga agaagacaag aagcatgaac gtcatcctat ttttggaaat 1200
atagtagatg aagttgctta tcatgagaaa tatccaacta tctatcatct gcgaaaaaaa 1260
ttggtagatt ctactgataa agcggatttg cgcttaatct atttggcctt agcgcatatg 1320
attaagtttc gtggtcattt tttgattgag ggagatttaa atcctgataa tagtgatgtg 1380
gacaaactat ttatccagtt ggtacaaacc tacaatcaat tatttgaaga aaaccctatt 1440
aacgcaagtg gagtagatgc taaagcgatt ctttctgcac gattgagtaa atcaagacga 1500
ttagaaaatc tcattgctca gctccccggt gagaagaaaa atggcttatt tgggaatctc 1560
attgctttgt cattgggttt gacccctaat tttaaatcaa attttgattt ggcagaagat 1620
gctaaattac agctttcaaa agatacttac gatgatgatt tagataattt attggcgcaa 1680
attggagatc aatatgctga tttgtttttg gcagctaaga atttatcaga tgctatttta 1740
ctttcagata tcctaagagt aaatactgaa ataactaagg ctcccctatc agcttcaatg 1800
attaaacgct acgatgaaca tcatcaagac ttgactcttt taaaagcttt agttcgacaa 1860
caacttccag aaaagtataa agaaatcttt tttgatcaat caaaaaacgg atatgcaggt 1920
tatattgatg ggggagctag ccaagaagaa ttttataaat ttatcaaacc aattttagaa 1980
aaaatggatg gtactgagga attattggtg aaactaaatc gtgaagattt gctgcgcaag 2040
caacggacct ttgacaacgg ctctattccc catcaaattc acttgggtga gctgcatgct 2100
attttgagaa gacaagaaga cttttatcca tttttaaaag acaatcgtga gaagattgaa 2160
aaaatcttga cttttcgaat tccttattat gttggtccat tggcgcgtgg caatagtcgt 2220
tttgcatgga tgactcggaa gtctgaagaa acaattaccc catggaattt tgaagaagtt 2280
gtcgataaag gtgcttcagc tcaatcattt attgaacgca tgacaaactt tgataaaaat 2340
cttccaaatg aaaaagtact accaaaacat agtttgcttt atgagtattt tacggtttat 2400

-continued

```
aacgaattga caaaggtcaa atatgttact gaaggaatgc gaaaaccagc atttctttca   2460
ggtgaacaga agaaagccat tgttgattta ctcttcaaaa caaatcgaaa agtaaccgtt   2520
aagcaattaa aagaagatta tttcaaaaaa atagaatgtt ttgatagtgt tgaaatttca   2580
ggagttgaag atagatttaa tgcttcatta ggtacctacc atgatttgct aaaaattatt   2640
aaagataaag atttttgga taatgaagaa aatgaagata tcttagagga tattgtttta   2700
acattgacct tatttgaaga tagggagatg attgaggaaa gacttaaaac atatgctcac   2760
ctctttgatg ataaggtgat gaaacagctt aaacgtcgcc gttatactgg ttggggacgt   2820
ttgtctcgaa aattgattaa tggtattagg gataagcaat ctggcaaaac aatattagat   2880
tttttgaaat cagatggttt tgccaatcgc aattttatgc agctgatcca tgatgatagt   2940
ttgacattta aagaagacat tcaaaaagca caagtgtctg gacaaggcga tagtttacat   3000
gaacatattg caaatttagc tggtagccct gctattaaaa aaggtatttt acagactgta   3060
aaagttgttg atgaattggt caaagtaatg gggcggcata agccagaaaa tatcgttatt   3120
gaaatggcac gtgaaaatca gacaactcaa aagggccaga aaaattcgcg agagcgtatg   3180
aaacgaatcg aagaaggtat caaagaatta ggaagtcaga ttcttaaaga gcatcctgtt   3240
gaaaatactc aattgcaaaa tgaaaagctc tatctctatt atctccaaaa tggaagagac   3300
atgtatgtgg accaagaatt agatattaat cgtttaagtg attatgatgt cgatcacatt   3360
gttccacaaa gtttccttaa agacgattca atagacaata aggtcttaac gcgttctgat   3420
aaaaatcgtg gtaaatcgga taacgttcca agtgaagaag tagtcaaaaa gatgaaaaac   3480
tattggagac aacttctaaa cgccaagtta atcactcaac gtaagtttga taatttaacg   3540
aaagctgaac gtggaggttt gagtgaactt gataaagctg gttttatcaa acgccaattg   3600
gttgaaactc gccaaatcac taagcatgtg gcacaaattt tggatagtcg catgaatact   3660
aaatacgatg aaaatgataa acttattcga gaggttaaag tgattacctt aaaatctaaa   3720
ttagtttctg acttccgaaa agatttccaa ttctataaag tacgtgagat taacaattac   3780
catcatgccc atgatgcgta tctaaatgcc gtcgttggaa ctgctttgat taagaaatat   3840
ccaaaacttg aatcggagtt tgtctatggt gattataaag tttatgatgt tcgtaaaatg   3900
attgctaagt ctgagcaaga aataggcaaa gcaaccgcaa aatatttctt ttactctaat   3960
atcatgaact tcttcaaaac agaaattaca cttgcaaatg gagagattcg caaacgccct   4020
ctaatcgaaa ctaatgggga aactggagaa attgtctggg ataaagggcg agattttgcc   4080
acagtgcgca aagtattgtc catgccccaa gtcaatattg tcaagaaaac agaagtacag   4140
acaggcggat tctccaagga gtcaatttta ccaaaaagaa attcggacaa gcttattgct   4200
cgtaaaaaag actgggatcc aaaaaaatat ggtggttttg atagtccaac ggtagcttat   4260
tcagtcctag tggttgctaa ggtggaaaaa gggaaatcga agaagttaaa atccgttaaa   4320
gagttactag ggatcacaat tatggaaaga agttcctttg aaaaaaatcc gattgacttt   4380
ttagaagcta aaggatataa ggaagttaaa aaagacttaa tcattaaact acctaaatat   4440
agtctttttg agttagaaaa cggtcgtaaa cggatgctgg ctagtgccgg agaattacaa   4500
aaaggaaatg agctggctct gccaagcaaa tatgtgaatt ttttatattt agctagtcat   4560
tatgaaaagt tgaagggtag tccagaagat aacgaacaaa aacaattgtt tgtggagcag   4620
cataagcatt atttagatga gattattgag caaatcagtg aattttctaa gcgtgttatt   4680
ttagcagatg ccaatttaga taaagttctt agtgcatata acaaacatag agacaaacca   4740
atacgtgaac aagcagaaaa tattattcat ttatttacgt tgacgaatct tggagctccc   4800
```

gctgctttta aatattttga tacaacaatt gatcgtaaac gatatacgtc tacaaaagaa 4860
gttttagatg ccactcttat ccatcaatcc atcactggtc tttatgaaac acgcattgat 4920
ttgagtcagc taggaggtga ccatcaccac caccatcac 4959

<210> SEQ ID NO 263
<211> LENGTH: 1059
<212> TYPE: DNA
<213> ORGANISM: Artificial Sequence
<220> FEATURE:
<223> OTHER INFORMATION: Synthetic Polynucleotide

<400> SEQUENCE: 263
atggcgagca atttactgac cgtacaccaa aatttgcctg cattgccggt cgatgcaacg 60
agtgatgagg ttcgcaagaa cctgatggac atgttcaggg atcgccaggc gttttctgag 120
catacctgga aaatgcttct gtccgtttgc cggtcgtggg cggcatggtg caagttgaat 180
aaccggaaat ggtttcccgc agaacctgaa gatgttcgcg attatcttct atatcttcag 240
gcgcgcggtc tggcagtaaa aactatccag caacatttgg gccagctaaa catgcttcat 300
cgtcggtccg ggctgccacg accaagtgac agcaatgctg tttcactggt tatgcggcgt 360
atccgaaaag aaaacgttga tgccggtgaa cgtgcaaaac aggctctagc gttcgaacgc 420
actgatttcg accaggttcg ttcactcatg gaaaatagcg atcgctgcca ggatatacgt 480
aatctggcat ttctggggat tgcttataac accctgttac gtatagccga aattgccagg 540
atcagggtta aagatatctc acgtactgac ggtgggagaa tgttaatcca tattggcaga 600
acgaaaacgc tggttagcac cgcaggtgta gagaaggcac ttagcctggg ggtaactaaa 660
ctggtcgagc gatggatttc cgtctctggt gtagctgatg atccgaataa ctacctgttt 720
tgccgggtca gaaaaaatgg tgttgccgcg ccatctgcca ccagccagct atcaactcgc 780
gccctggaag ggatttttga agcaactcat cgattgattt acggcgctaa ggatgactct 840
ggtcagagat acctggcctg gtctggacac agtgcccgtg tcggagccgc gcgagatatg 900
gcccgcgctg gagtttcaat accggagatc atgcaagctg gtggctggac caatgtaaat 960
attgtcatga actatatccg taacctggat agtgaaacag ggcaatggt gcgcctgctg 1020 gaagatggcg acggcggatc ccatcaccac caccatcac 1059

<210> SEQ ID NO 264
<211> LENGTH: 1860
<212> TYPE: DNA
<213> ORGANISM: Artificial Sequence
<220> FEATURE:
<223> OTHER INFORMATION: Synthetic Polynucleotide

<400> SEQUENCE: 264
atgggtgcta gcaaaggtga agagctgttt gacggtgtag taccgatctt agtggaatta 60
gacggcgacg tgaacggtca cgaatttagc gtgcgcggcg agggcgaagg tgacgctacc 120
gagggtgaat tgaccctgaa gtttatttgc acaacaggcg aattacccgt tccgtggccc 180
accttagtga ccaccctgac ctatggcgtt cagtgcttca gtgattaccc agatcatatg 240
gatcaacacg atttttcaa atcagccatg cctgaaggat atgttcaaga gcgtacaatc 300
agcttcaagg acgatggcac ctataaaacg cgtgcggaag tgaaatttga aggcgacaca 360
ttagtaaacc gtatcgaact gaaaggtatc gacttcaaag aagacggcaa cattttaggc 420
cataagctgg aatataactt taattctcat gacgtgtata ttacggccga taaacaggaa 480

-continued

```
aacggtatca aggcagaatt tgaaattcgc cataacgtgg aggacggcag cgttcaatta    540

gcggatcatt atcaacaaaa cacgccgatt ggtgatgggc ctgtactgtt acctgacgat    600

cactacctga gcacggagtc agccctgagc aaagatccga acgaagaccg cgatcacatg    660

gttctgttag aattcgtgac cgctgcaggc attgatcatg gaatggacga gctgtacaag    720

accggtggta gcggtggttc tggtggttct ggtggtagcg gcggtagcgg tggtagcggt    780

ggtagcggtg gcagcggcgg taccgcgagc aatttactga ccgtacacca aaatttgcct    840

gcattgccgg tcgatgcaac gagtgatgag gttcgcaaga acctgatgga catgttcagg    900

gatcgccagg cgttttctga gcatacctgg aaaatgcttc tgtccgtttg ccggtcgtgg    960

gcggcatggt gcaagttgaa taaccggaaa tggtttcccg cagaacctga agatgttcgc   1020

gattatcttc tatatcttca ggcgcgcggt ctggcagtaa aaactatcca gcaacatttg   1080

ggccagctaa acatgcttca tcgtcggtcc gggctgccac gaccaagtga cagcaatgct   1140

gtttcactgg ttatgcggcg tatccgaaaa gaaaacgttg atgccggtga acgtgcaaaa   1200

caggctctag cgttcgaacg cactgatttc gaccaggttc gttcactcat ggaaaatagc   1260

gatcgctgcc aggatatacg taatctggca tttctgggga ttgcttataa caccctgtta   1320

cgtatagccg aaattgccag gatcagggtt aaagatatct cacgtactga cggtgggaga   1380

atgttaatcc atattggcag aacgaaaacg ctggttagca ccgcaggtgt agagaaggca   1440

cttagcctgg gggtaactaa actggtcgag cgatggattt ccgtctctgg tgtagctgat   1500

gatccgaata actacctgtt ttgccgggtc agaaaaaatg gtgttgccgc gccatctgcc   1560

accagccagc tatcaactcg cgccctggaa gggatttttg aagcaactca tcgattgatt   1620

tacggcgcta aggatgactc tggtcagaga tacctggcct ggtctggaca cagtgcccgt   1680

gtcggagccg cgcgagatat ggcccgcgct ggagtttcaa taccggagat catgcaagct   1740

ggtggctgga ccaatgtaaa tattgtcatg aactatatcc gtaacctgga tagtgaaaca   1800

ggggcaatgg tgcgcctgct ggaagatggc gacggcggat cccatcacca ccaccatcac   1860
```

```
<210> SEQ ID NO 265
<211> LENGTH: 620
<212> TYPE: PRT
<213> ORGANISM: Artificial Sequence
<220> FEATURE:
<223> OTHER INFORMATION: Synthetic Polypeptide

<400> SEQUENCE: 265

Met Gly Ala Ser Lys Gly Glu Glu Leu Phe Thr Gly Val Val Pro Ile
1               5                   10                  15

Leu Val Glu Leu Asp Gly Asp Val Asn Gly His Lys Phe Ser Val Arg
            20                  25                  30

Gly Glu Gly Glu Gly Asp Ala Thr Asn Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Tyr Gly Val Gln Cys Phe Ser Arg Tyr Pro Asp His Met
65                  70                  75                  80

Lys Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125
```

-continued

```
Gly Ile Asp Phe Lys Glu Asp Gly Asn Ile Leu Gly His Lys Leu Glu
    130                 135                 140

Tyr Asn Phe Asn Ser His Asn Val Tyr Ile Thr Ala Asp Lys Gln Lys
145                 150                 155                 160

Asn Gly Ile Lys Ala Asn Phe Lys Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asn His Tyr Leu Ser Thr Gln Ser Ala
        195                 200                 205

Leu Ser Lys Asp Pro Asn Glu Lys Arg Asp His Met Val Leu Leu Glu
    210                 215                 220

Phe Val Thr Ala Ala Gly Ile Thr His Gly Met Asp Glu Leu Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Ser Asn Leu
            260                 265                 270

Leu Thr Val His Gln Asn Leu Pro Ala Leu Pro Val Asp Ala Thr Ser
        275                 280                 285

Asp Glu Val Arg Lys Asn Leu Met Asp Met Phe Arg Asp Arg Gln Ala
    290                 295                 300

Phe Ser Glu His Thr Trp Lys Met Leu Leu Ser Val Cys Arg Ser Trp
305                 310                 315                 320

Ala Ala Trp Cys Lys Leu Asn Asn Arg Lys Trp Phe Pro Ala Glu Pro
                325                 330                 335

Glu Asp Val Arg Asp Tyr Leu Leu Tyr Leu Gln Ala Arg Gly Leu Ala
            340                 345                 350

Val Lys Thr Ile Gln Gln His Leu Gly Gln Leu Asn Met Leu His Arg
        355                 360                 365

Arg Ser Gly Leu Pro Arg Pro Ser Asp Ser Asn Ala Val Ser Leu Val
    370                 375                 380

Met Arg Arg Ile Arg Lys Glu Asn Val Asp Ala Gly Glu Arg Ala Lys
385                 390                 395                 400

Gln Ala Leu Ala Phe Glu Arg Thr Asp Phe Asp Gln Val Arg Ser Leu
                405                 410                 415

Met Glu Asn Ser Asp Arg Cys Gln Asp Ile Arg Asn Leu Ala Phe Leu
            420                 425                 430

Gly Ile Ala Tyr Asn Thr Leu Leu Arg Ile Ala Glu Ile Ala Arg Ile
        435                 440                 445

Arg Val Lys Asp Ile Ser Arg Thr Asp Gly Gly Arg Met Leu Ile His
    450                 455                 460

Ile Gly Arg Thr Lys Thr Leu Val Ser Thr Ala Gly Val Glu Lys Ala
465                 470                 475                 480

Leu Ser Leu Gly Val Thr Lys Leu Val Glu Arg Trp Ile Ser Val Ser
                485                 490                 495

Gly Val Ala Asp Asp Pro Asn Asn Tyr Leu Phe Cys Arg Val Arg Lys
            500                 505                 510

Asn Gly Val Ala Ala Pro Ser Ala Thr Ser Gln Leu Ser Thr Arg Ala
        515                 520                 525

Leu Glu Gly Ile Phe Glu Ala Thr His Arg Leu Ile Tyr Gly Ala Lys
    530                 535                 540
```

-continued

Asp Asp Ser Gly Gln Arg Tyr Leu Ala Trp Ser Gly His Ser Ala Arg
545 550 555 560

Val Gly Ala Ala Arg Asp Met Ala Arg Ala Gly Val Ser Ile Pro Glu
565 570 575

Ile Met Gln Ala Gly Gly Trp Thr Asn Val Asn Ile Val Met Asn Tyr
580 585 590

Ile Arg Asn Leu Asp Ser Glu Thr Gly Ala Met Val Arg Leu Leu Glu
595 600 605

Asp Gly Asp Gly Gly Ser His His His His His His
610 615 620

<210> SEQ ID NO 266
<211> LENGTH: 1860
<212> TYPE: DNA
<213> ORGANISM: Artificial Sequence
<220> FEATURE:
<223> OTHER INFORMATION: Synthetic Polynucleotide

<400> SEQUENCE: 266
atgggtgcta gcaaaggtga agagctgttt acgggtgtag taccgatctt agtggaatta 60
gacggcgacg tgaacggtca caaatttagc gtgcgcggcg aaggcgaagg tgacgctacc 120
aatggtaaat tgaccctgaa gtttatttgc acaacaggca aattacccgt tccgtggccc 180
accttagtga ccaccctgac ctatggcgtt cagtgcttca gtcgttaccc agatcatatg 240
aaacaacacg attttttcaa atcagccatg cctgaaggat atgttcaaga gcgtacaatc 300
agcttcaagg acgatggcac ctataaaacg cgtgcggaag tgaaatttga aggcgacaca 360
ttagtaaacc gtatcgaact gaaaggtatc gacttcaaag aagacggcaa cattttaggc 420
cataagctgg aatataactt taattctcat aacgtgtata ttacggccga taaacagaaa 480
aacggtatca aggcaaattt caaaattcgc cataacgtgg aagacggcag cgttcaatta 540
gcggatcatt atcaacaaaa cacgccgatt ggtgacgggc ctgtactgtt acctgacaac 600
cactacctga gcacccagtc agcactgagc aaagatccga acgaaaaacg cgatcacatg 660
gttctgttag aattcgtgac cgctgcaggc attactcacg gaatggacga actctacaag 720
accggtggta gcggtggttc tggtggttct ggtggtagcg gcggtagcgg tggtagcggt 780
ggtagcggtg gcagcggcgg taccgcgagc aatttactga ccgtacacca aaatttgcct 840
gcattgccgg tcgatgcaac gagtgatgag gttcgcaaga acctgatgga catgttcagg 900
gatcgccagg cgttttctga gcatacctgg aaaatgcttc tgtccgtttg ccggtcgtgg 960
gcggcatggt gcaagttgaa taaccggaaa tggtttcccg cagaacctga agatgttcgc 1020
gattatcttc tatatcttca ggcgcgcggt ctggcagtaa aaactatcca gcaacatttg 1080
ggccagctaa acatgcttca tcgtcggtcc gggctgccac gaccaagtga cagcaatgct 1140
gtttcactgg ttatgcggcg tatccgaaaa gaaaacgttg atgccggtga acgtgcaaaa 1200
caggctctag cgttcgaacg cactgatttc gaccaggttc gttcactcat ggaaaatagc 1260
gatcgctgcc aggatatacg taatctggca tttctggggga ttgcttataa caccctgtta 1320
cgtatagccg aaattgccag gatcagggtt aaagatatct cacgtactga cggtgggaga 1380
atgttaatcc atattggcag aacgaaaacg ctggttagca ccgcaggtgt agagaaggca 1440
cttagcctgg gggtaactaa actggtcgag cgatggattt ccgtctctgg tgtagctgat 1500
gatccgaata actacctgtt ttgccgggtc agaaaaaatg gtgttgccgc gccatctgcc 1560
accagccagc tatcaactcg cgccctggaa gggatttttg aagcaactca tcgattgatt 1620

```
tacggcgcta aggatgactc tggtcagaga tacctggcct ggtctggaca cagtgcccgt   1680

gtcggagccg cgcgagatat ggcccgcgct ggagtttcaa taccggagat catgcaagct   1740

ggtggctgga ccaatgtaaa tattgtcatg aactatatcc gtaacctgga tagtgaaaca   1800

ggggcaatgg tgcgcctgct ggaagatggc gacggcggat cccatcacca ccaccatcac   1860


<210> SEQ ID NO 267
<211> LENGTH: 620
<212> TYPE: PRT
<213> ORGANISM: Artificial Sequence
<220> FEATURE:
<223> OTHER INFORMATION: Synthetic Polypeptide

<400> SEQUENCE: 267

Met Gly Ala Ser Lys Gly Glu Glu Leu Phe Thr Gly Val Val Pro Ile
1               5                   10                  15

Leu Val Glu Leu Asp Gly Asp Val Asn Gly His Lys Phe Ser Val Arg
            20                  25                  30

Gly Glu Gly Glu Gly Asp Ala Thr Asn Gly Lys Leu Thr Leu Lys Phe
        35                  40                  45

Ile Cys Thr Thr Gly Lys Leu Pro Val Pro Trp Pro Thr Leu Val Thr
    50                  55                  60

Thr Leu Thr Tyr Gly Val Gln Cys Phe Ser Arg Tyr Pro Asp His Met
65                  70                  75                  80

Asp Gln His Asp Phe Phe Lys Ser Ala Met Pro Glu Gly Tyr Val Gln
                85                  90                  95

Glu Arg Thr Ile Ser Phe Lys Asp Asp Gly Thr Tyr Lys Thr Arg Ala
            100                 105                 110

Glu Val Lys Phe Glu Gly Asp Thr Leu Val Asn Arg Ile Glu Leu Lys
        115                 120                 125

Gly Ile Asp Phe Lys Glu Asp Gly Asn Ile Leu Gly His Lys Leu Glu
    130                 135                 140

Tyr Asn Phe Asn Ser His Asp Val Tyr Ile Thr Ala Asp Lys Gln Glu
145                 150                 155                 160

Asn Gly Ile Lys Ala Glu Phe Glu Ile Arg His Asn Val Glu Asp Gly
                165                 170                 175

Ser Val Gln Leu Ala Asp His Tyr Gln Gln Asn Thr Pro Ile Gly Asp
            180                 185                 190

Gly Pro Val Leu Leu Pro Asp Asp His Tyr Leu Ser Thr Glu Ser Ala
        195                 200                 205

Leu Ser Lys Asp Pro Asn Glu Asp Arg Asp His Met Val Leu Leu Glu
    210                 215                 220

Phe Val Thr Ala Ala Gly Ile Asp His Gly Met Asp Glu Leu Tyr Lys
225                 230                 235                 240

Thr Gly Gly Ser Gly Gly Ser Gly Gly Ser Gly Gly Ser Gly Gly Ser
                245                 250                 255

Gly Gly Ser Gly Gly Ser Gly Gly Ser Gly Gly Thr Ala Ser Asn Leu
            260                 265                 270

Leu Thr Val His Gln Asn Leu Pro Ala Leu Pro Val Asp Ala Thr Ser
        275                 280                 285

Asp Glu Val Arg Lys Asn Leu Met Asp Met Phe Arg Asp Arg Gln Ala
    290                 295                 300

Phe Ser Glu His Thr Trp Lys Met Leu Leu Ser Val Cys Arg Ser Trp
305                 310                 315                 320

Ala Ala Trp Cys Lys Leu Asn Asn Arg Lys Trp Phe Pro Ala Glu Pro
```

-continued

```
                325                 330                 335

Glu Asp Val Arg Asp Tyr Leu Leu Tyr Leu Gln Ala Arg Gly Leu Ala
            340                 345                 350

Val Lys Thr Ile Gln Gln His Leu Gly Gln Leu Asn Met Leu His Arg
        355                 360                 365

Arg Ser Gly Leu Pro Arg Pro Ser Asp Ser Asn Ala Val Ser Leu Val
    370                 375                 380

Met Arg Arg Ile Arg Lys Glu Asn Val Asp Ala Gly Glu Arg Ala Lys
385                 390                 395                 400

Gln Ala Leu Ala Phe Glu Arg Thr Asp Phe Asp Gln Val Arg Ser Leu
                405                 410                 415

Met Glu Asn Ser Asp Arg Cys Gln Asp Ile Arg Asn Leu Ala Phe Leu
            420                 425                 430

Gly Ile Ala Tyr Asn Thr Leu Leu Arg Ile Ala Glu Ile Ala Arg Ile
        435                 440                 445

Arg Val Lys Asp Ile Ser Arg Thr Asp Gly Gly Arg Met Leu Ile His
    450                 455                 460

Ile Gly Arg Thr Lys Thr Leu Val Ser Thr Ala Gly Val Glu Lys Ala
465                 470                 475                 480

Leu Ser Leu Gly Val Thr Lys Leu Val Glu Arg Trp Ile Ser Val Ser
                485                 490                 495

Gly Val Ala Asp Asp Pro Asn Asn Tyr Leu Phe Cys Arg Val Arg Lys
            500                 505                 510

Asn Gly Val Ala Ala Pro Ser Ala Thr Ser Gln Leu Ser Thr Arg Ala
        515                 520                 525

Leu Glu Gly Ile Phe Glu Ala Thr His Arg Leu Ile Tyr Gly Ala Lys
    530                 535                 540

Asp Asp Ser Gly Gln Arg Tyr Leu Ala Trp Ser Gly His Ser Ala Arg
545                 550                 555                 560

Val Gly Ala Ala Arg Asp Met Ala Arg Ala Gly Val Ser Ile Pro Glu
                565                 570                 575

Ile Met Gln Ala Gly Gly Trp Thr Asn Val Asn Ile Val Met Asn Tyr
            580                 585                 590

Ile Arg Asn Leu Asp Ser Glu Thr Gly Ala Met Val Arg Leu Leu Glu
        595                 600                 605

Asp Gly Asp Gly Gly Ser His His His His His His
    610                 615                 620


<210> SEQ ID NO 268
<211> LENGTH: 1860
<212> TYPE: DNA
<213> ORGANISM: Artificial Sequence
<220> FEATURE:
<223> OTHER INFORMATION: Synthetic Polynucleotide

<400> SEQUENCE: 268

atgggtgcta gcaaaggtga agagctgttt acgggtgtag taccgatctt agtggaatta     60

gacggcgacg tgaacggtca caaatttagc gtgcgcggcg aaggcgaagg tgacgctacc    120

aatggtaaat tgaccctgaa gtttatttgc acaacaggca aattacccgt tccgtggccc    180

accttagtga ccaccctgac ctatggcgtt cagtgcttca gtcgttaccc agatcatatg    240

gatcaacacg attttttcaa atcagccatg cctgaaggat atgttcaaga gcgtacaatc    300

agcttcaagg acgatggcac ctataaaacg cgtgcggaag tgaaatttga aggcgacaca    360

ttagtaaacc gtatcgaact gaaaggtatc gacttcaaag aagacggcaa cattttaggc    420
```

cataagctgg aatataactt taattctcat gacgtgtata ttacggccga taaacaggaa 480
aacggtatca aggcagaatt tgaaattcgc cataacgtgg aggacggcag cgttcaatta 540
gcggatcatt atcaacaaaa cacgccgatt ggtgatgggc ctgtactgtt acctgacgat 600
cactacctga gcacggagtc agccctgagc aaagatccga acgaagaccg cgatcacatg 660
gttctgttag aattcgtgac cgctgcaggc attgatcatg gaatggacga gctgtacaag 720
accggtggta gcggtggttc tggtggttct ggtggtagcg gcggtagcgg tggtagcggt 780
ggtagcggtg gcagcggcgg taccgcgagc aatttactga ccgtacacca aaatttgcct 840
gcattgccgg tcgatgcaac gagtgatgag gttcgcaaga acctgatgga catgttcagg 900
gatcgccagg cgtttcctga gcatacctgg aaaatgcttc tgtccgtttg ccggtcgtgg 960
gcggcatggt gcaagttgaa taaccggaaa tggtttcccg cagaacctga agatgttcgc 1020
gattatcttc tatatcttca ggcgcgcggt ctggcagtaa aaactatcca gcaacatttg 1080
ggccagctaa acatgcttca tcgtcggtcc gggctgccac gaccaagtga cagcaatgct 1140
gtttcactgg ttatgcggcg tatccgaaaa gaaaacgttg atgccggtga acgtgcaaaa 1200
caggctctag cgttcgaacg cactgatttc gaccaggttc gttcactcat ggaaaatagc 1260
gatcgctgcc aggatatacg taatctggca tttctgggga ttgcttataa caccctgtta 1320
cgtatagccg aaattgccag gatcagggtt aaagatatct cacgtactga cggtgggaga 1380
atgttaatcc atattggcag aacgaaaacg ctggttagca ccgcaggtgt agagaaggca 1440
cttagcctgg gggtaactaa actggtcgag cgatggattt ccgtctctgg tgtagctgat 1500
gatccgaata actacctgtt ttgccgggtc agaaaaaatg gtgttgccgc gccatctgcc 1560
accagccagc tatcaactcg cgccctggaa gggatttttg aagcaactca tcgattgatt 1620
tacggcgcta aggatgactc tggtcagaga tacctggcct ggtctggaca cagtgcccgt 1680
gtcggagccg cgcgagatat ggcccgcgct ggagtttcaa taccggagat catgcaagct 1740
ggtggctgga ccaatgtaaa tattgtcatg aactatatcc gtaacctgga tagtgaaaca 1800
ggggcaatgg tgcgcctgct ggaagatggc gacggcggat cccatcacca ccaccatcac 1860

<210> SEQ ID NO 269
<211> LENGTH: 4401
<212> TYPE: DNA
<213> ORGANISM: Artificial Sequence
<220> FEATURE:
<223> OTHER INFORMATION: Synthetic Polynucleotide

<400> SEQUENCE: 269
atggataaga aatactcaat aggcttagct atcggcacaa atagcgtcgg atgggcggtg 60
atcactgatg aatataaggt tccgtctaaa aagttcaagg ttctgggaaa tacagaccgc 120
cacagtatca aaaaaaatct tataggggct cttttatttg acagtggaga gacagcggaa 180
gcgactcgtc tcaaacggac agctcgtaga aggtatacac gtcggaagaa tcgtatttgt 240
tatctacagg agatttttc aaatgagatg gcgaaagtag atgatagttt ctttcatcga 300
cttgaagagt cttttttggt ggaagaagac aagaagcatg aacgtcatcc tatttttgga 360
aatatagtag atgaagttgc ttatcatgag aaatatccaa ctatctatca tctgcgaaaa 420
aaattggtag attctactga taaagcggat ttgcgcttaa tctatttggc cttagcgcat 480
atgattaagt ttcgtggtca ttttttgatt gagggagatt taaatcctga taatagtgat 540
gtggacaaac tatttatcca gttggtacaa acctacaatc aattatttga agaaaaccct 600

-continued attaacgcaa gtggagtaga tgctaaagcg attctttctg cacgattgag taaatcaaga 660
cgattagaaa atctcattgc tcagctcccc ggtgagaaga aaaatggctt atttgggaat 720
ctcattgctt tgtcattggg tttgacccct aattttaaat caaattttga tttggcagaa 780
gatgctaaat tacagctttc aaaagatact tacgatgatg atttagataa tttattggcg 840
caaattggag atcaatatgc tgatttgttt ttggcagcta agaatttatc agatgctatt 900
ttactttcag atatcctaag agtaaatact gaaataacta aggctcccct atcagcttca 960
atgattaaac gctacgatga acatcatcaa gacttgactc ttttaaaagc tttagttcga 1020
caacaacttc cagaaaagta taaagaaatc ttttttgatc aatcaaaaaa cggatatgca 1080
ggttatattg atgggggagc tagccaagaa gaattttata aatttatcaa accaatttta 1140
gaaaaaatgg atggtactga ggaattattg gtgaaactaa atcgtgaaga tttgctgcgc 1200
aagcaacgga cctttgacaa cggctctatt ccccatcaaa ttcacttggg tgagctgcat 1260
gctattttga gaagacaaga agacttttat ccatttttaa aagacaatcg tgagaagatt 1320
gaaaaaatct tgacttttcg aattccttat tatgttggtc cattggcgcg tggcaatagt 1380
cgttttgcat ggatgactcg gaagtctgaa gaaacaatta ccccatggaa ttttgaagaa 1440
gttgtcgata aaggtgcttc agctcaatca tttattgaac gcatgacaaa ctttgataaa 1500
aatcttccaa atgaaaaagt actaccaaaa catagtttgc tttatgagta ttttacggtt 1560
tataacgaat tgacaaaggt caaatatgtt actgaaggaa tgcgaaaacc agcatttctt 1620
tcaggtgaac agaagaaagc cattgttgat ttactcttca aaacaaatcg aaaagtaacc 1680
gttaagcaat taaaagaaga ttatttcaaa aaaatagaat gttttgatag tgttgaaatt 1740
tcaggagttg aagatagatt taatgcttca ttaggtacct accatgattt gctaaaaatt 1800
attaaagata aagatttttt ggataatgaa gaaaatgaag atatcttaga ggatattgtt 1860
ttaacattga ccttatttga agatagggag atgattgagg aaagacttaa aacatatgct 1920
cacctctttg atgataaggt gatgaaacag cttaaacgtc gccgttatac tggttgggga 1980
cgtttgtctc gaaaattgat taatggtatt agggataagc aatctggcaa aacaatatta 2040
gatttttga aatcagatgg ttttgccaat cgcaatttta tgcagctgat ccatgatgat 2100
agtttgacat ttaaagaaga cattcaaaaa gcacaagtgt ctggacaagg cgatagttta 2160
catgaacata ttgcaaattt agctggtagc cctgctatta aaaaaggtat tttacagact 2220
gtaaaagttg ttgatgaatt ggtcaaagta atggggcggc ataagccaga aaatatcgtt 2280
attgaaatgg cacgtgaaaa tcagacaact caaaagggcc agaaaaattc gcgagagcgt 2340
atgaaacgaa tcgaagaagg tatcaaagaa ttaggaagtc agattcttaa agagcatcct 2400
gttgaaaata ctcaattgca aaatgaaaag ctctatctct attatctcca aaatggaaga 2460
gacatgtatg tggaccaaga attagatatt aatcgtttaa gtgattatga tgtcgatgcc 2520
attgttccac aaagtttcct taaagacgat tcaatagaca ataaggtctt aacgcgttct 2580
gataaaaatc gtggtaaatc ggataacgtt ccaagtgaag aagtagtcaa aaagatgaaa 2640
aactattgga gacaacttct aaacgccaag ttaatcactc aacgtaagtt tgataattta 2700
acgaaagctg aacgtggagg tttgagtgaa cttgataaag ctggttttat caaacgccaa 2760
ttggttgaaa ctcgccaaat cactaagcat gtggcacaaa ttttggatag tcgcatgaat 2820
actaaatacg atgaaaatga taaacttatt cgagaggtta aagtgattac cttaaaatct 2880
aaattagttt ctgacttccg aaaagatttc caattctata aagtacgtga gattaacaat 2940
taccatcatg cccatgatgc gtatctaaat gccgtcgttg gaactgcttt gattaagaaa 3000

```
tatccaaaac ttgaatcgga gtttgtctat ggtgattata aagtttatga tgttcgtaaa   3060

atgattgcta agtctgagca agaaataggc aaagcaaccg caaaatattt cttttactct   3120

aatatcatga acttcttcaa aacagaaatt acacttgcaa atggagagat tcgcaaacgc   3180

cctctaatcg aaactaatgg ggaaactgga gaaattgtct gggataaagg gcgagatttt   3240

gccacagtgc gcaaagtatt gtccatgccc caagtcaata ttgtcaagaa aacagaagta   3300

cagacaggcg gattctccaa ggagtcaatt ttaccaaaaa gaaattcgga caagcttatt   3360

gctcgtaaaa aagactggga tccaaaaaaa tatggtggtt ttgatagtcc aacggtagct   3420

tattcagtcc tagtggttgc taaggtggaa aaagggaaat cgaagaagtt aaaatccgtt   3480

aaagagttac tagggatcac aattatggaa agaagttcct ttgaaaaaaa tccgattgac   3540

tttttagaag ctaaaggata taaggaagtt aaaaaagact taatcattaa actacctaaa   3600

tatagtcttt ttgagttaga aaacggtcgt aaacggatgc tggctagtgc cggagaatta   3660

caaaaaggaa atgagctggc tctgccaagc aaatatgtga atttttata tttagctagt   3720

cattatgaaa agttgaaggg tagtccagaa gataacgaac aaaaacaatt gtttgtggag   3780

cagcataagc attatttaga tgagattatt gagcaaatca gtgaattttc taagcgtgtt   3840

attttagcag atgccaattt agataaagtt cttagtgcat ataacaaaca tagagacaaa   3900

ccaatacgtg aacaagcaga aaatattatt catttattta cgttgacgaa tcttggagct   3960

cccgctgctt ttaaatattt tgatacaaca attgatcgta aacgatatac gtctacaaaa   4020

gaagttttag atgccactct tatccatcaa tccatcactg gtctttatga aacacgcatt   4080

gatttgagtc agctaggagg tgacggttct cccaagaaga agaggaaagt ctcgagcgac   4140

tacaaagacc atgacggtga ttataaagat catgacatcg attacaagga tgacgatgac   4200

aaggctgcag gaggcggtgg aagcgggcgc gccgacgcgc tggacgattt cgatctcgac   4260

atgctgggtt ctgatgccct cgatgacttt gacctggata tgttgggaag cgacgcattg   4320

gatgactttg atctggacat gctcggctcc gatgctctgg acgatttcga tctcgatatg   4380

ttacatcacc accaccatca c                                             4401
```

<210> SEQ ID NO 270
<211> LENGTH: 1384
<212> TYPE: PRT
<213> ORGANISM: Artificial Sequence
<220> FEATURE:
<223> OTHER INFORMATION: Synthetic Polypeptide

<400> SEQUENCE: 270

```
Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110
```

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

Asp Leu Ala Glu Asp Ala Lys Leu Gln Leu Ser Lys Asp Thr Tyr Asp
260 265 270

Asp Asp Leu Asp Asn Leu Leu Ala Gln Ile Gly Asp Gln Tyr Ala Asp
275 280 285

Leu Phe Leu Ala Ala Lys Asn Leu Ser Asp Ala Ile Leu Leu Ser Asp
290 295 300

Ile Leu Arg Val Asn Thr Glu Ile Thr Lys Ala Pro Leu Ser Ala Ser
305 310 315 320

Met Ile Lys Arg Tyr Asp Glu His His Gln Asp Leu Thr Leu Leu Lys
325 330 335

Ala Leu Val Arg Gln Gln Leu Pro Glu Lys Tyr Lys Glu Ile Phe Phe
340 345 350

Asp Gln Ser Lys Asn Gly Tyr Ala Gly Tyr Ile Asp Gly Gly Ala Ser
355 360 365

Gln Glu Glu Phe Tyr Lys Phe Ile Lys Pro Ile Leu Glu Lys Met Asp
370 375 380

Gly Thr Glu Glu Leu Leu Val Lys Leu Asn Arg Glu Asp Leu Leu Arg
385 390 395 400

Lys Gln Arg Thr Phe Asp Asn Gly Ser Ile Pro His Gln Ile His Leu
405 410 415

Gly Glu Leu His Ala Ile Leu Arg Arg Gln Glu Asp Phe Tyr Pro Phe
420 425 430

Leu Lys Asp Asn Arg Glu Lys Ile Glu Lys Ile Leu Thr Phe Arg Ile
435 440 445

Pro Tyr Tyr Val Gly Pro Leu Ala Arg Gly Asn Ser Arg Phe Ala Trp
450 455 460

Met Thr Arg Lys Ser Glu Glu Thr Ile Thr Pro Trp Asn Phe Glu Glu
465 470 475 480

Val Val Asp Lys Gly Ala Ser Ala Gln Ser Phe Ile Glu Arg Met Thr
485 490 495

Asn Phe Asp Lys Asn Leu Pro Asn Glu Lys Val Leu Pro Lys His Ser
500 505 510

Leu Leu Tyr Glu Tyr Phe Thr Val Tyr Asn Glu Leu Thr Lys Val Lys
515 520 525

```
Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
```

```
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350
```

Gly Leu Tyr Glu Thr Arg Ile Asp Leu Ser Gln Leu Gly Gly Asp
1355 1360 1365

Pro Lys Lys Lys Arg Lys Val Met Asp Lys His His His His His
1370 1375 1380

His

<210> SEQ ID NO 271
<211> LENGTH: 4152
<212> TYPE: DNA
<213> ORGANISM: Artificial Sequence
<220> FEATURE:
<223> OTHER INFORMATION: Synthetic Polynucleotide

<400> SEQUENCE: 271
atggataaga aatactcaat aggcttagat atcggcacaa atagcgtcgg atgggcggtg 60
atcactgatg aatataaggt tccgtctaaa aagttcaagg ttctgggaaa tacagaccgc 120
cacagtatca aaaaaaatct tataggggct cttttatttg acagtggaga gacagcggaa 180
gcgactcgtc tcaaacggac agctcgtaga aggtatacac gtcggaagaa tcgtatttgt 240
tatctacagg agattttttc aaatgagatg gcgaaagtag atgatagttt ctttcatcga 300
cttgaagagt cttttttggt ggaagaagac aagaagcatg aacgtcatcc tatttttgga 360
aatatagtag atgaagttgc ttatcatgag aaatatccaa ctatctatca tctgcgaaaa 420
aaattggtag attctactga taaagcggat ttgcgcttaa tctatttggc cttagcgcat 480
atgattaagt ttcgtggtca tttttttgatt gagggagatt taaatcctga taatagtgat 540
gtggacaaac tatttatcca gttggtacaa acctacaatc aattatttga agaaaaccct 600
attaacgcaa gtggagtaga tgctaaagcg attctttctg cacgattgag taaatcaaga 660
cgattagaaa atctcattgc tcagctcccc ggtgagaaga aaaatggctt atttgggaat 720
ctcattgctt tgtcattggg tttgacccct aattttaaat caaattttga tttggcagaa 780
gatgctaaat tacagctttc aaaagatact tacgatgatg atttagataa tttattggcg 840
caaattggag atcaatatgc tgatttgttt ttggcagcta agaatttatc agatgctatt 900
ttactttcag atatcctaag agtaaatact gaaataacta aggctcccct atcagcttca 960
atgattaaac gctacgatga acatcatcaa gacttgactc ttttaaaagc tttagttcga 1020
caacaacttc cagaaaagta taaagaaatc ttttttgatc aatcaaaaaa cggatatgca 1080
ggttatattg atgggggagc tagccaagaa gaattttata aatttatcaa accaatttta 1140
gaaaaaatgg atggtactga ggaattattg gtgaaactaa atcgtgaaga tttgctgcgc 1200
aagcaacgga cctttgacaa cggctctatt ccccatcaaa ttcacttggg tgagctgcat 1260
gctattttga gaagacaaga agacttttat ccatttttaa aagacaatcg tgagaagatt 1320
gaaaaaatct tgacttttcg aattccttat tatgttggtc cattggcgcg tggcaatagt 1380
cgttttgcat ggatgactcg gaagtctgaa gaaacaatta ccccatggaa ttttgaagaa 1440
gttgtcgata aaggtgcttc agctcaatca tttattgaac gcatgacaaa ctttgataaa 1500
aatcttccaa atgaaaaagt actaccaaaa catagtttgc tttatgagta ttttacggtt 1560
tataacgaat tgacaaaggt caaatatgtt actgaaggaa tgcgaaaacc agcatttctt 1620
tcaggtgaac agaagaaagc cattgttgat ttactcttca aaacaaatcg aaaagtaacc 1680
gttaagcaat taaaagaaga ttatttcaaa aaaatagaat gttttgatag tgttgaaatt 1740
tcaggagttg aagatagatt taatgcttca ttaggtacct accatgattt gctaaaaatt 1800

-continued

```
attaaagata aagatttttt ggataatgaa gaaaatgaag atatcttaga ggatattgtt   1860
ttaacattga ccttatttga agatagggag atgattgagg aaagacttaa aacatatgct   1920
cacctctttg atgataaggt gatgaaacag cttaaacgtc gccgttatac tggttgggga   1980
cgtttgtctc gaaaattgat taatggtatt agggataagc aatctggcaa aacaatatta   2040
gatttttga aatcagatgg ttttgccaat cgcaatttta tgcagctgat ccatgatgat   2100
agtttgacat ttaaagaaga cattcaaaaa gcacaagtgt ctggacaagg cgatagttta   2160
catgaacata ttgcaaattt agctggtagc cctgctatta aaaaaggtat tttacagact   2220
gtaaaagttg ttgatgaatt ggtcaaagta atggggcggc ataagccaga aaatatcgtt   2280
attgaaatgg cacgtgaaaa tcagacaact caaaagggcc agaaaaattc gcgagagcgt   2340
atgaaacgaa tcgaagaagg tatcaaagaa ttaggaagtc agattcttaa agagcatcct   2400
gttgaaaata ctcaattgca aaatgaaaag ctctatctct attatctcca aaatggaaga   2460
gacatgtatg tggaccaaga attagatatt aatcgtttaa gtgattatga tgtcgatcac   2520
attgttccac aaagtttcct taaagacgat tcaatagaca ataaggtctt aacgcgttct   2580
gataaaaatc gtggtaaatc ggataacgtt ccaagtgaag aagtagtcaa aaagatgaaa   2640
aactattgga gacaacttct aaacgccaag ttaatcactc aacgtaagtt tgataattta   2700
acgaaagctg aacgtggagg tttgagtgaa cttgataaag ctggttttat caaacgccaa   2760
ttggttgaaa ctcgccaaat cactaagcat gtggcacaaa ttttggatag tcgcatgaat   2820
actaaatacg atgaaaatga taaacttatt cgagaggtta aagtgattac cttaaaatct   2880
aaattagttt ctgacttccg aaaagatttc caattctata aagtacgtga gattaacaat   2940
taccatcatg cccatgatgc gtatctaaat gccgtcgttg gaactgcttt gattaagaaa   3000
tatccaaaac ttgaatcgga gtttgtctat ggtgattata aagtttatga tgttcgtaaa   3060
atgattgcta agtctgagca agaaataggc aaagcaaccg caaaatattt cttttactct   3120
aatatcatga acttcttcaa aacagaaatt acacttgcaa atggagagat tcgcaaacgc   3180
cctctaatcg aaactaatgg ggaaactgga gaaattgtct gggataaagg gcgagatttt   3240
gccacagtgc gcaaagtatt gtccatgccc caagtcaata ttgtcaagaa aacagaagta   3300
cagacaggcg gattctccaa ggagtcaatt ttaccaaaaa gaaattcgga caagcttatt   3360
gctcgtaaaa aagactggga tccaaaaaaa tatggtggtt ttgatagtcc aacggtagct   3420
tattcagtcc tagtggttgc taaggtggaa aaagggaaat cgaagaagtt aaaatccgtt   3480
aaagagttac tagggatcac aattatggaa agaagttcct ttgaaaaaaa tccgattgac   3540
tttttagaag ctaaaggata taaggaagtt aaaaaagact taatcattaa actacctaaa   3600
tatagtcttt ttgagttaga aaacggtcgt aaacggatgc tggctagtgc cggagaatta   3660
caaaaaggaa atgagctggc tctgccaagc aaatatgtga atttttata tttagctagt   3720
cattatgaaa agttgaaggg tagtccagaa gataacgaac aaaaacaatt gtttgtggag   3780
cagcataagc attatttaga tgagattatt gagcaaatca gtgaattttc taagcgtgtt   3840
attttagcag atgccaattt agataaagtt cttagtgcat ataacaaaca tagagacaaa   3900
ccaatacgtg aacaagcaga aaatattatt catttattta cgttgacgaa tcttggagct   3960
cccgctgctt ttaaatattt tgatacaaca attgatcgta aacgatatac gtctacaaaa   4020
gaagttttag atgccactct tatccatcaa tccatcactg gtctttatga aacacgcatt   4080
gatttgagtc agctaggagg tgaccccaag aagaagagga aggtgatgga taagcatcac   4140
caccaccatc ac                                                        4152
```

<210> SEQ ID NO 272
<211> LENGTH: 1382
<212> TYPE: PRT
<213> ORGANISM: Artificial Sequence
<220> FEATURE:
<223> OTHER INFORMATION: Synthetic Polypeptide

<400> SEQUENCE: 272

Met Pro Lys Lys Lys Arg Lys Val Met Asp Lys Lys Tyr Ser Ile Gly
1 5 10 15

Leu Ala Ile Gly Thr Asn Ser Val Gly Trp Ala Val Ile Thr Asp Glu
20 25 30

Tyr Lys Val Pro Ser Lys Lys Phe Lys Val Leu Gly Asn Thr Asp Arg
35 40 45

His Ser Ile Lys Lys Asn Leu Ile Gly Ala Leu Leu Phe Asp Ser Gly
50 55 60

Glu Thr Ala Glu Ala Thr Arg Leu Lys Arg Thr Ala Arg Arg Arg Tyr
65 70 75 80

Thr Arg Arg Lys Asn Arg Ile Cys Tyr Leu Gln Glu Ile Phe Ser Asn
85 90 95

Glu Met Ala Lys Val Asp Asp Ser Phe Phe His Arg Leu Glu Glu Ser
100 105 110

Phe Leu Val Glu Glu Asp Lys Lys His Glu Arg His Pro Ile Phe Gly
115 120 125

Asn Ile Val Asp Glu Val Ala Tyr His Glu Lys Tyr Pro Thr Ile Tyr
130 135 140

His Leu Arg Lys Lys Leu Val Asp Ser Thr Asp Lys Ala Asp Leu Arg
145 150 155 160

Leu Ile Tyr Leu Ala Leu Ala His Met Ile Lys Phe Arg Gly His Phe
165 170 175

Leu Ile Glu Gly Asp Leu Asn Pro Asp Asn Ser Asp Val Asp Lys Leu
180 185 190

Phe Ile Gln Leu Val Gln Thr Tyr Asn Gln Leu Phe Glu Glu Asn Pro
195 200 205

Ile Asn Ala Ser Gly Val Asp Ala Lys Ala Ile Leu Ser Ala Arg Leu
210 215 220

Ser Lys Ser Arg Arg Leu Glu Asn Leu Ile Ala Gln Leu Pro Gly Glu
225 230 235 240

Lys Lys Asn Gly Leu Phe Gly Asn Leu Ile Ala Leu Ser Leu Gly Leu
245 250 255

Thr Pro Asn Phe Lys Ser Asn Phe Asp Leu Ala Glu Asp Ala Lys Leu
260 265 270

Gln Leu Ser Lys Asp Thr Tyr Asp Asp Asp Leu Asp Asn Leu Leu Ala
275 280 285

Gln Ile Gly Asp Gln Tyr Ala Asp Leu Phe Leu Ala Ala Lys Asn Leu
290 295 300

Ser Asp Ala Ile Leu Leu Ser Asp Ile Leu Arg Val Asn Thr Glu Ile
305 310 315 320

Thr Lys Ala Pro Leu Ser Ala Ser Met Ile Lys Arg Tyr Asp Glu His
325 330 335

His Gln Asp Leu Thr Leu Leu Lys Ala Leu Val Arg Gln Gln Leu Pro
340 345 350

Glu Lys Tyr Lys Glu Ile Phe Phe Asp Gln Ser Lys Asn Gly Tyr Ala
355 360 365

Gly Tyr Ile Asp Gly Gly Ala Ser Gln Glu Glu Phe Tyr Lys Phe Ile
    370                 375                 380

Lys Pro Ile Leu Glu Lys Met Asp Gly Thr Glu Glu Leu Leu Val Lys
385                 390                 395                 400

Leu Asn Arg Glu Asp Leu Leu Arg Lys Gln Arg Thr Phe Asp Asn Gly
                405                 410                 415

Ser Ile Pro His Gln Ile His Leu Gly Glu Leu His Ala Ile Leu Arg
            420                 425                 430

Arg Gln Glu Asp Phe Tyr Pro Phe Leu Lys Asp Asn Arg Glu Lys Ile
        435                 440                 445

Glu Lys Ile Leu Thr Phe Arg Ile Pro Tyr Tyr Val Gly Pro Leu Ala
    450                 455                 460

Arg Gly Asn Ser Arg Phe Ala Trp Met Thr Arg Lys Ser Glu Glu Thr
465                 470                 475                 480

Ile Thr Pro Trp Asn Phe Glu Glu Val Val Asp Lys Gly Ala Ser Ala
                485                 490                 495

Gln Ser Phe Ile Glu Arg Met Thr Asn Phe Asp Lys Asn Leu Pro Asn
            500                 505                 510

Glu Lys Val Leu Pro Lys His Ser Leu Leu Tyr Glu Tyr Phe Thr Val
        515                 520                 525

Tyr Asn Glu Leu Thr Lys Val Lys Tyr Val Thr Glu Gly Met Arg Lys
    530                 535                 540

Pro Ala Phe Leu Ser Gly Glu Gln Lys Lys Ala Ile Val Asp Leu Leu
545                 550                 555                 560

Phe Lys Thr Asn Arg Lys Val Thr Val Lys Gln Leu Lys Glu Asp Tyr
                565                 570                 575

Phe Lys Lys Ile Glu Cys Phe Asp Ser Val Glu Ile Ser Gly Val Glu
            580                 585                 590

Asp Arg Phe Asn Ala Ser Leu Gly Thr Tyr His Asp Leu Leu Lys Ile
        595                 600                 605

Ile Lys Asp Lys Asp Phe Leu Asp Asn Glu Glu Asn Glu Asp Ile Leu
    610                 615                 620

Glu Asp Ile Val Leu Thr Leu Thr Leu Phe Glu Asp Arg Glu Met Ile
625                 630                 635                 640

Glu Glu Arg Leu Lys Thr Tyr Ala His Leu Phe Asp Asp Lys Val Met
                645                 650                 655

Lys Gln Leu Lys Arg Arg Arg Tyr Thr Gly Trp Gly Arg Leu Ser Arg
            660                 665                 670

Lys Leu Ile Asn Gly Ile Arg Asp Lys Gln Ser Gly Lys Thr Ile Leu
        675                 680                 685

Asp Phe Leu Lys Ser Asp Gly Phe Ala Asn Arg Asn Phe Met Gln Leu
    690                 695                 700

Ile His Asp Asp Ser Leu Thr Phe Lys Glu Asp Ile Gln Lys Ala Gln
705                 710                 715                 720

Val Ser Gly Gln Gly Asp Ser Leu His Glu His Ile Ala Asn Leu Ala
                725                 730                 735

Gly Ser Pro Ala Ile Lys Lys Gly Ile Leu Gln Thr Val Lys Val Val
            740                 745                 750

Asp Glu Leu Val Lys Val Met Gly Arg His Lys Pro Glu Asn Ile Val
        755                 760                 765

Ile Glu Met Ala Arg Glu Asn Gln Thr Thr Gln Lys Gly Gln Lys Asn
    770                 775                 780

-continued

Ser Arg Glu Arg Met Lys Arg Ile Glu Glu Gly Ile Lys Glu Leu Gly
785 790 795 800

Ser Gln Ile Leu Lys Glu His Pro Val Glu Asn Thr Gln Leu Gln Asn
805 810 815

Glu Lys Leu Tyr Leu Tyr Tyr Leu Gln Asn Gly Arg Asp Met Tyr Val
820 825 830

Asp Gln Glu Leu Asp Ile Asn Arg Leu Ser Asp Tyr Asp Val Asp His
835 840 845

Ile Val Pro Gln Ser Phe Leu Lys Asp Asp Ser Ile Asp Asn Lys Val
850 855 860

Leu Thr Arg Ser Asp Lys Asn Arg Gly Lys Ser Asp Asn Val Pro Ser
865 870 875 880

Glu Glu Val Val Lys Lys Met Lys Asn Tyr Trp Arg Gln Leu Leu Asn
885 890 895

Ala Lys Leu Ile Thr Gln Arg Lys Phe Asp Asn Leu Thr Lys Ala Glu
900 905 910

Arg Gly Gly Leu Ser Glu Leu Asp Lys Ala Gly Phe Ile Lys Arg Gln
915 920 925

Leu Val Glu Thr Arg Gln Ile Thr Lys His Val Ala Gln Ile Leu Asp
930 935 940

Ser Arg Met Asn Thr Lys Tyr Asp Glu Asn Asp Lys Leu Ile Arg Glu
945 950 955 960

Val Lys Val Ile Thr Leu Lys Ser Lys Leu Val Ser Asp Phe Arg Lys
965 970 975

Asp Phe Gln Phe Tyr Lys Val Arg Glu Ile Asn Asn Tyr His His Ala
980 985 990

His Asp Ala Tyr Leu Asn Ala Val Val Gly Thr Ala Leu Ile Lys Lys
995 1000 1005

Tyr Pro Lys Leu Glu Ser Glu Phe Val Tyr Gly Asp Tyr Lys Val
1010 1015 1020

Tyr Asp Val Arg Lys Met Ile Ala Lys Ser Glu Gln Glu Ile Gly
1025 1030 1035

Lys Ala Thr Ala Lys Tyr Phe Phe Tyr Ser Asn Ile Met Asn Phe
1040 1045 1050

Phe Lys Thr Glu Ile Thr Leu Ala Asn Gly Glu Ile Arg Lys Arg
1055 1060 1065

Pro Leu Ile Glu Thr Asn Gly Glu Thr Gly Glu Ile Val Trp Asp
1070 1075 1080

Lys Gly Arg Asp Phe Ala Thr Val Arg Lys Val Leu Ser Met Pro
1085 1090 1095

Gln Val Asn Ile Val Lys Lys Thr Glu Val Gln Thr Gly Gly Phe
1100 1105 1110

Ser Lys Glu Ser Ile Leu Pro Lys Arg Asn Ser Asp Lys Leu Ile
1115 1120 1125

Ala Arg Lys Lys Asp Trp Asp Pro Lys Lys Tyr Gly Gly Phe Asp
1130 1135 1140

Ser Pro Thr Val Ala Tyr Ser Val Leu Val Val Ala Lys Val Glu
1145 1150 1155

Lys Gly Lys Ser Lys Lys Leu Lys Ser Val Lys Glu Leu Leu Gly
1160 1165 1170

Ile Thr Ile Met Glu Arg Ser Ser Phe Glu Lys Asn Pro Ile Asp
1175 1180 1185

Phe Leu Glu Ala Lys Gly Tyr Lys Glu Val Lys Lys Asp Leu Ile 1190 1195 1200

Ile Lys Leu Pro Lys Tyr Ser Leu Phe Glu Leu Glu Asn Gly Arg
1205 1210 1215

Lys Arg Met Leu Ala Ser Ala Gly Glu Leu Gln Lys Gly Asn Glu
1220 1225 1230

Leu Ala Leu Pro Ser Lys Tyr Val Asn Phe Leu Tyr Leu Ala Ser
1235 1240 1245

His Tyr Glu Lys Leu Lys Gly Ser Pro Glu Asp Asn Glu Gln Lys
1250 1255 1260

Gln Leu Phe Val Glu Gln His Lys His Tyr Leu Asp Glu Ile Ile
1265 1270 1275

Glu Gln Ile Ser Glu Phe Ser Lys Arg Val Ile Leu Ala Asp Ala
1280 1285 1290

Asn Leu Asp Lys Val Leu Ser Ala Tyr Asn Lys His Arg Asp Lys
1295 1300 1305

Pro Ile Arg Glu Gln Ala Glu Asn Ile Ile His Leu Phe Thr Leu
1310 1315 1320

Thr Asn Leu Gly Ala Pro Ala Ala Phe Lys Tyr Phe Asp Thr Thr
1325 1330 1335

Ile Asp Arg Lys Arg Tyr Thr Ser Thr Lys Glu Val Leu Asp Ala
1340 1345 1350

Thr Leu Ile His Gln Ser Ile Thr Gly Leu Tyr Glu Thr Arg Ile
1355 1360 1365

Asp Leu Ser Gln Leu Gly Gly Asp His His His His His His
1370 1375 1380

<210> SEQ ID NO 273
<211> LENGTH: 53
<212> TYPE: DNA
<213> ORGANISM: Artificial Sequence
<220> FEATURE:
<223> OTHER INFORMATION: Synthetic Polynucleotide

<400> SEQUENCE: 273
taatacgact cactataggg gccactaggg acaggatgaa aggacgaaac acc 53

<210> SEQ ID NO 274
<211> LENGTH: 200
<212> TYPE: DNA
<213> ORGANISM: Artificial Sequence
<220> FEATURE:
<223> OTHER INFORMATION: Synthetic Polynucleotide

<400> SEQUENCE: 274
cgaccacatg aagcagcacg acttcttcaa gtccgccatg cccgaaggct acgtccagga 60
gcgcaccatc ttcttcaagg acgacggcaa ctacaagacc cgcgccgagg tgaagttcga 120
gggcgacacc ctggtgaacc gcatcgagct gaagggcatc gacttcaagg aggacggcaa 180
catcctgggg cacaagctgg 200

<210> SEQ ID NO 275
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 275

Met Gly His His His His His His Gly Gly Ala Ser Lys Gly Glu Glu

-continued

```
1               5                   10                  15

Leu Phe Thr Gly Val Val Pro Ile Leu Val Glu Leu Asp Gly Asp Val
            20                  25                  30

Asn Gly His Lys Phe Ser Val Arg Gly Glu Gly Glu Gly Asp Ala Thr
        35                  40                  45

Asn Gly Lys Leu Thr Leu Lys Phe Ile Cys Thr Thr Gly Lys Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Asp His Met Lys Gln His Asp Phe Phe Lys Ser
                85                  90                  95

Ala Met Pro Glu Gly Tyr Val Gln Glu Arg Thr Ile Ser Phe Lys Asp
            100                 105                 110

Asp Gly Thr Tyr Lys Thr Arg Ala Glu Val Lys Phe Glu Gly Asp Thr
        115                 120                 125

Leu Val Asn Arg Ile Glu Leu Lys Gly Ile Asp Phe Lys Glu Asp Gly
    130                 135                 140

Asn Ile Leu Gly His Lys Leu Glu Tyr Asn Phe Asn Ser His Asn Val
145                 150                 155                 160

Tyr Ile Thr Ala Asp Lys Gln Lys Asn Gly Ile Lys Ala Asn Phe Lys
                165                 170                 175

Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asn
        195                 200                 205

His Tyr Leu Ser Thr Gln Ser Ala Leu Ser Lys Asp Pro Asn Glu Lys
    210                 215                 220

Arg Asp His Met Val Leu Leu Glu Phe Val Thr Ala Ala Gly Ile Thr
225                 230                 235                 240

His Gly Met Asp Glu Leu Tyr Lys
                245


<210> SEQ ID NO 276
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 276

Met Gly His His His His His His Gly Gly Ala Ser Lys Gly Glu Glu
1               5                   10                  15

Leu Phe Thr Gly Val Val Pro Ile Leu Val Glu Leu Asp Gly Asp Val
            20                  25                  30

Asn Gly His Glu Phe Ser Val Arg Gly Glu Gly Glu Gly Asp Ala Thr
        35                  40                  45

Glu Gly Glu Leu Thr Leu Lys Phe Ile Cys Thr Thr Gly Glu Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Asp His Met Lys Gln His Asp Phe Phe Lys Ser
                85                  90                  95

Ala Met Pro Glu Gly Tyr Val Gln Glu Arg Thr Ile Ser Phe Lys Asp
            100                 105                 110

Asp Gly Thr Tyr Lys Thr Arg Ala Glu Val Lys Phe Glu Gly Asp Thr
```

```
        115                 120                 125

Leu Val Asn Arg Ile Glu Leu Lys Gly Ile Asp Phe Lys Glu Asp Gly
    130                 135                 140

Asn Ile Leu Gly His Lys Leu Glu Tyr Asn Phe Asn Ser His Asp Val
145                 150                 155                 160

Tyr Ile Thr Ala Asp Lys Gln Glu Asn Gly Ile Lys Ala Glu Phe Glu
                165                 170                 175

Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asp
        195                 200                 205

His Tyr Leu Ser Thr Glu Ser Ala Leu Ser Lys Asp Pro Asn Glu Asp
    210                 215                 220

Arg Asp His Met Val Leu Leu Glu Phe Val Thr Ala Ala Gly Ile Asp
225                 230                 235                 240

His Gly Met Asp Glu Leu Tyr Lys
                245


<210> SEQ ID NO 277
<211> LENGTH: 248
<212> TYPE: PRT
<213> ORGANISM: Artificial Sequence
<220> FEATURE:
<223> OTHER INFORMATION: Synthetic Polypeptide

<400> SEQUENCE: 277

Met Gly His His His His His His Gly Gly Ala Ser Lys Gly Glu Glu
1               5                   10                  15

Leu Phe Asp Gly Glu Val Pro Ile Leu Val Glu Leu Asp Gly Asp Val
            20                  25                  30

Asn Gly His Glu Phe Ser Val Arg Gly Glu Gly Glu Gly Asp Ala Thr
        35                  40                  45

Glu Gly Glu Leu Thr Leu Lys Phe Ile Cys Thr Thr Gly Glu Leu Pro
    50                  55                  60

Val Pro Trp Pro Thr Leu Val Thr Thr Leu Thr Tyr Gly Val Gln Cys
65                  70                  75                  80

Phe Ser Arg Tyr Pro Asp His Met Asp Gln His Asp Phe Phe Lys Ser
                85                  90                  95

Ala Met Pro Glu Gly Tyr Val Gln Glu Arg Thr Ile Ser Phe Lys Asp
            100                 105                 110

Asp Gly Thr Tyr Lys Thr Arg Ala Glu Val Lys Phe Glu Gly Asp Thr
        115                 120                 125

Leu Val Asn Arg Ile Glu Leu Lys Gly Ile Asp Phe Lys Glu Asp Gly
    130                 135                 140

Asn Ile Leu Gly His Lys Leu Glu Tyr Asn Phe Asn Ser His Asp Val
145                 150                 155                 160

Tyr Ile Thr Ala Asp Lys Gln Glu Asn Gly Ile Lys Ala Glu Phe Glu
                165                 170                 175

Ile Arg His Asn Val Glu Asp Gly Ser Val Gln Leu Ala Asp His Tyr
            180                 185                 190

Gln Gln Asn Thr Pro Ile Gly Asp Gly Pro Val Leu Leu Pro Asp Asp
        195                 200                 205

His Tyr Leu Ser Thr Glu Ser Ala Leu Ser Lys Asp Pro Asn Glu Asp
    210                 215                 220

Arg Asp His Met Val Leu Leu Glu Phe Val Thr Ala Ala Gly Ile Asp
```

225 230 235 240

His Gly Met Asp Glu Leu Tyr Lys
245

<210> SEQ ID NO 278
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 278

Ala Ala Glu Ala Gly Ile Thr Gly Thr Trp Tyr Asn Gln Leu Gly Ser
1 5 10 15

Thr Phe Ile Val Thr Ala Gly Ala Asp Gly Ala Leu Thr Gly Thr Tyr
20 25 30

Glu Ser Ala Val Gly Asn Ala Glu Ser Arg Tyr Val Leu Thr Gly Arg
35 40 45

Tyr Asp Ser Ala Pro Ala Thr Asp Gly Ser Gly Thr Ala Leu Gly Trp
50 55 60

Thr Val Ala Trp Lys Asn Asn Tyr Arg Asn Ala His Ser Ala Thr Thr
65 70 75 80

Trp Ser Gly Gln Tyr Val Gly Gly Ala Glu Ala Arg Ile Asn Thr Gln
85 90 95

Trp Leu Leu Thr Ser Gly Thr Thr Glu Ala Asn Ala Trp Lys Ser Thr
100 105 110

Leu Val Gly His Asp Thr Phe Thr Lys Val Lys Pro Ser Ala Ala Ser
115 120 125

<210> SEQ ID NO 279
<211> LENGTH: 137
<212> TYPE: PRT
<213> ORGANISM: Artificial Sequence
<220> FEATURE:
<223> OTHER INFORMATION: Synthetic Polypeptide

<400> SEQUENCE: 279

Met Gly His His His His His His Gly Gly Ala Glu Ala Gly Ile Thr
1 5 10 15

Gly Thr Trp Tyr Asn Gln Leu Gly Ser Thr Phe Ile Val Thr Ala Gly
20 25 30

Ala Asp Gly Ala Leu Thr Gly Thr Tyr Glu Ser Ala Val Gly Asp Ala
35 40 45

Glu Ser Glu Tyr Val Leu Thr Gly Arg Tyr Asp Ser Ala Pro Ala Thr
50 55 60

Asp Gly Ser Gly Thr Ala Leu Gly Trp Thr Val Ala Trp Lys Asn Asp
65 70 75 80

Tyr Glu Asn Ala His Ser Ala Thr Thr Trp Ser Gly Gln Tyr Val Gly
85 90 95

Gly Ala Glu Ala Arg Ile Asn Thr Gln Trp Leu Leu Thr Ser Gly Thr
100 105 110

Thr Glu Ala Asp Ala Trp Lys Ser Thr Leu Val Gly His Asp Thr Phe
115 120 125

Thr Lys Val Glu Pro Ser Ala Ala Ser
130 135

<210> SEQ ID NO 280
<211> LENGTH: 137

-continued

```
<212> TYPE: PRT
<213> ORGANISM: Artificial Sequence
<220> FEATURE:
<223> OTHER INFORMATION: Synthetic Polypeptide

<400> SEQUENCE: 280

Met Gly His His His His His His Gly Gly Ala Lys Ala Gly Ile Thr
1               5                   10                  15

Gly Thr Trp Tyr Asn Gln Leu Gly Ser Thr Phe Ile Val Thr Ala Gly
            20                  25                  30

Ala Lys Gly Ala Leu Thr Gly Thr Tyr Glu Ser Ala Val Gly Asn Ala
        35                  40                  45

Lys Ser Arg Tyr Val Leu Thr Gly Arg Tyr Asp Ser Ala Pro Ala Thr
    50                  55                  60

Lys Gly Ser Gly Thr Ala Leu Gly Trp Thr Val Ala Trp Lys Asn Lys
65                  70                  75                  80

Tyr Arg Asn Ala His Ser Ala Leu Thr Trp Ser Gly Gln Tyr Val Gly
                85                  90                  95

Gly Ala Lys Ala Arg Ile Asn Thr Gln Trp Leu Leu Thr Ser Gly Thr
            100                 105                 110

Thr Lys Ala Lys Ala Trp Lys Ser Thr Leu Val Gly His Asp Thr Phe
        115                 120                 125

Thr Lys Val Lys Pro Ser Ala Ala Ser
    130                 135
```